US011242344B2

(12) United States Patent
Blaquiere et al.

(10) Patent No.: US 11,242,344 B2
(45) Date of Patent: Feb. 8, 2022

(54) (4-HYDROXYPYRROLIDIN-2-YL)-HETERO-CYCLIC COMPOUNDS AND METHODS OF USE THEREOF

(71) Applicant: Genentech, Inc., South San Francisco, CA (US)

(72) Inventors: Nicole Blaquiere, South San Francisco, CA (US); Peter Dragovich, South San Francisco, CA (US); Lewis J. Gazzard, South San Francisco, CA (US); Thomas Pillow, South San Francisco, CA (US); Steven T. Staben, South San Francisco, CA (US); Binqing Wei, South San Francisco, CA (US); Jianfeng Xin, Beijing (CN)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/858,004

(22) Filed: Apr. 24, 2020

(65) Prior Publication Data
US 2021/0309660 A1 Oct. 7, 2021

Related U.S. Application Data

(63) Continuation of application No. PCT/US2018/057135, filed on Oct. 23, 2018.

(30) Foreign Application Priority Data

Oct. 24, 2017 (WO) ................ PCT/CN2017/107445
Sep. 13, 2018 (WO) ................ PCT/CN2018/105402

(51) Int. Cl.
*C07D 471/16* (2006.01)
*C07D 493/10* (2006.01)
*A61P 35/00* (2006.01)
*C07D 417/14* (2006.01)
*C07D 413/14* (2006.01)
*C07D 403/04* (2006.01)

(52) U.S. Cl.
CPC ............ *C07D 471/16* (2013.01); *A61P 35/00* (2018.01); *C07D 403/04* (2013.01); *C07D 413/14* (2013.01); *C07D 417/14* (2013.01); *C07D 493/10* (2013.01)

(58) Field of Classification Search
None
See application file for complete search history.

(56) References Cited

U.S. PATENT DOCUMENTS

| 4,522,811 | A  | 6/1985  | Eppstein et al.  |
| 7,208,157 | B2 | 4/2007  | Dashaies et al.  |
| 7,723,485 | B2 | 5/2010  | Junutula et al.  |
| 7,989,595 | B2 | 8/2011  | Dennis et al.    |
| 8,226,945 | B2 | 7/2012  | Ebens, Jr. et al.|
| 8,449,883 | B2 | 5/2013  | Dennis et al.    |
| 2014/0356322 | A1 | 12/2014 | Crews et al.  |
| 2015/0291562 | A1 | 10/2015 | Crew et al.   |
| 2016/0045607 | A1 | 2/2016  | Crew et al.   |
| 2016/0058872 | A1 | 3/2016  | Crew et al.   |
| 2016/0185785 | A1 | 6/2016  | Ioannidis et al. |
| 2016/0229833 | A1 | 8/2016  | Ioannidis et al. |
| 2016/0229864 | A1 | 8/2016  | Ioannidis et al. |
| 2016/0229872 | A1 | 8/2016  | Ioannidis et al. |

FOREIGN PATENT DOCUMENTS

| WO | 2002022577 | 3/2002 |
| WO | 2007001851 | 1/2007 |
| WO | 2012078559 | 6/2012 |
| WO | 2013106643 | 7/2013 |
| WO | 2014143659 | 3/2014 |
| WO | 2014063061 | 4/2014 |
| WO | 2014123795 | 8/2014 |
| WO | 2014152588 | 9/2014 |
| WO | 2015000868 | 1/2015 |
| WO | 2015075483 | 5/2015 |
| WO | 2016138114 | 9/2016 |
| WO | 2016146985 | 9/2016 |
| WO | 2017004383 | 1/2017 |
| WO | 2017024317 | 2/2017 |
| WO | 2017030814 | 2/2017 |

OTHER PUBLICATIONS

Boitano et al., "Aryl Hydrocarbon Receptor Antagonists Promote the Expansion of Human Hematopoietic Stem Cells," Science, 329(5997): 1345-1348 (2010).
Brough et al., "4,5-Diarylisoxazole HSP90 Chaperone Inhibitors: Potential Therapeutic Agents for the Treatment of Cancer," Journal of Medicinal Chemistry, 51(2): 196-218 (2008).
Chang et al., "Structural Basis for G9a-Like Protein Lysine Methyltransferase Inhibition by BIX-01294," Nature Structural & Molecular Biology, 16(3): 312-317 (2009).
Chen et al., "Armed Antibodies Targeting the Mucin Repeats of the Ovarian Cancer Antigen, MUC16, Are Highly Efficacious in Animal Tumor Models," Cancer Research, 67(10): 4924-4932 (2007).
Chung et al., "Discovery and Characterization of Small Molecule Inhibitors of the BET Family Bromodomains," Journal of Medicinal Chemistry, 54(11): 3827-3838 (2011).
Dawson et al., "Inhibition of BET Recruitment to Chromatin as an Effective Treatment for MLL-fusion Leukemia," Nature, 478: 529-533 (2011).
Elkins et al., "Characterization of the Isomeric Configuration and Impurities of (Z)-endoxifen by 2D NMR, High Resolution LC-MS, and Quantitative HPLC Analysis," Journal of Pharmaceutical and Biomedical Analysis, 88: 174-179 (2014).

(Continued)

*Primary Examiner* — Samantha L Shterengarts
(74) *Attorney, Agent, or Firm* — Armstrong Teasdale LLP

(57) ABSTRACT

The present disclosure relates to bifunctional compounds, which can be used as modulators of targeted ubiquitination. In particular, the present disclosure is directed to compounds which contain on one end a VHL ligand moiety, which binds to the VHL E3 ubiquitin ligase, and on the other end a moiety that binds a target protein such that degradation of the target protein/polypeptide is effectuated. Also disclosed are VHL ligands.

29 Claims, No Drawings

(56) References Cited

OTHER PUBLICATIONS

Filippakopoulos et al. "Selective Inhibition of BET Bromodomains," Nature, 468(7237): 1067-1073 (2010).
Filippakoupoulos et al., "Targeting Bromodomains: Epigenetic Readers of Lysine Acetylation," Nature Reviews Drug Discovery, 13(5): 337-356 (2014).
Finnin et al., "Structures of A Histone Deacetylase Homologue Bound to the TSA and SAHA Inhibitors," Nature, 401(6749): 188-193 (1999).
Galdeano et al., "Structure-Guided Design and Optimization of Small Molecules Targeting the Protein-Protein Interaction between the von Hippel-Lindau (VHL) E3 Ubiquitin Ligase and the Hypoxia Inducible Factor (HIF) Alpha Subunit with in Vitro Nanomolar Affinities," Journal of Medicinal Chemistry, 57(20) 8657-8663 (2014).
Gerstenberger et al., "Identification of a Chemical Probe for Family VIII Bromodomains through Optimization of a Fragment Hit," Journal of Medicinal Chemistry, 59(10): 4800-4811 (2016).
Ghoshal et al., "BET Inhibitors in Cancer Therapeutics: A Patent Review," Expert Opinion on Therapeutic Patents, 26(4): 505-522 (2016).
Hewings et al., "3,5-Dimethylisoxazoles Act as Acetyl-lysine Bromodomain Ligands," Journal of Medicinal Chemistry, 54(19): 6761-6770 (2011).
Holderfield et al., "Targeting RAF Kinases for Cancer Therapy: BRAF-Mutated Melanoma and Beyond," Nature Reveviews Cancer, 14(7): 455-467 (2014).
Huang et al., "B-Raf and the Inhibitors: From Bench to Bedside," Journal of Hematology and Oncology 6(30), 9 pages (2013).
Iupac, "Definitive Rules for Nomenclature of Organic Chemistiy," Journal of American Chemical Society, 82(21): 5545-5574 (1960).
Jia et al., "Overcoming EGFR(T790M) and EGFR(C797S) Resistance With Mulant-Selective Allosteric Inhibitors," Nature 534 : 129-132 (2016).
Junutula et al., "Site-Specific Conjugation of a Cytotoxic Drug to an Antibody Impioves the Therapeutic Index," Nature Biotechnology, 26(8): 925-932 (2008).
Lee et al., "Targeted Degradation of the Aryl Hydrocarbon Receptor by the PROTAC Approach: A Useful Chemical Genetic Tool," ChemBioChem., 8(17): 2058-2062, (2007).
Li et al., "DCDT2980S, an Anti-CD22-Monomethyl Auristatin E Antibody-Drug Conjugate, Is a Potential Treatment for Non-Hodgkin Lymphoma," Molecular Cancer Therapeutics, 12(7): 1255-1265 (2013).
Liu et al., "Discovery of a 2,4-diamino-7-aminoalkoxyquinazoline as a Potent and Selective Inhibitor of Histone Lysine Methyltransferase G9a," Journal of Medicinal Chemistry, 52(24): 7950-7953 (2009).
Llinas-Brunet et al., "Discovery of a Potent and Selective Noncovalent Linear Inhibitor of the Hepatitis C Virus NS3 Protease (BI 201335)," Journal of Medicinal Chemistry, 53(17): 6466-6476 (2010).
Lountos et al., "Structural Characterization of Inhibitor Complexes with Checkpoint Kinase 2 (Chk2), a Drug Target for Cancer Therapy," Jounral of Structual Biology, 176(3): 292-301 (2011).
Mehellou et al., "Twenty-Six Years of Anti-HIV Drug Discovery: Where Do We Stand and Where Do We Go?," Journal of Medicinal Chemistry, 53(2): 521-538 (2010).
Mertz et al., "Targeting MYC Dependence in Cancer by Inhibiting BET Bromodomains," Proceedings of the National Academy of Scinces USA, 108(40): 16669-16674 (2011).
Millan et al., "Design and Synthesis of Inhaled P38 Inhibitors for the Treatment of Chronic Obstructive Pulmonary Disease," Journal of Medicinal Chemistry, 54(22): 7797-7814 (2011).
Nicodeme et al., "Supressionof Inflanuiiationby a Synthetic Histone Mimic," Nature, 468(7327): 1119-1123 (2010).
Nicolaou et al., "Calicheamicin θ: A Rationally Designed Molecule with Extremely Potent and Selective DNA Cleaving Properties and Apoptosis Inducing Activity," Angewandte Chemie International Edition in English, 33(2): 183-186 (1994).
Nishiguchi et al., "Design and Discovery of N-(2-methyl-5'-morpholino-6'-((tetrahydro-2H-pyran-4-yl)oxy)-[3,3'-bipyridin]-5-yl)-3-(trifluoromethyl)benzamide: A Potent, Selective and Efficacious RAF Inhibitor Targeting RAS Mutant Cancers," Journal of Medicinal Chemistry, 60(12): 4869-4881 (2017).
Papalia et al., "Thermodynamic Characterization of Pyrazole and Azaindole Derivatives Binding to p38 Mitogen-Activated Protein Kinase Using Biacore T100 Technology and van't Hoff Analysis," Analytical Biochemistry, 383(2): 255-264 (2008).
Polson et al., "Anti-CD22-MCC-DM1: An Antibody-Drug Conjugate with a Stable Linker for the Treatment of Non-Hodgkin's Lymphoma " Leukemia, 24(9): 1566-1573 (2010).
Polson et al., "Investigational Antibody-Drug Conjugates for Hematological Malignancies," Expert Opinion on Investigational Drugs, 20(1): 75-85 (2011).
Raina et al., "PROTAC-induced BET Protein Degradation as a Therapy for Castration-Resistant Prostate Cancer," Proceedings of the National Academy of Sciences USA, 113(26): 7124-7129 (2016).
Rich et al., "Why you Should be Using More SPR Biosensor Technology," Drug Discovery Today Technologies, 1(3): 301-308 (2004).
Rodriguez-Gonzalez et al., "Targeting Steroid Hormone Receptors for Ubiquitination and Degradation in Breast and Prostate Cancer," Oncogene, 27(57): 7201-7211 (2008).
Romero et al., "Disrupting Acetyl-Lysine Recognition: Progress in the Development of Bromodomain Inhibitors," Journal of Medicinal Chemistry, 59(4): 1271-1298 (2016).
Rusch et al., "Identification of Acyl Protein Thioesterases 1 and 2 as the Cellular Targets of the Ras-Signaling Modulators Palmostatin B and M," Angew. Chem. Int. Ed., 50(42): 9838-9842 (2011).
Sakamoto et al., "Development of Protacs to Target Cancer-promoting Proteins for Ubiquitination and Degradation," Molecular & Cellular Proteomics, 2(12): 1350-1358 (2003).
Sakamoto et al., "Protacs: Chimeric Molecules that Target Proteins to the Skp1-Cullin-F Box Complex for Ubiquitination and Degradation," Proceedings of the National Academy of Sciences USA, 98(15): 8554-8559 (2001).
Schenkel et al., "Discovery of Potent and Highly Selective Thienopyridine Janus Kinase 2 Inhibitors," Journal of Medicinal Chemistry, 54(24): 8440-8450 (2011).
Schneekloth et al., "Chemical Genetic Control of Protein Levels: Selective in Vivo Targeted Degradation," Journal of the American Chemical Society, 126(12): 3748-3754 (2004).
Schneekloth et al., "Targeted Intracellular Protein Degradation Induced by a Small Molecule: En Route to Chemical Proteomics," Bioorganic & Medicinal Chemistry Letters, 18(22): 5904-5908 (2008).
Spiegel et al., "Small-Molecule Modulation of Ras Signaling," Nature Chemical Biology, 10(8): 613-622 (2014).
Vallee et al., "Tricyclic Series of Heat Shock Protein 90 (HSP90) Inhibitors Part I: Discovery of Tricyclic Imidazo[4,5-C]Pyridines as Potent Inhibitors of the HSP90 Molecular Chaperone," Journal of Medicinal Chemistry, 54(20): 7206-7219 (2011).
Van Eis et al., "2,6-Naphthyridines as Potent and Selective Inhibitors of the Novel Protein Kinase C Isozymes," Biorganic & Medicinal Chemistry Letters, 21(24): 7367-7372 (2011).
Vassilev et al., "In Vivo Activation of the P53 Pathway by Small-Molecule Antagonists of MDM2," Science, 303(5659): 844-848 (2004).
Wang et al., "Next-generation EGFR/HER Tyrosine Kinase Inhibitors for the Treatment of Patients With Non-Small-Cell Lung Cancer Harboring EGFR Mulations: A Review of the Evidence," OncoTargets and Therapy, 9: 5461-5473 (2016).
Wright et al., "Structure-Activity Relationships in Purine-Based Inhibitor Binding to HSP90 Isoforms," Chemistry & Biology, 11(6): 775-785 (2004).
Zengerle et al., "Selective Small Molecule Induced Degradation of the BET Bromodomain Protein BRD4," ACS Chemical Biology, 10(8): 1770-1777 (2015).
Zhao et al., "Small-Molecule Inhibitors of the MDM2-p53 Protein-Protein Interaction (MDM2 Inhibitors) in Clinical Trials for Cancer Treatment," Journal of Medicinal Chemistry, 58(3): 1038-1052 (2015).

(56) References Cited

OTHER PUBLICATIONS

International Search Report and Written Opinion for International Application No. PCT/US2018/057135 dated Jan. 22, 2019 (14 pages).
International Preliminary Report on Patentability for International Application No. PCT/US2018/057135 dated May 7, 2020 (9 pages).

(4-HYDROXYPYRROLIDIN-2-YL)-HETEROCYCLIC COMPOUNDS AND METHODS OF USE THEREOF

CROSS-REFERENCE TO RELATED APPLICATIONS IDC

This application is a continuation of International Application No. PCT/US2018/057135 with an international filing date of Oct. 23, 2018, which is incorporated herein by reference in its entirety, and claims priority to PCT/CN2018/105402, which was filed on Sep. 13, 2018, and to PCT/CN2017/107445, which was filed on Oct. 24, 2017, both of which are herein incorporated by reference in their entirety.

FIELD OF THE DISCLOSURE

The present disclosure relates to bifunctional compounds, which can be used as modulators of targeted ubiquitination. In particular, the present disclosure is directed to compounds which contain on one end a VHL ligand moiety, which binds to the VHL E3 ubiquitin ligase, and on the other end a moiety that binds a target protein such that degradation of the target protein/polypeptide is effectuated. The present disclosure exhibits a broad range of pharmacological activities associated with compounds according to the present disclosure, consistent with the degradation/inhibition of targeted proteins/polypeptides.

BACKGROUND OF THE DISCLOSURE

Cell maintenance and normal function requires controlled degradation of cellular proteins. For example, degradation of regulatory proteins triggers events in the cell cycle, such as DNA replication, chromosome segregation, etc. Accordingly, such degradation of proteins has implications for the cell's proliferation, differentiation, and death.

While inhibitors of proteins can block or reduce protein activity in a cell, protein degradation in a cell can also reduce activity or remove altogether the target protein. Utilizing a cell's protein degradation pathway can, therefore, provide a means for reducing or removing protein activity. One of the cell's major degradation pathways is known as the ubiquitin-proteasome system. In this system, a protein is marked for degradation by the proteasome by ubiquitinating the protein. The ubiqitinization of the protein is accomplished by an E3 ubiquitin ligase that binds to a protein and adds ubiquitin molecules to the protein. The E3 ubiquitin ligase is part of a pathway that includes E1 and E2 ubiquitin ligases, which make ubiquitin available to the E3 ubiquitin ligase to add to the protein.

To harness this degradation pathway, PROTACs have been developed. PROTACs bring together an E3 ubiquitin ligase with a protein that is to be targeted for degradation. To facilitate a protein for degradation by the proteasome, the PROTAC is comprised of a group that binds to an E3 ubiquitin ligase and a group that binds to the protein one wishes to degrade. These groups are typically connected with a linker. This molecular construct can bring the E3 ubiquitin ligase in proximity with the protein so that it is ubiquitinated and marked for degradation.

One E3 ligase with therapeutic potential is the von Hippel-Lindau (VHL) tumor suppressor, the substrate recognition subunit of the E3 ligase complex VCB, which consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels. While HIF-1α is constitutively expressed, its intracellular levels are kept very low under normoxic conditions via its hydroxylation by prolyl hydroxylase domain (PHD) proteins and subsequent VHL-mediated ubiquitination.

The crystal structure of VHL with ligands has been obtained, confirming that a small compound can mimic the binding mode of the transcription factor HIF-la, the major substrate of VHL. Using rational design, the first small molecule ligands of Von Hippel Lindau (VHL) the substrate recognition subunit of the E3 ligase VCB (an important target in cancer, chronic anemia and ischemia) were generated.

However, an ongoing need exists in the art for effective small molecule therapeutics across disease indications. The present description provides means to recruit proteins to E3 ligases, and specifically VHL, for ubiquitination and degradation, to provide therapies based upon the degradation of targeted proteins.

BRIEF DESCRIPTION OF THE DISCLOSURE

In one aspect, the present disclosure is directed to a compound of Formula (I) or Formula (II), or a tautomer thereof:

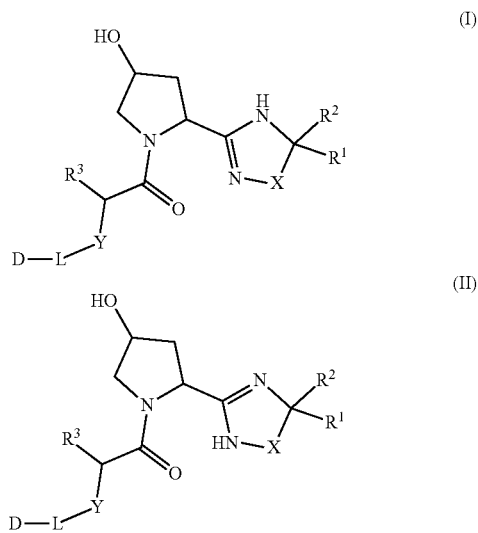

or a salt (e.g., a pharmaceutically acceptable salt) thereof; wherein: X is selected from the group consisting of —C(O)—, O, S, —SO$_2$—, —N(R$^4$)—, and —C(R$^{5a}$)(R$^{5b}$)—; R$^1$ is selected from the group consisting of H, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heterocyclyl, and substituted or unsubstituted heteroaryl; R$^2$ is selected from the group consisting of H, substituted or unsubstituted alkyl, substituted or unsubstituted alkenyl, substituted or unsubstituted alkynyl, and substituted or unsubstituted aryl; or R$^1$ and R$^2$, are taken together with the carbon to which they are attached to form a cycloalkyl or heterocyclyl, wherein the cycloalkyl or heterocyclyl is substituted or unsubstituted or fused with a ring selected from the group consisting of substituted or unsubstituted cycloalkyl, substituted or unsubstituted heterocyclyl, substituted or unsubstituted aryl, and substituted or unsubstituted heteroaryl; $R^3$ is substituted or unsubstituted alkyl, or $R^3$ is taken together with $R^6$, when present, and the atoms to which they are attached, to form a substituted or unsubstituted heterocyclylene; $R^4$, $R^{5a}$, and $R^{5b}$ are each independently selected from the group consisting of H, substituted or unsubstituted $C_1$-$C_3$ alkyl, and substituted or unsubstituted aryl; Y is selected from the group consisting of substituted or unsubstituted heteroarylene, substituted or unsubstituted heterocyclylene, O, S, —N($R^6$)—, —N($R^6$)—C(O)—, and —N($R^6$)—SO$_2$—; $R^6$ is selected from the group consisting of H and substituted or unsubstituted alkyl; or $R^6$ is taken together with $R^3$ and the atoms to which they are attached to form a substituted or unsubstituted heterocyclylene; L is a linker moiety; and D is a protein binding moiety.

In another aspect, the present disclosure is directed to a compound of Formula (I) or Formula (II), or a tautomer thereof.

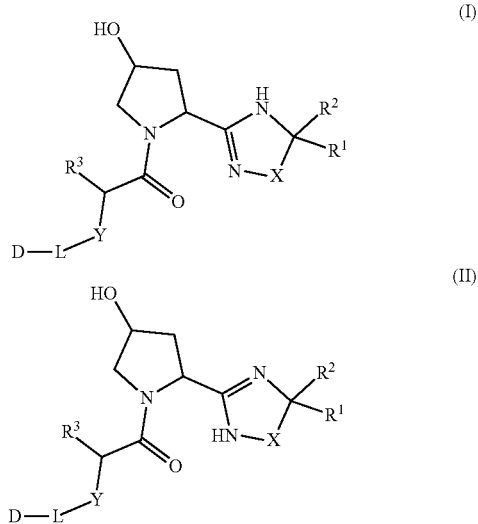

or a salt (e.g., a pharmaceutically acceptable salt) thereof; wherein: X is selected from the group consisting of —C(O)—, O, S, —SO$_2$—, —N($R^4$)—, and —C($R^{5a}$)($R^{5b}$)—; $R^1$ is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heterocyclyl, and substituted or unsubstituted heteroaryl; $R^2$ is selected from the group consisting of H, substituted or unsubstituted alkyl, substituted or unsubstituted alkenyl, and substituted or unsubstituted alkynyl; or $R^1$ and $R^2$, are taken together with the carbon to which they are attached to form a cycloalkyl or heterocyclyl, wherein the cycloalkyl or heterocyclyl is substituted or unsubstituted or fused with a ring selected from the group consisting of substituted or unsubstituted cycloalkyl, substituted or unsubstituted heterocyclyl, substituted or unsubstituted aryl, and substituted or unsubstituted heteroaryl; $R^3$ is substituted or unsubstituted alkyl, or $R^3$ is taken together with $R^6$, when present, and the atoms to which they are attached, to form a substituted or unsubstituted heterocyclylene; $R^4$, $R^{5a}$, and $R^{5b}$ are each independently selected from the group consisting of H and substituted or unsubstituted $C_1$-$C_3$ alkyl; Y is selected from the group consisting of substituted or unsubstituted heteroarylene, substituted or unsubstituted heterocyclylene, O, S, —N($R^6$)—, —N($R^6$)—C(O)—, and —N($R^6$)—SO$_2$—; $R^6$ is selected from the group consisting of H and substituted or unsubstituted alkyl; or $R^6$ is taken together with $R^3$ and the atoms to which they are attached to form a substituted or unsubstituted heterocyclylene; L is a linker moiety; and D is a protein binding moiety.

In another aspect, the present disclosure is directed to a compound of Formula (Ia) or Formula (IIa), or a tautomer thereof:

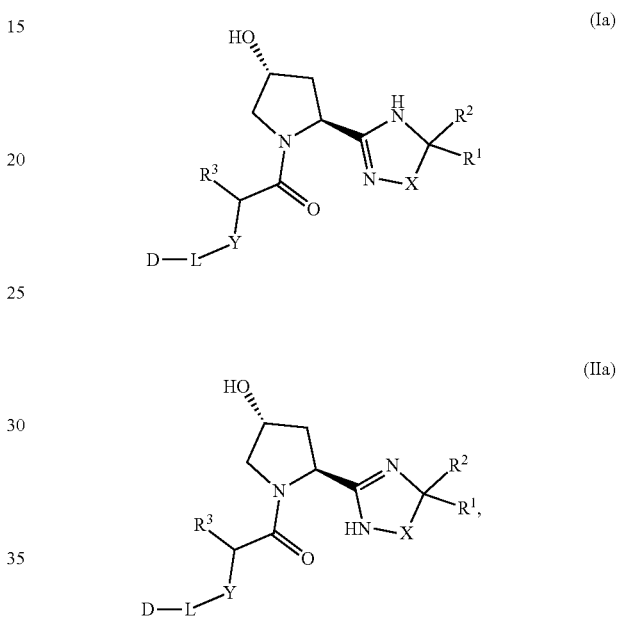

or a salt (e.g., a pharmaceutically acceptable salt) thereof, wherein X, $R^1$, $R^2$, $R^3$, Y, L, and D are defined the same as for Formulas (I) and (II).

In another aspect, the present disclosure is directed to a pharmaceutical composition comprising a compound of Formula (I), (II), (Ia), or (IIa), or a salt (e.g., a pharmaceutically acceptable salt) thereof, and one or more pharmaceutically acceptable excipients.

In another aspect, the present disclosure is directed to a method of treating a disease or disorder in a human in need thereof, comprising administering to said human an effective amount of a compound Formula (I), (II), (Ia), or (IIa), or a salt (e.g., a pharmaceutically acceptable salt) thereof, or a pharmaceutical composition comprising a compound Formula (I), (II), (Ia), or (IIa), or a salt (e.g., a pharmaceutically acceptable salt) thereof.

In another aspect, the present disclosure is directed to a method of degrading a target protein in a cell comprising exposing the cell to a composition comprising an effective amount of a compound Formula (I), (II), (Ia), or (IIa), or a salt (e.g., a pharmaceutically acceptable salt) thereof, wherein the compound effectuates the degradation of the target protein.

In another aspect, the present disclosure is directed to a compound of Formula (III) or Formula (IV), or a tautomer thereof:

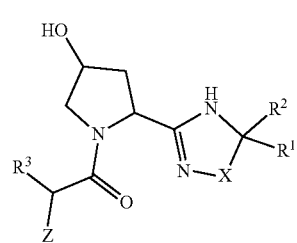

(III)

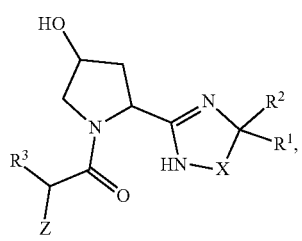

(IV)

or a salt (e.g., a pharmaceutically acceptable salt) thereof; wherein: X is selected from the group consisting of —C(O)—, O, S, —SO$_2$—, —N(R$^4$)—, and —C(R$^{5a}$)(R$^{5b}$)—; R$^1$ is selected from the group consisting of H, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heterocyclyl, and substituted or unsubstituted heteroaryl; R$^2$ is selected from the group consisting of H, substituted or unsubstituted alkyl, substituted or unsubstituted alkenyl, substituted or unsubstituted alkynyl, and substituted or unsubstituted aryl; or R$^1$ and R$^2$, are taken together with the carbon to which they are attached to form a cycloalkyl or heterocyclyl, wherein the cycloalkyl or heterocyclyl is substituted or unsubstituted or fused with a ring selected from the group consisting of substituted or unsubstituted cycloalkyl, substituted or unsubstituted heterocyclyl, substituted or unsubstituted aryl, and substituted or unsubstituted heteroaryl; R$^3$ is substituted or unsubstituted alkyl, or R$^3$ is taken together with R$^6$, when present, and the atoms to which they are attached, to form a substituted or unsubstituted heterocyclylene; R$^4$, R$^{5a}$, and R$^{5b}$ are each independently selected from the group consisting of H, substituted or unsubstituted C$_1$-C$_3$ alkyl, and substituted or unsubstituted aryl; Z is selected from the group consisting of substituted or unsubstituted heteroaryl, substituted or unsubstituted heterocyclyl, —N(R$^6$)R$^{6a}$, —OR$^{6a}$, —SR$^{6a}$, and —N(R$^6$)—SO$_2$—R; R$^6$ is selected from the group consisting of H and substituted or unsubstituted alkyl; or R$^6$ is taken together with R$^3$ and the atoms to which they are attached to form a substituted or unsubstituted heterocyclylene; each R$^{6a}$ is selected from the group consisting of H, substituted or unsubstituted acyl, and substituted or unsubstituted alkyl; and R$^{6b}$ is selected from the group consisting of substituted or unsubstituted alkyl and substituted or unsubstituted aryl.

In another aspect, the present disclosure is directed to a compound of Formula (III) or Formula (IV), or a tautomer thereof:

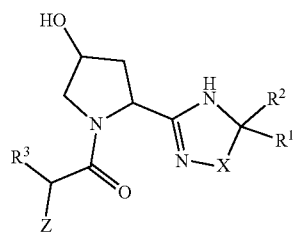

(III)

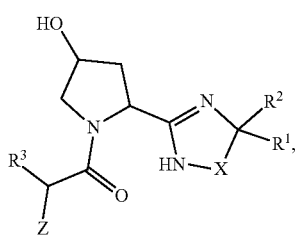

(IV)

or a salt (e.g., a pharmaceutically acceptable salt) thereof; wherein: X is selected from the group consisting of —C(O)—, O, S, —SO$_2$—, —N(R$^4$)—, and —C(R$^{5a}$)(R$^{5b}$)—; R$^1$ is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heterocyclyl, and substituted or unsubstituted heteroaryl; R$^2$ is selected from the group consisting of H, substituted or unsubstituted alkyl, substituted or unsubstituted alkenyl, and substituted or unsubstituted alkynyl; or R$^1$ and R$^2$, are taken together with the carbon to which they are attached to form a cycloalkyl or heterocyclyl, wherein the cycloalkyl or heterocyclyl is substituted or unsubstituted or fused with a ring selected from the group consisting of substituted or unsubstituted cycloalkyl, substituted or unsubstituted heterocyclyl, substituted or unsubstituted aryl, and substituted or unsubstituted heteroaryl; R$^3$ is substituted or unsubstituted alkyl, or R$^3$ is taken together with R$^6$, when present, and the atoms to which they are attached, to form a substituted or unsubstituted heterocyclylene; R$^4$, R$^{5a}$, and R$^{5b}$ are each independently selected from the group consisting of H and substituted or unsubstituted C$_1$-C$_3$ alkyl; Z is selected from the group consisting of substituted or unsubstituted heteroaryl, substituted or unsubstituted heterocyclyl, —N(R$^6$)R$^{6a}$, —OR$^{6a}$, —SR$^{6a}$, and —N(R$^6$)—SO$_2$—R$^{6b}$; R$^6$ is selected from the group consisting of H and substituted or unsubstituted alkyl; or R$^6$ is taken together with R$^3$ and the atoms to which they are attached to form a substituted or unsubstituted heterocyclylene; each R$^{6a}$ is selected from the group consisting of H, substituted or unsubstituted acyl, and substituted or unsubstituted alkyl; and R$^{6b}$ is selected from the group consisting of substituted or unsubstituted alkyl and substituted or unsubstituted aryl.

DETAILED DESCRIPTION OF THE DISCLOSURE

The present disclosure is directed to compounds that bind an E3 ubiquitin ligase protein complex. In particular, compounds are described that bind to Von Hippel-Lindau (VHL), the substrate recognition subunit of the E3 ligase complex VCB. In addition, the description provides bifunctional compounds and associated methods of use for effectuating the ubiquitination and/or degradation of a chosen target protein.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers alternatives, modifications, and equivalents. In the event that one or more of the incorporated literature, patents, and similar materials differs from or contradicts this application, including but not limited to defined terms, term usage, described techniques, or the like, this application controls. Unless otherwise defined, technical and scientific terms used herein have the same meaning as commonly understood by one of ordinary skill in the art to which this disclosure belongs, applying that term in context to its use in describing the present disclosure. The terminology used in the description is for describing particular embodiments only and is not intended to be limiting of the disclosure. All publications, patent applications, patents, and other references mentioned herein are incorporated by reference in their entirety.

I. DEFINITIONS

The term "PROTAC" refers to proteolysis-targeting chimera molecules having generally three components, an E3 ubiquitin ligase binding moiety (E3LB), a linker (L), and a protein binding moiety (PB moiety, also referred to herein as "D"). Specifically, the E3LB used herein is a VHL ligand moiety.

The terms "residue," "moiety" or "group" refers to a component that is covalently bound or linked to another component. For example a "VHL ligand moiety" in a PROTAC compound refers to a VHL ligand that is covalently linked to one or more groups such as a linker (L), which itself can be optionally further linked to another chemical component, such as a protein binding moiety (D).

The term "covalently bound" or "covalently linked" refers to a chemical bond formed by sharing of one or more pairs of electrons.

The term "linker", "linker unit", "linker group", "linker moiety", or "link" as used herein means a chemical moiety comprising a chain of atoms that covalently attaches a component of a PROTAC to another component of the PROTAC.

A "patient" or "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human. In some embodiments, the patient may be a "cancer patient," i.e. one who is suffering or at risk for suffering from one or more symptoms of cancer.

The terms "cancer" and "cancerous" refer to or describe the physiological condition in mammals that is typically characterized by unregulated cell growth/proliferation. A "tumor" comprises one or more cancerous cells. Examples of cancer are provided elsewhere herein.

A "chemotherapeutic agent" or "anti-cancer agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., Angew. Chem Intl. Ed. Engl., 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin;

losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®, an antisence oligonucleotide); pixantrone; EGFR inhibitors (see definition below); tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the compounds and compositions of the subject matter described herein are used to delay development of a disease or to slow the progression of a disease. In one embodiment, treatment is performed for prophylaxis only. In another embodiment, treatment is performed during the course of clinical pathology only (i.e., not for prophylaxis). In another embodiment, treatment is performed both during the course of clinical pathology and for prophylaxis.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

The term "effective" is used to describe an amount of a compound, composition or component which, when used within the context of its intended use, achieves the desired therapeutic or prophylactic result. The term effective subsumes other effective amount or effective concentration terms, including therapeutically effective amounts, which are otherwise described or used in the present application. As used herein, the term "therapeutically effective amount" means any amount which, as compared to a corresponding subject who has not received such amount, results in treatment of a disease, disorder, or side effect, or a decrease in the rate of advancement of a disease or disorder. The term also includes within its scope amounts effective to enhance normal physiological function. For use in therapy, therapeutically effective amounts of a PROTAC of the present disclosure, as well as salts thereof, may be administered as the raw chemical. Additionally, the active ingredient may be presented as a pharmaceutical composition.

As used herein, unless defined otherwise in a claim, the term "optionally" means that the subsequently described event(s) may or may not occur, and includes both event(s) that occur and event(s) that do not occur.

As used herein, unless defined otherwise, the phrase "optionally substituted", "substituted" or variations thereof denote an optional substitution, including multiple degrees of substitution, with one or more substituent group, for example, one, two, three, four or five. The phrase should not be interpreted as duplicative of the substitutions herein described and depicted.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical formulation, other than an active ingredient, which is nontoxic to a subject. A pharmaceutically acceptable excipient includes, but is not limited to, a buffer, carrier, stabilizer, or preservative.

The phrase "pharmaceutically acceptable salt," as used herein, refers to pharmaceutically acceptable organic or inorganic salts of a molecule. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Other salts, which are not pharmaceutically acceptable, may be useful in the preparation of compounds described herein and these should be considered to form a further aspect of the subject matter. These salts, such as oxalic or trifluoroacetate, while not in themselves pharmaceutically acceptable, may be useful in the preparation of salts useful as intermediates in obtaining the compounds described herein and their pharmaceutically acceptable salts.

A "small molecule" or "small molecular compound" generally refers to an organic molecule that is less than about 5 kilodaltons (Kd) in size. In some embodiments, the small molecule is less than about 4 Kd, 3 Kd, about 2 Kd, or about 1 Kd. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric. Small molecules are not proteins, polypeptides, oligopeptides, peptides, polynucleotides, oligonucleotides, polysaccharides, glycoproteins, proteoglycans, etc. A derivative of a small molecule refers to a molecule that shares the same structural core as the original small molecule, but which can be prepared by a series of chemical reactions from the original small molecule.

The term "alkyl" as used herein refers to a saturated linear or branched-chain monovalent hydrocarbon radical of any length from one to twelve carbon atoms ($C_1$-$C_{12}$), wherein the alkyl radical may be optionally substituted independently with one or more substituents described herein. In another embodiment, an alkyl radical is one to eight carbon atoms ($C_1$-$C_8$), or one to six carbon atoms ($C_1$-$C_6$), or one to four carbon atoms ($C_1$-$C_4$), or one to three carbon atoms ($C_1$-$C_3$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, isopropyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, tert-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkylene" as used herein refers to a saturated linear or branched-chain divalent hydrocarbon radical of any length from one to twelve carbon atoms ($C_1$-$C_{12}$), wherein the alkylene radical may be optionally substituted independently with one or more substituents described herein. In another embodiment, an alkylene radical is one to eight carbon atoms ($C_1$-$C_8$), one to six carbon atoms ($C_1$-$C_6$), or one to four carbon atoms ($C_1$-$C_4$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of any length from two to twelve carbon atoms ($C_2$-$C_{12}$) with at least one site of unsaturation, i.e., a carbon-carbon, sp2 double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of any length from two to twelve carbon atoms ($C_2$-$C_{12}$) with at least one site of unsaturation, i.e., a carbon-carbon, sp2 double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of any length from two to twelve carbon atoms ($C_2$-$C_{12}$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of any length from two to twelve carbon atoms ($C_2$-$C_{12}$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

The term "cycloalkylene" refer to a divalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic cycloalkylenes having 7 to 12 atoms can be arranged, for example, as a bicyclo [4,5], [5,5], [5,6] or [6,6] system, and bicyclic cycloalkylenes having 9 or 10 ring atoms can be arranged as a bicyclo [5,6] or [6,6] system, or as bridged systems such as bicyclo[2.2.1]heptane, bicyclo[2.2.2]octane and bicyclo [3.2.2]nonane. Spiro moieties are also included within the scope of this definition. Examples of monocyclic cycloalkylenes include, but are not limited to, cyclopropylene, cyclobutylene, cyclopentylene, 1-cyclopent-1-enylene, 1-cyclopent-2-enylene, 1-cyclopent-3-enylene, cyclohexylene, 1-cyclohex-1-enylene, 1-cyclohex-2-enylene, 1-cyclohex-3-enylene, cyclohexadienylene, cycloheptylene, cyclooctylene, cyclononylene, cyclodecylene, cycloundecylene, cyclododecylene, and the like. Cycloalkylene groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described herein. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heterocyclylene" refers to a divalent saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described herein. A heterocyclylene may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.;

"Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566. "Heterocyclylene" also includes divalent radicals where heterocycle radicals are fused with a saturated, partially unsaturated ring, or aromatic carbocyclic or heterocyclic ring. Examples of heterocyclylenes include, but are not limited to, morpholin-4-ylene, piperidin-1-ylene, piperazinylene, piperazin-4-ylene-2-one, piperazin-4-ylene-3-one, pyrrolidin-1-ylene, thiomorpholin-4-ylene, S-dioxothiomorpholin-4-ylene, azocan-1-ylene, azetidin-1-ylene, octahydropyrido[1,2-a]pyrazin-2-ylene, [1,4]diazepan-1-ylene, pyrrolidinylene, tetrahydrofuranylene, dihydrofuranylene, tetrahydrothienylene, tetrahydropyranylene, dihydropyranylene, tetrahydrothiopyranylene, piperidino, morpholino, thiomorpholino, thioxanylene, piperazinylene, homopiperazinylene, azetidinylene, oxetanylene, thietanylene, homopiperidinylene, oxepanylene, thiepanylene, oxazepinylene, diazepinylene, thiazepinylene, 2-pyrrolinylene, 3-pyrrolinylene, indolinylene, 2H-pyranylene, 4H-pyranylene, dioxanylene, 1,3-dioxolanylene, pyrazolinylene, dithianylene, dithiolanylene, dihydropyranylene, dihydrothienylene, dihydrofuranylene, pyrazolidinylimidazolinylene, imidazolidinylene, 3-azabicyco[3.1.0]hexanylene, 3-azabicyclo[4.1.0]heptanylene, azabicyclo[2.2.2]hexanylene, 3H-indolyl quinolizinyl and N-pyridyl ureas. Spiro moieties are also included within the scope of this definition. Examples of a heterocyclylene group wherein 2 ring atoms are substituted with oxo (=O) moieties are pyrimidinonylene and 1,1-dioxo-thiomorpholinylene. The heterocyclylene groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, 1-methyl-1H-benzo[d]imidazole, [1,2,4]triazolo[1,5-a]pyridine, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The term "heteroarylene" refers to a divalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroarylene groups are pyridinylene (including, for example, 2-hydroxypyridinylene), imidazolylene, imidazopyridinylene, 1-methyl-1H-benzo[d]imidazole, [1,2,4]triazolo[1,5-a]pyridine, pyrimidinylene (including, for example, 4-hydroxypyrimidinylene), pyrazolylene, triazolylene, pyrazinylene, tetrazolylene, furylene, thienylene, isoxazolylene, thiazolylene, oxadiazolylene, oxazolylene, isothiazolylene, pyrrolylene, quinolinylene, isoquinolinylene, tetrahydroisoquinolinylene, indolylene, benzimidazolylene, benzofuranylene, cinnolinylene, indazolylene, indolizinylene, phthalazinylene, pyridazinylene, triazinylene, isoindolylene, pteridinylene, purinylene, oxadiazolylene, thiadiazolylene, thiadiazolylene, furazanylene, benzofurazanylene, benzothiophenylene, benzothiazolylene, benzoxazolylene, quinazolinylene, quinoxalinylene, naphthyridinylene, and furopyridinylene. Heteroarylene groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The term "acyl" refers to both substituted and unsubstituted acyl. In certain embodiments, an "acyl" may be —C(O)—R$^{16}$, wherein R$^{16}$ is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, and substituted or unsubstituted heterocyclyl. In one particular embodiment, it is a substituted $C_1$-$C_3$ alkyl.

The term "oxo" refers to "=O".

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other stereoisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond  is shown, both a double bond and single bond are represented within the context of the compound shown. When a crossed double bond () is shown, both the E and Z configurations are represented within the context of the compound shown; and the compound may contain the E isomer or the Z isomer or a mixture of both the E and Z isomers.

The term "VCB E3 Ubiquitin Ligase," "Von Hippel-Lindau (or VHL) E3 Ubiquitin Ligase," "VHL," or "Ubiquitin Ligase," which are generally used interchangeably unless the context indicates otherwise, is used to describe a target enzyme(s) binding site of ubiquitin ligase moieties as described herein, e.g., in the bifunctional (chimeric) compounds as described herein. VCB E3 is a protein that in combination with an E2 ubiquitin-conjugating enzyme causes the attachment of ubiquitin to a lysine on a target protein; the E3 ubiquitin ligase targets specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

As used herein, a moiety that binds the E3 VHL ubiquitin ligase or a component thereof, is referred to a VHL ligand.

The term "protein binding moiety" ("PB") or "D" is used to describe a small molecule which binds to a target protein or other protein or polypeptide of interest and places/presents that protein or polypeptide in proximity to an ubiquitin ligase such that degradation of the protein or polypeptide by ubiquitin ligase may occur. Non-limiting examples of small molecule protein binding groups include Hsp90 inhibitors, kinase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, and compounds targeting the aryl hydrocarbon receptor (AHR), among numerous others. The compositions described herein exemplify some of the members of these and other types of small molecule target proteins. By coupling the VHL ligand to a protein binding moiety (PB), the target protein or polypeptide is ubiquitinated and/or degraded by the proteasome.

In certain embodiments disclosed herein, certain groups (e.g., alkyl, alkenyl, alkynyl, cycloalkyl, aryl, heteroaryl or heterocyclyl) are described as "substituted". In some such embodiments, the "substituted" group may be substituted with 1, 2, 3, 4, 5, or more substituents, as indicated herein. In certain embodiments, alkyl, alkenyl, alkynyl, cycloalkyl, aryl, heteroaryl or heterocyclyl may be substituted with one or more substituents independently selected from, but not limited to, alkyl, alkenyl, alkynyl, cycloalkyl heterocyclyl, aryl, heteroaryl, halo (i.e., halogen), haloalkyl, oxo, OH, CN, —O-alkyl, S-alkyl, NH-alkyl, N(alkyl)$_2$, O-cycloalkyl, S-cycloalkyl, NH-cycloalkyl, N(cycloalkyl)$_2$, N(cycloalkyl) (alkyl), NH$_2$, SH, SO$_2$-alkyl, P(O)(O-alkyl)(alkyl), P(O)(O-alkyl)$_2$, Si(OH)$_3$, Si(alkyl)$_3$, Si(OH)(alkyl)$_2$, CO-alkyl, CO$_2$H, NO$_2$, SF$_5$, SO$_2$NH-alkyl, SO$_2$N(alkyl)$_2$, SONH-alkyl, SON(alkyl)$_2$, CONH-alkyl, CON(alkyl)$_2$, N(alkyl) CONH(alkyl), N(alkyl)CON(alkyl)$_2$, NHCONH(alkyl), NHCON(alkyl)$_2$, NHCONH$_2$, N(alkyl)SO$_2$NH(alkyl), N(alkyl) SO$_2$N(alkyl)$_2$, NHSO$_2$NH(alkyl), NHSO$_2$N(alkyl)$_2$, and NHSO$_2$NH$_2$.

Still additional definitions and abbreviations are provided elsewhere herein.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

In the claims, as well as in the specification above, transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

As indicated above, the description relates to a bifunctional PROTAC compound that binds an E3 ubiquitin ligase protein, and specifically VHL, or component thereof and a target protein. The E3 ubiquitin ligase protein ubiquitinates the target protein once it and the target protein are placed in proximity by the PROTAC compound. Accordingly, the description provides such compounds that bind to such E3 ubiquitin ligase proteins, as well as bifunctional PROTAC compounds comprising the same.

II. PROTAC COMPOUNDS AND COMPOSITIONS

E3 ubiquitin ligases (of which over 600 are known in humans) confer substrate specificity for ubiquitination. There are known ligands which bind to these ligases. An E3 ubiquitin ligase binding group (E3LB) is a peptide or small molecule that can bind an E3 ubiquitin ligase.

A particular E3 ubiquitin ligase is von Hippel-Lindau (VHL) tumor suppressor, the substrate recognition subunit of the E3 ligase complex VCB, which also consists of elongins B and C, Cul2 and Rbx1. The primary substrate of VHL is Hypoxia Inducible Factor 1α (HIF-1α), a transcription factor that upregulates genes such as the pro-angiogenic growth factor VEGF and the red blood cell inducing cytokine erythropoietin in response to low oxygen levels.

In one aspect, the present disclosure is directed to proteolysis-targeting chimera (PROTAC) compounds that are useful for regulating protein activity, and specifically, for facilitating the degradation of target proteins. Specifically, the PROTAC compounds of the present disclosure are bifunctional compounds that can be used as modulators of targeted ubiquitination. The compounds comprise on one end a VHL ligand moiety, which binds to the VHL E3 ubiquitin ligase, and on the other end a moiety that binds a target protein, such that degradation of the target protein/polypeptide is effectuated.

Preferably the VHL ligand moiety is a small molecule (i.e., not peptide based). In certain aspects and embodiments, the VHL ligand moiety is chemically linked, via a bond or through a chemical linker, to a protein binding (PB) moiety (or "D"), wherein the VHL ligand moiety recognizes a VHL E3 ubiquitin ligase and the protein binding moiety recognizes a target protein or polypeptide, and wherein the VHL ligand moiety is coupled to the PB moiety.

In an additional aspect, the present disclosure is directed to a compound according to the structure: VHLM-L, where L is a linker group and VHLM is a VHL ligand moiety. In certain embodiments, the VHL ligand moiety is coupled directly or via a chemical linker to a protein binding (PB) moiety (or "D").

In another aspect, the description provides compounds that comprise a protein binding group according to the general structure: VHLM-L-PB or VHLM-L-D, where VHLM is a VHL ligand moiety, PB or D is a chemical moiety (protein binding moiety), which binds to a target protein or polypeptide, which is ubiquitinated by an ubiquitin ligase, and is chemically linked directly to the VHL ligand moiety or through a linker moiety L, which can be a bond or a chemical linker. In certain embodiments, the PB or D moiety is alternatively also a VHL E3 ubiquitin ligase binding moiety, which may be the same or different than the VHL ligand moiety and is linked to the VHL ligand moiety directly or through a linker or a pharmaceutically acceptable salt, enantiomer, stereoisomer, solvate or polymorph thereof. In certain embodiments, the VHL ligand moiety is coupled to a PB or D moiety directly (via a bond) or via a chemical linker.

In certain aspects of the disclosure, where PB or D is a VHL ligand moiety, the compound resembles a dimeric compound where both ends of the compound comprise a VHL ubiquitin ligase binding moiety as otherwise described herein.

Although the VHL ligand moiety and PB or D moiety may be covalently linked to the linker group through any group which is appropriate and stable to the chemistry of the linker, in certain embodiments, and as detailed further below, the linker may be independently covalently bonded to the VHL ligand moiety and the PB or D moiety through an amide, ester, thioester, keto group, carbamate (urethane), carbon or ether, each of which groups may be inserted anywhere on the VHL ligand moiety and PB or D moiety to provide maximum binding of the VHL ligand moiety on the VHL ubiquitin ligase and the PB or D moiety on the target protein to be degraded. (It is noted that in certain aspects where the PB or D group is a VHL ligand moiety, the target protein for degradation may be the ubiquitin ligase itself). In certain aspects, the linker may be linked to an optionally substituted alkyl, alkylene, alkene or alkyne group, an aryl group or a heterocyclic group on the VHL ligand moiety and/or PB or D moiety.

In one aspect, the present disclosure is directed to a compound (e.g. a PROTAC) of Formula (I) or Formula (II), or a tautomer thereof:

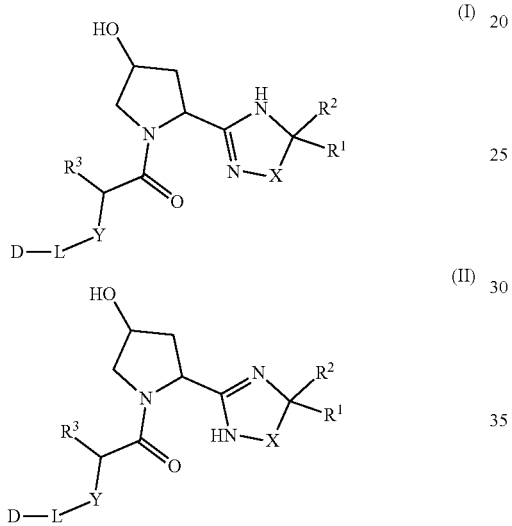

or a salt thereof (e.g., a pharmaceutically acceptable salt thereof);

wherein:

X is selected from the group consisting of —C(O)—, O, S, —SO$_2$—, —N(R$^4$)—, and —C(R$^{5a}$)(R$^{5b}$)—;

R$^1$ is selected from the group consisting of H, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heterocyclyl, and substituted or unsubstituted heteroaryl;

R$^2$ is selected from the group consisting of H, substituted or unsubstituted alkyl, substituted or unsubstituted alkenyl, substituted or unsubstituted alkynyl, and substituted or unsubstituted aryl;

or R$^1$ and R$^2$, are taken together with the carbon to which they are attached to form a cycloalkyl or heterocyclyl, wherein the cycloalkyl or heterocyclyl is substituted or unsubstituted or fused with a ring selected from the group consisting of substituted or unsubstituted cycloalkyl, substituted or unsubstituted heterocyclyl, substituted or unsubstituted aryl, and substituted or unsubstituted heteroaryl;

R$^3$ is substituted or unsubstituted alkyl, or R$^3$ is taken together with R$^6$, when present, and the atoms to which they are attached, to form a substituted or unsubstituted heterocyclylene;

R$^4$, R$^{5a}$, and R$^{5b}$ are each independently selected from the group consisting of H, substituted or unsubstituted C$_1$-C$_3$ alkyl, and substituted or unsubstituted aryl;

Y is selected from the group consisting of substituted or unsubstituted heteroarylene, substituted or unsubstituted heterocyclylene, O, S, —N(R$^6$)—, —N(R$^6$)—C(O)—, and —N(R$^6$)—SO$_2$—;

R$^6$ is selected from the group consisting of H and substituted or unsubstituted alkyl; or R$^6$ is taken together with R$^3$ and the atoms to which they are attached to form a substituted or unsubstituted heterocyclylene;

L is a linker moiety; and

D is a protein binding moiety.

In another aspect, the present disclosure is directed to a compound (e.g. a PROTAC) of Formula (I) or Formula (II), or a tautomer thereof, or a salt thereof (e.g., a pharmaceutically acceptable salt thereof); wherein:

X is selected from the group consisting of —C(O)—, O, S, —SO$_2$—, —N(R$^4$)—, and —C(R$^{5a}$)(R$^{5b}$)—;

R$^1$ is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heterocyclyl, and substituted or unsubstituted heteroaryl;

R$^2$ is selected from the group consisting of H, substituted or unsubstituted alkyl, substituted or unsubstituted alkenyl, and substituted or unsubstituted alkynyl;

or R$^1$ and R$^2$, are taken together with the carbon to which they are attached to form a cycloalkyl or heterocyclyl, wherein the cycloalkyl or heterocyclyl is substituted or unsubstituted or fused with a ring selected from the group consisting of substituted or unsubstituted cycloalkyl, substituted or unsubstituted heterocyclyl, substituted or unsubstituted aryl, and substituted or unsubstituted heteroaryl;

R$^3$ is substituted or unsubstituted alkyl, or R$^3$ is taken together with R$^6$, when present, and the atoms to which they are attached, to form a substituted or unsubstituted heterocyclylene;

R$^4$, R$^{5a}$, and R$^{5b}$ are each independently selected from the group consisting of H and substituted or unsubstituted C$_1$-C$_3$ alkyl;

Y is selected from the group consisting of substituted or unsubstituted heteroarylene, substituted or unsubstituted heterocyclylene, O, S, —N(R$^6$)—, —N(R$^6$)—C(O)—, and —N(R$^6$)—SO$_2$—;

R$^6$ is selected from the group consisting of H and substituted or unsubstituted alkyl; or R$^6$ is taken together with R$^3$ and the atoms to which they are attached to form a substituted or unsubstituted heterocyclylene;

L is a linker moiety; and

D is a protein binding moiety.

In another aspect, the compound (e.g. a PROTAC) is a compound of Formula (Ia) or Formula (IIa), or a tautomer thereof:

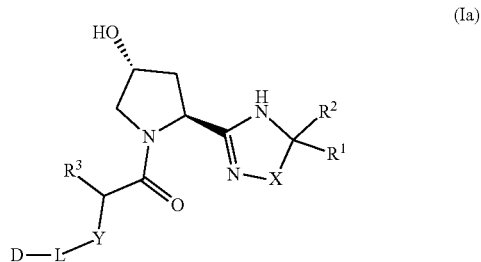

-continued

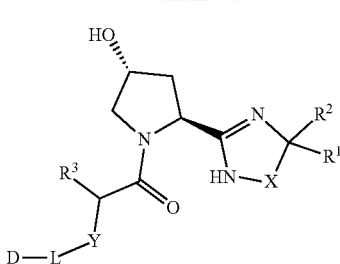
(IIa)

or a salt (e.g., a pharmaceutically acceptable salt) thereof, wherein each of X, $R^1$, $R^2$, $R^3$, Y, L, and D are as defined for Formula (I) or Formula (II).

In some embodiments of the compounds of Formula (I), (Ia), (II) or (IIa), or a salt (e.g. a pharmaceutically acceptable salt) thereof, X is —C(O)—, O, S, —N($R^4$)—, or —C($R^{5a}$)($R^{5b}$)—. In some embodiments, X is —C(O)— or —SO$_2$. In one particular embodiment, X is —C(O)—. In one embodiment, X is O. In one embodiment, X is —SO$_2$—. In one embodiment, X is —N($R^4$)—. In one embodiment, X is —N($R^4$)—, and $R^4$ is a substituted or unsubstituted $C_1$-$C_3$ alkyl. In one embodiment, X is —N($R^4$)—, and $R^4$ is selected from the group consisting of ethyl and —CH$_2$—CF$_3$. In one embodiment, X is —N($R^4$)—, and $R^4$ is phenyl. In one embodiment, X is —C($R^{5a}$)($R^{5b}$)—. In one embodiment, X is —C($R^{5a}$)($R^{5b}$)—, and $R^{5a}$ and $R^{5b}$ are each independently substituted or unsubstituted $C_1$-$C_3$ alkyl.

In some embodiments of the compounds of Formula (I), (Ia), (II) or (IIa), or a salt (e.g. a pharmaceutically acceptable salt) thereof, $R^1$ and $R^2$ are each H.

In some embodiments of the compounds of Formula (I), (Ia), (II) or (IIa), or a salt (e.g. a pharmaceutically acceptable salt) thereof, $R^1$ is a substituted or unsubstituted $C_1$-$C_3$ alkyl. In one particular embodiment, $R^1$ is methyl.

In some embodiments of the compounds of Formula (I), (Ia), (II) or (IIa), or a salt (e.g. a pharmaceutically acceptable salt) thereof, $R^1$ is substituted or unsubstituted phenyl. In one embodiment, $R^1$ is unsubstituted phenyl.

In some embodiments of the compounds of Formula (I), (Ia), (II) or (IIa), or a salt (e.g. a pharmaceutically acceptable salt) thereof, $R^1$ is —W—$R^7$, and W is selected from the group consisting of substituted or unsubstituted arylene, substituted or unsubstituted heteroarylene, substituted or unsubstituted heterocyclylene, and substituted or unsubstituted cycloalkylene; $R^7$ is selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, —OR$^8$, —N($R^{8a}$)$R^{8b}$, —C(O)$R^{8c}$, —C(O)N($R^{8a}$)$R^{8b}$, —N($R^{8a}$)C(O)$R^{8c}$, —SO$_2$N($R^{8a}$)$R^{8b}$, and —SO$_2$$R^{8c}$; $R^8$, $R^{8a}$, and $R^{8b}$ are independently selected from the group consisting of H and substituted or unsubstituted alkyl; and $R^{8c}$ is selected from the group consisting of substituted or unsubstituted alkyl and substituted or unsubstituted aryl. In some embodiments, $R^7$ is selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, —OR$^8$, —N($R^{8a}$)$R^{8b}$, and —SO$_2$$R^{8c}$, wherein $R^8$, $R^{8a}$, $R^{8b}$, and $R^{8c}$ are as defined above. In some embodiments, $R^7$ is selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, and —SO$_2$$R^{8c}$, wherein $R^{8c}$ is as defined above. In some embodiments, $R^7$ is selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, —C(O)$R^{8c}$, —C(O)N($R^{8a}$)$R^{8b}$, —N($R^{8a}$)C(O)$R^{8c}$, —SO$_2$N($R^{8a}$)$R^{8b}$, and —SO$_2$$R^{8c}$, wherein $R^{8a}$, $R^{8b}$, and $R^{8c}$ are as defined above.

In one embodiment, $R^7$ is a haloalkyl, for example, a —CF$_3$.

In one aspect, $R^1$ is —W—$R^7$; W is substituted or unsubstituted phenylene; and $R^7$ is as defined above.

In another aspect, $R^1$ is

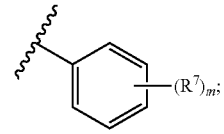

m is 0, 1, 2, 3, 4, or 5; $R^7$ is selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, —OR$^8$, —N($R^{8a}$)$R^{8b}$, —C(O)$R^{8c}$, —C(O)N($R^{8a}$)$R^{8b}$, —N($R^{8a}$)C(O)$R^{8c}$, —SO$_2$N($R^{8a}$)$R^{8b}$, and —SO$_2$$R^{8c}$; $R^8$, $R^{8a}$, and $R^{8b}$ are independently selected from the group consisting of H and substituted or unsubstituted alkyl; $R^{8c}$ is selected from the group consisting of substituted or unsubstituted alkyl and substituted or unsubstituted aryl; and ∽ is the point of attachment to the remaining structure of the compound. In one particular embodiment, $R^1$ is

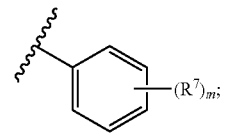

m is 0, 1, 2, or 3; and $R^7$ is as defined above.

In another aspect, $R^1$ is

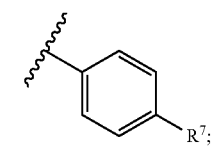

$R^7$ is as defined above; and ∽ is the point of attachment to the remaining structure of the compound.

In one particular embodiment, $R^7$ is selected from the group consisting of substituted or unsubstituted heteroaryl, substituted or unsubstituted heterocyclyl, and substituted or unsubstituted aryl.

In certain aspects, $R^7$ is selected from the group consisting of

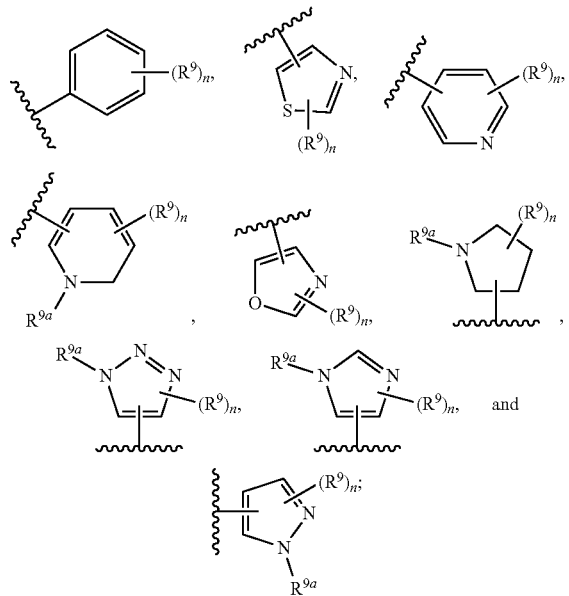

wherein: n is 0, 1, 2, 3, 4, or 5; $R^9$ is selected from the group consisting of oxo, alkyl, haloalkyl, cycloalkyl, halo, —CN, —NH$_2$, and substituted or unsubstituted alkynyl; ⁓, when present, is the point of attachment to the remaining structure of the compound; $R^{9a}$, when present, is selected from the group consisting of H and $R^9$; or $R^{9a}$ is the point of attachment to the remaining structure of the compound and ⁓ is absent.

Non-limiting examples of $R^7$ include

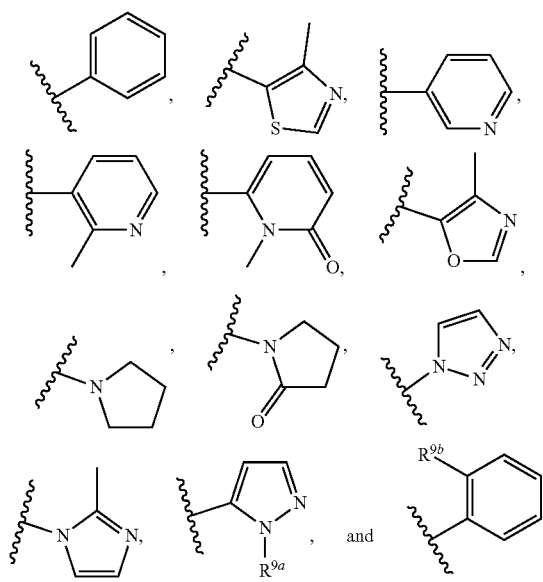

wherein $R^{9a}$ is alkyl, and $R^{9b}$ is halo. In some embodiments, $R^7$ is chlorophenyl, chloro-thiazolyl or trifluoromethyl-thiazolyl.

In one particular embodiment, $R^7$ is

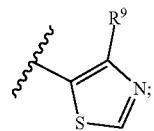

and $R^9$ is a substituted or unsubstituted alkynyl. In one embodiment, the alkynyl is substituted with a substituted or unsubstituted aryl, such as phenyl. In one embodiment, the aryl is phenyl, and the phenyl is substituted with at least one $R^{10}$, wherein $R^{10}$ is halo.

In one particular embodiment, $R^7$ is selected from the group consisting of

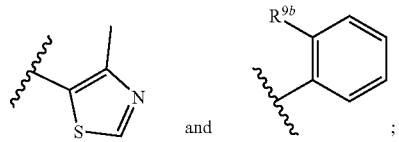

wherein $R^{9b}$ is halo and ⁓ is the point of attachment to the remaining structure of the compound.

In one particular embodiment, $R^7$ is selected from the group consisting of a substituted or unsubstituted 5-membered heteroaryl, and a substituted or unsubstituted 5-membered heterocyclyl. $R^7$ may be, for example, 1-pyrrolidinyl or 1-pyrrolidonyl. In one particular embodiment, $R^7$ is methylthiazolyl.

In some embodiments of the compounds of Formula (I), (Ia), (II) or (IIa), or a salt (e.g. a pharmaceutically acceptable salt) thereof, $R^2$ is substituted or unsubstituted alkyl. In one embodiment, $R^2$ is a substituted or unsubstituted $C_1$-$C_3$ alkyl. In one particular embodiment, $R^2$ is an alkyl (e.g., a $C_1$-$C_3$ alkyl) substituted with at least one substituent selected from the group consisting of halo, hydroxyl, and carboxyl. Examples of suitable $R^2$ groups include, but are not limited to, —CH$_3$, —CF$_3$, —CH$_2$OH, and —C(O)OH. In one embodiment, $R^2$ is —CH$_3$ or —CF$_3$.

In another embodiment, $R^2$ is a substituted or unsubstituted alkynyl. In one particular embodiment, $R^2$ is a $C_1$-$C_3$ alkynyl.

In some embodiments of the compounds of Formula (I), (Ia), (II) or (IIa), or a salt (e.g. a pharmaceutically acceptable salt) thereof, $R^2$ is a substituted or unsubstituted aryl. In one particular embodiment, $R^2$ is an unsubstituted phenyl.

In some embodiments of the compounds of Formula (I), (Ia), (II) or (IIa), or a salt (e.g. a pharmaceutically acceptable salt) thereof, $R^1$ and $R^2$, are taken together with the carbon to which they are attached to form a cycloalkyl or heterocyclyl, wherein the cycloalkyl or heterocyclyl is substituted or unsubstituted or fused with a ring selected from the group consisting of substituted or unsubstituted cycloalkyl, substituted or unsubstituted heterocyclyl, substituted or unsubstituted aryl, and substituted or unsubstituted heteroaryl.

In one embodiment, $R^1$ and $R^2$ are taken together with the carbon to which they are attached to form an unsubstituted cycloalkyl.

In another embodiment, $R^1$ and $R^2$ are taken together with the carbon to which they are attached to form a cycloalkyl, wherein the cycloalkyl is fused with a substituted or unsubstituted aryl.

In one particular embodiment, $R^1$ and $R^2$ are taken together with the carbon to which they are attached to form a cycloalkyl fused with a ring selected from the group consisting of substituted aryl and substituted heteroaryl. For example, $R^1$ and $R^2$ can be taken together with the carbon to which they are attached to form a substituted 1,2,3,4-tetrahydronaphthyl. In one particular embodiment, the 1,2,3,4-tetrahydronaphthyl is substituted with at least one $R^7$, and each $R^7$ is independently selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, —OR$^8$, —N(R$^{8a}$)R$^{8b}$, and —SO$_2$R$^{8c}$; R$^8$, R$^{8a}$, and R$^{8b}$ are independently selected from the group consisting of H and substituted or unsubstituted alkyl; and R$^{8c}$ is selected from the group consisting of substituted or unsubstituted alkyl and substituted or unsubstituted aryl.

In one embodiment, $R^1$ and $R^2$ are taken together with the carbon to which they are attached to form a cycloalkyl selected from the group consisting of:

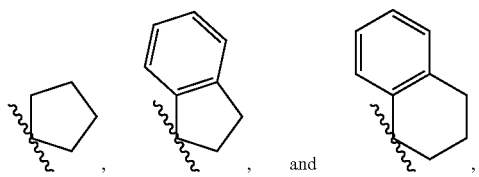

wherein ⌇⌇⌇ is the point of attachment to the remaining structure of the compound.

In some embodiments of the compounds of Formula (I), (Ia), (II) or (IIa), or a salt (e.g. a pharmaceutically acceptable salt) thereof, $R^3$ is a substituted or unsubstituted $C_1$-$C_6$ alkyl. In certain embodiments, $R^3$ isopropyl or tert-butyl.

In some embodiments of the compounds of Formula (I), (Ia), (II) or (IIa), or a salt (e.g. a pharmaceutically acceptable salt) thereof, Y is selected from the group consisting of substituted or unsubstituted heteroarylene, substituted or unsubstituted heterocyclylene, O, S, —N(R$^6$)—, —N(R$^6$)—C(O)—, and —N(R$^6$)—SO$_2$—. In some embodiments, Y is substituted or unsubstituted heteroarylene, or a substituted or unsubstituted heterocyclylene.

In certain aspects, Y is a substituted or unsubstituted heteroarylene. Examples of Y include, but are not limited to

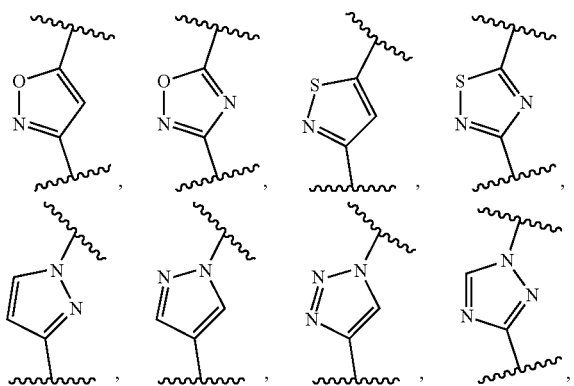

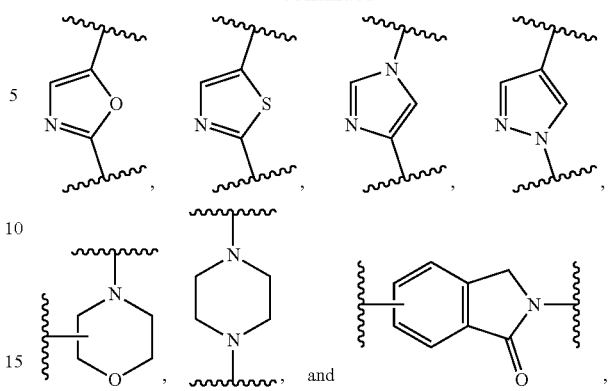

wherein ⌇⌇⌇ indicates the point of attachment to the remaining structure of the compound or L, and wherein Y may be attached to the compound in either orientation.

In other embodiments, Y is selected from the group consisting of —N(R$^6$)—, —N(R$^6$)—C(O)—, and —N(R$^6$)—SO$_2$—; and R$^6$ is selected from the group consisting of H and substituted or unsubstituted alkyl. In one embodiment, Y is selected from the group consisting of —N(R$^6$)—, —N(R$^6$)—C(O)—, and —N(R$^6$)—SO$_2$—; and R$^6$ is selected from the group consisting of H and substituted or unsubstituted $C_1$-$C_6$ alkyl. In one embodiment, Y is —N(R$^6$)—C(O)— and R$^6$ is H. In another embodiment, Y is —N(R$^6$)—SO$_2$—; and R$^6$ is H.

In other embodiments, Y is selected from the group consisting of —N(R$^6$)—, —N(R$^6$)—C(O)—, and —N(R$^6$)—SO$_2$—; and R$^6$ is taken together with R$^3$ and the atoms to which they are attached to form a substituted or unsubstituted heterocyclylene. In one particular embodiment, the heterocyclylene is substituted with —(R$^{11}$)$_p$; wherein p is 0, 1, 2, 3, or 4; R$^{11}$ is selected from the group consisting of substituted or unsubstituted $C_1$-$C_3$ alkyl, halo, —CN, and —OR$^{11a}$; and each R$^{11a}$ is independently selected from the group consisting of H and substituted or unsubstituted alkyl (e.g., a $C_1$-$C_3$ alkyl). In one embodiment, $R_{11}$ is —OR$^{11a}$, and is selected from the group consisting of —OCH$_3$, —OCF$_3$, and —OH. In one embodiment, p is 1 and R$^{11}$ is selected from the group consisting of —OCH$_3$, —OCF$_3$, and —OH. In one embodiment, p is 2, and R$^{11}$ is methyl. In another embodiment, p is 0. In another embodiment, R$^6$ is taken together with R$^3$ and the atoms to which they are attached to form a substituted or unsubstituted 5- or 6-membered heterocyclylene. For instance, in one embodiment, Y is —N(R$^6$)—C(O)—, and R$^3$ and R$^6$ are taken together with the atoms to which they are attached to form a substituted or unsubstituted 5- or 6-membered heterocyclylene. In another embodiment, Y is —N(R$^6$)—SO$_2$—; and R$^3$ and R$^6$ are taken together with the atoms to which they are attached to form a substituted or unsubstituted 5- or 6-membered heterocyclylene. In one embodiment, the 5- or 6-membered heterocyclylene is substituted with at least one alkyl.

In other embodiments, Y is a substituted or unsubstituted heterocyclylene. For instance, in one embodiment, the heterocyclylene is substituted with oxo. In another embodiment, the heterocyclylene is fused with a substituted or unsubstituted aryl. In another embodiment, Y is

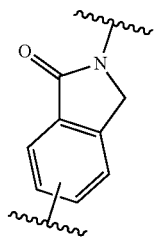

wherein ∼∼∼ indicates the point of attachment to the remaining structure of the compound or L.

It is intented and understood that any of the Y moieties detailed herein for the compound of Formula (I), (Ia), (II) or (IIa) may be combined with any of the X, $R^1$, $R^2$, and/or $R^3$ groups detailed herein, as if each and every combination has been individually described. For example, in some embodiments of the compound of Formula (I), (Ia), (II), or (IIa), or a salt (e.g., a pharmaceutically acceptable salt) thereof, X is —C(O)—; $R^1$ is unsubstituted alkyl or

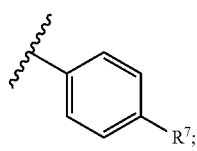

$R^2$ is unsubstituted alkyl; $R^3$ is a $C_1$-$C_6$ alkyl, such as isopropyl or tert-butyl; Y is —N($R^6$)—C(O)— or

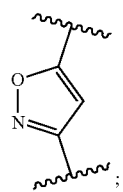

$R^6$ is H; and $R^7$ is substituted or unsubstituted heteroaryl or halo.

In one aspect, the present disclosure is directed to a compound of Formula (I), (Ia), (II), or (IIa), or a salt (e.g., a pharmaceutically acceptable salt) thereof, wherein X is —C(O)—; $R^1$ is unsubstituted alkyl (e.g., a $C_1$-$C_3$ alkyl) or

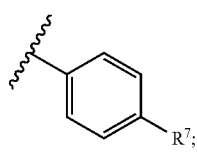

$R^2$ is unsubstituted alkyl (e.g., a $C_1$-$C_3$ alkyl); $R^3$ is tert-butyl; Y is —N($R^6$)—C(O)—; $R^6$ is H; and $R^7$ is substituted or unsubstituted heteroaryl or halo. In one such embodiment, $R^7$ is a substituted or unsubstituted 5- or 6-membered heteroaryl.

In another aspect, the present disclosure is directed to a compound of Formula (I), (Ia), (II), or (IIa), or a salt (e.g., a pharmaceutically acceptable salt) thereof, wherein X is —C(O)—; $R^1$ is unsubstituted alkyl (e.g., a $C_1$-$C_3$ alkyl) or

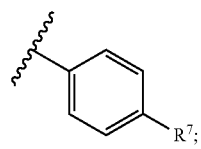

$R^2$ is unsubstituted alkyl (e.g., a $C_1$-$C_3$ alkyl); $R^3$ is isopropyl; Y is

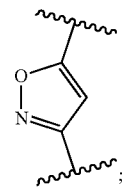

and $R^7$ is substituted or unsubstituted heteroaryl or halo. In one such embodiment, $R^7$ is a substituted or unsubstituted 5- or 6-membered heteroaryl. In one such embodiment, $R^7$ is halo.

In another aspect, the present disclosure is directed to a compound of Formula (I), (Ia), (II), or (IIa), or a salt (e.g., a pharmaceutically acceptable salt) thereof, wherein X is —C(O)—; $R^1$ is

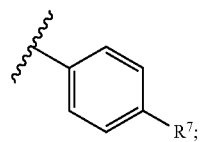

$R^2$ is unsubstituted alkyl (e.g., a $C_1$-$C_3$ alkyl); $R^3$ is isopropyl or tert-butyl; Y is —N($R^6$)—C(O)— or substituted or unsubstituted heteroarylene; $R^6$ is H; $R^7$ is

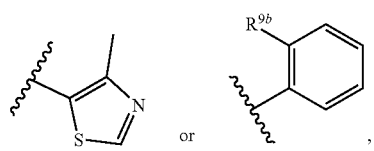

and $R^{9b}$ is halo. In one particular such embodiment, $R^3$ is isopropyl, and Y is selected from the group consisting of

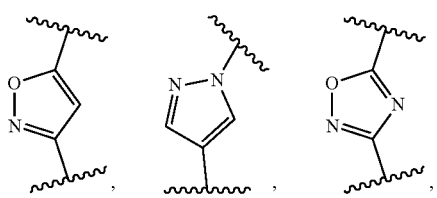

-continued

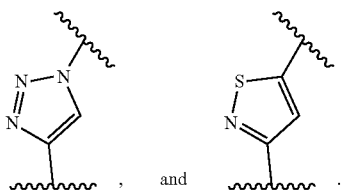, and

In another aspect, the present disclosure is directed to a compound of Formula (I), (Ia), (II), or (IIa), or a salt (e.g., a pharmaceutically acceptable salt) thereof, wherein X is —C(O)—; $R^1$ is

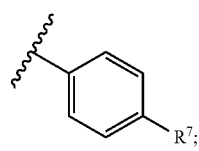

$R^2$ is unsubstituted alkyl (e.g., a $C_1$-$C_3$ alkyl); Y is —N($R^6$)—C(O)— or —N($R^6$) $SO_2$—; $R^7$ is

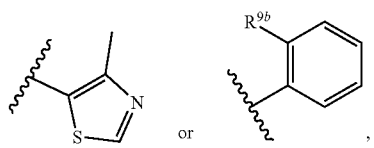

and $R^{9b}$ is halo; wherein $R^3$ is taken together with $R^6$, and the atoms to which they are attached, to form a substituted or unsubstituted 5- or 6-membered heterocyclylene.

In another aspect, the present disclosure is directed to a compound of Formula (I), (Ia), (II), or (IIa), or a salt (e.g., a pharmaceutically acceptable salt) thereof, wherein X is O; $R^1$ is unsubstituted alkyl, phenyl, or

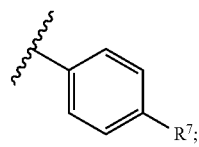

$R^2$ is unsubstituted alkyl (e.g., a $C_1$-$C_3$ alkyl), —$CF_3$, or phenyl; $R^3$ is isopropyl or tert-butyl; Y is —N($R^6$)—C(O)— or

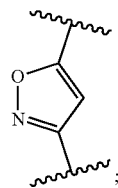 [SMILES: *c1cc(*)on1];

$R^6$ is H; $R^7$ is halo,

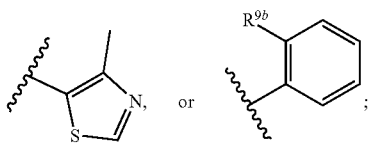

and $R^{9b}$ is halo. In one particular embodiment, Y is —N($R^6$)—C(O)—; $R^3$ is tert-butyl; and $R^6$ is H. In another embodiment, Y is

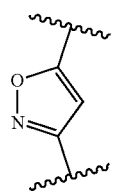 [SMILES: *c1cc(*)on1]

and $R^3$ is isopropyl.

In another aspect, the present disclosure is directed to a compound of Formula (I), (Ia), (II), or (IIa), or a salt (e.g., a pharmaceutically acceptable salt) thereof, wherein X is O; $R^1$ and $R^2$, are taken together with the carbon to which they are attached to form a 5- or 6-membered cycloalkyl, wherein the cycloalkyl is unsubstituted or fused with an unsubstituted phenyl; $R^3$ is isopropyl; and Y is

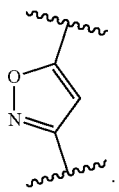 [SMILES: *c1cc(*)on1].

In another aspect, the present disclosure is directed to a compound of Formula (I), (Ia), (II), or (IIa), or a salt (e.g., a pharmaceutically acceptable salt) thereof, wherein X is —N($R^4$)—; $R^1$ and $R^2$ are each unsubstituted alkyl (e.g., a $C_1$-$C_3$ alkyl); $R^3$ is isopropyl; $R^4$ is substituted or unsubstituted $C_1$-$C_3$ alkyl or phenyl; and Y is

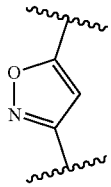.

In one particular embodiment, $R^4$ is ethyl or —$CH_2$—$CF_3$.

In another aspect, the present disclosure is directed to a compound of Formula (I), (Ia), (II), or (IIa), or a salt (e.g., a pharmaceutically acceptable salt) thereof, wherein X is —$SO_2$—; $R^1$ and $R^2$ are each hydrogen; $R^3$ is isopropyl; and Y is

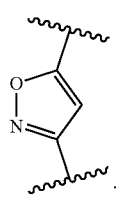

In another aspect, the present disclosure is directed to a compound of Formula (I), (Ia), (II), or (a), or a salt (e.g., a pharmaceutically acceptable salt) thereof, wherein X is —C(R$^{5a}$)(R$^{5b}$)—; R$^1$ and R$^2$ are each unsubstituted alkyl; R$^3$ is isopropyl; and Y is

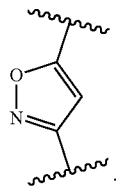

In one embodiment, the PROTAC is a compound of Formula (I) or a tautomer thereof, or a salt (e.g., a pharmaceutically acceptable salt) thereof, and has a structure selected from the group consisting of those structures in Table 1, wherein X, R$^1$, R$^2$, L, and D are as defined herein; p is 0, 1, 2, 3, or 4; R$^{11}$ is selected from the group consisting of substituted or unsubstituted C$_1$-C$_3$ alkyl, halo, —CN, and —OR$^{11a}$; and R$^{11a}$ is selected from the group consisting of H and substituted or unsubstituted alkyl.

TABLE 1-continued

| Formula Number | Structure |
|---|---|
| I-A-1f | (structure) |
| I-A-1g | (structure) |
| I-A-2 | (structure) |
| I-A-2a | (structure) |
| I-A-2b | (structure) |
| I-A-3 | (structure) |
| I-A-3a | (structure) |
| I-A-3b | (structure) |
| I-A-4 | (structure) |

TABLE 1-continued

| Formula Number | Structure |
|---|---|
| I-A-4a | (chemical structure) |
| I-A-4b | (chemical structure) |
| I-A-4c | (chemical structure) |
| I-A-5 | (chemical structure) |
| I-A-5a | (chemical structure) |
| I-A-6 | (chemical structure) |
| I-A-6a | (chemical structure) |
| I-A-6b | (chemical structure) |
| I-A-7 | (chemical structure) |
| I-A-7a | (chemical structure) |

TABLE 1-continued

| Formula Number | Structure |
|---|---|
| I-A-8 | (structure) |
| I-A-8a | (structure) |
| I-A-9 | (structure) |
| I-A9a | (structure) |
| I-A-10 | (structure) |
| I-A-10a | (structure) |
| I-A-10b | (structure) |
| I-A-11 | (structure) |
| I-A-11a | (structure) |

TABLE 1-continued
| Formula Number | Structure |
|---|---|
| I-A-12 | 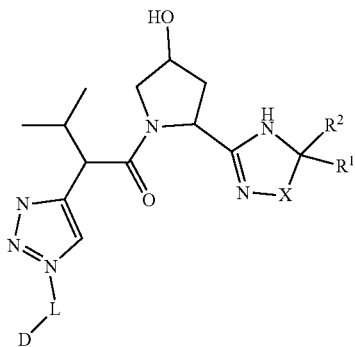 |
| I-A-12a | 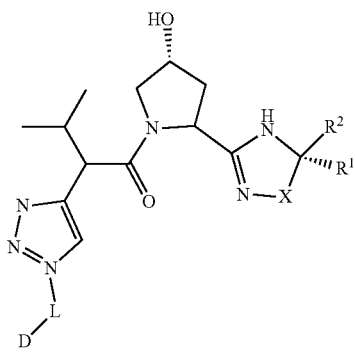 |
| I-A-13 | 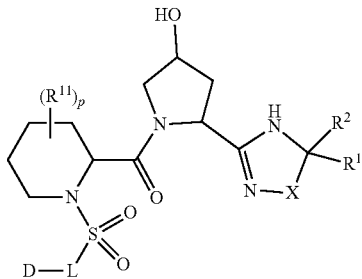 |
| I-A-13a | 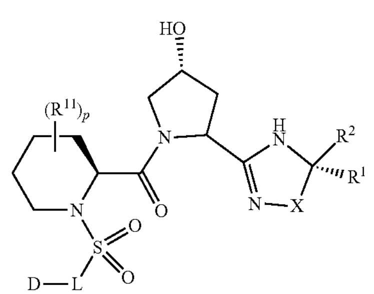 |
| I-A-14 | 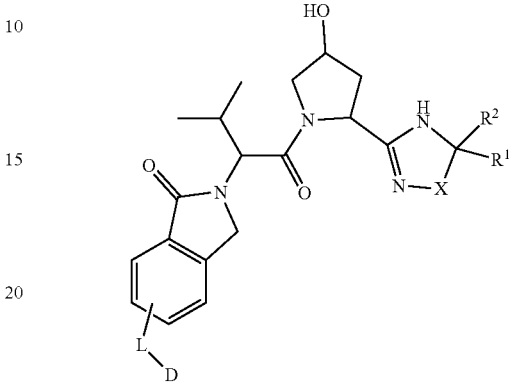 |
| I-A-14a | 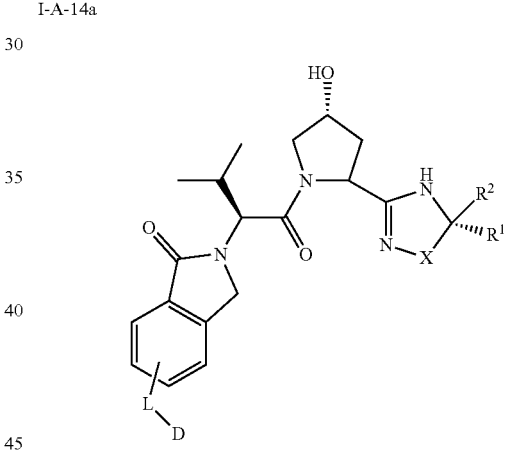 |
| I-A-14b | 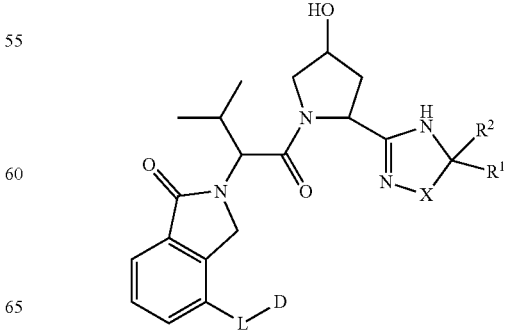 |

TABLE 1-continued

| Formula Number | Structure |
|---|---|
| I-A-14c | (structure) |
| I-A-14d | (structure) |

In one embodiment, the PROTAC is a compound of Formula (I) or a tautomer thereof, or a salt (e.g., a pharmaceutically acceptable salt) thereof, and has a structure selected from the group consisting of those structures in Table 2, wherein $R^3$, $R^7$, L, and D are as defined herein; $R^{10}$ is halo; and m is 0, 1, 2, 3, 4, or 5.

TABLE 2

| Formula Number | Structure |
|---|---|
| I-B-1 | (structure) |
| I-B-1a | (structure) |
| I-B-2 | (structure) |

TABLE 2-continued
| Formula Number | Structure |
| --- | --- |
| I-B-2a | 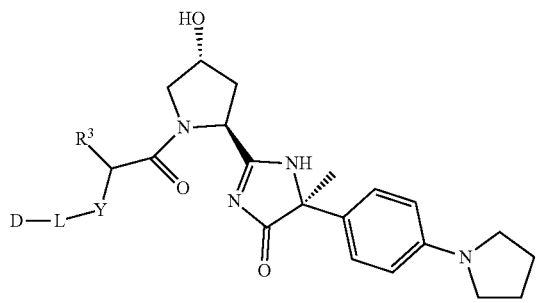 |
| I-B-3 | 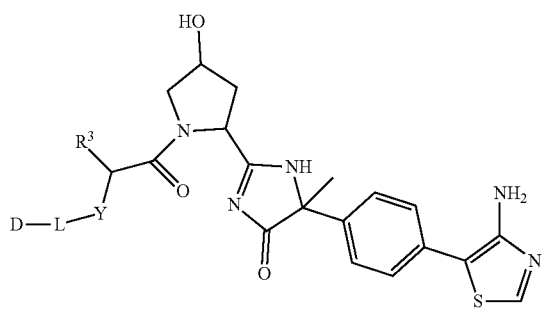 |
| I-B-3a | 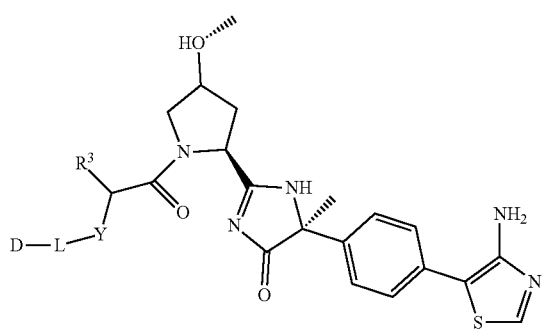 |
| I-B-4 | 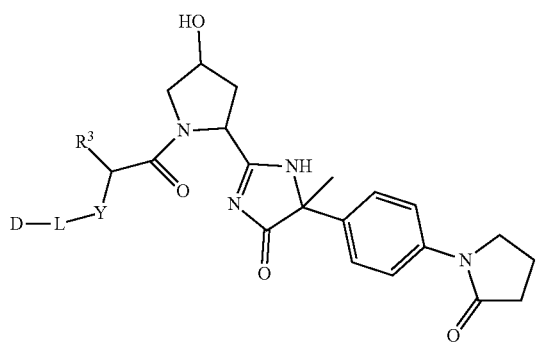 |

TABLE 2-continued
| Formula Number | Structure |
|---|---|
| I-B-4a | 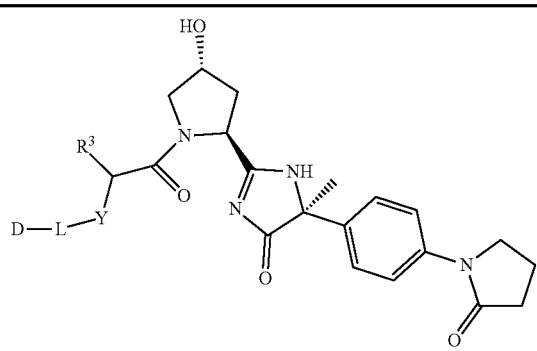 |
| I-B-5 | 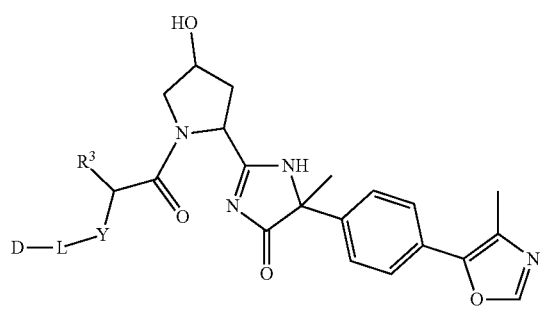 |
| I-B-5a | 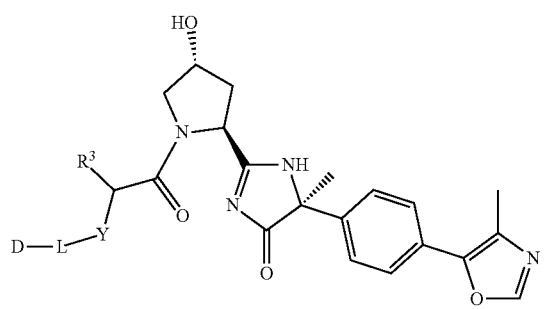 |
| I-B-6 | 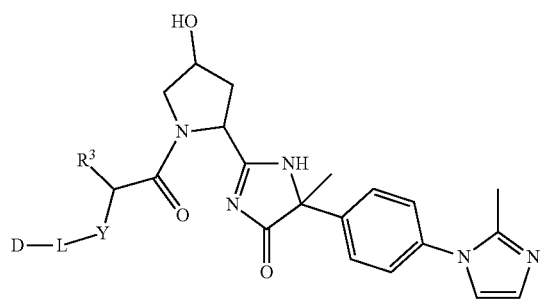 |
| I-B-6a | 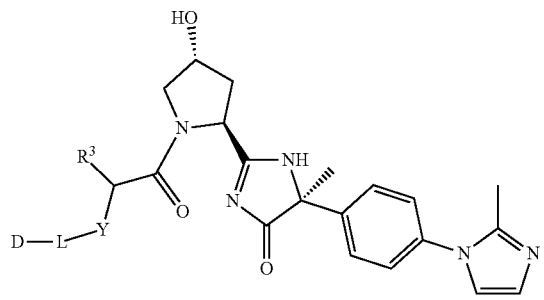 |

TABLE 2-continued
| Formula Number | Structure |
|---|---|
| I-B-7 | 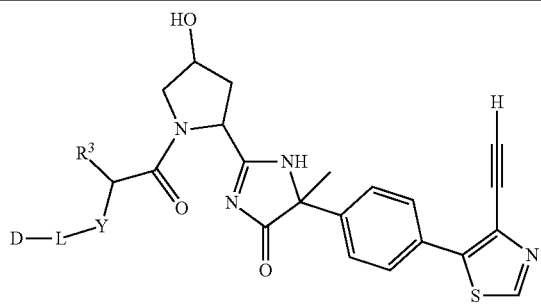 |
| I-B-7a | 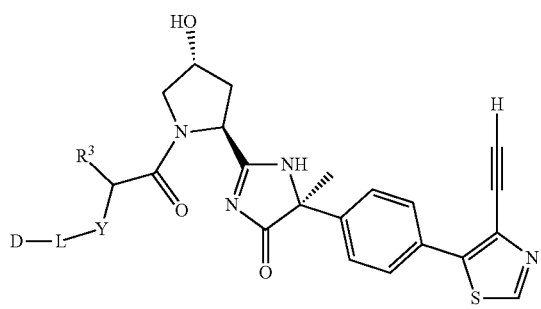 |
| I-B-8 | 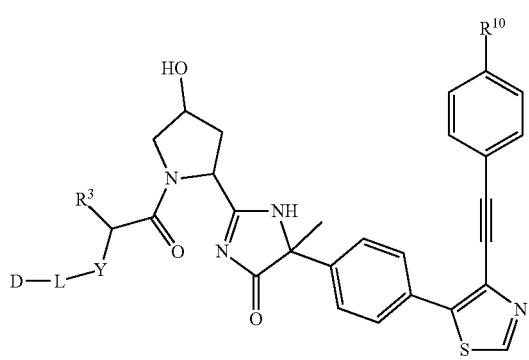 |
| I-B-8a | 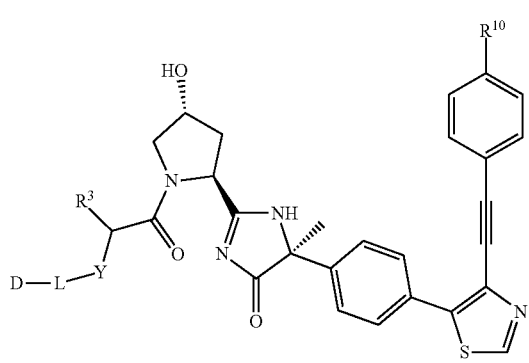 |
| I-B-9 | 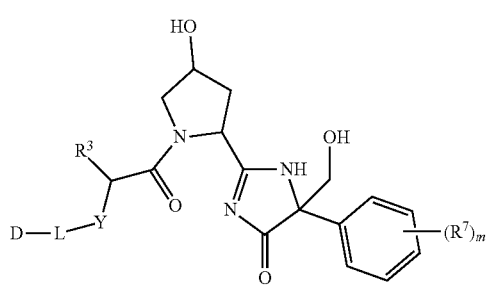 |

TABLE 2-continued
| Formula Number | Structure |
|---|---|
| I-B-9a | 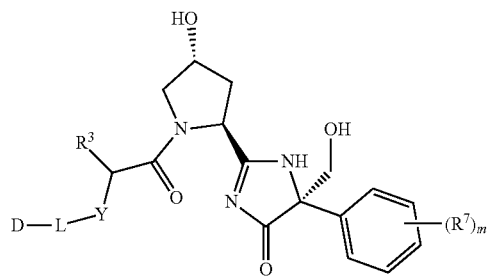 |
| I-B-10 | 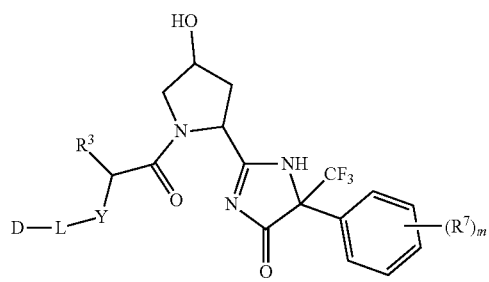 |
| I-B-10a | 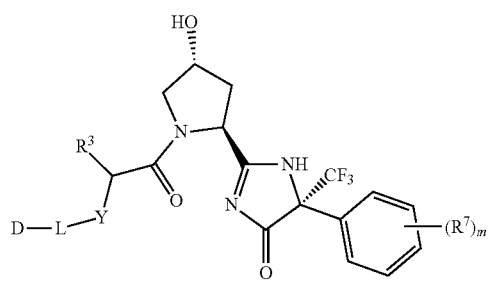 |
| I-B-11 | 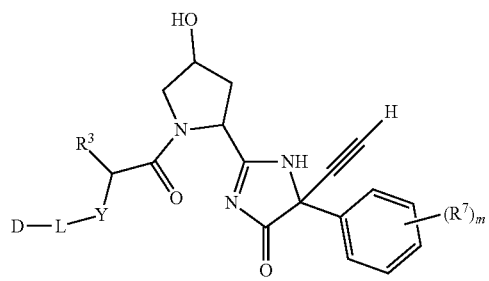 |
| I-B-11a | 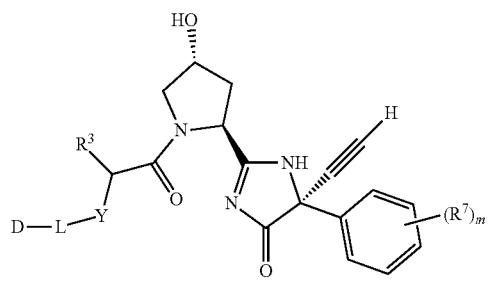 |

TABLE 2-continued
| Formula Number | Structure |
|---|---|
| I-B-12 | 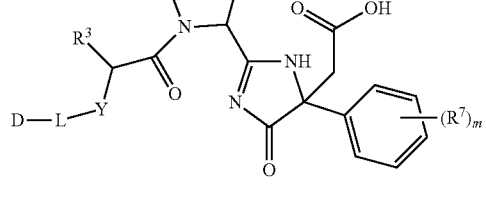 |
| I-B-12a | 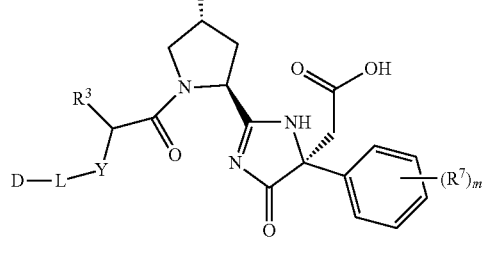 |
| I-B-13 | 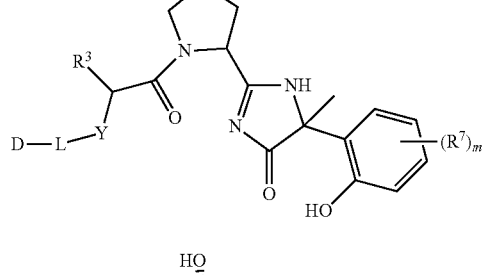 |
| I-B-13a | 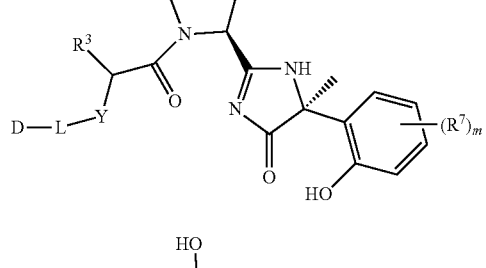 |
| I-B-14 | 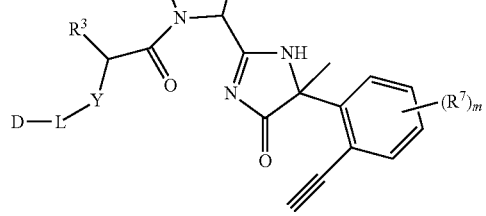 |

TABLE 2-continued
| Formula Number | Structure |
|---|---|
| I-B-14a | 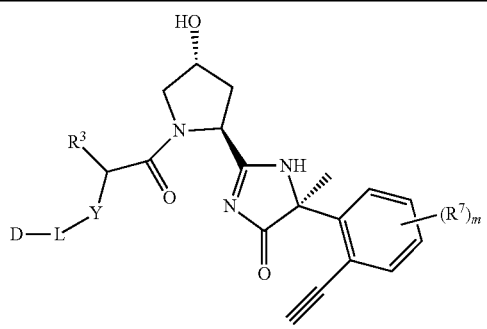 |
| I-B-15 | 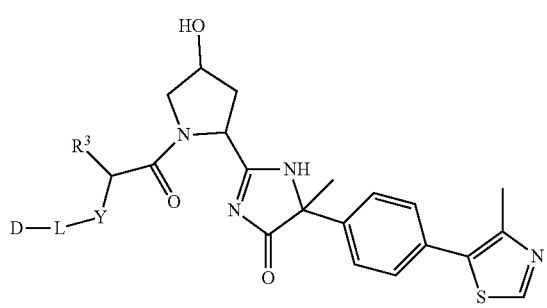 |
| I-B-15a | 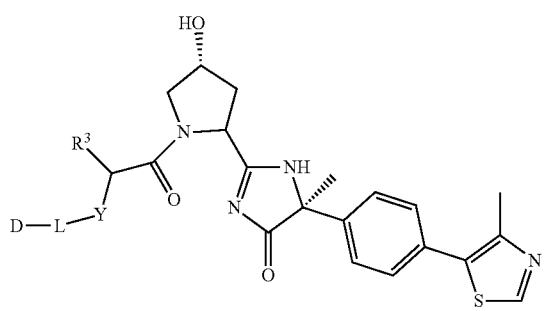 |
| I-B-15b | 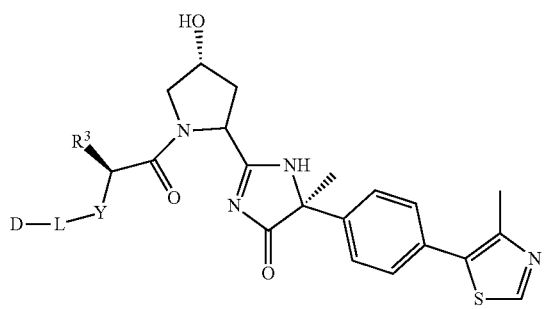 |
| I-B-15c | 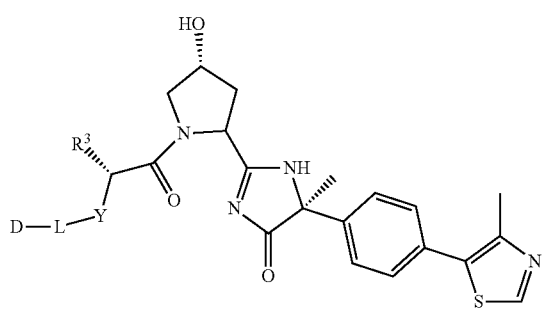 |

TABLE 2-continued
| Formula Number | Structure |
| --- | --- |
| I-B-15d | 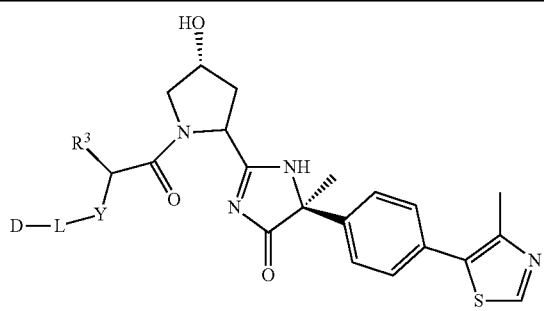 |
| I-B-16 | 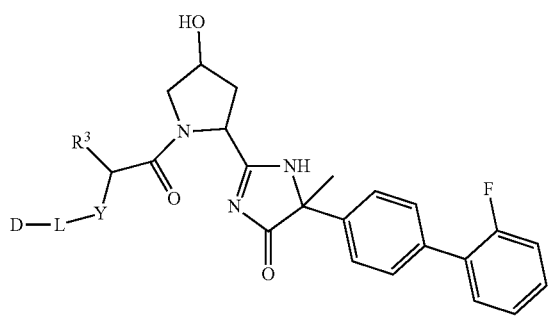 |
| I-B-16a | 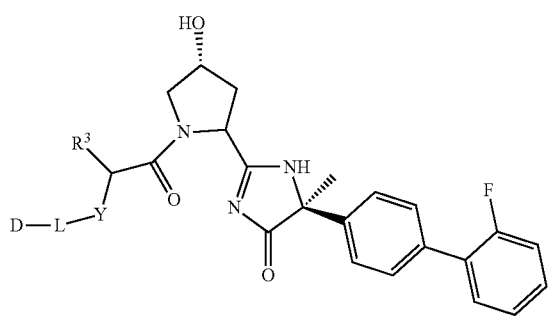 |
| I-B-17 | 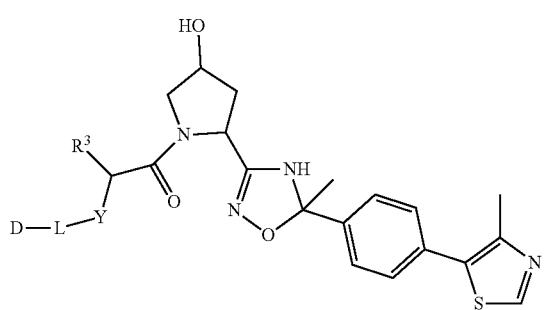 |
| I-B-17a | 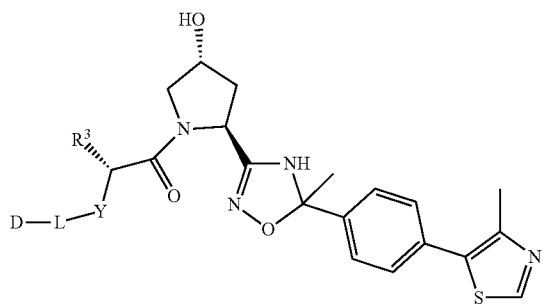 |

TABLE 2-continued
| Formula Number | Structure |
|---|---|
| I-B-17b | 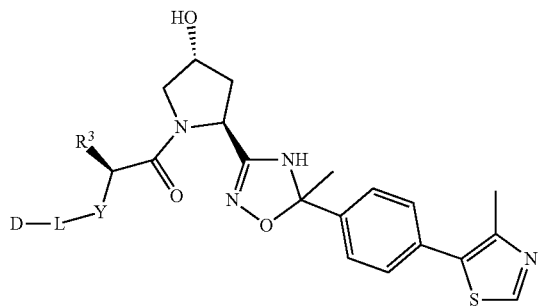 |
| I-B-18 | 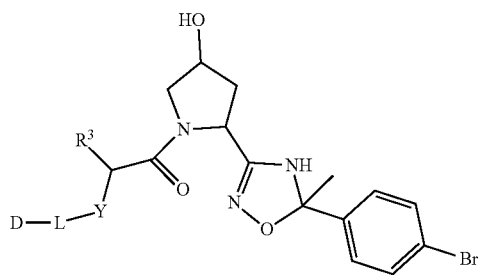 |
| I-B-18a | 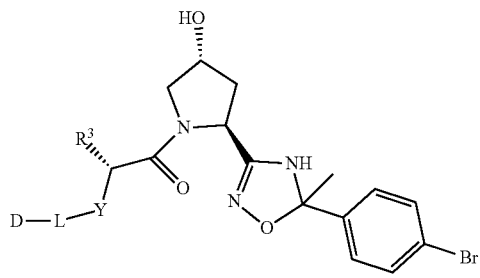 |
| I-B-18b | 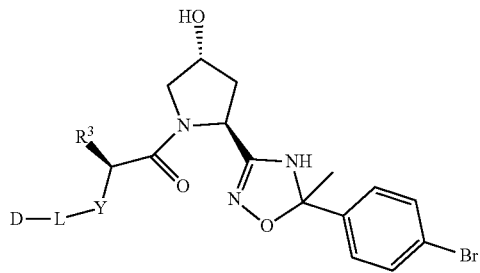 |
| I-B-19 | 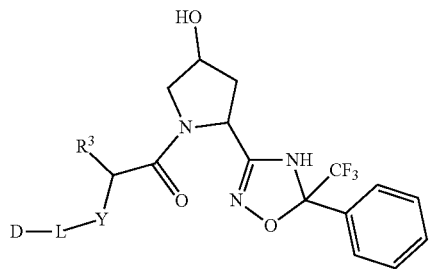 |

TABLE 2-continued
| Formula Number | Structure |
|---|---|
| I-B-19a | 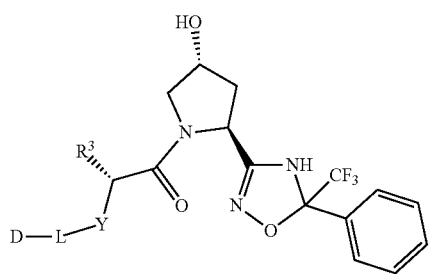 |
| I-B-19b | 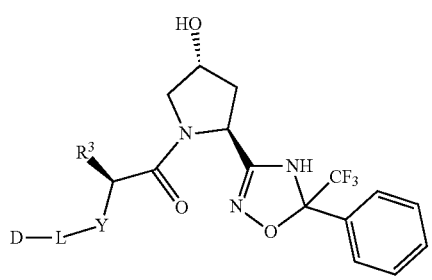 |
| I-B-20 | 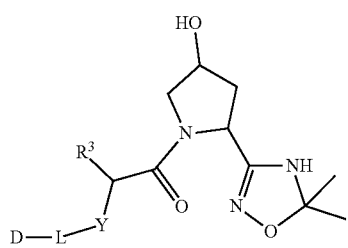 |
| I-B-20a | 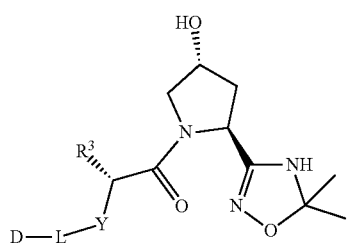 |
| I-B-20b | 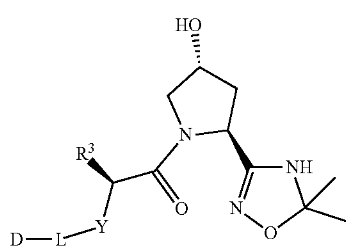 |
| I-B-21 | 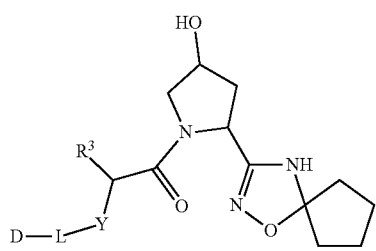 |

TABLE 2-continued
| Formula Number | Structure |
| --- | --- |
| I-B-21a | 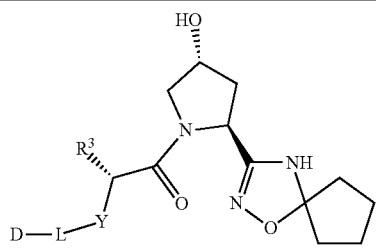 |
| I-B-21b | 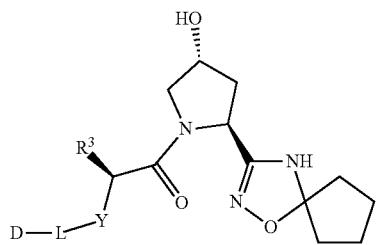 |
| I-B-22 | 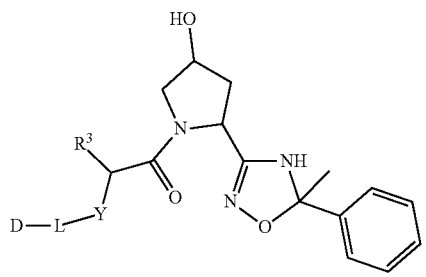 |
| I-B-22a | 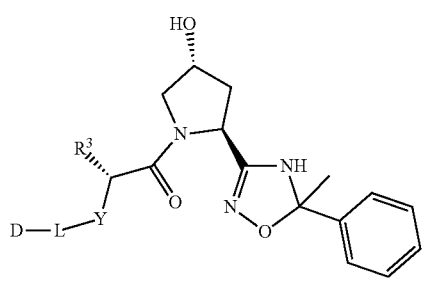 |
| I-B-22b | 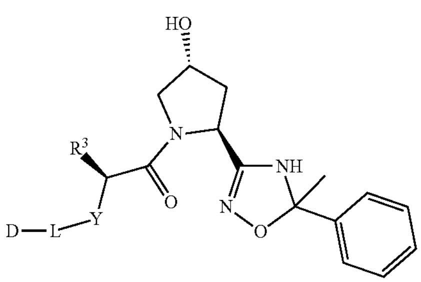 |
| I-B-23 | 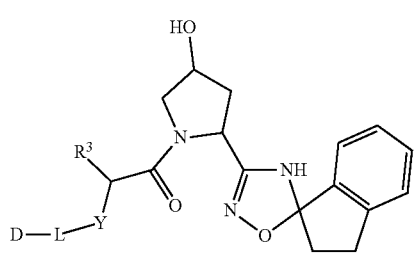 |

TABLE 2-continued
| Formula Number | Structure |
|---|---|
| I-B-23a | 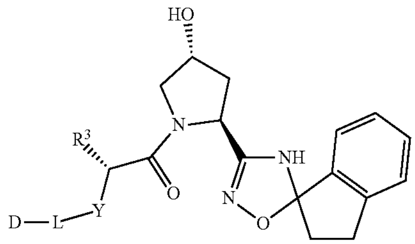 |
| I-B-23b | 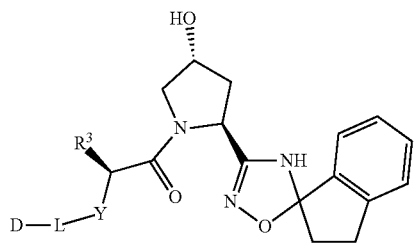 |
| I-B-24 | 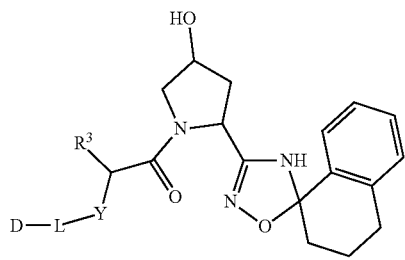 |
| I-B-24a | 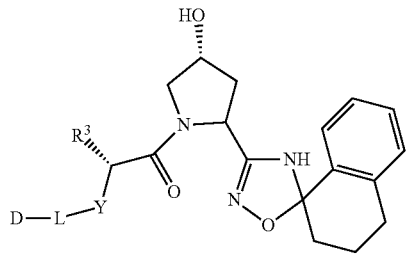 |
| I-B-24b | 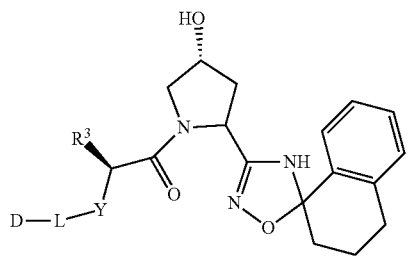 |
| I-B-25 | 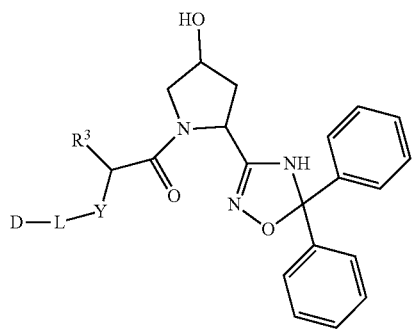 |

TABLE 2-continued
| Formula Number | Structure |
|---|---|
| I-B-25a | 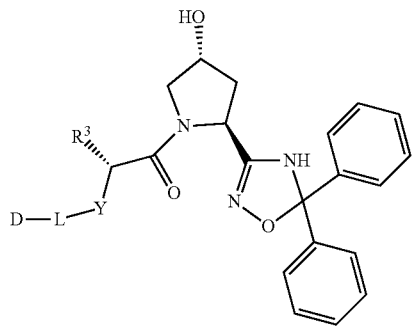 |
| I-B-25b | 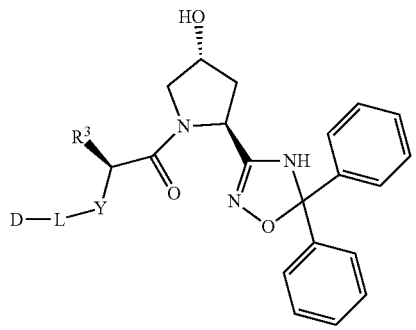 |
| I-B-26 | 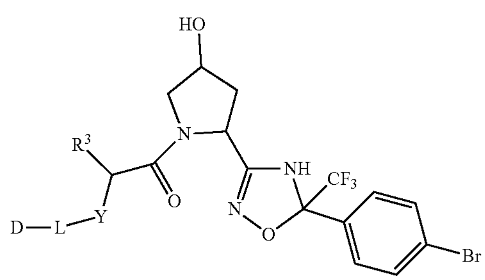 |
| I-B 26a | 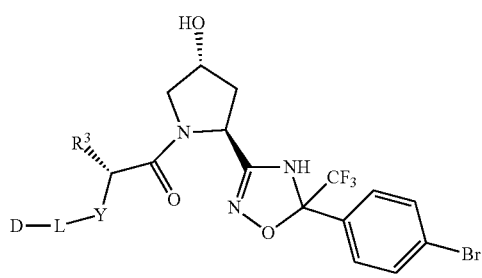 |
| I-B-26b | 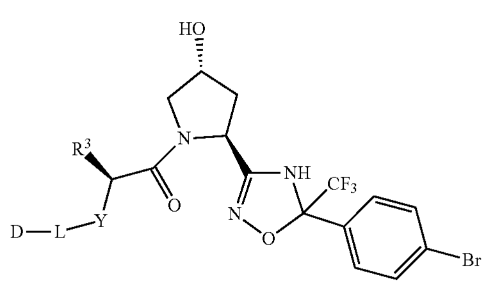 |

TABLE 2-continued
| Formula Number | Structure |
|---|---|
| I-B-27 | 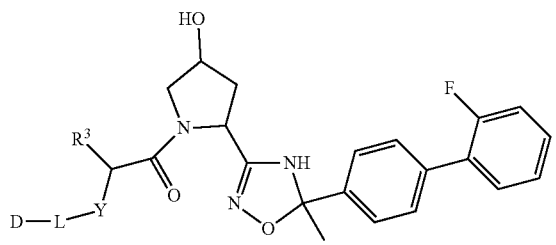 |
| I-B-27a | 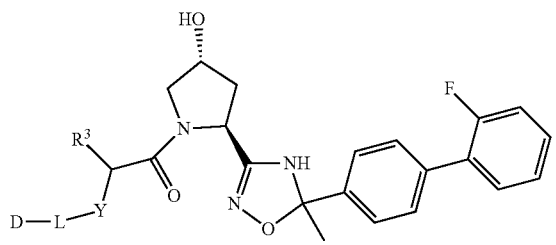 |
| I-B-28 | 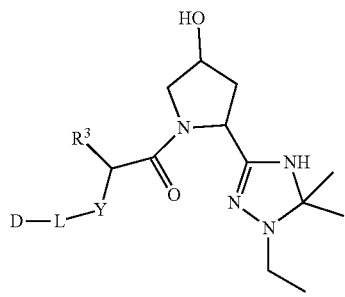 |
| I-B-28a | 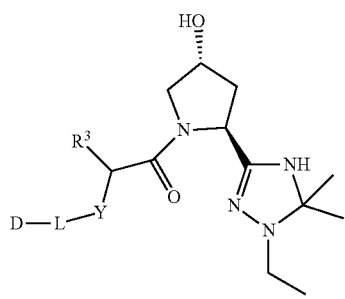 |
| I-B-29 | 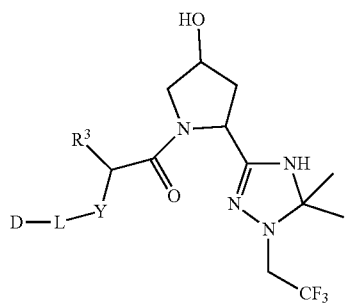 |

TABLE 2-continued
| Formula Number | Structure |
|---|---|
| I-B-29a | 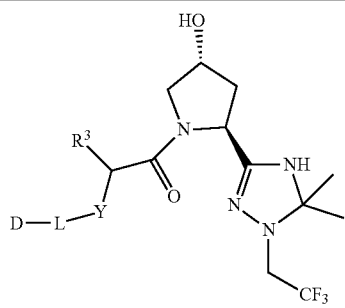 |
| I-B-30 | 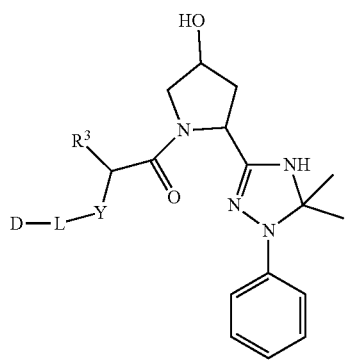 |
| I-B-30a | 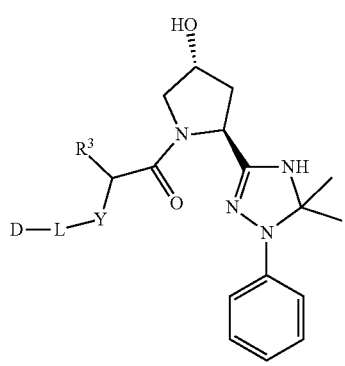 |
| I-B-31 | 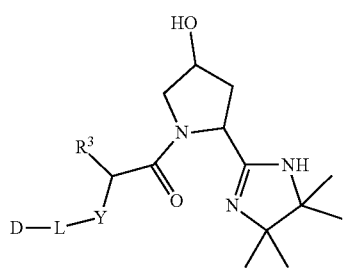 |
| I-B-31a | 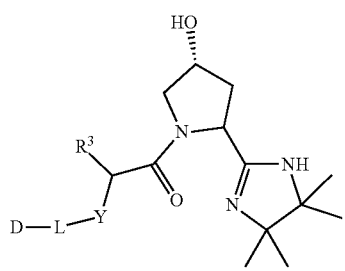 |

TABLE 2-continued
| Formula Number | Structure |
| --- | --- |
| I-B-32 | 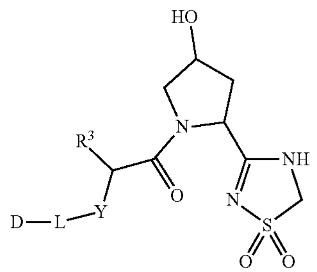 |
| I-B-32a | 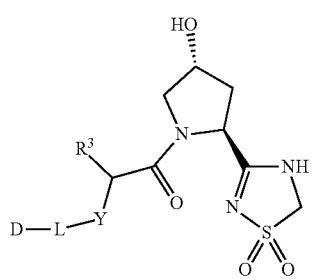 |
| I-B-33 | 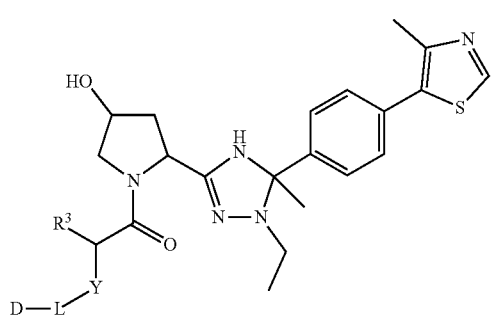 |
| I-B-33a | 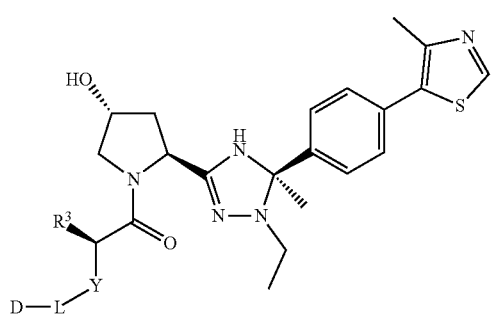 |
| I-B-33b | 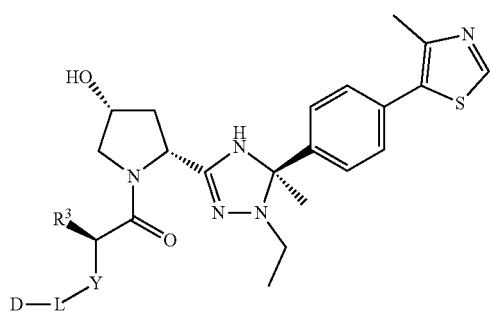 |

TABLE 2-continued
| Formula Number | Structure |
|---|---|
| I-B-34 | 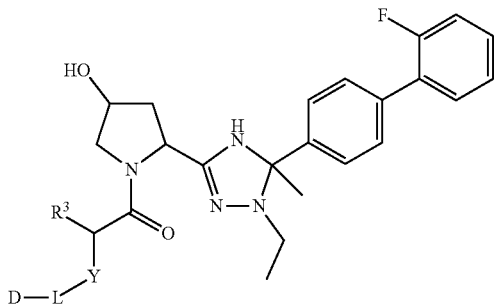 |
| I-B-34a | 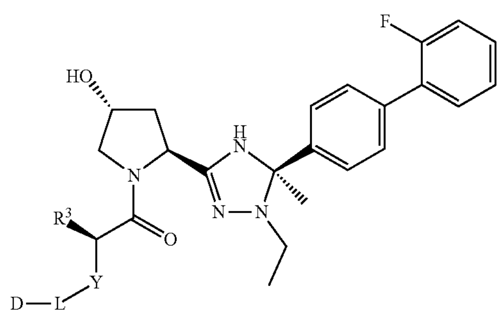 |
| I-B-34b | 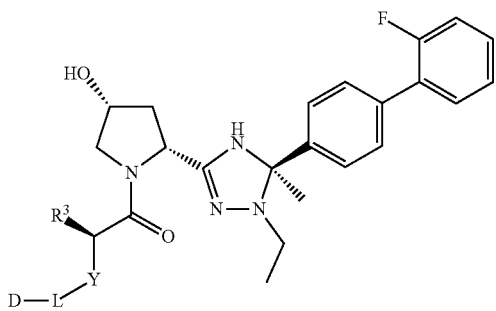 |
| I-B-35 | 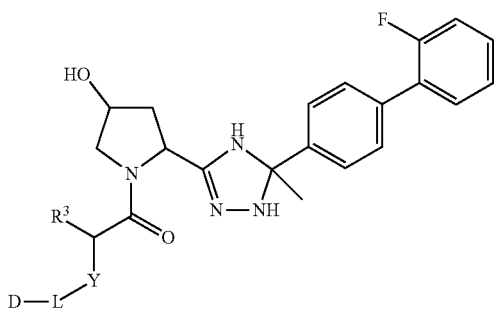 |

TABLE 2-continued

| Formula Number | Structure |
| --- | --- |
| I-B-35a | 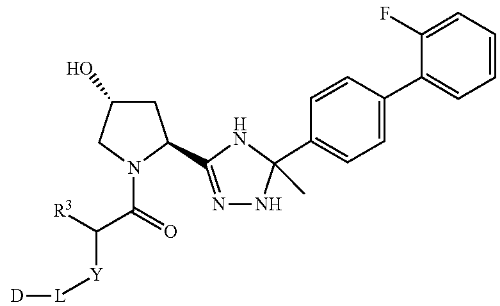 |
| I-B-35b | 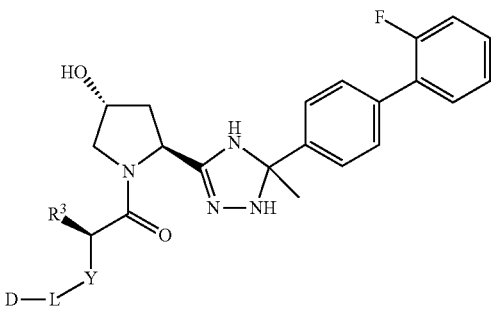 |

In one embodiment, the PROTAC is a compound of Formula I-B-9 or a salt (e.g., a pharmaceutically acceptable salt) thereof, having the structure

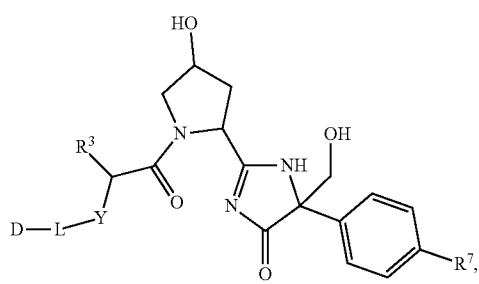

wherein $R^7$ is as defined above.

In one embodiment, the PROTAC is a compound of Formula I-B-9a or a salt (e.g., a pharmaceutically acceptable salt) thereof, having the structure

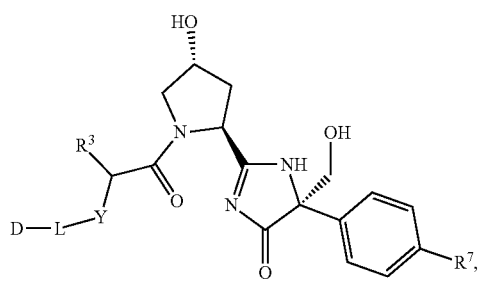

wherein $R^7$ is as defined above.

In one embodiment, the PROTAC is a compound of Formula I-B-10 or a salt (e.g., a pharmaceutically acceptable salt) thereof, having the structure

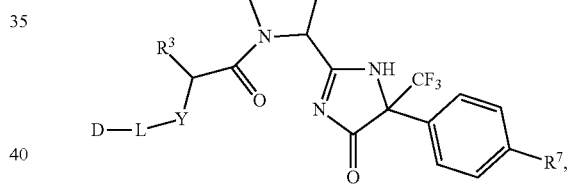

wherein $R^7$ is as defined above.

In one embodiment, the PROTAC is a compound of Formula I-B-10a or a salt (e.g., a pharmaceutically acceptable salt) thereof, having the structure

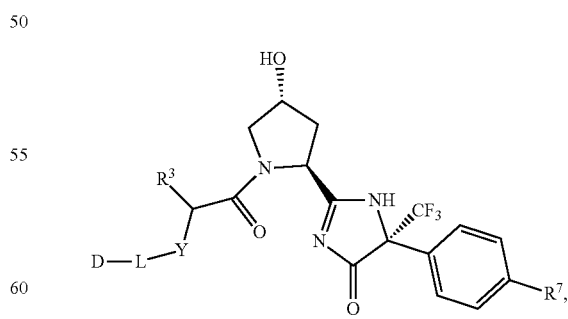

wherein $R^7$ is as defined above.

In one embodiment, the PROTAC is a compound of Formula I-B-11 or a salt (e.g., a pharmaceutically acceptable salt) thereof, having the structure

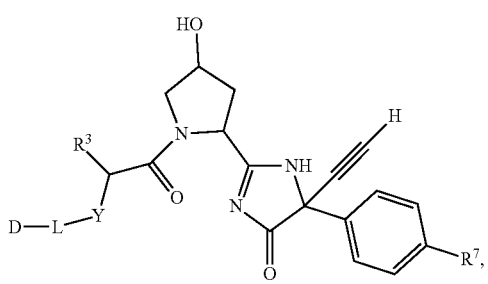

wherein R[7] is as defined above.

In one embodiment, the PROTAC is a compound of Formula I-B-11a or a salt (e.g., a pharmaceutically acceptable salt) thereof, having the structure

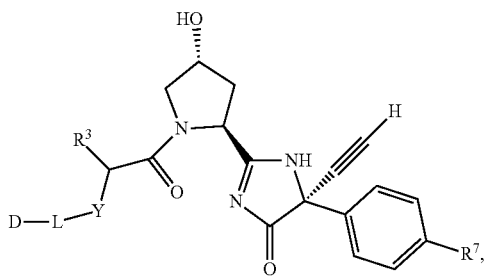

wherein R[7] is as defined above.

In one embodiment, the PROTAC is a compound of Formula I-B-12 or a salt (e.g., a pharmaceutically acceptable salt) thereof, having the structure

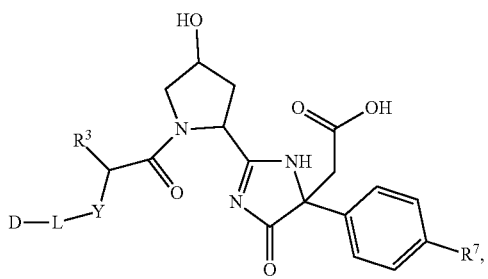

wherein R[7] is as defined above.

In one embodiment, the PROTAC is a compound of Formula I-B-12a or a salt (e.g., a pharmaceutically acceptable salt) thereof, having the structure

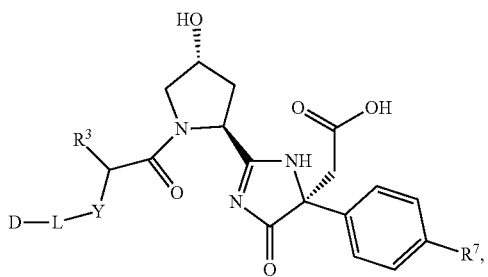

wherein R[7] is as defined above.

In one embodiment, the PROTAC is a compound of Formula I-B-13 or a salt (e.g., a pharmaceutically acceptable salt) thereof, having the structure

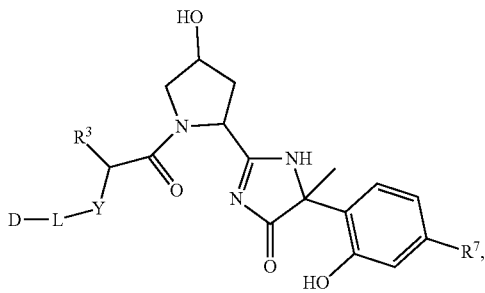

wherein R[7] is as defined above.

In one embodiment, the PROTAC is a compound of Formula I-B-13a or a salt (e.g., a pharmaceutically acceptable salt) thereof, having the structure

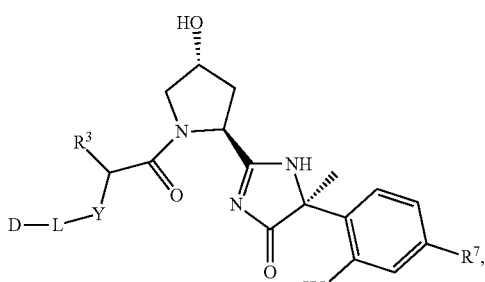

wherein R[7] is as defined above.

In one embodiment, the PROTAC is a compound of Formula I-B-14 or a salt (e.g., a pharmaceutically acceptable salt) thereof, having the structure

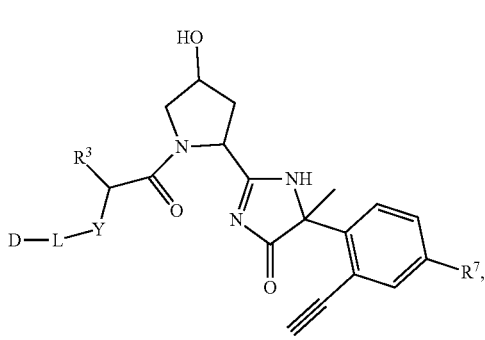

wherein R[7] is as defined above.

In one embodiment, the PROTAC is a compound of Formula I-B-14a or a salt (e.g., a pharmaceutically acceptable salt) thereof, having the structure

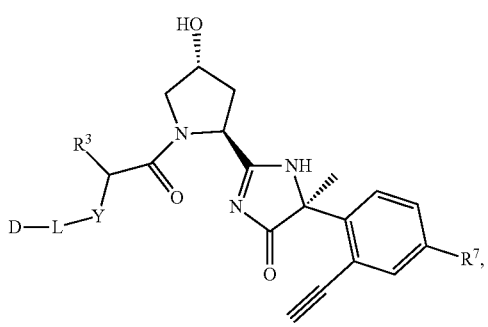

wherein R⁷ is as defined above.

In one embodiment, the PROTAC is a compound of Formula I-B-15 or a salt (e.g., a pharmaceutically acceptable salt) thereof, having the structure

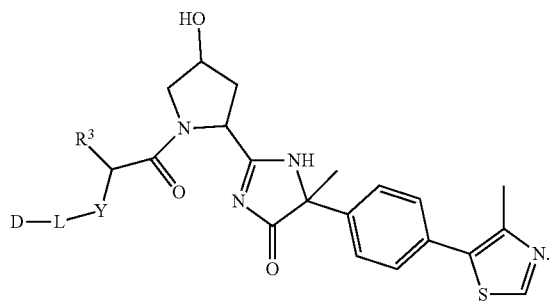

In one embodiment, the PROTAC is a compound of Formula I-B-15a or a salt (e.g., a pharmaceutically acceptable salt) thereof, having the structure

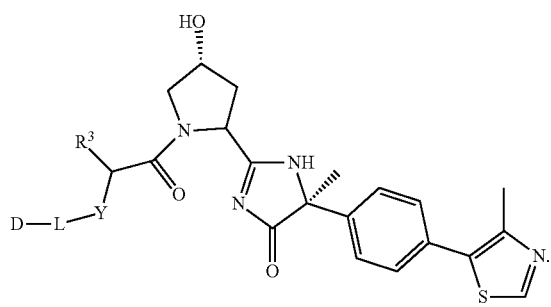

In one embodiment, the PROTAC is a compound of Formula (II) or a tautomer thereof, or a salt (e.g., a pharmaceutically acceptable salt) thereof, and has a structure selected from the group consisting of those structures in Table 3, wherein X, R¹, R², L, and D are as defined herein; p is 0, 1, 2, 3, or 4; $R^{11}$ is selected from the group consisting of substituted or unsubstituted $C_1$-$C_3$ alkyl, halo, —CN, and —$OR^{11a}$; and $R^{11a}$ is selected from the group consisting of H and substituted or unsubstituted alkyl.

TABLE 3

| Formula Number | Structure |
|---|---|
| II-A-1 | 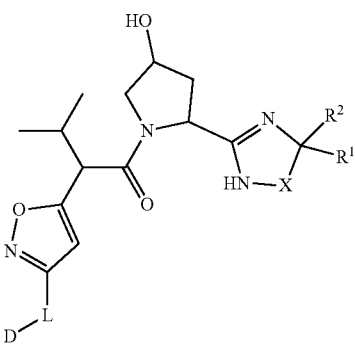 |
| II-A-1a | 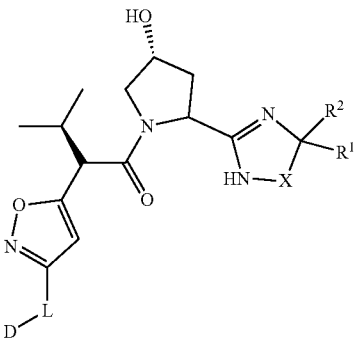 |
| II-A-1b | 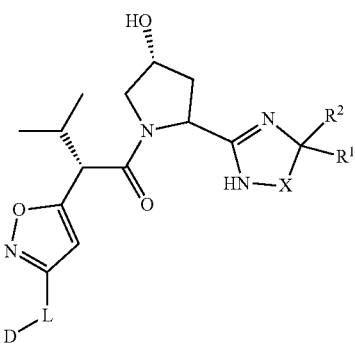 |
| II-A-1c | 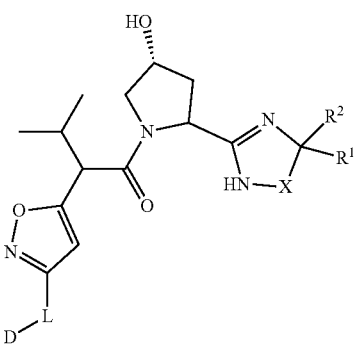 |

TABLE 3-continued
| Formula Number | Structure |
|---|---|
| II-A-1d | 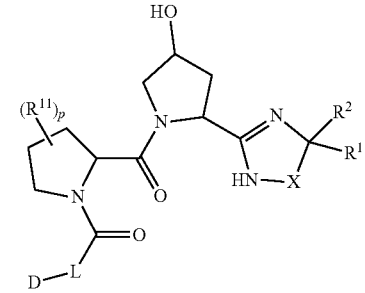 |
| II-A-1e | 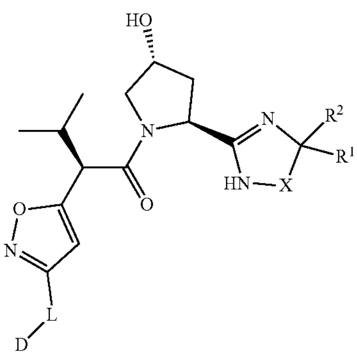 |
| II-A-1f | 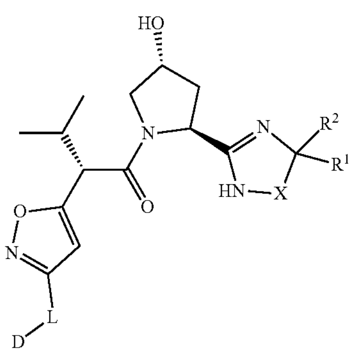 |
| I-IA-1g | 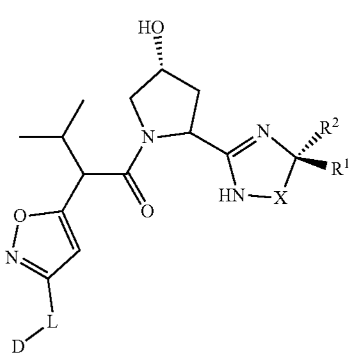 |
TABLE 3-continued
| Formula Number | Structure |
|---|---|
| II-A-2 | 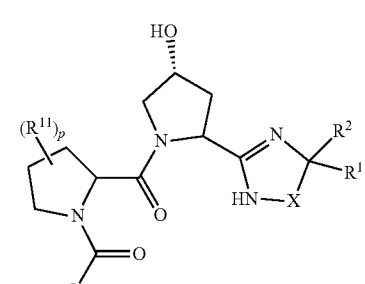 |
| II-A-2a | 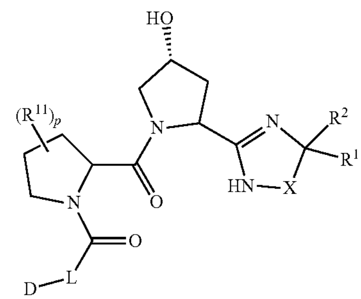 |
| II-A-2b | 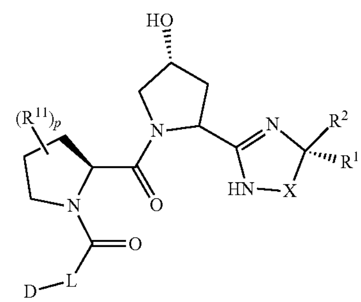 |
| II-A-3 | 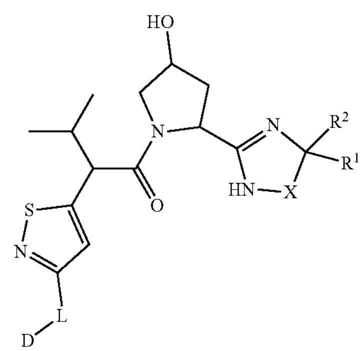 |
| II-A-3a | 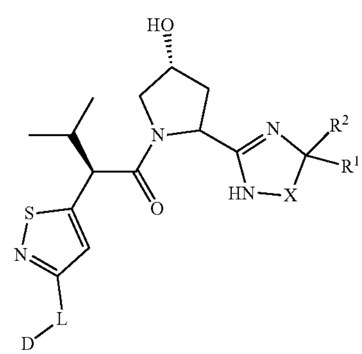 |

TABLE 3-continued

| Formula Number | Structure |
|---|---|
| II-A-3b | (structure) |
| II-A-4 | (structure) |
| II-A-4a | (structure) |
| II-A-4b | (structure) |
| II-A-4c | (structure) |
| II-A-5 | (structure) |
| II-A-5a | (structure) |
| II-A-6 | (structure) |
| II-A-6a | (structure) |
| II-A-6b | (structure) |

TABLE 3-continued

| Formula Number | Structure |
|---|---|
| II-A-7 | |
| II-A-7a | |
| II-A-8 | |
| II-A-8a | |
| II-A-9 | 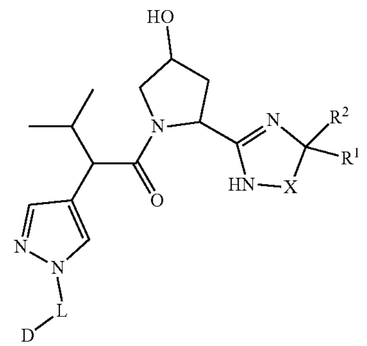 |
| II-A-9a | 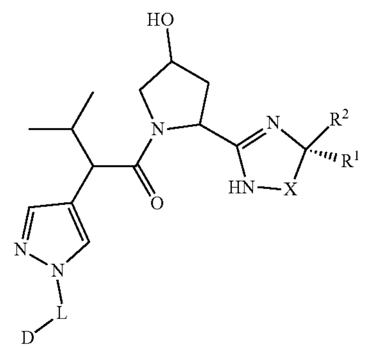 |
| II-A-10 | 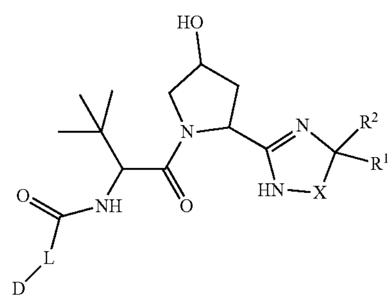 |
| II-A-10a | 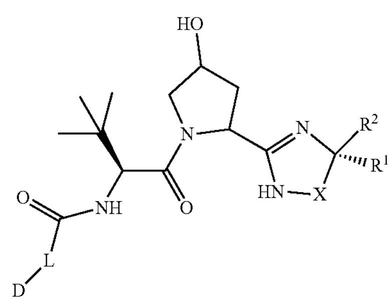 |
| II-A-10b | 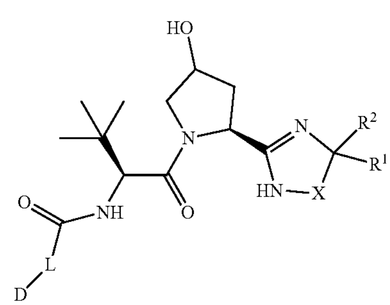 |

TABLE 3-continued

| Formula Number | Structure |
|---|---|
| II-A-11 | 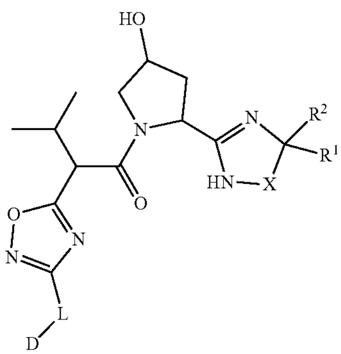 |
| II-A-11a | 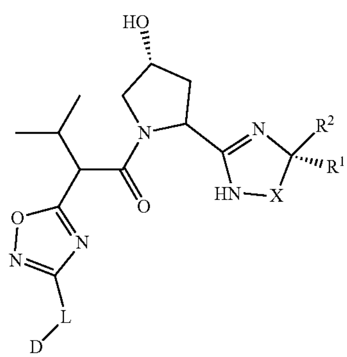 |
| II-A-12 | 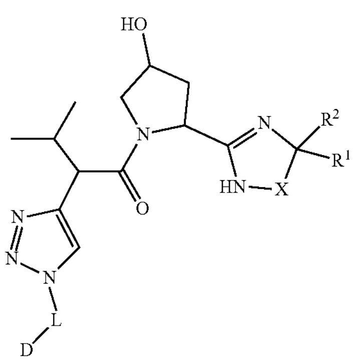 |
| II-A-12a | 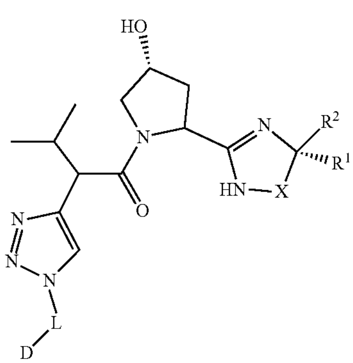 |
| II-A-13 | |
| II-A-13a | |
| I-A-14 | |
| II-A-14a | |

TABLE 3-continued

| Formula Number | Structure |
|---|---|
| II-A-14b | 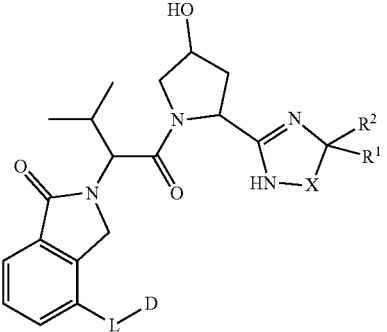 |
| II-A-14c | 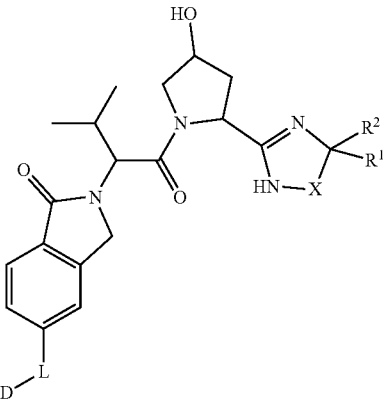 |
| II-A-14d | 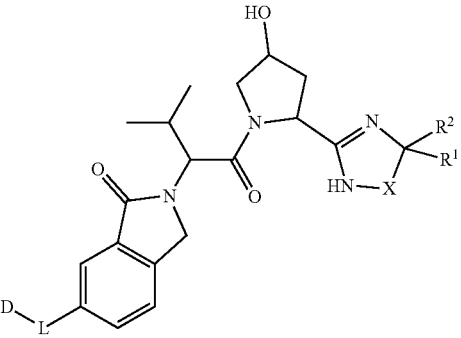 |

In one embodiment, the PROTAC is a compound of Formula (II) or a tautomer thereof, or a salt (e.g., a pharmaceutically acceptable salt) thereof, and has a structure selected from the group consisting of those structures in Table 4, wherein $R^3$, $R^7$, L, and D are as defined herein; $R^{10}$ is halo; and m is 0, 1, 2, 3, 4, or 5.

TABLE 4

| Formula Number | Structure |
|---|---|
| II-B-1 | 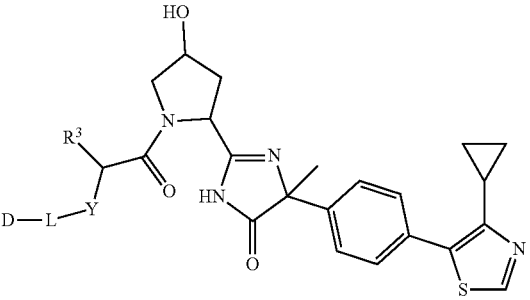 |
| II-B-1a | 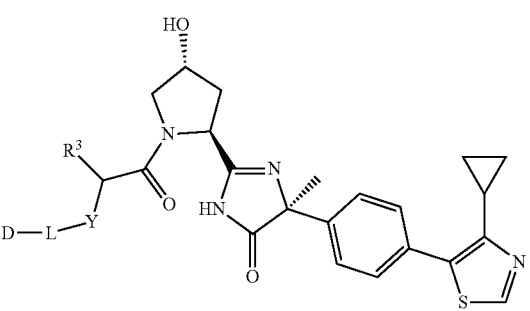 |

TABLE 4-continued
| Formula Number | Structure |
|---|---|
| II-B-2 | 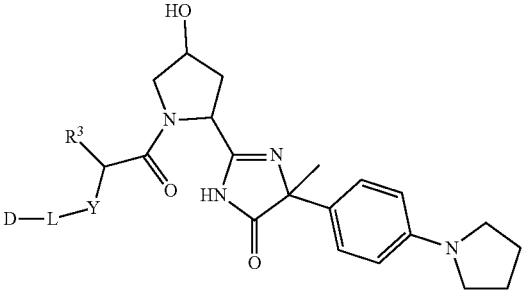 |
| II-B-2a | 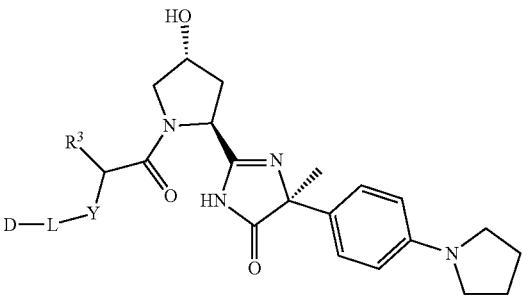 |
| II-B-3 | 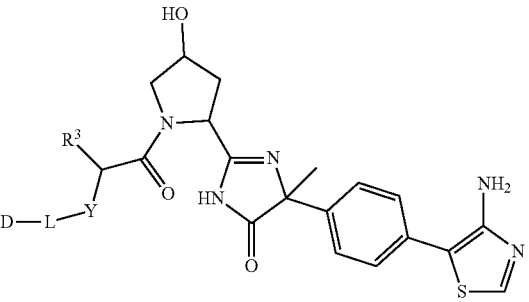 |
| II-B-3a | 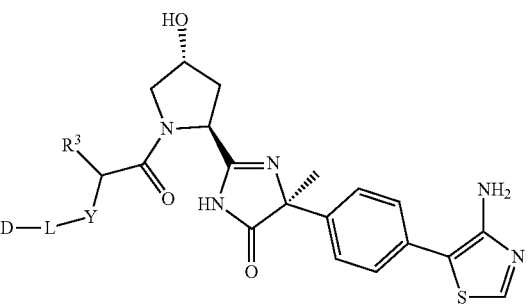 |
| II-B-4 | 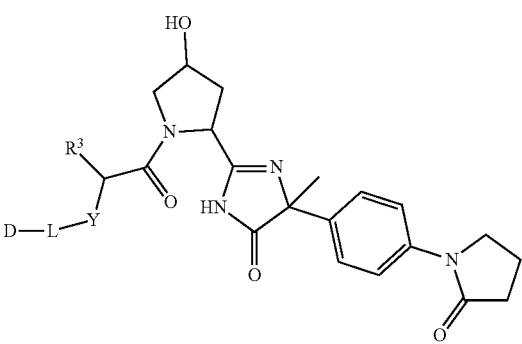 |

TABLE 4-continued
| Formula Number | Structure |
|---|---|
| II-B-4a | 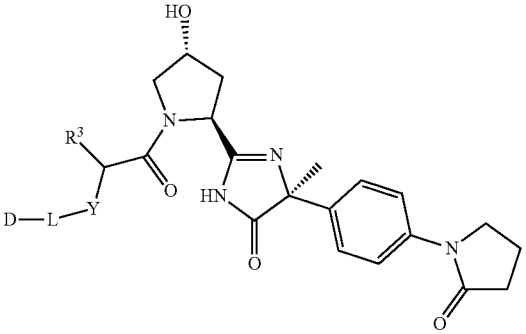 |
| II-B-5 | 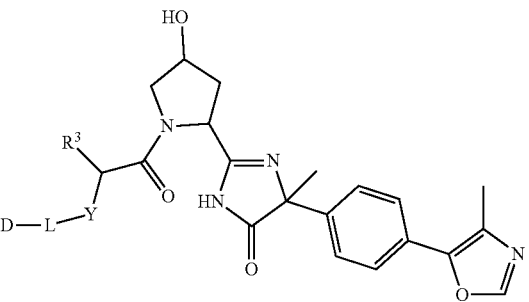 |
| II-B-5a | 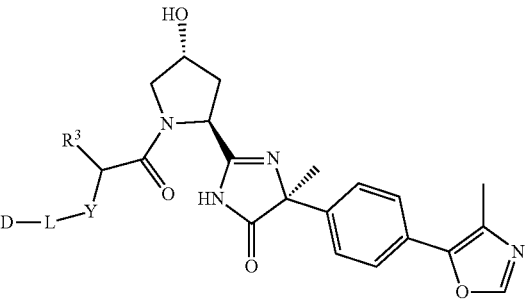 |
| II-B-6 | 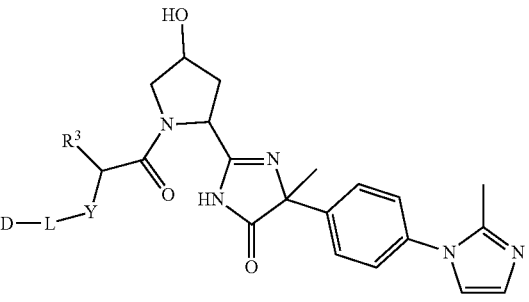 |
| II-B-6a | 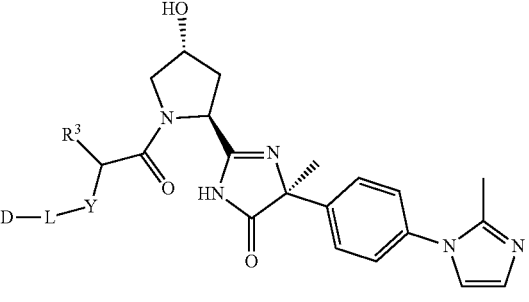 |

TABLE 4-continued

| Formula Number | Structure |
|---|---|
| II-B-7 | (structure) |
| II-B-7a | (structure) |
| II-B-8 | (structure) |
| II-B-8a | (structure) |
| II-B-9 | (structure) |

TABLE 4-continued

| Formula Number | Structure |
|---|---|
| II-B-9a | (chemical structure) |
| II-B-10 | (chemical structure) |
| II-B-10a | (chemical structure) |
| II-B-11 | (chemical structure) |
| II-B-11a | (chemical structure) |

TABLE 4-continued
| Formula Number | Structure |
|---|---|
| II-B-12 | 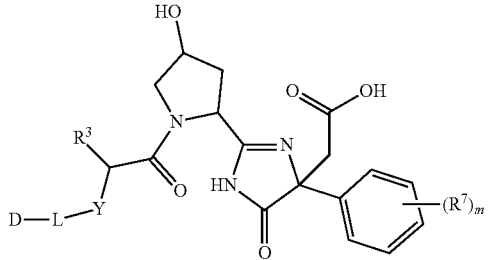 |
| II-B-12a | 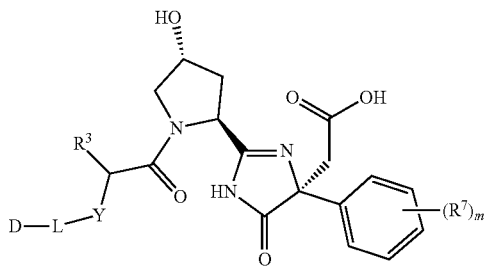 |
| II-B-13 | 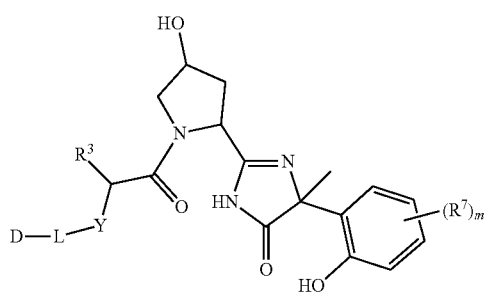 |
| II-B-13a | 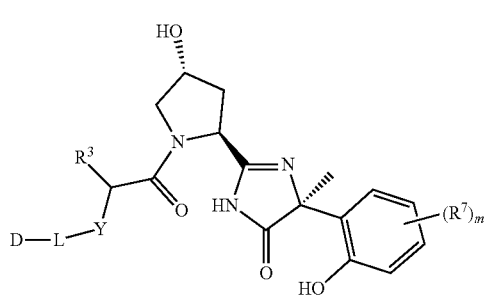 |
| II-B-14 | 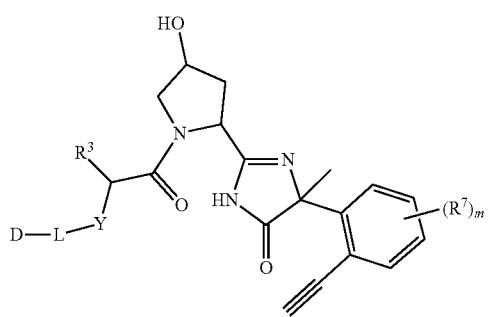 |

TABLE 4-continued

| Formula Number | Structure |
|---|---|
| II-B-14a | 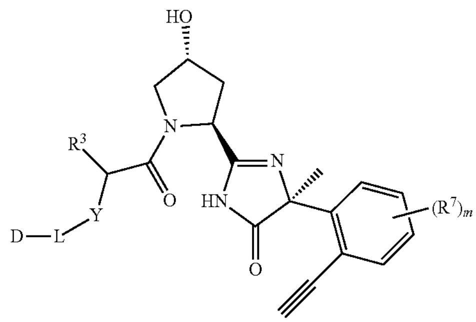 |
| II-B-15 | 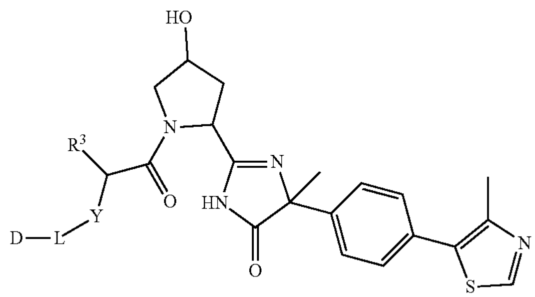 |
| II-B-15a | 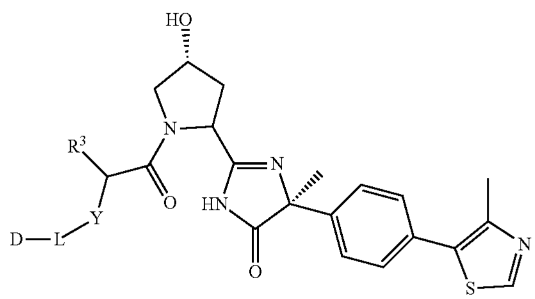 |
| II-B-15b | 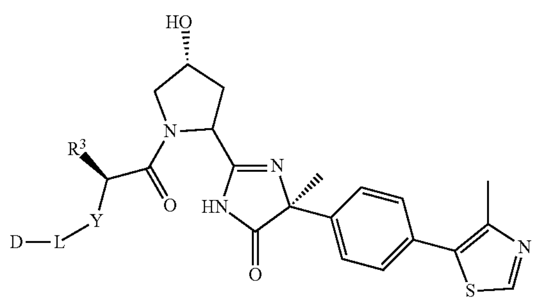 |
| II-B-15c | 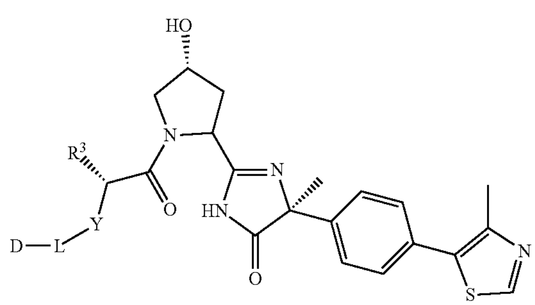 |

TABLE 4-continued
| Formula Number | Structure |
|---|---|
| II-B-15d | 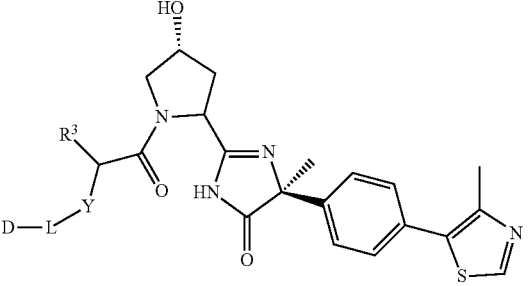 |
| II-B-16 | 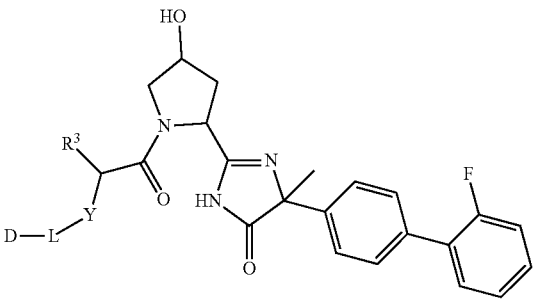 |
| II-B-16a | 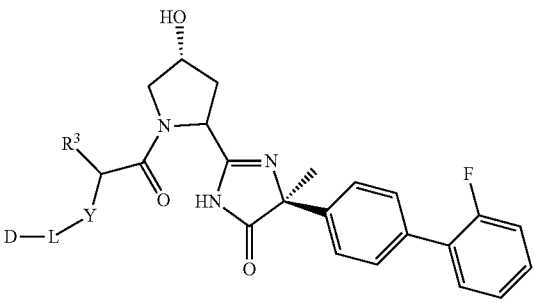 |
| II-B-17 | 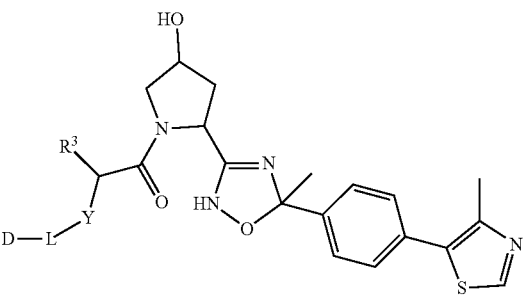 |
| II-B-17a | 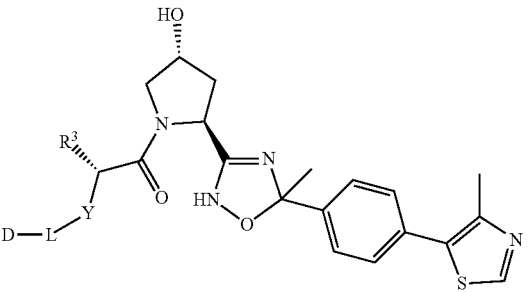 |

TABLE 4-continued

| Formula Number | Structure |
|---|---|
| II-B-17b | 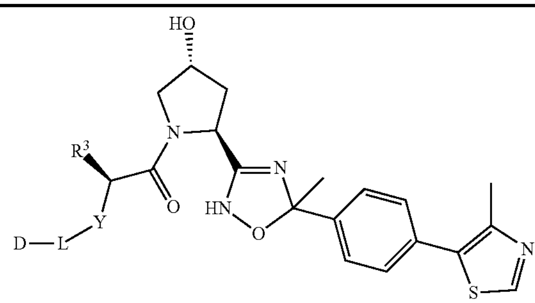 |
| II-B-18 | 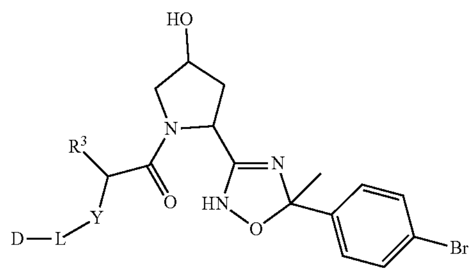 |
| II-B-18a | 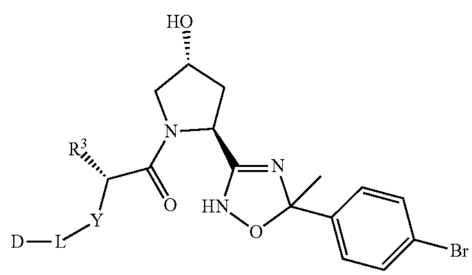 |
| II-B-18b | 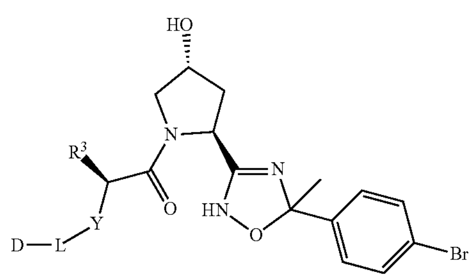 |
| II-B-19 | 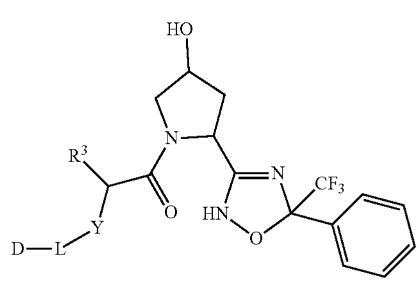 |

TABLE 4-continued
| Formula Number | Structure |
|---|---|
| II-B-19a | 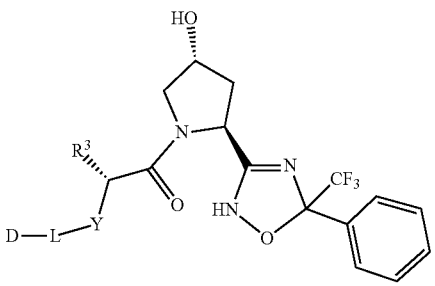 |
| II-B-19b | 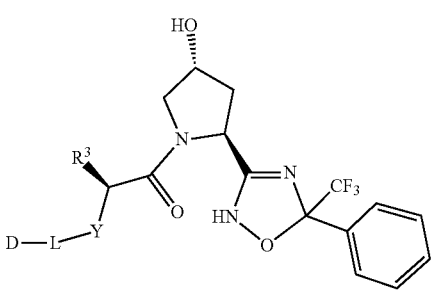 |
| II-B-20 | 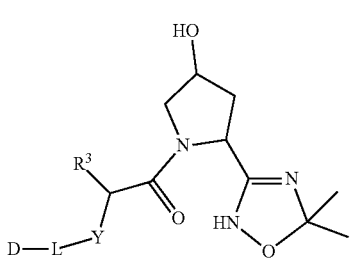 |
| II-B-20a | 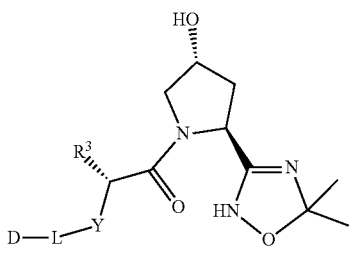 |
| II-B-20b | 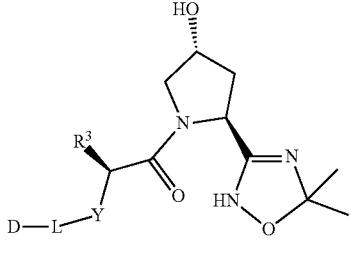 |
| II-B-21 | 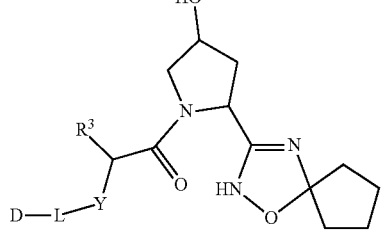 |

TABLE 4-continued
| Formula Number | Structure |
|---|---|
| II-B-21a | 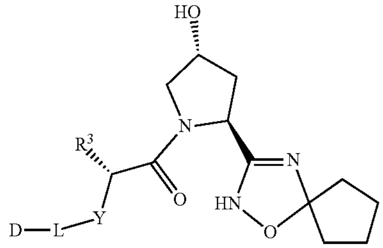 |
| II-B-21b | 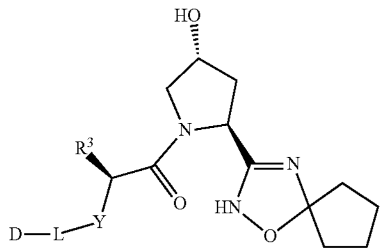 |
| II-B-22 | 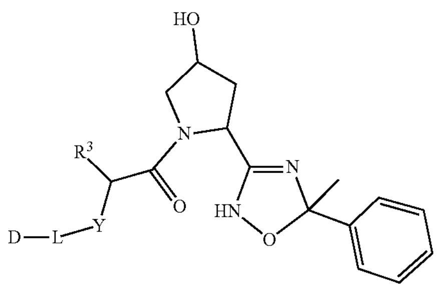 |
| II-B-22a | 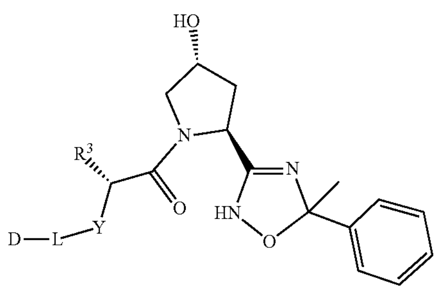 |
| II-B-22b | 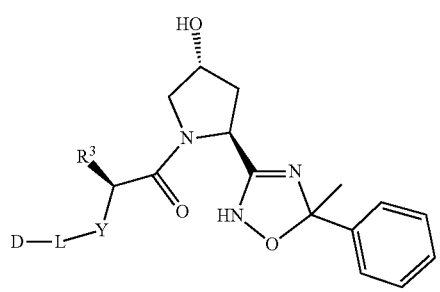 |

TABLE 4-continued
| Formula Number | Structure |
|---|---|
| II-B-23 | 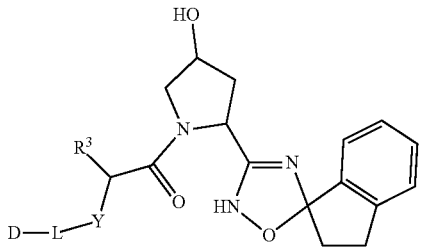 |
| II-B-23a | 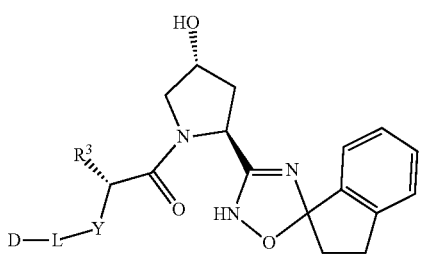 |
| II-B-23b | 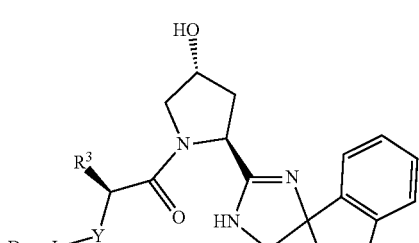 |
| II-B-24 | 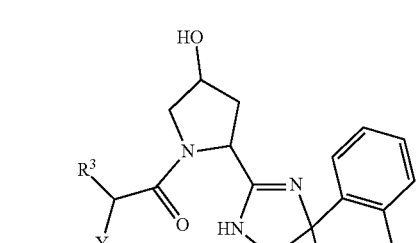 |
| II-B-24a | 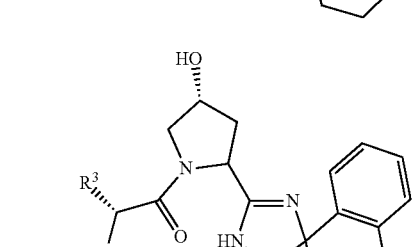 |
| II-B-24b | 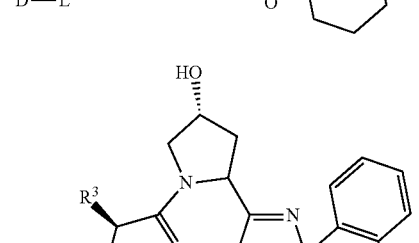 |

TABLE 4-continued

| Formula Number | Structure |
| --- | --- |
| II-B-25 | 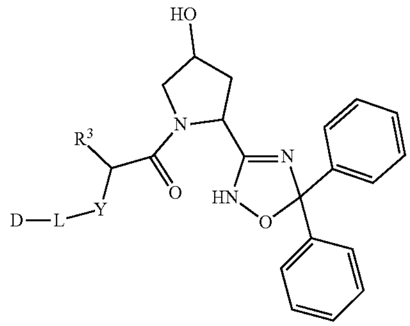 |
| II-B-25a | 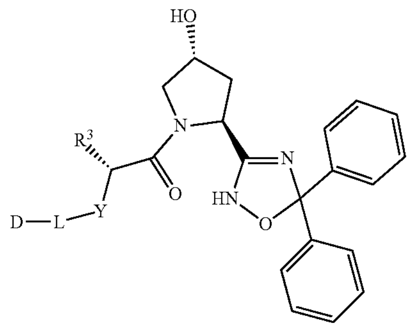 |
| II-B-25b | 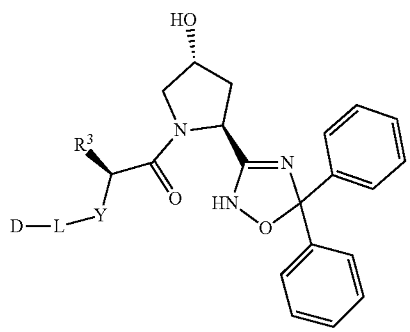 |
| II-B-26 | 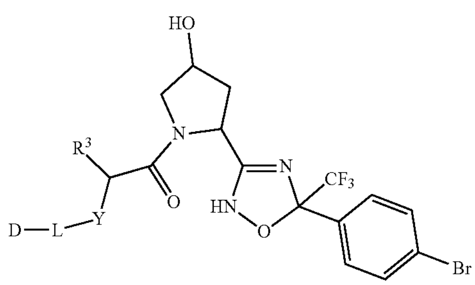 |
| II-B-26a | 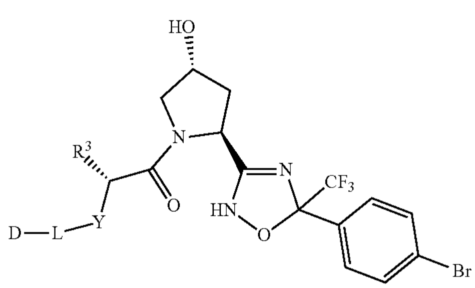 |

TABLE 4-continued
| Formula Number | Structure |
|---|---|
| II-B-26b | 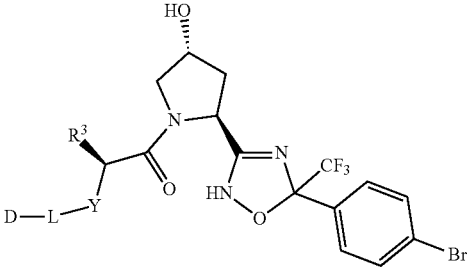 |
| II-B-27 | 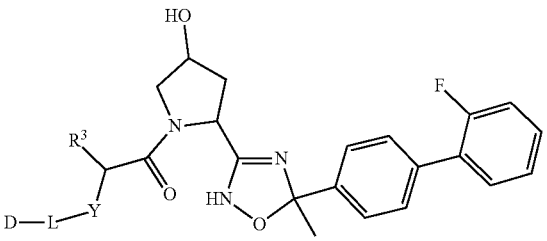 |
| II-B-27a | 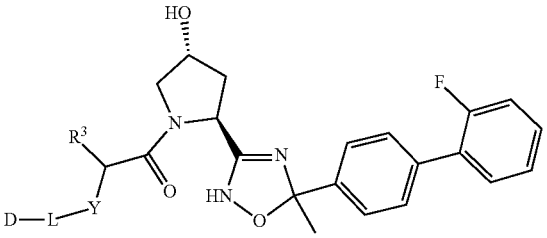 |
| II-B-28 | 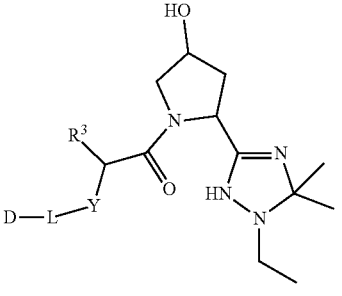 |
| II-B-28a | 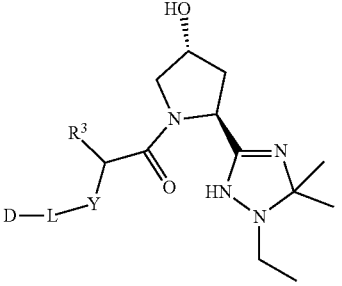 |

TABLE 4-continued
| Formula Number | Structure |
|---|---|
| II-B-29 | 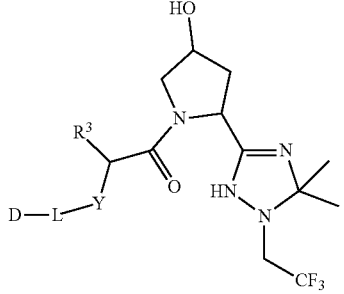 |
| II-B-29a | 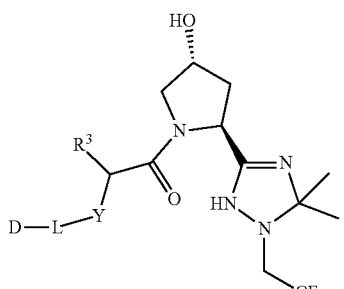 |
| II-B-30 | 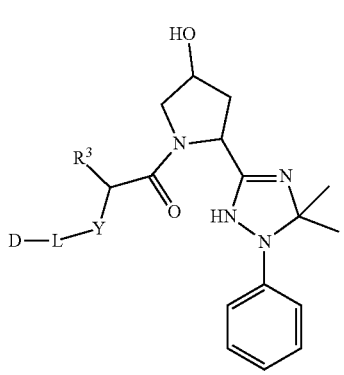 |
| II-B-30a | 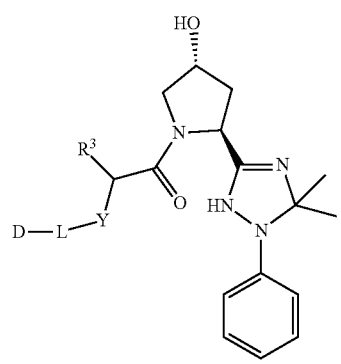 |
| II-B-31 | 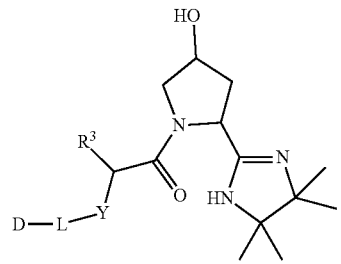 |

TABLE 4-continued
| Formula Number | Structure |
| --- | --- |
| II-B-31a | 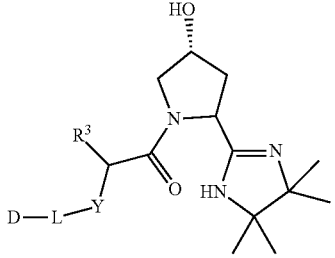 |
| II-B-32 | 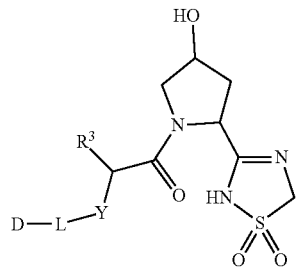 |
| II-B-32a | 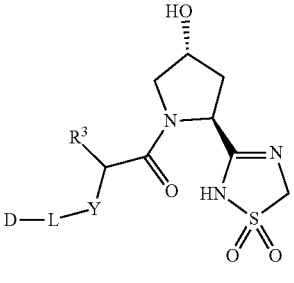 |
| II-B-33 | 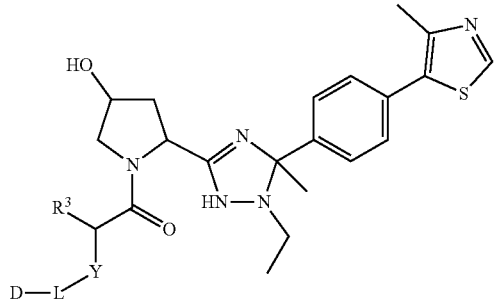 |
| II-B-33a | 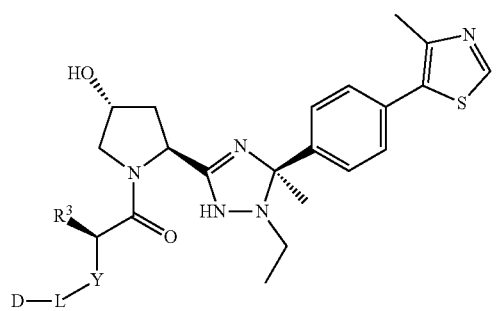 |

TABLE 4-continued
| Formula Number | Structure |
|---|---|
| II-B-33b | 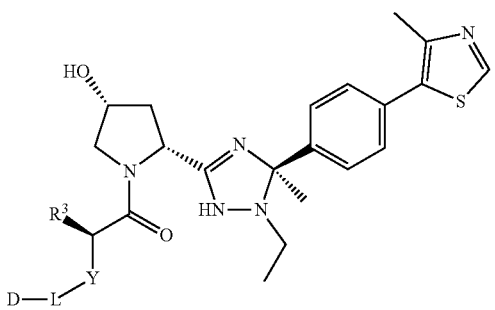 |
| II-B-34 | 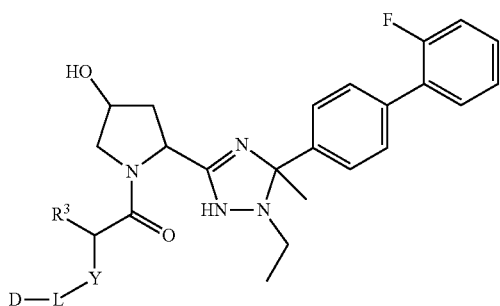 |
| II-B-34a | 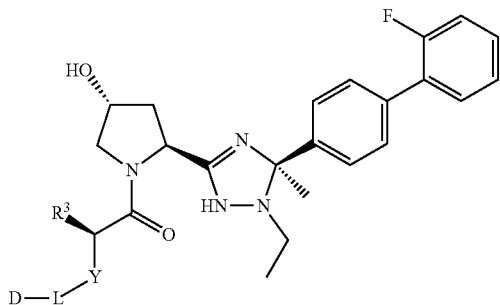 |
| II-B-34b | 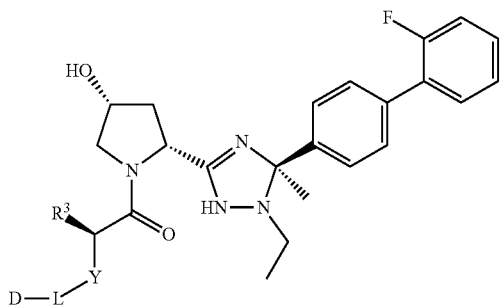 |
| II-B-35 | 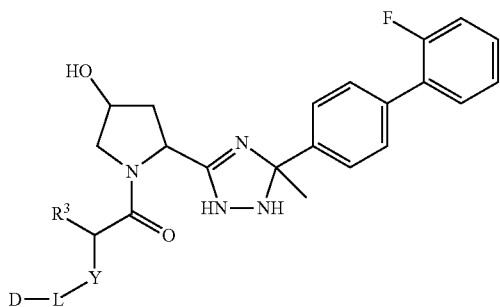 |

TABLE 4-continued

| Formula Number | Structure |
| --- | --- |
| II-B-35a | 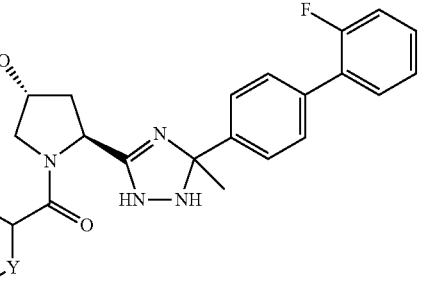 |
| II-B-35b | 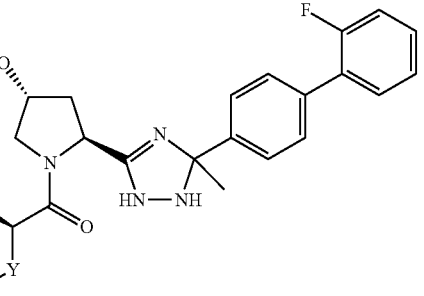 |

In one embodiment, the PROTAC is a compound of Formula II-B-9, or a salt (e.g., a pharmaceutically acceptable salt) thereof, having the structure

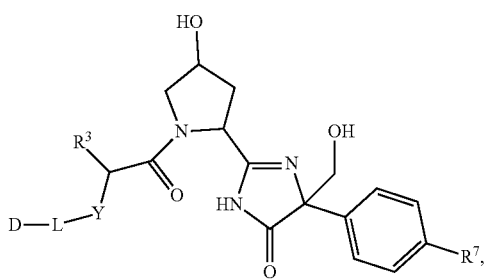

wherein $R^7$ is as defined above.

In one embodiment, the PROTAC is a compound of Formula II-B-9a or a salt (e.g., a pharmaceutically acceptable salt) thereof, having the structure

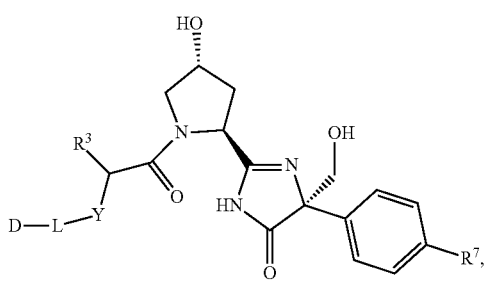

wherein $R^7$ is as defined above.

In one embodiment, the PROTAC is a compound of Formula II-B-10 or a salt (e.g., a pharmaceutically acceptable salt) thereof, having the structure

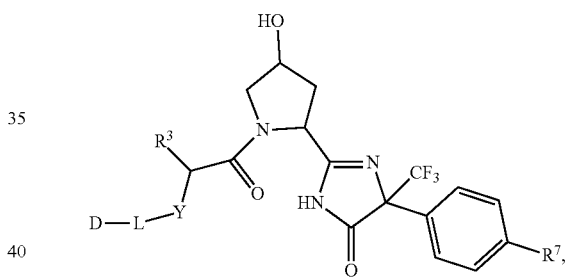

wherein $R^7$ is as defined above.

In one embodiment, the PROTAC is a compound of Formula II-B-10a or a salt (e.g., a pharmaceutically acceptable salt) thereof, having the structure

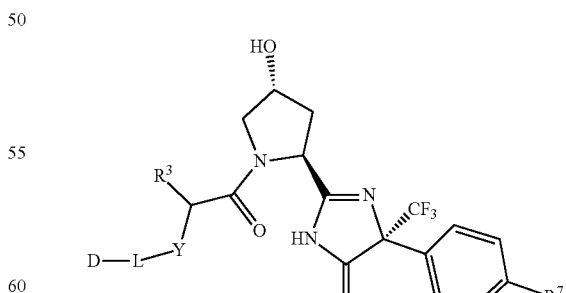

wherein $R^7$ is as defined above.

In one embodiment, the PROTAC is a compound of Formula II-B-11 or a salt (e.g., a pharmaceutically acceptable salt) thereof, having the structure

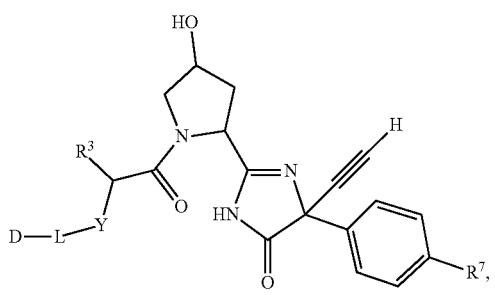

wherein R[7] is as defined above.

In one embodiment, the PROTAC is a compound of Formula II-B-11a or a salt (e.g., a pharmaceutically acceptable salt) thereof, having the structure

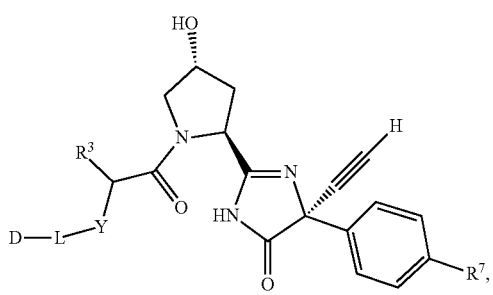

wherein R[7] is as defined above.

In one embodiment, the PROTAC is a compound of Formula II-B-12 or a salt (e.g., a pharmaceutically acceptable salt) thereof, having the structure

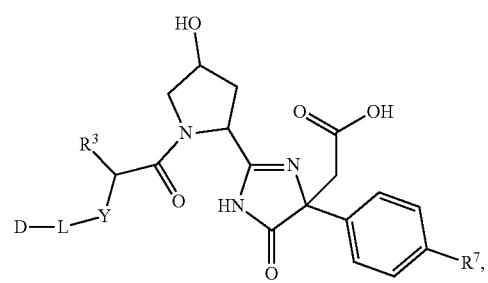

wherein R[7] is as defined above.

In one embodiment, the PROTAC is a compound of Formula II-B-12a or a salt (e.g., a pharmaceutically acceptable salt) thereof, having the structure

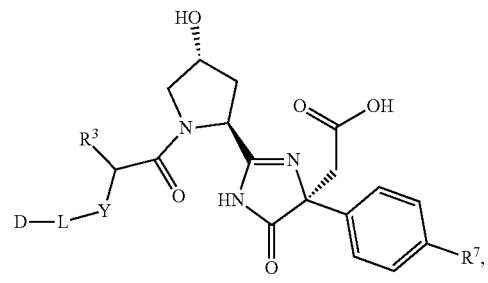

wherein R[7] is as defined above.

In one embodiment, the PROTAC is a compound of Formula II-B-13 or a salt (e.g., a pharmaceutically acceptable salt) thereof, having the structure

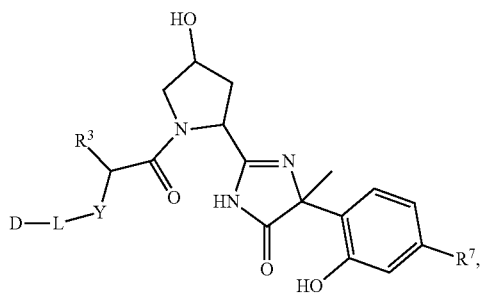

wherein R[7] is as defined above.

In one embodiment, the PROTAC is a compound of Formula II-B-13a or a salt (e.g., a pharmaceutically acceptable salt) thereof, having the structure

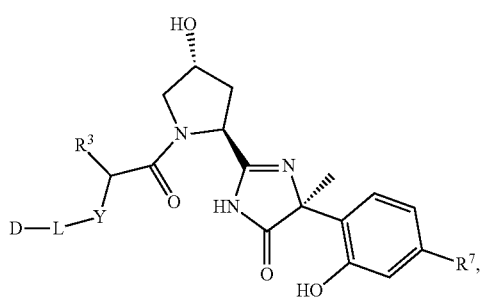

wherein R[7] is as defined above.

In one embodiment, the PROTAC is a compound of Formula II-B-14 or a salt (e.g., a pharmaceutically acceptable salt) thereof, having the structure

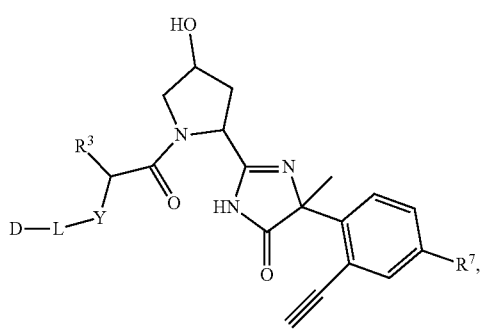

wherein R[7] is as defined above.

In one embodiment, the PROTAC is a compound of Formula II-B-14a or a salt (e.g., a pharmaceutically acceptable salt) thereof, having the structure

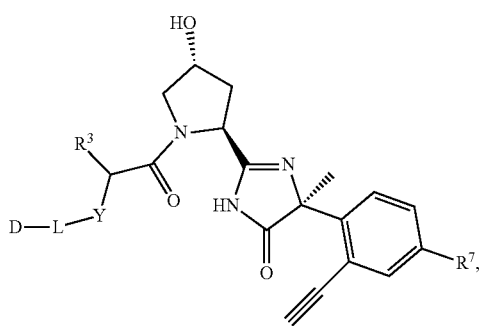

wherein R⁷ is as defined above.

In one embodiment, the PROTAC is a compound of Formula II-B-15 or a salt (e.g., a pharmaceutically acceptable salt) thereof, having the structure

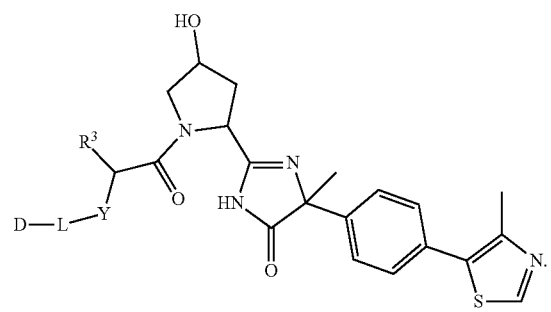

In one embodiment, the PROTAC is a compound of Formula II-B-15a or a salt (e.g., a pharmaceutically acceptable salt) thereof, having the structure In one embodiment, the PROTAC is a compound of Formula (I), or a salt (e.g., a pharmaceutically acceptable salt) thereof, and has a structure selected from the group consisting of those structures in Table 5, wherein L and D are as defined herein. Although the tautomers of the compounds as shown in Formula (I) or (Ia) are depicted in Table 5, the corresponding tautomers as shown in Formula (II) or (IIa) are intended and embraced by the current disclosure, as if each and every one of the tautomers as shown in Formula (II) or (IIa) is individually depicted.

TABLE 5

| Formula Number | Structure |
|---|---|
| I-C-1 | 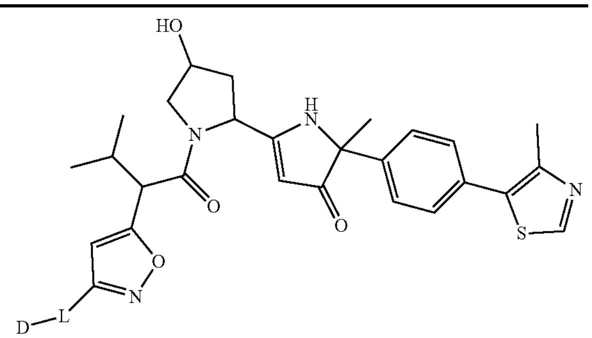 |
| I-C-1a | 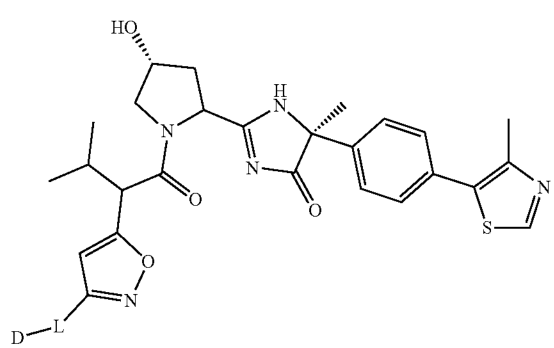 |

TABLE 5-continued
| Formula Number | Structure |
| --- | --- |
| I-C-1b | 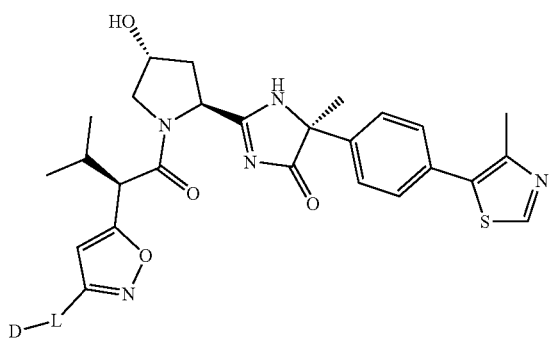 |
| I-C-1c | 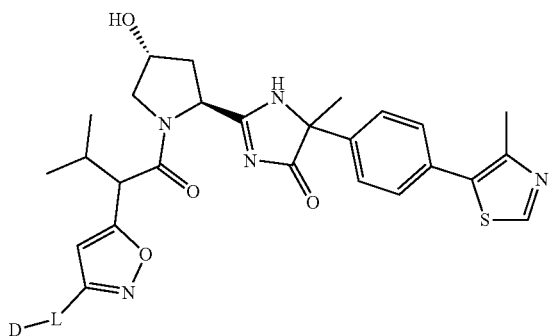 |
| I-C-2 | 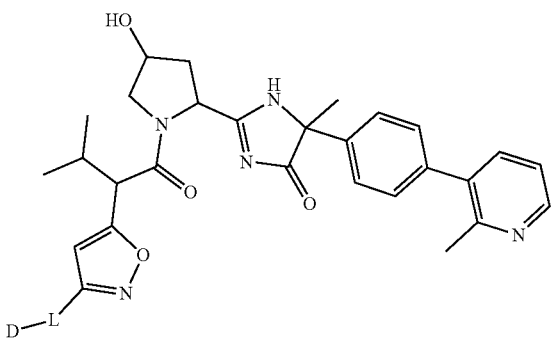 |
| I-C-2a | 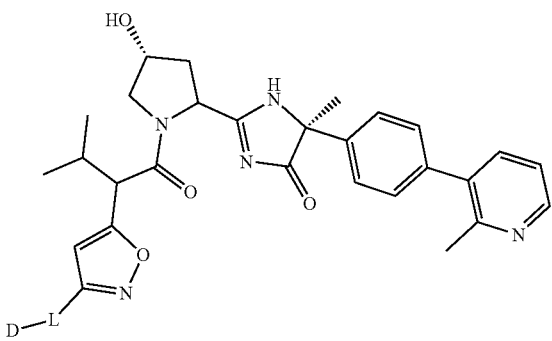 |

TABLE 5-continued
| Formula Number | Structure |
| --- | --- |
| I-C-2b | 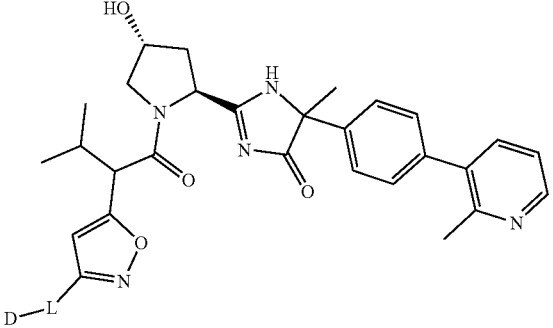 |
| I-C-3 | 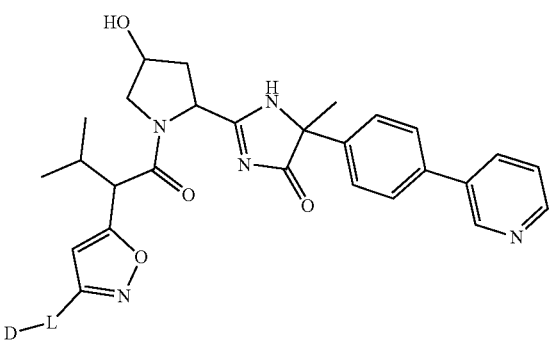 |
| I-C-3a | 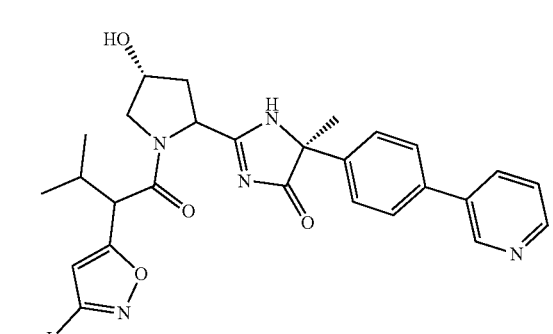 |
| I-C-3b | 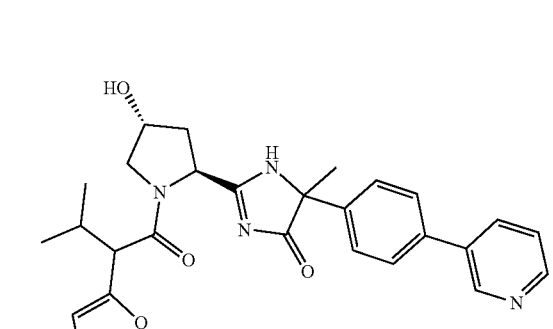 |

TABLE 5-continued
| Formula Number | Structure |
|---|---|
| I-C-4 | 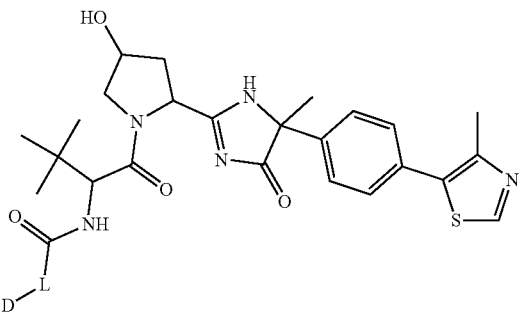 |
| I-C-4a | 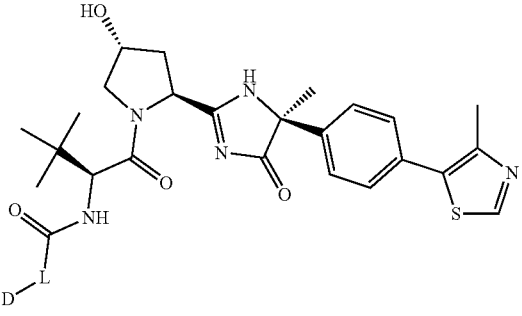 |
| I-C-4b | 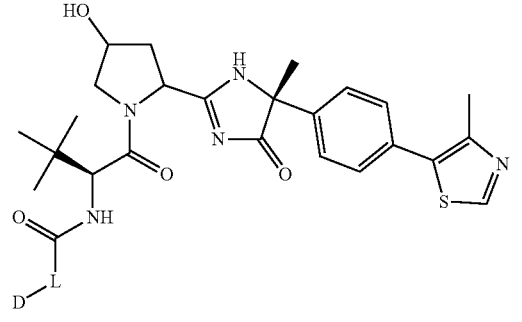 |
| I-C-4c | 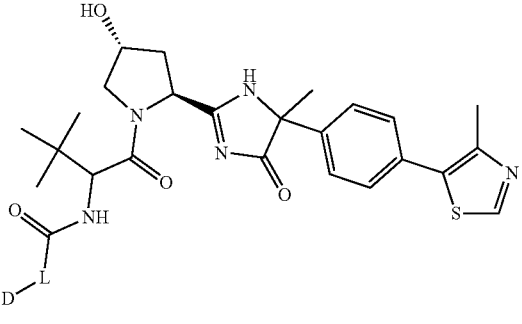 |
| I-C-4d | 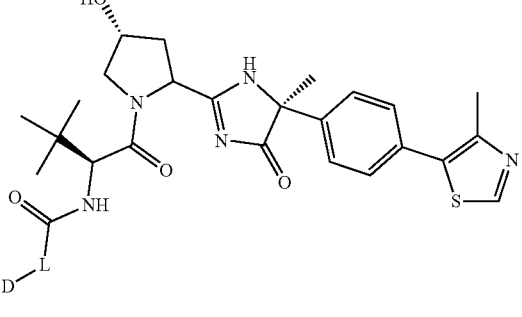 |

TABLE 5-continued
| Formula Number | Structure |
|---|---|
| I-C-5 | 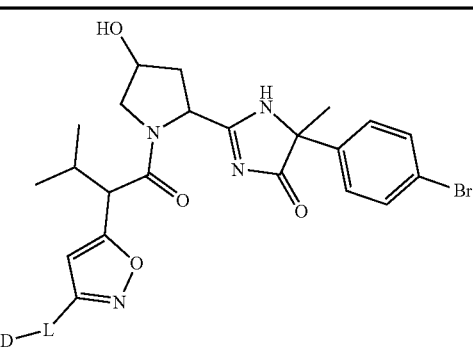 |
| I-C-5a | 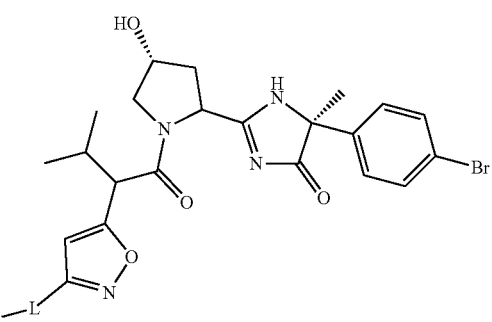 |
| I-C-5b | 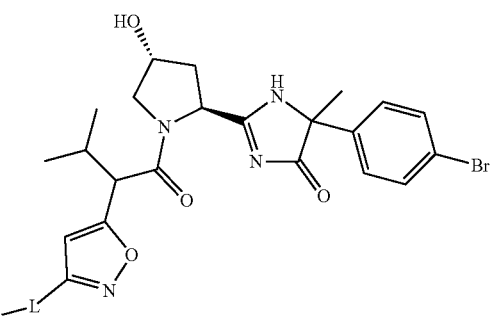 |
| I-C-6 | 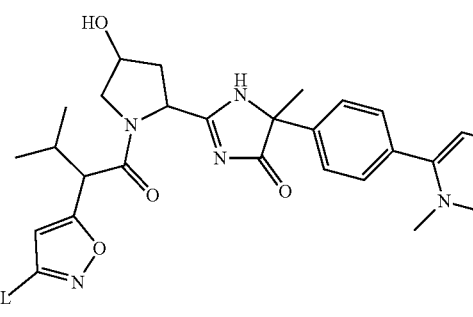 |
| I-C-6a | 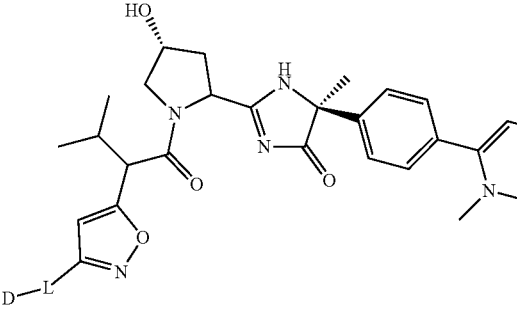 |

TABLE 5-continued
| Formula Number | Structure |
| --- | --- |
| I-C-6b | 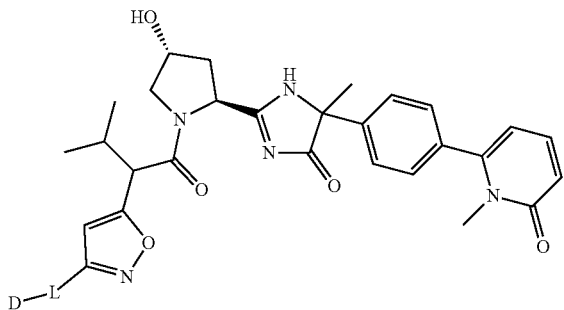 |
| I-C-7 | 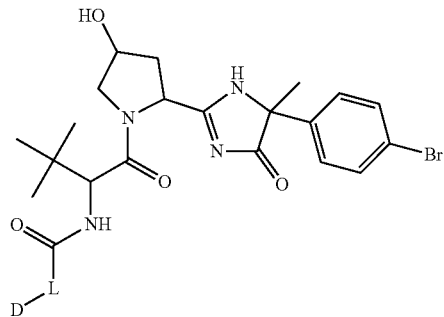 |
| I-C-7a | 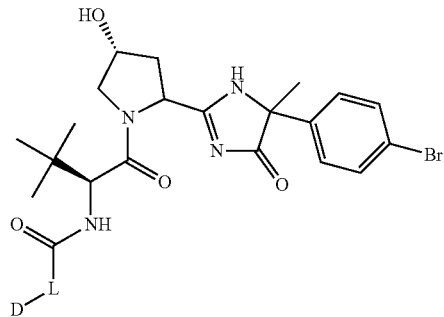 |
| I-C-7b | 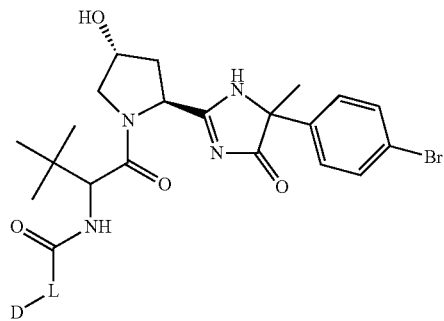 |

| Formula Number | Structure |
|---|---|
| I-C-8 | 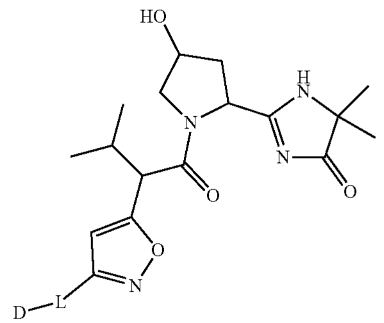 |
| I-C-8a | 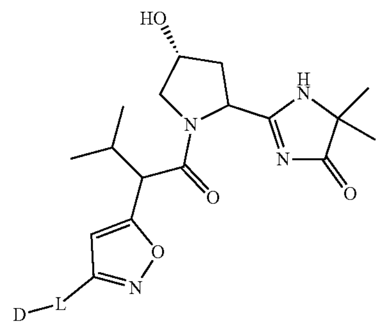 |
| I-C-8b | 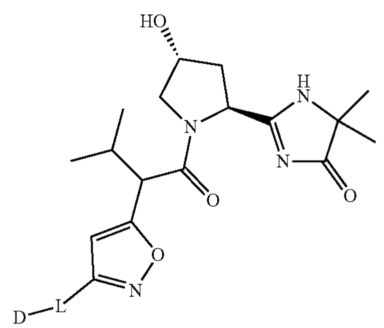 |
| I-C-9 | 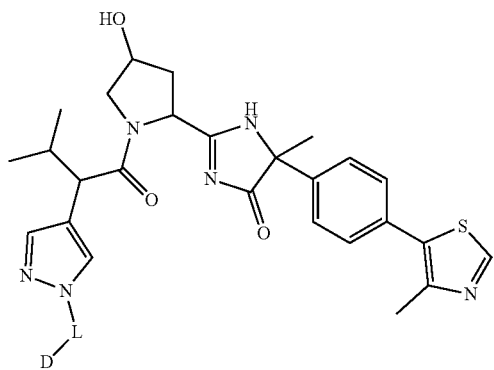 |

TABLE 5-continued
| Formula Number | Structure |
|---|---|
| I-C-9a | 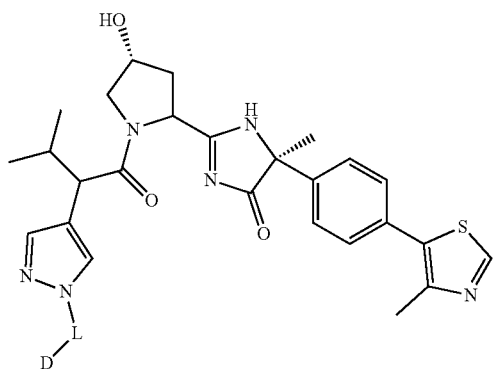 |
| I-C-10 | 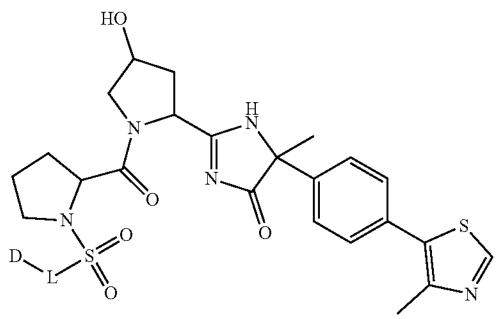 |
| I-C-10a | 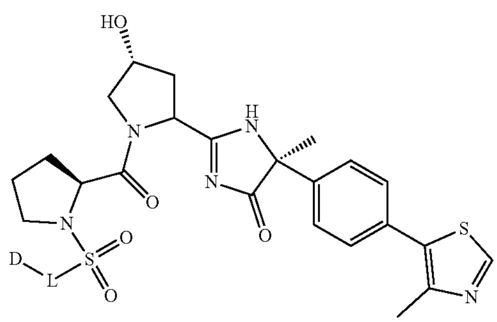 |
| I-C-10b | 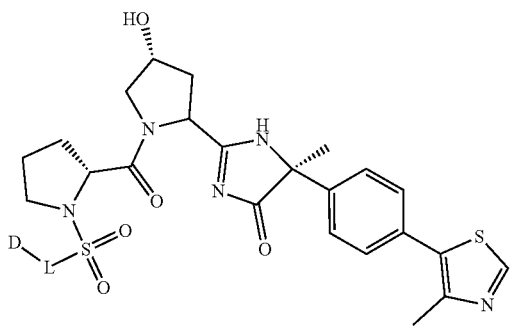 |

TABLE 5-continued
| Formula Number | Structure |
|---|---|
| I-C-11 | 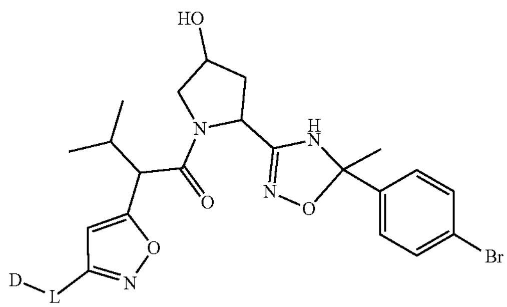 |
| I-C-11a | 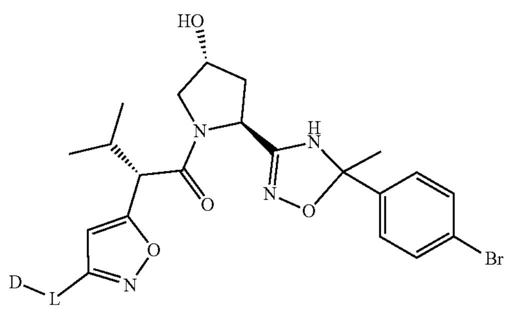 |
| I-C-11b | 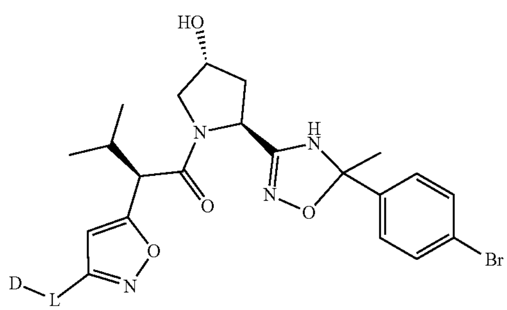 |
| I-C-12 | 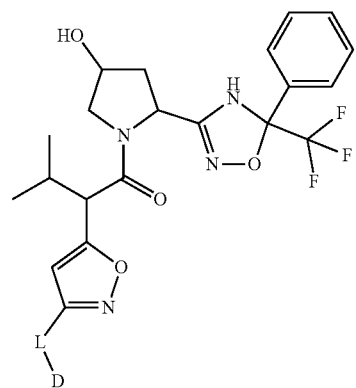 |

TABLE 5-continued
| Formula Number | Structure |
|---|---|
| I-C-12a | 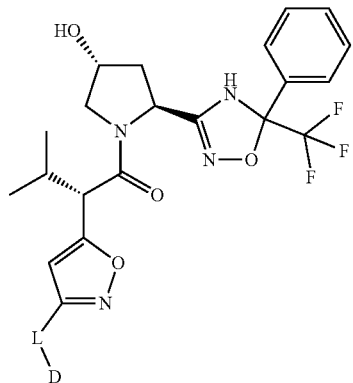 |
| I-C-12b | 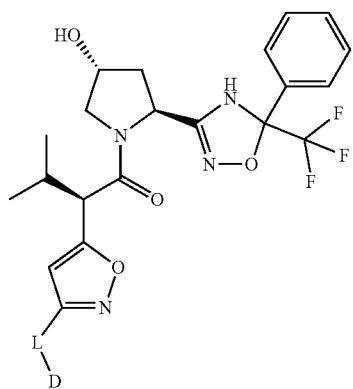 |
| I-C-13 | 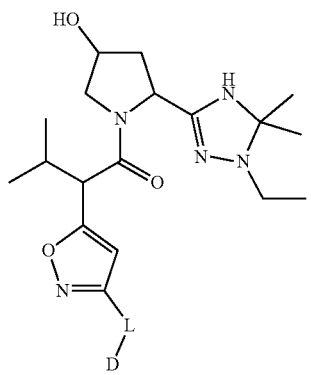 |
| I-C-13a | 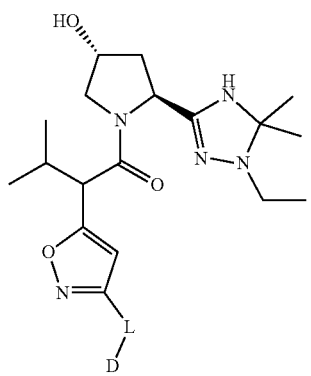 |

US 11,242,344 B2
TABLE 5-continued
| Formula Number | Structure |
|---|---|
| I-C-14 | 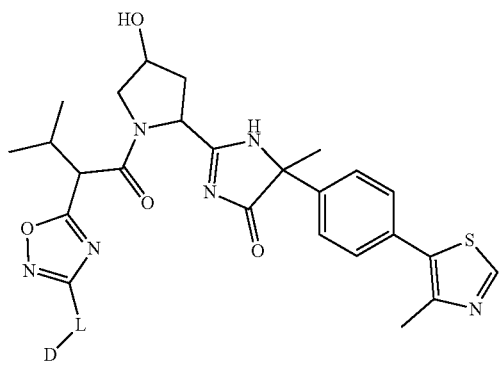 |
| I-C-14a | 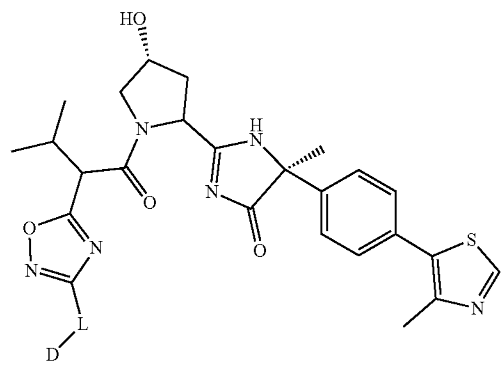 |
| I-C-15 | 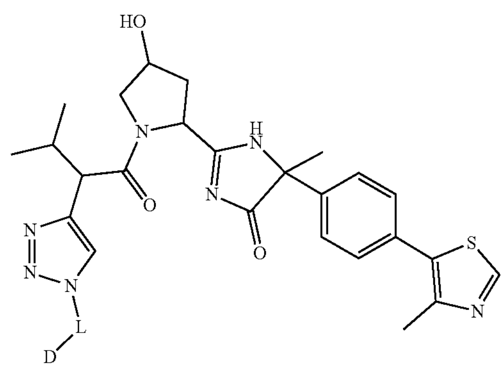 |
| I-C-15a | 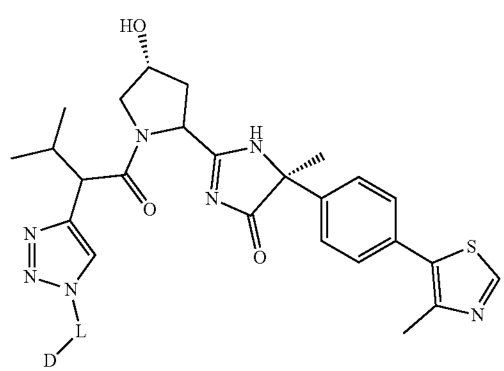 |

TABLE 5-continued
| Formula Number | Structure |
| --- | --- |
| I-C-16 | 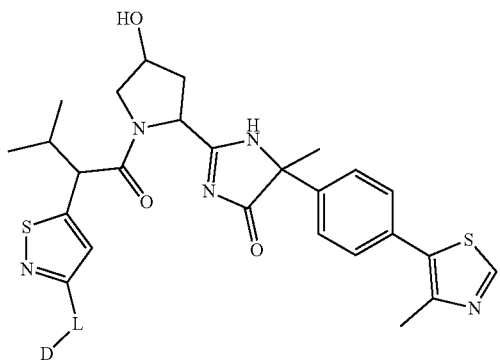 |
| I-C-16a | 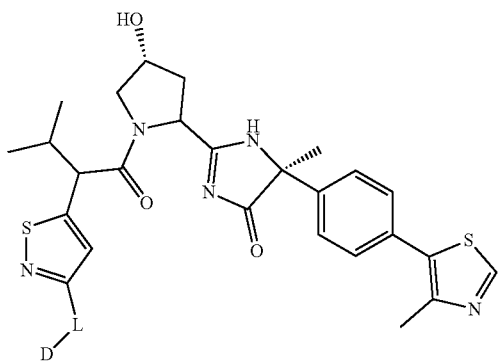 |
| I-C-17 | 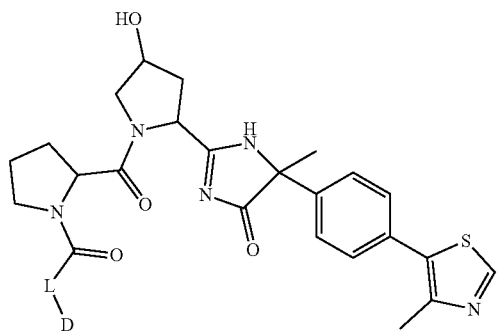 |
| I-C-17a | 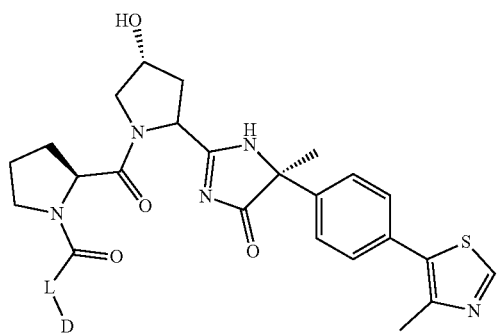 |

TABLE 5-continued

| Formula Number | Structure |
| --- | --- |
| I-C-18 | 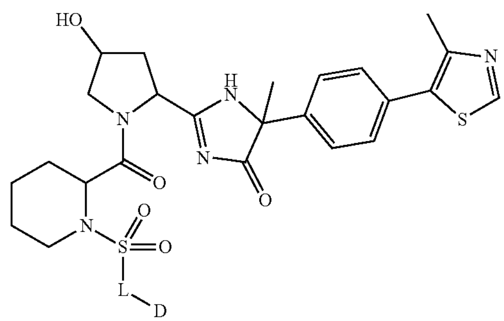 |
| I-C-18a | 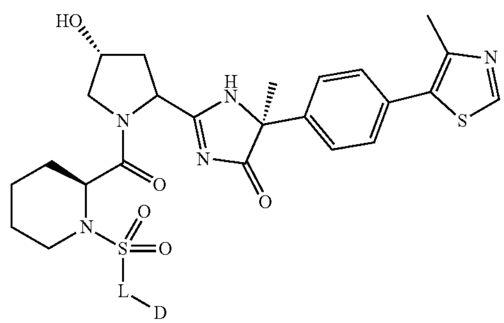 |
| I-C-19 | 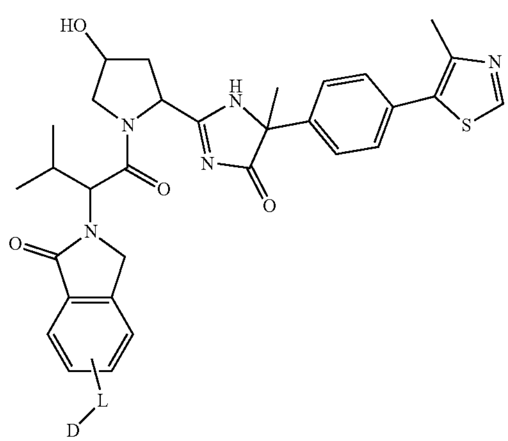 |
| I-C-19a | 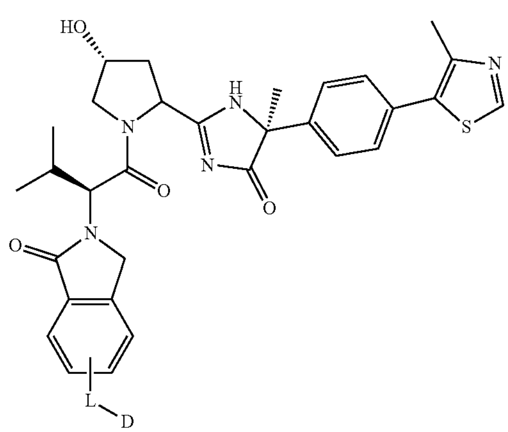 |

TABLE 5-continued

| Formula Number | Structure |
| --- | --- |
| I-C-19b | (structure) |
| I-C-19c | (structure) |
| I-C-19d | (structure) |
| I-C-20 | (structure) |

TABLE 5-continued
| Formula Number | Structure |
|---|---|
| I-C-20a | 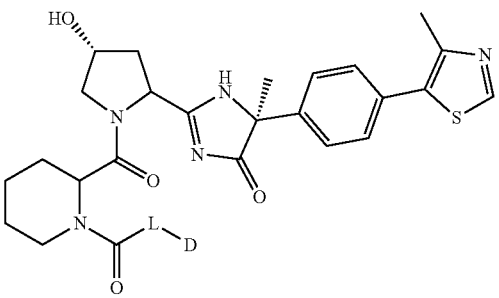 |
| I-C-21 | 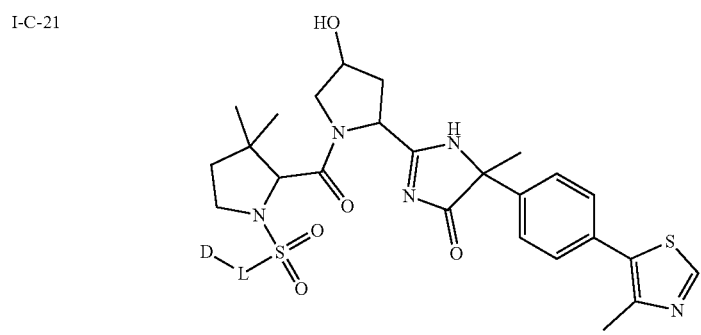 |
| I-C-21a | 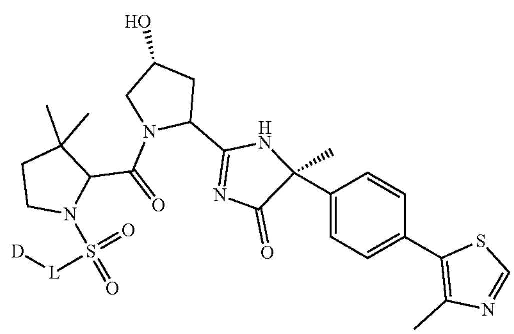 |
| I-C-22 | 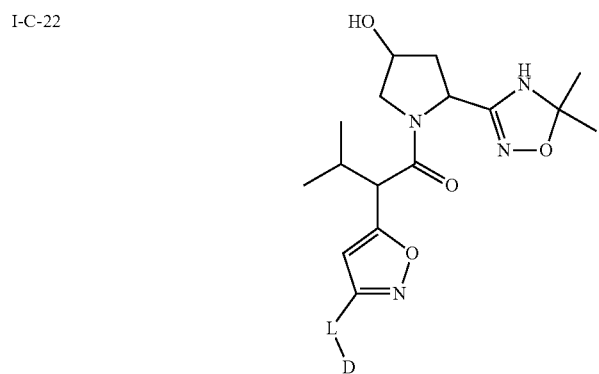 |

TABLE 5-continued

| Formula Number | Structure |
| --- | --- |
| I-C-22a | (structure) |
| I-C-22b | (structure) |
| I-C-23 | (structure) |
| I-C-23a | (structure) |

TABLE 5-continued
| Formula Number | Structure |
|---|---|
| I-C-23b | 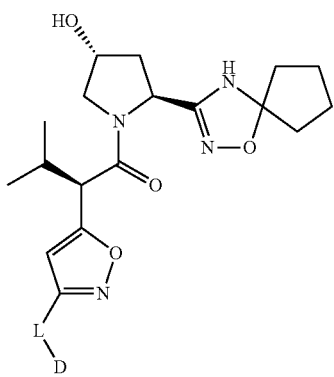 |
| I-C-24 | 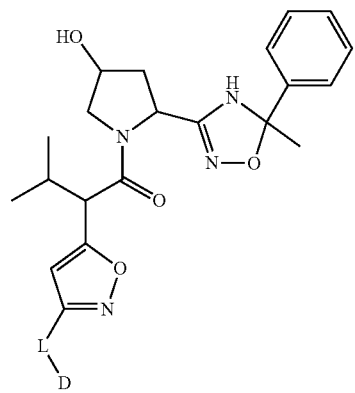 |
| I-C-24a | 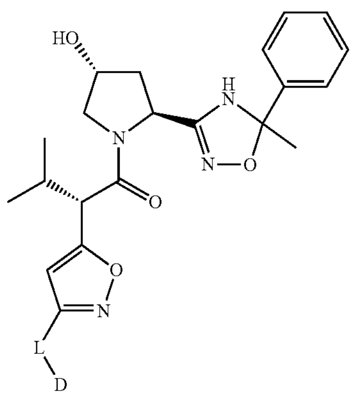 |
| I-C-24b | 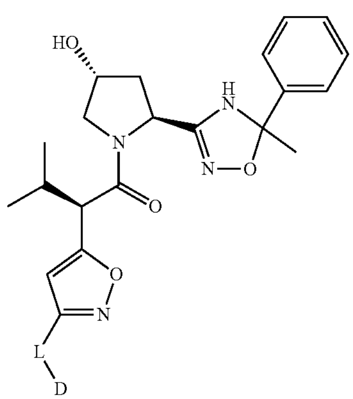 |

TABLE 5-continued
| Formula Number | Structure |
| --- | --- |
| I-C-25 | 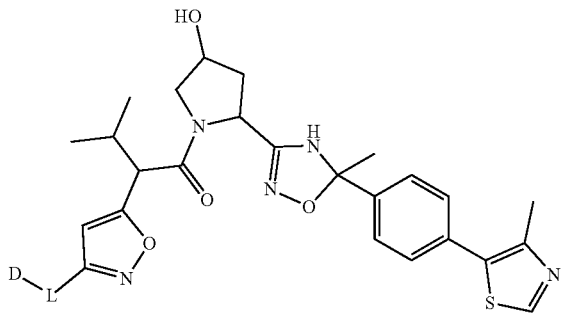 |
| I-C-25a | 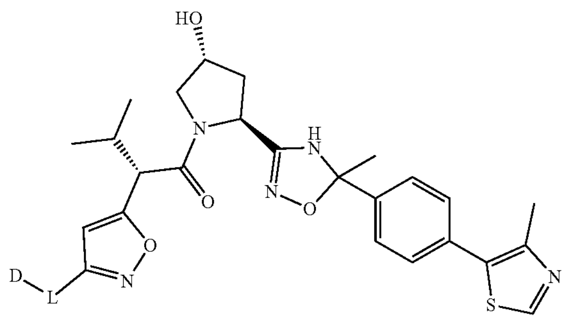 |
| I-C-25b | 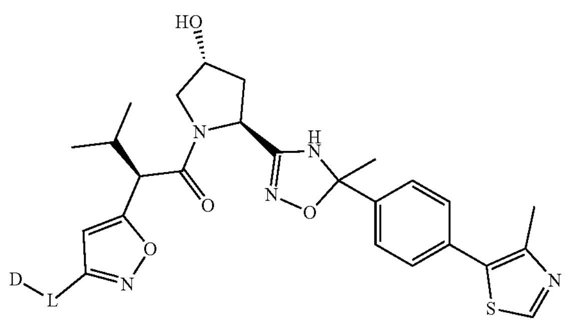 |
| I-C-26 | 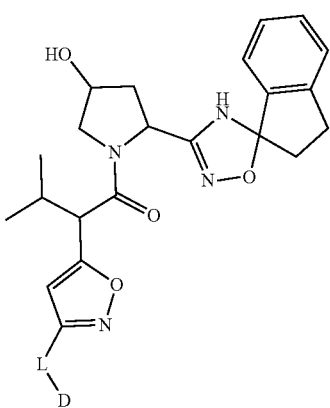 |

TABLE 5-continued

| Formula Number | Structure |
|---|---|
| I-C-26a | 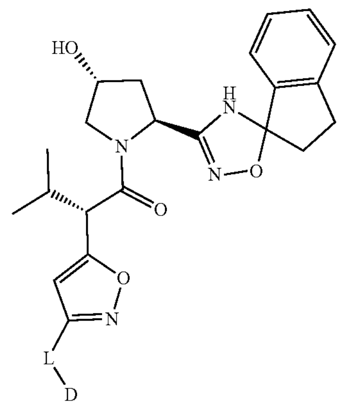 |
| I-C-26b | 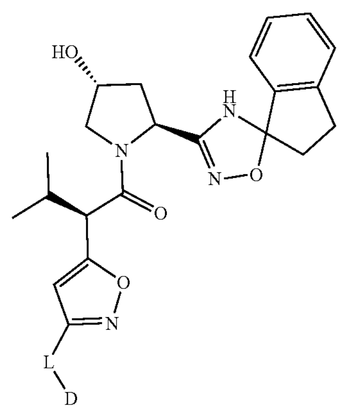 |
| I-C-27 | 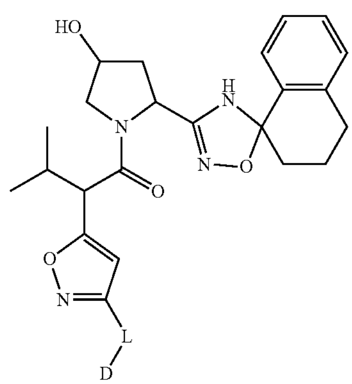 |
| I-C-27a | 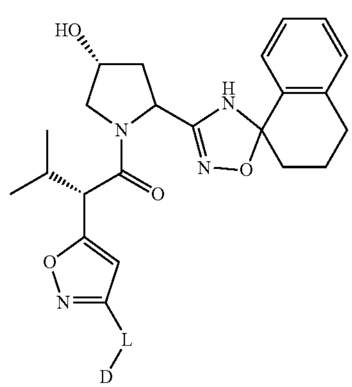 |

TABLE 5-continued
| Formula Number | Structure |
|---|---|
| I-C-27b | 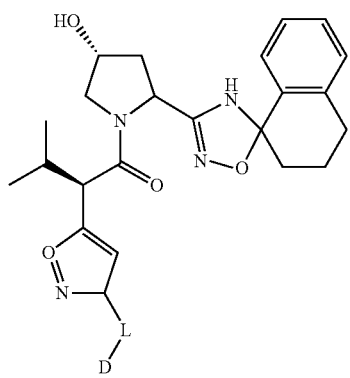 |
| I-C-28 | 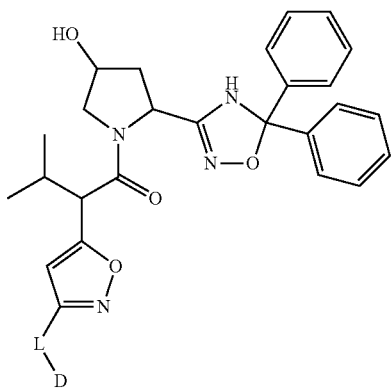 |
| I-C-28a | 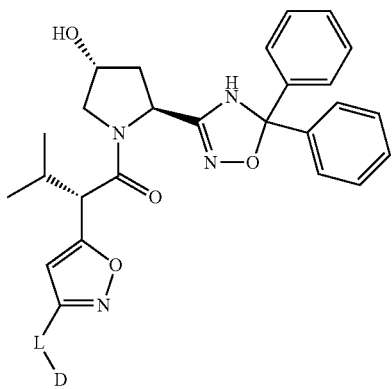 |
| I-C-28b | 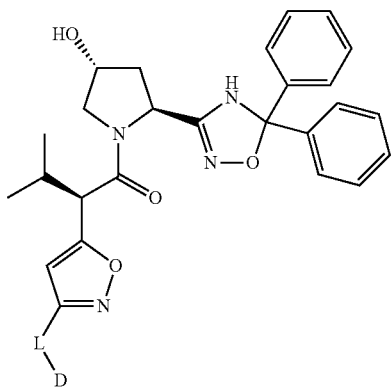 |

TABLE 5-continued
| Formula Number | Structure |
|---|---|
| I-C-29 | 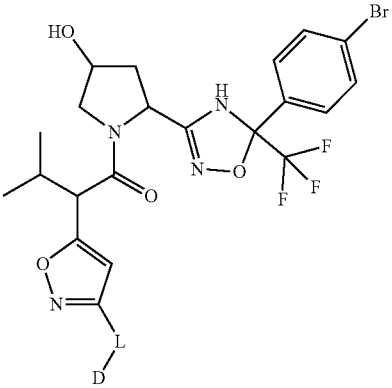 |
| I-C-29a | 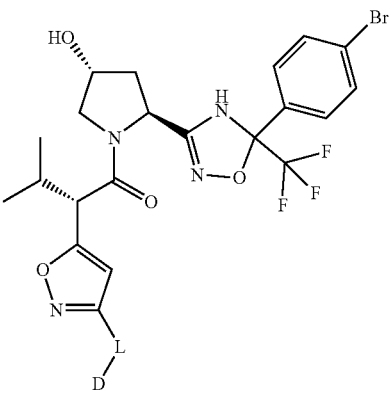 |
| I-C-29b | 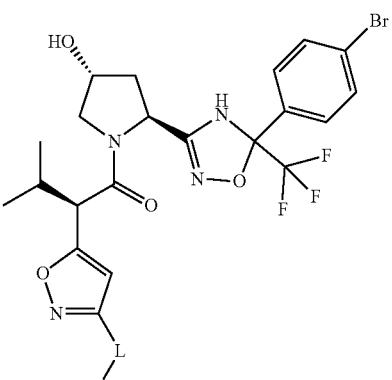 |
| I-C-30 | 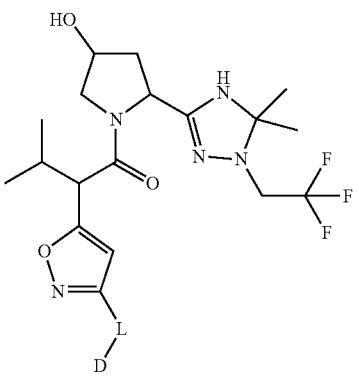 |

TABLE 5-continued

| Formula Number | Structure |
|---|---|
| I-C-30a | (structure) |
| I-C-31 | (structure) |
| I-C-31a | (structure) |
| I-C-32 | (structure) |

TABLE 5-continued
| Formula Number | Structure |
|---|---|
| I-C-32a | 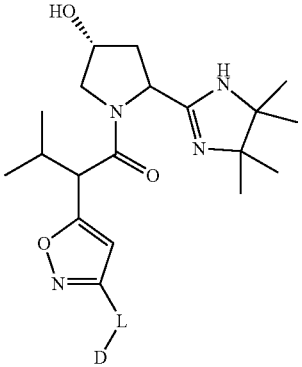 |
| I-C-33 | 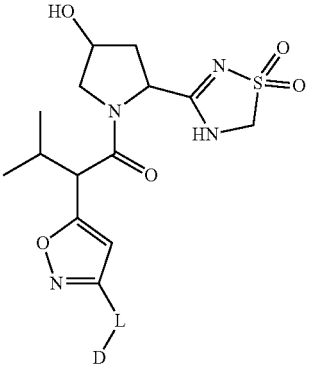 |
| I-C-33a | 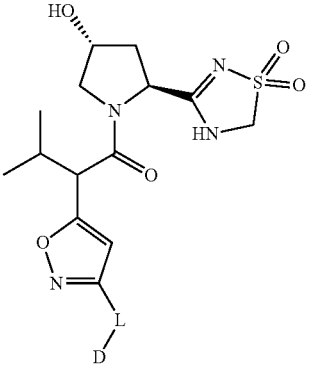 |
| I-C-34 | 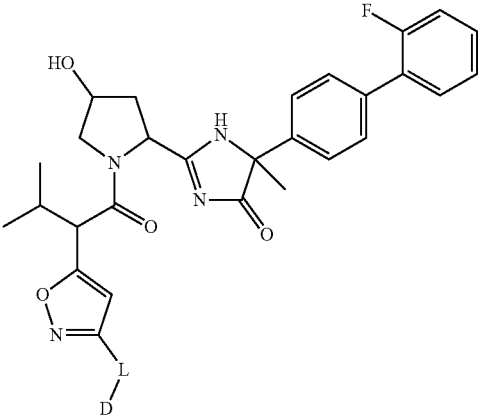 |

TABLE 5-continued
| Formula Number | Structure |
|---|---|
| I-C-34a | 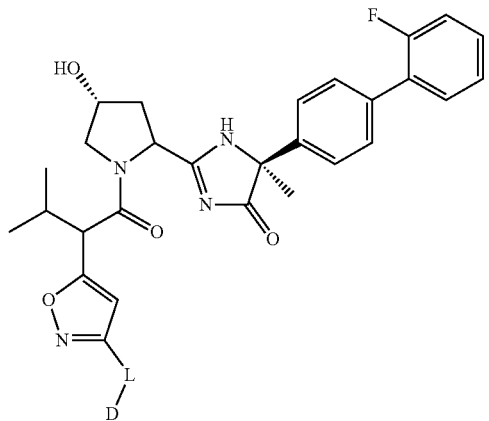 |
| I-C-35 | 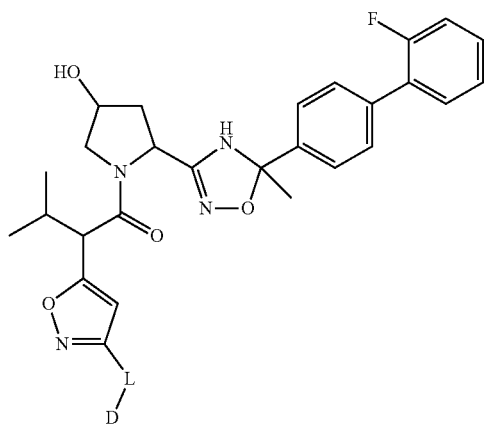 |
| I-C-35a | 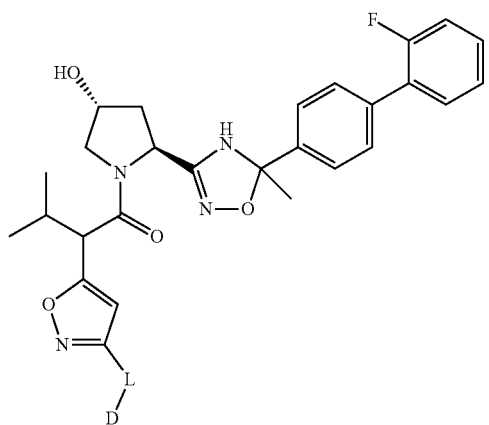 |

TABLE 5-continued
| Formula Number | Structure |
|---|---|
| I-C-36 | 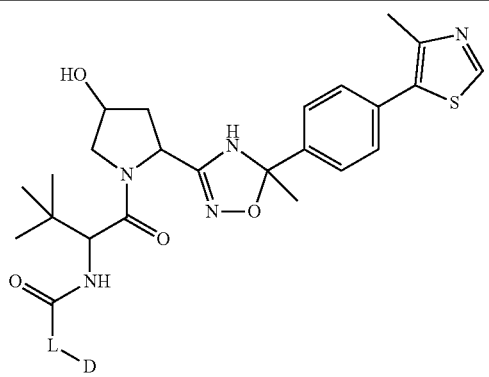 |
| I-C-36a | 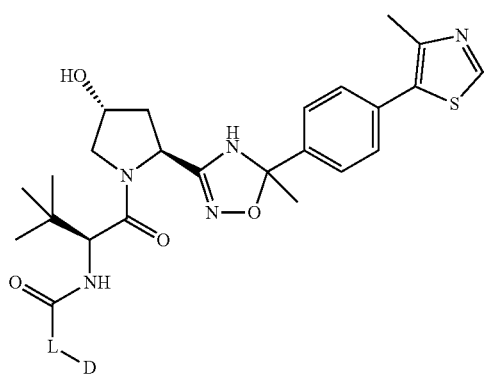 |
| I-C-37 | 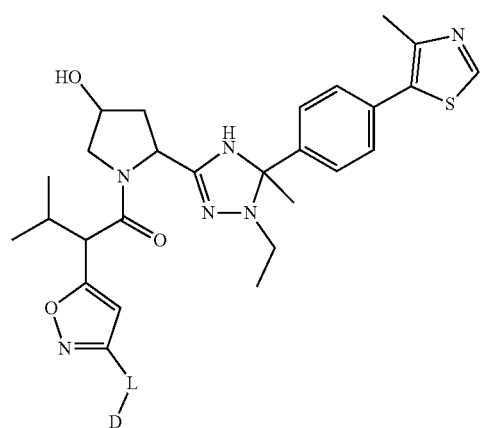 |
| I-C-37a | 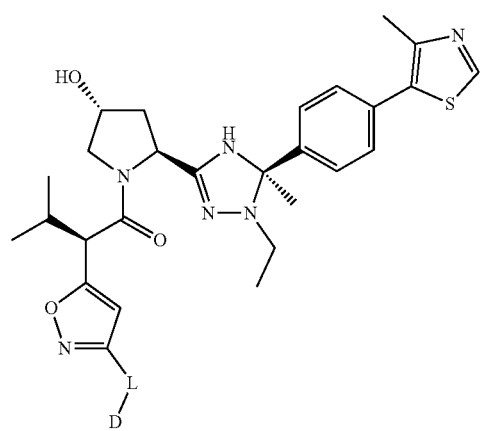 |

TABLE 5-continued
| Formula Number | Structure |
|---|---|
| I-C-37b | 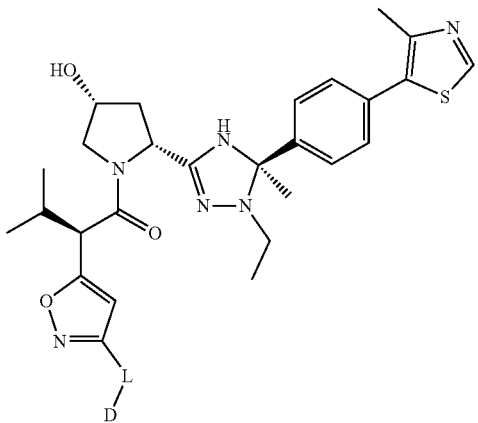 |
| I-C-38 | 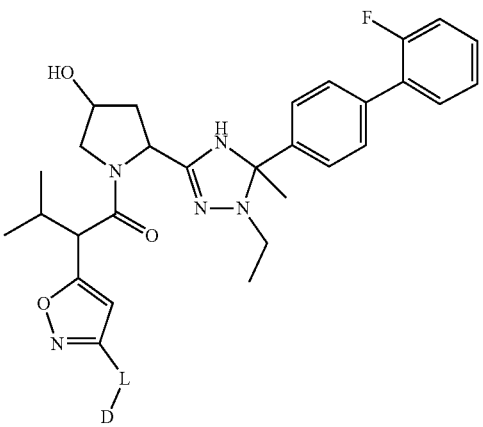 |
| I-C-38a | 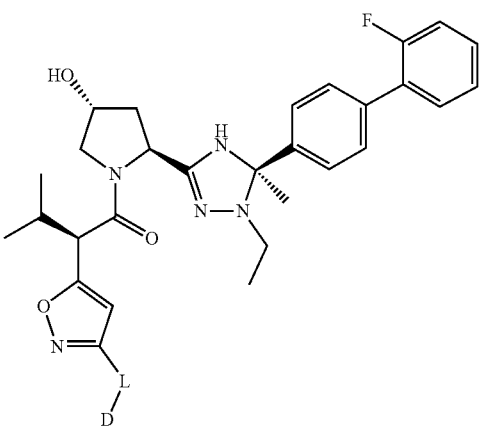 |

181 182
TABLE 5-continued
| Formula Number | Structure |
|---|---|
| I-C-38b | 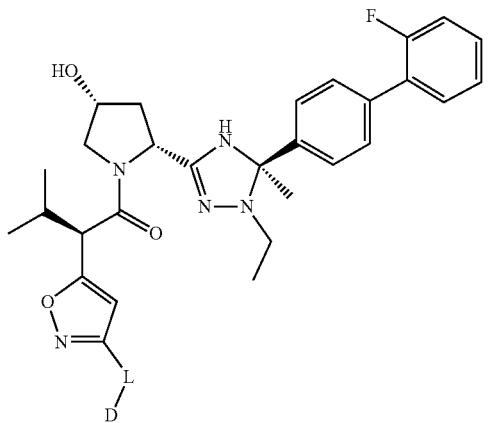 |
| I-C-39 | 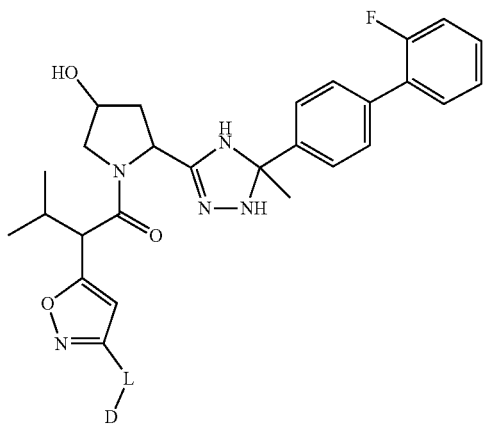 |
| I-C-39a | 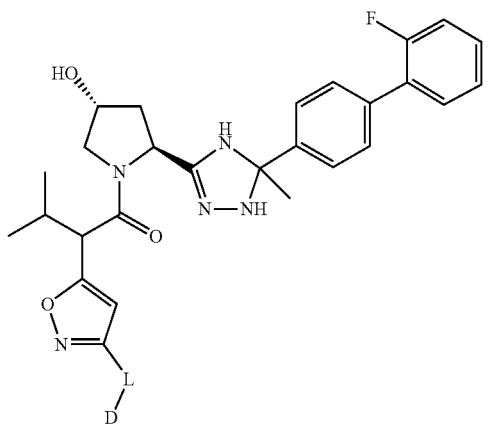 |

TABLE 5-continued

| Formula Number | Structure |
|---|---|
| I-C-39b | 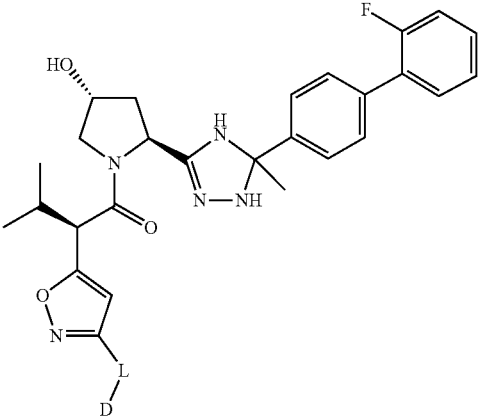 |

In one embodiment, the PROTAC is a compound of Formula (I) or (Ia), or a salt (e.g., a pharmaceutically acceptable salt) thereof, and is selected from the group consisting of those compounds in Table 6. Although the tautomers of the compounds as shown in Formula (I) or (Ia) are depicted in Table 6, the corresponding tautomers as shown in Formula (II) or (IIa) are intended and embraced by the current disclosure, as if each and every one of the tautomers as shown in Formula (II) or (IIa) is individually depicted.

TABLE 6

| Compound No. | Structure/Name [1] |
|---|---|
| 1001 | 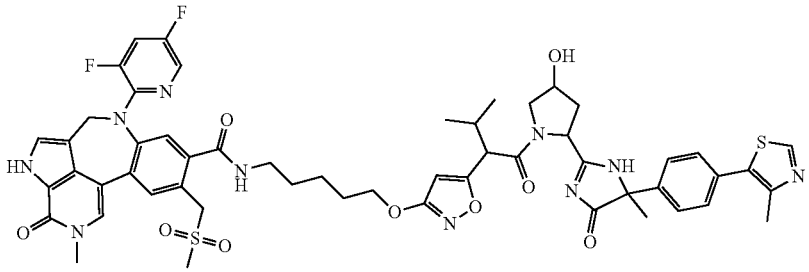 [SMILES: Cc1ncsc1-c1ccc(C2(C)NC(C3CC(O)CN3C(=O)C(c3cc(OCCCCCNC(=O)c4cc5c(cc4CS(C)(=O)=O)-c4cn(C)c(=O)c6[nH]cc(c46)CN5c4ncc(F)cc4F)no3)C(C)C)=NC2=O)cc1]<br>7-(3,5-difluoropyridin-2-yl)-N-(5-((5-(1-(4-hydroxy-2-(5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide |
| 1001a | 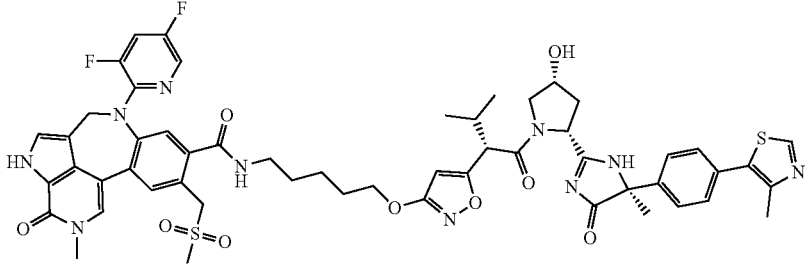 [SMILES: Cc1ncsc1-c1ccc([C@]2(C)NC([C@H]3C[C@@H](O)CN3C(=O)[C@H](c3cc(OCCCCCNC(=O)c4cc5c(cc4CS(C)(=O)=O)-c4cn(C)c(=O)c6[nH]cc(c46)CN5c4ncc(F)cc4F)no3)C(C)C)=NC2=O)cc1]<br>7-(3,5-difluoropyridin-2-yl)-N-(5-((5-((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide |

… 185                                                                          186

TABLE 6-continued

| Compound No. | Structure/Name [1] |
|---|---|
| 1001b | 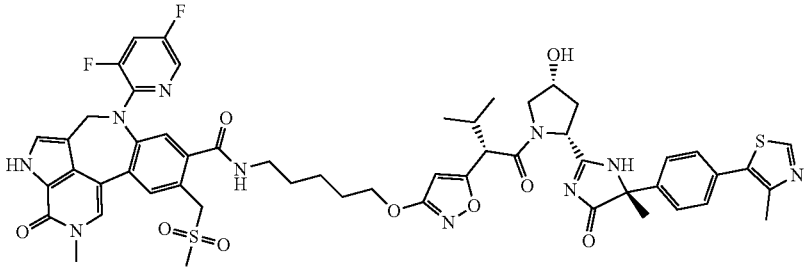 [SMILES: Cc1ncsc1-c1ccc([C@@]2(C)NC([C@H]3C[C@@H](O)CN3C(=O)[C@H](c3cc(OCCCCCNC(=O)c4cc5c(cc4CS(C)(=O)=O)-c4cn(C)c(=O)c6[nH]cc(c46)CN5c4ncc(F)cc4F)no3)C(C)C)=NC2=O)cc1]<br>7-(3,5-difluoropyridin-2-yl)-N-(5-((5-((S)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide |
| 1001c | 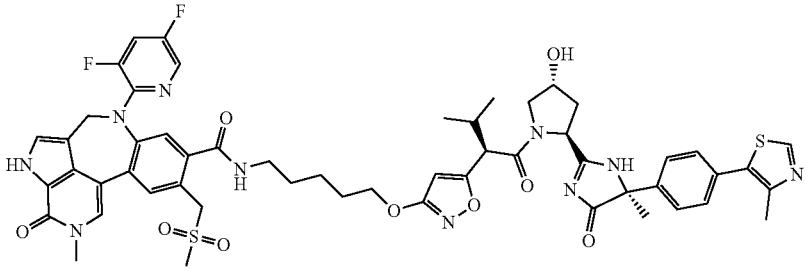 [SMILES: Cc1ncsc1-c1ccc([C@]2(C)NC([C@@H]3C[C@@H](O)CN3C(=O)[C@@H](c3cc(OCCCCCNC(=O)c4cc5c(cc4CS(C)(=O)=O)-c4cn(C)c(=O)c6[nH]cc(c46)CN5c4ncc(F)cc4F)no3)C(C)C)=NC2=O)cc1]<br>7-(3,5-difluoropyridin-2-yl)-N-(5-((5-((R)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide |
| 1001d | 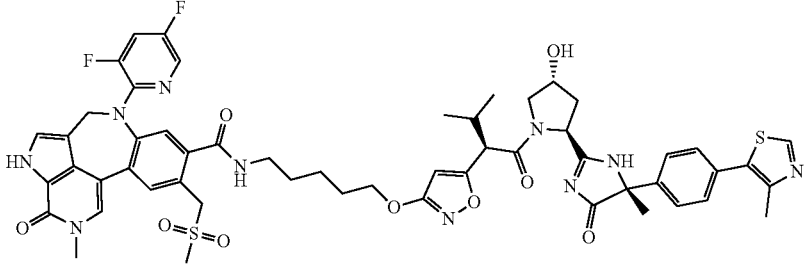 [SMILES: Cc1ncsc1-c1ccc([C@@]2(C)NC([C@@H]3C[C@@H](O)CN3C(=O)[C@@H](c3cc(OCCCCCNC(=O)c4cc5c(cc4CS(C)(=O)=O)-c4cn(C)c(=O)c6[nH]cc(c46)CN5c4ncc(F)cc4F)no3)C(C)C)=NC2=O)cc1]<br>7-(3,5-difluoropyridin-2-yl)-N-(5-((5-((R)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide |
| 1001e | 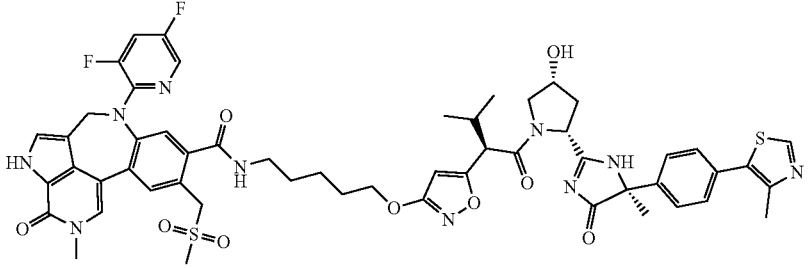 [SMILES: Cc1ncsc1-c1ccc([C@]2(C)NC([C@H]3C[C@@H](O)CN3C(=O)[C@@H](c3cc(OCCCCCNC(=O)c4cc5c(cc4CS(C)(=O)=O)-c4cn(C)c(=O)c6[nH]cc(c46)CN5c4ncc(F)cc4F)no3)C(C)C)=NC2=O)cc1]<br>7-(3,5-difluoropyridin-2-yl)-N-(5-((5-((R)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide |

TABLE 6-continued

| Compound No. | Structure/Name [1] |
|---|---|
| 1001f | 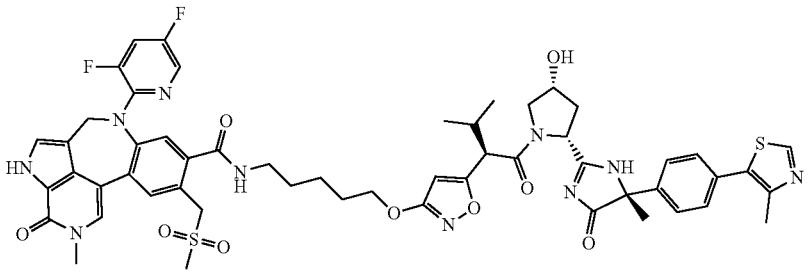 [SMILES: Cc1ncsc1-c1ccc([C@@]2(C)NC([C@H]3C[C@@H](O)CN3C(=O)[C@@H](c3cc(OCCCCCNC(=O)c4cc5c(cc4CS(C)(=O)=O)-c4cn(C)c(=O)c6[nH]cc(c46)CN5c4ncc(F)cc4F)no3)C(C)C)=NC2=O)cc1]<br>7-(3,5-difluoropyridin-2-yl)-N-(5-((5-((R)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide |
| 1001g | 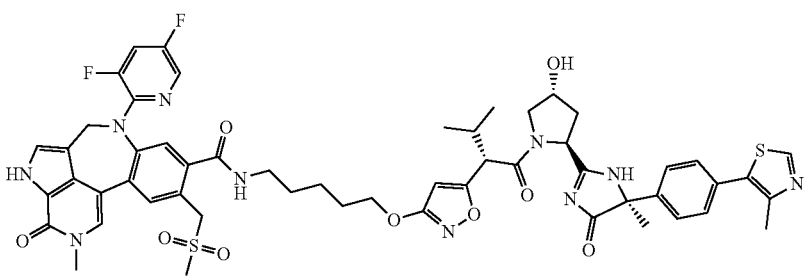 [SMILES: Cc1ncsc1-c1ccc([C@]2(C)NC([C@@H]3C[C@@H](O)CN3C(=O)[C@H](c3cc(OCCCCCNC(=O)c4cc5c(cc4CS(C)(=O)=O)-c4cn(C)c(=O)c6[nH]cc(c46)CN5c4ncc(F)cc4F)no3)C(C)C)=NC2=O)cc1]<br>7-(3,5-difluoropyridin-2-yl)-N-(5-((5-((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide |
| 1001h | 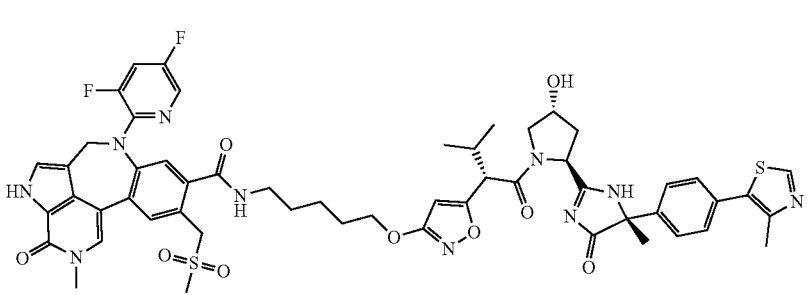 [SMILES: Cc1ncsc1-c1ccc([C@@]2(C)NC([C@@H]3C[C@@H](O)CN3C(=O)[C@H](c3cc(OCCCCCNC(=O)c4cc5c(cc4CS(C)(=O)=O)-c4cn(C)c(=O)c6[nH]cc(c46)CN5c4ncc(F)cc4F)no3)C(C)C)=NC2=O)cc1]<br>7-(3,5-difluoropyridin-2-yl)-N-(5-((5-((S)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide |

TABLE 6-continued

| Compound No. | Structure/Name [1] |
|---|---|
| 1002 | 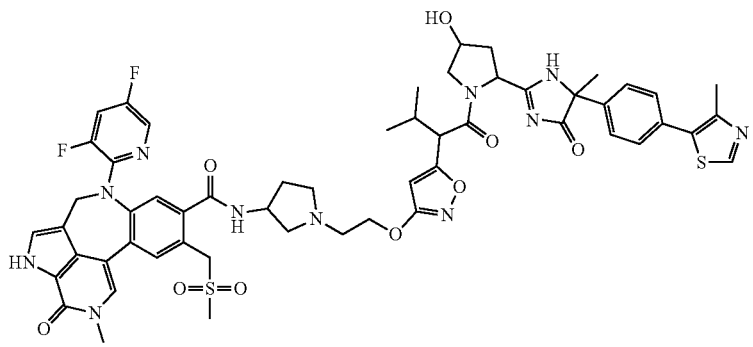 [SMILES: Cc1ncsc1-c1ccc(C2(C)NC(C3CC(O)CN3C(=O)C(c3cc(OCCN4CCC(NC(=O)c5cc6c(cc5CS(C)(=O)=O)-c5cn(C)c(=O)c7[nH]cc(c57)CN6c5ncc(F)cc5F)C4)no3)C(C)C)=NC2=O)cc1]<br>4-(3,5-difluoropyridin-2-yl)-N-(1-(2-((5-(1-(4-hydroxy-2-(5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide |
| 1002a | 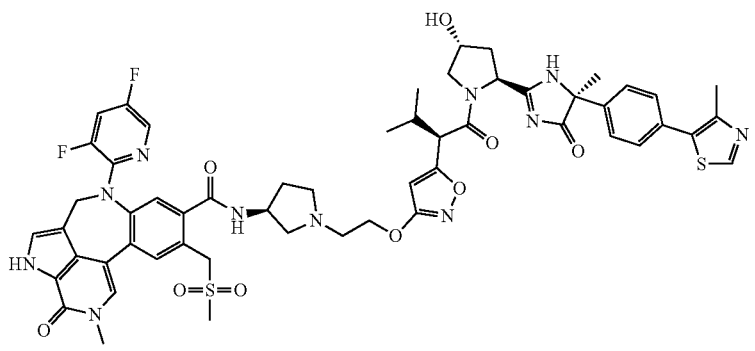 [SMILES: Cc1ncsc1-c1ccc([C@]2(C)NC([C@@H]3C[C@@H](O)CN3C(=O)[C@@H](c3cc(OCCN4CC[C@H](NC(=O)c5cc6c(cc5CS(C)(=O)=O)-c5cn(C)c(=O)c7[nH]cc(c57)CN6c5ncc(F)cc5F)C4)no3)C(C)C)=NC2=O)cc1]<br>4-(3,5-difluoropyridin-2-yl)-N-((S)-1-(2-((5-((R)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide |
| 1002b | 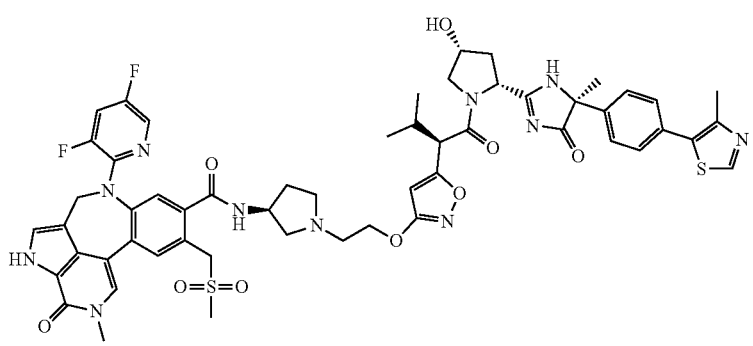 [SMILES: Cc1ncsc1-c1ccc([C@]2(C)NC([C@H]3C[C@@H](O)CN3C(=O)[C@@H](c3cc(OCCN4CC[C@H](NC(=O)c5cc6c(cc5CS(C)(=O)=O)-c5cn(C)c(=O)c7[nH]cc(c57)CN6c5ncc(F)cc5F)C4)no3)C(C)C)=NC2=O)cc1]<br>4-(3,5-difluoropyridin-2-yl)-N-((S)-1-(2-((5-((R)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide |

| Compound No. | Structure/Name [1] |
|---|---|
| 1002c | 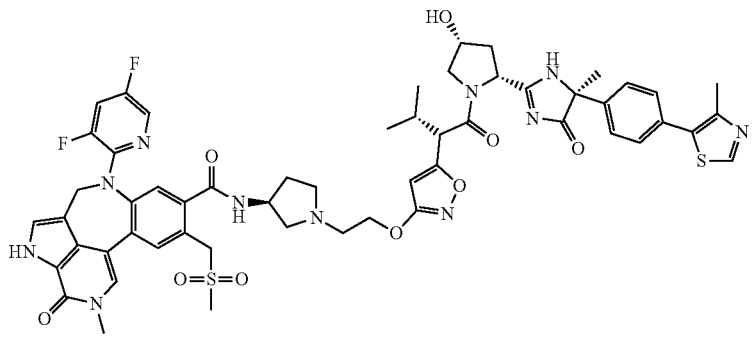<br>4-(3,5-difluoropyridin-2-yl)-N-((S)-1-(2-((5-((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide |
| 1002d | 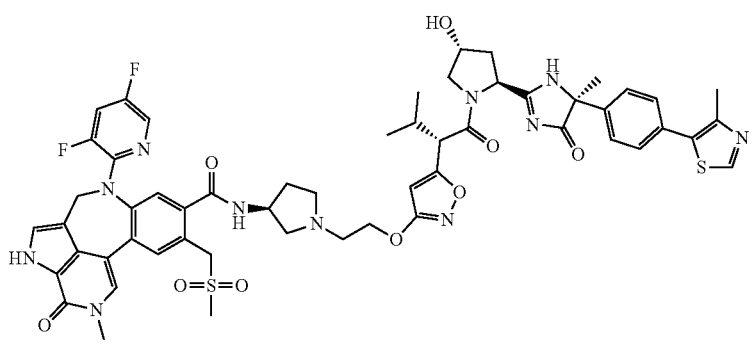 [SMILES: Cc1ncsc1-c1ccc([C@]2(C)NC([C@@H]3C[C@@H](O)CN3C(=O)[C@H](c3cc(OCCN4CC[C@H](NC(=O)c5cc6c(cc5CS(C)(=O)=O)-c5cn(C)c(=O)c7[nH]cc(c57)CN6c5ncc(F)cc5F)C4)no3)C(C)C)=NC2=O)cc1]<br>4-(3,5-difluoropyridin-2-yl)-N-((S)-1-(2-((5-((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide |
| 1002e | 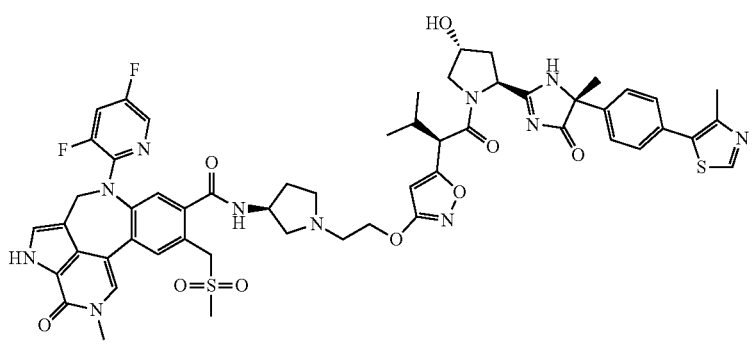 [SMILES: Cc1ncsc1-c1ccc([C@@]2(C)NC([C@@H]3C[C@@H](O)CN3C(=O)[C@@H](c3cc(OCCN4CC[C@H](NC(=O)c5cc6c(cc5CS(C)(=O)=O)-c5cn(C)c(=O)c7[nH]cc(c57)CN6c5ncc(F)cc5F)C4)no3)C(C)C)=NC2=O)cc1]<br>4-(3,5-difluoropyridin-2-yl)-N-((S)-1-(2-((5-((R)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide |

TABLE 6-continued

| Compound No. | Structure/Name [1] |
|---|---|
| 1002f | 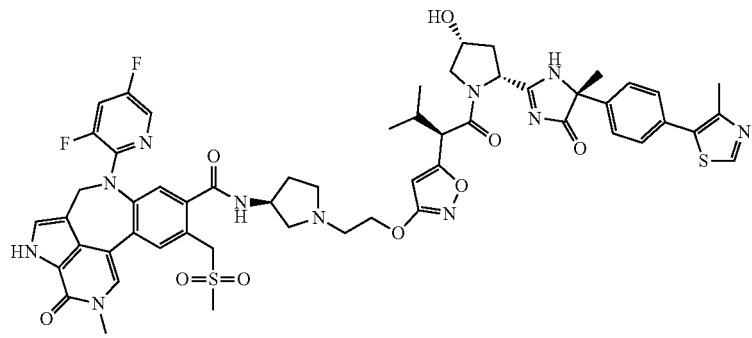 [SMILES: Cc1ncsc1-c1ccc([C@@]2(C)NC([C@H]3C[C@@H](O)CN3C(=O)[C@@H](c3cc(OCCN4CC[C@H](NC(=O)c5cc6c(cc5CS(C)(=O)=O)-c5cn(C)c(=O)c7[nH]cc(c57)CN6c5ncc(F)cc5F)C4)no3)C(C)C)=NC2=O)cc1]<br>4-(3,5-difluoropyridin-2-yl)-N-((S)-1-(2-((5-((R)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide |
| 1002g | 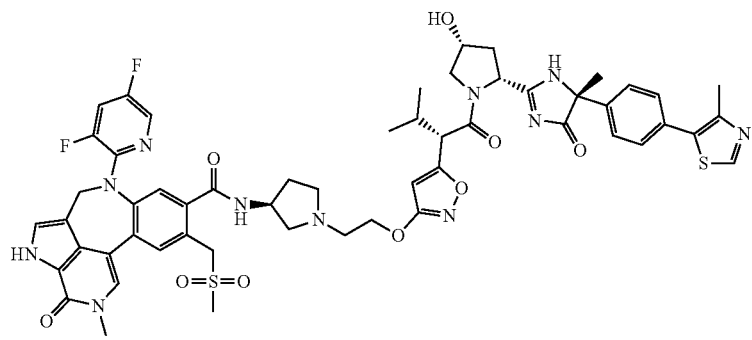 [SMILES: Cc1ncsc1-c1ccc([C@@]2(C)NC([C@H]3C[C@@H](O)CN3C(=O)[C@H](c3cc(OCCN4CC[C@H](NC(=O)c5cc6c(cc5CS(C)(=O)=O)-c5cn(C)c(=O)c7[nH]cc(c57)CN6c5ncc(F)cc5F)C4)no3)C(C)C)=NC2=O)cc1]<br>4-(3,5-difluoropyridin-2-yl)-N-((S)-1-(2-((5-((S)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide |
| 1002h | 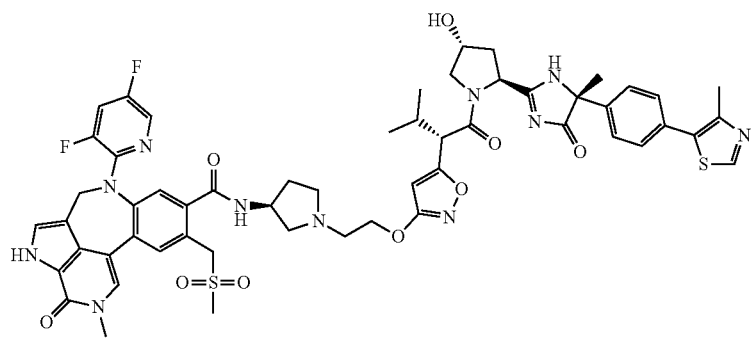 [SMILES: Cc1ncsc1-c1ccc([C@@]2(C)NC([C@@H]3C[C@@H](O)CN3C(=O)[C@H](c3cc(OCCN4CC[C@H](NC(=O)c5cc6c(cc5CS(C)(=O)=O)-c5cn(C)c(=O)c7[nH]cc(c57)CN6c5ncc(F)cc5F)C4)no3)C(C)C)=NC2=O)cc1]<br>4-(3,5-difluoropyridin-2-yl)-N-((S)-1-(2-((5-((S)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide |

TABLE 6-continued

| Compound No. | Structure/Name [1] |
|---|---|
| 1003 | 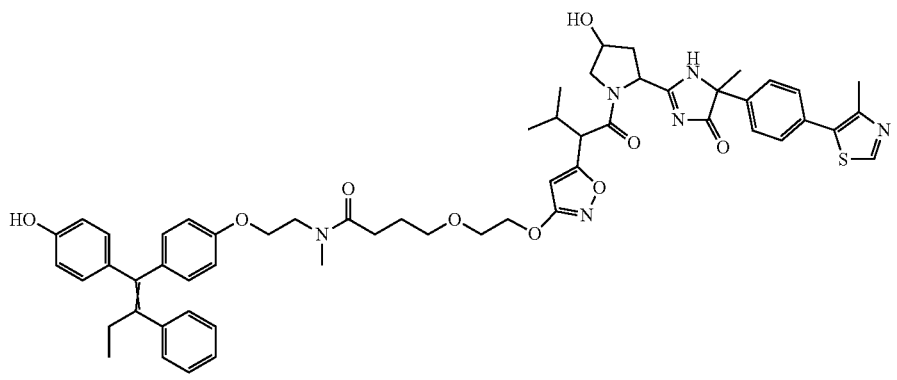 [SMILES: CCC(=C(c1ccc(O)cc1)c1ccc(OCCN(C)C(=O)CCCOCCOc2cc(C(C(=O)N3CC(O)CC3C3=NC(=O)C(C)(c4ccc(-c5scnc5C)cc4)N3)C(C)C)on2)cc1)c1ccccc1] 4-(2-((5-(1-(4-hydroxy-2-(5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-(1-(4-hydroxyphenyl)-2-phenylbut-1-en-1-yl)phenoxy)ethyl)-N-methylbutanamide |
| 1003a | 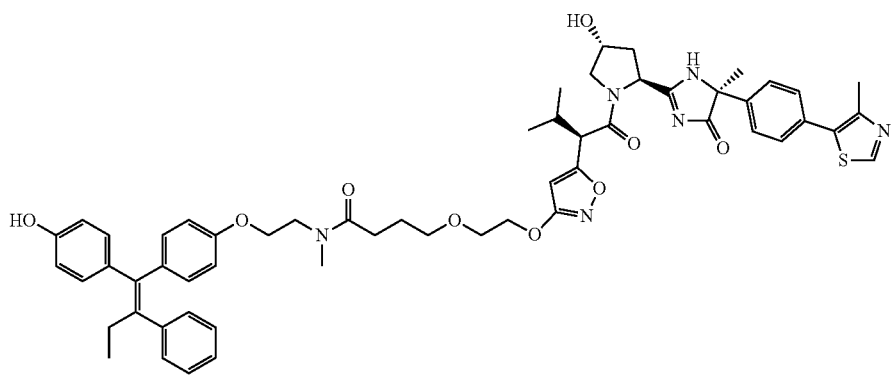 [SMILES: CC/C(=C(\c1ccc(O)cc1)c1ccc(OCCN(C)C(=O)CCCOCCOc2cc([C@H](C(=O)N3C[C@H](O)C[C@H]3C3=NC(=O)[C@](C)(c4ccc(-c5scnc5C)cc4)N3)C(C)C)on2)cc1)c1ccccc1] 4-(2-((5-((R)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide |
| 1003b | 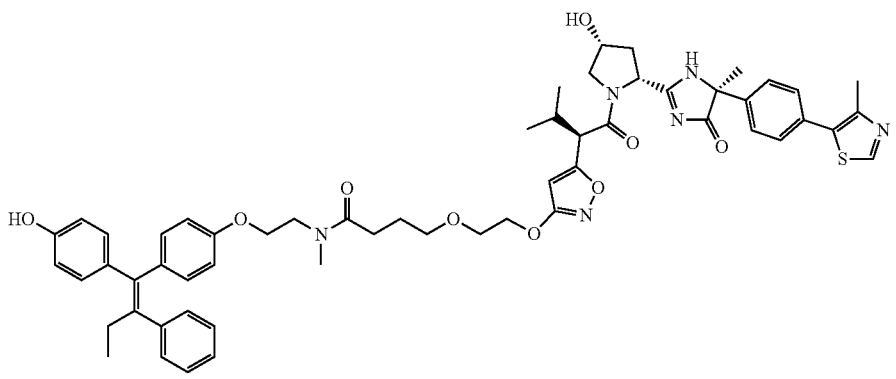 [SMILES: CC/C(=C(\c1ccc(O)cc1)c1ccc(OCCN(C)C(=O)CCCOCCOc2cc([C@H](C(=O)N3C[C@H](O)C[C@@H]3C3=NC(=O)[C@](C)(c4ccc(-c5scnc5C)cc4)N3)C(C)C)on2)cc1)c1ccccc1] 4-(2-((5-((R)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide |

| Compound No. | Structure/Name [1] |
|---|---|
| 1003c | 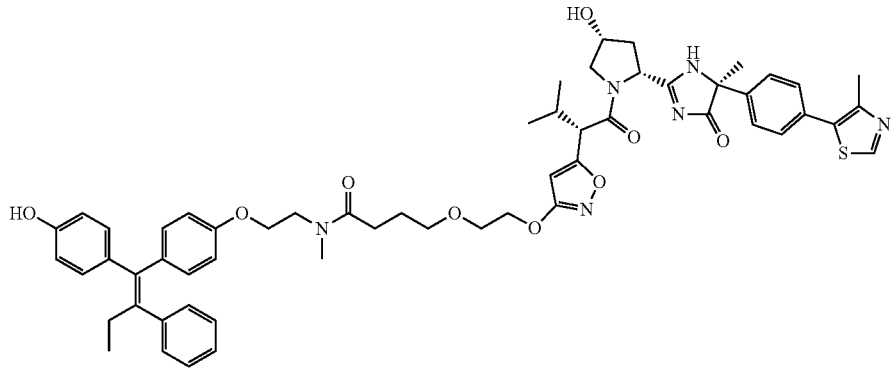 [SMILES: CC/C(=C(\c1ccc(O)cc1)c1ccc(OCCN(C)C(=O)CCCOCCOc2cc([C@@H](C(=O)N3C[C@H](O)C[C@@H]3C3=NC(=O)[C@](C)(c4ccc(-c5scnc5C)cc4)N3)C(C)C)on2)cc1)c1ccccc1]<br>4-(2-((5-((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide |
| 1003d | 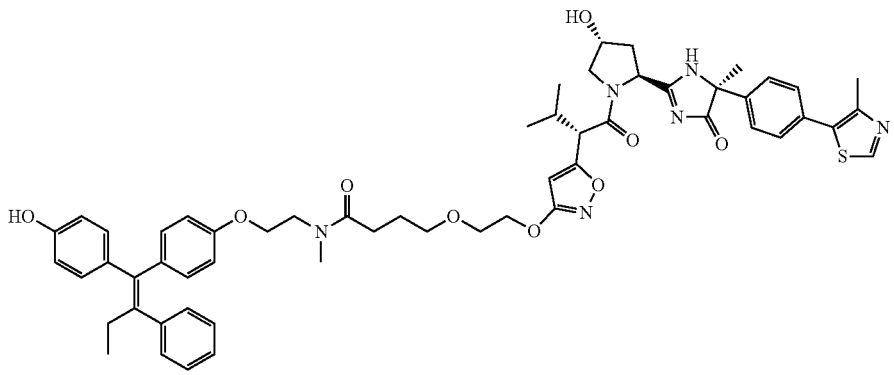 [SMILES: CC/C(=C(\c1ccc(O)cc1)c1ccc(OCCN(C)C(=O)CCCOCCOc2cc([C@@H](C(=O)N3C[C@H](O)C[C@H]3C3=NC(=O)[C@](C)(c4ccc(-c5scnc5C)cc4)N3)C(C)C)on2)cc1)c1ccccc1]<br>4-(2-((5-((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide |
| 1003e | 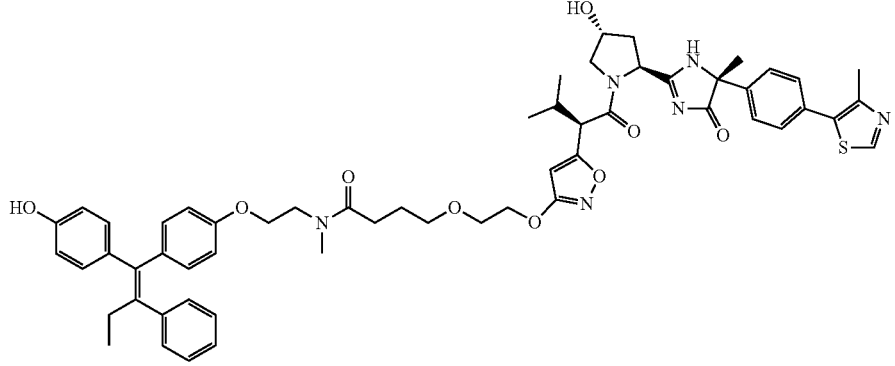 [SMILES: CC/C(=C(\c1ccc(O)cc1)c1ccc(OCCN(C)C(=O)CCCOCCOc2cc([C@H](C(=O)N3C[C@H](O)C[C@H]3C3=NC(=O)[C@@](C)(c4ccc(-c5scnc5C)cc4)N3)C(C)C)on2)cc1)c1ccccc1]<br>4-(2-((5-((R)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide |

TABLE 6-continued

| Compound No. | Structure/Name [1] |
|---|---|
| 1003f | 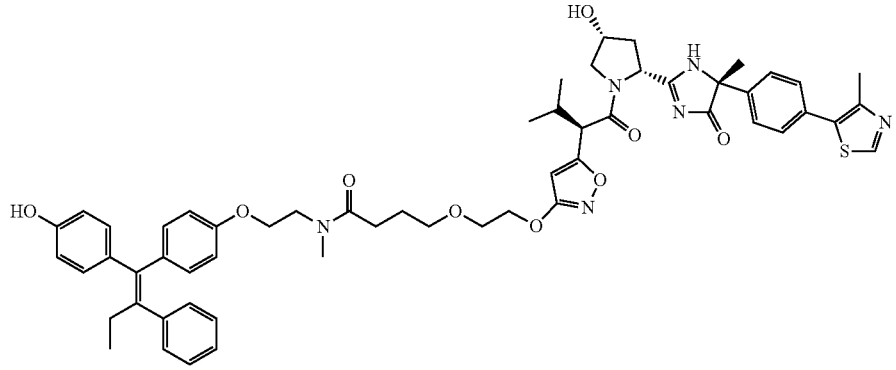 [SMILES: CC/C(=C(\c1ccc(O)cc1)c1ccc(OCCN(C)C(=O)CCCOCCOc2cc([C@H](C(=O)N3C[C@H](O)C[C@@H]3C3=NC(=O)[C@@](C)(c4ccc(-c5scnc5C)cc4)N3)C(C)C)on2)cc1)c1ccccc1]
4-(2-((5-((R)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide |
| 1003g | 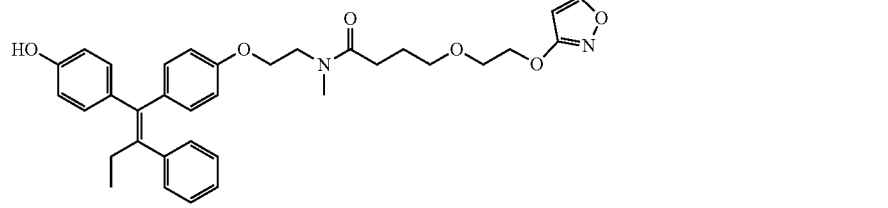
4-(2-((5-((S)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide |
| 1003h | 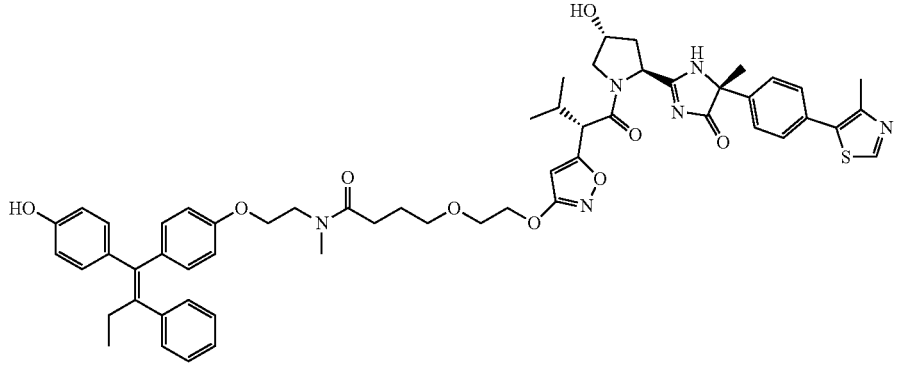 [SMILES: CC/C(=C(\c1ccc(O)cc1)c1ccc(OCCN(C)C(=O)CCCOCCOc2cc([C@@H](C(=O)N3C[C@H](O)C[C@H]3C3=NC(=O)[C@@](C)(c4ccc(-c5scnc5C)cc4)N3)C(C)C)on2)cc1)c1ccccc1]
4-(2-((5-((S)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide |

| Compound No. | Structure/Name [1] |
|---|---|
| 1003i | 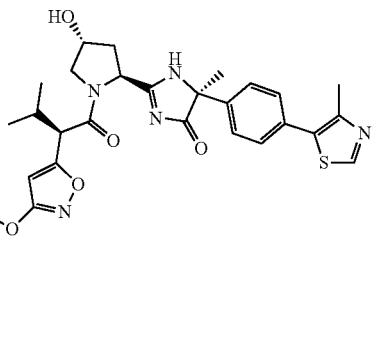<br>4-(2-((5-((R)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide |
| 1003j | 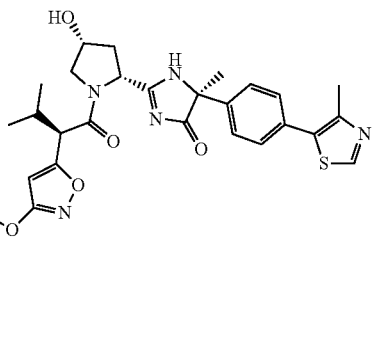<br>4-(2-((5-((R)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide |
| 1003k | 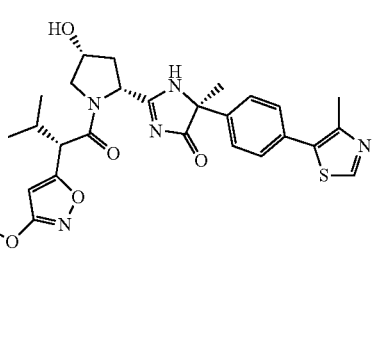<br>4-(2-((5-((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide |

TABLE 6-continued

| Compound No. | Structure/Name [1] |
|---|---|
| 1003l | 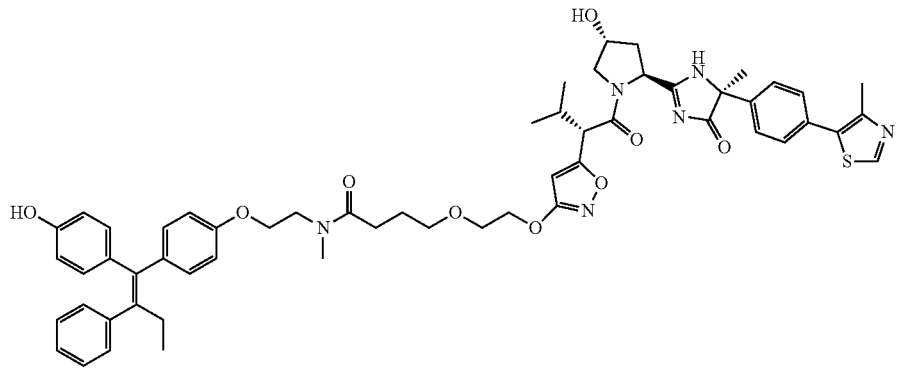 [SMILES: CC/C(=C(/c1ccc(O)cc1)c1ccc(OCCN(C)C(=O)CCCOCCOc2cc([C@@H](C(=O)N3C[C@H](O)C[C@H]3C3=NC(=O)[C@](C)(c4ccc(-c5scnc5C)cc4)N3)C(C)C)on2)cc1)c1ccccc1]<br>4-(2-((5-((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide |
| 1003m | 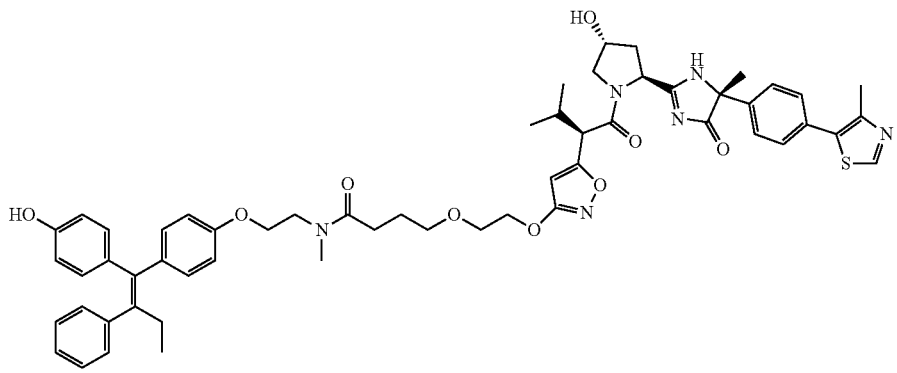 [SMILES: CC/C(=C(/c1ccc(O)cc1)c1ccc(OCCN(C)C(=O)CCCOCCOc2cc([C@H](C(=O)N3C[C@H](O)C[C@H]3C3=NC(=O)[C@@](C)(c4ccc(-c5scnc5C)cc4)N3)C(C)C)on2)cc1)c1ccccc1]<br>4-(2-((5-((R)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide |
| 1003n | 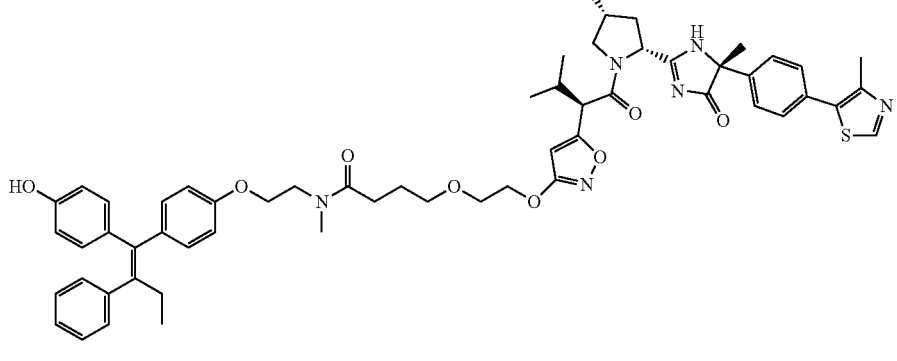<br>4-(2-((5-((R)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide |

TABLE 6-continued

| Compound No. | Structure/Name [1] |
| --- | --- |
| 1003o | 4-(2-((5-((S)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide |
| 1003p | 4-(2-((5-((S)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide |
| 1004 | 2-(1-(2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one |

| Compound No. | Structure/Name [1] |
|---|---|
| 1004a | 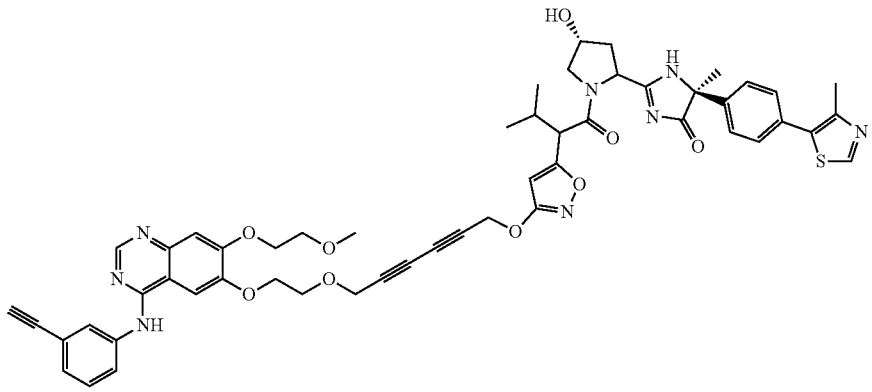 [SMILES: C#Cc1cccc(Nc2ncnc3cc(OCCOC)c(OCCOCC#CC#CCOc4cc(C(C(=O)N5C[C@H](O)CC5C5=NC(=O)[C@](C)(c6ccc(-c7scnc7C)cc6)N5)C(C)C)on4)cc23)c1]<br>(5S)-2-((4R)-1-(2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one |
| 1004b | 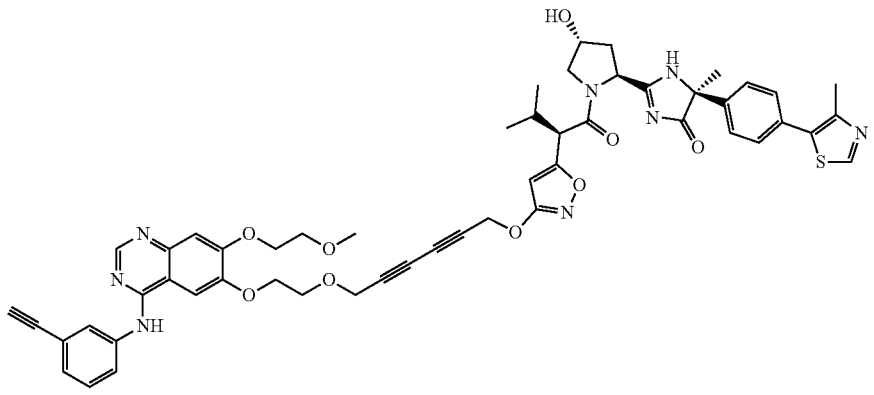 [SMILES: C#Cc1cccc(Nc2ncnc3cc(OCCOC)c(OCCOCC#CC#CCOc4cc([C@H](C(=O)N5C[C@H](O)C[C@H]5C5=NC(=O)[C@](C)(c6ccc(-c7scnc7C)cc6)N5)C(C)C)on4)cc23)c1]<br>(S)-2-((2S,4R)-1-((R)-2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one |
| 1004c | 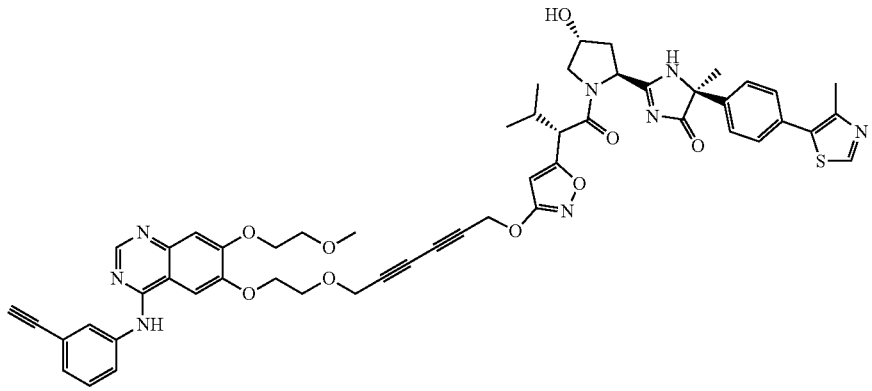 [SMILES: C#Cc1cccc(Nc2ncnc3cc(OCCOC)c(OCCOCC#CC#CCOc4cc([C@@H](C(=O)N5C[C@H](O)C[C@H]5C5=NC(=O)[C@](C)(c6ccc(-c7scnc7C)cc6)N5)C(C)C)on4)cc23)c1]<br>(S)-2-((2S,4R)-1-((S)-2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one |

TABLE 6-continued

| Compound No. | Structure/Name [1] |
|---|---|
| 1004d | 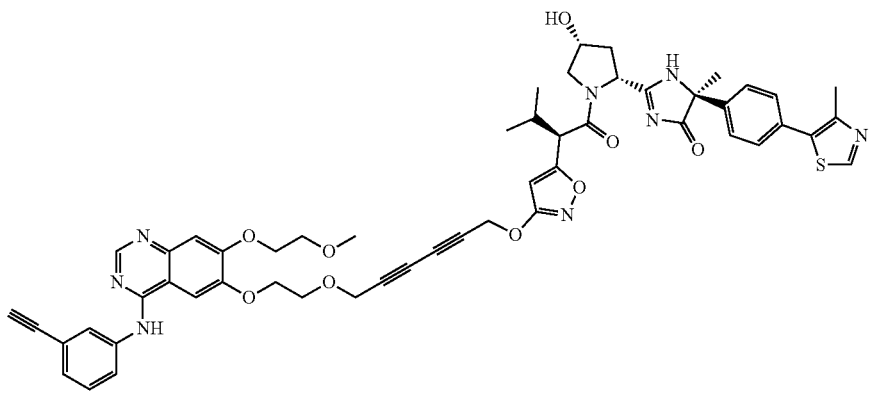 [SMILES: C#Cc1cccc(Nc2ncnc3cc(OCCOC)c(OCCOCC#CC#CCOc4cc([C@H](C(=O)N5C[C@H](O)C[C@@H]5C5=NC(=O)[C@](C)(c6ccc(-c7scnc7C)cc6)N5)C(C)C)on4)cc23)c1] |

(S)-2-((2R,4R)-1-((R)-2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one

| 1004e | 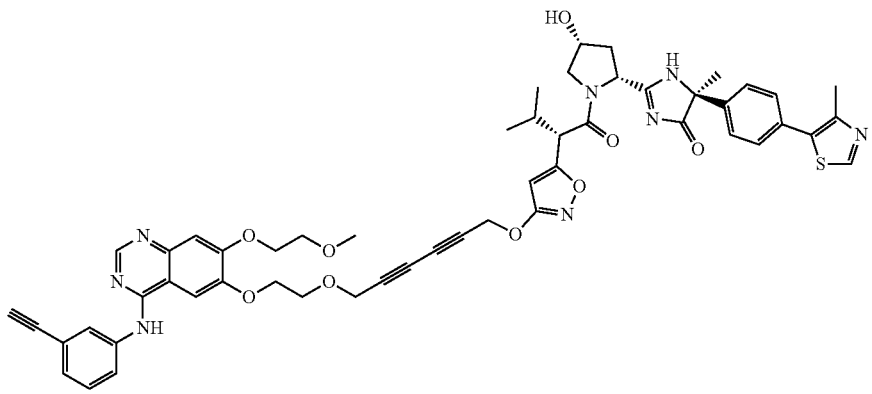 [SMILES: C#Cc1cccc(Nc2ncnc3cc(OCCOC)c(OCCOCC#CC#CCOc4cc([C@@H](C(=O)N5C[C@H](O)C[C@@H]5C5=NC(=O)[C@](C)(c6ccc(-c7scnc7C)cc6)N5)C(C)C)on4)cc23)c1] |

(S)-2-((2R,4R)-1-((S)-2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one

| 1005 | 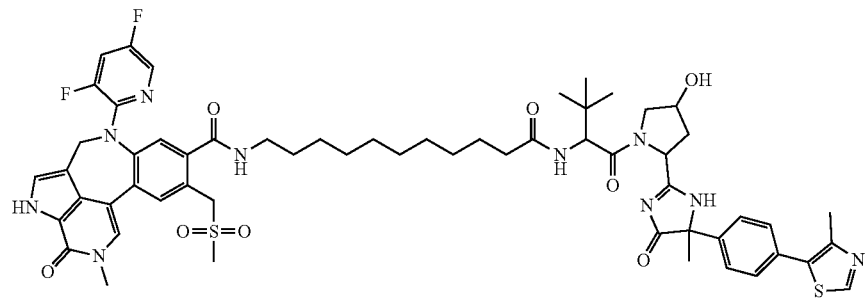 [SMILES: Cc1ncsc1-c1ccc(C2(C)NC(C3CC(O)CN3C(=O)C(NC(=O)CCCCCCCCCCNC(=O)c3cc4c(cc3CS(C)(=O)=O)-c3cn(C)c(=O)c5[nH]cc(c35)CN4c3ncc(F)cc3F)C(C)(C)C)=NC2=O)cc1] |

4-(3,5-difluoropyridin-2-yl)-N-(11-((1-(4-hydroxy-2-(5-methyl-5-(4-(4-methylthiazol-5-yl)phenyl)-4-oxo-4,5-dihydro-1H-imidazol-2-yl)pyrrolidin-1-yl))-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide

| Compound No. | Structure/Name [1] |
|---|---|
| 1005a | 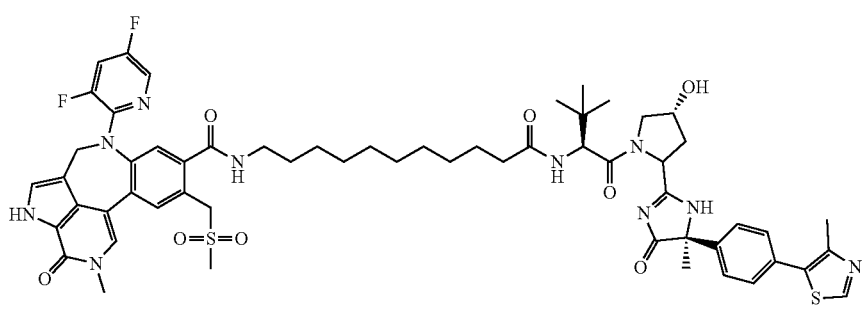 [SMILES: Cc1ncsc1-c1ccc([C@]2(C)NC(C3C[C@@H](O)CN3C(=O)[C@@H](NC(=O)CCCCCCCCCCNC(=O)c3cc4c(cc3CS(C)(=O)=O)-c3cn(C)c(=O)c5[nH]cc(c35)CN4c3ncc(F)cc3F)C(C)(C)C)=NC2=O)cc1]<br>4-(3,5-difluoropyridin-2-yl)-N-(11-(((2S)-1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide |
| 1005b | 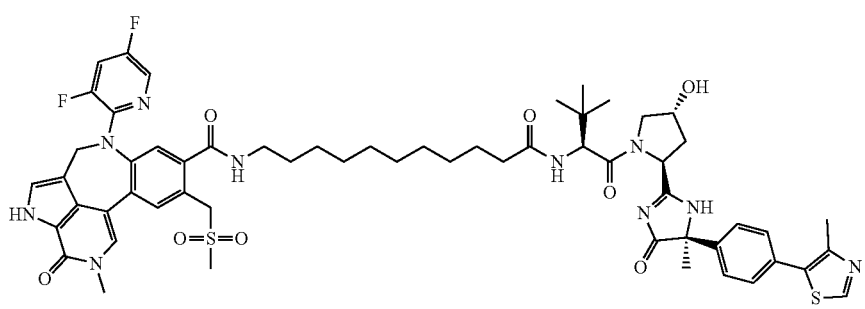 [SMILES: Cc1ncsc1-c1ccc([C@]2(C)NC([C@@H]3C[C@@H](O)CN3C(=O)[C@@H](NC(=O)CCCCCCCCCCNC(=O)c3cc4c(cc3CS(C)(=O)=O)-c3cn(C)c(=O)c5[nH]cc(c35)CN4c3ncc(F)cc3F)C(C)(C)C)=NC2=O)cc1]<br>4-(3,5-difluoropyridin-2-yl)-N-(11-(((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide |
| 1005c | 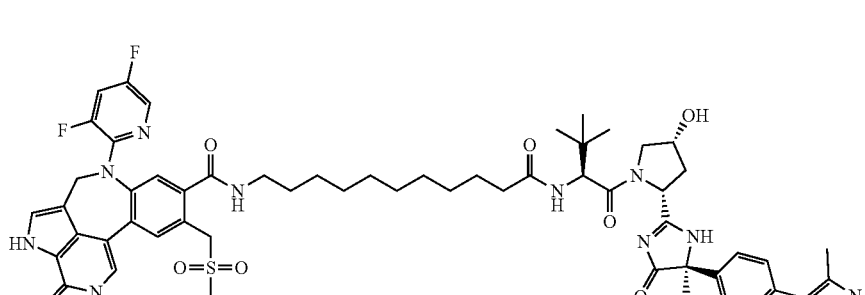<br>4-(3,5-difluoropyridin-2-yl)-N-(11-(((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide |

TABLE 6-continued

| Compound No. | Structure/Name [1] |
|---|---|
| 1006 | 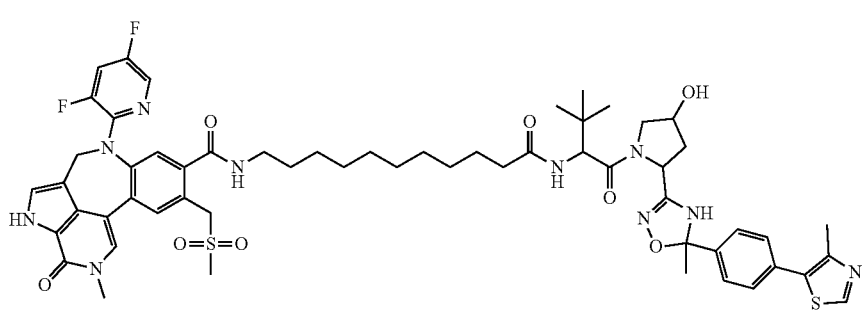 [SMILES: Cc1ncsc1-c1ccc(C2(C)NC(C3CC(O)CN3C(=O)C(NC(=O)CCCCCCCCCCNC(=O)c3cc4c(cc3CS(C)(=O)=O)-c3cn(C)c(=O)c5[nH]cc(c35)CN4c3ncc(F)cc3F)C(C)(C)C)=NO2)cc1]
4-(3,5-difluoropyridin-2-yl)-N-(11-((1-(4-hydroxy-2-(5-methyl-5-(4-(4-methylthiazol-5-yl)phenyl)-4,5-dihydro-1,2,4-oxadiazol-3-yl)pyrrolidin-1-yl-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide |
| 1006a | 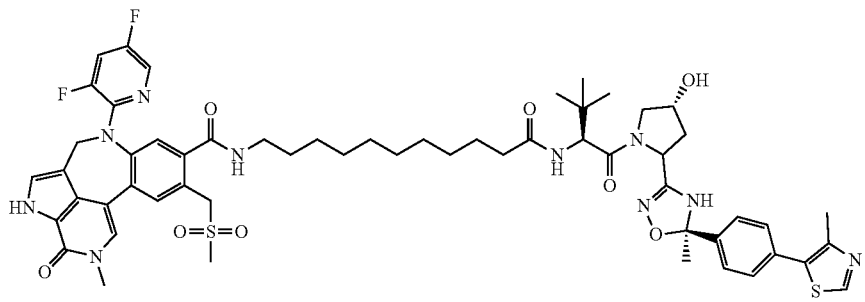 [SMILES: Cc1ncsc1-c1ccc([C@]2(C)NC(C3C[C@@H](O)CN3C(=O)[C@@H](NC(=O)CCCCCCCCCCNC(=O)c3cc4c(cc3CS(C)(=O)=O)-c3cn(C)c(=O)c5[nH]cc(c35)CN4c3ncc(F)cc3F)C(C)(C)C)=NO2)cc1]
4-(3,5-difluoropyridin-2-yl)-N-(11-(((2S)-1-((4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide |
| 1006b | 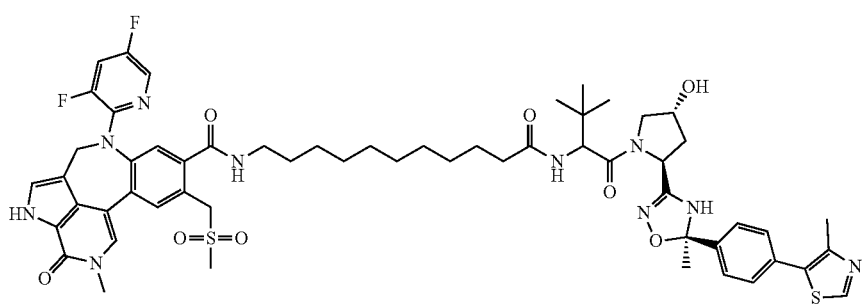
4-(3,5-difluoropyridin-2-yl)-N-(11-((1-((2S,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide |

TABLE 6-continued

| Compound No. | Structure/Name [1] |
|---|---|
| 1006c | 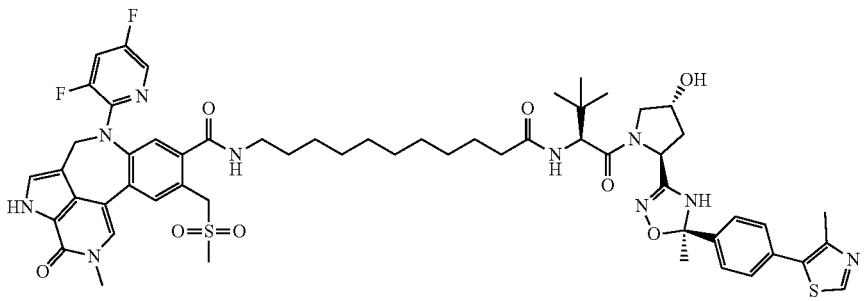 [SMILES: Cc1ncsc1-c1ccc([C@]2(C)NC([C@@H]3C[C@@H](O)CN3C(=O)[C@@H](NC(=O)CCCCCCCCCCNC(=O)c3cc4c(cc3CS(C)(=O)=O)-c3cn(C)c(=O)c5[nH]cc(c35)CN4c3ncc(F)cc3F)C(C)(C)C)=NO2)cc1] 4-(3,5-difluoropyridin-2-yl)-N-(11-(((S)-((2S,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide |
| 1006d | 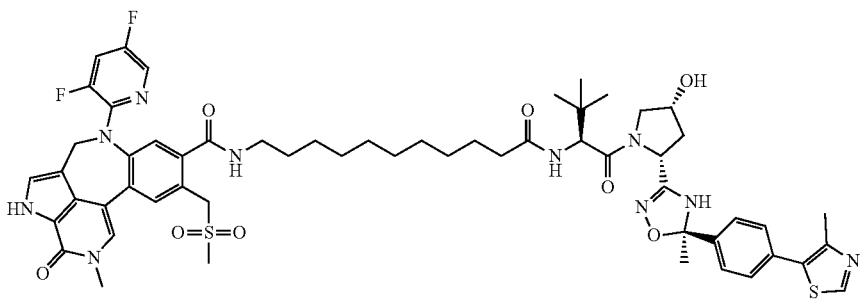 [SMILES: Cc1ncsc1-c1ccc([C@]2(C)NC([C@H]3C[C@@H](O)CN3C(=O)[C@@H](NC(=O)CCCCCCCCCCNC(=O)c3cc4c(cc3CS(C)(=O)=O)-c3cn(C)c(=O)c5[nH]cc(c35)CN4c3ncc(F)cc3F)C(C)(C)C)=NO2)cc1] 4-(3,5-difluoropyridin-2-yl)-N-(11-(((S)-((2R,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide |
| 1006e | 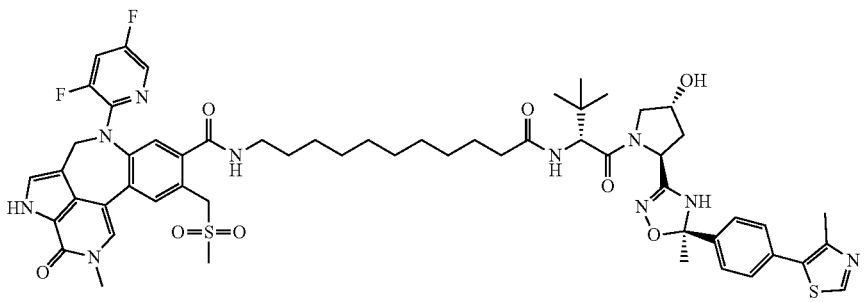 [SMILES: Cc1ncsc1-c1ccc([C@]2(C)NC([C@@H]3C[C@@H](O)CN3C(=O)[C@H](NC(=O)CCCCCCCCCCNC(=O)c3cc4c(cc3CS(C)(=O)=O)-c3cn(C)c(=O)c5[nH]cc(c35)CN4c3ncc(F)cc3F)C(C)(C)C)=NO2)cc1] 4-(3,5-difluoropyridin-2-yl)-N-(11-(((R)-((2S,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide |

| Compound No. | Structure/Name [1] |
|---|---|
| 1007 | 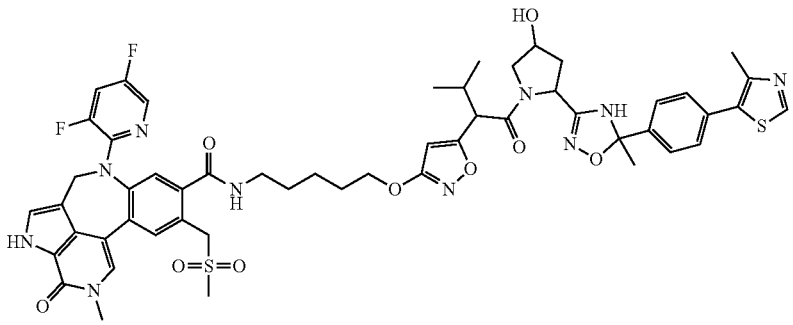 [SMILES: Cc1ncsc1-c1ccc(C2(C)NC(C3CC(O)CN3C(=O)C(c3cc(OCCCCCNC(=O)c4cc5c(cc4CS(C)(=O)=O)-c4cn(C)c(=O)c6[nH]cc(c46)CN5c4ncc(F)cc4F)no3)C(C)C)=NO2)cc1]<br>4-(3,5-difluoropyridin-2-yl)-N-(5-((5-(1-(4-hydroxy-2-(5-methyl-5-(4-(4-methylthiazol-5-yl)phenyl)-4,5-dihydro-1,2,4-oxadiazol-3-yl)pyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide |
| 1007a | 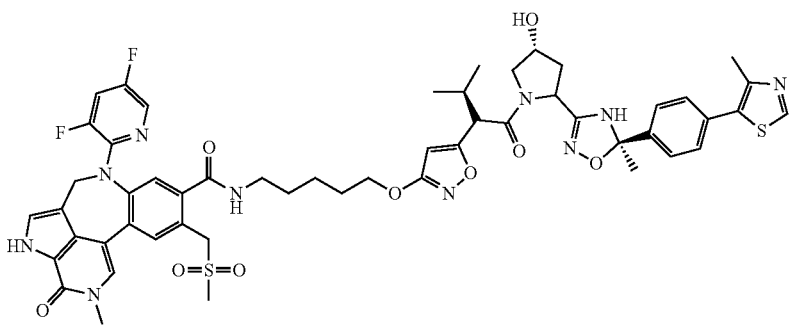<br>4-(3,5-difluoropyridin-2-yl)-N-(5-((5-((2R)-1-((4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide |
| 1007b | 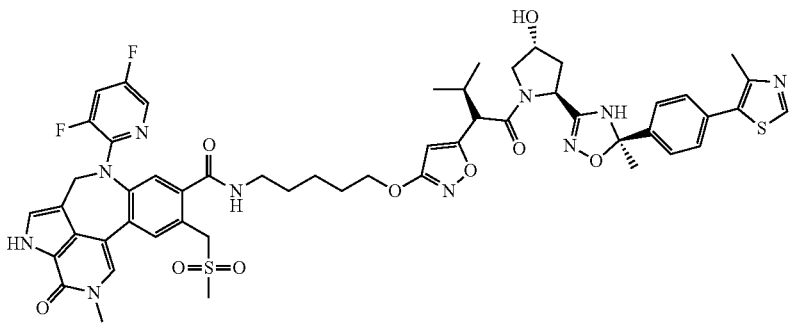<br>4-(3,5-difluoropyridin-2-yl)-N-(5-((5-((R)-1-((2S,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide |

TABLE 6-continued

| Compound No. | Structure/Name [1] |
|---|---|
| 1007c | 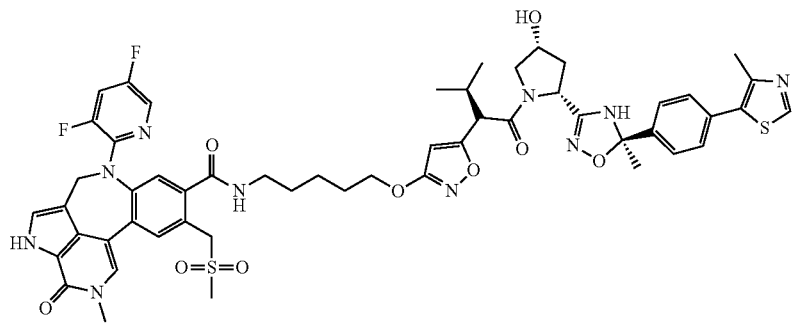<br>4-(3,5-difluoropyridin-2-yl)-N-(5-((5-((R)-1-((2R,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide |
| 1008 | 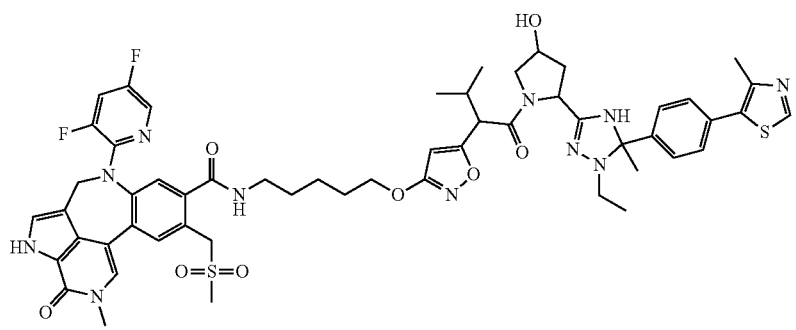 [SMILES: CCN1N=C(C2CC(O)CN2C(=O)C(c2cc(OCCCCCNC(=O)c3cc4c(cc3CS(C)(=O)=O)-c3cn(C)c(=O)c5[nH]cc(c35)CN4c3ncc(F)cc3F)no2)C(C)C)NC1(C)c1ccc(-c2scnc2C)cc1]<br>4-(3,5-difluoropyridin-2-yl)-N-(5-((5-(1-(2-(1-ethyl-5-methyl-5-(4-(4-methylthiazol-5-yl)phenyl)-4,5-dihydro-1,2,4-triazol-3-yl)-4-hydroxypyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide |
| 1008a | 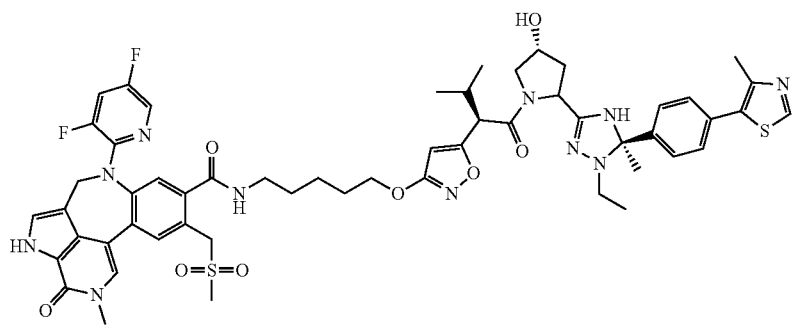 [SMILES: CCN1N=C(C2C[C@@H](O)CN2C(=O)[C@@H](c2cc(OCCCCCNC(=O)c3cc4c(cc3CS(C)(=O)=O)-c3cn(C)c(=O)c5[nH]cc(c35)CN4c3ncc(F)cc3F)no2)C(C)C)N[C@@]1(C)c1ccc(-c2scnc2C)cc1]<br>4-(3,5-difluoropyridin-2-yl)-N-(5-((5-((2R)-1-((4R)-2-((R)-1-ethyl-5-methyl-5-(4-(4-methylthiazol-5-yl)phenyl)-4,5-dihydro-1,2,4-triazol-3-yl)-4-hydroxypyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide |

TABLE 6-continued

| Compound No. | Structure/Name [1] |
|---|---|
| 1008b | 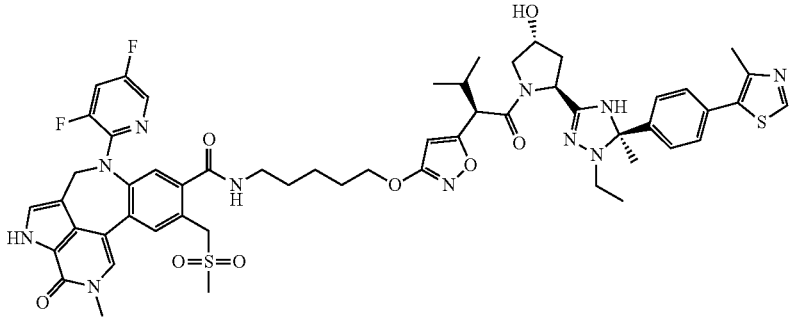 [SMILES: CCN1N=C([C@@H]2C[C@@H](O)CN2C(=O)[C@@H](c2cc(OCCCCCNC(=O)c3cc4c(cc3CS(C)(=O)=O)-c3cn(C)c(=O)c5[nH]cc(c35)CN4c3ncc(F)cc3F)no2)C(C)C)N[C@@]1(C)c1ccc(-c2scnc2C)cc1]<br>4-(3,5-difluoropyridin-2-yl)-N-(5-((5-((R)-1-((2S,4R)-2-((R)-1-ethyl-5-methyl-5-(4-(4-methylthi-azol-5-yl)phenyl)-4,5-dihydro-1,2,4-triazol-3-yl)-4-hydroxypyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide |
| 1008c | 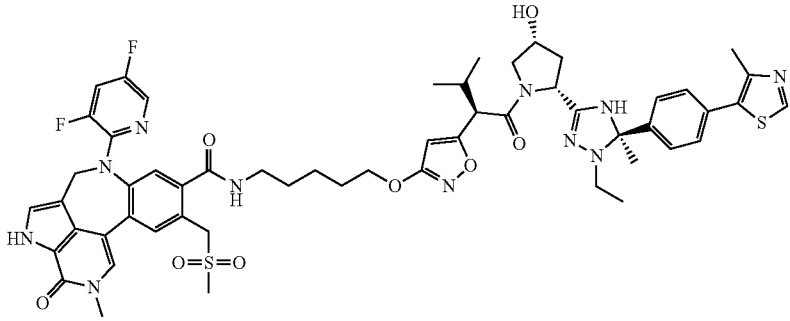 [SMILES: CCN1N=C([C@H]2C[C@@H](O)CN2C(=O)[C@@H](c2cc(OCCCCCNC(=O)c3cc4c(cc3CS(C)(=O)=O)-c3cn(C)c(=O)c5[nH]cc(c35)CN4c3ncc(F)cc3F)no2)C(C)C)N[C@@]1(C)c1ccc(-c2scnc2C)cc1]<br>4-(3,5-difluoropyridin-2-yl)-N-(5-((5-((R)-1-((2R,4R)-2-((R)-1-ethyl-5-methyl-5-(4-(4-methylthi-azol-5-yl)phenyl)-4,5-dihydro-1,2,4-triazol-3-yl)-4-hydroxypyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide |

[1] Compound names are auto-generated using ChemDraw ® software version 15.1.0.144 or 17.1.0.105.

Referring now to a PROTAC compound or a VHL ligand, as described herein, these can exist in solid or liquid form. In the solid state, the compound may exist in crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The subject matter described herein includes such solvates.

The skilled artisan will further appreciate that certain compounds (PROTACs and VHL ligands) described herein that exist in crystalline form, including the various solvates thereof, may exhibit polymorphism (i.e. the capacity to occur in different crystalline structures). These different crystalline forms are typically known as "polymorphs." The subject matter disclosed herein includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

PROTACs and VHL ligands described herein or a salt thereof may exist in stereoisomeric forms (e.g., it contains one or more asymmetric carbon atoms). The individual stereoisomers (enantiomers and diastereomers) and mixtures of these are included within the scope of the subject matter disclosed herein. Likewise, it is understood that a compound or salt of Formulas (I), (II), (III), and (IV) may exist in tautomeric forms other than that shown in the formula and these are also included within the scope of the subject matter disclosed herein. It is to be understood that the subject matter disclosed herein includes combinations and subsets of the particular groups described herein. The scope of the subject matter disclosed herein includes mixtures of stereoisomers as well as purified enantiomers or enantiomerically/ diastereomerically enriched mixtures. It is to be understood that the subject matter disclosed herein includes combinations and subsets of the particular groups defined hereinabove.

The subject matter disclosed herein also includes isotopically-labelled forms of the compounds described herein, but for the fact that one or more atoms are replaced by an atom having an atomic mass or mass number different from the atomic mass or mass number usually found in nature. Examples of isotopes that can be incorporated into compounds described herein and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

PROTAC compounds and VHL ligands as disclosed herein and pharmaceutically acceptable salts thereof that contain the aforementioned isotopes and/or other isotopes of other atoms are within the scope of the subject matter disclosed herein. Isotopically-labelled compounds are disclosed herein, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are commonly used for their ease of preparation and detectability. $^{11}$C and $^{18}$F isotopes are useful in PET (positron emission tomography), and $^{125}$I isotopes are useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula I can generally be prepared by carrying out the procedures disclosed in the Schemes and/or in the Examples below, by substituting a readily available isotopically labelled reagent for a non-isotopically labelled reagent.

1. VHL Ligands and VHL Ligand Moieties

In another aspect, the present disclosure is directed to VHL ligands, and specifically, VHL ligands that bind to a VHL E3 ubiquitin ligase. The VHL ligands of the present disclosure may be derivatized, e.g., by coupling the VHL ligand directly or via a chemical linker to a protein binding moiety to form a PROTAC, as discussed elsewhere herein.

In one aspect, the VHL ligand is a compound of Formula (III) or Formula (IV), or a tautomer thereof:

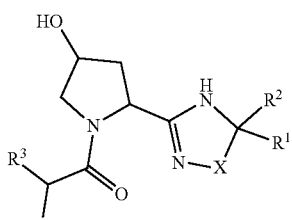

(III)

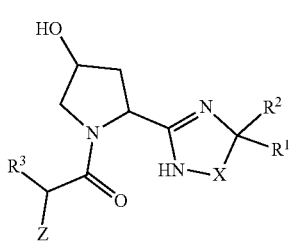

(IV)

or a salt (e.g., a pharmaceutically acceptable salt) thereof;
wherein:

X, $R^1$, $R^2$, and $R^3$ are as defined above; Z is selected from the group consisting of substituted or unsubstituted heteroaryl, substituted or unsubstituted heterocyclyl, —N($R^6$)$R^{6a}$, —O$R^{6a}$, —S$R^{6a}$a, and —N($R^6$)—SO$_2$—$R^{6b}$.

$R^6$ is selected from the group consisting of H and substituted or unsubstituted alkyl; or $R^6$, when present, is taken together with $R^3$ and the atoms to which they are attached to form a substituted or unsubstituted heterocyclylene;

$R^{6a}$ is selected from the group consisting of H, substituted or unsubstituted acyl, and substituted or unsubstituted alkyl; and $R^{6b}$ is selected from the group consisting of substituted or unsubstituted alkyl and substituted or unsubstituted aryl.

In one aspect, the VHL ligand is a compound of Formula (III) or Formula (IV), or a tautomer thereof, or a salt (e.g., a pharmaceutically acceptable salt) thereof; wherein:

X is selected from the group consisting of —C(O)—, O, S, —SO$_2$—, —N($R^4$)—, and —C($R^{5a}$)($R^{5b}$)—;

$R^1$ is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heterocyclyl, and substituted or unsubstituted heteroaryl;

$R^2$ is selected from the group consisting of H, substituted or unsubstituted alkyl, substituted or unsubstituted alkenyl, and substituted or unsubstituted alkynyl;

or $R^1$ and $R^2$, are taken together with the carbon to which they are attached to form a cycloalkyl or heterocyclyl, wherein the cycloalkyl or heterocyclyl is substituted or unsubstituted or fused with a ring selected from the group consisting of substituted or unsubstituted cycloalkyl, substituted or unsubstituted heterocyclyl, substituted or unsubstituted aryl, and substituted or unsubstituted heteroaryl;

$R^3$ is substituted or unsubstituted alkyl, or $R^3$ is taken together with $R^6$, when present, and the atoms to which they are attached, to form a substituted or unsubstituted heterocyclylene;

$R^4$, $R^{5a}$, and $R^{5b}$ are each independently selected from the group consisting of H and substituted or unsubstituted $C_1$-$C_3$ alkyl;

and Z is as defined above.

In another embodiment, the VHL ligand may be a compound of Formula (IIIa) or Formula (IVa), or a tautomer thereof:

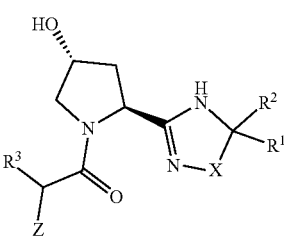

(IIIa)

-continued

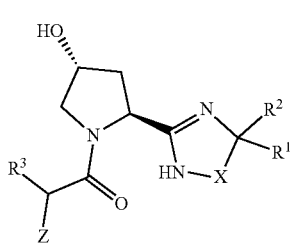

(IVa)

or a salt (e.g., a pharmaceutically acceptable salt) thereof; wherein each of X, $R^1$, $R^2$, $R^3$, and Z are as defined above.

In one particular embodiment, X is —C(O)—. In one embodiment, X is O. In one embodiment, X is —SO$_2$—. In one embodiment, X is —N($R^4$)—. In one embodiment, X is —N($R^4$)—, and $R^4$ is a substituted or unsubstituted $C_1$-$C_3$ alkyl. In one embodiment, X is —N($R^4$)—, and $R^4$ is selected from the group consisting of ethyl and —CH$_2$—CF$_3$. In one embodiment, X is —N($R^4$)—, and $R^4$ is phenyl. In one embodiment, X is —C($R^{5a}$)($R^{5b}$)—. In one embodiment, X is —C($R^{5a}$)($R^{5b}$)—, and $R^{5a}$ and $R^{5b}$ are each independently substituted or unsubstituted $C_1$-$C_3$ alkyl.

In some embodiments of the compounds of Formula (III), (IIIa), (IV) or (IVa), or a salt (e.g. a pharmaceutically acceptable salt) thereof, $R^1$ and $R^2$ are each H.

In some embodiments of the compounds of Formula (III), (IIIa), (IV) or (IVa), or a salt (e.g. a pharmaceutically acceptable salt) thereof, $R^1$ is a substituted or unsubstituted $C_1$-$C_3$ alkyl. In one particular embodiment, $R^1$ is methyl.

In some embodiments of the compounds of Formula (III), (IIIa), (IV) or (IVa), or a salt (e.g. a pharmaceutically acceptable salt) thereof, $R^1$ is substituted or unsubstituted phenyl. In one embodiment, $R^1$ is unsubstituted phenyl.

In one aspect, $R^1$ is —W—$R^7$, and W is selected from the group consisting of substituted or unsubstituted arylene, substituted or unsubstituted heteroarylene, substituted or unsubstituted heterocyclylene, and substituted or unsubstituted cycloalkylene; $R^7$ is selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, —OR$^8$, —N($R^{8a}$)$R^{8b}$, —C(O)$R^{8c}$, —C(O)N($R^{8a}$)$R^{8b}$, —N($R^{8a}$)C(O)$R^{8c}$, —SO$_2$N($R^{8a}$)$R^{8b}$, and —SO$_2$$R^{8c}$; $R^8$, $R^{8a}$, and $R^{8b}$ are independently selected from the group consisting of H and substituted or unsubstituted alkyl; and $R^{8c}$ is selected from the group consisting of substituted or unsubstituted alkyl and substituted or unsubstituted aryl. In some embodiments, $R^7$ is selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, and —SO$_2$$R^{8c}$, wherein $R^{8c}$ is as defined above. In some embodiments, $R^7$ is selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, —C(O)$R^{8c}$, —C(O)N($R^{8a}$)$R^{8b}$, —N($R^{8a}$)C(O)$R^{8c}$, —SO$_2$N($R^{8a}$)$R^{8b}$, and —SO$_2$$R^{8c}$, wherein $R^{8a}$, $R^{8b}$, and $R^{8c}$ are as defined above.

In one embodiment, $R^7$ is a haloalkyl, for example, a —CF$_3$.

In another aspect, $R^1$ is —W—$R^7$; W is substituted or unsubstituted phenylene; and $R^7$ is as defined above.

In one embodiment, $R^1$ is substituted or unsubstituted phenyl.

In another aspect, $R^1$ is

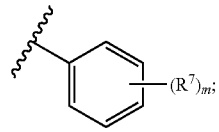

m is 0, 1, 2, 3, 4, or 5; $R^7$ is selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, —OR$^8$, —N($R^{8a}$)$R^{8b}$, —C(O)$R^{8c}$, —C(O)N($R^{8a}$)$R^{8b}$, —N($R^{8a}$)C(O)$R^{8c}$, —SO$_2$N($R^{8a}$)$R^{8b}$, and —SO$_2$$R^{8c}$; $R^8$, $R^{8a}$, and $R^{8b}$ are independently selected from the group consisting of H and substituted or unsubstituted alkyl; $R^{8c}$ is selected from the group consisting of substituted or unsubstituted alkyl and substituted or unsubstituted aryl; and ∿∿∿ is the point of attachment to the remaining structure of the compound. In one particular embodiment, $R^1$ is

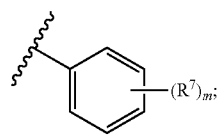

m is 0, 1, 2, or 3; and $R^7$ is as defined above.

In another aspect, $R^1$ is

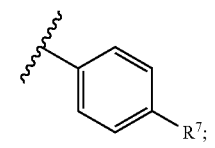

$R^7$ is as defined above; and ∿∿∿ is the point of attachment to the remaining structure of the compound.

In one particular embodiment, $R^7$ is selected from the group consisting of substituted or unsubstituted heteroaryl, substituted or unsubstituted heterocyclyl, and substituted or unsubstituted aryl.

In certain aspects, $R^7$ is selected from the group consisting of

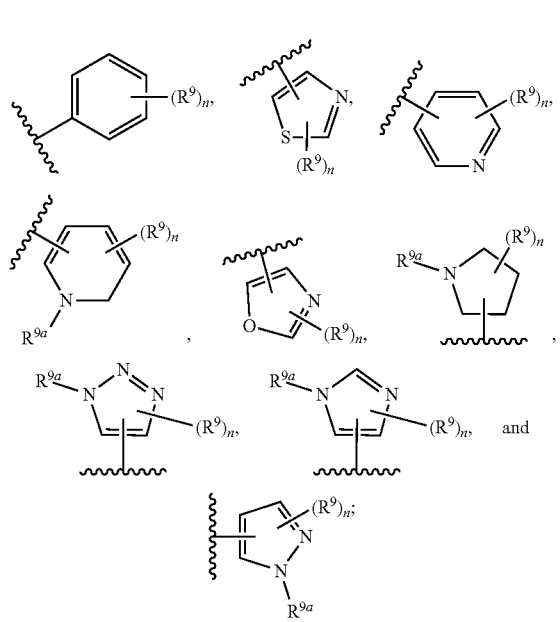

wherein: n is 0, 1, 2, 3, 4, or 5; $R^9$ is selected from the group consisting of oxo, alkyl, haloalkyl, cycloalkyl, halo, —CN, —NH$_2$, and substituted or unsubstituted alkynyl; ⁓, when present, is the point of attachment to the remaining structure of the compound; $R^{9a}$, when present, is selected from the group consisting of H and $R^9$; or $R^{9a}$ is the point of attachment to the remaining structure of the compound and ⁓ is absent.

Non-limiting examples of $R^7$ include

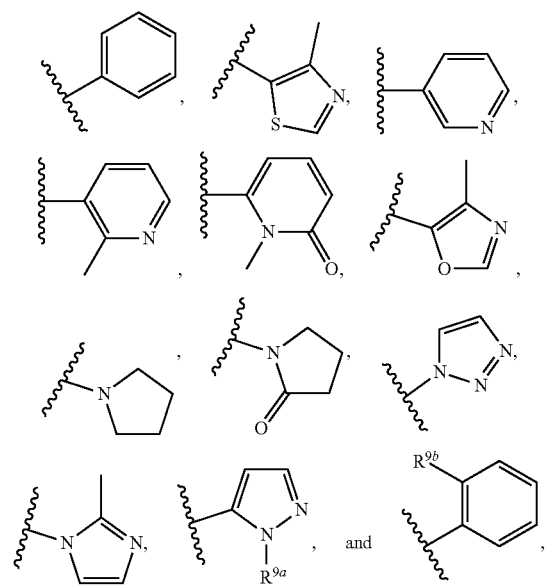

wherein $R^{9a}$ is alkyl, and $R^{9b}$ is halo. In some embodiments, $R^7$ is chlorophenyl, chloro-thiazolyl or trifluoromethyl-thiazolyl.

In one particular embodiment, $R^7$ is

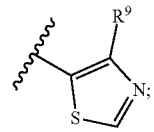

and $R^9$ is a substituted or unsubstituted alkynyl. In one embodiment, the alkynyl is substituted with a substituted or unsubstituted aryl, such as phenyl. In one embodiment, the aryl is phenyl, and the phenyl is substituted with at least one $R^{10}$, wherein $R^{10}$ is halo.

In one particular embodiment, $R^7$ is selected from the group consisting of

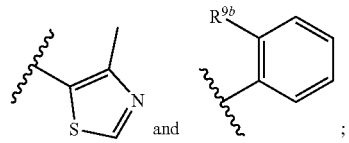

wherein $R^{9b}$ is halo and ⁓ is the point of attachment to the remaining structure of the compound.

In one particular embodiment, $R^7$ is selected from the group consisting of a substituted or unsubstituted 5-membered heteroaryl, and a substituted or unsubstituted 5-membered heterocyclyl. $R^7$ may be, for example, 1-pyrrolidinyl or 1-pyrrolidonyl.

In another aspect, $R^2$ is substituted or unsubstituted alkyl. In one embodiment, $R^2$ is a substituted or unsubstituted $C_1$-$C_3$ alkyl. In one particular embodiment, $R^2$ is an alkyl (e.g., a $C_1$-$C_3$ alkyl) substituted with at least one substituent selected from the group consisting of halo, hydroxyl, and carboxyl. Examples of suitable $R^2$ groups include, but are not limited to, —CH$_3$, —CF$_3$, —CH$_2$OH, and —C(O)OH. In one embodiment, $R^2$ is —CH$_3$ or —CF$_3$.

In another embodiment, $R^2$ is a substituted or unsubstituted alkynyl. In one particular embodiment, $R^2$ is a $C_1$-$C_3$ alkynyl.

In some embodiments of the compounds of Formula (III), (IIIa), (IV) or (IVa), or a salt (e.g. a pharmaceutically acceptable salt) thereof, $R^2$ is a substituted or unsubstituted aryl. In one particular embodiment, $R^2$ is an unsubstituted phenyl.

In some embodiments of the compounds of Formula (III), (IIIa), (IV) or (IVa), or a salt (e.g. a pharmaceutically acceptable salt) thereof, $R^1$ and $R^2$, are taken together with the carbon to which they are attached to form a cycloalkyl or heterocyclyl, wherein the cycloalkyl or heterocyclyl is substituted or unsubstituted or fused with a ring selected from the group consisting of substituted or unsubstituted cycloalkyl, substituted or unsubstituted heterocyclyl, substituted or unsubstituted aryl, and substituted or unsubstituted heteroaryl.

In one embodiment, $R^1$ and $R^2$ are taken together with the carbon to which they are attached to form an unsubstituted cycloalkyl.

In another embodiment, $R^1$ and $R^2$ are taken together with the carbon to which they are attached to form a cycloalkyl, wherein the cycloalkyl is fused with a substituted or unsubstituted aryl.

In one particular embodiment, $R^1$ and $R^2$ are taken together with the carbon to which they are attached to form a cycloalkyl fused with a ring selected from the group consisting of substituted aryl and substituted heteroaryl. For example, $R^1$ and $R^2$ can be taken together with the carbon to which they are attached to form a substituted 1,2,3,4-tetrahydronaphthyl. In one particular embodiment, the 1,2,3,4-tetrahydronaphthyl is substituted with at least one $R^7$, and each $R^7$ is independently selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, —OR$^8$, —N(R$^{8a}$)R$^{8b}$, and —SO$_2$R$^{8c}$; R$^8$, R$^{8a}$, and R$^{8b}$ are independently selected from the group consisting of H and substituted or unsubstituted alkyl; and R$^{8c}$ is selected from the group consisting of substituted or unsubstituted alkyl and substituted or unsubstituted aryl.

In one embodiment, $R^1$ and $R^2$ are taken together with the carbon to which they are attached to form a cycloalkyl selected from the group consisting of:

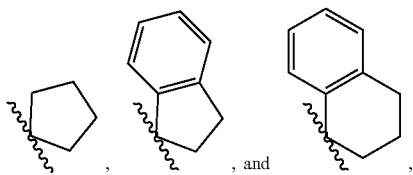

wherein ⌇⌇⌇ is the point of attachment to the remaining structure of the compound.

In some embodiments of the compounds of Formula (III), (IIIa), (IV) or (IVa), or a salt (e.g. a pharmaceutically acceptable salt) thereof, $R^3$ is a substituted or unsubstituted $C_1$-$C_6$ alkyl. In certain embodiments, $R^3$ isopropyl or tert-butyl.

In some embodiments of the compounds of Formula (III), (IIIa), (IV) or (IVa), or a salt (e.g. a pharmaceutically acceptable salt) thereof, Z may be a substituted or unsubstituted heteroaryl or substituted or unsubstituted heterocyclyl. Examples of Z include, but are not limited to

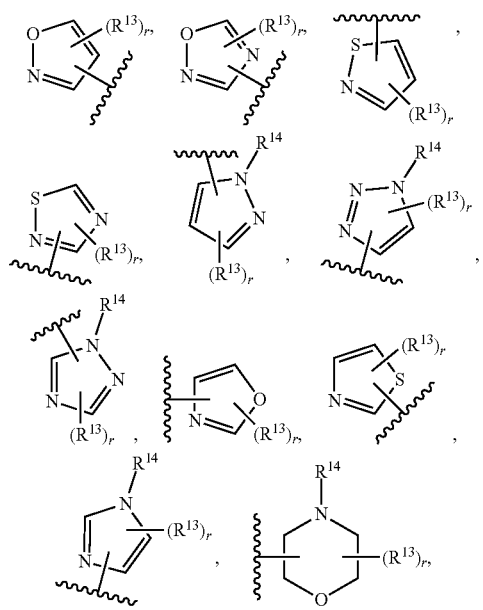

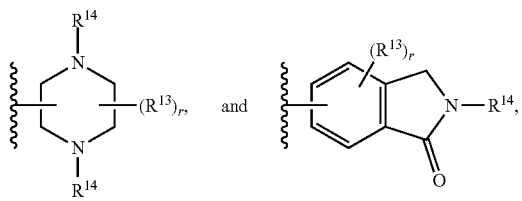

wherein ⌇⌇⌇ indicates the point of attachment to the remaining structure of the compound; r is 0, 1, 2, or 3; each $R^{13}$ is independently selected from the group consisting of —OR$^{13a}$ and substituted or unsubstituted alkyl; each $R^{14}$ is independently selected from the group consisting of H, substituted or unsubstituted alkyl, and the point of attachment to the remaining structure of the compound; and each $R^{13a}$ is independently selected from the group consisting of H and substituted or unsubstituted alkyl; wherein when $R^{14}$ is the point of attachment to the remaining structure of the compound, ⌇⌇⌇ is absent.

In some embodiments, r is 0, 1, or 2. In one embodiment, r is 1.

In some embodiments, $R^{13}$ is a $C_1$-$C_3$ alkyl. In one embodiment, r is 1 and $R^{13}$ is —CH$_3$.

In some embodiments, $R^{13}$ is —OR$^{13a}$, and $R^{13a}$ is selected from the group consisting of $C_1$-$C_3$ alkyl and H. In one embodiment, r is 1, $R^{13}$ is —OR$^{13a}$, and $R^{13a}$ is —CH$_3$ or H.

In one embodiment, Z is

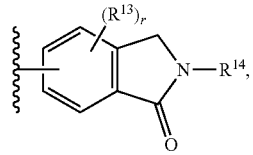

r is 0, $R^{14}$ is the point of attachment to the remaining structure of the compound, and ⌇⌇⌇ is absent.

In one embodiment, Z is a 5- or 6-membered substituted or unsubstituted heteroaryl. In another embodiment, Z is a 5-membered substituted or unsubstituted heteroaryl. Examples of Z include, but are not limited to

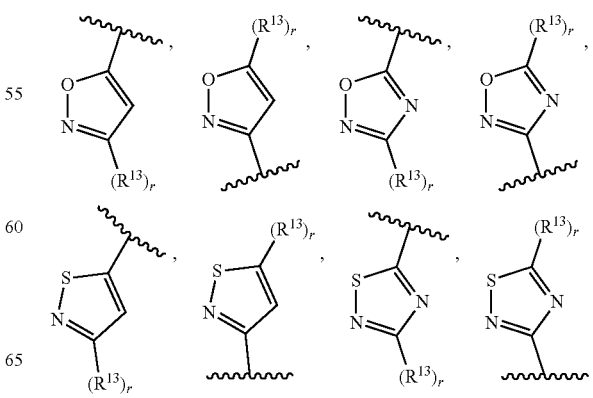

-continued

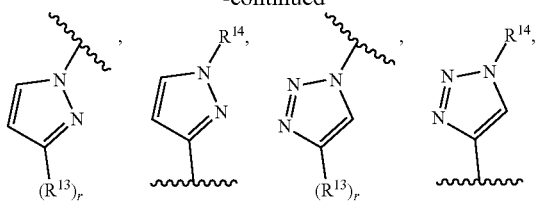

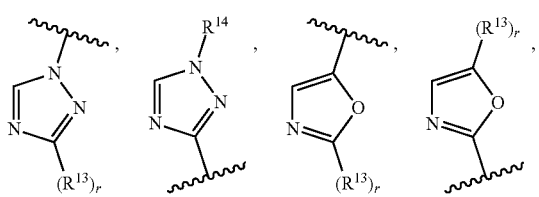

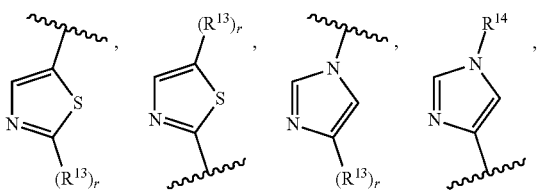

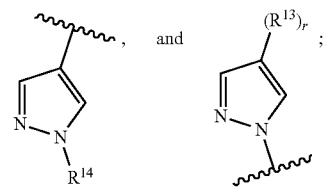, and 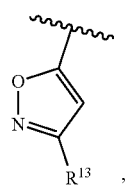;

wherein ⌇⌇⌇ indicates the point of attachment to the remaining structure of the compound; r is 0 or 1; $R^{13}$ is selected from the group consisting of —$OR^{13a}$ and substituted or unsubstituted alkyl; $R^{14}$ is selected from the group consisting of H and substituted or unsubstituted alkyl; and $R^{13a}$ is selected from the group consisting of H and substituted or unsubstituted alkyl.

In one embodiment, r is 1 and $R^{13}$ is a $C_1$-$C_3$ alkyl. In one embodiment, r is 1 and $R^{13}$ is —$CH_3$. In one embodiment, r is 0.

In another embodiment, r is 1; $R^{13}$ is —$OR^{13a}$; and $R^{13a}$ is selected from the group consisting of $C_1$-$C_3$ alkyl and H. In one embodiment, r is 1, $R^{13}$ is —$OR^{13a}$, and $R^{13a}$ is —$CH_3$ or H.

In one specific embodiment, Z is

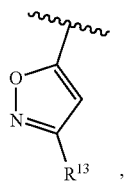

wherein $R^{13}$ is selected from the group consisting of —$OR^{13a}$ and substituted or unsubstituted alkyl; and $R^{13a}$ is selected from the group consisting of H and substituted or unsubstituted alkyl. More specifically, Z may be wherein $R^{13}$ is selected from the group consisting of —$CH_3$ and —$OR^{13a}$, and $R^{13a}$ is H or —$CH_3$.

In another embodiment, Z is selected from the group consisting of

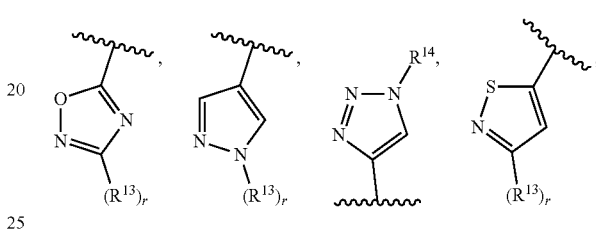

wherein r is 1, $R^{13}$ is —$CH_3$, and $R^{14}$ is —$CH_3$.

In another aspect, Z is selected from the group consisting of —$N(R^6)R^{6a}$, —$OR^{6a}$, —$SR^{6a}$, and —$N(R^6)$—$SO_2$—$R^{6b}$; wherein $R^6$ is selected from the group consisting of H and substituted or unsubstituted alkyl; or $R^6$, when present, is taken together with $R^3$ and the atoms to which they are attached to form a substituted or unsubstituted heterocyclylene; $R^{6a}$ is selected from the group consisting of H, substituted or unsubstituted acyl, and substituted or unsubstituted alkyl; and $R^{6b}$ is selected from the group consisting of substituted or unsubstituted alkyl and substituted or unsubstituted aryl. In particular embodiments, $R^6$ is selected from the group consisting of H and substituted or unsubstituted $C_1$-$C_6$ alkyl and $R^{6a}$ is selected from the group consisting of H, substituted or unsubstituted $C_1$-$C_6$ acyl, and substituted or unsubstituted $C_1$-$C_6$ alkyl. In one embodiment, $R^{6a}$ is —C(O)—$R^{16}$, wherein $R^{16}$ is selected from the group consisting of substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heteroaryl, and substituted or unsubstituted heterocyclyl. In one particular embodiment, $R^a$ is —C(O)—$R^{16}$, wherein $R^{16}$ is a substituted $C_1$-$C_3$ alkyl. In another embodiment, $R^{6a}$ is

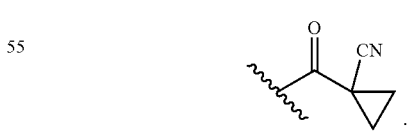

In one particular embodiment, Z is —$N(R^6)R^{6a}$, and $R^6$ and $R^{6a}$ are as defined above. In another embodiment, Z is —$N(R^6)R^{6a}$, $R^6$ is H, and $R^{6a}$ is a substituted or unsubstituted acyl (e.g., a substituted or unsubstituted $C_1$-$C_6$ acyl). In one specific embodiment, Z is —$N(R^6)R^{6a}$, $R^6$ is H, and $R^{6a}$ is —C(O)$CH_3$. In another embodiment, Z is —$N(R^6)R^{6a}$, $R^6$ is H, and $R^{6a}$ is

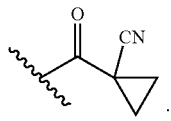 [SMILES: *C(=O)C1(C#N)CC1]

In one particular embodiment, Z is —N(R$^6$)R$^{6a}$ or —N(R$^6$)—SO$_2$—R$^{6b}$, R$^{6a}$ and R$^{6b}$ are as defined above, and R$^6$ is taken together with R$^3$ and the atoms to which they are attached form a substituted or unsubstituted heterocyclylene. In one such embodiment, R$^6$ is taken together with R$^3$ and the atoms to which they are attached to form a substituted or unsubstituted 5- or 6-membered heterocyclylene. In one embodiment, the heterocyclylene is an unsubstituted 5- or 6-membered heterocyclylene. In other embodiments, the heterocyclylene is substituted with —(R$^{11}$)$_p$; wherein p is 0, 1, 2, 3, or 4; R$^{11}$ is selected from the group consisting of substituted or unsubstituted C$_1$-C$_3$ alkyl, halo, —CN, and —OR$^{11a}$; and each R$^{11a}$ is independently selected from the group consisting of H and substituted or unsubstituted alkyl (e.g., a C$_1$-C$_3$ alkyl). In one embodiment, R$^{11}$ is —OR$^{11a}$, and is selected from the group consisting of —OCH$_3$, —OCF$_3$, and —OH. In one embodiment, p is 1 and R$^{11}$ is selected from the group consisting of —OCH$_3$, —OCF$_3$, and —OH. In one embodiment, p is 2, and R$^{11}$ is methyl. In another embodiment, p is 0.

In one particular embodiment, Z is —N(R$^6$)R$^{6a}$, and R$^{6a}$ is —C(O)—R$^{16}$, wherein R$^{16}$ is substituted or unsubstituted alkyl, and R$^6$ is taken together with R$^3$ and the atoms to which they are attached to form a substituted or unsubstituted 5- or 6-membered heterocyclylene. In one particular embodiment, R$^{6a}$ is —C(O)—R$^{16}$, wherein R$^{16}$ is an unsubstituted substituted C$_1$-C$_3$ alkyl, such as methyl.

In one particular embodiment, Z is —N(R$^6$)—SO$_2$—R$^{6b}$, wherein R$^{6b}$ is as defined above, and R$^6$ is taken together with R$^3$ and the atoms to which they are attached to form a substituted or unsubstituted 5- or 6-membered heterocyclylene. In one such embodiment, R$^6$ is taken together with R$^3$ and the atoms to which they are attached to form an unsubstituted 5- or 6-membered heterocyclylene. In another embodiment, the heterocyclylene is substituted with —(R$^{11}$)$_p$; wherein p is 2, and R$^{11}$ is an unsubstituted C$_1$-C$_3$ alkyl, such as methyl. In one such embodiment, R$^{6b}$ is unsubstituted alkyl. In one embodiment, R$^{6b}$ is a C$_1$-C$_3$ alkyl, such as methyl.

It is intented and understood that any of the Z moieties detailed herein for the compound of Formula (III), (IIIa), (IV), or (IVa) may be combined with any of the X, R$^1$, R$^2$, and/or R$^3$ groups detailed herein, as if each and every combination has been individually described. For example, in some embodiments, the present disclosure is directed to a compound of Formula (III), (IIIa), (IV), or (IVa), or a salt (e.g., a pharmaceutically acceptable salt) thereof, wherein X is —C(O)—; R$^1$ is unsubstituted alkyl or

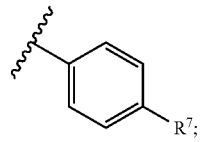

R$^2$ is unsubstituted alkyl; R$^3$ is a C$_1$-C$_6$ alkyl, such as isopropyl or tert-butyl; Z is —N(R$^6$)R$^{6a}$ or

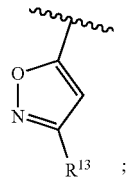

R$^6$ is H; R$^{6a}$ is substituted or unsubstituted acyl; R$^7$ is substituted or unsubstituted heteroaryl or halo; R$^{13}$ is selected from the group consisting of —OR$^{13a}$ and substituted or unsubstituted alkyl (e.g., a C$_1$-C$_6$ alkyl); and R$^{13a}$ is selected from the group consisting of H and substituted or unsubstituted alkyl (e.g., a C$_1$-C$_6$ alkyl).

In one aspect, the present disclosure is directed to a compound of Formula (III), (IIIa), (IV), or (IVa), or a salt (e.g., a pharmaceutically acceptable salt) thereof, wherein X is —C(O)—; R$^1$ is unsubstituted alkyl (e.g., a C$_1$-C$_3$ alkyl) or

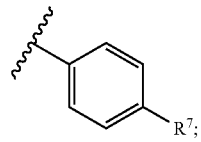

R$^2$ is unsubstituted alkyl (e.g. a C$_1$-C$_3$ alkyl); R$^3$ is tert-butyl; Z is —N(R$^6$)R$^{6a}$; R$^6$ is H; R$^{6a}$ is substituted or unsubstituted C$_1$-C$_6$ acyl, and R$^7$ is substituted or unsubstituted heteroaryl or halo. In one such embodiment, R$_7$ is a substituted or unsubstituted 5- or 6-membered heteroaryl, and R$^{6a}$ is —C(O)CH$_3$.

In another aspect, the present disclosure is directed to a compound of Formula (III), (IIIa), (IV), or (IVa), or a salt (e.g., a pharmaceutically acceptable salt) thereof, wherein X is —C(O)—; R$^1$ is unsubstituted alkyl (e.g., a C$_1$-C$_3$ alkyl) or

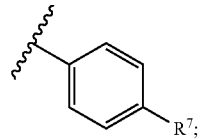

R$^2$ is unsubstituted alkyl (e.g., a C$_1$-C$_3$ alkyl); R$^3$ is isopropyl; Z is

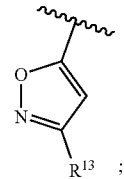

R$^7$ is substituted or unsubstituted heteroaryl or halo; R$^{13}$ is —OR$^{13a}$ or a C$_1$-C$_6$ alkyl; and R$^{13a}$ is H or a C$_1$-C$_6$ alkyl. In one such embodiment, R$^7$ is a substituted or unsubstituted 5- or 6-membered heteroaryl; R$^{13}$ is —CH$_3$ or —OR$^{13a}$; and R$^{13a}$ is H or —CH$_3$. In one such embodiment, R$^7$ is halo; R$^{13}$ is —CH$_3$ or —OR$^{13a}$; and R$^{13a}$ is H or —CH$_3$.

In another aspect, the present disclosure is directed to a compound of Formula (III), (IIIa), (IV), or (IVa), or a salt (e.g., a pharmaceutically acceptable salt) thereof, wherein X is —C(O)—; $R^1$ is

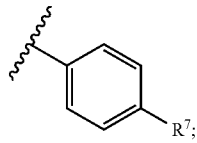

$R^2$ is unsubstituted alkyl (e.g., a $C_1$-$C_3$ alkyl); $R^3$ is isopropyl or tert-butyl; Z is —N($R^6$)$R^{6a}$ or substituted or unsubstituted heteroaryl; $R^6$ is H; $R^{6a}$ is substituted or unsubstituted $C_1$-$C_6$ acyl; $R^7$ is

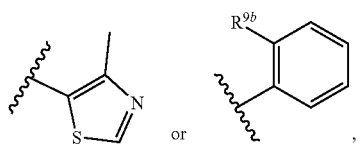

and $R^{9b}$ is halo. In one particular such embodiment, $R^3$ is isopropyl, and Z is selected from the group consisting of

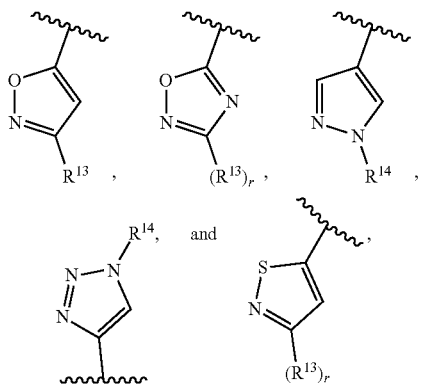

wherein r is 1, $R^{13}$ is —$CH_3$ or —O—$R^{13a}$, $R^{13a}$ is H, and $R^{14}$ is —$CH_3$.

In another aspect, the present disclosure is directed to a compound of Formula (III), (IIIa), (IV), or (IVa), or a salt (e.g., a pharmaceutically acceptable salt) thereof, wherein X is —C(O)—; $R^1$ is

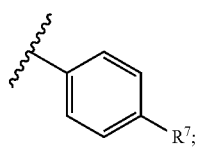

$R^2$ is unsubstituted alkyl (e.g., a $C_1$-$C_3$ alkyl); Z is —N($R^6$)$R^{6a}$ or —N($R^6$)—$SO_2$—$R^{6b}$; $R^{6a}$ is substituted or unsubstituted $C_1$-$C_6$ acyl; $R^{6b}$ is substituted or unsubstituted C1-$C_6$ alkyl; $R^7$ is

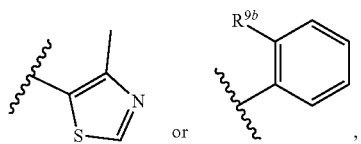

and $R^{9b}$ is halo; wherein $R^3$ is taken together with $R^6$, and the atoms to which they are attached, to form a substituted or unsubstituted 5- or 6-membered heterocyclylene. In one such embodiment, $R^{6a}$ is —C(O)$CH_3$ or $R^{6b}$ is methyl.

In another aspect, the present disclosure is directed to a compound of Formula (III), (IIIa), (IV), or (IVa), or a salt (e.g., a pharmaceutically acceptable salt) thereof, wherein X is O; $R^1$ is unsubstituted alkyl, phenyl, or

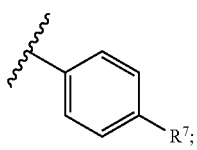

$R^2$ is unsubstituted alkyl (e.g., a $C_1$-$C_3$ alkyl), —$CF_3$, or phenyl; $R^3$ is isopropyl or tert-butyl; Z is —N($R^6$)$R^{6a}$ or

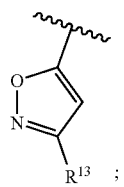

$R^6$ is H; $R^{6a}$ is —C(O)$CH_3$; $R^7$ is halo,

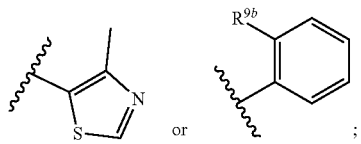

and $R^{9b}$ is halo. In one particular embodiment, Z is —N($R^6$)$R^{6a}$; $R^3$ is tert-butyl; and $R^6$ is H. In another embodiment, Z is

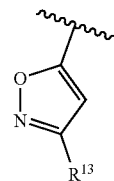

and $R^3$ is isopropyl.

In another aspect, the present disclosure is directed to a compound of Formula (III), (IIIa), (IV), or (IVa), or a salt (e.g., a pharmaceutically acceptable salt) thereof, wherein X is O; $R^1$ and $R^2$, are taken together with the carbon to which they are attached to form a 5- or 6-membered cycloalkyl, wherein the cycloalkyl is unsubstituted or fused with an unsubstituted phenyl; $R^3$ is isopropyl; Z is

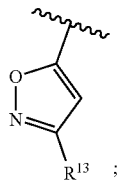

and R¹³ is a $C_1$-$C_6$ alkyl. In one such embodiment, R¹³ is —CH₃.

In another aspect, the present disclosure is directed to a compound of Formula (III), (IIIa), (IV), or (IVa), or a salt (e.g., a pharmaceutically acceptable salt) thereof, wherein X is —N(R⁴)—; R¹ and R² are each unsubstituted alkyl (e.g., a $C_1$-$C_3$ alkyl); R³ is isopropyl; R⁴ is substituted or unsubstituted $C_1$-$C_3$ alkyl or phenyl; Z is

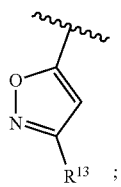

and R¹³; and R¹³ is a $C_1$-$C_6$ alkyl. In one particular embodiment, R⁴ is ethyl or —CH₂—CF₃. In one such embodiment, R¹³ is —CH₃.

In another aspect, the present disclosure is directed to a compound of Formula (III), (IIIa), (IV), or (IVa), or a salt (e.g., a pharmaceutically acceptable salt) thereof, wherein X is —SO₂—; R¹ and R² are each hydrogen; R³ is isopropyl; Z is

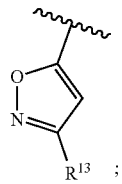

and R¹³; and R¹³ is a $C_1$-$C_6$ alkyl. In one such embodiment, R¹³ is —CH₃.

In another aspect, the present disclosure is directed to a compound of Formula (III), (IIIa), (IV), or (IVa), or a salt (e.g., a pharmaceutically acceptable salt) thereof, wherein X is —C(R⁵ᵃ)(R⁵ᵇ)—; R and R² are each unsubstituted alkyl; R³ is isopropyl; Z is

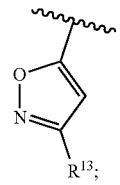

and R¹³; and R¹³ is a $C_1$-$C_6$ alkyl. In one such embodiment, R¹³ is —CH₃.

In one embodiment, the VHL ligand is a compound of Formula (III) or (IIIa), or a salt (e.g., a pharmaceutically acceptable salt) thereof, and has a structure selected from the group consisting of those structures in Table 7. Although the tautomers of the compounds as shown in Formula (III) or (IIIa) are depicted in the Table 7, the corresponding tautomers as shown in Formula (IV) or (IVa) are intended and embraced by the current disclosure, as if each and every one of the tautomers as shown in Formula (IV) or (IVa) is individually depicted.

TABLE 7

| | VHL ligands | |
|---|---|---|
| Compound No. | Structure | Name[1] |
| 101 | HO [structure] | N-(1-(2-(5-(4-bromophenyl)-5-methyl-4-oxo-4,5-dihydro-1H-imidazol-2-yl)-4-hydroxypyrrolidin-1-yl)-3,3-dimethyl-1-oxobutan-2-yl)acetamide |

TABLE 7-continued

VHL ligands

| Compound No. | Structure | Name[1] |
|---|---|---|
| 101a | 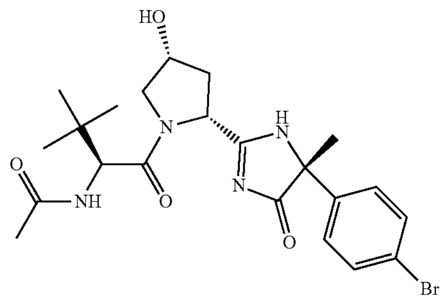 | N-((S)-1-((2R,4R)-2-((R)-5-(4-bromophenyl)-5-methyl-4-oxo-4,5-dihydro-1H-imidazol-2-yl)-4-hydroxypyrrolidin-1-yl)-3,3-dimethyl-1-oxobutan-2-yl)acetamide |
| 101b | 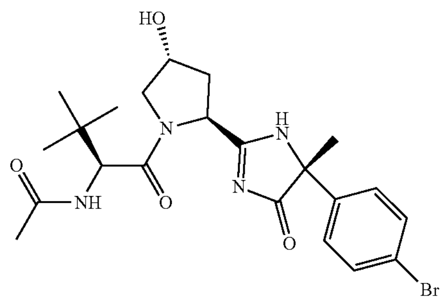 | N-((S)-1-((2S,4R)-2-((R)-5-(4-bromophenyl)-5-methyl-4-oxo-4,5-dihydro-1H-imidazol-2-yl)-4-hydroxypyrrolidin-1-yl)-3,3-dimethyl-1-oxobutan-2-yl)acetamide |
| 101c | 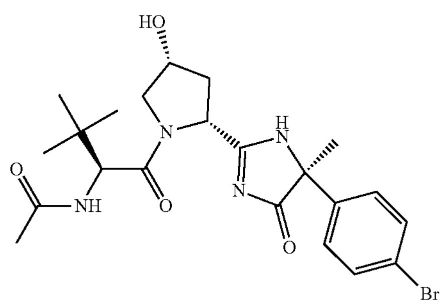 | N-((S)-1-((2R,4R)-2-((S)-5-(4-bromophenyl)-5-methyl-4-oxo-4,5-dihydro-1H-imidazol-2-yl)-4-hydroxypyrrolidin-1-yl)-3,3-dimethyl-1-oxobutan-2-yl)acetamide |
| 101d | 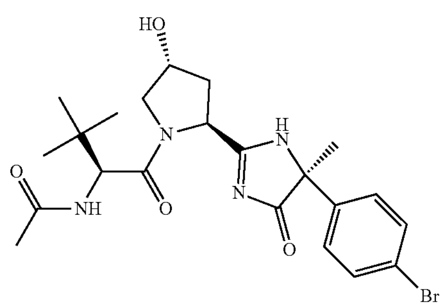 | N-((S)-1-((2S,4R)-2-((S)-5-(4-bromophenyl)-5-methyl-4-oxo-4,5-dihydro-1H-imidazol-2-yl)-4-hydroxypyrrolidin-1-yl)-3,3-dimethyl-1-oxobutan-2-yl)acetamide |
| 102 | 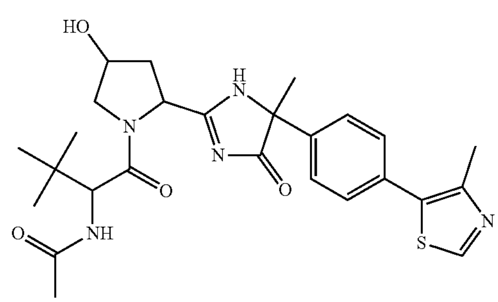 [SMILES: CC(=O)NC(C(=O)N1CC(O)CC1C1=NC(=O)C(C)(c2ccc(-c3scnc3C)cc2)N1)C(C)(C)C] | N-(1-(4-hydroxy-2-(5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)acetamide |

TABLE 7-continued

VHL ligands

| Compound No. | Structure | Name[1] |
|---|---|---|
| 102a | 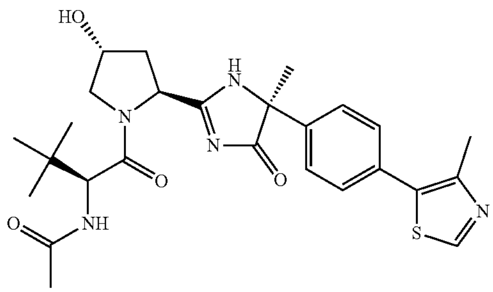 [SMILES: CC(=O)N[C@H](C(=O)N1C[C@H](O)C[C@H]1C1=NC(=O)[C@](C)(c2ccc(-c3scnc3C)cc2)N1)C(C)(C)C] | N-((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)acetamide |
| 102b | 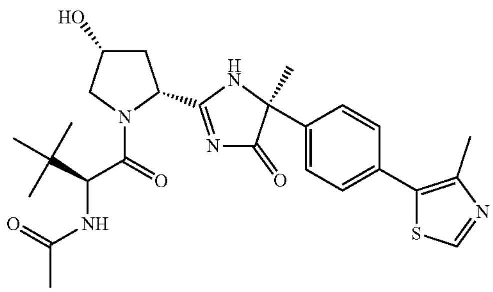 [SMILES: CC(=O)N[C@H](C(=O)N1C[C@H](O)C[C@@H]1C1=NC(=O)[C@](C)(c2ccc(-c3scnc3C)cc2)N1)C(C)(C)C] | N-((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)acetamide |
| 102c | 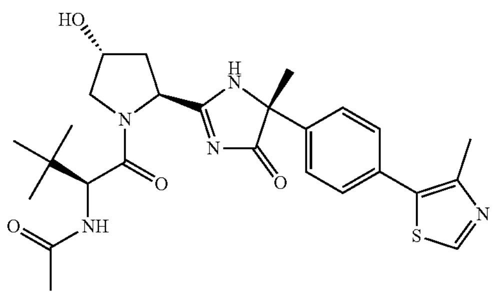 [SMILES: CC(=O)N[C@H](C(=O)N1C[C@H](O)C[C@H]1C1=NC(=O)[C@@](C)(c2ccc(-c3scnc3C)cc2)N1)C(C)(C)C] | N-((S)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)acetamide |
| 102d | 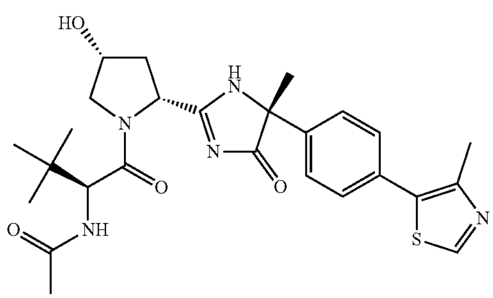 [SMILES: CC(=O)N[C@H](C(=O)N1C[C@H](O)C[C@@H]1C1=NC(=O)[C@@](C)(c2ccc(-c3scnc3C)cc2)N1)C(C)(C)C] | N-((S)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)acetamide |
| 103 | 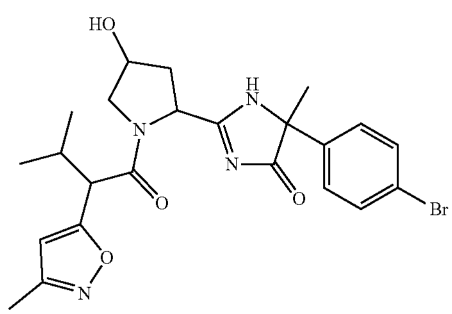 [SMILES: Cc1cc(C(C(=O)N2CC(O)CC2C2=NC(=O)C(C)(c3ccc(Br)cc3)N2)C(C)C)on1] | 5-(4-bromophenyl)-2-(4-hydroxy-1-(3-methyl-2-(3-methylisoxazol-5-yl)butanoyl)pyrrolidin-2-yl)-5-methyl-1,5-dihydro-4H-imidazol-4-one |

TABLE 7-continued

VHL ligands

| Compound No. | Structure | Name |
|---|---|---|
| 103a | 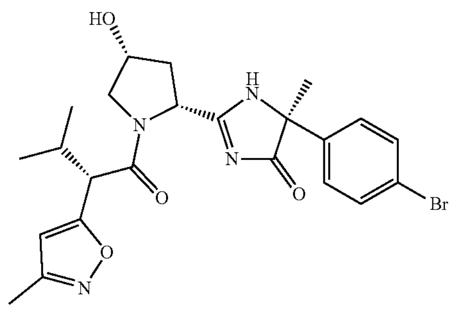 [SMILES: Cc1cc([C@@H](C(=O)N2C[C@H](O)C[C@@H]2C2=NC(=O)[C@](C)(c3ccc(Br)cc3)N2)C(C)C)on1] | (S)-5-(4-bromophenyl)-2-((2R,4R)-4-hydroxy-1-((S)-3-methyl-2-(3-methylisoxazol-5-yl)butanoyl)pyrrolidin-2-yl)-5-methyl-1,5-dihydro-4H-imidazol-4-one |
| 103b | 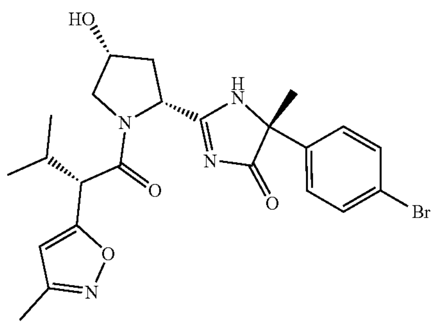 [SMILES: Cc1cc([C@@H](C(=O)N2C[C@H](O)C[C@@H]2C2=NC(=O)[C@@](C)(c3ccc(Br)cc3)N2)C(C)C)on1] | (R)-5-(4-bromophenyl)-2-((2R,4R)-4-hydroxy-1-((S)-3-methyl-2-(3-methylisoxazol-5-yl)butanoyl)pyrrolidin-2-yl)-5-methyl-1,5-dihydro-4H-imidazol-4-one |
| 103c | 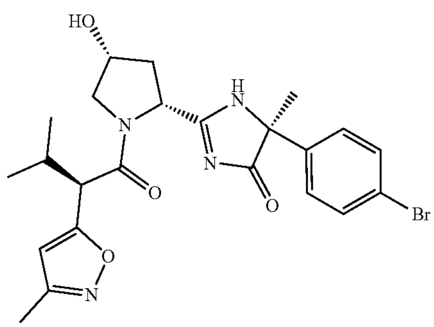 [SMILES: Cc1cc([C@H](C(=O)N2C[C@H](O)C[C@@H]2C2=NC(=O)[C@](C)(c3ccc(Br)cc3)N2)C(C)C)on1] | (S)-5-(4-bromophenyl)-2-((2R,4R)-4-hydroxy-1-((R)-3-methyl-2-(3-methylisoxazol-5-yl)butanoyl)pyrrolidin-2-yl)-5-methyl-1,5-dihydro-4H-imidazol-4-one |
| 103d | 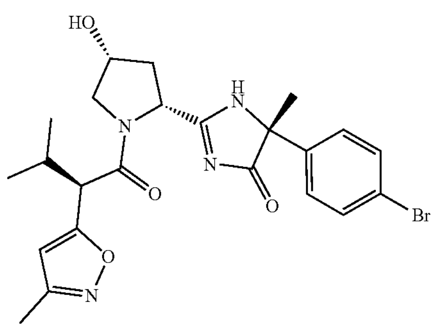 [SMILES: Cc1cc([C@H](C(=O)N2C[C@H](O)C[C@@H]2C2=NC(=O)[C@@](C)(c3ccc(Br)cc3)N2)C(C)C)on1] | (R)-5-(4-bromophenyl)-2-((2R,4R)-4-hydroxy-1-((R)-3-methyl-2-(3-methylisoxazol-5-yl)butanoyl)pyrrolidin-2-yl)-5-methyl-1,5-dihydro-4H-imidazol-4-one |

TABLE 7-continued

VHL ligands

| Compound No. | Structure | Name |
|---|---|---|
| 103e | 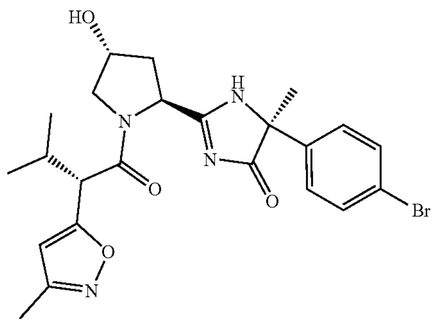 [SMILES: Cc1cc([C@@H](C(=O)N2C[C@H](O)C[C@H]2C2=NC(=O)[C@](C)(c3ccc(Br)cc3)N2)C(C)C)on1] | (S)-5-(4-bromophenyl)-2-((2S,4R)-4-hydroxy-1-((S)-3-methyl-2-(3-methylisoxazol-5-yl)butanoyl)pyrrolidin-2-yl)-5-methyl-1,5-dihydro-4H-imidazol-4-one |
| 103f | 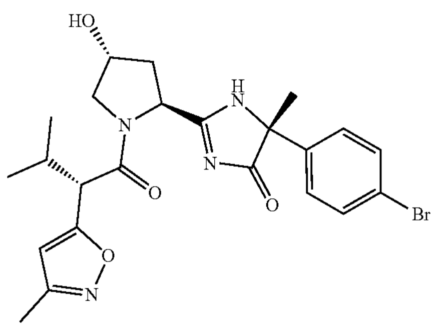 [SMILES: Cc1cc([C@@H](C(=O)N2C[C@H](O)C[C@H]2C2=NC(=O)[C@@](C)(c3ccc(Br)cc3)N2)C(C)C)on1] | (R)-5-(4-bromophenyl)-2-((2S,4R)-4-hydroxy-1-((S)-3-methyl-2-(3-methylisoxazol-5-yl)butanoyl)pyrrolidin-2-yl)-5-methyl-1,5-dihydro-4H-imidazol-4-one |
| 103g | 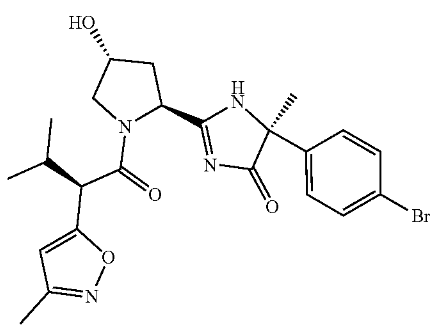 [SMILES: Cc1cc([C@H](C(=O)N2C[C@H](O)C[C@H]2C2=NC(=O)[C@](C)(c3ccc(Br)cc3)N2)C(C)C)on1] | (S)-5-(4-bromophenyl)-2-((2R,4R)-4-hydroxy-1-((S)-3-methyl-2-(3-methylisoxazol-5-yl)butanoyl)pyrrolidin-2-yl)-5-methyl-1,5-dihydro-4H-imidazol-4-one |
| 103h | 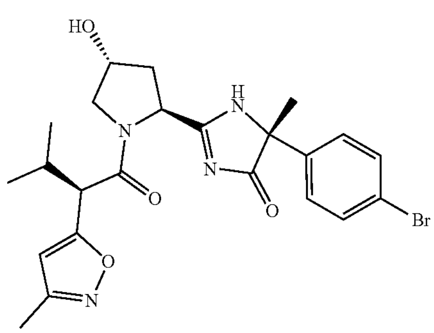 [SMILES: Cc1cc([C@H](C(=O)N2C[C@H](O)C[C@H]2C2=NC(=O)[C@@](C)(c3ccc(Br)cc3)N2)C(C)C)on1] | (R)-5-(4-bromophenyl)-2-((2S,4R)-4-hydroxy-1-((R)-3-methyl-2-(3-methylisoxazol-5-yl)butanoyl)pyrrolidin-2-yl)-5-methyl-1,5-dihydro-4H-imidazol-4-one |

TABLE 7-continued

VHL ligands

| Compound No. | Structure | Name |
|---|---|---|
| 104 | 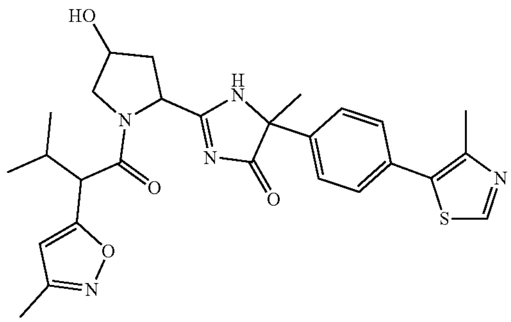 [SMILES: Cc1cc(C(C(=O)N2CC(O)CC2C2=NC(=O)C(C)(c3ccc(-c4scnc4C)cc3)N2)C(C)C)on1] | 2-(4-hydroxy-1-(3-methyl-2-(3-methylisoxazol-5-yl)butanoyl)pyrrolidin-2-yl)-5-methyl-5-(4-(4-methylthiazol-5-yl)phenyl)-1,5-dihydro-4H-imidazol-4-one |
| 104a | 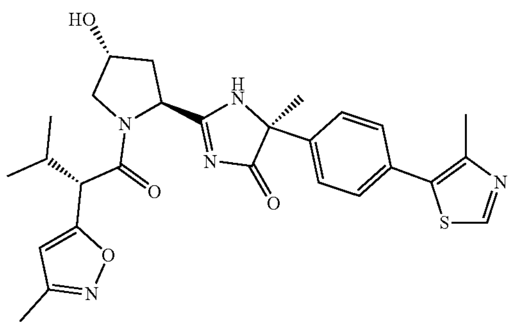 [SMILES: Cc1cc([C@@H](C(=O)N2C[C@H](O)C[C@H]2C2=NC(=O)[C@](C)(c3ccc(-c4scnc4C)cc3)N2)C(C)C)on1] | (S)-2-((2S,4R)-4-hydroxy-1-((S)-3-methyl-2-(3-methylisoxazol-5-yl)butanoyl)pyrrolidin-2-yl)-5-methyl-5-(4-(4-methylthiazol-5-yl)phenyl)-1,5-dihydro-4H-imidazol-4-one |
| 104b | 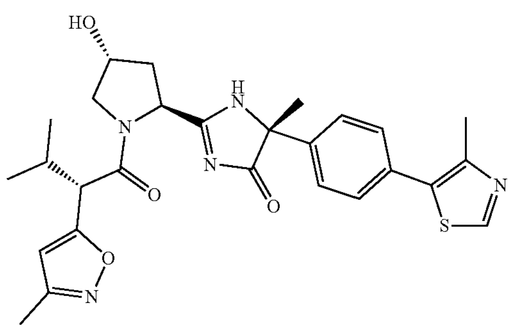 [SMILES: Cc1cc([C@@H](C(=O)N2C[C@H](O)C[C@H]2C2=NC(=O)[C@@](C)(c3ccc(-c4scnc4C)cc3)N2)C(C)C)on1] | (R)-2-((2S,4R)-4-hydroxy-1-((S)-3-methyl-2-(3-methylisoxazol-5-yl)butanoyl)pyrrolidin-2-yl)-5-methyl-5-(4-(4-methylthiazol-5-yl)phenyl)-1,5-dihydro-4H-imidazol-4-one |
| 104c | 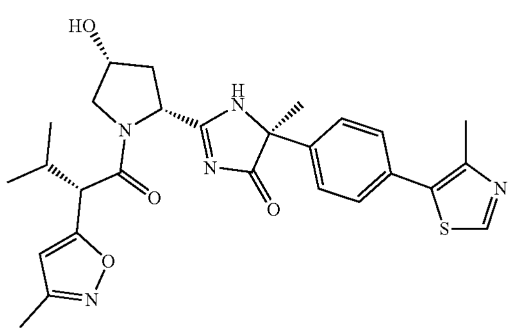 [SMILES: Cc1cc([C@@H](C(=O)N2C[C@H](O)C[C@@H]2C2=NC(=O)[C@](C)(c3ccc(-c4scnc4C)cc3)N2)C(C)C)on1] | (S)-2-((2R,4R)-4-hydroxy-1-((S)-3-methyl-2-(3-methylisoxazol-5-yl)butanoyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 104d | 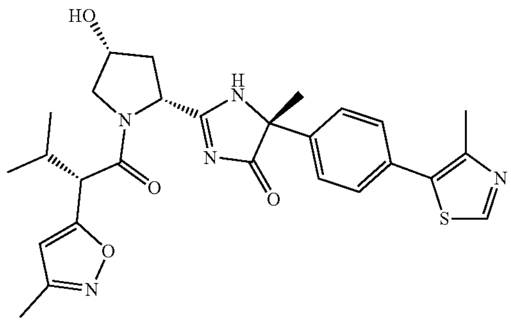 [SMILES: Cc1cc([C@@H](C(=O)N2C[C@H](O)C[C@@H]2C2=NC(=O)[C@@](C)(c3ccc(-c4scnc4C)cc3)N2)C(C)C)on1] | (R)-2-((2R,4R)-4-hydroxy-1-((S)-3-methyl-2-(3-methylisoxazol-5-yl)butanoyl)pyrrolidin-2-yl)-5-methyl-5-(4-(4-methylthiazol-5-yl)phenyl)-1,5-dihydro-4H-imidazol-4-one |
| 104e | 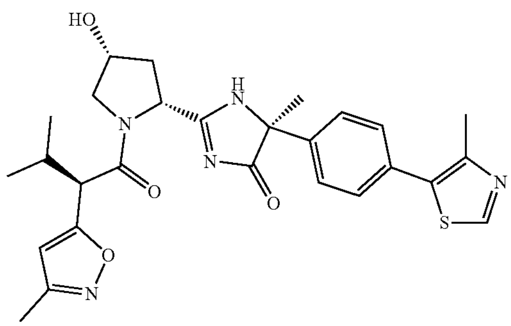 [SMILES: Cc1cc([C@H](C(=O)N2C[C@H](O)C[C@@H]2C2=NC(=O)[C@](C)(c3ccc(-c4scnc4C)cc3)N2)C(C)C)on1] | (S)-2-((2R,4R)-4-hydroxy-1-((R)-3-methyl-2-(3-methylisoxazol-5-yl)butanoyl)pyrrolidin-2-yl)-5-methyl-5-(4-(4-methylthiazol-5-yl)phenyl)-1,5-dihydro-4H-imidazol-4-one |
| 104f | 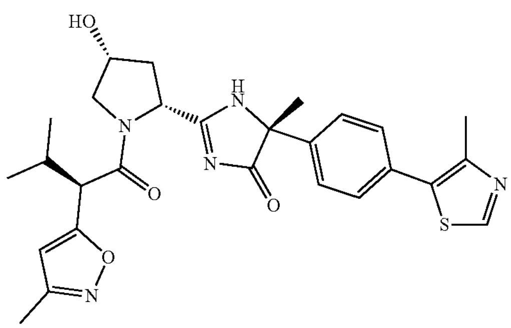 [SMILES: Cc1cc([C@H](C(=O)N2C[C@H](O)C[C@@H]2C2=NC(=O)[C@@](C)(c3ccc(-c4scnc4C)cc3)N2)C(C)C)on1] | (R)-2-((2R,4R)-4-hydroxy-1-((R)-3-methyl-2-(3-methylisoxazol-5-yl)butanoyl)pyrrolidin-2-yl)-5-methyl-5-(4-(4-methylthiazol-5-yl)phenyl)-1,5-dihydro-4H-imidazol-4-one |
| 104g | 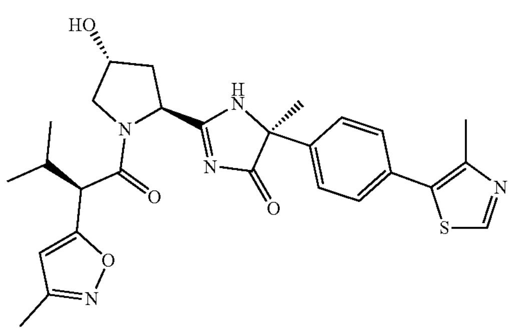 [SMILES: Cc1cc([C@H](C(=O)N2C[C@H](O)C[C@H]2C2=NC(=O)[C@](C)(c3ccc(-c4scnc4C)cc3)N2)C(C)C)on1] | (S)-2-((2S,4R)-4-hydroxy-1-((R)-3-methyl-2-(3-methylisoxazol-5-yl)butanoyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 104h | 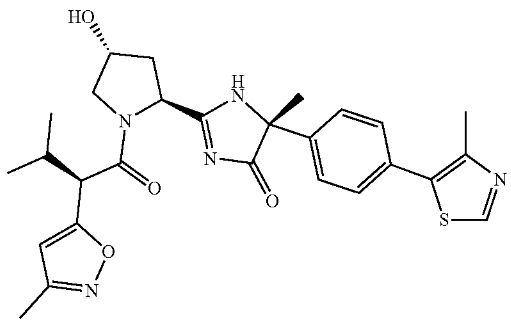 [SMILES: Cc1cc([C@H](C(=O)N2C[C@H](O)C[C@H]2C2=NC(=O)[C@@](C)(c3ccc(-c4scnc4C)cc3)N2)C(C)C)on1] | (R)-2-((2S,4R)-4-hydroxy-1-((R)-3-methyl-2-(3-methylisoxazol-5-yl)butanoyl)pyrrolidin-2-yl)-5-methyl-5-(4-(4-methylthiazol-5-yl)phenyl)-1,5-dihydro-4H-imidazol-4-one |
| 105 | 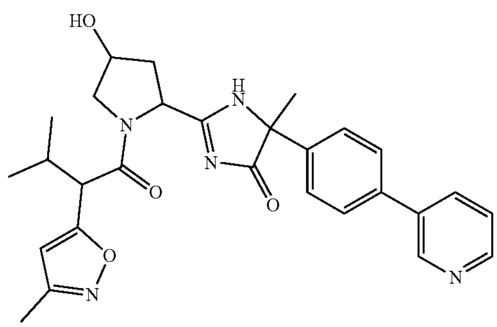 [SMILES: Cc1cc(C(C(=O)N2CC(O)CC2C2=NC(=O)C(C)(c3ccc(-c4cccnc4)cc3)N2)C(C)C)on1] | 2-(4-hydroxy-1-(3-methyl-2-(3-methylisoxazol-5-yl)butanoyl)pyrrolidin-2-yl)-5-methyl-5-(4-(pyridin-3-yl)phenyl)-1,5-dihydro-4H-imidazol-4-one |
| 105a | 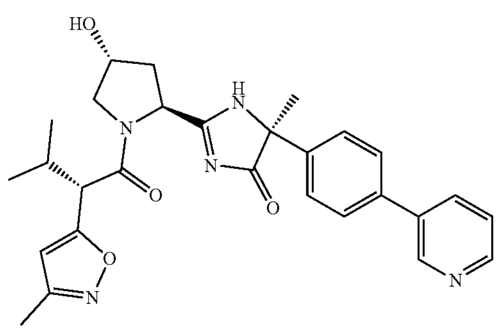 [SMILES: Cc1cc([C@@H](C(=O)N2C[C@H](O)C[C@H]2C2=NC(=O)[C@](C)(c3ccc(-c4cccnc4)cc3)N2)C(C)C)on1] | (S)-2-((2S,4R)-4-hydroxy-1-((S)-3-methyl-2-(3-methylisoxazol-5-yl)butanoyl)pyrrolidin-2-yl)-5-methyl-5-(4-(pyridin-3-yl)phenyl)-1,5-dihydro-4H-imidazol-4-one |
| 105b | 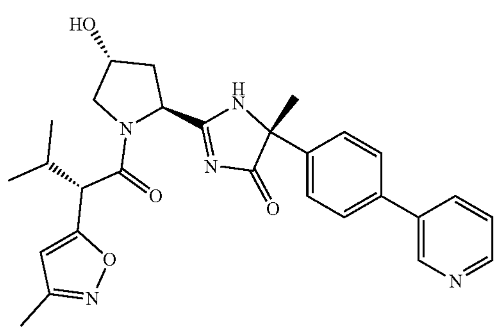 [SMILES: Cc1cc([C@@H](C(=O)N2C[C@H](O)C[C@H]2C2=NC(=O)[C@@](C)(c3ccc(-c4cccnc4)cc3)N2)C(C)C)on1] | (R)-2-((2S,4R)-4-hydroxy-1-((S)-3-methyl-2-(3-methylisoxazol-5-yl)butanoyl)pyrrolidin-2-yl)-5-methyl-5-(4-(pyridin-3-yl)phenyl)-1,5-dihydro-4H-imidazol-4-one |

TABLE 7-continued

VHL ligands

| Compound No. | Structure | Name[1] |
|---|---|---|
| 105c | 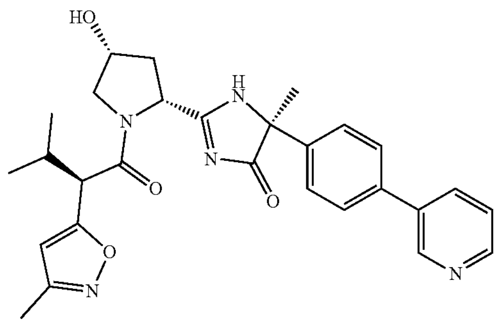 [SMILES: Cc1cc([C@H](C(=O)N2C[C@H](O)C[C@@H]2C2=NC(=O)[C@](C)(c3ccc(-c4cccnc4)cc3)N2)C(C)C)on1] | (S)-2-((2R,4R)-4-hydroxy-1-((R)-3-methyl-2-(3-methylisoxazol-5-yl)butanoyl)pyrrolidin-2-yl)-5-methyl-5-(4-(pyridin-3-yl)phenyl)-1,5-dihydro-4H-imidazol-4-one |
| 105d | 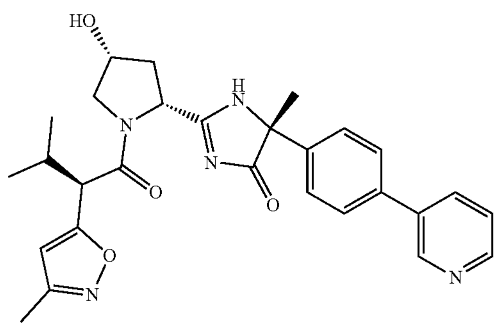 [SMILES: Cc1cc([C@H](C(=O)N2C[C@H](O)C[C@@H]2C2=NC(=O)[C@@](C)(c3ccc(-c4cccnc4)cc3)N2)C(C)C)on1] | (R)-2-((2R,4R)-4-hydroxy-1-((R)-3-methyl-2-(3-methylisoxazol-5-yl)butanoyl)pyrrolidin-2-yl)-5-methyl-5-(4-(pyridin-3-yl)phenyl)-1,5-dihydro-4H-imidazol-4-one |
| 105e | 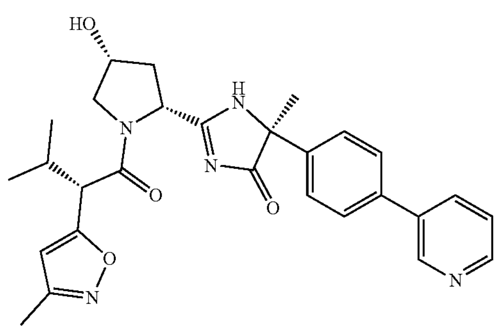 [SMILES: Cc1cc([C@@H](C(=O)N2C[C@H](O)C[C@@H]2C2=NC(=O)[C@](C)(c3ccc(-c4cccnc4)cc3)N2)C(C)C)on1] | (S)-2-((2R,4R)-4-hydroxy-1-((S)-3-methyl-2-(3-methylisoxazol-5-yl)butanoyl)pyrrolidin-2-yl)-5-methyl-5-(4-(pyridin-3-yl)phenyl)-1,5-dihydro-4H-imidazol-4-one |
| 105f | 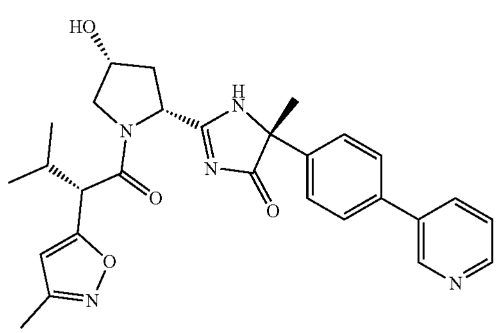 [SMILES: Cc1cc([C@@H](C(=O)N2C[C@H](O)C[C@@H]2C2=NC(=O)[C@@](C)(c3ccc(-c4cccnc4)cc3)N2)C(C)C)on1] | (R)-2-((2R,4R)-4-hydroxy-1-((S)-3-methyl-2-(3-methylisoxazol-5-yl)butanoyl)pyrrolidin-2-yl)-5-methyl-5-(4-(pyridin-3-yl)phenyl)-1,5-dihydro-4H-imidazol-4-one |

TABLE 7-continued

VHL ligands

| Compound No. | Structure | Name[1] |
|---|---|---|
| 105g | 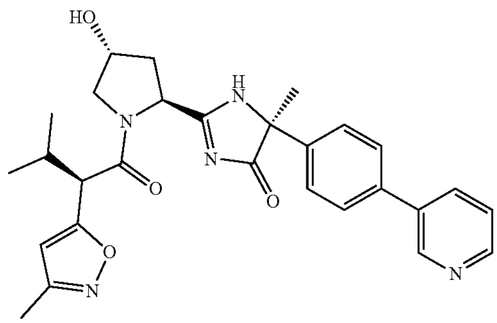 [SMILES: Cc1cc([C@H](C(=O)N2C[C@H](O)C[C@H]2C2=NC(=O)[C@](C)(c3ccc(-c4cccnc4)cc3)N2)C(C)C)on1] | (S)-2-((2S,4R)-4-hydroxy-1-((R)-3-methyl-2-(3-methylisoxazol-5-yl)butanoyl)pyrrolidin-2-yl)-5-methyl-5-(4-(pyridin-3-yl)phenyl)-1,5-dihydro-4H-imidazol-4-one |
| 105h | 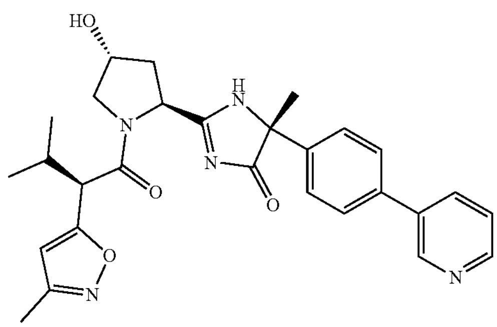 [SMILES: Cc1cc([C@H](C(=O)N2C[C@H](O)C[C@H]2C2=NC(=O)[C@@](C)(c3ccc(-c4cccnc4)cc3)N2)C(C)C)on1] | (R)-2-((2S,4R)-4-hydroxy-1-((R)-3-methyl-2-(3-methylisoxazol-5-yl)butanoyl)pyrrolidin-2-yl)-5-methyl-5-(4-(pyridin-3-yl)phenyl)-1,5-dihydro-4H-imidazol-4-one |
| 106 | 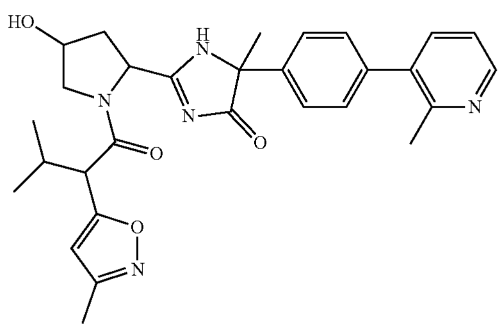 [SMILES: Cc1cc(C(C(=O)N2CC(O)CC2C2=NC(=O)C(C)(c3ccc(-c4cccnc4C)cc3)N2)C(C)C)on1] | 2-(4-hydroxy-1-(3-methyl-2-(3-methylisoxazol-5-yl)butanoyl)pyrrolidin-2-yl)-5-methyl-5-(4-(2-methylpyridin-3-yl)phenyl)-1,5-dihydro-4H-imidazol-4-one |
| 106a | 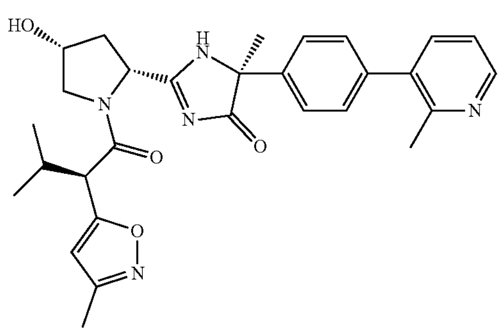 [SMILES: Cc1cc([C@H](C(=O)N2C[C@H](O)C[C@@H]2C2=NC(=O)[C@](C)(c3ccc(-c4cccnc4C)cc3)N2)C(C)C)on1] | (S)-2-((2R,4R)-4-hydroxy-1-((R)-3-methyl-2-(3-methylisoxazol-5-yl)butanoyl)pyrrolidin-2-yl)-5-methyl-5-(4-(2-methylpyridin-3-yl)phenyl)-1,5-dihydro-4H-imidazol-4-one |

TABLE 7-continued

VHL ligands

| Compound No. | Structure | Name[1] |
|---|---|---|
| 106b | 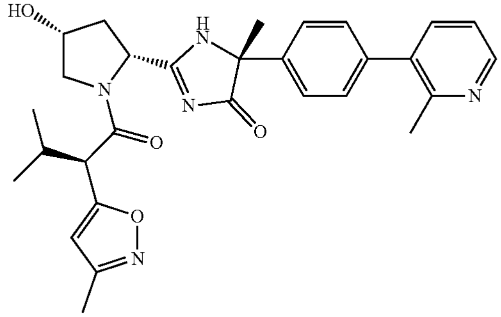 [SMILES: Cc1cc([C@H](C(=O)N2C[C@H](O)C[C@@H]2C2=NC(=O)[C@@](C)(c3ccc(-c4cccnc4C)cc3)N2)C(C)C)on1] | (R)-2-((2R,4R)-4-hydroxy-1-((R)-3-methyl-2-(3-methylisoxazol-5-yl)butanoyl)pyrrolidin-2-yl)-5-methyl-5-(4-(2-methylpyridin-3-yl)phenyl)-1,5-dihydro-4H-imidazol-4-one |
| 106c | 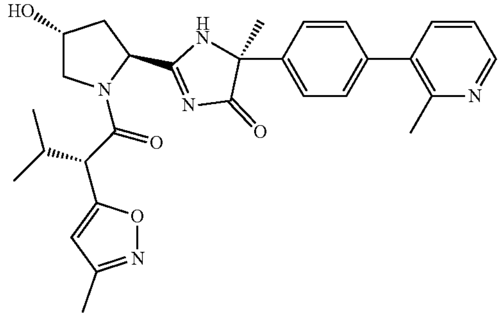 [SMILES: Cc1cc([C@@H](C(=O)N2C[C@H](O)C[C@H]2C2=NC(=O)[C@](C)(c3ccc(-c4cccnc4C)cc3)N2)C(C)C)on1] | (S)-2-((2S,4R)-4-hydroxy-1-((S)-3-methyl-2-(3-methylisoxazol-5-yl)butanoyl)pyrrolidin-2-yl)-5-methyl-5-(4-(2-methylpyridin-3-yl)phenyl)-1,5-dihydro-4H-imidazol-4-one |
| 106d | 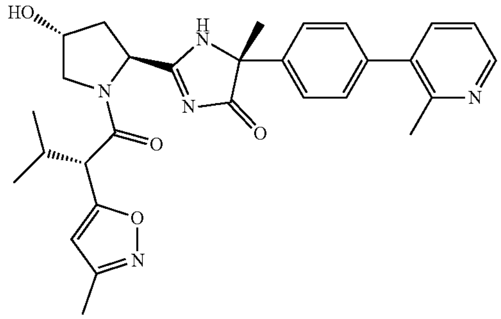 [SMILES: Cc1cc([C@@H](C(=O)N2C[C@H](O)C[C@H]2C2=NC(=O)[C@@](C)(c3ccc(-c4cccnc4C)cc3)N2)C(C)C)on1] | (R)-2-((2S,4R)-4-hydroxy-1-((S)-3-methyl-2-(3-methylisoxazol-5-yl)butanoyl)pyrrolidin-2-yl)-5-methyl-5-(4-(2-methylpyridin-3-yl)phenyl)-1,5-dihydro-4H-imidazol-4-one |
| 106e | 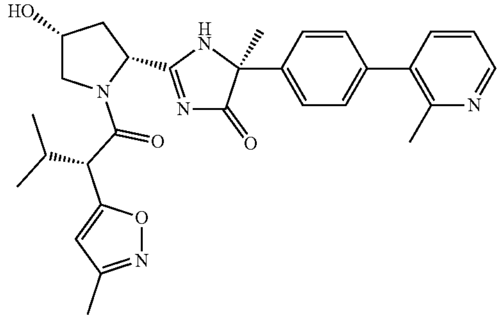 [SMILES: Cc1cc([C@@H](C(=O)N2C[C@H](O)C[C@@H]2C2=NC(=O)[C@](C)(c3ccc(-c4cccnc4C)cc3)N2)C(C)C)on1] | (S)-2-((2R,4R)-4-hydroxy-1-((S)-3-methyl-2-(3-methylisoxazol-5-yl)butanoyl)pyrrolidin-2-yl)-5-methyl-5-(4-(2-methylpyridin-3-yl)phenyl)-1,5-dihydro-4H-imidazol-4-one |

TABLE 7-continued

VHL ligands

| Compound No. | Structure | Name[1] |
|---|---|---|
| 106f | 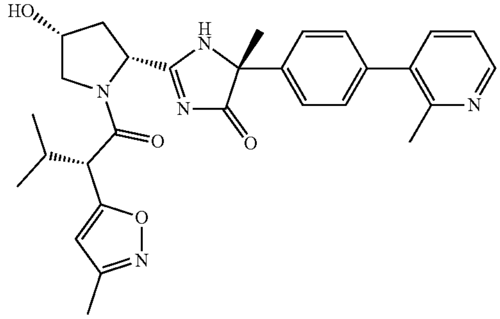 [SMILES: Cc1cc([C@@H](C(=O)N2C[C@H](O)C[C@@H]2C2=NC(=O)[C@@](C)(c3ccc(-c4cccnc4C)cc3)N2)C(C)C)on1] | (R)-2-((2R,4R)-4-hydroxy-1-((S)-3-methyl-2-(3-methylisoxazol-5-yl)butanoyl)pyrrolidin-2-yl)-5-methyl-5-(4-(2-methylpyridin-3-yl)phenyl)-1,5-dihydro-4H-imidazol-4-one |
| 106g | 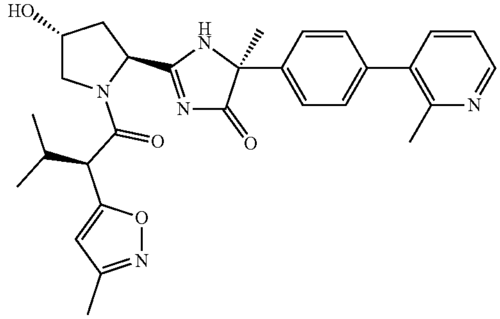 [SMILES: Cc1cc([C@H](C(=O)N2C[C@H](O)C[C@H]2C2=NC(=O)[C@](C)(c3ccc(-c4cccnc4C)cc3)N2)C(C)C)on1] | (S)-2-((2S,4R)-4-hydroxy-1-((R)-3-methyl-2-(3-methylisoxazol-5-yl)butanoyl)pyrrolidin-2-yl)-5-methyl-5-(4-(2-methylpyridin-3-yl)phenyl)-1,5-dihydro-4H-imidazol-4-one |
| 106h | 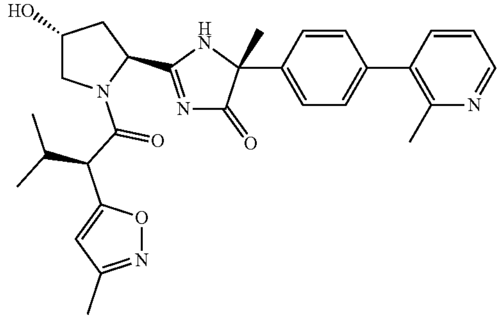 [SMILES: Cc1cc([C@H](C(=O)N2C[C@H](O)C[C@H]2C2=NC(=O)[C@@](C)(c3ccc(-c4cccnc4C)cc3)N2)C(C)C)on1] | (R)-2-((2S,4R)-4-hydroxy-1-((R)-3-methyl-2-(3-methylisoxazol-5-yl)butanoyl)pyrrolidin-2-yl)-5-methyl-5-(4-(2-methylpyridin-3-yl)phenyl)-1,5-dihydro-4H-imidazol-4-one |
| 107 | 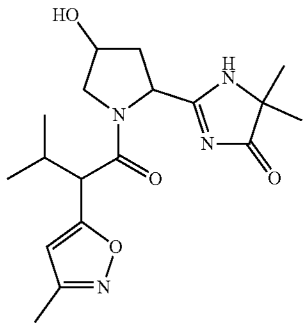 [SMILES: Cc1cc(C(C(=O)N2CC(O)CC2C2=NC(=O)C(C)(C)N2)C(C)C)on1] | 2-(4-hydroxy-1-(3-methyl-2-(3-methylisoxazol-5-yl)butanoyl)pyrrolidin-2-yl)-5,5-dimethyl-1,5-dihydro-4H-imidazol-4-one |

TABLE 7-continued

VHL ligands

| Compound No. | Structure | Name[1] |
|---|---|---|
| 107a | 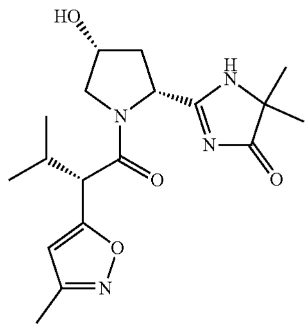 [SMILES: Cc1cc([C@@H](C(=O)N2C[C@H](O)C[C@@H]2C2=NC(=O)C(C)(C)N2)C(C)C)on1] | 2-((2R,4R)-4-hydroxy-1-((S)-3-methyl-2-(3-methylsoxazol-5-yl)butanoyl)pyrrolidin-2-yl)-5,5-dimethyl-1,5-dihydro-4H-imidazol-4-one |
| 107b | 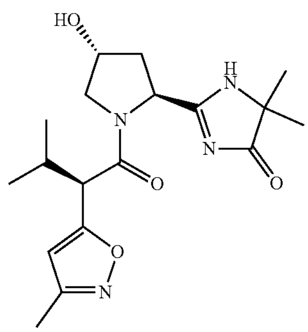 [SMILES: Cc1cc([C@H](C(=O)N2C[C@H](O)C[C@H]2C2=NC(=O)C(C)(C)N2)C(C)C)on1] | 2-((2S,4R)-4-hydroxy-1-((R)-3-methyl-2-(3-methylisoxazol-5-yl)butanoyl)pyrrolidin-2-yl)-5,5-dimethyl-1,5-dihydro-4H-imidazol-4-one |
| 107c | 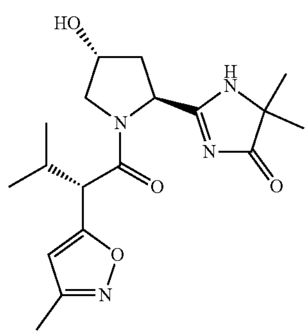 [SMILES: Cc1cc([C@@H](C(=O)N2C[C@H](O)C[C@H]2C2=NC(=O)C(C)(C)N2)C(C)C)on1] | 2-((2S,4R)-4-hydroxy-1-((S)-3-methyl-2-(3-methylisoxazol-5-yl)butanoyl)pyrrolidin-2-yl)-5,5-dimethyl-1,5-dihydro-4H-imidazol-4-one |
| 107d | 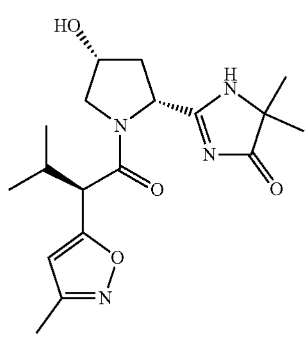 [SMILES: Cc1cc([C@H](C(=O)N2C[C@H](O)C[C@@H]2C2=NC(=O)C(C)(C)N2)C(C)C)on1] | 2-((2R,4R)-4-hydroxy-1-((R)-3-methyl-2-(3-methylisoxazol-5-yl)butanoyl)pyrrolidin-2-yl)-5,5-dimethyl-1,5-dihydro-4H-imidazol-4-one |

TABLE 7-continued

VHL ligands

| Compound No. | Structure | Name[1] |
|---|---|---|
| 108 | 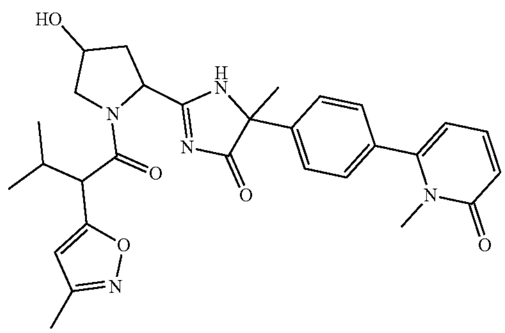 [SMILES: Cc1cc(C(C(=O)N2CC(O)CC2C2=NC(=O)C(C)(c3ccc(-c4cccc(=O)n4C)cc3)N2)C(C)C)on1] | 6-(4-(2-(4-hydroxy-1-(3-methyl-2-(3-methylisoxazol-5-yl)butanoyl)pyrrolidin-2-yl)-5-methyl-4-oxo-4,5-dihydro-1H-imidazol-5-yl)phenyl)-1-methylpyridin-2(1H)-one |
| 108a | 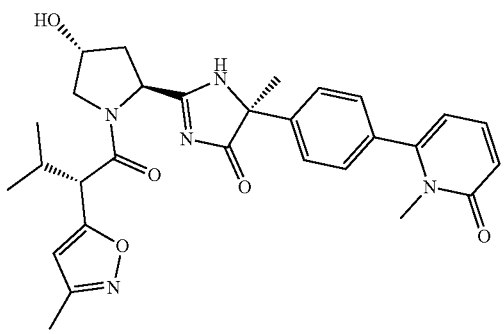 [SMILES: Cc1cc([C@@H](C(=O)N2C[C@H](O)C[C@H]2C2=NC(=O)[C@](C)(c3ccc(-c4cccc(=O)n4C)cc3)N2)C(C)C)on1] | 6-(4-((S)-2-((2S,4R)-4-hydroxy-1-((S)-3-methyl-2-(3-methylisoxazol-5-yl)butanoyl)pyrrolidin-2-yl)-5-methyl-4-oxo-4,5-dihydro-1H-imidazol-5-yl)phenyl)-1-methylpyridin-2(1H)-one |
| 108b | 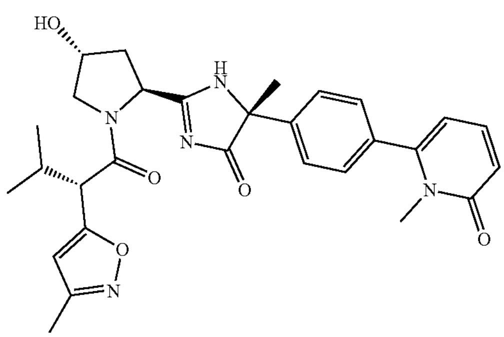 [SMILES: Cc1cc([C@@H](C(=O)N2C[C@H](O)C[C@H]2C2=NC(=O)[C@@](C)(c3ccc(-c4cccc(=O)n4C)cc3)N2)C(C)C)on1] | 6-(4-((R)-2-((2S,4R)-4-hydroxy-1-((S)-3-methyl-2-(3-methylisoxazol-5-yl)butanoyl)pyrrolidin-2-yl)-5-methyl-4-oxo-4,5-dihydro-1H-imidazol-5-yl)phenyl)-1-methylpyridin-2(1H)-one |
| 108c | 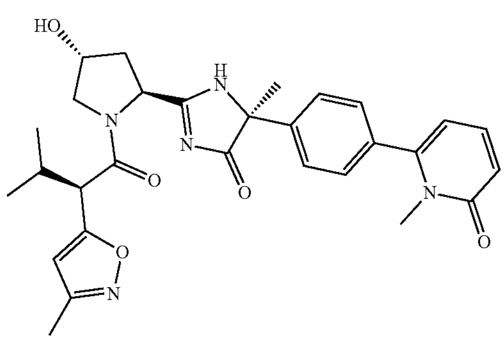 [SMILES: Cc1cc([C@H](C(=O)N2C[C@H](O)C[C@H]2C2=NC(=O)[C@](C)(c3ccc(-c4cccc(=O)n4C)cc3)N2)C(C)C)on1] | 6-(4-((S)-2-((2S,4R)-4-hydroxy-1-((R)-3-methyl-2-(3-methylisoxazol-5-yl)butanoyl)pyrrolidin-2-yl)-5-methyl-4-oxo-4,5-dihydro-1H-imidazol-5-yl)phenyl)-1-methylpyridin-2(1H)-one |

TABLE 7-continued

VHL ligands

| Compound No. | Structure | Name[1] |
|---|---|---|
| 108d | 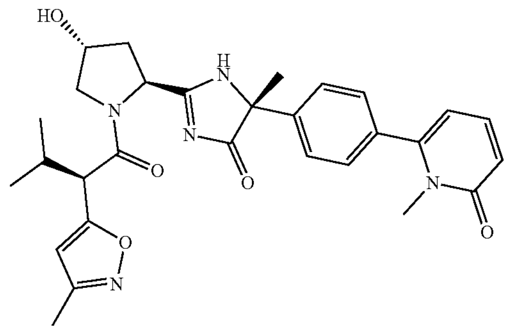 [SMILES: Cc1cc([C@H](C(=O)N2C[C@H](O)C[C@H]2C2=NC(=O)[C@@](C)(c3ccc(-c4cccc(=O)n4C)cc3)N2)C(C)C)on1] | 6-(4-((R)-2-((2S,4R)-4-hydroxy-1-((R)-3-methyl-2-(3-methylisoxazol-5-yl)butanoyl)pyrrolidin-2-yl)-5-methyl-4-oxo-4,5-dihydro-1H-imidazol-5-yl)phenyl)-1-methylpyridin-2(1H)-one |
| 108e | 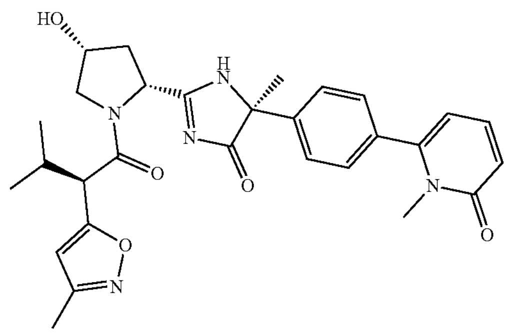 [SMILES: Cc1cc([C@H](C(=O)N2C[C@H](O)C[C@@H]2C2=NC(=O)[C@](C)(c3ccc(-c4cccc(=O)n4C)cc3)N2)C(C)C)on1] | 6-(4-((S)-2-((2R,4R)-4-hydroxy-1-((R)-3-methyl-2-(3-methylisoxazol-5-yl)butanoyl)pyrrolidin-2-yl)-5-methyl-4-oxo-4,5-dihydro-1H-imidazol-5-yl)phenyl)-1-methylpyridin-2(1H)-one |
| 108f | 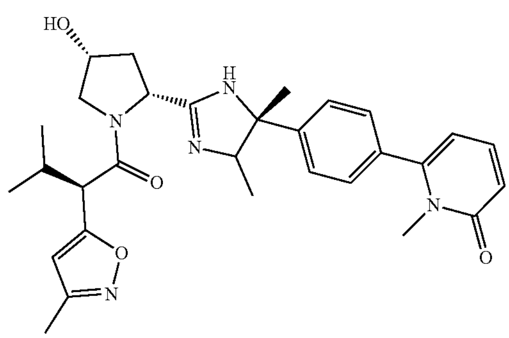 [SMILES: Cc1cc([C@H](C(=O)N2C[C@H](O)C[C@@H]2C2=NC(C)[C@@](C)(c3ccc(-c4cccc(=O)n4C)cc3)N2)C(C)C)on1] | 6-(4-((R)-2-((2R,4R)-4-hydroxy-1-((R)-3-methyl-2-(3-methylisoxazol-5-yl)butanoyl)pyrrolidin-2-yl)-5-methyl-4-oxo-4,5-dihydro-1H-imidazol-5-yl)phenyl)-1-methylpyridin-2(1H)-one |
| 108g | 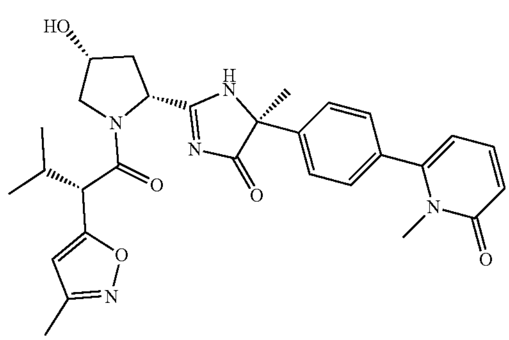 [SMILES: Cc1cc([C@@H](C(=O)N2C[C@H](O)C[C@@H]2C2=NC(=O)[C@](C)(c3ccc(-c4cccc(=O)n4C)cc3)N2)C(C)C)on1] | 6-(4-((S)-2-((2R,4R)-4-hydroxy-1-((S)-3-methyl-2-(3-methylisoxazol-5-yl)butanoyl)pyrrolidin-2-yl)-5-methyl-4-oxo-4,5-dihydro-1H-imidazol-5-yl)phenyl)-1-methylpyridin-2(1H)-one |

TABLE 7-continued

VHL ligands

| Compound No. | Structure | Name[1] |
|---|---|---|
| 108h | 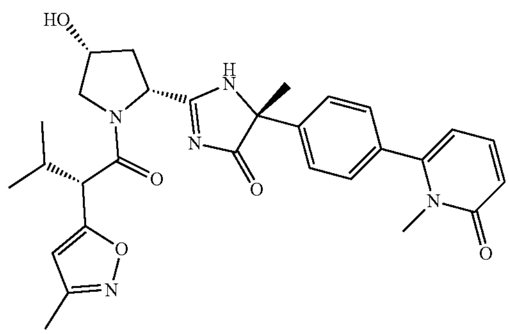 [SMILES: Cc1cc([C@@H](C(=O)N2C[C@H](O)C[C@@H]2C2=NC(=O)[C@@](C)(c3ccc(-c4cccc(=O)n4C)cc3)N2)C(C)C)on1] | 6-(4-((R)-2-((2R,4R)-4-hydroxy-1-((S)-3-methyl-2-(3-methylisoxazol-5-yl)butanoyl)pyrrolidin-2-yl)-5-methyl-4-oxo-4,5-dihydro-1H-imidazol-5-yl)phenyl)-1-methylpyridin-2(1H)-one |
| 109 | 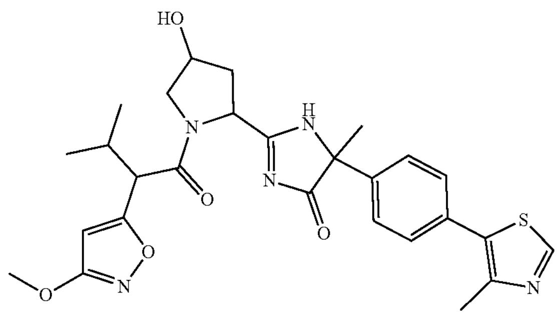 [SMILES: COc1cc(C(C(=O)N2CC(O)CC2C2=NC(=O)C(C)(c3ccc(-c4scnc4C)cc3)N2)C(C)C)on1] | 2-(4-hydroxy-1-(2-(3-methoxyisoxazol-5-yl)-3-methylbutanoyl) pyrrolidin-2-yl)-5-methyl-5-(4-(4-methylthiazol-5-yl)phenyl)-1,5-dihydro-4H-imidazol-4-one |
| 109a | 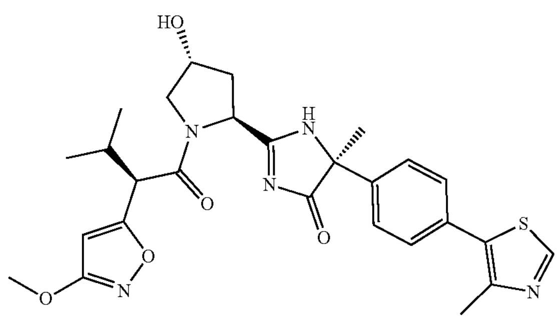 [SMILES: COc1cc([C@H](C(=O)N2C[C@H](O)C[C@H]2C2=NC(=O)[C@](C)(c3ccc(-c4scnc4C)cc3)N2)C(C)C)on1] | (S)-2-((2S,4R)-4-hydroxy-1-((R)-2-(3-methoxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |
| 109b | 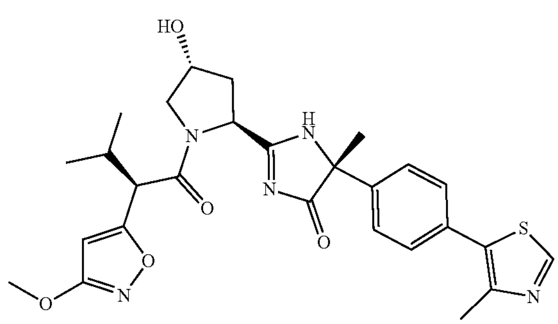 [SMILES: COc1cc([C@H](C(=O)N2C[C@H](O)C[C@H]2C2=NC(=O)[C@@](C)(c3ccc(-c4scnc4C)cc3)N2)C(C)C)on1] | (R)-2-((2S,4R)-4-hydroxy-1-((R)-2-(3-methoxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 109c | 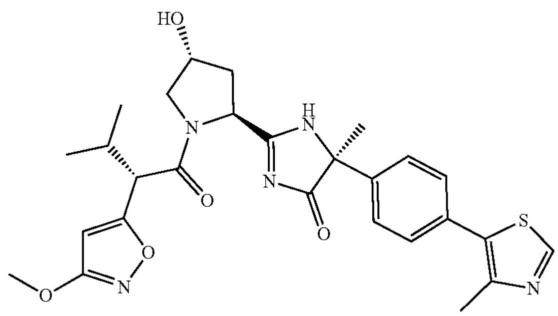 [SMILES: COc1cc([C@@H](C(=O)N2C[C@H](O)C[C@H]2C2=NC(=O)[C@](C)(c3ccc(-c4scnc4C)cc3)N2)C(C)C)on1] | (S)-2-((2S,4R)-4-hydroxy-1-((S)-2-(3-methoxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |
| 109d | 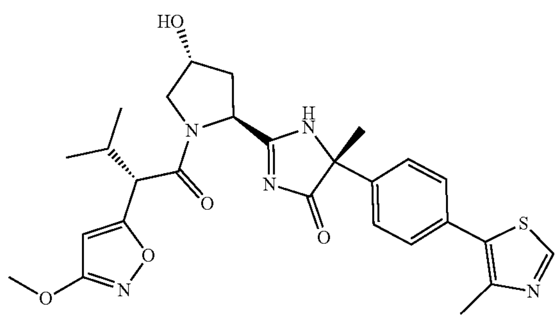 [SMILES: COc1cc([C@@H](C(=O)N2C[C@H](O)C[C@H]2C2=NC(=O)[C@@](C)(c3ccc(-c4scnc4C)cc3)N2)C(C)C)on1] | (R)-2-((2S,4R)-4-hydroxy-1-((S)-2-(3-methoxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |
| 109e | 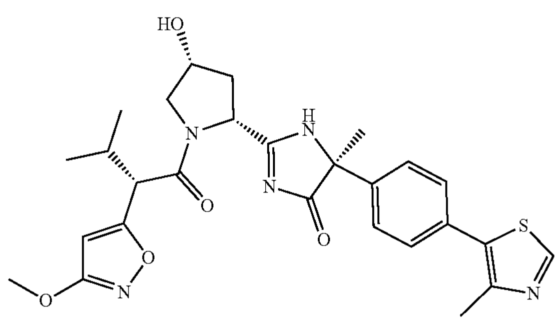 [SMILES: COc1cc([C@@H](C(=O)N2C[C@H](O)C[C@@H]2C2=NC(=O)[C@](C)(c3ccc(-c4scnc4C)cc3)N2)C(C)C)on1] | (S)-2-((2R,4R)-4-hydroxy-1-((S)-2-(3-methoxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |
| 109f | 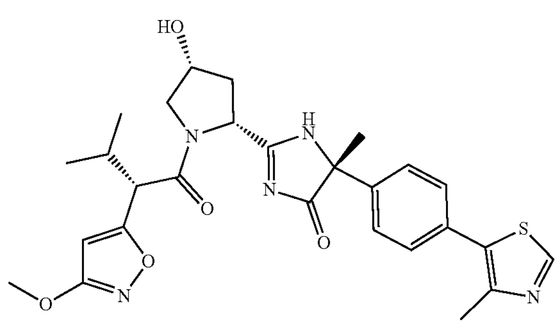 [SMILES: COc1cc([C@@H](C(=O)N2C[C@H](O)C[C@@H]2C2=NC(=O)[C@@](C)(c3ccc(-c4scnc4C)cc3)N2)C(C)C)on1] | (R)-2-((2R,4R)-4-hydroxy-1-((S)-2-(3-methoxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 109g | 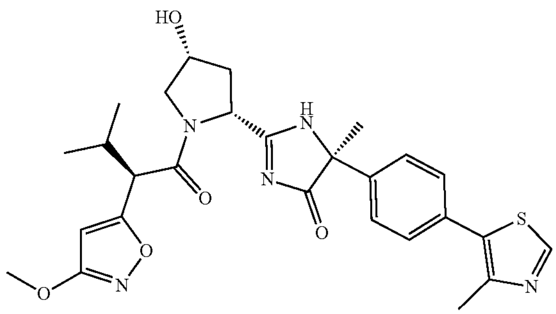 [SMILES: COc1cc([C@H](C(=O)N2C[C@H](O)C[C@@H]2C2=NC(=O)[C@](C)(c3ccc(-c4scnc4C)cc3)N2)C(C)C)on1] | (S)-2-((2R,4R)-4-hydroxy-1-((R)-2-(3-methoxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |
| 109h | 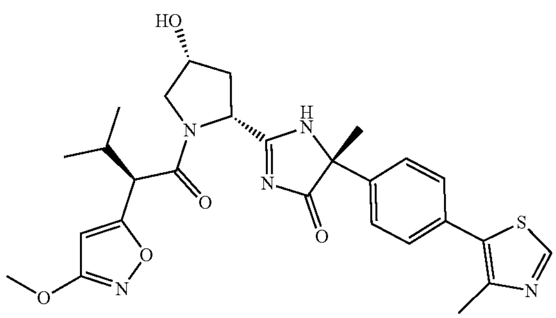 [SMILES: COc1cc([C@H](C(=O)N2C[C@H](O)C[C@@H]2C2=NC(=O)[C@@](C)(c3ccc(-c4scnc4C)cc3)N2)C(C)C)on1] | (R)-2-((2R,4R)-4-hydroxy-1-((R)-2-(3-methoxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |
| 110 | 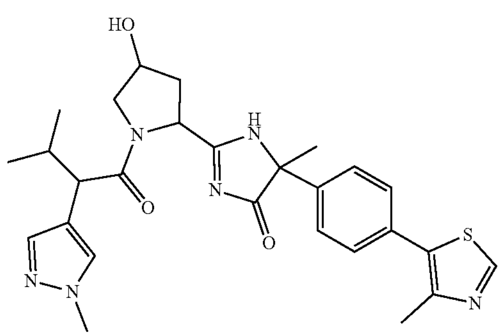 [SMILES: Cc1ncsc1-c1ccc(C2(C)NC(C3CC(O)CN3C(=O)C(c3cnn(C)c3)C(C)C)=NC2=O)cc1] | 2-(4-hydroxy-1-(3-methyl-2-(1-methyl-1H-pyrazol-4-yl)butanoyl)pyrrolidin-2-yl)-5-methyl-5-(4-(4-methylthiazol-5-yl)phenyl)-1,5-dihydro-4H-imidazol-4-one |
| 110a | 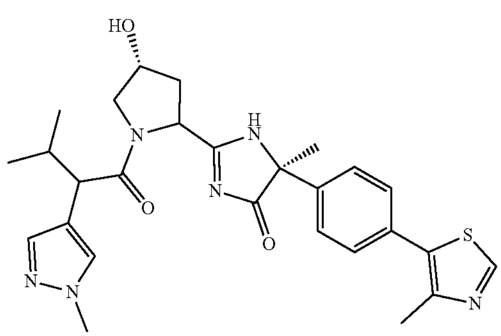 [SMILES: Cc1ncsc1-c1ccc([C@]2(C)NC(C3C[C@@H](O)CN3C(=O)C(c3cnn(C)c3)C(C)C)=NC2=O)cc1] | (5S)-2-((4R)-4-hydroxy-1-(3-methyl-2-(1-methyl-1H-pyrazol-4-yl)butanoyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 110b | 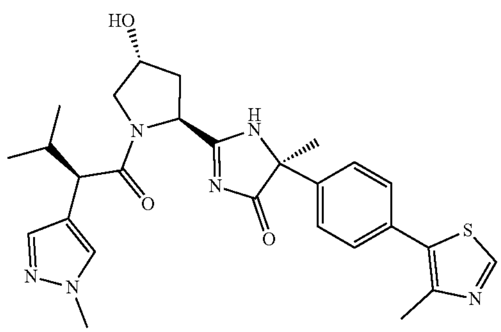 [SMILES: Cc1ncsc1-c1ccc([C@]2(C)NC([C@@H]3C[C@@H](O)CN3C(=O)[C@@H](c3cnn(C)c3)C(C)C)=NC2=O)cc1] | (S)-2-((2S,4R)-4-hydroxy-1-((R)-3-methyl-2-(1-methyl-1H-pyrazol-4-yl)butanoyl)pyrrolidin-2-yl)-5-methyl-5-(4-(4-methylthiazol-5-yl)phenyl)-1,5-dihydro-4H-imidazol-4-one |
| 110c | 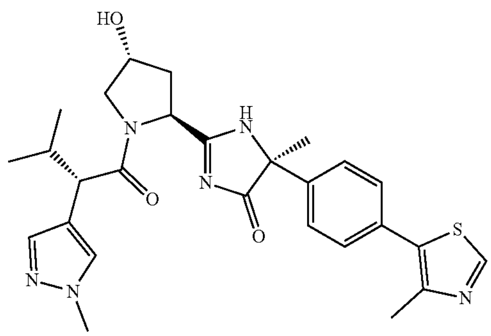 [SMILES: Cc1ncsc1-c1ccc([C@]2(C)NC([C@@H]3C[C@@H](O)CN3C(=O)[C@H](c3cnn(C)c3)C(C)C)=NC2=O)cc1] | (S)-2-((2S,4R)-4-hydroxy-1-((S)-3-methyl-2-(1-methyl-1H-pyrazol-4-yl)butanoyl)pyrrolidin-2-yl)-5-methyl-5-(4-(4-methylthiazol-5-yl)phenyl)-1,5-dihydro-4H-imidazol-4-one |
| 110d | 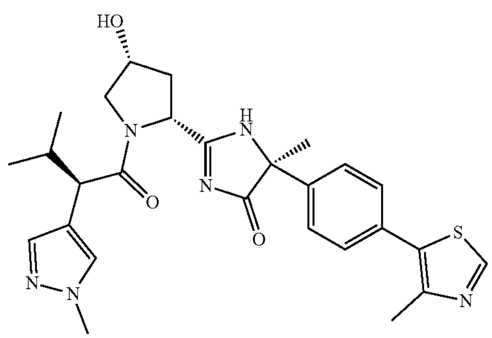 [SMILES: Cc1ncsc1-c1ccc([C@]2(C)NC([C@H]3C[C@@H](O)CN3C(=O)[C@@H](c3cnn(C)c3)C(C)C)=NC2=O)cc1] | (S)-2-((2R,4R)-4-hydroxy-1-((R)-3-methyl-2-(1-methyl-1H-pyrazol-4-yl)butanoyl)pyrrolidin-2-yl)-5-methyl-5-(4-(4-methylthiazol-5-yl)phenyl)-1,5-dihydro-4H-imidazol-4-one |
| 110e | 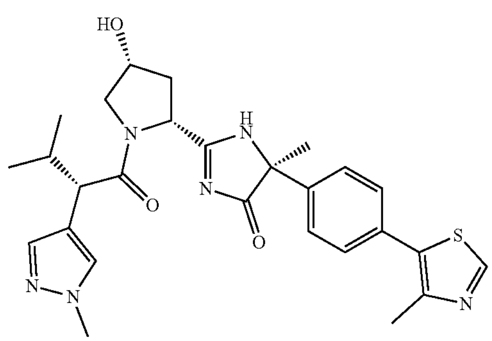 [SMILES: Cc1ncsc1-c1ccc([C@]2(C)NC([C@H]3C[C@@H](O)CN3C(=O)[C@H](c3cnn(C)c3)C(C)C)=NC2=O)cc1] | (S)-2-((2R,4R)-4-hydroxy-1-((S)-3-methyl-2-(1-methyl-1H-pyrazol-4-yl)butanoyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 111 | 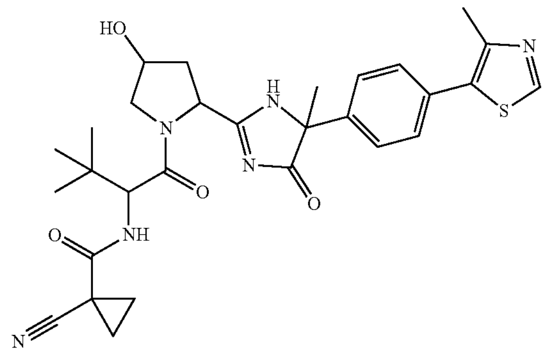 [SMILES: Cc1ncsc1-c1ccc(C2(C)NC(C3CC(O)CN3C(=O)C(NC(=O)C3(C#N)CC3)C(C)(C)C)=NC2=O)cc1] | 1-cyano-N-(1-(4-hydroxy-2-(5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)cyclopropane-1-carboxamide |
| 111a | 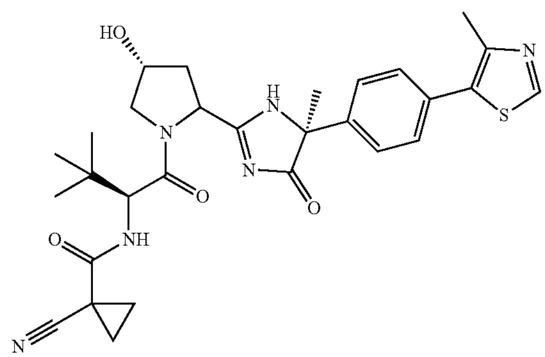 [SMILES: Cc1ncsc1-c1ccc([C@]2(C)NC(C3C[C@@H](O)CN3C(=O)[C@@H](NC(=O)C3(C#N)CC3)C(C)(C)C)=NC2=O)cc1] | 1-cyano-N-((2S)-1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)cyclopropane-1-carboxamide |
| 111b | 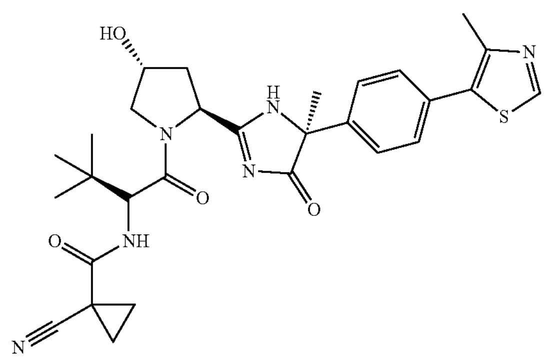 | 1-cyano-N-((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)cyclopropane-1-carboxamide |
| 111c | 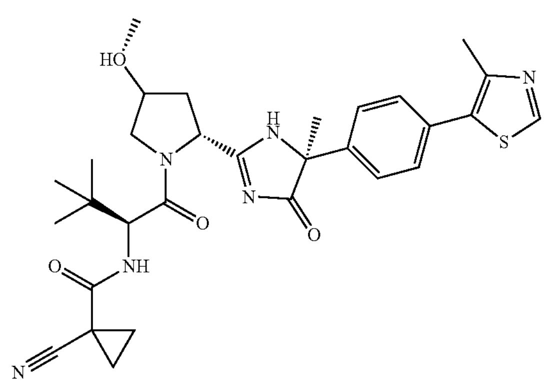 | 1-cyano-N-((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)cyclopropane-1-carboxamide |

TABLE 7-continued

VHL ligands

| Compound No. | Structure | Name[1] |
|---|---|---|
| 112 and 120 | 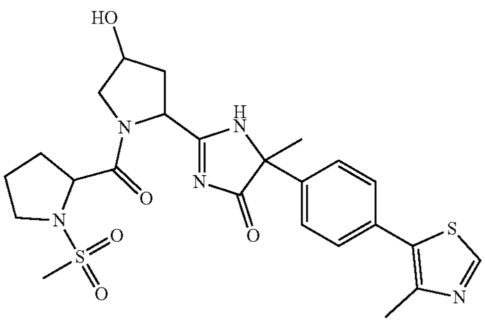 [SMILES: Cc1ncsc1-c1ccc(C2(C)NC(C3CC(O)CN3C(=O)C3CCCN3S(C)(=O)=O)=NC2=O)cc1] | 2-(4-hydroxy-1-((methylsulfonyl)prolyl)pyrrolidin-2-yl)-5-methyl-5-(4-(4-methylthiazol-5-yl)phenyl)-1,5-dihydro-4H-imidazol-4-one |
| 112a | 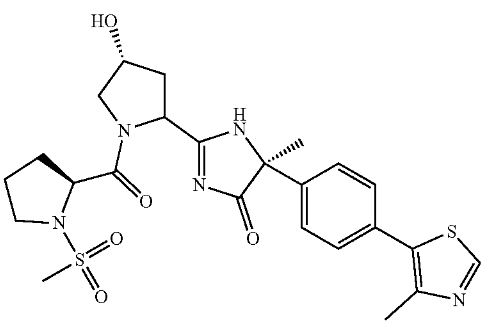 | (5S)-2-((4R)-4-hydroxy-1-((methylsulfonyl)-L-prolyl)pyrrolidin-2-yl)-5-methyl-5-(4-(4-methylthiazol-5-yl)phenyl)-1,5-dihydro-4H-imidazol-4-one |
| 112b | 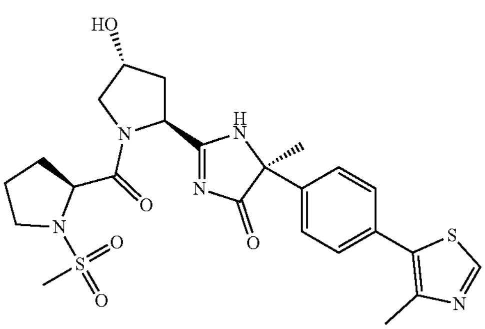 [SMILES: Cc1ncsc1-c1ccc([C@]2(C)NC([C@@H]3C[C@@H](O)CN3C(=O)[C@@H]3CCCN3S(C)(=O)=O)=NC2=O)cc1] | (S)-2-((2S,4R)-4-hydroxy-1-((methylsulfonyl)-L-prolyl)pyrrolidin-2-yl)-5-methyl-5-(4-(4-methylthiazol-5-yl)phenyl)-1,5-dihydro-4H-imidazol-4-one |
| 112c | 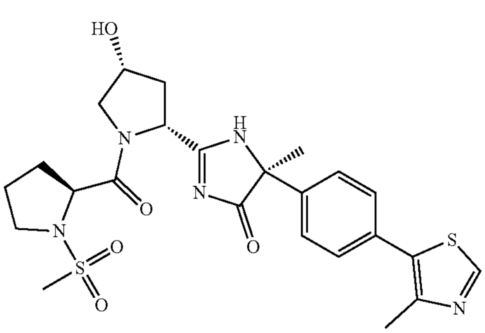 [SMILES: Cc1ncsc1-c1ccc([C@]2(C)NC([C@H]3C[C@@H](O)CN3C(=O)[C@@H]3CCCN3S(C)(=O)=O)=NC2=O)cc1] | (S)-2-((2R,4R)-4-hydroxy-1-((methylsulfonyl)-L-prolyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 113 | 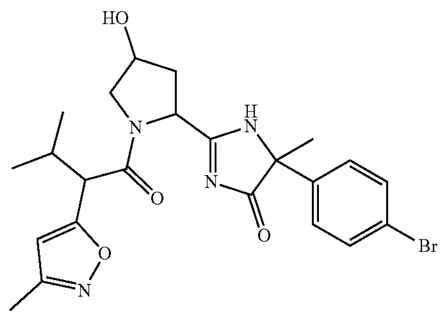 [SMILES: Cc1cc(C(C(=O)N2CC(O)CC2C2=NC(=O)C(C)(c3ccc(Br)cc3)N2)C(C)C)on1] | 1-(2-(5-(4-bromophenyl)-5-(5-4,5-dihydro-1,2,4-oxadiazol-3-yl)-4-hydroxypyrrolidin-1-yl)-3-methyl-2-(3-methylisoxazol-5-yl)butan-1-one |
| 113a | 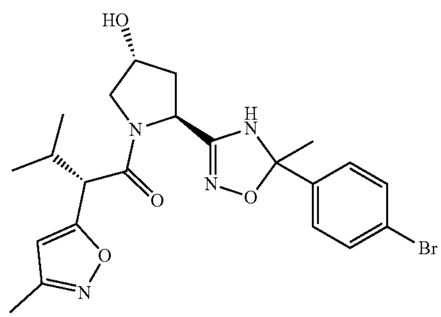 [SMILES: Cc1cc([C@@H](C(=O)N2C[C@H](O)C[C@H]2C2=NOC(C)(c3ccc(Br)cc3)N2)C(C)C)on1] | (2S)-1-((2S,4R)-2-(5-(4-bromophenyl)-5-methyl-4,5-dihydro-1,2,4-oxadiazol-3-yl)-4-hydroxypyrrolidin-1-yl)-3-methyl-2-(3-methylisoxazol-5-yl)butan-1-one |
| 113b | 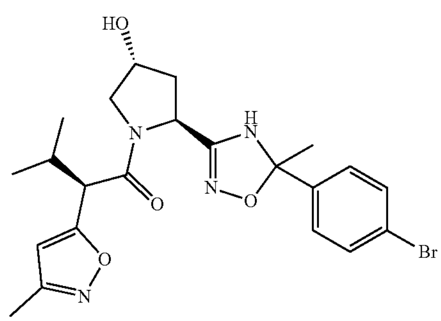 [SMILES: Cc1cc([C@H](C(=O)N2C[C@H](O)C[C@H]2C2=NOC(C)(c3ccc(Br)cc3)N2)C(C)C)on1] | (2R)-1-((2S,4R)-2-(5-(4-bromophenyl)-5-methyl-4,5-dihydro-1,2,4-oxadiazol-3-yl)-4-hydroxypyrrolidin-1-yl)-3-methyl-2-(3-methylisoxazol-5-yl)butan-1-one |
| 113c | 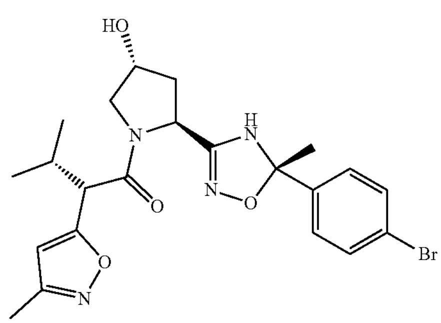 | (S)-1-((2S,4R)-2-((S)-5-(4-bromophenyl)-5-methyl-4,5-dihydro-1,2,4-oxadiazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 113d | 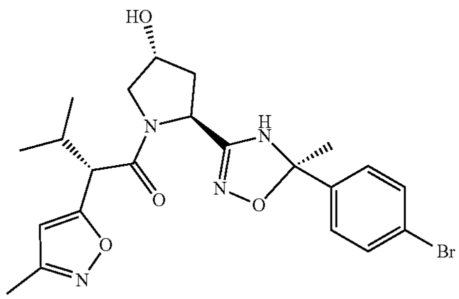 [SMILES: Cc1cc([C@@H](C(=O)N2C[C@H](O)C[C@H]2C2=NO[C@](C)(c3ccc(Br)cc3)N2)C(C)C)on1] | (S)-1-((2S,4R)-2-((R)-5-(4-bromophenyl)-5-methyl-4,5-dihydro-1,2,4-oxadiazol-3-yl)-4-hydroxypyrrolidin-1-yl)-3-methyl-2-(3-methylisoxazol-5-yl)butan-1-one |
| 113e | 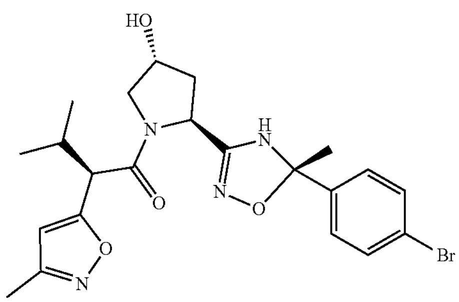 [SMILES: Cc1cc([C@H](C(=O)N2C[C@H](O)C[C@H]2C2=NO[C@@](C)(c3ccc(Br)cc3)N2)C(C)C)on1] | (R)-1-((2S,4R)-2-((S)-5-(4-bromophenyl)-5-methyl-4,5-dihydro-1,2,4-oxadiazol-3-yl)-4-hydroxypyrrolidin-1-yl)-3-methyl-2-(3-methylisoxazol-5-yl)butan-1-one |
| 113f | 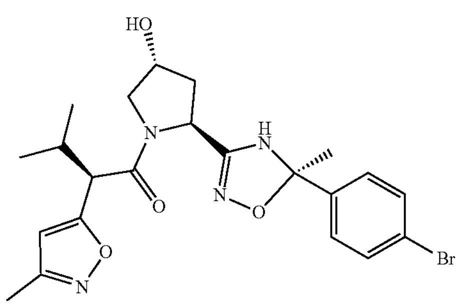 [SMILES: Cc1cc([C@H](C(=O)N2C[C@H](O)C[C@H]2C2=NO[C@](C)(c3ccc(Br)cc3)N2)C(C)C)on1] | (R)-1-((2S,4R)-2-((R)-5-(4-bromophenyl)-5-methyl-4,5-dihydro-1,2,4-oxadiazol-3-yl)-4-hydroxypyrrolidin-1-yl)-3-methyl-2-(3-methylisoxazol-5-yl)butan-1-one |
| 114 | 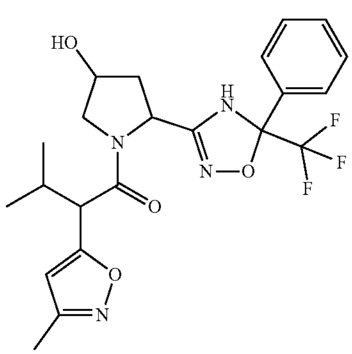 [SMILES: Cc1cc(C(C(=O)N2CC(O)CC2C2=NOC(c3ccccc3)(C(F)(F)F)N2)C(C)C)on1] | 1-(4-hydroxy-2-(5-phenyl-5-(trifluoromethyl)-4,5-dihydro-1,2,4-oxadiazol-3-yl)pyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 114a | 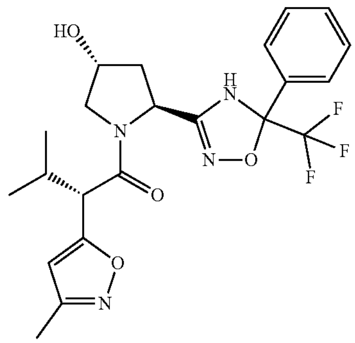 [SMILES: Cc1cc([C@@H](C(=O)N2C[C@H](O)C[C@H]2C2=NOC(c3ccccc3)(C(F)(F)F)N2)C(C)C)on1] | (2S)-1-((2S,4R)-4-hydroxy-2-(5-phenyl-5-(trifluoromethyl)-4,5-dihydro-1,2,4-oxadiazol-3-yl)pyrrolidin-1-yl)-3-methyl-2-(3-methylisoxazol-5-yl)butan-1-one |
| 114b | 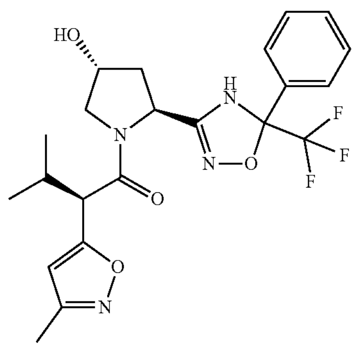 [SMILES: Cc1cc([C@H](C(=O)N2C[C@H](O)C[C@H]2C2=NOC(c3ccccc3)(C(F)(F)F)N2)C(C)C)on1] | (2R)-1-((2S,4R)-4-hydroxy-2-(5-phenyl-5-(trifluoromethyl)-4,5-dihydro-1,2,4-oxadiazol-3-yl)pyrrolidin-1-yl)-3-methyl-2-(3-methylisoxazol-5-yl)butan-1-one |
| 114c | 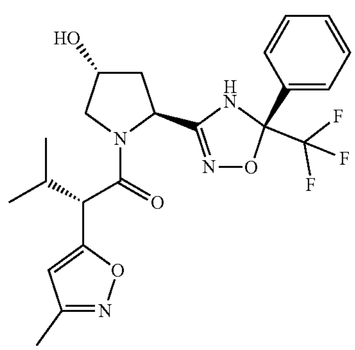 [SMILES: Cc1cc([C@@H](C(=O)N2C[C@H](O)C[C@H]2C2=NO[C@@](c3ccccc3)(C(F)(F)F)N2)C(C)C)on1] | (S)-1-((2S,4R)-4-hydroxy-2-((S)-5-phenyl-5-(trifluoromethyl)-4,5-dihydro-1,2,4-oxadiazol-3-yl)pyrrolidin-1-yl)-3-methyl-2-(3-methylisoxazol-5-yl)butan-1-one |
| 114d | 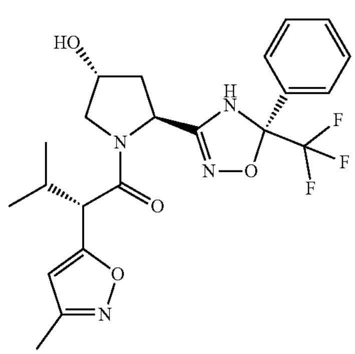 [SMILES: Cc1cc([C@@H](C(=O)N2C[C@H](O)C[C@H]2C2=NO[C@](c3ccccc3)(C(F)(F)F)N2)C(C)C)on1] | (S)-1-((2S,4R)-4-hydroxy-2-((R)-5-phenyl-5-(trifluoromethyl)-4,5-dihydro-1,2,4-oxadiazol-3-yl)pyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 114e | 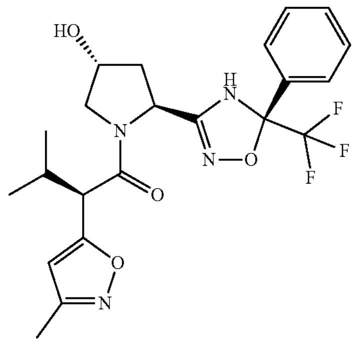 [SMILES: Cc1cc([C@H](C(=O)N2C[C@H](O)C[C@H]2C2=NO[C@@](c3ccccc3)(C(F)(F)F)N2)C(C)C)on1] | (R)-1-((2S,4R)-4-hydroxy-2-((S)-5-phenyl-5-(trifluoromethyl)-4,5-dihydro-1,2,4-oxadiazol-3-yl)pyrrolidin-1-yl)-3-methyl-2-(3-methylisoxazol-5-yl)butan-1-one |
| 114f | 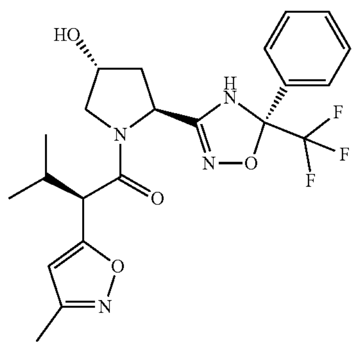 [SMILES: Cc1cc([C@H](C(=O)N2C[C@H](O)C[C@H]2C2=NO[C@](c3ccccc3)(C(F)(F)F)N2)C(C)C)on1] | (R)-1-((2S,4R)-4-hydroxy-2-((R)-5-phenyl-5-(trifluoromethyl)-4,5-dihydro-1,2,4-oxadiazol-3-yl)pyrrolidin-1-yl)-3-methyl-2-(3-methylisoxazol-5-yl)butan-1-one |
| 115 | 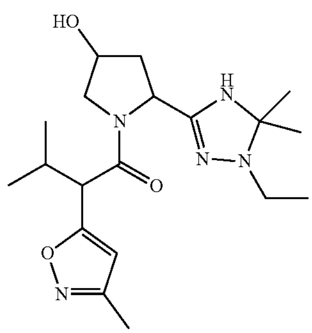 [SMILES: CCN1N=C(C2CC(O)CN2C(=O)C(c2cc(C)no2)C(C)C)NC1(C)C] | 1-(2-(1-ethyl-5,5-dimethyl-4,5-dihydro-1H-1,2,4-triazol-3-yl)-4-hydroxypyrrolidin-1-yl)-3-methyl-2-(3-methylisoxazol-5-yl)butan-1-one |
| 115a | 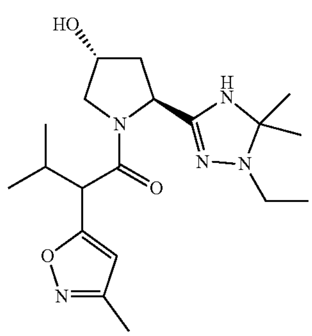 [SMILES: CCN1N=C([C@@H]2C[C@@H](O)CN2C(=O)C(c2cc(C)no2)C(C)C)NC1(C)C] | 1-((2S,4R)-2-(1-ethyl-5,5-dimethyl-4,5-dihydro-1H-1,2,4-triazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 115b | 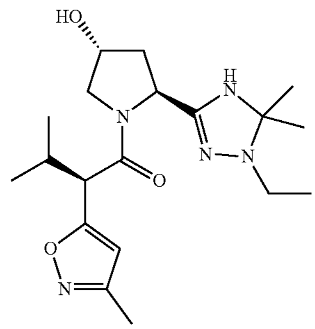 [SMILES: CCN1N=C([C@@H]2C[C@@H](O)CN2C(=O)[C@@H](c2cc(C)no2)C(C)C)NC1(C)C] | (R)-1-((2S,4R)-2-(1-ethyl-5,5-dimethyl-4,5-dihydro-1H-1,2,4-triazol-3-yl)-4-hydroxypyrrolidin-1-yl)-3-methyl-2-(3-methylisoxazol-5-yl)butan-1-one |
| 115c | 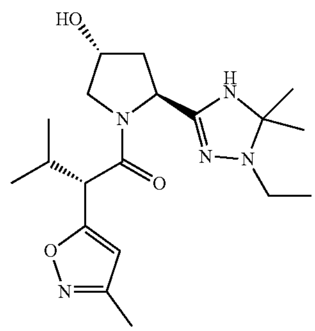 [SMILES: CCN1N=C([C@@H]2C[C@@H](O)CN2C(=O)[C@H](c2cc(C)no2)C(C)C)NC1(C)C] | (S)-1-((2S,4R)-2-(1-ethyl-5,5-dimethyl-4,5-dihydro-1H-1,2,4-triazol-3-yl)-4-hydroxypyrrolidin-1-yl)-3-methyl-2-(3-methylisoxazol-5-yl)butan-1-one |
| 116 | 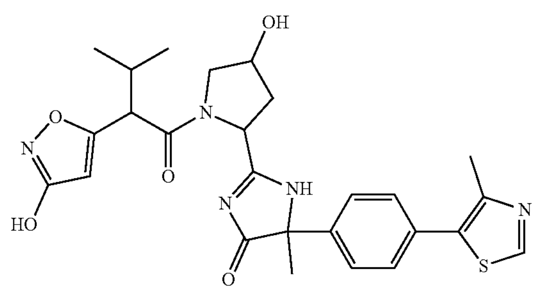 [SMILES: Cc1ncsc1-c1ccc(C2(C)NC(C3CC(O)CN3C(=O)C(c3cc(O)no3)C(C)C)=NC2=O)cc1] | 2-(4-hydroxy-1-(2-(3-hydroxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |
| 116a | 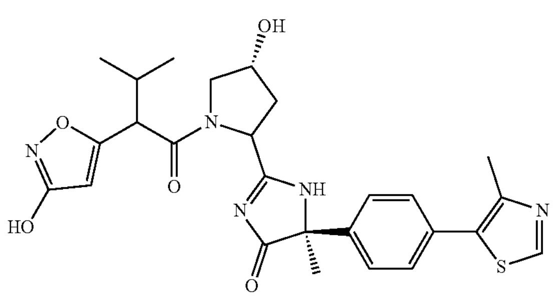 [SMILES: Cc1ncsc1-c1ccc([C@]2(C)NC(C3C[C@@H](O)CN3C(=O)C(c3cc(O)no3)C(C)C)=NC2=O)cc1] | (5S)-2-((4R)-4-hydroxy-1-(2-(3-hydroxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |
| 116b | 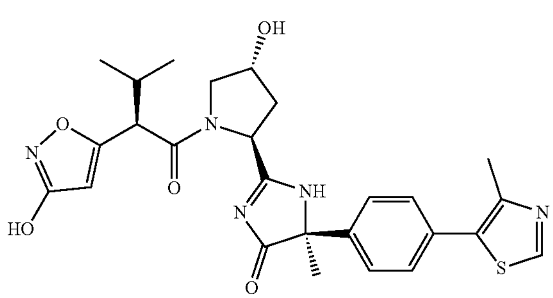 [SMILES: Cc1ncsc1-c1ccc([C@]2(C)NC([C@@H]3C[C@@H](O)CN3C(=O)[C@@H](c3cc(O)no3)C(C)C)=NC2=O)cc1] | (S)-2-((2S,4R)-4-hydroxy-1-((R)-2-(3-hydroxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 116c | 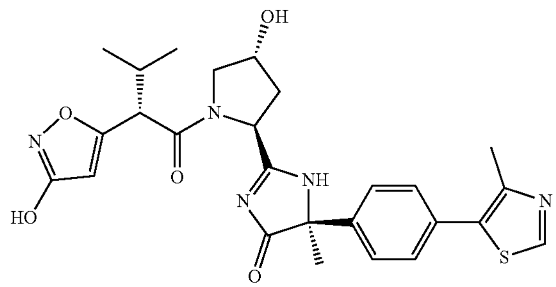 [SMILES: Cc1ncsc1-c1ccc([C@]2(C)NC([C@@H]3C[C@@H](O)CN3C(=O)[C@H](c3cc(O)no3)C(C)C)=NC2=O)cc1] | (S)-2-((2S,4R)-4-hydroxy-1-((S)-2-(3-hydroxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |
| 116d | 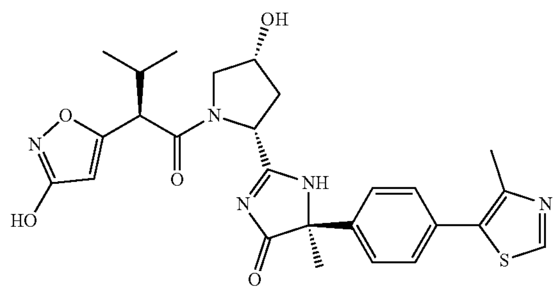 [SMILES: Cc1ncsc1-c1ccc([C@]2(C)NC([C@H]3C[C@@H](O)CN3C(=O)[C@@H](c3cc(O)no3)C(C)C)=NC2=O)cc1] | (S)-2-((2R,4R)-4-hydroxy-1-((R)-2-(3-hydroxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |
| 116e | 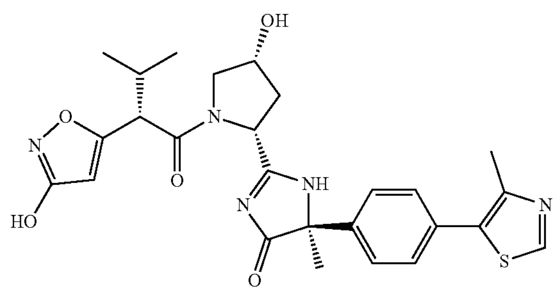 [SMILES: Cc1ncsc1-c1ccc([C@]2(C)NC([C@H]3C[C@@H](O)CN3C(=O)[C@H](c3cc(O)no3)C(C)C)=NC2=O)cc1] | (S)-2-((2R,4R)-4-hydroxy-1-((S)-2-(3-hydroxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one |
| 117 | 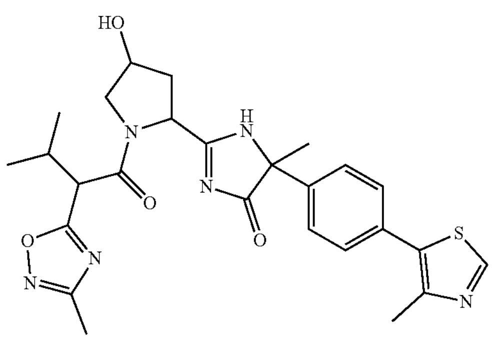 [SMILES: Cc1noc(C(C(=O)N2CC(O)CC2C2=NC(=O)C(C)(c3ccc(-c4scnc4C)cc3)N2)C(C)C)n1] | 2-(4-hydroxy-1-(3-methyl-2-(3-methyl-1,2,4-oxadiazol-5-yl)butanoyl)pyrrolidin-2-yl)-5-methyl-5-(4-(4-methylthiazol-5-yl)phenyl)-1,5-dihydro-4H-imidazol-4-one |
| 117a | 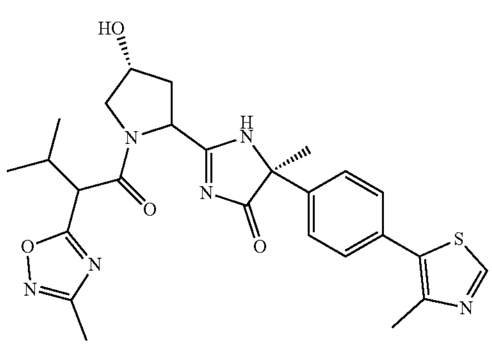 [SMILES: Cc1noc(C(C(=O)N2C[C@H](O)CC2C2=NC(=O)[C@](C)(c3ccc(-c4scnc4C)cc3)N2)C(C)C)n1] | (5S)-2-((4R)-4-hydroxy-1-(3-methyl-2-(3-methyl-1,2,4-oxadiazol-5-yl)butanoyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name |
|---|---|---|
| 117b | 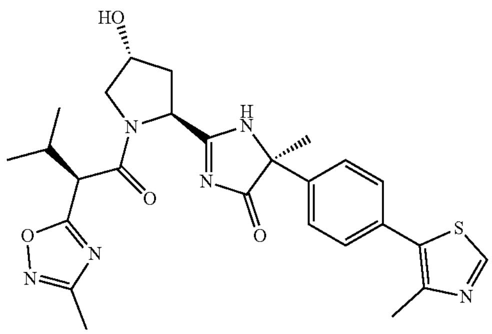 [SMILES: Cc1noc([C@H](C(=O)N2C[C@H](O)C[C@H]2C2=NC(=O)[C@](C)(c3ccc(-c4scnc4C)cc3)N2)C(C)C)n1] | (S)-2-((2S,4R)-4-hydroxy-1-((R)-3-methyl-2-(3-methyl-1,2,4-oxadiazol-5-yl)butanoyl)pyrrolidin-2-yl)-5-methyl-5-(4-(4-methylthiazol-5-yl)phenyl)-1,5-dihydro-4H-imidazol-4-one |
| 117c | 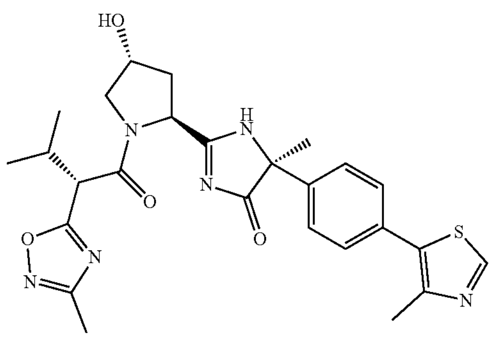 | (S)-2-((2S,4R)-4-hydroxy-1-((S)-3-methyl-2-(3-methyl-1,2,4-oxadiazol-5-yl)butanoyl)pyrrolidin-2-yl)-5-methyl-5-(4-(4-methylthiazol-5-yl)phenyl)-1,5-dihydro-4H-imidazol-4-one |
| 117d | 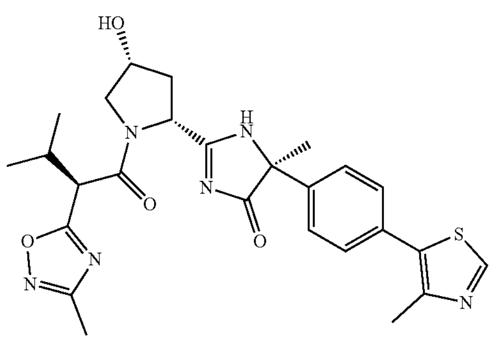 [SMILES: Cc1noc([C@H](C(=O)N2C[C@H](O)C[C@@H]2C2=NC(=O)[C@](C)(c3ccc(-c4scnc4C)cc3)N2)C(C)C)n1] | (S)-2-((2R,4R)-4-hydroxy-1-((R)-3-methyl-2-(3-methyl-1,2,4-oxadiazol-5-yl)butanoyl)pyrrolidin-2-yl)-5-methyl-5-(4-(4-methylthiazol-5-yl)phenyl)-1,5-dihydro-4H-imidazol-4-one |
| 117e | 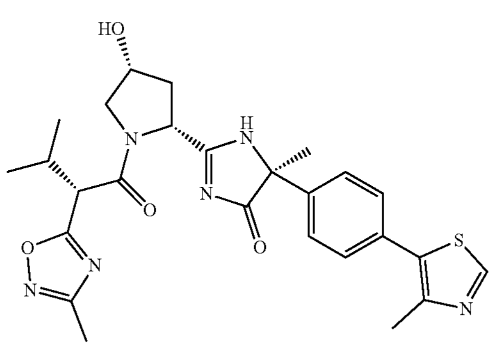 [SMILES: Cc1noc([C@@H](C(=O)N2C[C@H](O)C[C@@H]2C2=NC(=O)[C@](C)(c3ccc(-c4scnc4C)cc3)N2)C(C)C)n1] | (S)-2-((2R,4R)-4-hydroxy-1-((S)-3-methyl-2-(3-methyl-1,2,4-oxadiazol-5-yl)butanoyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name |
|---|---|---|
| 117f | 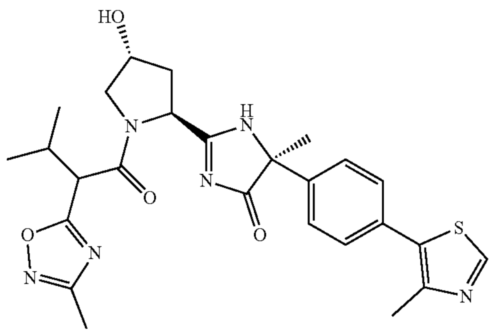 [SMILES: Cc1noc(C(C(=O)N2C[C@H](O)C[C@H]2C2=NC(=O)[C@](C)(c3ccc(-c4scnc4C)cc3)N2)C(C)C)n1] | (5S)-2-((2S,4R)-4-hydroxy-1-(3-methyl-2-(3-methyl-1,2,4-oxadiazol-5-yl)butanoyl)pyrrolidin-2-yl)-5-methyl-5-(4-(4-methylthiazol-5-yl)phenyl)-1,5-dihydro-4H-imidazol-4-one |
| 118 | 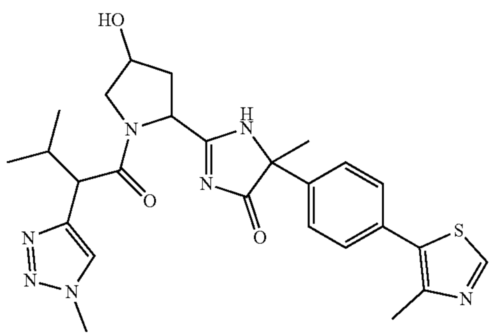 [SMILES: Cc1ncsc1-c1ccc(C2(C)NC(C3CC(O)CN3C(=O)C(c3cn(C)nn3)C(C)C)=NC2=O)cc1] | 2-(4-hydroxy-1-(3-methyl-2-(1-methyl-1H-1,2,3-triazol-4-yl)butanoyl)pyrrolidin-2-yl)-5-methyl-5-(4-(4-methylthiazol-5-yl)phenyl)-1,5-dihydro-4H-imidazol-4-one |
| 118a | 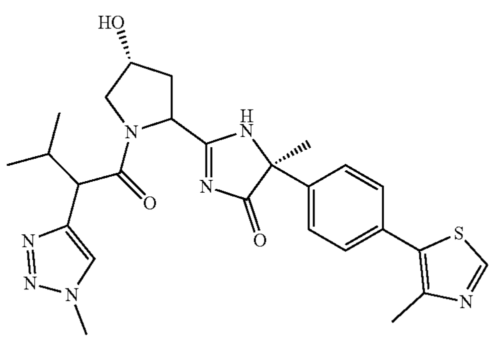 [SMILES: Cc1ncsc1-c1ccc([C@]2(C)NC(C3C[C@@H](O)CN3C(=O)C(c3cn(C)nn3)C(C)C)=NC2=O)cc1] | (5S)-2-((4R)-4-hydroxy-1-(3-methyl-2-(1-methyl-1H-1,2,3-triazol-4-yl)butanoyl)pyrrolidin-2-yl)-5-methyl-5-(4-(4-methylthiazol-5-yl)phenyl)-1,5-dihydro-4H-imidazol-4-one |
| 118b | 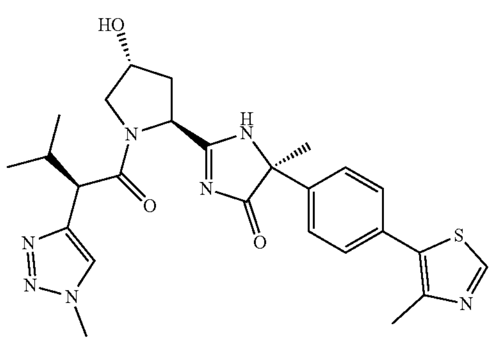 [SMILES: Cc1ncsc1-c1ccc([C@]2(C)NC([C@@H]3C[C@@H](O)CN3C(=O)[C@@H](c3cn(C)nn3)C(C)C)=NC2=O)cc1] | (S)-2-((2S,4R)-4-hydroxy-1-((R)-3-methyl-2-(1-methyl-1H-1,2,3-triazol-4-yl)butanoyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 118c | 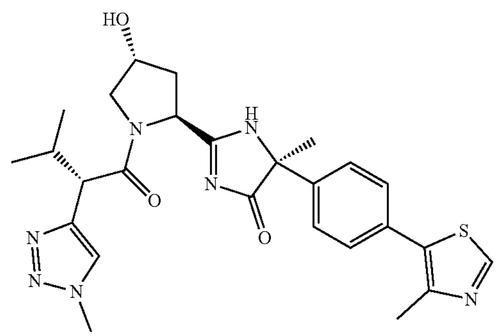 [SMILES: Cc1ncsc1-c1ccc([C@]2(C)NC([C@@H]3C[C@@H](O)CN3C(=O)[C@H](c3cn(C)nn3)C(C)C)=NC2=O)cc1] | (S)-2-((2S,4R)-4-hydroxy-1-((S)-3-methyl-2-(1-methyl-1H-1,2,3-triazol-4-yl)butanoyl)pyrrolidin-2-yl)-5-methyl-5-(4-(4-methylthiazol-5-yl)phenyl)-1,5-dihydro-4H-imidazol-4-one |
| 118d | 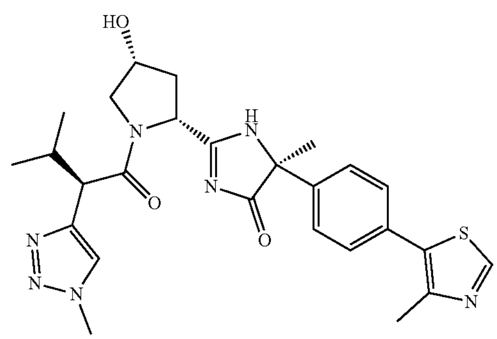 [SMILES: Cc1ncsc1-c1ccc([C@]2(C)NC([C@H]3C[C@@H](O)CN3C(=O)[C@@H](c3cn(C)nn3)C(C)C)=NC2=O)cc1] | (S)-2-((2R,4R)-4-hydroxy-1-((R)-3-methyl-2-(1-methyl-1H-1,2,3-triazol-4-yl)butanoyl)pyrrolidin-2-yl)-5-methyl-5-(4-(4-methylthiazol-5-yl)phenyl)-1,5-dihydro-4H-imidazol-4-one |
| 118e | 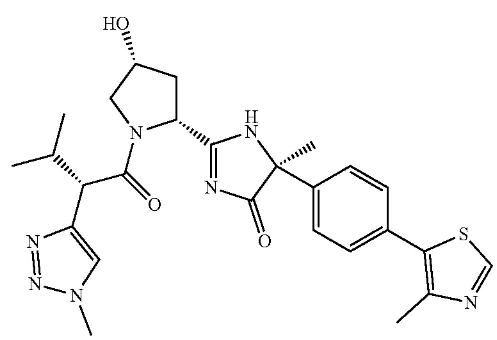 [SMILES: Cc1ncsc1-c1ccc([C@]2(C)NC([C@H]3C[C@@H](O)CN3C(=O)[C@H](c3cn(C)nn3)C(C)C)=NC2=O)cc1] | (S)-2-((2R,4R)-4-hydroxy-1-((S)-3-methyl-2-(1-methyl-1H-1,2,3-triazol-4-yl)butanoyl)pyrrolidin-2-yl)-5-methyl-5-(4-(4-methylthiazol-5-yl)phenyl)-1,5-dihydro-4H-imidazol-4-one |
| 119 | 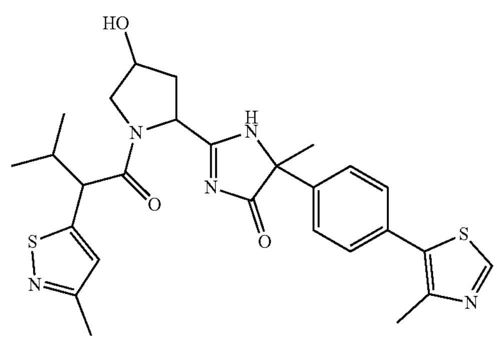 [SMILES: Cc1cc(C(C(=O)N2CC(O)CC2C2=NC(=O)C(C)(c3ccc(-c4scnc4C)cc3)N2)C(C)C)sn1] | 2-(4-hydroxy-1-(3-methyl-2-(3-methylisothiazol-5-yl)butanoyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 119a | 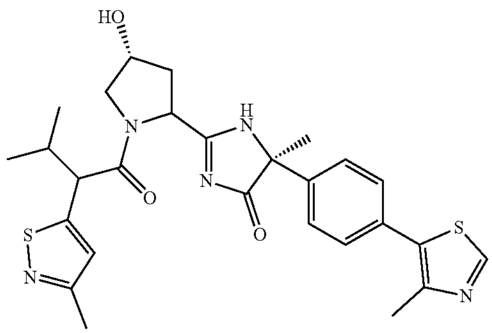 [SMILES: Cc1cc(C(C(=O)N2C[C@H](O)CC2C2=NC(=O)[C@](C)(c3ccc(-c4scnc4C)cc3)N2)C(C)C)sn1] | (5S)-2-((4R)-4-hydroxy-1-(3-methyl-2-(3-methylisothiazol-5-yl)butanoyl)pyrrolidin-2-yl)-5-methyl-5-(4-(4-methylthiazol-5-yl)phenyl)-1,5-dihydro-4H-imidazol-4-one |
| 119b | 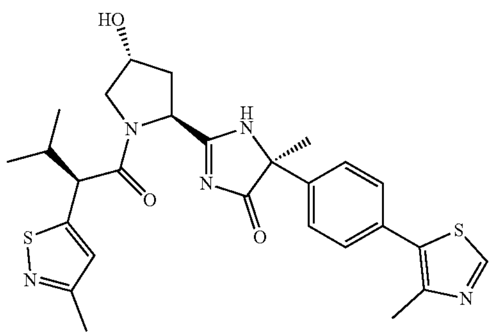 [SMILES: Cc1cc([C@H](C(=O)N2C[C@H](O)C[C@H]2C2=NC(=O)[C@](C)(c3ccc(-c4scnc4C)cc3)N2)C(C)C)sn1] | (S)-2-((2S,4R)-4-hydroxy-1-((S)-3-methyl-2-(3-methylisothiazol-5-yl)butanoyl)pyrrolidin-2-yl)-5-methyl-5-(4-(4-methylthiazol-5-yl)phenyl)-1,5-dihydro-4H-imidazol-4-one |
| 119c | 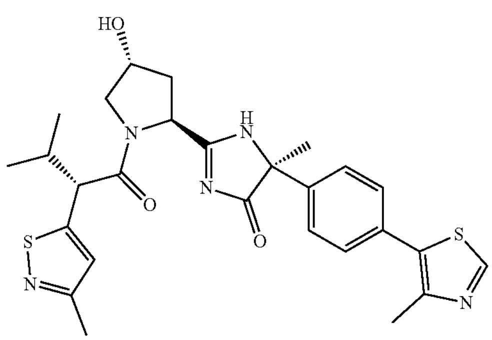 [SMILES: Cc1cc([C@@H](C(=O)N2C[C@H](O)C[C@H]2C2=NC(=O)[C@](C)(c3ccc(-c4scnc4C)cc3)N2)C(C)C)sn1] | (S)-2-((2S,4R)-4-hydroxy-1-((R)-3-methyl-2-(3-methylisothiazol-5-yl)butanoyl)pyrrolidin-2-yl)-5-methyl-5-(4-(4-methylthiazol-5-yl)phenyl)-1,5-dihydro-4H-imidazol-4-one |
| 119d | 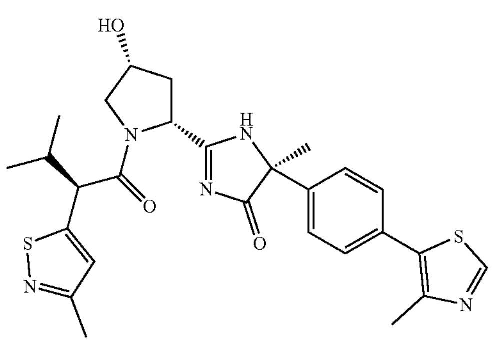 [SMILES: Cc1cc([C@H](C(=O)N2C[C@H](O)C[C@@H]2C2=NC(=O)[C@](C)(c3ccc(-c4scnc4C)cc3)N2)C(C)C)sn1] | (S)-2-((2R,4R)-4-hydroxy-1-((S)-3-methyl-2-(3-methylisothiazol-5-yl)butanoyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 119e | 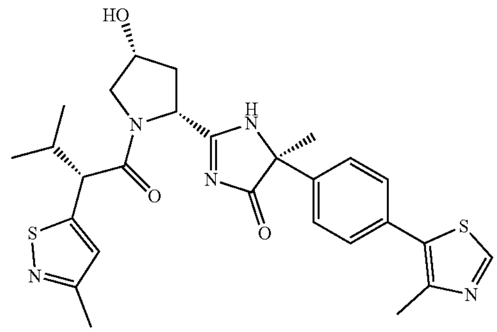 [SMILES: Cc1cc([C@@H](C(=O)N2C[C@H](O)C[C@@H]2C2=NC(=O)[C@](C)(c3ccc(-c4scnc4C)cc3)N2)C(C)C)sn1] | (S)-2-((2R,4R)-4-hydroxy-1-((R)-3-methyl-2-(3-methylisothiazol-5-yl)butanoyl)pyrrolidin-2-yl)-5-methyl-5-(4-(4-methylthiazol-5-yl)phenyl)-1,5-dihydro-4H-imidazol-4-one |
| 112 and 120 | 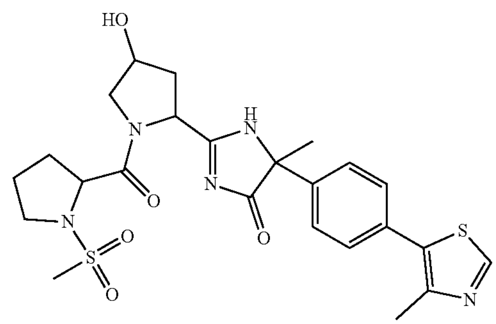 [SMILES: Cc1ncsc1-c1ccc(C2(C)NC(C3CC(O)CN3C(=O)C3CCCN3S(C)(=O)=O)=NC2=O)cc1] | 2-(4-hydroxy-1-((methylsulfonyl)prolyl)pyrrolidin-2-yl)-5-methyl-5-(4-(4-methylthiazol-5-yl)phenyl)-1,5-dihydro-4H-imidazol-4-one |
| 120a | 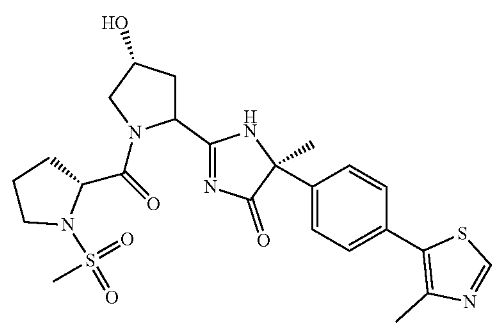 [SMILES: Cc1ncsc1-c1ccc([C@]2(C)NC(C3C[C@@H](O)CN3C(=O)[C@H]3CCCN3S(C)(=O)=O)=NC2=O)cc1] | (5S)-2-((4R)-4-hydroxy-1-((methylsulfonyl)-D-prolyl)pyrrolidin-2-yl)-5-methyl-5-(4-(4-methylthiazol-5-yl)phenyl)-1,5-dihydro-4H-imidazol-4-one |
| 120b | 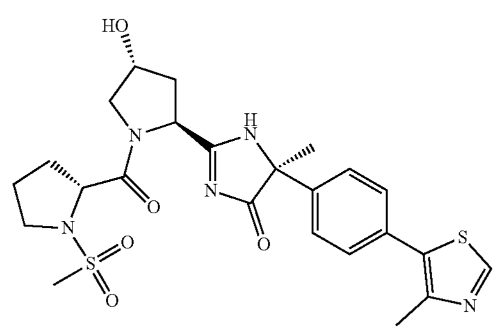 [SMILES: Cc1ncsc1-c1ccc([C@]2(C)NC([C@@H]3C[C@@H](O)CN3C(=O)[C@H]3CCCN3S(C)(=O)=O)=NC2=O)cc1] | (S)-2-((2S,4R)-4-hydroxy-1-((methylsulfonyl)-D-prolyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 120c | 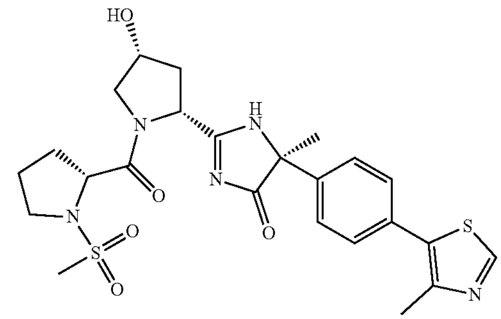 [SMILES: Cc1ncsc1-c1ccc([C@]2(C)NC([C@H]3C[C@@H](O)CN3C(=O)[C@H]3CCCN3S(C)(=O)=O)=NC2=O)cc1] | (S)-2-((2R,4R)-4-hydroxy-1-((methylsulfonyl)-D-prolyl)pyrrolidin-2-yl)-5-methyl-5-(4-(4-methylthiazol-5-yl)phenyl)-1,5-dihydro-4H-imidazol-4-one |
| 121 | 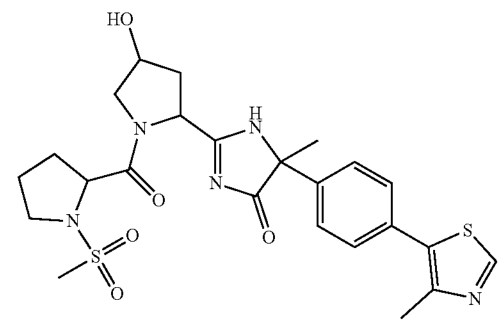 [SMILES: Cc1ncsc1-c1ccc(C2(C)NC(C3CC(O)CN3C(=O)C3CCCN3S(C)(=O)=O)=NC2=O)cc1] | 2-(1-(acetylprolyl)-4-hydroxypyrrolidin-2-yl)-5-methyl-5-(4-(4-methylthiazol-5-yl)phenyl)-1,5-dihydro-4H-imidazol-4-one |
| 121a | 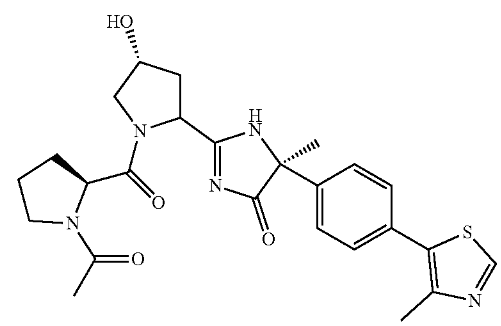 [SMILES: CC(=O)N1CCC[C@H]1C(=O)N1C[C@H](O)CC1C1=NC(=O)[C@](C)(c2ccc(-c3scnc3C)cc2)N1] | (5S)-2-((4R)-1-(acetyl-L-prolyl)-4-hydroxypyrrolidin-2-yl)-5-methyl-5-(4-(4-methylthiazol-5-yl)phenyl)-1,5-dihydro-4H-imidazol-4-one |
| 121b | 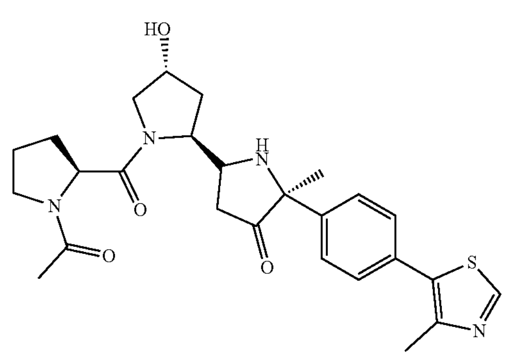 [SMILES: CC(=O)N1CCC[C@H]1C(=O)N1C[C@H](O)C[C@H]1C1CC(=O)[C@](C)(c2ccc(-c3scnc3C)cc2)N1] | (S)-2-((2S,4R)-1-(acetyl-L-prolyl)-4-hydroxypyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 121c | 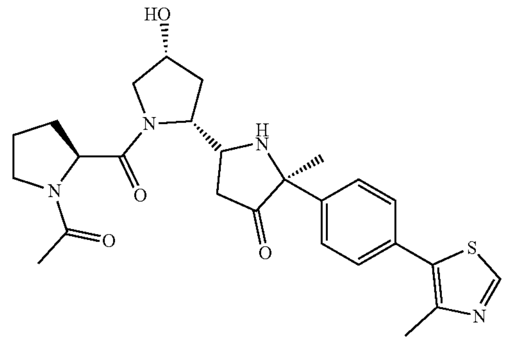 [SMILES: CC(=O)N1CCC[C@H]1C(=O)N1C[C@H](O)C[C@@H]1C1CC(=O)[C@](C)(c2ccc(-c3scnc3C)cc2)N1] | (S)-2-((2R,4R)-1-(acetyl-L-prolyl)-4-hydroxypyrrolidin-2-yl)-5-methyl-5-(4-(4-methylthiazol-5-yl)phenyl)-1,5-dihydro-4H-imidazol-4-one |
| 122 | 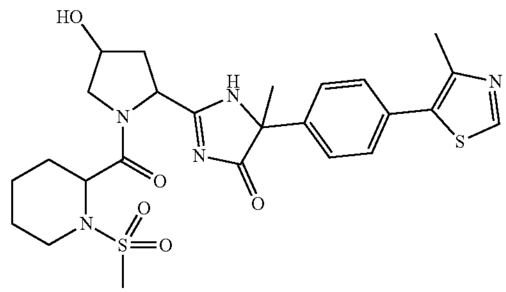 [SMILES: Cc1ncsc1-c1ccc(C2(C)NC(C3CC(O)CN3C(=O)C3CCCCN3S(C)(=O)=O)=NC2=O)cc1] | 2-(4-hydroxy-1-(1-(methylsulfonyl)piperidine-2-carbonyl)pyrrolidin-2-yl)-5-methyl-5-(4-(4-methylthiazol-5-yl)phenyl)-1,5-dihydro-4H-imidazol-4-one |
| 122a | 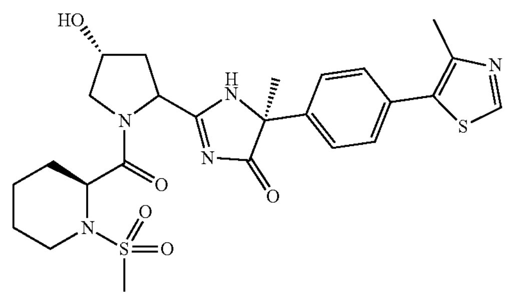 [SMILES: Cc1ncsc1-c1ccc([C@]2(C)NC(C3C[C@@H](O)CN3C(=O)[C@@H]3CCCCN3S(C)(=O)=O)=NC2=O)cc1] | (5S)-2-((4R)-4-hydroxy-1-((S)-1-(methylsulfonyl)piperidine-2-carbonyl)pyrrolidin-2-yl)-5-methyl-5-(4-(4-methylthiazol-5-yl)phenyl)-1,5-dihydro-4H-imidazol-4-one |
| 122b | 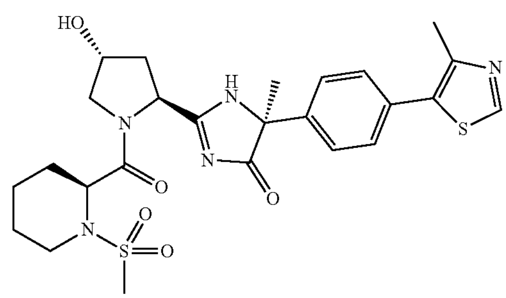 [SMILES: Cc1ncsc1-c1ccc([C@]2(C)NC([C@@H]3C[C@@H](O)CN3C(=O)[C@@H]3CCCCN3S(C)(=O)=O)=NC2=O)cc1] | (S)-2-((2S,4R)-4-hydroxy-1-((S)-1-(methylsulfonyl)piperidine-2-carbonyl)pyrrolidin-2-yl)-5-methyl-5-(4-(4-methylthiazol-5-yl)phenyl)-1,5-dihydro-4H-imidazol-4-one |
| 122c | 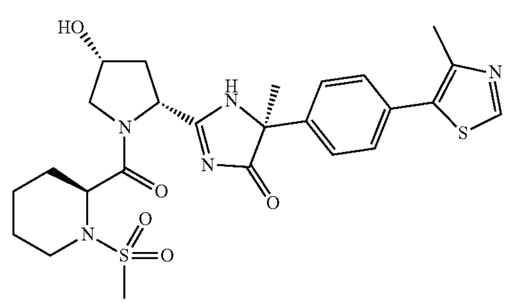 [SMILES: Cc1ncsc1-c1ccc([C@]2(C)NC([C@H]3C[C@@H](O)CN3C(=O)[C@@H]3CCCCN3S(C)(=O)=O)=NC2=O)cc1] | (S)-2-((2R,4R)-4-hydroxy-1-((S)-1-(methylsulfonyl)piperidine-2-carbonyl)pyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 123 | 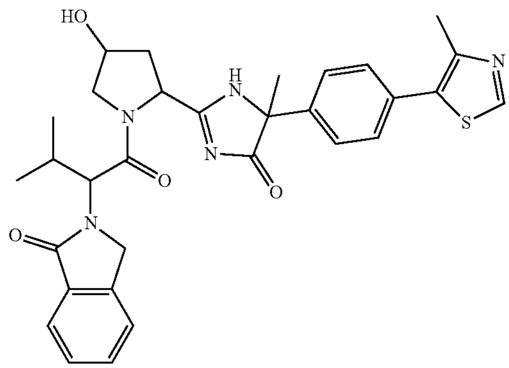 [SMILES: Cc1ncsc1-c1ccc(C2(C)NC(C3CC(O)CN3C(=O)C(C(C)C)N3Cc4ccccc4C3=O)=NC2=O)cc1] | 2-(1-(4-hydroxy-2-(5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoindolin-1-one |
| 123a | 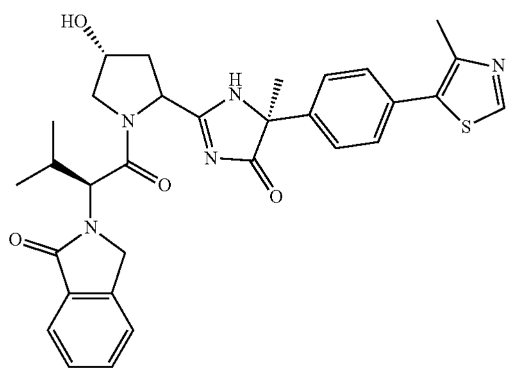 [SMILES: Cc1ncsc1-c1ccc([C@]2(C)NC(C3C[C@@H](O)CN3C(=O)[C@H](C(C)C)N3Cc4ccccc4C3=O)=NC2=O)cc1] | 2-((2S)-1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoindolin-1-one |
| 123b | 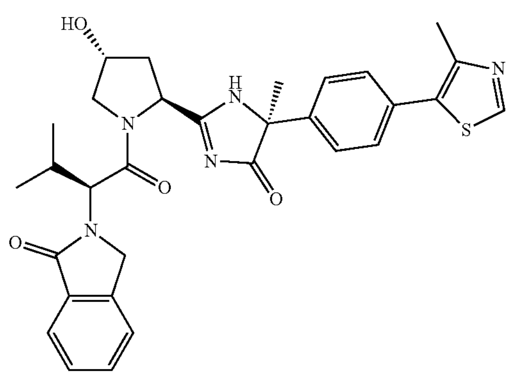 [SMILES: Cc1ncsc1-c1ccc([C@]2(C)NC([C@@H]3C[C@@H](O)CN3C(=O)[C@H](C(C)C)N3Cc4ccccc4C3=O)=NC2=O)cc1] | 2-((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoindolin-1-one |
| 123c | 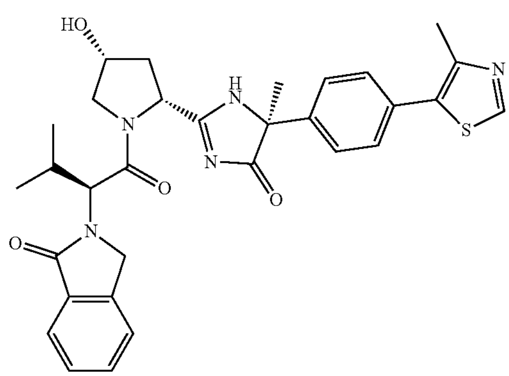 | 2-((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoindolin-1-one |

TABLE 7-continued

VHL ligands

| Compound No. | Structure | Name[1] |
|---|---|---|
| 124 | 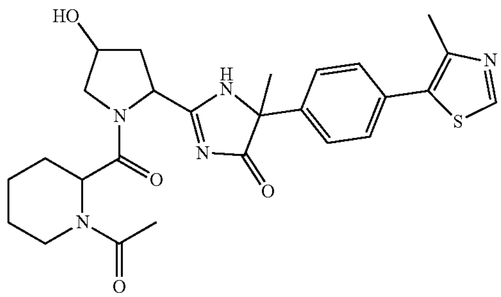 [SMILES: CC(=O)N1CCCCC1C(=O)N1CC(O)CC1C1=NC(=O)C(C)(c2ccc(-c3scnc3C)cc2)N1] | 2-(1-(1-acetylpiperidine-2-carbonyl)-4-hydroxypyrrolidin-2-yl)-5-methyl-5-(4-(4-methylthiazol-5-yl)phenyl)-1,5-dihydro-4H-imidazol-4-one |
| 124a | 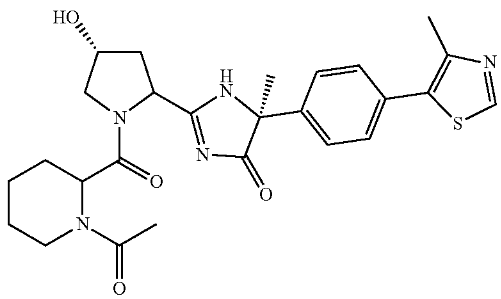 [SMILES: CC(=O)N1CCCCC1C(=O)N1C[C@H](O)CC1C1=NC(=O)[C@](C)(c2ccc(-c3scnc3C)cc2)N1] | (5S)-2-((4R)-1-(1-acetylpiperidine-2-carbonyl)-4-hydroxypyrrolidin-2-yl)-5-methyl-5-(4-(4-methylthiazol-5-yl)phenyl)-1,5-dihydro-4H-imidazol-4-one |
| 124b | 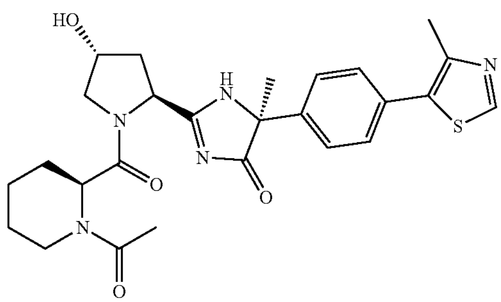 [SMILES: CC(=O)N1CCCC[C@H]1C(=O)N1C[C@H](O)C[C@H]1C1=NC(=O)[C@](C)(c2ccc(-c3scnc3C)cc2)N1] | (S)-2-((2S,4R)-1-((S)-1-acetylpiperidine-2-carbonyl)-4-hydroxypyrrolidin-2-yl)-5-methyl-5-(4-(4-methylthiazol-5-yl)phenyl)-1,5-dihydro-4H-imidazol-4-one |
| 124c | 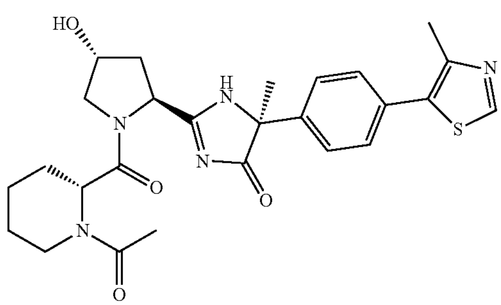 [SMILES: CC(=O)N1CCCC[C@@H]1C(=O)N1C[C@H](O)C[C@H]1C1=NC(=O)[C@](C)(c2ccc(-c3scnc3C)cc2)N1] | (S)-2-((2S,4R)-1-((R)-1-acetylpiperidine-2-carbonyl)-4-hydroxypyrrolidin-2-yl)-5-methyl-5-(4-(4-methylthiazol-5-yl)phenyl)-1,5-dihydro-4H-imidazol-4-one |
| 124d | 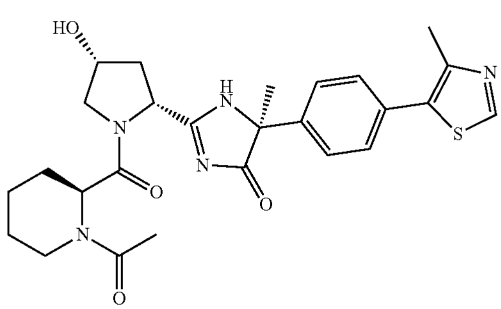 [SMILES: CC(=O)N1CCCC[C@H]1C(=O)N1C[C@H](O)C[C@@H]1C1=NC(=O)[C@](C)(c2ccc(-c3scnc3C)cc2)N1] | (S)-2-((2R,4R)-1-((S)-1-acetylpiperidine-2-carbonyl)-4-hydroxypyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 124e | 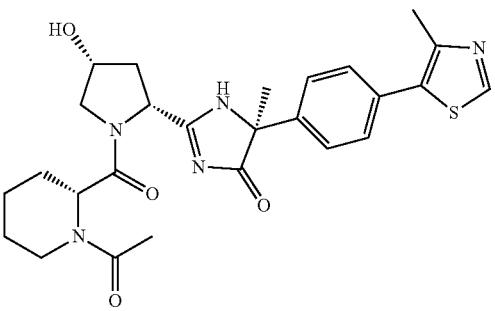 [SMILES: CC(=O)N1CCCC[C@@H]1C(=O)N1C[C@H](O)C[C@@H]1C1=NC(=O)[C@](C)(c2ccc(-c3scnc3C)cc2)N1] | (S)-2-((2R,4R)-1-((R)-1-acetylpiperidine-2-carbonyl)-4-hydroxypyrrolidin-2-yl)-5-methyl-5-(4-(4-methylthiazol-5-yl)phenyl)-1,5-dihydro-4H-imidazol-4-one |
| 125 | 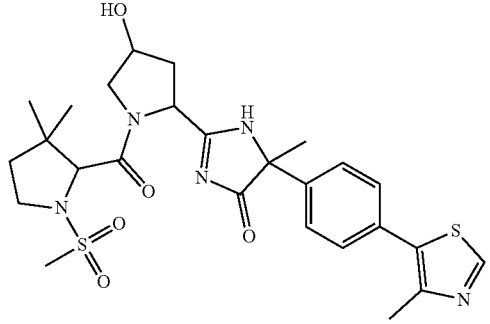 | 2-(1-(3,3-dimethyl-1-(methylsulfonyl)pyrrolidine-2-carbonyl)-4-hydroxypyrrolidin-2-yl)-5-methyl-5-(4-(4-methylthiazol-5-yl)phenyl)-1,5-dihydro-4H-imidazol-4-one |
| 125a | 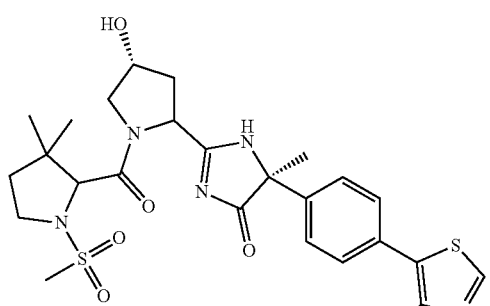 | (5S)-2-((4R)-1-(3,3-dimethyl-1-(methylsulfonyl)pyrrolidine-2-carbonyl)-4-hydroxypyrrolidin-2-yl)-5-methyl-5-(4-(4-methylthiazol-5-yl)phenyl)-1,5-dihydro-4H-imidazol-4-one |
| 125b | 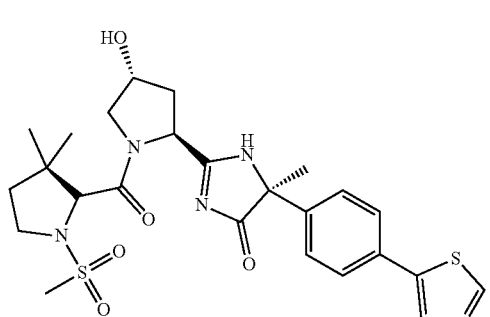 | (S)-2-((2S,4R)-1-((S)-3,3-dimethyl-1-(methylsulfonyl)pyrrolidine-2-carbonyl)-4-hydroxypyrrolidin-2-yl)-5-methyl-5-(4-(4-methylthiazol-5-yl)phenyl)-1,5-dihydro-4H-imidazol-4-one |

TABLE 7-continued

VHL ligands

| Compound No. | Structure | Name[1] |
|---|---|---|
| 125c | 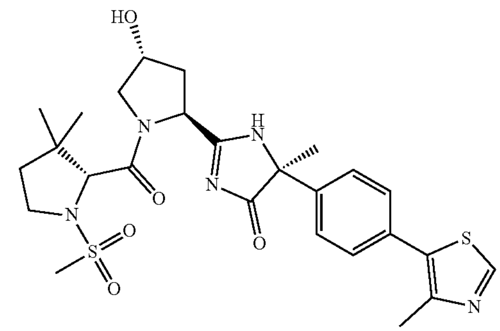 | (S)-2-((2S,4R)-1-((R)-3,3-dimethyl-1-(methylsulfonyl)pyrrolidine-2-carbonyl)-4-hydroxypyrrolidin-2-yl)-5-methyl-5-(4-(4-methylthiazol-5-yl)phenyl)-1,5-dihydro-4H-imidazol-4-one |
| 125d | 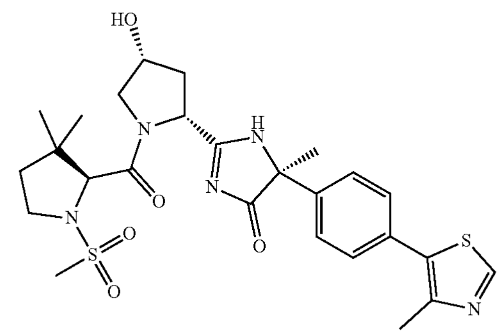 | (S)-2-((2R,4R)-1-((S)-3,3-dimethyl-1-(methylsulfonyl)pyrrolidine-2-carbonyl)-4-hydroxypyrrolidin-2-yl)-5-methyl-5-(4-(4-methylthiazol-5-yl)phenyl)-1,5-dihydro-4H-imidazol-4-one |
| 125e | 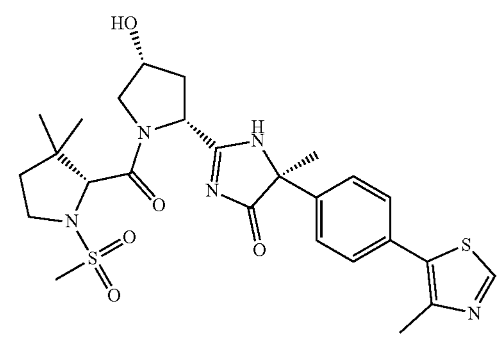 | (S)-2-((2R,4R)-1-((R)-3,3-dimethyl-1-(methylsulfonyl)pyrrolidine-2-carbonyl)-4-hydroxypyrrolidin-2-yl)-5-methyl-5-(4-(4-methylthiazol-5-yl)phenyl)-1,5-dihydro-4H-imidazol-4-one |
| 126 | 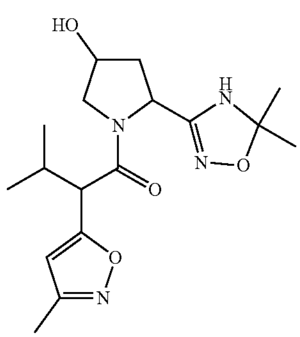 [SMILES: Cc1cc(C(C(=O)N2CC(O)CC2C2=NOC(C)(C)N2)C(C)C)on1] | 1-(2-(5,5-dimethyl-4,5-dihydro-1,2,4-oxadiazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 126a | 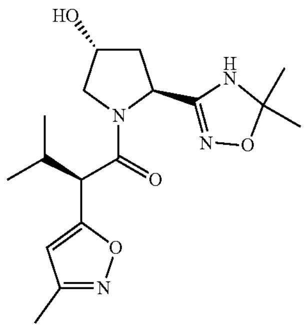 [SMILES: Cc1cc([C@H](C(=O)N2C[C@H](O)C[C@H]2C2=NOC(C)(C)N2)C(C)C)on1] | (R)-1-((2S,4R)-2-(5,5-dimethyl-4,5-dihydro-1,2,4-oxadiazol-3-yl)-4-hydroxypyrrolidin-1-yl)-3-methyl-2-(3-methylisoxazol-5-yl)butan-1-one |
| 126b | 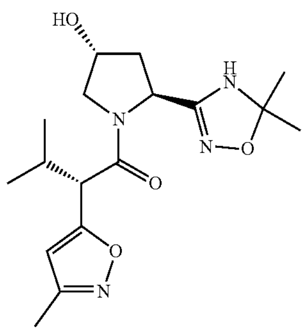 [SMILES: Cc1cc([C@@H](C(=O)N2C[C@H](O)C[C@H]2C2=NOC(C)(C)N2)C(C)C)on1] | (S)-1-((2S,4R)-2-(5,5-dimethyl-4,5-dihydro-1,2,4-oxadiazol-3-yl)-4-hydroxypyrrolidin-1-yl)-3-methyl-2-(3-methylisoxazol-5-yl)butan-1-one |
| 127 | 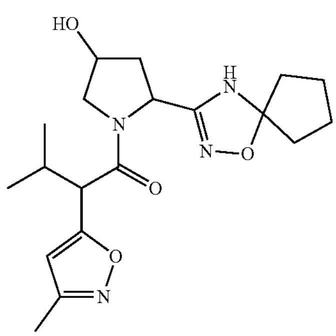 [SMILES: Cc1cc(C(C(=O)N2CC(O)CC2C2=NOC3(CCCC3)N2)C(C)C)on1] | 1-(4-hydroxy-2-(1-oxa-2,4-diazaspiro[4.4]non-2-en-3-yl)pyrrolidin-1-yl)-3-methyl-2-(3-methylisoxazol-5-yl)butan-1-one |
| 127a | 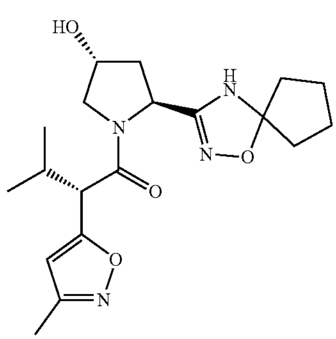 [SMILES: Cc1cc([C@@H](C(=O)N2C[C@H](O)C[C@H]2C2=NOC3(CCCC3)N2)C(C)C)on1] | (S)-1-((2S,4R)-4-hydroxy-2-(1-oxa-2,4-diazaspiro[4.4]non-2-en-3-yl)pyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 127b | 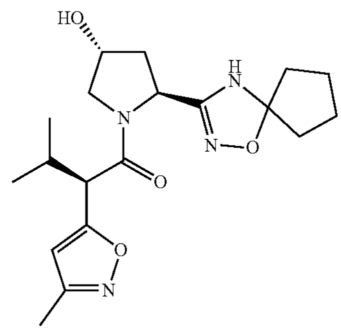 [SMILES: Cc1cc([C@H](C(=O)N2C[C@H](O)C[C@H]2C2=NOC3(CCCC3)N2)C(C)C)on1] | (R)-1-((2S,4R)-4-hydroxy-2-(1-oxa-2,4-diazaspiro[4.4]non-2-en-3-yl)pyrrolidin-1-yl)-3-methyl-2-(3-methylisoxazol-5-yl)butan-1-one |
| 128 | 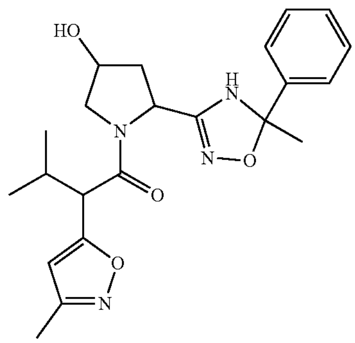 [SMILES: Cc1cc(C(C(=O)N2CC(O)CC2C2=NOC(C)(c3ccccc3)N2)C(C)C)on1] | 1-(4-hydroxy-2-(5-methyl-5-phenyl-4,5-dihydro-1,2,4-oxadiazol-3-yl)pyrrolidin-1-yl)-3-methyl-2-(3-methylisoxazol-5-yl)butan-1-one |
| 128a | 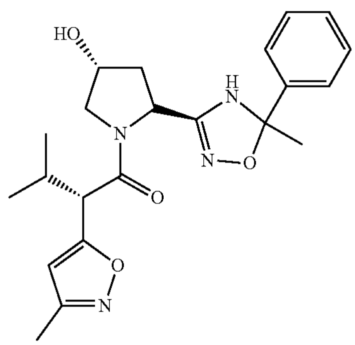 | (2S)-1-((2S,4R)-4-hydroxy-2-(5-methyl-5-phenyl-4,5-dihydro-1,2,4-oxadiazol-3-yl)pyrrolidin-1-yl)-3-methyl-2-(3-methylisoxazol-5-yl)butan-1-one |
| 128b | 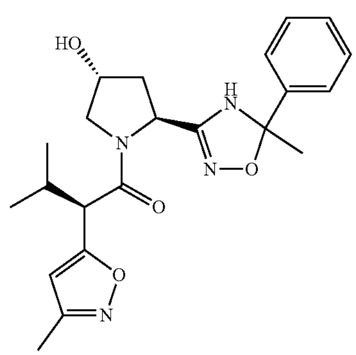 [SMILES: Cc1cc([C@H](C(=O)N2C[C@H](O)C[C@H]2C2=NOC(C)(c3ccccc3)N2)C(C)C)on1] | (2R)-1-((2S,4R)-4-hydroxy-2-(5-methyl-5-phenyl-4,5-dihydro-1,2,4-oxadiazol-3-yl)pyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 128c | 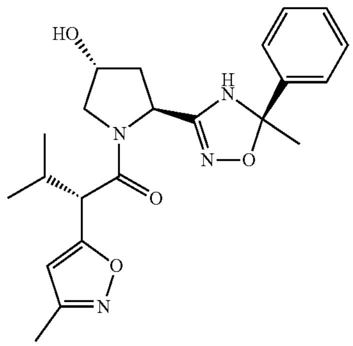 [SMILES: Cc1cc([C@@H](C(=O)N2C[C@H](O)C[C@H]2C2=NO[C@](C)(c3ccccc3)N2)C(C)C)on1] | (S)-1-((2S,4R)-4-hydroxy-2-((R)-5-methyl-5-phenyl-4,5-dihydro-1,2,4-oxadiazol-3-yl)pyrrolidin-1-yl)-3-methyl-2-(3-methylisoxazol-5-yl)butan-1-one |
| 128d | 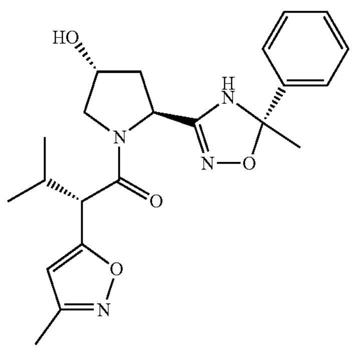 [SMILES: Cc1cc([C@@H](C(=O)N2C[C@H](O)C[C@H]2C2=NO[C@@](C)(c3ccccc3)N2)C(C)C)on1] | (S)-1-((2S,4R)-4-hydroxy-2-((S)-5-methyl-5-phenyl-4,5-dihydro-1,2,4-oxadiazol-3-yl)pyrrolidin-1-yl)-3-methyl-2-(3-methylisoxazol-5-yl)butan-1-one |
| 128e | 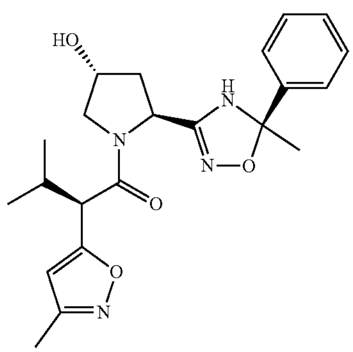 [SMILES: Cc1cc([C@H](C(=O)N2C[C@H](O)C[C@H]2C2=NO[C@](C)(c3ccccc3)N2)C(C)C)on1] | (R)-1-((2S,4R)-4-hydroxy-2-((R)-5-methyl-5-phenyl-4,5-dihydro-1,2,4-oxadiazol-3-yl)pyrrolidin-1-yl)-3-methyl-2-(3-methylisoxazol-5-yl)butan-1-one |
| 128f | 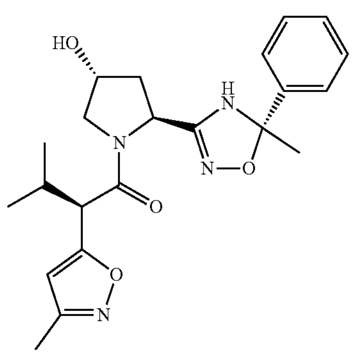 | (R)-1-((2S,4R)-4-hydroxy-2-((S)-5-methyl-5-phenyl-4,5-dihydro-1,2,4-oxadiazol-3-yl)pyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 129 | 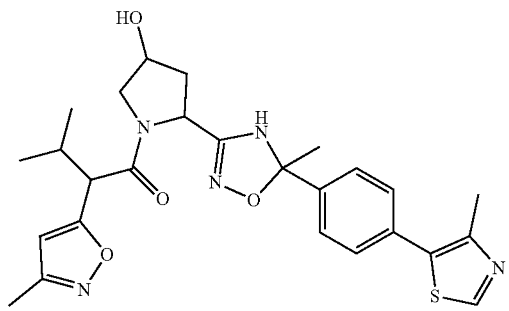 [SMILES: Cc1cc(C(C(=O)N2CC(O)CC2C2=NOC(C)(c3ccc(-c4scnc4C)cc3)N2)C(C)C)on1] | 1-(4-hydroxy-2-(5-methyl-5-(4-(4-methylthiazol-5-yl)phenyl)-4,5-dihydro-1,2,4-oxadiazol-3-yl)pyrrolidin-1-yl)-3-methyl-2-(3-methylisoxazol-5-yl)butan-1-one |
| 129a | 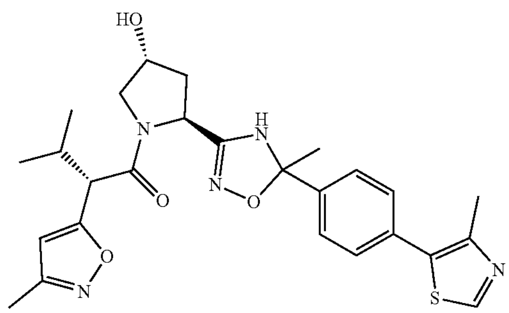 [SMILES: Cc1cc([C@@H](C(=O)N2C[C@H](O)C[C@H]2C2=NOC(C)(c3ccc(-c4scnc4C)cc3)N2)C(C)C)on1] | (2S)-1-((2S,4R)-4-hydroxy-2-(5-methyl-5-(4-(4-methylthiazol-5-yl)phenyl)-4,5-dihydro-1,2,4-oxadiazol-3-yl)pyrrolidin-1-yl)-3-methyl-2-(3-methylisoxazol-5-yl)butan-1-one |
| 129b | 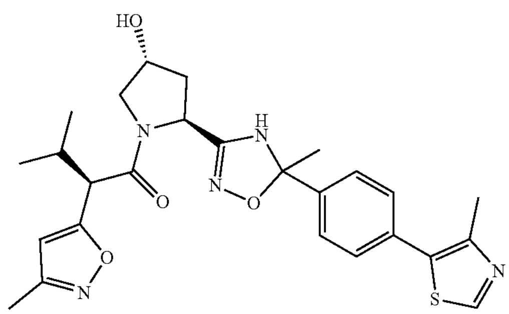 [SMILES: Cc1cc([C@H](C(=O)N2C[C@H](O)C[C@H]2C2=NOC(C)(c3ccc(-c4scnc4C)cc3)N2)C(C)C)on1] | (2R)-1-((2S,4R)-4-hydroxy-2-(5-methyl-5-(4-(4-methylthiazol-5-yl)phenyl)-4,5-dihydro-1,2,4-oxadiazol-3-yl)pyrrolidin-1-yl)-3-methyl-2-(3-methylisoxazol-5-yl)butan-1-one |
| 129c | 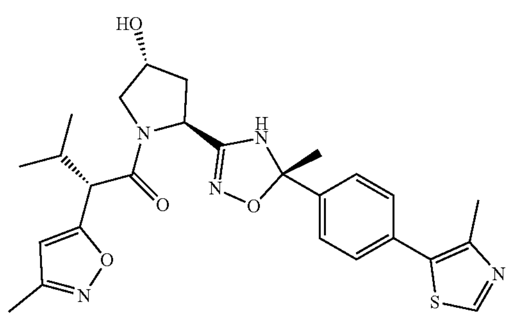 [SMILES: Cc1cc([C@@H](C(=O)N2C[C@H](O)C[C@H]2C2=NO[C@@](C)(c3ccc(-c4scnc4C)cc3)N2)C(C)C)on1] | (S)-1-((2S,4R)-4-hydroxy-2-((S)-5-methyl-5-(4-(4-methylthiazol-5-yl)phenyl)-4,5-dihydro-1,2,4-oxadiazol-3-yl)pyrrolidin-1-yl)-3-methyl-2-(3-methylisoxazol-5-yl)butan-1-one |
| 129d | 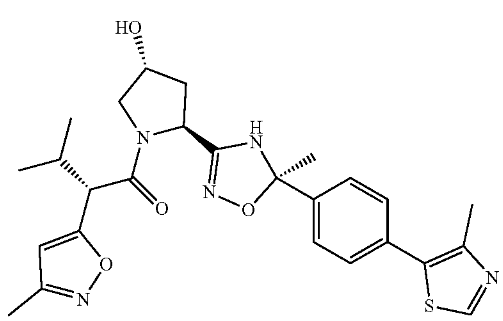 [SMILES: Cc1cc([C@@H](C(=O)N2C[C@H](O)C[C@H]2C2=NO[C@](C)(c3ccc(-c4scnc4C)cc3)N2)C(C)C)on1] | (S)-1-((2S,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3-methyl-2-(3methylisoxazol-5-yl)butan-1-one |

TABLE 7-continued

VHL ligands

| Compound No. | Structure | Name[1] |
|---|---|---|
| 129e | 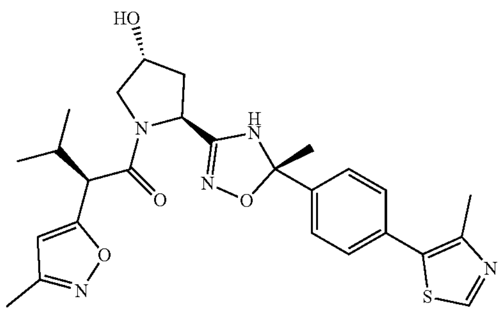 [SMILES: Cc1cc([C@H](C(=O)N2C[C@H](O)C[C@H]2C2=NO[C@@](C)(c3ccc(-c4scnc4C)cc3)N2)C(C)C)on1] | (R)-1-((2S,4R)-4-hydroxy-2-((S)-5-methyl-5-(4-(4-methylthiazol-5-yl)phenyl)-4,5-dihydro-1,2,4-oxadiazol-3-yl)pyrrolidin-1-yl)-3-methyl-2-(3-methylisoxazol-5-yl)butan-1-one |
| 129f | 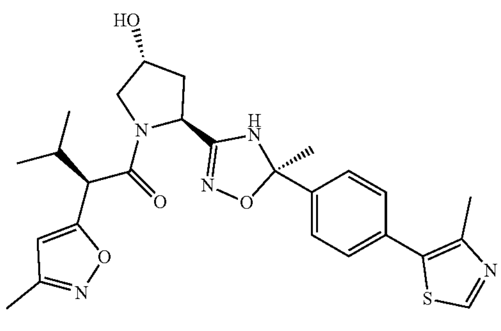 [SMILES: Cc1cc([C@H](C(=O)N2C[C@H](O)C[C@H]2C2=NO[C@](C)(c3ccc(-c4scnc4C)cc3)N2)C(C)C)on1] | (R)-1-((2S,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3-methyl-2-(3-methylisoxazol-5-yl)butan-1-one |
| 130 | 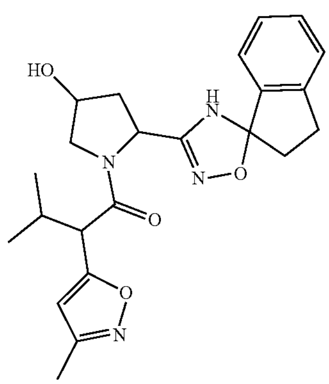 [SMILES: Cc1cc(C(C(=O)N2CC(O)CC2C2=NOC3(CCc4ccccc43)N2)C(C)C)on1] | 1-(2-(2,3-dihydro-4'H-spiro[indene-1,5'-[1,2,4]oxadiazol]-3'-yl)-4-hydroxypyrrolidin-1-yl)-3-methyl-2-(3-methylisoxazol-5-yl)butan-1-one |
| 130a | 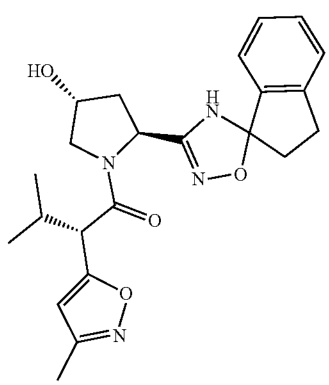 [SMILES: Cc1cc([C@@H](C(=O)N2C[C@H](O)C[C@H]2C2=NOC3(CCc4ccccc43)N2)C(C)C)on1] | (2S)-1-((2S,4R)-2-(2,3-dihydro-4'H-spiro[indene-1,5'-[1,2,4]oxadiazol]-3'-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 130b | 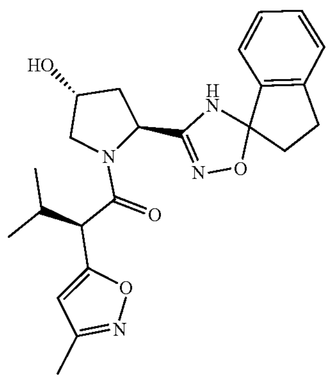 [SMILES: Cc1cc([C@H](C(=O)N2C[C@H](O)C[C@H]2C2=NOC3(CCc4ccccc43)N2)C(C)C)on1] | (2R)-1-((2S,4R)-2-(2,3-dihydro-4'H-spiro[indene-1,5'-[1,2,4]oxadiazol]-3'-yl)-4-hydroxypyrrolidin-1-yl)-3-methyl-2-(3-methylisoxazol-5-yl)butan-1-one |
| 130c | 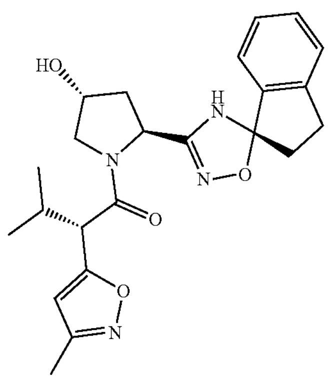 [SMILES: Cc1cc([C@@H](C(=O)N2C[C@H](O)C[C@H]2C2=NO[C@]3(CCc4ccccc43)N2)C(C)C)on1] | (S)-1-((2S,4R)-2-((S)-2,3-dihydro-4'H-spiro[indene-1,5'-[1,2,4]oxadiazol]-3'-yl)-4-hydroxypyrrolidin-1-yl)-3-methyl-2-(3-methylisoxazol-5-yl)butan-1-one |
| 130d | 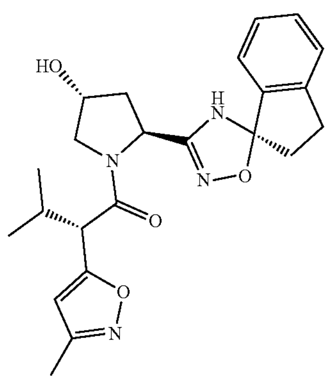 [SMILES: Cc1cc([C@@H](C(=O)N2C[C@H](O)C[C@H]2C2=NO[C@@]3(CCc4ccccc43)N2)C(C)C)on1] | (S)-1-((2S,4R)-2-((R)-2,3-dihydro-4'H-spiro[indene-1,5'-[1,2,4]oxadiazol]-3'-yl)-4-hydroxypyrrolidin-1-yl)-3-methyl-2-(3-methylisoxazol-5-yl)butan-1-one |
| 130e | 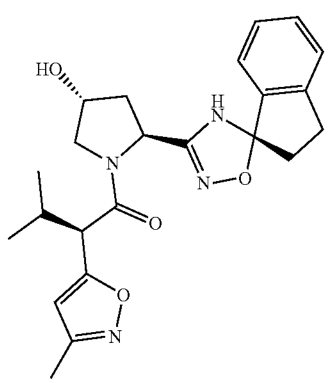 [SMILES: Cc1cc([C@H](C(=O)N2C[C@H](O)C[C@H]2C2=NO[C@]3(CCc4ccccc43)N2)C(C)C)on1] | (R)-1-((2S,4R)-2-((S)-2,3-dihydro-4'H-spiro[indene-1,5'-[1,2,4]oxadiazol]-3'-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 130f | 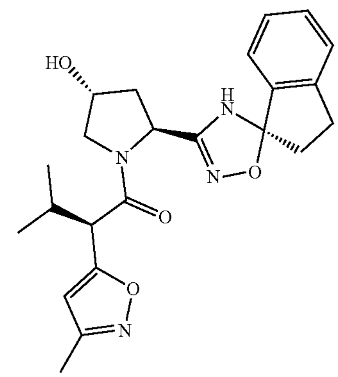 [SMILES: Cc1cc([C@H](C(=O)N2C[C@H](O)C[C@H]2C2=NO[C@@]3(CCc4ccccc43)N2)C(C)C)on1] | (R)-1-((2S,4R)-2-((R)-2,3-dihydro-4'H-spiro[indene-1,5'-[1,2,4]oxadiazol]-3'-yl)-4-hydroxypyrrolidin-1-yl)-3-methyl-2-(3-methylisoxazol-5-yl)butan-1-one |
| 131 | 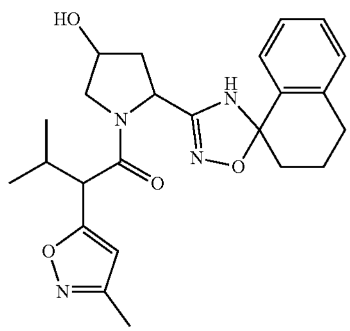 [SMILES: Cc1cc(C(C(=O)N2CC(O)CC2C2=NOC3(CCCc4ccccc43)N2)C(C)C)on1] | 1-(2-(3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one |
| 131a | 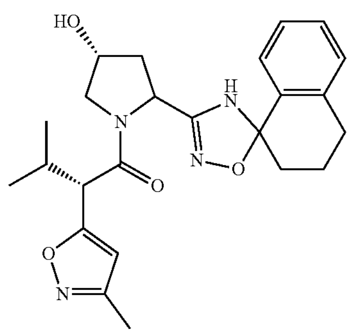 [SMILES: Cc1cc([C@@H](C(=O)N2C[C@H](O)CC2C2=NOC3(CCCc4ccccc43)N2)C(C)C)on1] | (2S)-1-((4R)-2-(3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one |
| 131b | 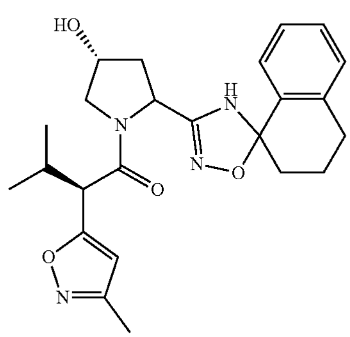 [SMILES: Cc1cc([C@H](C(=O)N2C[C@H](O)CC2C2=NOC3(CCCc4ccccc43)N2)C(C)C)on1] | (2R)-1-((4R)-2-(3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 131c | 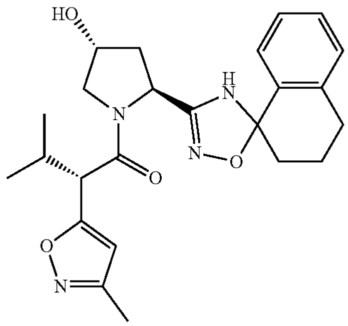 [SMILES: Cc1cc([C@@H](C(=O)N2C[C@H](O)C[C@H]2C2=NOC3(CCCc4ccccc43)N2)C(C)C)on1] | (2S)-1-((2S,4R)-2-(3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one |
| 131d | 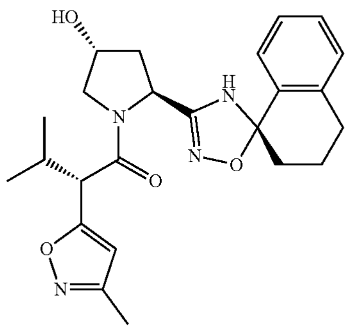 [SMILES: Cc1cc([C@@H](C(=O)N2C[C@H](O)C[C@H]2C2=NO[C@]3(CCCc4ccccc43)N2)C(C)C)on1] | (S)-1-((2S,4R)-2-((S)-3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one |
| 131e | 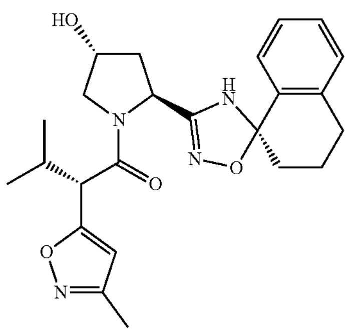 [SMILES: Cc1cc([C@@H](C(=O)N2C[C@H](O)C[C@H]2C2=NO[C@@]3(CCCc4ccccc43)N2)C(C)C)on1] | (S)-1-((2S,4R)-2-((R)-3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one |
| 131f | 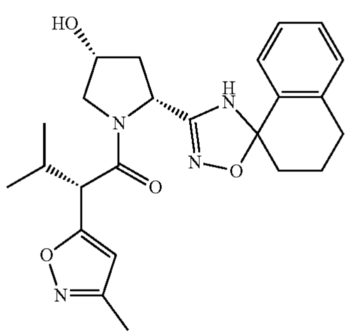 [SMILES: Cc1cc([C@@H](C(=O)N2C[C@H](O)C[C@@H]2C2=NOC3(CCCc4ccccc43)N2)C(C)C)on1] | (2S)-1-((2R,4R)-2-(3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 131g | 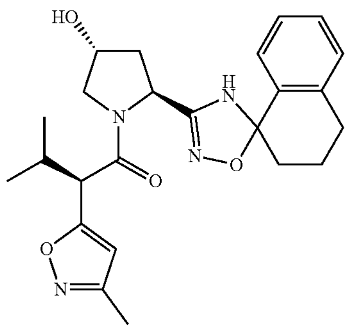 [SMILES: Cc1cc([C@H](C(=O)N2C[C@H](O)C[C@H]2C2=NOC3(CCCc4ccccc43)N2)C(C)C)on1] | (2R)-1-((2S,4R)-2-(3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one |
| 131h | 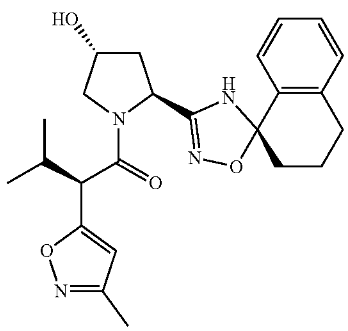 [SMILES: Cc1cc([C@H](C(=O)N2C[C@H](O)C[C@H]2C2=NO[C@]3(CCCc4ccccc43)N2)C(C)C)on1] | (R)-1-((2S,4R)-2-((S)-3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one |
| 131i | 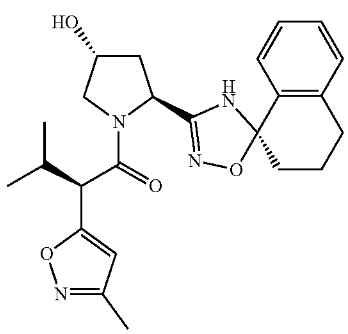 [SMILES: Cc1cc([C@H](C(=O)N2C[C@H](O)C[C@H]2C2=NO[C@@]3(CCCc4ccccc43)N2)C(C)C)on1] | (R)-1-((2S,4R)-2-((R)-3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one |
| 131j | 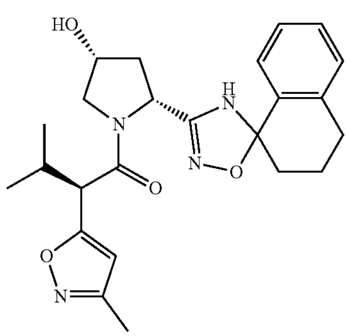 [SMILES: Cc1cc([C@H](C(=O)N2C[C@H](O)C[C@@H]2C2=NOC3(CCCc4ccccc43)N2)C(C)C)on1] | (2R)-1-((2R,4R)-2-(3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 132 | 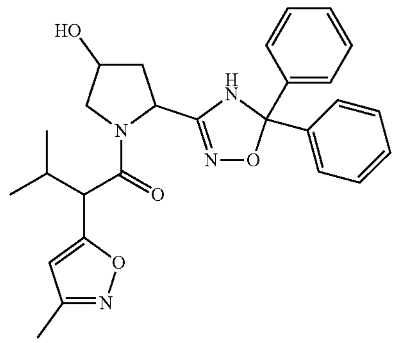 [SMILES: Cc1cc(C(C(=O)N2CC(O)CC2C2=NOC(c3ccccc3)(c3ccccc3)N2)C(C)C)on1] | 1-(2-(5,5-diphenyl-4,5-dihydro-1,2,4-oxadiazol-3-yl)-4-hydroxypyrrolidin-1-yl)-3-methyl-2-(3-methylisoxazol-5-yl)butan-1-one |
| 132a | 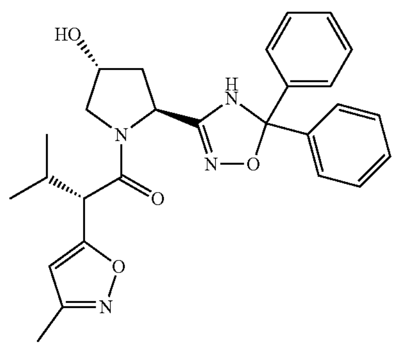 [SMILES: Cc1cc([C@@H](C(=O)N2C[C@H](O)C[C@H]2C2=NOC(c3ccccc3)(c3ccccc3)N2)C(C)C)on1] | (S)-1-((2S,4R)-2-(5,5-diphenyl-4,5-dihydro-1,2,4-oxadiazol-3-yl)-4-hydroxypyrrolidin-1-yl)-3-methyl-2-(3-methylisoxazol-5-yl)butan-1-one |
| 132b | 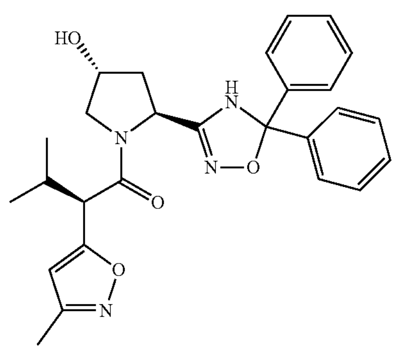 [SMILES: Cc1cc([C@H](C(=O)N2C[C@H](O)C[C@H]2C2=NOC(c3ccccc3)(c3ccccc3)N2)C(C)C)on1] | (R)-1-((2S,4R)-2-(5,5-diphenyl-4,5-dihydro-1,2,4-oxadiazol-3-yl)-4-hydroxypyrrolidin-1-yl)-3-methyl-2-(3-methylisoxazol-5-yl)butan-1-one |
| 133 | 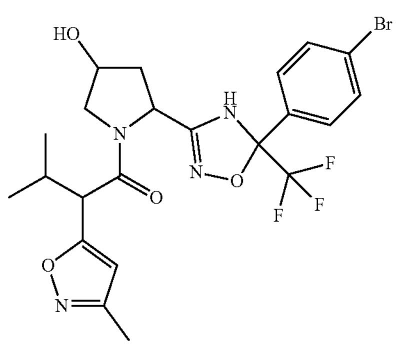 [SMILES: Cc1cc(C(C(=O)N2CC(O)CC2C2=NOC(c3ccc(Br)cc3)(C(F)(F)F)N2)C(C)C)on1] | 1-(2-(5-(4-bromophenyl)-5-(trifluoromethyl)-4,5-dihydro-1,2,4-oxadiazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 133a | 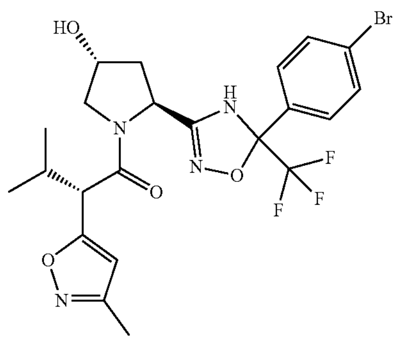 [SMILES: Cc1cc([C@@H](C(=O)N2C[C@H](O)C[C@H]2C2=NOC(c3ccc(Br)cc3)(C(F)(F)F)N2)C(C)C)on1] | (2S)-1-((2S,4R)-2-(5-(4-bromophenyl)-5-(trifluoromethyl)-4,5-dihydro-1,2,4-oxadiazol-3-yl)-4-hydroxypyrrolidin-1-yl)-3-methyl-2-(3-methylisoxazol-5-yl)butan-1-one |
| 133b | 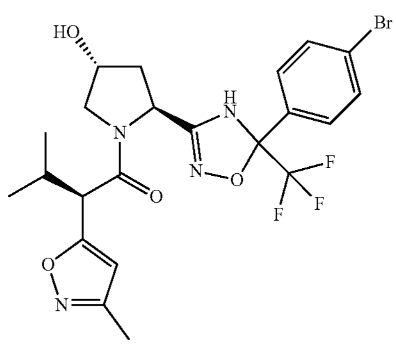 [SMILES: Cc1cc([C@H](C(=O)N2C[C@H](O)C[C@H]2C2=NOC(c3ccc(Br)cc3)(C(F)(F)F)N2)C(C)C)on1] | (2R)-1-((2S,4R)-2-(5-(4-bromophenyl)-5-(trifluoromethyl)-4,5-dihydro-1,2,4-oxadiazol-3-yl)-4-hydroxypyrrolidin-1-yl)-3-methyl-2-(3-methylisoxazol-5-yl)butan-1-one |
| 133c | 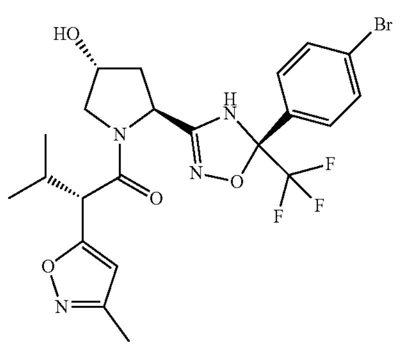 [SMILES: Cc1cc([C@@H](C(=O)N2C[C@H](O)C[C@H]2C2=NO[C@@](c3ccc(Br)cc3)(C(F)(F)F)N2)C(C)C)on1] | (S)-1-((2S,4R)-2-((S)-5-(4-bromophenyl)-5-(trifluoromethyl)-4,5-dihydro-1,2,4-oxadiazol-3-yl)-4-hydroxypyrrolidin-1-yl)-3-methyl-2-(3-methylisoxazol-5-yl)butan-1-one |
| 133d | 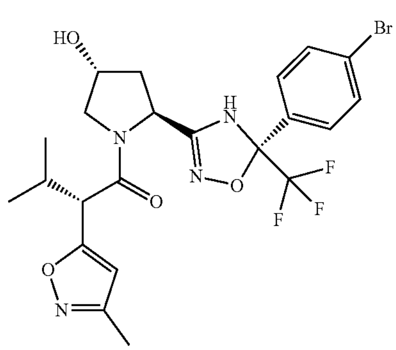 [SMILES: Cc1cc([C@@H](C(=O)N2C[C@H](O)C[C@H]2C2=NO[C@](c3ccc(Br)cc3)(C(F)(F)F)N2)C(C)C)on1] | (S)-1-((2S,4R)-2-((R)-5-(4-bromophenyl)-5-(trifluoromethyl)-4,5-dihydro-1,2,4-oxadiazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 133e | 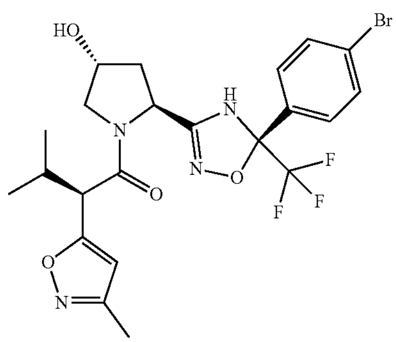 [SMILES: Cc1cc([C@H](C(=O)N2C[C@H](O)C[C@H]2C2=NO[C@@](c3ccc(Br)cc3)(C(F)(F)F)N2)C(C)C)on1] | (R)-1-((2S,4R)-2-((S)-5-(4-bromophenyl)-5-(trifluoromethyl)-4,5-dihydro-1,2,4-oxadiazol-3-yl)-4-hydroxypyrrolidin-1-yl)-3-methyl-2-(3-methylisoxazol-5-yl)butan-1-one |
| 133f | 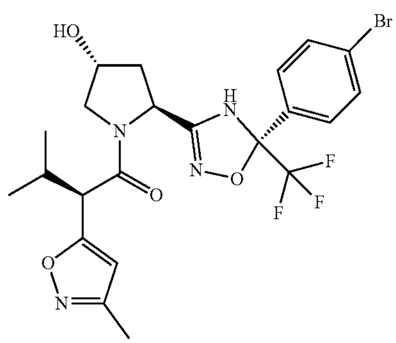 [SMILES: Cc1cc([C@H](C(=O)N2C[C@H](O)C[C@H]2C2=NO[C@](c3ccc(Br)cc3)(C(F)(F)F)N2)C(C)C)on1] | (R)-1-((2S,4R)-2-((R)-5-(4-bromophenyl)-5-(trifluoromethyl)-4,5-dihydro-1,2,4-oxadiazol-3-yl)-4-hydroxypyrrolidin-1-yl)-3-methyl-2-(3-methylisoxazol-5-yl)butan-1-one |
| 134 | 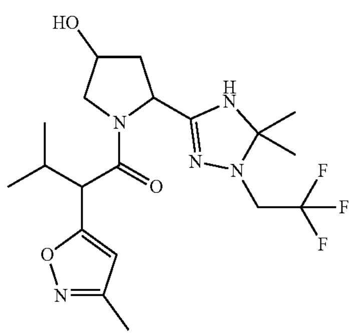 [SMILES: Cc1cc(C(C(=O)N2CC(O)CC2C2=NN(CC(F)(F)F)C(C)(C)N2)C(C)C)on1] | 1-(2-(5,5-dimethyl-1-(2,2,2-trifluoroethyl)-4,5-dihydro-1H-1,2,4-triazol-3-yl)-4-hydroxypyrrolidin-1-yl)-3-methyl-2-(3-methylisoxazol-5-yl)butan-1-one |
| 134a | 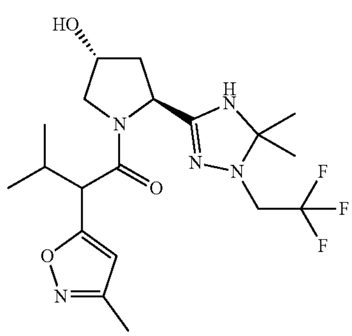 [SMILES: Cc1cc(C(C(=O)N2C[C@H](O)C[C@H]2C2=NN(CC(F)(F)F)C(C)(C)N2)C(C)C)on1] | 1-((2S,4R)-2-(5,5-dimethyl-1-(2,2,2-trifluoroethyl)-4,5-dihydro-1H-1,2,4-triazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 134b | 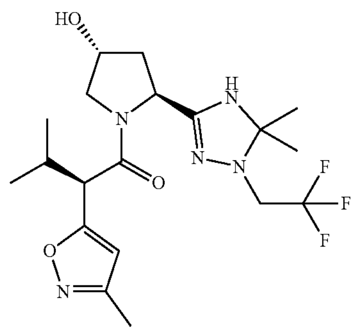 [SMILES: Cc1cc([C@H](C(=O)N2C[C@H](O)C[C@H]2C2=NN(CC(F)(F)F)C(C)(C)N2)C(C)C)on1] | (R)-1-((2S,4R)-2-(5,5-dimethyl-1-(2,2,2-trifluoroethyl)-4,5-dihydro-1H-1,2,4-triazol-3-yl)-4-hydroxypyrrolidin-1-yl)-3-methyl-2-(3-methylisoxazol-5-yl)butan-1-one |
| 134c | 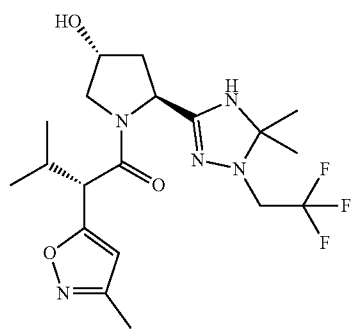 [SMILES: Cc1cc([C@@H](C(=O)N2C[C@H](O)C[C@H]2C2=NN(CC(F)(F)F)C(C)(C)N2)C(C)C)on1] | (S)-1-((2S,4R)-2-(5,5-dimethyl-1-(2,2,2-trifluoroethyl)-4,5-dihydro-1H-1,2,4-triazol-3-yl)-4-hydroxypyrrolidin-1-yl)-3-methyl-2-(3-methylisoxazol-5-yl)butan-1-one |
| 135 | 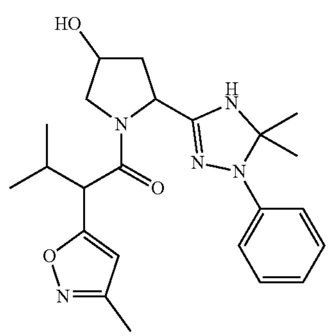 [SMILES: Cc1cc(C(C(=O)N2CC(O)CC2C2=NN(c3ccccc3)C(C)(C)N2)C(C)C)on1] | 1-(2-(5,5-dimethyl-1-phenyl-4,5-dihydro-1H-1,2,4-triazol-3-yl)-4-hydroxypyrrolidin-1-yl)-3-methyl-2-(3-methylisoxazol-5-yl)butan-1-one |
| 135a | 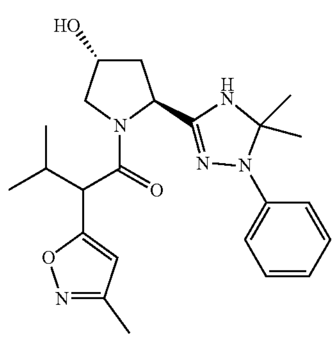 | 1-((2S,4R)-2-(5,5-dimethyl-1-phenyl-4,5-dihydro-1H-1,2,4-triazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 135b | 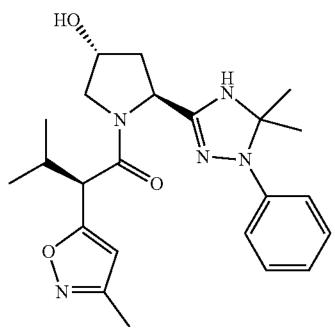 [SMILES: Cc1cc([C@H](C(=O)N2C[C@H](O)C[C@H]2C2=NN(c3ccccc3)C(C)(C)N2)C(C)C)on1] | (R)-1-((2S,4R)-2-(5,5-dimethyl-1-phenyl-4,5-dihydro-1H-1,2,4-triazol-3-yl)-4-hydroxypyrrolidin-1-yl)-3-methyl-2-(3-methylisoxazol-5-yl)butan-1-one |
| 135c | 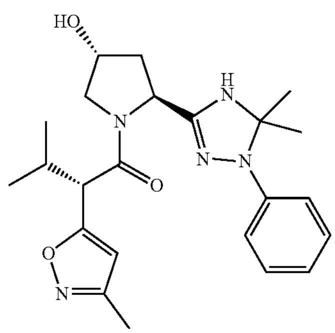 [SMILES: Cc1cc([C@@H](C(=O)N2C[C@H](O)C[C@H]2C2=NN(c3ccccc3)C(C)(C)N2)C(C)C)on1] | (S)-1-((2S,4R)-2-(5,5-dimethyl-1-phenyl-4,5-dihydro-1H-1,2,4-triazol-3-yl)-4-hydroxypyrrolidin-1-yl)-3-methyl-2-(3-methylisoxazol-5-yl)butan-1-one |
| 136 | 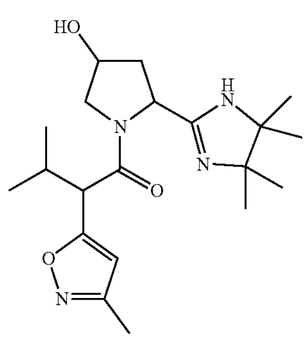 [SMILES: Cc1cc(C(C(=O)N2C[C@H](O)CC2C2=NC(C)(C)C(C)(C)N2)C(C)C)on1] | 1-(4-hydroxy-2-(4,4,5,5-tetramethyl-4,5-dihydro-1H-imidazol-2-yl)pyrrolidin-1-yl)-3-methyl-2-(3-methylisoxazol-5-yl)butan-1-one |
| 136a | 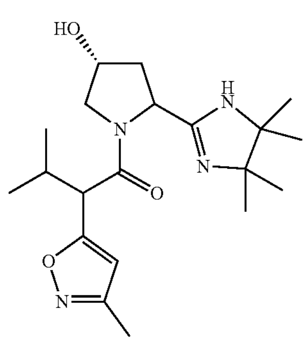 | 1-((4R)-4-hydroxy-2-(4,4,5,5-tetramethyl-4,5-dihydro-1H-imidazol-2-yl)pyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 136b | 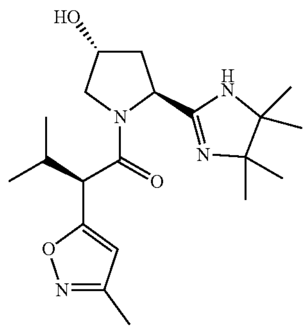 [SMILES: Cc1cc([C@H](C(=O)N2C[C@H](O)C[C@H]2C2=NC(C)(C)C(C)(C)N2)C(C)C)on1] | (R)-1-((2S,4R)-4-hydroxy-2-(4,4,5,5-tetramethyl-4,5-dihydro-1H-imidazol-2-yl)pyrrolidin-1-yl)-3-methyl-2-(3-methylisoxazol-5-yl)butan-1-one |
| 136c | 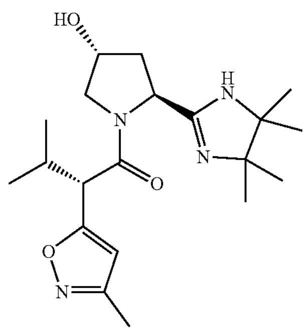 [SMILES: Cc1cc([C@@H](C(=O)N2C[C@H](O)C[C@H]2C2=NC(C)(C)C(C)(C)N2)C(C)C)on1] | (S)-1-((2S,4R)-4-hydroxy-2-(4,4,5,5-tetramethyl-4,5-dihydro-1H-imidazol-2-yl)pyrrolidin-1-yl)-3-methyl-2-(3-methylisoxazol-5-yl)butan-1-one |
| 136d | 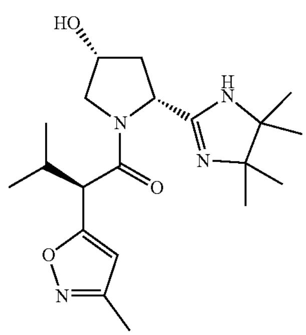 [SMILES: Cc1cc([C@H](C(=O)N2C[C@H](O)C[C@@H]2C2=NC(C)(C)C(C)(C)N2)C(C)C)on1] | (R)-1-((2R,4R)-4-hydroxy-2-(4,4,5,5-tetramethyl-4,5-dihydro-1H-imidazol-2-yl)pyrrolidin-1-yl)-3-methyl-2-(3-methylisoxazol-5-yl)butan-1-one |
| 136e | 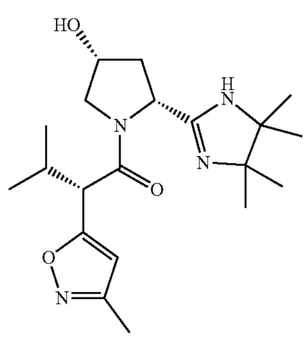 [SMILES: Cc1cc([C@@H](C(=O)N2C[C@H](O)C[C@@H]2C2=NC(C)(C)C(C)(C)N2)C(C)C)on1] | (S)-1-((2R,4R)-4-hydroxy-2-(4,4,5,5-tetramethyl-4,5-dihydro-1H-imidazol-2-yl)pyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 137 | 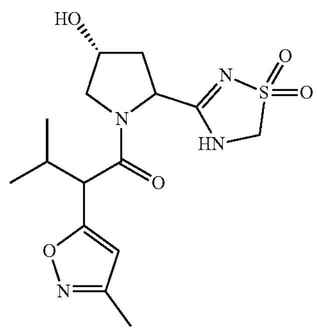 [SMILES: Cc1cc(C(C(=O)N2C[C@H](O)CC2C2=NS(=O)(=O)CN2)C(C)C)on1] | 1-(2-(1,1-dioxido-4,5-dihydro-1,2,4-thiadiazol-3-yl)-4-hydroxypyrrolidin-1-yl)-3-methyl-2-(3-methylisoxazol-5-yl)butan-1-one |
| 137a | 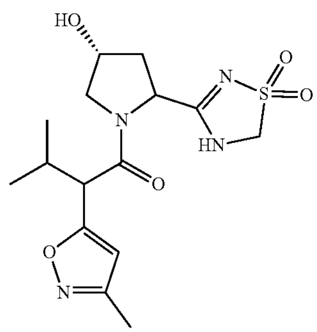 [SMILES: Cc1cc(C(C(=O)N2C[C@H](O)CC2C2=NS(=O)(=O)CN2)C(C)C)on1] | 1-((4R)-2-(1,1-dioxido-4,5-dihydro-1,2,4-thiadiazol-3-yl)-4-hydroxypyrrolidin-1-yl)-3-methyl-2-(3-methylisoxazol-5-yl)butan-1-one |
| 137b | 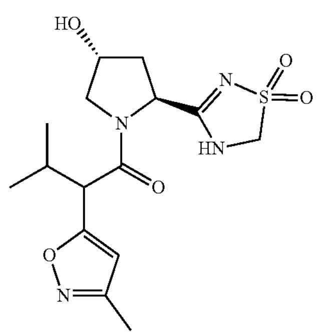 [SMILES: Cc1cc(C(C(=O)N2C[C@H](O)C[C@H]2C2=NS(=O)(=O)CN2)C(C)C)on1] | 1-((2S,4R)-2-(1,1-dioxido-4,5-dihydro-1,2,4-thiadiazol-3-yl)-4-hydroxypyrrolidin-1-yl)-3-methyl-2-(3-methylisoxazol-5-yl)butan-1-one |
| 137c | 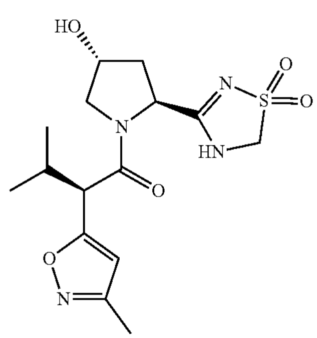 [SMILES: Cc1cc([C@H](C(=O)N2C[C@H](O)C[C@H]2C2=NS(=O)(=O)CN2)C(C)C)on1] | (R)-1-((2S,4R)-2-(1,1-dioxido-4,5-dihydro-1,2,4-thiadiazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 137d | 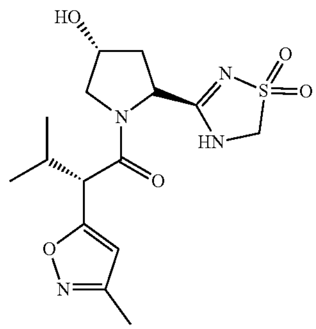 | (S)-1-((2S,4R)-2-(1,1-dioxido-4,5-dihydro-1,2,4-thiadiazol-3-yl)-4-hydroxypyrrolidin-1-yl)-3-methyl-2-(3-methylisoxazol-5-yl)butan-1-one |
| 137e | 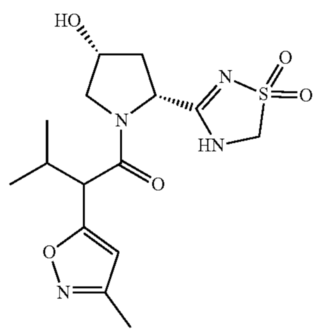 | 1-((2R,4R)-2-(1,1-dioxido-4,5-dihydro-1,2,4-thiadiazol-3-yl)-4-hydroxypyrrolidin-1-yl)-3-methyl-2-(3-methylisoxazol-5-yl)butan-1-one |
| 137f | 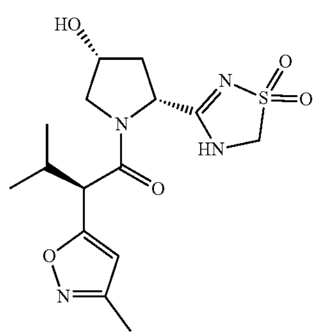 [SMILES: Cc1cc([C@H](C(=O)N2C[C@H](O)C[C@@H]2C2=NS(=O)(=O)CN2)C(C)C)on1] | (R)-1-((2R,4R)-2-(1,1-dioxido-4,5-dihydro-1,2,4-thiadiazol-3-yl)-4-hydroxypyrrolidin-1-yl)-3-methyl-2-(3-methylisoxazol-5-yl)butan-1-one |
| 137g | 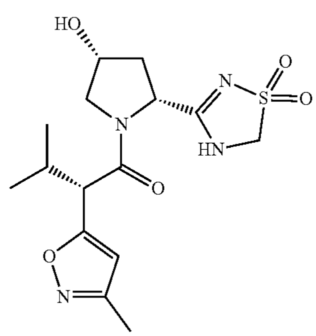 [SMILES: Cc1cc([C@@H](C(=O)N2C[C@H](O)C[C@@H]2C2=NS(=O)(=O)CN2)C(C)C)on1] | (S)-1-((2R,4R)-2-(1,1-dioxido-4,5-dihydro-1,2,4-thiadiazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 138 | 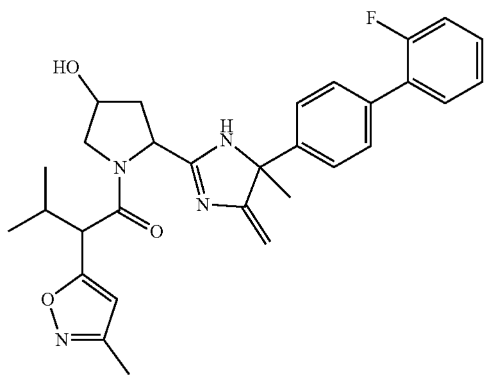 [SMILES: C=C1N=C(C2CC(O)CN2C(=O)C(c2cc(C)no2)C(C)C)NC1(C)c1ccc(-c2ccccc2F)cc1] | 5-(2'-fluoro-[1,1'-biphenyl]-4-yl)-2-(4-hydroxy-1-(3-methyl-2-(3-methylisoxazol-5-yl)butanoyl)pyrrolidin-2-yl)-5-methyl-1,5-dihydro-4H-imidazol-4-one |
| 138a | 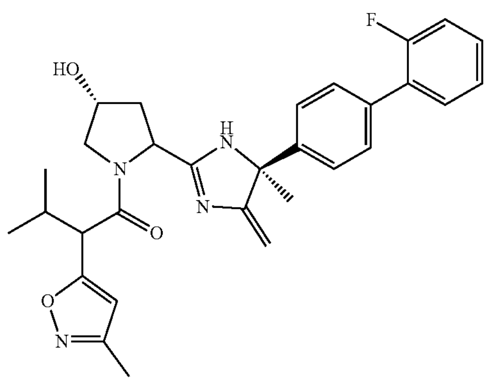 | (5S)-5-(2'-fluoro-[1,1'-biphenyl]-4-yl)-2-((4R)-4-hydroxy-1-(3-methyl-2-(3-methylisoxazol-5-yl)butanoyl)pyrrolidin-2-yl)-5-methyl-1,5-dihydro-4H-imidazol-4-one |
| 138b | 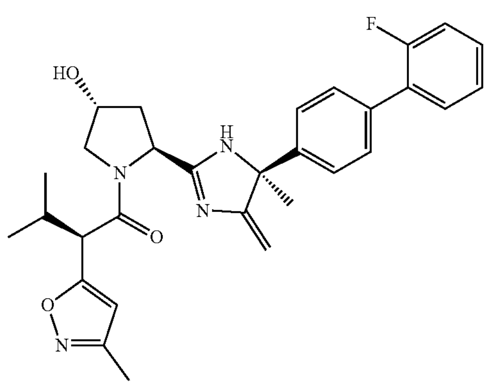 [SMILES: C=C1N=C([C@@H]2C[C@@H](O)CN2C(=O)[C@@H](c2cc(C)no2)C(C)C)N[C@@]1(C)c1ccc(-c2ccccc2F)cc1] | (S)-5-(2'-fluoro-[1,1'-biphenyl]-4-yl)-2-((2S,4R)-4-hydroxy-1-((R)-3-methyl-2-(3-methylisoxazol-5-yl)butanoyl)pyrrolidin-2-yl)-5-methyl-1,5-dihydro-4H-imidazol-4-one |
| 138c | 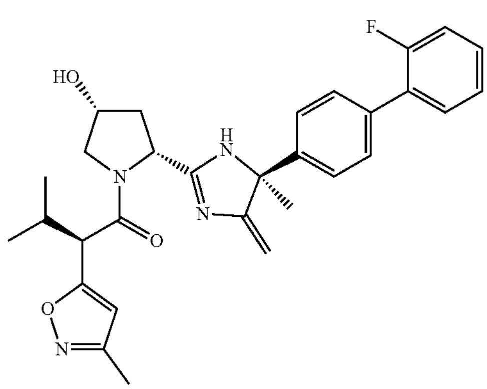 [SMILES: C=C1N=C([C@H]2C[C@@H](O)CN2C(=O)[C@@H](c2cc(C)no2)C(C)C)N[C@@]1(C)c1ccc(-c2ccccc2F)cc1] | (S)-5-(2'-fluoro-[1,1'-biphenyl]-4-yl)-2-((2R,4R)-4-hydroxy-1-((R)-3-methyl-2-(3-methylisoxazol-5-yl)butanoyl)pyrrolidin-2-yl)-5-methyl-1,5-dihydro-4H-imidazol-4-one |

TABLE 7-continued

VHL ligands

| Compound No. | Structure | Name[1] |
|---|---|---|
| 138d | 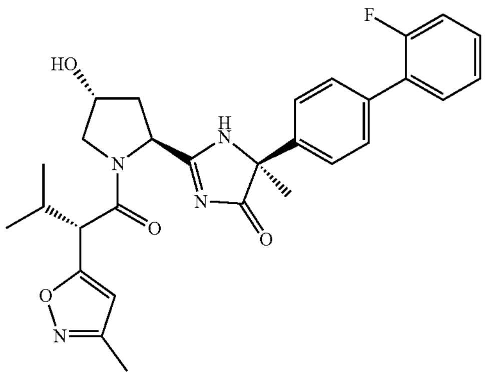 [SMILES: Cc1cc([C@@H](C(=O)N2C[C@H](O)C[C@H]2C2=NC(=O)[C@](C)(c3ccc(-c4ccccc4F)cc3)N2)C(C)C)on1] | (S)-5-(2'-fluoro-[1,1'-biphenyl]-4-yl)-2-((2S,4R)-4-hydroxy-1-((S)-3-methyl-2-(3-methylisoxazol-5-yl)butanoyl)pyrrolidin-2-yl)-5-methyl-1,5-dihydro-4H-imidazol-4-one |
| 138e | 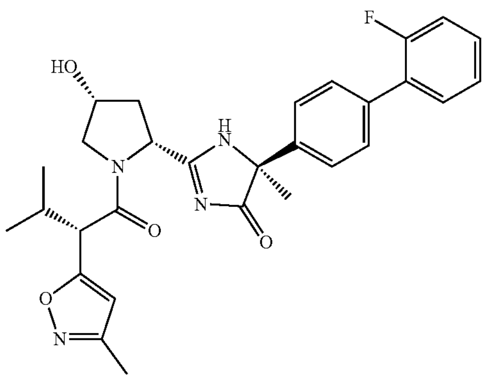 [SMILES: Cc1cc([C@@H](C(=O)N2C[C@H](O)C[C@@H]2C2=NC(=O)[C@](C)(c3ccc(-c4ccccc4F)cc3)N2)C(C)C)on1] | (S)-5-(2'-fluoro-[1,1'-biphenyl]-4-yl)-2-((2R,4R)-4-hydroxy-1-((S)-3-methyl-2-(3-methylisoxazol-5-yl)butanoyl)pyrrolidin-2-yl)-5-methyl-1,5-dihydro-4H-imidazol-4-one |
| 139 | 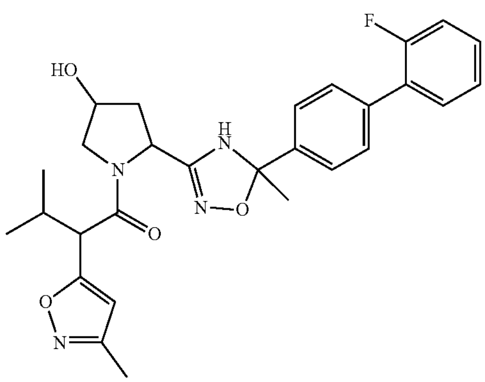 [SMILES: Cc1cc(C(C(=O)N2CC(O)CC2C2=NOC(C)(c3ccc(-c4ccccc4F)cc3)N2)C(C)C)on1] | 1-(2-(5-(2'-fluoro-[1,1'-biphenyl]-4-yl)-5-methyl-4,5-dihydro-1,2,4-oxadiazol-3-yl)-4-hydroxypyrrolidin-1-yl)-3-methyl-2-(3-methylisoxazol-5-yl)butan-1-one |
| 139a | 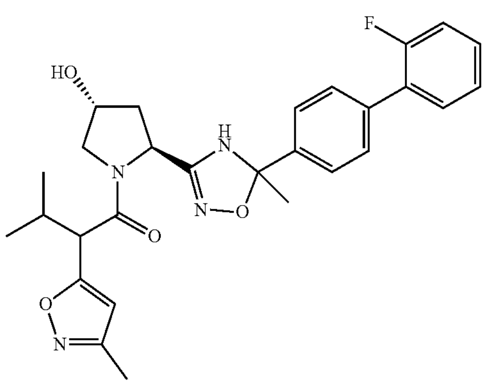 [SMILES: Cc1cc(C(C(=O)N2C[C@H](O)C[C@H]2C2=NOC(C)(c3ccc(-c4ccccc4F)cc3)N2)C(C)C)on1] | 1-((2S,4R)-2-(5-(2'-fluoro-[1,1'-biphenyl]-4-yl)-5-methyl-4,5-dihydro-1,2,4-oxadiazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 139b | 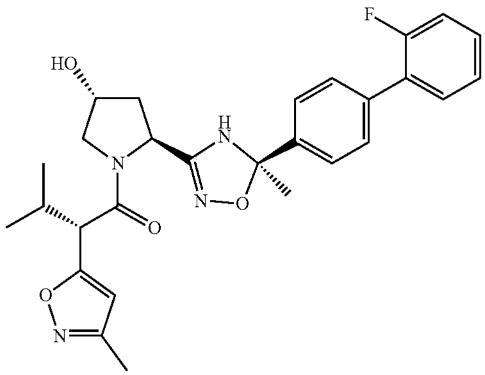 [SMILES: Cc1cc([C@@H](C(=O)N2C[C@H](O)C[C@H]2C2=NO[C@](C)(c3ccc(-c4ccccc4F)cc3)N2)C(C)C)on1] | (S)-1-((2S,4R)-2-((R)-5-(2'-fluoro-[1,1'-biphenyl]-4-yl)-5-methyl-4,5-dihydro-1,2,4-oxadiazol-3-yl)-4-hydroxypyrrolidin-1-yl)-3-methyl-2-(3-methylisoxazol-5-yl)butan-1-one |
| 139c | 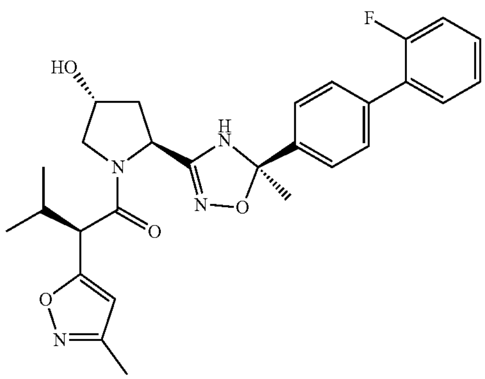 [SMILES: Cc1cc([C@H](C(=O)N2C[C@H](O)C[C@H]2C2=NO[C@](C)(c3ccc(-c4ccccc4F)cc3)N2)C(C)C)on1] | (R)-1-((2S,4R)-2-((R)-5-(2'-fluoro-[1,1'-biphenyl]-4-yl)-5-methyl-4,5-dihydro-1,2,4-oxadiazol-3-yl)-4-hydroxypyrrolidin-1-yl)-3-methyl-2-(3-methylisoxazol-5-yl)butan-1-one |
| 139d | 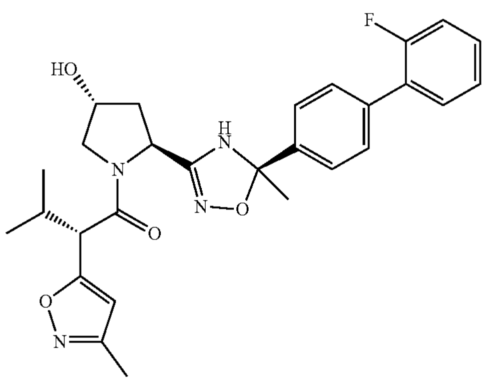 [SMILES: Cc1cc([C@@H](C(=O)N2C[C@H](O)C[C@H]2C2=NO[C@](C)(c3ccc(-c4ccccc4F)cc3)N2)C(C)C)on1] | (S)-1-((2S,4R)-2-((S)-5-(2'-fluoro-[1,1'-biphenyl]-4-yl)-5-methyl-4,5-dihydro-1,2,4-oxadiazol-3-yl)-4-hydroxypyrrolidin-1-yl)-3-methyl-2-(3-methylisoxazol-5-yl)butan-1-one |
| 139e | 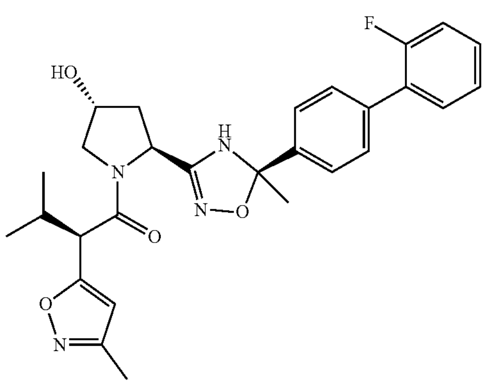 [SMILES: Cc1cc([C@H](C(=O)N2C[C@H](O)C[C@H]2C2=NO[C@](C)(c3ccc(-c4ccccc4F)cc3)N2)C(C)C)on1] | (R)-1-((2S,4R)-2-((S)-5-(2'-fluoro-[1,1'-biphenyl]-4-yl)-5-methyl-4,5-dihydro-1,2,4-oxadiazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 140 | 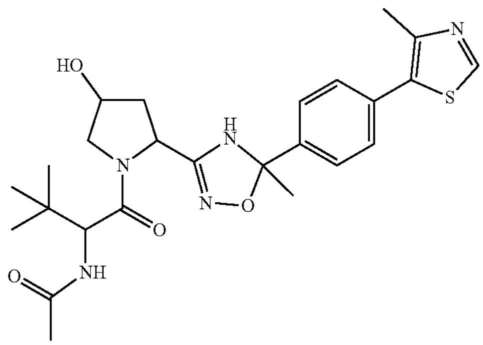 [SMILES: CC(=O)NC(C(=O)N1CC(O)CC1C1=NOC(C)(c2ccc(-c3scnc3C)cc2)N1)C(C)(C)C] | N-(1-(4-hydroxy-2-(5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)acetamide |
| 140a | 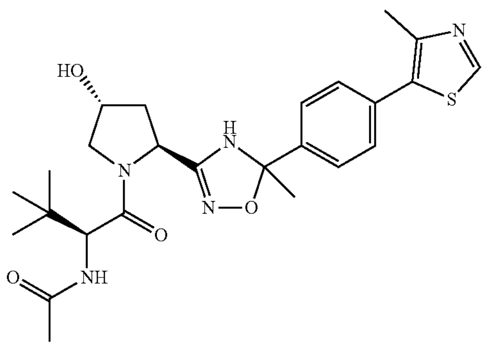 [SMILES: CC(=O)N[C@H](C(=O)N1C[C@H](O)C[C@H]1C1=NOC(C)(c2ccc(-c3scnc3C)cc2)N1)C(C)(C)C] | N-((2S)-1-((2S,4R)-4-hydroxy-2-(5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)acetamide |
| 140b | 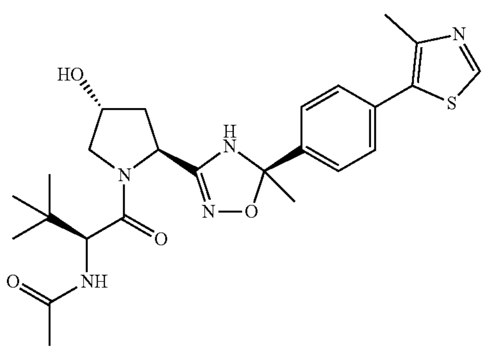 [SMILES: CC(=O)N[C@H](C(=O)N1C[C@H](O)C[C@H]1C1=NO[C@](C)(c2ccc(-c3scnc3C)cc2)N1)C(C)(C)C] | N-((S)-1-((2S,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)acetamide |
| 140c | 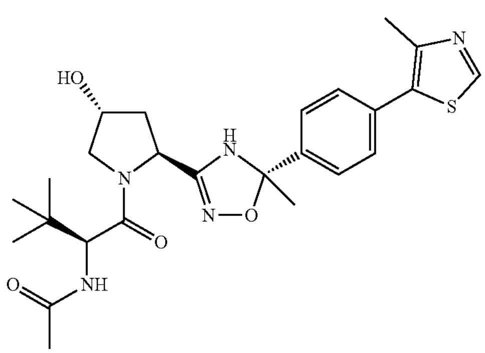 [SMILES: CC(=O)N[C@H](C(=O)N1C[C@H](O)C[C@H]1C1=NO[C@@](C)(c2ccc(-c3scnc3C)cc2)N1)C(C)(C)C] | N-((S)-1-((2S,4R)-4-hydroxy-2-((S)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)acetamide |

TABLE 7-continued

VHL ligands

| Compound No. | Structure | Name[1] |
|---|---|---|
| 141 | 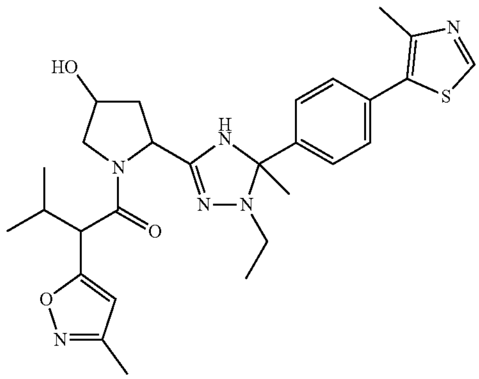 [SMILES: CCN1N=C(C2CC(O)CN2C(=O)C(c2cc(C)no2)C(C)C)NC1(C)c1ccc(-c2scnc2C)cc1] | 1-(2-(1-ethyl-5-methyl-5-(4-(4-methylthiazol-5-yl)phenyl)-4,5-dihydro-1H-1,2,4-triazol-3-yl)-4-hydroxypyrrolidin-1-yl)-3-methyl-2-(3-methylisoxazol-5-yl)butan-1-one |
| 141a | 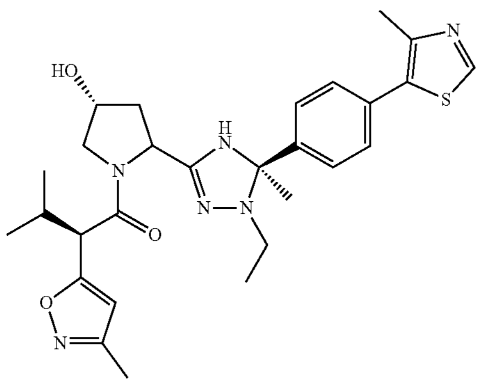 [SMILES: CCN1N=C(C2C[C@@H](O)CN2C(=O)[C@@H](c2cc(C)no2)C(C)C)N[C@@]1(C)c1ccc(-c2scnc2C)cc1] | (2R)-1-((4R)-2-((R)-1-ethyl-5-methyl-5-(4-(4-methylthiazol-5-yl)phenyl)-4,5-dihydro-1H-1,2,4-triazol-3-yl)-4-hydroxypyrrolidin-1-yl)-3-methyl-2-(3-methylisoxazol-5-yl)butan-1-one |
| 141b | 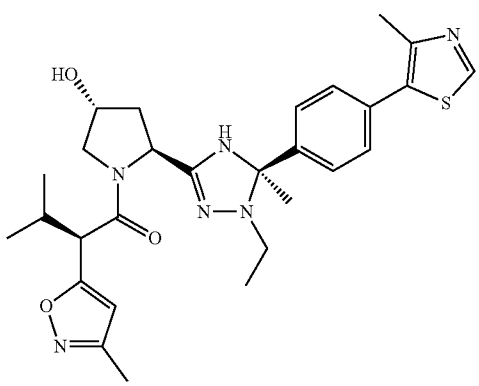 [SMILES: CCN1N=C([C@@H]2C[C@@H](O)CN2C(=O)[C@@H](c2cc(C)no2)C(C)C)N[C@@]1(C)c1ccc(-c2scnc2C)cc1] | (R)-1-((2S,4R)-2-((R)-1-ethyl-5-methyl-5-(4-(4-methylthiazol-5-yl)phenyl)-4,5-dihydro-1H-1,2,4-triazol-3-yl)-4-hydroxypyrrolidin-1-yl)-3-methyl-2-(3-methylisoxazol-5-yl)butan-1-one |
| 141c | 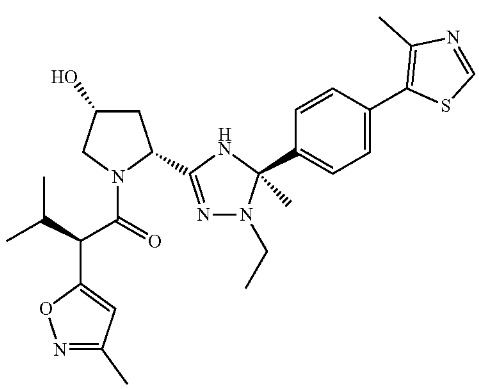 | (R)-1-((2R,4R)-2-((R)-1-ethyl-5-methyl-5-(4-(4-methylthiazol-5-yl)phenyl)-4,5-dihydro-1H-1,2,4-triazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 142 | 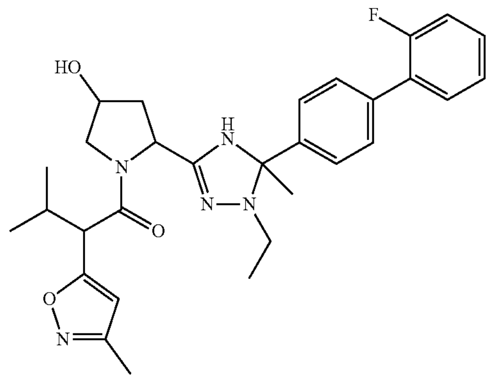 [SMILES: CCN1N=C(C2CC(O)CN2C(=O)C(c2cc(C)no2)C(C)C)NC1(C)c1ccc(-c2ccccc2F)cc1] | 1-(2-(1-ethyl-5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one |
| 142a | 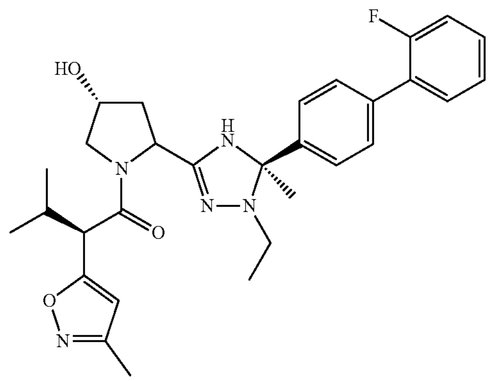 [SMILES: CCN1N=C(C2C[C@@H](O)CN2C(=O)[C@@H](c2cc(C)no2)C(C)C)N[C@@]1(C)c1ccc(-c2ccccc2F)cc1] | (2R)-1-((4R)-2-((R)-1-ethyl-5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one |
| 142b | 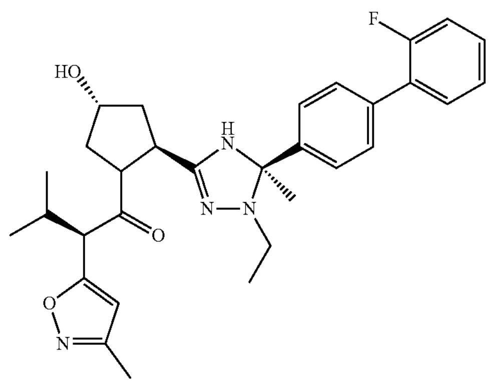 [SMILES: CCN1N=C([C@@H]2C[C@@H](O)CC2C(=O)[C@@H](c2cc(C)no2)C(C)C)N[C@@]1(C)c1ccc(-c2ccccc2F)cc1] | (R)-1-((2S,4R)-2-((R)-1-ethyl-5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one |
| 142c | 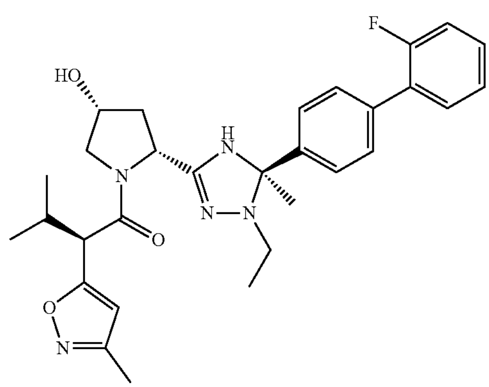 [SMILES: CCN1N=C([C@H]2C[C@@H](O)CN2C(=O)[C@@H](c2cc(C)no2)C(C)C)N[C@@]1(C)c1ccc(-c2ccccc2F)cc1] | (R)-1-((2R,4R)-2-((R)-1-ethyl-5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one |

TABLE 7-continued

VHL ligands

| Compound No. | Structure | Name[1] |
|---|---|---|
| 143 | 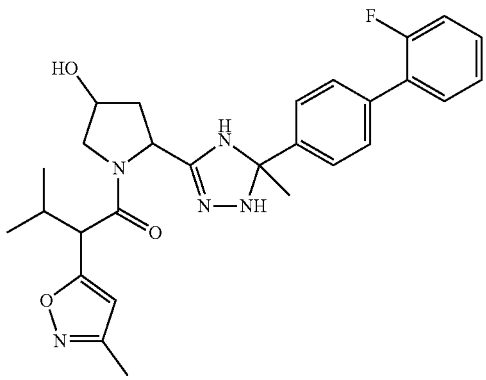 [SMILES: Cc1cc(C(C(=O)N2CC(O)CC2C2=NNC(C)(c3ccc(-c4ccccc4F)cc3)N2)C(C)C)on1] | 1-(2-(5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one |
| 143a | 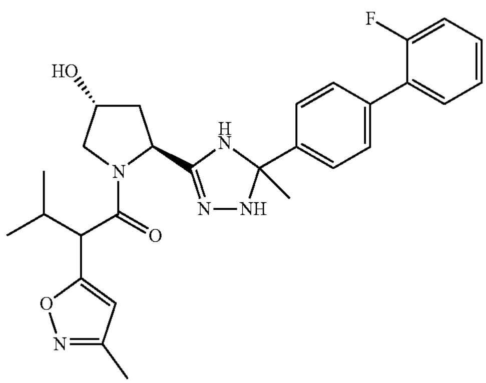 [SMILES: Cc1cc(C(C(=O)N2C[C@H](O)C[C@H]2C2=NNC(C)(c3ccc(-c4ccccc4F)cc3)N2)C(C)C)on1] | 1-((2S,4R)-2-(5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one |
| 143b | 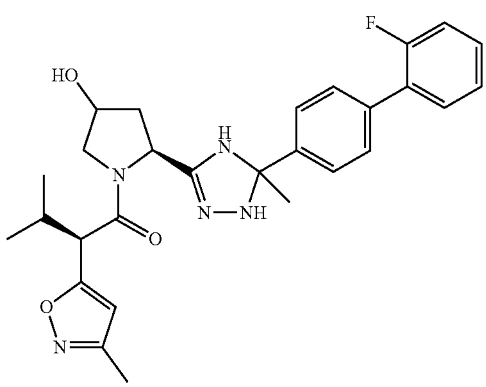 [SMILES: Cc1cc([C@H](C(=O)N2CC(O)C[C@H]2C2=NNC(C)(c3ccc(-c4ccccc4F)cc3)N2)C(C)C)on1] | (2R)-1-((2S,4R)-2-(5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one |
| 143c | 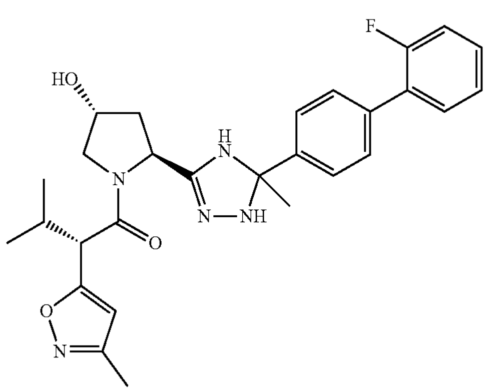 [SMILES: Cc1cc([C@@H](C(=O)N2C[C@H](O)C[C@H]2C2=NNC(C)(c3ccc(-c4ccccc4F)cc3)N2)C(C)C)on1] | (2S)-1-((2S,4R)-2-(5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one |

[1]Compound names were auto-generated using ChemDraw ®software version 15.1.0.144 or 17.1.0.105.

As discussed herein, the VHL ligands of the present disclosure may be derivatized, e.g., by coupling the VHL ligand directly or via a chemical linker to a protein binding moiety to form a PROTAC, as discussed elsewhere herein.

The VHL ligand and PB moiety ("D") may be covalently linked to one another and/or to the linker group through any group which is appropriate and stable to the chemistry of the linker. In certain embodiments, and as detailed herein, the linker may be independently covalently bonded to the VHL ligand and the PB moiety through an amide, ester, thioester, keto group, carbamate (urethane), carbon or ether, among others, each of which groups may be inserted anywhere on the VHL ligand and PB moiety to provide maximum binding of the VHL ligand on the VHL ubiquitin ligase and the PB moiety on the target protein to be degraded. In certain aspects, the linker may be linked to a substituted or unsubstituted alkyl group, substituted or unsubstituted alkenyl group, substituted or unsubstituted alkynyl group, substituted or unsubstituted aryl group, or to a substituted or unsubstituted heterocyclic group on the VHL ligand and/or PB moiety.

In one particular embodiment, a linker and PB moiety ("-L-D") are linked to a VHL ligand of Formula (III), (IIIa), (IV), or (IVa), or a salt (e.g., a pharmaceutically acceptable salt) thereof, through the Z substituent to form a PROTAC. In one such embodiment, the resulting PROTAC has a structure of Formula (I), (Ia), (II), or (IIa) or a salt (e.g., a pharmaceutically acceptable salt) thereof.

In another embodiment, a linker and PB moiety ("-L-D") are linked to a VHL ligand of Formula (III), (IIIa), (IV), or (IVa), or a salt (e.g., a pharmaceutically acceptable salt) thereof, through R² substituent to form a PROTAC. For example, R² may be an alkenyl or alkynyl, or may be an alkyl, alkenyl, or alkynyl that is substituted with a substituent suitable for linker attachment, such as halo, hydroxyl, or carboxyl. Alternatively, the R² substituent may be further modified to introduce a substituent suitable for linker attachment (e.g., introducing a hydroxyl group to a phenyl). Examples of VHL ligands of the present disclosure that may be derivatized at the R² position to attach a linker and PB moiety ("-L-D") include the following:

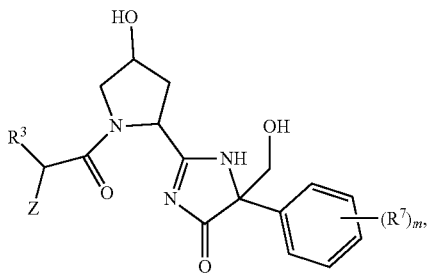

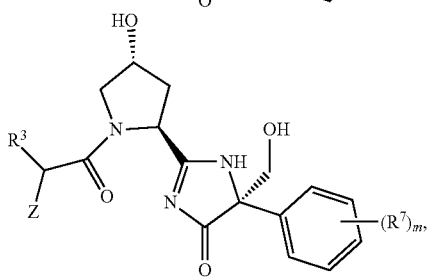

-continued

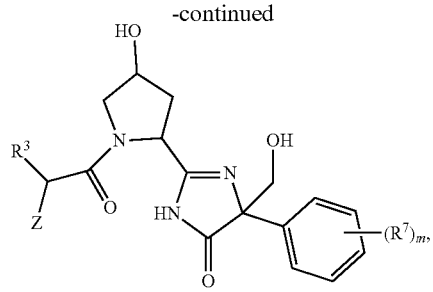

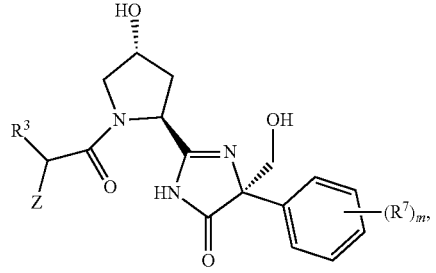

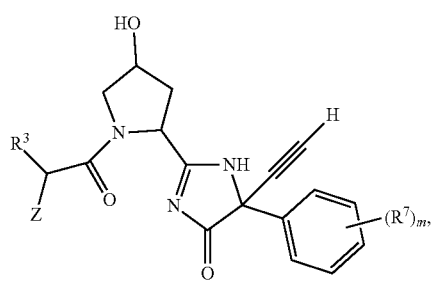

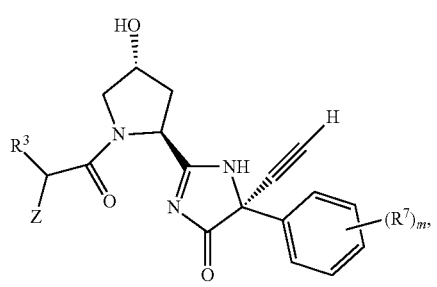

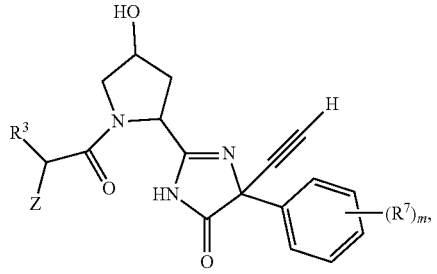

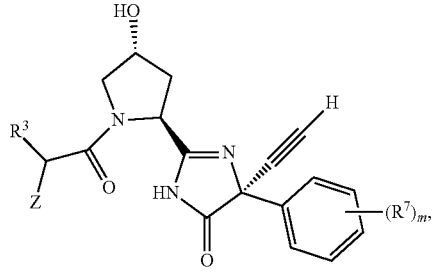

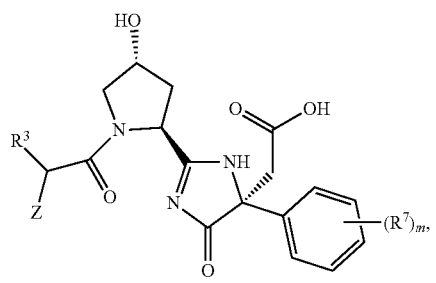

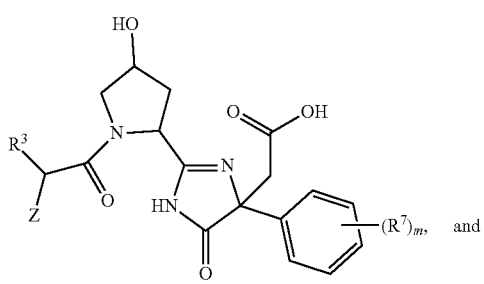 and

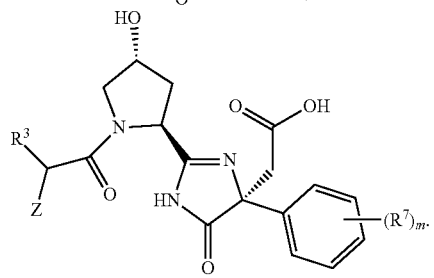

It is to be understood that these structures are exemplary, and other structures or compounds illustrated in the tables set forth herein that contain a suitable $R^2$ substituent may be linked to a linker and PB moiety ("-L-D") at the $R^2$ position, or alternately, may be modified at the $R^2$ substituent to introduce a substituent suitable for linker attachment.

In another embodiment, a linker and PB moiety ("-L-D") are linked to a VHL ligand of Formula (III), (IIIa), (IV), or (IVa), or a salt (e.g., a pharmaceutically acceptable salt) thereof, through the $R^1$ substituent to form a PROTAC. For example, $R^1$ may be an alkenyl or alkynyl, or may be an alkyl, alkenyl, alkynyl, cycloalkyl, aryl, heterocyclyl, or heteroaryl that is substituted with a substituent suitable for linker attachment. Alternatively, the $R^1$ substituent may be further modified to introduce a substituent suitable for linker attachment (e.g., introducing a hydroxyl group to a phenyl). Examples of VHL ligands of the present disclosure that may be derivatized at the $R^1$ position to attach a linker and PB moiety ("-L-D") include the following:

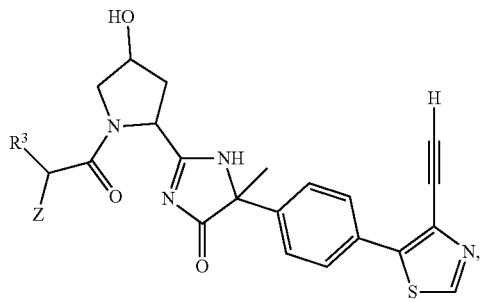

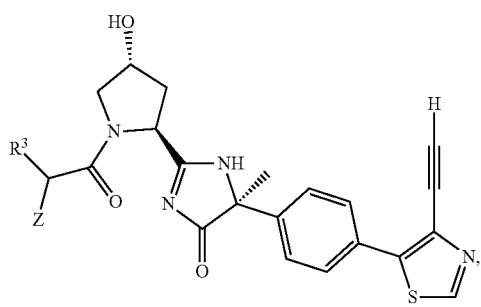

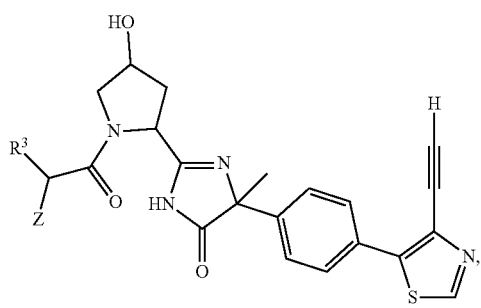

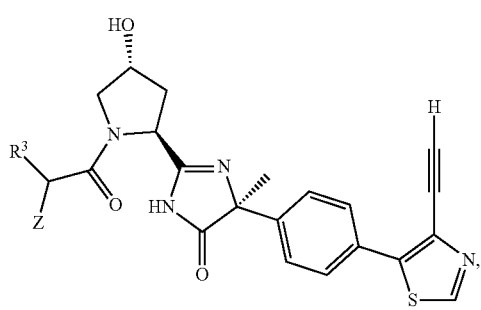

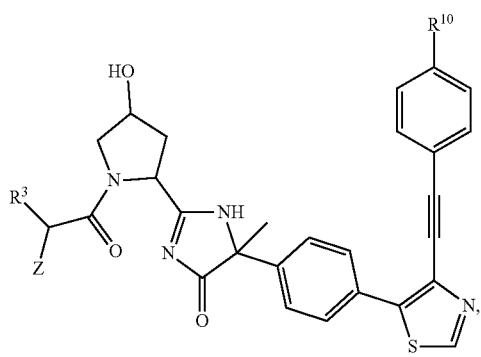

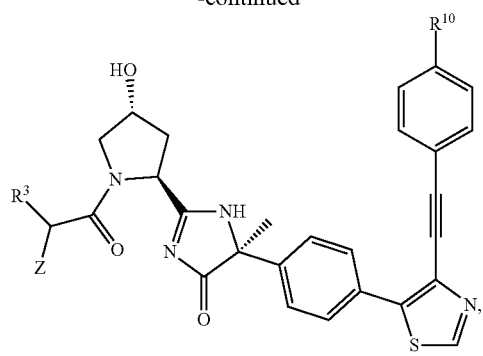
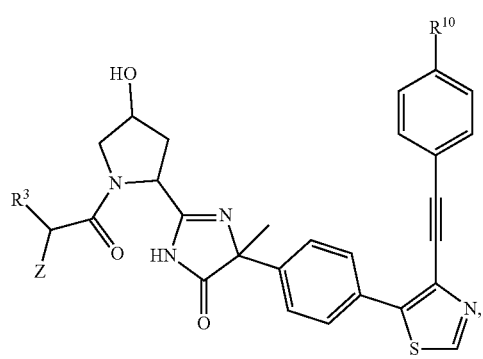
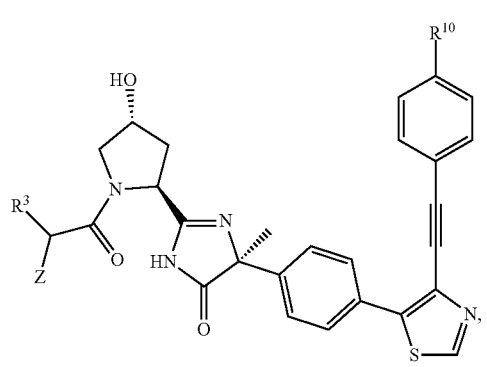
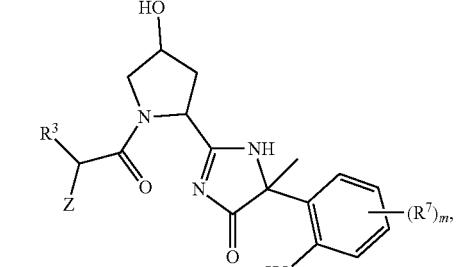
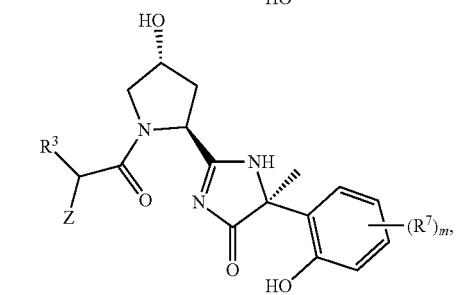
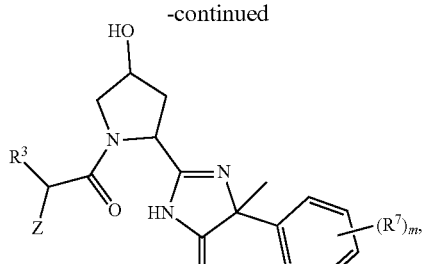
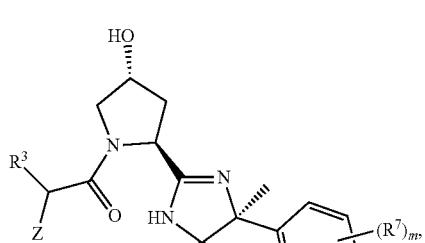
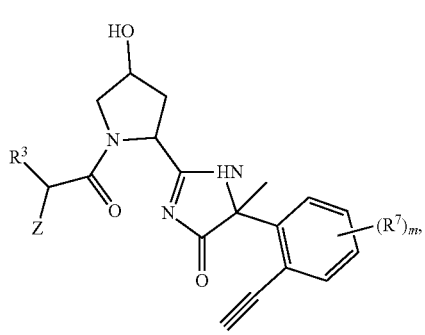
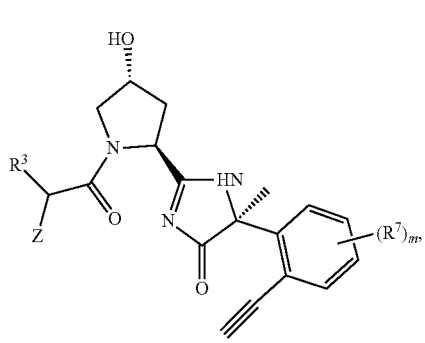
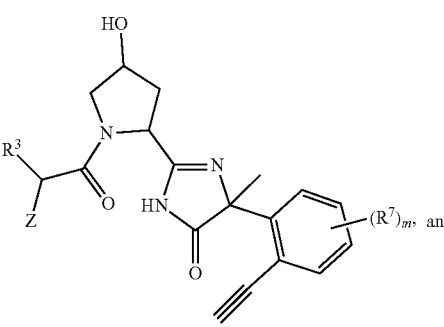

-continued

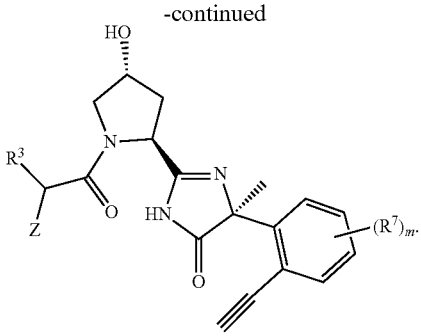

It is to be understood that these structures are exemplary, and other structures or compounds illustrated in the tables set forth herein that contain a suitable $R^1$ substituent may be linked to a linker and PB moiety ("-L-D") at the $R^1$ position, or alternately, may be modified at the $R^1$ substituent to introduce a substituent suitable for linker attachment.

In the above embodiments, the linker group L may be any linker group as described hereinafter. In the above embodiments, the PB moiety ("D") may be any protein binding moiety as described hereinafter.

2. Protein Binding (PB) Moiety ("D")

The PB moiety ("D") is a group which binds to a target protein intended to be degraded. The term "protein" includes oligopeptides and polypeptide sequences of sufficient length that they can bind to a PB moiety. Any protein in a eukaryotic system or a microbial system, including a virus, bacteria or fungus, as otherwise described herein, are targets for ubiquitination mediated by the compounds described herein. In some embodiments, the target protein may be a eukaryotic protein.

PB moieties include, for example, any moiety which binds to a protein specifically (binds to a target protein) and includes the following non-limiting examples of small molecule target protein moieties: heat shock protein 90 (Hsp90) inhibitors, kinase inhibitors and phosphatase inhibitors, MDM2 inhibitors, compounds targeting Human BET Bromodomain-containing proteins, HDAC inhibitors, human lysine methyltransferase inhibitors, angiogenesis inhibitors, immunosuppressive compounds, RAS inhibitors, EGFR inhibitors, and BRM inhibitors, as well as compounds that bind to the aryl hydrocarbon receptor (AHR), RAF receptor kinase, FKBP, Androgen Receptor (AR), estrogen receptor (ER), thyroid hormone receptor, HIV protease, HIV integrase, HCV protease, acyl-protein thioesterase-1 and -2 (APT1 and APT2), USP7, and BRG1, among numerous others. The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. These protein binding moieties are linked to the VHL ligand moiety through a linker, in order to present a target protein (to which the protein binding moiety is bound) in proximity to the ubiquitin ligase for ubiquitination and degradation.

Any protein, which can bind to a PB moiety and can be acted on or degraded by a ubiquitin ligase may be a target protein. In general, target proteins may include, for example, structural proteins, receptors, enzymes, cell surface proteins, proteins pertinent to the integrated function of a cell, including proteins involved in catalytic activity, proteins involved in aromatase activity, proteins involved in motor activity, proteins involved in helicase activity, proteins involved in metabolic processes (anabolism and catabolism), proteins involved in antioxidant activity, proteins involved in proteolysis, proteins involved in biosynthesis, proteins with kinase activity, proteins with oxidoreductase activity, proteins with transferase activity, proteins with hydrolase activity, proteins with lyase activity, proteins with isomerase activity, proteins with ligase activity, proteins with enzyme regulator activity, proteins with signal transducer activity, proteins with structural molecule activity, proteins with binding activity (protein, lipid carbohydrate), proteins with receptor activity, proteins with cell motility, membrane fusion proteins, cell communication proteins, proteins involved in regulation of biological processes, proteins that regulate development, proteins that regulate cell differentiation, proteins that regulate response to stimulus, behavioral proteins, cell adhesion proteins, proteins involved in cell death, proteins involved in transport (including protein transporter activity, proteins involved in nuclear transport, proteins involved in ion transporter activity, proteins involved in channel transporter activity, proteins involved in carrier activity, proteins involved in permease activity, proteins involved in secretion activity, proteins involved in electron transporter activity, proteins involved in pathogenesis, proteins involved in chaperone regulator activity, proteins involved in nucleic acid binding activity, proteins involved in transcription regulator activity, proteins involved in extracellular organization and biogenesis activity, proteins involved in translation regulator activity, and proteins involved in deubiquitinase activity. Proteins of interest can include proteins from eukaryotes and prokaryotes including humans as targets for drug therapy, other animals, including domesticated animals, microbials for the determination of targets for antibiotics and other antimicrobials and plants, and even viruses, among numerous others.

Accordingly, the PB moiety of a PROTAC may be any peptide or small molecule that bind protein targets such as FoxOl, HDAC, DP-1, E2F, ABL, AMPK, BRK, BRSK I, BRSK2, BTK, CAMKK1, CAMKK alpha, CAMKK beta, Rb, Suv39HI, SCF, p19INK4D, GSK-3, pi 8 INK4, myc, cyclin E, CDK2, CDK9, CDG4/6, Cycline D, p16 INK4A, cdc25A, BMI1, Akt, CHKl/2, C 1 delta, CK1 gamma, C 2, CLK2, CSK, DDR2, DYRK1A/2/3, EF2K, EPH-A2/A4/B1/B2/B3/B4, EIF2A 3, Smad2, Smad3, Smad4, Smad7, p53, p21 Cipl, PAX, Fyn, CAS, C3G, SOS, Tal, Raptor, RACK-1, CRK, Rapl, Rac, KRas, NRas, HRas, GRB2, FAK, PI3K, spred, Spry, mTOR, MPK, LKB1, PAK 1/2/4/5/6, PDG-FRA, PYK2, Src, SRPK1, PLC, PKC, PKA, PKB alpha/beta, PKC alpha/gamma/zeta, PKD, PLKl, PRAK, PRK2, WAVE-2, TSC2, DAPKl, BAD, IMP, C-TAK1, TAKl, TAOl, TBK1, TESK1, TGFBR1, TIE2, TLK1, TrkA, TSSK1, TTBKl/2, TTK, Tpl2/cotl, MEK1, MEK2, PLDL Erkl, Erk2, Erk5, Erk8, p90RSK, PEA-15, SRF, p27 KIP1, TIF la, HMGN1, ER81, MKP-3, c-Fos, FGF-R1, GCK, GSK3 beta, HER4, HIPK1/2/3/, IGF-1R, cdc25, UBF, LAMTOR2, Statl, StaO, CREB, JAK, PTEN, NF-kappaB, HECTH9, Bax, HSP70, HSP90, Apaf-1, Cyto c, BCL-2, Bcl-xL, Smac, XIAP, Caspase-9, Caspase-3, Caspase-6, Caspase-7, CDC37, TAB, IKK, TRADD, TRAF2, R1P1, FLIP, JNKl/2/3, Lck, A-Raf, B-Raf, C-Raf, MOS, MLKl/3, MN l/2, MSKl, MST2/3/4, MPSK1, MEKKl, ME K4, MEL, ASK1, MINK1, MKK 1/2/3/4/6/7, NE 2a/6/7, NUAK1, OSR1, SAP, STK33, Syk, Lyn, PDK1, PHK, PIM 1/2/3, Ataxin-1, mTORCl, MDM2, p21 Wafl, Cyclin Dl, Lamln A, Tpl2, Myc, catenin, Wnt, IKK-beta, IKK-gamma, IKK-alpha, IKK-epsilon, ELK, p65RelA, IRAKI, IRA 2, IRAK4, IRR, FADD, TRAF6, TRAF3, MKK3, MKK6, ROCK2, RSK1/2, SGK 1, SmMLCK, SIK2/3, ULK1/2, VEGFR1, WNK 1, YES1, ZAP70, MAP4K3, MAP4K5, MAPKlb, MAPKAP-K2 K3, p38 alpha/beta/delta/gamma MAPK, Aurora A, Aurora B, Aurora C, MCAK, Clip, MAPKAPK, MARK 1/2/3/4, Mucl, SHC, CXCR4, Gap-1, beta-catenin/ TCF, Cbl, BRM, Mcl-1, BRD2, BRD3, BRD4, AR, RAS, ErbB3, EGFR, IRE1, HPK1, RIPK2, and ERα, including variants, mutations, splice variants, indels and fusions of these target proteins listed. Other examples of protein targets include Ras proteins, P13K, Ral-GDS, H-Ras, N-Ras, KRas4A, K-Ras4B, BRG1, RAF, BRAF, CRAF, and BET. In one embodiment, the protein target is selected from the group consisting of EGRF, RAS, BRM, BRG1, MDM2, RAF (BRAF and CRAF), BET, and USP7.

A number of drug targets for human therapeutics also represent protein targets to which a protein binding moiety may be bound and incorporated into compounds according to the present disclosure. These include proteins which may be used to restore function in numerous polygenic diseases, including for example B7.1 and B7, TINFRlm, TNFR2, NADPH oxidase, BclIBax and other partners in the apotosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, i.e., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuramimidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-αR, ICAM1, Cat+ channels, VCAM, VLA-4 integrin, selectins, CD40/CD40L, newokinins and receptors, inosine monophosphate dehydrogenase, p38 MAP Kinase, RaslRaflMEWERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-21 neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further target proteins include Acetyl-CoA carboxylase, adenylosuccinate synthetase, protoporphyrinogen oxidase, and enolpyruvyl-shikimate-phosphate synthase.

Haloalkane dehalogenase enzymes are another target of specific compounds according to the present disclosure. Compounds according to the present disclosure which contain chloroalkane peptide binding moieties ($C_1$-$C_{12}$ often about $C_2$-$C_{10}$ alkyl halo groups) may be used to inhibit and/or degrade haloalkane dehalogenase enzymes which are used in fusion proteins or related diagnostic proteins as described in WO 2012/078559, the contents of which is incorporated by reference herein.

In still other embodiments, the PB moiety is a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl PB moieties for use in the present disclosure may be represented by the chemical structure -$(CH_2)_v$-Halo where v is any integer from 2 to about 12, often about 3 to about 8, more often about 4 to about 6. Halo may be any halogen, but is preferably Cl or Br, more often Cl.

In still other embodiments, the PB moiety has the structure

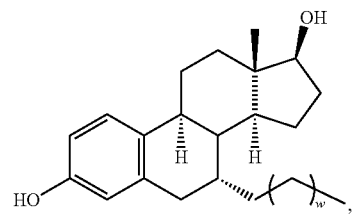

where w is 0 to 3, preferably 1 or 2. This group binds selectively to estrogen receptors and is useful for treating diseases which are modulated through estrogen receptors, and in particular cancers, such as breast cancer, endometrial cancer, ovarian cancer and uterine cancer, among others.

The compositions described below exemplify some of the members of these types of small molecule target protein binding moieties. Such small molecule target protein binding moieties also include pharmaceutically acceptable salts, enantiomers, solvates and polymorphs of these compositions, as well as other small molecules that may target a protein of interest. References which are cited hereinbelow are incorporated by reference herein in their entirety.

Heat Shock Protein 90 (HSP90) Inhibitors

HSP90 inhibitors as used herein include, but are not limited to:

1. The HSP90 inhibitors identified in Vallee, et al., "Tricyclic Series of Heat Shock Protein 90 (HSP90) Inhibitors Part I: Discovery of Tricyclic Imidazo[4,5-C]Pyridines as Potent Inhibitors of the HSP90 Molecular Chaperone (2011) *J. Med. Chem.*, 54: 7206, including YKB:

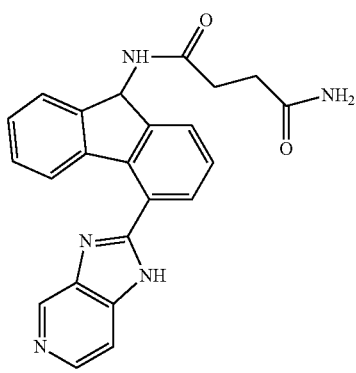 [SMILES: NC(=O)CCC(=O)NC1c2ccccc2-c2c(-c3nc4cnccc4[nH]3)cccc21]

(N-[4-(3H-imidazo[4,5-C]pyridin-2-yl)-9H-fluoren-9-yl]-succinamide)
derivatized where a linker group L or a -L-(VHL ligand moiety) group is attached via the terminal amide group;

2. The HSP90 inhibitor p54 (modified):
8-[(2,4-dimethylphenyl)sulfanyl]-3-pent-4-yn-1-yl-3H-purin-6-amine

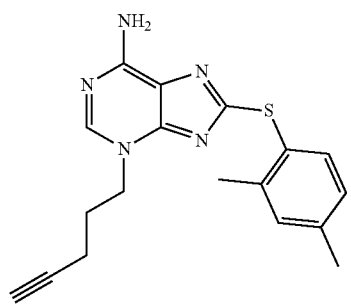 [SMILES: C#CCCCn1cnc(N)c2nc(Sc3ccc(C)cc3C)nc1-2]

where a linker group L or a -L-(VHL ligand moiety) group is attached via the terminal acetylene group;

3. The HSP90 inhibitors (modified) identified in Brough, et al., "4,5-Diarylisoxazole HSP90 Chaperone Inhibitors: Potential Therapeutic Agents for the Treatment of Cancer", *J. Med. Chem.*, Vol: 51, p.:196 (2008), including the compound 2GJ (5-[2,4-dihydroxy-5-(1-methylethyl)phenyl]-N-ethyl-4-[4-(morpholin-4-ylmethyl)phenyl]isoxazole-3-carboxamide) having the structure:

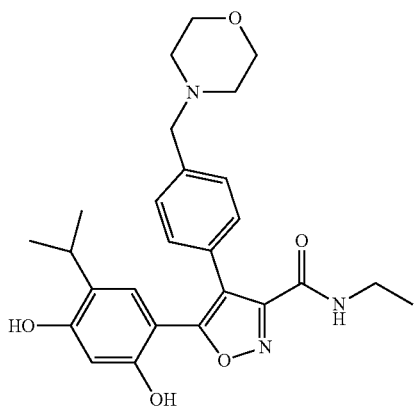 [SMILES: CCNC(=O)c1noc(-c2cc(C(C)C)c(O)cc2O)c1-c1ccc(CN2CCOCC2)cc1]

(derivatized, where a linker group L or a -L-(VHL ligand moiety) group is attached via the amide group (at the amine or at the alkyl group on the amine));

4. The HSP90 inhibitors (modified) identified in Wright, et al., "Structure-Activity Relationships in Purine-Based Inhibitor Binding to HSP90 Isoforms," *Chem Biol.* 2004 June; 11(6):775-85, including the HSP90 inhibitor PU3 having the structure:

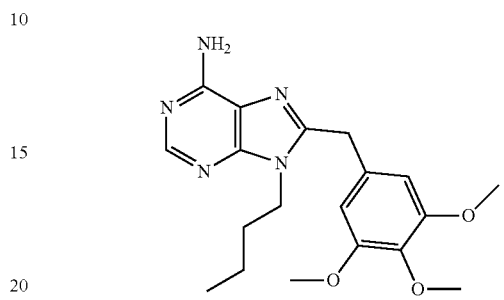

where a linker group L or -L-(VHL ligand moiety) is attached via the butyl group; and 5. The HSP90 inhibitor Geldanamycin ((4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1] (derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")) (derivatized, where a linker group L or -L-(VHL ligand moiety) group is attached via the amide group).

Kinase and Phosphatase Inhibitors

Kinase inhibitors as used herein include, but are not limited to:

1. Erlotinib Derivative Tyrosine Kinase Inhibitor

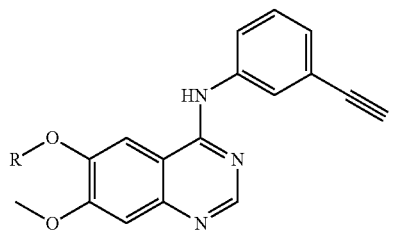

where R is a linker group L or a -L-(VHL ligand moiety) group attached via the ether group;

2. The kinase inhibitor Sunitanib (derivatized):

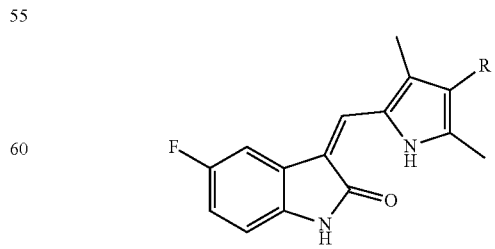

(derivatized where R is a linker group L or a -L-(VHL ligand moiety) group attached to the pyrrole moiety);

3. Kinase Inhibitor Sorafenib (derivatized)

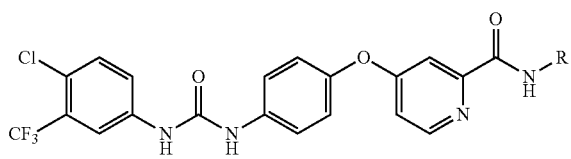

(derivatized where R is a linker group L or a -L-(VHL ligand moiety) group attached to the phenyl moiety);

4. The kinase inhibitor Desatinib (derivatized)

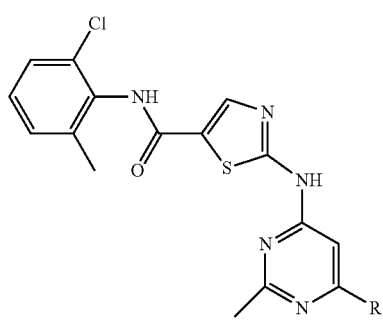

(derivatized where R is a linker group L or a -L-(VHL ligand moiety) group attached to the pyrimidine);

5. The kinase inhibitor Lapatinib (derivatized)

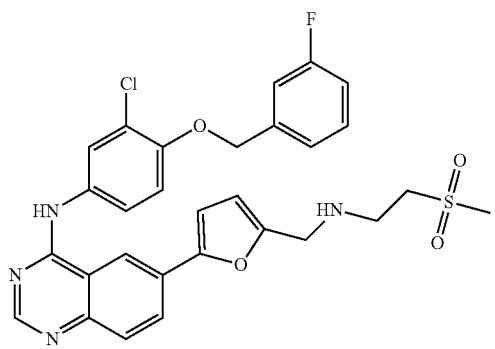 [SMILES: CS(=O)(=O)CCNCc1ccc(-c2ccc3ncnc(Nc4ccc(OCc5cccc(F)c5)c(Cl)c4)c3c2)o1]

derivatized where a linker group L or a -L-(VHL ligand moiety) group is attached via the terminal methyl of the sulfonyl methyl group;

6. The kinase inhibitor U09-CX-5279 (Derivatized)

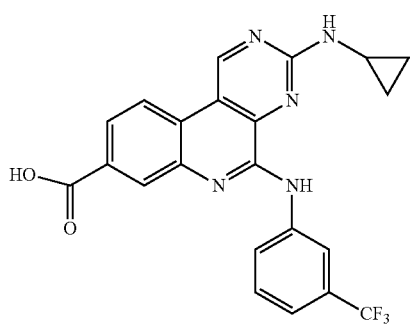 [SMILES: O=C(O)c1ccc2c(c1)nc(Nc1cccc(C(F)(F)F)c1)c1nc(NC3CC3)ncc12]

(derivatized where a linker group L or a -L-(VHL ligand moiety) group is attached via the amine (aniline), carboxylic acid or amine alpha to cyclopropyl group, or cyclopropyl group);

7. The kinase inhibitors identified in Millan, et al., "Design and Synthesis of Inhaled P38 Inhibitors for the Treatment of Chronic Obstructive Pulmonary Disease," *J. Med. Chem.*, Vol:54, pag:7797 (2011), including the kinase inhibitors Y1W and Y1X (Derivatized) having the structures:

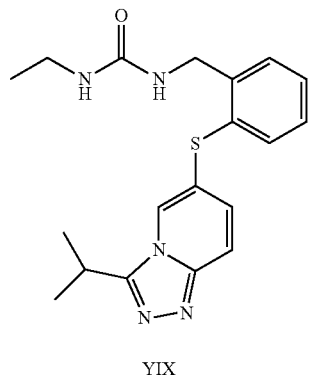

YIX 1-ethyl-3-(2-{[3-(1-methylethyl)[1,2,4]triazolo[4,3-a]pyridin-6-yl]sulfanyl}benzyl)urea (derivatized where a linker group L or a -L-(VHL ligand moiety) group is attached preferably via the propyl group);

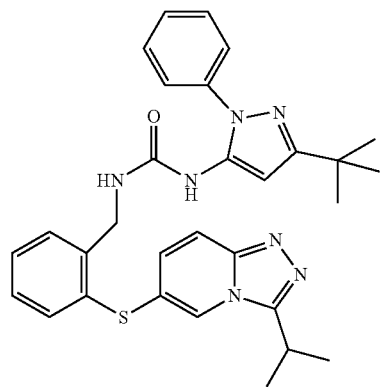

YIW 1-(3-tert-butyl-1-phenyl-1H-pyrazol-5-yl)-3-(2-{[3-(1-methylethyl)[1,2,4]triazolol[4,3-a]pyridin-6-yl]sulfanyl}benzyl)urea (derivatized where a linker group L or a -L-(VHL ligand moiety) group is attached preferably via either the propyl group or the butyl group);

8. The kinase inhibitors identified in Schenkel, et al., "Discovery of Potent and Highly Selective Thienopyridine Janus Kinase 2 Inhibitors", *J. Med. Chem.*, 2011, 54 (24), pp 8440-8450, including the compounds 6TP and 0TP (derivatized) having the structures:

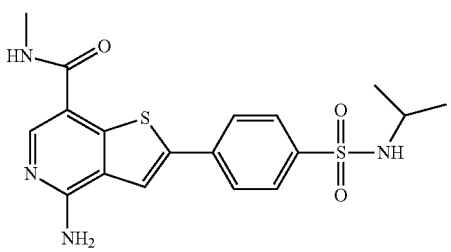

6TP 4-amino-2-[4-(tert-butylsulfamoyl)phenyl]-N-methylthieno[3,2-c]pyridine-7-carboxamide Thienopyridine (derivatized where a linker group L or a -L-(VHL ligand moiety) group is attached preferably via the terminal methyl group bound to amide moiety);

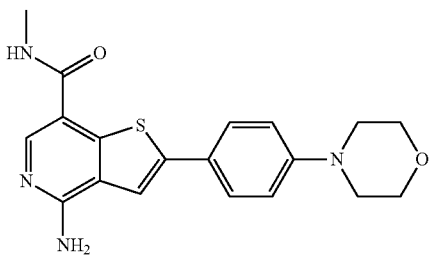

OTP 4-amino-N-methyl-2-[4-(morpholin-4-yl)phenyl]thieno[3,2-c]pyridine-7-carboxamide Thienopyridine (derivatized where a linker group L or a -L-(VHL ligand moiety) group is attached preferably via the terminal methyl group bound to amide moiety);

9. The kinase inhibitors identified in Van Eis, et al., "2,6-Naphthyridines as potent and selective inhibitors of the novel protein kinase C isozymes", *Biorg. Med. Chem. Lett.*, 2011 Dec. 15; 21(24):7367-72, including the kinase inhibitor O7U having the structure:

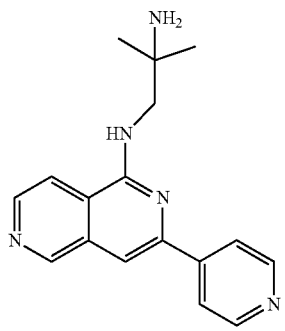

O7U 2-methyl-N~1~-[3-(pyridin-4-yl)-2,6-naphthyridin-1-yl]propane-1,2-diamine (derivatized where a linker group L or a -L-(VHL ligand moiety) group is attached preferably via the secondary amine or terminal amino group);

10. The kinase inhibitors identified in Lountos, et al., "Structural Characterization of Inhibitor Complexes with Checkpoint Kinase 2 (Chk2), a Drug Target for Cancer Therapy", *J. Struct. Biol.*, Vol:176, p.:292 (2011), including the kinase inhibitor YCF having the structure:

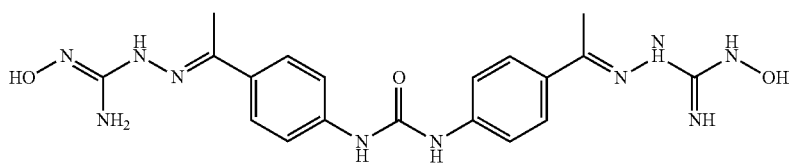 [SMILES: C/C(=N\NC(=N)NO)c1ccc(NC(=O)Nc2ccc(/C(C)=N/N/C(N)=N/O)cc2)cc1]

(derivatized where a linker group L or a -L-(VHL ligand moiety) group is attached preferably via either of the terminal hydroxyl groups);

11. The kinase inhibitors identified in Lountos, et al., "Structural Characterization of Inhibitor Complexes with Checkpoint Kinase 2 (Chk2), a Drug Target for Cancer Therapy", *J. Struct. Biol.*, Vol:176, p.:292 (2011), including the kinase inhibitors XK9 and NXP (derivatized) having the structures:

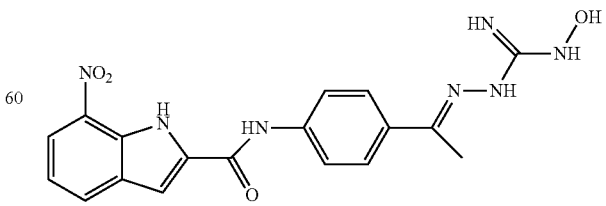

XK9

N-(4-[(1E)-N—(N-hydroxycarbamimidoyl)ethanehydrazonoyl]phenyl)-7-nitro-1H-indole-2-carboxamide

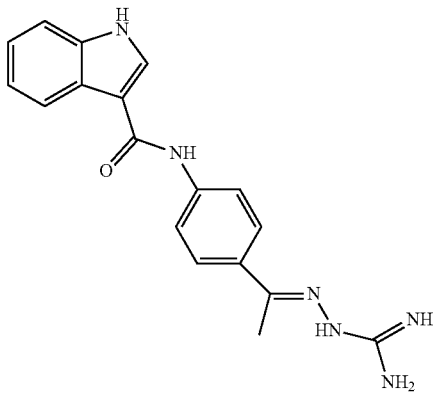

NXP

N-(4-[(1E)-N-carbamimidoylethanehydrazonoyl]phenyl)-1H-indole-3-carboxamide (derivatized where a linker group L or a -L-(VHL ligand moiety) group is attached preferably via the terminal hydroxyl group (XK9) or the hydrazine group (NXP));

12. The kinase inhibitor Afatinib (derivatized) (N-[4-[(3-Chloro-4-fluorophenyl)amino]-7-[[(3S)-tetrahydro-3-furanyl]oxy]-6-quinazolinyl]-4(dimethylamino)-2-butenamide) (derivatized where a linker group L or a -L-(VHL ligand moiety) group is attached preferably via the aliphatic amine group);

13. The kinase inhibitor Fostamatinib (derivatized) ([6-({5-fluoro-2-[(3,4,5-trimethoxyphenyl)amino]pyrimidin-4-yl}amino)-2,2-dimethyl-3-oxo-2,3-dihydro-4H-pyrido[3,2-b]-1,4-oxazin-4-yl]methyl disodium phosphate hexahydrate) (derivatized where a linker group L or a -L-(VHL ligand moiety) group is attached preferably via a methoxy group);

14. The kinase inhibitor Gefitinib (derivatized) (N-(3-chloro-4-fluoro-phenyl)-7-methoxy-6-(3-morpholin-4-yl-propoxy)quinazolin-4-amine) (derivatized where a linker group L or a -L-(VHL ligand moiety) group is attached preferably via a methoxy or ether group);

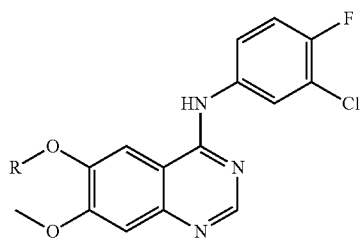

15. The kinase inhibitor Lenvatinib (derivatized) (4-[3-chloro-4-(cyclopropylcarbamoylamino)phenoxy]-7-methoxy-quinoline-6-carboxamide) (derivatized where a linker group L or a -L-(VHL ligand moiety) group is attached preferably via the cyclopropyl group);

16. The kinase inhibitor Vandetanib (derivatized) (N-(4-bromo-2-fluorophenyl)-6-methoxy-7-[(1-methylpiperidin-4-yl)methoxy]quinazolin-4-amine) (derivatized where a linker group L or a -L-(VHL ligand moiety) group is attached preferably via the methoxy or hydroxyl group);

17. The kinase inhibitor Vemurafenib (derivatized) (propane-1-sulfonic acid {3-[5-(4-chlorophenyl)-1H-pyrrolo[2,3-b]pyridine-3-carbonyl]-2,4-difluoro-phenyl}-amide) (derivatized where a linker group L or a -L-(VHL ligand moiety) group is attached preferably via the sulfonyl propyl group);

18. The kinase inhibitor Gleevee (derivatized):

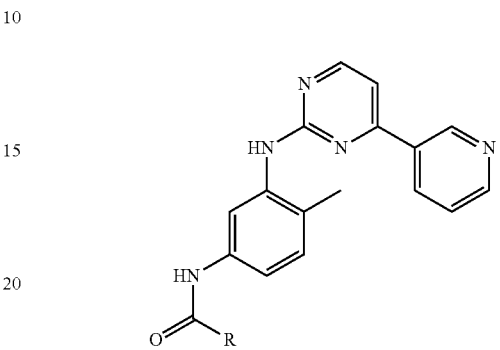

(derivatized where R is a linker group L or a -L-(VHL ligand moiety) group is attached preferably via the amide group or via the aniline amine group);

19. The kinase inhibitor Pazopanib (derivatized) (VEGFR3 inhibitor):

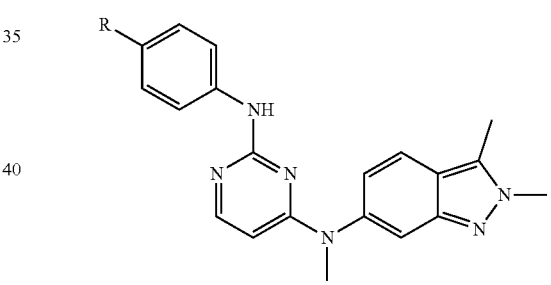

(derivatized where R is a linker group L or a -L-(VHL ligand moiety) group preferably attached to the phenyl moiety or via the aniline amine group);

20. The kinase inhibitor AT-9283 (Derivatized) Aurora Kinase Inhibitor

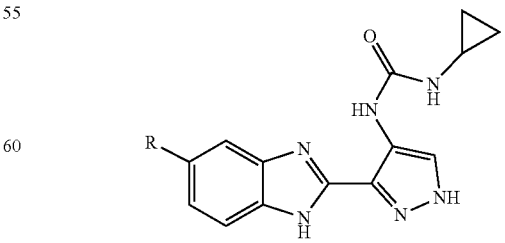

(where R is a linker group L or a -L-(VHL ligand moiety) group attached preferably to the phenyl moiety);

21. The kinase inhibitor TAE684 (derivatized) ALK inhibitor

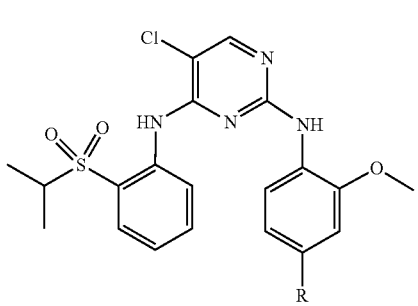

(where R is a linker group L or a -L-(VHL ligand moiety) group attached preferably to the phenyl moiety);

22. The kinase inhibitor Nilotanib (derivatized) Abl inhibitor:

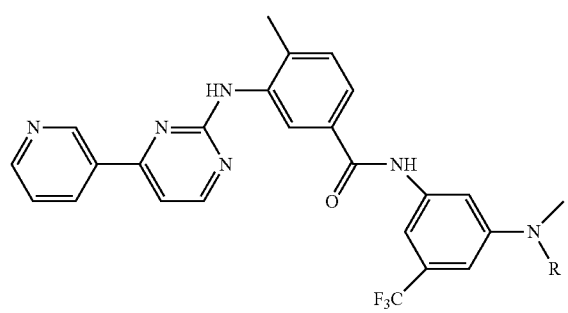

(derivatized where R is a linker group L or a -L-(VHL ligand moiety) group attached preferably to the phenyl moiety or the aniline amine group);

23. Kinase InhibitorNVP-BSK805 (derivatized) JAK2 Inhibitor:

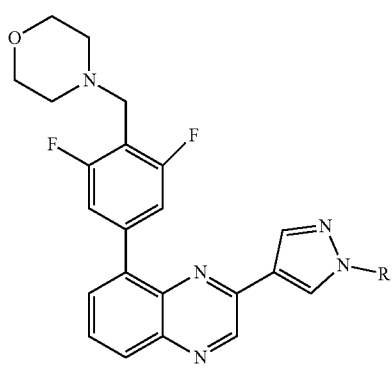

(derivatized where R is a linker group L or a -L-(VHL ligand moiety) group attached to the phenyl moiety or the diazole group);

24. Kinase Inhibitor Crizotinib Derivatized Alk Inhibitor:

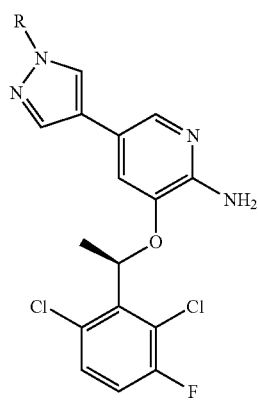

(derivatized where R is a linker group L or a -L-(VHL ligand moiety) group attached to the phenyl moiety or the diazole group);

25. Kinase Inhibitor JNJ FMS (derivatized) Inhibitor:

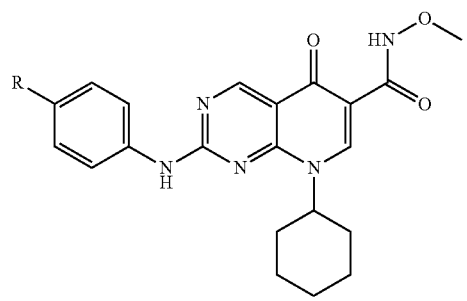

(derivatized where R is a linker group L or a -L-(VHL ligand moiety) group attached preferably to the phenyl moiety);

26. The kinase inhibitor Foretinib (derivatized) Met Inhibitor:

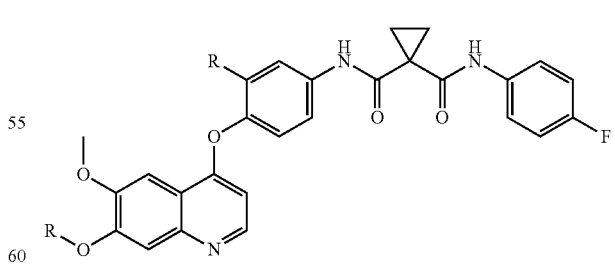

(derivatized where R is a linker group L or a -L-(VHL ligand moiety) group attached to the phenyl moiety or a hydroxyl or ether group on the quinoline moiety);

27. The allosteric Protein Tyrosine Phosphatase Inhibitor PTP1B (derivatized):

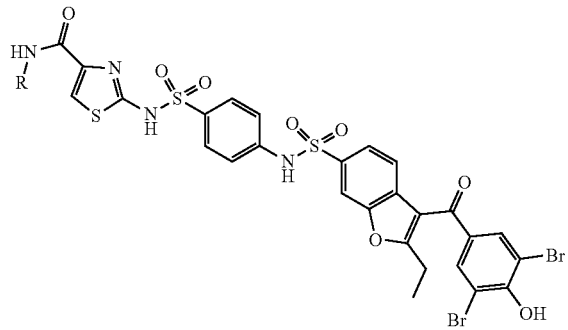

(derivatized where a linker group L or a -L-(VHL ligand moiety) group is preferably attached at R, as indicated);

28. The inhibitor of SHP-2 Domain of Tyrosine Phosphatase (derivatized):

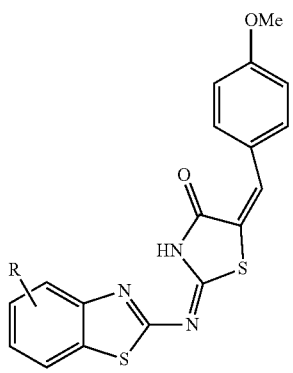

(derivatized where a linker group L or a -L-(VHL ligand moiety) group is attached preferably at R);

29. The inhibitor (derivatized) of BRAF (BRAF$^{V600E}$)/MEK:

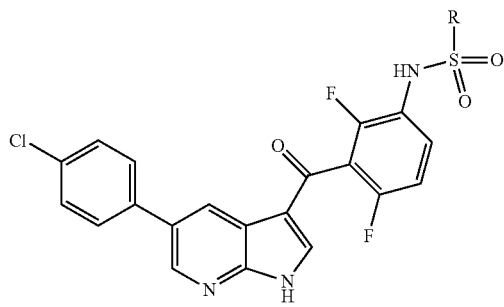

(derivatized where a linker group L or a -L-(VHL ligand moiety) group is attached preferably at R); and 30. Inhibitor (derivatized) of Tyrosine Kinase ABL:

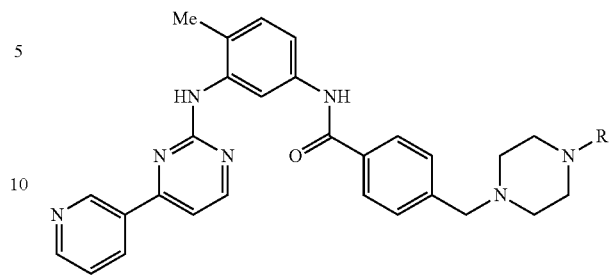

(derivatized where "R" designates a site for attachment of a linker group L or a -L-(VHL ligand moiety) group on the piperazine moiety).

MDM2 Inhibitors

MDM2 inhibitors as used herein include, but are not limited to:

1. The MDM2 inhibitors identified in Vassilev, et al., "In vivo activation of the p53 pathway by small-molecule antagonists of MDM2," *Science*, vol:303, p.:844-848 (2004), and Schneekloth, et al., "Targeted intracellular protein degradation induced by a small molecule: En route to chemical proteomics", *Bioorg. Med. Chem. Lett.*, 18 (2008) 5904-5908, including (or additionally) the compounds nutlin-3, nutlin-2, and nutlin-1 (derivatized) as described below, as well as derivatives and analogs thereof:

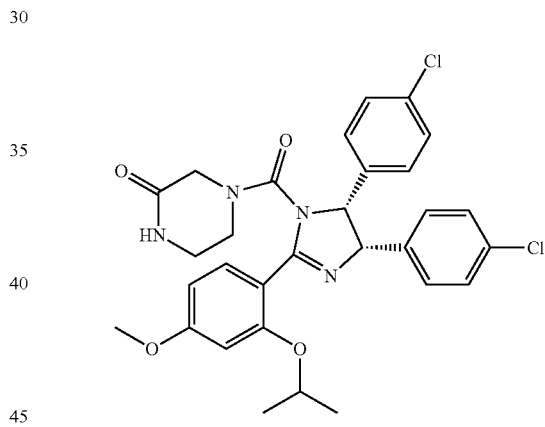

(derivatized where a linker group L or a -L-(VHL ligand moiety) group is attached preferably at the methoxy group or as a hydroxyl group);

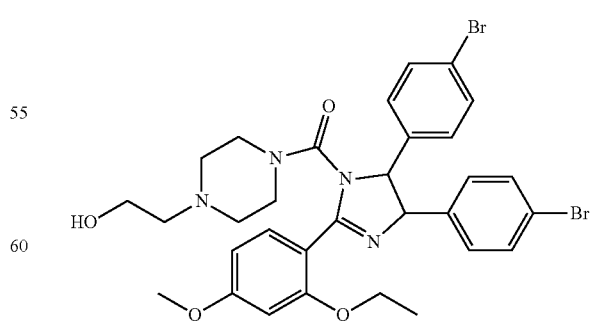

(derivatized where a linker group L or a -L-(VHL ligand moiety) group is attached preferably at the methoxy group or hydroxyl group);

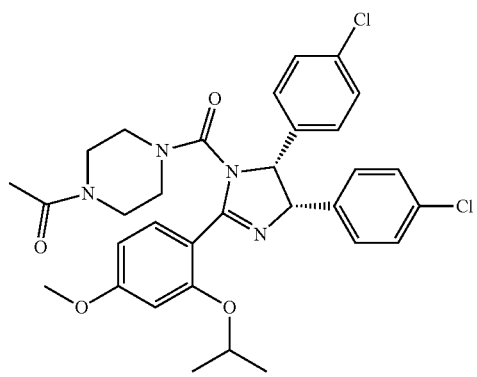 [SMILES: COc1ccc(C2=N[C@@H](c3ccc(Cl)cc3)[C@@H](c3ccc(Cl)cc3)N2C(=O)N2CCN(C(C)=O)CC2)c(OC(C)C)c1]

(derivatized where a linker group L or a -L-(VHL ligand moiety) group is attached via the methoxy group or as a hydroxyl group); and 2. Trans-4-Iodo-4'-Boranyl-Chalcone

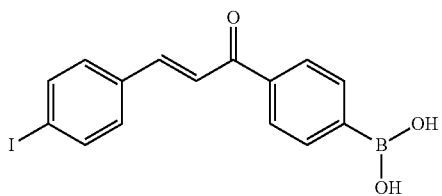 [SMILES: O=C(/C=C/c1ccc(I)cc1)c1ccc(B(O)O)cc1]

(derivatized where a linker group L or a -L-(VHL ligand moiety) group is attached via a hydroxy group);

3. The MDM2 inhibitors identified in Zhao, Y. "Small-Molecule Inhibitors of the MDM2-p53 Protein-Protein Interaction (MDM2 Inhibitors) in Clinical Trials for Cancer Treatment" *J. Med. Chem.* 2015, 58, 1038-1052, including but not limited to:

a. RG7112

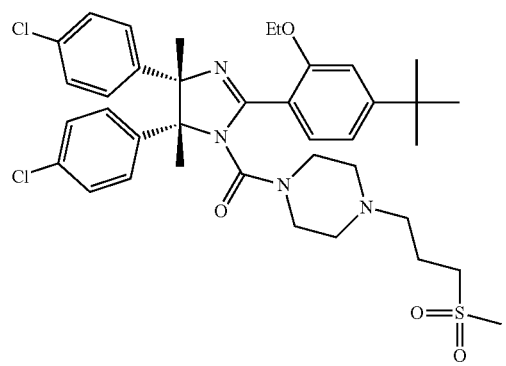 [SMILES: CCOc1cc(C(C)(C)C)ccc1C1=N[C@@](C)(c2ccc(Cl)cc2)[C@@](C)(c2ccc(Cl)cc2)N1C(=O)N1CCN(CCCS(C)(=O)=O)CC1]

(derivatized such that a linker group L or a -L-(VHL ligand moiety) is attached);

b. RG7388

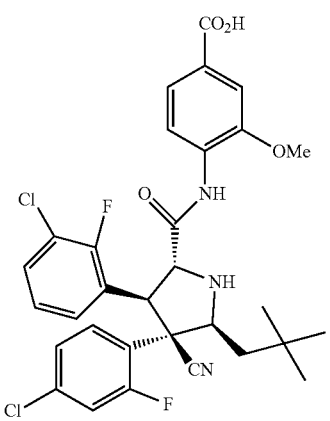 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

(derivatized such that a linker group L or a -L-(VHL ligand moiety) is attached);

c. MI-77301

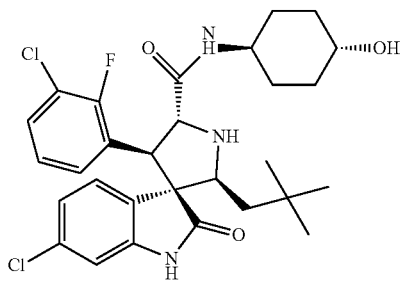

(derivatized such that a linker group L or a -L-(VHL ligand moiety) is attached);

d. AMG 232

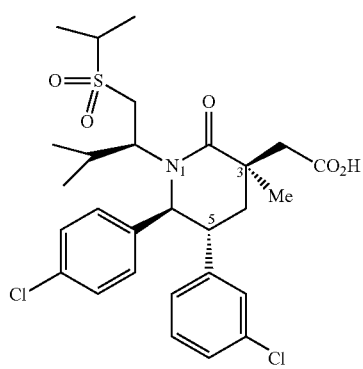

(derivatized such that a linker group L or a -L-(VHL ligand moiety) is attached);

e. PB12WK23

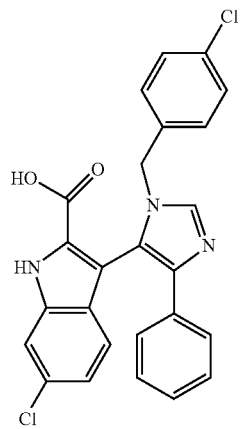 [SMILES: O=C(O)c1[nH]c2cc(Cl)ccc2c1-c1c(-c2ccccc2)ncn1Cc1ccc(Cl)cc1]

(derivatized such that a linker group L or a -L-(VHL ligand moiety) is attached);

f. MCL0527-3

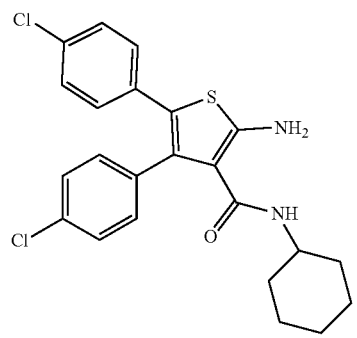 [SMILES: Nc1sc(-c2ccc(Cl)cc2)c(-c2ccc(Cl)cc2)c1C(=O)NC1CCCCC1]

(derivatized such that a linker group L or a -L-(VHL ligand moiety) is attached);

g. AM-8735

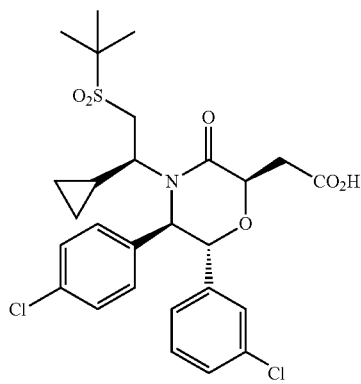 [SMILES: CC(C)(C)S(=O)(=O)C[C@H](C1CC1)N1C(=O)[C@@H](CC(=O)O)O[C@H](c2cccc(Cl)c2)[C@H]1c1ccc(Cl)cc1]

(derivatized such that a linker group L or a -L-(VHL ligand moiety) is attached);

h. RO2468

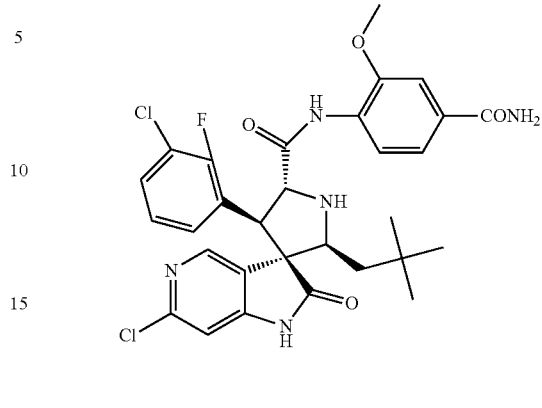

(derivatized such that a linker group L or a -L-(VHL ligand moiety) is attached);

i. PB11

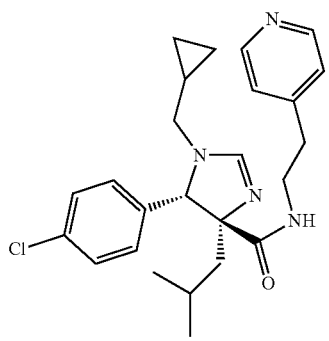 [SMILES: CC(C)C[C@@]1(C(=O)NCCc2ccncc2)N=CN(CC2CC2)[C@H]1c1ccc(Cl)cc1]

(derivatized such that a linker group L or a -L-(VHL ligand moiety) is attached);

j. AM-6761

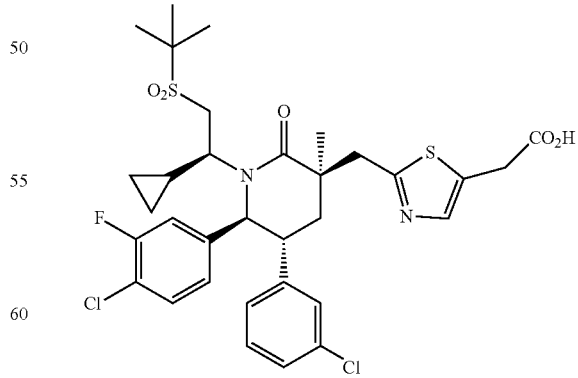

(derivatized such that a linker group L or a -L-(VHL ligand moiety) is attached);

k. RO5353

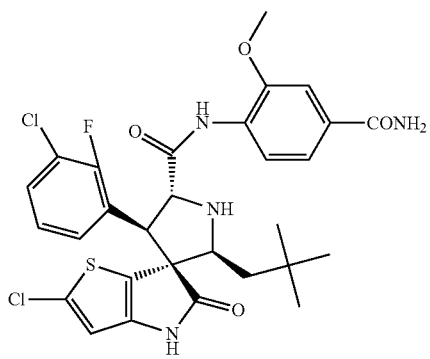

(derivatized such that a linker group L or a -L-(VHL ligand moiety) is attached);

l. RO8994

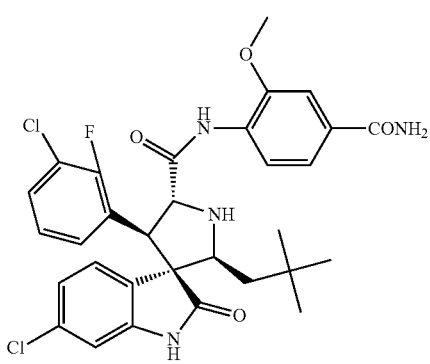

(derivatized such that a linker group L or a -L-(VHL ligand moiety) is attached);

m.

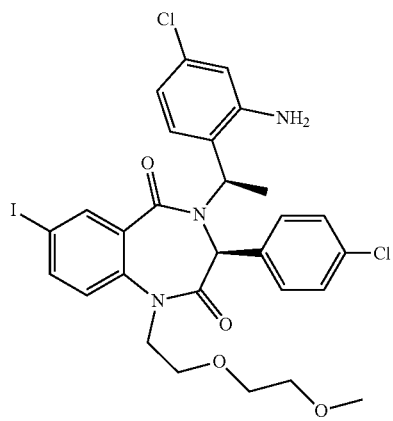 [SMILES: COCCOCCN1C(=O)[C@H](c2ccc(Cl)cc2)N([C@H](C)c2ccc(Cl)cc2N)C(=O)c2cc(I)ccc21]

(derivatized such that a linker group L or a -L-(VHL ligand moiety) is attached);

n.

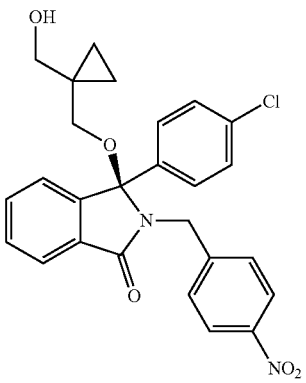 [SMILES: O=C1c2ccccc2[C@](OCC2(CO)CC2)(c2ccc(Cl)cc2)N1Cc1ccc([N+](=O)[O-])cc1]

(derivatized such that a linker group L or a -L-(VHL ligand moiety) is attached);

o.

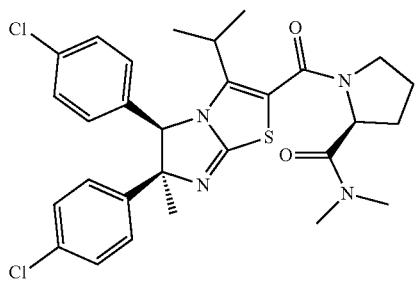 [SMILES: CC(C)C1=C(C(=O)N2CCC[C@H]2C(=O)N(C)C)SC2=N[C@@](C)(c3ccc(Cl)cc3)[C@@H](c3ccc(Cl)cc3)N21]

(derivatized such that a linker group L or a -L-(VHL ligand moiety) is attached);

p.

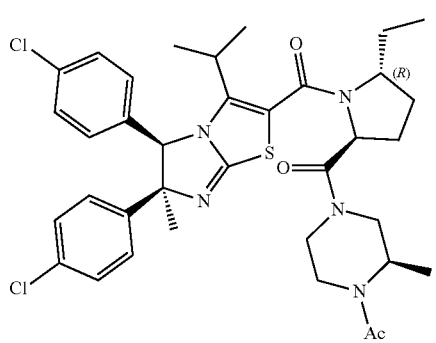

(derivatized such that a linker group L or a -L-(VHL ligand moiety) is attached);

q.

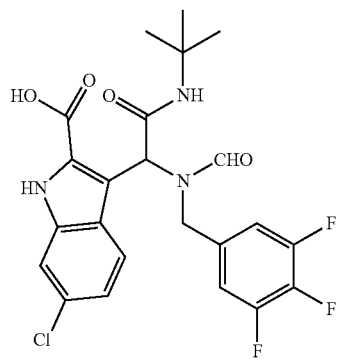 [SMILES: CC(C)(C)NC(=O)C(c1c(C(=O)O)[nH]c2cc(Cl)ccc12)N(C=O)Cc1cc(F)c(F)c(F)c1]

(derivatized such that a linker group L or a -L-(VHL ligand moiety) is attached);

r.

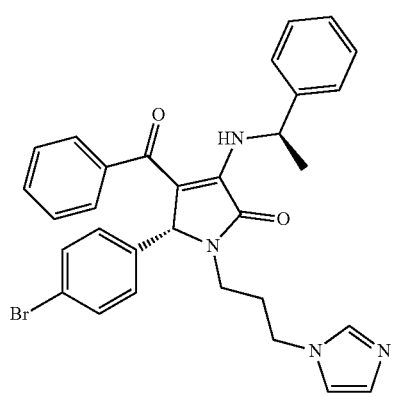 [SMILES: C[C@@H](NC1=C(C(=O)c2ccccc2)[C@@H](c2ccc(Br)cc2)N(CCCn2ccnc2)C1=O)c1ccccc1]

(derivatized such that a linker group L or a -L-(VHL ligand moiety) is attached);

s.

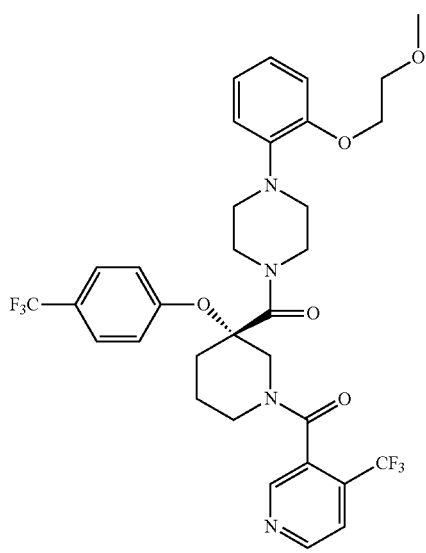 [SMILES: COCCOc1ccccc1N1CCN(C(=O)[C@]2(Oc3ccc(C(F)(F)F)cc3)CCCN(C(=O)c3cnccc3C(F)(F)F)C2)CC1]

(derivatized such that a linker group L or a -L-(VHL ligand moiety) is attached);

t.

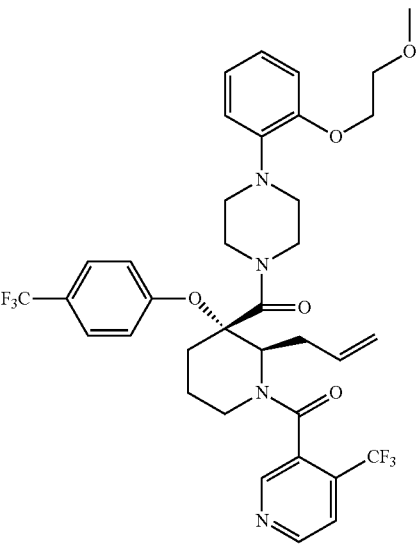 [SMILES: C=CC[C@H]1N(C(=O)c2cnccc2C(F)(F)F)CCC[C@@]1(Oc1ccc(C(F)(F)F)cc1)C(=O)N1CCN(c2ccccc2OCCOC)CC1]

(derivatized such that a linker group L or a -L-(VHL ligand moiety) is attached);

u.

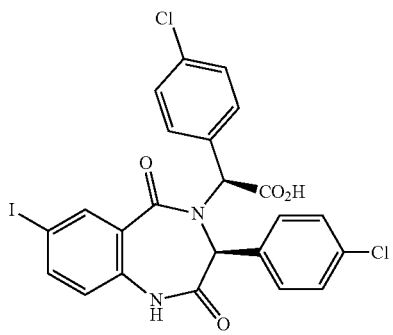 [SMILES: O=C(O)[C@H](c1ccc(Cl)cc1)N1C(=O)c2cc(I)ccc2NC(=O)[C@@H]1c1ccc(Cl)cc1]

(derivatized such that a linker group L or a -L-(VHL ligand moiety) is attached);

v.

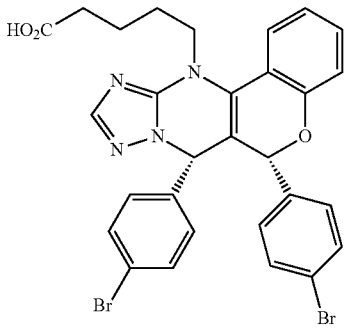 [SMILES: O=C(O)CCCCN1C2=C([C@H](c3ccc(Br)cc3)n3ncnc31)[C@@H](c1ccc(Br)cc1)Oc1ccccc12]

(derivatized such that a linker group L or a -L-(VHL ligand moiety) is attached);

w.

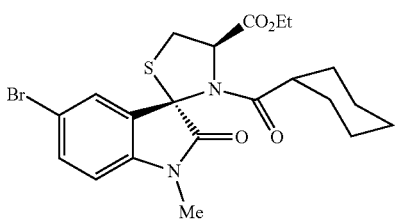 [SMILES: CCOC(=O)[C@@H]1CS[C@@]2(C(=O)N(C)c3ccc(Br)cc32)N1C(=O)C1CCCCC1]

(derivatized such that a linker group L or a -L-(VHL ligand moiety) is attached); and x.

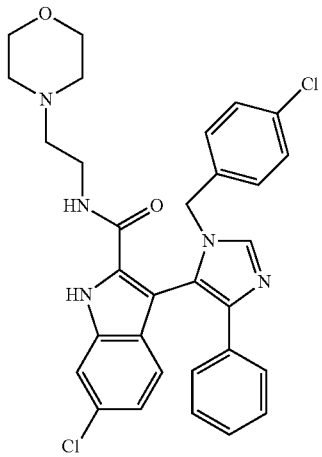 [SMILES: O=C(NCCN1CCOCC1)c1[nH]c2cc(Cl)ccc2c1-c1c(-c2ccccc2)ncn1Cc1ccc(Cl)cc1]

(derivatized such that a linker group L or a -L-(VHL ligand moiety) is attached).

Compounds Targeting Human BET Bromodomain-Containing Proteins

Compounds targeting Human BET Bromodomain-containing proteins include, but are not limited to the compounds associated with the targets as described below, where "R" designates a site for linker group L or a -L-(VHL ligand moiety) group attachment. For example:

1.

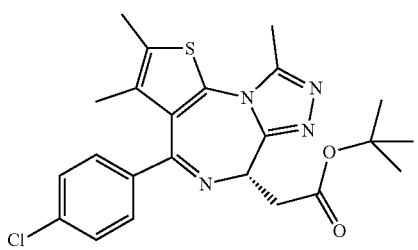

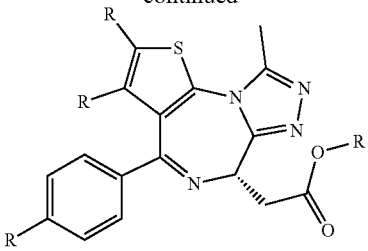

JQ1, Filippakopoulos et al. "Selective inhibition of BET bromodomains," *Nature* (2010), 468, 1067-1073; Romero, et al., *J. Med. Chem.* 59, 1271-1298 (2016);

2.

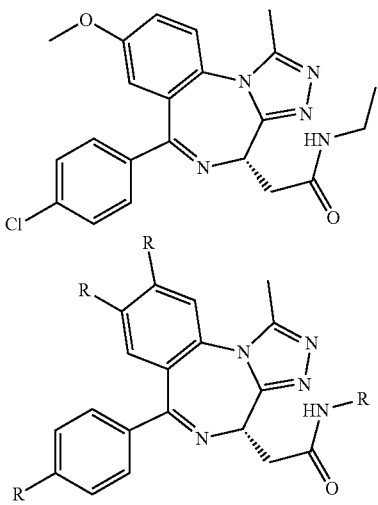

I-BET, Nicodeme et al., "Supression of Inflammation by a Synthetic Histone Mimic," *Nature* (2010), 468, 1119-1123; Chung et al., "Discovery and Characterization of Small Molecule Inhibitors of the BET Family Bromodomains," *J. Med Chem.* (2011), 54, 3827-3838; Romero, et al., *J. Med. Chem.* 59, 1271-1298 (2016);

3.

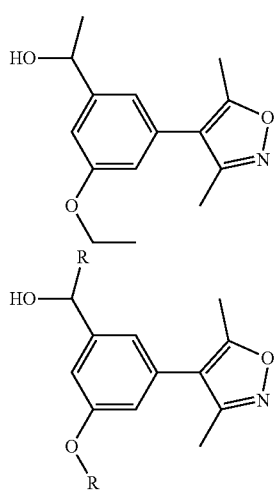

Hewings et al., "3,5-Dimethylisoxazoles Act as Acetyllysine Bromodomain Ligands," *J. Med. Chem.*, (2011), 54, 6761-6770;

4.

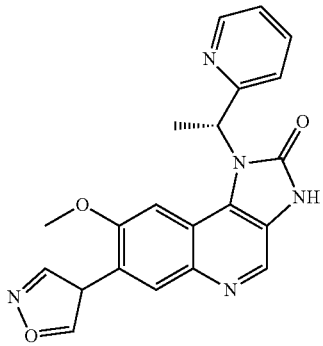

I-BET151, Dawson et al., "Inhibition of BET Recruitment to Chromatin as an Effective Treatment for MLL-fusion Leukemia," *Nature* (2011), 478, 529-523;

5. The BET bromodomain inhibitors identified in Romero, et al., *J. Med. Chem.* 59, 1271-1298 (2016), including, but not limited to:

a. I-BET151

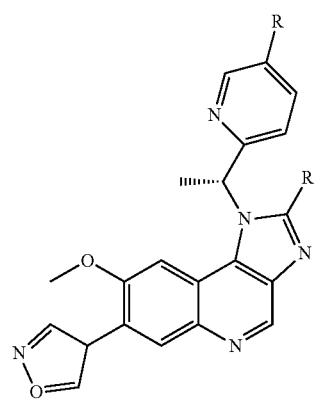

(derivatized such that a linker group L or a -L-(VHL ligand moiety) is attached);

b. PFI-1

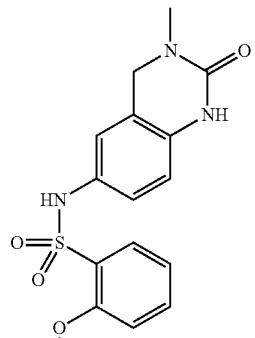

(derivatized such that a linker group L or a -L-(VHL ligand moiety) is attached);

c. OTX015

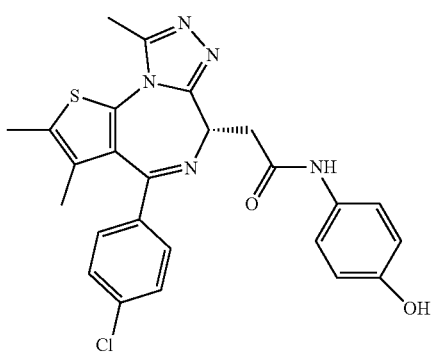 [SMILES: Cc1sc2c(c1C)C(c1ccc(Cl)cc1)=N[C@@H](CC(=O)Nc1ccc(O)cc1)c1nnc(C)n1-2]

(derivatized such that a linker group L or a -L-(VHL ligand moiety) is attached);

d.

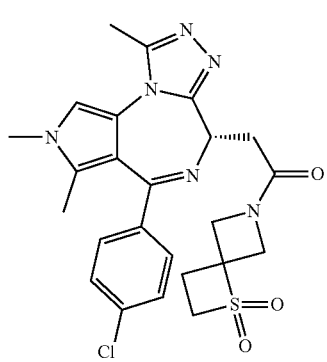 [SMILES: Cc1c2c(cn1C)-n1c(C)nnc1[C@H](CC(=O)N1CC3(CCS3(=O)=O)C1)N=C2c1ccc(Cl)cc1]

(derivatized such that a linker group L or a -L-(VHL ligand moiety) is attached);

e.

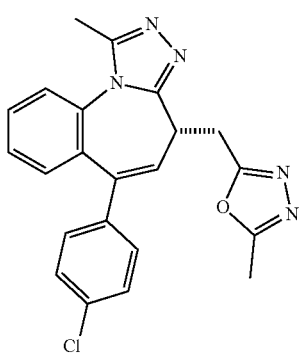 [SMILES: Cc1nnc(C[C@@H]2C=C(c3ccc(Cl)cc3)c3ccccc3-n3c(C)nnc32)o1]

(derivatized such that a linker group L or a -L-(VHL ligand moiety) is attached);

f.

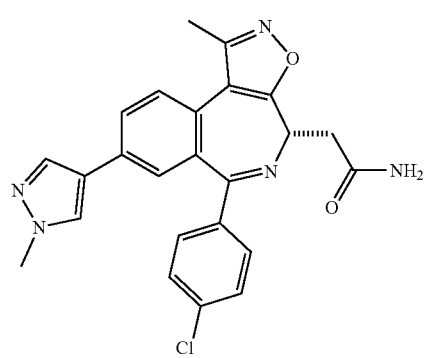 [SMILES: Cc1noc2c1-c1ccc(-c3cnn(C)c3)cc1C(c1ccc(Cl)cc1)=N[C@H]2CC(N)=O]

(derivatized such that a linker group L or a -L-(VHL ligand moiety) is attached);

g.

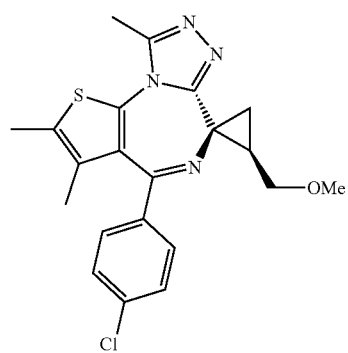

(derivatized such that a linker group L or a -L-(VHL ligand moiety) is attached);

h.

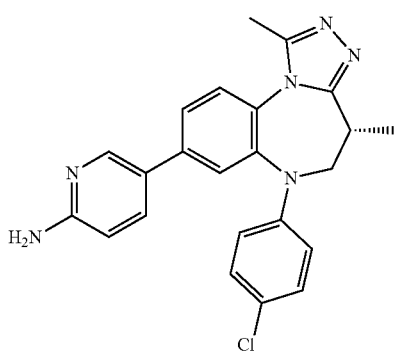 [SMILES: Cc1nnc2n1-c1ccc(-c3ccc(N)nc3)cc1N(c1ccc(Cl)cc1)C[C@H]2C]

(derivatized such that a linker group L or a -L-(VHL ligand moiety) is attached);

i.

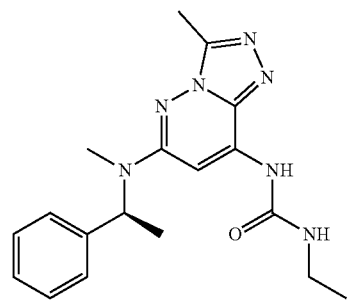 [SMILES: CCNC(=O)Nc1cc(N(C)[C@@H](C)c2ccccc2)nn2c(C)nnc12]

(derivatized such that a linker group L or a -L-(VHL ligand moiety) is attached);

j.

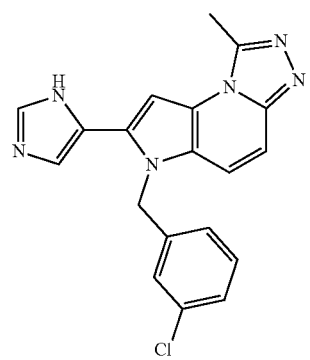

(derivatized such that a linker group L or a -L-(VHL ligand moiety) is attached);

k.

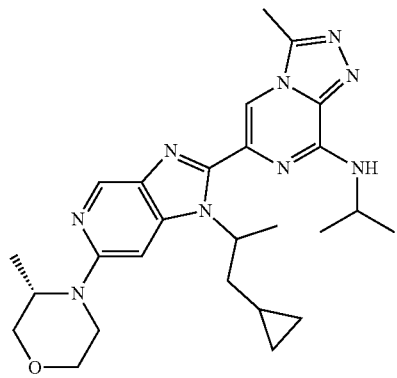 [SMILES: Cc1nnc2c(NC(C)C)nc(-c3nc4cnc(N5CCOC[C@@H]5C)cc4n3C(C)CC3CC3)cn12]

(derivatized such that a linker group L or a -L-(VHL ligand moiety) is attached);

l.

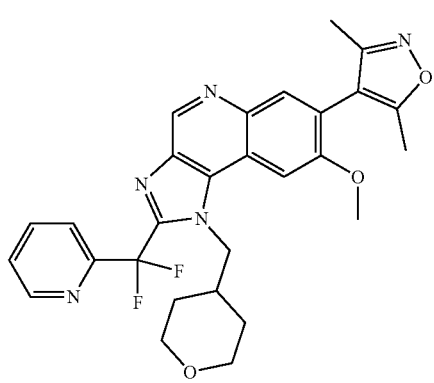 [SMILES: COc1cc2c(cc1-c1c(C)noc1C)ncc1nc(C(F)(F)c3ccccn3)n(CC3CCOCC3)c12]

(derivatized such that a linker group L or a -L-(VHL ligand moiety) is attached);

m.

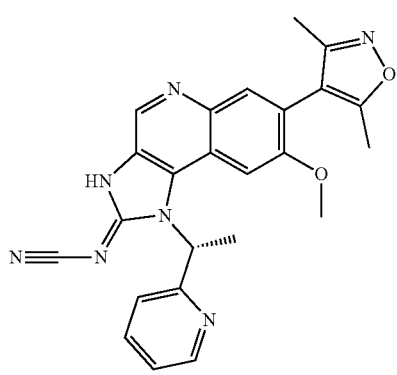 [SMILES: COc1cc2c(cc1-c1c(C)noc1C)ncc1[nH]/c(=N\C#N)n([C@H](C)c3ccccn3)c12]

(derivatized such that a linker group L or a -L-(VHL ligand moiety) is attached);

n.

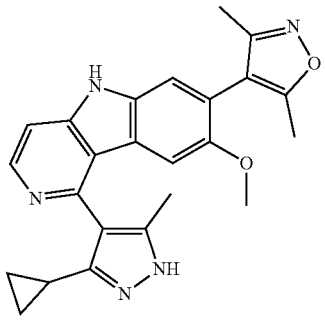 [SMILES: COc1cc2c(cc1-c1c(C)noc1C)[nH]c1ccnc(-c3c(C4CC4)n[nH]c3C)c12]

(derivatized such that a linker group L or a -L-(VHL ligand moiety) is attached);

o.

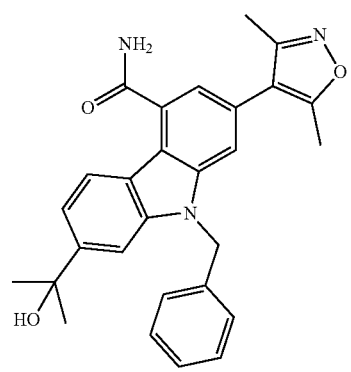 [SMILES: Cc1noc(C)c1-c1cc(C(N)=O)c2c3ccc(C(C)(C)O)cc3n(Cc3ccccc3)c2c1]

(derivatized such that a linker group L or a -L-(VHL ligand moiety) is attached);

p.

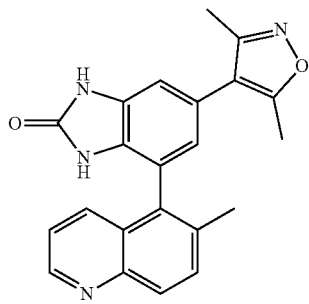 [SMILES: Cc1ccc2ncccc2c1-c1cc(-c2c(C)noc2C)cc2[nH]c(=O)[nH]c12]

(derivatized such that a linker group L or a -L-(VHL ligand moiety) is attached);

q.

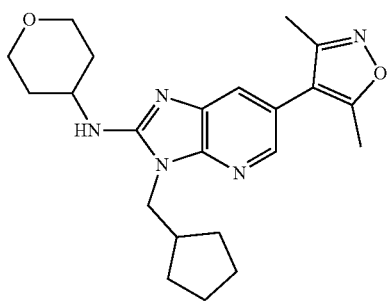 [SMILES: Cc1noc(C)c1-c1cnc2c(c1)nc(NC1CCOCC1)n2CC1CCCC1]

(derivatized such that a linker group L or a -L-(VHL ligand moiety) is attached);

r.

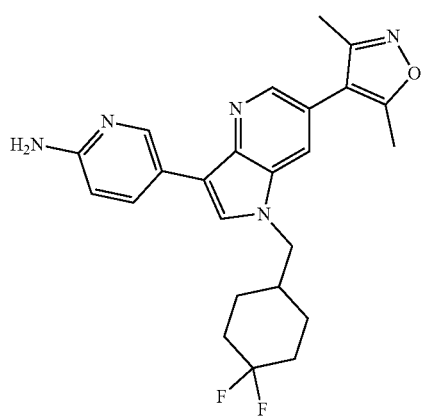 [SMILES: Cc1noc(C)c1-c1cnc2c(-c3ccc(N)nc3)cn(CC3CCC(F)(F)CC3)c2c1]

(derivatized such that a linker group L or a -L-(VHL ligand moiety) is attached);

s.

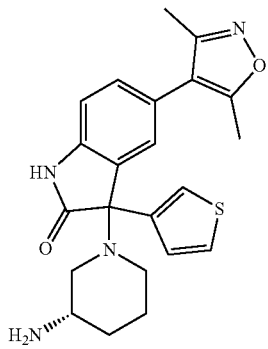 [SMILES: Cc1noc(C)c1-c1ccc2c(c1)C(c1ccsc1)(N1CCC[C@H](N)C1)C(=O)N2]

(derivatized such that a linker group L or a -L-(VHL ligand moiety) is attached);

t.

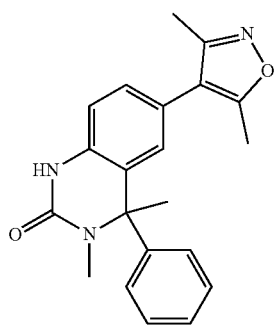 [SMILES: Cc1noc(C)c1-c1ccc2c(c1)C(C)(c1ccccc1)N(C)C(=O)N2]

(derivatized such that a linker group L or a -L-(VHL ligand moiety) is attached);

u.

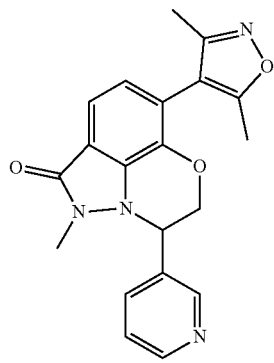 [SMILES: Cc1noc(C)c1-c1ccc2c(=O)n(C)n3c2c1OCC3c1cccnc1]

(derivatized such that a linker group L or a -L-(VHL ligand moiety) is attached);

v.

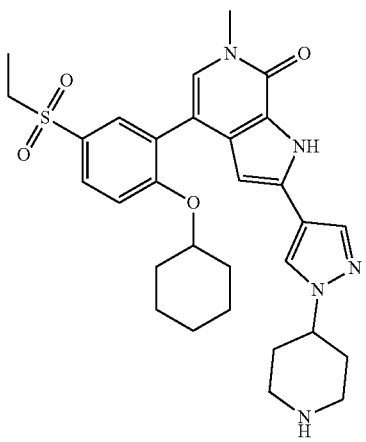 [SMILES: CCS(=O)(=O)c1ccc(OC2CCCCC2)c(-c2cn(C)c(=O)c3[nH]c(-c4cnn(C5CCNCC5)c4)cc23)c1]

(derivatized such that a linker group L or a -L-(VHL ligand moiety) is attached);

w.

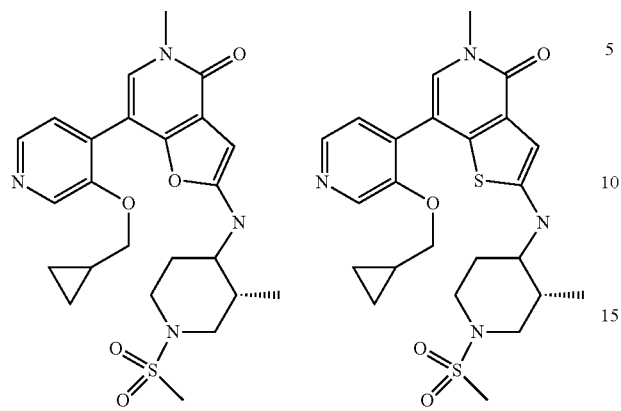

(derivatized such that a linker group L or a -L-(VHL ligand moiety) is attached);

x.

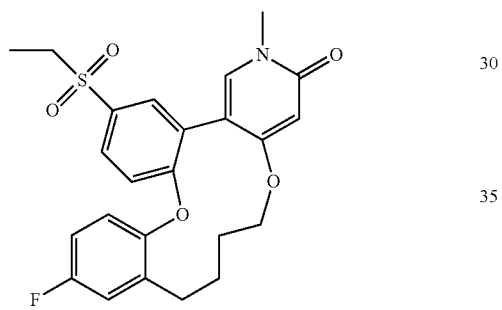

(derivatized such that a linker group L or a -L-(VHL ligand moiety) is attached);

y.

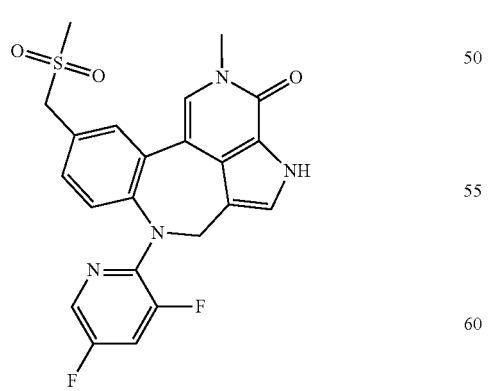

(derivatized such that a linker group L or a -L-(VHL ligand moiety) is attached);

z.

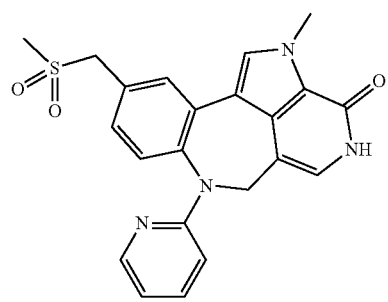 [SMILES: Cn1cc2c3c(c[nH]c(=O)c31)CN(c1ccccn1)c1ccc(CS(C)(=O)=O)cc1-2]

(derivatized such that a linker group L or a -L-(VHL ligand moiety) is attached);

aa.

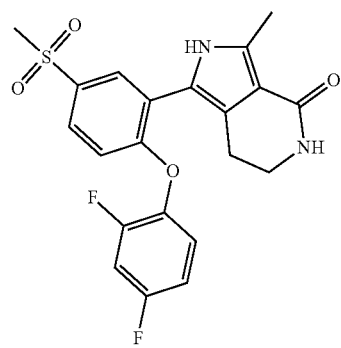 [SMILES: Cc1[nH]c(-c2cc(S(C)(=O)=O)ccc2Oc2ccc(F)cc2F)c2c1C(=O)NCC2]

(derivatized such that a linker group L or a -L-(VHL ligand moiety) is attached);

bb.

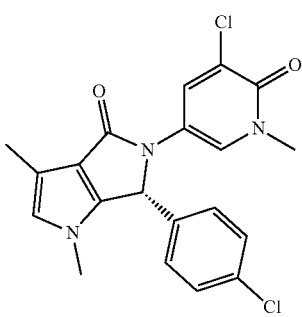

(derivatized such that a linker group L or a -L-(VHL ligand moiety) is attached);

cc.

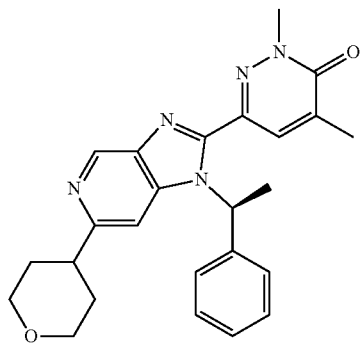 [SMILES: Cc1cc(-c2nc3cnc(C4CCOCC4)cc3n2[C@@H](C)c2ccccc2)nn(C)c1=O]

(derivatized such that a linker group L or a -L-(VHL ligand moiety) is attached);

dd.

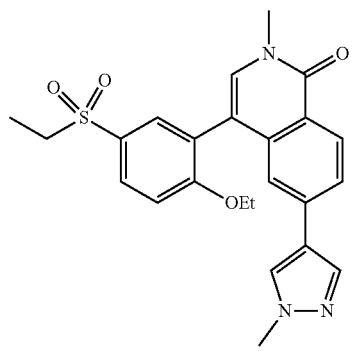 [SMILES: CCOc1ccc(S(=O)(=O)CC)cc1-c1cn(C)c(=O)c2ccc(-c3cnn(C)c3)cc12]

(derivatized such that a linker group L or a -L-(VHL ligand moiety) is attached);

ee.

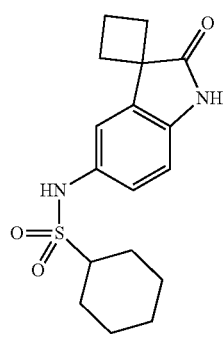 [SMILES: O=C1Nc2ccc(NS(=O)(=O)C3CCCCC3)cc2C12CCC2]

(derivatized such that a linker group L or a -L-(VHL ligand moiety) is attached);

ff.

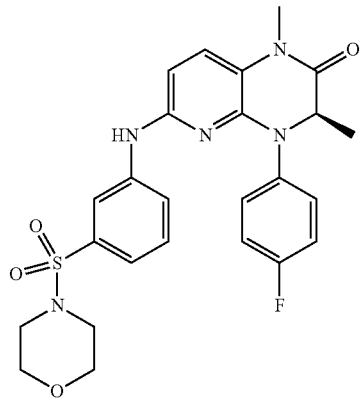 [SMILES: C[C@@H]1C(=O)N(C)c2ccc(Nc3cccc(S(=O)(=O)N4CCOCC4)c3)nc2N1c1ccc(F)cc1]

(derivatized such that a linker group L or a -L-(VHL ligand moiety) is attached);

gg.

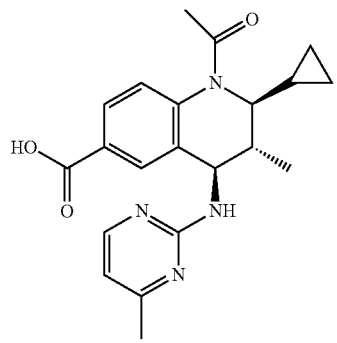 [SMILES: CC(=O)N1c2ccc(C(=O)O)cc2[C@H](Nc2nccc(C)n2)[C@@H](C)[C@@H]1C1CC1]

(derivatized such that a linker group L or a -L-(VHL ligand moiety) is attached);

hh.

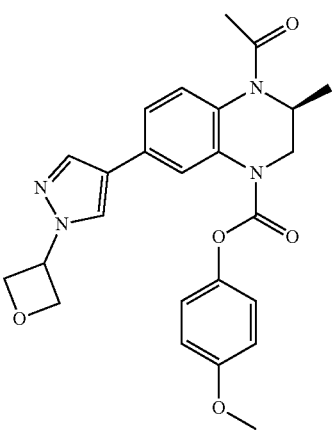

(derivatized such that a linker group L or a -L-(VHL ligand moiety) is attached);

ii.

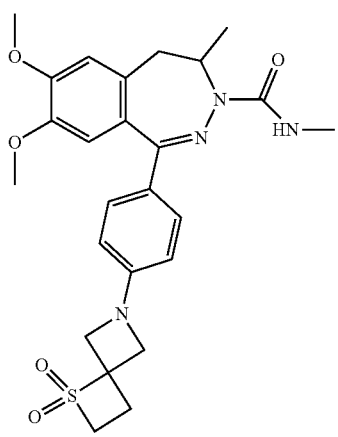 [SMILES: CNC(=O)N1N=C(c2ccc(N3CC4(CCS4(=O)=O)C3)cc2)c2cc(OC)c(OC)cc2CC1C]

(derivatized such that a linker group L or a -L-(VHL ligand moiety) is attached);

jj.

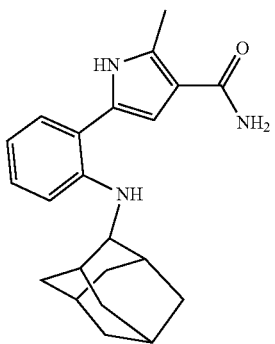 [SMILES: Cc1[nH]c(-c2ccccc2NC2C3CC4CC(C3)CC2C4)cc1C(N)=O]

(derivatized such that a linker group L or a -L-(VHL ligand moiety) is attached);

kk.

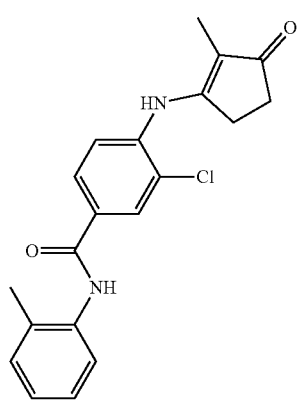 [SMILES: CC1=C(Nc2ccc(C(=O)Nc3ccccc3C)cc2Cl)CCC1=O]

(derivatized such that a linker group L or a -L-(VHL ligand moiety) is attached);

ll.

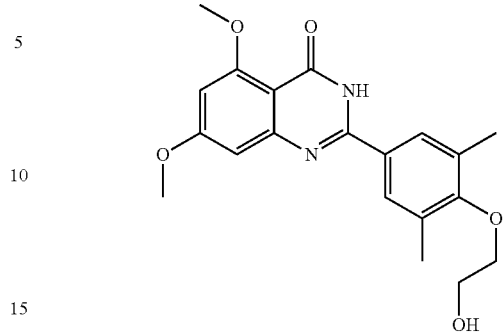

(derivatized such that a linker group L or a -L-(VHL ligand moiety) is attached);

mm.

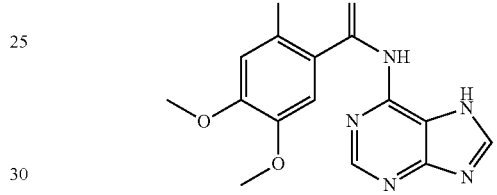

(derivatized such that a linker group L or a -L-(VHL ligand moiety) is attached);

nn.

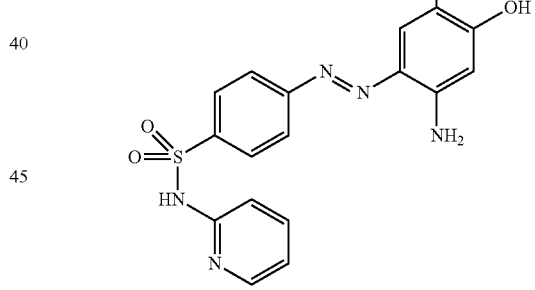

(derivatized such that a linker group L or a -L-(VHL ligand moiety) is attached);

oo.

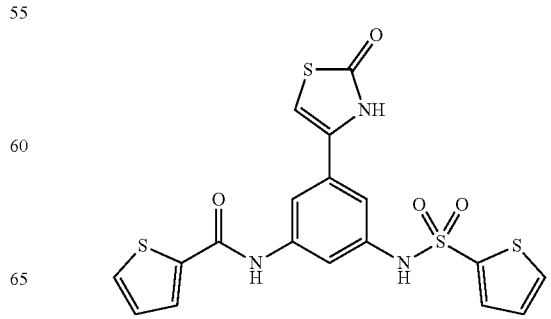

(derivatized such that a linker group L or a -L-(VHL ligand moiety) is attached);

pp. RVX-208

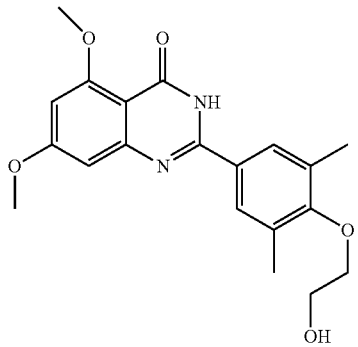 [SMILES: COc1cc(OC)c2c(=O)[nH]c(-c3cc(C)c(OCCO)c(C)c3)nc2c1]

(derivatized such that a linker group L or a -L-(VHL ligand moiety) is attached);

qq. BI2536

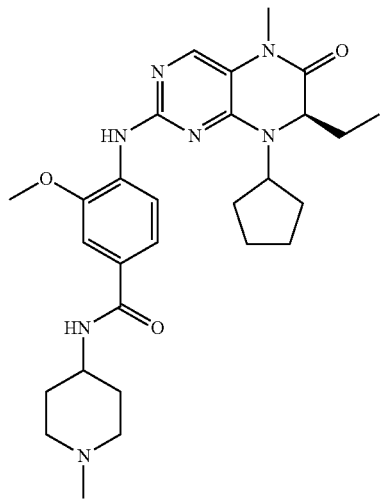 [SMILES: CC[C@@H]1C(=O)N(C)c2cnc(Nc3ccc(C(=O)NC4CCN(C)CC4)cc3OC)nc2N1C1CCCC1]

(derivatized such that a linker group L or a -L-(VHL ligand moiety) is attached);

rr. LY294002

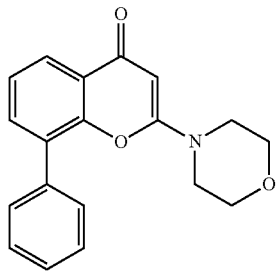 [SMILES: O=c1cc(N2CCOCC2)oc2c(-c3ccccc3)cccc12]

(derivatized such that a linker group L or a -L-(VHL ligand moiety) is attached); and ss. LY303511

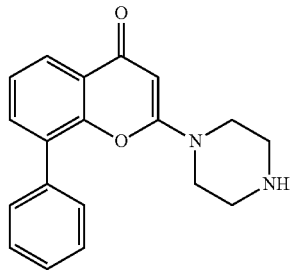 [SMILES: O=c1cc(N2CCNCC2)oc2c(-c3ccccc3)cccc12]

(derivatized such that a linker group L or a -L-(VHL ligand moiety) is attached); and 6. The BET inhibitors identified in Ghoshal, et al., "BET inhibitors in cancer therapeutics: a patent review," *Expert Opinion on Therapeutic Patents,* 26:4, 505-522, (2016)) (hereinafter Ghoshal, et al. (2016)), including but not limited to:

a. TEN010

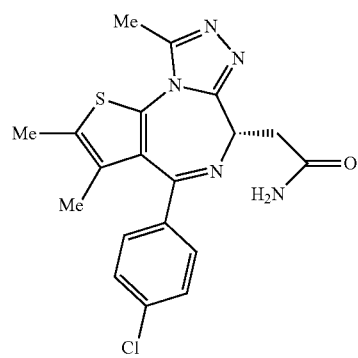 [SMILES: Cc1sc2c(c1C)C(c1ccc(Cl)cc1)=N[C@@H](CC(N)=O)c1nnc(C)n1-2]

(derivatized such that a linker group L or a -L-(VHL ligand moiety) is attached);

b. CPI-0610

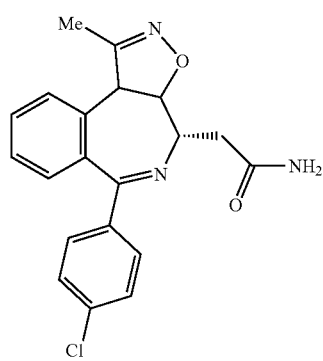 [SMILES: CC1=NOC2C1c1ccccc1C(c1ccc(Cl)cc1)=N[C@H]2CC(N)=O]

(derivatized such that a linker group L or a -L-(VHL ligand moiety) is attached);

c. Diazepines

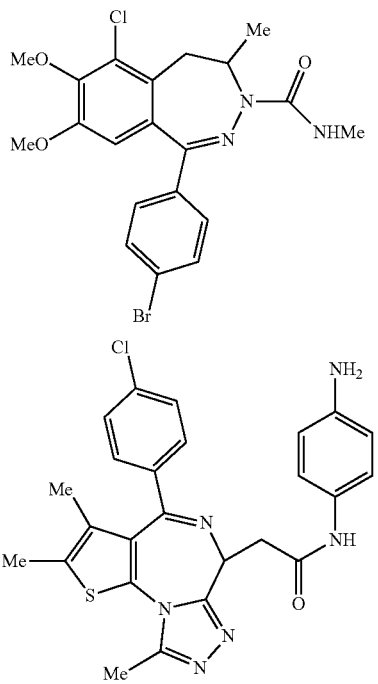

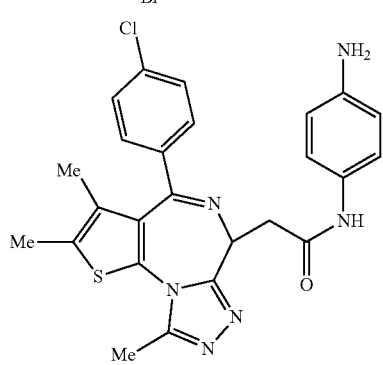

(derivatized such that a linker group L or a -L-(VHL ligand moiety) is attached);

d. Pyrroles and Pyrazoles

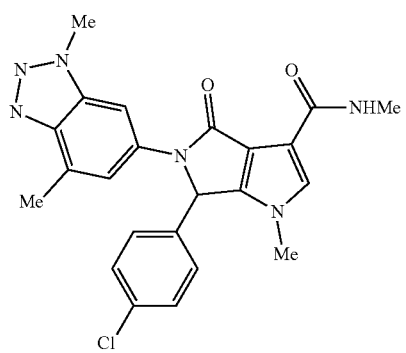

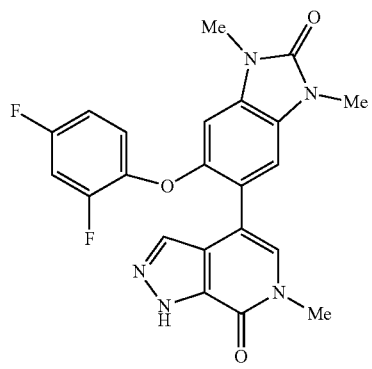

(derivatized such that a linker group L or a -L-(VHL ligand moiety) is attached);

e. Isoxazoles

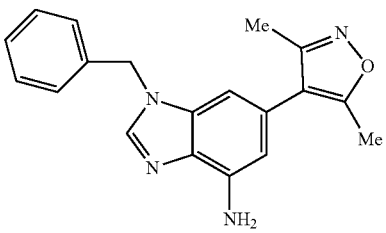

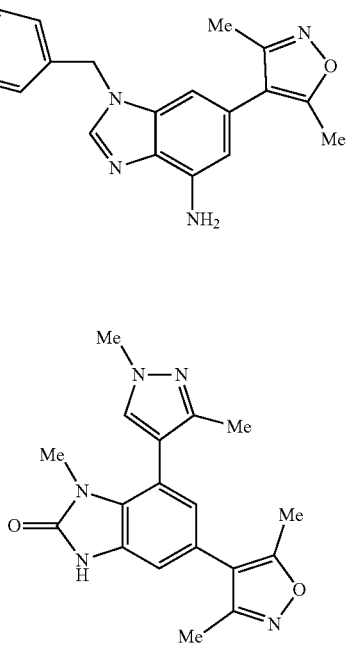

(derivatized such that a linker group L or a -L-(VHL ligand moiety) is attached);

f. Quinoline and quinazoline

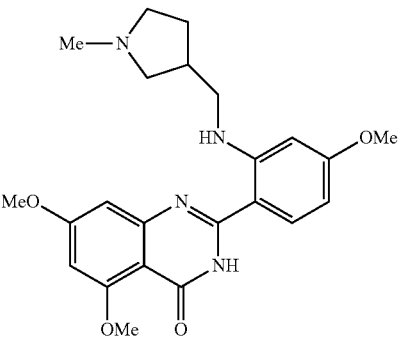

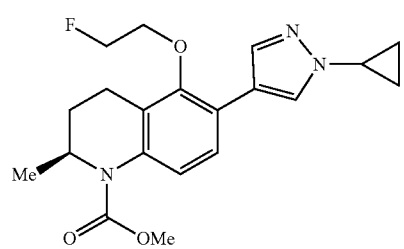

(derivatized such that a linker group L or a -L-(VHL ligand moiety) is attached);

g. Oxazine

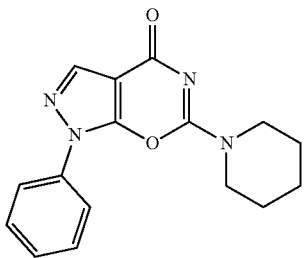 [SMILES: O=c1nc(N2CCCCC2)oc2c1cnn2-c1ccccc1]

(derivatized such that a linker group L or a -L-(VHL ligand moiety) is attached);

h. Benzopiperazine

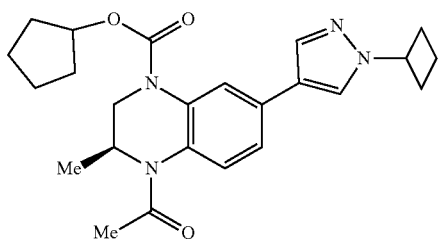 [SMILES: CC(=O)N1c2ccc(-c3cnn(C4CCC4)c3)cc2N(C(=O)OC2CCCC2)C[C@@H]1C]

(derivatized such that a linker group L or a -L-(VHL ligand moiety) is attached);

i. MS436

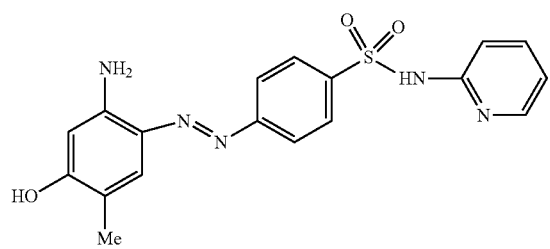 [SMILES: Cc1cc(/N=N/c2ccc(S(=O)(=O)Nc3ccccn3)cc2)c(N)cc1O]

(derivatized such that a linker group L or a -L-(VHL ligand moiety) is attached);

j. CPI-203

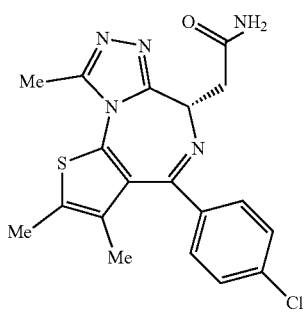 [SMILES: Cc1sc2c(c1C)C(c1ccc(Cl)cc1)=N[C@@H](CC(N)=O)c1nnc(C)n1-2]

(derivatized such that a linker group L or a -L-(VHL ligand moiety) is attached);

k. Y803

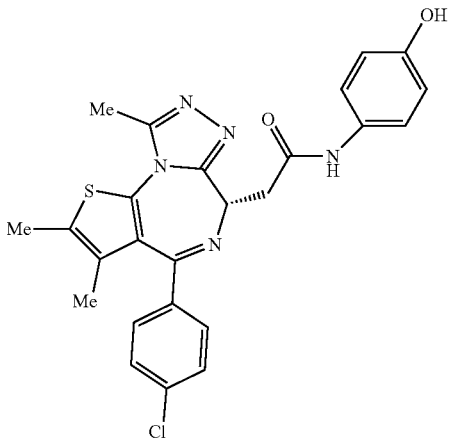 [SMILES: Cc1sc2c(c1C)C(c1ccc(Cl)cc1)=N[C@@H](CC(=O)Nc1ccc(O)cc1)c1nnc(C)n1-2]

(derivatized such that a linker group L or a -L-(VHL ligand moiety) is attached); and 1. Benzodiazepine-based BET inhibitors reported in any one of FIG. 1 or 4-27 of Ghoshal, et al. (2016) (derivatized such that a linker group L or a -L-(VHL ligand moiety) is attached).

HDAC Inhibitors

HDAC Inhibitors (derivatized) include, but are not limited to:

1. Compounds as described in Finnin, M. S. et al., "Structures of a histone deacetylase homologue bound to the TSA and SAHA inhibitors," *Nature,* 401, 188-193 (1999):

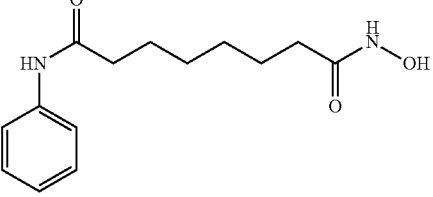

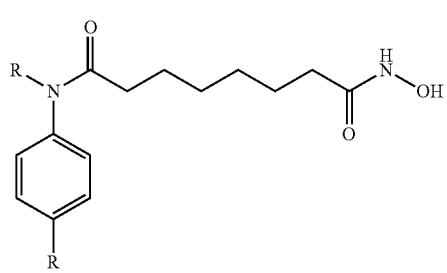

(derivatized where "R" designates a site for attachment of a linker group L or a -L-(VHL ligand moiety) group); and 2. Compounds as defined by formula (I) of PCT Application WO 02/22577 ("DEACETYLASE INHIBITORS") (derivatized where a linker group L or a -L-(VHL ligand moiety) group is attached via the hydroxyl group).

Human Lysine Methyltransferase Inhibitors
Human Lysine Methyltransferase inhibitors include, but are not limited to:
1.

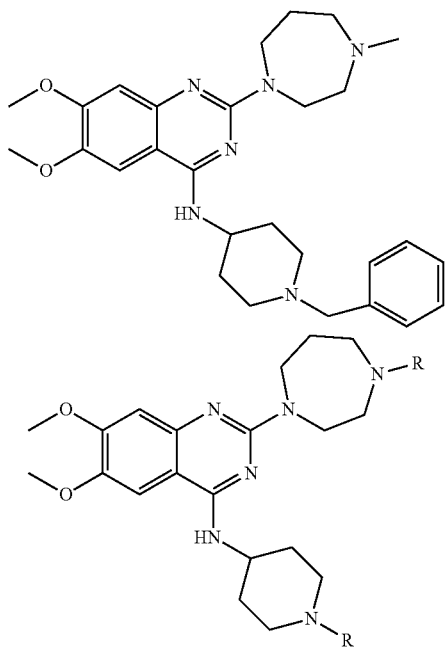

(Chang, et al., "Structural basis for G9a-like protein lysine methyltransferase inhibition by BIX-01294," *Nat. Str. Mol. Biol.* (2009), vol. 16, pp. 312-7) (derivatized where "R" designates a site for attachment of a linker group L or a -L-(VHL ligand moiety) group);

2.

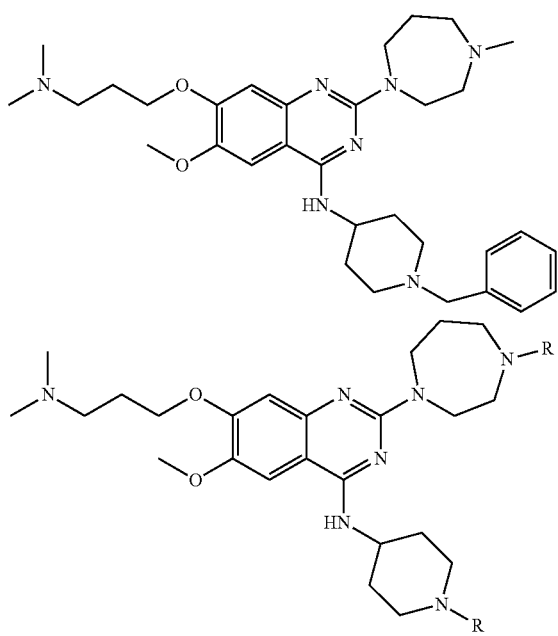

(Liu, et al., "Discovery of a 2,4-diamino-7-aminoalkoxyquinazoline as a potent and selective inhibitor of histone lysine methyltransferase G9a," *J. Med. Chem.*, 2009, Vol. 52(24), pp. 7950-3) (derivatized where "R" designates a potential site for attachment of a linker group L or a -L-(VHL ligand moiety) group);

3. Azacitidine (derivatized) (4-amino-1-β-D-ribofuranosyl-1,3,5-triazin-2(1H)-one) (derivatized where a linker group L or a -L-(VHL ligand moiety) group is attached via the hydroxy or amino groups); and 4. Decitabine (derivatized) (4-amino-1-(2-deoxy-b-D-erythro-pentofuranosyl)-1, 3, 5-triazin-2(1H)-one) (derivatized where a linker group L or a -L-(VHL ligand moiety) group is attached via either of the hydroxy groups or at the amino group).

Angiogenesis Inhibitors
Angiogenesis inhibitors include, but are not limited to:

1. GA-1 (derivatized) and derivatives and analogs thereof, having the structure(s) and binding to linkers as described in Sakamoto, et al., "Development of Protacs to target cancer-promoting proteins for ubiquitination and degradation," *Mol Cell Proteomics,* 2003 December; 2(12):1350-8;

2. Estradiol (derivatized), which may be bound to a linker group L or a -L-(VHL ligand moiety) group as is generally described in Rodriguez-Gonzalez, et al., "Targeting steroid hormone receptors for ubiquitination and degradation in breast and prostate cancer," *Oncogene* (2008) 27, 7201-7211;

3. Estradiol, testosterone (derivatized) and related derivatives, including but not limited to DHT and derivatives and analogs thereof, having the structure(s) and binding to a linker group L or a -L-(VHL ligand moiety) group as generally described in Sakamoto, et al., "Development of Protacs to target cancer-promoting proteins for ubiquitination and degradation," *Mol Cell Proteomics* 2003 December; 2(12):1350-8; and 4. Ovalicin, fumagillin (derivatized), and derivatives and analogs thereof, having the structure(s) and binding to a linker group L or a -L-(VHL ligand moiety) group as is generally described in Sakamoto, et al., "Protacs: chimeric molecules that target proteins to the Skp1-Cullin-F box complex for ubiquitination and degradation," *Proc Natl Acad Sci USA.* 2001 Jul. 17; 98(15):8554-9 and U.S. Pat. No. 7,208,157.

Immunosuppressive Compounds
Immunosuppressive compounds include, but are not limited to:

1. AP21998 (derivatized), having the structure(s) and binding to a linker group L or a -L-(VHL ligand moiety) group as is generally described in Schneekloth, et al., "Chemical Genetic Control of Protein Levels: Selective in Vivo Targeted Degradation," J. Am. Chem. Soc. 2004, 126, 3748-3754;

2. Glucocorticoids (e.g., hydrocortisone, prednisone, prednisolone, and methylprednisolone) (derivatized where a linker group L or a -L-(VHL ligand moiety) group is to bound, e.g. to any of the hydroxyls) and beclomethasone dipropionate (derivatized where a linker group or a -L-(VHL ligand moiety) is bound, e.g. to a proprionate);

3. Methotrexate (derivatized where a linker group or a -L-(VHL ligand moiety) group can be bound, e.g. to either of the terminal hydroxyls);

4. Ciclosporin (derivatized where a linker group or a -L-(VHL ligand moiety) group can be bound, e.g. at any of the butyl groups);

5. Tacrolimus (FK-506) and rapamycin (derivatized where a linker group L or a -L-(VHL ligand moiety) group can be bound, e.g. at one of the methoxy groups); and 6. Actinomycins (derivatized where a linker group L or a -L-(VHL ligand moiety) group can be bound, e.g. at one of the isopropyl groups).

Compounds Targeting the Aryl Hydrocarbon Receptor (AHR)

Compounds targeting the aryl hydrocarbon receptor (AHR) include, but are not limited to:

1. Apigenin (derivatized in a way which binds to a linker group L or a -L-(VHL ligand moiety) group as is generally illustrated in Lee, et al., "Targeted Degradation of the Aryl Hydrocarbon Receptor by the PROTAC Approach: A Useful Chemical Genetic Tool," *Chem. BioChem.*, Volume 8, Issue 17, pages 2058-2062, Nov. 23, 2007); and 2. SR1 and LGC006 (derivatized such that a linker group L or a -L-(VHL ligand moiety) is bound), as described in Boitano, et al., "Aryl Hydrocarbon Receptor Antagonists Promote the Expansion of Human Hematopoietic Stem Cells," *Science* 10 Sep. 2010: Vol. 329 no. 5997 pp. 1345-1348.

Compounds Targeting RAF Receptor (Kinase)

Compounds targeting RAF Receptor (kinase) include, but are not limited to:

1. PLX4032

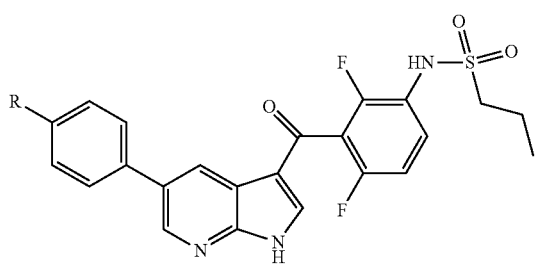

(derivatized where "R" designates a site for linker group L or -L-(VHL ligand moiety) group attachment);

2. The B-Raf inhibitors identified in Huang, T. et al "B-Raf and the inhibitors: from bench to bedside" *Journal of Hematology and Oncology* 2013, including but not limited to:

a. Sorafenib

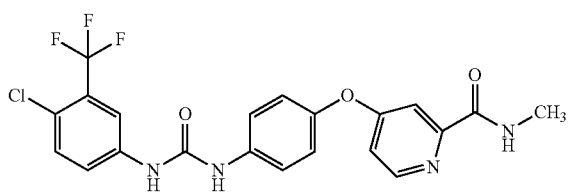 [SMILES: CNC(=O)c1cc(Oc2ccc(NC(=O)Nc3ccc(Cl)c(C(F)(F)F)c3)cc2)ccn1]

(derivatized such that a linker group L or a -L-(VHL ligand moiety) is attached);

b. RAF265

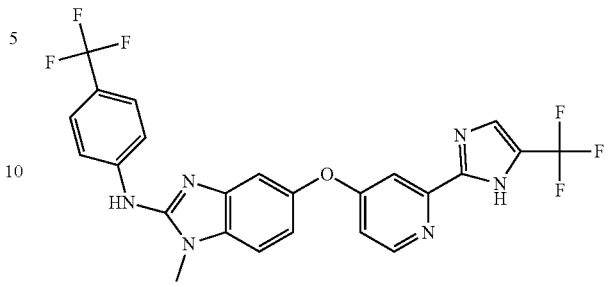

(derivatized such that a linker group L or a -L-(VHL ligand moiety) is attached);

c. GDC0879

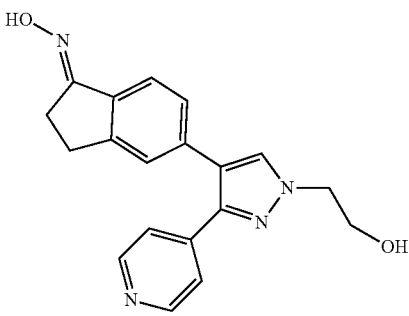 [SMILES: OCCn1cc(-c2ccc3c(c2)CC/C3=N\O)c(-c2ccncc2)n1]

(derivatized such that a linker group L or a -L-(VHL ligand moiety) is attached); and d. Dabrafenib

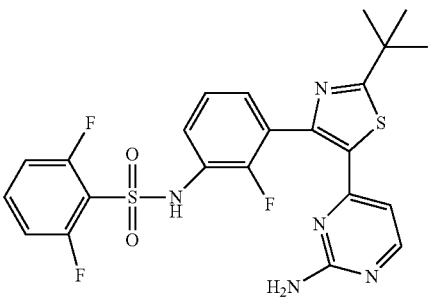 [SMILES: CC(C)(C)c1nc(-c2cccc(NS(=O)(=O)c3c(F)cccc3F)c2F)c(-c2ccnc(N)n2)s1]

(derivatized such that a linker group L or a -L-(VHL ligand moiety) is attached);

3. The RAF inhibitors described in WO 2015/075483, including but not limited to, the compounds having the structure set forth on page 31 of WO 2015/075483, as defined therein, (derivatized such that a linker group L or a -L-(VHL ligand moiety) is attached); and 4. The RAF inhibitors described in Nishiguchi, et al., "Design and Discovery of N-(2-methyl-5'-morpholino-6'-((tetrahydro-2H-pyran-4-yl)oxy)-[3,3'-bipyridin]-5-yl)-3-(trifluoromethyl)benzamide: A potent, selective and efficacious RAF inhibitor targeting RAS mutant cancers," *J. Med. Chem.*, 2017, 60, 4869-4881, including, but not limited to:

a. LY3009120

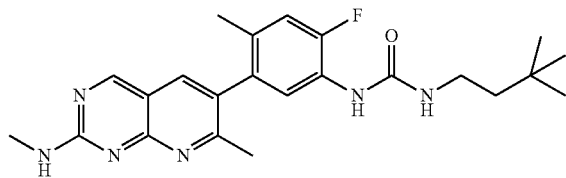 [SMILES: CNc1ncc2cc(-c3cc(NC(=O)NCCC(C)(C)C)c(F)cc3C)c(C)nc2n1]

(derivatized such that a linker group L or a -L-(VHL ligand moiety) is attached); and b. RAF709

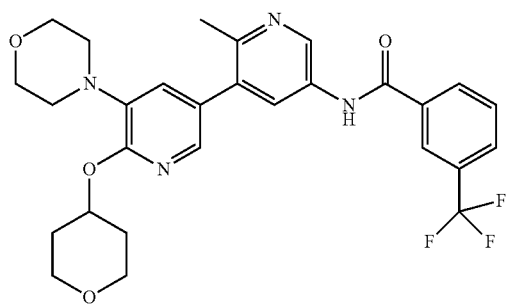 [SMILES: Cc1ncc(NC(=O)c2cccc(C(F)(F)F)c2)cc1-c1cnc(OC2CCOCC2)c(N2CCOCC2)c1]

(derivatized such that a linker group L or a -L-(VHL ligand moiety) is attached).

Compounds Targeting FKBP

Compounds targeting FKBP include, but are not limited to:

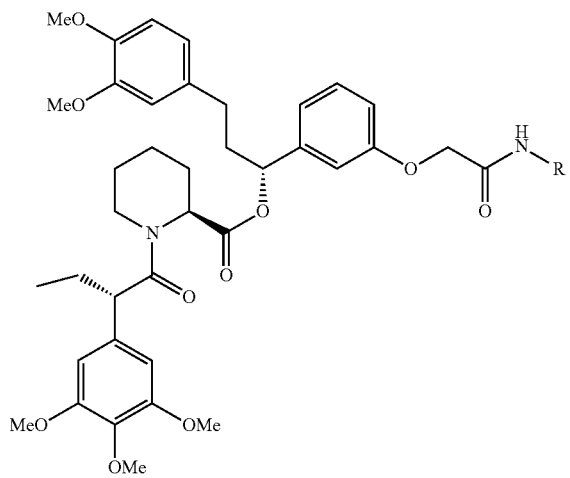

(derivatized where "R" designates a site for a linker group L or a -L-(VHL ligand moiety) group attachment).

Compounds Targeting Androgen Receptor (AR)

1. RU59063 Ligand (derivatized) of Androgen Receptor

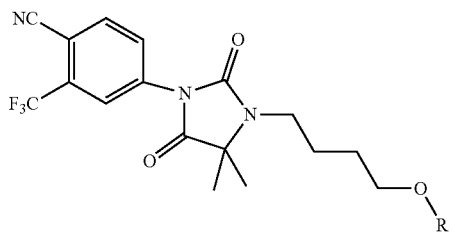

(derivatized where "R" designates a site for a linker group L or a -L-(VHL ligand moiety) group attachment);

2. SARM Ligand (derivatized) of Androgen Receptor

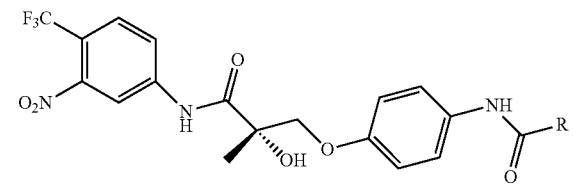

(derivatized where "R" designates a site for a linker group L or a -L-(VHL ligand moiety) group attachment);

3. Androgen Receptor Ligand DHT (derivatized)

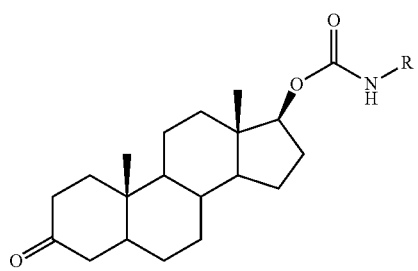

(derivatized where "R" designates a site for a linker group L or -L-(VHL ligand moiety) group attachment);

4. MDV3100-like Ligand (derivatized)

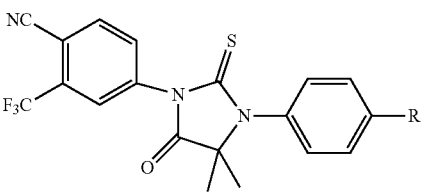

where R designates a linker group L or a -L-(VHL ligand moiety) group;

5. ARN-509-like Ligand (derivatized)

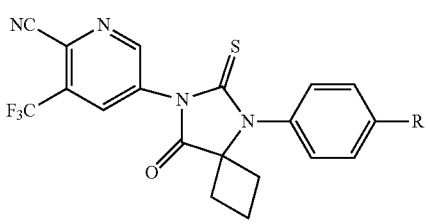

where R designates a linker group L or a -L-(VHL ligand moiety) group;

6. Hexahydrobenzisoxazoles

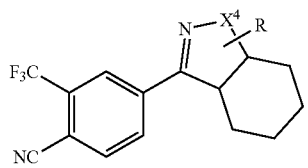

where R designates a linker group L or a -L-(VHL ligand moiety) group; and

7. Tetramethylcyclobutanes

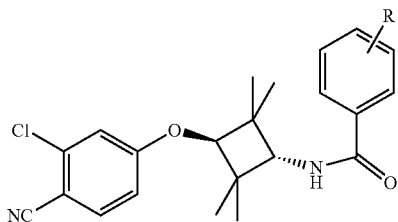

where R designates a linker group L or a -L-(VHL ligand moiety) group.

Compounds Targeting Estrogen Receptor (ER) ICI-182780

1. Estrogen Receptor Ligand

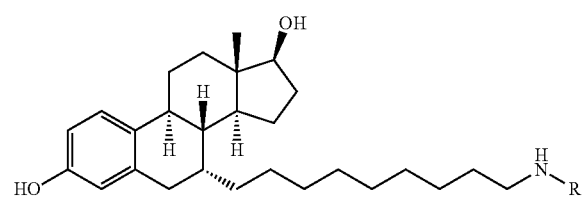

(derivatized where "R" designates a site for linker group L or -L-(VHL ligand moiety) group attachment).

Compounds Targeting Thyroid Hormone Receptor (TR)

Thyroid Hormone Receptor Ligand (derivatized)

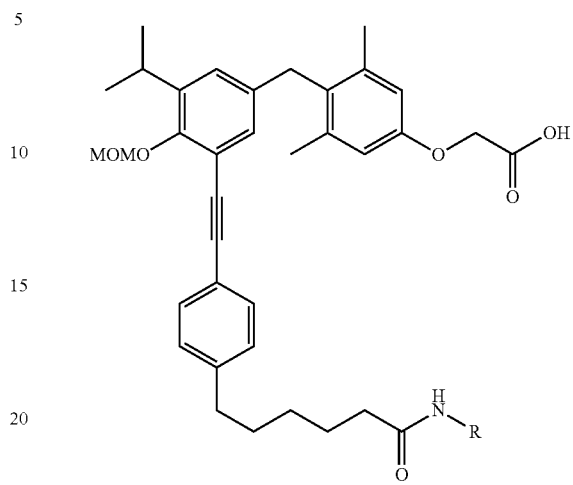

(derivatized where "R" designates a site for linker group L or -L-(VHL ligand moiety) group attachment and MOMO indicates a methoxymethoxy group).

Compounds Targeting HIV Protease

1. Inhibitor of HIV Protease (derivatized)

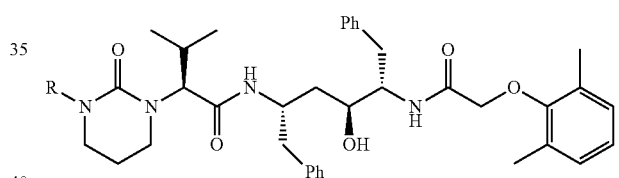

(derivatized where "R" designates a site for linker group L or -L-(VHL ligand moiety) group attachment). See, *J. Med. Chem.*, 2010, 53, 521-538; and 2. Inhibitor of HIV Protease

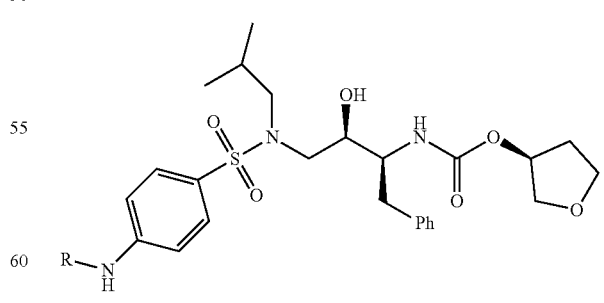

(derivatized where "R" designates a potential site for linker group L or -L-(VHL ligand moiety) group attachment). See, *J. Med. Chem.* 2010, 53, 521-538.

Compounds Targeting HIV Integrase
1. Inhibitor of HIV Integrase (derivatized)

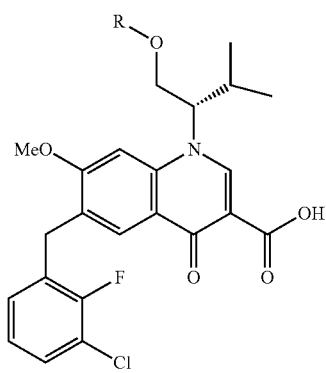

(derivatized where "R" designates a site for linker group L or -L-(VHL ligand moiety) group attachment). See, *J. Med. Chem.* 2010, 53, 6466; and 2. Inhibitor of HIV Integrase (derivatized)

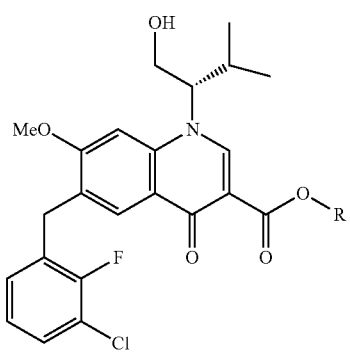

(derivatized where "R" designates a site for linker group L or -L-(VHL ligand moiety) group attachment). See, *J. Med. Chem.*, 2010, 53, 6466.

Compounds Targeting HCV Protease
Inhibitors of HCV Protease (derivatized)

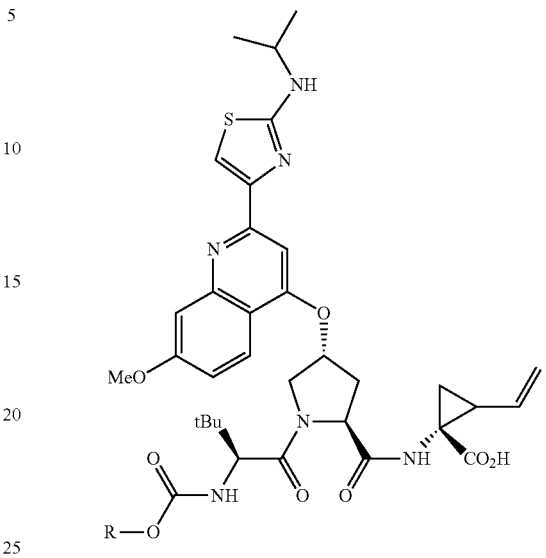

(derivatized where "R" designates a site for linker group L or -L-(VHL ligand moiety) group attachment).

Compounds Targeting Acyl-Protein Thioesterase-1 and -2 (APT1 and APT2)
Inhibitor of APT1 and APT2 (derivatized)

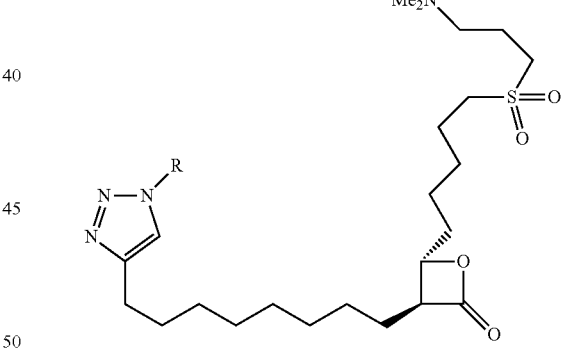

(derivatized where "R" designates a site for linker group L or -L-(VHL ligand moiety) group attachment). See, *Angew. Chem. Int. Ed.* 2011, 50, 9838-9842, where L is a linker group as otherwise described herein and said VHL ligand moiety is as otherwise described herein such that -L-(VHL ligand moiety) binds the VHL ligand moiety to a protein binding moiety as otherwise described herein.

RAS Family Inhibitors

RAS family inhibitors used herein include, but are not limited to:

1. The RAS inhibitors identified in (Spiegel, J. et al "Small-molecule modulation of Ras signaling" *Nature Chemical Biology* 2014, 10, 613-622):

a. SCH53239

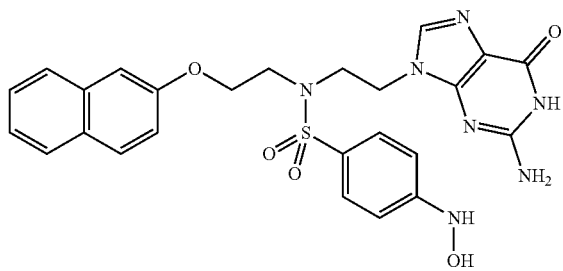 [SMILES: Nc1nc2c(ncn2CCN(CCOc2ccc3ccccc3c2)S(=O)(=O)c2ccc(NO)cc2)c(=O)[nH]1]

(derivatized such that a linker group L or -L-(VHL ligand moiety) is attached);
b. SCH53239 Sulindac Sulfide

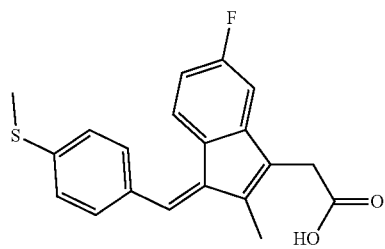 [SMILES: CSc1ccc(/C=C2/C(C)=C(CC(=O)O)c3cc(F)ccc32)cc1]

(derivatized such that a linker group L or a -L-(VHL ligand moiety) is attached);
c. VSA9

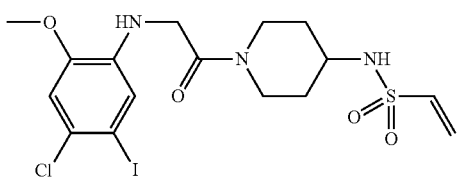

(derivatized such that a linker group L or a -L-(VHL ligand moiety) is attached);
d. AA12

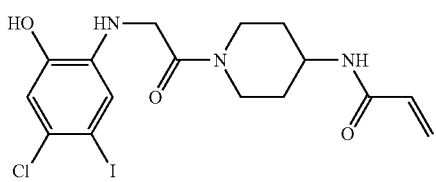 [SMILES: C=CC(=O)NC1CCN(C(=O)CNc2cc(I)c(Cl)cc2O)CC1]

(derivatized such that a linker group L or a -L-(VHL ligand moiety) is attached);

e. MCP110

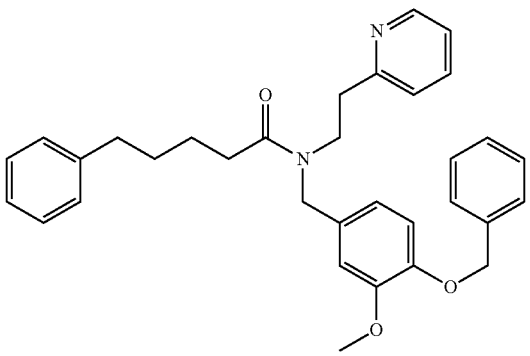 [SMILES: COc1cc(CN(CCc2ccccn2)C(=O)CCCCc2ccccc2)ccc1OCc1ccccc1]

(derivatized such that a linker group L or a -L-(VHL ligand moiety) is attached);
f. Kobe0065

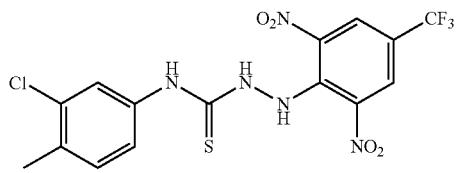 [SMILES: Cc1ccc(NC(=S)NNc2c([N+](=O)[O-])cc(C(F)(F)F)cc2[N+](=O)[O-])cc1Cl]

(derivatized such that a linker group L or a -L-(VHL ligand moiety) is attached); and
g. Kobe2602

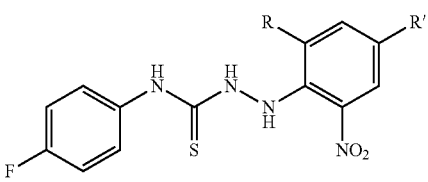

(derivatized such that a linker group L or a -L-(VHL ligand moiety) is attached); and
2. The RAS inhibitors disclosed in WO 2014/143659, including the compounds of Formulas (I) and (II) in WO 2014/143659 (derivatized such that a linker group L or a -L-(VHL ligand moiety) is attached).

EGFR Family Inhibitors

EGFR family inhibitors used herein include, but are not limited to:
1. The EGFR tyrosine kinase inhibitors (TKIs) identified in Jia et al "Overcoming EGFR(T790M) and EGFR(C797S) resistance with mutant-selective allosteric inhibitors" *Nature* 2016, 534, 129-132, such as EAI045

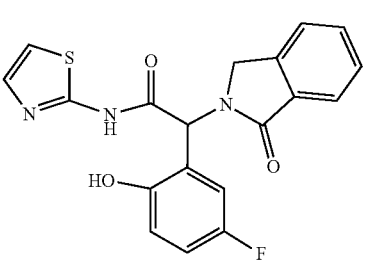 [SMILES: O=C(Nc1nccs1)C(c1cc(F)ccc1O)N1Cc2ccccc2C1=O]

(derivatized such that a linker group L or a -L-(VHL ligand moiety) is attached); and 2. The EGFR tyrosine kinase inhibitors (TKIs) inhibitors identified in Wang et. al "Next-generation EGFR/HER tyrosine kinase inhibitors for the treatment of patients with non-small-cell lung cancer harboring EGFR mutations: a review of the evidence" *OncoTargets and Therapy*, Vol. 9 p. 5461-5473, including but not limited to:

a. Getfitinib

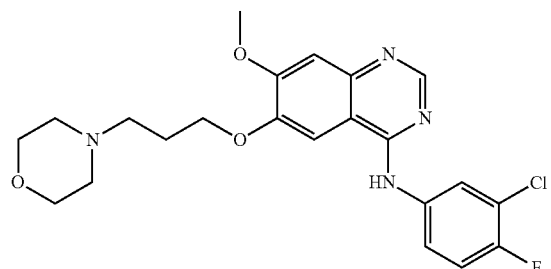

(derivatized such that a linker group L or a -L-(VHL ligand moiety) is attached);

b. Erlotinib

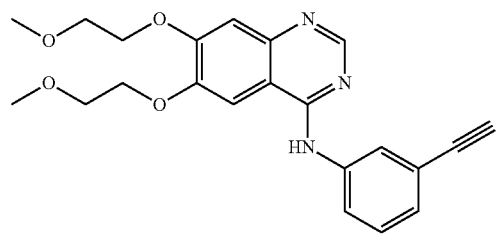 [SMILES: C#Cc1cccc(Nc2ncnc3cc(OCCOC)c(OCCOC)cc23)c1]

(derivatized such that a linker group L or a -L-(VHL ligand moiety) is attached);

c. Afatinib

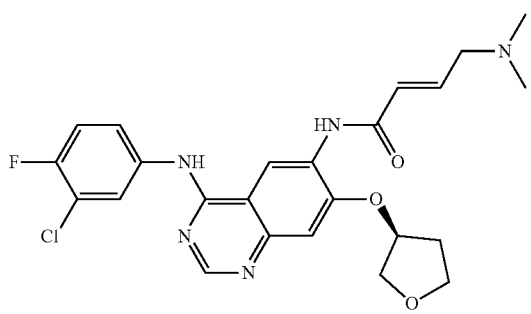 [SMILES: CN(C)C/C=C/C(=O)Nc1cc2c(Nc3ccc(F)c(Cl)c3)ncnc2cc1O[C@H]1CCOC1]

(derivatized such that a linker group L or a -L-(VHL ligand moiety) is attached);

d. Dacomitinib

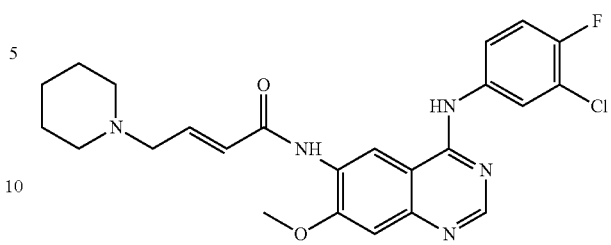

(derivatized such that a linker group L or a -L-(VHL ligand moiety) is attached);

e. Neratinib

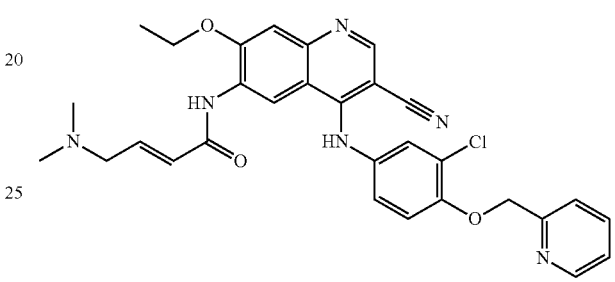

(derivatized such that a linker group L or a -L-(VHL, ligand moiety) is attached);

f. Osimeritinib

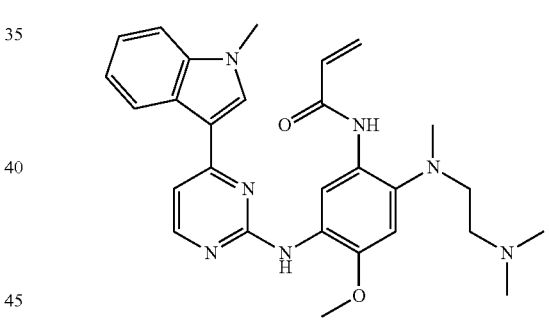

(derivatized such that a linker group L or a -L-(VHL ligand moiety) is attached); and g. Rociletinib

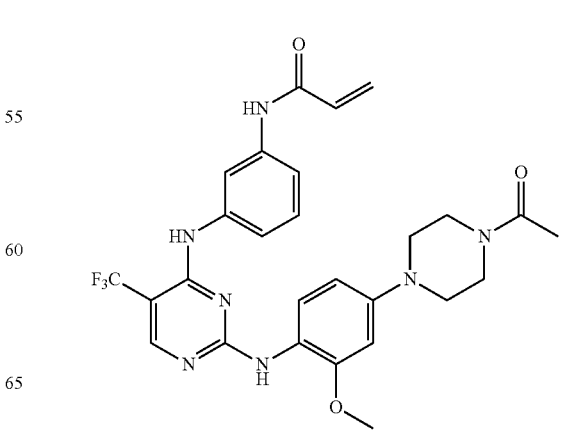

(derivatized such that a linker group L or a -L-(VHL ligand moiety) is attached).

BRM/BRG Family Inhibitors

BRM family inhibitors used herein include, but are not limited to, the BRM tyrosine kinase inhibitors (TKIs) inhibitors identified in Gerstenberger, B S. et al "Identification of a Chemical Probe for Family VIII Bromodomains through Optimization of a Fragment Hit" *J. Med. Chem.* 2016, 59, 4800-4811, such as:

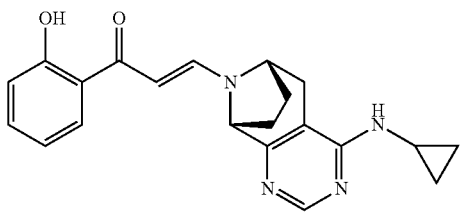 [SMILES: O=C(/C=C/N1[C@H]2CC[C@@H]1c1ncnc(NC3CC3)c1C2)c1ccccc1O]

(derivatized such that a linker group L or a -L-(VHL ligand moiety) group is attached).

BRG/BRG1 family inhibitors used herein include but are not limited to the BRG/BRG1 inhibitors described in WO 2016/138114A1 (e.g., in Formula (I) of WO 2016/138114A1) (derivatized such that a linker group L or a -L-(VHL ligand moiety) group is attached).

USP7 Family Inhibitors

USP7 family inhibitors used herein include but are not limited to the USP7 inhibitors as defined in Formula (I) of US Patent Application No. 2016/0185785A1 (derivatized such that a linker group L or a -L-(VHL ligand moiety) group is attached).

The term "target protein" is used to describe a protein or polypeptide, which is a target for binding to a compound according to the present disclosure and degradation by ubiquitin ligase hereunder. Such small molecule target protein binding moieties also include pharmaceutically acceptable salts, enantiomers, solvates and polymorphs of these compositions, as well as other small molecules that may target a protein of interest. These binding moieties are linked to VHL ligand moieties through linker groups L.

Specific PB moieties may also be small molecule compounds such as those disclosed in US Patent Application No. 2014/0356322 and US Patent Application No. 2016/0045607. Compounds disclosed therein can be classified as Heat Shock Protein 90 (HSP90) inhibitors, Kinase and Phosphatase inhibitors, MDM2 inhibitors, HDAC inhibitors, Human Lysine Methyltransferase Inhibitors, Angiogenesis inhibitors, Immunosuppressive compounds, as well as compounds that bind to: Human BET Bromodomain-containing proteins, the aryl hydrocarbon receptor (AHR), RAF receptor kinase, FKBP, Androgen Receptor (AR), Estrogen receptor (ER), Thyroid Hormone Receptor, HIV Protease, HIV Integrase, HCV Protease, Acyl-protein Thioesterase-1 and -2 (APT1 and APT2). Other specific PB moieties may also be small molecule compounds such as those disclosed in US Patent Application No. 2016/0185785 (USP7 inhibitors) and WO 2016/138114 (BRG1).

Target proteins and/or PB moieties are also described in: Holderfield, et al., "Targeting RAF kinases for cancer therapy: BRAF mutated melanoma and beyond," *Nat. Rev. Cancer*, 2014, 14, 455-467 (RAF); and Filippakoupoulos, et al., "Targeting bromodomains: epigenetic readers of lysine acetylation," Nature Reviews Drug Discovery, 2014, 13, 337-356 (BET).

3. Linker (L)

The VHL ligand moiety and PB moiety (D) of PROTACs as described herein can be connected with a linker (L). In certain embodiments, the linker group L is a group comprising one or more covalently connected structural units of A, wherein each A unit is a group coupled to at least one of a VHL ligand moiety, a PB moiety, another A unit, or a combination thereof. In certain embodiments, an A unit links a VHL ligand moiety, a PB moiety, or a combination thereof directly to another VHL ligand, PB moiety, or combination thereof. In other embodiments, an A unit links a VHL ligand moiety, a PB moiety, or a combination thereof indirectly to another VHL ligand moiety, PB moiety, or combination thereof through one or more different A unit(s). In any of the embodiments disclosed herein, one or more covalently connected structural units of A may be coupled to the VHL ligand moiety of the PROTAC of the present disclosure at substituent Y. Thus, in certain embodiments, the linker L may be coupled to Y, D, or combinations thereof. In other embodiments, one or more covalently connected structural units of A may be coupled to a PB moiety and also to a VHL ligand of the present disclosure at $R^1$, $R^2$, or Z, as described herein, to form a PROTAC.

In certain embodiments, the linker "L" is $(A)_q$, and each A is independently selected from the group consisting of a bond, $CR^{La}R^{Lb}$, O, S, SO, $SO_2$, $NR^{Lc}$, $SO_2NR^{Lc}$, $SONR^{Lc}$, $CONR^{Lc}$, $NR^{Lc}CONR^{Ld}$, $NR^{Lc}SO_2NR^{Ld}$, CO, $CR^{La}=CR^{Lb}$, C≡C, $SiR^{La}R^{Lb}$, $P(O)R^{La}$, $P(O)OR^{La}$, $NR^{Lc}C(=NCN)NR^{Ld}$, $NR^{Lc}C(=NCN)$, $NR^{Lc}C(=CNO_2)NR^{Ld}$, $C_3$-$C_{11}$ cycloalkylene, $C_3$-$C_{11}$ heterocyclylene, arylene, and heteroarylene, wherein the $C_3$-$C_{11}$ cycloalkylene, $C_3$-$C_{11}$ heteocyclylene, arylene, and heteroarylene are independently either unsubstituted or substituted with 1, 2, 3, 4, 5, or 6 substituents selected from the group consisting of $R^{La}$, $R^{Lb}$, and combinations thereof, where $R^{La}$ or $R^{Lb}$, each independently, can be linked to other A groups to form cycloalkylene and/or heterocyclylene moiety, wherein the cycloalkylene and heterocyclylene moieties are independently unsubstituted or substituted with 1, 2, 3, or 4 $R^{Le}$ groups; wherein $R^{La}$, $R^{Lb}$, $R^{Lc}$, $R^{Ld}$ and $R^{Le}$ are, each independently, selected from the group consisting of H, halogen, $R^{Lf}$, $-OR^{Lh}$, $-SR^{Lh}$, $-NR^{Lh}$, $-N(R^{Lh})_2$, $C_3$-$C_{11}$ cycloalkyl, aryl, heteroaryl, $C_3$-$C_{11}$ heterocyclyl, $-N(R^{Lg})(R^{Lf})$, $-OH$, $-NH_2$, $-SH$, $-SO_2R^{Lf}$, $-P(O)(OR^{Lf})(R^{Lf})$, $-P(O)(OR^{Lf})_2$, $-C≡C-R^{Lf}$, $-C≡CH$, $-CH=CH(R^{Lf})$, $-C(R^{Lf})=CH(R^{Lf})$, $-C(R^{Lf})=C(R^{Lf})_2$, $-Si(OH)_3$, $-Si(R^{Lf})_3$, $-Si(OH)(R^{Lf})_2$, $-COR^{Lf}$, $-CO_2H$, $-CN$, $-CF_3$, $-CHF_2$, $-CH_2F$, $-NO_2$, $-SF_5$, $-SO_2NHR^{Lf}$, $-SO_2N(R^{Lf})_2$, $-SONHR^{Lf}$, $-SON(R^{Lf})_2$, $-CONHR^{Lf}$, $-CON(R^{Lf})_2$, $-N(R^{Lf})CONH(R^{Lf})$, $-N(R^{Lf})CON(R^{Lf})_2$, $-NHCONH(R^{Lf})$, $-NHCON(R^{Lf})_2$, $-NHCONH_2$, $-N(R^{Lf})SO_2NH(R^{Lf})$, $-N(R^{Lf})SO_2N(R^{Lf})_2$, $-NHSO_2NH(R^{Lf})$, $-NHSO_2N(R^{Lf})_2$, and $-NHSO_2NH_2$, wherein $R^{Lf}$ is a substituted or unsubstituted $C_1$-$C_8$ alkyl; $R^{Lg}$ is a substituted or unsubstituted $C_1$-$C_8$ cycloalkyl; and $R^{Lh}$ is $R^{Lf}$ or $R^{Lg}$.

In certain embodiments, q is an integer greater than or equal to 1.

In certain embodiments, q is greater than 2.

In certain embodiments, q is 2.

In certain embodiments, e.g., where q is 1, and A is a group which is connected to a VHL ligand moiety and a PB moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, the linker is selected from the group consisting of:
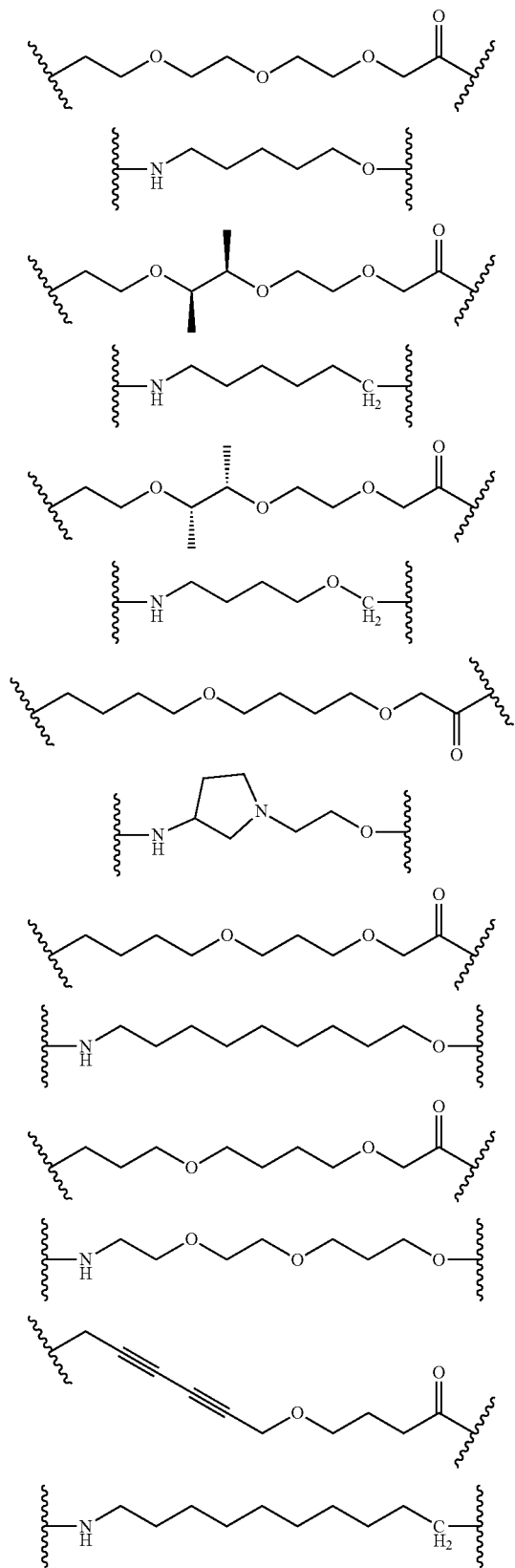
-continued
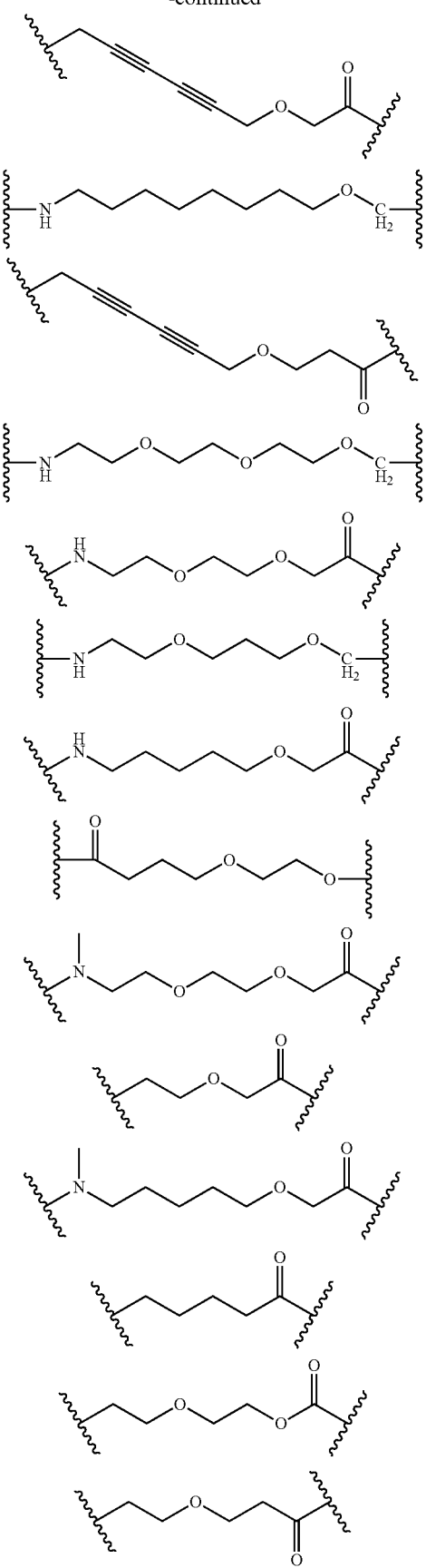

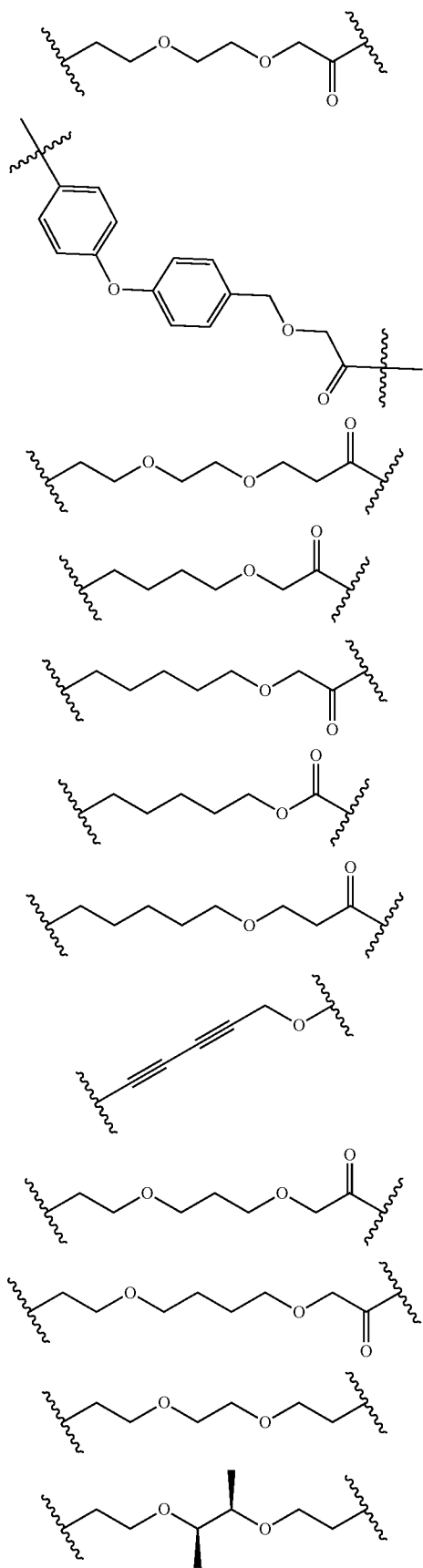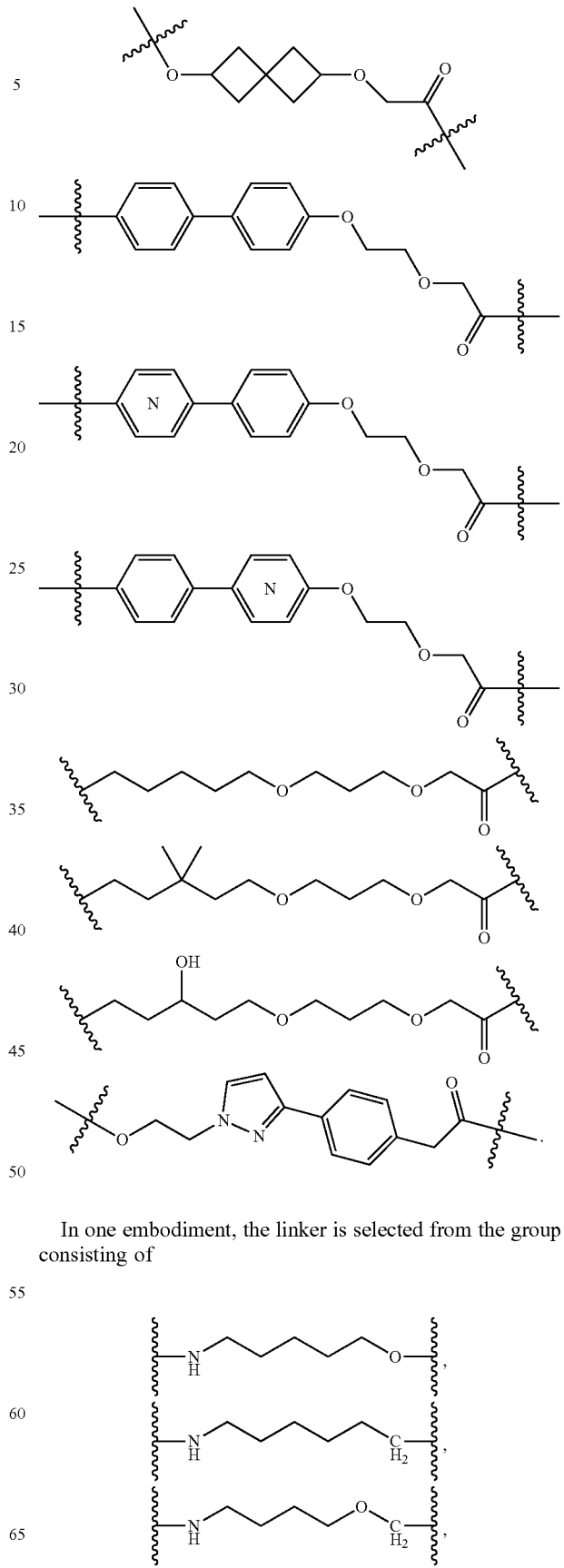
In one embodiment, the linker is selected from the group consisting of
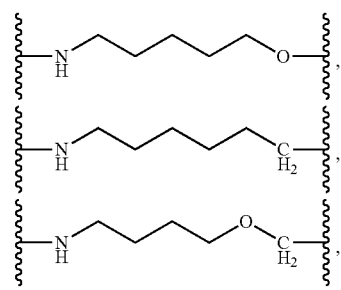

-continued

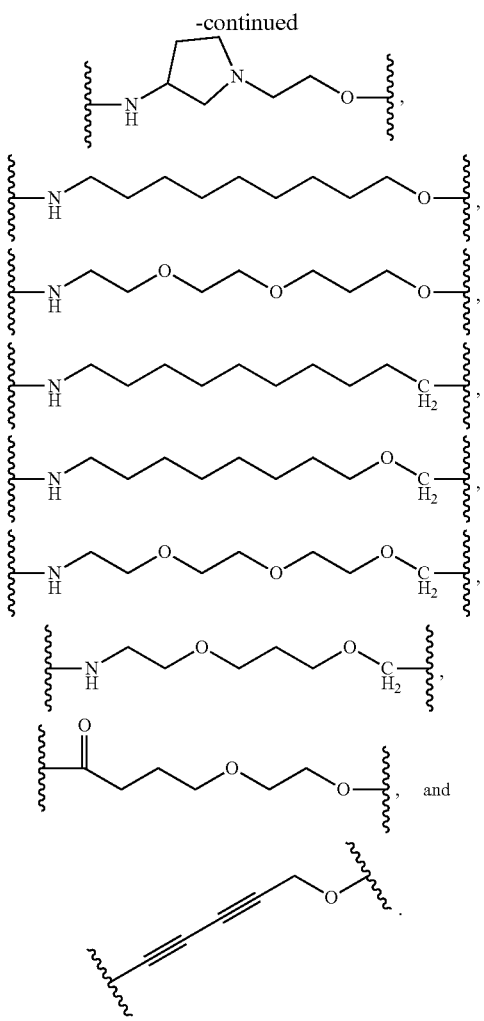

In additional embodiments, the linker group is an optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

The VHL ligand moiety and PB moiety may be covalently linked to the linker group through any group which is appropriate and stable to the chemistry of the linker. The linker is independently covalently bonded to the VHL ligand moiety and the PB moiety preferably through an amide, ester, thioester, keto group, carbamate (urethane), carbon or ether, each of which groups may be inserted anywhere on the VHL ligand moiety and PB moiety to provide maximum binding of the VHL ligand moiety on the ubiquitin ligase and the PB moiety on the target protein to be degraded. In certain aspects where the PB moiety is a VHL ligand moiety, the target protein for degradation may be the ubiquitin ligase itself. In certain aspects, the linker may be linked to an optionally substituted alkyl, alkylene, alkene or alkyne group, an aryl group or a heterocyclic group on the VHL ligand moiety and/or PB moiety. It is noted that a VHL ligand moiety or a PB moiety may need to be derivatized to make a chemical functional group that is reactive with a chemical functional group on the linker. Alternatively, the linker may need to be derivatized to include a chemical functional group that can react with a functional group found on the VHL ligand moiety and/or PB moiety.

The linker L can also be represented by the formula:

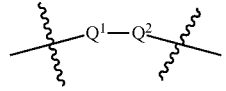

where $Q^1$ is a group which links the VHL ligand moiety to $Q^2$; and $Q^2$ is a group linking $Q^1$ to the PB moiety.

In some embodiments, $Q^1$ is absent (a bond), —(CH$_2$)i-O, —(CHR$^{15}$)i-O, —[C(R$^{15}$)$_2$]i-O, —(CH$_2$)i-S, —(CH$_2$)i-N—R$^{15}$, —S, —S(O), —S(O)$_2$, —OP(O)OR$^{15}$, —Si(R$^{15}$)$_2$, or a (CH$_2$)i-Q$^3$Q$^4$ group wherein Q$^3$Q$^4$ forms an amide group, or a urethane group, ester or thioester group, or a

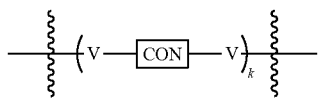

where, each R$^{15}$ is H, or a C$_1$-C$_3$ alkyl, an alkanol group or a heterocycle (including a water soluble heterocycle, preferably, a morpholino, piperidine or piperazine group to promote water solubility of the linker group); each U is independently a bond, O, S or N—R$^{15}$; and each i is independently 0 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5.

In embodiments, $Q^2$ is a

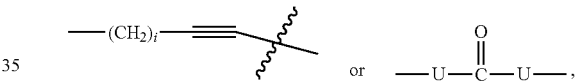

where each V is independently a bond (absent),

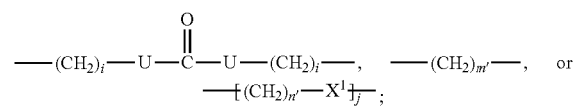

j is 1 to 100, 1 to 75, 1 to 60, 1 to 55, 1 to 50, 1 to 45, 1 to 40, 2 to 35, 3 to 30, 1 to 5, 1 to 10, 1 to 8, 1 to 6, 1, 2, 3, 4 or 5;

k is 1 to 100, 1 to 75, 1 to 60, 1 to 55, 1 to 50, 1 to 45, 1 to 40, 2 to 35, 3 to 30, 1 to 5, 1 to 10, 1 to 8, 1 to 6, 1, 2, 3, 4 or 5; preferably k is 1, 2, 3, 4, or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

$X^1$ is O, S or N—$R^{15}$, preferably O;

U is the same as above;

and CON is a connector group (which may be a bond) which connects $Q^1$ to $Q^2$, when present in the linker group.

In embodiments, CON is a bond (absent), a heterocycle including a water soluble heterocycle such as a piperazinyl or other group or a group,

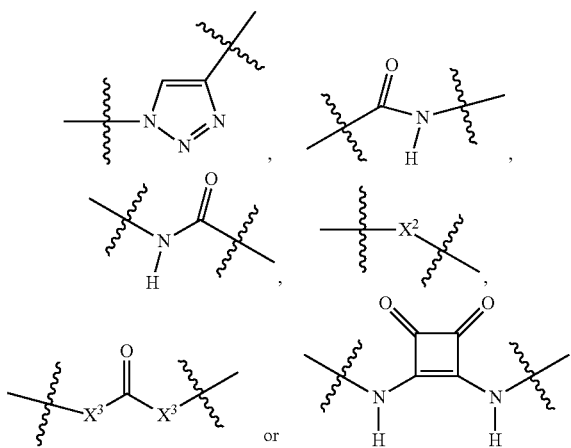

where $X^2$ is cycloalkyl, heterocyclyl, O, S, $NR^{12}$, S(O), $S(O)_2$, —$S(O)_2O$, —$OS(O)_2$, $OP(O)OR^{15}$, $Si(R^{15})_2$, or $OS(O)_2O$;

$X^3$ is O, S, $CHR^{12}$, $NR^{12}$;

$R^{12}$ is H or a $C_1$-$C_3$ alkyl group optionally substituted with one or two hydroxyl groups, or a pharmaceutically acceptable salt, enantiomer or stereoisomer thereof; and $R^{15}$ is as defined above.

In alternative preferred aspects, the linker group is a (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units. In certain embodiments, the linker is optionally substituted; i.e., comprises chemical groups interdispersed within or on the PEG linker. In certain embodiments, the PEG linker is substituted with an alkyl, alkylene, aromatic group, or aryl group, e.g., phenyl, benzyl, or heterocyclyl group, or amino acid side chain and is optionally interdispersed with optionally substituted O, N, S, P, or Si atoms.

In embodiments, CON is

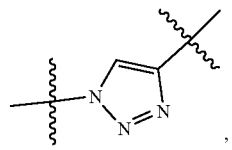 [SMILES: *c1cn(*)nn1]

or an amide group.

The linker may be asymmetrical or symmetrical.

Although the VHL ligand moiety and PB moiety may be covalently linked to the linker group through any group which is appropriate and stable to the chemistry of the linker, in preferred aspects, the linker is independently covalently bonded to the VHL ligand moiety and the PB moiety through an amide, ester, thioester, keto group, carbamate (urethane) or ether, each of which groups may be inserted anywhere on the VHL ligand moiety and PB moiety to allow binding of the VHL ligand moiety to the ubiquitin ligase and the PB moiety to the target protein to be degraded. In other words, as shown herein, the linker can be designed and connected to VHL ligand moiety and PB moiety to minimize, eliminate, or neutralize any impact its presence might have on the binding of VHL ligand moiety and PB moiety to their respective binding partners. In certain aspects, the targeted protein for degradation may be an ubiquitin ligase. In some embodiments, the linker may be linked to an optionally substituted alkyl, alkylene, alkene, or alkyne group, an aryl group, or a heterocyclic group on the VHL ligand moiety and/or PB moiety. In one aspect, the linker is connected to the VHL ligand moiety through substituent Y.

Additional linkers are disclosed in U.S. Patent Application Publication NOs. 2016/0058872, 2016/0045607, 2014/0356322, and 2015/0291562; and in WO2014/063061.

III. FORMULATIONS

In an additional aspect, the description provides therapeutic or pharmaceutical compositions comprising an effective amount of at least one of the compounds as described herein, including, e.g., at least one VHL ligand, at least one PROTAC, and combinations thereof. Pharmaceutical compositions comprising an effective amount of at least one bifunctional compound according to the present disclosure, and optionally one or more of the compounds otherwise described herein, in effective amounts, in combination with a pharmaceutically effective amount of a carrier, additive or excipient, and optionally an additional bioactive agent, represents a further aspect of the disclosure.

In certain embodiments, the compositions comprise pharmaceutically acceptable salts, in particular, acid or base addition salts of compounds as described herein. The acids that are used to prepare the pharmaceutically acceptable acid addition salts of the aforementioned base compounds include those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compositions as described herein may in certain embodiments be administered in single or divided unit doses by the oral, parenteral or topical routes. Administration of the compounds may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, by inhalation spray, rectally, vaginally, or via an implanted reservoir, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound according to the present disclosure, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but may also be administered in suppository and transdermal or other topical forms. Intramuscular injections in liposomal form may also be used to control or sustain the release of compound at an injection site.

Thus in one aspect, pharmaceutical formulations of VHL ligands and/or PROTACs as described herein can be prepared for parenteral administration with a pharmaceutically acceptable parenteral vehicle and in a unit dosage injectable form. The term "parenteral" as used herein includes subcutaneous, intravenous, intramuscular, intra-articular, intrasynovial, intrasternal, intrathecal, intrahepatic, intralesional and intracranial injection or infusion techniques. Preferably, the compositions are administered orally, intraperitoneally or intravenously. A PROTAC having the desired degree of purity is optionally mixed with one or more pharmaceutically acceptable excipients (Remington's Pharmaceutical Sciences (1980) 16th edition, Osol, A. Ed.), in the form of a lyophilized formulation for reconstitution or an aqueous solution.

The compositions of the present disclosure may be formulated in a conventional manner using one or more pharmaceutically acceptable carriers and may also be administered in controlled-release formulations. The compounds of the disclosure can be formulated in accordance with standard pharmaceutical practice as a pharmaceutical composition. According to this aspect, there is provided a pharmaceutical composition comprising a PROTAC or VHL ligand in association with one or more pharmaceutically acceptable excipients.

A typical formulation is prepared by mixing the compounds of the disclosure with excipients, such as carriers and/or diluents. Suitable carriers, diluents and other excipients are well known to those skilled in the art and include materials such as carbohydrates, waxes, water soluble and/or swellable polymers, hydrophilic or hydrophobic materials, gelatin, oils, solvents, water and the like. The particular carrier, diluent or other excipient used will depend upon the means and purpose for which the compound is being applied. Other pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ PLURONICS™ or polyethylene glycol (PEG).

The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the PROTAC or aid in the manufacturing of the pharmaceutical product. The formulations may be prepared using conventional dissolution and mixing procedures.

Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The pharmaceutical compositions may be in the form of a sterile injectable preparation, such as a sterile injectable aqueous or oleaginous suspension. In particular, formulations to be used for in vivo administration must be sterile. Such sterilization is readily accomplished by filtration through sterile filtration membranes. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables, as well as natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The PROTAC and VHL ligand compositions ordinarily can be stored as a solid composition, a lyophilized formulation or as an aqueous solution.

The pharmaceutical compositions comprising a PROTAC or VHL ligand of the present disclosure can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the disorder. Such amount is preferably below the amount that is toxic to the host or renders the host significantly more susceptible to unwanted side effects.

The PROTAC can be formulated into pharmaceutical dosage forms to provide an easily controllable dosage of the drug and to enable patient compliance with the prescribed regimen. The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the present disclosure can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for the herein-mentioned conditions is in the range from about 10 ng/kg to 300 mg/kg, preferably 0.1 to 100 mg/kg per day, more generally 0.5 to about 25 mg per kilogram body weight of the recipient/patient per day. One typical daily dosage might range from about 1 µg/kg to 100 mg/kg or more, depending on the factors mentioned above. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 mM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

The term "pharmaceutically acceptable salt" is used throughout the specification to describe, where applicable, a salt form of one or more of the compounds described herein which are presented to increase the solubility of the compound in the gastric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

The subject matter further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally or by any other desired route.

IV. INDICATIONS AND METHODS OF TREATMENT

It is contemplated that the PROTACs disclosed herein may be used to treat various diseases or disorders. Exemplary hyperproliferative disorders include benign or malignant solid tumors and hematological disorders such as leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the PROTAC may be used in treatment include rheumatologic disorders (such as, for example, rheumatoid arthritis, Sjögren's syndrome, scleroderma, lupus such as systemic lupus erythematosus (SLE) and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Other disease states or disorders which may be treated using compounds or compositions according to the present disclosure include, for example, asthma, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease (PKD1) or 4 (PKD2) Prader-Willi syndrome, Sickle-cell disease, Tay-Sachs disease, and Turner syndrome.

Further diseases or disorders which may be treated by compounds or compositions according to the present disclosure include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional diseases or disorders which can be treated by compounds or compositions according to the present disclosure include acernloplasminemia, Achondrogenesis type H, Acrocephaly, Gaucher disease type 2, acute intermittent porphyria, Adenomatous Polyposis Coli, adenylosuccinate lyase deficiency, Adrenogenital syndrome, Adrenoleukodystrophy, ALA-D porphyria, ALA dehydratase deficiency, Alkaptonuria, Alkaptonuric ochronosis, alpha 1-antitrypsin deficiency, alpha-1 proteinase inhibitor, emphysema, amyotrophic lateral sclerosis, Alström syndrome, Alexander disease, Amelogenesis imperfecta, Anderson-Fabry disease, Anemia, Angiokeratoma Corporis Diffusum, Angiomatosis retinae (von Hippel-Lindau disease) Apert syndrome, Arachnodactyly (Marfan syndrome), Arthrochalasis multiplex congenital (Ehlers-Danlos syndrome arthrochalasia type), ataxia telangiectasia, Rett syndrome, Sandhoff disease, neurofibromatosis type II, Mediterranean fever, familial, Benjamin syndrome, Bilateral Acoustic Neurofibromatosis (neurofibromatosis type II), factor V Leiden thrombophilia, Bloch-Sulzberger syndrome (incontinentia pigmenti), Bloom syndrome, Bonnevie-Ullrich syndrome (Turner syndrome), Bourneville disease (tuberous sclerosis), Birt-Hogg-Dube syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat CAVD (congenital absence of the vas deferens), Caylor cardiofacial syndrome (CBAVD), CEP (congenital erythropoietic porphyria), congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, Diffuse Globoid Body Sclerosis (Krabbe disease), Di George's syndrome, Dihydrotestosterone receptor deficiency, Down syndrome, Dwarfism, Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, genetic brain disorders, Giant cell hepatitis (Neonatal hemochromatosis), Gronblad-.Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Joubert syndrome, Lesch-Nyhan syndrome, Jackson-Weiss syndrome, Kidney diseases, including hyperoxaluria, Lacunar dementia, Langer-Saldino achondrogenesis, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber Rendu disease, Peutz-Jeghers syndrome, Polycystic kidney disease, polyostotic fibrous dysplasia (McCune-Albright syndrome), Prader-Labhart-Willi syndrome, hemochromatosis, primary hyperuricemia, primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South African genetic porphyria (variegate porphyria), infantile-onset ascending hereditary spastic paralysis, Speech and communication disorders, sphingolipidosis, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymüller syndrome, Wolf-Hirschhorn syndrome, Wolff Periodic disease, and Xeroderma pigmentosum, among others.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas, Hodgkin's disease, Wilms' tumor and teratocarcinomas. Additional cancers which may be treated using compounds according to the present disclosure include, for example, T-lineage Acute lymphoblastic Leukemia ('T-ALL), Tlineage lymphoblastic Lymphoma (T-LL), Peripheral T-cell lymphoma, Adult T-cell Leukemia, Pre.B ALL, Pre-B Lymphomas, Large B-cell Lymphoma, Burkitts Lymphoma, B-cell ALL Philadelphia chromosome positive ALL and Philadelphia chromosome positive CML.

In certain embodiments, the present disclosure is directed to a method of treating a disease or disorder in a human in need thereof, comprising administering to the human an effective amount of a compound of the present disclosure (e.g., a PROTAC of Formula (I), (Ia), (II), or (IIa)), or a pharmaceutically acceptable salt thereof, or a pharmaceutical composition of the present disclosure that comprises said PROTAC.

In certain embodiments, a PROTAC of the present disclosure is used in a method of treating solid tumor, e.g., ovarian.

In another embodiment, a PROTAC of the present disclosure is used in a method of treating hematological malignancies such as non-Hodgkin's lymphoma (NHL), diffuse large hematopoietic lymphoma, follicular lymphoma, mantle cell lymphoma, chronic lymphocytic leukemia, multiple myeloma, acute myeloid leukemia (AML), and myeloid cell leukemia (MCL), and including B-cell related cancers and proliferative disorders. See, e.g., U.S. Pat. No. 8,226,945; Li et al (2013) *Mol. Cancer. Ther.* 12(7):1255-1265; Polson et al (2010) Leukemia 24:1566-1573; Polson et al (2011) *Expert Opin. Investig. Drugs* 20(1):75-85.

In another embodiment, a PROTAC of the present disclosure is used in a method of treating ovarian, breast and pancreatic cancers. The cancer may be associated with the expression or activity of a MUC16/CA125/0772P polypeptide. See, e.g., WO 2007/001851; U.S. Pat. Nos. 7,989,595; 8,449,883; 7,723,485; Chen et al (2007) *Cancer Res.* 67(10): 4924-4932; Junutula, et al., (2008) *Nature Biotech.,* 26(8): 925-932.

In certain embodiments, a PROTAC of the present disclosure is used in a method of treating cancer, e.g., breast or gastric cancer, more specifically HER2 positive breast or gastric cancer, wherein the method comprises administering such PROTAC to a patient in need of such treatment.

A PROTAC of the present disclosure may be administered by any route appropriate to the condition to be treated. The PROTAC or VHL will typically be administered parenterally, i.e. infusion, subcutaneous, intramuscular, intravenous, intradermal, intrathecal and epidural.

A PROTAC can be used either alone or in combination with other agents in a therapy. For instance, a PROTAC may be co-administered with at least one additional therapeutic agent. Such combination therapies noted above encompass combined administration (where two or more therapeutic agents are included in the same or separate formulations), and separate administration, in which case, administration of the PROTAC can occur prior to, simultaneously, and/or following, administration of the additional therapeutic agent and/or adjuvant. A PROTAC can also be used in combination with radiation therapy.

The term "coadministration" or "combination therapy" shall mean that at least two compounds or compositions are administered to the patient at the same time, such that effective amounts or concentrations of each of the two or more compounds may be found in the patient at a given point in time. Although compounds according to the present disclosure may be co-administered to a patient at the same time, the term embraces both administration of two or more agents at the same time or at different times, provided that effective concentrations of coadministered compounds or compositions are found in the subject at a given time.

In an additional aspect, the description provides combination therapies comprising an effective amount of a compound as described herein in combination with an additional bioactive agent. The term "bioactive agent" is used to describe an agent, other than a compound as described herein, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc. In certain embodiments, the compound as described herein, the additional bioactive agent or both are present in an effective amount or, in certain embodiments, a synergistically effective amount.

The term "additional anti-cancer agent" is used to describe an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR1 KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu$^t$)6,Azgly$^{10}$] or pyro-Glu-His-Trp-Ser-Tyr-D-Ser(Bu$^t$)-Leu-Arg-Pro-Azgly-NH$_2$ acetate $[C_{29}H_{84}N_{18}O_{14}\cdot(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

The term "anti-HIV agent" or "additional anti-HIV agent" includes, for example, nucleoside reverse transcriptase inhibitors (NRTI), other non-nucloeoside reverse transcriptase inhibitors (i.e., those which are not representative of the present disclosure), protease inhibitors, fusion inhibitors, among others, exemplary compounds of which may include, for example, 3TC (Lamivudine), AZT (Zidovudine), (−)-FTC, ddI (Didanosine), ddC (zalcitabine), abacavir (ABC), tenofovir (PMPA), D-D4FC (Reverset), D4T (Stavudine), Racivir, L-FddC, L-FD4C, NVP (Nevirapine), DLV (Delavirdine), EFV (Efavirenz), SQVM (Saquinavir mesylate), RTV (Ritonavir), IDV (Indinavir), SQV (Saquinavir), NFV (Nelfinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in coadministration with compounds according to the present disclosure include, for example, other NNRTI's (i.e., other than the NNRTI's according to the present disclosure) may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furancarbothiamide), etravirine (TMC125), Trovirdine (Ly300046.HCl), MKC-442 (emivirine, coactinon), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl) phenyl)hept-1-enyl)-2-methoxybenzoate (Alkenyldiarylmethane analog, Adam analog), 5Cl3PhS-2Indo1CONH2 (5-chloro-3-(phenylsulfinyl)-2'-indolecarboxamide), AAP-BHAP (U-104489 or PNU-104489), Capravirine (AG-1549, 5-1153), atevirdine (U-87201E), aurin tricarboxylic acid (SD-095345), 1-[(6-Cyano-2-indoyly)carbonyl]-4-[3-(isopropylamino)-2-pyridinyl]piperazine (piperazine1 pyridine 4 indolyl derivative), 1-[5-[[N-(methyl)methylsulfonylamino]-2-indolylcarbonyl-4-[3-(isopropylamino)-2-pyridinyl]piperazine (piperazine 1pyridine 5 indolyl derivative), 1-[3-(Ethylamino)-2-[pyridinyl]-4-[(5-hydroxy-2-indolyl)carbonyl]piperazine, 1-[(6-Formyl-2-indoyly) carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S (1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl)]hiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 3-[2-(4,7-Difluorobenzoxazol-2-yl)ethyl]-5-ethyl-6-methyl (pyridin-2(1H)-thione (2-Pyridinone Derivative), 3-[[(2-Methoxy-5,6-dimethyl-3-pyridyl)methyl]amine]-5-ethyl-6-methyl(pyridin-2(1H)-thione (2-Pyridinone 3pyrid 3MeNH Derivative), R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5(9bH)-one, Tivirapine (R86183), UC-38 and UC-84, among others.

A PROTAC or VHL ligand (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

For the prevention or treatment of disease, the appropriate dosage of a PROTAC (when used alone or in combination with one or more other additional therapeutic agents) will depend on the type of disease to be treated, the type of PROTAC, the severity and course of the disease, whether the PROTAC is administered for preventive or therapeutic purposes, previous therapy, the patient's clinical history and response to the PROTAC, and the discretion of the attending physician. The PROTAC is suitably administered to the patient at one time or over a series of treatments. Depending on the type and severity of the disease, about 10 ng/kg to 300 mg/kg (e.g. 0.1 mg/kg-10 mg/kg) of a PROTAC can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of a PROTAC would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses). An initial higher loading dose, followed by one or more lower doses may be administered. However, other dosage regimens may be useful. The progress of this therapy is easily monitored by conventional techniques and assays.

Thus, in one aspect, present disclosure may be used to treat a number of disease states and/or disorders, including any disease state and/or disorder in which proteins are dysregulated and where a patient would benefit from the degradation of proteins.

In alternative aspects, the present disclosure relates to a method for treating a disease state by degrading a protein or polypeptide through which a disease or disorder is modulated comprising administering to said patient or subject an effective amount of at least one compound as described hereinabove, optionally in combination with an additional bioactive agent. The method according to the present disclosure may be used to treat a large number of diseases or disorders including cancer, by virtue of the administration of effective amounts of at least one compound described herein.

In still another aspect, the description provides a method of ubiquitinating/degrading a target protein in a cell. The method comprises administering a bifunctional compound or a pharmaceutical composition comprising a bifunctional compound that comprises a VHL ligand moiety and a protein binding moiety, preferably linked through a linker moiety, as otherwise described herein, wherein the VHL ligand moiety is coupled to the protein binding moiety and wherein the VHL ligand moiety recognizes a ubiquitin pathway protein (e.g., an ubiquitin ligase, preferably a VHL E3 ubiquitin ligase) and the protein binding moiety recognizes the target protein such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition, which is modulated through the target protein by lowering the level of that protein in the cells of a patient.

In another aspect, the present disclosure is directed to a method of degrading a target protein in a cell comprising exposing the cell to a composition comprising an effective amount of a compound Formula (I), (II), (Ia), or (IIa), or a pharmaceutically acceptable salt thereof, wherein the compound effectuates the degradation of the target protein.

In still another aspect, the description provides a method of treating or preventing in a patient in need thereof a disease or disorder modulated through a protein where the degradation of that protein will produce a therapeutic effect in that patient, the method comprising administering to a patient in need an effective amount of a compound according to the present disclosure, optionally in combination with another bioactive agent. The disease state or condition may be a disease caused by a microbial agent or other exogenous agent such as a virus, bacteria, fungus, protozoa or other microbe or may be a disease state, which is caused by overexpression of a protein, which leads to a disease state and/or condition.

V. ARTICLES OF MANUFACTURE

In another aspect, described herein are articles of manufacture, for example, a "kit", containing materials useful for the treatment of the diseases and disorders described above is provided. The kit comprises a container comprising a PROTAC. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products.

Suitable containers include, for example, bottles, vials, syringes, blister pack, etc. A "vial" is a container suitable for holding a liquid or lyophilized preparation. In one embodiment, the vial is a single-use vial, e.g. a 20-cc single-use vial with a stopper. The container may be formed from a variety of materials such as glass or plastic. The container may hold a PROTAC or a formulation thereof which is effective for treating the condition and may have a sterile access port (for example, the container may be an intravenous solution bag or a vial having a stopper pierceable by a hypodermic injection needle).

At least one active agent in the composition is a PROTAC of the present disclosure. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a PROTAC can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the PROTAC and, if present, the second pharmaceutical formulation. For example, if the kit comprises a first composition comprising a PROTAC, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a PROTAC, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a PROTAC contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a PROTAC and a second therapeutic agent, the kit may comprise a container for containing the separate compositions such as a divided bottle or a divided foil packet; however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

VI. EXAMPLES

The following examples are offered by way of illustration and not by way of limitation. Some of the compounds used in the following examples are tautomers. Although the illustrations of these compounds provided below depict only a single tautomer, these illustrations should not be viewed in a limiting sense, but rather, the corresponding tautomers are also intended and embraced by the following examples, as if each and every one of the tautomers of the compound is individually depicted.

Abbreviations

The following abbreviations are used in the examples:
ABPR—automated back pressure regulator
$Ac_2O$—acetic anhydride
ACN—acetonitrile
AIBN—2,2'-Azobis(2-methylpropionitrile)
Boc—tert-butyloxycarbonyl
Cbz—carboxybenzyl
CbzCl—Benzyl chloroformate
$CDCl_3$—Deuterochloroform
$Cy_3PHBF_4$—Tricyclohexylphosphine tetrafluoroborate
DBU—1,8-Diazabicyclo[5.4.0]undec-7-ene
DCE—1,2-Dichloroethane
DCM—dichloromethane
DEA—diethanolamine
DIAD—diisopropyl azodicarboxylate
DIPEA or DIEA—N,N-diisopropylethylamine
DMA—dimethylacetamide
DMAP—4-(dimethylamino)pyridine
DME—dimethoxyethane
DMF—dimethylformamide
DMFA—dimethylforamide dimethyl acetal
DMSO—dimethyl sulfoxide
DTT—dithiothreitol
EDCI—N-(3-Dimethylaminopropyl)-N'-ethylcarbodiimide hydrochloride
EDTA—ethylenediaminetetraacetic acid
ESI—electrospray ionization
$Et_3N$—trimethylamine
EtOAc—ethyl acetate
EtOH—ethanol
FA—formic acid
FBS—fetal bovine serum
Fmoc—Fluorenylmethyloxycarbonyl
GAPDH—Glyceraldehyde 3-phosphate dehydrogenase
HATU—1-[Bis(dimethylamino)methylene]-1H-1,2,3-triazolo[4,5-b]pyridinium 3-oxide hexafluorophosphate
HEPES—4-(2-Hydroxyethyl)piperazine-1-ethanesulfonic acid
Hex—hexane
HOAc—acetic acid
HOBt or HOBT—hydroxybenzotriazole
HPLC—high performance liquid chromatography
KOAc—potassium acetate
LC/MS or LCMS—liquid chromatography-mass spectrometry
LDA—Lithium diisopropylamide
LiHMDS—lithium bis(trimethylsilyl)amide
MeI—methyl iodide
MeOH—methanol or methyl alcohol
MeONa or NaOMe—sodium methoxide
MSD—mass selective detector
$MeSO_2Na$—sodium methanesulphinate
MTBE—methyl tert-butyl ether
NBS—N-bromosuccinimide
n-BuLi—butyllithium
$(n-Bu)_3SnCl$—tributylin chloride
NIS—N-iodosuccinimide
NMP—N-Methyl-2-pyrrolidone
NMR—nuclear magnetic resonance
OBD—optimum bed density
PBS—phosphate buffered saline
Pd/C—palladium on carbon
$PdCl_2(dppf)$ or $Pd(dppf)Cl_2$—[1,1'-Bis(diphenylphosphino)ferrocene]dichloropalladium(II)
$Pd(dppf)Cl_2.CH_2Cl_2$—[1,1'-Bis(diphenylphosphino)ferrocene]dichloropalladium(II) dichloromethane
$PdCl_2(PPH_3)_2$—Bis(triphenylphosphine)palladium(II) dichloride
$Pd(OAc)_2$—Palladium(II) acetate
$Pd(PPh_3)_4$—Palladium-tetrakis(triphenylphosphine)
PEG—polyethylene glycol
$Ph_3P$—triphenylphosphine
PivOH—pivalic acid
PPTS—Pyridinium p-toluenesulfonate
SFC—supercritical fluid chromatography
TAMRA—carboxytetramethylrhodamine
TBAF—tetrabutylammonium fluoride
TBS—tert-Butyldimethylsilyl
TBSCl—tert-Butyldimethylsilyl chloride
tBuOK—potassium tert-butoxide
TCEP—Tris(2-carboxyethyl)phosphine
TEA—triethylamine
TFA—trifluoroacetic acid
TFAA—trifluoroacetic anhydride
THF—tetrahydrofuran
TLC—thin layer chromatography
TMSCN—Trimethylsilyl cyanide
TMSI—trimethylsilyl iodide
TMSOTf—Trimethylsilyl trifluoromethanesulfonate
TsCl—4-toluenesulfonyl chloride
TsOH—toluenesulfonic acid
UV—ultraviolet LC/MS Methods Method A: Experiments performed on an SHIMADZU 2020 HPLC with SHIMADZU MSD mass spectrometer using ESI as ionization source using an Shim-Pack XR-ODS C18 50×3.0 mm 2.2 μm column and a 1.2 ml/minute flow rate. The solvent A is water with 0.05% TFA and solvent B is acetonitrile with 0.05% TFA, The gradient consisted with 20-80% solvent B over 3.6 minutes, 80-100% solvent B over 0.4 minutes and hold 100% B for 0.5 minutes. LC column temperature is 40° C. UV absorbance was collected from 190 nm to 400 nm.

Method B: Experiments performed on an SHIMADZU 2020 HPLC with SHIMADZU MSD mass spectrometer using ESI as ionization source using a Shim-pack XR-ODS C18 50×3.0 mm column and a 1.2 ml/minute flow rate. The solvent system was a gradient starting with 95% water with 0.05% TFA (solvent A) and 5% acetonitrile with 0.05% TFA (solvent B), ramping up to 100% solvent B over 1.1 minutes. The final solvent system was held constant for a further 0.6 minutes. LC column temperature is 40° C. UV absorbance was collected from 190 nm to 400 nm.

Method C: Experiments performed on an SHIMADZU 2020 HPLC with SHIMADZU MSD mass spectrometer using ESI as ionization source using an Ascentis Express C18 50×2.1 mm column and a 1.0 ml/minute flow rate. The solvent system was a gradient starting with 95% water with 0.05% TFA (solvent A) and 5% acetonitrile with 0.05% TFA (solvent B), ramping up to 100% solvent B over 1.1 minutes. The final solvent system was held constant for a further 0.5 minutes. LC column temperature is 40° C. UV absorbance was collected from 190 nm to 400 nm.

Method D: Experiments performed on an SHIMADZU 2020 HPLC with SHIMADZU MSD mass spectrometer using ESI as ionization source using a Shim-pack XR-ODS, 50×3.0 mm column and a 1.2 ml/minute flow rate. The solvent system was a gradient starting with 95% water with 0.05% TFA (solvent A) and 5% acetonitrile with 0.05% TFA (solvent B), ramping up to 95% solvent B over 2.0 minutes. The final solvent system was held constant for a further 0.7 minutes. LC column temperature is 40° C. UV absorbance was collected from 190 nm to 400 nm.

Method E: Experiments performed on an SHIMADZU 2020 HPLC with SHIMADZU MSD mass spectrometer using ESI as ionization source using a CORTECS C18 50×3.1 mm column and a 1.0 ml/minute flow rate. The solvent system was a gradient starting with 95% water with 0.05% TFA (solvent A) and 5% acetonitrile with 0.05% TFA (solvent B), ramping up to 100% solvent B over 1.1 minutes. The final solvent system was held constant for a further 0.5 minutes. LC column temperature is 45° C. UV absorbance was collected from 190 nm to 400 nm.

Method F: Experiments performed on a Shimadzu 2020 HPLC with Shimadzu MSD mass spectrometer using ESI as ionization source using a Poroshell HPH-C18 50×3.0 mm column and a 1.2 mL/minute flow rate. The solvent A is water with 0.05% $NH_4HCO_3$ and solvent B is acetonitrile. The gradient consisted with 10-50% solvent B over 3.5 minutes then 50-95% solvent B over 0.5 minutes and hold 95% B for 0.7 minutes. LC column temperature is 40° C. UV absorbance was collected from 190 nm to 400 nm.

Method G: Experiments performed on an SHIMADZU 2020 HPLC with SHIMADZU MSD mass spectrometer using ESI as ionization source using an XSELECT CSH C18 50×3.0 mm column and a 1.5 ml/minute flow rate. The solvent system was a gradient starting with 90% water with 0.1% FA (solvent A) and 10% acetonitrile with 0.1% FA (solvent B), ramping up to 100% solvent B over 1.1 minutes. The final solvent system was held constant for a further 0.6 minutes. LC column temperature is 40° C. UV absorbance was collected from 190 nm to 400 nm.

Method H: Experiments performed on an SHIMADZU 2020 HPLC with SHIMADZU MSD mass spectrometer using ESI as ionization source using an Accucore C18 50×2.1 mm column and a 1.0 ml/minute flow rate. The solvent system was a gradient starting with 90% water with 0.1% FA (solvent A) and 10% acetonitrile with 0.1% FA (solvent B), ramping up to 95% solvent B over 2 minutes. The final solvent system was held constant for a further 0.7 minutes. LC column temperature is 40° C. UV absorbance was collected from 190 nm to 400 nm.

Method I: Experiments performed on a Shimadzu LCMS-2020 coupled with SHIMADZU MSD mass spectrometer using ESI as ionization source. The LC separation was using a CAPCELL CORE C18, 50×2.1 mm column with a 1 ml/minute flow rate. Solvent A is water with 0.05% TFA and solvent B is acetonitrile with 0.05% TFA. The gradient consisted with 5-95% solvent B over 2.0 minutes and hold 95% B for 0.7 minutes. LC column temperature is 40° C. UV absorbance was collected from 190 nm to 400 nm.

Method J: Experiments performed on a Shimadzu LCMS-2020 coupled with SHIMADZU MSD mass spectrometer using ESI as ionization source. The LC separation was using a Shim-pack XR-ODS, 50×3.0 mm column with a 1.2 ml/minute flow rate. Solvent A is water with 0.05% TFA and solvent B is acetonitrile with 0.05% TFA. The gradient consisted with 5-70% solvent B over 3.7 minutes, 70-95% solvent B over 0.2 minutes and hold 95% B for 0.7 minutes. LC column temperature is 40° C. UV absorbance was collected from 190 nm to 400 nm.

Method K: Experiments performed on a Shimadzu LCMS-2020. The LC separation was using a Ascentis Express C18, 100×4.6 mm column with a 1.2 ml/minute flow rate. Solvent A is water with 0.05% TFA and solvent B is methanol. The gradient consisted with 30-95% solvent B over 10 minutes and hold 95% B for 2 minutes. LC column temperature is 40° C. UV absorbance was collected from 190 nm to 400 nm.

Method L: Experiments performed on a Shimadzu LCMS-2020 coupled with SHIMADZU MSD mass spectrometer using ESI as ionization source. The LC separation was using a Kinetex EVO C18, 50×2.1 mm column with a 1.0 ml/minute flow rate. Solvent A is water with 0.05% $NH_4HCO_3$ and solvent B is acetonitrile. The gradient consisted with 10-95% solvent B over 1.1 minutes, and hold 95% B for 0.5 minutes. LC column temperature is 35° C. UV absorbance was collected from 190 nm to 400 nm.

Method M: Experiments were performed on a HPLC column coupled with a mass spectrometer using ESI as an ionization source. The LC separation was using MK RP18e, 25×2 mm column with a 1.5 mL/minute flow rate. Solvent A was 1.5 mL TFA in 4 L water, and solvent B was 0.75 mL TFA in 4 L acetonitrile. The gradient consisted of 5-95% solvent B over 0.7 minutes, and holding at 95% for 0.4 minutes. LC column temperature was 50° C. UV absorbance was collected from 220 nm to 254 nm.

Method N: Experiments were performed on a HPLC column coupled with a mass spectrometer using ESI as an ionization source. The LC separation was using MK RP18e, 25×2 mm column with a 1.5 mL/minute flow rate. Solvent A was 1.5 mL TFA in 4 L water, and solvent B was 0.75 mL TFA in 4 L acetonitrile. The gradient consisted of 10-80% solvent B over 7 minutes, and holding at 95% for 0.4 minutes. LC column temperature was 50° C. UV absorbance was collected from 220 nm to 254 nm.

Method O: Experiments were performed on a HPLC column coupled with a mass spectrometer using ESI as an ionization source. The LC separation was using MK RP18e, 25×2 mm column with a 1.5 mL/minute flow rate. Solvent A was 1.5 mL TFA in 4 L water, and solvent B was 0.75 mL TFA in 4 L acetonitrile. The gradient consisted of 0-60% solvent B over 7 minutes, and holding at 95% for 0.4 minutes. LC column temperature was 50° C. UV absorbance was collected from 220 nm to 254 nm.

Method P: Experiments performed on SHIMADZU 2020 HPLC with SHIMADZU MSD mass spectrometer using ESI as ionization source using Shim-Pack XR-ODS C18 50×3.0 mm 2.2 μm column and a 1.2 ml/minute flow rate. The solvent A is water with 0.05% TFA and solvent B is acetonitrile with 0.05% TFA. The gradient consisted with 5-95% solvent B over 2.0 minutes, hold 95% B for 0.7 minutes. LC column temperature is 40° C. UV absorbance was collected from 190 nm to 400 nm.

Method Q: Experiments performed on SHIMADZU 2020 HPLC with SHIMADZU MSD mass spectrometer using ESI as ionization source using Shim-Pack XR-ODS C18 50×3.0 mm 2.2 μm column and a 1.2 ml/minute flow rate. The solvent A is water with 0.05% TFA and solvent B is acetonitrile with 0.05% TFA. The gradient consisted with 5-60% solvent B over 3.2 minutes, 60-100% solvent B over 0.5 minutes, hold 100% B for 0.8 minutes. LC column temperature is 40° C. UV absorbance was collected from 190 nm to 400 nm.

Method R: Experiments performed on SHIMADZU 2020 HPLC with SHIMADZU MSD mass spectrometer using ESI as ionization source using Shim-Pack XR-ODS C18 50×3.0 mm 2.2 μm column and a 1.2 ml/minute flow rate. The solvent A is water with 0.05% TFA and solvent B is acetonitrile with 0.05% TFA. The gradient consisted with 20-60% solvent B over 3.6 minutes, 60-100% solvent B over 0.4 minutes, hold 100% B for 0.5 minutes. LC column temperature is 40° C. UV absorbance was collected from 190 nm to 400 nm.

Method S: Experiments performed on Shimadzu LCMS-2020. The LC separation was using Ascentis Express C18, 100×4.6 mm column with a 1.5 ml/minute flow rate. Solvent A is water with 0.05% TFA and solvent B is ACN/0.05% TFA. The gradient consisted with 5% B hold 0.8 min, 5-40% solvent B over 7.2 minutes, 40-95% solvent B over 2.0 minutes and hold 95% B for 2.0 minutes. LC column temperature is 60° C. UV absorbance was collected from 190 nm to 400 nm.

Method T: Experiments performed on Shimadzu LCMS-2020. The LC separation was using Ascentis Express C18, 100×4.6 mm column with a 1.5 ml/minute flow rate. Solvent A is water with 0.05% TFA and solvent B is ACN/0.05% TFA. The gradient consisted with 10-60% solvent B over 10 minutes, 60-95% solvent B over 1.0 minutes and hold 95% B for 2.0 minutes. LC column temperature is 60° C. UV absorbance was collected from 190 nm to 400 nm.

Method U: Experiments performed on Shimadzu LCMS-2020. The LC separation was using Ascentis Express C18, 100×4.6 mm column with a 1.0 ml/minute flow rate. Solvent A is water with 0.05% TFA and solvent B is ACN/0.05% TFA. The gradient consisted with 10-60% solvent B over 10 minutes, 60-95% solvent B over 2.0 minutes and hold 95% B for 2.0 minutes. LC column temperature is 60° C. UV absorbance was collected from 190 nm to 400 nm.

Method V. Experiments performed on Shimadzu LCMS-2020. The LC separation was using Ascentis Express C18, 100×4.6 mm column with a 1.0 ml/minute flow rate. Solvent A is water with 0.05% TFA and solvent B is ACN/0.05% TFA. The gradient consisted with 5-95% solvent B over 8 minutes, hold 95% B for 2.0 minutes. LC column temperature is 60° C. UV absorbance was collected from 190 nm to 400 nm.

Method W: Experiments performed on Shimadzu 2020 HPLC with Shimadzu MSD mass spectrometer using ESI as ionization source using Poroshell HPH-C18 50×3.0 mm column and a 1.2 mL/minute flow rate. The solvent A is water with 0.05% $NH_4HCO_3$ and solvent B is acetonitrile. The gradient consisted with 10-95% solvent B over 2.0 minutes and hold 95% B for 0.7 minutes. LC column temperature is 40° C. UV absorbance was collected from 190 nm to 400 nm.

Method X: Experiments performed on Shimadzu 2020 HPLC with Shimadzu MSD mass spectrometer using ESI as ionization source using Poroshell HPH-C18 50×3.0 mm column and a 1.2 mL/minute flow rate. The solvent A is water with 0.05% $NH_4HCO_3$ and solvent B is acetonitrile. The gradient consisted with 10-70% solvent B over 3.5 minutes, 70-95% solvent B over 0.5 minutes and hold 95% B for 0.7 minutes. LC column temperature is 40° C. UV absorbance was collected from 190 nm to 400 nm.

Method Y: Experiments performed on Shimadzu 2020 HPLC with Shimadzu MSD mass spectrometer using ESI as ionization source using Poroshell HPH-C18 50×3.0 mm column and a 1.2 mL/minute flow rate. The solvent A is water with 0.05% $NH_4HCO_3$ and solvent B is acetonitrile. The gradient consisted with 30-70% solvent B over 4.0 minutes, 70-95% solvent B over 0.5 minutes and hold 95% B for 0.3 minutes. LC column temperature is 40° C. UV absorbance was collected from 190 nm to 400 nm.

Method Z: Experiments performed on Shimadzu 2020 HPLC with Shimadzu MSD mass spectrometer using ESI as ionization source using Poroshell HPH-C18 50×3.0 mm column and a 1.2 mL/minute flow rate. The solvent A is water with 0.05% $NH_4HCO_3$ and solvent B is acetonitrile. The gradient consisted with 30-95% solvent B over 4.0 minutes and hold 95% B for 0.7 minutes. LC column temperature is 40° C. UV absorbance was collected from 190 nm to 400 nm.

Method AA: Experiments performed on SHIMADZU 2020 HPLC with SHIMADZU MSD mass spectrometer using ESI as ionization source using Accucore C18 50×2.1 mm column and a 1.0 ml/minute flow rate. The solvent A is water with 0.1% FA and solvent B is acetonitrile with 0.1% FA. The gradient consisted with 10-95% solvent B over 3.0 minutes and hold 95% B for 0.7 minutes. LC column temperature is 40° C. UV absorbance was collected from 190 nm to 400 nm.

Method BB: Experiments performed on SHIMADZU 2020 HPLC with SHIMADZU MSD mass spectrometer using ESI as ionization source using Accucore C18 50×2.1 mm column and a 1.0 ml/minute flow rate. The solvent A is water with 0.1% FA and solvent B is acetonitrile with 0.1% FA. The gradient consisted with 10-50% solvent B over 3.5, 50-95% solvent B over 0.5 minutes and hold 95% B for 0.7 minutes. LC column temperature is 40° C. UV absorbance was collected from 190 nm to 400 nm.

Method CC: Experiments performed on Shimadzu LCMS-2020 coupled with SHIMADZU MSD mass spectrometer using ESI as ionization source. The LC separation was using Shim-pack XR-ODS, 50×3.0 mm column with a 1.2 ml/minute flow rate. Solvent A is water with 0.05% TFA and solvent B is acetonitrile with 0.05% TFA. The gradient consisted with 5-50% solvent B over 3.5 minutes, 50-100% solvent B over 0.2 minutes and hold 100% B for 1.0 minutes. LC column temperature is 40° C. UV absorbance was collected from 190 nm to 400 nm.

Method DD: Experiments performed on Shimadzu LCMS-2020 coupled with SHIMADZU MSD mass spectrometer using ESI as ionization source. The LC separation was using Shim-pack XR-ODS, 50×3.0 mm column with a 1.2 ml/minute flow rate. Solvent A is water with 0.05% TFA and solvent B is acetonitrile with 0.05% TFA. The gradient consisted with 5-95% solvent B over 2.0 minutes and hold 95% B for 0.7 minutes. LC column temperature is 40° C. UV absorbance was collected from 190 nm to 400 nm.

Method EE: Experiments performed on SHIMADZU 2020 HPLC with SHIMADZU MSD mass spectrometer using ESI as ionization source using Ascentis Express C18

50×2.1 mm column and a 1.2 ml/minute flow rate. Solvent A is water with 0.05% TFA and solvent B is MeOH. The gradient consisted with 30-85% solvent B over 10 minutes and hold 80% B for 3.2 minutes. LC column temperature is 40° C. UV absorbance was collected from 190 nm to 400 nm.

Method FF: Experiments performed on MK RP18e 25-2 mm column with mass spectrometer using ESI as ionization source. Solvent A was 1.5 mL/4 L of TFA in water and solvent B was 0.75 mL/4 L of TFA in acetonitrile. The gradient consisted of 5-95% solvent B over 0.7 minutes, and holding at 95% for 0.4 minutes at a flow rate of 1.5 mL/min. LC column temperature was 50° C. UV absorbance was collected at 220 nm and 254 nm.

Method GG: Experiments performed on Xtimate C18 2.1*30 mm, 3 μm column, with mass spectrometer using ESI as ionization source. Solvent A was 1.5 mL/4 L of TFA in water, and solvent B was 0.75 mL/4 L of TFA in acetonitrile. The gradient consisted of 10-80% solvent B over 6 minutes, holding at 80% for 0.5 minutes at a flow rate of 0.8 mL/min. LC column temperature was 50° C. UV absorbance was collected at 220 nm and 254 nm.

SFC Methods

Method 1: Column: Chiralpak AD-3 150×4.6 mm I.D., 3 um; Mobile phase: A: $CO_2$; B: ethanol (0.05% DEA); Gradient: from 5% to 40% of B in 5 minutes and from 40% to 5% of B in 0.5 minutes hold 5% of B for 1.5 minutes; Flow rate: 2.5 mL/minute; Column temperature: 35° C.; ABPR: 1500 psi.

Method 2: Column: Chiralcel OD-3 100×4.6 mm I.D., 3 um; Mobile phase: A: $CO_2$; B: ethanol (0.05% DEA); Gradient: from 5% to 40% of B in 4.5 minutes and hold 40% for 2.5 minutes, then 5% of B for 1 minute; Flow rate: 2.8 mL/minute; Column temperature: 40° C.

Method 3: Column: Chiralcel OJ-3 100×4.6 mm I.D., 3 um; Mobile phase: A: $CO_2$; B: methanol (0.05% DEA); Gradient: from 5% to 40% of B in 4.5 minutes and hold 40% for 0.5 minutes, then 5% of B for 1 minute; Flow rate: 2.8 mL/minute; Column temperature: 40° C.

Method 4: Column: ChiralCel OJ-H 150×4.6 mm I.D., 5 um; Mobile phase: A: $CO_2$; B: ethanol (0.05% DEA); Gradient: from 5% to 40% of B in 5.5 minutes, then 5% of B for 1.5 minutes; Flow rate: 2.5 mL/minute; Column temperature: 40° C.

Method 5: Column: Chiralcel OJ-H 150*4.6 mm I.D., 5 um; Mobile phase: A: $CO_2$; B: ethanol (0.05% DEA); Gradient: hold 5% for 0.5 minutes, then from 5% to 40% of B in 3.5 minutes and hold 40% for 2.5 minutes, then 5% of B for 1.5 minutes; Flow rate: 3 mL/minute; Column temperature: 40° C.

Method 6: Column: Chiralpak AD-3 150×4.6 mm I.D., 3 um; Mobile phase: A: $CO_2$; B: iso-propanol (0.05% DEA); Gradient: from 5% to 40% of B in 5 minutes and hold 40% for 2.5 minutes, then 5% of B for 2.5 minutes; Flow rate: 2.5 mL/minute; Column temperature: 35° C.; ABPR: 1500 psi.

Method 7: Column: Chiralcel OJ-3 100×4.6 mm I.D., 3 um; Mobile phase: A: $CO_2$; B: ethanol (0.05% DEA); Gradient: from 5% to 40% of B in 4.5 minutes and hold 40% for 2.5 minutes, then 5% of B for 1 minute; Flow rate: 2.8 mL/minute; Column temperature: 40° C.

Examples 1 and 2

Ethyl 2-amino-2-(4-bromophenyl)propanoate (2 Single Isomers)

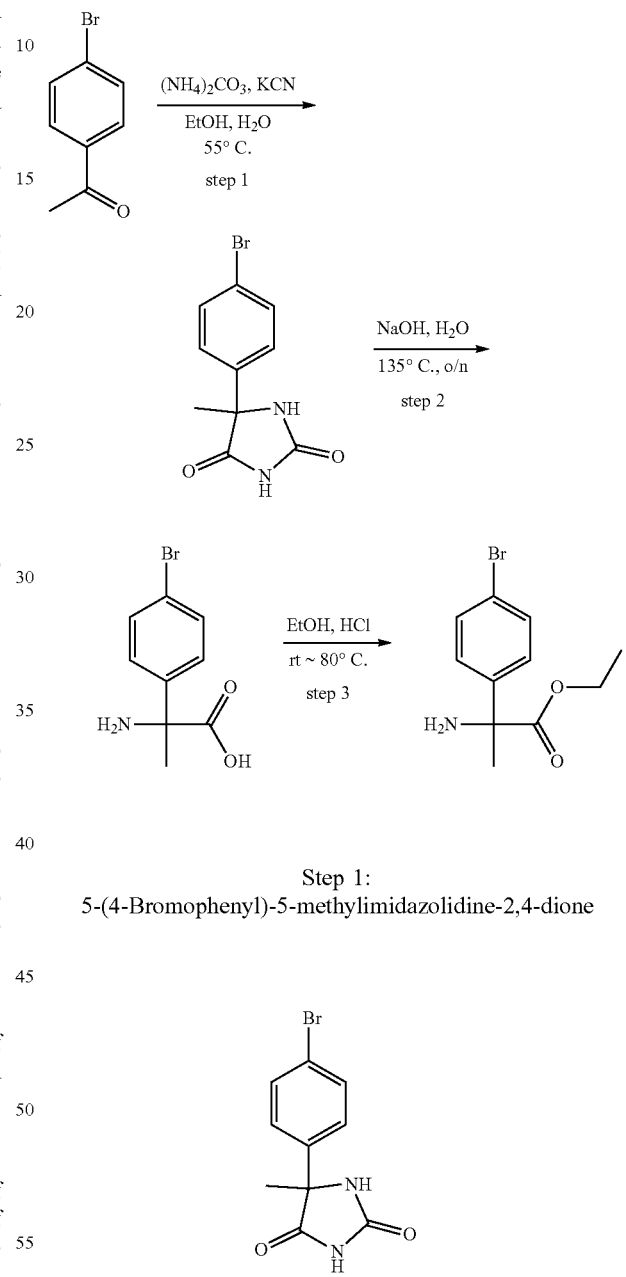

Step 1:
5-(4-Bromophenyl)-5-methylimidazolidine-2,4-dione

A solution of 1-(4-bromophenyl)ethan-1-one (40.0 g, 200 mmol), $(NH_4)_2CO_3$ (100.0 g, 1.04 mol) and KCN (17.0 g, 262 mmol) in EtOH (400 mL) and $H_2O$ (400 mL) was stirred at 55° C. for 6 hours. The reaction mixture was cooled to room temperature and filtered. The solid was collected and washed with water, dried in vacuo to yield 46.0 g (85%) of the title compound as a light yellow solid. $^1$H NMR (300 MHz, DMSO-$d_6$) δ 10.84 (s, 1H), 8.65 (s, 1H), 7.81-7.54 (m, 2H), 7.50-7.28 (m, 2H), 1.64 (s, 3H).

Step 2: 2-Amino-2-(4-bromophenyl)propanoic acid

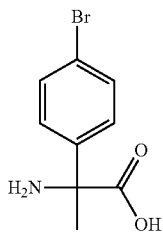

A solution of 5-(4-bromophenyl)-5-methylimidazolidine-2,4-dione (40.0 g, 148 mmol) and NaOH (24.0 g, 600 mmol) in H$_2$O (500 mL) was heated at reflux with stirring for 16 hours. The reaction mixture was cooled to 0° C. 2 N HCl aqueous solution was added to the cold solution until pH~6. The solid was collected and washed with water, dried in vacuo to yield 28.0 g (77%) of the title compound as a white solid. LCMS (ESI):R$_T$ (min)=0.848, [M+H]$^+$=244/246, method=B.

Step 3: Ethyl (S) 2-amino-2-(4-bromophenyl)propanoate and Ethyl (R) 2-amino-2-(4-bromophenyl) propanoate (Two Single Isomers)

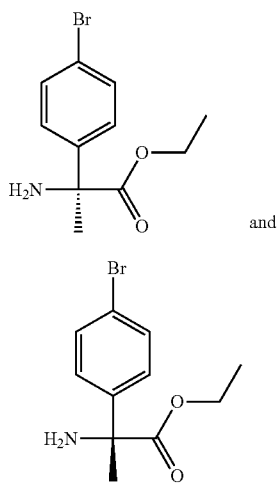

Intermediate 1 and

Intermediate 2

HCl (gas) was bubbled through the solution of 2-amino-2-(4-bromophenyl) propanoic acid (28.0 g, 115 mmol) in EtOH (500 mL) at room temperature for 6 hours. The reaction mixture was stirred at 80° C. for 16 hours. The mixture was concentrated under reduced pressure. The residue was purified by flash chromatography on silica gel (gradient: 0%-20% EtOH/DCM) to afford 20 g (64%) of the title compound (mixture of enantiomer) as a light yellow oil. The enantiomers were separated by prep-SFC (Column: EnantioPak-A1-5(02), 5*25 cm, 5 um; Mobile Phase A: CO$_2$: 80, Mobile Phase B: MeOH (0.2% DEA): 20; Flow rate: 150 mL/min; 220 nm; RT1: 6.01; RT2: 7.58). Two single unknown stereoisomers were obtained: Intermediate 1 (the faster peak):7.85 g and Intermediate 2 (the slower peak): 7.95 g. LCMS (ESI): R$_T$ (min)=0.622, [M+H]$^+$=272/274, method=C. The structures for the two isomers (Intermediates 1 and 2) set forth above are assumed, but were not definitively determined.

Example 3 tert-Butyl (4R)-2-(5-(4-bromophenyl)-5-methyl-4-oxo-4,5-dihydro-1H-imidazol-2-yl)-4-hydroxypyrrolidine-1-carboxylate (Intermediate 3)

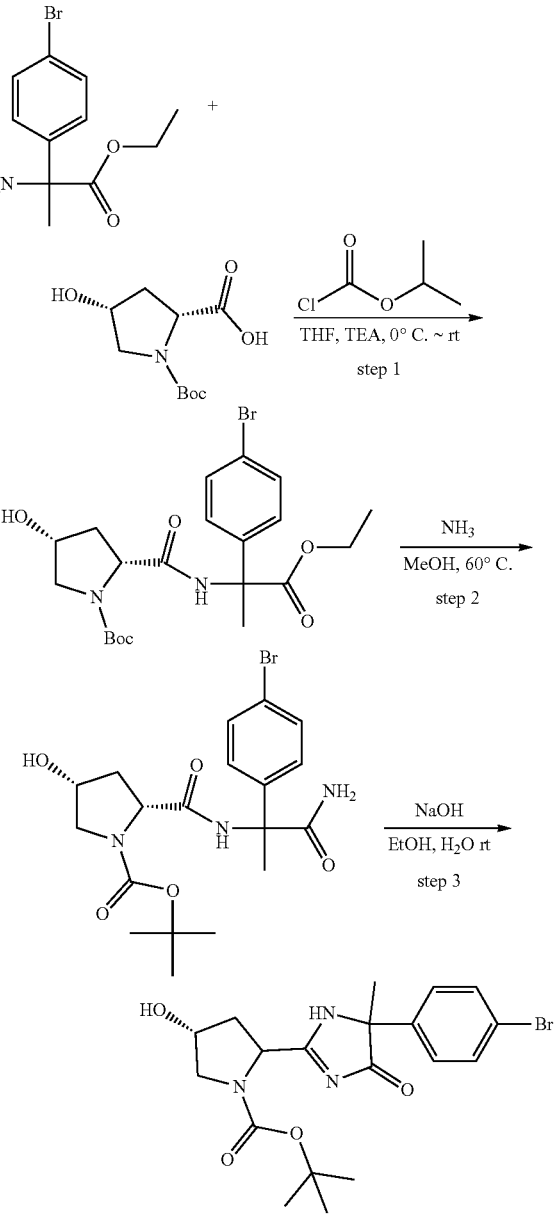

Step 1: tert-Butyl (2R, 4R)-2-((2-(4-bromophenyl)-1-ethoxy-1-oxopropan-2-yl) carbamoyl)-4-hydroxypyrrolidine-1-carboxylate To a solution of (2R,4R)-1-(tert-butoxycarbonyl)-4-hydroxypyrrolidine-2-carboxylic acid (8.94 g, 38.7 mmol) in THF (200 mL) was added triethylamine (7.78 g, 76.8 mmol)

and isopropyl carbonochloridate (7.85 g, 64.1 mmol) at 0° C. The resulting solution was stirred at 0° C. for 0.5 hours. Then Intermediate 2 (ethyl 2-amino-2-(4-bromophenyl) propanoate, the slower peak on chiral SFC) (7.01 g, 25.7 mmol) was added. The reaction mixture was stirred at room temperature for 3 hours. The mixture was diluted with water, extracted with DCM. The combined organic layers were dried over anhydrous Na$_2$SO$_4$ and concentrated under reduced pressure. The residue was purified by flash chromatography on silica gel (gradient: 0%-20% MeOH/DCM) to yield 8.56 g (69%) of the title compound as a white solid. LCMS (ESI): R$_T$ (min)=1.17, [M+H]$^+$=485/487, method=F.

Step 2: tert-Butyl (2R,4R)-2-((1-amino-2-(4-bromophenyl)-1-oxopropan-2-yl)carbamoyl)-4-hydroxypyrrolidine-1-carboxylate

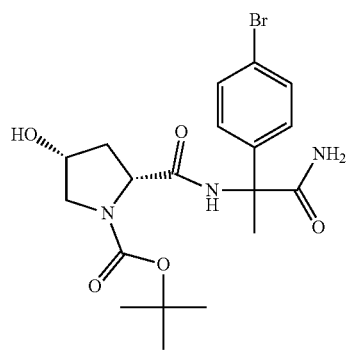 [SMILES: CC(C)(C)OC(=O)N1C[C@H](O)C[C@@H]1C(=O)NC(C)(C(N)=O)c1ccc(Br)cc1]

A solution of tert-butyl (2R, 4R)-2-((2-(4-bromophenyl)-1-ethoxy-1-oxopropan-2-yl)carbamoyl)-4-hydroxypyrrolidine-1-carboxylate (8.56 g, 17.6 mmol) in ammonia methanol solution (800 mL, 7M solution in MeOH) was stirred at 80° C. for 48 hours. The reaction mixture was concentrated under reduced pressure to yield 7.01 g (87%) the title compound as a light yellow solid. LCMS (ESI): R$_T$ (min)=1.11, [M+H]$^+$=456/458, method=J.

Step 3: tert-Butyl (4R)-2-(5-(4-bromophenyl)-5-methyl-4-oxo-4,5-dihydro-1H-imidazol-2-yl)-4-hydroxypyrrolidine-1-carboxylate

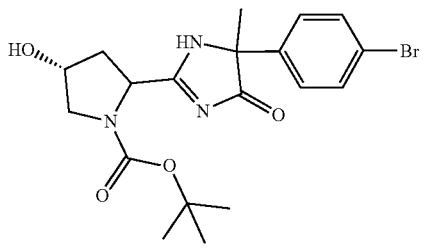 [SMILES: CC(C)(C)OC(=O)N1C[C@H](O)CC1C1=NC(=O)C(C)(c2ccc(Br)cc2)N1]

A solution of tert-butyl (2R,4R)-2-((1-amino-2-(4-bromophenyl)-1-oxopropan-2-yl)carbamoyl)-4-hydroxypyrrolidine-1-carboxylate (7.01 g, 15.4 mmol) and NaOH (1.84 g, 46.0 mmol) in EtOH (50 mL) and H$_2$O (50 mL) was stirred at 50° C. for 6 hours. The reaction mixture was extracted with DCM, the combined organic layers were dried over anhydrous Na$_2$SO$_4$ and concentrated under reduced pressure. The residue was purified by flash chromatography on silica gel (gradient: 0%-10% MeOH/DCM) to yield 5.90 g (87%) of the title compound as a white solid. LCMS (ESI): R$_T$ (min)=1.041, [M+H]$^+$=438/440, method=F.

Example 4 tert-Butyl (4R)-2-(5-(4-bromophenyl)-5-methyl-4-oxo-4,5-dihydro-1H-imidazol-2-yl)-4-hydroxypyrrolidine-1-carboxylate (Intermediate 4)

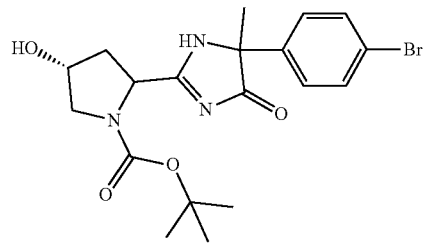 [SMILES: CC(C)(C)OC(=O)N1C[C@H](O)CC1C1=NC(=O)C(C)(c2ccc(Br)cc2)N1]

Analogous to the preparation of Intermediate 3, Intermediate 4 was prepared from Intermediate 1 (ethyl 2-amino-2-(4-bromophenyl) propanoate, the faster peak on chiral SFC).

Example 5

3-Methyl-2-(3-methylisoxazol-5-yl) butanoic acid (Intermediate 5)

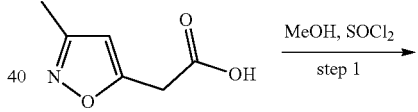

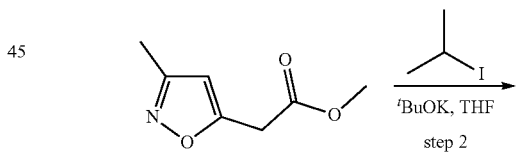

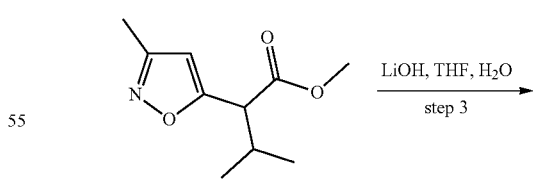

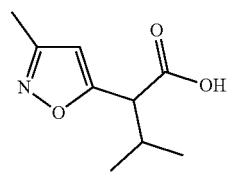

Step 1: Methyl 2-(3-methylisoxazol-5-yl) acetate

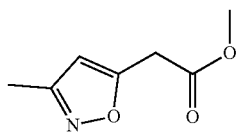

To a stirred solution of (3-methyl-5-isoxazolyl)acetic acid (5.64 g, 40.0 mmol) in methanol (30 mL) was added thionyl chloride (5.71 g, 48 mmol) dropwise at 0° C. The resulting solution was stirred at 0° C. for 3 hours. Then the solvent was removed under reduced pressure. The residue was purified by flash chromatography on silica gel (gradient: 0%-20% ethyl acetate/petroleum ether) to yield 5.6 g (90.2%) of the title compound as a colorless oil. LCMS (ESI): $R_T$ (min)=0.46. [M+H]$^+$=156, method=H.

Step 2: Methyl 3-methyl-2-(3-methylisoxazol-5-yl)butanoate

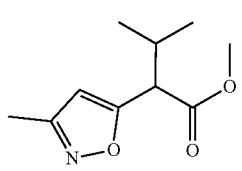

To a stirred solution of methyl 2-(3-methylisoxazol-5-yl)acetate (5.60 g, 36.0 mmol) and tBuOK (8.20 g, 73.1 mmol) in THF (100 mL) was added 2-iodopropane (8.59 g, 50.5 mmol) dropwise at 0° C. The resulting solution was stirred for 16 hours at 25° C. and then quenched with water/ice (400 mL). The mixture was extracted with ethyl acetate. The combine organic layers were washed with brine, dried over anhydrous sodium sulfate and concentrated reduced procedure. The residue was purified by flash chromatography on silica gel (gradient: 0%-20% ethyl acetate/petroleum ether) to yield 5.7 g (80.1%) of the title compound as yellow oil. LCMS (ESI): $R_T$ (min)=1.28. [M+H]$^+$=198, method=A.

Step 3: 3-Methyl-2-(3-methylisoxazol-5-yl)butanoic acid (Intermediate 5)

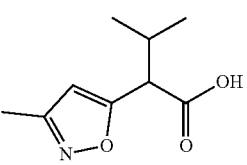

To a stirred solution of methyl 3-methyl-2-(3-methylisoxazol-5-yl)butanoate (5.7 g, 28.9 mmol) in THF (20 mL) and water (20 mL) was added LiOH.H$_2$O (3.64 g, 86.7 mmol) at 0° C. The resulting solution was stirred at 0° C. for 5 hours and then neutralized by addition of 1 N HCl aqueous solution until pH~7. The resulting solution was concentrated under reduced pressure to dryness. The residue was purified by reverse phase flash chromatography (gradient: 5%-40%/ ACN in water (0.1% formic acid)) to yield 5.1 g (96.3%) of the title compound as a white solid. LCMS (ESI): $R_T$ (min)=0.90. [M+H]$^+$=184, method=G. $^1$H NMR (300 MHz, DMSO-d$_6$) δ 12.89 (br, 1H), 6.25 (s, 1H), 3.56 (d, J=8.7 Hz, 1H), 2.35-2.22 (m, 1H), 2.20 (s, 3H), 0.95 (d, J=6.7 Hz, 3H), 0.81 (d, J=6.7 Hz, 3H).

Example 6

2-(3-Methoxyisoxazol-5-yl)-3-methylbutanoic acid (Intermediate 6)

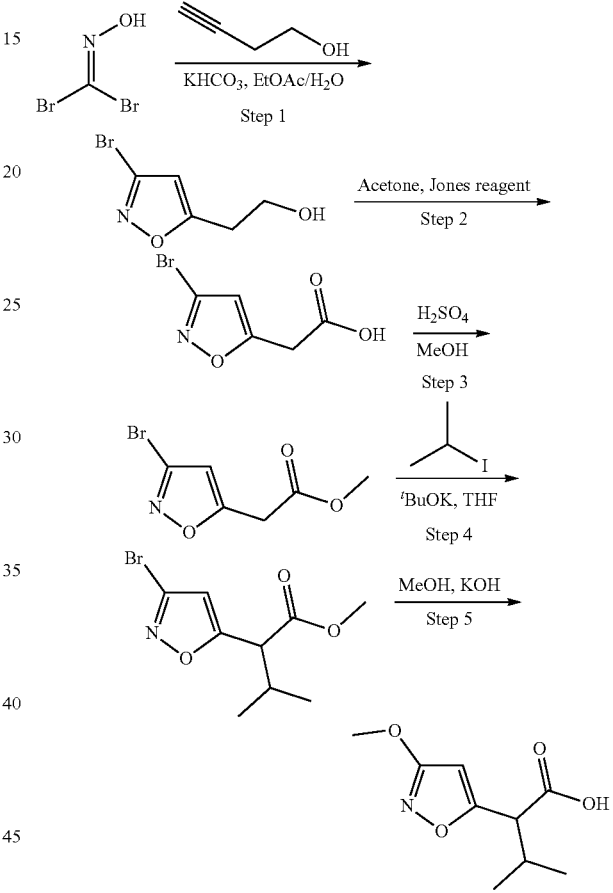

Step 1: 2-(3-Bromoisoxazol-5-yl) ethanol

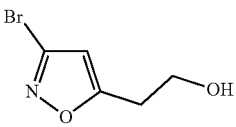

To a stirred solution of but-3-yn-1-ol (28.0 g, 399 mmol) and potassium bicarbonate (30.0 g, 300 mmol) in ethyl acetate/water (200/20 mL) was added a solution of hydroxycarbonimidic dibromide (20.0 g, 98.6 mmol) in ethyl acetate (50 mL) dropwise at room temperature. The resulting solution was stirred at room temperature for 16 hours and then diluted with water. The organic layer was separated, and the aqueous layer was extracted with ethyl acetate. The combined organic layers were washed with brine (150 mL), dried over anhydrous sodium sulfate and concentrated under reduced pressure. The residue was purified by flash chromatography on silica gel column (gradient: 0%-25% ethyl acetate/petroleum ether) to yield 18.5 g (97.7%) of the title compound as a yellow oil. LCMS (ESI): $R_T$ (min)=0.540, [M+H]$^+$=192/194, method=E. $^1$H NMR (400 MHz, DMSO-d$_6$) δ 6.61 (s, 1H), 4.91 (t, J=5.3 Hz, 1H), 3.75-3.65 (m, 2H), 2.95-2.85 (m, 2H).

Step 2: 2-(3-Bromoisoxazol-5-yl) acetic acid

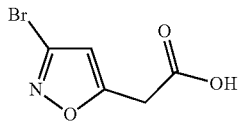

To a stirred solution of 2-(3-bromoisoxazol-5-yl) ethanol (18.5 g, 96.3 mmol) in acetone (220 mL) was added Jones reagent (90 mL) dropwise at 0° C. The resulting solution was stirred at 25° C. for 12 hours. The mixture was diluted with water, extracted with ethyl acetate. The combined organic layers were washed with brine, dried over anhydrous sodium sulfate and concentrated under reduced pressure to yield 17.9 g (90.2%) of the title compound as yellow oil. LCMS (ESI): $R_T$ (min)=0.970, [M+H]$^+$=206/208, method=A.

Step 3: Methyl 2-(3-bromoisoxazol-5-yl) acetate

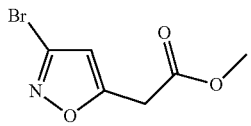

A solution of 2-(3-bromoisoxazol-5-yl) acetic acid (17.9 g, 86.9 mmol) and concentrated H$_2$SO$_4$ (1.5 mL, 28.1 mmol) in methanol (150 mL) was stirred at 70° C. for 2 hours. The resulting solution was concentrated under reduced pressure. The residue was diluted with water, extracted with ethyl acetate. The combined organic layers were washed with brine, dried over anhydrous sodium sulfate and concentrated under reduced pressure. The residue was purified by flash chromatography on silica gel column (gradient: 0%-25% ethyl acetate/petroleum ether) to yield 12.4 g (64.9%) of the title compound as a yellow oil. LCMS (ESI): $R_T$ (min)=1.13, [M+H]$^+$=220/222, method=A. $^1$H NMR (400 MHz, DMSO-d$_6$) δ 6.75 (s, 1H), 4.11 (s, 2H), 3.67 (s, 3H).

Step 4: Methyl 2-(3-bromoisoxazol-5-yl)-3-methylbutanoate

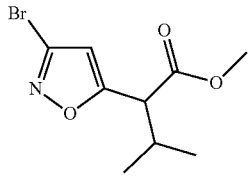

To a stirred solution of methyl 2-(3-bromoisoxazol-5-yl) acetate (12.4 g, 56.3 mmol) and $^t$BuOK (9.17 g, 81.7 mmol) in THF (120 mL) was added 2-iodopropane (12.2 g, 71.7 mmol) dropwise at 0° C. The resulting solution was stirred at room temperature for 16 hours and then quenched with water/ice. The organic layer was separated, and the aqueous was extracted with ethyl acetate. The combined organic layers were washed with brine, dried over anhydrous sodium sulfate and concentrated under reduced pressure. The residue was purified by flash chromatography on silica gel (gradient: 0%-20% ethyl acetate/petroleum ether) to yield 8.2 g (55.5%) of the title compound as yellow oil. LCMS (ESI): $R_T$ (min)=1.34, [M+H]$^+$=262/264, method=A. $^1$H NMR (400 MHz, DMSO-d$_6$) δ 6.83 (s, 1H), 3.93 (d, J=8.3 Hz, 1H), 3.67 (s, 3H), 2.40-2.30 (m, 1H), 0.93 (d, J=6.7 Hz, 3H), 0.85 (d, J=6.7 Hz, 3H).

Step 5: 2-(3-Methoxyisoxazol-5-yl)-3-methylbutanoic acid (Intermediate 6)

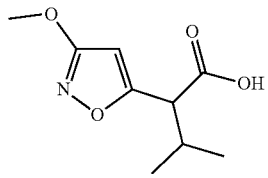

To a stirred solution of methyl 2-(3-bromoisoxazol-5-yl)-3-methylbutanoate (3.0 g, 11.4 mmol) in methanol (22 mL) was added KOH (6.6 g, 115 mmol) at room temperature. The resulting solution was stirred at 100° C. for 4 hours, and allowed to cool to room temperature. The resulting solution was acidified to pH~5 with 1 N HCl aqueous solution and concentrated under reduced pressure. The residue was purified by reverse phase chromatography (gradient: 5%-40% ACN in water (0.1% formic acid)) to yield 1.51 g (66.2%) of the title compound as a colorless thick oil. LCMS (ESI): $R_T$ (min)=1.11, [M+H]$^+$=200, method=A. $^1$H NMR (400 MHz, DMSO-d$_6$) δ 13.03 (br, 1H), 6.13 (s, 1H), 3.87 (s, 3H), 3.48 (d, J=8.7 Hz, 1H), 2.32-2.19 (m, 1H), 0.95 (d, J=6.7 Hz, 3H), 0.83 (d, J=6.7 Hz, 3H).

Example 7

2-(3-Hydroxyisoxazol-5-yl)-3-methylbutanoic acid (Intermediate 7)

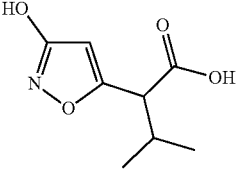

A solution of 2-(3-methoxyisoxazol-5-yl)-3-methylbutanoic acid (Intermediate 6, 500 mg, 2.51 mmol) in HOAc (5 mL) and HBr acid (5 mL, 40% aqueous) was stirred at 60° C. for 16 hours. The solvent was concentrated under reduced pressure. The residue was purified by reverse phase chromatography (gradient: 5%-40% ACN in water (0.1% formic acid)) to yield 348 mg (74.9%) of the title compound as yellow solid. LCMS (ESI): $R_T$ (min)=0.980, $[M+H]^+$=186, method=D.

Example 8

Methyl 2-(3-hydroxyisoxazol-5-yl)-3-methylbutanoate (Intermediate 8)

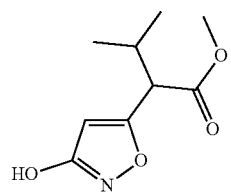

A solution of 2-(3-hydroxyisoxazol-5-yl)-3-methylbutanoic acid (900 mg, 4.86 mmol,) and $SOCl_2$ (1.5 mL, 21.9 mmol) in methanol (3 mL) was stirred at room temperature for 3 hours. The solvent was concentrated under reduced pressure. The residue was dilute with water and extracted with ethyl acetate. The combined organic layers were washed with brine, dried over anhydrous sodium sulfate and concentrated under reduced pressure. The residue was purified by flash chromatography on silica gel (gradient: 0-10% MeOH in DCM) to yield 810 mg (83.7%) of the title compound as a yellow oil. LCMS (ESI): $R_T$ (min)=0.779. $[M+H]^+$=200, method=I.

Example 9

7-(3,5-Difluoropyridin-2-yl)-2-methyl-10-((methylsulfonyl)methyl)-3-oxo-3,4,6,7-tetrahydro-2H-2,4,7-triazadibenzo[cd,f]azulene-9-carboxylic acid (Intermediate 9)

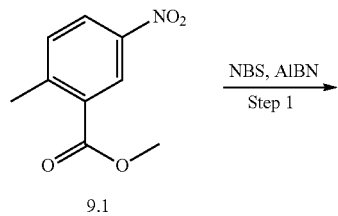

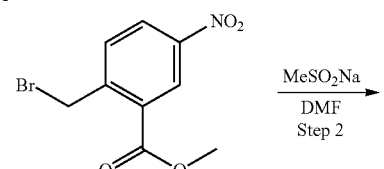

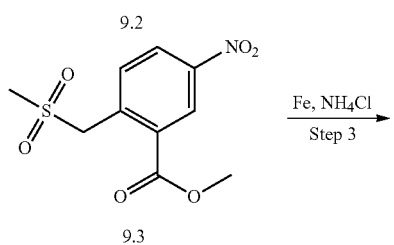

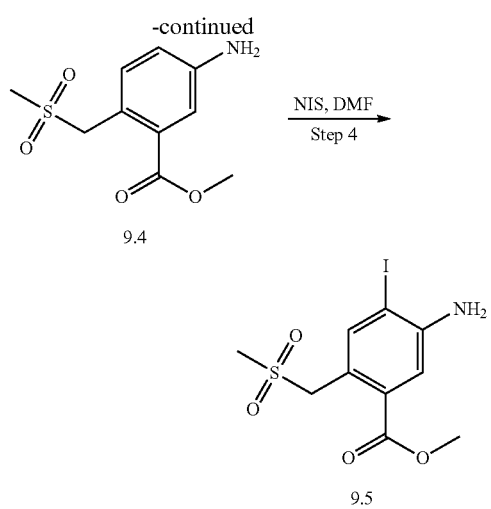

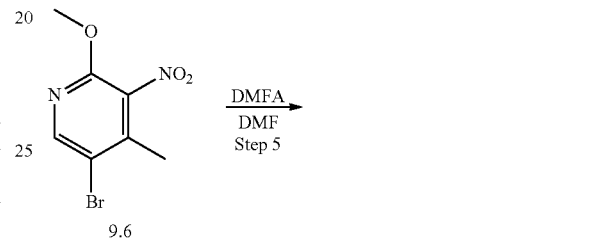

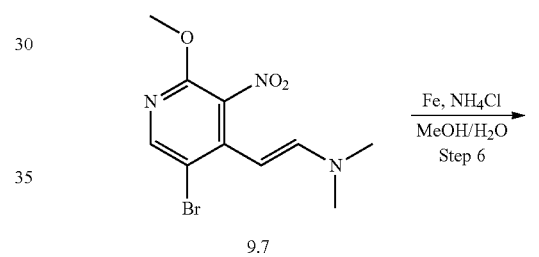

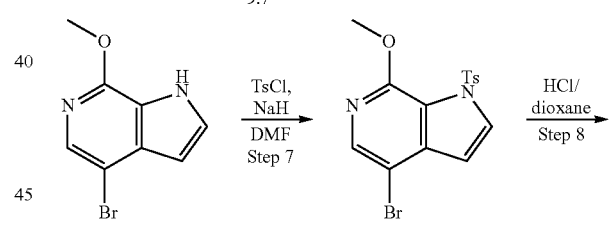

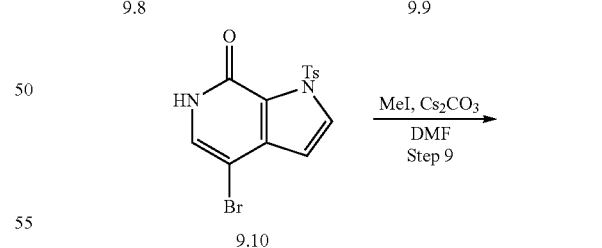

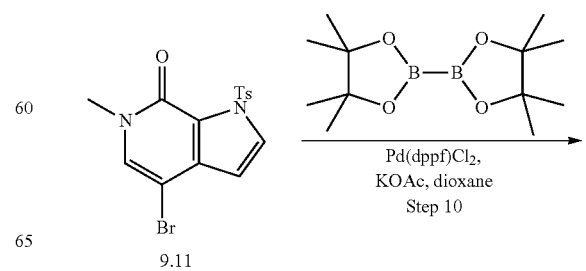

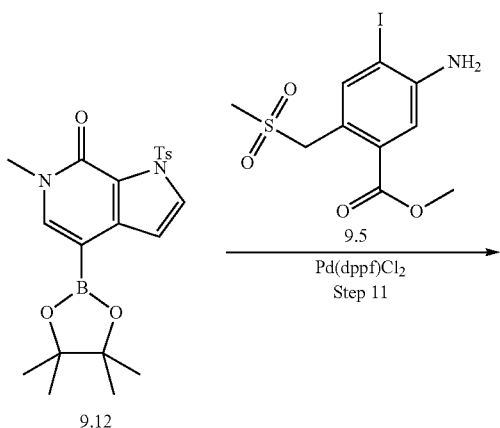

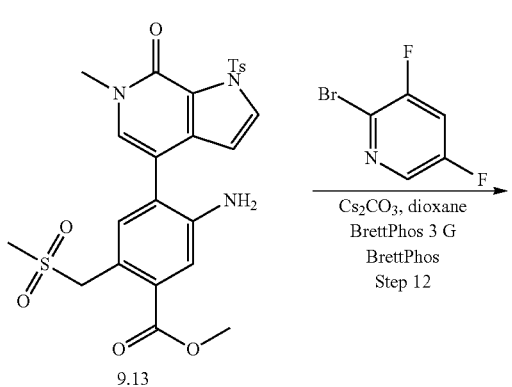

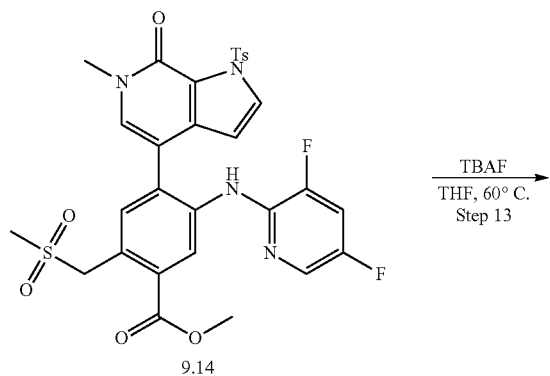

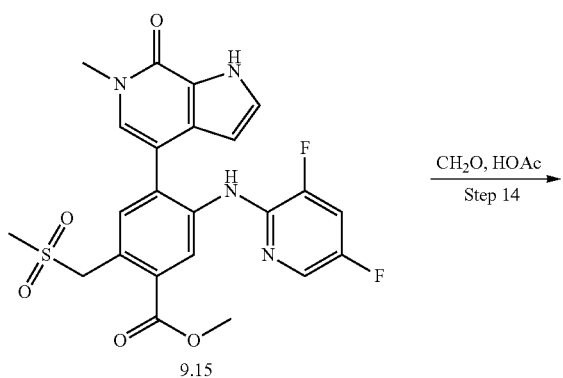

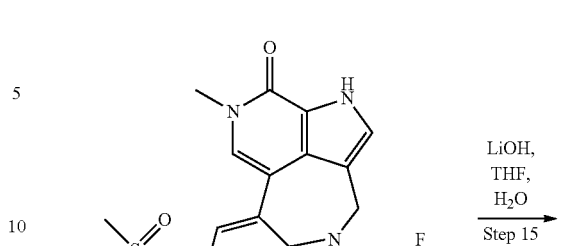

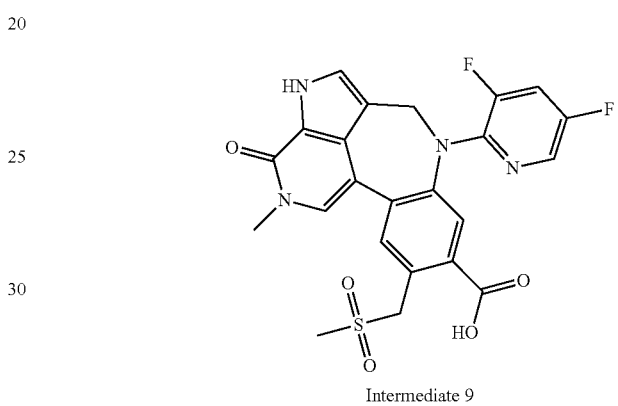

Step 1: methyl 2-(bromomethyl)-5-nitro-benzoate

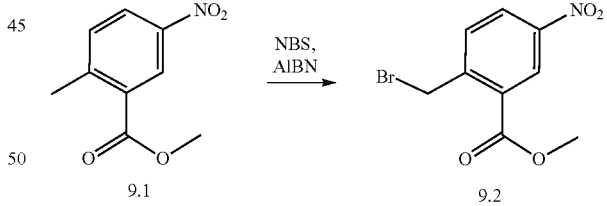

To a solution of methyl 2-methyl-5-nitrobenzoate (compound 9.1, 10.00 g, 51.24 mmol) in 1,2-dichloroethane (100 mL) was added NBS (13.678 g, 76.86 mmol) and AIBN (420.68 mg, 2.56 mmol). The reaction mixture was stirred at 80° C. for 1 hour. TLC (15% EtOAc in petroleum ether, Rf=0.6) showed the starting material consumed, two new spots found. The mixture was concentrated and purified by flash chromatography (0-10% 0 EtOAc in petroleum ether) to afford methyl 2-(bromomethyl)-5-nitro-benzoate (compound 9.2, 8.00 g, 570%) as a yellow solid. $^1$H NMR (400 MHz, CDCl$_3$) δ 8.82-8.81 (d, J=2.8 Hz, 1H), 8.34-8.31 (m, 1H), 7.69-7.67 (d, J=8.4 Hz, 1H), 4.99 (s, 2H), 4.00 (s, 3H).

Step 2: methyl 2-(methylsulfonylmethyl)-5-nitro-benzoate

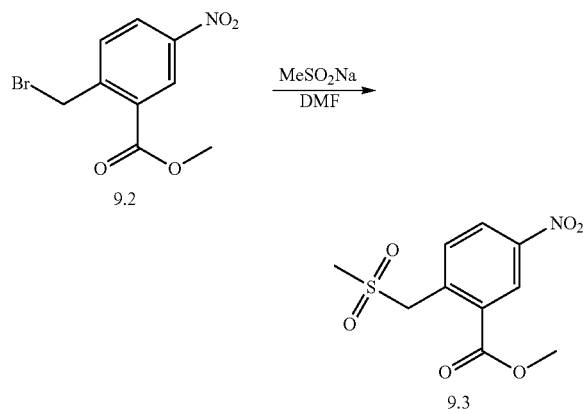

To a solution of methyl 2-(bromomethyl)-5-nitro-benzoate (compound 9.2, 8.00 g, 29.19 mmol) in DMF (150 mL) was added MeSO₂Na (14.899 g, 145.95 mmol). The mixture was stirred at 60° C. for 1 hour. TLC (15% EtOAc in petroleum ether, Rf=0.5) showed the starting material consumed, two new spots were found. The mixture was quenched with water (100 mL), extracted with EtOAc (100 mL×2). The organic layer was washed with water (100 mL×3) and brine (100 mL×3), dried over Na₂SO₄, concentrated and purified by flash column chromatography (0-35% EtOAc in petroleum ether) to afford methyl 2-(methylsulfonylmethyl)-5-nitro-benzoate (compound 9.3, 7.500 g, 94%) as a yellow solid. ¹H NMR (400 MHz, CDCl₃) δ 8.88 (d, J=2.8 Hz, 1H), 8.42-8.39 (m, 1H), 7.78-7.76 (d, J=8.4 Hz, 1H), 5.03 (s, 2H), 4.00 (s, 3H), 2.91 (s, 3H).

Step 3: methyl 5-amino-2-(methylsulfonylmethyl)benzoate

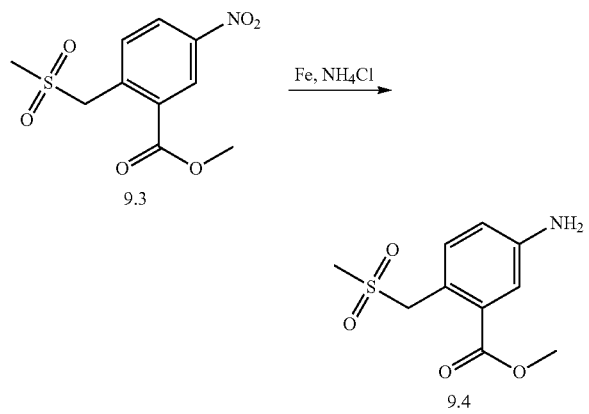

To a solution of methyl 2-(methylsulfonylmethyl)-5-nitro-benzoate (compound 9.3, 7.500 g, 27.45 mmol) in MeOH (150 mL) and water (20 mL) was added iron (7.664 g, 137.23 mmol) and NH₄Cl (7.340 g, 137.23 mmol), and the mixture was stirred at 75° C. for 16 hours. TLC (50% EtOAc in petroleum ether, Rf=0.4) showed the starting material consumed. The mixture was filtered and washed with MeOH (50 mL×3). The filtrate was concentrated and purified by flash column chromatography (50-85% EtOAc in petroleum ether, TLC:60% EtOAc in petroleum ether, Rf=0.5) to give methyl 5-amino-2-(methylsulfonylmethyl) benzoate (compound 9.4, 6.500 g, 97.3%) as a yellow solid. ¹H NMR (400 MHz, DMSO-d6) δ 7.12 (d, J=8.4 Hz, 1H), 7.07 (d, J=2.4 Hz, 1H), 6.72-6.69 (m, 1H), 5.54 (s, 2H), 4.67 (s, 2H), 3.75 (s, 3H), 2.75 (s, 3H).

Step 4: methyl 5-amino-4-iodo-2-(methylsulfonylmethyl)benzoate

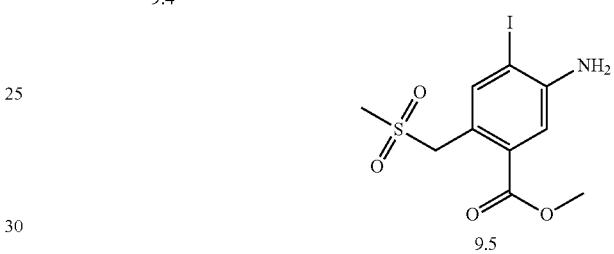

To a solution of methyl 5-amino-2-(methylsulfonylmethyl)benzoate (compound 9.4, 2.500 g, 10.28 mmol) in DMF (30 mL) was added NIS (3.467 g, 15.41 mmol). The reaction mixture was stirred at 22° C. for 16 hours. TLC (50% EtOAc in petroleum ether, Rf=0.5) showed the starting material consumed. The mixture was quenched with Na₂S₂O₃ (aq. 20 mL) and NaHCO₃ (aq. 20 mL). It was extracted with EtOAc (30 mL×2). The organic layer was washed with water (20 mL×3) and brine (20 mL×3), dried over Na₂SO₄, concentrated and purified by flash column chromatography (20%-50% EtOAc in petroleum ether, Rf=0.5) to afford methyl 5-amino-4-iodo-2-(methylsulfonylmethyl)benzoate (compound 9.5, 1.700 g, 44.8%) as a yellow solid. ¹H NMR (400 MHz, CDCl₃) δ 7.78 (s, 1H), 7.31 (s, 1H), 4.68 (s, 2H), 4.33 (s, 2H), 3.87 (s, 3H), 2.77 (s, 3H).

Step 5: (E)-2-(5-bromo-2-methoxy-3-nitro-4-pyridyl)-N,N-dimethyl-ethenamine

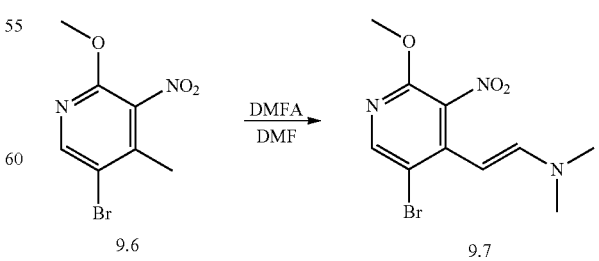

To a solution of 5-bromo-2-methoxy-4-methyl-3-nitropyridine (compound 9.6, 33.0 g, 133.58 mmol) and MeOLi (507.19 mg, 13.36 mmol) in DMF (250 mL) was added DMFA (141.96 mL, 1068.6 mmol) at 100° C., and the reaction mixture was stirred at 100° C. for 16 hours. TLC (15% EtOAc in petroleum ether, Rf=0.5) showed the starting material consumed. The mixture was cooled to 20° C., and quenched with water (60 mL) carefully. The resulting precipitate was collected by vacuum filtration, washed with water (50 mL×3) and dried to afford (E)-2-(5-bromo-2-methoxy-3-nitro-4-pyridyl)-N,N-dimethyl-ethenamine (compound 9.7, 37.0 g, 91.7%) as a red solid. The crude was used in the next step without further purification.

Step 6: 4-bromo-7-methoxy-1H-pyrrolo[2,3-c]pyridine

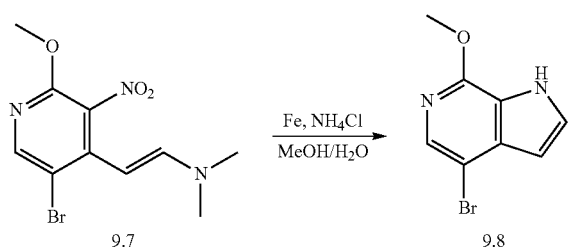

To a solution of (E)-2-(5-bromo-2-methoxy-3-nitro-4-pyridyl)-N,N-dimethyl-ethenamine (compound 9.7, 10.0 g, 33.1 mmol) in MeOH (50 mL) and water (10 mL) was added iron (9.24 g, 165.5 mmol) and NH$_4$Cl (8.85 g, 165.5 mmol). The mixture was stirred at 75° C. for 16 hours. TLC (20% EtOAc in petroleum ether Rf=0.5) showed the starting material consumed and the desired product found. The mixture was filtered and washed with MeOH (10 mL×3), the filtrate was concentrated and purified by flash column chromatography (0-15% EtOAc in petroleum ether) to give 4-bromo-7-methoxy-1H-pyrrolo[2,3-c]pyridine (compound 9.8, 3.3 g, 43.2%) as a white solid. LCMS: RT (220/254 nm)=0.598 min, [M+H]+226.9, Method=M.

Step 7: 4-bromo-7-methoxy-1-(p-tolylsulfonyl)pyrrolo[2,3-c]pyridine

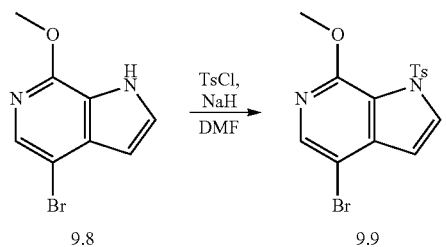

To a solution of NaH (858 mg, 21.45 mmol) in DMF (15 mL) was added 4-bromo-7-methoxy-1H-pyrrolo[2,3-c]pyridine (compound 9.8, 3.30 g, 14.3 mmol) at 0° C., and the mixture was stirred at 0° C. for 10 minutes. Then TsCl (5.452 g, 28.6 mmol) was added portion-wise, and the mixture was stirred at 0° C. under N$_2$ for 16 hours. TLC (30% EtOAc in petroleum ether Rf=0.6) showed the starting material consumed, and the desired product found. The mixture was quenched with water (10 mL), and the resulting precipitate was collected by vacuum filtration, washed with water (10 mL×3), and dried to afford 4-bromo-7-methoxy-1-(p-tolylsulfonyl)pyrrolo[2,3-c]pyridine (compound 9.9, 3.30 g, 60%) as a white solid which was used next step without further purification.

Step 8: 4-bromo-1-(p-tolylsulfonyl)-6H-pyrrolo[2,3-c]pyridin-7-one

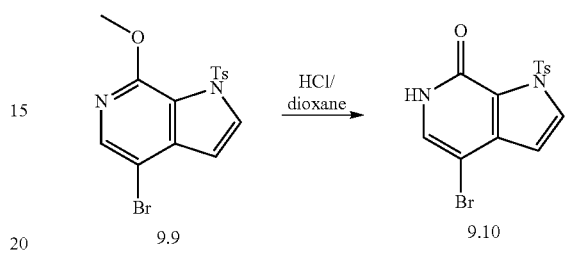

To a solution of 4-bromo-7-methoxy-1-(p-tolylsulfonyl) pyrrolo[2,3-c]pyridine (compound 9.9, 3.300 g, 8.65 mmol) in 1,4-dioxane (15 mL) was added a HCl solution in dioxane (4.0 M, 19.08 mL, 76.33 mmol). The solution was stirred at 40° C. for 16 hours. TLC (20% EtOAc in petroleum ether Rf=0.4) showed the starting material consumed, and the desired product found. The mixture was concentrated and MTBE (20 mL) was added. The resulting precipitate was collected by vacuum filtration, washed with MTBE (20 mL×2), and dried to give 4-bromo-1-(p-tolylsulfonyl)-6H-pyrrolo[2,3-c]pyridin-7-one (compound 9.10, 3.00 g, 94%) as a beige solid. LCMS: RT (220/254 nm)=1.016 min, [M+H]+368.9, Method=M.

Step 9: 4-bromo-6-methyl-1-(p-tolylsulfonyl)pyrrolo[2,3-c]pyridin-7-one

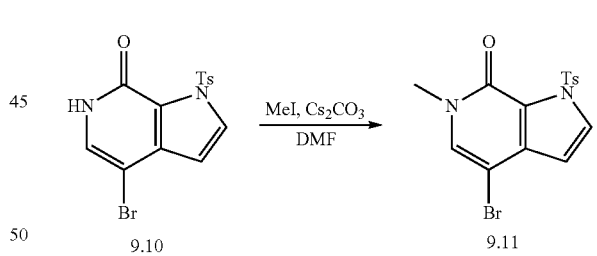

To a solution of 4-bromo-1-(p-tolylsulfonyl)-6H-pyrrolo[2,3-c]pyridin-7-one (compound 9.10, 3.00 g, 8.17 mmol) in DMF (20 mL) was added Cs$_2$CO$_3$ (3.194 g, 9.8 mmol) under N$_2$ at 20° C., and the mixture was stirred at 20° C. for 30 minutes. MeI (1.80 mL, 28.6 mmol) was added and the solution was stirred at 20° C. for 3 hours. TLC (50% EtOAc in petroleum ether, Rf=0.5) showed the starting material consumed, and the desired product found. The mixture was quenched with water (50 mL), and the resulting precipitate was collected by vacuum filtration, washed with MTBE (50 mL×3), and dried to afford 4-bromo-6-methyl-1-(p-tolylsulfonyl)pyrrolo[2,3-c]pyridin-7-one (compound 9.11, 2.50 g, 80%) as a white solid. LCMS: RT (220/254 nm)=0.95 min, [M+H]+383, Method=M.

Step 10: 6-methyl-1-(p-tolylsulfonyl)-4-(4,4,5,5-tetramethyl-1,3,2-dioxaborolan-2-yl)pyrrolo[2,3-c]pyridin-7-one

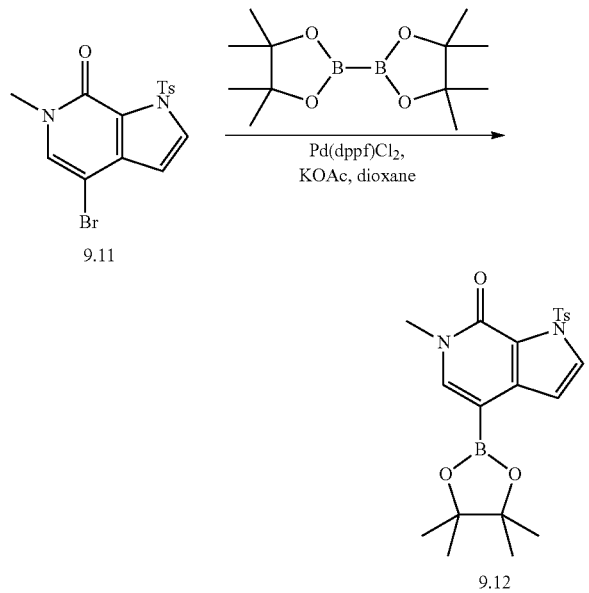

A mixture of 4-bromo-6-methyl-1-(p-tolylsulfonyl)pyrrolo[2,3-c]pyridin-7-one (compound 9.11, 2.00 g, 5.25 mmol), bis(pinacolato)diboron (3.330 g, 13.12 mmol), KOAc (1.287 g, 13.12 mmol), Pd(dppf)Cl$_2$ (433.7 mg, 0.520 mmol) in 1,4-dioxane (15 mL) was stirred at 90° C. under N$_2$ for 16 hours. TLC (50% EtOAc in petroleum ether, Rf=0.5) indicated the reaction was completed. The mixture was concentrated and purified by column chromatography (30%-50% EtOAc in petroleum ether) to afford 6-methyl-1-(p-tolylsulfonyl)-4-(4,4,5,5-tetramethyl-1,3,2-dioxaborolan-2-yl)pyrrolo[2,3-c]pyridin-7-one (compound 9.12, 1.320 g, 57.6%) as a yellow oil. LCMS: RT (220/254 nm)=0.928 min, [M+H]+429.0, Method=M.

Step 11: methyl 5-amino-4-[6-methyl-7-oxo-1-(p-tolylsulfonyl)pyrrolo [2,3-c]pyridin-4-yl]-2-(methylsulfonylmethyl)benzoate

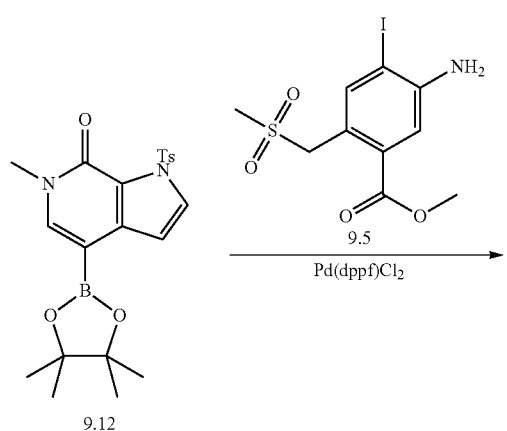

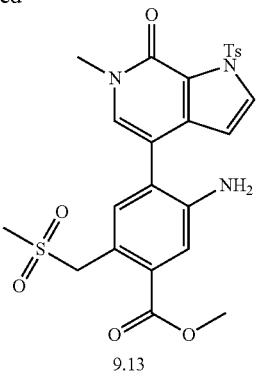

A mixture of 6-methyl-1-(p-tolylsulfonyl)-4-(4,4,5,5-tetramethyl-1,3,2-dioxaborolan-2-yl)pyrrolo[2,3-c]pyridin-7-one (compound 9.12, 812.12 mg, 1.9 mmol), Pd(dppf)Cl$_2$ (115.7 mg, 0.1400 mmol), methyl 5-amino-4-iodo-2-(methylsulfonylmethyl)benzoate (compound 9.5, 500.0 mg, 1.35 mmol), NaHCO$_3$ (284.45 mg, 3.39 mmol) in 1,4-dioxane (2.0 mL) and water (1.0 mL) was stirred at 90° C. under N$_2$ for 1 hour. LCMS showed the starting material consumed, the desired product found. The mixture was concentrated and purified by prep-TLC (5% MeOH in DCM, Rf=0.5) to afford methyl 5-amino-4-[6-methyl-7-oxo-1-(p-tolylsulfonyl)pyrrolo [2,3-c]pyridin-4-yl]-2-(methylsulfonylmethyl)benzoate (compound 9.13, 550 mg, 74.7%) as a yellow solid.

Step 12: methyl 5-[(3,5-difluoro-2-pyridyl)amino]-4-[6-methyl-7-oxo-1-(p-tolylsulfonyl)pyrrolo[2,3-c]pyridin-4-yl]-2-(methylsulfonylmethyl)benzoate

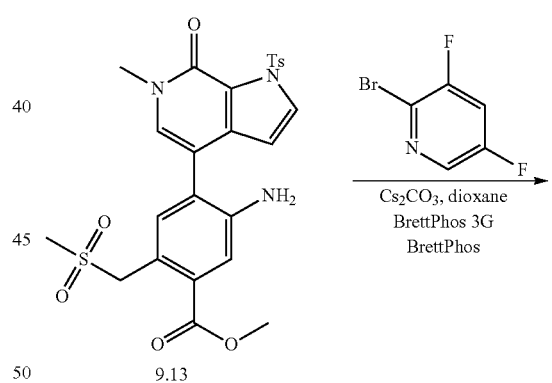

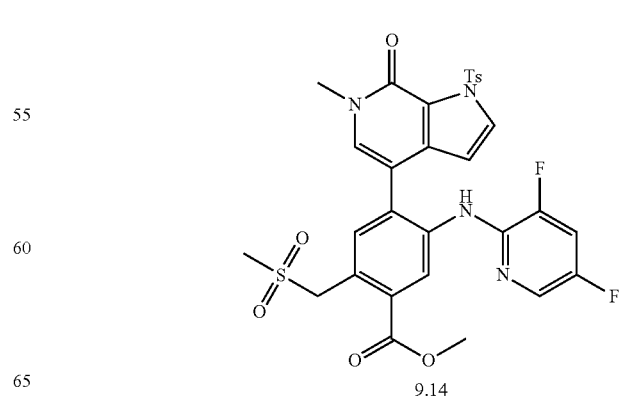

To a solution of methyl 5-amino-4-[6-methyl-7-oxo-1-(p-tolylsulfonyl)pyrrolo [2,3-c]pyridin-4-yl]-2-(methylsulfonylmethyl)benzoate (compound 9.13, 400.0 mg, 0.7400 mmol) in 1,4-dioxane (6.0 mL) was added Cs$_2$CO$_3$ (479.49 mg, 1.47 mmol), BrettPhos (197.48 mg, 0.370 mmol), BrettPhos 3G (133.4 mg, 0.1500 mmol) and 2-bromo-3,5-difluoro-pyridine (428.2 mg, 2.21 mmol). The reaction mixture was purged with N$_2$ and was stirred at 90° C. under N$_2$ for 12 hours. The reaction was filtered and washed with MeOH (10 mL×3). The filtrate was dried (Na$_2$SO$_4$), and the residue was purified by prep-TLC (5% MeOH in DCM, Rf=0.5) to afford methyl 5-[(3,5-difluoro-2-pyridyl)amino]-4-[6-methyl-7-oxo-1-(p-tolylsulfonyl)pyrrolo[2,3-c]pyridin-4-yl]-2-(methylsulfonylmethyl)benzoate (compound 9.14, 300 mg, 54%) as a yellow solid. LCMS: RT=0.851 min, [M+H]+656.9, Method=M.

Step 13: methyl 5-[(3,5-difluoro-2-pyridyl)amino]-4-(6-methyl-7-oxo-1H-pyrrolo[2,3-c]pyridin-4-yl)-2-(methylsulfonylmethyl)benzoate

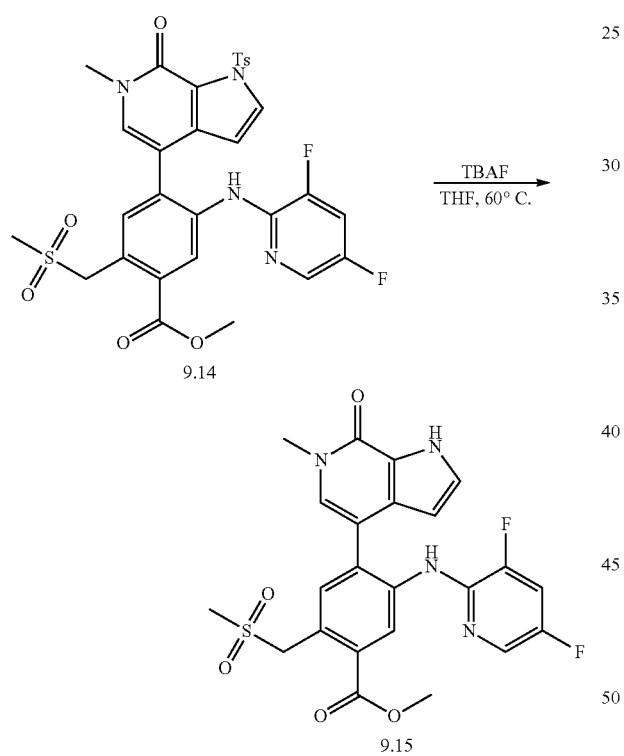

To a solution of methyl 5-[(3,5-difluoro-2-pyridyl)amino]-4-[6-methyl-7-oxo-1-(p-tolylsulfonyl)pyrrolo[2,3-c]pyridin-4-yl]-2-(methylsulfonylmethyl)benzoate (compound 9.14, 270.0 mg, 0.360 mmol) in THF (10 mL) was added TBAF (338.6 mg, 1.07 mmol). The mixture was stirred at 60° C. for 2 hours. TLC (5% MeOH in DCM, Rf=0.4) showed the starting material was consumed, the desired product found. Water (10 mL) was added, and it was extracted with EtOAc (10 mL×2). The organic layer was washed with brine (10 mL×3), dried over Na$_2$SO$_4$, concentrated and purified by prep-TLC (5% MeOH in DCM) to afford methyl 5-[(3,5-difluoro-2-pyridyl)amino]-4-(6-methyl-7-oxo-1H-pyrrolo[2,3-c]pyridin-4-yl)-2-(methylsulfonylmethyl)benzoate (compound 9.15, 80 mg, 40.1%) as a yellow solid. LCMS: RT (220/254 nm)=0.764 min, [M+Na]+525.0, Method=M.

Step 14: methyl 7-(3,5-difluoropyridin-2-yl)-2-methyl-10-((methylsulfonyl)methyl)-3-oxo-3,4,6,7-tetrahydro-2H-2,4,7-triazadibenzo[cd,f]azulene-9-carboxylate

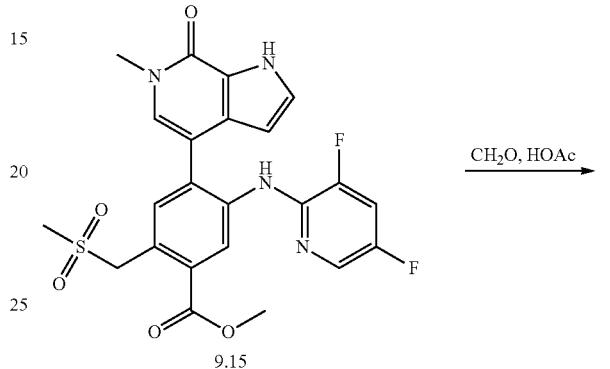

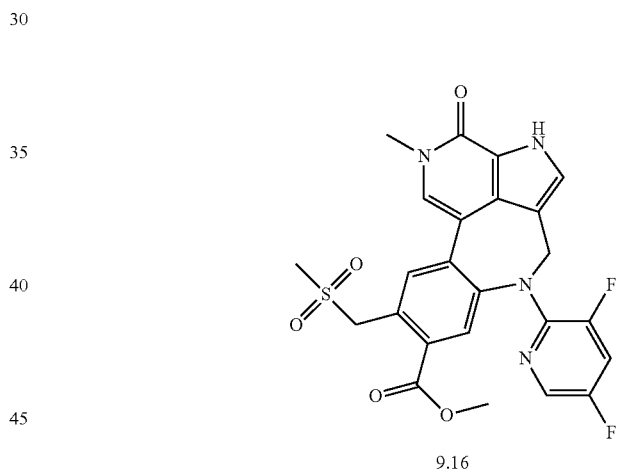

To a solution of methyl 5-[(3,5-difluoro-2-pyridyl)amino]-4-(6-methyl-7-oxo-1H-pyrrolo[2,3-c]pyridin-4-yl)-2-(methylsulfonylmethyl)benzoate (compound 9.15, 20.0 mg, 0.0400 mmol) in acetic acid (2.0 mL) was added paraformaldehyde (3.55 mg, 0.1200 mmol) under N$_2$, and the reaction mixture was stirred at 90° C. for 1.5 hours. The mixture was concentrated and purified by prep-HPLC (36-66 water (0.225% FA)-ACN) to afford the desired product (5 mg, 25%) as a white solid. $^1$H NMR (400 MHz, DMSO-d6) δ 11.89 (s, 1H), 8.04 (d, J=2.0 Hz, 1H), 7.96 (s, 1H), 7.79 (s, 1H), 7.63-7.58 (m, 1H), 7.53 (s, 1H), 7.24 (d, J=1.6 Hz, 1H), 5.86 (brs, 1H), 5.06-4.85 (br, 2H), 4.27 (brs, 1H), 3.74 (s, 3H), 3.59 (s, 3H), 2.92 (s, 3H). LCMS: RT (220/254 nm)=0.693 min, [M+Na]+515.0, Method=M.

Step 15: 7-(3,5-difluoropyridin-2-yl)-2-methyl-10-((methylsulfonyl)methyl)-3-oxo-3,4,6,7-tetrahydro-2H-2,4,7-triazadibenzo[cd,f]azulene-9-carboxylic acid (Intermediate 9)

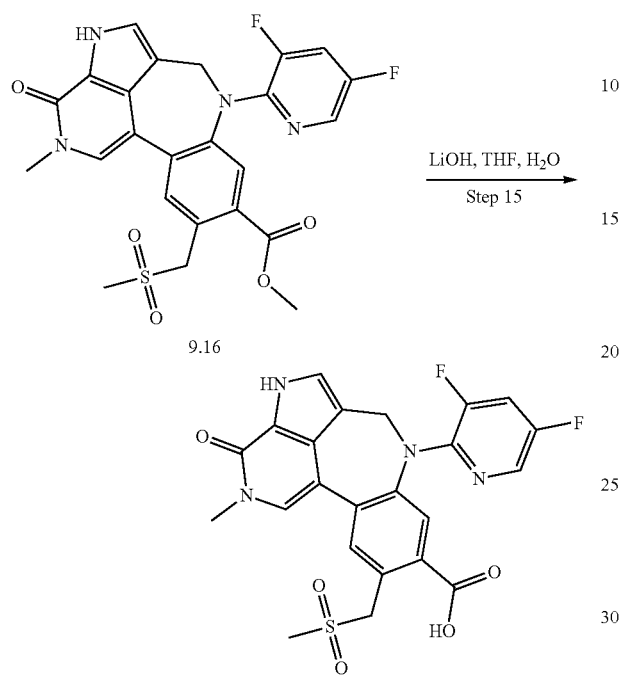

A solution of methyl 7-(3,5-difluoropyridin-2-yl)-2-methyl-10-((methylsulfonyl)methyl)-3-oxo-3,4,6,7-tetrahydro-2H-2,4,7-triazadibenzo[cd,f]azulene-9-carboxylate (compound 9.16, 108 mg, 0.210 mmol) and LiOH·H$_2$O (13.2 mg, 0.310 mmol) in THF (5 mL) and water (5 mL) was stirred at 25° C. for 6 hours. The solvent was concentrated under reduced pressure. The residue was purified by reverse phase chromatography (gradient: 5%-40% ACN in water (0.1% formic acid)) to yield 97 mg (92.3%) of the title compound as a yellow solid. LCMS (ESI): R$_T$ (min)=1.06, [M+H]$^+$=501, method=A.

Example 10

(2S,4R)-4-hydroxy-1-((R)-3-methyl-2-(3-methyl-isoxazol-5-yl)butanoyl)pyrrolidine-2-carboxylic acid (Intermediate 11)

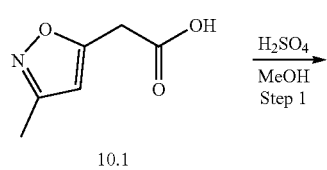

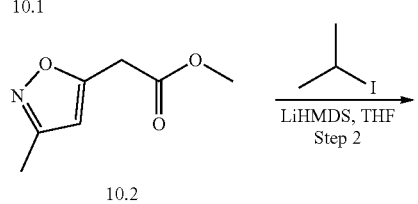

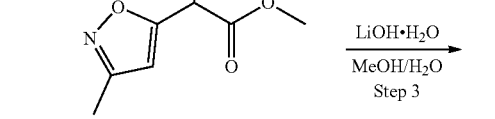

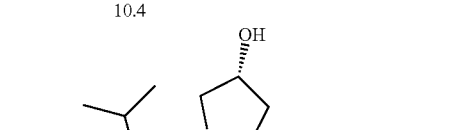

Intermediate 11

Step 1: methyl 2-(3-methylisoxazol-5-yl)acetate

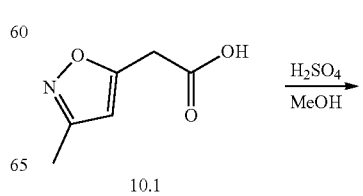

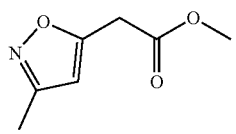

10.2

To a solution of 2-(3-methylisoxazol-5-yl)acetic acid (compound 10.1, 15.0 g, 106.29 mmol) in MeOH (150 mL) was added H$_2$SO$_4$ (0.28 mL, 5.31 mmol). The reaction was stirred at 70° C. for 2 hours. TLC (33% EtOAc in petroleum ether, R$_f$=0.5) showed the desired product was formed. The solution was concentrated under reduced pressure, and the residue was diluted with saturated NaHCO$_3$ solution (50 mL), and extracted with EtOAc (60 mL×3). The combined organic layers were dried over Na$_2$SO$_4$, filtered, and concentrated in vacuo to afford methyl 2-(3-methylisoxazol-5-yl)acetate (compound 10.2, 15.0 g, 91%) as light yellow oil. $^1$H NMR (400 MHz, CDCl$_3$) δ ppm 6.09 (s, 1H), 3.77 (s, 2H), 3.73 (s, 3H), 2.27 (s, 3H).

Step 2: methyl 3-methyl-2-(3-methylisoxazol-5-yl)butanoate

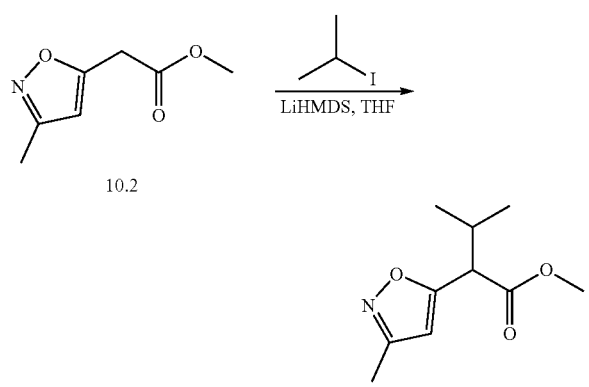

To a solution of methyl 2-(3-methylisoxazol-5-yl)acetate (compound 10.2, 17.0 g, 109.57 mmol) in anhydrous THF (100 mL) was added LiHMDS (1.0 M, 131.49 mL, 131.49 mmol) in THF at −78° C. The mixture was stirred at −78° C. for 30 minutes, then 2-iodopropane (21.87 mL, 219.14 mmol) was added dropwise. The reaction mixture was stirred at −78° C. to 15° C. for 16 hours. TLC (33% EtOAc in petroleum ether, R$_f$=0.6) showed desired product was formed. LCMS: R$_T$=0.810 min, [M+H]$^+$ 197.9, Method=M, showed 58% of desired product. The mixture was quenched with saturated NH$_4$Cl solution (60 mL), and extracted with EtOAc (80 mL×3). The combined organic layers were dried over Na$_2$SO$_4$, filtered, and concentrated. The residue was purified by chromatography on silica (solvent gradient: 0-15% EtOAc in petroleum ether) to afford methyl 3-methyl-2-(3-methylisoxazol-5-yl)butanoate (compound 10.3, 15.0 g, 60.4%) as a pale yellow oil. LCMS: RT (220/254 nm)=0.810 minutes, [M+Na]+197.9, Method=M. H NMR (400 MHz, CDCl$_3$) δ 6.09 (s, 1H), 3.72 (s, 3H), 3.59 (d, J=8.8 Hz, 1H), 2.39-2.33 (m, 1H), 2.28 (s, 3H), 0.99 (d, J=6.8 Hz, 3H), 0.89 (d, J=6.4 Hz, 3H).

Step 3: 3-methyl-2-(3-methylisoxazol-5-yl)butanoic acid

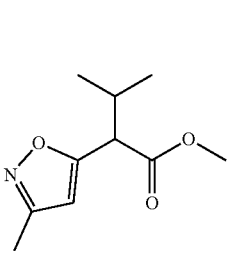

10.3

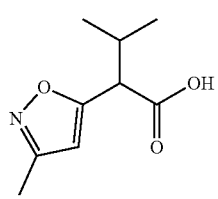

10.4

To a solution of methyl 3-methyl-2-(3-methylisoxazol-5-yl)butanoate (compound 10.3, 15.0 g, 76.05 mmol) in MeOH (50 mL)/water (25 mL) was added LiOH H$_2$O (9.57 g, 228.2 mmol). The reaction mixture was stirred at 15° C. for 16 hours. LCMS (Method=M) showed the reaction was completed. The mixture was concentrated in vacuo to remove most of MeOH, diluted with H$_2$O (40 mL), and extracted with EtOAc (30 mL) to remove byproduct. Then the aqueous phase was adjusted to pH 2.0 by a concentrated HCl solution, and extracted with EtOAc/MeOH (10:1, 50 mL×6). The combined organic layers were dried over Na$_2$SO$_4$, filtered, and concentrated in vacuo to afford 3-methyl-2-(3-methylisoxazol-5-yl)butanoic acid (compound 10.4, 13 g, 93.3%) as a white solid. LCMS: RT (220/254 nm)=0.738 minutes, [M+Na]+183.9, Method=M.

Step 4: methyl (2S,4R)-4-hydroxy-1-(3-methyl-2-(3-methylisoxazol-5-yl)butanoyl)pyrrolidine-2-carboxylate

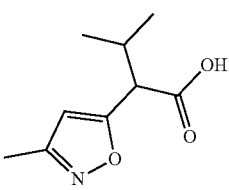

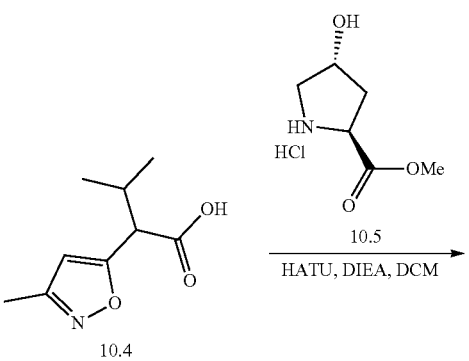

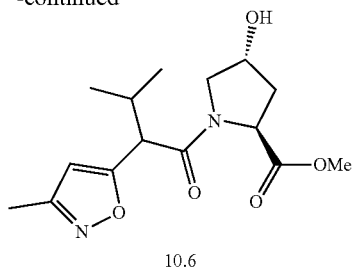

10.6

To a solution of 3-methyl-2-(3-methylisoxazol-5-yl)butanoic acid (compound 10.4, 3.00 g, 16.38 mmol) in anhydrous DCM (50 mL) was added HATU (8.094 g, 21.29 mmol) and DIEA (6.349 g, 49.13 mmol). The mixture was stirred at 15° C. for 15 minutes, then methyl (2S,4R)-4-hydroxypyrrolidine-2-carboxylate hydrochloride (compound 10.5, 3.866 g, 21.29 mmol) was added. The resulting reaction mixture was stirred at 15° C. for 16 hours. LCMS: $R_T$=0.706 min, [M+H]$^+$ 311.0, Method=M, showed 92% of desired product. The mixture was diluted with DCM (50 mL), washed with sat. citric acid solution (40 mL), satd. NaHCO$_3$ solution (40 mL), and brine (40 mL). It was dried over Na$_2$SO$_4$, filtered, and concentrated. The residue was purified by prep-HPLC (Phenomenex luna C18 250*50 mm*10 um, acetonitrile 10-40/0.1% TFA in water) to afford methyl (2S,4R)-4-hydroxy-1-(3-methyl-2-(3-methylisoxazol-5-yl)butanoyl)pyrrolidine-2-carboxylate (compound 10.6, 4.20 g, 82.6%) as sandy beige oil. LCMS: peak 1, $R_T$=2.378 min, [M+H]$^+$ 310.9, Method=O, showed 46% of desired mass; peak 2, $R_T$=2.543 minutes, [M+H]$^+$ 310.9 showed 53% of desired mass.

Step 5: (2S,4R)-4-hydroxy-1-(3-methyl-2-(3-methylisoxazol-5-yl)butanoyl)pyrrolidine-2-carboxylic acid

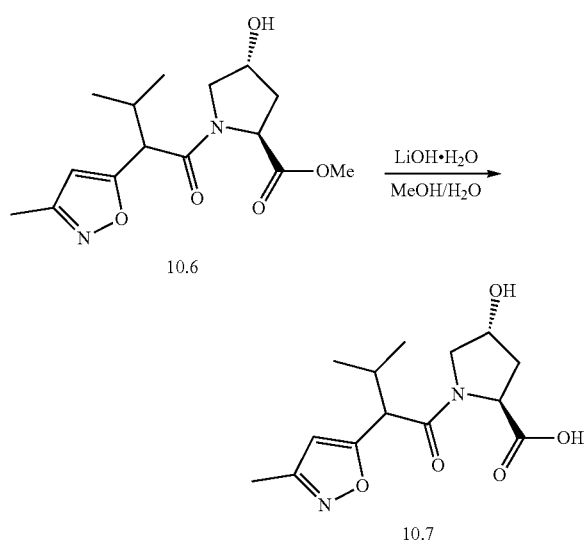

To a solution of methyl (2S,4R)-4-hydroxy-1-(3-methyl-2-(3-methylisoxazol-5-yl)butanoyl)pyrrolidine-2-carboxylate (compound 10.6, 2.1 g, 6.77 mmol) in MeOH (15 mL)/water (5 mL) was added LiOH H$_2$O (851.77 mg, 20.3 mmol). The reaction was stirred at 15° C. for 12 hours. LCMS (Method=M) showed the reaction was completed. The solution was concentrated under reduced pressure. The residue was diluted with H$_2$O (40 mL), and extracted with EtOAc (30 mL×3) to remove the byproduct. Then the aq. phase was adjusted to pH 2.0 by concentrated HCl, and extracted with EtOAc/MeOH (10:1, 50 mL×4). The combined organic layers were dried over Na$_2$SO$_4$, filtered, and concentrated in vacuo to afford (2S,4R)-4-hydroxy-1-(3-methyl-2-(3-methylisoxazol-5-yl)butanoyl)pyrrolidine-2-carboxylic acid (compound 10.7, 1.9 g, 92.9%) as a white solid. LCMS: RT (220/254 nm)=0.635 minutes, [M+H]+ 297.1, Method=M. SFC: peak 1, Rt=2.402 minutes, 45.59%; peak 2, Rt=2.699 minutes, 54.41%.

Step 6: (2S,4R)-4-hydroxy-1-((R)-3-methyl-2-(3-methylisoxazol-5-yl)butanoyl)pyrrolidine-2-carboxylic acid

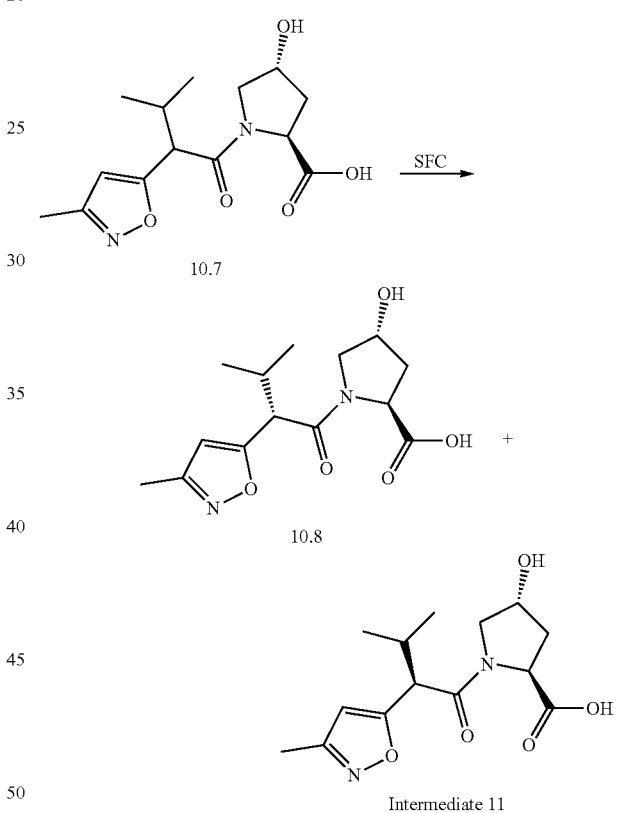

(2S,4R)-4-hydroxy-1-(3-methyl-2-(3-methylisoxazol-5-yl)butanoyl)pyrrolidine-2-carboxylic acid (compound 10.7, 300 g, 10.12 mmol) was separated by chiral SFC (SFC13; Chiralpak AD 250×30 mm I.D. 10 μm; Supercritical CO$_2$/MeOH-0.1% NH$_3$H$_2$O=15%; 50 ml/minute) to afford (2S,4R)-4-hydroxy-1-((S)-3-methyl-2-(3-methylisoxazol-5-yl)butanoyl)pyrrolidine-2-carboxylic acid (compound 10.8, 1.300 g, 42.5%) and (2S,4R)-4-hydroxy-1-((R)-3-methyl-2-(3-methylisoxazol-5-yl)butanoyl)pyrrolidine-2-carboxylic acid (crude) (Intermediate 11, 1.400 g, 46.7%) both as thick colorless oils. SFC (GNEWX-535-125-2A_G1) showed 89% of ee. Then 700 mg of Intermediate 11 (crude) was purified again by chiral SFC (SFC13; Chiralpak AD 250×30 mm I.D. 10 μm; Supercritical CO$_2$/MeOH-0.1% NH$_3$H$_2$O=15%; 50 ml/min) to afford the pure product (Intermediate 11, 620 mg, 88.6%) as thick colorless oil (99% ee). LCMS: $R_T$=0.632 minutes, [M+H]$^+$ 296.9, Method=M. $^1$H NMR (400 MHz, MeOD) δ 6.22 (d, J=16.4 Hz, 1H), 4.54-4.37 (m, 2H), 3.90-3.59 (m, 3H), 2.41-1.96 (m, 6H), 1.10-1.03 (m, 3H), 0.85 (d, J=6.4 Hz, 3H).
Example 12
(5S)-2-((4R)-4-Hydroxypyrrolidin-2-yl)-5-methyl-5-(4-(4-methylthiazol-5-yl) phenyl)-1,5-dihydro-4H-imidazol-4-one (Intermediate 12)
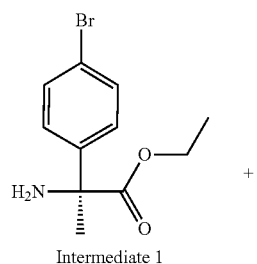
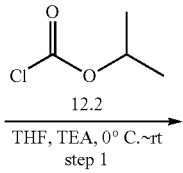
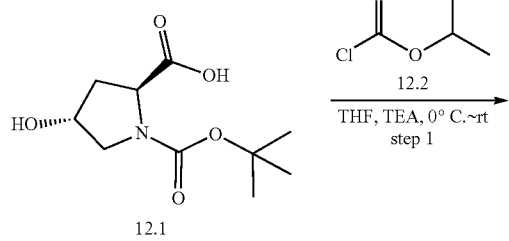
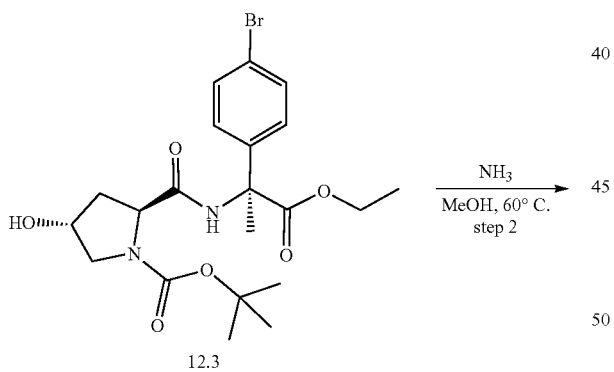
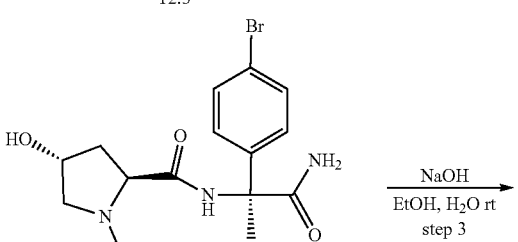
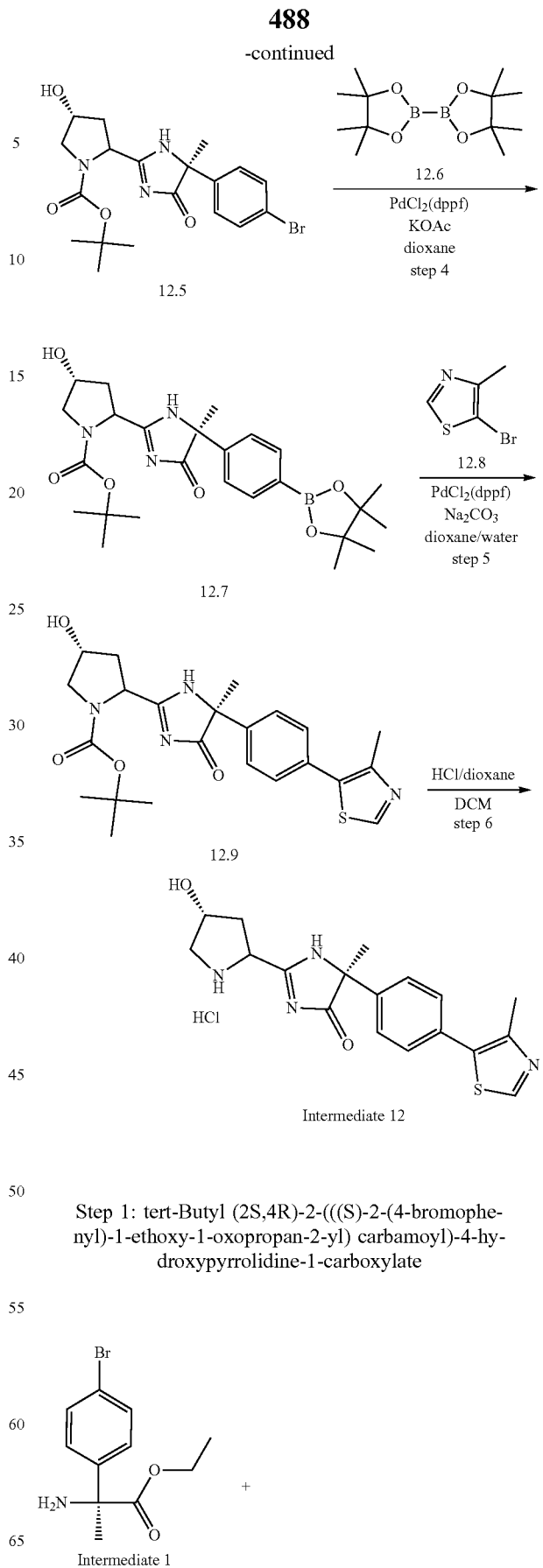
Step 1: tert-Butyl (2S,4R)-2-(((S)-2-(4-bromophenyl)-1-ethoxy-1-oxopropan-2-yl) carbamoyl)-4-hydroxypyrrolidine-1-carboxylate

489
-continued

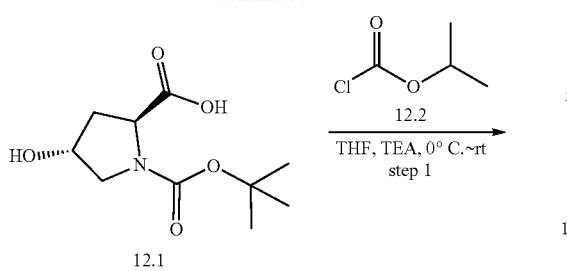

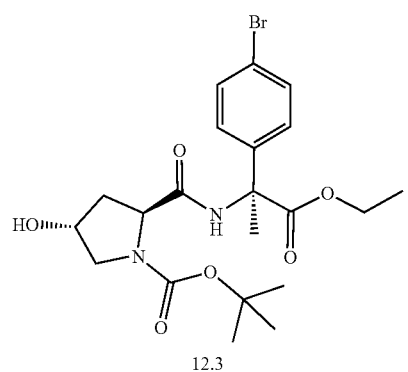

To a solution of (2S,4R)-1-(tert-butoxycarbonyl)-4-hydroxypyrrolidine-2-carboxylic acid (compound 12.1, 8.94 g, 38.7 mmol) in THF (200 mL) was added triethylamine (7.78 g, 76.8 mmol) and isopropyl carbonochloridate (compound 12.2, 7.85 g, 64.1 mmol) at 0° C. The resulting solution was stirred at 0° C. for 0.5 hours. Then ethyl (S)-2-amino-2-(4-bromophenyl) propanoate (Intermediate 1, the faster peak produced in Example 1, step 3) (7.01 g, 25.7 mmol) was added. The reaction mixture was stirred at room temperature for 3 hours. The mixture was diluted with water, extracted with DCM. The combined organic layers were dried over anhydrous $Na_2SO_4$ and concentrated under reduced pressure. The residue was purified by flash chromatography on silica gel (gradient: 0%-20% MeOH/DCM) to yield 8.56 g (69% yield) of the title compound as a white solid. LCMS (ESI): $[M+H]^+=485/487$.

Step 2: tert-Butyl (2S,4R)-2-(((S)-1-amino-2-(4-bromophenyl)-1-oxopropan-2-yl) carbamoyl)-4-hydroxypyrrolidine-1-carboxylate

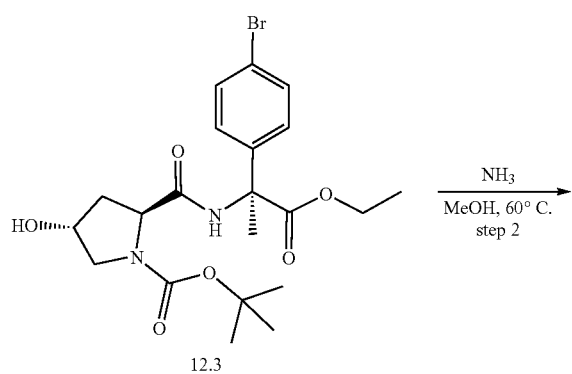

490
-continued

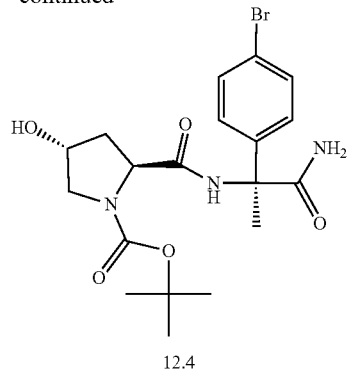

A solution of tert-butyl (2S,4R)-2-(((S)-2-(4-bromophenyl)-1-ethoxy-1-oxopropan-2-yl) carbamoyl)-4-hydroxypyrrolidine-1-carboxylate (compound 12.3, 8.56 g, 17.6 mmol) in ammonia methanol solution (800 mL, 7M solution in MeOH) was stirred at 80° C. for 48 hours. The reaction mixture was concentrated under reduced pressure to yield 7.01 g (87% yield) the title compound as a light yellow solid. LCMS (ESI): $[M+H]^+=456/458$.

Step 3: tert-Butyl (4R)-2-((S)-5-(4-bromophenyl)-5-methyl-4-oxo-4,5-dihydro-1H-imidazol-2-yl)-4-hydroxypyrrolidine-1-carboxylate

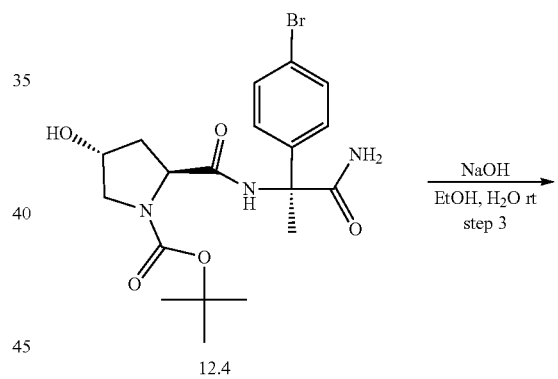

A solution of tert-butyl (2S,4R)-2-(((S)-1-amino-2-(4-bromophenyl)-1-oxopropan-2-yl) carbamoyl)-4-hydroxypyrrolidine-1-carboxylate (compound 12.4, 7.01 g, 15.4 mmol) and NaOH (1.84 g, 46.0 mmol) in EtOH (50 mL) and $H_2O$ (50 mL) was stirred at 50° C. for 6 hours. The reaction mixture was extracted with DCM, the combined organic layers were dried over anhydrous $Na_2SO_4$ and concentrated under reduced pressure. The residue was purified by flash chromatography on silica gel (gradient: 0%-10% MeOH/DCM) to yield 5.90 g (87% yield) of the title compound as a white solid. LCMS (ESI): [M+H]⁺=438/440.

Step 4: tert-Butyl (4R)-4-hydroxy-2-((S)-5-methyl-4-oxo-5-(4-(4,4,5,5-tetramethyl-1,3,2-dioxaborolan-2-yl) phenyl)-4,5-dihydro-1H-imidazol-2-yl) pyrrolidine-1-carboxylate

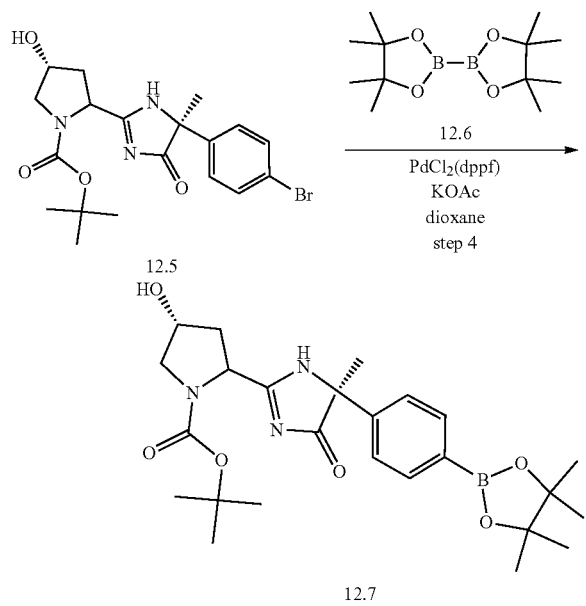

A solution of intermediate tert-butyl (4R)-2-((S)-5-(4-bromophenyl)-5-methyl-4-oxo-4,5-dihydro-1H-imidazol-2-yl)-4-hydroxypyrrolidine-1-carboxylate (compound 12.5, 200 mg, 0.460 mmol), 4,4,4',4',5,5,5',5'-octamethyl-2,2'-bi(1,3,2-dioxaborolane) (compound 12.6, 139 mg, 0.547 mmol), PdCl₂(dppf) (66.7 mg, 0.0911 mmol) and KOAc (89.4 mg, 0.910 mmol) in dioxane (10 mL) was stirred at 95° C. for 16 hours. The mixture was concentrated under reduced pressure. The residue was purified by flash chromatography on silica gel (gradient: 0%-10% MeOH/DCM) to yield 160 mg (72% yield) of the title compound as a light yellow solid. LCMS (ESI): [M+H]⁺=486.

Step 5: tert-Butyl (4R)-4-hydroxy-2-((S)-5-methyl-5-(4-(4-methylthiazol-5-yl) phenyl)-4-oxo-4,5-dihydro-1H-imidazol-2-yl) pyrrolidine-1-carboxylate

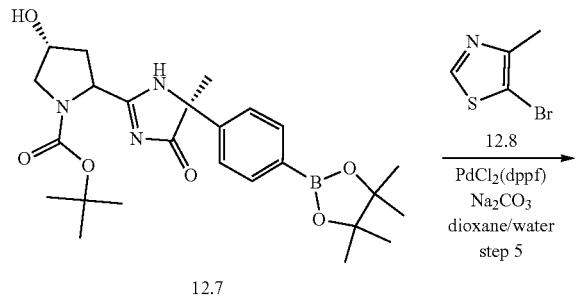

A solution of tert-butyl (4R)-4-hydroxy-2-((S)-5-methyl-4-oxo-5-(4-(4,4,5,5-tetramethyl-1,3,2-dioxaborolan-2-yl) phenyl)-4,5-dihydro-1H-imidazol-2-yl)pyrrolidine-1-carboxylate (compound 12.7, 150 mg, 0.310 mmol), 5-bromo-4-methylthiazole (compound 12.8, 66.1 mg, 0.370 mmol), PdCl₂(dppf) (45.2 mg, 0.0618 mmol) and Na₂CO₃ (98.3 mg, 0.930 mmol) in dioxane (4 mL) and water (0.6 mL) was stirred at 100° C. for 70 minutes in microwave. The mixture was concentrated under reduced pressure. The residue was purified by flash chromatography on silica gel (gradient: 0%-10% MeOH/DCM) to yield 110 mg (78% yield) of the title compound as a light yellow solid. LCMS (ESI): [M+H]⁺=457. ¹H NMR (300 MHz, Chloroform-d) δ 9.10 (br, 1H), 8.68 (s, 1H), 7.70-7.60 (m, 2H), 7.45-7.35 (m, 2H), 4.90-4.75 (m, 1H), 4.60-4.45 (m, 1H), 3.45-3.55 (m, 2H), 2.98-2.65 (m, 1H), 2.50 (s, 3H), 2.40-2.10 (m, 1H), 2.65 (s, 3H), 1.48 (1.45) (s, 9H).

Step 6: (5S)-2-((4R)-4-hydroxypyrrolidin-2-yl)-5-methyl-5-(4-(4-methylthiazol-5-yl) phenyl)-1,5-dihydro-4H-imidazol-4-one hydrochloride (Intermediate 12)

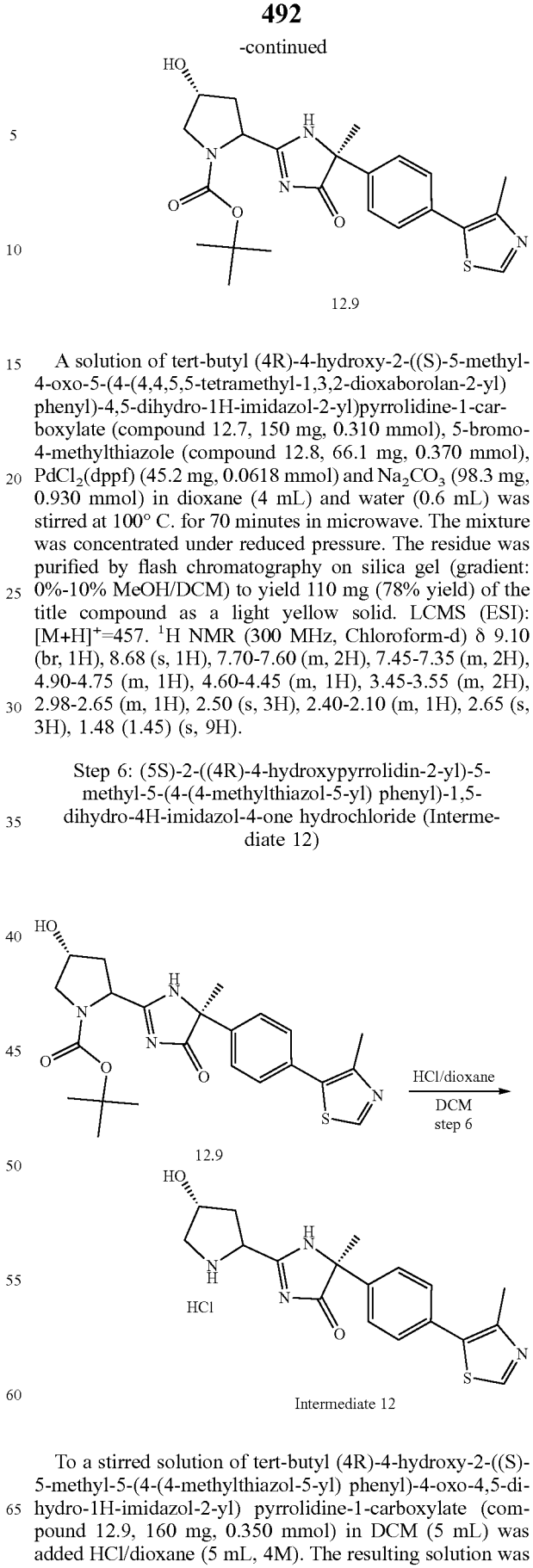

To a stirred solution of tert-butyl (4R)-4-hydroxy-2-((S)-5-methyl-5-(4-(4-methylthiazol-5-yl) phenyl)-4-oxo-4,5-dihydro-1H-imidazol-2-yl) pyrrolidine-1-carboxylate (compound 12.9, 160 mg, 0.350 mmol) in DCM (5 mL) was added HCl/dioxane (5 mL, 4M). The resulting solution was stirred at room temperature for 2 hours and then concentrated under reduced pressure. The residue was purified by flash chromatography on silica gel (gradient: 0%-20% MeOH/DCM) to yield 99.0 mg (79% yield) of the title compound as a light yellow solid. LCMS (ESI): [M+H]⁺ =357.

Example 13

3-Methyl-2-(1-methyl-1H-pyrazol-4-yl) butanoic acid (Intermediate 13)

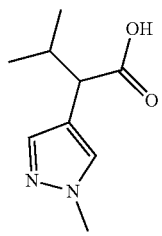

Intermediate 13 was prepared from 2-(1-methyl-1H-pyrazol-4-yl) acetic acid following a procedure analogous to Intermediate 5.

Example 14

3-Methyl-2-(3-methyl-1,2,4-oxadiazol-5-yl) butanoic acid (Intermediate 14)

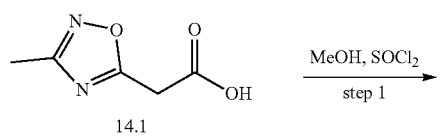

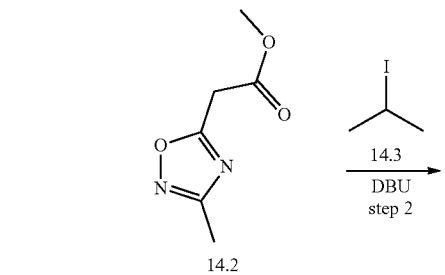

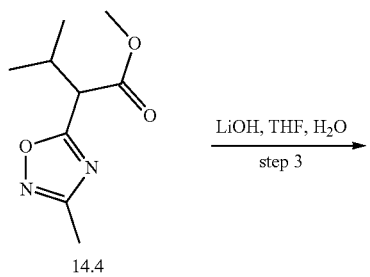

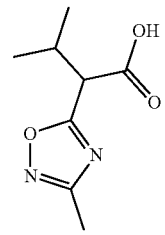

Intermediate 14

Step 1: Methyl 2-(3-methyl-1,2,4-oxadiazol-5-yl) acetate

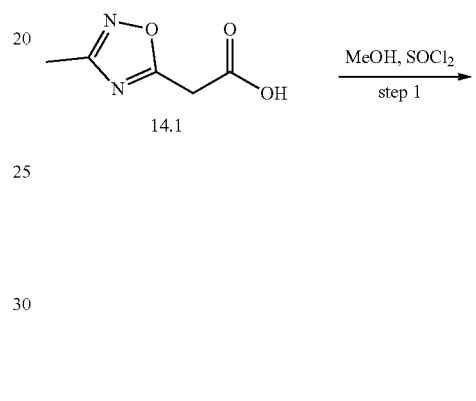

The title compound was generated from 2-(3-methyl-1,2,4-oxadiazol-5-yl) acetic acid (compound 14.1) following a procedure analogous to that set forth in Step 1 in Example 5.

Step 2: Methyl 3-methyl-2-(3-methyl-1,2,4-oxadiazol-5-yl) butanoate

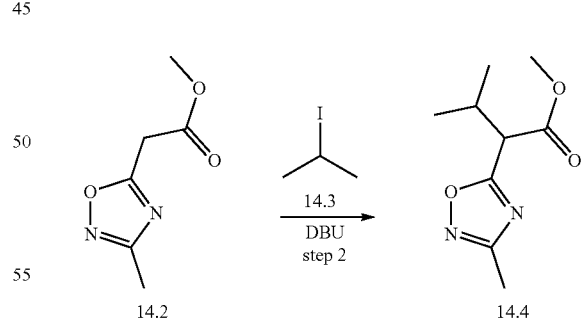

A solution of methyl 2-(3-methyl-1,2,4-oxadiazol-5-yl) acetate (compound 14.2, 750 mg, 4.81 mmol) and 2-iodopropane (compound 14.3, 1.63 g, 9.61 mmol) in DBU (1.5 mL) was stirring at 0° C. for 2 hours. The resulting solution was diluted with water (50 mL), extracted with ethyl acetate. The combined organic layers were washed with brine, dried over anhydrous sodium sulfate and concentrated under vacuum to afford the crude product (445 mg) as yellow oil. The crude product was used for next step without further purification. LCMS (ESI): [M+H]⁺=199. ¹H NMR (400 MHz, DMSO-d₆) δ 4.14 (d, J=7.7 Hz, 1H), 3.68 (s, 3H), 2.50-2.40 (m, 1H), 2.35 (s, 3H), 0.97 (d, J=6.8 Hz, 3H), 0.95 (d, J=6.8 Hz, 3H).

Step 3: 3-Methyl-2-(3-methyl-1,2,4-oxadiazol-5-yl) butanoic acid

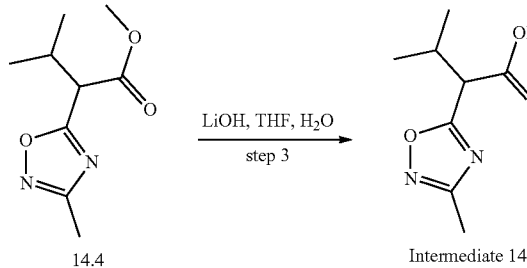

Intermediate 13 was generated from methyl 3-methyl-2-(3-methyl-1,2,4-oxadiazol-5-yl) butanoate (compound 14.4) following a procedure analogous to that set forth in Step 3 in Example 5.

Example 15

3-Methyl-2-(3-methylisothiazol-5-yl) butanoic acid (Intermediate 15)

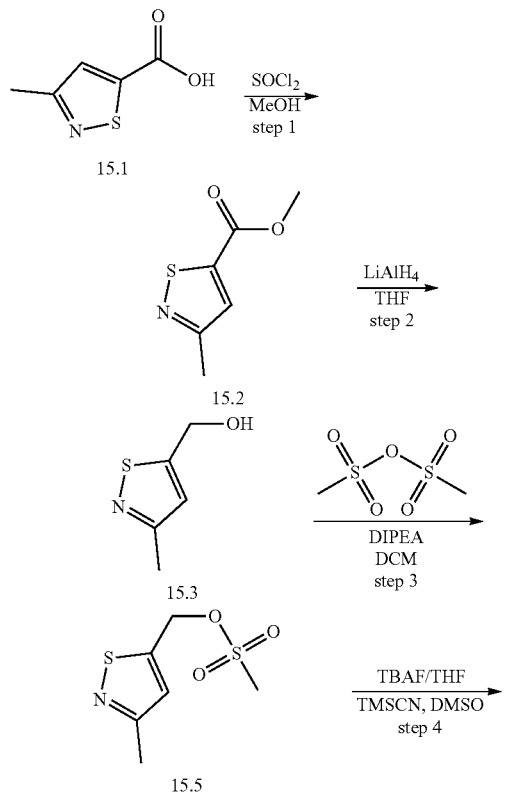

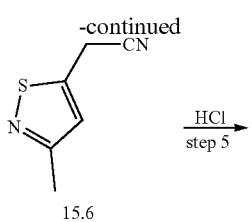

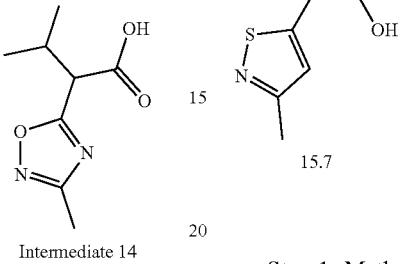

Step 1: Methyl 3-methylisothiazole-5-carboxylate

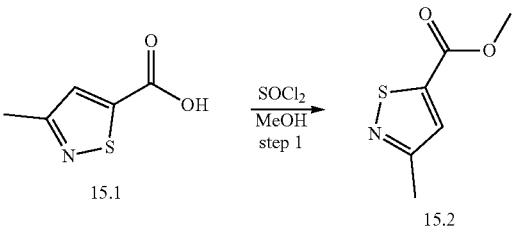

To a stirred solution of 3-methylisothiazole-5-carboxylic acid (compound 15.1, 1.50 g, 10.5 mmol) in methyl alcohol (30 mL) was added SOCl₂ (1.00 mL, 10.5 mmol) at 0° C. The resulting solution was stirred at 25° C. for 2 hours. The solvent was concentrated under vacuum. The residue was purified by flash chromatography on silica gel (gradient: 0%-30% ethyl acetate/petroleum ether) to afford the title compound 1.23 g (75% yield) as a white solid. LCMS (ESI): [M+H]⁺=158.

Step 2: (3-Methylisothiazol-5-yl) methanol

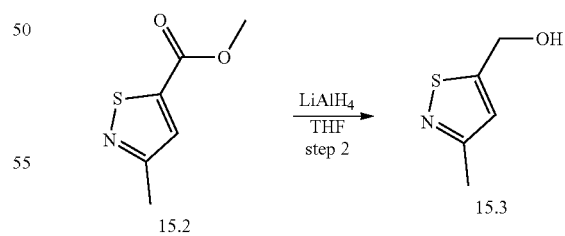

To a stirred solution of methyl 3-methylisothiazole-5-carboxylate (compound 15.2, 1.20 g, 7.63 mmol) in THF (20 mL) was added LiAlH₄ (348 mg, 9.16 mmol) at −40° C. The resulting solution was stirred for 2 hours at −40° C. and then quenched with water (5 mL) at −40° C. The reaction system was diluted with water, extracted with ethyl acetate. The combined organic layers were dried over anhydrous sodium sulfate and concentrated under vacuum to afford the product 893 mg (crude) as a yellow oil. The crude product was used for next step without further purification. LCMS (ESI): [M+H]⁺=130.

Step 3: (3-Methylisothiazol-5-yl) methyl methanesulfonate

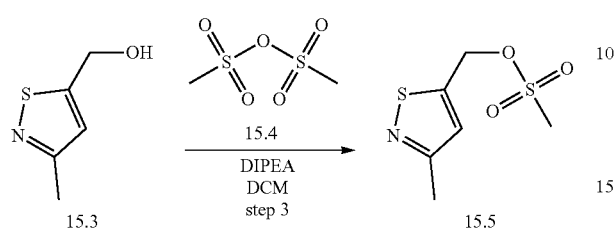

To a stirred solution of (3-methylisothiazol-5-yl) methanol (compound 15.3, 893 mg, 6.91 mmol) and DIPEA (1.78 g, 13.8 mmol) in DCM (30 mL) was added methanesulfonic anhydride (compound 15.4, 181 g, 10.4 mmol) at 0° C. The resulting solution was stirred at 25° C. for 1 hour. The reaction mixture was diluted with water, extracted with DCM. The combined organic layers were dried over anhydrous sodium sulfate and concentrated under vacuum to afford the product 952 mg (crude) as a yellow oil. The crude product was used for next step without further purification. LCMS (ESI): [M+H]⁺=208.

Step 4: 2-(3-Methylisothiazol-5-yl) acetonitrile

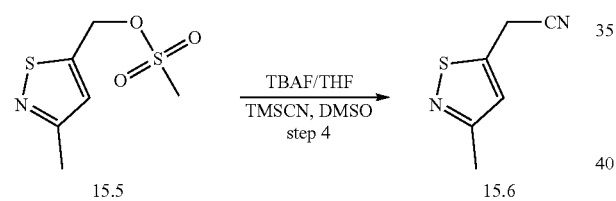

To a stirred solution of (3-methylisothiazol-5-yl) methyl methanesulfonate (compound 15.5, 950 mg, 4.58 mmol) and TMSCN (908 mg, 9.17 mmol) in DMSO (20 mL) was added TBAF/THF (9.1 mL, 1M) at 0° C. The resulting solution was stirred at 25° C. for 2 hours. The reaction mixture was diluted with water, extracted with ethyl acetate. The combined organic layers were washed with brine, dried over anhydrous sodium sulfate and concentrated under vacuum to afford the product 793 mg (crude) as a yellow oil. The crude product was used for next step without further purification. LCMS (ESI): [M+H]⁺=139.

Step 5: 2-(3-Methylisothiazol-5-yl) acetic acid

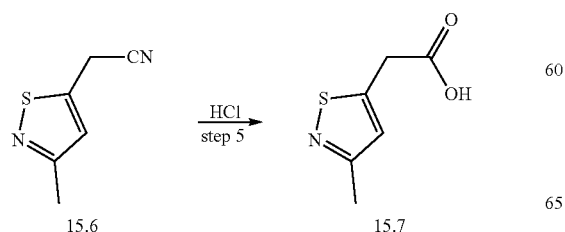

A solution of 2-(3-methylisothiazol-5-yl) acetonitrile (compound 15.6, 793 mg, 5.74 mmol) in concentrated HCl (15 mL) was stirred at 60° C. for 1 hour. The solvent was concentrated under vacuum to afford the product 723 mg (crude) as a yellow solid. The crude product was used for next step without further purification. LCMS (ESI): [M+H]⁺=158.

Step 6: 3-Methyl-2-(3-methylisothiazol-5-yl) butanoic acid

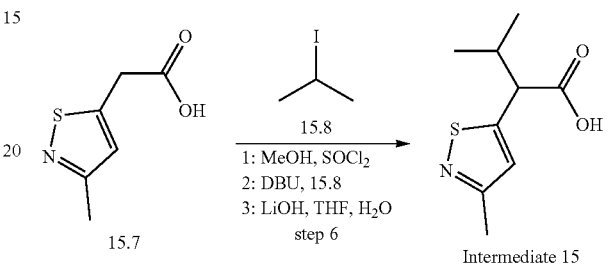

The title compound was generated from 2-(3-methylisothiazol-5-yl) acetic acid (compound 15.7) following procedures analogous to Steps 1-3 of Example 14.

Example 16

3-Methyl-2-(1-methyl-11H-1,2,3-triazol-4-yl) butanoic acid (Intermediate 16)

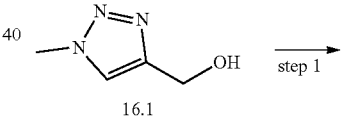

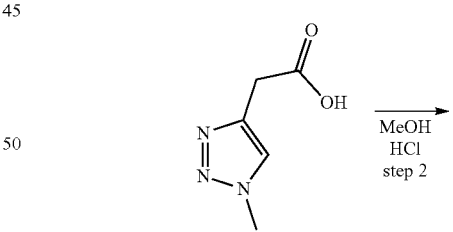

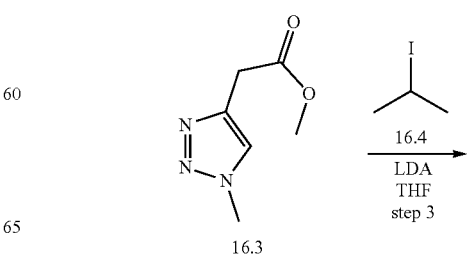

Step 3: Methyl 3-methyl-2-(1-methyl-1H-1,2,3-triazol-4-yl) butanoate

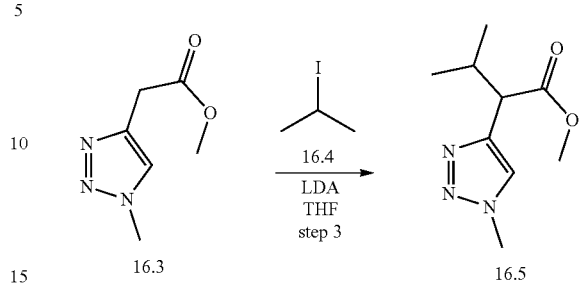

Under nitrogen, to a stirred solution of methyl 2-(1-methyltriazol-4-yl) acetate (compound 16.3, 323 mg, 2.08 mmol) in THF (5 mL) was added LDA (4.2 mL, 1M in THF) at −78° C. and the solution was stirred for 30 mins at −78° C. Then 2-iodopropane (compound 16.4, 708 mg, 4.16 mmol) was added at −78° C. The resulting solution was stirred at 25° C. for 16 hours and then quenched with water. The resulting solution was extracted with ethyl acetate and the combined organic layers were dried over anhydrous sodium sulfate and concentrated under vacuum. The residue was purified by flash chromatography on silica gel (gradient: 0%-5% MeOH/DCM) to afford the title compound 293 mg as a yellow oil. LCMS (ESI): [M+H]⁺=198.

Step 4: 3-Methyl-2-(1-methyl-1H-1,2,3-triazol-4-yl) butanoic acid

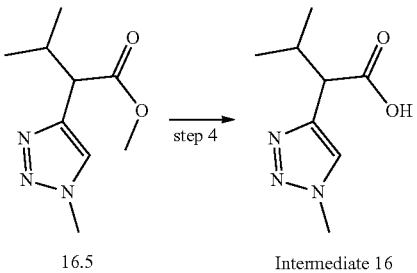

The title compound was generated from methyl 3-methyl-2-(1-methyl-1H-1,2,3-triazol-4-yl) butanoate (compound 16.5) following a procedure analogous to that set forth in Example 5, Step 3.

Example 17

(Methylsulfonyl)-L-proline (Intermediate 17)

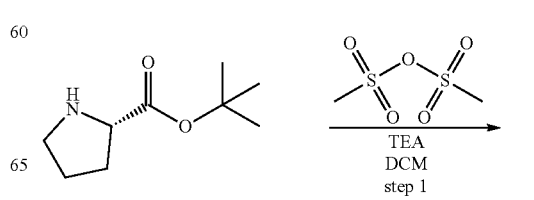

---

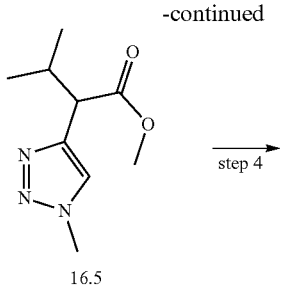

Step 1: 2-(1-methyl-1H-1,2,3-triazol-4-yl)acetic acid

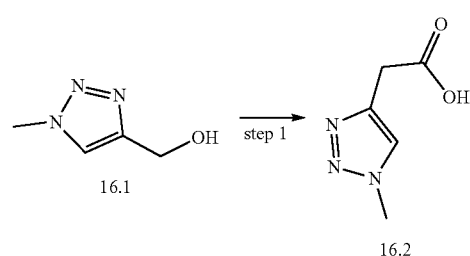

The title compound was generated from (1-methyl-1H-1,2,3-triazol-4-yl) methanol (compound 16.1) following procedures analogous to those set forth in Example 15, Step 3-5.

Step 2: Methyl 2-(1-methyl-1H-1,2,3-triazol-4-yl) acetate

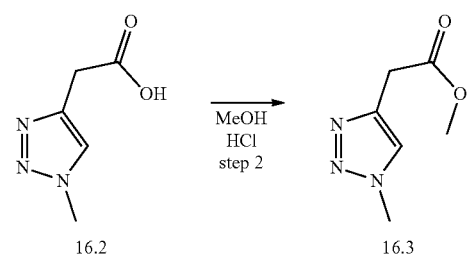

A solution of 2-(1-methyl-1H-1,2,3-triazol-4-yl) acetic acid (compound 16.2, 723 mg, 5.13 mmol) in concentrated HCl (10 mL) and MeOH (10 mL) was stirred at 60° C. for 1 hour. The solvent was concentrated under vacuum. The residue was purified by flash chromatography on silica gel (gradient: 0%-10% MeOH/DCM) to afford the title compound 323 mg (40% yield) as a yellow oil. LCMS (ESI): [M+H]⁺=156.

-continued

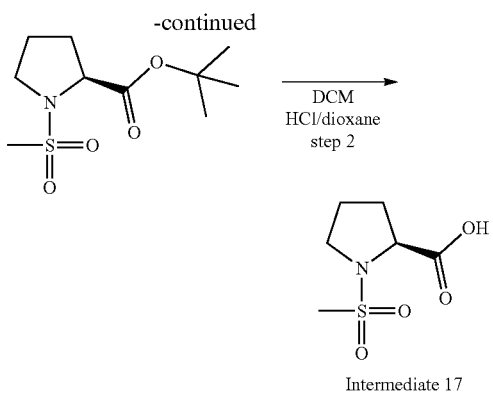

Step 1: tert-Butyl (methylsulfonyl)-L-prolinate

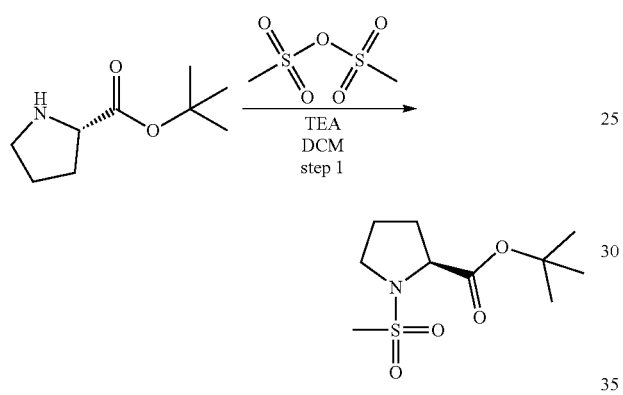

A solution of tert-butyl L-prolinate (1.05 g, 6.13 mmol), triethylamine (1.86 g, 18.4 mmol) and methanesulfonic anhydride (1.28 g, 7.36 mmol) in DCM (30.0 mL) was stirred at room temperature for 3 hours. The solvent was concentrated under vacuum. The residue was purified by flash chromatography on silica gel (gradient: 0%-50% ethyl acetate/petroleum ether) to afford the title compound 1.06 g (69.3% yield) as a white solid. LCMS (ESI): [M+H]$^+$=250. $^1$H NMR (300 MHz, Chloroform-d) δ 4.45-4.35 (m, 1H), 3.62-3.57 (m, 1H), 3.50-3.40 (m, 1H), 3.03 (s, 3H), 2.36-2.17 (m, 1H), 2.12-1.93 (m, 3H), 1.49 (s, 9H).

Step 2: (Methylsulfonyl)-L-proline

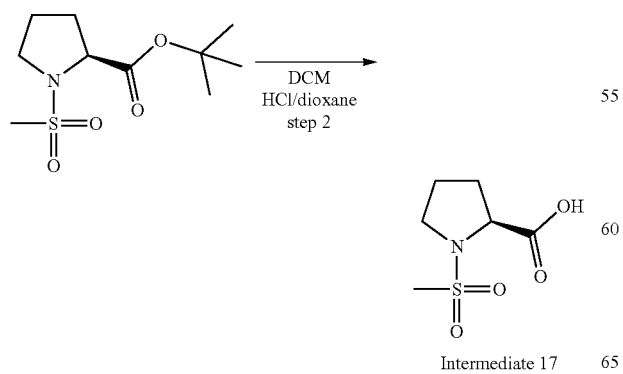

To a stirred solution of tert-butyl (methylsulfonyl)-L-prolinate (130 mg, 0.520 mmol) in DCM (1.00 mL) was added HCl/dioxane (1.00 mL, 4 M). The resulting solution was stirred at room temperature overnight. The solvent was concentrated under vacuum. The crude product was used for the next step without further purification. LCMS (ESI): [M+H]$^+$=194.

Examples 18-22—Intermediates 18-22

Intermediates 18-22, depicted in Table 8, were prepared using methods analogous to those described above for Intermediate 17.

TABLE 8

Intermediates 18-22

| Intermediate No. | Structure | LCMS (ESI): [M + H]$^+$ |
|---|---|---|
| Intermediate 18 | 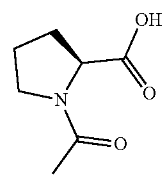 | 158 |
| Intermediate 19 | 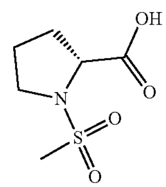 | 194 |
| Intermediate 20 | 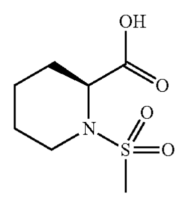 | 208 |
| Intermediate 21 | 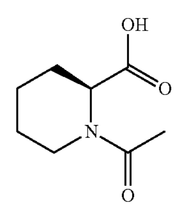 | 172 |
| Intermediate 22 | 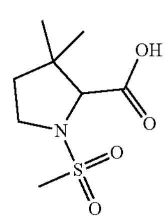 | 222 |

Example 23

(2S,4R, Z)—N',4-Dihydroxy-1-(3-methyl-2-(3-methylisoxazol-5-yl) butanoyl) pyrrolidine-2-carboximidamide (Intermediate 23)

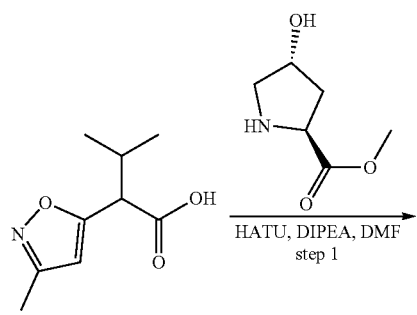

Intermediate 5

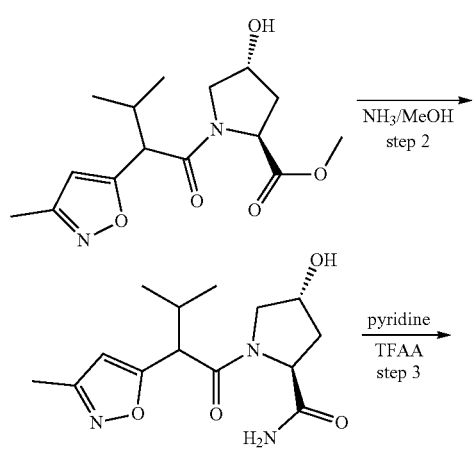

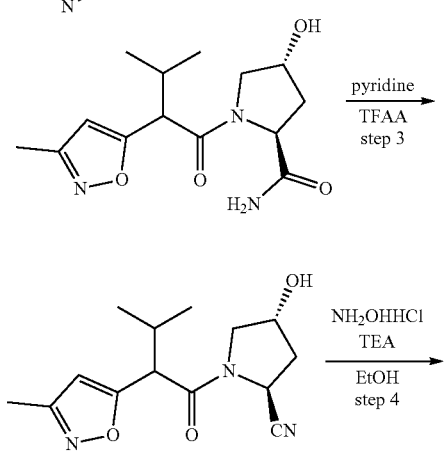

Intermediate 23

Step 1: Methyl (2S,4R)-4-hydroxy-1-(3-methyl-2-(3-methylisoxazol-5-yl) butanoyl) pyrrolidine-2-carboxylate

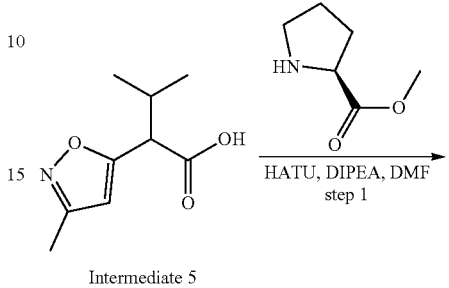

Intermediate 5

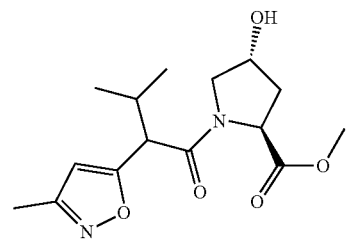

To a stirred solution of methyl (2S,4R)-4-hydroxypyrrolidine-2-carboxylate (800 mg, 5.51 mmol) in DMF (20 mL) was added 3-methyl-2-(3-methylisoxazol-5-yl) butanoic acid (Intermediate 5, 1.01 g, 5.51 mmol), HATU (2.52 g, 6.63 mmol) and DIPEA (2.14 g, 16.6 mmol). The resulting solution was stirred at room temperature for 1 hour. The reaction mixture was loaded directly onto a pre-packed C18 column (120 g, C18, 40-60 m, 60 Å, Agela Technologies) eluting with acetonitrile/water (0.1% FA) (5-100%), appropriate fractions were collected and concentrated under reduced pressure to afford the title compound 1.30 g (76% yield) as a colorless oil. LCMS (ESI): $[M+H]^+=311$.

Step 2: (2S,4R)-4-Hydroxy-1-(3-methyl-2-(3-methylisoxazol-5-yl) butanoyl) pyrrolidine-2-carboxamide

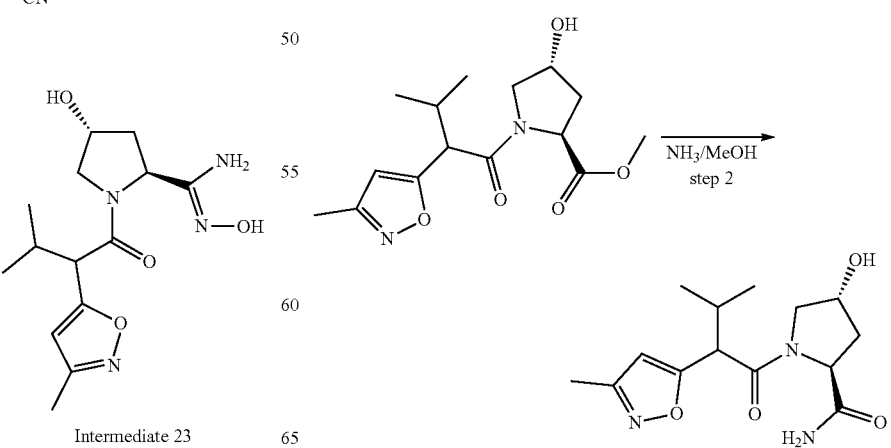

A solution of methyl (2S,4R)-4-hydroxy-1-[3-methyl-2-(3-methylisoxazol-5-yl) butanoyl] pyrrolidine-2-carboxylate (1.30 g, 4.19 mmol) in NH$_3$/MeOH (30 mL, 7M) was stirred at 70° C. for 15 hours. The resulting mixture was concentrated under vacuum to afford the title compound 1.20 g (crude). The crude product was used for next step without further purification. LCMS (ESI): [M+H]$^+$=296.

Step 3: (2S,4R)-4-Hydroxy-1-(3-methyl-2-(3-methylisoxazol-5-yl) butanoyl) pyrrolidine-2-carbonitrile

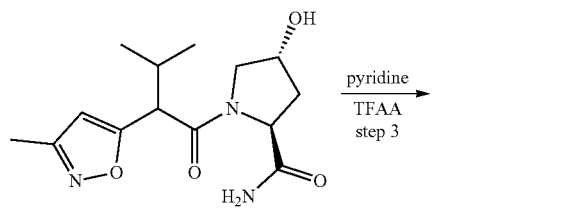

To a stirred solution of (2S,4R)-4-hydroxy-1-[3-methyl-2-(3-methylisoxazol-5-yl) butanoyl] pyrrolidine-2-carboxamide (1.20 g, 4.07 mmol) in pyridine (15 mL) was added TFAA (1.71 g, 8.14 mmol) dropwised at 0° C. over 10 minutes. The resulting solution was stirred at room temperature for 15 hours. The reaction mixture was diluted with water, extracted with ethyl acetate. The combined organic layers were dried over Na$_2$SO$_4$ and concentrated under vacuum. The residue was purified by flash chromatography on silica gel eluting with ethyl acetate/petroleum ether (0-60%) to afford the title compound 1.00 g (78% yield) as colorless oil. LCMS (ESI): [M+H]$^+$=278.

Step 4: (2S, 4R, Z)—N',4-Dihydroxy-1-(3-methyl-2-(3-methylisoxazol-5-yl)butanoyl)pyrrolidine-2-carboximidamide

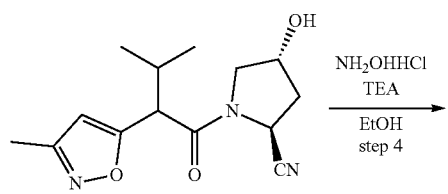

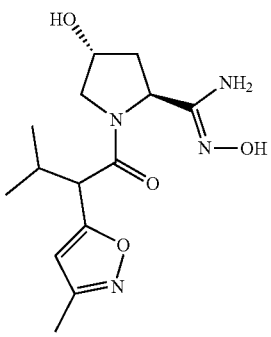

Intermediate 23

A solution of (2S,4R)-4-hydroxy-1-[3-methyl-2-(3-methylisoxazol-5-yl) butanoyl]pyrrolidine-2-carbonitrile (1.00 g, 3.61 mmol), NH$_2$OHHCl (519 mg, 7.52 mmol) and triethylamine (760 mg, 7.52 mmol) in ethanol (10 mL) was stirred at 90° C. for 2 hours. The solvent was evaporated under vacuum. The residue was purified by reverse phase flash chromatography on C18 column (80 g, C18, 25-35 m, 100 Å, Agela Technologies) eluting with CH$_3$CN/H$_2$O (0.1% FA) (0-50%) to afford the title compound 956 mg (85% yield) as a colorless oil. LCMS (ESI): [M+H]$^+$=311.

Example 24

(2S,4R, Z)—N,4-Dihydroxy-1-(3-methyl-2-(3-methylisoxazol-5-yl)butanoyl)pyrrolidine-2-carbimidoyl chloride (Intermediate 24)

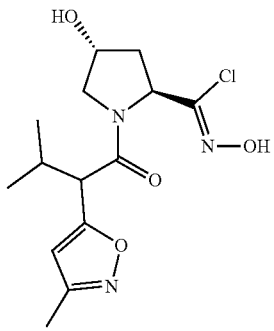 [SMILES: Cc1cc(C(C(=O)N2C[C@H](O)C[C@H]2/C(Cl)=N/O)C(C)C)on1]

To a stirred solution of (2S,4R)—N',4-dihydroxy-1-[3-methyl-2-(3-methylisoxazol-5-yl) butanoyl]pyrrolidine-2-carboxamidine (Intermediate 23, 150 mg, 0.480 mmol) in water (5 mL) and concentrated HCl (1.5 mL) was added NaNO$_2$ (167 mg, 2.42 mmol) at 0° C. The resulting solution was stirred at 0° C. for 3 hours. The solution was diluted with water and then adjusted the pH~7 with aqueous NaHCO$_3$. The mixture was extracted with ethyl acetate. The combined organic layers were dried over MgSO$_4$ and concentrated under vacuum to afford the title compound 150 mg (crude) as yellow solid. The crude product was used for the next step without further purification. LCMS (ESI): [M+H]$^+$=330.

Example 25

Methyl (2S,4R)-4-hydroxy-1-(3-methyl-2-(3-methylisoxazol-5-yl) butanoyl) pyrrolidine-2-carbimidate (Intermediate 25)

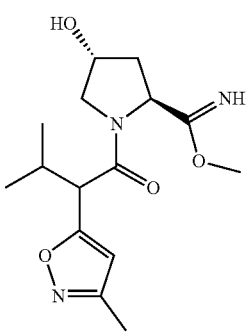 [SMILES: COC(=N)[C@@H]1C[C@@H](O)CN1C(=O)C(c1cc(C)no1)C(C)C]

Under nitrogen, to a stirred solution of (2S,4R)-4-hydroxy-1-(3-methyl-2-(3-methylisoxazol-5-yl) butanoyl) pyrrolidine-2-carbonitrile (Example 23, step 3, 340 mg, 1.23 mmol) in methyl alcohol (10 mL) was added MeONa (221 mg, 4.18 mmol) at 0° C. The resulting solution was stirred for 12 hours at room temperature. The reaction was quenched with water and extracted with ethyl acetate. The combined organic layer was dried over anhydrous $Na_2SO_4$ and concentrated under vacuum to afford the title compound 325 mg (crude) as yellow oil. The crude product was used for next step without further purification. LCMS (ESI): $[M+H]^+=310$.

Example 26

5-(4-(1,1-Dimethoxyethyl) phenyl)-4-methylthiazole (Intermediate 26)

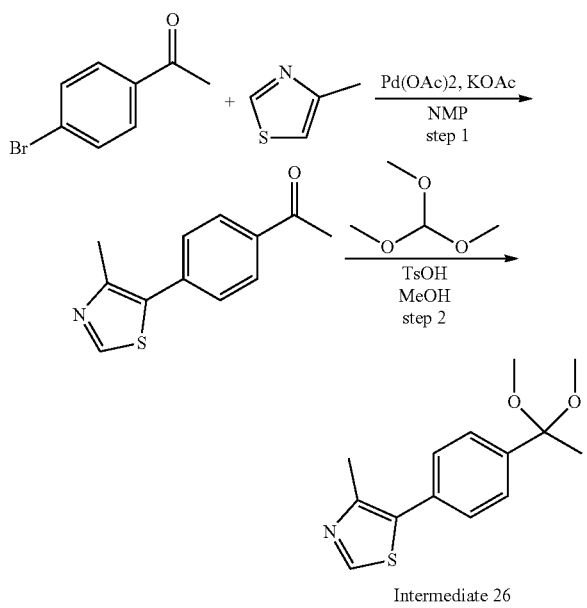

Step 1: 1-(4-(4-Methylthiazol-5-yl) phenyl) ethan-1-one

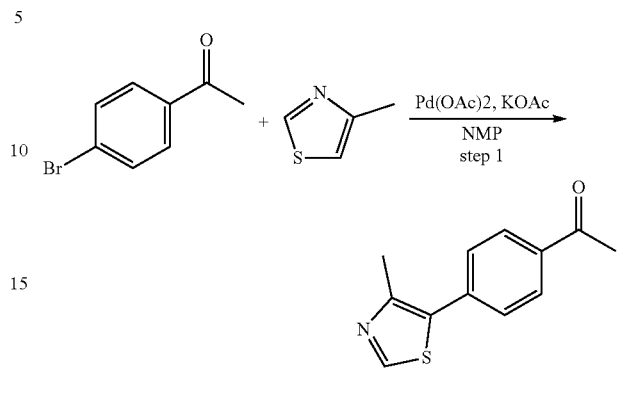

Under nitrogen, a solution of 1-(4-bromophenyl) ethanone (2.00 g, 10.0 mmol), 4-methylthiazole (2.00 g, 20.2 mmol), $Pd(OAc)_2$ (224 mg, 1 mmol) and KOAc (2.00 g, 20.4 mmol) in NMP (15 mL) was stirred at 110° C. for 3 hours. The resulting solution was diluted with DCM. The solids were filter out. The filtrate was concentrated under vacuum. The residue was purified by reverse phase chromatography (gradient: 5-40% acetonitrile/water (0.1% FA)) to afford the title compound 1.7 g (78% yield) as a brown solid. LCMS (ESI): $[M+H]^+=218$.

Step 2: 5-(4-(1,1-Dimethoxyethyl) phenyl)-4-methylthiazole

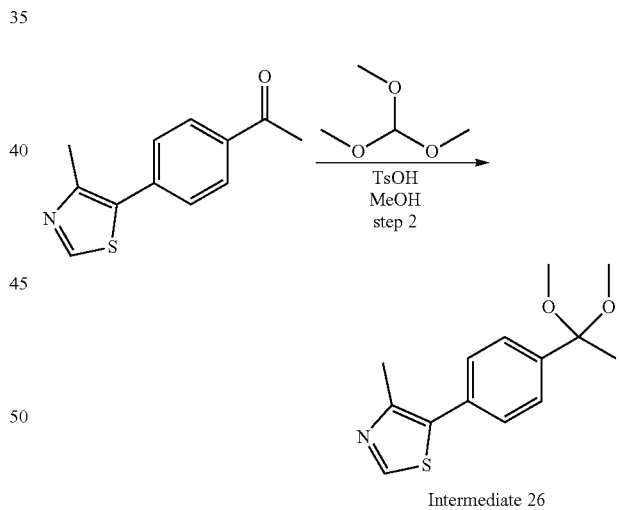

A solution of 1-(4-(4-methylthiazol-5-yl) phenyl) ethan-1-one (1.80 g, 8.28 mmol), trimethoxymethane (1.76 g, 16.6 mmol) and TsOH (71.3 mg, 0.410 mmol) in methyl alcohol (10 mL) was stirred at 70° C. for 8 hours. Then the reaction was quenched with MeONa/MeOH (10 mL, 30% wt) at room temperature. The solvent was concentrated under vacuum. The residue was diluted with water and extracted with ethyl acetate. The combined organic layers were dried over $MgSO_4$ and concentrated under reduce pressure. The residue was purified by chromatography on silica gel (gradient: 0-20% ethyl acetate/petroleum ether) to afford the title compound 1.96 g (90% yield) as colorless oil. LCMS (ESI):

[M+H]+=264. 1H NMR (400 MHz, DMSO-d6) δ 9.00 (s, 1H), 7.56-7.46 (m, 4H), 3.11 (s, 6H), 2.48 (s, 3H), 1.49 (s, 3H).

Examples 27-29—Intermediates 27-29

Intermediates 27-29, depicted in Table 9, were prepared using methods analogous to those described above for Intermediate 26.

TABLE 9

| Intermediates 27-29 | | |
|---|---|---|
| Intermediate No. | Structure | LCMS (ESI): [M + H]+/HNMR |
| Intermediate 27 | | 1H NMR (400 MHz, DMSO-d6) δ 7.60-7.52 (m, 2H), 7.41-7.33 (m, 2H), 3.07 (s, 6H), 1.44 (s, 3H). |
| Intermediate 28 | | No analytical data, crude was used for next step. |
| Intermediate 29 | | No analytical data, crude was used for next step. |

Example 30

(5R)-2-((4R)-4-Hydroxypyrrolidin-2-yl)-5-methyl-5-(4-(4-methylthiazol-5-yl) phenyl)-1,5-dihydro-4H-imidazol-4-one hydrochloride (Intermediate 30)

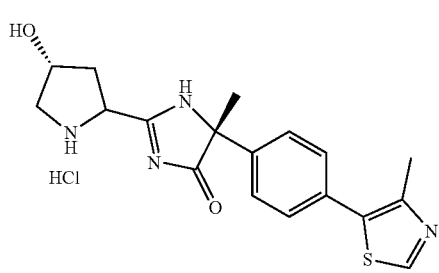 [SMILES: Cc1ncsc1-c1ccc([C@@]2(C)NC(C3C[C@@H](O)CN3)=NC2=O)cc1 ; Cl]

Intermediate 30 was generated from (R)-2-amino-2-(4-bromophenyl) propanoate (Intermediate 2, step 3 of Example 2, the slower peak) following procedures analogous to those used to produce Intermediate 12.

Example 91

(2S,4R)—N-(2-(2-(3',6'-bis(dimethylamino)-3-oxo-3H-spiro[isobenzofuran-1,9'-xanthene]-5-carboxamido)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide (FP Probe)

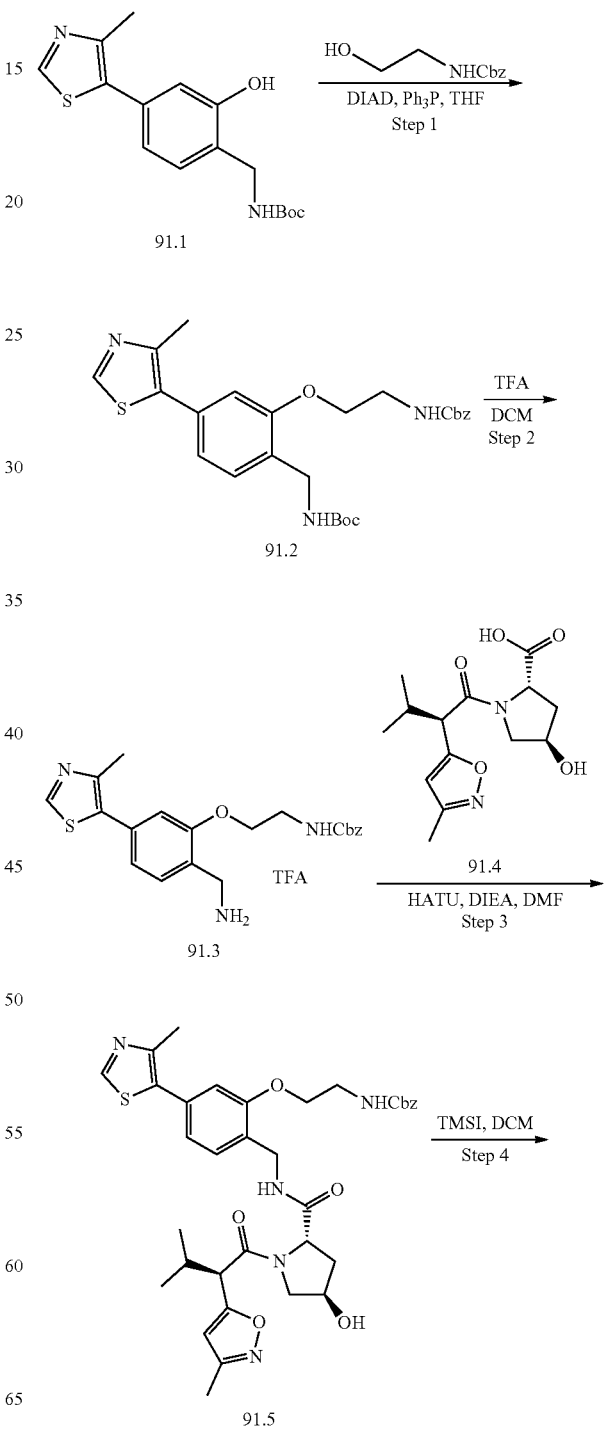

511
-continued

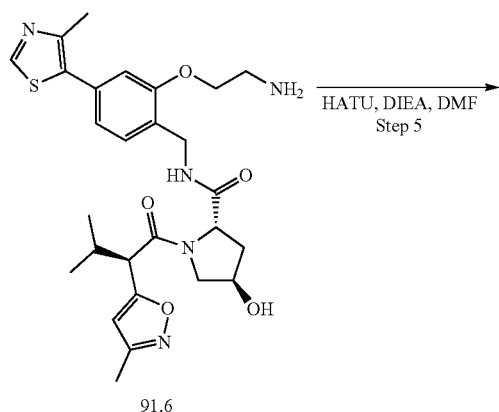

91.6

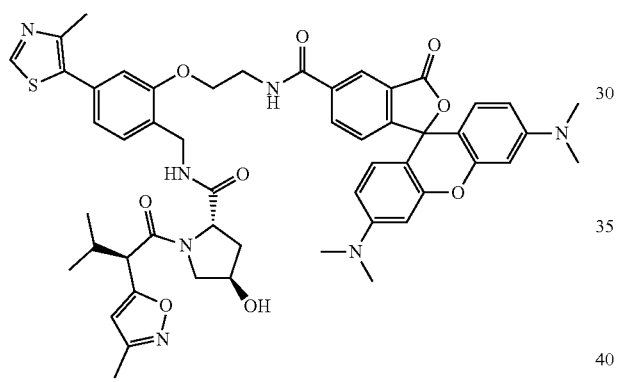

Step 1: tert-butyl (2-(2-(((benzyloxy)carbonyl)amino)ethoxy)-4-(4-methylthiazol-5-yl)benzyl)carbamate

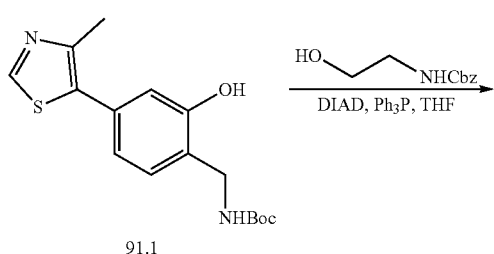

91.1

512
-continued

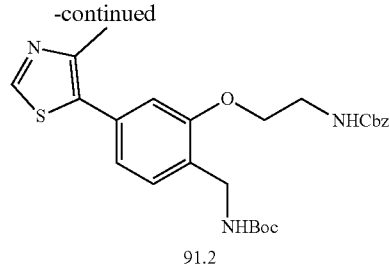

91.2

To a stirred solution of benzyl 2-hydroxyethylcarbamate (182.8 mg, 0.940 mmol), tert-butyl (2-hydroxy-4-(4-methylthiazol-5-yl)benzyl)carbamate (compound 91.1, 200.0 mg, 0.6200 mmol) and Ph$_3$P (245.58 mg, 0.940 mmol) in THF (10 mL) was added DIAD (189.3 mg, 0.940 mmol), at 20° C. After the mixture was stirred for 12 hours, TLC (10% MeOH in DCM, R$_f$=0.5) indicated the reaction was completed and the starting materials were consumed. The reaction solvent was removed under reduced pressure and the residue was purified by flash chromatography on silica gel (0-10% MeOH in DCM) to give tert-butyl (2-(2-(((benzyloxy)carbonyl)amino)ethoxy)-4-(4-methylthiazol-5-yl)benzyl)carbamate (compound 91.2, 200 mg, 64%) as a yellow oil. LCMS: RT (220/254 nm)=0.909 min, [M+Na]+520.0, Method=M.

Step 2: TFA salt of benzyl (2-(2-(aminomethyl)-5-(4-methylthiazol-5-yl)phenoxy)ethyl)carbamate

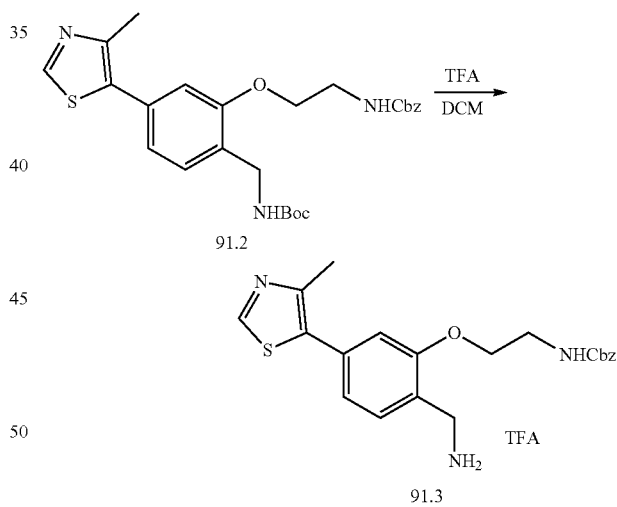

To a solution of tert-butyl (2-(2-(((benzyloxy)carbonyl)amino)ethoxy)-4-(4-methylthiazol-5-yl)benzyl)carbamate (compound 91.2, 200.0 mg, 0.4000 mmol) in DCM (4.0 mL) was added TFA (1.0 mL, 13.46 mmol). The reaction solution was stirred at 20° C. for 2 hours. LCMS: R$_T$=0.755 min, [M+H]$^+$ 398.1, Method=M, showed 54% of desired product. The solution was concentrated in vacuo to remove the solvent, the residue was purified by prep-HPLC (Xtimate C18 150*25 mm*5 um, acetonitrile 18-48/0.225% FA in water) to afford the TFA salt of benzyl (2-(2-(aminomethyl)-5-(4-methylthiazol-5-yl)phenoxy)ethyl)carbamate (compound 91.3, 60 mg, 29.2%) as a white solid. LCMS: RT (220/254 nm)=0.768 min, [M+H]+398.1, Method=M.

513

Step 3: benzyl (2-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)ethyl)carbamate

514

Step 4: (2S,4R)—N-(2-(2-aminoethoxy)-4-(4-methylthiazol-5-yl)benzyl)-4-hydroxy-1-((R)-3-methyl-2-(3-methylisoxazol-5-yl)butanoyl)pyrrolidine-2-carboxamide

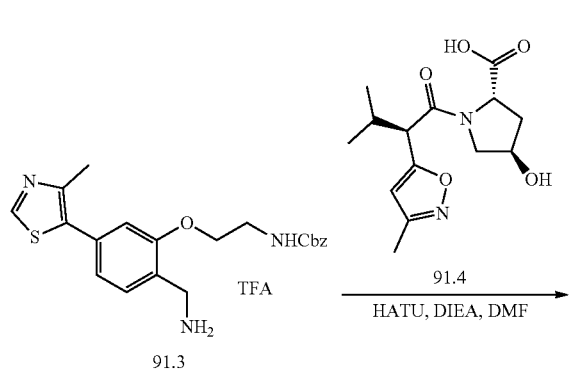

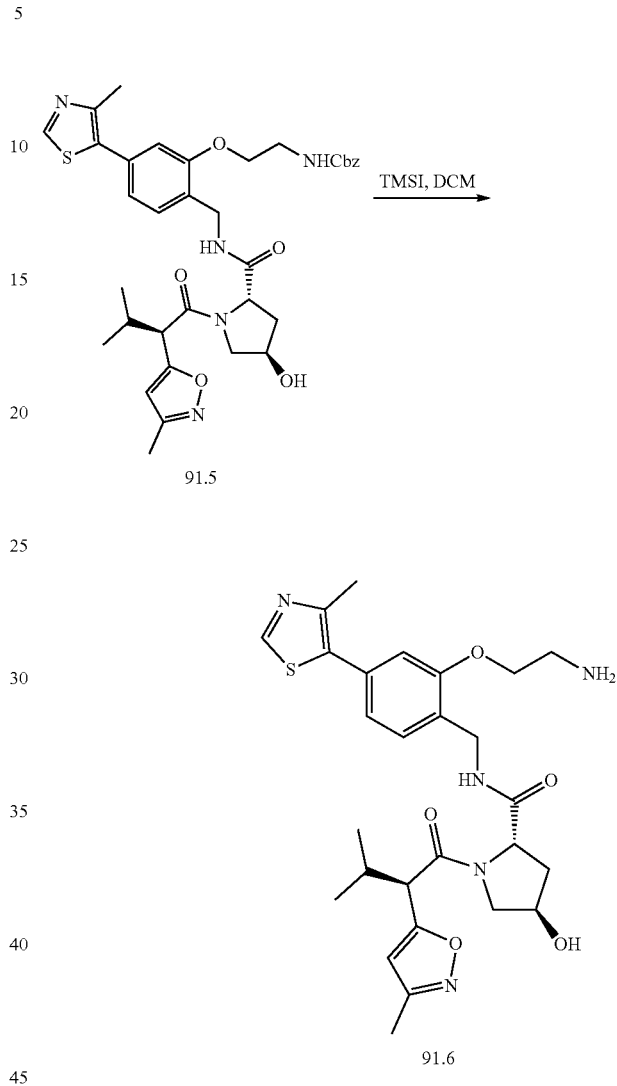

To a solution of (2S,4R)-4-hydroxy-1-((R)-3-methyl-2-(3-methylisoxazol-5-yl)butanoyl)pyrrolidine-2-carboxylic acid (compound 91.4, 30.12 mg, 0.1000 mmol) in anhydrous DMF (5.0 mL) was added DIEA (30.32 mg, 0.2300 mmol) and HATU (59.47 mg, 0.1600 mmol). After the solution was stirred at 20° C. for 15 minutes, then the TFA salt of benzyl (2-(2-(aminomethyl)-5-(4-methylthiazol-5-yl)phenoxy)ethyl)carbamate (compound 91.3, 40.0 mg, 0.0800 mmol) was added. The resulting reaction solution was stirred at 20° C. for 16 hours. LCMS: $R_T$=0.873 min, [M+H]$^+$ 676.2, Method=M, showed 71% of desired product. The mixture was purified by prep-HPLC (Xtimate C18 150*25 mm*5 μm, acetonitrile 20-50/0.225% FA in water) to afford benzyl (2-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)ethyl)carbamate (compound 91.5, 33 mg, 61.8%) as a white solid. LCMS: RT (220/254 nm)=0.828 min, [M+Na]+698.1, Method=M.

To a solution of benzyl (2-(2-(((2S,4R)-4-hydroxy-1-((R)-3-methyl-2-(3-methylisoxazol-5-yl)butanoyl)pyrrolidine-2-carboxamido)methyl)-5-(4-methylthiazol-5-yl)phenoxy)ethyl)carbamate (compound 91.5, 25.0 mg, 0.0400 mmol) in anhydrous DCM (4 mL) was added TMSI (74.02 mg, 0.3700 mmol). The reaction mixture was stirred at 20° C. for 2 hours. LCMS: $R_T$=0.682 min, [M+Na]$^+$ 564.0, Method=M, showed 54% of desired product. MeOH (4.0 mL) was added to quench the reaction, and the mixture was stirred at 20° C. for another 0.5 hours. The solvent was removed in vacuo, and the residue was diluted with EtOAc (15 mL) and aq. NaHCO$_3$ solution (10 mL), and extracted with EtOAc/MeOH (15 mL×5). The combined organic layers were dried over Na$_2$SO$_4$, filtered, and concentrated in vacuo to afford (2S,4R)—N-(2-(2-aminoethoxy)-4-(4-methylthiazol-5-yl)benzyl)-4-hydroxy-1-((R)-3-methyl-2-(3-methylisoxazol-5-yl)butanoyl)pyrrolidine-2-carboxamide (compound 91.6, 20 mg, 44.9%) as a brown oil. LCMS: RT (220/254 nm)=0.695 min, [M+Na]+564.1, Method=M.

515

Step 5: (2S,4R)—N-(2-(2-(3',6'-bis(dimethylamino)-3-oxo-3H-spiro[isobenzofuran-1,9'-xanthene]-5-carboxamido)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide (FP Probe)

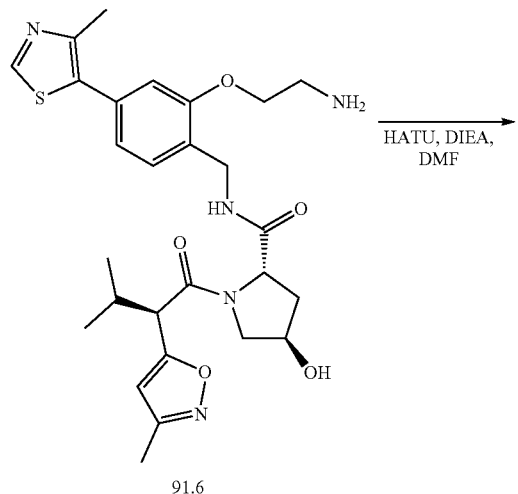

91.6

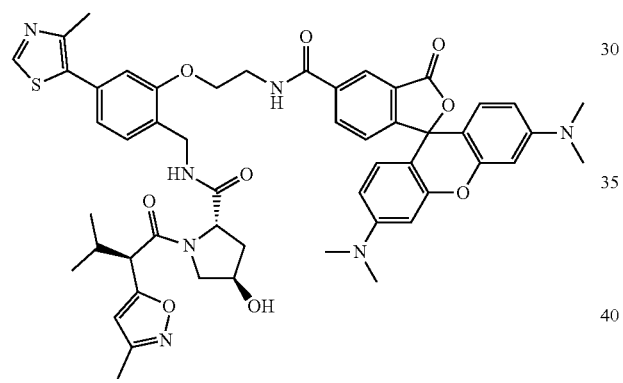

To a solution of 3',6'-bis(dimethylamino)-3-oxo-spiro[isobenzofuran-1,9'-xanthene]-5-carboxylic acid (9.54 mg, 0.020 mmol) in anhydrous DCM (5 mL) was added DIEA (9.54 mg, 0.0700 mmol) and HATU (10.53 mg, 0.0300 mmol). The mixture was stirred at 20° C. for 15 minutes, then (2S,4R)—N-(2-(2-aminoethoxy)-4-(4-methylthiazol-5-yl)benzyl)-4-hydroxy-1-((R)-3-methyl-2-(3-methylisoxazol-5-yl)butanoyl)pyrrolidine-2-carboxamide (compound 91.6, 10.0 mg, 0.0200 mmol) was added. The reaction mixture was stirred at 20° C. for 2 hours. LCMS: $R_T$=3.061 min, [M+H]$^+$ 953.9, Method=N, showed 43% of desired product. The mixture was concentrated and purified by prep-TLC (9% MeOH in DCM, $R_f$=0.2) to afford the crude product, which was purified again by prep-HPLC (Xtimate C18 150*25 mm*5 um, acetonitrile 30-60/0.225% FA in water) to afford (2S,4R)—N-(2-(2-(3',6'-bis(dimethylamino)-3-oxo-3H-spiro[isobenzofuran-1,9'-xanthene]-5-carboxamido)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide (4.2 mg, 23.4%) as a purple solid. LCMS: RT (220/254 nm)=0.845 min, [M+H]+ 955.3, Method=M.

516

Examples 101.1, 101.2, 101.3 and 101.4

N-((2S)-1-((4R)-2-(5-(4-Bromophenyl)-5-methyl-4-oxo-4,5-dihydro-1H-imidazol-2-yl)-4-hydroxypyrrolidin-1-yl)-3,3-dimethyl-1-oxobutan-2-yl)acetamide (4 Single Stereoisomers)

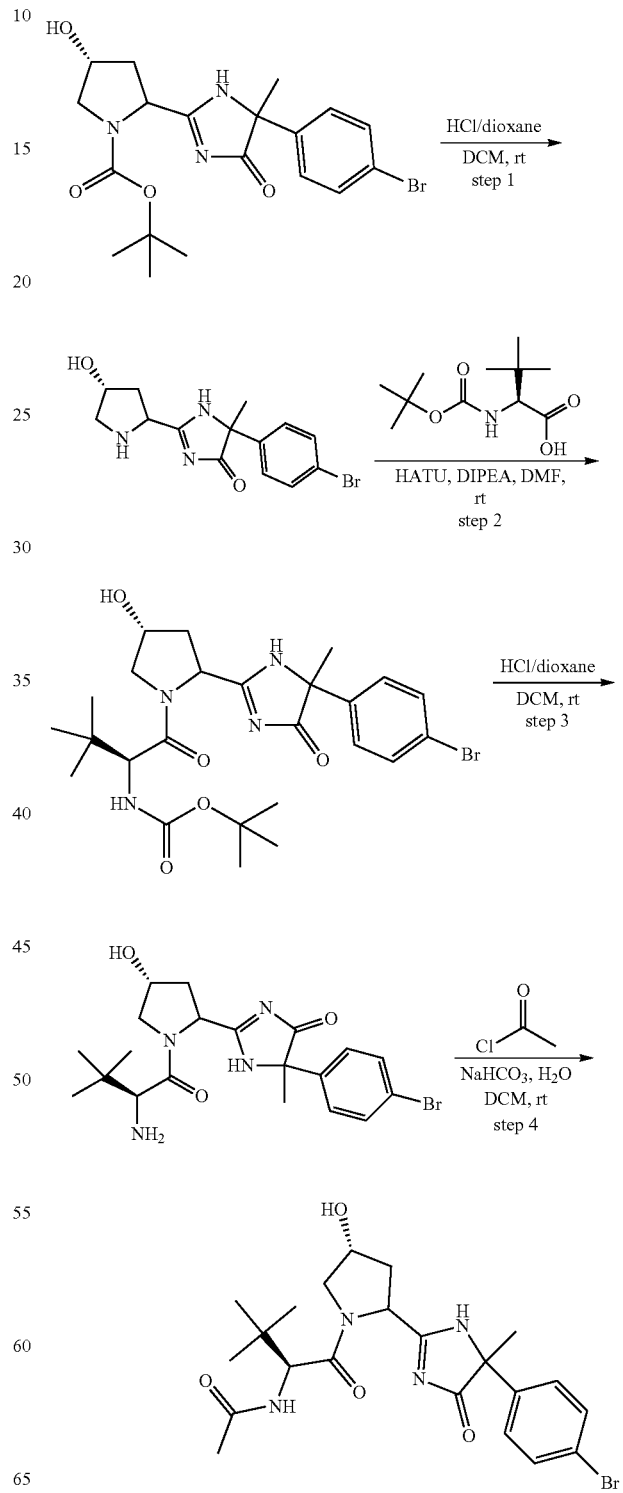

Step 1: 5-(4-Bromophenyl)-2-((4R)-4-hydroxypyrrolidin-2-yl)-5-methyl-1,5-dihydro-4H-imidazol-4-one

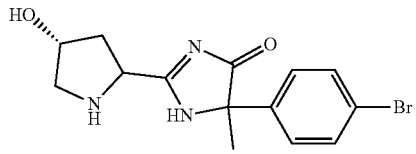 [SMILES: CC1(c2ccc(Br)cc2)NC(C2C[C@@H](O)CN2)=NC1=O]

To a stirred solution of Intermediate 3 (500 mg, 1.14 mmol) in DCM (10 mL) was added HCl/dioxane (4M) (5 mL). The resulting solution was stirred at room temperature for 2 hours and concentrated under reduced pressure. The residue was dissolved in DCM/MeOH (10 mL/10 mL), and then triethylamine (3 mL) was added. The resulting solution was concentrated under reduced pressure. The residue was purified by flash chromatography on silica gel (gradient: 0%-20% MeOH/DCM) to yield 340 mg (88%) of the title compound as a light yellow solid. LCMS (ESI): $R_T$ (min) =0.827, [M+H]$^+$=338/340, method=F.

Step 2: tert-Butyl ((2S)-1-((4R)-2-(5-(4-bromophenyl)-5-methyl-4-oxo-4,5-dihydro-1H-imidazol-2-yl)-4-hydroxypyrrolidin-1-yl)-3,3-dimethyl-1-oxobutan-2-yl)carbamate

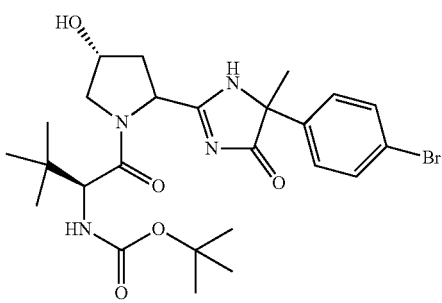 [SMILES: CC(C)(C)OC(=O)N[C@H](C(=O)N1C[C@H](O)CC1C1=NC(=O)C(C)(c2ccc(Br)cc2)N1)C(C)(C)C]

A solution of 5-(4-bromophenyl)-2-((4R)-4-hydroxypyrrolidin-2-yl)-5-methyl-1,5-dihydro-4H-imidazol-4-one (300 mg, 0.888 mmol), (S)-2-((tert-butoxycarbonyl)amino)-3,3-dimethylbutanoic acid (250 mg, 1.08 mmol), HATU (510 mg, 1.34 mmol) and DIPEA (290 mg, 2.24 mmol) in DMF (10 mL) was stirred at room temperature for 0.5 hours. The reaction solution was loaded directly onto a pre-packed C18 column (solvent gradient: 0-100% ACN in water (0.05% NH$_4$HCO$_3$)) to yield 350 mg (72%) of the title compound as an off-white solid. LCMS (ESI): $R_T$(min)=1.19, [M+H]$^+$=551/553, method=F.

Step 3: 2-((4R)-1-((S)-2-Amino-3,3-dimethylbutanoyl)-4-hydroxypyrrolidin-2-yl)-5-(4-bromophenyl)-5-methyl-1,5-dihydro-4H-imidazol-4-one hydrochloride

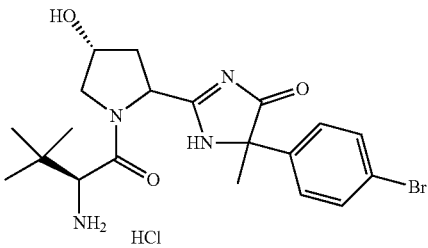 [SMILES: CC1(c2ccc(Br)cc2)NC(C2C[C@@H](O)CN2C(=O)[C@@H](N)C(C)(C)C)=NC1=O ; Cl]

To a stirred solution of tert-butyl ((2S)-1-((4R)-2-(5-(4-bromophenyl)-5-methyl-4-oxo-4,5-dihydro-1H-imidazol-2-yl)-4-hydroxypyrrolidin-1-yl)-3,3-dimethyl-1-oxobutan-2-yl)carbamate (300 mg, 0.554 mmol) in DCM (10 mL) was added HCl/dioxane (5 mL, 4M). The resulting solution was stirred at room temperature for 2 hours. The resulting mixture was concentrated under reduced pressure. The residue was purified by flash chromatography on silica gel (gradient: 0%-20% MeOH/DCM) to yield 200 mg (81%) of the title compound as a light yellow solid. LCMS (ESI): $R_T$ (min)=0.965, [M+H]$^+$=451/453, method=F.

Step 4: N-((2S)-1-((4R)-2-(5-(4-Bromophenyl)-5-methyl-4-oxo-4,5-dihydro-1H-imidazol-2-yl)-4-hydroxypyrrolidin-1-yl)-3,3-dimethyl-1-oxobutan-2-yl)acetamide (2 single Stereoisomers: Example 101.1 and Example 101.2)

To a stirring solution of 2-((4R)-1-((S)-2-amino-3,3-dimethylbutanoyl)-4-hydroxypyrrolidin-2-yl)-5-(4-bromophenyl)-5-methyl-1,5-dihydro-4H-imidazol-4-one hydrochloride (200 mg, 0.409 mmol) and NaHCO$_3$ (2.23 g, 26.5 mmol) in DCM (20 mL) and H$_2$O (20 mL) was added acetyl chloride (520 mg, 6.62 mmol) at room temperature. The reaction mixture was stirred at room temperature for 1 hour. Phases were separated, and the aqueous phase was extracted with DCM. The combined organic layers were dried over anhydrous Na$_2$SO$_4$ and concentrated under reduced pressure. The residue was purified by prep-HPLC (Column: XBridge Prep C18 OBD column 19×150 mm 5 um; Mobile Phase A: water (10 mmol/L NH$_4$HCO$_3$), Mobile Phase B: ACN; Flow rate: 20 mL/min; Gradient: 20% B to 45% B in 10 min; 254, 220 nm) to yield 31.4 mg (14%) of Example 101.1 and 18.9 mg (9%) of Example 101.2 as white solids.

Analogous to method described for Examples 101.1 and 102.2, Example 101.3 (38.6 mg) and Example 101.4 (34.7 mg) were prepared from Intermediate 4.

Example 101.1: LCMS (ESI): $R_T$ (min)=1.36, [M+H]$^+$=493/495, method=J; $^1$H NMR (400 MHz, CDCl$_3$) δ 7.47-7.45 (m, 2H), 7.34-7.25 (m, 2H), 6.55-6.47 (m, 1H), 5.07 (d, J=8.8 Hz, 1H), 4.64-4.52 (m, 2H), 4.13 (d, J=11.2 Hz, 1H), 3.87-3.84 (m, 1H), 2.55 (d, J=14.1 Hz, 1H), 2.39-2.36 (m, 1H), 1.96 (s, 3H), 1.69 (s, 3H), 1.04 (s, 9H);

Example 101.2: LCMS (ESI): $R_T$ (min)=1.48, [M+H]$^+$=493/495, method=J; $^1$H NMR (400 MHz, CDCl$_3$) δ 10.28 (s, 1H), 7.51-7.41 (m, 5H), 5.29-5.26 (m, 1H), 4.66 (s, 1H), 4.52 (d, J=8.7 Hz, 1H), 4.33 (d, J=11.5 Hz, 1H), 3.67 (s, 1H), 3.03 (s, 1H), 2.29-2.27 (m, 1H), 1.73 (s, 3H), 1.60 (s, 3H), 1.03 (s, 9H).

Example 101.3: LCMS (ESI): $R_T$ (min)=1.37, [M+H]$^+$=493/495, method=J; $^1$H NMR (400 MHz, CDCl$_3$) δ 7.48 (s, 4H), 6.39 (d, J=7.9 Hz, 1H), 5.33 (s, 1H), 5.12 (d, J=8.8 Hz, 1H), 4.66-4.63 (m, 1H), 4.49 (d, J=8.1 Hz, 1H), 4.09 (d, J=11.1 Hz, 1H), 3.88-3.85 (m, 1H), 2.64 (d, J=14.2 Hz, 1H), 2.39-2.36 (m, 1H), 2.04 (s, 3H), 1.65 (s, 3H), 1.02 (s, 9H).

Example 101.4: LCMS (ESI): $R_T$ (min)=1.48, [M+H]$^+$=493/495, method=J; $^1$H NMR (400 MHz, CDCl$_3$) δ 10.22 (s, 1H), 7.66 (s, 1H), 7.44 (d, J=8.3 Hz, 2H), 7.32 (d, J=8.6 Hz, 2H), 5.34-5.31 (m, 1H), 4.67 (s, 1H), 4.50 (d, J=8.8 Hz, 1H), 4.39 (d, J=11.7 Hz, 1H), 3.60 (d, J=11.4 Hz, 1H), 3.01 (s, 1H), 2.29-2.26 (m, 1H), 2.02 (s, 3H), 1.66 (s, 3H), 0.89 (s, 9H).

Example 102.1

N-((2S)-1-((4R)-4-Hydroxy-2-(5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)acetamide (Single Stereoisomer)

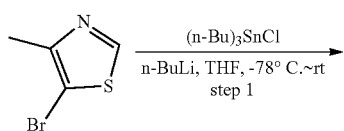

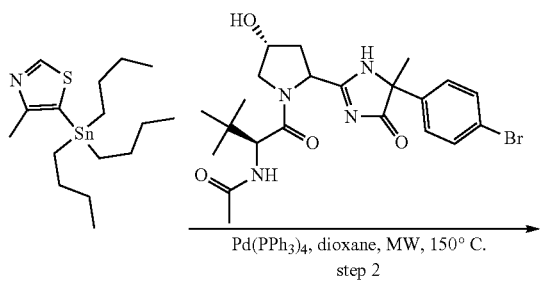

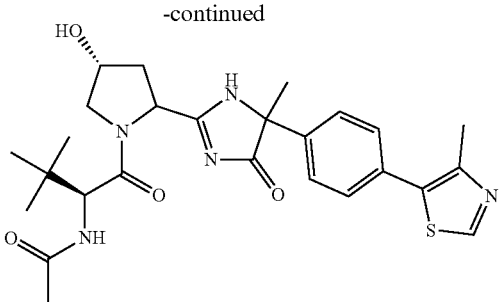

Step 1: 4-Methyl-5-(tributylstannyl)thiazole

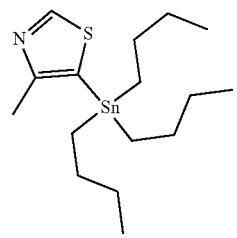 [SMILES: CCC[CH2][Sn]([CH2]CCC)([CH2]CCC)[c]1scnc1C]

To a −78° C. solution of 5-bromo-4-methylthiazole (1.50 g, 8.42 mmol) in THF (200 mL) was added butyllithium (6.7 mL, 2.5M in n-hexane) dropwise over 5 minutes with stirring. The reaction mixture was stirred at −78° C. for 0.5 hours and then tributylchlorostannane (3.29 g, 10.1 mmol) was added at −78° C. The resulting solution was allowed to warm to room temperature gradually and stirred for 16 hours. The reaction mixture was quenched with water, extracted with EtOAc. The combined organic layers were dried over anhydrous Na$_2$SO$_4$ and concentrated under reduced pressure. The residue was purified by flash chromatography on silica gel (gradient: 0%-5% ethyl acetate/petroleum ether) to yield 0.330 g (10%) of the title compound as a yellow oil. LCMS (ESI): $R_T$ (min)=1.57, [M+H]$^+$=390, method=J.

Step 2: N-((2S)-1-((4R)-4-Hydroxy-2-(5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)acetamide (Example 102.1)

A solution of N-((2S)-1-((4R)-2-(5-(4-bromophenyl)-5-methyl-4-oxo-4,5-dihydro-1H-imidazol-2-yl)-4-hydroxypyrrolidin-1-yl)-3,3-dimethyl-1-oxobutan-2-yl)acetamide (Example 101.4) (70.0 mg, 0.142 mmol), Pd(PPh$_3$)$_4$ (33.0 mg, 0.0290 mmol) and 4-methyl-5-(tributylstannyl)thiazole (138 mg, 0.355 mmol) in dioxane (4 mL) was stirred at 150° C. for 2 h in microwave. The reaction mixture was concentrated under reduced pressure. The residue was purified by reverse phase flash chromatography (solvent gradient: 5-50% ACN in water (0.1% FA)) to yield 6.10 mg (8%) of the title compound as a white solid. LCMS (ESI): $R_T$ (min)=2.49, [M+H]$^+$=512, method=J. $^1$H NMR (400 MHz, CDCl$_3$) δ 9.77 (s, 1H), 8.71 (s, 1H), 7.54-7.46 (m, 2H), 7.44-7.37 (m, 2H), 7.13 (s, 1H), 5.31-5.28 (m, 1H), 4.67 (s, 1H), 4.51 (d, J=8.7 Hz, 1H), 4.39 (d, J=11.6 Hz, 1H), 3.68-3.60 (m, 1H), 3.10-2.98 (m, 1H), 2.54 (s, 3H), 2.33-2.30 (m, 1H), 2.04 (s, 3H), 1.74 (s, 3H), 1.14-1.06 (m, 1H), 0.94 (s, 9H).

Examples 102.2 and 102.3

N-((2S)-1-((4R)-2-(5-(4-Bromophenyl)-5-methyl-4-oxo-4,5-dihydro-1H-imidazol-2-yl)-4-hydroxypyrrolidin-1-yl)-3,3-dimethyl-1-oxobutan-2-yl)acetamide (2 Single Stereoisomers)

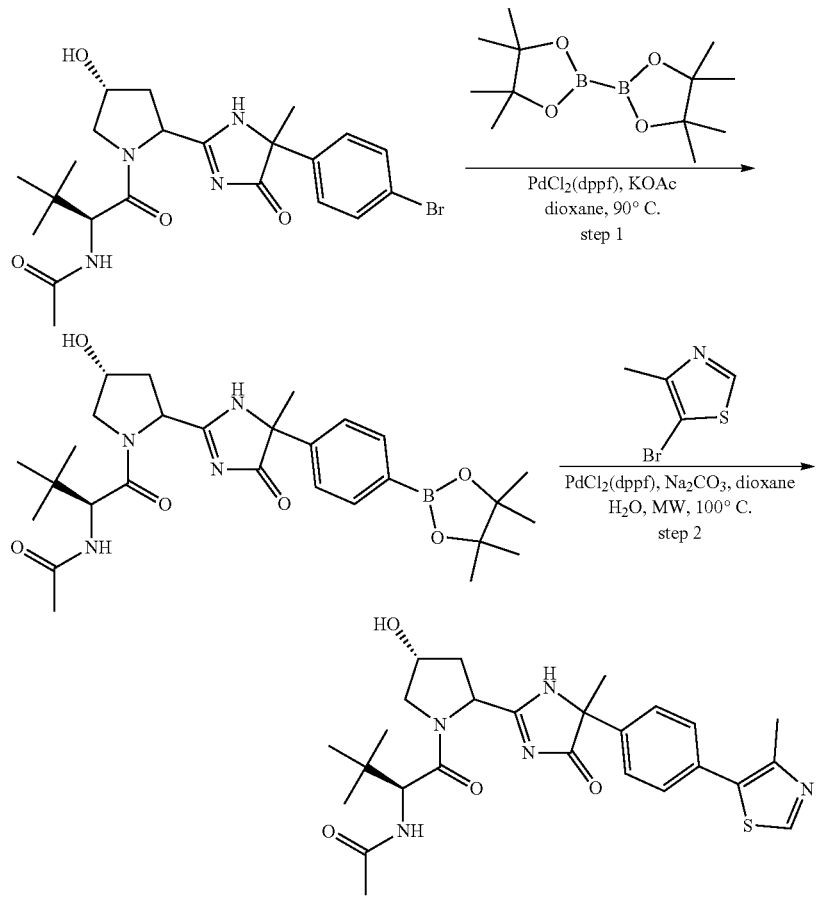

Step 1: N-((2S)-1-((4R)-4-Hydroxy-2-(5-methyl-4-oxo-5-(4-(4,4,5,5-tetramethyl-1,3,2-dioxaborolan-2-yl)phenyl)-4,5-dihydro-1H-imidazol-2-yl)pyrrolidin-1-yl)-3,3-dimethyl-1-oxobutan-2-yl)acetamide

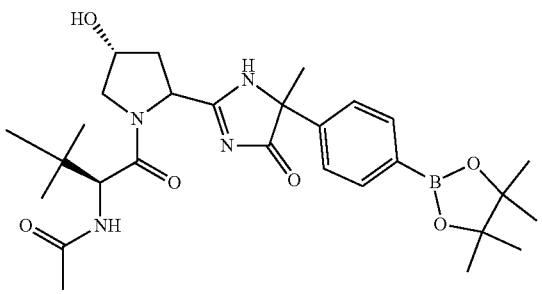 [SMILES: CC(=O)N[C@H](C(=O)N1C[C@H](O)CC1C1=NC(=O)C(C)(c2ccc(B3OC(C)(C)C(C)(C)O3)cc2)N1)C(C)(C)C]

A solution of N-((2S)-1-((4R)-2-(5-(4-bromophenyl)-5-methyl-4-oxo-4,5-dihydro-1H-imidazol-2-yl)-4-hydroxypyrrolidin-1-yl)-3,3-dimethyl-1-oxobutan-2-yl)acetamide (Example 101.2) (40.0 mg, 0.0810 mmol), 4,4,4',4',5,5,5',5'-octamethyl-2,2'-bi(1,3,2-dioxaborolane)(25.0 mg, 0.0980 mmol), PdCl$_2$(dppf) (13.0 mg, 0.0180 mmol) and KOAc (17.0 mg, 0.173 mmol) in dioxane (4 mL) was stirred at 95° C. for 16 hours. The reaction mixture was concentrated under reduced pressure. The residue was purified by flash chromatography on silica gel (gradient: 0%-10% MeOH/DCM) to yield 33.0 mg (75%) of the title compound as a gray solid. LCMS (ESI): R$_T$ (min)=1.11, [M+H]$^+$=541, method=J.

Step 2: N-((2S)-1-((4R)-4-Hydroxy-2-(5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)acetamide (2 Single Stereoisomers)

A solution of N-((2S)-1-((4R)-4-hydroxy-2-(5-methyl-4-oxo-5-(4-(4,4,5,5-tetramethyl-1,3,2-dioxaborolan-2-yl)phenyl)-4,5-dihydro-1H-imidazol-2-yl)pyrrolidin-1-yl)-3,3-dimethyl-1-oxobutan-2-yl)acetamide (33.0 mg, 0.0610 mmol), PdCl$_2$(dppf) (9.00 mg, 0.0120 mmol), Na$_2$CO$_3$ (13.0 mg, 0.123 mmol) and 5-bromo-4-methylthiazole (13.1 mg, 0.0740 mmol) in dioxane (10 mL) and water (1.5 mL) was stirred at 100° C. for 1 hour in microwave. The reaction mixture was concentrated under reduced pressure. The residue was purified by reverse phase flash chromatography (solvent gradient: 5-50% ACN in water (0.1% FA)) to yield 5.60 mg (18%) of Example 102.2 and 6.80 mg (22%) of Example 102.3 as white solids.

Example 102.2: LCMS (ESI): $R_T$ (min)=2.03, [M+H]$^+$=512, method=A; $^1$H NMR (400 MHz, CDCl$_3$) δ 8.70 (d, J=3.3 Hz, 1H), 7.51 (d, J=8.2 Hz, 2H), 7.47-7.41 (m, 2H), 6.21 (d, J=8.0 Hz, 1H), 5.22 (d, J=10.4 Hz, 1H), 4.66 (s, 1H), 4.54 (d, J=9.7 Hz, 1H), 4.14 (d, J=11.0 Hz, 1H), 3.88 (d, J=10.6 Hz, 1H), 2.68 (s, 1H), 2.54 (s, 3H), 2.43 (s, 1H), 1.93 (d, J=12.5 Hz, 3H), 1.78 (s, 3H), 1.66 (s, 1H), 1.28 (s, 1H), 1.06 (d, J=4.9 Hz, 9H).

Example 102.3: LCMS (ESI): $R_T$ (min)=2.57, [M+H]$^+$=512, method=J. $^1$H NMR (400 MHz, CDCl$_3$) δ 10.15 (s, 1H), 8.70 (s, 1H), 7.66-7.58 (m, 2H), 7.54 (d, J=8.8 Hz, 1H), 7.46-7.38 (m, 2H), 5.33-5.30 (m, 1H), 4.67 (d, J=3.3 Hz, 1H), 4.53 (d, J=8.9 Hz, 1H), 4.38 (d, J=11.7 Hz, 1H), 3.66-3.63 (m, 1H), 3.15-3.05 (m, 1H), 2.52 (s, 3H), 2.30-2.28 (m, 1H), 1.70 (s, 3H), 1.66 (s, 4H), 1.05 (s, 9H).

Examples 103.1, 103.2, 103.3 and 103.4

5-(4-Bromophenyl)-2-((4R)-4-hydroxy-1-(3-methyl-2-(3-methylisoxazol-5-yl)butanoyl)pyrrolidin-2-yl)-5-methyl-1,5-dihydro-4H-imidazol-4-one (4 Single Stereoisomers)

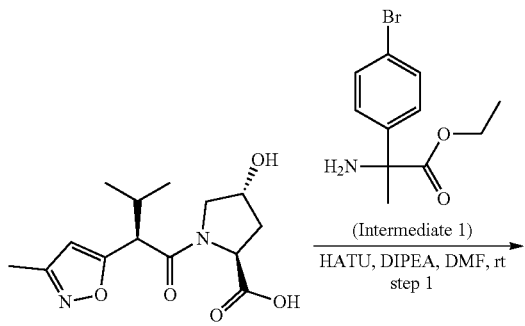

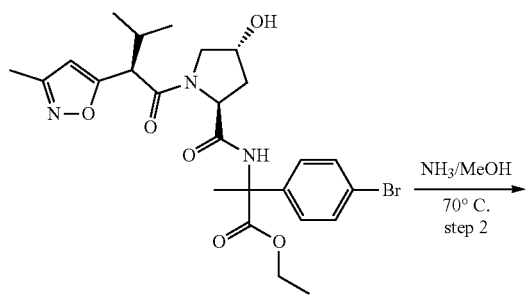

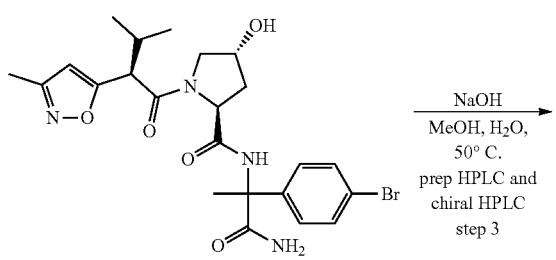

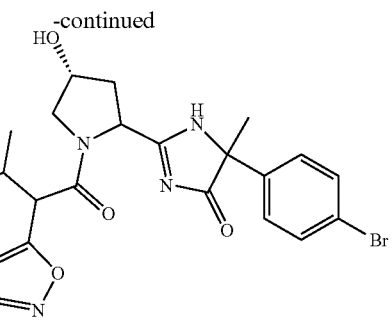

Step 1: Ethyl 2-(4-bromophenyl)-2-((2S,4R)-4-hydroxy-1-((R)-3-methyl-2-(3-methylisoxazol-5-yl)butanoyl)pyrrolidine-2-carboxamido)propanoate

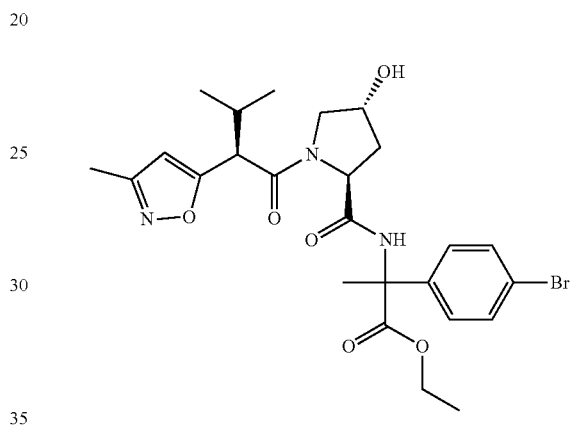

A solution of intermediate 1 (50.0 mg, 0.180 mmol), (2S,4R)-4-hydroxy-1-((R)-3-methyl-2-(3-methylisoxazol-5-yl)butanoyl)pyrrolidine-2-carboxylic acid (Intermediate 11, 54.4 mg, 0.180 mmol), HATU (140 mg, 0.368 mmol) and DIPEA (118 mg, 0.915 mmol) in DMF (4 mL) was stirred at room temperature for 1 hour. The residue was purified by reverse phase flash chromatography (solvent gradient: 5-50% ACN in water (0.1% NH$_4$HCO$_3$)) to yield 65.0 mg (64.3%) of the title compound as a white solid. LCMS (ESI): $R_T$ (min)=1.18, [M+H]+=550/552, method=F.

Step 2: (2S,4R)—N-(1-Amino-2-(4-bromophenyl)-1-oxopropan-2-yl)-4-hydroxy-1-((R)-3-methyl-2-(3-methylisoxazol-5-yl)butanoyl)pyrrolidine-2-carboxamide

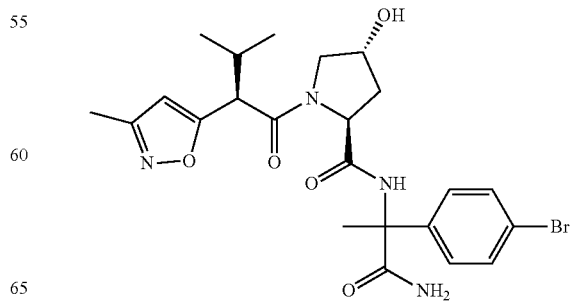

A solution of ethyl 2-(4-bromophenyl)-2-((2S,4R)-4-hydroxy-1-((R)-3-methyl-2-(3-methylisoxazol-5-yl)butanoyl)pyrrolidine-2-carboxamido)propanoate (65.0 mg, 0.120 mmol) in ammonia methanol solution (7M solution in MeOH) (20 mL) was stirred at 70° C. for 48 hours. The reaction solution was concentrated under reduced pressure to yield 50.0 mg (81%) of the title compound as a light yellow solid. LCMS (ESI): $R_T$ (min)=1.12, [M+H]$^+$=521/523, method=J.

Step 3: 5-(4-Bromophenyl)-2-((4R)-4-hydroxy-1-(3-methyl-2-(3-methylisoxazol-5-yl)butanoyl)pyrrolidin-2-yl)-5-methyl-1,5-dihydro-4H-imidazol-4-one (4 Single Stereoisomers)

A solution of (2S,4R)—N-(1-amino-2-(4-bromophenyl)-1-oxopropan-2-yl)-4-hydroxy-1-(3-methyl-2-(3-methylisoxazol-5-yl)butanoyl)pyrrolidine-2-carboxamide (50.0 mg, 0.0960 mmol) and NaOH (12.0 mg, 0.300 mmol) in MeOH (4 mL) and H$_2$O (4 mL) was stirred at 50° C. for 5 hours. The reaction mixture was concentrated under reduced pressure and the residue was purified by flash chromatography on silica gel (gradient: 0%-20% MeOH/DCM) to obtained two peaks. The first peak was separated again by chiral HPLC (Column: CHIRAL ART Cellulose-SB, 2*25 cm, 5 um; Mobile Phase A: Hex-HPLC, Mobile Phase B: EtOH; Flow rate: 20 mL/min; Gradient: 50 B to 50 B in 9 min; 254/220 nm; RT1: 6.769; RT2: 8.351) and obtained two single diastereomers: Example 103.1 (first peak on chiral HPLC) and Example 103.2 (second peak on chiral HPLC). The second peak was separated again by prep-HPLC (Column: SunFire Prep C18 OBD Column 19×150 mm 5 um 10 nm; Mobile Phase A: Water (0.1% FA), Mobile Phase B: ACN; Flow rate: 25 mL/min; Gradient: 30% B to 50% B in 7 min; 254/220 nm; Rt: 6.67, 6.70 min) and obtained two single diastereomers: first peak Example 103.3 and second peak Example 103.4. Finally, 4 diastereomers were obtained (Example 103.1: 2.20 mg, 9.4% yield; Example 103.2: 5.70 mg, 11.8% yield; Example 103.3: 5.70 mg, 11.8% yield; Example 103.4: 8.50 mg, 17.6% yield).

Example 103.1: LCMS (ESI): $R_T$ (min)=1.21, [M+H]$^+$=503/505, method=I. $^1$H NMR (300 MHz, CDCl$_3$) δ 7.55-7.39 (m, 4H), 6.06 (s, 1H), 5.16 (d, J=8.8 Hz, 1H), 4.64-4.61 (m, 1H), 3.86-3.83 (m, 1H), 3.69-3.66 (m, 2H), 2.78 (d, J=14.2 Hz, 1H), 2.50-2.26 (m, 5H), 1.56 (s, 3H), 1.05 (d, J=6.6 Hz, 3H), 0.92 (d, J=6.7 Hz, 3H).

Example 103.2: LCMS (ESI): $R_T$ (min)=1.52, [M+H]$^+$=503/505, method=J. $^1$H NMR (300 MHz, CDCl$_3$) δ 7.55-7.42 (m, 4H), 6.13 (s, 1H), 5.04 (d, J=8.9 Hz, 1H), 4.62-4.59 (m, 1H), 3.94-3.77 (m, 2H), 3.65 (d, J=9.9 Hz, 1H), 2.73 (d, J=14.5 Hz, 1H), 2.53-2.27 (m, 5H), 1.63 (s, 3H), 1.01 (d, J=6.6 Hz, 3H), 0.93 (d, J=6.7 Hz, 3H).

Example 103.3: LCMS (ESI): $R_T$ (min)=2.37, [M+H]$^+$=503/505, method=J. $^1$H NMR (400 MHz, CDCl$_3$) δ 7.51-7.42 (m, 3H), 7.32 (s, 1H), 6.07 (d, J=56.6 Hz, 1H), 5.10 (d, J=38.2 Hz, 1H), 4.68 (d, J=54.5 Hz, 1H), 3.78 (d, J=67.7 Hz, 3H), 2.99 (s, 1H), 2.43 (s, 1H), 2.32 (s, 1H), 2.19 (s, 3H), 1.64 (d, J=7.8 Hz, 3H), 1.05-1.03 (m, 3H), 0.94-0.91 (m, 3H).

Example 103.4: LCMS (ESI): $R_T$ (min)=2.45, [M+H]$^+$=503/505, method=F. $^1$H NMR (400 MHz, CDCl$_3$) δ 9.09 (s, 1H), 7.51-7.37 (m, 4H), 6.11 (s, 1H), 4.97 (s, 1H), 4.70 (s, 1H), 3.86 (s, 1H), 3.73 (s, 1H), 3.60 (d, J=8.9 Hz, 1H), 2.91 (s, 1H), 2.41 (s, 1H), 2.29 (d, J=3.2 Hz, 4H), 1.74-1.63 (m, 3H), 0.95-0.83 (m, 6H).

Examples 104.1, 104.2, 104.3 and 104.4

2-((4R)-4-Hydroxy-1-(3-methyl-2-(3-methylisoxazol-5-yl)butanoyl) pyrrolidin-2-yl)-5-methyl-5-(4-(4-methylthiazol-5-yl)phenyl)-1,5-dihydro-4H-imidazol-4-one (4 Single Stereoisomers)

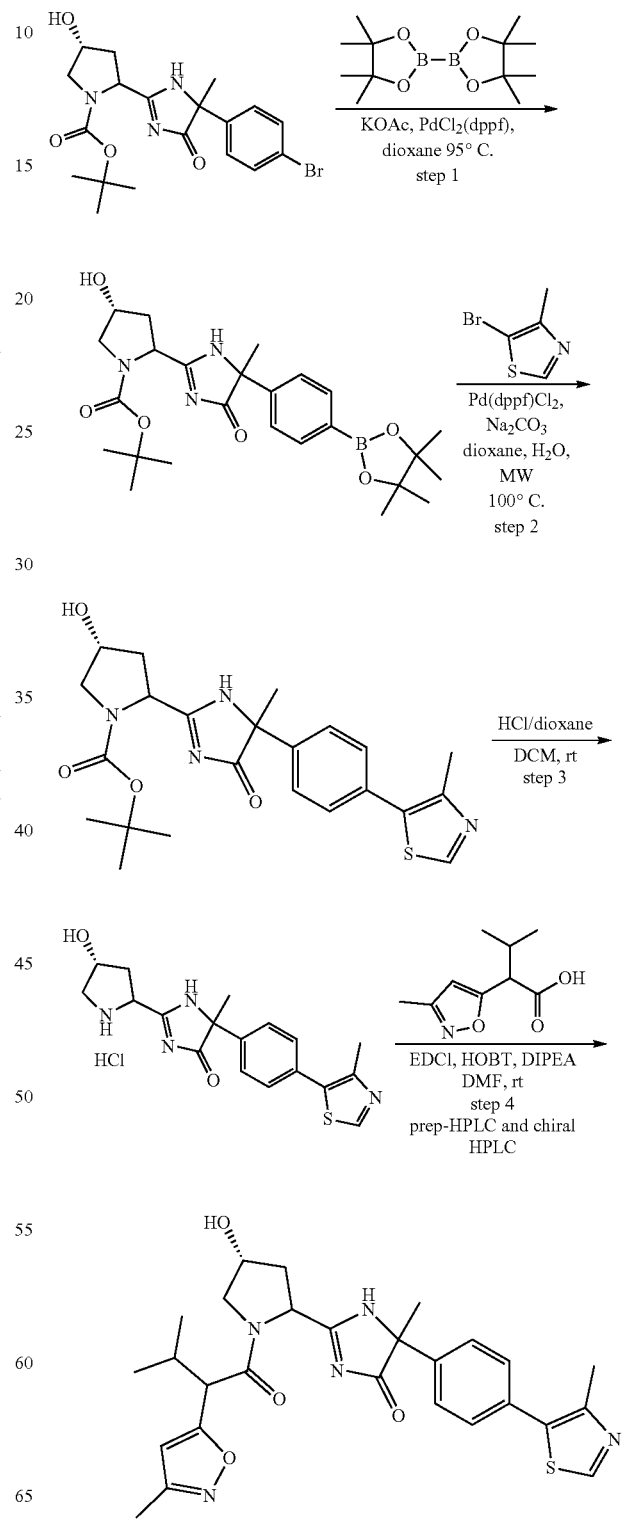

Step 1: tert-Butyl (4R)-4-hydroxy-2-(5-methyl-4-oxo-5-(4-(4,4,5,5-tetramethyl-1,3,2-dioxaborolan-2-yl)phenyl)-4,5-dihydro-1H-imidazol-2-yl)pyrrolidine-1-carboxylate

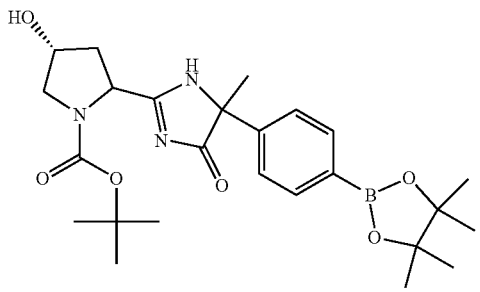 [SMILES: CC(C)(C)OC(=O)N1C[C@H](O)CC1C1=NC(=O)C(C)(c2ccc(B3OC(C)(C)C(C)(C)O3)cc2)N1]

A solution of Intermediate 4 (200 mg, 0.460 mmol), 4,4,4',4',5,5,5',5'-octamethyl-2,2'-bi(1,3,2-dioxaborolane) (139 mg, 0.547 mmol), PdCl$_2$(dppf) (66.7 mg, 0.0911 mmol) and KOAc (89.4 mg, 0.910 mmol) in dioxane (10 mL) was stirred at 95° C. for 16 hours. The mixture was concentrated under reduced pressure. The residue was purified by flash chromatography on silica gel (gradient: 0%-10% MeOH/DCM) to yield 160 mg (72%) of the title compound as a light yellow solid. LCMS (ESI): R$_T$ (min)=1.167, [M+H]$^+$=486, method=J.

Step 2: tert-Butyl (4R)-4-hydroxy-2-(5-methyl-5-(4-(4-methylthiazol-5-yl)phenyl)-4-oxo-4,5-dihydro-1H-imidazol-2-yl)pyrrolidine-1-carboxylate

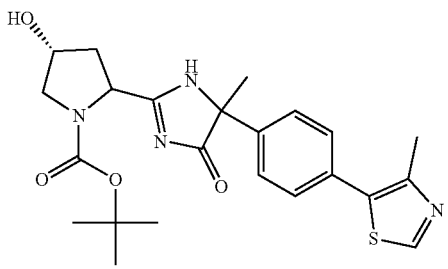 [SMILES: Cc1ncsc1-c1ccc(C2(C)NC(C3C[C@@H](O)CN3C(=O)OC(C)(C)C)=NC2=O)cc1]

A solution of tert-butyl (4R)-4-hydroxy-2-(5-methyl-4-oxo-5-(4-(4,4,5,5-tetramethyl-1,3,2-dioxaborolan-2-yl)phenyl)-4,5-dihydro-1H-imidazol-2-yl)pyrrolidine-1-carboxylate (150 mg, 0.310 mmol), 5-bromo-4-methylthiazole (66.1 mg, 0.37 mmol), PdCl$_2$(dppf) (45.2 mg, 0.0618 mmol) and Na$_2$CO$_3$ (98.3 mg, 0.930 mmol) in dioxane (4 mL) and water (0.6 mL) was stirred at 100° C. for 70 minutes in microwave. The mixture was concentrated under reduced pressure. The residue was purified by flash chromatography on silica gel (gradient: 0%-10% MeOH/DCM) to yield 110 mg (78%) of the title compound as a light yellow solid. LCMS (ESI): R$_T$(min)=0.98, [M+H]$^+$=457, method=J.

Step 3: 2-((4R)-4-Hydroxypyrrolidin-2-yl)-5-methyl-5-(4-(4-methylthiazol-5-yl)phenyl)-1,5-dihydro-4H-imidazol-4-one hydrochloride (Intermediate 10)

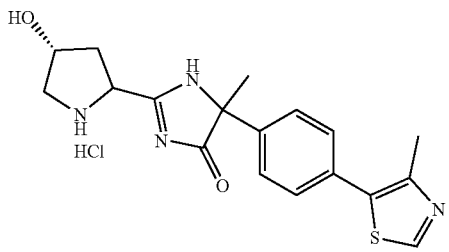 [SMILES: Cc1ncsc1-c1ccc(C2(C)NC(C3C[C@@H](O)CN3)=NC2=O)cc1 ; Cl]

To a stirred solution of tert-butyl (4R)-4-hydroxy-2-(5-methyl-5-(4-(4-methylthiazol-5-yl)phenyl)-4-oxo-4,5-dihydro-1H-imidazol-2-yl)pyrrolidine-1-carboxylate (160 mg, 0.350 mmol) in DCM (5 mL) was added HCl/dioxane (5 mL, 4M). The resulting solution was stirred at room temperature for 2 hours and then concentrated under reduced pressure. The residue was purified by flash chromatography on silica gel (gradient: 0%-20% MeOH/DCM) to yield 99.0 mg (79%) of the title compound as a light yellow solid. LCMS (ESI): R$_T$ (min)=0.736, [M+H]$^+$=357, method=F.

Step 4: 2-((4R)-4-Hydroxy-1-(3-methyl-2-(3-methylisoxazol-5-yl)butanoyl) pyrrolidin-2-yl)-5-methyl-5-(4-(4-methylthiazol-5-yl)phenyl)-1, 5-dihydro-4H-imidazol-4-one (4 Single Stereoisomers)

A solution of 2-((4R)-4-hydroxypyrrolidin-2-yl)-5-methyl-5-(4-(4-methylthiazol-5-yl)phenyl)-1,5-dihydro-4H-imidazol-4-one hydrochloride (100 mg, 0.254 mmol), 3-methyl-2-(3-methylisoxazol-5-yl)butanoic acid (intermediate 5, 56.5 mg, 0.310 mmol), EDCI.HCl (192 mg, 0.84 mmol), HOBT (113 mg, 0.837 mmol) and DIPEA (181 mg, 1.40 mmol) in DMF (5 mL) was stirred at room temperature for 0.5 hours. The reaction system was purified directly by prep-HPLC (Column: XBridge Shield RP18 OBD Column 30*150 mm, 5 um; Mobile Phase A: Water (10 mmol/L NH$_4$HCO$_3$), Mobile Phase B: ACN; Flow rate: 60 mL/min; Gradient: 10% B to 33% B in 15 min; 254/220 nm; Rt: 13.25, 14.00, 15.00 min). Three peaks were observed on prep HPLC. The first and second peaks were collected separately and freeze drying to get two single structures: first peak Example 104.3 and second peak Example 104.4. The third peak contained a mixture of two diastereomers. It was separated again by chiral HPLC (Column: CHIRAL ART Cellulose-SB, 2*25 cm, 5 um; Mobile Phase A: MTBE, Mobile Phase B: EtOH; Flow rate: 20 mL/min; Gradient: 30 B to 30 B in 10 min; 254/220 nm; RT1: 5.581; RT2: 6.923) and got two the other single diastereomers: Example 104.1 (first peak on chiral HPLC) and Example 104.2 (second peak on chiral HPLC)]. Finally, 4 diastereomers were obtained (Example 104.1: 13.7 mg, 9.4% yield; Example 104.2: 11.3 mg, 7.7% yield; Example 104.3: 14.2 mg, 9.7% yield; Example 104.4: 14.9 mg, 10.2% yield).

Example 104.1: LCMS (ESI): R$_T$ (min)=1.39, [M+H]$^+$=522, method=J. $^1$H NMR (300 MHz, CDCl$_3$) δ 8.74 (s, 1H), 7.68-7.58 (m, 2H), 7.50-7.39 (m, 2H), 6.08 (s, 1H), 5.20 (d, J=8.9 Hz, 1H), 4.66-4.63 (m, 1H), 3.87-3.84 (m, 1H), 3.74 (d, J=10.9 Hz, 1H), 3.64 (d, J=9.5 Hz, 1H), 2.83

(d, J=14.4 Hz, 1H), 2.55 (s, 3H), 2.61-2.35 (m, 2H), 2.30 (s, 3H), 1.64 (s, 3H), 1.05 (d, J=6.6 Hz, 3H), 0.93 (d, J=6.7 Hz, 3H).

Example 104.2: LCMS (ESI): R$_T$ (min)=1.40, [M+H]$^+$=522, method=J. $^1$H NMR (300 MHz, CDCl$_3$) δ 8.74 (s, 1H), 7.72-7.61 (m, 2H), 7.51-7.40 (m, 2H), 6.14 (s, 1H), 5.08 (d, J=9.0 Hz, 1H), 4.65-4.62 (m, 1H), 3.97-3.78 (m, 2H), 3.68 (d, J=9.9 Hz, 1H), 2.78 (d, J=14.3 Hz, 1H), 2.56 (s, 3H), 2.54-2.31 (m, 2H), 2.31 (s, 3H), 1.71 (s, 3H), 1.03 (d, J=6.6 Hz, 3H), 0.94 (d, J=6.7 Hz, 3H).

Example 104.3: LCMS34 (ESI): R$_T$ (min)=2.56, [M+H]$^+$=522, method=F. $^1$H NMR (400 MHz, CDCl$_3$) δ 8.71 (s, 1H), 7.49 (d, J=8.0 Hz, 2H), 7.49-7.37 (m, 2H), 6.09 (d, J=43.5 Hz, 1H), 5.14-5.11 (m, 1H), 4.77 (s, 1H), 3.70 (d, J=11.2 Hz, 3H), 3.02 (s, 1H), 2.55 (s, 3H), 2.43 (s, 1H), 2.23 (s, 1H), 2.17 (s, 3H), 1.70 (s, 3H), 1.07-1.04 (m, 3H), 0.93-0.90 (m, 3H).

Example 104.4: LCMS(ESI): R$_T$ (min)=7.16, [M+H]$^+$=522, method=K. $^1$H NMR (300 MHz, CDCl$_3$) δ 9.09 (s, 1H), 8.70 (s, 1H), 7.65-7.52 (m, 2H), 7.48-7.37 (m, 2H), 6.12 (s, 1H), 5.03-5.01 (m, 1H), 4.72 (s, 1H), 3.86-3.83 (m, 1H), 3.76-3.72 (m, 1H), 3.61 (d, J=9.7 Hz, 1H), 2.99-2.96 (m, 1H), 2.55 (s, 3H), 2.42-2.40 (m, 1H), 2.30 (s, 4H), 1.72 (s, 3H), 0.89-0.86 (m, 6H).

Examples 105.1, 105.2, 105.3 and 105.4

2-((4R)-4-Hydroxy-1-(3-methyl-2-(3-methylisoxazol-5-yl)butanoyl) pyrrolidin-2-yl)-5-methyl-5-(4-(pyridin-3-yl) phenyl)-1,5-dihydro-4H-imidazol-4-one (4 Single Stereoisomers)

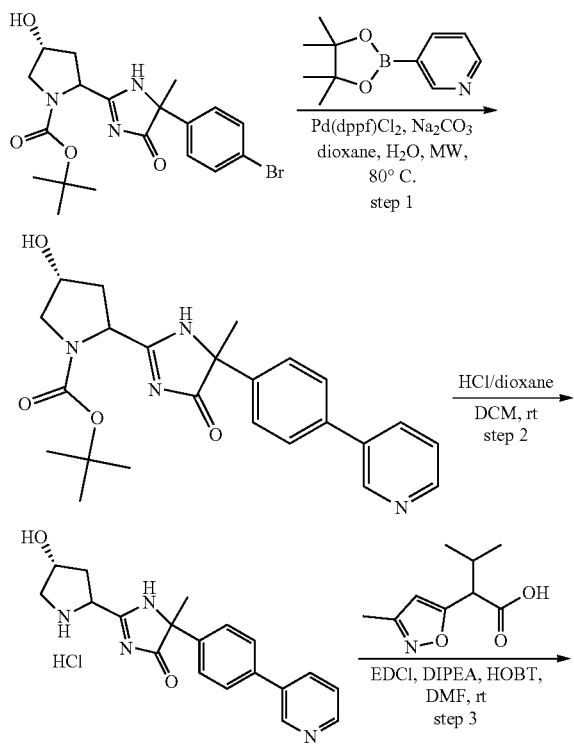

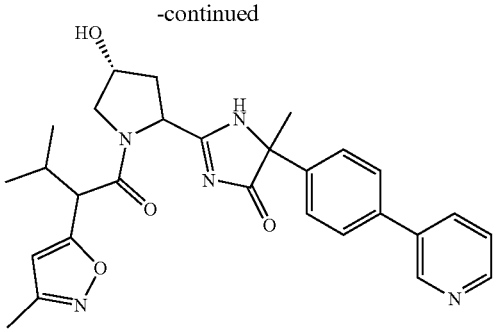

Step 1: tert-Butyl (4R)-4-hydroxy-2-(5-methyl-4-oxo-5-(4-(pyridin-3-yl) phenyl)-4,5-dihydro-1H-imidazol-2-yl)pyrrolidine-1-carboxylate

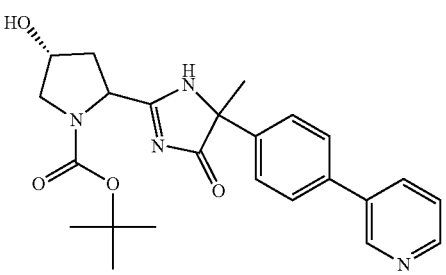 [SMILES: CC(C)(C)OC(=O)N1C[C@H](O)CC1C1=NC(=O)C(C)(c2ccc(-c3cccnc3)cc2)N1]

A solution of Intermediate 4 (300 mg, 0.680 mmol), 3-(4,4,5,5-tetramethyl-1,3,2-dioxaborolan-2-yl)pyridine (168 mg, 0.820 mmol), PdCl$_2$(dppf) (100 mg, 0.140 mmol) and Na$_2$CO$_3$ (217 mg, 2.05 mmol) in dioxane (10 mL) and water (1.5 mL) was stirred at 80° C. for 1 hour in microwave. The mixture was concentrated under reduced pressure. The residue was purified by flash chromatography on silica gel (gradient: 0%-10% MeOH/DCM) to yield 240 mg (80%) of the title compound as a light yellow solid. LCMS (ESI): R$_T$ (min)=0.847, [M+H]$^+$=437, method=J.

Step 2: 2-((4R)-4-Hydroxypyrrolidin-2-yl)-5-methyl-5-(4-(pyridin-3-yl) phenyl)-1, 5-dihydro-4H-imidazol-4-one hydrochloride

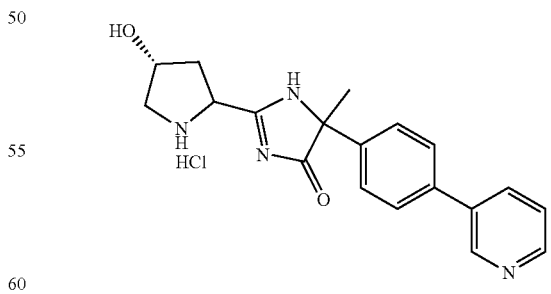

To a stirred solution of tert-butyl (4R)-4-hydroxy-2-(5-methyl-4-oxo-5-(4-(pyridin-3-yl)phenyl)-4,5-dihydro-1H-imidazol-2-yl)pyrrolidine-1-carboxylate (200 mg, 0.460 mmol) in DCM (5 mL) was added HCl/dioxane (5 mL, 4M). The resulting solution was stirred at room temperature for 2 hours and then concentrated under reduced pressure. The residue was purified by flash chromatography on silica gel (gradient: 0%-20% MeOH/DCM) to yield 130 mg (84%) of the title compound as a light yellow solid. LCMS (ESI): $R_T$ (min)=0.702, [M+H]$^+$=337, method=F.

Step 3: 2-((4R)-4-Hydroxy-1-(3-methyl-2-(3-methylisoxazol-5-yl) butanoyl) pyrrolidin-2-yl)-5-methyl-5-(4-(pyridin-3-yl) phenyl)-1,5-dihydro-4H-imidazol-4-one (4 Single Stereoisomers)

A solution of 2-((4R)-4-hydroxypyrrolidin-2-yl)-5-methyl-5-(4-(pyridin-3-yl)phenyl)-1,5-dihydro-4H-imidazol-4-one hydrochloride (80.0 mg, 0.214 mmol), 3-methyl-2-(3-methylisoxazol-5-yl)butanoic acid (intermediate 5, 47.9 mg, 0.260 mmol), EDCI.HCl (163 mg, 0.715 mmol), HOBT (96.3 mg, 0.710 mmol) and DIPEA (153 mg, 1.19 mmol) in DMF (5 mL) was stirred at room temperature for 0.5 hours. The reaction mixture was purified directly by prep-HPLC (Column: XBridge Shield RP18 OBD Column 30*150 mm, 5 um; Mobile Phase A: Water (10 mmol/L NH$_4$HCO$_3$), Mobile Phase B: ACN; Flow rate: 60 mL/min; Gradient: 10% B to 33% B in 15 min; 254/220 nm; Rt: 13.25, 14.00, 15.00 min). Three peaks were observed on prep HPLC. The first and second peaks were collected and freeze drying to get two single structures: first peak Example 105.3 and second peak Example 105.4. The third peak was a mixture of two diastereomers. It was separated by chiral HPLC (Column: CHIRAL ART Cellulose-SB S-5 um, 2*25 cm, 5 um; Mobile Phase A: HEX:DCM=3:1, Mobile Phase B: EtOH; Flow rate: 20 mL/min; Gradient: 30 B to 30 B in 20 min; 220/254 nm; RT1: 9.369; RT2: 15.013) and got two the other single diastereomers: Example 105.1 (first peak on chiral HPLC) and Example 105.2 (second peak on chiral HPLC). Finally, 4 diastereomers were obtained (Example 105.1: 7.60 mg, 6.4% yield; Example 105.2: 6.00 mg, 5.0% yield; Example 105.3: 10.7 mg, 9.0% yield; Example 105.4: 8.30 mg, 7.0% yield).

Example 105.1: LCMS (ESI): $R_T$ (min)=2.03, [M+H]$^+$=502, method=J. $^1$H NMR (300 MHz, CDCl$_3$) δ 8.86 (s, 1H), 8.63 (d, J=4.8 Hz, 1H), 7.94-7.92 (m, 1H), 7.68 (d, J=8.4 Hz, 2H), 7.65-7.53 (m, 2H), 7.45-7.42 (m, 1H), 6.08 (s, 1H), 5.17 (d, J=8.8 Hz, 1H), 4.66-4.63 (m, 1H), 3.89-3.86 (m, 1H), 3.73 (d, J=10.9 Hz, 1H), 3.64 (d, J=9.5 Hz, 1H), 2.78 (d, J=14.4 Hz, 1H), 2.53-2.27 (m, 2H), 2.29 (s, 3H), 1.61 (s, 3H), 1.06 (d, J=6.6 Hz, 3H), 0.93 (d, J=6.7 Hz, 3H).

Example 105.2: LCMS (ESI): $R_T$ (min)=2.07, [M+H]$^+$=502, method=J. $^1$H NMR (300 MHz, CDCl$_3$) δ 8.88 (s, 1H), 8.65 (d, J=4.8 Hz, 1H), 7.95 (d, J=8.0 Hz, 1H), 7.76-7.66 (m, 2H), 7.65-7.52 (m, 2H), 7.47-7.44 (m, 1H), 6.15 (s, 1H), 5.08 (d, J=9.0 Hz, 1H), 4.65-4.62 (m, 1H), 3.96-3.80 (m, 2H), 3.67 (d, J=10.0 Hz, 1H), 2.76 (d, J=14.5 Hz, 1H), 2.43-2.41 (m, 1H), 2.32 (s, 3H), 1.70 (s, 3H), 1.03 (d, J=6.6 Hz, 3H), 0.94 (d, J=6.7 Hz, 3H).

Example 105.3: LCMS (ESI): $R_T$ (min)=2.45, [M+H]$^+$=502, method=F. $^1$H NMR (300 MHz, CDCl$_3$) δ 8.84 (d, J=2.5 Hz, 1H), 8.72-8.48 (m, 1H), 8.00-7.82 (m, 1H), 7.54 (s, 4H), 7.40-7.37 (m, 1H), 6.09 (d, J=38.5 Hz, 1H), 5.34-5.00 (m, 1H), 4.80-4.77 (m, 1H), 4.06-3.57 (m, 3H), 3.09-3.06 (m, 1H), 2.44-2.41 (m, 1H), 2.32 (s, 1H), 2.15 (s, 3H), 1.70 (d, J=3.1 Hz, 3H), 1.06-1.04 (m, 3H), 0.93-0.90 (m, 3H).

Example 105.4: LCMS (ESI): $R_T$ (min)=2.56, [M+H]$^+$=502, method=F. $^1$H NMR (400 MHz, CDCl$_3$) δ 9.12 (d, J=2.2 Hz, 1H), 8.78-8.75 (m, 1H), 8.57 (d, J=8.3 Hz, 1H), 7.89-7.86 (m, 1H), 7.84-7.73 (m, 2H), 7.65-7.48 (m, 2H), 6.27 (s, 1H), 4.74-4.71 (m, 1H), 4.45 (s, 1H), 3.98-3.95 (m, 1H), 3.83 (d, J=9.3 Hz, 1H), 3.47 (d, J=10.0 Hz, 1H), 2.42-2.33 (m, 1H), 2.22 (s, 4H), 2.18-2.07 (m, 1H), 1.64 (d, J=13.1 Hz, 3H), 1.04-0.94 (m, 3H), 0.88-0.75 (m, 3H).

Examples 106.1, 106.2, 106.3 and 106.4

2-((4R)-4-Hydroxy-1-(3-methyl-2-(3-methylisoxazol-5-yl)butanoyl)pyrrolidin-2-yl)-5-methyl-5-(4-(2-methylpyridin-3-yl)phenyl)-1,5-dihydro-4H-imidazol-4-one (4 Single Stereoisomers)

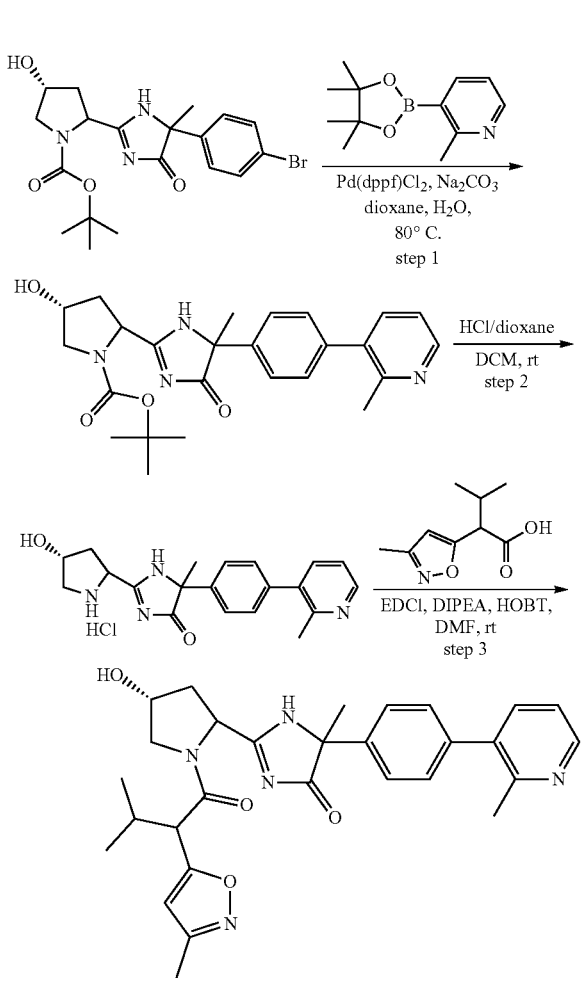

Step 1: tert-Butyl (4R)-4-hydroxy-2-(5-methyl-5-(4-(2-methylpyridin-3-yl)phenyl)-4-oxo-4,5-dihydro-1H-imidazol-2-yl)pyrrolidine-1-carboxylate

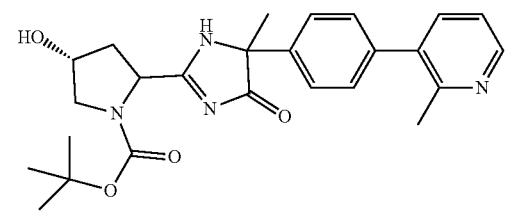 [SMILES: Cc1ncccc1-c1ccc(C2(C)NC(C3C[C@@H](O)CN3C(=O)OC(C)(C)C)=NC2=O)cc1]

A solution of tert-butyl (4R)-2-(5-(4-bromophenyl)-5-methyl-4-oxo-4,5-dihydro-1H-imidazol-2-yl)-4-hydroxypyrrolidine-1-carboxylate (Intermediate 4, 200 mg, 0.460 mmol), 2-methyl-3-(4,4,5,5-tetramethyl-1,3,2-dioxaborolan-2-yl)pyridine (120 mg, 0.548 mmol), PdCl$_2$(dppf) (66.8 mg, 0.0913 mmol) and Na$_2$CO$_3$ (145 mg, 1.37 mmol) in dioxane (10 mL) and water (1.5 mL) was stirred at 80° C. for 1 hour in microwave. The mixture was concentrated under reduced pressure. The residue was purified by flash chromatography on silica gel (gradient: 0%-10% MeOH/DCM) to yield 150 mg (73%) of the title compound as a light yellow solid. LCMS (ESI): R$_T$ (min)=0.860, [M+H]$^+$=451, method=J.

Step 2: 2-((4R)-4-Hydroxypyrrolidin-2-yl)-5-methyl-5-(4-(2-methylpyridin-3-yl)phenyl)-1,5-dihydro-4H-imidazol-4-one hydrochloride

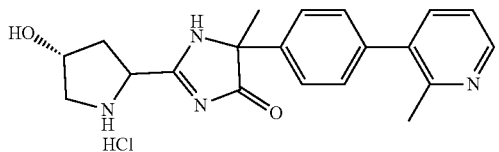 [SMILES: Cc1ncccc1-c1ccc(C2(C)NC(C3C[C@@H](O)CN3)=NC2=O)cc1 ; Cl]

To a stirred solution of tert-butyl (4R)-4-hydroxy-2-(5-methyl-5-(4-(2-methylpyridin-3-yl)phenyl)-4-oxo-4,5-dihydro-1H-imidazol-2-yl)pyrrolidine-1-carboxylate (150 mg, 0.333 mmol) in DCM (5 mL) was added HCl/dioxane (5 mL, 4M). The resulting solution was stirred at room temperature for 2 hours and then concentrated under reduced pressure. The residue was purified by flash chromatography on silica gel (gradient: 0%-20% MeOH/DCM) to yield 100 mg (85%) of the title compound as a light yellow solid. LCMS (ESI): R$_T$ (min)=0.725, [M+H]$^+$=351, method=F.

Step 3: 2-((4R)-4-Hydroxy-1-(3-methyl-2-(3-methylisoxazol-5-yl)butanoyl)pyrrolidin-2-yl)-5-methyl-5-(4-(2-methylpyridin-3-yl)phenyl)-1,5-dihydro-4H-imidazol-4-one (4 Single Stereoisomers)

A solution of 2-((4R)-4-hydroxypyrrolidin-2-yl)-5-methyl-5-(4-(2-methylpyridin-3-yl)phenyl)-1,5-dihydro-4H-imidazol-4-one hydrochloride (100 mg, 0.258 mmol), 3-methyl-2-(3-methylisoxazol-5-yl)butanoic acid (Intermediate 5, 57.5 mg, 0.310 mmol), EDCI.HCl (195 mg, 0.853 mmol), HOBT (116 mg, 0.860 mmol) and DIPEA (184 mg, 1.43 mmol) in DMF (5 mL) was stirred at room temperature for 0.5 hours. The reaction mixture was purified directly by prep-HPLC (Column: XBridge Shield RP18 OBD Column 30*150 mm, 5 um; Mobile Phase A: Water (10 mmol/L NH$_4$HCO$_3$), Mobile Phase B: ACN; Flow rate: 60 mL/min; Gradient: 20% B to 32% B in 13 min; 254/220 nm; Rt: 9.57, 10.52, 12.12 min). Three peaks were observed on prep HPLC. The first and second peaks were collected and freeze drying to obtain two single structures: first peak Example 106.3 and second peak Example 106.4. The third peak is a mixture of two diastereomers. It was separated again by chiral HPLC (Column: CHIRAL ART Cellulose-SB, 2*25 cm, 5 um; Mobile Phase A: Hex, Mobile Phase B: EtOH; Flow rate: 20 mL/min; Gradient: 50 B to 50 B in 13 min; 254/220 nm; RT1: 6.843; RT2:10.199) and obtained two the other single isomers Example 106.1 (first peak on chiral HPLC) and Example 106.2 (second peak on chiral HPLC)]. Finally, 4 diastereomers were obtained (Example 106.1: 9.10 mg, 6.2% yield; Example 106.2: 3.90 mg, 2.7% yield; Example 106.3: 16.5 mg, 11.2% yield; Example 106.4: 10.4 mg, 7.1% yield).

Example 106.1: LCMS (ESI): R$_T$ (min)=2.03, [M+H]$^+$=516, method=J. $^1$H NMR (300 MHz, CDCl$_3$) δ 8.79 (s, 1H), 8.55-8.53 (m, 1H), 7.62-7.60 (m, 3H), 7.38-7.30 (m, 2H), 7.25 (s, 1H), 6.08 (s, 1H), 5.56 (s, 1H), 5.18 (d, J=8.8 Hz, 1H), 4.64 (s, 1H), 3.88-3.85 (m, 1H), 3.72 (d, J=10.9 Hz, 1H), 3.64 (d, J=9.5 Hz, 1H), 2.79 (d, J=14.2 Hz, 1H), 2.56 (s, 3H), 2.42-2.39 (m, 2H), 2.30 (s, 3H), 1.62 (s, 3H), 1.06 (d, J=6.6 Hz, 3H), 0.93 (d, J=6.7 Hz, 3H).

Example 106.2: LCMS (ESI): R$_T$ (min)=2.07, [M+H]$^+$=516, method=J. $^1$H NMR (300 MHz, CDCl$_3$) δ 8.87 (s, 1H), 8.55-8.52 (m, 1H), 7.67 (d, J=8.1 Hz, 2H), 7.58 (d, J=7.6 Hz, 1H), 7.38-7.29 (m, 2H), 7.25 (s, 1H), 6.15 (s, 1H), 5.76 (s, 1H), 5.09 (d, J=9.0 Hz, 1H), 4.63 (s, 1H), 3.88 (d, J=3.9 Hz, 2H), 3.67 (d, J=10.0 Hz, 1H), 2.78 (d, J=14.4 Hz, 1H), 2.56 (s, 3H), 2.32 (s, 5H), 1.70 (s, 3H), 1.01-0.98 (m, 6H).

Example 106.3: LCMS (ESI): R$_T$ (min)=1.85, [M+H]$^+$=516, method=F. H NMR (300 MHz, CDCl$_3$) δ 8.78 (s, 1H), 8.55-8.53 (m, 1H), 7.74-7.44 (m, 3H), 7.29 (s, 1H), 7.28-7.20 (m, 2H), 6.06 (s, 1H), 5.23-5.04 (m, 1H), 4.79-4.77 (m, 1H), 3.81-3.62 (m, 3H), 3.15-3.00 (m, 1H), 2.54 (s, 3H), 2.51-2.35 (m, 1H), 2.35-2.17 (m, 1H), 2.18 (s, 3H), 1.71 (s, 3H), 1.08 (d, J=6.6 Hz, 3H), 0.91 (d, J=6.7 Hz, 3H).

Example 106.4: LCMS (ESI): R$_T$ (min)=1.92, [M+H]$^+$=516, method=F. $^1$H NMR (300 MHz, CDCl$_3$) δ 9.13 (s, 1H), 8.55-8.53 (m, 1H), 7.58 (d, J=8.1 Hz, 3H), 7.32 (s, 3H), 6.12 (s, 1H), 5.06-4.94 (m, 1H), 4.74 (s, 1H), 3.88 (d, J=8.2 Hz, 1H), 3.82-3.71 (m, 1H), 3.63 (d, J=9.6 Hz, 1H), 2.95 (s, 1H), 2.55 (s, 3H), 2.49-2.35 (m, 1H), 2.30 (s, 4H), 1.75 (s, 3H), 0.90-0.88 (m, 6H).

Examples 107.1, 107.2, 107.3 and 107.4

2-((4R)-4-Hydroxy-1-(3-methyl-2-(3-methylisoxazol-5-yl) butanoyl)pyrrolidin-2-yl)-5,5-dimethyl-1H-imidazol-4(5H)-one (4 Single Stereoisomers)

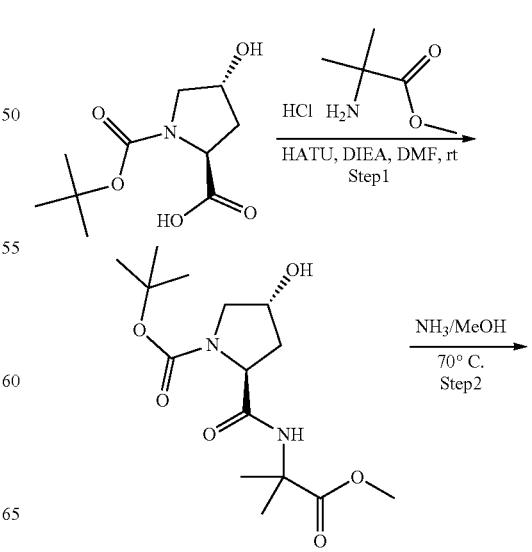

-continued

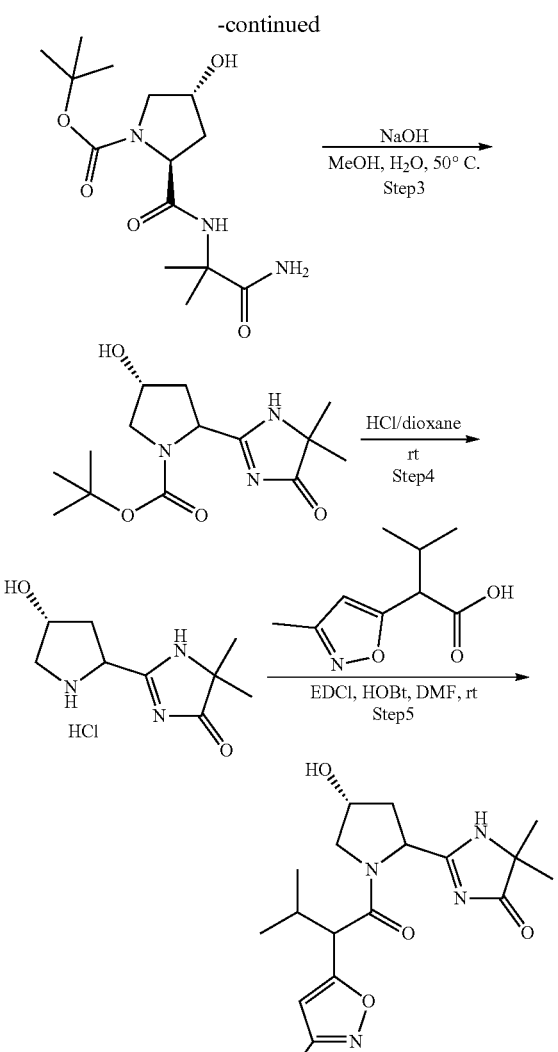

Step 1: (2S,4R)-tert-Butyl 4-hydroxy-2-(1-methoxy-2-methyl-1-oxopropan-2-ylcarbamoyl)pyrrolidine-1-carboxylate

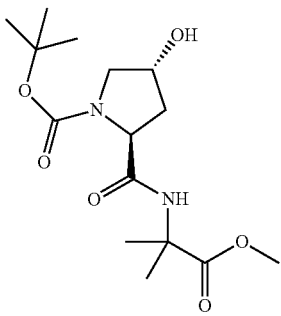 [SMILES: COC(=O)C(C)(C)NC(=O)[C@@H]1C[C@@H](O)CN1C(=O)OC(C)(C)C]

A solution of (2S,4R)-1-(tert-butoxycarbonyl)-4-hydroxypyrrolidine-2-carboxylic acid (500 mg, 2.16 mmol), HATU (1233 mg, 3.24 mmol), DIPEA (1.88 mL, 10.8 mmol) and methyl 2-amino-2-methylpropanoate hydrochloride (332 mg, 2.16 mmol) in DMF (8.00 mL) was stirred at 25° C. for 0.5 hours. The reaction mixture was loaded directly onto a pre-packed C18 column (120 g, C18, 20-35 m, Agela Technologies) eluting with acetonitrile/water (solvent gradient: 5-100% acetonitrile in water (0.05% NH$_4$HCO$_3$) to yield 500 mg (70%) of the title compound as a yellow solid. LCMS (ESI): R$_T$ (min)=1.01, [M+H]$^+$=331, method=J.

Step 2: (2S, 4R)-tert-Butyl 2-(1-amino-2-methyl-1-oxopropan-2-ylcarbamoyl)-4-hydroxypyrrolidine-1-carboxylate

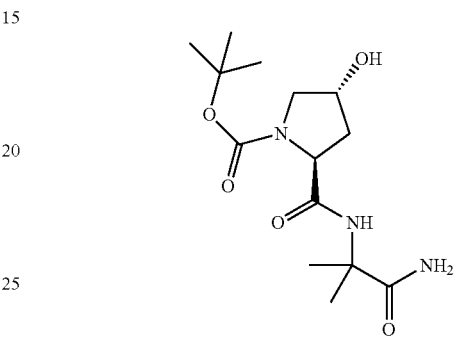

A solution of (2S,4R)-tert-butyl 4-hydroxy-2-(1-methoxy-2-methyl-1-oxopropan-2-ylcarbamoyl)pyrrolidine-1-carboxylate (500 mg, 1.51 mmol) in ammonia methanol solution (20 mL, 7M solution in MeOH) was stirred at 70° C. for 3 days. The solvent was removed under reduced pressure to yield 450 mg (94%) of the crude product as yellow oil. The crude product was used for next step without further purification. LCMS (ESI): R$_T$ (min)=0.866, [M+H]$^+$=316, method=J.

Step 3: (4R)-tert-Butyl 2-(5,5-dimethyl-4-oxo-4,5-dihydro-1H-imidazol-2-yl)-4-hydroxypyrrolidine-1-carboxylate

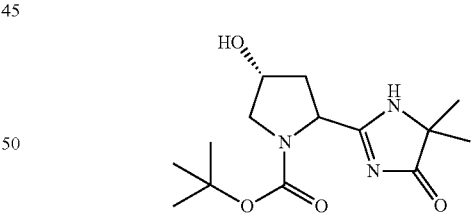

A solution of (2S,4R)-tert-Butyl 2-(1-amino-2-methyl-1-oxopropan-2-ylcarbamoyl)-4-hydroxypyrrolidine-1-carboxylate (450 mg, 1.45 mmol) and NaOH (317 mg, 7.93 mmol) in MeOH (10 mL) and water (10 ml) was stirred for 3 hours at 50° C. The reaction mixture was diluted with DCM and water. The organic layers were separated and the aqueous phase was extracted with DCM (2×). The combined organic layers were dried over anhydrous Na$_2$SO$_4$ and concentrated under reduced pressure. The residue was purified by flash chromatography on silica gel (gradient: 0%-10% MeOH/DCM) to yield 300 mg (60%) of the title compound as a yellow oil. LCMS (ESI): R$_T$ (min)=0.863, [M+H]$^+$=298, method=J.

Step 4: 2-((4R)-4-Hydroxypyrrolidin-2-yl)-5, 5-dimethyl-1H-imidazol-4(5H)-one hydrochloride

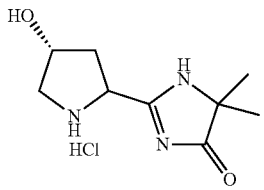

To a stirred solution of (4R)-tert-butyl 2-(5,5-dimethyl-4-oxo-4,5-dihydro-1H-imidazol-2-yl)-4-hydroxypyrrolidine-1-carboxylate (300 mg, 1.02 mmol) in DCM (5 mL) was added HCl/dioxane (5 mL, 4M). The resulting solution was stirred at 25° C. for 1 hour and then concentrated under vacuum to yield 150 mg (75%) of the crude product as yellow oil. The crude product was used for next step without further purification. LCMS (ESI): $R_T$ (min)=0.108, [M+H]$^+$=198, method=J.

Step 5: 2-((4R)-4-Hydroxy-1-(3-methyl-2-(3-methylisoxazol-5-yl) butanoyl)pyrrolidin-2-yl)-5,5-dimethyl-1H-imidazol-4(5H)-one (4 Single Stereoisomers)

To a stirring solution of 3-methyl-2-(3-methylisoxazol-5-yl)butanoic acid (Intermediate 5, 139 mg, 0.760 mmol) in DMF (10 mL) were added 2-((4R)-4-Hydroxypyrrolidin-2-yl)-5,5-dimethyl-1H-imidazol-4(5H)-one hydrochloride salt (150 mg, 0.641 mmol), EDCI (209 mg, 1.52 mmol), HOBT (205 mg, 1.52 mmol) and DIPEA (490 mg, 3.80 mmol). The resulting solution was stirred at 25° C. for 0.5 hours. The reaction mixture was purified directly by prep-HPLC (Column: XBridge Prep C18 OBD Column, 5 um, 19*150 mm; Mobile Phase A: Water (10 mmol/L NH$_4$HCO$_3$), Mobile Phase B: ACN; Flow rate: 20 mL/minute; Gradient: 10% B to 21% B in 13 minutes; 254/220 nm; Rt: 10.78 minutes, 12.33 minutes). Two peaks were observed on prep-HPLC and both of them were mixture of diastereoisomers. They were collected (faster peak and slower peak) and freeze-drying then separated by chiral-HPLC. Two single isomers Example 107.1 and Example 107.2 were obtained for the faster peak after chiral-HPLC (Column: CHIRALPAK IE, 2*25 cm, 5 um; Mobile Phase A: HEX:DCM=3:1, Mobile Phase B: EtOH; Flow rate: 20 mL/min; Gradient: 10 B to 10 B in 15 min; 254/220 nm; RT1: 8.039; RT2:10.882) and the other two single isomers Example 107.3 and Example 107.4 were obtained for the slower peak after chiral-HPLC (Column: (R,R)WHELK-01 5/100 Kromasil, 2.11 cm*25 cm (5 um); Mobile Phase A: Hex, Mobile Phase B: EtOH; Flow rate: 20 mL/minute; Gradient: 30 B to 30 B in 14 min; 220/254 nm; RT1: 9.415; RT2: 12.072). Finally, 4 diastereoisomers were obtained (Example 107.1: 28.3 mg, 10% yield; Example 107.2: 18.5 mg, 6.4% yield; Example 107.3: 9.2 mg, 3.3% yield; Example 107.4: 9.2 mg, 3.3% yield).

Example 107.1: LCMS (ESI): $R_T$ (min)=1.09, [M+H]$^+$=363, method=J. $^1$H NMR (300 MHz, CDCl$_3$) δ 6.11 (s, 1H), 5.15-5.05 (m, 1H), 4.76-4.65 (m, 1H), 3.80-3.65 (m, 3H), 2.91-2.83 (m, 1H), 2.50-2.35 (m, 1H), 2.28 (s, 3H), 2.19-2.10 (m, 1H), 1.29 (d, J=12 Hz, 6H), 1.07 (d, J=9 Hz, 3H), 0.89 (d, J=9 Hz, 3H).

Example 107.2: LCMS (ESI): $R_T$ (min)=1.11, [M+H]$^+$=363, method=J. $^1$H NMR (300 MHz, CDCl$_3$) δ 6.11 (s, 1H), 4.85-4.77 (m, 1H), 4.65-4.60 (m, 1H), 3.94-3.87 (m, 1H), 3.75 (d, J=11.1 Hz, 1H), 3.59 (d, J=9.0 Hz, 1H), 2.73-2.65 (m, 1H), 2.48-2.38 (m, 1H), 2.29-2.19 (m, 4H), 1.39 (d, J=12 Hz, 6H), 0.98 (d, J=9 Hz, 3H), 0.87 (d, J=9 Hz, 3H).

Example 107.3: LCMS (ESI): $R_T$ (min)=0.925, [M+H]$^+$=363, method=F. $^1$H NMR (300 MHz, DMSO-d$_6$) δ 6.04 (s, 1H), 5.11 (d, J=9.0 Hz, 1H), 4.59-4.56 (m, 1H), 3.84-3.78 (m, 1H), 3.65-3.58 (m, 2H), 2.69 (d, J=12 Hz, 1H), 2.46-2.31 (m, 2H), 2.27 (s, 3H), 1.34 (s, 3H), 1.25 (s, 3H), 1.03 (d, J=9 Hz, 3H), 0.91 (d, J=9 Hz, 3H).

Example 107.4: LCMS (ESI): $R_T$ (min)=1.78, [M+H]$^+$=363, method=J. $^1$H NMR (300 MHz, CDCl$_3$) δ 6.12 (s, 1H), 5.01 (d, J=9.0 Hz, 1H), 4.56-4.54 (m, 1H), 3.84-3.80 (m, 2H), 3.62 (d, J=12 Hz, 1H), 2.64 (d, J=12 Hz, 1H), 2.46-2.33 (m, 1H), 2.30-2.26 (m, 4H), 1.41 (s, 3H), 1.32 (s, 3H), 1.03 (d, J=9 Hz, 3H), 0.91 (d, J=9 Hz, 3H).

Examples 108.1, 108.2, 108.3 and 108.4

6-(4-(2-((4R)-4-Hydroxy-1-(3-methyl-2-(3-methylisoxazol-5-yl)butanoyl) pyrrolidin-2-yl)-5-methyl-4-oxo-4,5-dihydro-1H-imidazol-5-yl) phenyl)-1-methylpyridin-2(1H)-one (4 Single Stereoisomers)

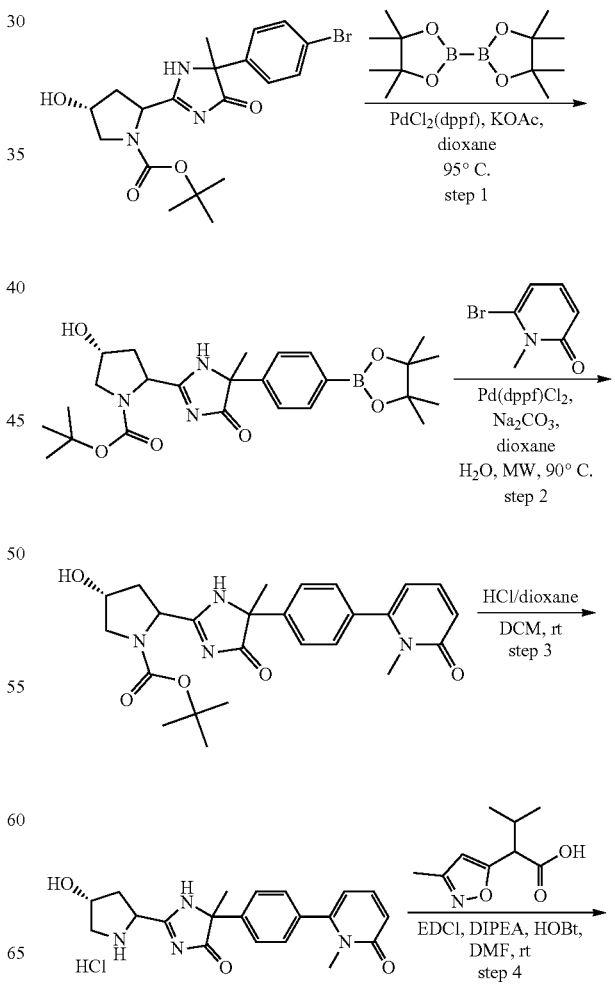

-continued

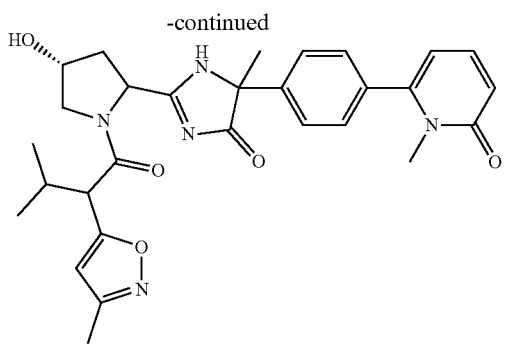

Step 1: tert-Butyl (4R)-4-hydroxy-2-(5-methyl-4-oxo-5-(4-(4,4,5,5-tetramethyl-1,3,2-dioxaborolan-2-yl)phenyl)-4,5-dihydro-1H-imidazol-2-yl)pyrrolidine-1-carboxylate

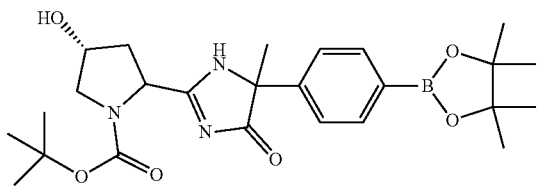 [SMILES: CC(C)(C)OC(=O)N1C[C@H](O)CC1C1=NC(=O)C(C)(c2ccc(B3OC(C)(C)C(C)(C)O3)cc2)N1]

A solution of tert-butyl (4R)-2-(5-(4-bromophenyl)-5-methyl-4-oxo-4,5-dihydro-1H-imidazol-2-yl)-4-hydroxypyrrolidine-1-carboxylate (Intermediate 4, 500 mg, 1.14 mmol), 4,4,4',4',5,5,5',5'-octamethyl-2,2'-bi(1,3,2-dioxaborolane) (348 mg, 1.37 mmol), PdCl$_2$(dppf) (167 mg, 0.230 mmol) and KOAc (279 mg, 2.85 mmol) in dioxane (15 mL) was stirred at 95° C. for 16 hours. The mixture was concentrated under reduced pressure. The residue was purified by flash chromatography on silica gel (gradient: 0%-10% MeOH/DCM) to yield 360 mg (65%) of the title compound as a light yellow solid. LCMS (ESI): R$_T$ (min)=1.17, [M+H]$^+$=486, method=J.

Step 2: tert-Butyl (4R)-4-hydroxy-2-(5-methyl-5-(4-(1-methyl-6-oxo-1,6-dihydropyridin-2-yl)phenyl)-4-oxo-4,5-dihydro-1H-imidazol-2-yl)pyrrolidine-1-carboxylate

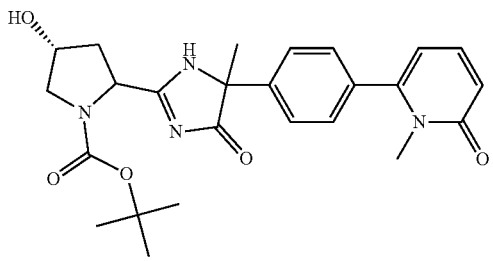 [SMILES: Cn1c(-c2ccc(C3(C)NC(C4C[C@@H](O)CN4C(=O)OC(C)(C)C)=NC3=O)cc2)cccc1=O]

A solution of tert-butyl (4R)-4-hydroxy-2-(5-methyl-4-oxo-5-(4-(4,4,5,5-tetramethyl-1,3,2-dioxaborolan-2-yl)phenyl)-4,5-dihydro-1H-imidazol-2-yl)pyrrolidine-1-carboxylate (360 mg, 0.741 mmol), 6-bromo-1-methylpyridin-2(1H)-one (140 mg, 0.740 mmol), PdCl$_2$(dppf) (109 mg, 0.150 mmol) and Na$_2$CO$_3$ (158 mg, 1.49 mmol) in dioxane (10 mL) and water (1.5 mL) was stirred at 90° C. for 1 hour in microwave. The mixture was concentrated under reduced pressure. The residue was purified by flash chromatography on silica gel (gradient: 0%-10% MeOH/DCM) to yield 270 mg (78%) of the title compound as a light yellow solid. LCMS (ESI): R$_T$(min)=0.991, [M+H]$^+$=467, method=J.

Step 3: 6-(4-(2-((4R)-4-Hydroxypyrrolidin-2-yl)-5-methyl-4-oxo-4,5-dihydro-1H-imidazol-5-yl) phenyl)-1-methylpyridin-2(1H)-one hydrochloride

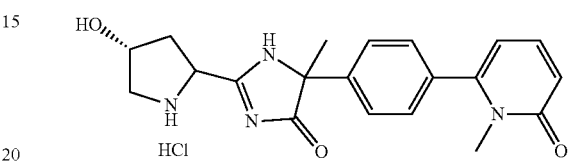

To a stirred solution of tert-butyl (4R)-4-hydroxy-2-(5-methyl-5-(4-(1-methyl-6-oxo-1,6-dihydropyridin-2-yl)phenyl)-4-oxo-4,5-dihydro-1H-imidazol-2-yl)pyrrolidine-1-carboxylate (270 mg, 0.580 mmol) in DCM (6 mL) was added HCl/dioxane (6 mL, 4M). The resulting solution was stirred at room temperature for 2 hours and then concentrated under reduced pressure. The residue was purified by flash chromatography on silica gel (gradient: 0%-20% MeOH/DCM) to yield 170 mg (80%) of the title compound as a light yellow solid. LCMS (ESI): R$_T$ (min)=0.731, [M+H]$^+$=367, method=F.

Step 4: 6-(4-(2-((4R)-4-Hydroxy-1-(3-methyl-2-(3-methylisoxazol-5-yl) butanoyl) pyrrolidin-2-yl)-5-methyl-4-oxo-4, 5-dihydro-1H-imidazol-5-yl) phenyl)-1-methylpyridin-2(1H)-one (4 Single Stereoisomers)

A solution of 6-(4-(2-((4R)-4-hydroxypyrrolidin-2-yl)-5-methyl-4-oxo-4,5-dihydro-1H-imidazol-5-yl)phenyl)-1-methylpyridin-2(1H)-one hydrochloride (100 mg, 0.248 mmol), 3-methyl-2-(3-methylisoxazol-5-yl)butanoic acid (intermediate 5, 50.0 mg, 0.270 mmol), EDCI.HCl (187 mg, 0.818 mmol), HOBT (111 mg, 0.820 mmol) and DIPEA (176 mg, 1.36 mmol) in DMF (7 mL) was stirred at room temperature for 0.5 hours. The reaction mixture was purified directly by prep-HPLC (Column: XBridge Shield RP18 OBD Column 30*150 mm, 5 um; Mobile Phase A: Water (10 mmol/L NH$_4$HCO$_3$), Mobile Phase B: ACN; Flow rate: 60 mL/min; Gradient: 20% B to 33% B in 10 min; 254/220 nm; Rt: 5.33, 5.87, 6.83 min). Three peaks were observed on prep HPLC. The first and second peaks were collected and freeze drying to obtain two single structures: first peak Example 108.1 and second peak Example 108.2. The third peak was a mixture of two diastereomers. It was separated again by chiral HPLC (Column: CHIRALPAK IA, 2*25 cm, 5 um; Mobile Phase A: Hex, Mobile Phase B: EtOH; Flow rate: 20 mL/min; Gradient: 60% B to 60% B in 10 min; 220/254 nm; RTL: 5.56; RT2: 14.35) and obtained two the other single isomers Example 108.3 (first peak on chiral HPLC) and Example 108.4 (second peak on chiral HPLC)]. Finally, 4 diastereomers were obtained (Example 108.1: 5.90 mg, 4.1% yield; Example 108.2: 7.40 mg, 5.1% yield; Example 108.3: 10.0 mg, 6.9% yield; Example 108.4: 9.40 mg, 6.5% yield).

Example 108.1: LCMS (ESI): $R_T$ (min)=4.74, [M+H]$^+$=532, method=K; $^1$H NMR (300 MHz, CDCl$_3$) δ 8.80 (s, 1H), 7.59-7.49 (m, 2H), 7.42-7.28 (m, 3H), 6.62-6.60 (m, 1H), 6.13-6.04 (m, 2H), 5.18-5.16 (m, 1H), 4.76 (d, J=5.5 Hz, 1H), 3.82-3.64 (m, 3H), 3.38 (s, 3H), 3.08 (d, J=13.2 Hz, 1H), 2.43-2.41 (m, 1H), 2.30-2.15 (m, 5H), 1.70 (s, 3H), 1.08 (d, J=6.6 Hz, 3H), 0.91 (d, J=6.7 Hz, 3H).

Example 108.2: LCMS (ESI): $R_T$ (min)=1.91, [M+H]$^+$=532, method=F; $^1$H NMR (300 MHz, CDCl$_3$) δ 9.14 (s, 1H), 7.66-7.55 (m, 2H), 7.42-7.28 (m, 3H), 6.62-6.60 (m, 1H), 6.15-6.03 (m, 2H), 4.99-4.97 (m, 1H), 4.77-4.67 (m, 1H), 3.86-3.84 (m, 1H), 3.78-3.76 (m, 1H), 3.62 (d, J=9.7 Hz, 1H), 3.37 (s, 3H), 2.95-2.93 (m, 1H), 2.56 (d, J=4.9 Hz, 1H), 2.51-2.32 (m, 1H), 2.30 (s, 4H), 1.73 (s, 3H), 0.89-0.87 (m, 6H).

Example 108.3: LCMS (ESI): $R_T$ (min)=1.77, [M+H]$^+$=532, method=F; $^1$H NMR (300 MHz, CDCl$_3$) δ 7.67 (d, J=8.3 Hz, 2H), 7.42-7.29 (m, 3H), 6.62-6.60 (m, 1H), 6.09 (d, J=5.3 Hz, 2H), 5.19 (d, J=8.9 Hz, 1H), 4.66-4.64 (m, 1H), 3.88-3.86 (m, 1H), 3.75 (d, J=10.9 Hz, 1H), 3.64 (d, J=9.5 Hz, 1H), 3.38 (s, 3H), 2.80 (d, J=14.4 Hz, 1H), 2.43-2.41 (m, 2H), 2.30 (s, 3H), 1.63 (s, 3H), 1.06 (d, J=6.6 Hz, 3H), 0.93 (d, J=6.7 Hz, 3H).

Example 108.4: LCMS (ESI): $R_T$ (min)=1.82, [M+H]$^+$=532, method=F; H NMR (300 MHz, CDCl$_3$) δ 7.76-7.65 (m, 2H), 7.42-7.30 (m, 3H), 6.64-6.62 (m, 1H), 6.17-6.05 (m, 2H), 5.09 (d, J=9.0 Hz, 1H), 4.65-4.63 (m, 1H), 3.93 (d, J=10.9 Hz, 1H), 3.84-3.82 (m, 1H), 3.69 (d, J=9.9 Hz, 1H), 3.38 (s, 3H), 2.76 (d, J=14.4 Hz, 1H), 2.54-2.31 (m, 2H), 2.32 (s, 3H), 1.71 (s, 3H), 1.03 (d, J=6.6 Hz, 3H), 0.94 (d, J=6.7 Hz, 3H).

Examples 109.1, 109.2, 109.3 and 109.4

2-((4R)-4-Hydroxy-1-(2-(3-methoxyisoxazol-5-yl)-3-methylbutanoyl) pyrrolidin-2-yl)-5-methyl-5-(4-(4-methylthiazol-5-yl) phenyl)-1,5-dihydro-4H-imidazol-4-one (4 Single Stereoisomers)

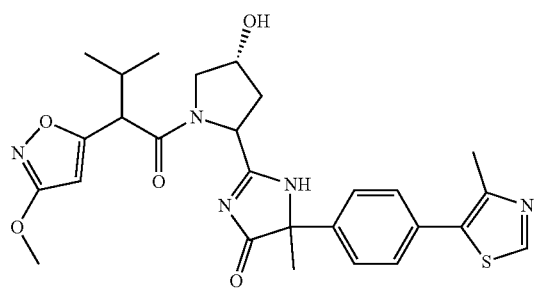 [SMILES: COc1cc(C(C(=O)N2C[C@H](O)CC2C2=NC(=O)C(C)(c3ccc(-c4scnc4C)cc3)N2)C(C)C)on1]

To a stirring solution of 2-((4R)-4-hydroxypyrrolidin-2-yl)-5-methyl-5-(4-(4-methylthiazol-5-yl)phenyl)-1,5-dihydro-4H-imidazol-4-one hydrochloride (Intermediate 10, Example 104) (85.0 mg, 0.220 mmol) and 2-(3-methoxyisoxazol-5-yl)-3-methylbutanoic acid (Intermediate 6, 43.0 mg, 0.220 mmol) in DMF (2 mL) was added HATU (82.2 mg, 0.220 mmol) at 0° C. The resulting solution was stirred for 5 minutes and then DIPEA (0.11 mL, 0.650 mmol) was added. The resulting mixture was stirred at room temperature for 3 hours. The reaction mixture was partitioned between water and EtOAc. Phases were separated. The aqueous phase was extracted with EtOAc. The combined organic layers were dried over anhydrous sodium sulfate and concentrated under reduced pressure. The residue was purified by prep-TLC (eluent: MeOH/DCM=1:20) to yield four isomers. Example 109.1: (10.5 mg, 9% yield, Rf=0.20); Example 109.2: (4.8 mg, 4.1% yield, R$_f$=0.23); Example 109.3: (7.3 mg, 6.3% yield, R$_f$=0.30); Example 109.4: (5 mg, 4.3% yield, R$_f$=0.35). All of the samples are white solids.

Example 109.1: LCMS (ESI): $R_T$ (min)=0.93. [M+H]$^+$=538, method C; $^1$H NMR (400 MHz, DMSO-d6) 10.93 (s, 1H), 9.00 (d, J=5.7 Hz, 1H), 7.65-7.27 (m, 4H), 6.18-6.06 (m, 1H), 5.29 (dd, J=16.7, 3.8 Hz, 1H), 4.85-4.63 (m, 1H), 4.51-4.35 (m, 1H), 3.98-3.43 (m, 6H), 2.45 (s, 3H), 2.24 (m, 2H), 2.05 (m, 1H), 1.66-1.42 (m, 3H), 1.01-0.66 (m, 6H).

Example 109.2: LCMS (ESI): $R_T$ (min)=0.95. [M+H]$^+$=538, method C; $^1$H NMR (400 MHz, DMSO-d6) 10.96 (s, 1H), 9.00 (d, J=1.1 Hz, 1H), 7.73-7.37 (m, 4H), 6.12 (s, 1H), 5.29-5.13 (m, 1H), 4.74-4.58 (m, 1H), 4.42 (d, J=4.5 Hz, 1H), 4.00-3.63 (m, 5H), 3.45 (d, J=10.6 Hz, 1H), 2.46 (d, J=6.4 Hz, 3H), 2.33-2.23 (m, 1H), 2.17 (td, J=9.9, 8.0, 5.5 Hz, 1H), 2.05 (m, 1H), 1.68-1.40 (m, 3H), 1.04-0.61 (m, 6H).

Example 109.3: LCMS (ESI): $R_T$ (min)=2.13. [M+H]$^+$=538, method C. $^1$H NMR (400 MHz, DMSO-d6) 10.87 (d, J=42.6 Hz, 1H), 9.06-8.95 (m, 1H), 7.71-7.36 (m, 4H), 6.16-6.00 (m, 1H), 5.52-5.31 (m, 1H), 4.88-4.68 (m, 1H), 4.41-4.27 (m, 1H), 3.99-3.71 (m, 4H), 3.68-3.50 (m, 1H), 3.50-3.39 (m, 1H), 2.45 (d, J=8.4 Hz, 3H), 2.31-2.06 (m, 2H), 1.94 (dt, J=13.2, 4.9 Hz, 1H), 1.63-1.39 (m, 3H), 0.98-0.58 (m, 6H).

Example 109.4: LCMS (ESI): $R_T$ (min)=1.00. [M+H]$^+$=538, method C; $^1$H NMR (400 MHz, DMSO-d6) 10.91 (d, J=15.9 Hz, 1H), 9.09-8.93 (m, 1H), 7.66-7.30 (m, 4H), 6.15 (d, J=3.2 Hz, 1H), 5.57 (d, J=5.5 Hz, 1H), 4.72 (m, 1H), 4.35 (q, J=5.2 Hz, 1H), 3.90-3.67 (m, 5H), 3.40 (d, J=12.8 Hz, 1H), 2.44 (d, J=11.7 Hz, 3H), 2.32-2.22 (m, 1H), 2.21-1.86 (m, 2H), 1.63-1.38 (m, 3H), 1.01-0.69 (m, 6H).

Examples 110.1, 110.2, 110.3, and 110.4

(5S)-2-((4R)-4-Hydroxy-1-(3-methyl-2-(1-methyl-1H-pyrazol-4-yl) butanoyl) pyrrolidin-2-yl)-5-methyl-5-(4-(4-methylthiazol-5-yl) phenyl)-1,5-dihydro-4H-imidazol-4-one (4 Single Stereoisomers)

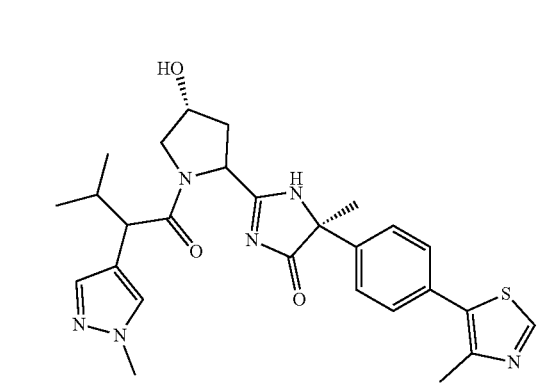 [SMILES: Cc1ncsc1-c1ccc([C@]2(C)NC(C3C[C@@H](O)CN3C(=O)C(c3cnn(C)c3)C(C)C)=NC2=O)cc1]

A solution of (5S)-2-((4R)-4-hydroxypyrrolidin-2-yl)-5-methyl-5-(4-(4-methylthiazol-5-yl)phenyl)-1,5-dihydro-4H-imidazol-4-one hydrochlorid (Intermediate 12,170 mg, 0.430 mmol), 3-methyl-2-(1-methyl-1H-pyrazol-4-yl)butanoic acid (Intermediate 13, 65.0 mg, 0.360 mmol), HATU (163 mg, 0.430 mmol) and DIPEA (230 mg, 1.78 mmol) in N,N-dimethylformamide (2 mL) was stirred at room temperature for 1 hour. The reaction system was diluted with water, extracted with ethyl acetate. The combined organic layers were washed with brine, dried over Na$_2$SO$_4$ and concentrated under reduce pressure. The crude product was purified by TLC (MeOH:DCM=1:10) to afford Example 110.1 (8.4 mg, 4.5% yield, R$_f$=0.30), Example 110.2 (8.8 mg, 4.7% yield, R$_f$=0.40) and the mixture of Example 110.3 and Example 110.4 (32.0 mg, R$_f$=0.60) as white solids. The mixture of Example 110.3 and Example 110.4 were separated again by Chiral-Prep-HPLC with the following conditions (Column: CHIRALPAK IA, 2*25 cm, 5 um; Mobile Phase A: Hex-HPLC, Mobile Phase B: EtOH-HPLC; Flow rate: 17 mL/min; Gradient: 50 B to 50 B in 16 min; 220/254 nm; RT1: 6.364; RT2:13.028) to afford the Example 110.3 (6.9 mg, 3.7% yield) and Example 110.4 (11.5 mg, 0.0221 mmol, 6.2% yield) as white solids.

Example 110.1: LCMS (ESI): R$_T$ (min)=1.26. [M+H]$^+$=521, method=P; $^1$H NMR (400 MHz, DMSO-d$_6$) δ 10.89 (s, 1H), 8.99 (s, 1H), 7.59-7.34 (m, 5H), 7.30 (s, 1H), 5.18-5.10 (m, 1H), 4.58 (t, J=7.8 Hz, 1H), 4.45-4.39 (m, 1H), 3.90-3.85 (m, 1H), 3.79 (s, 3H), 3.42 (d, J=10.6 Hz, 1H), 3.27 (s, 1H), 2.45 (s, 3H), 2.15-2.00 (m, 3H), 1.54 (s, 3H), 0.89 (d, J=6.5 Hz, 3H), 0.71 (d, J=6.7 Hz, 3H).

Example 110.2: LCMS (ESI): R$_T$ (min)=6.39. [M+H]$^+$=521, method=S; $^1$H NMR (400 MHz, DMSO-d$_6$) δ 10.85 (s, 1H), 9.00 (s, 1H), 7.57-7.41 (m, 2H), 7.39-7.24 (m, 4H), 5.25 (5.20, 4.90) (s, 1H), 4.81-4.60 (m, 1H), 4.45-4.35 (m, 1H), 3.75 (d, J=38.3 Hz, 4H), 3.61-3.54 (m, 1H), 3.43 (d, J=8.7 Hz, 1H), 2.46 (d, J=3.3 Hz, 3H), 2.21-1.97 (m, 3H), 1.65 (1.55, 1.45) (s, 3H), 0.96-0.57 (m, 6H).

Example 110.3: LCMS (ESI): R$_T$ (min)=1.12. [M+H]$^+$=521, method=W; $^1$H NMR (400 MHz, DMSO-d$_6$) δ 8.99 (d, J=4.8 Hz, 1H), 7.68 (d, J=8.2 Hz, 1H), 7.55-7.48 (m, 2H), 7.48-7.42 (m, 2H), 7.27 (s, 1H), 4.75-4.60 (m, 1H), 4.40-4.20 (m, 1H), 3.87 (dd, J=10.9, 5.5 Hz, 1H), 3.80 (3.70) (s, 3H), 3.49-3.36 (m, 2H), 2.50-2.40 (m, 4H), 2.10-1.90 (m, 2H), 1.53 (s, 3H), 0.98-0.38 (m, 6H). (proton of OH and NH didn't come out).

Example 110.4: LCMS (ESI): R$_T$ (min)=1.30. [M+H]$^+$=521, method=P; $^1$H NMR (400 MHz, DMSO-d$_6$) δ 10.83 (s, 1H), 8.99 (s, 1H), 7.68-7.52 (m, 3H), 7.40-7.30 (m, 2H), 7.31 (s, 1H), 5.55 (s, 1H), 4.76-4.53 (m, 1H), 4.35-4.20 (m, 1H), 3.78 (s, 3H), 3.72-3.53 (m, 2H), 3.40-3.20 (m, 1H), 2.50-2.30 (m, 4H), 2.12-1.90 (m, 2H), 1.66-1.41 (m, 3H), 0.95-0.80 (m, 3H), 0.75-0.65 (m, 3H).

Examples 111.1 and 111.2

1-Cyano-N-((2S)-1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)cyclopropane-1-carboxamide (2 Single Stereoisomers)

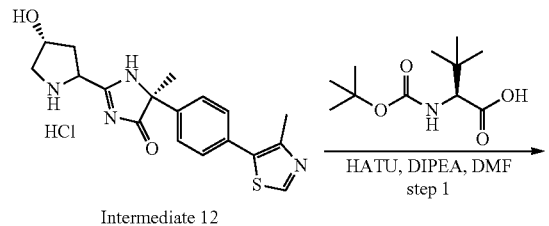

Intermediate 12

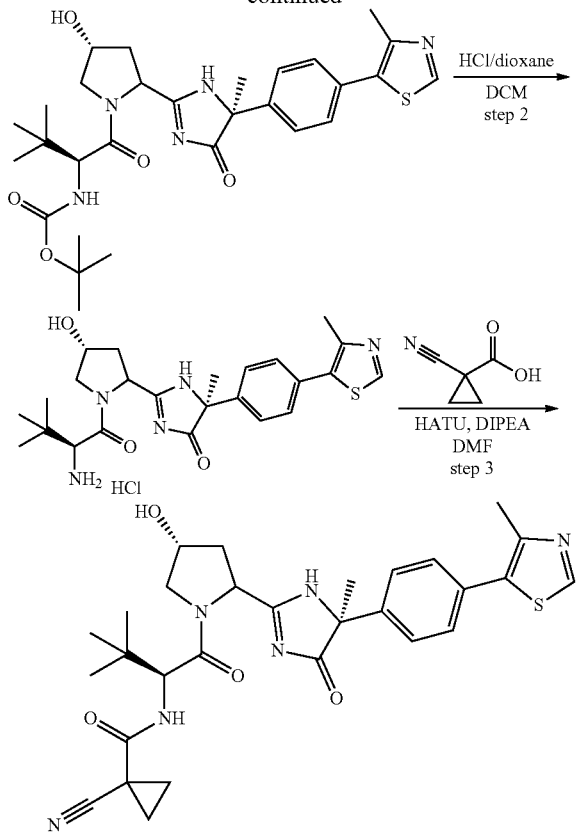

Step 1: tert-Butyl ((2S)-1-((4R)-4-hydroxy-2-((S)-5-methyl-5-(4-(4-methylthiazol-5-yl) phenyl)-4-oxo-4,5-dihydro-1H-imidazol-2-yl) pyrrolidin-1-yl)-3,3-dimethyl-1-oxobutan-2-yl) carbamate

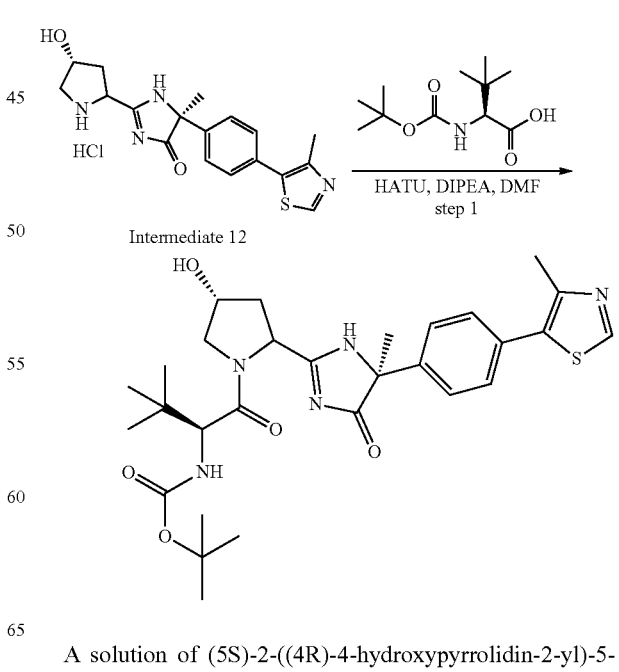

A solution of (5S)-2-((4R)-4-hydroxypyrrolidin-2-yl)-5-methyl-5-(4-(4-methylthiazol-5-yl)phenyl)-1,5-dihydro- 4H-imidazol-4-one hydrochloride (Intermediate 12, 145.0 mg, 0.410 mmol), (S)-2-((tert-butoxycarbonyl)amino)-3,3-dimethylbutanoic acid (94.0 mg, 0.410 mmol), HATU (155 mg, 0.410 mol) and N,N-diisopropylethylamine (0.360 mL, 2.04 mmol) in N,N-dimethylformamide (5 mL) was stirred at room temperature for 1 hour. The crude product was purified by reverse phase chromatography (gradient: 5-100% acetonitrile/water (0.1% FA) to afford the title compound (205 mg, 86.1% yield) as a yellow oil. LCMS (ESI): [M+H]$^+$=570.

Step 2: tert-Butyl ((2S)-1-((4R)-4-hydroxy-2-((S)-5-methyl-5-(4-(4-methylthiazol-5-yl) phenyl)-4-oxo-4, 5-dihydro-1H-imidazol-2-yl) pyrrolidin-1-yl)-3,3-dimethyl-1-oxobutan-2-yl)carbamate hydrochloride

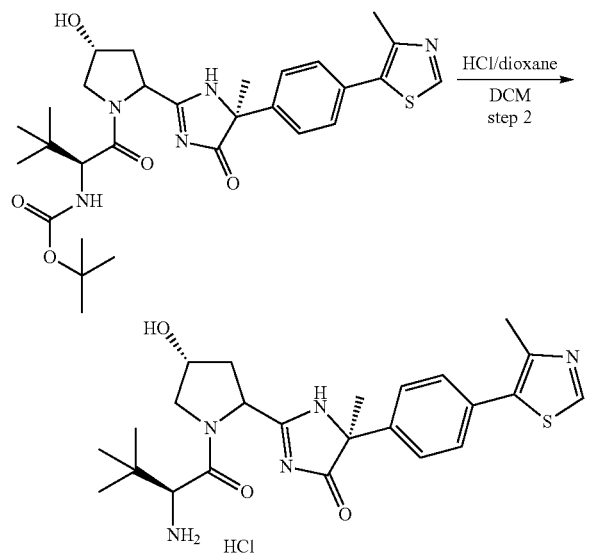

A solution of tert-butyl ((2S)-1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)carbamate (205 mg, 0.360 mmol) in DCM (3 mL) and HCl/dioxane (3 mL, 4M) was stirred for 1 hour at room temperature. The resulting solution was concentrated under vacuum to afford the title compound (158 mg crude) as a brown solid. The crude product was used for next step without further purification. LCMS (ESI): [M+H]$^+$=470.

Step 3: 1-Cyano-N-((2S)-1-((4R)-4-hydroxy-2-((S)-5-methyl-5-(4-(4-methylthiazol-5-yl) phenyl)-4-oxo-4,5-dihydro-1H-imidazol-2-yl) pyrrolidin-1-yl)-3,3-dimethyl-1-oxobutan-2-yl)cyclopropane-1-carboxamide (Two Single Stereoisomers)

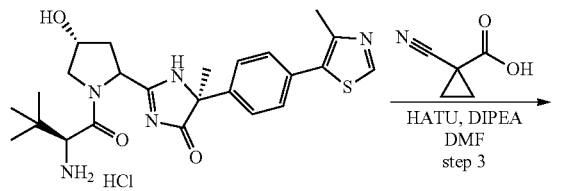

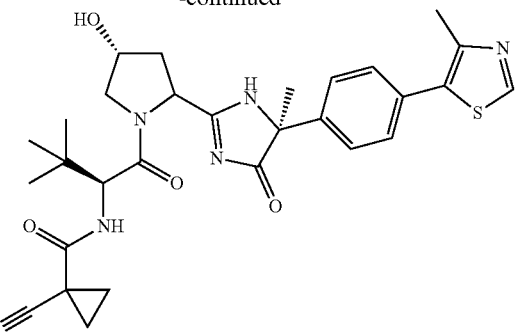

A solution of tert-butyl ((2S)-1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)carbamate hydrochloride (158 mg, 0.336 mmol), 1-cyanocyclopropane-1-carboxylic acid (37.0 mg, 0.330 mmol), HATU (124 mg, 0.330 mmol) and DIPEA (0.280 mL, 1.61 mmol) in N,N-dimethylformamide (5 mL) was stirred at room temperature for 1 hour. The reaction system was diluted with water, extracted with dichloromethane. The combined organic layers were washed with brine, dried over anhydrous sodium sulfate and concentrated under vacuum. The crude product was purified by TLC (MeOH/DCM=1:20) to afford Example 111.1 (11.4 mg, 6.0% yield, R$_f$=0.50) and Example 111.2 (19.2 mg, 10.1% yield, R$_f$=0.45) as white solids.

Example 111.1: LCMS (ESI): R$_T$ (min)=1.14. [M+H]$^+$=563.2, method=AA; $^1$H NMR (400 MHz, DMSO-d$_6$) δ 10.38 (br, 1H), 8.98 (d, J=5.5 Hz, 1H), 7.69-7.30 (m, 5H), 5.53 (br, 1H), 4.90-4.70 (m, 1H), 4.55-4.43 (m, 1H), 4.40-4.25 (m, 1H), 3.85-3.75 (m, 1H), 3.70-3.50 (m, 1H), 2.4d-2.35 (m, 4H), 2.10-1.95 (m, 1H), 1.70-1.39 (m, 7H), 0.98 (0.80) (s, 9H).

Example 111.2: LCMS (ESI): R$_T$ (min)=1.19, [M+H]$^+$=563.2, method=AA; $^1$H NMR (400 MHz, DMSO-d$_6$) δ 10.99 (br, 1H), 8.99 (s, 1H), 7.61-7.20 (m, 5H), 5.25 (5.10) (s, 1H), 4.73 (t, J=8.1 Hz, 1H), 4.57 (d, J=9.0 Hz, 1H), 4.45-4.35 (m, 1H), 3.80-3.70 (m, 1H), 3.69-3.42 (m, 1H), 2.44 (s, 3H), 2.30-2.20 (m, 1H), 2.11-1.81 (m, 1H), 1.73-1.57 (m, 2H), 1.56-1.37 (m, 5H), 0.96 (s, 9H).

Examples 112.1 and 112.2

(5S)-2-((4R)-4-hydroxy-1-((methylsulfonyl)-L-prolyl) pyrrolidin-2-yl)-5-methyl-5-(4-(4-methylthiazol-5-yl) phenyl)-1,5-dihydro-4H-imidazol-4-one (2 Single Stereoisomers)

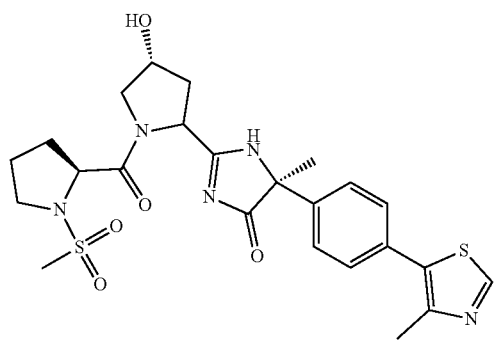 [SMILES: Cc1ncsc1-c1ccc([C@]2(C)NC(C3C[C@@H](O)CN3C(=O)[C@@H]3CCCN3S(C)(=O)=O)=NC2=O)cc1]

A solution of (methylsulfonyl)-L-proline (Intermediate 17, 55.0 mg, 0.280 mmol), (5S)-2-((4R)-4-hydroxypyrrolidin-2-yl)-5-methyl-5-(4-(4-methylthiazol-5-yl)phenyl)-1,5-dihydro-4H-imidazol-4-one hydrochloride (Intermediate 12, 134 mg, 0.340 mmol), HATU (130 mg, 0.340 mmol) and DIPEA (220 mg, 1.71 mmol) in N,N-dimethylformamide (5 mL) was stirred at room temperature for 1.5 hours. The solvent was concentrated under vacuum. The resulting residue was purified by reverse phase chromatography (gradient: 5-40% acetonitrile/water (0.1% FA)) to afford the mixture of Example 112.1 and Example 112.2 (75.0 mg). The mixture was separated by Chiral-Prep-HPLC with the following conditions (Column: CHIRAL ART Cellulose-SB, 2*25 cm, 5 um; Mobile Phase A: Hex-HPLC, Mobile Phase B: EtOH-HPLC (4:1); Flow rate: 20 mL/min; RT1: 14.43 min, RT2: 23.24 min) to afford Example 112.1 (19.9 mg, 13.1% yield) and Example 112.2 (23.7 mg, 15.7% yield) as white solids.

Example 112.1: LCMS (ESI): $R_T$ (min)=1.79. [M+H]$^+$=532.2, method=Q; $^1$H NMR (400 MHz, DMSO-d6) δ 10.91 (s, 1H), 8.99 (s, 1H), 7.67-7.36 (m, 4H), 5.28 (d, J=4.1 Hz, 1H), 4.69 (t, J=7.5 Hz, 1H), 4.60-4.55 (m, 1H), 4.50-4.40 (m, 1H), 3.75-3.70 (m, 1H), 3.65-3.50 (m, 1H), 3.40-3.30 (m, 2H), 2.97 (s, 3H), 2.44 (s, 3H), 2.20-1.80 (m, 6H), 1.57 (s, 3H).

Example 112.2: LCMS (ESI): $R_T$ (min)=1.79. [M+H]$^+$=532.2, method=Q; $^1$H NMR (400 MHz, DMSO-d$_6$) δ 10.90 (10.50, 10.30, 9.80) (s, 1H), 8.89 (s, 1H), 7.61-7.50 (m, 2H), 7.48-7.37 (m, 2H), 5.80-4.69 (m, 2H), 4.61-4.31 (m, 2H), 3.80-3.70 (m, 1H), 3.65-3.55 (m, 1H), 3.45-3.25 (m, 2H), 2.95-2.85 (m, 3H), 2.45 (s, 3H), 2.35-2.15 (m, 2H), 2.11-1.70 (m, 4H), 1.55 (1.45) (s, 3H).

Examples 113.1, 113.2, 113.3, and 113.4

(2S)-1-((2S,4R)-2-(5-(4-Bromophenyl)-5-methyl-4,5-dihydro-1,2,4-oxadiazol-3-yl)-4-hydroxypyrrolidin-1-yl)-3-methyl-2-(3-methylisoxazol-5-yl)butan-1-one and (2R)-1-((2S,4R)-2-(5-(4-Bromophenyl)-5-methyl-4,5-dihydro-1,2,4-oxadiazol-3-yl)-4-hydroxypyrrolidin-1-yl)-3-methyl-2-(3-methylisoxazol-5-yl)butan-1-one (4 Single Stereoisomers)

Examples 113.1 and 113.3

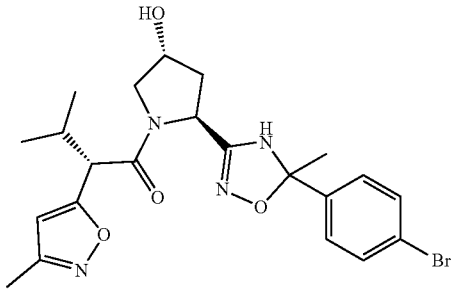

Examples 113.2 and 113.4

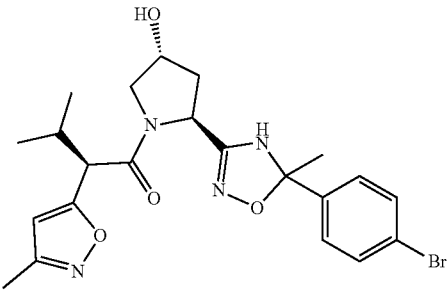

A solution of (2S,4R,Z)—N',4-dihydroxy-1-(3-methyl-2-(3-methylisoxazol-5-yl)butanoyl)pyrrolidine-2-carboximidamide (Intermediate 23, 150 mg, 0.480 mmol) and 1-bromo-4-(1,1-dimethoxyethyl)benzene (Intermediate 27, 592 mg, 2.42 mmol) in 1,2-dichloroethane (7 mL) and acetic acid (1 mL) was stirred at 95° C. for 12 hours. The solvent was evaporated under reduce pressure and the residue was purified by flash chromatography on silica gel column eluting with ethyl acetate (100%) to afford the mixture of four isomers. Then the mixture was further separated by chiral HPLC (Column: CHIRALPAK IE, 2*25 cm, 5 um; Mobile Phase A: Hex-HPLC, Mobile Phase B: IPA-HPLC; Flow rate: 20 mL/min; Gradient: 20 B to 20 B in 20 min; 220/254 nm; RT1: 9.814; RT2:11.798; RT3:16.083) to afford three peaks (Example 113.1: 5.2 mg, the second peak; Example 113.3: 6.1 mg, the first peak; the mixture of Example 113.2 and Example 113.4: 21 mg, the third peak). The third peak was further separated by chiral HPLC (Column: Lux 5u Cellulose-3, AXIA Packed, 2.12*25 cm, 5 um; Mobile Phase A: Hex-HPLC, Mobile Phase B: EtOH-HPLC; Flow rate: 20 mL/min; Gradient: 15 B to 15 B in 16 min; 220/254 nm; RT1: 8.791; RT2:12.555) to afford two single isomers (Example 113.2: 7.5 mg, the first peak; Example 113.4: 6.7 mg, the second peak).

Example 113.1: LCMS (ESI): $R_T$ (min)=1.33. [M+H]$^+$=491, method=W. $^1$H NMR (400 MHz, DMSO-d6) δ 7.90-7.29 (m, 5H), 6.17 (d, J=5.7 Hz, 1H), 5.15 (4.95) (d, J=3.6 Hz, 1H), 4.75-4.55 (m, 1H), 4.35-4.24 (m, 1H), 3.84-3.40 (m, 3H), 2.32-1.88 (m, 6H), 1.65 (1.55) (s, 3H), 0.98-0.51 (m, 6H).

Example 113.2: LCMS (ESI): $R_T$ (min)=2.57. [M+H]$^+$=491, method=X. $^1$H NMR (400 MHz, DMSO-d6) δ 7.75-7.35 (m, 5H), 6.20 (6.12) (s, 1H), 5.10 (5.05) (s, 1H), 4.80 (4.60) (m, 1H), 4.39-4.26 (m, 1H), 3.90-3.60 (m, 2H), 3.48-3.32 (m, 1H), 2.20-2.10 (m, 4H), 2.05-1.90 (m, 2H), 1.60 (1.50) (s, 3H), 0.95-0.60 (m, 6H).

Example 113.3: LCMS (ESI): $R_T$ (min)=2.64. [M+H]$^+$=491, method=X. $^1$H NMR (400 MHz, DMSO-d6) δ 7.99-7.16 (m, 5H), 6.15 (6.12) (s, 1H), 5.15 (4.95) (d, J=3.7 Hz, 1H), 4.75-4.55 (m, 1H), 4.37-4.25 (m, 1H), 3.80-3.40 (m, 3H), 2.34-2.23 (m, 1H), 2.19 (d, J=6.5 Hz, 3H), 2.10-1.95 (m, 2H), 1.70 (1.50) (s, 3H), 1.02-0.45 (m, 6H).

Example 113.4: LCMS (ESI): $R_T$ (min)=2.50. [M+H]$^+$=491, method=X. $^1$H NMR (400 MHz, DMSO-d6) δ 7.69-7.29 (m, 5H), 6.20 (5.80) (s, 1H), 5.10 (5.05) (d, J=3.5 Hz, 1H), 4.85 (4.55) (t, J=7.5 Hz, 1H), 4.35-4.25 (m, 1H), 3.84-3.64 (m, 2H), 3.40-3.30 (m, 1H), 2.30-2.10 (m, 4H), 2.00-1.90 (m, 2H), 1.60 (1.55) (s, 3H), 0.95-0.75 (m, 6H).

549

Examples 114.1, 114.2, 114.3, and 114.4

(2S)-1-((2S,4R)-4-Hydroxy-2-(5-phenyl-5-(trifluoromethyl)-4,5-dihydro-1,2,4-oxadiazol-3-yl)pyrrolidin-1-yl)-3-methyl-2-(3-methylisoxazol-5-yl)butan-1-one and (2R)-1-((2S,4R)-4-Hydroxy-2-(5-phenyl-5-(trifluoromethyl)-4,5-dihydro-1,2,4-oxadiazol-3-yl)pyrrolidin-1-yl)-3-methyl-2-(3-methylisoxazol-5-yl)butan-1-one (4 Single Stereoisomers)

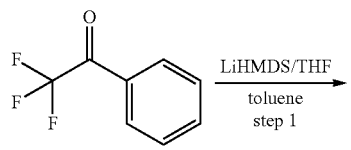

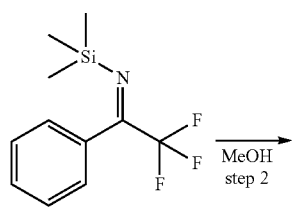

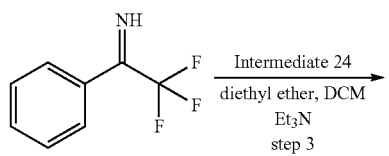

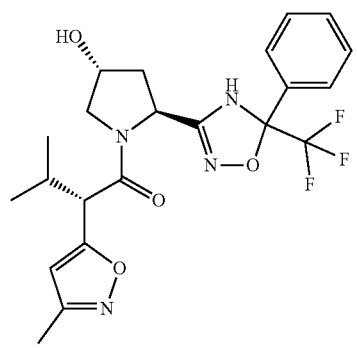

Examples 114.1 and 114.2

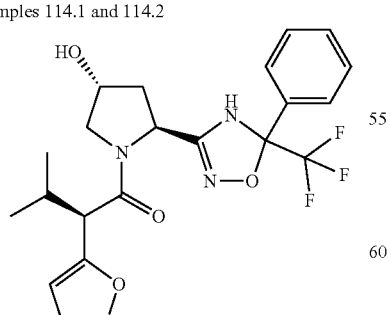

Examples 114.3 and 114.4

550

Step 1: 2,2,2-Trifluoro-1-phenyl-N-(trimethylsilyl)ethan-1-imine

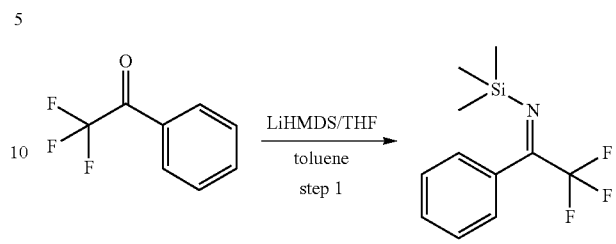

Under nitrogen, to a stirred solution of 2,2,2-trifluoro-1-phenylethan-1-one (1.00 g, 5.74 mmol) in toluene (5.6 mL) was added LiHMDS/THF (6 mL, 1M) at 0° C. The resulting solution was stirred for 1 hour at 0° C. Then the solution was concentrated under vacuum to afford the title compound (1.35 g, crude) as a yellow oil. The crude product was used for next step without further purification. LCMS (ESI): [M+H]$^+$=246.

Step 2: 2,2,2-Trifluoro-1-phenylethan-1-imine

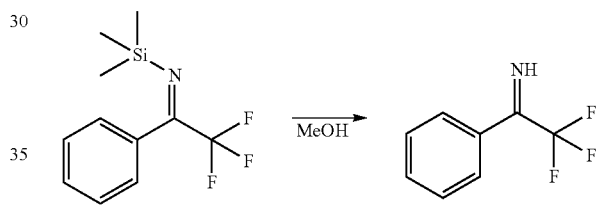

A solution of 2,2,2-trifluoro-1-phenyl-N-(trimethylsilyl)ethan-1-imine (1.35 g, 5.50 mmol) in MeOH (50 mL) was stirred at room temperature for 18 hours. Then the solvent was concentrated under vacuum to afford the title compound as a MeOH adduct (0.70 g, crude). The crude product was used for the next step without further purification. LCMS (ESI): [M+H+MeOH]$^+$=206.

Step 3: (2S)-1-((2S,4R)-4-Hydroxy-2-(5-phenyl-5-(trifluoromethyl)-4,5-dihydro-1,2,4-oxadiazol-3-yl)pyrrolidin-1-yl)-3-methyl-2-(3-methylisoxazol-5-yl)butan-1-one and (2R)-1-((2S,4R)-4-Hydroxy-2-(5-phenyl-5-(trifluoromethyl)-4,5-dihydro-1,2,4-oxadiazol-3-yl)pyrrolidin-1-yl)-3-methyl-2-(3-methylisoxazol-5-yl)butan-1-one (4 Single Stereoisomers)

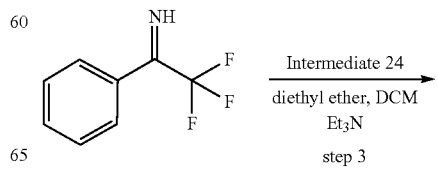

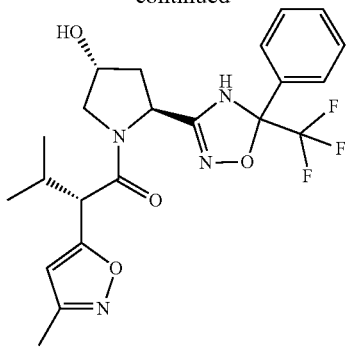

Examples 114.1 and 114.2

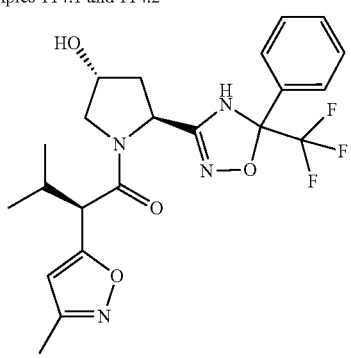

Examples 114.3 and 114.4

To a stirred solution of (2Z,2S,4R)—N,4-dihydroxy-1-[3-methyl-2-(3-methylisoxazol-5-yl)butanoyl]pyrrolidine-2-carboximidoyl chloride (Intermediate 24, 100 mg, 0.300 mmol) and 2,2,2-trifluoro-1-phenylethan-1-imine (263 mg, 1.52 mmol) in diethyl ether (10 mL) and DCM (10 mL) was added Et₃N (153 mg, 1.52 mmol) at 0° C. The resulting solution was stirred at room temperature for 12 hours. The solvent was concentrated under vacuum. The residue was purified by flash chromatography on silica gel (gradient: 0-50% ethyl acetate in petroleum) to afford a mixture of four stereoisomers of the desired product which were further separated by chiral HPLC (Column: Chiralpak ID-2, 2*25 cm, 5 um; Mobile Phase A: Hex-HPLC, Mobile Phase B: IPA-HPLC; Flow rate: 20 mL/min; Gradient: 10 B to 10 B in 22 min; 220/254 nm; RT1:8.748; RT2:13.669; RT3:18.81) to afford Example 114.1 (the first peak, 7.6 mg, 5.4% yield), mixture of Example 114.2 and Example 114.3 (the second peak, 19.2 mg) and Example 114.4 (the third peak, 5.2 mg, 3.7% yield) as white solids. The mixture of Example 114.2 and Example 114.3 was separated again by chiral HPLC (Column: chiralpak IE, 2*25 cm, 5 um; Mobile Phase A: Hex-HPLC, Mobile Phase B: EtOH-HPLC; Flow rate: 20 mL/min; Gradient: 10 B to 10 B in 20 min; 220/254 nm; RT1: 11.228; RT2: 13.794) to afford Example 114.2 (the first peak, 8.6 mg, 6.1% yield) and Example 114.3 (the second peak, 5.2 mg, 3.7% yield) as white solids.

Example 114.1: LCMS (ESI): $R_T$ (min)=1.97, [M+H]⁺=467, method=X. ¹H NMR (400 MHz, DMSO-d₆) δ 9.20 (8.60) (s, 1H), 7.63-7.42 (m, 5H), 6.15 (6.08) (s, 1H), 5.20 (5.00) (d, J=3.7 Hz, 1H), 4.77-4.64 (m, 1H), 4.36-4.25 (m, 1H), 3.85-3.43 (m, 3H), 2.31-1.94 (m, 6H), 0.99-0.56 (m, 6H).

Example 114.2: LCMS (ESI): $R_T$ (min)=1.90. [M+H]⁺=467, method=X. ¹H NMR (400 MHz, DMSO-d₆) δ 9.10 (8.84) (s, 1H), 7.60-7.38 (m, 5H), 6.16 (6.09) (s, 1H), 5.20 (5.00) (d, J=3.5 Hz, 1H), 4.76-4.67 (m, 1H), 4.39-4.26 (m, 1H), 3.86-3.46 (m, 3H), 2.25-1.93 (m, 6H), 0.97-0.46 (m, 6H).

Example 114.3: LCMS (ESI): $R_T$ (min)=1.98. [M+H]⁺=467, method=X. ¹H NMR (400 MHz, DMSO-d₆) δ 8.70 (s, 1H), 7.63-7.45 (m, 5H), 6.21 (s, 1H), 5.31-5.11 (m, 1H), 4.66 (t, J=7.4 Hz, 1H), 4.35 (q, J=4.3 Hz, 1H), 3.90-3.35 (m, 3H), 2.29-1.97 (m, 6H), 0.85 (dd, J=66.7, 6.7 Hz, 6H).

Example 114.4: LCMS (ESI): $R_T$ (min)=1.52. [M+H]⁺=467, method=W. ¹H NMR (400 MHz, DMSO-d₆) δ 8.90 (8.75) (s, 1H), 7.57-7.41 (m, 5H), 6.20 (5.55) (s, 1H), 5.15 (5.10) (d, J=3.4 Hz, 1H), 4.90 (4.65) (t, J=7.8 Hz, 1H), 4.35-4.25 (m, 1H), 3.93-3.34 (m, 3H), 2.34-1.76 (m, 6H), 0.97-0.67 (m, 6H).

Examples 115.1 and 115.2

1-((2S,4R)-2-(1-ethyl-5,5-dimethyl-4,5-dihydro-1H-1,2,4-triazol-3-yl)-4-hydroxypyrrolidin-1-yl)-3-methyl-2-(3-methylisoxazol-5-yl) butan-1-one (2 Single Stereoisomers)

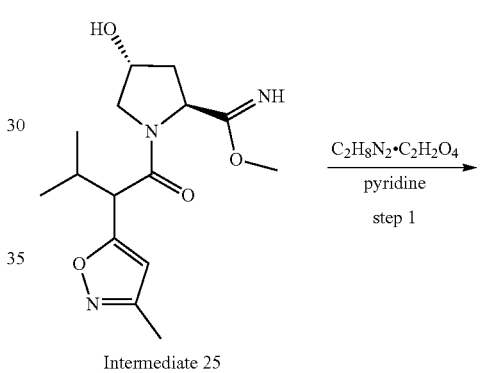

Intermediate 25

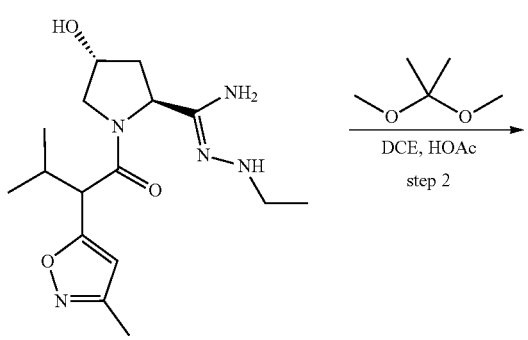

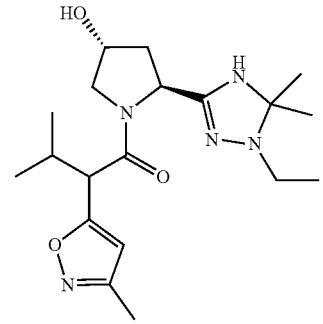

Step 1: (2S,4R, Z)—N'-Ethyl-4-hydroxy-1-(3-methyl-2-(3-methylisoxazol-5-yl) butanoyl) pyrrolidine-2-carbohydrazonamide

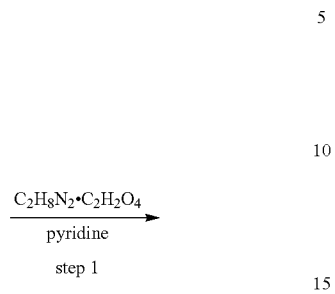

Intermediate 25

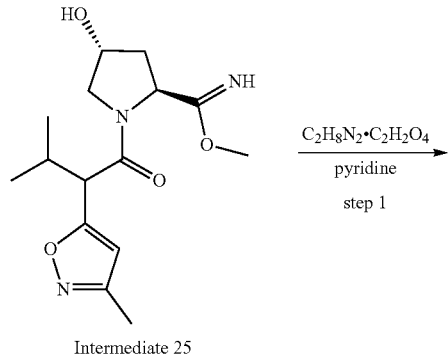

A solution of methyl (2S,4R)-4-hydroxy-1-(3-methyl-2-(3-methylisoxazol-5-yl) butanoyl) pyrrolidine-2-carbimidate (Intermediate 25, 400 mg, 1.29 mmol) and ethylhydrazine oxalate (971 mg, 6.46 mmol) in pyridine (5 mL) was stirred at 25° C. for 12 hours. The solvent was evaporated under vacuum. The residue was purified by reverse phase chromatography (gradient: 5-40% acetonitrile/water (0.1% FA)) to afford the titled compound (200 mg, 46% yield) as a white solid. LCMS (ESI): [M+H]$^+$=338.

Step 2: 1-((2S,4R)-2-(1-Ethyl-5,5-dimethyl-4,5-dihydro-1H-1,2,4-triazol-3-yl)-4-hydroxypyrrolidin-1-yl)-3-methyl-2-(3-methylisoxazol-5-yl) butan-1-one (2 Single Stereoisomers)

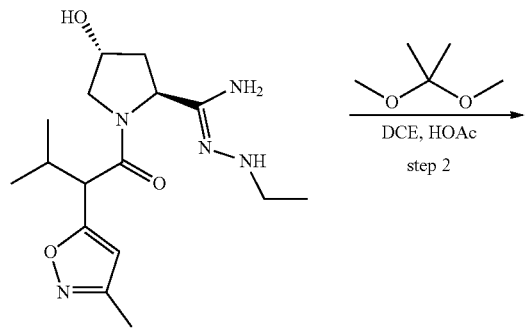

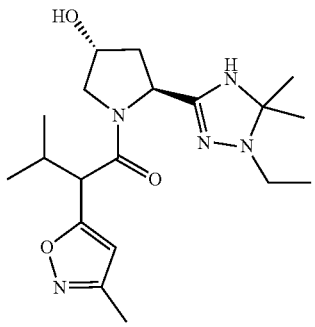

A solution of (2S,4R, Z)—N'-ethyl-4-hydroxy-1-(3-methyl-2-(3-methylisoxazol-5-yl) butanoyl) pyrrolidine-2-carbohydrazonamide (90.0 mg, 0.270 mmol) and 2,2-dimethoxypropane (5 mL, 40.4 mmol) in 1,2-dichloroethane (2 mL) and acetic acid (0.50 mL) was stirred for 12 hours at 25° C. The solvent was concentrated under vacuum. The residue was dissolved with DCM (20 mL), adjust the pH to 12 with triethylamine. After evaporation, the residue was purified by prep-TLC eluting with DCM/MeOH (10:1) to afford a mixture of two diastereoisomers. The mixture was further separated by prep-chiral-HPLC (Column: CHIRAL ART Cellulose-SB S-5 um-02, 250*20 mm; Mobile Phase A: Hex (0.2% IPA)-HPLC, Mobile Phase B: EtOH-HPLC; Flow rate: 20 mL/min; Gradient: 5 B to 5 B in 20 min; 254/220 nm; RT1:11.53; RT2:16.46) to afford two single stereoisomers (Example 115.1, 4.1 mg, 89.9% purity, the first peak; Example 115.2, 5.3 mg, 82.1% purity, the second peak) as white solids.

Example 115.1: LCMS (ESI): R$_T$ (min)=1.11. [M+H]$^+$=378, method=W. $^1$H NMR (400 MHz, Chloroform-d) δ 6.04 (s, 1H), 5.06 (s, 1H), 4.86 (dd, J=8.2, 5.3 Hz, 1H), 4.65 (p, J=5.2 Hz, 1H), 3.70-3.51 (m, 3H), 2.75-2.58 (m, 3H), 2.48-2.39 (m, 1H), 2.25 (s, 4H), 2.07-1.99 (m, 1H), 1.28 (s, 3H), 1.22 (t, J=7.1 Hz, 3H), 1.09-0.96 (m, 6H), 0.88 (d, J=6.7 Hz, 3H).

Example 115.2: LCMS (ESI): R$_T$ (min)=1.12. [M+H]$^+$=378, method=W. $^1$H NMR (400 MHz, Chloroform-d) δ 6.11 (s, 1H), 5.34 (s, 1H), 4.79 (m, 1H), 4.63 (m, 1H), 3.79 (m, 1H), 3.71-3.57 (m, 2H), 2.83-2.66 (m, 3H), 2.43 (m, 1H), 2.32-2.17 (m, 4H), 2.04 (m, 1H), 1.50-1.13 (m, 9H), 1.05 (m, 3H), 0.90 (m, 3H).

Examples 1161-135.2

The examples listed in Table 10 were prepared following procedures analogous to those described for the above Examples. The number of the Example describing the relevant procedure, and the corresponding intermediate, used to prepare each example is listed in the table.

In the following table, when two examples have the same structure and compound name (e.g., Examples 116.1, 116.2, 116.3, and 116.4), the examples are directed to single unknown stereoisomers of the presented structure.

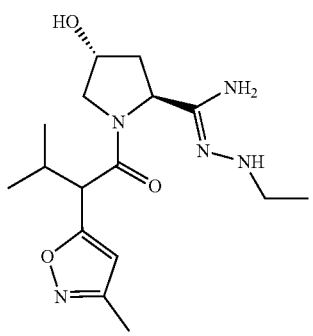

TABLE 10

Examples 116.1-135.2

| Example | Structure/Name | LCMS [M + H]+ | LCMS R$^T$ (min), method | Synthesis Method/ Example# (Intermediate #) |
|---|---|---|---|---|
| 116.1 | (5S)-2-((4R)-4-hydroxy-1-(2-(3-hydroxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one | 524.2 | 1.26, P | 110.1-110.4 (7) |
| 116.2 | (5S)-2-((4R)-4-hydroxy-1-(2-(3-hydroxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one | 524.2 | 2.26, Q | 110.1-110.4 (7) |
| 116.3 | (5S)-2-((4R)-4-hydroxy-1-(2-(3-hydroxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one | 524.2 | 4.21/ 5.16 T | 110.1-110.4 (7) |
| 116.4 | (5S)-2-((4R)-4-hydroxy-1-(2-(3-hydroxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one | 524.2 | 7.16 U | 110.1-110.4 (7) |

TABLE 10-continued

Examples 116.1-135.2

| Example | Structure/Name | LCMS [M + H]⁺ | LCMS R$^T$ (min), method | Synthesis Method/ Example# (Intermediate #) |
|---|---|---|---|---|
| 117.1 | (5S)-2-((4R)-4-hydroxy-1-(3-methyl-2-(3-methyl-1,2,4-oxadiazol-5-yl)butanoyl)pyrrolidin-2-yl)-5-methyl-5-(4-(4-methylthiazol-5-yl)phenyl)-1,5-dihydro-4H-imidazol-4-one | 523.2 | 1.31 P | 110.1-110.4 (14) |
| 117.2 | (5S)-2-((4R)-4-hydroxy-1-(3-methyl-2-(3-methyl-1,2,4-oxadiazol-5-yl)butanoyl)pyrrolidin-2-yl)-5-methyl-5-(4-(4-methylthiazol-5-yl)phenyl)-1,5-dihydro-4H-imidazol-4-one | 523.2 | 1.33 P | 110.1-110.4 (14) |
| 117.3 | (5S)-2-((4R)-4-hydroxy-1-(3-methyl-2-(3-methyl-1,2,4-oxadiazol-5-yl)butanoyl)pyrrolidin-2-yl)-5-methyl-5-(4-(4-methylthiazol-5-yl)phenyl)-1,5-dihydro-4H-imidazol-4-one | 523.2 | 1.37 P | 110.1-110.4 (14) |

TABLE 10-continued

Examples 116.1-135.2

| Example | Structure/Name | LCMS [M + H]+ | LCMS R$^T$ (min), method | Synthesis Method/ Example# (Intermediate #) |
|---|---|---|---|---|
| 117.4 | (5S)-2-((4R)-4-hydroxy-1-(3-methyl-2-(3-methyl-1,2,4-oxadiazol-5-yl)butanoyl)pyrrolidin-2-yl)-5-methyl-5-(4-(4-methylthiazol-5-yl)phenyl)-1,5-dihydro-4H-imidazol-4-one | 523.2 | 1.36 P | 110.1-110.4 (14) |
| 118.1 | (5S)-2-((4R)-4-hydroxy-1-(3-methyl-2-(1-methyl-1H-1,2,3-triazol-4-yl)butanoyl)pyrrolidin-2-yl)-5-methyl-5-(4-(4-methylthiazol-5-yl)phenyl)-1,5-dihydro-4H-imidazol-4-one | 522.2 | 1.20 P | 110.1-110.4 (16) |
| 118.2 | (5S)-2-((4R)-4-hydroxy-1-(3-methyl-2-(1-methyl-1H-1,2,3-triazol-4-yl)butanoyl)pyrrolidin-2-yl)-5-methyl-5-(4-(4-methylthiazol-5-yl)phenyl)-1,5-dihydro-4H-imidazol-4-one | 522.2 | 1.23 P | 110.1-110.4 (16) |

TABLE 10-continued

Examples 116.1-135.2

| Example | Structure/Name | LCMS [M + H]+ | LCMS R$^T$ (min), method | Synthesis Method/ Example# (Intermediate #) |
|---|---|---|---|---|
| 118.3 | (5S)-2-((4R)-4-hydroxy-1-(3-methyl-2-(1-methyl-1H-1,2,3-triazol-4-yl)butanoyl)pyrrolidin-2-yl)-5-methyl-5-(4-(4-methylthiazol-5-yl)phenyl)-1,5-dihydro-4H-imidazol-4-one | 522.2 | 1.25 P | 110.1-110.4 (16) |
| 118.4 | (5S)-2-((4R)-4-hydroxy-1-(3-methyl-2-(1-methyl-1H-1,2,3-triazol-4-yl)butanoyl)pyrrolidin-2-yl)-5-methyl-5-(4-(4-methylthiazol-5-yl)phenyl)-1,5-dihydro-4H-imidazol-4-one | 522.2 | 2.04 Q | 110.1-110.4 (16) |
| 119.1 | (5S)-2-((4R)-4-hydroxy-1-(3-methyl-2-(3-methylisothiazol-5-yl)butanoyl)pyrrolidin-2-yl)-5-methyl-5-(4-(4-methylthiazol-5-yl)phenyl)-1,5-dihydro-4H-imidazol-4-one | 538.2 | 2.36 Q | 110.1-110.4 (15) |

TABLE 10-continued

Examples 116.1-135.2

| Example | Structure/Name | LCMS [M + H]⁺ | LCMS R$^T$ (min), method | Synthesis Method/ Example# (Intermediate #) |
|---|---|---|---|---|
| 119.2 | (5S)-2-((4R)-4-hydroxy-1-(3-methyl-2-(3-methylisothiazol-5-yl)butanoyl)pyrrolidin-2-yl)-5-methyl-5-(4-(4-methylthiazol-5-yl)phenyl)-1,5-dihydro-4H-imidazol-4-one | 538.2 | 2.52 Q | 110.1-110.4 (15) |
| 119.3 | (5S)-2-((4R)-4-hydroxy-1-(3-methyl-2-(3-methylisothiazol-5-yl)butanoyl)pyrrolidin-2-yl)-5-methyl-5-(4-(4-methylthiazol-5-yl)phenyl)-1,5-dihydro-4H-imidazol-4-one | 538.2 | 2.35 Q | 110.1-110.4 (15) |
| 119.4 | (5S)-2-((4R)-4-hydroxy-1-(3-methyl-2-(3-methylisothiazol-5-yl)butanoyl)pyrrolidin-2-yl)-5-methyl-5-(4-(4-methylthiazol-5-yl)phenyl)-1,5-dihydro-4H-imidazol-4-one | 538.2 | 2.25 Q | 110.1-110.4 (15) |

TABLE 10-continued

Examples 116.1-135.2

| Example | Structure/Name | LCMS [M + H]+ | LCMS R$^T$ (min), method | Synthesis Method/ Example# (Intermediate #) |
|---|---|---|---|---|
| 120.1 | (5S)-2-((4R)-4-hydroxy-1-((methylsulfonyl)-D-prolyl)pyrrolidin-2-yl)-5-methyl-5-(4-(4-methylthiazol-5-yl)phenyl)-1,5-dihydro-4H-imidazol-4-one | 532.2 | 1.12 P | 112.1 and 112.2 (19) |
| 120.2 | (5S)-2-((4R)-4-hydroxy-1-((methylsulfonyl)-D-prolyl)pyrrolidin-2-yl)-5-methyl-5-(4-(4-methylthiazol-5-yl)phenyl)-1,5-dihydro-4H-imidazol-4-one | 532.2 | 1.01 W | 112.1 and 112.2 (19) |
| 121.1 | (5S)-2-((4R)-1-(acetyl-L-prolyl)-4-hydroxypyrrolidin-2-yl)-5-methyl-5-(4-(4-methylthiazol-5-yl)phenyl)-1,5-dihydro-4H-imidazol-4-one | 496.2 | 3.10 V | 112.1 and 112.2 (18) |

TABLE 10-continued

Examples 116.1-135.2

| Example | Structure/Name | LCMS [M + H]⁺ | LCMS R$^T$ (min), method | Synthesis Method/ Example# (Intermediate #) |
|---|---|---|---|---|
| 121.2 | (5S)-2-((4R)-1-(acetyl-L-prolyl)-4-hydroxypyrrolidin-2-yl)-5-methyl-5-(4-(4-methylthiazol-5-yl)phenyl)-1,5-dihydro-4H-imidazol-4-one | 496.2 | 1.10 DD | 112.1 and 112.2 (18) |
| 122.1 | (5S)-2-((4R)-4-hydroxy-1-((S)-1-(methylsulfonyl)piperidine-2-carbonyl) pyrrolidin-2-yl)-5-methyl-5-(4-(4-methylthiazol-5-yl)phenyl)-1,5-dihydro-4H-imidazol-4-one | 546.2 | 5.71 U | 112.1 and 112.2 (20) |
| 122.2 | (5S)-2-((4R)-4-hydroxy-1-((S)-1-(methylsulfonyl)piperidine-2-carbonyl) pyrrolidin-2-yl)-5-methyl-5-(4-(4-methylthiazol-5-yl)phenyl)-1,5-dihydro-4H-imidazol-4-one | 546.2 | 2.16 CC | 112.1 and 112.2 (20) |

TABLE 10-continued

Examples 116.1-135.2

| Example | Structure/Name | LCMS [M + H]⁺ | LCMS R$^T$ (min), method | Synthesis Method/ Example# (Intermediate #) |
|---|---|---|---|---|
| 123.1 | 2-((2S)-1-((4R)-4-hydroxy-2-((S)-5-methyl-5-(4-(4-methylthiazol-5-yl) phenyl)-4-oxo-4,5-dihydro-1H-imidazol-2-yl)pyrrolidin-1-yl)-3-methyl-1-oxobutan-2-yl)isoindolin-1-one | 572.2 | 2.08 BB | 112.1 and 112.2 |
| 123.2 | 2-((2S)-1-((4R)-4-hydroxy-2-((S)-5-methyl-5-(4-(4-methylthiazol-5-yl) phenyl)-4-oxo-4,5-dihydro-1H-imidazol-2-yl)pyrrolidin-1-yl)-3-methyl-1-oxobutan-2-yl)isoindolin-1-one | 572.2 | 7.18 T | 112.1 and 112.2 |
| 124.1 | (5S)-2-((4R)-1-(1-acetylpiperidine-2-carbonyl)-4-hydroxypyrrolidin-2-yl)-5-methyl-5-(4-(4-methylthiazol-5-yl)phenyl)-1,5-dihydro-4H-imidazol-4-one | 510.2 | 0.748 AA | 112.1 and 112.2 (21) |

TABLE 10-continued

Examples 116.1-135.2

| Example | Structure/Name | LCMS [M + H]+ | LCMS R$^T$ (min), method | Synthesis Method/ Example# (Intermediate #) |
|---|---|---|---|---|
| 124.2 | (5S)-2-((4R)-1-(1-acetylpiperidine-2-carbonyl)-4-hydroxypyrrolidin-2-yl)-5-methyl-5-(4-(4-methylthiazol-5-yl)phenyl)-1,5-dihydro-4H-imidazol-4-one | 510.2 | 0.751 P | 112.1 and 112.2 (21) |
| 124.3 | (5S)-2-((4R)-1-(1-acetylpiperidine-2-carbonyl)-4-hydroxypyrrolidin-2-yl)-5-methyl-5-(4-(4-methylthiazol-5-yl)phenyl)-1,5-dihydro-4H-imidazol-4-one | 510.2 | 1.31 BB | 112.1 and 112.2 (21) |
| 124.4 | (5S)-2-((4R)-1-(1-acetylpiperidine-2-carbonyl)-4-hydroxypyrrolidin-2-yl)-5-methyl-5-(4-(4-methylthiazol-5-yl)phenyl)-1,5-dihydro-4H-imidazol-4-one | 510.2 | 1.57 BB | 112.1 and 112.2 (21) |

TABLE 10-continued

Examples 116.1-135.2

| Example | Structure/Name | LCMS [M + H]⁺ | LCMS R$^T$ (min), method | Synthesis Method/ Example# (Intermediate #) |
|---|---|---|---|---|
| 125.1 | (5S)-2-((4R)-1-(3,3-dimethyl-1-(methylsulfonyl)pyrrolidine-2-carbonyl)-4-hydroxypyrrolidin-2-yl)-5-methyl-5-(4-(4-methylthiazol-5-yl)phenyl)-1,5-dihydro-4H-imidazol-4-one | 560.1 | 1.93 EE | 112.1 and 112.2 (22) |
| 125.2 | (5S)-2-((4R)-1-(3,3-dimethyl-1-(methylsulfonyl)pyrrolidine-2-carbonyl)-4-hydroxypyrrolidin-2-yl)-5-methyl-5-(4-(4-methylthiazol-5-yl)phenyl)-1,5-dihydro-4H-imidazol-4-one | 560.1 | 1.84 X | 112.1 and 112.2 (22) |
| 125.3 | (5S)-2-((4R)-1-(3,3-dimethyl-1-(methylsulfonyl)pyrrolidine-2-carbonyl)-4-hydroxypyrrolidin-2-yl)-5-methyl-5-(4-(4-methylthiazol-5-yl)phenyl)-1,5-dihydro-4H-imidazol-4-one | 560.1 | 1.14 W | 112.1 and 112.2 (22) |

TABLE 10-continued

Examples 116.1-135.2

| Example | Structure/Name | LCMS [M + H]+ | LCMS R$^T$ (min), method | Synthesis Method/ Example# (Intermediate #) |
|---|---|---|---|---|
| 125.4 | 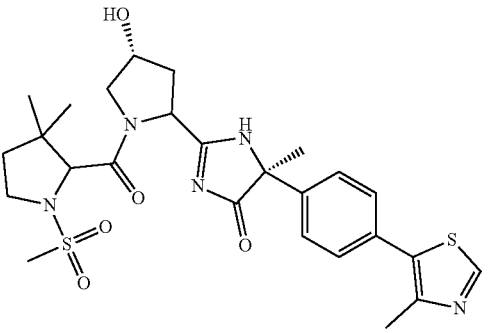 [SMILES: Cc1ncsc1-c1ccc([C@]2(C)NC(C3C[C@@H](O)CN3C(=O)C3N(S(C)(=O)=O)CCC3(C)C)=NC2=O)cc1]<br>(5S)-2-((4R)-1-(3,3-dimethyl-1-(methylsulfonyl)pyrrolidine-2-carbonyl)-4-hydroxypyrrolidin-2-yl)-5-methyl-5-(4-(4-methylthiazol-5-yl)phenyl)-1,5-dihydro-4H-imidazol-4-one | 560.1 | 2.35 CC | 112.1 and 112.2 (21) |
| 126.1 | 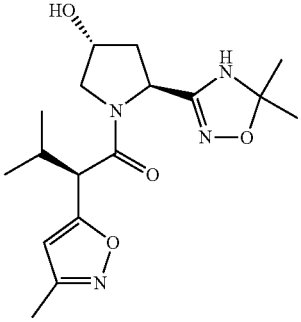 [SMILES: Cc1cc([C@H](C(=O)N2C[C@H](O)C[C@H]2C2=NOC(C)(C)N2)C(C)C)on1]<br>(R)-1-((2S,4R)-2-(5,5-dimethyl-4,5-dihydro-1,2,4-oxadiazol-3-yl)-4-hydroxypyrrolidin-1-yl)-3-methyl-2-(3-methylisoxazol-5-yl)butan-1-one | 351.2 | 1.28 P | 113.1-113.4 |
| 126.2 | 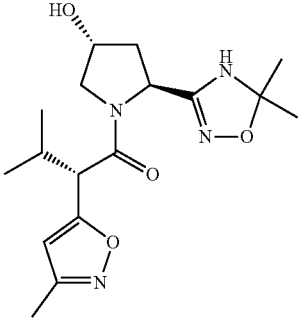 [SMILES: Cc1cc([C@@H](C(=O)N2C[C@H](O)C[C@H]2C2=NOC(C)(C)N2)C(C)C)on1]<br>(S)-1-((2S,4R)-2-(5,5-dimethyl-4,5-dihydro-1,2,4-oxadiazol-3-yl)-4-hydroxypyrrolidin-1-yl)-3-methyl-2-(3-methylisoxazol-5-yl)butan-1-one | 351.2 | 2.11 Q | 113.1-113.4 |

TABLE 10-continued

Examples 116.1-135.2

| Example | Structure/Name | LCMS [M + H]+ | LCMS R$^T$ (min), method | Synthesis Method/ Example# (Intermediate #) |
|---|---|---|---|---|
| 127.1 | (S)-1-((2S,4R)-4-hydroxy-2-(1-oxa-2,4-diazaspiro[4.4]non-2-en-3-yl)pyrrolidin-1-yl)-3-methyl-2-(3-methylisoxazol-5-yl)butan-1-one | 377.1 | 2.18 Q | 113.1-113.4 |
| 127.2 | (R)-1-((2S,4R)-4-hydroxy-2-(1-oxa-2,4-diazaspiro[4.4]non-2-en-3-yl)pyrrolidin-1-yl)-3-methyl-2-(3-methylisoxazol-5-yl)butan-1-one | 377.1 | 2.16 Q | 113.1-113.4 |
| 128.1 | (2S)-1-((2S,4R)-4-hydroxy-2-(5-methyl-5-phenyl-4,5-dihydro-1,2,4-oxadiazol-3-yl)pyrrolidin-1-yl)-3-methyl-2-(3-methylisoxazol-5-yl)butan-1-one | 413.2 | 2.49 Q | 113.1-113.4 |

TABLE 10-continued

Examples 116.1-135.2

| Example | Structure/Name | LCMS [M + H]+ | LCMS R$^T$ (min), method | Synthesis Method/ Example# (Intermediate #) |
|---|---|---|---|---|
| 128.2 | (2S)-1-((2S,4R)-4-hydroxy-2-(5-methyl-5-phenyl-4,5-dihydro-1,2,4-oxa-diazol-3-yl)pyrrolidin-1-yl)-3-methyl-2-(3-methylisoxazol-5-yl)butan-1-one | 413.2 | 1.55 P | 113.1-113.4 |
| 128.3 | (2R)-1-((2S,4R)-4-hydroxy-2-(5-methyl-5-phenyl-4,5-dihydro-1,2,4-oxa-diazol-3-yl)pyrrolidin-1-yl)-3-methyl-2-(3-methylisoxazol-5-yl)butan-1-one | 413.2 | 2.48 Q | 113.1-113.4 |
| 128.4 | (2R)-1-((2S,4R)-4-hydroxy-2-(5-methyl-5-phenyl-4,5-dihydro-1,2,4-oxa-diazol-3-yl)pyrrolidin-1-yl)-3-methyl-2-(3-methylisoxazol-5-yl)butan-1-one | 413.2 | 1.56 P | 113.1-113.4 |

TABLE 10-continued

Examples 116.1-135.2

| Example | Structure/Name | LCMS [M + H]+ | LCMS R$^T$ (min), method | Synthesis Method/ Example# (Intermediate #) |
|---|---|---|---|---|
| 129.1 | (2S)-1-((2S,4R)-4-hydroxy-2-(5-methyl-5-(4-(4-methylthiazol-5-yl)phenyl)-4,5-dihydro-1,2,4-oxadiazol-3-yl)pyrrolidin-1-yl)-3-methyl-2-(3-methylisoxazol-5-yl)butan-1-one | 510.2 | 2.48 X | 113.1-113.4 (26) |
| 129.2 | (2S)-1-((2S,4R)-4-hydroxy-2-(5-methyl-5-(4-(4-methylthiazol-5-yl)phenyl)-4,5-dihydro-1,2,4-oxadiazol-3-yl)pyrrolidin-1-yl)-3-methyl-2-(3-methylisoxazol-5-yl)butan-1-one | 510.2 | 1.34 W | 113.1-113.4 (26) |
| 129.3 | (2R)-1-((2S,4R)-4-hydroxy-2-(5-methyl-5-(4-(4-methylthiazol-5-yl)phenyl)-4,5-dihydro-1,2,4-oxadiazol-3-yl)pyrrolidin-1-yl)-3-methyl-2-(3-methylisoxazol-5-yl)butan-1-one | 510.2 | 2.36 X | 113.1-113.4 (26) |

TABLE 10-continued

Examples 116.1-135.2

| Example | Structure/Name | LCMS [M + H]⁺ | LCMS $R^T$ (min), method | Synthesis Method/ Example# (Intermediate #) |
|---|---|---|---|---|
| 129.4 | (2R)-1-((2S,4R)-4-hydroxy-2-(5-methyl-5-(4-(4-methylthiazol-5-yl)phenyl)-4,5-dihydro-1,2,4-oxadiazol-3-yl)pyrrolidin-1-yl)-3-methyl-2-(3-methylisoxazol-5-yl)butan-1-one | 510.2 | 2.42 X | 113.1-113.4 (26) |
| 130.1 | (2S)-1-((2S,4R)-2-(2,3-dihydro-4'H-spiro[indene-1,5'-[1,2,4]oxadiazol]-3'-yl)-4-hydroxypyrrolidin-1-yl)-3-methyl-2-(3-methylisoxazol-5-yl)butan-1-one | 425.2 | 2.45/ 2.50 Q | 113.1-113.4 (28) |
| 130.2 | (2S)-1-((2S,4R)-2-(2,3-dihydro-4'H-spiro[indene-1,5'-[1,2,4]oxadiazol]-3'-yl)-4-hydroxypyrrolidin-1-yl)-3-methyl-2-(3-methylisoxazol-5-yl)butan-1-one | 425.2 | 1.30/ 1.32 W | 113.1-113.4 (28) |

TABLE 10-continued

Examples 116.1-135.2

| Example | Structure/Name | LCMS [M + H]⁺ | LCMS R$^T$ (min), method | Synthesis Method/ Example# (Intermediate #) |
|---|---|---|---|---|
| 130.3 | (2R)-1-((2S,4R)-2-(2,3-dihydro-4'H-spiro[indene-1,5'-[1,2,4]oxadiazol]-3'-yl)-4-hydroxypyrrolidin-1-yl)-3-methyl-2-(3-methylisoxazol-5-yl)butan-1-one | 425.2 | 2.34 R | 113.1-113.4 (28) |
| 130.4 | (2R)-1-((2S,4R)-2-(2,3-dihydro-4'H-spiro[indene-1,5'-[1,2,4]oxadiazol]-3'-yl)-4-hydroxypyrrolidin-1-yl)-3-methyl-2-(3-methylisoxazol-5-yl)butan-1-one | 425.2 | 2.34 R | 113.1-113.4 (28) |
| 131.1 | (2S)-1-((4R)-2-(3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one | 439.2 | 2.39 X | 113.1-113.4 (29) |

TABLE 10-continued

Examples 116.1-135.2

| Example | Structure/Name | LCMS [M + H]+ | LCMS R^T (min), method | Synthesis Method/ Example# (Intermediate #) |
|---|---|---|---|---|
| 131.2 | (2S)-1-((4R)-2-(3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one | 439.2 | 2.33 X | 113.1-113.4 (29) |
| 131.3 | (2R)-1-((4R)-2-(3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one | 439.2 | 2.38 X | 113.1-113.4 (29) |
| 131.4 | (2R)-1-((4R)-2-(3,4-dihydro-2H,4'H-spiro[naphthalene-1,5'-[1,2,4]oxadiazol]-3'-yl)-4-hydroxypyrrolidin-1-yl)-3-methyl-2-(3-methylisoxazol-5-yl)butan-1-one | 439.2 | 2.38 X | 113.1-113.4 (29) |

TABLE 10-continued

Examples 116.1-135.2

| Example | Structure/Name | LCMS [M + H]⁺ | LCMS R$^T$ (min), method | Synthesis Method/ Example# (Intermediate #) |
|---|---|---|---|---|
| 132.1 | (S)-1-((2S,4R)-2-(5,5-diphenyl-4,5-dihydro-1,2,4-oxadiazol-3-yl)-4-hydroxypyrrolidin-1-yl)-3-methyl-2-(3-methylisoxazol-5-yl)butan-1-one | 475.2 | 2.58 X | 114.1-114.4 |
| 132.2 | (R)-1-((2S,4R)-2-(5,5-diphenyl-4,5-dihydro-1,2,4-oxadiazol-3-yl)-4-hydroxypyrrolidin-1-yl)-3-methyl-2-(3-methylisoxazol-5-yl)butan-1-one | 475.2 | 2.61 X | 114.1-114.4 |
| 133.1 | (2S)-1-((2S,4R)-2-(5-(4-bromophenyl)-5-(trifluoromethyl)-4,5-dihydro-1,2,4-oxadiazol-3-yl)-4-hydroxypyrrolidin-1-yl)-3-methyl-2-(3-methylisoxazol-5-yl)butan-1-one | 547.1 | 2.53 Y | 114.1-114.4 |

TABLE 10-continued

Examples 116.1-135.2

| Example | Structure/Name | LCMS [M + H]⁺ | LCMS R$^T$ (min), method | Synthesis Method/ Example# (Intermediate #) |
|---|---|---|---|---|
| 133.2 | (2S)-1-((2S,4R)-2-(5-(4-bromophenyl)-5-(trifluoromethyl)-4,5-dihydro-1,2,4-oxadiazol-3-yl)-4-hydroxypyrrolidin-1-yl)-3-methyl-2-(3-methyl-isoxazol-5-yl)butan-1-one | 547.1 | 1.89 Z | 114.1-114.4 |
| 133.3 | (2R)-1-((2S,4R)-2-(5-(4-bromophenyl)-5-(trifluoromethyl)-4,5-dihydro-1,2,4-oxadiazol-3-yl)-4-hydroxypyrrolidin-1-yl)-3-methyl-2-(3-methyl-isoxazol-5-yl)butan-1-one | 547.1 | 2.35 Z | 114.1-114.4 |
| 133.4 | (2R)-1-((2S,4R)-2-(5-(4-bromophenyl)-5-(trifluoromethyl)-4,5-dihydro-1,2,4-oxadiazol-3-yl)-4-hydroxypyrrolidin-1-yl)-3-methyl-2-(3-methyl-isoxazol-5-yl)butan-1-one | 547.1 | 2.31 Z | 114.1-114.4 |

TABLE 10-continued

Examples 116.1-135.2

| Example | Structure/Name | LCMS [M + H]⁺ | LCMS $R^T$ (min), method | Synthesis Method/ Example# (Intermediate #) |
|---|---|---|---|---|
| 134.1 | 1-((2S,4R)-2-(5,5-dimethyl-1-(2,2,2-trifluoroethyl)-4,5-dihydro-1H-1,2,4-triazol-3-yl)-4-hydroxypyrrolidin-1-yl)-3-methyl-2-(3-methylisoxazol-5-yl)butan-1-one | 432.2 | 1.27 W | 115.1 and 115.2 |
| 134.2 | 1-((2S,4R)-2-(5,5-dimethyl-1-(2,2,2-trifluoroethyl)-4,5-dihydro-1H-1,2,4-triazol-3-yl)-4-hydroxypyrrolidin-1-yl)-3-methyl-2-(3-methylisoxazol-5-yl)butan-1-one | 432.2 | 1.27 W | 115.1 and 115.2 |
| 135.1 | 1-((2S,4R)-2-(5,5-dimethyl-1-phenyl-4,5-dihydro-1H-1,2,4-triazol-3-yl)-4-hydroxypyrrolidin-1-yl)-3-methyl-2-(3-methylisoxazol-5-yl)butan-1-one | 426.2 | 2.37 X | 115.1 and 115.2 |

TABLE 10-continued

Examples 116.1-135.2

| Example | Structure/Name | LCMS [M + H]+ | LCMS R$^T$ (min), method | Synthesis Method/ Example# (Intermediate #) |
|---|---|---|---|---|
| 135.2 | HO,,,, [structure]<br>1-((2S,4R)-2-(5,5-dimethyl-1-phenyl-4,5-dihydro-1H-1,2,4-triazol-3-yl)-4-hydroxypyrrolidin-1-yl)-3-methyl-2-(3-methylisoxazol-5-yl)butan-1-one | 426.2 | 2.40 X | 115.1 and 115.2 |

Example 136.1

1-((4R)-4-Hydroxy-2-(4,4,5,5-tetramethyl-4,5-dihydro-1H-imidazol-2-yl) pyrrolidin-1-yl)-3-methyl-2-(3-methylisoxazol-5-yl) butan-1-one (Mixture of 4 Stereoisomers)

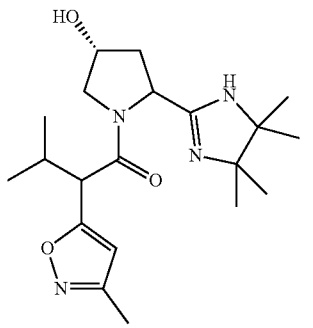 [SMILES: Cc1cc(C(C(=O)N2C[C@H](O)CC2C2=NC(C)(C)C(C)(C)N2)C(C)C)on1]

A solution of methyl (2S,4R)-4-hydroxy-1-[3-methyl-2-(3-methylisoxazol-5-yl) butanoyl] pyrrolidine-2-carboximidate (Intermediate 25, 100 mg, 0.320 mmol), 2,3-dimethylbutane-2,3-diamine (75.1 mg, 0.650 mmol) and DIPEA (417 mg, 3.23 mmol) in ethanol (4 mL) was stirred at 80° C. for 48 hours. The solvent was concentrated under vacuum. The residue was purified by prep HPLC (Column: XSelect CSH Prep C18 OBD Column, 5 um, 19*150 mm; Mobile Phase A: Water (0.1% FA), Mobile Phase B: ACN; Flow rate: 25 mL/min; Gradient: 5% B to 25% B in 7 min; 254/220 nm; R$_T$: 6.13 min) to afford the title compound (19.8 mg, 16.3% yield) as a light yellow solid. LCMS (ESI): R$_T$ (min)=2.18, 2.24, 2.30. [M+H]+=377, method=CC. $^1$H NMR (400 MHz, DMSO-d$_6$) δ 8.33 (s, 1H), 6.26-6.15 (m, 1H), 4.64-4.18 (m, 2H), 3.93-3.71 (m, 2H), 3.57-3.31 (m, 2H), 2.33-2.16 (m, 4H), 2.10-1.85 (m, 2H), 1.17-0.67 (m, 18H).

Examples 137.1, 137.2, and 137.3

1-((4R)-2-(1,1-dioxido-4,5-dihydro-1,2,4-thiadiazol-3-yl)-4-hydroxypyrrolidin-1-yl)-3-methyl-2-(3-methylisoxazol-5-yl)butan-1-one (3 Single Stereoisomers)

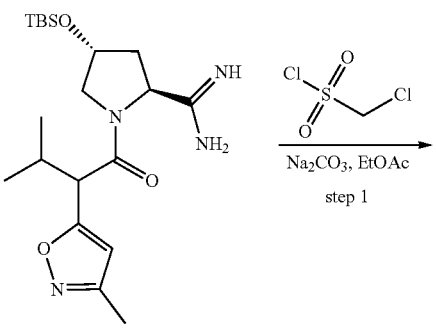

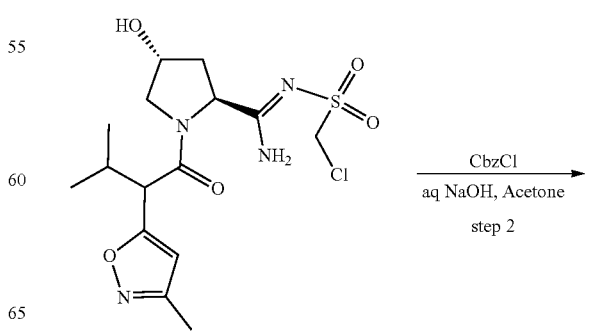

-continued

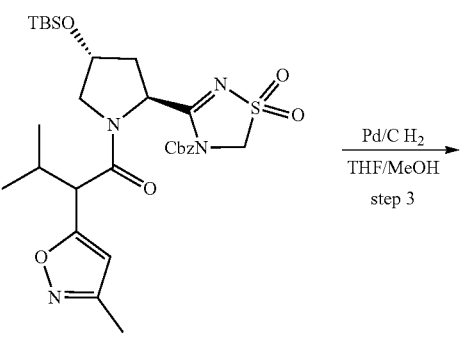

Pd/C H₂
THF/MeOH
step 3

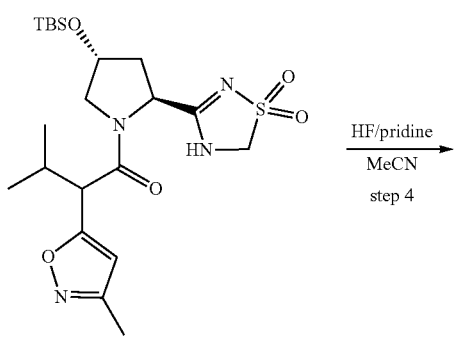

HF/pridine
MeCN
step 4

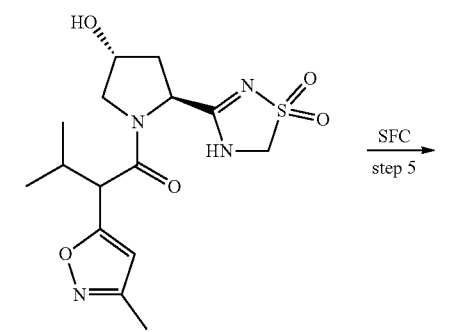

SFC
step 5

Examples 137.1, 137.2, and 137.3

Step 1: (2S,4R,Z)—N'-((chloromethyl)sulfonyl)-4-hydroxy-1-(3-methyl-2-(3-methylisoxazol-5-yl)butanoyl)pyrrolidine-2-carboximidamide

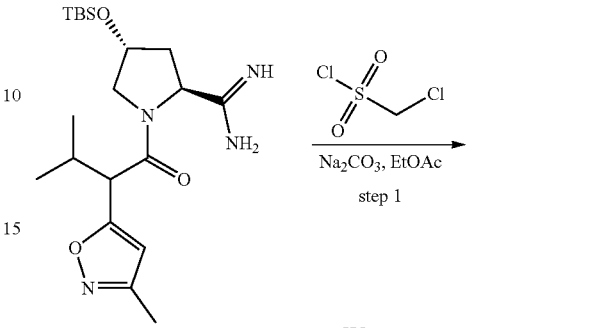

Na₂CO₃, EtOAc
step 1

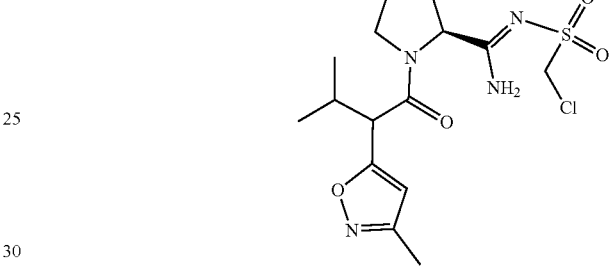

To a mixture of Na₂CO₃ (648.48 mg, 6.12 mmol) and (2S,4R)-4-((tert-butyldimethylsilyl)oxy)-1-(3-methyl-2-(3-methylisoxazol-5-yl)butanoyl)pyrrolidine-2-carboximidamide (500.0 mg, 1.22 mmol) in EtOAc (20 mL) was added chloromethanesulfonyl chloride (364.65 mg, 2.45 mmol) at 20° C. The mixture was stirred at 60° C. for 14 hours. The mixture was filtrated, concentrated, and purified by flash chromatography on silica gel (20-50% EtOAc in petroleum ether, Rf=0.4) to give (2S,4R,Z)—N'-((chloromethyl)sulfonyl)-4-hydroxy-1-(3-methyl-2-(3-methylisoxazol-5-yl)butanoyl)pyrrolidine-2-carboximidamide (135 mg, 21%) as an off-white solid. LCMS (Method FF): RT=1.066 min, m z=521.0 [M+1]⁺.

Step 2: benzyl 3-((2S,4R)-4-((tert-butyldimethylsilyl)oxy)-1-(3-methyl-2-(3-methylisoxazol-5-yl)butanoyl)pyrrolidin-2-yl)-1,2,4-thiadiazole-4(5H)-carboxylate 1,1-dioxide

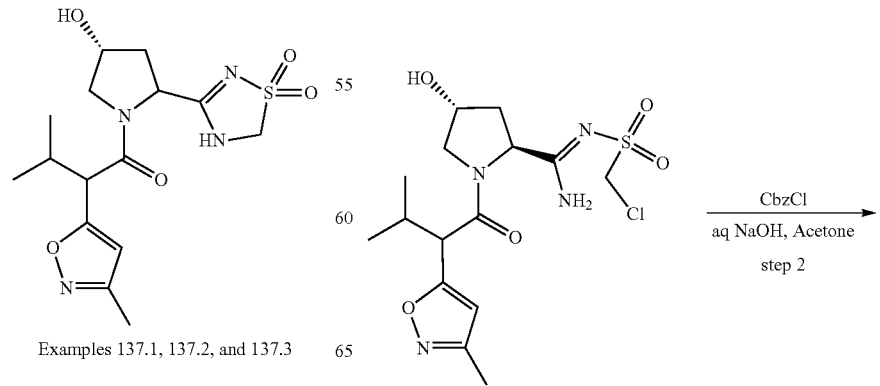

CbzCl
aq NaOH, Acetone
step 2

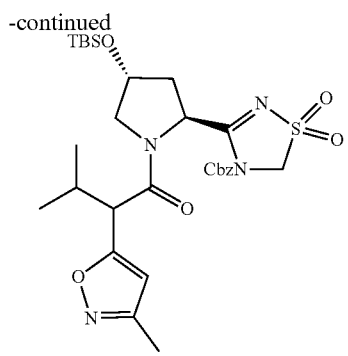

To a solution of (2S,4R,Z)—N'-((chloromethyl)sulfonyl)-4-hydroxy-1-(3-methyl-2-(3-methylisoxazol-5-yl)butanoyl)pyrrolidine-2-carboximidamide (120.0 mg, 0.2300 mmol) in acetone (10 mL) was added a solution of NaOH in water (46.05 mg, 0.4600 mmol) at 50° C. CbzCl (785.6 mg, 4.61 mmol) was added to the above mixture. After the mixture was stirred at 50° C. for 0.5 hours, it was quenched with water (10 mL). The mixture was extracted with EtOAc (20 mL×2), and washed with brine (20 mL×2). The organic layer was concentrated and purified by flash chromatography on silica gel (10-30% EtOAc in petroleum ether, Rf=0.4) to afford benzyl 3-((2S,4R)-4-((tert-butyldimethylsilyl)oxy)-1-(3-methyl-2-(3-methylisoxazol-5-yl)butanoyl)pyrrolidin-2-yl)-1,2,4-thiadiazole-4(5H)-carboxylate 1,1-dioxide (84 mg, 59%) as an off white solid. LCMS (Method FF): RT=1.157 min and 1.186 min, m z=619.1 [M+1]⁺.

Step 3: 1-((2S,4R)-4-((tert-butyldimethylsilyl)oxy)-2-(1,1-dioxido-4,5-dihydro-1,2,4-thiadiazol-3-yl)pyrrolidin-1-yl)-3-methyl-2-(3-methylisoxazol-5-yl)butan-1-one

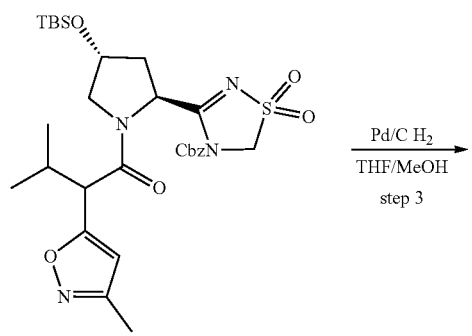

A mixture of benzyl 3-((2S,4R)-4-((tert-butyldimethylsilyl)oxy)-1-(3-methyl-2-(3-methylisoxazol-5-yl)butanoyl)pyrrolidin-2-yl)-1,2,4-thiadiazole-4(5H)-carboxylate 1,1-dioxide (80.0 mg, 0.1300 mmol) in MeOH (4.0 mL) and THF (4.0 mL) was added 10% Pd/C (5.66 mg) at 20° C. The mixture was stirred under H₂ (15 psi) for 1 hour. The mixture was filtrated, and the filtrate was concentrated to give 1-((2S,4R)-4-((tert-butyldimethylsilyl)oxy)-2-(1,1-dioxido-4,5-dihydro-1,2,4-thiadiazol-3-yl)pyrrolidin-1-yl)-3-methyl-2-(3-methylisoxazol-5-yl)butan-1-one (61 mg, 97%) as a colorless oil, which was used in next step directly. LCMS (Method FF): RT=1.01 min and 1.036, m z=485.1 [M+1]⁺.

Step 4: 1-((2S,4R)-2-(1,1-dioxido-4,5-dihydro-1,2,4-thiadiazol-3-yl)-4-hydroxypyrrolidin-1-yl)-3-methyl-2-(3-methylisoxazol-5-yl)butan-1-one

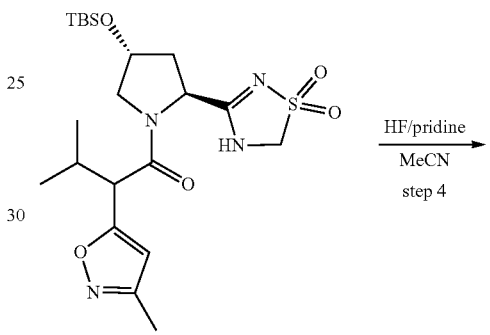

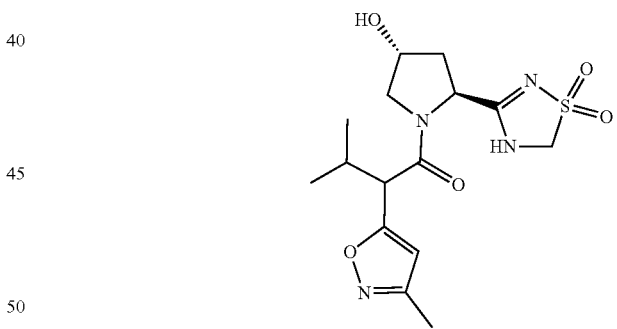

A mixture of 1-((2S,4R)-4-((tert-butyldimethylsilyl)oxy)-2-(1,1-dioxido-4,5-dihydro-1,2,4-thiadiazol-3-yl)pyrrolidin-1-yl)-3-methyl-2-(3-methylisoxazol-5-yl)butan-1-one (60.0 mg, 0.1200 mmol) in CH₃CN (4.0 mL) was added HF/pyridine (0.60 mL) at 20° C., and the reaction mixture was stirred at 20° C. for 1 hour. The mixture was concentrated and purified by prep-HPLC (acetonitrile 15-45/0.225% FA in water) to afford 1-((2S,4R)-2-(1,1-dioxido-4,5-dihydro-4,5-dihydro-1,2,4-thiadiazol-3-yl)-4-hydroxypyrrolidin-1-yl)-3-methyl-2-(3-methylisoxazol-5-yl)butan-1-one (25 g, 54%) as a brown solid. LCMS (Method FF): RT=0.746 min, m z=393.0 [M+23]⁺.

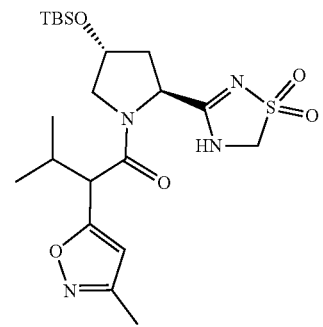

Step 5: 1-((4R)-2-(1,1-dioxido-4,5-dihydro-1,2,4-thiadiazol-3-yl)-4-hydroxypyrrolidin-1-yl)-3-methyl-2-(3-methylisoxazol-5-yl)butan-1-one (3 single stereoisomers) (Examples 137.1, 137.2, and 137.3)

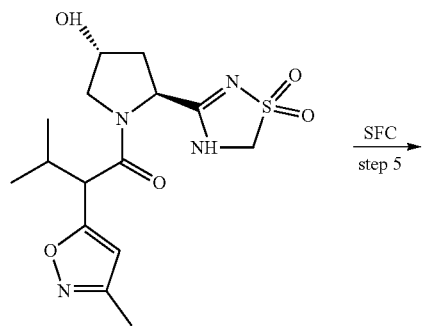

Examples 137.1, 137.2, and 137.3

The 1-((2S,4R)-2-(1,1-dioxido-4,5-dihydro-1,2,4-thiadiazol-3-yl)-4-hydroxypyrrolidin-1-yl)-3-methyl-2-(3-methylisoxazol-5-yl)butan-1-one (25.0 mg, 0.0700 mmol) was separated by SFC (0.1% $NH_3H_2O$ in EtOH, 50 mL/min) to give three products as off-white solids: Example 137.1 (7.5 mg, 28%). Example 137.2 (8.4 mg, 32%), Example 137.3 (3.2 mg, 12.8%).

Example 137.1: H NMR (400 MHz, $CD_3OD$) δ 6.19 (s, 1H), 4.67 (t, J=8.0 Hz, 1H), 4.53-4.46 (m, 1H), 4.43-4.32 (m, 2H), 3.81 (d, J=8.8 Hz, 1H), 3.73-3.70 (m, 1H), 3.62-3.60 (m, 1H), 2.33-2.26 (m, 2H), 2.23 (s, 3H), 2.13-2.10 (m, 1H), 1.01 (d, J=6.4 Hz, 3H), 0.87 (d, J=6.4 Hz, 3H). LCMS (Method FF): RT=0.735 min, m/z=393.0 [M+23]+. SFC: Method 1, RT=3.993 min, ee=100%.

Example 137.2: $^1$H NMR (400 MHz, $CD_3OD$) δ 6.20 (s, 1H), 4.61-4.59 (m, 1H), 4.53-4.50 (br, 1H), 4.46-4.35 (m, 2H), 3.91 (dd, J=4.0, 10.8 Hz, 1H), 3.76 (d, J=9.6 Hz, 1H), 3.64-3.61 (m, 1H), 2.38-2.26 (m, 2H), 2.23 (s, 3H), 2.22-2.15 (m, 1H), 1.04 (d, J=6.4 Hz, 3H), 0.84 (d, J=6.4 Hz, 3H). LCMS (Method FF): RT=0.775 min, m/z=393.0 [M+23]+. SFC: Method 1, RT=5.294 min, ee=100%.

Example 137.3: $^1$H NMR (400 MHz, $CD_3OD$) δ 6.22 (s, 1H), 4.73-4.69 (m, 2H), 4.44-4.35 (m, 2H), 3.84-3.81 (m, 1H), 3.62 (d, J=3.2 Hz, 1H), 3.53-3.49 (m, 1H), 2.51-2.49 (m, 1H), 2.33-2.25 (m, 1H), 2.23 (s, 3H), 2.05-2.01 (m, 1H), 098 (d, J=6.4 Hz, 3H), 0.86 (d, J=6.4 Hz, 3H). LCMS (Method FF): RT=0.743 min, m/z=393.0 [M+23]+. SFC: Method 1, RT=3.591 min, ee=98%.

Examples 138.1, 138.2, 138.3, and 138.4

(S)-5-(2'-fluoro-[1,1'-biphenyl]-4-yl)-2-((2S,4R)-4-hydroxy-1-((R)-3-methyl-2-(3-methylisoxazol-5-yl)butanoyl)pyrrolidin-2-yl)-5-methyl-1,5-dihydro-4H-imidazol-4-one (S)-5-(2'-fluoro-[1,1'-biphenyl]-4-yl)-2-((2R,4R)-4-hydroxy-1-((R)-3-methyl-2-(3-methylisoxazol-5-yl)butanoyl)pyrrolidin-2-yl)-5-methyl-1,5-dihydro-4H-imidazol-4-one (S)-5-(2'-fluoro-[1,1'-biphenyl]-4-yl)-2-((2S,4R)-4-hydroxy-1-((S)-3-methyl-2-(3-methylisoxazol-5-yl)butanoyl)pyrrolidin-2-yl)-5-methyl-1,5-dihydro-4H-imidazol-4-one (S)-5-(2'-fluoro-[1,1'-biphenyl]-4-yl)-2-((2R,4R)-4-hydroxy-1-((S)-3-methyl-2-(3-methylisoxazol-5-yl)butanoyl)pyrrolidin-2-yl)-5-methyl-1,5-dihydro-4H-imidazol-4-one

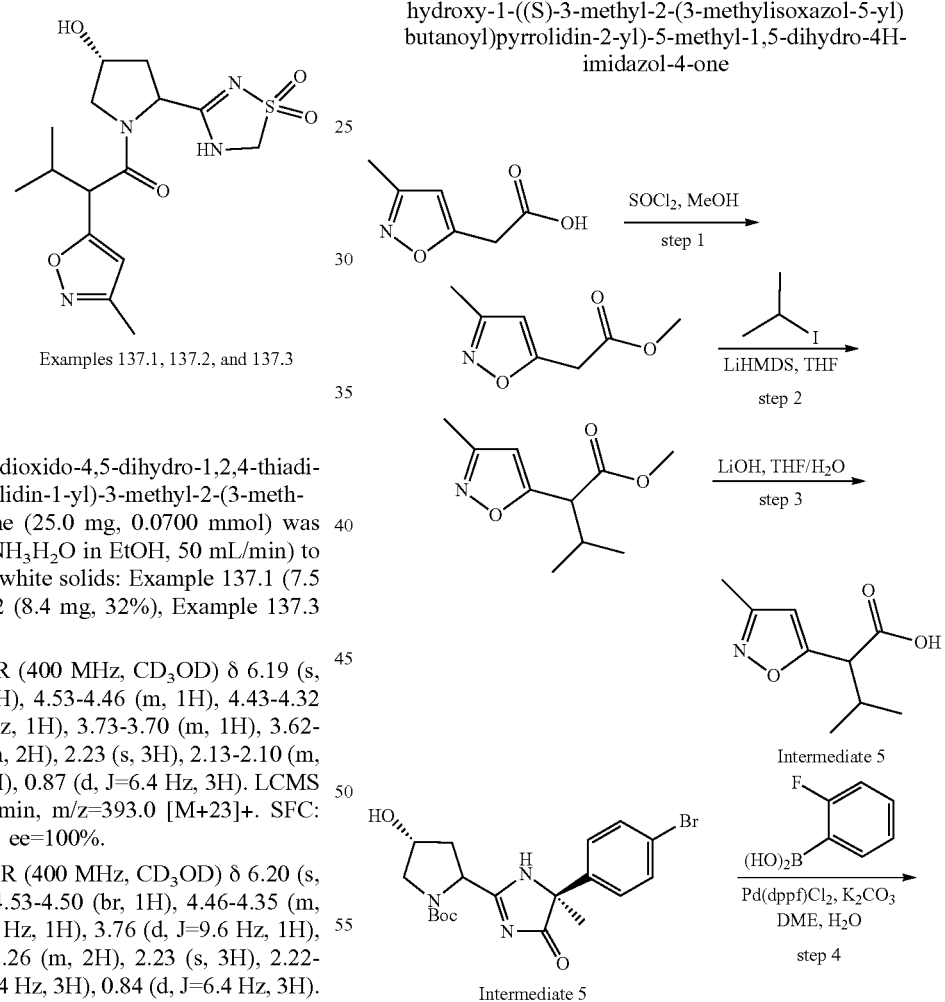

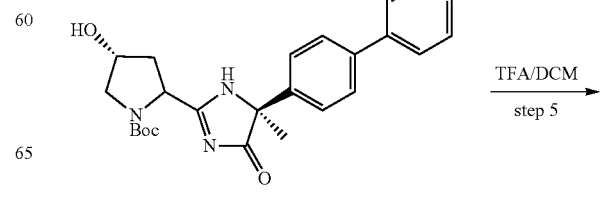

603

-continued

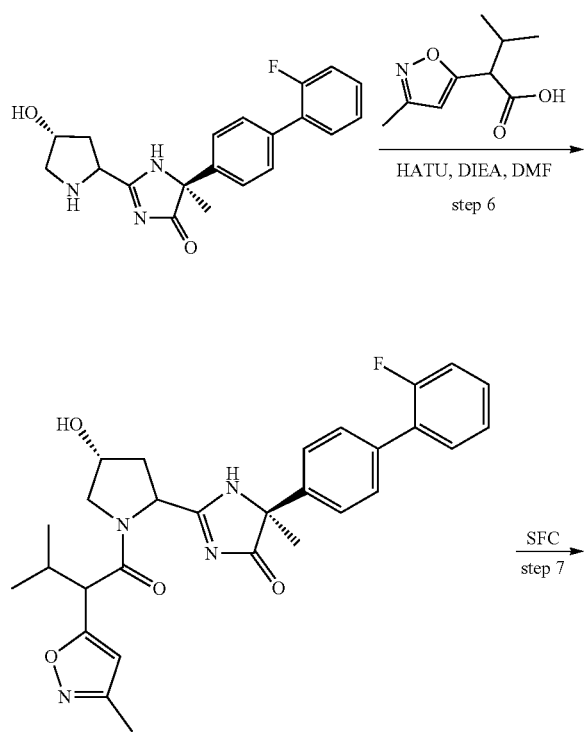

604

-continued

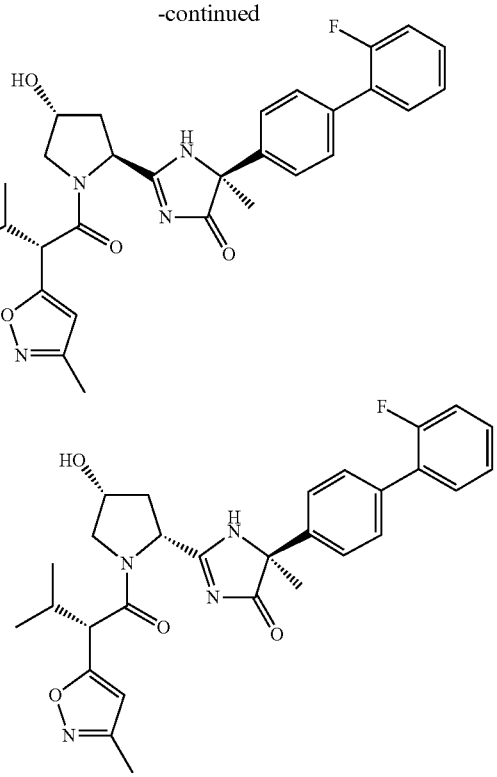

Step 1: methyl 2-(3-methylisoxazol-5-yl)acetate

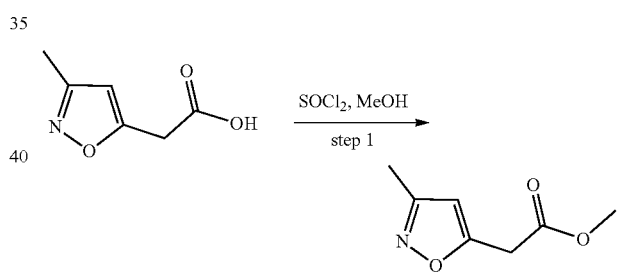

A mixture of 2-(3-methylisoxazol-5-yl)acetic acid (1.800 g, 12.76 mmol) in MeOH (50 mL) was added SOCl$_2$ (1.39 mL, 19.13 mmol) slowly at 0° C. The mixture was stirred at 50° C. for 12 hours. The mixture was concentrated and diluted with water (20 mL). The mixture was extracted with EtOAc (50 mL×3), washed with brine (20 mL×2). The organic layer was concentrated to give the desired product (1.700 g, 85.9%) which was used in next step directly. H NMR (400 MHz, CDCl$_3$) δ 6.10 (s, 1H), 3.78 (s, 2H), 3.74 (s, 3H), 2.28 (s, 3H).

Step 2: methyl 3-methyl-2-(3-methylisoxazol-5-yl)butanoate

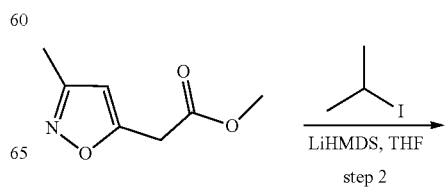

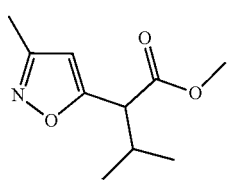

To a solution of methyl 2-(3-methylisoxazol-5-yl)acetate (1.100 g, 7.09 mmol) in THF (20 mL) was added LiHMDS (12.76 mL, 12.76 mmol) in THF at −78° C. The mixture was stirred at −78° C. for 30 minutes, then 2-iodopropane (1.42 mL, 14.18 mmol) was added dropwise. The reaction temperature increased from −78° C. to −15° C. over 16 hours. The mixture was quenched with saturated NH$_4$Cl solution (20 mL), and extracted with EtOAc (30 mL×3). The combined organic layers were dried over Na$_2$SO$_4$, filtered, and concentrated. The residue was purified by column chromatography on silica gel (0~20% EtOAc in petroleum ether) to afford the desired product (550 mg, 39%) as a colorless oil. $^1$H NMR (400 MHz, CDCl$_3$) δ 6.09 (s, 1H), 3.72 (s, 3H), 3.58 (d, J=8.4 Hz, 1H), 2.45-2.32 (m, 1H), 2.28 (s, 3H), 0.99 (d, J=6.8 Hz, 3H), 0.89 (d, J=6.8 Hz, 3H).

Step 3: 3-methyl-2-(3-methylisoxazol-5-yl)butanoic acid (Intermediate 5)

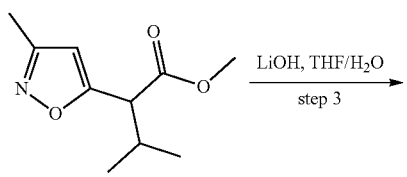

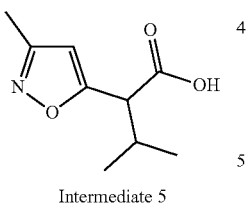

Intermediate 5

A mixture of methyl 3-methyl-2-(3-methylisoxazol-5-yl) butanoate (650.0 mg, 3.3 mmol) in THF (5.0 mL) and H$_2$O (1.0 mL) was added LiOH H$_2$O (691.43 mg, 16.48 mmol). The mixture was stirred for 12 hours at 25° C. The mixture was extracted with EtOAc (20 mL×2). The aqueous phase was adjusted to pH=5.0 with conc. HCl. The mixture was extracted with EtOAc (20 mL×3). The organic layer was concentrated to give the desired product (540 mg, 89%) as a white solid which was used in next step directly. $^1$H NMR (400 MHz, CDCl$_3$) δ 10.65 (s, 1H), 6.14 (s, 1H), 3.63 (d, J=8.4 Hz, 1H), 2.49-2.33 (m, 1H), 2.30 (s, 3H), 1.05 (d, J=6.8 Hz, 3H), 0.93 (d, J=6.8 Hz, 3H).

Step 4: tert-butyl (4R)-2-((S)-5-(2'-fluoro-[1,1'-biphenyl]-4-yl)-5-methyl-4-oxo-4,5-dihydro-1H-imidazol-2-yl)-4-hydroxypyrrolidine-1-carboxylate

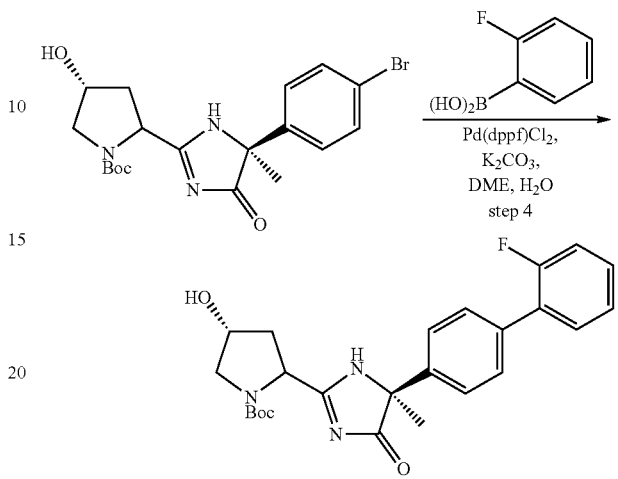

To a mixture of tert-butyl (4R)-2-((S)-5-(4-bromophenyl)-5-methyl-4-oxo-4,5-dihydro-1H-imidazol-2-yl)-4-hydroxypyrrolidine-1-carboxylate (400.0 mg, 0.910 mmol) and (2-fluorophenyl)boronic acid (165.99 mg, 1.19 mmol), K$_2$CO$_3$ (252.25 mg, 1.83 mmol) in DME (6.0 mL)/H$_2$O (1.0 mL) was added Pd(dppf)Cl$_2$ (66.77 mg, 0.0900 mmol). After the mixture was stirred at 80° C. for 12 hours under N$_2$, it was filtered and the organic layer was concentrated. Water (20 mL) was added and it was extracted with EtOAc (20 mL×3). The organic layer was dried over Na$_2$SO$_4$, concentrated, and purified by chromatography on silica gel (0-100% EtOAc in petroleum ether) to afford the desired product (500 mg) as a yellow solid. LCMS (Method GG): R$_T$=3.047 min, m z=454.0 [M+1]$^+$.

Step 5: (5S)-5-(2'-fluoro-[1,1'-biphenyl]-4-yl)-2-((4R)-4-hydroxypyrrolidin-2-yl)-5-methyl-1,5-dihydro-4H-imidazol-4-one

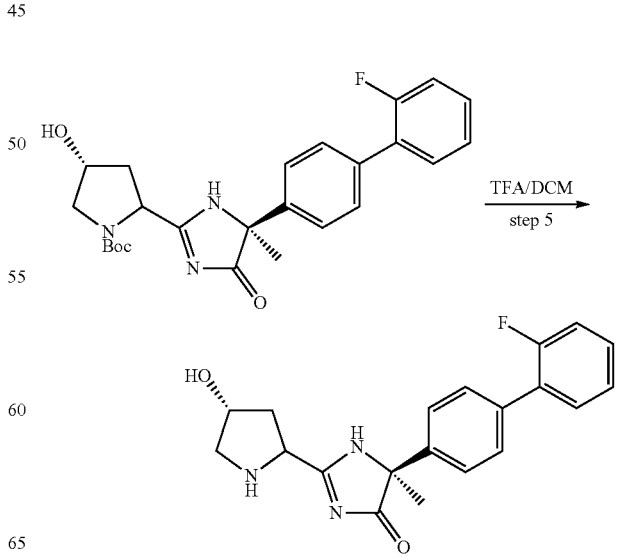

607

To a solution of TFA (3.28 mL) in DCM (10 mL) was added tert-butyl (4R)-2-((S)-5-(2'-fluoro-[1,1'-biphenyl]-4-yl)-5-methyl-4-oxo-4,5-dihydro-1H-imidazol-2-yl)-4-hydroxypyrrolidine-1-carboxylate (500.0 mg, 1.1 mmol) at 15° C. The mixture was stirred at 15° C. for 12 hours. The mixture was concentrated and basified to pH=8.0 by NH₃ H₂O. It was concentrated and purified by chromatography on silica gel (0-10% MeOH in DCM, Rf=0.1) to afford the desired product (380 mg, 98%). LCMS (Method FF): $R_T$=0.790 min, m z=354.0 [M+1]⁺.

Steps 6 and 7: Examples 138.1, 138.2, 138.3, and 138.4

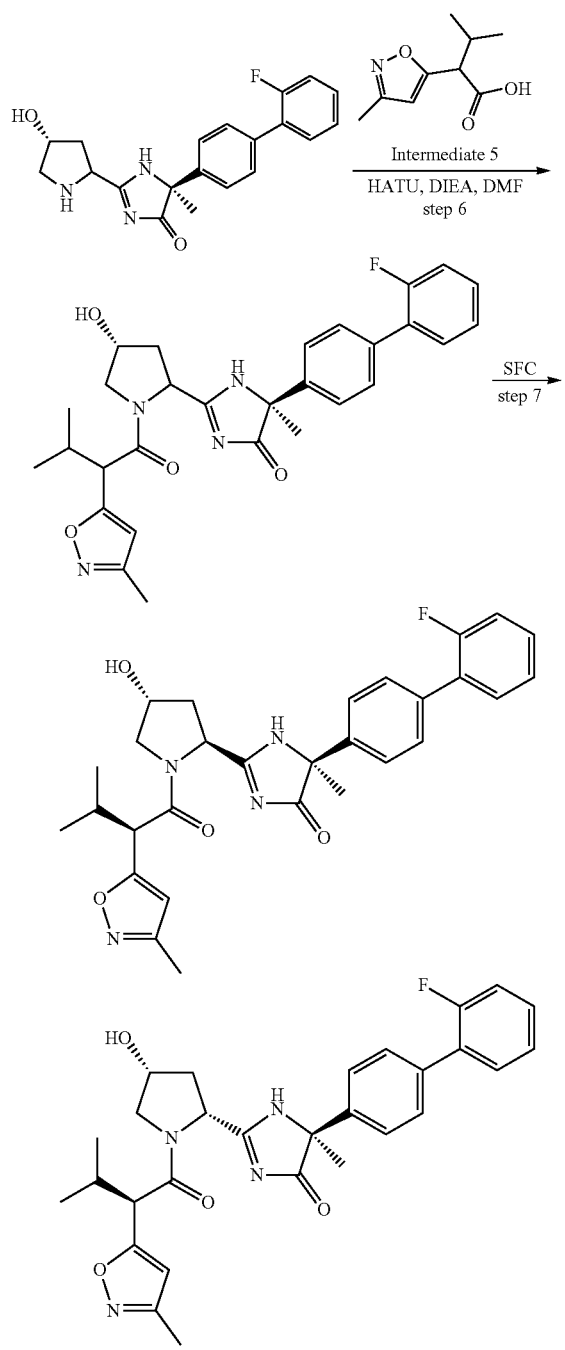

608

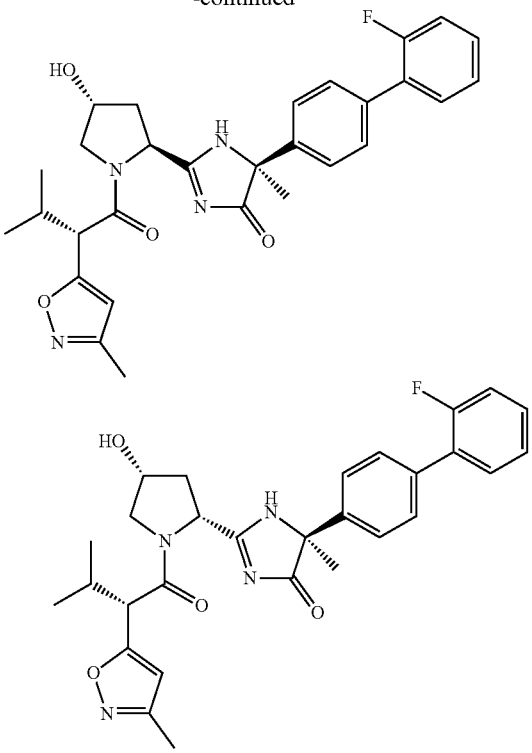

To a solution of HATU (199.25 mg, 0.5200 mmol), 3-methyl-2-(3-methylisoxazol-5-yl)butanoic acid (Intermediate 5, 80.0 mg, 0.4400 mmol) and DIEA (0.22 mL, 1.31 mmol) in DMF (2.0 mL) was added (5S)-5-(2'-fluoro-[1,1'-biphenyl]-4-yl)-2-((4R)-4-hydroxypyrrolidin-2-yl)-5-methyl-1,5-dihydro-4H-imidazol-4-one (154.32 mg, 0.4400 mmol) at 15° C. and stirred at 15° C. for 2 hours. The reaction mixture was quenched with water (20 mL), and extracted with EtOAc (30 mL×3). The organic layer was concentrated, and purified by prep-HPLC (acetonitrile 38-68/0.225% FA in water), followed by SFC separation to afford four compounds as white solids.

Example 138.1 (10.8 mg, 4.7%): ¹H NMR (400 MHz, CDCl₃) δ 8.75 (s, 1H), 7.62 (d, J=8.8 Hz, 2H), 7.53 (d, J=6.8 Hz, 2H), 7.44-7.38 (m, 1H), 7.36-7.28 (m, 1H), 7.24-7.18 (m, 1H), 7.17-7.10 (m, 1H), 6.07 (s, 1H), 5.61 (d, J=8.8 Hz, 1H), 5.15 (d, J=8.8 Hz, 1H), 4.63-4.61 (m, 1H), 3.85 (dd, J=10.8, 4.4 Hz, 1H), 3.70 (d, J=10.4 Hz, 1H), 3.62 (d, J=9.6 Hz, 1H), 2.78 (d, J=14.0 Hz, 1H), 2.45-2.37 (m, 2H), 2.29 (s, 3H), 1.59 (s, 3H), 1.04 (d, J=6.4 Hz, 3H), 0.91 (d, J=6.8 Hz, 3H). LCMS (Method FF): $R_T$=0.923 min, m z=519.1 [M+1]⁺. SFC: Method 2, RT=2.971 min, de=99%.

Example 138.2 (1.1 mg, 0.48%): ¹H NMR (400 MHz, CDCl₃) δ 8.83 (s, 1H), 7.65 (d, J=8.8 Hz, 2H), 7.54 (d, J=7.2 Hz, 2H), 7.42 (t, J=7.2 Hz, 1H), 7.36-7.29 (m, 1H), 7.25-7.19 (m, 1H), 7.18-7.11 (m, 1H), 6.14 (s, 1H), 5.82 (d, J=8.8 Hz, 1H), 5.06 (d, J=9.2 Hz, 1H), 4.65-4.61 (m, 1H), 3.89-3.81 (m, 2H), 3.65 (d, J=10.0 Hz, 1H), 2.77 (d, J=14.8 Hz, 1H), 2.49-2.32 (m, 2H), 2.30 (s, 3H), 1.67 (s, 3H), 1.02 (d, J=6.4 Hz, 3H), 0.93 (d, J=6.8 Hz, 3H). LCMS (Method FF): $R_T$=0.929 min, m z=519.1[M+1]⁺. SFC: Method 2, $R_T$=3.318 min, de=99%.

Example 138.3 (9.4 mg, 4.2%): ¹H NMR (400 MHz, CDCl₃) δ 8.83 (s, 1H), 7.48 (brs, 4H), 7.40 (t, J=7.6 Hz, 1H), 7.34-7.28 (m, 1H), 7.24-7.14 (m, 2H), 6.00 (s, 1H), 5.14 (dd, J=7.6, 3.6 Hz, 1H), 4.74 (brs, 1H), 3.71-3.67 (m, 3H), 3.04-3.00 (m, 1H), 2.44-2.35 (m, 2H), 2.19-2.17 (m, 1H), 2.13 (s, 3H), 1.69 (s, 3H), 1.06 (d, J=6.8 Hz, 3H), 0.88 (d, J=6.8 Hz, 3H). LCMS (Method FF): $R_T$=0.906 min, m z=519.1[M+1]$^+$. SFC: Method 7, RT=2.017 min, de=95.7%.

Example 138.4 (6.0 mg, 2.6%): $^1$H NMR (400 MHz, CDCl$_3$) δ 9.06 (s, 1H), 7.57 (d, J=8.4 Hz, 2H), 7.52 (d, J=8.0 Hz, 2H), 7.41-7.38 (m, 1H), 7.32-7.27 (m, 1H), 7.24-7.12 (m, 3H), 6.11 (s, 1H), 5.01 (t, J=6.8 Hz, 1H), 4.77-4.71 (m, 1H), 3.83-3.79 (m, 1H), 3.71-3.68 (m, 1H), 3.59 (d, J=10.0 Hz, 1H), 3.02-2.97 (m, 1H), 2.36-2.33 (m, 1H), 2.29 (s, 3H), 2.23-2.18 (m, 1H), 1.72 (s, 3H), 0.88 (d, J=6.4 Hz, 3H), 0.84 (d, J=6.4 Hz, 3H). LCMS (Method FF): $R_T$=0.931 min, m/z=519.1[M+1]$^+$. SFC: Method 2, RT=2.794 Min, de=96%.

Examples 139.1 and 139.2

1-((2S,4R)-2-((R)-5-(2'-fluoro-[1,1'-biphenyl]-4-yl)-5-methyl-4,5-dihydro-1,2,4-oxadiazol-3-yl)-4-hydroxypyrrolidin-1-yl)-3-methyl-2-(3-methylisoxazol-5-yl)butan-1-one (2 Stereoisomers)

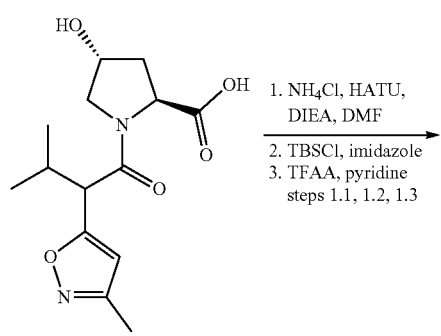

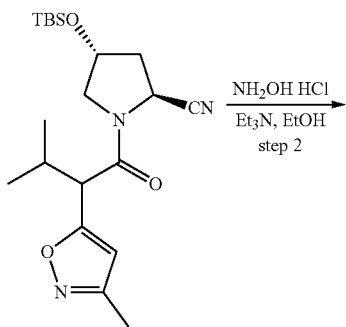

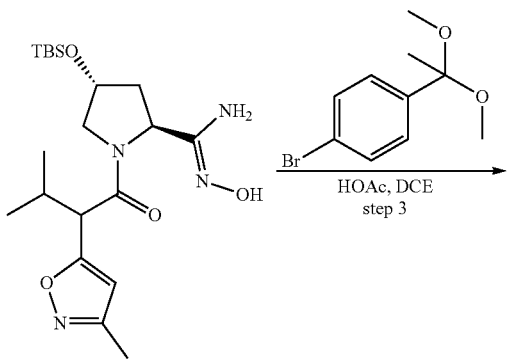

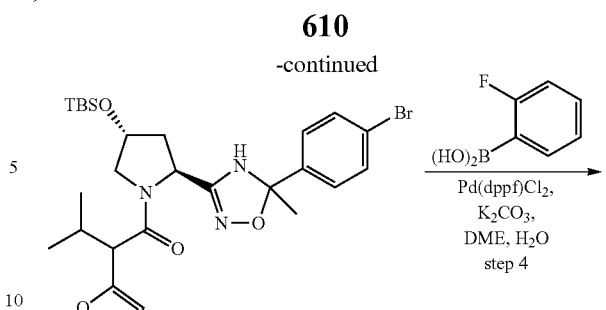

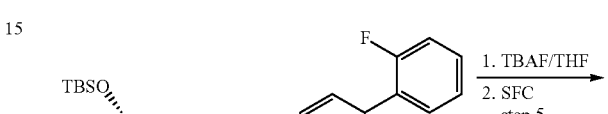

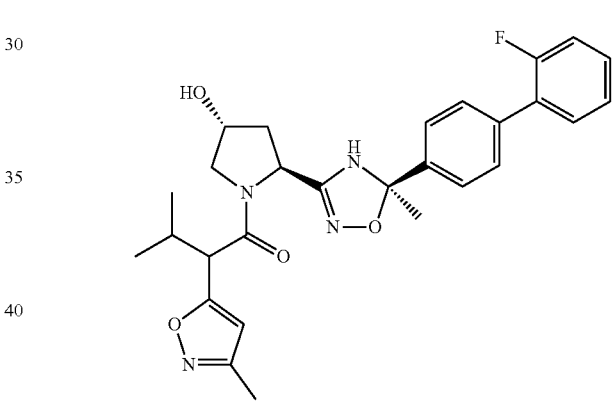

Examples 139.1 and 139.2

Step 1.1: (2S,4R)-4-hydroxy-1-(3-methyl-2-(3-methylisoxazol-5-yl)butanoyl)pyrrolidine-2-carboxamide

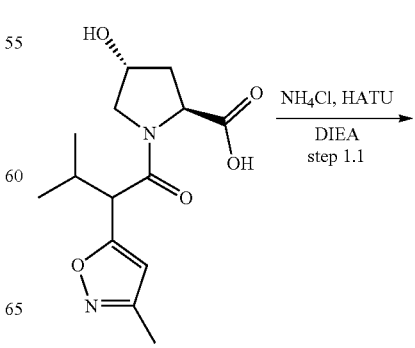

-continued

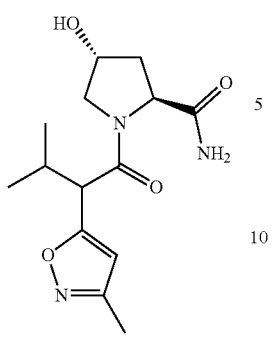

To a solution of (2S,4R)-4-hydroxy-1-(3-methyl-2-(3-methylisoxazol-5-yl)butanoyl)pyrrolidine-2-carboxylic acid (5.00 g, 16.87 mmol) in DMF (33.3 mL) was added HATU (7.699 g, 20.25 mmol) and DIEA (6.542 g, 50.62 mmol) at 20° C. The reaction mixture was stirred at 20° C. for 30 minutes. NH$_4$Cl (1.805 g, 33.75 mmol) was added and stirred for 2 hours at 20° C. The reaction mixture was concentrated under reduced pressure to remove DMF, and was diluted with H$_2$O (10 mL). The mixture was acidified to pH=2.0 with HCl (1.0 M), washed with EtOAc (20 mL), and the organic layer was extracted with water (10 mL×2). The aqueous layer was lyophilized to afford crude (2S,4R)-4-hydroxy-1-(3-methyl-2-(3-methylisoxazol-5-yl)butanoyl)pyrrolidine-2-carboxamide (4.90 g, 98% yield) as a yellow solid, which was used directly in the next step.

Step 1.2: (2S,4R)-4-(((tert-butyldimethylsilyl)oxy)-1-(3-methyl-2-(3-methylisoxazol-5-yl)butanoyl)pyrrolidine-2-carboxamide

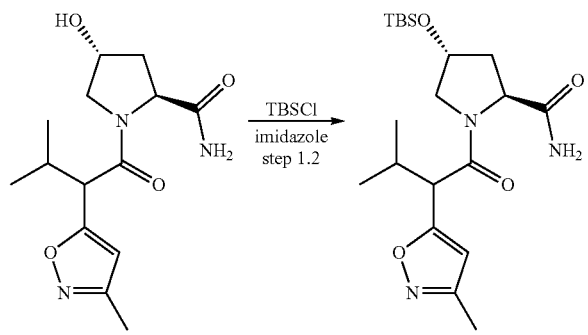

A mixture of TBSCl (3.751 g, 24.89 mmol), (2S,4R)-4-hydroxy-1-(3-methyl-2-(3-methylisoxazol-5-yl)butanoyl)pyrrolidine-2-carboxamide (4.900 g, 16.59 mmol), DMAP (202.7 mg, 1.66 mmol) and imidazole (3.388 g, 49.77 mmol) in THF (30 mL) was stirred at 25° C. for 12 hours. Water (30.0 mL) was added and it was extracted with DCM (40 mL×3), washed with brine (30 mL×3). The organic layer was dried over Na$_2$SO$_4$, concentrated, and purified by flash column chromatography on silica gel (0-100% EtOAc in petroleum ether, Rf=0.5) to give (2S,4R)-4-((tert-butyldimethylsilyl)oxy)-1-(3-methyl-2-(3-methylisoxazol-5-yl)butanoyl)pyrrolidine-2-carboxamide (6.700 g, 98.6%) as a colorless oil, which was used in next step directly. LCMS (Method FF): RT=1.078 min, m/z=392.1 [M+1]$^+$.

Step 1.3: (2S,4R)-4-(((tert-butyldimethylsilyl)oxy)-1-(3-methyl-2-(3-methylisoxazol-5-yl)butanoyl)pyrrolidine-2-carbonitrile

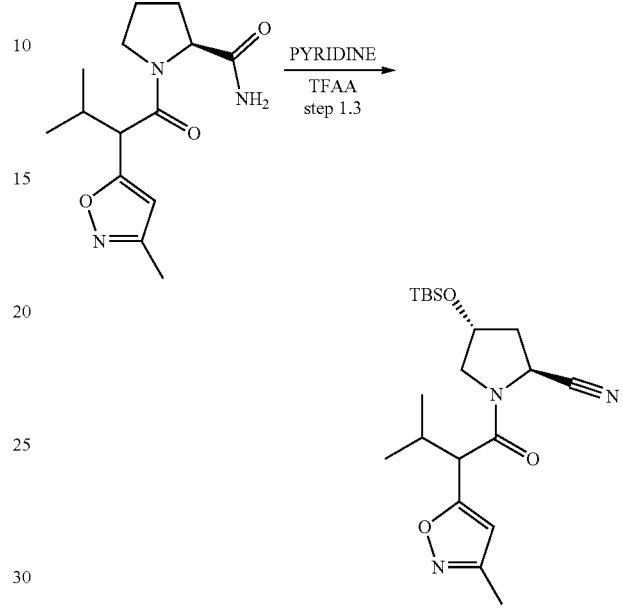

To a solution of (2S,4R)-4-((tert-butyldimethylsilyl)oxy)-1-(3-methyl-2-(3-methylisoxazol-5-yl)butanoyl)pyrrolidine-2-carboxamide (6.700 g, 16.36 mmol) and pyridine (3.881 g, 49.07 mmol) in EtOAc (20 mL) was added TFAA (3.779 g, 17.99 mmol). After the mixture was stirred at 20° C. for 1 hour, it was concentrated, and dissolved in DCM (90 mL). The organic layer was washed with brine (20 mL×2), dried over Na$_2$SO$_4$, concentrated, and purified by flash chromatography on silica (0-30% EtOAc in petroleum ether, Rf=0.4) to (2S,4R)-4-(((tert-butyldimethylsilyl)oxy)-1-(3-methyl-2-(3-methylisoxazol-5-yl)butanoyl)pyrrolidine-2-carbonitrile (5.700 g, 89%) as a yellow solid. LCMS (Method FF): RT=1.078 min, m/z=392.1 [M+1]$^+$.

Step 2: (2S,4R,Z)-4-(((tert-butyldimethylsilyl)oxy)-N'-hydroxy-1-(3-methyl-2-(3-methylisoxazol-5-yl)butanoyl)pyrrolidine-2-carboximidamide

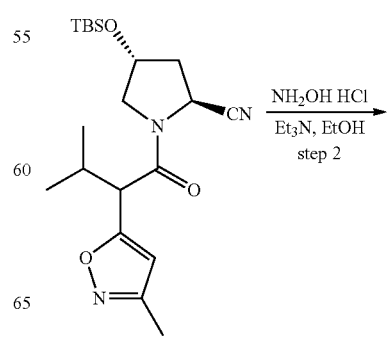

-continued

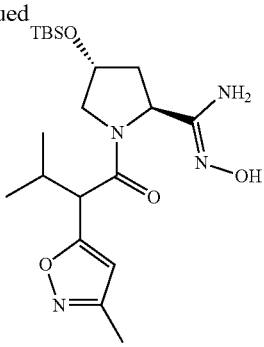

A mixture of Et₃N (1.353 g, 12.77 mmol) and (2S,4R)-4-((tert-butyldimethylsilyl)oxy)-1-(3-methyl-2-(3-methylisoxazol-5-yl)butanoyl)pyrrolidine-2-carbonitrile (1.000 g, 2.55 mmol) and NH₂OH HCl (887.3 mg, 12.77 mmol) in EtOH (10 mL) was stirred at 60° C. for 2 hours. The reaction solution was diluted with EtOAc (40 mL) and washed with water (10 mL×2). The organic layers were dried over Na₂SO₄, and concentrated to afford crude (2S,4R,Z)-4-((tert-butyldimethylsilyl)oxy)-N'-hydroxy-1-(3-methyl-2-(3-methylisoxazol-5-yl)butanoyl)pyrrolidine-2-carboximidamide (1084 mg, 100%) as a white solid. LCMS (Method FF): RT=0.854 min, m/z=425.2 [M+1]⁺.

Step 3: 1-((2S,4R)-2-(5-(4-bromophenyl)-5-methyl-4,5-dihydro-1,2,4-oxadiazol-3-yl)-4-((tert-butyldimethylsilyl)oxy)pyrrolidin-1-yl)-3-methyl-2-(3-methylisoxazol-5-yl)butan-1-one

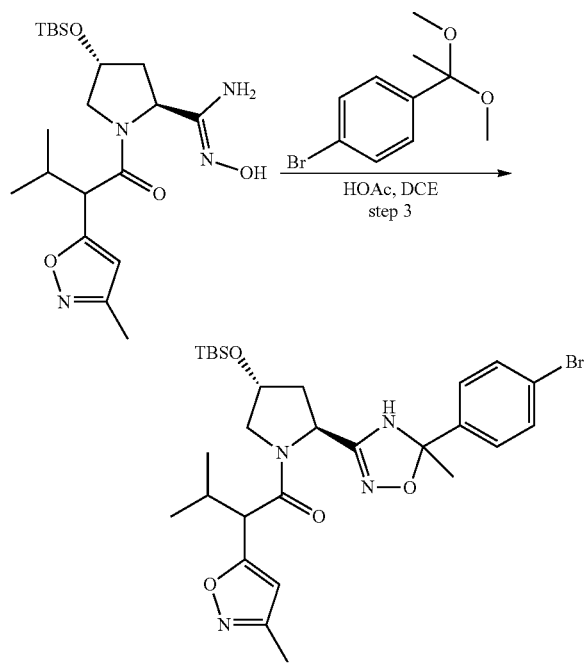

A mixture of (2S,4R,Z)-4-((tert-butyldimethylsilyl)oxy)-N'-hydroxy-1-(3-methyl-2-(3-methylisoxazol-5-yl)butanoyl)pyrrolidine-2-carboximidamide (1.084 g, 2.55 mmol), 1-bromo-4-(1,1-dimethoxyethyl)benzene (3.128 g, 12.76 mmol) in DCE (6.0 mL) and HOAc (6 mL) was stirred at 85° C. for 14 hours. The reaction solution was diluted with EtOAc (40 mL) and washed with water (10 mL×2). The organic layers were dried over Na₂SO₄, concentrated, and purified by flash column chromatography (0-30% EtOAc in petroleum ether, Rf=0.5) to afford 1-((2S,4R)-2-(5-(4-bromophenyl)-5-methyl-4,5-dihydro-1,2,4-oxadiazol-3-yl)-4-((tert-butyldimethylsilyl)oxy)pyrrolidin-1-yl)-3-methyl-2-(3-methylisoxazol-5-yl)butan-1-one (1.200 g, 78%) as a white solid. LCMS (Method FF): RT=1.183 min, m/z=606.9 [M+1+2]⁺.

Step 4: 1-((2S,4R)-4-((tert-butyldimethylsilyl)oxy)-2-(5-(2'-fluoro-[1,1'-biphenyl]-4-yl)-5-methyl-4,5-dihydro-1,2,4-oxadiazol-3-yl)pyrrolidin-1-yl)-3-methyl-2-(3-methylisoxazol-5-yl)butan-1-one

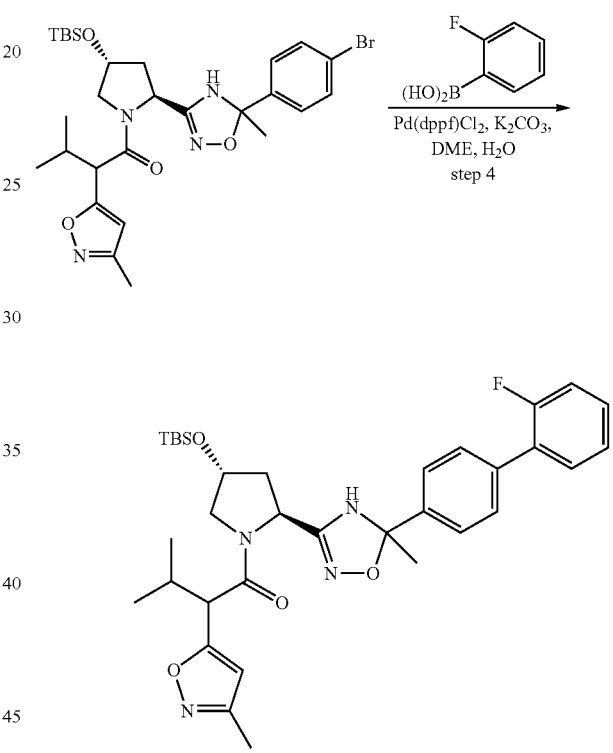

To a mixture of 1-((2S,4R)-2-(5-(4-bromophenyl)-5-methyl-4,5-dihydro-1,2,4-oxadiazol-3-yl)-4-((tert-butyldimethylsilyl)oxy)pyrrolidin-1-yl)-3-methyl-2-(3-methylisoxazol-5-yl)butan-1-one (1.200 g, 1.98 mmol) and (2-fluorophenyl)boronic acid (360.4 mg, 2.58 mmol), K₂CO₃ (821.54 mg, 5.94 mmol) in 1,4-dioxane (20 mL)/water (5 mL) was added Pd(dppf)Cl₂ (144.98 mg, 0.2000 mmol). After the mixture was stirred at 90° C. for 12 hours under N₂, it was filtrated and filtrate was concentrated. The residue was dissolved in EtOAc (60 mL), washed with water (20 mL), dried over Na₂SO₄, concentrated and purified by chromatography on silica (0-30% EtOAc in petroleum ether, Rf=0.4) to afford 1-((2S,4R)-4-((tert-butyldimethylsilyl)oxy)-2-(5-(2'-fluoro-[1,1'-biphenyl]-4-yl)-5-methyl-4,5-dihydro-1,2,4-oxadiazol-3-yl)pyrrolidin-1-yl)-3-methyl-2-(3-methylisoxazol-5-yl)butan-1-one (900 mg, 73.2%) as yellow solid. LCMS (Method FF): RT=1.130 min, m/z=621.3 [M+1]⁺.

Step 5: Examples 139.1 and 139.2

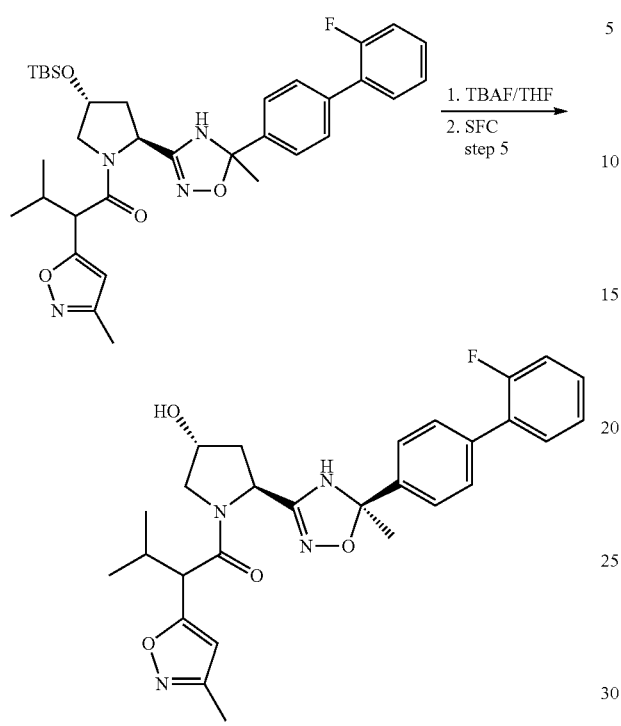

Examples 139.1 and 139.2

A mixture of 1-((2S,4R)-4-(((tert-butyldimethylsilyl)oxy)-2-(5-(2'-fluoro-[1,1'-biphenyl]-4-yl)-5-methyl-4,5-dihydro-1,2,4-oxadiazol-3-yl)pyrrolidin-1-yl)-3-methyl-2-(3-methylisoxazol-5-yl)butan-1-one (900.0 mg, 1.45 mmol), TBAF (1.829 g, 5.8 mmol) and in THF (10 mL) was stirred at 50° C. for 2 hours. The reaction solution was diluted with EtOAc (20 mL) and washed with water (10 mL×2). The organic layers were dried over $Na_2SO_4$, concentrated, and purified by prep-HPLC (acetonitrile 50-80/0.225% FA in water) to afford a mixture of isomers, which were separated by SFC (MeOH 20-20/0.1% $NH_3H_2O$) to afford the stereoisomers Example 139.1 (130 mg, 18%), Example 139.2 (130 mg, 18%) as white solids. Examples 139.1 and 139.2 each form a mixture of tautomers.

Example 139.1: $^1H$ NMR (400 MHz, $CDCl_3$) δ 7.60-7.55 (m, 4H), 7.43-7.41 (m, 1H), 7.34-7.31 (m, 1H), 7.24-7.11 (m, 2H), 6.20 (s, 1H), 6.04 (s, 1H), 5.02-4.99 (m, 1H), 4.75-4.73 (m, 1H), 3.75-3.71 (s, 1H), 3.67-3.64 (m, 1H), 2.73-2.69 (m, 1H), 2.47-2.43 (s, 1 H), 2.27 (s, 3H), 2.17-2.07 (m, 3H), 1.64 (s, 3H), 1.07-1.03 (m, 3H), 0.91-0.85 (m, 3H). LCMS (Method FF): RT=0.830 min, m/z 507.1 $[M+1]^+$. SFC: Method 3, RT=2.035 min and 2.700 min.

Example 139.2: $^1H$ NMR (400 MHz, $CDCl_3$) δ 7.62-7.52 (m, 4H), 7.45-7.42 (m, 1H), 7.36-7.32 (m, 1H), 7.24-7.14 (m, 2H), 6.37 (s, 1H), 6.11 (s, 1H), 4.90-4.87 (m, 1H), 4.73-4.70 (m, 1H), 3.86-3.83 (m, 1H), 3.69-3.67 (m, 1H), 3.64-3.61 (m, 1H), 2.73-2.67 (m, 1H), 2.49-2.44 (m, 1H), 2.29 (s, 3H), 2.14-2.13 (m, 1H), 1.88-1.85 (m, 1H), 1.80 (s, 3H), 1.08 (d, J=6.4 Hz, 3H), 0.92 (d, J=6.4 Hz, 3H). LCMS (Method FF): RT=0.824 min, m/z 507.1 $[M+H]^+$. SFC: Method 3, RT=2.304 min and 3.065 min.

Examples 140.1 and 140.2

N-((2S)-1-((2S,4R)-4-hydroxy-2-(5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)acetamide (2 Mixtures of Stereoisomers)

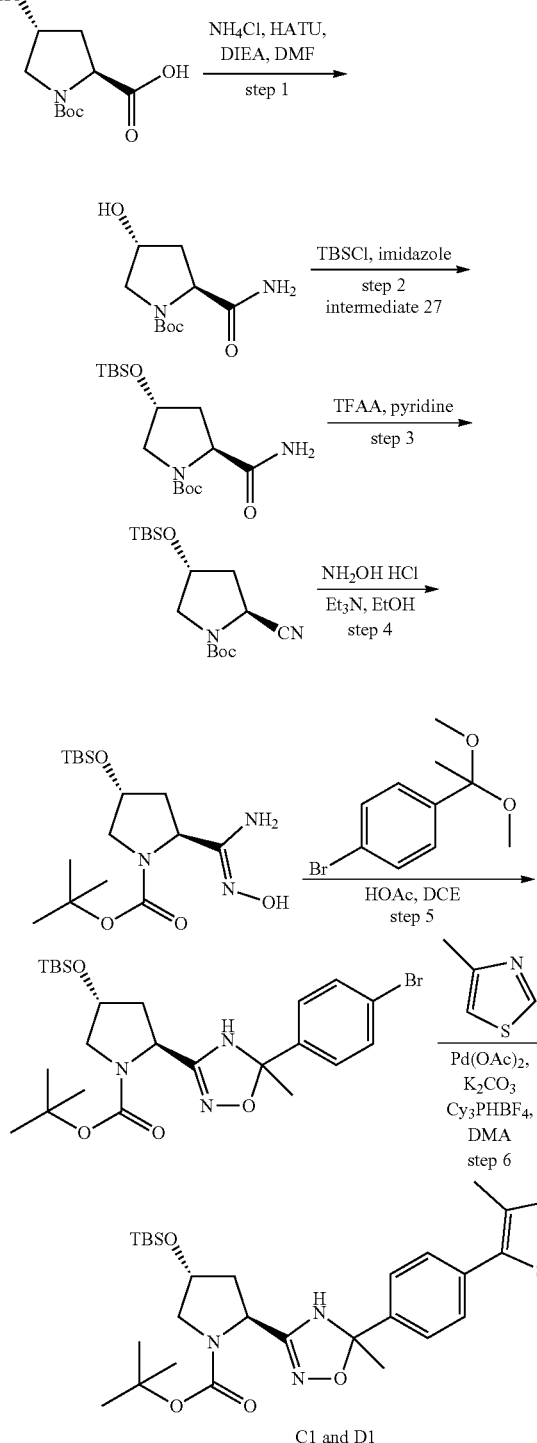

C1 and D1

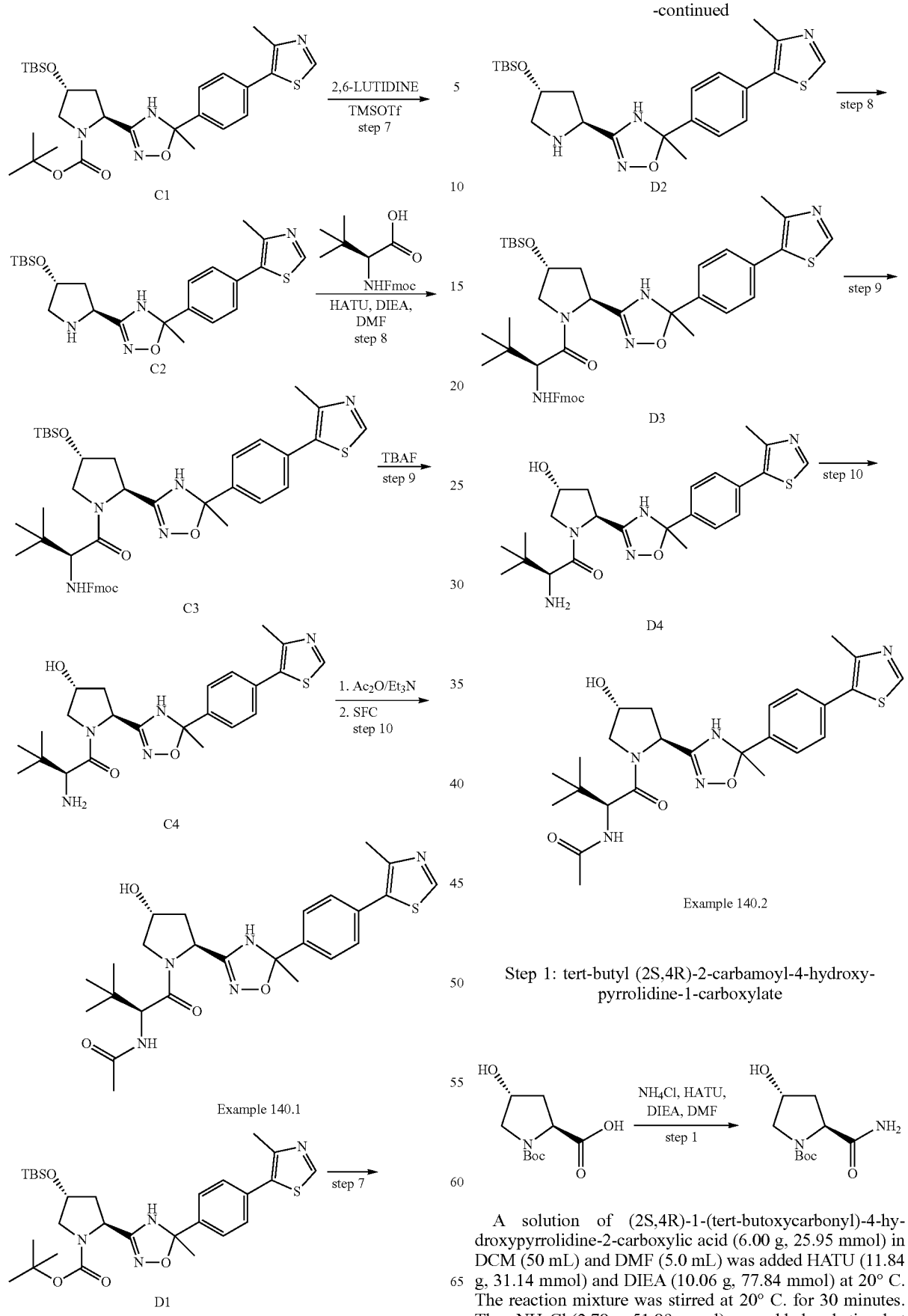
Example 140.2
Step 1: tert-butyl (2S,4R)-2-carbamoyl-4-hydroxy-pyrrolidine-1-carboxylate
A solution of (2S,4R)-1-(tert-butoxycarbonyl)-4-hydroxypyrrolidine-2-carboxylic acid (6.00 g, 25.95 mmol) in DCM (50 mL) and DMF (5.0 mL) was added HATU (11.84 g, 31.14 mmol) and DIEA (10.06 g, 77.84 mmol) at 20° C. The reaction mixture was stirred at 20° C. for 30 minutes. Then NH$_4$Cl (2.78 g, 51.89 mmol) was added and stirred at 20° C. for 2 hours. The reaction mixture was concentrated under reduced pressure to remove solvents. The crude tert-butyl (2S,4R)-2-carbamoyl-4-hydroxypyrrolidine-1-carboxylate (5.974 g, 99%) as a yellow oil, which was used directly in the next step.

Step 2: tert-butyl (2S,4R)-4-((tert-butyldimethylsilyl)oxy)-2-carbamoylpyrrolidine-1-carboxylate

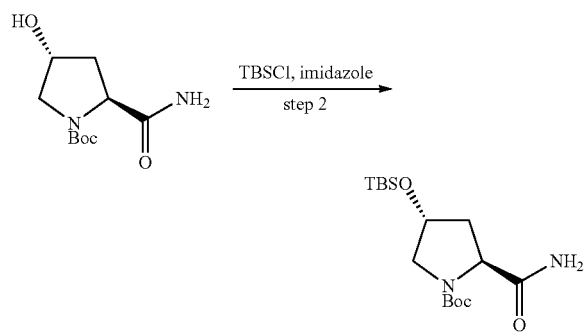

A mixture of TBSCl (5.87 g, 38.92 mmol), tert-butyl (2S,4R)-2-carbamoyl-4-hydroxypyrrolidine-1-carboxylate (5.974 g, 25.94 mmol), DMAP (316.96 mg, 2.59 mmol) and imidazole (5.300 g, 77.83 mmol) in THF (80 mL) was stirred at 25° C. for 12 hours. Water (80 mL) was added and it was extracted with DCM (100 mL×3), washed by brine (50 mL×3). The organics were dried over Na$_2$SO$_4$, concentrated, and purified by flash column chromatography (0-50% EtOAc in petroleum ether, Rf=0.6) to give tert-butyl (2S,4R)-4-((tert-butyldimethylsilyl)oxy)-2-carbamoylpyrrolidine-1-carboxylate (8.900 g, 99.6%) as a colorless oil used in next step directly. $^1$H NMR (400 MHz, CD$_3$OD) δ 4.83-4.76 (m, 1H), 4.05-4.0 (m, 1H), 3.95-3.92 (m, 1H), 3.81-3.80 (m, 1H), 2.70-2.67 (m, 1H), 2.52-2.48 (m, 1H), 1.96-1.91 (m, 9H),1.39 (s, 1H), 0.60 (s, 6H).

Step 3: tert-butyl (2S,4R)-4-((tert-butyldimethylsilyl)oxy)-2-cyanopyrrolidine-1-carboxylate

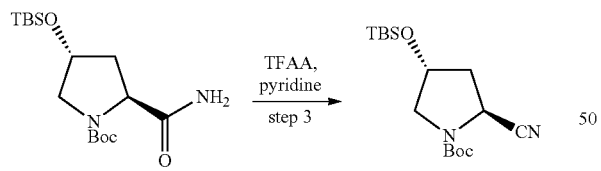

A solution of tert-butyl (2S,4R)-4-((tert-butyldimethylsilyl)oxy)-2-carbamoylpyrrolidine-1-carboxylate (8.900 g, 25.83 mmol), TFAA (5.968 g, 28.42 mmol) and pyridine (6.130 g, 77.5 mmol) in EtOAc (50 mL) was stirred at 20° C. for 1 hour. The mixture was diluted with EtOAc (150 mL), washed with brine (80 mL×2). The organic layer was dried over Na$_2$SO$_4$, concentrated, and purified by flash chromatography on silica (0-10% EtOAc in petroleum ether, Rf=0.7) to tert-butyl (2S,4R)-4-((tert-butyldimethylsilyl)oxy)-2-cyanopyrrolidine-1-carboxylate (8.00 g, 95%) as colorless oil. $^1$HNMR (400 MHz, DMSO-d6) δ 4.59 (t, J=8.0 Hz, 1H), 4.47-4.44 (m, 1H), 3.45-3.41 (m, 1H), 3.28-3.25 (m, 1H), 2.31-2.21 (m, 2H), 1.43 (d, J=7.2 Hz, 9H), 0.83 (s, 9H), 0.06 (s, 6H).

Step 4: tert-butyl (2S,4R)-4-((tert-butyldimethylsilyl)oxy)-2-((Z)—N'-hydroxycarbamimidoyl)pyrrolidine-1-carboxylate

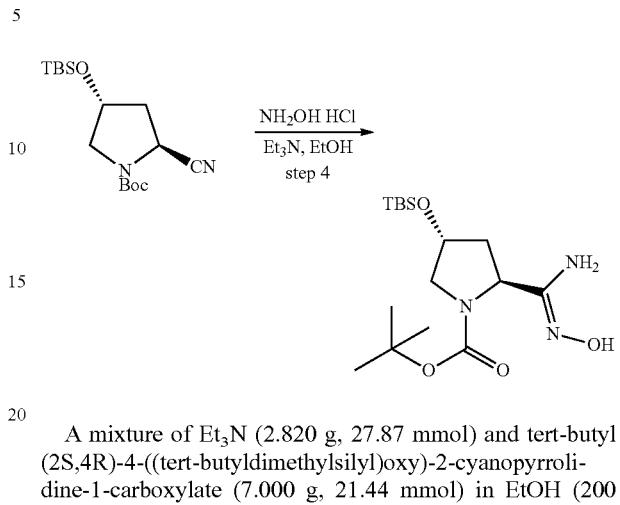

A mixture of Et$_3$N (2.820 g, 27.87 mmol) and tert-butyl (2S,4R)-4-((tert-butyldimethylsilyl)oxy)-2-cyanopyrrolidine-1-carboxylate (7.000 g, 21.44 mmol) in EtOH (200 mL) was stirred at 90° C. for 13 hours. The reaction solution was diluted with EtOAc (200 mL) and washed with water (100 mL×2). The organic layer was dried over Na$_2$SO$_4$ and concentrated to afford tert-butyl (2S,4R)-4-((tert-butyldimethylsilyl)oxy)-2-((Z)—N'-hydroxycarbamimidoyl)pyrrolidine-1-carboxylate (7500 mg, 97%) as a white solid.

Step 5: tert-butyl (2S,4R)-2-(5-(4-bromophenyl)-5-methyl-4,5-dihydro-1,2,4-oxadiazol-3-yl)-4-((tert-butyldimethylsilyl)oxy)pyrrolidine-1-carboxylate

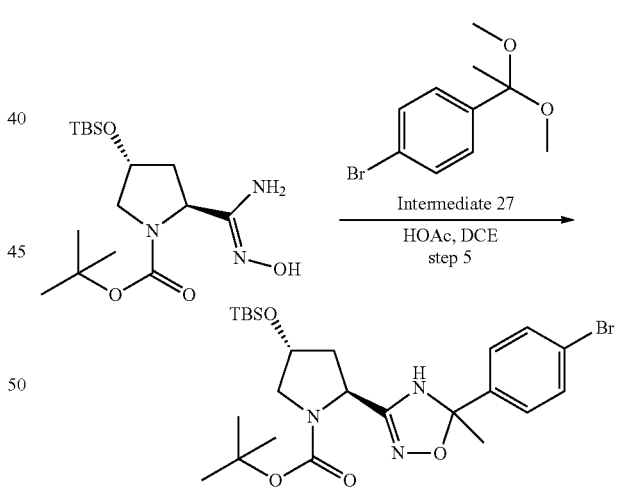

A mixture of tert-butyl (2S,4R)-4-((tert-butyldimethylsilyl)oxy)-2-((Z)—N'-hydroxycarbamimidoyl)pyrrolidine-1-carboxylate (2.500 g, 6.95 mmol), 1-bromo-4-(1,1-dimethoxyethyl)benzene (Intermediate 27, 8.521 g, 34.77 mmol) in 1,2-dichloroethane (15 mL) and HOAc (15 mL) was stirred at 85° C. for 13 hours. The reaction solution was diluted with EtOAc (100 mL) and washed with water (100 mL×2). The organic layers were dried over Na$_2$SO$_4$, concentrated, and purified by flash chromatography on silica gel (0-20% ethyl acetate in petroleum ether, Rf=0.6) to afford tert-butyl (2S,4R)-2-(5-(4-bromophenyl)-5-methyl-4,5-dihydro-1,2,4-oxadiazol-3-yl)-4-((tert-butyldimethylsilyl)

oxy)pyrrolidine-1-carboxylate (2.900 g, 77.2%) as a yellow solid. LCMS (Method FF): RT=1.085 min, m/z=540.1[M+H]⁺.

Step 6: tert-butyl (2S,4R)-4-((tert-butyldimethylsilyl)oxy)-2-(5-methyl-5-(4-(4-methylthiazol-5-yl)phenyl)-4,5-dihydro-1,2,4-oxadiazol-3-yl)pyrrolidine-1-carboxylate (Compounds C1 and D1)

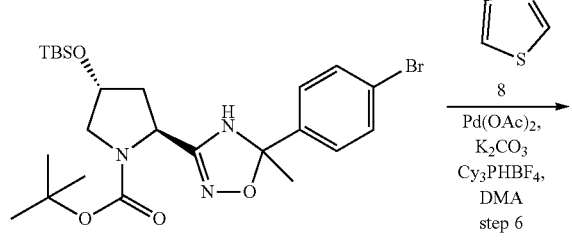

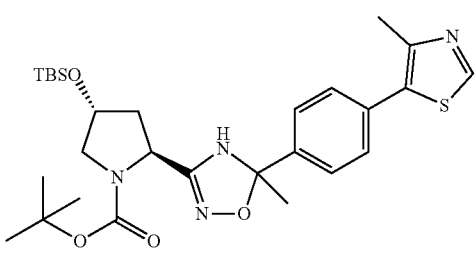

C1 and D1

To a solution of tert-butyl (2S,4R)-2-(5-(4-bromophenyl)-5-methyl-4,5-dihydro-1,2,4-oxadiazol-3-yl)-4-((tert-butyldimethylsilyl)oxy)pyrrolidine-1-carboxylate (1.000 g, 1.85 mmol) in DMF (8.0 mL) was added Pd(OAc)₂ (41.53 mg, 0.1800 mmol), 4-methylthiazole (1.834 g, 18.5 mmol), K₂CO₃ (383.51 mg, 2.77 mmol), Cy₃PHBF₄ (68.12 mg, 0.1800 mmol) and pivalic acid (56.68 mg, 0.5500 mmol). The mixture was stirred at 100° C. for 16 hours. The mixture was concentrated and 20 mL of water was added. The resulting solution was extracted with EtOAc (30 mL×3) and the organic layer was washed with brine (30 mL), dried over Na₂SO₄, and concentrated. The residue was purified by flash chromatography on silica gel (0-20% EtOAc in petroleum ether, Rf=0.4) to afford Compound C1 (0.7500 g, 1.34 mmol, 73%) and Compound D1 (240 mg, 23%) as yellow oils.

Compound C1 (Peak 1): ¹H NMR (400 MHz, CDCl₃) δ 8.69 (s, 1H), 7.63-7.40 (m, 4H), 4.67-4.62 (m, 1H), 4.51-4.41 (m, 1H), 3.49 (s, 3H), 3.42-3.32 (m, 1H), 2.56-2.54 (m, 4H), 2.07-2.05 (m, 1H), 1.87 (s, 3H), 1.49 (s, 9H), 0.87 (m, 9H), 0.07 (s, 6H). LCMS (Method FF): RT=1.120 min, m/z=559.3 [M+1]⁺.

Compound D1 (Peak 2): LCMS (Method FF): RT=1.201 min, m/z=559.1 [M+1]⁺.

Step 7: 3-((2S,4R)-4-((tert-butyldimethylsilyl)oxy)pyrrolidin-2-yl)-5-methyl-5-(4-(4-methylthiazol-5-yl)phenyl)-4,5-dihydro-1,2,4-oxadiazole

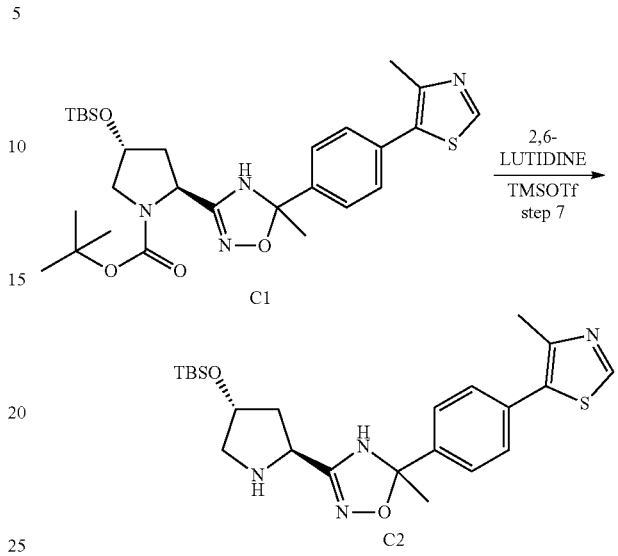

To a stirred solution of Compound C1 (200.0 mg, 0.3600 mmol) and 2,6-lutidine (115.05 mg, 1.07 mmol) in dry DCM (8 mL) at 0° C. was added dropwise TMSOTf (0.10 mL, 0.5400 mmol). The reaction mixture was stirred at 0° C. for 15 minutes, and quenched with MeOH (15 mL). The solution was concentrated to give crude Compound C2 (160 mg, 98%) as a yellow solid, which was used directly in the next step.

Step 8: (9H-fluoren-9-yl)methyl ((2S)-1-((2S,4R)-4-((tert-butyldimethylsilyl)oxy)-2-(5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)carbamate

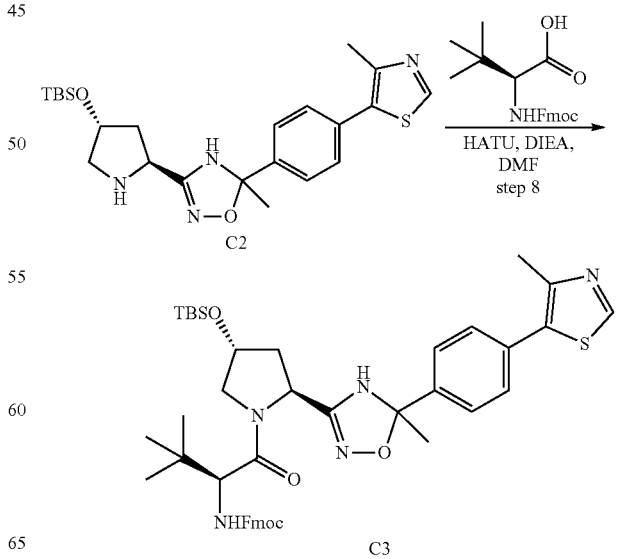

A solution of (S)-2-((((9H-fluoren-9-yl)methoxy)carbonyl)amino)-3,3-dimethylbutanoic acid (147.93 mg, 0.420 mmol), HATU (198.95 mg, 0.520 mmol) and DIEA (0.29 mL, 1.74 mmol) in DMF (10 mL) was stirred at 25° C. for 10 minutes and then Compound C2 (160.0 mg, 0.350 mmol) was added. After the mixture was stirred at 25° C. for 1 hour, it was concentrated and purified by prep-TLC (50% EtOAc in petroleum ether, Rf=0.4) to give Compound C3 (150 mg, 54%) as a yellow oil. LCMS (Method FF): RT=1.092 min, m/z=794.4 [M+1]$^+$.

Step 9: (2S)-2-amino-1-((2S,4R)-4-hydroxy-2-(5-methyl-5-(4-(4-methylthiazol-5-yl)phenyl)-4,5-dihydro-1,2,4-oxadiazol-3-yl)pyrrolidin-1-yl)-3,3-dimethylbutan-1-one

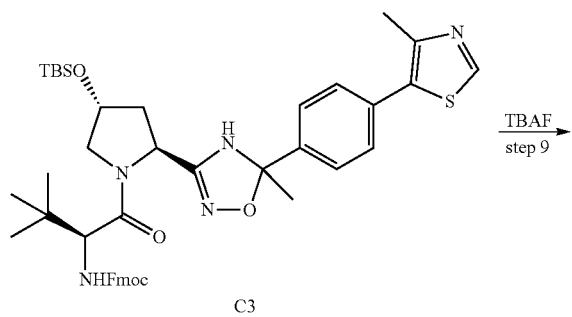

To a stirred solution of Compound C3 (190.0 mg, 0.2400 mmol) in DMF (8.0 mL) was added a TBAF solution in THF (1.0 M, 0.72 mL, 0.7200 mmol). After the reaction mixture was stirred at 50° C. for 2 hours, it was concentrated to afford the crude Compound C4 (109 mg, 99.6%) as a yellow oil, which was used directly in the next step.

Step 10: N-((2S)-1-((2S,4R)-4-hydroxy-2-(5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)acetamide (Mixture of Isomers)

To a stirred solution of Compound C4 (109.0 mg, 0.2400 mmol) in DMF (3.0 mL) was added Ac$_2$O (72.95 mg, 0.710 mmol) and Et$_3$N (72.31 mg, 0.7100 mmol). The reaction mixture was stirred at 25° C. for 1 hour. The mixture was concentrated and purified by prep-HPLC (acetonitrile 15-45/ 0.225% FA in water) to afford the desired product. It showed as two isomers on SFC. After SFC separation, they became mixture spontaneously, so it was submitted as a mixture Example 140.1 (11.61 mg, 10%). $^1$H NMR (400 MHz, CDCl$_3$) δ 8.70 (s, 1H), 7.61-7.39 (m, 4H), 6.45 (s, 0.5H), 6.31 (s, 0.5H), 6.16 (d, J=8.8 Hz, 0.5H), 6.03 (d, J=8.8 Hz, 0.5H), 4.95-4.88 (m, 1H), 4.57-4.36 (m, 2H), 4.15 (d, J=11.2 Hz, 0.5H), 4.08 (d, J=11.2 Hz, 0.5H), 3.66, 3.46 (dd, J=3.2 Hz, 11.6 Hz, 1H), 3.15 (brs, 1H), 2.66-2.59 (m, 1H), 2.55 (s, 1.5H), 2.53 (s, 1.5H), 2.31-2.27 (m, 1H), 2.04, (s, 1.5H), 2.00 (s, 1.5H), 1.89 (s, 2H), 1.77 (s, 1H), 1.06 (s, 3H), 0.70 (s, 6H). LCMS (Method FF): RT=0.833 min, m/z=522.1 [M+23]$^+$. SFC (Method 4): RT=2.687 min, and 3.027 min.

Example 140.2 (16.3 mg, 15% over 4 steps) was prepared from compound D1 (120 mg), with similar procedure.

Example 140.2: H NMR (400 MHz, CDCl$_3$) δ 7.94 and 7.87 (d, J=8.4 Hz, 2H), 7.58 (d, J=8.4 Hz, 1H), 7.47 (d, J=8.4 Hz, 1H), 6.89 (s, 1H), 6.42 and 6.29 (s, 1H), 6.19 (d, J=8.8 Hz, 0.5H), 6.06 (d, J=8.8 Hz, 0.5H), 4.94-4.90 (m, 1H), 4.57-4.35 (m, 2H), 4.16 (d, J=11.6 Hz, 0.5H), 4.06 (d, J=11.6 Hz, 0.5H), 3.63 (dd, J=3.6 Hz, 11.2 Hz, 0.5H), 3.46 (dd, J=3.6 Hz, 11.2 Hz, 0.5H), 2.63-2.59 (m, 1H), 2.52 (s, 3H), 2.26-2.20 (m, 1H), 2.04 and 1.98 (s, 3H), 1.87 (s, 1.5H), 1.75 (s, 1.5H), 1.06 (s, 3H), 0.69 (s, 6H). LCMS (Method FF): RT=0.879 min, m/z=500.2 [M+1]$^+$. SFC (Method 4): RT=3.182 min, and 3.859 min.

Examples 143.1 and 143.2
1-((2S,4R)-2-(5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one and (2R)-1-((2S,4R)-2-(5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one
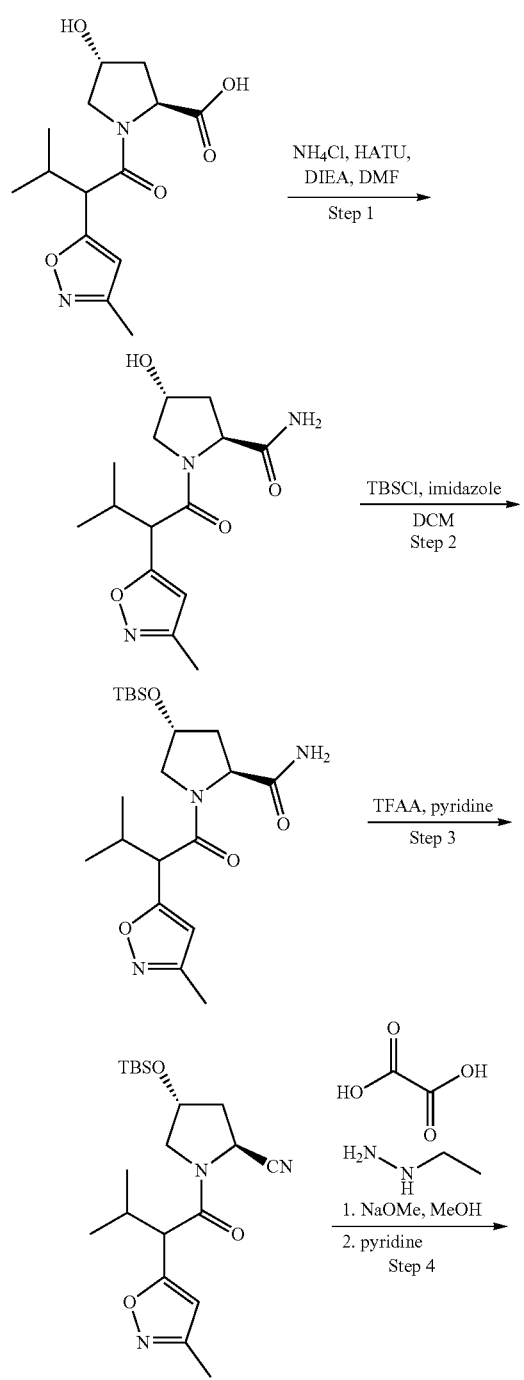
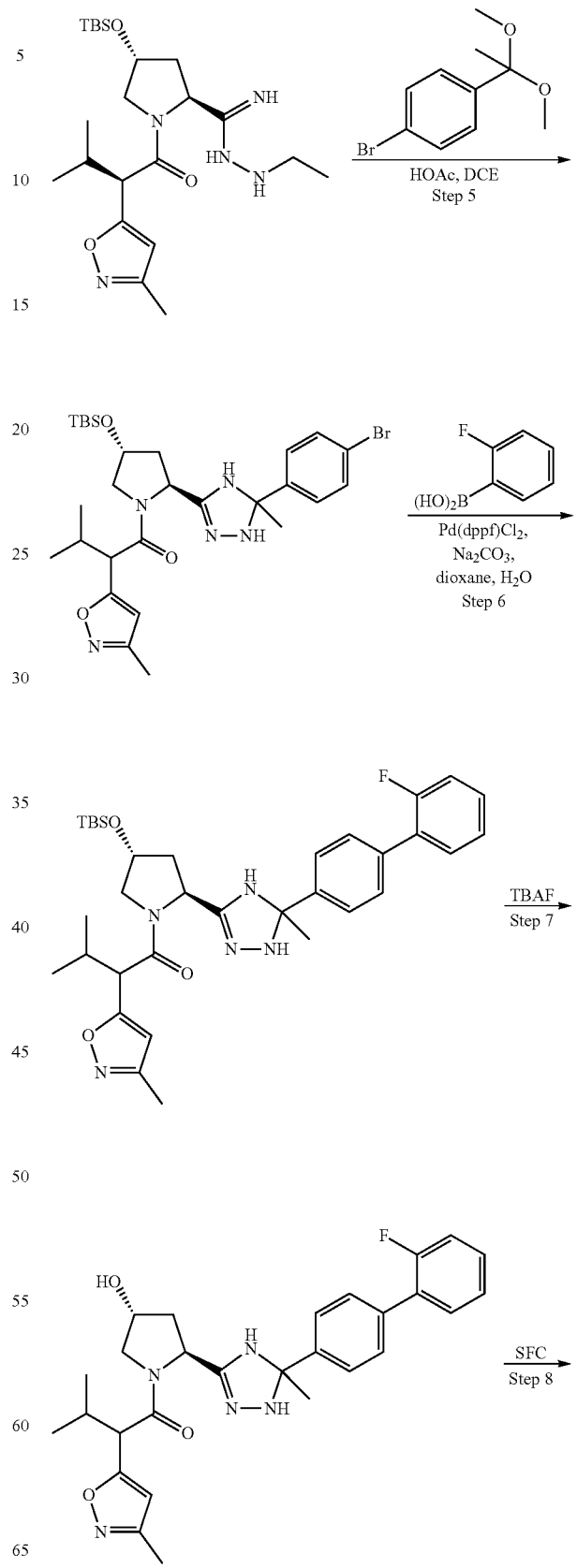

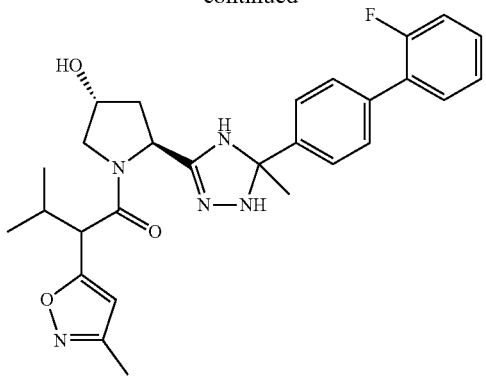

Example 143.1

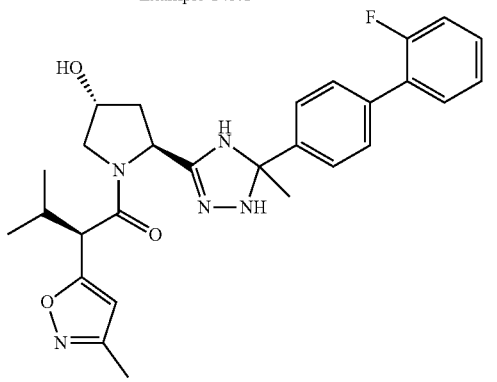

Example 143.2

Step 1: (2S,4R)-4-hydroxy-1-(3-methyl-2-(3-methylisoxazol-5-yl)butanoyl)pyrrolidine-2-carboxamide

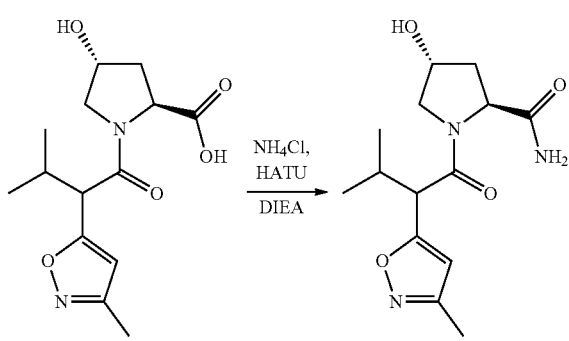 [SMILES: Cc1cc(C(C(=O)N2C[C@H](O)C[C@H]2C(=O)O)C(C)C)on1 ; Cc1cc(C(C(=O)N2C[C@H](O)C[C@H]2C(N)=O)C(C)C)on1]

To a solution of (2S,4R)-4-hydroxy-1-(3-methyl-2-(3-methylisoxazol-5-yl)butanoyl)pyrrolidine-2-carboxylic acid (5.000 g, 16.87 mmol) in DMF (33 mL) was added HATU (7.699 g, 20.25 mmol) and DIEA (6.542 g, 50.62 mmol) at 20° C. The reaction mixture was stirred at 20° C. for 30 minutes. NH₄Cl (1.805 g, 33.75 mmol) was added at 20° C. and the mixture was stirred for 2 hours. DMF was concentrated under reduced pressure, and H₂O (10 mL) was added. The mixture was extracted with EtOAc (20 mL) and the organic layer was washed with water (10 mL×2). The combined aqueous layer was lyophilized to afford crude (2S,4R)-4-hydroxy-1-(3-methyl-2-(3-methylisoxazol-5-yl)butanoyl)pyrrolidine-2-carboxamide (4.900 g, 98%) as a yellow solid, which was used directly in the next step. LCMS (Method FF): $R_T$=0.521 min, m/z=296.1[M+H]+

Step 2: (2S,4R)-4-((tert-butyldimethylsilyl)oxy)-1-(3-methyl-2-(3-methylisoxazol-5-yl)butanoyl)pyrrolidine-2-carboxamide

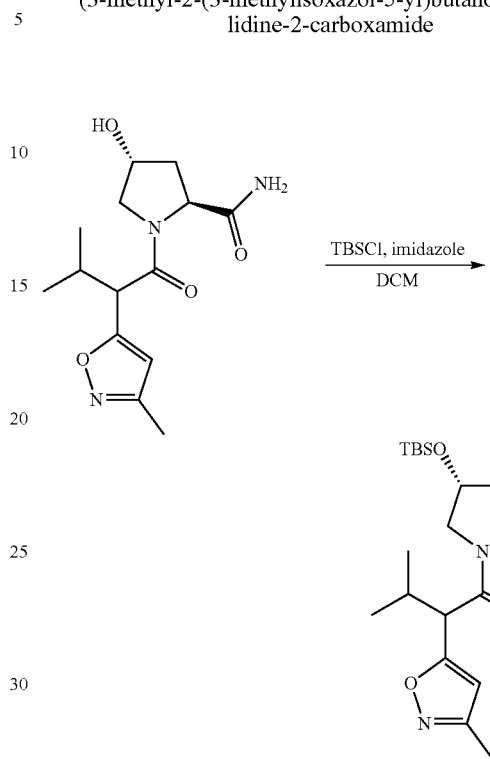

A mixture of TBSCl (3.751 g, 24.89 mmol), (2S,4R)-4-hydroxy-1-(3-methyl-2-(3-methylisoxazol-5-yl)butanoyl) pyrrolidine-2-carboxamide (4.900 g, 16.59 mmol), DMAP (202.7 mg, 1.66 mmol) and imidazole (3.388 g, 49.77 mmol) in THF (30 mL) was stirred at 25° C. for 12 hours. Water (30 mL) was added and extracted with DCM (40 mL×3), washed with brine (30 mL×3). The organic layer was dried over Na₂SO₄ and concentrated. The residue was purified by flash column chromatography (0-100% EtOAc in petroleum ether, Rf=0.5) to give (2S,4R)-4-((tert-butyldimethylsilyl)oxy)-1-(3-methyl-2-(3-methylisoxazol-5-yl)butanoyl)pyrrolidine-2-carboxamide (6.700 g, 98.6%) as a colorless oil which was used in next step directly. LCMS (Method FF): RT=0.979 min, m/z=410.3 [M+1]+.

Step 3: (2S,4R)-4-((tert-butyldimethylsilyl)oxy)-1-(3-methyl-2-(3-methylisoxazol-5-yl)butanoyl)pyrrolidine-2-carbonitrile

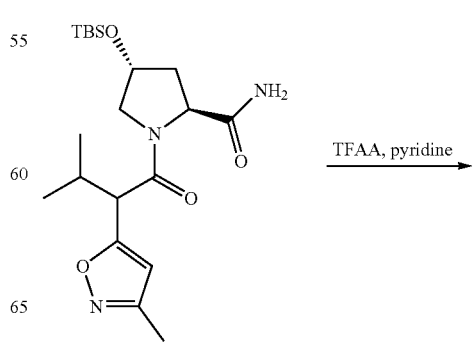

-continued

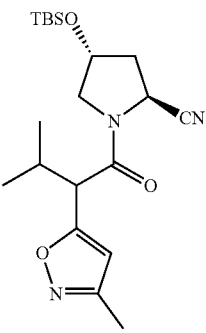

To a solution of (2S,4R)-4-((tert-butyldimethylsilyl)oxy)-1-(3-methyl-2-(3-methylisoxazol-5-yl)butanoyl)pyrrolidine-2-carboxamide (6.700 g, 16.36 mmol) and pyridine (3.881 g, 49.07 mmol) in EtOAc (20 mL) was added TFAA (3.779 g, 17.99 mmol). The mixture was stirred at 20° C. for 1 hour. The organic layer was concentrated under vacuum and the mixture was extracted with DCM (30 mL×3), washed with brine (20 mL×2). The organic layer was dried over anhydrous sodium sulfate and concentrated under vacuum to give crude product, which was purified by flash chromatography on silica (0-30% EtOAc in petroleum ether, Rf=0.4) to give (2S,4R)-4-((tert-butyldimethylsilyl)oxy)-1-(3-methyl-2-(3-methylisoxazol-5-yl)butanoyl)pyrrolidine-2-carbonitrile (5.700 g, 89%) as a yellow solid. LCMS (Method FF): RT=1.078 and 1.101 min, m/z=392.1 [M+H]+.

Step 4: (2S,4R)-4-((tert-butyldimethylsilyl)oxy)-N'-ethyl-1-((R)-3-methyl-2-(3-methylisoxazol-5-yl)butanoyl)pyrrolidine-2-carboximidhydrazide

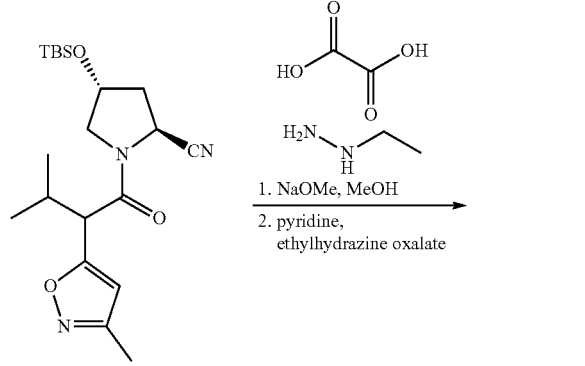

To a solution of MeONa (331.09 mg, 6.13 mmol) in MeOH (8.0 mL) was added (2S,4R)-4-((tert-butyldimethylsilyl)oxy)-1-(3-methyl-2-(3-methylisoxazol-5-yl)butanoyl)pyrrolidine-2-carbonitrile (2.000 g, 5.11 mmol) and stirred at 25° C. for 12 hours. Et₃N (1.343 g, 13.28 mmol) and ethylhydrazine oxalate (996.83 mg, 6.64 mmol) in MeOH (8.0 mL) was added and the reaction mixture stirred at 25° C. for 3 hours. The mixture was concentrated to give crude (2S,4R)-4-((tert-butyldimethylsilyl)oxy)-N'-ethyl-1-((R)-3-methyl-2-(3-methylisoxazol-5-yl)butanoyl)pyrrolidine-2-carboximidhydrazide (2.300 g, 99.7%) as a white solid, which was used in next step directly. LCMS (Method FF): RT=0.738 min, m/z=424.5 [M+H]+.

Step 5: 1-((2S,4R)-2-(5-(4-bromophenyl)-5-methyl-4,5-dihydro-1H-1,2,4-triazol-3-yl)-4-((tert-butyldimethylsilyl)oxy)pyrrolidin-1-yl)-3-methyl-2-(3-methylisoxazol-5-yl)butan-1-one

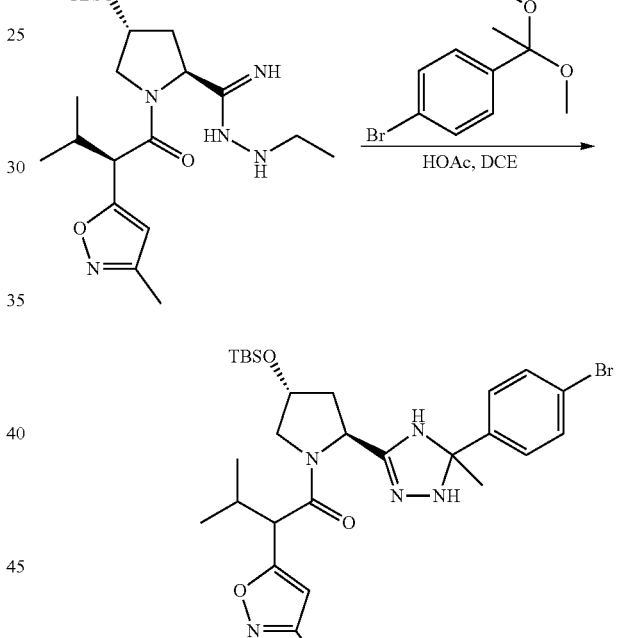

To a mixture of (2S,4R)-4-((tert-butyldimethylsilyl)oxy)-N'-ethyl-1-((R)-3-methyl-2-(3-methylisoxazol-5-yl)butanoyl)pyrrolidine-2-carboximidhydrazide (2.200 g, 4.87 mmol) in 1,2-dichloroethane (8.0 mL) and acetic acid (8.0 mL) was added 1-bromo-4-(1,1-dimethoxyethyl)benzene (4.775 g, 19.48 mmol). After the mixture was stirred at 25° C. for 14 hours, it was concentrated and diluted with EtOAc (90 mL) and washed with water (10 mL×2). The organic layers were dried over Na₂SO₄ and evaporated in vacuo. The residue was purified by prep-HPLC (water (0.04% NH₃H₂O+10 mM NH₄HCO₃)-(70-100)% ACN) to give 1-((2S,4R)-2-(5-(4-bromophenyl)-5-methyl-4,5-dihydro-1H-1,2,4-triazol-3-yl)-4-((tert-butyldimethylsilyl)oxy)pyrrolidin-1-yl)-3-methyl-2-(3-methylisoxazol-5-yl)butan-1-one based on MS (190 mg, 6.5%) as a white solid. LCMS (30-90, CD, 3 min): RT=2.351 min, m/z=604.2 [M+1]+.

Step 6: 1-((2S,4R)-4-((tert-butyldimethylsilyl)oxy)-2-(5-(2'-fluoro-[1,1'-biphenyl]-4-yl)-5-methyl-4,5-dihydro-1H-1,2,4-triazol-3-yl)pyrrolidin-1-yl)-3-methyl-2-(3-methylisoxazol-5-yl)butan-1-one

Step 7: 1-((2S,4R)-2-(5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one

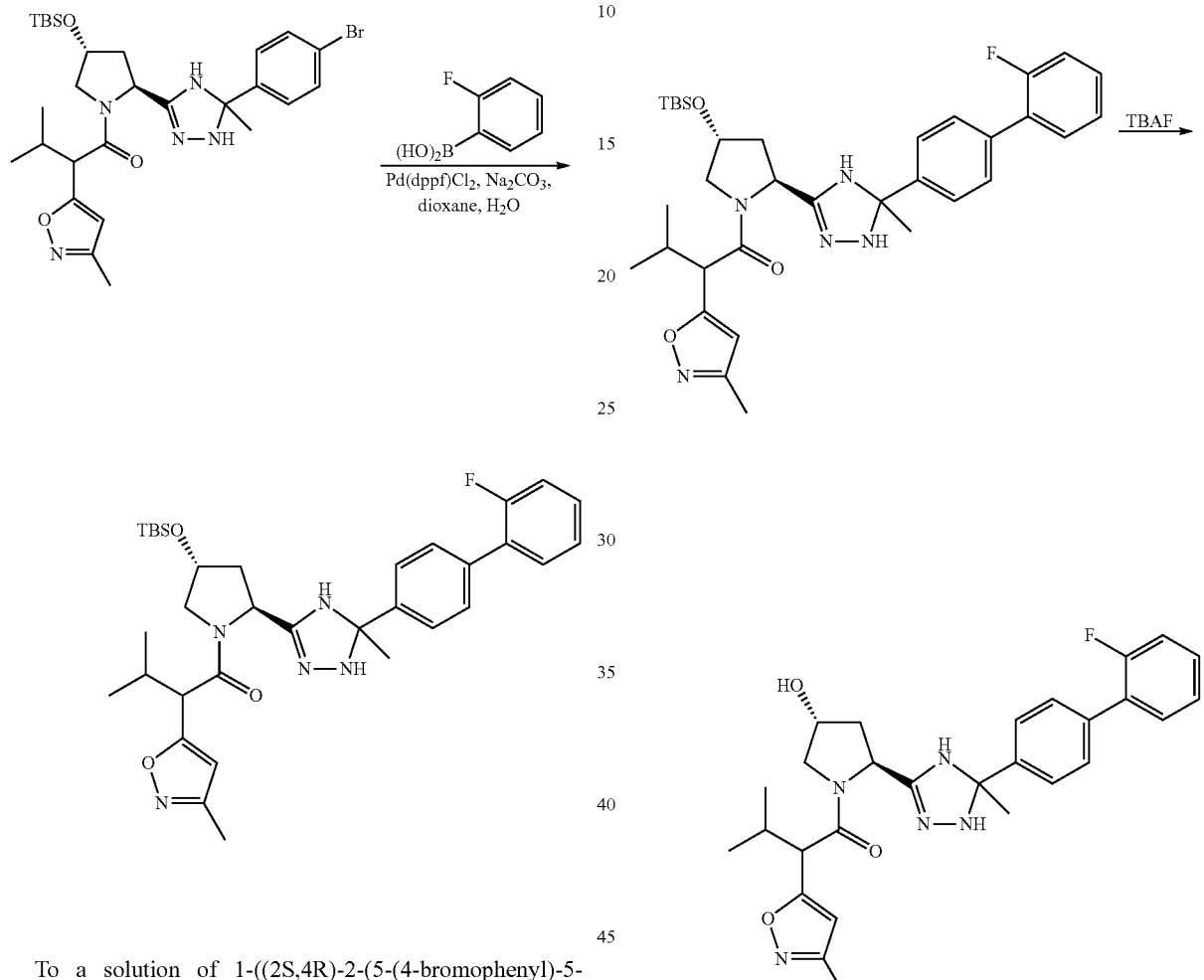

To a solution of 1-((2S,4R)-2-(5-(4-bromophenyl)-5-methyl-4,5-dihydro-1H-1,2,4-triazol-3-yl)-4-((tert-butyldimethylsilyl)oxy)pyrrolidin-1-yl)-3-methyl-2-(3-methylisoxazol-5-yl)butan-1-one (100.0 mg, 0.1700 mmol) in 1,4-dioxane (3.0 mL) and water (1.0 mL) was added (2-fluorophenyl)boronic acid (46.28 mg, 0.3300 mmol), $Cs_2CO_3$ (161.66 mg, 0.500 mmol) and $Pd(dppf)Cl_2$ (24.2 mg, 0.0300 mmol), the resulting mixture was stirred at 90° C. for 3 hours under $N_2$. The reaction mixture was concentrated and diluted with EtOAc (60 mL), washed with brine (10 mL×2), the organic layer was dried over anhydrous sodium sulfate and concentrated under vacuum to give crude product, which was purified by flash chromatography on silica (1-10% MeOH in DCM, Rf=0.7) to give 1-((2S,4R)-4-((tert-butyldimethylsilyl)oxy)-2-(5-(2'-fluoro-[1,1'-biphenyl]-4-yl)-5-methyl-4,5-dihydro-1H-1,2,4-triazol-3-yl)pyrrolidin-1-yl)-3-methyl-2-(3-methylisoxazol-5-yl)butan-1-one (60 mg, 59%) as a yellow solid. LCMS (Method FF): RT=0.862 min, m/z=620.3 [M+1]+.

To a solution of 1-((2S,4R)-4-((tert-butyldimethylsilyl)oxy)-2-(5-(2'-fluoro-[1,1'-biphenyl]-4-yl)-5-methyl-4,5-dihydro-1H-1,2,4-triazol-3-yl)pyrrolidin-1-yl)-3-methyl-2-(3-methylisoxazol-5-yl)butan-1-one (35.0 mg, 0.0600 mmol) in THF (2.0 mL) was added TBAF/THF (0.17 mL, 0.1700 mmol) at 25° C., and the resulting mixture was stirred at 25° C. for 1 hour. The mixture was purified by prep-HPLC (acetonitrile 26-56/0.225% FA in water) to afford 1-((2S,4R)-2-(5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one (20 mg, 70%) as a yellow solid. LCMS (Method FF): RT=0.752 min, m/z=506.2 [M+1]+.

Step 8: Examples 143.1 and 143.2

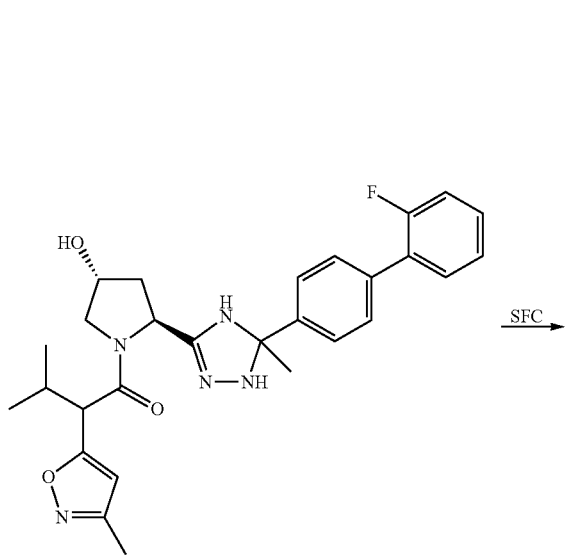

Example 143.1

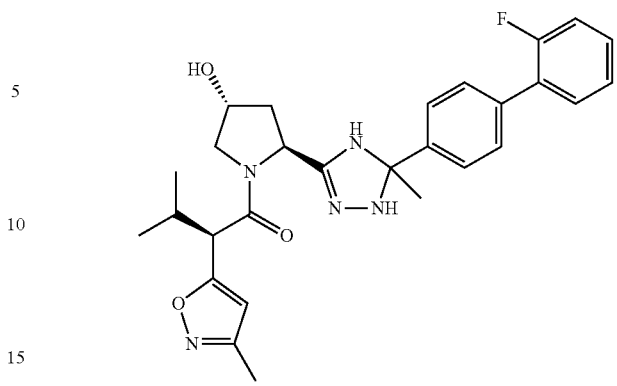

Example 143.2

1-((2S,4R)-2-(5-(2'-fluoro-[1,1'-biphenyl]-4-yl)-5-methyl-4,5-dihydro-1H-1,2,4-triazol-3-yl)-4-hydroxypyrrolidin-1-yl)-3-methyl-2-(3-methylisoxazol-5-yl)butan-1-one (20.0 mg, 0.0400 mmol) was separated by chiral SFC (Method 7) and further purified by prep-TLC (10% MeOH in DCM, Rf=0.5) to afford Example 143.1 (2.6 mg) and Example 143.2 (1.72 mg) both as white solids.

Example 143.1 (peak 1): $^1$H NMR (400 MHz, MeOD-d4) δ ppm 7.97-7.92 (m, 2H), 7.58-7.50 (m, 3H), 7.37-7.35 (m, 1H), 7.27-7.18 (m, 2H), 6.21 (s, 0.5H), 6.11 (s, 0.5H), 4.72-4.68 (m, 1H), 4.56-4.52 (m, 0.5H), 4.47 (br s, 0.5H), 4.01-3.99 (m, 0.5H), 3.93-3.90 (m, 0.5H), 3.84-3.77 (m, 1H), 3.69-3.65 (m, 0.5H), 3.57-3.55 (m, 0.5H), 2.52-2.14 (m, 7H), 2.11 (s, 2H), 1.12-1.01 (m, 3H), 0.87-0.77 (m, 3H). LCMS (Method FF): $R_T$=0.747 min, m/z=506.6[M+1]$^+$. SFC (Method 7): ee %=100%.

Example 143.2 (peak 2): $^1$H NMR (400 MHz, METHANOL-d4) δ ppm 8.00 (d, J=8.0 Hz, 1H), 7.91 (d, J=8.8 Hz, 1H), 7.63-7.55 (m, 3H), 7.42-7.33 (m, 1H), 7.26-7.19 (m, 2H), 6.25 (s, 1H), 4.79-4.75 (m, 0.5H), 4.72-4.66 (m, 0.5H), 4.59-4.56 (m, 0.5H), 4.51-4.46 (m, 0.5H), 3.91-3.88 (m, 2H), 3.77-3.75 (m, 1H), 2.48 (s, 1H), 2.45-2.40 (m, 1H), 2.38-2.35 (m, 1H), 2.31-2.28 (m, 1H), 2.27-2.16 (m, 3H), 1.09-1.07 (m, 2H), 0.97-0.95 (m, 1H), 0.892-0.89 (m, 2H), 0.81-0.73 (m, 1H). LCMS (Method FF): $R_T$=0.751 min, m/z=506.2[M+1]$^+$. SFC (Method 7): ee %=100%.

Examples 1001.1, 1001.2, 1001.3 and 1001.4

7-(3,5-Difluoropyridin-2-yl)-N-(5-((5-(1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide (4 Single Stereoisomers)

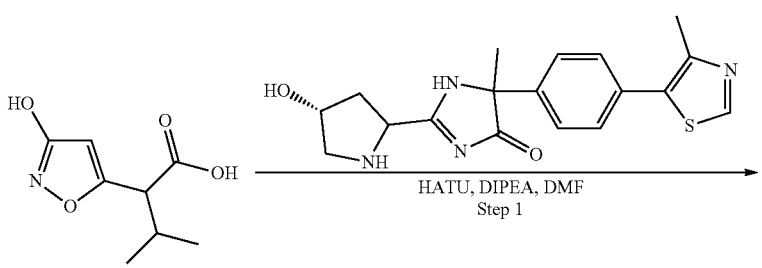

HATU, DIPEA, DMF
Step 1

-continued
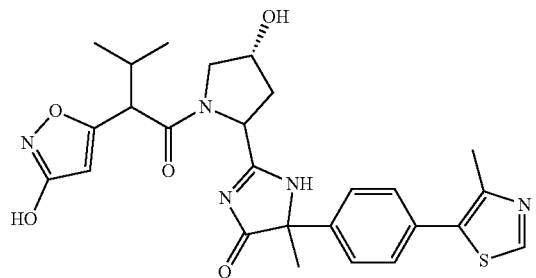
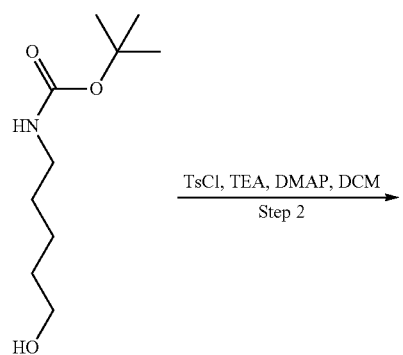
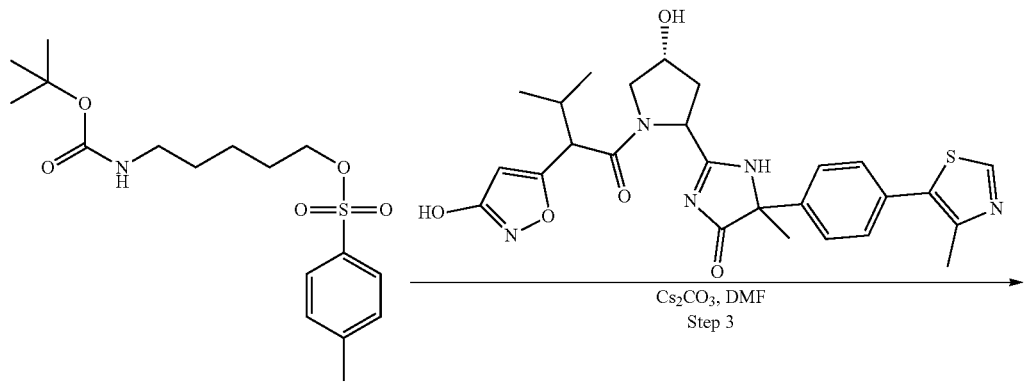
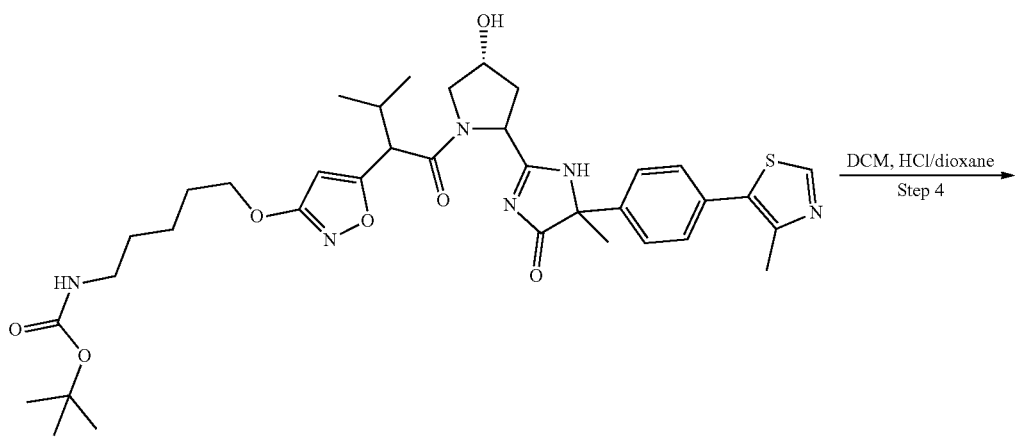

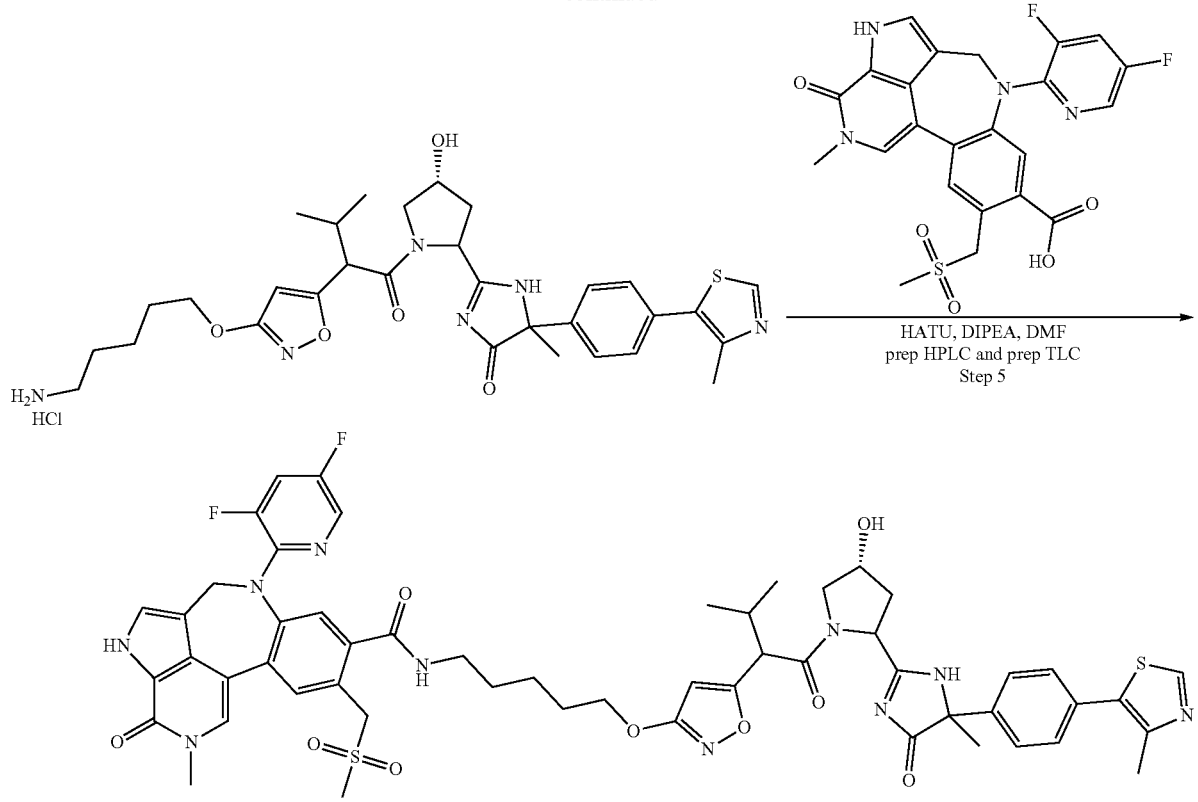

Step 1: 2-((4R)-4-Hydroxy-1-(2-(3-hydroxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one

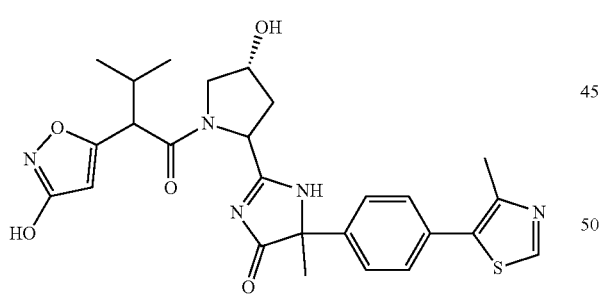

A solution of 2-((4R)-4-hydroxypyrrolidin-2-yl)-5-methyl-5-(4-(4-methylthiazol-5-yl)phenyl)-1,5-dihydro-4H-imidazol-4-one hydrochloride salt (Intermediate 10, Example 104, 100 mg, 0.255 mmol), 2-(3-hydroxyisoxazol-5-yl)-3-methylbutanoic acid (Intermediate 7, 62.3 mg, 0.340 mmol), HATU (213 mg, 0.560 mmol) and DIPEA (181 mg, 1.40 mmol) in DMF (4 mL) was stirred at 25° C. for 30 minutes. The solution was purified directly by reverse phase chromatography (gradient: 5%-40% ACN in water (0.1% formic acid)) to yield 50 mg (34%) of the title compound as a light yellow solid. LCMS (ESI): $R_T$ (min)=0.92, 1.07. [M+H]$^+$=524, method=D.

Step 2: 5-(tert-Butoxycarbonylamino)pentyl 4-methylbenzenesulfonate

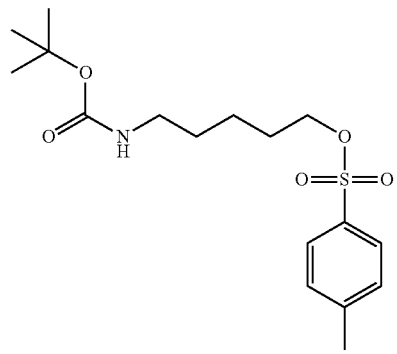 [SMILES: Cc1ccc(S(=O)(=O)OCCCCCNC(=O)OC(C)(C)C)cc1]

Under nitrogen, to a stirred solution of tert-butyl 5-hydroxypentylcarbamate (4.00 g, 19.7 mmol), DMAP (0.24 g, 1.99 mmol) and Et$_3$N (5.51 mL, 39.5 mmol) in DCM (70 mL) was added TsCl (5.68 g, 29.8 mmol) portionwise at 0° C. The resulting solution was stirred at 25° C. for 12 hours. The reaction mixture was diluted with water. The organic layers were separated, and the aqueous was extracted with DCM. The combined organic layers were dried over Na$_2$SO$_4$ and concentrated under reduced pressure. The residue was purified by flash chromatography on silica gel (gradient: 0-30% ethyl acetate/petroleum ether) to yield 6.4 g (91%) of the title compound as a colorless oil. LCMS (ESI): $R_T$ (min)=1.38. [M+H]$^+$=358, method A.

Step 3: tert-Butyl (5-((5-(1-((4R)-4-hydroxy-2-(5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)carbamate

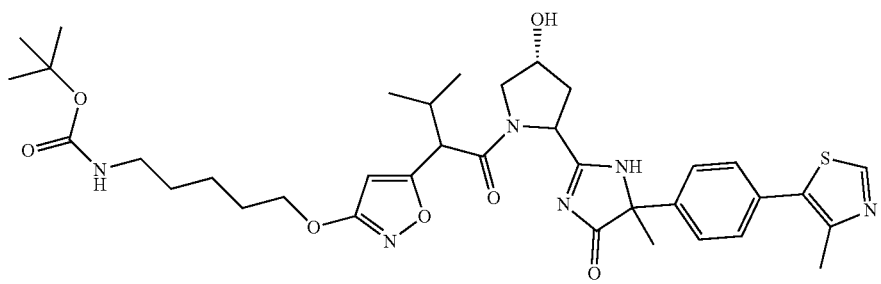 [SMILES: Cc1ncsc1-c1ccc(C2(C)NC(C3C[C@@H](O)CN3C(=O)C(c3cc(OCCCCCNC(=O)OC(C)(C)C)no3)C(C)C)=NC2=O)cc1]

A solution of 5-(tert-butoxycarbonylamino)pentyl 4-methylbenzenesulfonate (102 mg, 0.290 mmol), 2-((4R)-4-hydroxy-1-(2-(3-hydroxyisoxazol-5-yl)-3-methylbutanoyl)pyrrolidin-2-yl)-5-methyl-5-(4-(4-methylthiazol-5-yl)phenyl)-1,5-dihydro-4H-imidazol-4-one (150 mg, 0.290 mmol) and $Cs_2CO_3$ (167 mg, 0.510 mmol) in DMF (6 mL) was stirred at 25° C. for 3 hours. The resulting mixture was purified directly by reverse phase chromatography (gradient: 5%-40% ACN in water (0.1% formic acid)) to yield 90 mg (44.3%) of the title compound as a yellow solid. LCMS (ESI): $R_T$ (min)=0.94, 1.23. [M+H]$^+$=709, method=F.

Step 4: 2-((4R)-1-(2-(3-((5-Aminopentyl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one Hydrochloride Salt methyl-1-oxobutan-2-yl)isoxazol-3-yl)oxy)pentyl)carbamate (90.0 mg, 0.130 mmol) in DCM (4 mL) was added HCl/dioxane (1 mL, 4 M) dropwise at 0° C. The resulting solution was stirred at 25° C. for 3 hours. The solution was concentrated under reduced pressure to afford the crude title compound. The crude was used for the next step without further purification. LCMS (ESI): $R_T$ (min)=0.930, 1.07. [M+H]$^+$=609, method=A.

Step 5: 7-(3,5-Difluoropyridin-2-yl)-N-(5-((5-(1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide (4 Single Stereoisomers)

A solution of 7-(3,5-difluoropyridin-2-yl)-2-methyl-10-((methylsulfonyl)methyl)-3-oxo-3,4,6,7-tetrahydro-2H-2,4,7-triazadibenzo[cd,f]azulene-9-carboxylic acid (intermediate 9, 33.3 mg, 0.070 mmol), (S)-2-((4R)-1-(2-(3-(5-aminopentyloxy)isoxazol-5-yl)-3-methylbutanoyl)-4-

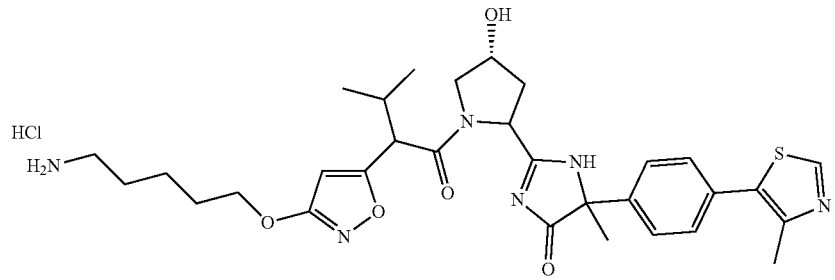 [SMILES: Cl ; Cc1ncsc1-c1ccc(C2(C)NC(C3C[C@@H](O)CN3C(=O)C(c3cc(OCCCCCN)no3)C(C)C)=NC2=O)cc1]

To a stirred solution of tert-butyl (5-((5-(1-((4R)-4-hydroxy-2-(5-methyl-5-(4-(4-methylthiazol-5-yl)phenyl)-4-oxo-4,5-dihydro-1H-imidazol-2-yl)pyrrolidin-1-yl)-3- hydroxypyrrolidin-2-yl)-5-methyl-5-(4-(4-methylthiazol-5-yl)phenyl)-]H-imidazol-4(5H)-one hydrochloride (43.0 mg, 0.070 mmol), HATU (27.9 mg, 0.070 mmol) and DIPEA (0.03 mL, 0.20 mmol) in N,N-Dimethylformamide (2 mL) was stirred at 25° C. for 3 hours. The mixture was purified by prep-HPLC (column: Kinetex EVO C18 column 21.2*150, 5 um; mobile phase A: water (10 mmol/L NH₄HCO₃), mobile phase B: acetonitrile; flow rate: 25 mL/min; gradient: 15% B to 50% B in 15 min; 220 nm; Rt: 13.5/14.6/15.2). Three peaks were observed on prep-HPLC. The first peak is a single stereoisomer Example 1001.1. The second peak was a mixture of two isomers Example 1001.2 and Example 1001.3. The third peak is a single stereoisomer Example 1001.4. The second peak was separated again by prep-TLC (MeOH/DCM=1/10) (Example 1001.2 is the low Rf value point and Example 1001.3 is the high Rf value point). Finally, four single unknown stereoisomers were obtained as white solids. Example 1001.1 (8.8 mg, 12.1% yield), Example 1001.2 (8.9 mg, 12.2% yield), Example 1001.3 (5.9 mg, 8.1% yield) and Example 1001.4 (4.4 mg, 6.1% yield).

Example 1001.1: LCMS (ESI): $R_T$ (min)=2.47. [M+H]⁺=1091, method=C; ¹H NMR (400 MHz, DMSO-d6) 11.93 (s, 1H), 10.93 (s, 1H), 9.04-8.95 (m, 1H), 8.40 (t, J=5.7 Hz, 1H), 8.05 (t, J=2.9 Hz, 1H), 7.91 (s, 1H), 7.75 (s, 1H), 7.66-7.43 (m, 2H), 7.43-7.21 (m, 5H), 6.11 (d, J=17.2 Hz, 1H), 5.94 (s, 1H), 5.35-5.14 (m, 2H), 4.68 (t, J=7.6 Hz, 1H), 4.59 (s, 1H), 4.48-4.40 (m, 1H), 4.28 (s, 1H), 4.05-3.89 (m, 2H), 3.88-3.65 (m, 3H), 3.62 (s, 3H), 3.11 (s, 2H), 2.91 (s, 3H), 2.44 (d, J=2.7 Hz, 3H), 2.30-2.17 (m, 2H), 2.09-2.00 (m, 1H), 1.63-1.35 (m, 7H), 1.23 (s, 2H), 0.98 (d, J=6.4 Hz, 3H), 0.84 (dd, J=6.7, 3.9 Hz, 3H).

Example 1001.2: LCMS (ESI): $R_T$ (min)=2.61. [M+H]⁺=1091, method=C; ¹H NMR (400 MHz, DMSO-d6) 11.93 (s, 1H), 10.96 (s, 1H), 9.00 (d, J=4.6 Hz, 1H), 8.44 (t, J=5.6 Hz, 1H), 8.07 (d, J=2.6 Hz, 1H), 7.92 (s, 1H), 7.76 (s, 1H), 7.61 (ddd, J=11.3, 8.2, 2.7 Hz, 1H), 7.56-7.34 (m, 4H), 7.34-7.21 (m, 2H), 6.10 (s, 1H), 5.95 (s, 1H), 5.26 (dd, J=17.8, 4.0 Hz, 2H), 4.74-4.57 (m, 2H), 4.45-4.38 (m, 1H), 4.26 (d, J=32.2 Hz, 1H), 4.11 (t, J=6.5 Hz, 2H), 3.90 (dd, J=10.3, 4.6 Hz, 1H), 3.71 (dd, J=9.4, 5.7 Hz, 1H), 3.62 (s, 3H), 3.45 (d, J=10.9 Hz, 1H), 3.17 (s, 2H), 2.92 (s, 3H), 2.44 (d, J=4.6 Hz, 3H), 2.31-2.24 (m, 1H), 2.21-2.13 (m, 1H), 2.05 (dt, J=12.4, 5.6 Hz, 1H), 1.70 (t, J=7.4 Hz, 2H), 1.64-1.44 (m, 5H), 1.37 (t, J=8.5 Hz, 2H), 1.00-0.86 (m, 3H), 0.85-0.75 (m, 3H).

Example 1001.3: LCMS (ESI): $R_T$ (min)=1.17. [M+H]⁺=1091, method=C; ¹H NMR (400 MHz, DMSO-d6) 11.93 (s, 1H), 10.81 (s, 1H), 8.98 (d, J=8.0 Hz, 1H), 8.42 (d, J=14.7 Hz, 1H), 8.06 (dd, J=6.8, 2.5 Hz, 1H), 7.91 (d, J=4.9 Hz, 1H), 7.75 (d, J=2.7 Hz, 1H), 7.69-7.54 (m, 2H), 7.54-7.40 (m, 3H), 7.36-7.24 (m, 2H), 6.07 (d, J=26.6 Hz, 1H), 5.96 (s, 1H), 5.50 (s, 1H), 5.21 (s, 1H), 4.73 (dd, J=15.7, 12.2 Hz, 1H), 4.59 (s, 1H), 4.38 (s, 1H), 4.30 (s, 1H), 4.11 (t, J=6.5 Hz, 1H), 4.01 (t, J=6.6 Hz, 1H), 3.93 (dd, J=10.4, 5.4 Hz, 1H), 3.78 (d, J=8.7 Hz, 1H), 3.67-3.59 (m, 3H), 3.46 (d, J=12.7 Hz, 1H), 3.14 (s, 2H), 2.91 (d, J=7.6 Hz, 3H), 2.44 (d, J=2.1 Hz, 3H), 2.30-2.21 (m, 1H), 2.16 (d, J=13.5 Hz, 1H), 1.94 (s, 1H), 1.72-1.25 (m, 9H), 0.96 (d, J=6.6 Hz, 2H), 0.82 (d, J=6.6 Hz, 2H), 0.73 (d, J=6.6 Hz, 1H), 0.59 (d, J=6.7 Hz, 1H).

Example 1001.4: LCMS (ESI): $R_T$ (min)=2.65. [M+H]⁺=1091, method=C; ¹H NMR (400 MHz, DMSO-d6) 11.93 (s, 1H), 10.89 (s, 1H), 8.98 (d, J=14.9 Hz, 1H), 8.43 (t, J=5.5 Hz, 1H), 8.06 (dd, J=7.0, 2.5 Hz, 1H), 7.91 (d, J=4.8 Hz, 1H), 7.75 (d, J=2.5 Hz, 1H), 7.67-7.53 (m, 3H), 7.53-7.44 (m, 2H), 7.33-7.26 (m, 2H), 6.12 (s, 1H), 5.95 (s, 1H), 5.57 (s, 1H), 5.20 (s, 1H), 4.79-4.61 (m, 2H), 4.32 (d, J=31.3 Hz, 2H), 4.13-4.01 (m, 2H), 3.81-3.67 (m, 3H), 3.62 (s, 3H), 3.17 (s, 2H), 2.91 (d, J=7.3 Hz, 3H), 2.43 (d, J=16.6 Hz, 3H), 2.29 (d, J=15.1 Hz, 1H), 2.21-2.08 (m, 1H), 1.95 (d, J=13.5 Hz, 1H), 1.70 (m, 2H), 1.64-1.43 (m, 5H), 1.39 (d, J=9.4 Hz, 2H), 0.94 (t, J=5.9 Hz, 3H), 0.81 (dd, J=13.8, 6.6 Hz, 3H).

Examples 1002.1, 1002.2, 1002.3 and 1002.4

7-(3,5-Difluoropyridin-2-yl)-N-((3S)-1-(2-((5-(1-((4R)-4-hydroxy-2-(5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-2-methyl-10-((methylsulfonyl)methyl)-3-oxo-3,4,6,7-tetrahydro-2H-2,4,7-triazadibenzo[cd,f]azulene-9-carboxamide
(4 Single Stereoisomers)

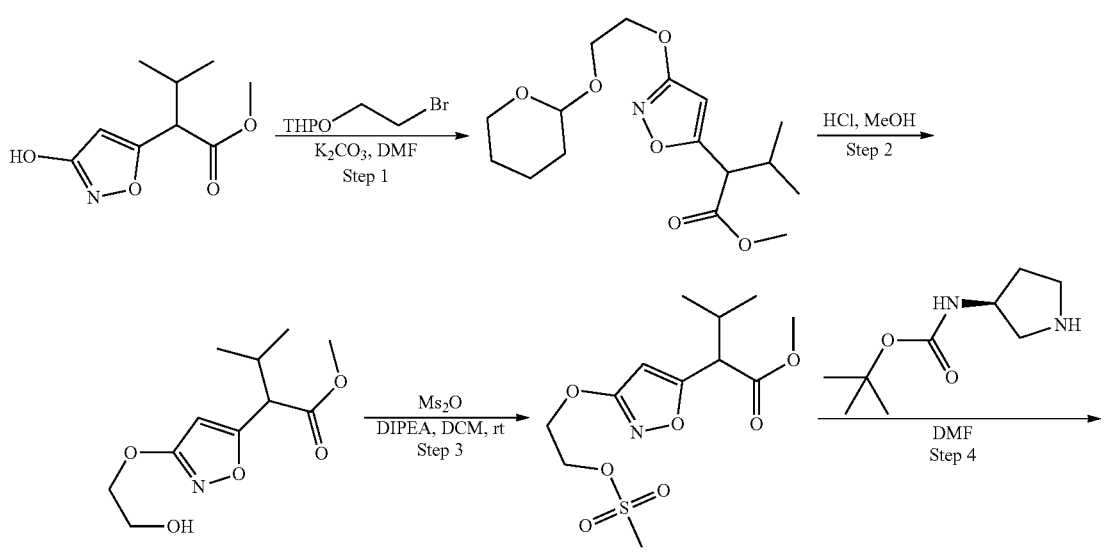

-continued
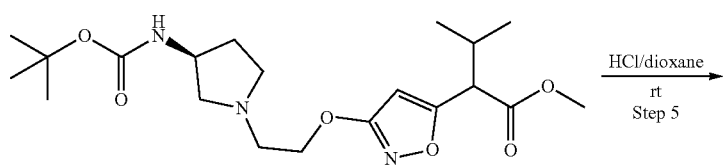
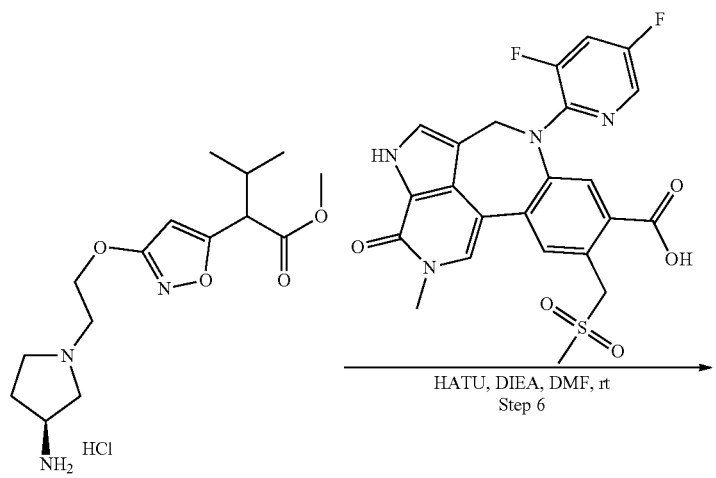
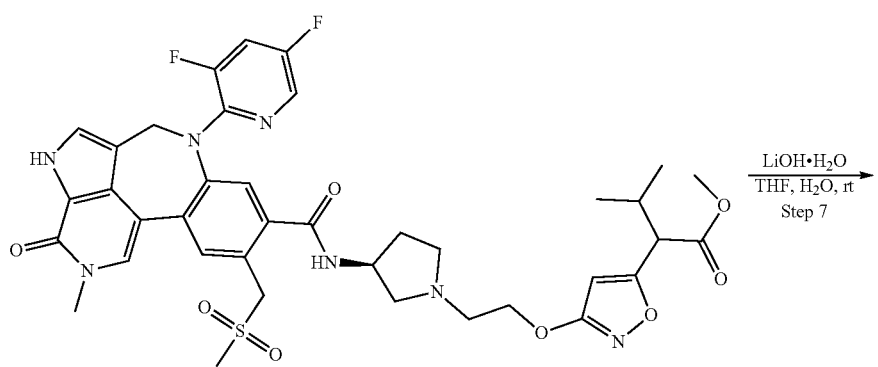
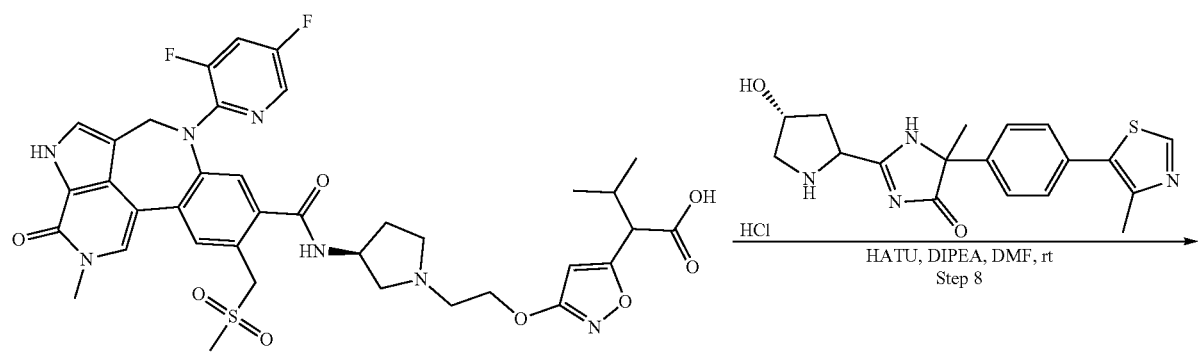

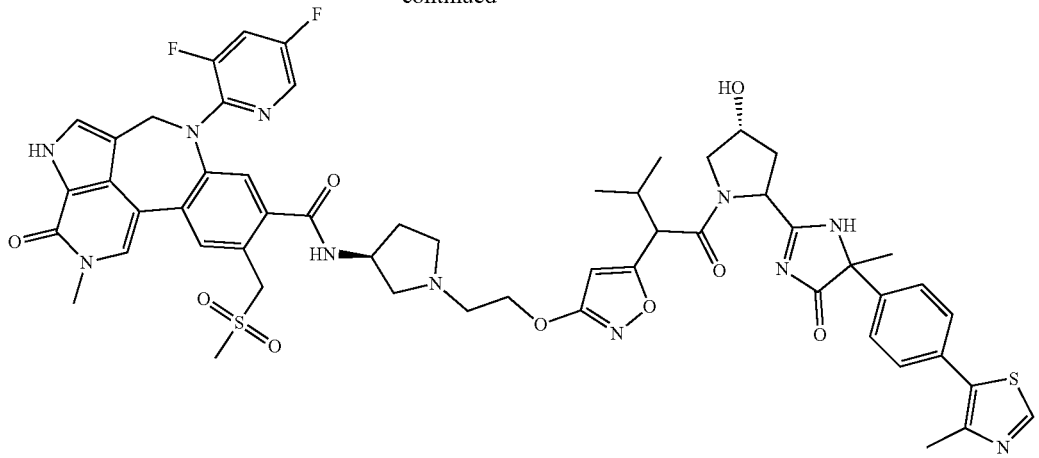

Step 1: Methyl 3-methyl-2-(3-(2-((tetrahydro-2H-pyran-2-yl) oxy)ethoxy)isoxazol-5-yl)butanoate

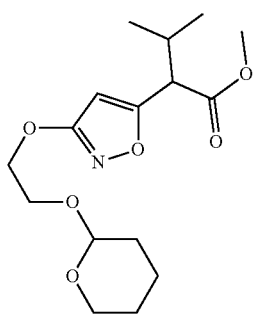 [SMILES: COC(=O)C(c1cc(OCCOC2CCCCO2)no1)C(C)C]

A mixture of methyl 2-(3-hydroxyisoxazol-5-yl)-3-methyl-butanoate (intermediate 3, 300 mg, 1.51 mmol), 2-(2-bromoethoxy) tetrahydro-2H-pyran (787 mg, 3.77 mmol) and K$_2$CO$_3$ (623 mg, 4.52 mmol) in DMF (3 mL) was stirred at 50° C. for 1 hour. The reaction solution was portioned between ethyl acetate and water. Phases were separated. The organic phase was dried over anhydrous sodium sulfate and the concentrated under reduced pressure. The residue was purified by flash chromatography on silica gel (gradient: 0%-80% ethyl acetate/petroleum ether) to yield 299 mg (60%) of the title compound as a colorless oil. LCMS (ESI): R$_T$ (min)=1.03, [M+H]$^+$=328, method=I.

Step 2: Methyl 2-(3-(2-hydroxyethoxy) isoxazol-5-yl)-3-methylbutanoate

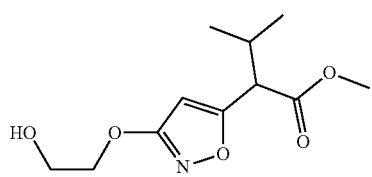 [SMILES: COC(=O)C(c1cc(OCCO)no1)C(C)C]

A solution of methyl 3-methyl-2-(3-(2-((tetrahydro-2H-pyran-2-yl)oxy)ethoxy)isoxazol-5-yl)butanoate (299 mg, 0.910 mmol) in methanol (3 mL) and aqueous hydrochloric acid (0.3 mL, 1 M) was stirred at 50° C. for 1 hour. The resulting mixture was concentrated under reduced pressure to yield 222 mg (crude) of the title compound as colorless oil, which was sufficient for next step without further purification. LCMS (ESI): R$_T$ (min)=1.10, [M+H]$^+$=244, method=J.

Step 3: Methyl 3-methyl-2-(3-(2-((methylsulfonyl) oxy) ethoxy) isoxazol-5-yl) butanoate

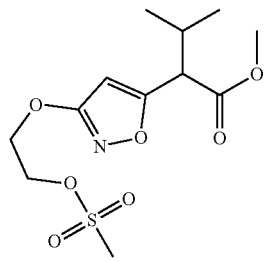 [SMILES: COC(=O)C(c1cc(OCCOS(C)(=O)=O)no1)C(C)C]

A solution of methyl 2-(3-(2-hydroxyethoxy)isoxazol-5-yl)-3-methylbutanoate (222 mg, 0.910 mmol), methanesulfonic anhydride (317 mg, 1.83 mmol) and DIPEA (588 mg, 4.56 mmol) in DCM (5 mL) was stirred at room temperature for 3 hours. The resulting solution was diluted with DCM and washed with water. The organic layer was dried over anhydrous sodium sulfate and concentrated under reduced pressure to yield 330 mg (crude) of the title compound as yellow oil. LCMS (ESI): R$_T$ (min)=1.22, [M+H]$^+$=322, method=J.

Step 4: Methyl 2-(3-(2-((S)-3-((tert-butoxycarbonyl) amino)pyrrolidin-1-yl)ethoxy)isoxazol-5-yl)-3-methylbutanoate

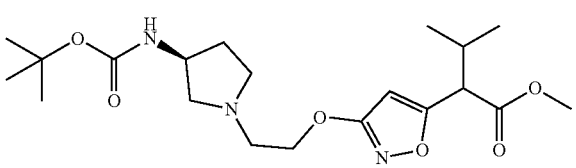 [SMILES: COC(=O)C(c1cc(OCCN2CC[C@H](NC(=O)OC(C)(C)C)C2)no1)C(C)C]

Under nitrogen, a solution of methyl 3-methyl-2-(3-(2-((methylsulfonyl)oxy)ethoxy)isoxazol-5-yl)butanoate (235 mg, 0.730 mmol) and tert-butyl (S)-pyrrolidin-3-ylcarbamate (408 mg, 2.19 mmol) in DMF (3 mL) was stirred at 80° C. for 3 hours. The reaction mixture was partitioned between ethyl acetate, and water. Phases were separated. The organic layer was dried over anhydrous sodium sulfate and concentrated under reduced pressure. The residue was purified by flash chromatography on silica gel (gradient: 0%-80% ethyl acetate/petroleum ether) to yield 172 mg (57%) of the title compound as yellow oil. LCMS (ESI): $R_T$ (min)=1.07, $[M+H]^+$=412, method=J.

Step 5: Methyl 2-(3-(2-((S)-3-aminopyrrolidin-1-yl)ethoxy) isoxazol-5-yl)-3-methylbutanoate hydrochloride

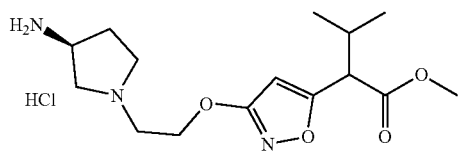 [SMILES: Cl ; COC(=O)C(c1cc(OCCN2CC[C@H](N)C2)no1)C(C)C]

A solution of methyl 2-(3-(2-((S)-3-((tert-butoxycarbonyl) amino) pyrrolidin-1-yl) ethoxy)isoxazol-5-yl)-3-methylbutanoate (172 mg, 0.420 mmol) in DCM (1.5 mL) and HCl/dioxane (1.5 mL, 4 M) was stirred at room temperature for 0.5 hours. The resulting mixture was concentrated under reduced pressure to yield 140 mg (crude) of the title compound as a yellow solid. LCMS (ESI): $R_T$ (min)=0.74, $[M+H]^+$=312, method=L.

Step 6: Methyl 2-(3-(2-((S)-3-(7-(3,5-difluoropyridin-2-yl)-2-methyl-10-((methylsulfonyl)methyl)-3-oxo-3,4,6,7-tetrahydro-2H-2,4,7-triazadibenzo[cd,f]azulene-9-carboxamido)pyrrolidin-1-yl)ethoxy)isoxazol-5-yl)-3-methylbutanoate

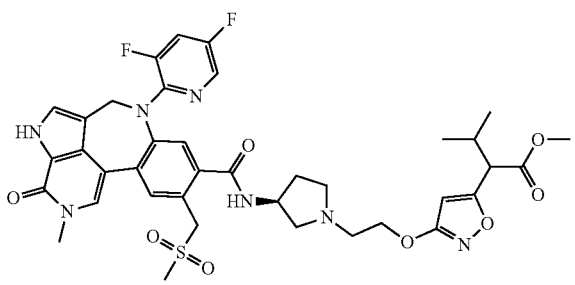 [SMILES: COC(=O)C(c1cc(OCCN2CC[C@H](NC(=O)c3cc4c(cc3CS(C)(=O)=O)-c3cn(C)c(=O)c5[nH]cc(c35)CN4c3ncc(F)cc3F)C2)no1)C(C)C]

A solution of methyl 2-(3-(2-((S)-3-aminopyrrolidin-1-yl)ethoxy)isoxazol-5-yl)-3-methylbutanoate hydrochloride (130 mg, 0.420 mmol), 7-(3,5-difluoropyridin-2-yl)-2-methyl-10-((methylsulfonyl)methyl)-3-oxo-3,4,6,7-tetrahydro-2H-2,4,7-triazadibenzo[cd,f]azulene-9-carboxylic acid (208 mg, 0.42 mmol), HATU (174 mg, 0.46 mmol) and DIPEA (215 mg, 1.67 mmol) in DMF (10 mL) was stirred at room temperature for 0.5 h. The reaction solution was purified by reverse phase flash chromatography (solvent gradient: 5-80% acetonitrile in water (0.05% NH$_4$HCO$_3$)) to yield 152 mg (46%) of the title compound as a yellow solid. LCMS (ESI): $R_T$ (min)=1.05, $[M+H]^+$=794, method=J.

Step 7: 2-(3-(2-((S)-3-(7-(3,5-Difluoropyridin-2-yl)-2-methyl-10-((methylsulfonyl)methyl)-3-oxo-3,4,6,7-tetrahydro-2H-2,4,7-triazadibenzo[cd,f]azulene-9-carboxamido)pyrrolidin-1-yl)ethoxy)isoxazol-5-yl)-3-methylbutanoic acid

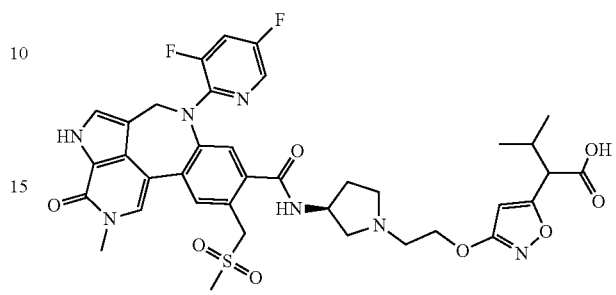

A solution of methyl 2-(3-(2-((S)-3-(7-(3,5-difluoropyridin-2-yl)-2-methyl-10-((methylsulfonyl)methyl)-3-oxo-3,4,6,7-tetrahydro-2H-2,4,7-triazadibenzo[cd,f]azulene-9-carboxamido)pyrrolidin-1-yl)ethoxy)isoxazol-5-yl)-3-methylbutanoate (152 mg, 0.190 mmol) and LiOH.H$_2$O (16.0 mg, 0.380 mmol) in tetrahydrofuran (1.5 mL) and water (1.5 mL) was stirred at room temperature for 1 hour. The resulting mixture was concentrated under reduced pressure to yield 145 mg (crude) of the title compound as a yellow solid. LCMS (ESI): $R_T$ (min)=1.00, $[M+H]^+$=780, method=J.

Step 8: 7-(3,5-Difluoropyridin-2-yl)-N-((3S)-1-(2-((5-(1-((4R)-4-hydroxy-2-(5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-2-methyl-10-((methylsulfonyl)methyl)-3-oxo-3,4,6,7-tetrahydro-2H-2,4,7-triazadibenzo[cd,f]azulene-9-carboxamide (4 Single Stereoisomers)

A solution of 2-(3-(2-((S)-3-(7-(3,5-difluoropyridin-2-yl)-2-methyl-10-((methylsulfonyl)methyl)-3-oxo-3,4,6,7-tetrahydro-2H-2,4,7-triazadibenzo[cd,f]azulene-9-carboxamido)pyrrolidin-1-yl)ethoxy)isoxazol-5-yl)-3-methylbutanoic acid (180 mg, 0.230 mmol), 2-((4R)-4-hydroxypyrrolidin-2-yl)-5-methyl-5-(4-(4-methylthiazol-5-yl)phenyl)-1,5-dihydro-4H-imidazol-4-one hydrochloride (Intermediate 10, Example 104) (90.7 mg, 0.230 mmol), HATU (96.5 mg, 0.250 mmol) and DIPEA (99.4 mg, 0.920 mmol) in DMF (2.5 mL) was stirred at room temperature for 0.5 hour. The resulting solution was purified by reverse phase chromatography (solvent gradient: 5-100% acetonitrile in water (0.05% NH$_4$HCO$_3$)) to yield 120 mg of the mixture of four isomers. The mixture was separated again by Prep-HPLC (Column: Kinetex EVO C18 Column 21.2*150.5 um; Mobile Phase A: Water (10 mM ammonium formate), Mobile Phase B: ACN; Flow rate: 25 mL/min; Gradient: 20% B to 40% B in 18 minutes; 220 nm; RT (min): 12.7, 14.1, 14.8) to yield 17.9 mg (7%) of Example 1002.1, 22.1 mg of a mixture of Example 1002.2 and Example 1002.3, and 4.0 mg (2%) of Example 1002.4 as white solids. Example 1002.2 and Example 1002.3 were separated again by Chiral-Prep-HPLC (Column: (R,R)Whelk-O 1, 21.1*250 mm, 5 um; Mobile Phase A: Hex:DCM=1:1-HPLC, Mobile Phase B: EtOH-HPLC; Flow rate: 20 mL/minute; Gradient: 20 B to 20 B in 25 min; 220/254 nm; $R_T$1:13.4; $R_T$2:17.3)

to yield 6.9 mg (3%) of Example 1002.2 and 9.4 mg (4%) of Example 1002.3 as white solids.

Example 1002.1: LCMS (ESI): $R_T$ (min)=2.38, [M+H]$^+$=1118, method=L. $^1$H NMR (300 MHz, DMSO-d$_6$) δ11.92 (s, 1H), 10.92 (10.26) (s, 1H), 9.00-8.93 (m, 1H), 8.50 (d, J=7.3 Hz, 1H), 8.02 (d, J=2.6 Hz, 1H), 7.89 (s, 1H), 7.74 (s, 1H), 7.64-7.45 (m, 2H), 7.49-7.00 (m, 5H), 6.12 (s, 1H), 5.91 (br, 1H), 5.28 (d, J=3.8 Hz, 1H), 5.17 (br, 1H), 4.92-4.55 (m, 2H), 4.43 (s, 1H), 4.40-4.15 (m, 2H), 4.15-3.97 (m, 2H), 3.88-3.65 (m, 3H), 3.60 (s, 3H), 2.89 (s, 3H), 2.80-2.60 (m, 3H), 2.48-2.20 (m, 8H), 2.12-1.90 (m, 2H), 1.80-1.40 (m, 4H), 0.96 (d, J=6.5 Hz, 3H), 0.82 (d, J=6.6 Hz, 3H).

Example 1002.2: LCMS (ESI): $R_T$ (min)=2.48, [M+H]$^+$=1118, method=A. $^1$H NMR (300 MHz, DMSO-d$_6$) δ11.92 (s, 1H), 11.17 (10.95, 10.43) (s, 1H), 8.99 (8.98, 8.97) (d, J=3.5 Hz, 1H), 8.54 (d, J=6.9 Hz, 1H), 8.03 (d, J=2.5 Hz, 1H), 7.89 (s, 1H), 7.74 (s, 1H), 7.66-7.57 (m, 1H), 7.57-7.35 (m, 4H), 7.34-7.14 (m, 2H), 6.12 (s, 1H), 6.02 (s, 1H), 5.35-5.10 (m, 2H), 4.75-4.50 (m, 2H), 4.50-4.40 (m, 1H), 4.40-4.11 (m, 4H), 3.95-3.82 (m, 1H), 3.68 (d, J=9.4 Hz, 1H), 3.60 (s, 3H), 3.52-3.42 (m, 1H), 2.91 (s, 3H), 2.85-2.70 (m, 3H), 2.70-2.60 (m, 1H), 2.48-2.41 (m, 4H), 2.40-2.30 (m, 1H), 1.80-1.50 (m, 4H), 0.94 (d, J=6.6 Hz, 3H), 0.80 (d, J=5.9 Hz, 3H).

Example 1002.3: LCMS (ESI): $R_T$ (min)=2.45, [M+H]$^+$=1118, method=A. $^1$H NMR (300 MHz, DMSO-d$_6$) δ11.93 (s, 1H), 10.90 (10.81, 10.65) (s, 1H), 8.97 (8.95) (s, 1H), 8.57-8.47 (m, 1H), 8.05-7.99 (m, 1H), 7.92-7.87 (m, 1H), 7.75-7.71 (m, 1H), 7.70-7.29 (m, 5H), 7.30-7.24 (m, 2H), 6.13 (6.05, 6.04) (s, 1H), 5.93 (br, 1H), 5.49 (d, J=5.3 Hz, 1H), 5.32 (br, 1H), 4.83-4.70 (m, 1H), 4.64-4.45 (m, 1H), 4.41-4.32 (m, 1H), 4.31-4.15 (m, 3H), 4.14-4.00 (m, 1H), 3.97-3.86 (m, 1H), 3.70-3.57 (m, 4H), 3.55 (m, 1H), 2.90 (d, J=5.5 Hz, 3H), 2.85-2.73 (m, 1H), 2.70-2.65 (m, 1H), 2.46-2.32 (m, 6H), 2.19-1.79 (m, 4H), 1.77-1.35 (m, 5H), 0.98-0.89 (m, 2H), 0.86-0.75 (m, 2H), 0.71 (d, J=6.6 Hz, 1H), 0.58 (d, J=6.6 Hz, 1H).

Example 1002.4: LCMS (ESI): $R_T$ (min)=2.53, [M+H]$^+$=1118, method=A. $^1$H NMR (300 MHz, DMSO-d$_6$) δ11.93 (s, 1H), 10.90 (10.81, 10.65) (s, 1H), 8.97 (8.95) (s, 1H), 8.57-8.47 (m, 1H), 8.05-7.99 (m, 1H), 7.92-7.87 (m, 1H), 7.75-7.71 (m, 1H), 7.70-7.29 (m, 5H), 7.30-7.24 (m, 2H), 6.13 (6.05, 6.04) (s, 1H), 5.93 (br, 1H), 5.49 (d, J=5.3 Hz, 1H), 5.32 (br, 1H), 4.83-4.70 (m, 1H), 4.64-4.45 (m, 1H), 4.41-4.32 (m, 1H), 4.31-4.15 (m, 3H), 4.14-4.00 (m, 1H), 3.97-3.86 (m, 1H), 3.70-3.57 (m, 4H), 3.55 (m, 1H), 2.90 (d, J=5.5 Hz, 3H), 2.85-2.73 (m, 1H), 2.70-2.65 (m, 1H), 2.46-2.32 (m, 6H), 2.19-1.79 (m, 4H), 1.77-1.35 (m, 5H), 0.98-0.89 (m, 2H), 0.86-0.75 (m, 2H), 0.71 (d, J=6.6 Hz, 1H), 0.58 (d, J=6.6 Hz, 1H).

Examples 1003.1, 1003.2, 1003.3 and 1003.4

4-(2-((5-(1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide (4 Stereoisomers)

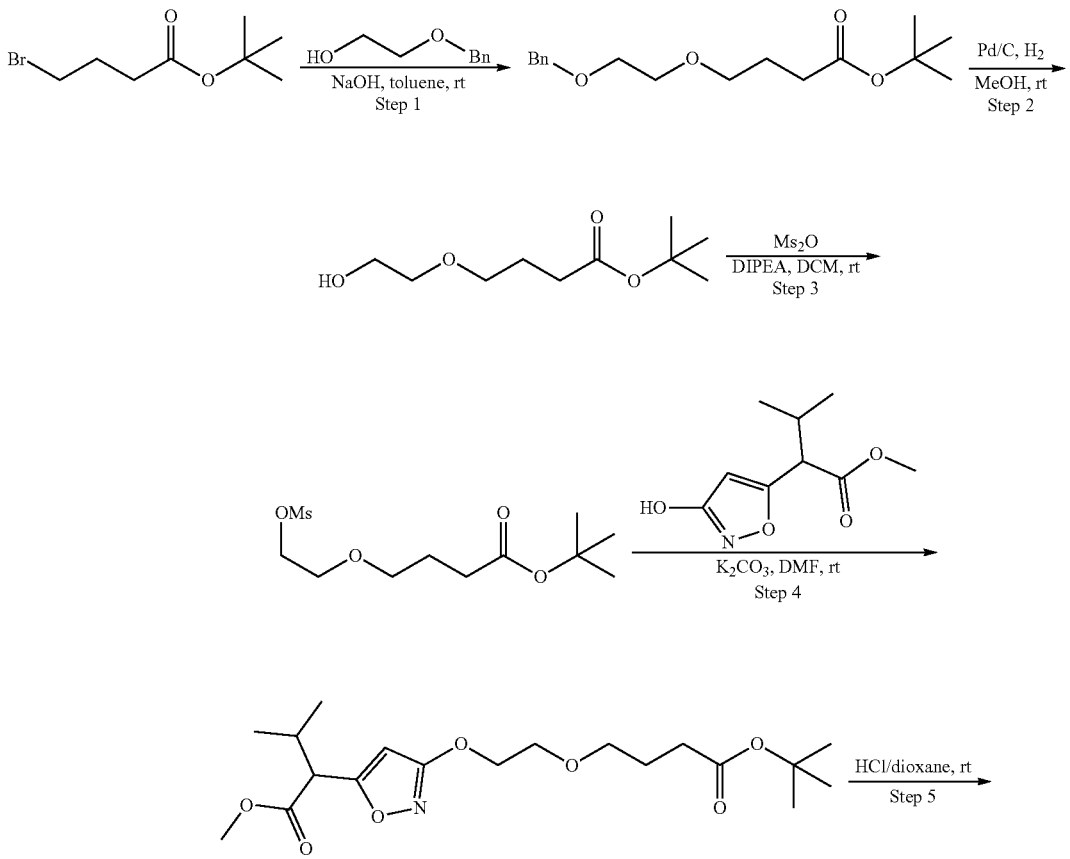

-continued

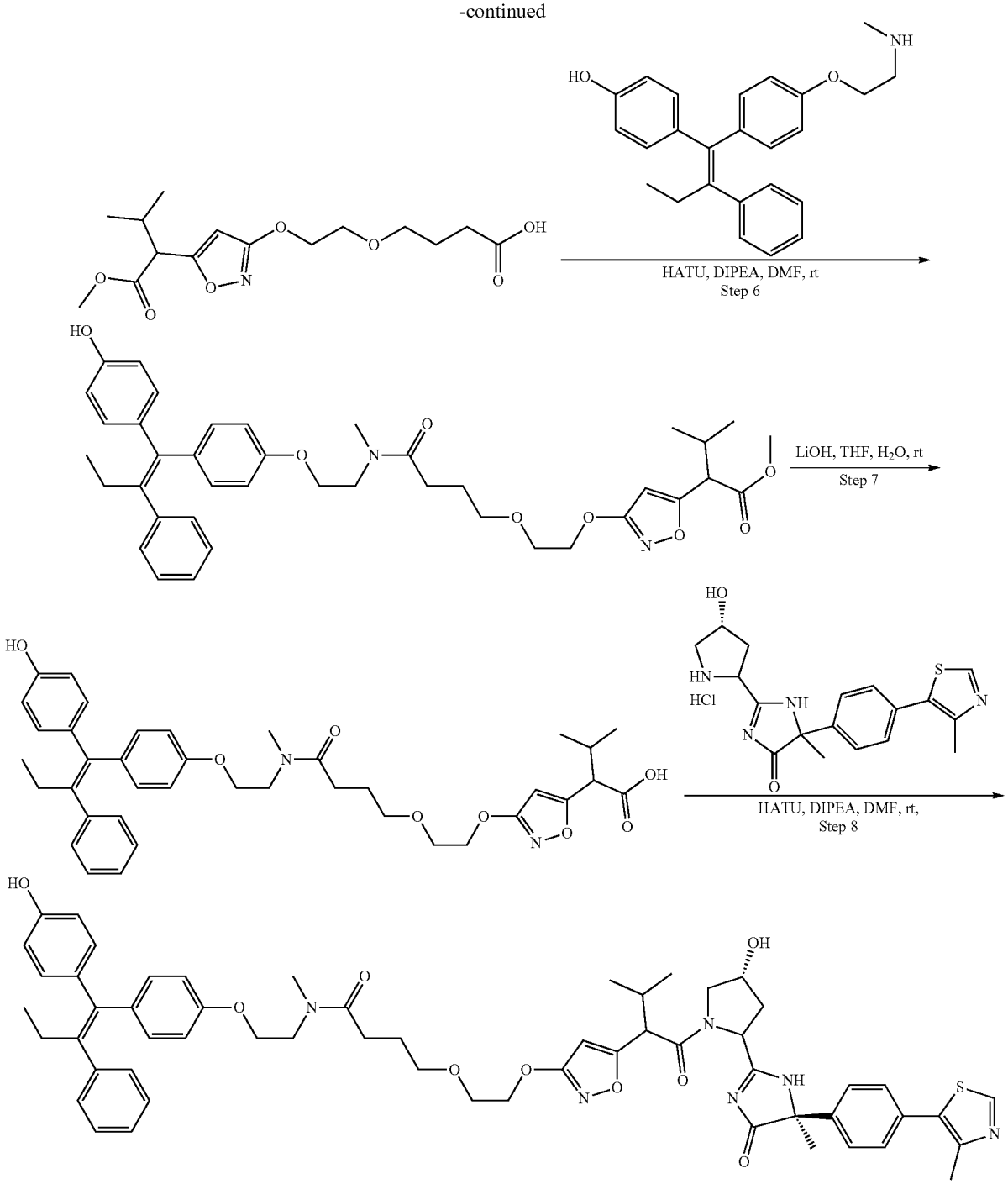

Step 1: tert-Butyl 4-(2-(benzyloxy)ethoxy)butanoate

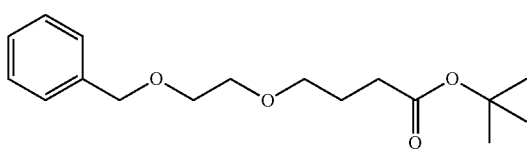 [SMILES: CC(C)(C)OC(=O)CCCOCCOCc1ccccc1]

A mixture of tert-butyl 4-bromobutanoate (22.0 g, 98.6 mmol), 2-(benzyloxy)ethanol (6.00 g, 39.4 mmol) and sodium hydroxide (3.23 g, 78.9 mmol) in toluene (75.0 mL) was stirred at room temperature for 16 hours. The resulting solution was partitioned between water and EtOAc. Phases were separated. The aqueous phase was extracted with EtOAc. The combined organic layers were dried over anhydrous Na₂SO₄ and concentrated under reduced pressure. The residue was purified by flash chromatography on silica gel (gradient: 0%-20% ethyl acetate/petroleum ether) to yield 530 mg (5%) of the title compound as a colorless oil. LCMS (ESI): $R_T$ (min)=1.45, [M+Na]$^+$=317, method=A.

Step 2: tert-Butyl 4-(2-hydroxyethoxy)butanoate

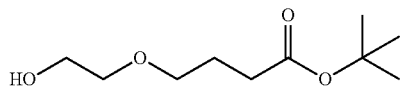

To a solution of tert-butyl 4-(2-(benzyloxy)ethoxy)butanoate (530 mg, 1.80 mmol) in MeOH (8.00 mL) was added 10% wet Pd/C (65.0 mg). The resulting mixture was evacuated and back filled with H$_2$ from a balloon. The resulting solution was stirred at room temperature for 2 hours and then filtered through a pad of Celite, The filtrate was concentrated under reduced pressure to yield 352 mg (crude) of the title compound as colorless oil. LCMS (ESI): $R_T$ (min)=0.78, [M+Na]$^+$=227, method=I.

Step 3: tert-Butyl 4-(2-((methylsulfonyl)oxy)ethoxy)butanoate

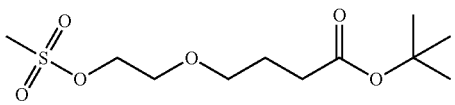 [SMILES: CC(C)(C)OC(=O)CCCOCCOS(C)(=O)=O]

A solution of tert-butyl 4-(2-hydroxyethoxy)butanoate (300 mg, 1.47 mmol), methanesulfonic anhydride (512 mg, 2.94 mmol) and DIPEA (1.00 mL, 5.87 mmol) in DCM (1.5 mL) was stirred at room temperature for 3 hours. The resulting solution was quenched with water and extracted with DCM. The organic layers were washed with brine, dried over anhydrous Na$_2$SO$_4$ and concentrated under reduced pressure to yield 392 mg (crude) of the title compound as yellow oil. LCMS (ESI): $R_T$ (min)=1.25, [M+Na]$^+$=305, method=A.

Step 4: Methyl 2-(3-(2-(4-(tert-butoxy)-4-oxobutoxy) ethoxy)isoxazol-5-yl)-3-methylbutanoate

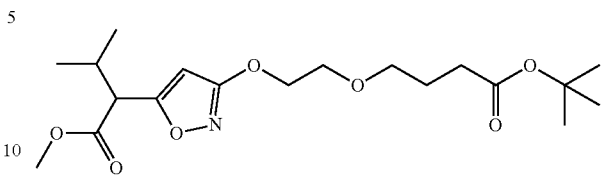

A solution of tert-butyl 4-(2-((methylsulfonyl)oxy) ethoxy)butanoate (425 mg, 1.51 mmol), methyl 2-(3-hydroxyisoxazol-5-yl)-3-methyl-butanoate (150 mg, 0.750 mmol) and potassium carbonate (422 mg, 3.01 mmol) in DMF (4 mL) was stirred at room temperature for 15 hours. The crude was purified by reverse phase flash chromatography (solvent gradient: 5-75% acetonitrile in water (0.05% NH$_4$HCO$_3$)) to yield 134 mg (46%) of the title compound as a colorless oil. LCMS (ESI): $R_T$ (min)=1.47, [M+Na]$^+$=408, method=A.

Step 5: 4-(2-((5-(1-Methoxy-3-methyl-1-oxobutan-2-yl) isoxazol-3-yl) oxy)ethoxy)butanoic acid

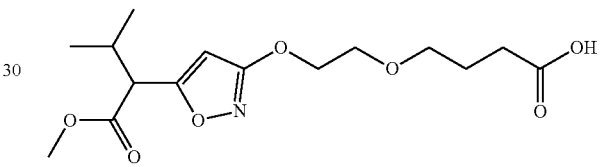

A solution of methyl 2-(3-(2-(4-(tert-butoxy)-4-oxobutoxy) ethoxy) isoxazol-5-yl)-3-methylbutanoate (100 mg, 0.260 mmol) in HCl/dioxane (4 M, 3.0 mL) was stirred at room temperature for 3 hours. The volatiles were removed under reduced pressure to yield 101 mg (crude) of the title compound as colorless oil. LCMS (ESI): $R_T$ (min)=1.18, [M+H]$^+$=330, method=A.

Step 6: Methyl (Z)-2-(3-(2-(4-((2-(4-(1-(4-hydroxyphenyl)-2-phenylbut-1-en-1-yl) phenoxy) ethyl) (methyl) amino)-4-oxobutoxy) ethoxy) isoxazol-5-yl)-3-methylbutanoate

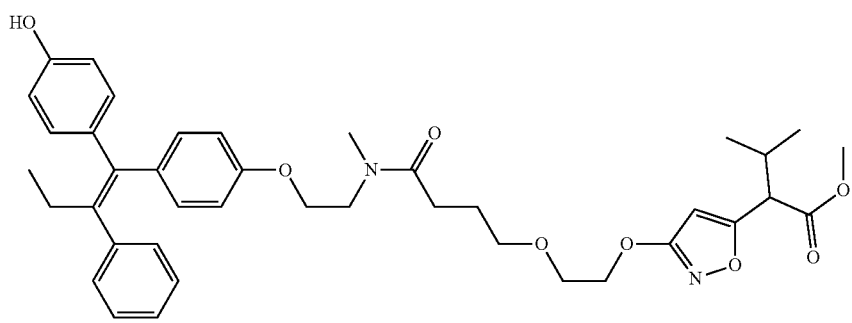 [SMILES: CC/C(=C(\c1ccc(O)cc1)c1ccc(OCCN(C)C(=O)CCCOCCOc2cc(C(C(=O)OC)C(C)C)on2)cc1)c1ccccc1]

A solution of 4-(2-((5-(1-methoxy-3-methyl-1-oxobutan-2-yl)isoxazol-3-yl)oxy)ethoxy)butanoic acid (100.0 mg, 0.300 mmol), (Z)-4-(1-(4-(2-(methylamino)ethoxy)phenyl)-2-phenylbut-1-en-1-yl)phenol (113 mg, 0.300 mmol), HATU (115 mg, 0.300 mmol) and DIPEA (136.7 mg, 1.06 mmol) in DMF (3.0 mL) was stirred at room temperature for 30 mins. The resulting solution was purified by reverse phase flash chromatography (solvent gradient: 5-80% acetonitrile in water (0.05% NH$_4$HCO$_3$)) to yield 137 mg (66%) of the title compound as a white solid. LCMS (ESI): R$_T$ (min)=1.16, [M+H]$^+$=685, method=E.

Step 7: (Z)-2-(3-(2-(4-((2-(4-(1-(4-Hydroxyphenyl)-2-phenylbut-1-en-1-yl)phenoxy) ethyl) (methyl) amino)-4-oxobutoxy) ethoxy) isoxazol-5-yl)-3-methylbutanoic acid

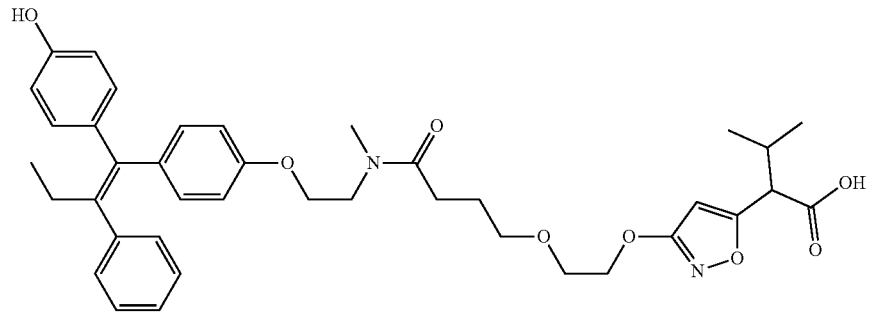 [SMILES: CC/C(=C(\c1ccc(O)cc1)c1ccc(OCCN(C)C(=O)CCCOCCOc2cc(C(C(=O)O)C(C)C)on2)cc1)c1ccccc1]

A solution of methyl (Z)-2-(3-(2-(4-((2-(4-(1-(4-hydroxyphenyl)-2-phenylbut-1-en-1-yl)phenoxy)ethyl)(methyl)amino)-4-oxobutoxy)ethoxy)isoxazol-5-yl)-3-methylbutanoate (137 mg, 0.200 mmol) and anhydrous lithium hydroxide (14.4 mg, 0.600 mmol) in THF (7.0 mL) and water (2.5 mL) was stirred at room temperature for 1.5 hours. The reaction mixture was acidified with 1N HCl aqueous solution to pH 4-5. The resulting solution was partitioned between water and DCM. Phases were separated and the aqueous phase was extracted with DCM. The combined organic phases were washed with brine, dried over anhydrous Na$_2$SO$_4$ and concentrated under reduced pressure to yield 129 mg (crude) of the title compound as a white solid. LCMS (ESI): R$_T$ (min)=1.11, [M+H]$^+$=671, method=I.

Step 8: 4-(2-((5-(1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide (4 Diastereoisomers: The Imidazolinone Piece are the Single Unknown Stereoisomers, the Double Bond Piece are the Mixture of Geometric Isomers)

A solution of 2-((4R)-4-hydroxypyrrolidin-2-yl)-5-methyl-5-(4-(4-methylthiazol-5-yl)phenyl)-1,5-dihydro-4H-imidazol-4-one hydrochloride (Intermediate 10, Example 104) (70.6 mg, 0.180 mmol), (Z)-2-(3-(2-(4-((2-(4-(1-(4-hydroxyphenyl)-2-phenylbut-1-en-1-yl)phenoxy) ethyl)(methyl)amino)-4-oxobutoxy)ethoxy)isoxazol-5-yl)-3-methylbutanoic acid (120 mg, 0.180 mmol), HATU (68.0 mg, 0.180 mmol) and DIPEA (81.3 mg, 0.630 mmol) in DMF (3.0 mL) was stirred at room temperature for 20 minutes. The resulting solution was purified by reverse phase chromatography (solvent gradient: 5-75% acetonitrile in water (0.05% NH$_4$HCO$_3$)) to afford 130 mg of the mixture of four isomers. The four single unknown stereoisomers were in the imidazolinone portion of the compound. The endoxifen portion of the compound was a mixture of geometric isomers (see, e.g., Elkins, et al., "Characterization of the isomeric configuration and impurities of (Z)-endoxifen by 2D NMR, high resolution LC-MS, and quantitative HPLC analysis", *J. Pharm. Biomed. Anal.*, 2014, 88, 174-179). Then it was separated by flash chromatography on silica gel (gradient: 0%-7% MeOH/DCM) to afford 55.0 mg of the faster peak (mixture of two isomers) and 50.0 mg of the slower peak (mixture of two isomers). The faster peak on silica gel column (55.0 mg) was separated by Chiral-Prep-HPLC (conditions: Column: CHIRALPAK IA-SFC-03, 5*25 cm, 5 um; Mobile Phase A: Hex:DCM=5:1, Mobile Phase B: EtOH; Flow rate: 20 mL/minute; Gradient: 50 B to 50 B in 20 minutes; 254/220 nm; R$_{T1}$:7.91; R$_{T2}$:13.2) to afford 26.2 mg (14%) of Example 1003.2 as a white solid and 10.1 mg (6%) Example 1003.4 as a light yellow solid. The slower peak on silica gel column (50.0 mg) was separated by Chiral-Prep-HPLC (conditions: Column: CHIRAL ART Cellulose-SB, 2*25 cm, 5 um; Mobile Phase A: Hex:DCM=5:1, Mobile Phase B: EtOH; Flow rate: 20 mL/minute; Gradient: 10 B to 10 B in 16 minutes; 254/220 nm; R$_{T1}$:8.93; R$_{T2}$:12.0) to afford the Example 1003.1 20.1 mg (11%) as a white solid and the Example 1003.3 10.9 mg (6%) as a yellow solid.

Example 1003.1: LCMS (ESI): R$_T$ (min)=1.85, [M+H]$^+$=1009, method=A. $^1$H NMR (300 MHz, DMSO-d$_6$) δ11.39 (10.94, 10.29) (s, 1H), 9.41 (9.16) (s, 1H), 9.03-8.90 (m, 1H), 7.56-7.33 (m, 4H), 7.23-7.03 (m, 6H), 7.01-6.87 (m, 2H), 6.77-6.72 (m, 1H), 6.72-6.64 (m, 1H), 6.62-6.53 (m, 2H), 6.42-6.35 (m, 1H), 6.18-6.08 (m, 1H), 5.32-5.24 (m, 1H), 4.90-4.62 (m, 1H), 4.44 (s, 1H), 4.34-3.99 (m, 4H), 3.99-3.79 (m, 2H), 3.79-3.61 (m, 3H), 3.61-3.43 (m, 3H), 3.32-3.22 (m, 1H), 3.12-2.70 (m, 3H), 2.49-2.12 (m, 9H), 2.12-1.96 (m, 1H), 1.76-1.55 (m, 2H), 1.56 (1.47) (s, 3H), 1.03-0.93 (m, 3H), 0.90-0.77 (m, 6H).

Example 1003.2: LCMS (ESI): R$_T$ (min)=2.30, [M+H]$^+$=1009, method=A. $^1$H NMR (300 MHz, DMSO-d$_6$) δ10.94 (10.86, 10.64) (s, 1H), 9.43 (9.18) (s, 1H), 9.06-8.95 (m, 1H), 7.78-7.39 (m, 4H), 7.26-7.14 (m, 2H), 7.14-7.05 (m, 4H), 7.05-6.88 (m, 2H), 6.76 (d, J=8.4 Hz, 1H), 6.73-6.65 (m, 1H), 6.62-6.55 (m, 2H), 6.40 (d, J=8.4 Hz, 1H), 6.22-6.06 (m, 1H), 5.99-5.30 (m, 1H), 4.94-4.67 (m, 1H), 4.43-4.21 (m, 2H), 4.21-3.86 (m, 4H), 3.86-3.39 (m, 8H), 3.10-2.72 (m, 3H), 2.49-1.90 (m, 10H), 1.85-1.40 (m, 5H), 1.01-0.90 (m, 2H), 0.90-0.77 (m, 5H), 0.78-0.55 (m, 2H).

Example 1003.3: LCMS (ESI): R$_T$ (min)=2.30, [M+H]$^+$=1009, method=A. $^1$H NMR (300 MHz, DMSO-d$_6$) δ11.21 (10.97, 10.46) (s, 1H), 9.43 (9.18) (s, 1H), 9.02 (9.01) (s, 1H), 7.67-7.36 (m, 4H), 7.22-7.12 (m, 2H), 7.16-7.08 (m, 4H), 7.00-6.87 (m, 2H), 6.76 (d, J=8.5 Hz, 1H), 6.74-6.68 (m, 1H), 6.65-6.56 (m, 2H), 6.40 (d, J=8.5 Hz, 1H), 6.23-6.05 (m, 1H), 5.32-5.13 (m, 1H), 4.77-4.58 (m, 1H), 4.43 (br, 1H), 4.33-4.26 (m, 2H), 4.21-3.80 (m, 3H), 3.80-3.40 (m, 8H), 3.05 (2.96, 2.88, 2.80) (s, 3H), 2.46 (d, J=3.1 Hz, 4H), 2.42-2.24 (m, 4H), 2.24-1.97 (m, 2H), 1.84-1.49 (m, 5H), 1.01-0.92 (m, 3H), 0.92-0.72 (m, 6H).

Example 1003.4: LCMS (ESI): $R_T$ (min)=2.01, $[M+H]^+$ =1009, method=A. $^1$H NMR (300 MHz, DMSO-$d_6$) δ10.91 (10.74) (s, 1H), 9.43 (9.18) (s, 1H), 9.01 (8.98) (s, 1H), 7.66-7.33 (m, 4H), 7.23-7.15 (m, 2H), 7.15-7.04 (m, 4H), 7.00-6.87 (m, 2H), 6.76 (d, J=8.5 Hz, 1H), 6.73-6.65 (m, 1H), 6.65-6.54 (m, 2H), 6.40 (d, J=8.5 Hz, 1H), 6.24-6.15 (m, 1H), 6.06-5.11 (m, 1H), 4.86-4.61 (m, 1H), 4.37 (br, 1H), 4.31-3.89 (m, 4H), 3.86-3.51 (m, 7H), 3.45 (t, J=6.6 Hz, 2H), 3.13-2.73 (m, 3H), 2.50-2.24 (m, 9H), 2.03-1.89 (m, 1H), 1.82-1.68 (m, 2H), 1.68-1.37 (m, 3H), 0.99-0.91 (m, 3H), 0.91-0.75 (m, 6H).

Examples 1004.1, 1004.2, 1004.3, and 1004.4

(5S)-2-((4R)-1-(2-(3-((6-(2-((4-((3-Ethynylphenyl) amino)-7-(2-methoxyethoxy)quinazolin-6-yl)oxy) ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one (4 Single Stereoisomers)

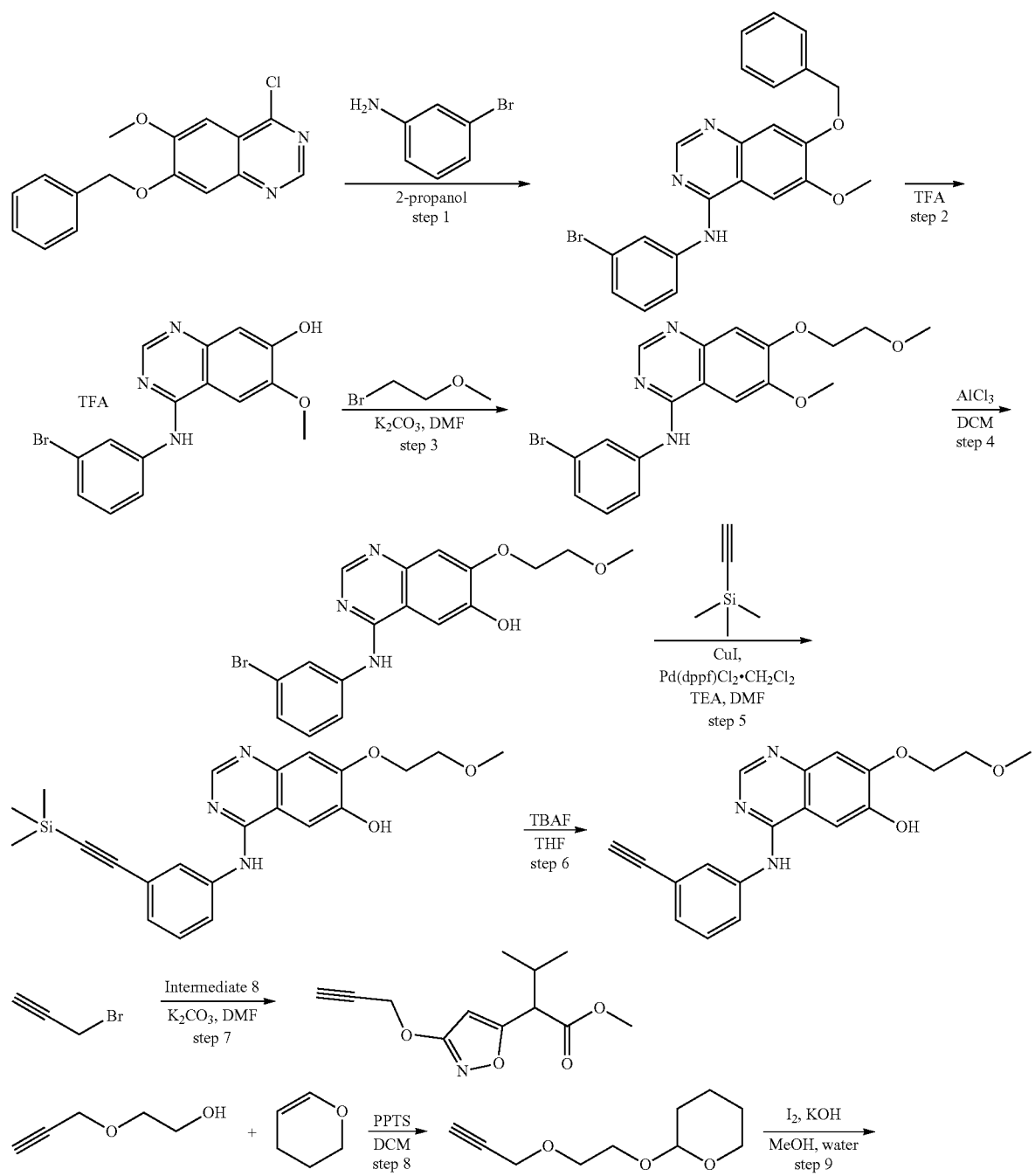

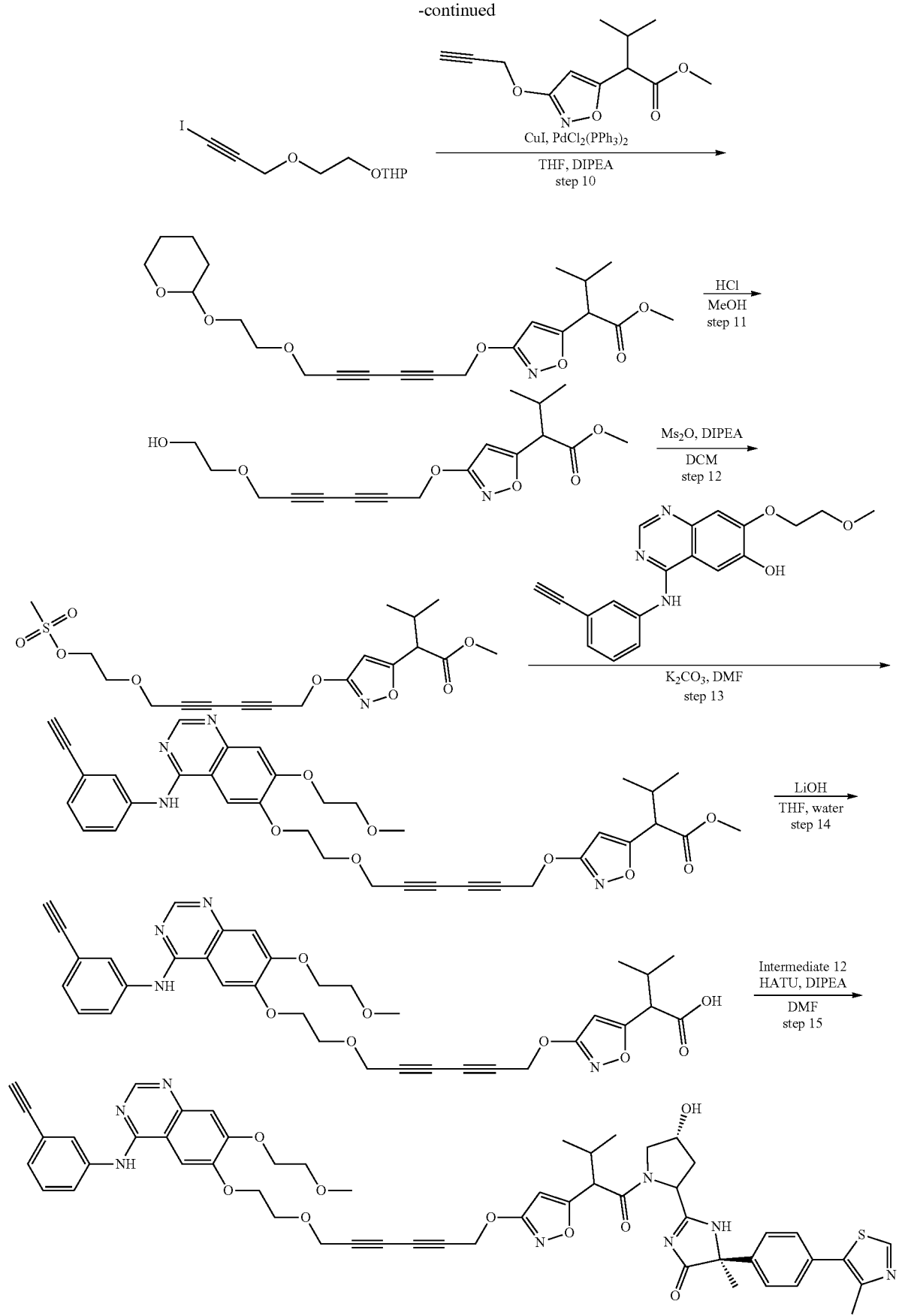

Step 1: 7-(Benzyloxy)-N-(3-bromophenyl)-6-methoxyquinazolin-4-amine

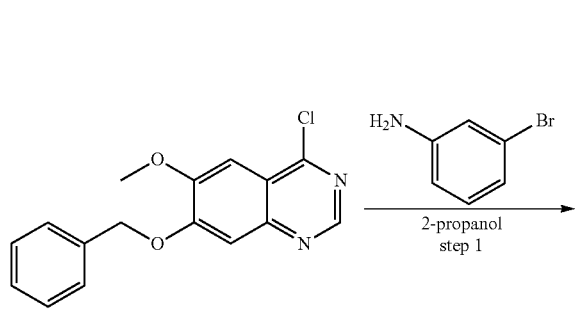

A solution of 7-benzyloxy-4-chloro-6-methoxy-quinazoline (8.50 g, 28.2 mmol) and 3-bromoaniline (9.72 g, 56.5 mmol) in 2-propanol (100 mL) was stirred at 80° C. for 1 hour. After filtration, the solids were collected and washed by 2-propanol to afford 11.4 g (crude) of the title compound as a white solid. The crude was used for next step without further purification. (ESI): [M+H]⁺=436.

Step 2: 4-((3-Bromophenyl) amino)-6-methoxyquinazolin-7-ol (TFA Salt)

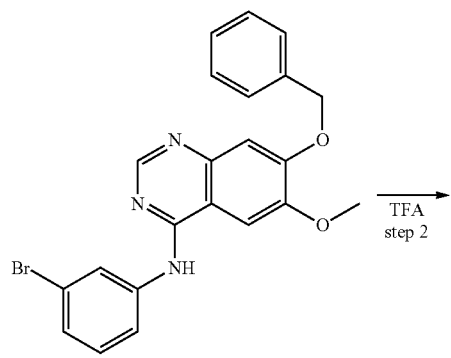

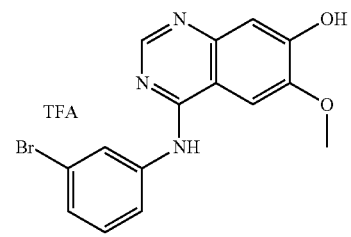

A solution of 7-benzyloxy-N-(3-bromophenyl)-6-methoxy-quinazolin-4-amine (11.4 g, 26.1 mmol) in TFA (100 mL) was refluxed for 2 hours. The solvent was concentrated under vacuum to afford 14.1 g (crude) of the title compound as a yellow solid. The crude was used for next step without further purification. LCMS (ESI): [M+H]⁺=346.

Step 3: N-(3-Bromophenyl)-6-methoxy-7-(2-methoxyethoxy) quinazolin-4-amine

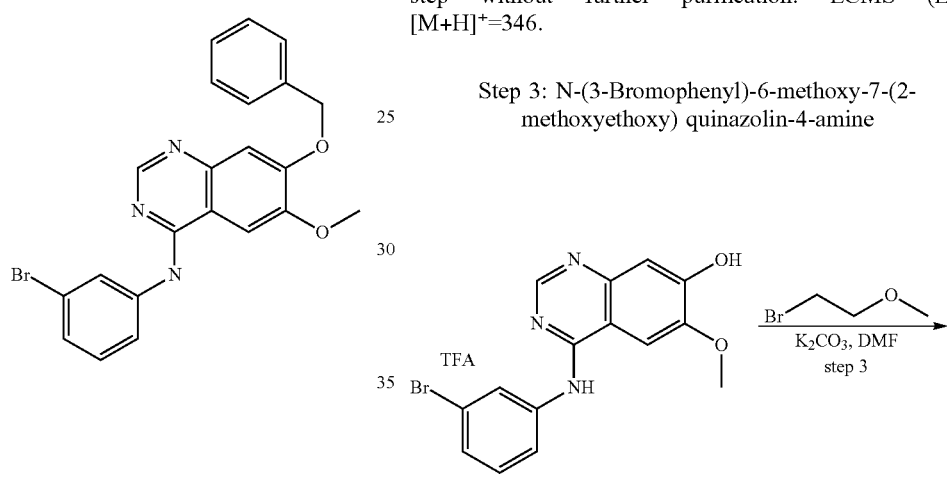

A solution of 4-(3-bromoanilino)-6-methoxy-quinazolin-7-ol (TFA salt, 14.1 g, 26.1 mmol), 1-bromo-2-methoxyethane (4.3 g, 31.3 mmol) and K₂CO₃ (12.8 g, 91.2 mmol) in DMF (150 mL) was stirred at 60° C. for 10 hours. The solution was diluted with water and extracted with ethyl acetate. The combined organic layers were dried over anhydrous Na₂SO₄ and concentrated under vacuum. The residue was purified by flash chromatography on silica gel eluting with MeOH/DCM (0-7%) to afford 7.93 g (75% yield) of the title compound as a yellow solid. LCMS (ESI): [M+H]⁺=404.

Step 4: 4-((3-Bromophenyl) amino)-7-(2-methoxyethoxy) quinazolin-6-ol

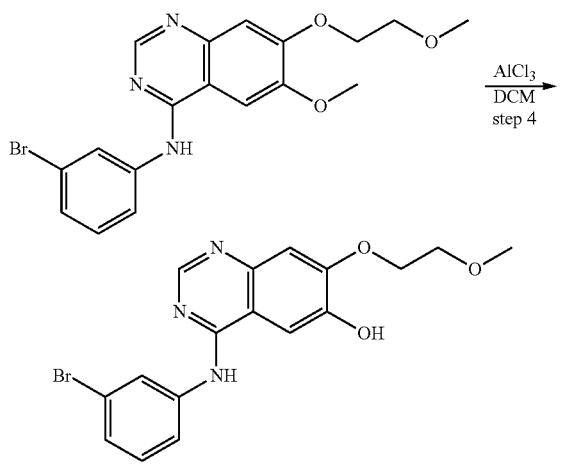

Under nitrogen, a solution of N-(3-bromophenyl)-6-methoxy-7-(2-methoxyethoxy) quinazolin-4-amine (6.93 g, 17.1 mmol) and AlCl₃ (114 g, 85.7 mmol) in DCM (70 mL) was stirred at 40° C. for overnight. The solvent was concentrated under vacuum. The residue was purified by flash chromatography on silica gel eluting with MeOH/DCM (0-10%) to afford 16.7 g (25%) of the title compound as a brown solid. LCMS (ESI): [M+H]⁺=390.

Step 5: 7-(2-Methoxyethoxy)-4-((3-((trimethylsilyl) ethynyl) phenyl) amino) quinazolin-6-ol

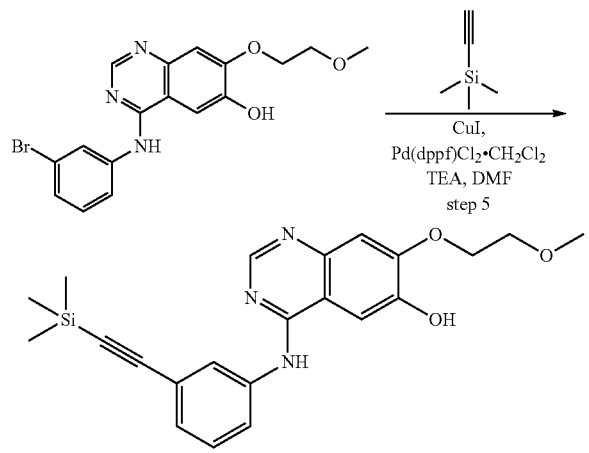

Under nitrogen, a solution of 4-((3-bromophenyl)amino)-7-(2-methoxyethoxy)quinazolin-6-ol (1.67 g, 4.28 mmol), ethynyltrimethylsilane (4.20 g, 42.8 mmol), CuI (406.6 mg, 2.14 mmol), Pd(dppf)Cl₂·CH₂Cl₂ (1.50 g, 2.14 mmol) in TEA (5 mL) and DMF (12 mL) was stirred at 100° C. for 5 hours. The resulting solution was diluted with water and extracted with ethyl acetate. The combined organic layers were dried over anhydrous Na₂SO₄ and concentrated under vacuum. The residue was purified by flash chromatography on silica gel eluting with ethyl acetate/petroleum ether (0-100%) to afford 1.23 g (70% yield) of the title compound as a brown solid. LCMS (ESI): [M+H]⁺=408.

Step 6: 4-((3-Ethynylphenyl) amino)-7-(2-methoxyethoxy) quinazolin-6-ol

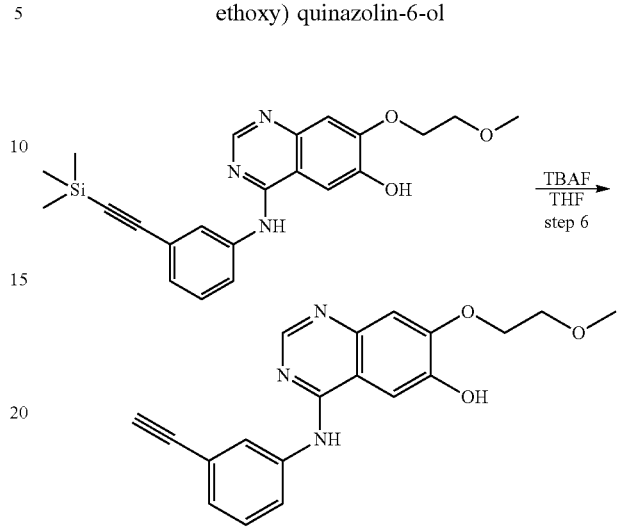

A solution of 7-(2-methoxyethoxy)-4-((3-((trimethylsilyl) ethynyl) phenyl) amino)quinazolin-6-ol (1.23 g, 3.02 mmol) and TBAF (6 mL, 1 M in THF) in THF (10 mL) was stirred at room temperature for 20 minutes. The solvent was concentrated under vacuum. The residue was purified by flash chromatography on silica gel eluting with ethyl acetate/petroleum ether (0-100%) to afford 560 mg (55% yield) of the title compound as a light yellow solid. LCMS (ESI): [M+H]⁺=336. ¹H NMR (300 MHz, DMSO-d6) δ 9.65 (s, 1H), 9.43 (s, 1H), 8.47 (s, 1H), 8.08 (t, J=1.9 Hz, 1H), 7.92-7.85 (m, 1H), 7.80 (s, 1H), 7.37 (t, J=7.9 Hz, 1H), 7.20 (s, 1H), 7.18-7.12 (m, 1H), 4.36-4.26 (m, 2H), 4.19 (s, 1H), 3.83-3.73 (m, 2H), 3.35 (s, 3H).

Step 7: Methyl 3-methyl-2-(3-(prop-2-yn-1-yloxy) isoxazol-5-yl) butanoate

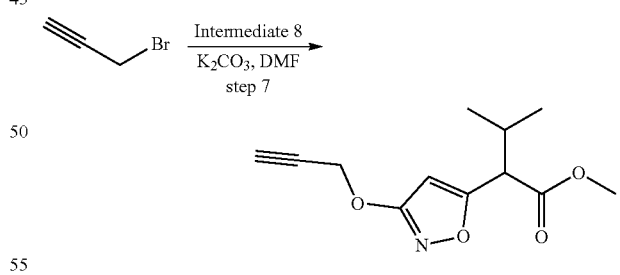

A solution of methyl 2-(3-hydroxyisoxazol-5-yl)-3-methylbutanoate (Intermediate 8, 500 mg, 2.51 mmol), 3-bromoprop-1-yne (328 mg, 2.76 mmol) and K₂CO₃ (693 mg, 5.02 mmol) in DMF (5 mL) was stirred at room temperature for 2 hours. The reaction was diluted with ethyl acetate, washed with water. The organic layers were dried over anhydrous Na₂SO₄ and evaporated under vacuum. The crude was purified by flash chromatography on silica gel eluting with ethyl acetate/petroleum ether (0%-30%) to yield 370 mg (62% yield) of the title compound as a colorless oil. LCMS (ESI): [M+H]⁺=238.

Step 8: 2-(2-(Prop-2-yn-1-yloxy) ethoxy) tetrahydro-2H-pyran

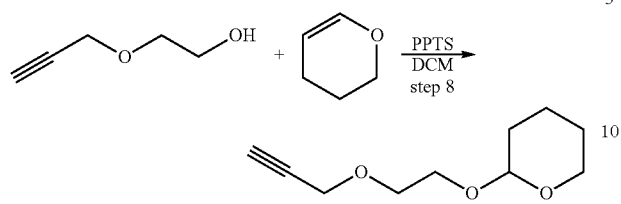

A solution of 2-(prop-2-yn-1-yloxy) ethan-1-ol (2.20 g, 21.9 mmol), 3,4-dihydro-2H-pyran (2.70 g, 32.9 mmol) and PPTS (1.10 g, 4.39 mmol) in DCM (30 mL) was stirred at room temperature overnight. Solvent was evaporated under vacuum and the crude was purified by flash chromatography on silica gel eluting with ethyl acetate/petroleum ether (0%-50%) to yield 1.80 g (44% yield) of the title compound as a colorless oil. H NMR (300 MHz, DMSO-$d_6$) δ 4.60-4.51 (m, 1H), 4.14 (d, J=2.4 Hz, 2H), 3.78-3.65 (m, 2H), 3.60-3.35 (m, 5H), 1.73-1.58 (m, 2H), 1.50-1.40 (m, 4H).

Step 9: 2-(2-((3-Iodoprop-2-yn-1-yl) oxy) ethoxy) tetrahydro-2H-pyran

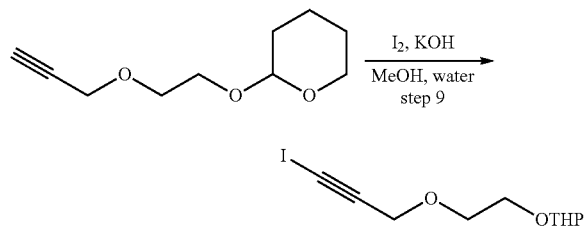

To a solution of 2-(2-prop-2-ynoxyethoxy) tetrahydropyran (2.00 g, 10.8 mmol) and KOH (1.50 g, 27.1 mmol) in MeOH (20 mL) and water (4 mL) was added iodine (3.00 g, 11.9 mmol) at 0° C. The mixture was stirred at room temperature for 2 hours. The resulting solution was diluted with ethyl acetate, washed with aqueous $Na_2S_2O_3$ and water. The combined organic layers were dried over anhydrous $Na_2SO_4$ and evaporated under vacuum. The crude was purified by flash chromatography on silica gel eluting with ethyl acetate/petroleum ether (0%-50%) to yield 2.00 g (59% yield) of the title compound as a colorless oil. LCMS (ESI): [M+Na]$^+$=333.

Step 10: Methyl 3-methyl-2-(3-((6-(2-((tetrahydro-2H-pyran-2-yl) oxy) ethoxy) hexa-2,4-diyn-1-yl) oxy)isoxazol-5-yl)butanoate

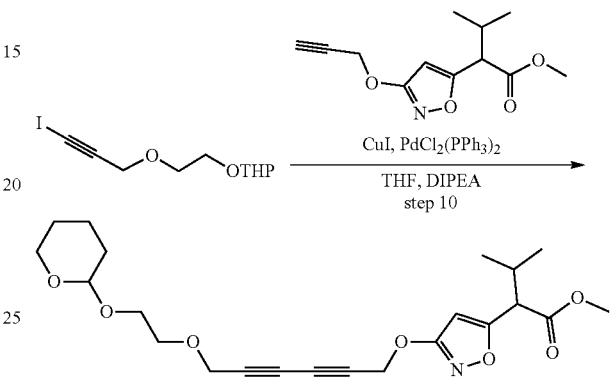

To a mixture of methyl 3-methyl-2-(3-prop-2-ynoxy-isoxazol-5-yl)butanoate (370 mg, 1.56 mmol), 2-(2-((3-Iodoprop-2-yn-1-yl)oxy)ethoxy)tetrahydro-2H-pyran (967 mg, 3.12 mmol), CuI (59.2 mg, 0.310 mmol) and $PdCl_2(PPh_3)_2$ (109 mg, 0.160 mmol) in THF (5 mL) was added DIPEA (805 mg, 6.24 mmol) at 0° C. The solution was stirred at room temperature overnight. The reaction was diluted with ethyl acetate and washed with water. The combined organic layers were dried over anhydrous $Na_2SO_4$ and evaporated under vacuum. The crude was purified by flash chromatography on silica gel eluting with ethyl acetate/petroleum ether (0%-50%) to yield 310 mg (47% yield) of the title compound as a yellow oil. LCMS (ESI): [M+H]$^+$=420.

Step 11: Methyl 2-(3-((6-(2-hydroxyethoxy) hexa-2,4-diyn-1-yl) oxy) isoxazol-5-yl)-3-methylbutanoate

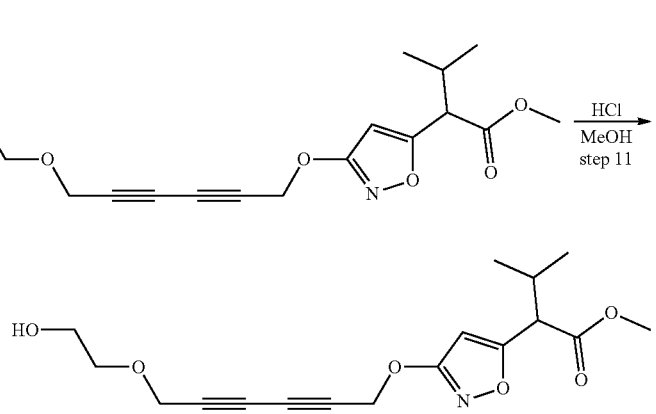

A solution of methyl 3-methyl-2-(3-((6-(2-((tetrahydro-2H-pyran-2-yl) oxy) ethoxy) hexa-2,4-diyn-1-yl)oxy) isoxazol-5-yl)butanoate (310 mg, 0.740 mmol) and HCl (0.2 mL, 1M aqueous) in MeOH (4 mL) was stirred at 50° C. for 2 hours. Solvent was evaporated under reduced pressure and the crude was purified by flash chromatography on silica gel eluting with ethyl acetate/petroleum ether (0%-80%) to yield 107 mg (43% yield) of the title compound as a colorless oil. LCMS (ESI): [M+H]$^+$=336.

Step 12: Methyl 3-methyl-2-(3-((6-(2-((methylsulfonyl)oxy) ethoxy) hexa-2,4-diyn-1-yl) oxy)isoxazol-5-yl)butanoate

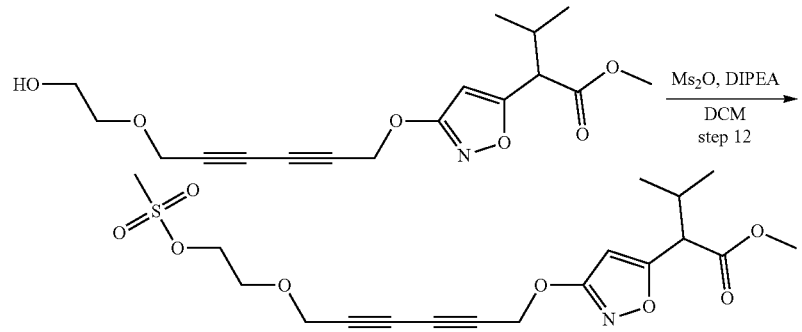

A solution of methyl 2-(3-((6-(2-hydroxyethoxy) hexa-2,4-diyn-1-yl) oxy) isoxazol-5-yl)-3-methylbutanoate (107 mg, 0.320 mmol), Ms$_2$O (111 mg, 0.640 mmol) and DIPEA (165 mg, 1.28 mmol) in DCM (4 mL) was stirred at room temperature for 1 hour. The reaction was diluted with DCM, washed with water. The combined organic layers were dried over anhydrous Na$_2$SO$_4$ and evaporated under vacuum to yield 145 mg (crude) of the title compound as a yellow oil. The crude product was used for next step without further purification. LCMS (ESI): [M+H]$^+$=414.

Step 13: Methyl 2-(3-((6-(2-((4-((3-ethynylphenyl)amino)-7-(2-methoxyethoxy) quinazolin-6-yl)oxy) ethoxy) hexa-2,4-diyn-1-yl)oxy)isoxazol-5-yl)-3-methylbutanoate

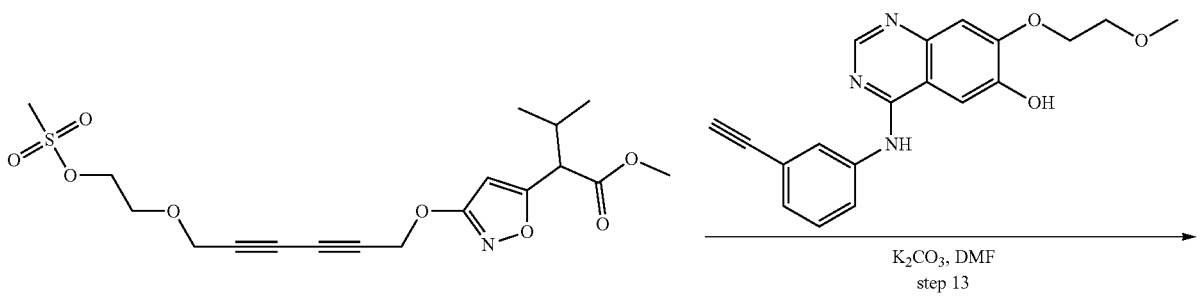

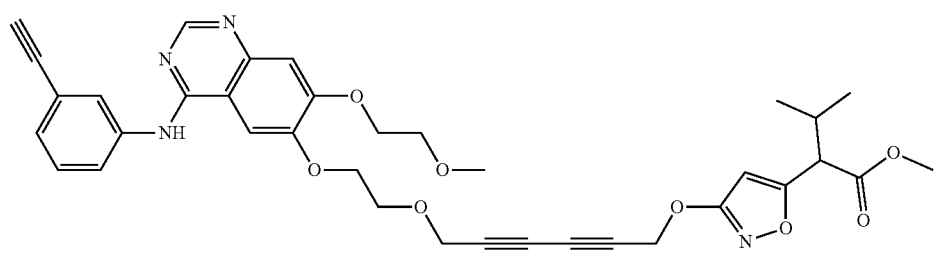

Under nitrogen, a solution of methyl 3-methyl-2-(3-((6-(2-((methylsulfonyl)oxy)ethoxy)hexa-2,4-diyn-1-yl)oxy)isoxazol-5-yl) butanoate (145 mg, 0.350 mmol), 4-((3-ethynylphenyl)amino)-7-(2-methoxyethoxy)quinazolin-6-ol (118 mg, 0.350 mmol) and K$_2$CO$_3$ (96.8 mg, 0.700 mmol) in DMF (2 mL) was stirred at 50° C. overnight. Solids were filtered out and the crude was purified by reverse phase flash chromatography (gradient: 5%-100% CH$_3$CN/H$_2$O (0.05% NH$_4$HCO$_3$)) to yield 150 mg (65% yield) of the title compound as a yellow oil. LCMS (ESI): [M+H]$^+$=653.

Step 14: 2-(3-((6-(2-((4-((3-Ethynylphenyl) amino)-7-(2-methoxyethoxy) quinazolin-6-yl)oxy)ethoxy) hexa-2,4-diyn-1-yl)oxy)isoxazol-5-yl)-3-methylbutanoic acid

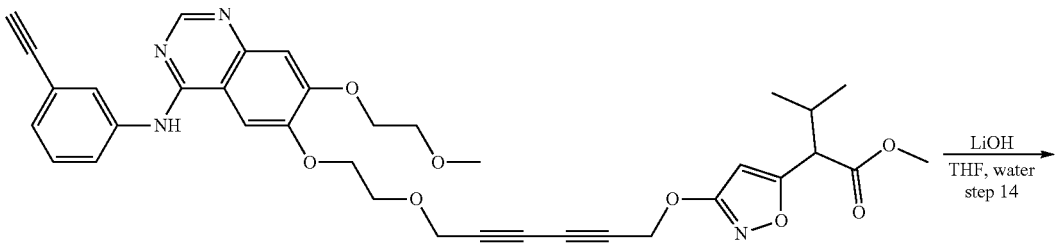

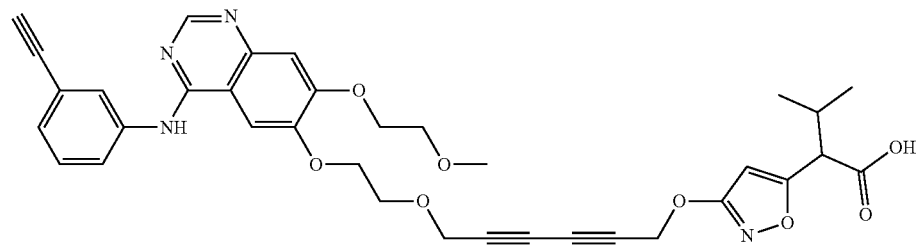

A solution of methyl 2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoate (150 mg, 0.230 mmol) and LiOH (11.0 mg, 0.460 mmol) in THF (2 mL) and water (2 mL) was stirred at room temperature for 2 hours. The solvent was evaporated to yield 160 mg (crude) of the title compound as a yellow oil. The crude product was used for next step without further purification. LCMS (ESI): [M+H]$^+$=639.

Step 15: (5S)-2-((4R)-1-(2-(3-((6-(2-((4-((3-Ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one (4 Single Stereoisomers)

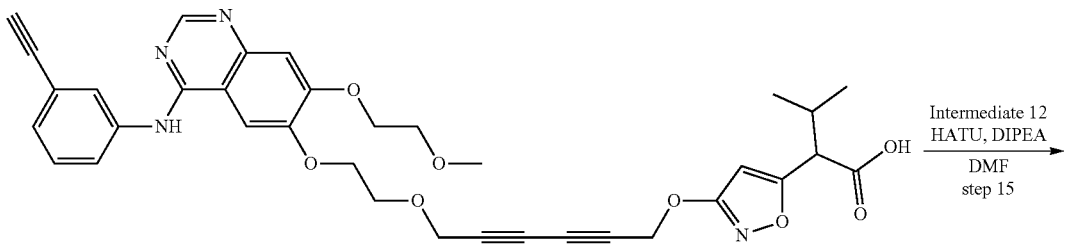

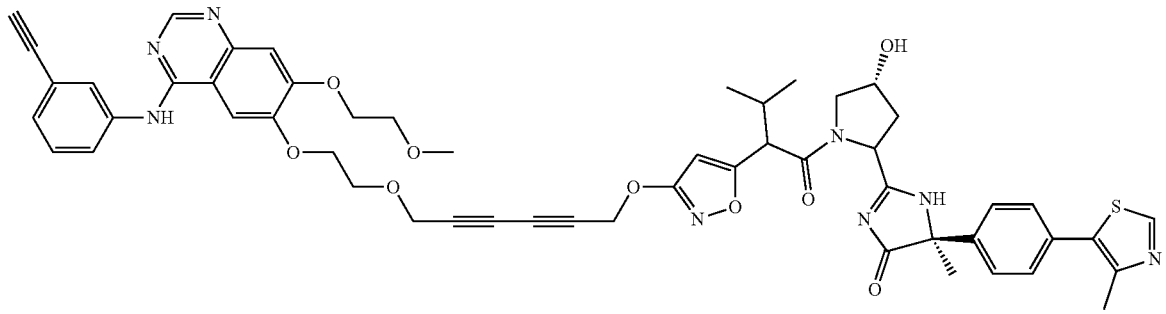

A solution of 2-(3-((6-(2-((4-((3-Ethynylphenyl)amino)-7-(2-methoxyethoxy)quinazolin-6-yl)oxy)ethoxy)hexa-2,4-diyn-1-yl)oxy)isoxazol-5-yl)-3-methylbutanoic acid (150 mg, 0.230 mmol), (5S)-2-((4R)-4-hydroxypyrrolidin-2-yl)-5-methyl-5-(4-(4-methylthiazol-5-yl)phenyl)-1,5-dihydro-4H-imidazol-4-one hydrochloride (Intermediate 12, 102 mg, 0.260 mmol), HATU (89.3 mg, 0.23 mmol) and DIPEA (121 mg, 0.940 mmol) in DMF (2 mL) was stirred at room temperature for 1 hour. The reaction was diluted with ethyl acetate, washed with water. The organic layers were dried over anhydrous $Na_2SO_4$ and evaporated under vacuum. The crude was purified by flash chromatography on silica gel eluting with MeOH/DCM (0%-5%) to yield 60 mg the mixture of Example 1004.1 and Example 1004.2 (the first peak) and 90 mg of the mixture of Example 1004.3 and Example 1004.4 (the second peak). The first peak was separated by chiral HPLC(Column: CHIRAL ART Cellulose-SB S-5 um, 2*25 cm, 5 um; Mobile Phase A: MTBE, Mobile Phase B: MeOH; Flow rate: 20 mL/min; Gradient: 15% B to 15% B in 12 min; 254/220 nm; RT1: 7.372; RT2: 8.9) to yield Example 1004.1 (the faster peak, 38.6 mg, 17% yield) and Example 1004.2 (the slower peak, 12.1 mg, 5.3% yield) as white solids. The second peak was separated by chiral HPLC(Column: CHIRAL ART Cellulose-SB, 2*25 cm, 5 um; Mobile Phase A: MTBE, Mobile Phase B: MeOH; Flow rate: 20 mL/min; Gradient: 20% B to 20% B in 15 min; 254/220 nm; RT1: 8.601; RT2: 13.015) to yield Example 1004.3 (the faster peak, 23.1 mg, 10% yield) and Example 1004.4 (the slower peak, 6.1 mg, 2.7% yield) as white solids.

Example 1004.1: LCMS (ESI): $R_T$ (min)=2.46, [M+H]$^+$=977, method=Y. $^1$H NMR (300 MHz, DMSO-$d_6$) δ 10.94 (s, 1H), 9.49 (s, 1H), 9.00 (s, 1H), 8.52 (s, 1H), 8.01 (t, J=1.8 Hz, 1H), 7.96-7.85 (m, 2H), 7.60-7.32 (m, 5H), 7.28-7.17 (m, 2H), 6.21 (s, 1H), 5.33 (s, 1H), 4.99 (s, 2H), 4.71 (br, 1H), 4.55-4.40 (m, 3H), 4.38-4.24 (m, 4H), 4.21 (s, 1H), 3.96-3.83 (m, 3H), 3.80-3.67 (m, 4H), 3.53-3.38 (m, 2H), 3.30-3.25 (m, 1H), 2.47 (s, 3H), 2.33-2.13 (m, 2H), 2.12-1.97 (m, 1H), 1.50 (s, 3H), 1.02-0.70 (m, 6H).

Example 1004.2: LCMS (ESI): $R_T$ (min)=2.67, [M+H]$^+$=977, method=Y. $^1$H NMR (300 MHz, DMSO-$d_6$) δ 11.00 (s, 1H), 9.53 (s, 1H), 9.01 (s, 1H), 8.49 (s, 1H), 8.02 (t, J=1.8 Hz, 1H), 7.92-7.83 (m, 2H), 7.60-7.36 (m, 5H), 7.28-7.17 (m, 2H), 6.24 (s, 1H), 5.05 (s, 2H), 4.67 (br, 1H), 4.49 (s, 2H), 4.44-4.38 (m, 1H), 4.37-4.21 (m, 4H), 4.21 (s, 1H), 3.96-3.83 (m, 3H), 3.82-3.71 (m, 3H), 3.55-3.40 (m, 2H), 3.33-3.25 (m, 2H), 2.47 (s, 3H), 2.40-2.27 (m, 1H), 2.27-2.15 (m, 1H), 2.15-1.97 (m, 1H), 1.65-1.40 (m, 3H), 1.06-0.77 (m, 6H). (—OH didn't come out).

Example 1004.3: LCMS (ESI): $R_T$ (min)=2.75, [M+H]$^+$=977, method=Y. $^1$H NMR (300 MHz, DMSO-$d_6$) δ 10.86 (s, 1H), 9.53-9.45 (m, 1H), 8.99 (d, J=4.2 Hz, 1H), 8.52 (s, 1H), 8.01 (d, J=1.9 Hz, 1H), 7.96-7.84 (m, 2H), 7.70-7.36 (m, 5H), 7.28-7.18 (m, 2H), 6.25 (6.16) (s, 1H), 5.08 (5.00) (s, 2H), 4.85-4.72 (m, 1H), 4.49 (d, J=12.3 Hz, 2H), 4.40-4.23 (m, 5H), 4.19 (s, 1H), 4.01-3.62 (m, 6H), 3.53-3.36 (m, 3H), 3.32-3.22 (m, 1H), 2.45 (s, 3H), 2.33-2.14 (m, 2H), 2.04-1.90 (m, 1H), 1.70-1.40 (m, 3H), 0.98-0.53 (m, 6H). (—OH didn't come out).

Example 1004.4: LCMS (ESI): $R_T$ (min)=2.85, [M+H]$^+$=977, method=Y. $^1$H NMR (300 MHz, DMSO-$d_6$) δ 10.91 (s, 1H), 9.50 (s, 1H), 8.98 (s, 1H), 8.52 (s, 1H), 8.01 (t, J=1.9 Hz, 1H), 7.97-7.84 (m, 2H), 7.62-7.31 (m, 5H), 7.28-7.17 (m, 2H), 6.26 (s, 1H), 5.20-4.93 (m, 2H), 4.70 (s, 1H), 4.49 (s, 2H), 4.41-4.23 (m, 5H), 4.21 (s, 1H), 3.97-3.88 (m, 2H), 3.88-3.71 (m, 5H), 3.50-3.40 (m, 1H), 3.33-3.20 (m, 2H), 2.50-2.39 (m, 4H), 2.39-2.22 (m, 1 H), 2.17-1.90 (m, 1H), 1.64-1.37 (m, 3H), 1.00-0.90 (m, 3H), 0.90-0.73 (m, 3H). (—OH didn't come out).

Examples 1005.1 and 1005.2
4-(3,5-difluoropyridin-2-yl)-N-(11-(((2S)-1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide (2 Single Diastereomers)
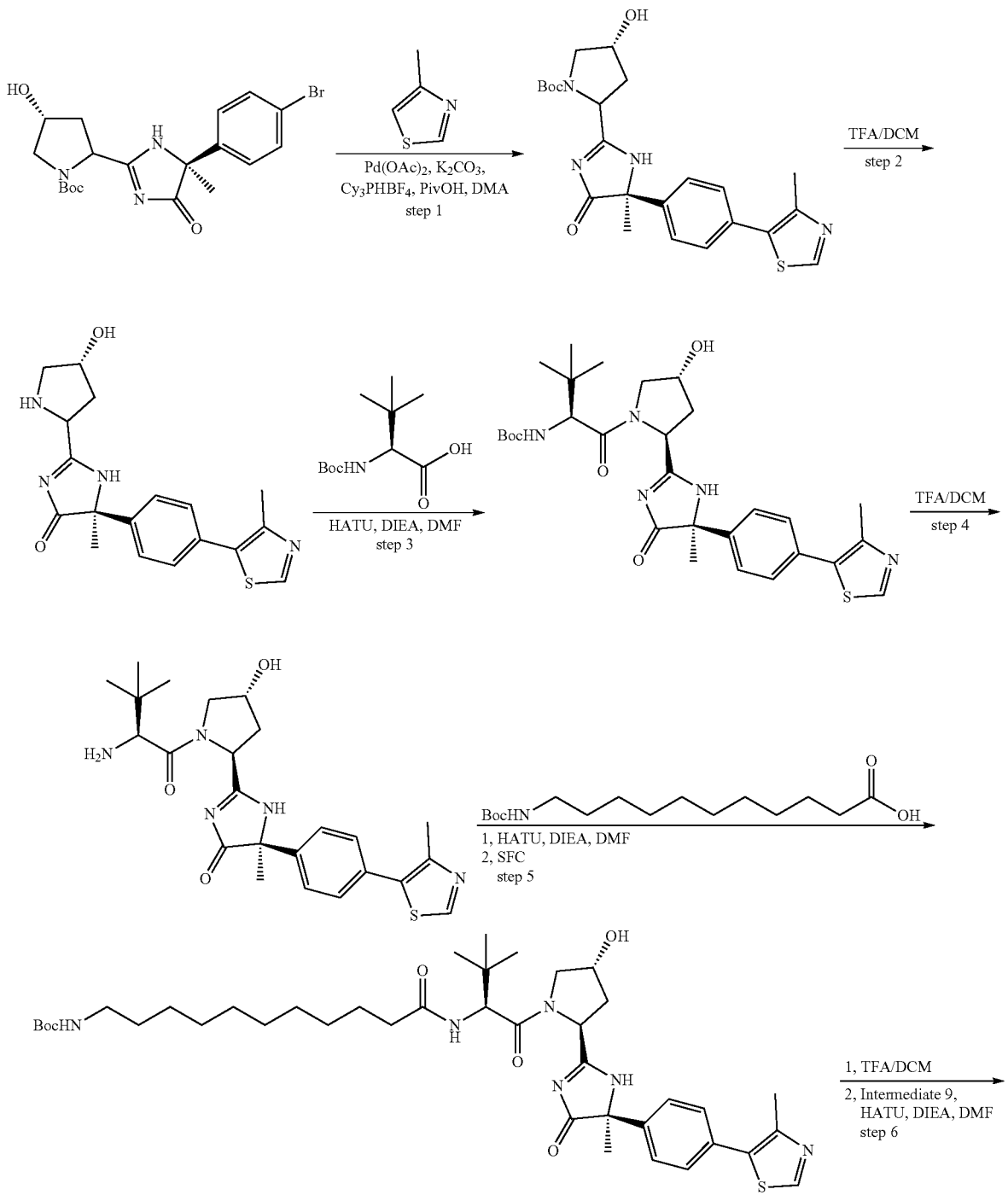
A1 and B1

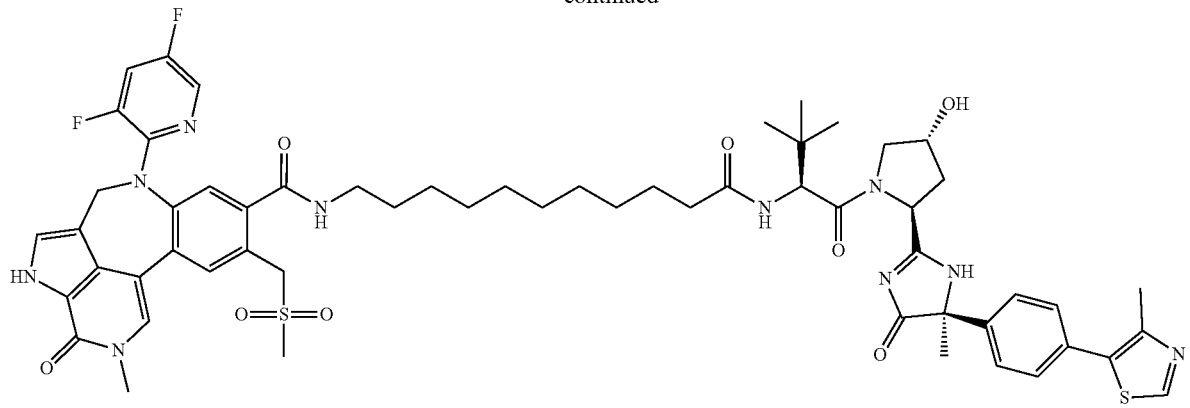

Examples 1005.1 and 1005.2

Step 1: tert-butyl (4R)-4-hydroxy-2-((S)-5-methyl-5-(4-(4-methylthiazol-5-yl)phenyl)-4-oxo-4,5-dihydro-1H-imidazol-2-yl)pyrrolidine-1-carboxylate Step 2: (5S)-2-((4R)-4-hydroxypyrrolidin-2-yl)-5-methyl-5-(4-(4-methylthiazol-5-yl)phenyl)-1,5-dihydro-4H-imidazol-4-one

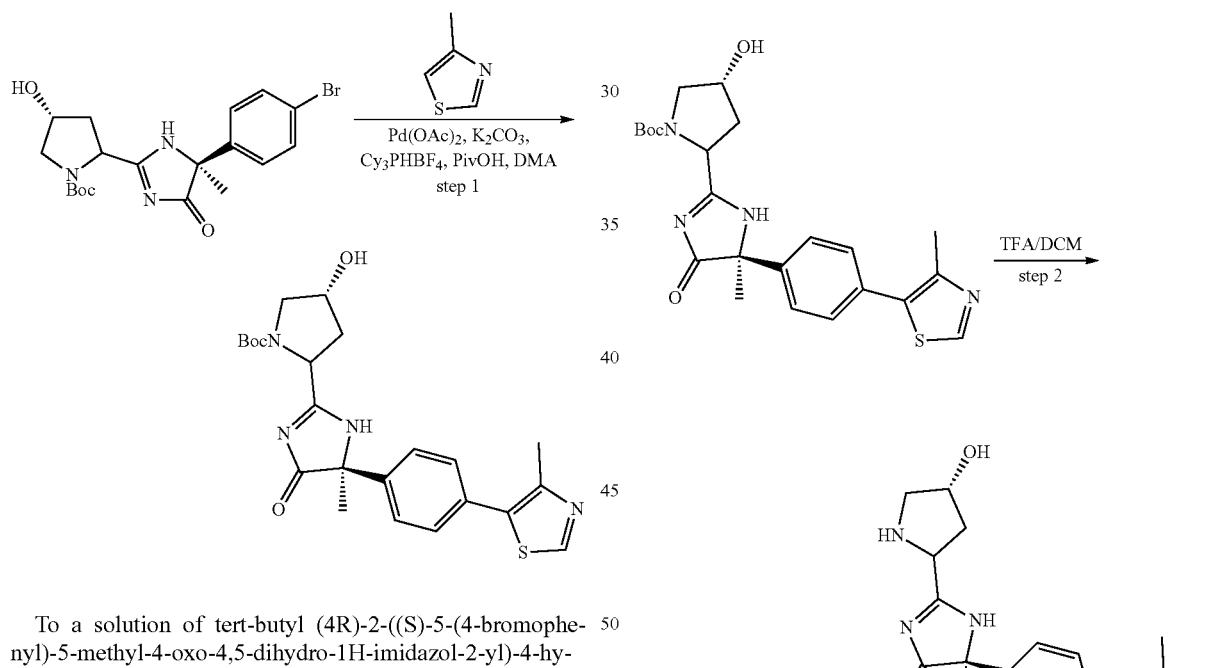

To a solution of tert-butyl (4R)-2-((S)-5-(4-bromophenyl)-5-methyl-4-oxo-4,5-dihydro-1H-imidazol-2-yl)-4-hydroxypyrrolidine-1-carboxylate (300.0 mg, 0.680 mmol) in DMF (10.0 mL) was added Pd(OAc)$_2$ (15.37 mg, 0.0700 mmol), 4-methylthiazole (678.61 mg, 6.84 mmol), K$_2$CO$_3$ (141.9 mg, 1.03 mmol), Cy$_3$PHBF$_4$ (25.2 mg, 0.0700 mmol) and pivalic acid (20.97 mg, 0.210 mmol). The mixture was stirred at 100° C. for 16 hours. The mixture was concentrated under reduced pressure and 20 mL of water was added. The resulting mixture was extracted with EtOAc (30 mL×3). The organic layer was washed with brine (10 mL), dried over anhydrous Na$_2$SO$_4$, concentrated, and purified by prep-TLC (10% MeOH in DCM) to give tert-butyl (4R)-4-hydroxy-2-((S)-5-methyl-5-(4-(4-methylthiazol-5-yl)phenyl)-4-oxo-4,5-dihydro-1H-imidazol-2-yl)pyrrolidine-1-carboxylate (0.250 g, 80%) as a yellow solid. LCMS (Method FF): RT=0.709 min, m/z=457.1[M+1]$^+$.

A solution of tert-butyl (4R)-4-hydroxy-2-((S)-5-methyl-5-(4-(4-methylthiazol-5-yl)phenyl)-4-oxo-4,5-dihydro-1H-imidazol-2-yl)pyrrolidine-1-carboxylate (250.0 mg, 0.550 mmol) in a mixture of 20% TFA in DCM (5.0 mL) was stirred for 16 hours at 25° C. The mixture was concentrated to give the crude (5S)-2-((4R)-4-hydroxypyrrolidin-2-yl)-5-methyl-5-(4-(4-methylthiazol-5-yl)phenyl)-1,5-dihydro-4H-imidazol-4-one TFA salt (230 mg, 89%) as a colorless oil, which was used in the next step directly.

Step 3: tert-butyl ((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)carbamate Step 4: (S)-2-((2S,4R)-1-((S)-2-amino-3,3-dimethylbutanoyl)-4-hydroxypyrrolidin-2-yl)-5-methyl-5-(4-(4-methylthiazol-5-yl)phenyl)-1,5-dihydro-4H-imidazol-4-one

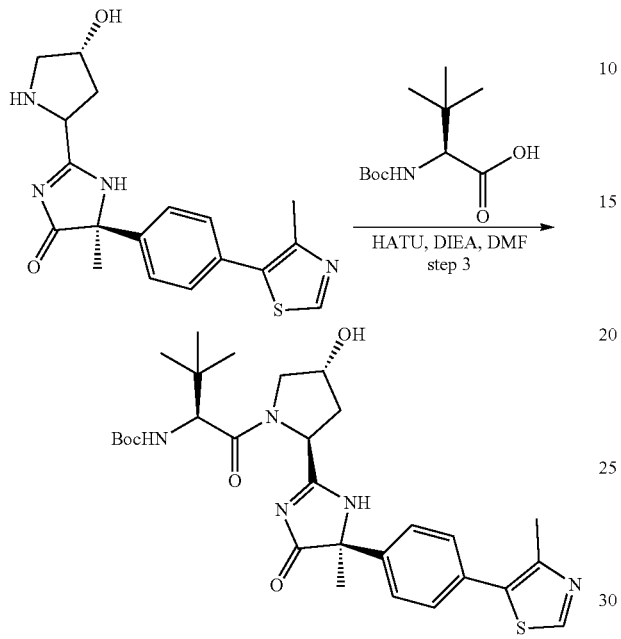

To a solution of (S)-2-((tert-butoxycarbonyl)amino)-3,3-dimethylbutanoic acid (216.3 mg, 0.940 mmol), HATU (355.6 mg, 0.940 mmol) and (5S)-2-((4R)-4-hydroxypyrrolidin-2-yl)-5-methyl-5-(4-(4-methylthiazol-5-yl)phenyl)-1,5-dihydro-4H-imidazol-4-one (220.0 mg, 0.470 mmol) in DMF (3.0 mL) was added DIEA (0.390 mL, 2.34 mmol). The mixture was stirred at 25° C. for 1 hour. The mixture was extracted with EtOAc (20 mL×3), washed with brine (10 mL×2). The organic layer was dried over $Na_2SO_4$, concentrated, and purified by flash chromatography on silica (0-5% MeOH in DCM) to give tert-butyl ((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)carbamate (250 mg, 94%) as a white solid. LCMS (Method FF): RT=0.673 min, m/z=570.3[M+1]$^+$.

To a solution of tert-butyl ((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)carbamate (250.0 mg, 0.4400 mmol) in DCM (4.0 mL) was added TFA (1.0 mL). The mixture was stirred at 25° C. for 2 hours. The mixture was concentrated to give (S)-2-((2S,4R)-1-((S)-2-amino-3,3-dimethylbutanoyl)-4-hydroxypyrrolidin-2-yl)-5-methyl-5-(4-(4-methylthiazol-5-yl)phenyl)-1,5-dihydro-4H-imidazol-4-one with TFA salt (200 mg, 78%) as colorless oil.

Step 5: tert-butyl (11-(((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)amino)-11-oxoundecyl)carbamate (2 Isomers, A1 and B1)

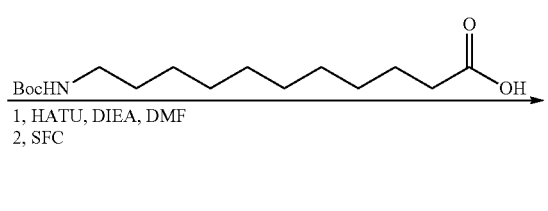

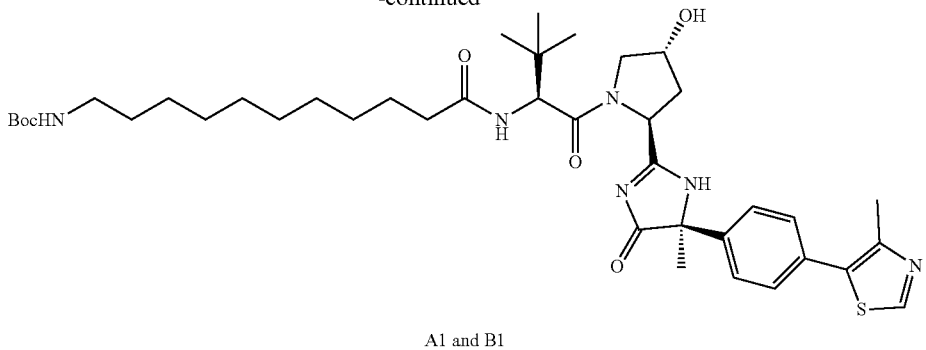

A1 and B1

To a solution of (S)-2-((2S,4R)-1-((S)-2-amino-3,3-dimethylbutanoyl)-4-hydroxypyrrolidin-2-yl)-5-methyl-5-(4-(4-methylthiazol-5-yl)phenyl)-1,5-dihydro-4H-imidazol-4-one (200.0 mg, 0.3400 mmol), HATU (260.6 mg, 0.6900 mmol) and 11-((tert-butoxycarbonyl)amino)undecanoic acid (206.59 mg, 0.6900 mmol) in DMF (4.0 mL) was added DIEA (0.28 mL, 1.71 mmol). The mixture was stirred at 25° C. for 1 hour. The mixture was concentrated, and purified by flash chromatography on silica (0-5% MeOH in DCM) to give a mixture of diastereomers which was separated by SFC to give compound A1 (90 mg) and B1 (15 mg) as colorless oils.

Compound A1: $^1$H NMR (400 MHz, CDCl$_3$) δ 8.69 (s, 1H), 7.63 (d, J=8.4 Hz, 2H), 7.42 (d, J=8.4 Hz, 2H), 6.24 (brs, 1H), 5.09-5.07 (m, 1H), 4.69-4.61 (m, 1H), 4.64-4.60 (m, 1H), 4.55 (br, 2H), 4.12 (d, J=11.6 Hz, 1H), 3.92-3.85 (m, 1H), 3.10-3.08 (m, 2H), 2.66-2.62 (m, 1H), 2.53 (s, 3H), 2.41-2.38 (m, 1H), 2.36-2.23 (m, 2H), 1.62-1.58 (m, 4H), 1.44 (s, 12H), 1.26 (s, 12H), 1.02 (s, 9H). LCMS (Method FF): RT=0.957 min, m/z=753.4 [M+1]$^+$. SFC: Method 6, RT=5.304 min.

Compound B1: SFC: Method 6, RT=6.702 min.

Step 6: 4-(3,5-difluoropyridin-2-yl)-N-(11-(((2S)-1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide (2 Single Diastereomers) (Examples 1005.1 and 1005.2)

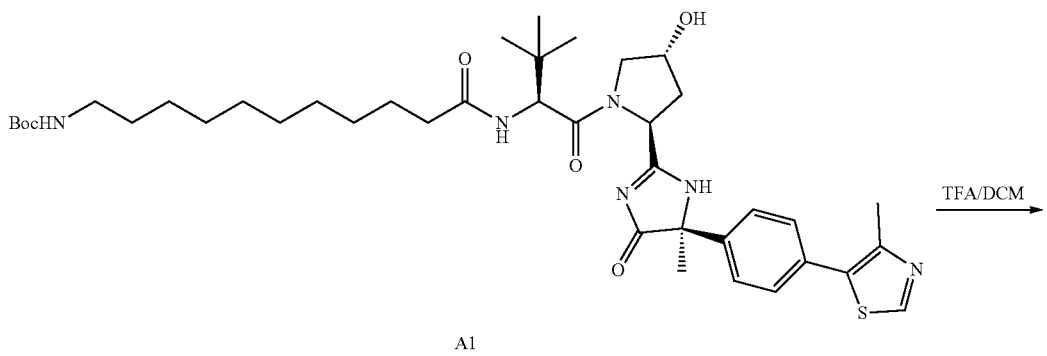

A1

TFA/DCM

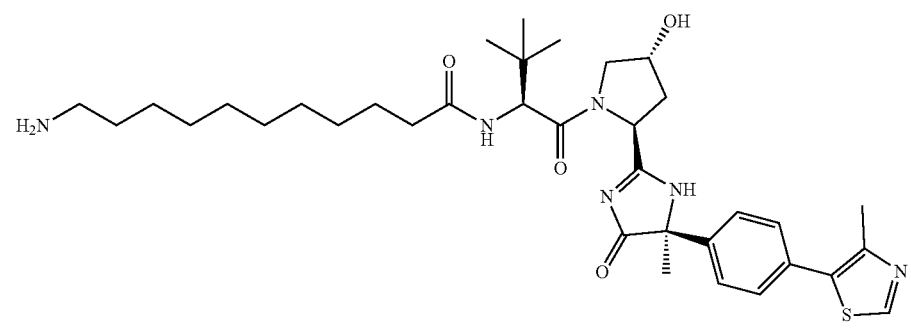

A2

TFA (1.0 mL) was added to a solution of compound A1 (80.0 mg, 0.1100 mmol) in DCM (4.0 mL) at 25° C., and the mixture was stirred at 25° C. for 1 hour. The mixture was concentrated to give compound A2 TFA salt (80.0 mg, 98%) as a colorless oil, which was directly used in next step.

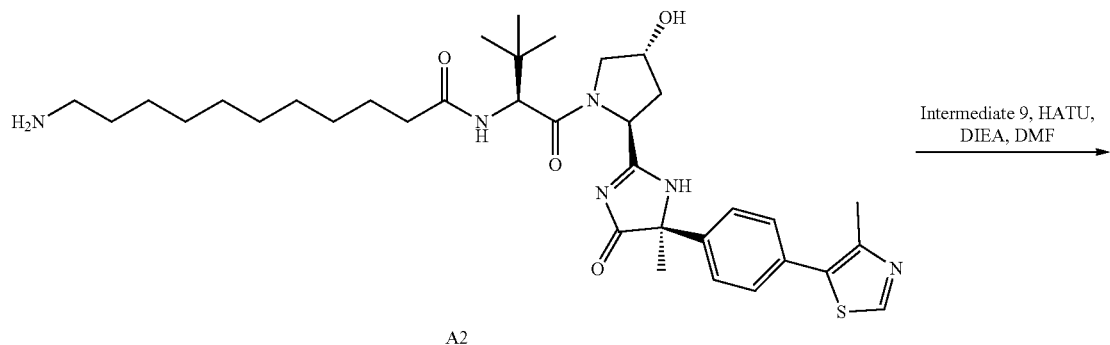

A2

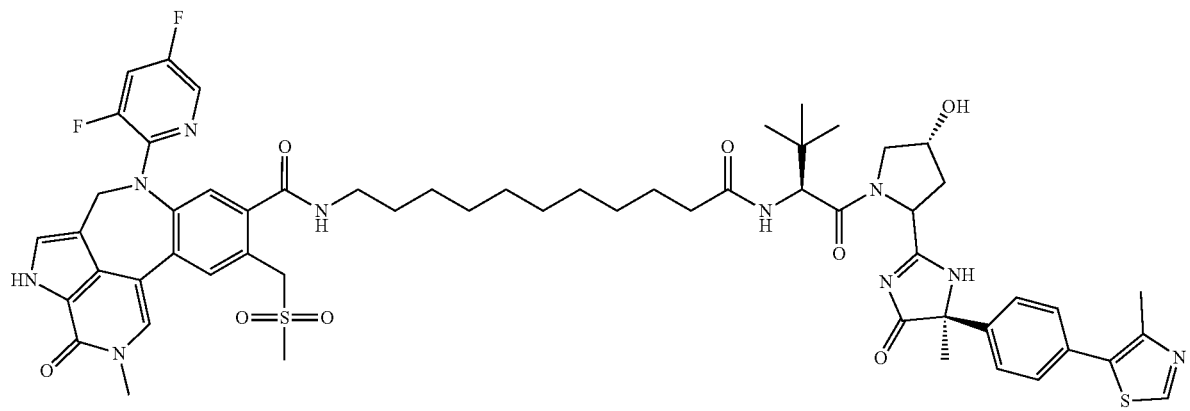

Examples 1005.1

A solution of compound A2 (76.35 mg, 0.1000 mmol), HATU (49.21 mg, 0.1300 mmol) and DIEA (64.33 mg, 0.500 mmol) in DMF (2.0 mL) was stirred 5 min, then Intermediate 9 (64.77 mg, 0.1300 mmol) was added. The mixture was stirred for 2 hours at 25° C. The mixture was concentrated, diluted with H$_2$O (20 mL) and extracted with EtOAc (30 mL×3). The combined organic layers were washed with brine (50 mL), dried over Na$_2$SO$_4$, concentrated, and purified by prep-TLC (10% MeOH in DCM) to give Example 1005.1 (23.3 mg, 21%) as a white solid.

Example 1005.1: $^1$H NMR (400 MHz, CD$_3$OD) δ 8.84 (s, 1H), 7.96 (s, 1H), 7.86 (d, J=2.4 Hz, 1H), 7.71 (s, 1H), 7.68-7.60 (m, 2H), 7.43 (d, J=8.0 Hz, 2H), 7.32 (s, 1H), 7.25-7.17 (m, 2H), 4.62-4.59 (m, 5H), 4.36-4.32 (m, 1H), 4.11-4.08 (m, 1H), 3.96-3.86 (m, 1H), 3.71 (s, 3H), 3.29-3.24 (m, 2H), 2.97 (s, 3H), 2.62-2.52 (m, 1H), 2.46 (s, 3H), 2.32-2.20 (m, 3H), 1.68 (s, 3H), 1.58-1.45 (m, 4H), 1.28-1.11 (m, 12H), 1.09 (s, 9H). LCMS (Method FF): RT=0.840 min, m/z=568.7 [M/2+1]$^+$. SFC: Method 5, RT=4.013 min, de=97.5%.

Example 1005.2 (1.3 mg, 7% over 2 steps) was prepared from compound B1 (15 mg) with procedure similar to Example 1005.1.

Example 1005.2: $^1$H NMR (400 MHz, CD$_3$OD) δ 8.87 (s, 1H), 7.95 (s, 1H), 7.89-7.85 (m, 2H), 7.71 (s, 1H), 7.57-7.55 (m, 2H), 7.48-7.36 (m, 2H), 7.33 (s, 1H), 7.25-7.21 (m, 2H), 4.66-4.63 (m, 1H), 4.58 (s, 5H), 4.57-4.53 (m, 1H), 4.01-3.95 (m, 1H), 3.94-3.85 (m, 1H), 3.73 (s, 3H), 3.31-3.26 (m, 2H), 2.97 (s, 3H), 2.46 (s, 3H), 2.41-2.23 (m, 4H), 1.70 (s, 3H), 1.63-1.53 (m, 4H), 1.36-1.28 (m, 12H), 1.01 (s, 9H). LCMS (Method FF): RT=0.848 min, m/z=568.6 [M/2+1]$^+$. SFC: Method 5, RT=4.20 min, de=81%.

Examples 1006.1 and 1006.2

4-(3,5-difluoropyridin-2-yl)-N-(11-((1-((2S,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide (2 Single Diastereomers)

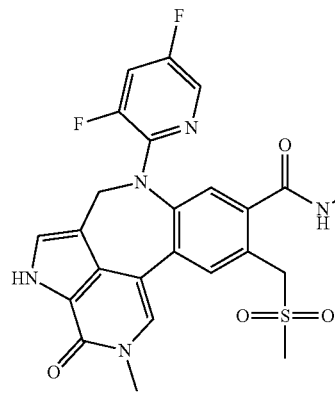
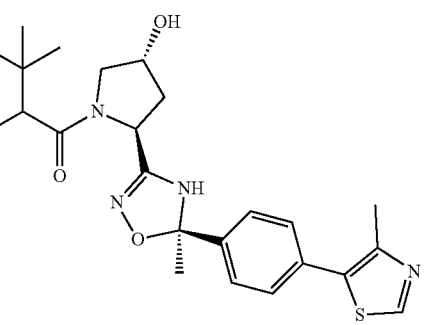

Examples 1006.1 and 1006.2 were synthesized from intermediates C4 and D4 (prepared in Examples 140.1 and 140.2), using procedures equivalent to those used to convert intermediates A1 and B1 to Examples 1005.1 and 1005.2.

Biological Assays

Example A: Fluorescence Polarization (FP) VHL Binding Assay

The binding of test compounds to the VHL Elongin B/C complex was measured using a fluorescence polarization tracer competition assay. The VHL/Elongin B/C protein complex used in the assay was generated as follows. The coding region for amino acids E55-D213 of human VHL with N-terminal His6 tag with a TEV-protease cleavage site was co-expressed with Elongin B (residues M1-Q118) and Elongin C (Residues M17-C112) in *E. coli*. The VHL/Elongin B/C complex was purified using an affinity nickel column, anion exchange HiTrap QP HP column chromatography, and gel filtration using a Superdex 75 26/60 column. The purified VHL/Elongin B/C complex was dialyzed into formulation buffer: 20 mM Bis-Tris pH7.0, 150 mM NaCl, 1 mM DTT. A VHL fluorescence polarization probe (prepared in Example 91), consisted of a VHL ligand coupled to carboxytetramethylrhodamine (TAMRA); (2S,4R)—N-(2-(2-(3',6'-bis(dimethylamino)-3-oxo-3H-spiro[isobenzofuran-1,9'-xanthene]-5-carboxamido)ethoxy)-4-(4-methylthiazol-5-yl)benzyl)-4-hydroxy-1-((R)-3-methyl-2-(3-methylisoxazol-5-yl)butanoyl)pyrrolidine-2-carboxamide. The Kd of the VHL fluorescence polarization probe binding to VHL/Elongin B/C was 18.2 nM. Compounds were prepared as a serial dilution in DMSO at a concentration 25-fold higher than the final desired concentration and acoustically dispensed (400 nl) into a ProxiPlate-384 Plus F, Black 384-shallow well Microplate (Part Number 6008260). DMSO was dispensed into wells designated for "VHL control" (without compound) wells. The "Assay Buffer" consisted of 50 mM Tris pH 8.0, 120 mM NaCl, 0.005% Nonidet P-40, and 1% DMSO (v/v). Assay Buffer containing 5.28 µM VHL Elongin B/C complex was prepared and 5 µl dispensed using a BioRapTR (Beckman Coulter) into each well of the assay plate. Assay Buffer was also dispensed into "no VHL control" wells using the same method. A "pre-assay" fluorescence measurement was made using an Infinite® M1000 (Tecan) plate reader (Excitation 530 nm, Emission 574 nm, Bandwidth 10 nm). Assay Buffer containing 3.34 nM of the VHL FP probe was prepared in Assay Buffer and 5 µl dispensed into each well of the assay plate using a BioRapTR (Beckman Coulter). The final VHL/Elongin B/C protein concentration is 2.64 nM and the final probe concentration is 1.67 nM. Assay plates were briefly centrifuged and incubated for 1 hour at room temperature. "Post-assay" fluorescence polarization measurements were made as described for the "pre-assay" fluorescence measurement. Fluorescence polarization was calculated for each sample; taking into account the "pre-assay" fluorescence measurements and subtracting the fluorescence signal of the compound/VHL only ("pre-assay") measurements from the "post-assay" fluorescence polarization measurements, for each plane of polarization. The data were analyzed using Genedata Screener software and normalized to the "no VHL control" and "VHL control" (without compound). $IC_{50}$ values were calculated using a four parameter curve fit (Robust method).

Example B: Surface Plasmon Resonance Assay

Using a Biacore T200, Avidin tagged VHL co-expressed with Elongins B and C were immobilized to a Biacore SA chip in running buffer without DMSO. Compounds were tested individually at varying concentrations in running buffer (50 mM HEPES pH 7.2, 150 mM NaCl, 0.5 mM TCEP, 0.001% Tween 20, 0.2% PEG3350, 2% DMSO) at 20° C. Sensorgrams were run in order from low to high concentration using a flow rate of 80 µL/min. Association and disassociation times were varied depending on the estimated potency of the compound tested. All sensor chips were monitored for loss of activity with the injection of a control compound (((2S,4R)-1-((S)-2-acetamido-3,3-dimethylbutanoyl)-4-hydroxy-N-(4-(4-methylthiazol-5-yl)benzyl) pyrrolidine-2-carboxamide, which is Compound 7 in C. Galdeano et al, *J. Med. Chem.* 2014, 57, 8657-8663, herein incorporated by reference) which retained greater than 75% of the activity over the course of the run. Analysis of the binding curves and determination of the kinetic parameters were done using evaluation software (Version 2.0, Biacore).

Example C: VHL HEK-293 BRET Assay

The VHL NanoBRET™ Target Engagement Assay analyzes the apparent affinity of test compounds for VHL in cells by competitive displacement of a VHL NanoBRET™ tracer reversibly bound to a NanoLuc® VHL fusion protein stably expressed in the cells.

Test compounds were transferred to the assay plate (384 Well White Non-Binding Corning Assay Plates (Corning-3574)) using an Echo 555 Liquid Handler (Labcyte) in 2.5 nL increments and, as appropriate, intermediate stock concentrations of compounds, in order to prepare a titration series. 50 nL of control compound (10 mM; parental unlabeled VHL antagonist; see structure below) and 50 nL of DMSO (negative control) were dispensed into the appropriate control wells. DMSO was backfilled to a final volume of 50 nL as required. 50 nl per well of 1 mM VHL NanoBRET™ Tracer in DMSO (NanoBRET™ Tracer-PEG2-590 (see structure below)) was transferred into each well using an Echo 555 (ultimately yielding a final concentration of 1 uM). HEK 293 RT VHL-NanoLuc® stable cells were cultured in DMEM High Glucose with Pyruvate, 10% fetal bovine serum, 2 mg/mL of Geneticin Selective Antibiotic (50 mg/ml) and 2 mM HEPES (1 M). Cells were seeded in Opti-MEM (Life Technologies-11058-021), 1.7×10$^5$ cells/mL, 40 µl per well into the assay plate, centrifuged at 500 rpm for 30 seconds and incubated for 2 hours. Max Signal control wells consisted of DMSO only treated wells. Minimum Signal control wells contained of 10 uM parental unlabeled VHL antagonist (control compound—see structure below). 3× Complete Substrate plus Inhibitor Solution was prepared in Opti-MEM (consists of a 1:166 dilution of NanoBRET™ Nano-Glo® Substrate plus a 1:500 dilution of Extracellular NanoLuc® Inhibitor in Opti-MEM), and 20 ul was dispensed into each well of the 384-well plate and centrifuged at 1000 rpm for 1 minute, then incubated for 2 minutes at room temperature. Background Signal control wells were prepared without tracer for background correction steps.

Plates were read using a PerkinElmer Envision Reader (model 2104-0020) equipped with Luminescence option (Mirror: BRET2 Enh (PE Barcode 659), Emission Filter: Omega 610LP (Barcode 504), 2nd Emission Filter: Umbelliferone 460 (Barcode 207), Measurement height: 6.5 mm, Measurement time: 1 s). The raw BRET ratio values were calculated by dividing the acceptor emission value (610 nm) by the donor emission value (460 nm) for each sample. To correct for background, the BRET ratio in the absence of tracer (average of no-tracer control samples) was subtracted from the BRET ratio of each sample. Raw BRET units were converted to milliBRET units (mBU) by multiplying each raw BRET value by 1,000. The normalized NanoBRET™ signal was calculated relative to the Max Signal control wells (DMSO treated control wells) and the Minimum Signal control wells. Percentage inhibition was calculated relative to the Minimum Signal control and Maximum Signal control wells. IC$_{50}$ values were derived by four parameter curve fitting using the Robust method.

NanoBRET™ Tracer-PEG2-590:

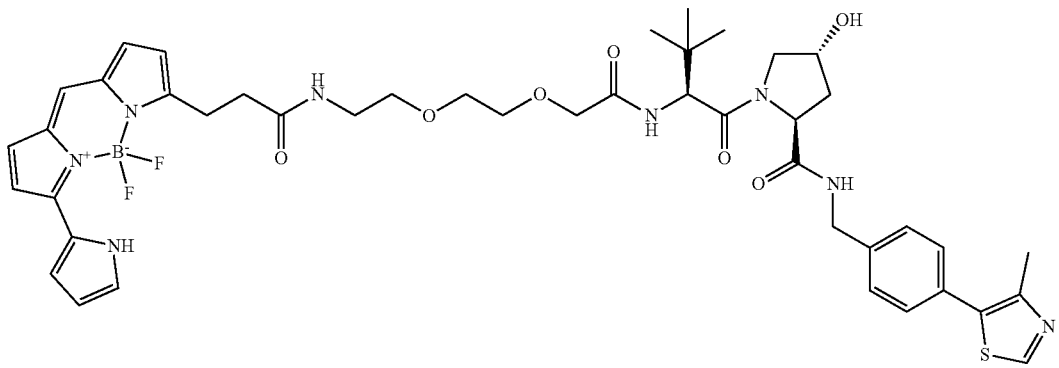 [SMILES: Cc1ncsc1-c1ccc(CNC(=O)[C@@H]2C[C@@H](O)CN2C(=O)[C@@H](NC(=O)COCCOCCNC(=O)CCc2ccc3n2[B-](F)(F)[N+]2=C(c4ccc[nH]4)C=CC2=C3)C(C)(C)C)cc1]

Parental Unlabeled VHL Antagonist (Control Compound):

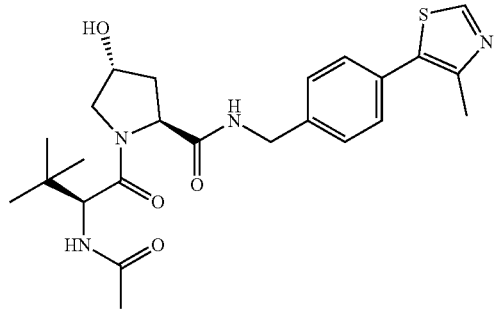 [SMILES: CC(=O)N[C@H](C(=O)N1C[C@H](O)C[C@H]1C(=O)NCc1ccc(-c2scnc2C)cc1)C(C)(C)C]

The results for VHL binding IC$_{50}$ values from the FP assay and the HEK-293 BRET assay and K$_d$ values measured in the SPR assay are shown in Table 11. Where more than one measurement was performed for the same assay, the value reported is the geometric mean of all values.

TABLE 11

VHL inhibition data (i.e., IC$_{50}$, µM) for the FP assay and HEK-293 BRET assay, and SPR measured VHL affinity

| Example Number | IC$_{50}$ (µM) (FP) | K$_d$ (µM) (SPR) | IC$_{50}$ (µM) (HEK-293) | Example Number | IC$_{50}$ (µM) (FP) | K$_d$ (µM) (SPR) | IC$_{50}$ (µM) (HEK-293) |
|---|---|---|---|---|---|---|---|
| 101.1 | >200 | >500 | — | 120.1 | — | 150 | — |
| 101.2 | >200 | 41.6 | — | 120.2 | — | 150 | — |
| 101.3 | >200 | 332 | — | 121.1 | 65.5 | 29.2 | 100 |

TABLE 11-continued

VHL inhibition data (i.e., IC$_{50}$, μM) for the FP assay and HEK-293 BRET assay, and SPR measured VHL affinity

| Example Number | IC$_{50}$ (μM) (FP) | Kd (μM) (SPR) | IC$_{50}$ (μM) (HEK-293) | Example Number | IC$_{50}$ (μM) (FP) | Kd (μM) (SPR) | IC$_{50}$ (μM) (HEK-293) |
|---|---|---|---|---|---|---|---|
| 101.4 | 108 | 26.7 | — | 121.2 | — | 150 | — |
| 102.1 | 6.17 | 1.96 | — | 122.1 | 400 | 150 | 100 |
| 102.2 | 93.1 | 43.8 | — | 122.2 | 16.7 | 6.83 | 39 |
| 102.3 | 43.3 | 10.7 | — | 123.1 | 400 | 55.6 | 100 |
| 103.1 | >400 | >150 | — | 123.2 | 4.68 | 3.98 | 5.48 |
| 103.2 | >400 | >150 | — | 124.1 | 400 | 150 | 100 |
| 103.3 | 292 | >150 | — | 124.2 | 32.9 | 10.1 | 54.6 |
| 103.4 | 6.73 | 1.09 | — | 124.3 | 400 | 150 | 100 |
| 104.1 | 203 | 35.9 | — | 124.4 | 400 | 150 | 100 |
| 104.2 | >400 | >150 | — | 125.1 | 179 | 14.7 | 100 |
| 104.3 | 230 | 44.6 | — | 125.2 | 400 | 150 | 100 |
| 104.4 | 0.422 | 0.171 | — | 125.3 | 400 | 150 | 100 |
| 105.1 | 375 | 241 | — | 125.4 | 400 | 150 | 100 |
| 105.2 | 136 | 113 | — | 126.1 | 31.4 | 12.8 | 45.4 |
| 105.3 | >400 | >150 | — | 126.2 | — | 150 | — |
| 105.4 | 5.39 | 1.58 | — | 127.1 | 400 | 150 | 100 |
| 106.1 | >400 | >150 | — | 127.2 | 50.8 | 16.4 | 73.2 |
| 106.2 | >400 | >150 | — | 128.1 | — | 150 | — |
| 106.3 | >400 | >150 | — | 128.2 | — | 150 | — |
| 106.4 | 2.96 | 0.895 | — | 128.3 | 33.6 | 5.7 | 10.7 |
| 107.1 | — | >150 | — | 128.4 | 17.3 | 7.5 | 24.5 |
| 107.2 | 24.1 | 14.9 | — | 129.1 | 79 | 48.1 | 100 |
| 107.3 | >50 | >150 | — | 129.2 | 58.4 | 57 | 77.9 |
| 107.4 | >50 | >150 | — | 129.3 | 0.418 | 0.0293 | 0.304 |
| 108.1 | 57.5 | 13.9 | — | 129.4 | 0.202 | 0.0438 | 0.239 |
| 108.2 | 11.0 | 3.95 | — | 130.1 | 96.1 | 83 | 100 |
| 108.3 | >400 | >0.3 | — | 130.2 | 362 | 121 | 100 |
| 108.4 | >400 | >0.3 | — | 130.3 | 17.6 | 4.69 | 16.2 |
| 110.1 | 20.6 | 7.42 | 28.1 | 130.4 | 17.5 | 4.24 | 34.5 |
| 110.2 | 400 | 104 | 100 | 131.1 | 160 | — | 100 |
| 110.3 | 400 | 150 | 100 | 131.2 | 242 | — | 100 |
| 110.4 | 400 | 150 | 100 | 131.3 | 19.6 | — | 23 |
| 111.1 | 111 | 31.8 | 100 | 131.4 | 19.9 | — | 20 |
| 111.2 | 4.97 | 1.86 | 5.11 | 132.1 | 400 | 150 | 100 |
| 112.1 | 23.3 | 12.1 | 66.4 | 132.2 | 45.7 | 12.6 | 39.4 |
| 112.2 | — | 150 | — | 133.1 | 400 | 150 | 100 |
| 113.1 | 70.6 | 24.1 | 96.9 | 133.2 | 400 | 150 | 100 |
| 113.2 | 6.3 | 2.49 | 2.94 | 133.3 | 34.4 | 36.3 | 22.6 |
| 113.3 | 400 | 90.8 | 100 | 133.4 | 54.9 | 17.4 | 52.3 |
| 113.4 | 2.28 | 3.17 | 2.92 | 134.1 | 400 | 150 | 100 |
| 114.1 | 400 | 150 | 100 | 134.2 | 48.2 | 57.4 | 41.3 |
| 114.2 | 400 | 150 | 100 | 135.1 | 400 | 150 | 100 |
| 114.3 | 47 | 8.8 | 48.8 | 135.2 | 9.32 | 6.55 | 5.67 |
| 114.4 | 58.3 | 5.86 | 59.9 | 136.1 | 93.6 | 150 | 77.1 |
| 115.1 | 400 | 150 | 100 | 137.1 | 400 | — | 100 |
| 115.2 | 40.7 | 4.03 | 25.7 | 137.2 | 47.3 | — | 100 |
| 116.1 | 4.35 | 5.1 | 100 | 137.3 | 400 | — | 100 |
| 116.2 | — | 150 | — | 139.1 | 10 | — | 21.7 |
| 116.3 | — | 150 | — | 139.2 | 0.0628 | — | 0.0678 |
| 116.4 | 35.4 | 5.3 | 100 | 1001.1 | 16.9 | — | — |
| 117.1 | 400 | 155 | 100 | 1001.2 | 0.795 | — | — |
| 117.2 | 1.62 | 0.625 | 1.9 | 1001.3 | >100 | — | — |
| 117.3 | 400 | 217 | 100 | 1001.4 | >100 | — | — |
| 117.4 | 400 | 150 | 100 | 1003.1 | 400 | 67.1 | 100 |
| 118.1 | 157 | 61.5 | 100 | 1003.2 | 400 | 67.1 | 100 |
| 118.2 | 0.418 | 0.128 | 0.939 | 1003.3 | 30.4 | 67.1 | 51.6 |
| 118.3 | 150 | 21.2 | 100 | 1003.4 | 100 | 67.1 | 100 |
| 118.4 | 400 | 102 | 100 | 1004.1 | 6.25 | — | 68.3 |
| 119.1 | 400 | 150 | 100 | 1004.2 | 75.8 | — | 46.4 |
| 119.2 | 400 | 150 | 100 | 1004.3 | 75.8 | — | 100 |
| 119.3 | 72.4 | 17.5 | 71.1 | 1004.4 | 6.25 | — | 100 |
| 119.4 | 400 | 150 | 100 | 1005.1 | 255 | — | 64.6 |

Example D: Inhibition of MYC Expression

Pharmacologic inhibition of MYC is achievable through targeting BET bromodomains through small molecule binder or degrader mechanisms. Such inhibitors may have clinical utility given the widespread pathogenetic role of MYC in cancer. See, e.g., Mertz J, et al., "Targeting MYC dependence in cancer by inhibiting BET bromodomains," (2011) *Proc. Natl. Acad. Sci. USA*, Vol. 108 (40), pp. 16669-16674.

To determine the inhibition of MYC expression, MV-4-11 cells (ATCC) were plated at 10,000 cells per well in 96-well plates in RPMI1640 media supplemented with 10% fetal bovine serum and 2 mM L-glutamine. Test compounds diluted in DMSO were transferred to the cell plates, keeping final DMSO concentration consistent at 0.1%, and incubated for 4 h at 37° C. Lysis and analysis for MYC expression were carried out using QuantiGene 2.0 reagents (Affymetrix/eBioscience, probe set cat #SA-50182) and following the vendor's instructions. Luminescence was read using an EnVision plate reader (PerkinElmer) and IC$_{50}$s generated in Genedata Screener using a 4-parameter non-linear regression fit.

Bromobinder molecules that potently inhibit, but do not degrade, the target will block up to 80% of the endogenous MYC expression in the MV-4-11 cells. Effective degraders will surpass this and inhibit >95% of MYC, thus following the maximum inhibition within this assay provides valuable SAR. Where more than one measurement was performed for the same assay, the value reported is the geometric mean of all values.

The results are set forth in Table 12.

TABLE 12

Inhibition of MYC expression

| Example Number | IC$_{50}$ (μM) | Maximum Inhibition (%) |
|---|---|---|
| 1001.1 | 0.0174 | 82.3 |
| 1001.2 | 0.00171 | 98.4 |
| 1001.3 | 0.0274 | 79.2 |
| 1001.4 | 0.0261 | 75.7 |
| 1002.1 | 0.0515 | 76.4 |
| 1002.2 | 0.0257 | 90.3 |
| 1002.3 | 0.123 | 69.8 |
| 1002.4 | 0.0804 | 69.9 |

Example E: BRD4 Degradation Assay in PC3 (Steap-1) Prostate Cancer Cells and ELO-1 Cells, High Content Fluorescence Imaging Assays PC3 (Steap-1) prostate cancer cells: PC3 (Steap-1) prostate cancer cells (PC3 cells overexpressing the surface protein Steap-1) were seeded on day 1 at a density of 200,000 cells/mL in 45 μl/well in cell plates in a 384 well Greiner/Perkin Elmer Cell Carrier TC Treated plate (part #6007430) in Assay Medium (RPMI, 10% FBS, 2 mM Glutamax). Cells were incubated overnight at 37° C. degrees. On day 2, compounds were serially diluted 3-fold in DMSO spanning the concentrations 10 mM to 8.6 nM, in 384 well clear polypropylene plates (Greiner Cat #781201). DMSO and 10 mM of a control PROTAC (dBET1, as described in WO 2017/024317, p. 235, structure below) (control compound) were added to designated wells. Compounds and controls were diluted 50-fold (2 μl of DMSO stock into 98 μl) into Assay Medium. 5 μl of the diluted compounds was transferred to the cell plates. The final top concentration of the test compounds in the cell plates was 20 μM. Cell plates were incubated at 37° C., for 4 hours. Fixation and permeabilization were carried out using a Biotek EL406 plate washer and dispenser as follows. Cells were fixed by addition of 15 μL of 16% paraformaldehyde (Electron Microscopy Sciences #15710-S) directly to the 50 µL cell culture medium in each well using the peristaltic pump 5 µL cassette on a Biotek EL406 (final concentration of formaldehyde was 3.7% w/v). Samples were incubated 30 minutes. Well contents were aspirated and 50 µL/well of Phosphate Buffered Saline (PBS) containing 0.5% w/v bovine serum albumen, 0.5% v/v Triton X-100 (Antibody Dilution Buffer) was added to each well. Samples were incubated for 30 minutes. Well contents were aspirated and washed 3 times with 100 µL/well of PBS.

EOL-1 cells: The BRD4 degradation assay was performed on EOL-1 cells using the same procedure as described above for PC3 (Steap-1) prostate cancer cells, except EOL-1 cells were seeded at 1,000,000 cells/mL. Following aspiration and washing of the well contents with 100 µL/well of PBS, 40 µL PBS plus 10% normal goat serum was added per well for 20 minutes at room temperature.

For both the PC3 and EOL-1 cell assays, immunofluorescence staining of BRD4 was carried out using a Biotek EL406 plate washer and dispenser as follows. The well supernatant was aspirated from the wells and 25 µL/well of rabbit mAb Anti-BRD4 [EPR5150(2)] abeam 128874 diluted 1:500 in Antibody Dilution Buffer is dispensed. Samples were incubated for 2 hours at room temperature. Samples were washed 4 times with 100 µL/well of PBS. 25 µL/well of secondary antibody solution (Goat Anti-Rabbit IgG, DyLight 488 Conjugated Highly Cross-adsorbed #35553 1:1000) diluted 1:1000 and Hoechst 33342 1 µg/ml diluted in Antibody Dilution Buffer) were dispensed into each well. 16 wells of the plate, which were designated as 'no primary antibody" wells, received only Antibody Dilution Buffer (without anti-BRD4 antibody). Samples were incubated for 2 hours at room temperature. Samples were washed 3 times with 100 µL/well of PBS using a Biotek EL406. Quantitative fluorescence imaging of BRD4 was carried out using a Phenix (Perkin Elmer). Fluorescence images of the samples (Channel 1: Hoechst33342 (DNA stain); Channel 2: 488 nm (BRD4 stain)) were acquired. Channel 1 (DNA stain) was used to define the "Region of Interest" (ROI) nuclear region. Measurements of BRD4 average immunofluorescence intensity within the ROI (nuclear region), were made on a per cell basis and averaged over all the measured cells. Data analysis was carried out using Genedata Screener Software, with DMSO and "no primary antibody" samples being used to define the 0% and 100% changes in BRD4. The "Robust Fit" method was used to define the inflexion point of curve ($EC_{50}$) and the plateau of the maximal effect ($S_{inf}$). The $S_{inf}$ value reports degradation as percent change in protein level, so complete loss of the protein target is −100%. $S_{inf}$ is the maximum degradation achieved, obtained by determining the bottom of a dose-response (where the S-shaped curve levels out).

TABLE 13

Degradation of BRD4 in PC3 (Steap-1) cells and EOL-1 cells

| Example Number | PC3 (Steap-1) | | EOL-1 | |
|---|---|---|---|---|
| | $EC_{50}$ (µM) | $S_{inf}$ (%) | $EC_{50}$ (µM) | $S_{inf}$ (%) |
| 1001.1 | >20 | — | >20 | — |
| 1001.2 | 0.0033 | −97.2 | 0.000865 | −96.4 |
| 1001.3 | 0.140 | −29.0 | >20 | — |
| 1002.1 | — | — | >20 | — |
| 1002.2 | — | — | 0.000310 | −65.0 |
| 1005.1 | — | — | >20 | — |
| 1006.1 | — | — | 0.00102 | −92.6 |

Examples F1 and F2: Protein Degradation Assays

The following assays may be used to measure protein degradation. These assays are amenable for measuring degradation of all protein types. Protocol 1 (Western blot) is based on assays for an RTK (membrane) protein. Protocol 2 is based on assays for BRD4 (nuclear and cytosolic) protein.

1. Protocol 1: Western Blot (Example F1)

New PROTAC compounds may be initially screened by a cell viability assay (CTG). Compounds that impact cell viability are subjected to a Western blot to determine if reduced cell growth is a result of targeted protein degradation by the PROTAC.

To begin, cell lines are treated with a dose titration of selected compounds (PROTAC and parent ligands). At the desired time point, the media and compound is aspirated, and the cells are rinsed in PBS. Lysis buffer is added to the cells, and the cells are lifted using a cell scraper and lysed on ice for 20 minutes in NP40 lysis buffer (10 mM Tris pH 7.4, 50 mM NaCl, 1 mM EDTA, 0.5% NP-40) supplemented with protease (Roche #058927910001) and phosphatase inhibitors (Thermo #78426). The lysates are centrifuged at 15,000 rpm for 10 minutes and the protein concentration is determined using BCA reagent (Thermo #23227).

Equal amounts of protein are subjected to SDS-PAGE (NuPAGE, 4-12% Bis-Tris Gel, #WG-1403, Novex) and transferred to a nitrocellulose membrane (BioRad, #170-4159). The membranes are blocked for 30 minutes in blocking buffer (#927-40000, Li-Cor) and incubated overnight at 4° C. on a rocking platform with the appropriate primary antibodies diluted in blocking buffer.

The membranes are washed in TBST for 40-60 minutes, while changing the buffer every 10-15 minutes, followed by incubation with the appropriate secondary antibodies (#926-68050, goat anti-mouse, #926-32211, goat anti-rabbit, Li-Cor) for 40-60 minutes. The antibodies are diluted in blocking buffer. The membranes are washed again as described above, followed by visualization on LiCor Odyssey CLx Scanner (LiCor) to assess the expression of protein.

Reduced expression of the desired protein by a PROTAC (but not by parent ligands) without a change in expression of loading control protein (actin, GAPDH, etc.) suggests degradation by the PROTAC.

Observations may be confirmed by further experiments (e.g., VHL ligand competition assay, rescue by proteasome inhibitors, etc.).

2. Protocol 2: Measuring Loss of Protein Expression (Example F2)

Cell lysates are extracted by boiling in 6M Urea buffer (6 M Urea, 20 mM Tris pH 7.5, 12.5 mM NaCl, 2.5 mM $MgCl_2$, and 0.1% Triton X-100), supplemented with HALT protease and phosphatase inhibitor cocktail. Protein quanti-

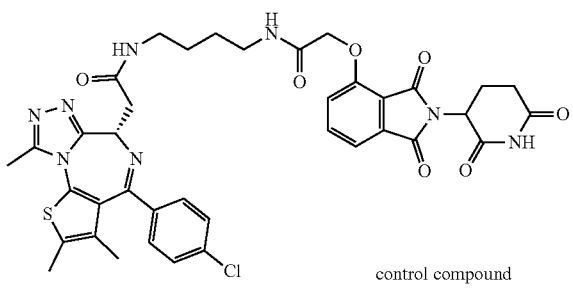 [SMILES: Cc1sc2c(c1C)C(c1ccc(Cl)cc1)=N[C@@H](CC(=O)NCCCCNC(=O)COc1cccc3c1C(=O)N(C1CCC(=O)NC1=O)C3=O)c1nnc(C)n1-2]

control compound fication is performed using a Pierce™ BCA Protein Assay Kit, and equal amounts of protein lysate are loaded onto the NuPAGE Bis-Tris Gel. Immunodetection and quantification of proteins is performed by a Quantitative Western Blot method using LI-COR® Odyssey. Protein expression is normalized to an internal loading control to accurately determine the loss of protein expression.

In a typical experiment, the concentration dependent influence of compound treated cells on protein levels is determined in comparison to DMSO alone treated cells. From this experiment a DC50 (concentration in which ~50% of protein is depleted) and Dmax (concentration and %-amount of protein remaining where maximal effect is observed) is determined.

Additional description of protein degradation assays can be found in Zengerle, M., et al., "Selective Small Molecule Induced Degradation of the BET Bromodomain Protein BRD4," ACS *Chem Biol.* 2015, Vol. 10, p. 1770; and Raina, K., et al., "PROTAC-induced BET protein degradation as a therapy for castration-resistant prostate cancer," *Proc. Natl. Acad. Sci. U.S.A.,* 2016, Vol. 113, pp. 7124-7129.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A compound of Formula (III) or (IV)

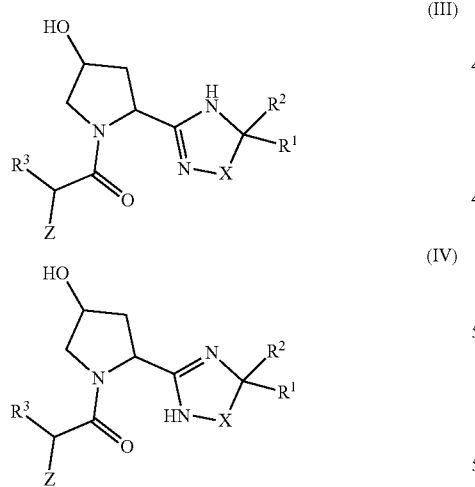

or a pharmaceutically acceptable salt thereof, wherein:
X is selected from the group consisting of —C(O)—, O, S, —SO$_2$—, —N(R$^4$)—, and —C(R$^{5a}$)(R$^{5b}$)— wherein R$^4$, R$^{5a}$, and R$^{5b}$ are each independently selected from the group consisting of H, substituted or unsubstituted C$_1$-C$_3$ alkyl, and substituted or unsubstituted aryl;
R$^1$ is selected from the group consisting of H, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heterocyclyl, and substituted or unsubstituted heteroaryl;
R$^2$ is selected from the group consisting of H, substituted or unsubstituted alkyl, substituted or unsubstituted alkenyl, substituted or unsubstituted alkynyl, and substituted or unsubstituted aryl;
or R$^1$ and R$^2$ are taken together with the carbon to which they are attached to form a cycloalkyl or heterocyclyl, wherein the cycloalkyl or heterocyclyl is substituted or unsubstituted or fused with a ring selected from the group consisting of substituted or unsubstituted cycloalkyl, substituted or unsubstituted heterocyclyl, substituted or unsubstituted aryl, and substituted or unsubstituted heteroaryl;
R$^3$ is substituted or unsubstituted alkyl, or R$^3$ is taken together with R$^6$, when present, and the atoms to which they are attached, to form a substituted or unsubstituted heterocyclylene;
Z is selected from the group consisting of —N(R$^6$)R$^{6a}$, —OR$^{6a}$, —N(R$^6$)—SO$_2$—R$^{6b}$,

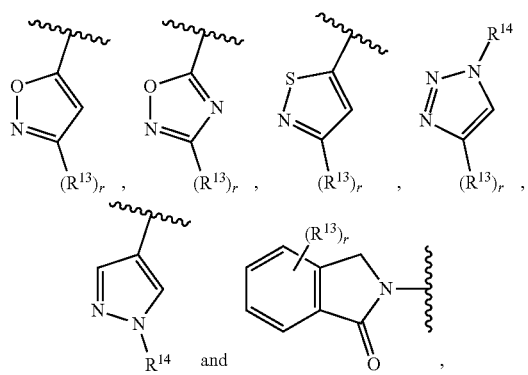

wherein
R$^6$ is selected from the group consisting of H and substituted or unsubstituted alkyl; or R$^6$, when present, is taken together with R$^3$ and the atoms to which they are attached to form a substituted or unsubstituted heterocyclylene;
R$^{6a}$ is selected from the group consisting of H, substituted or unsubstituted acyl, and substituted or unsubstituted alkyl;
R$^{6b}$ is selected from the group consisting of substituted or unsubstituted alkyl and substituted or unsubstituted aryl;
∿∿∿ indicates the point of attachment to the remaining structure of the compound;
r is 0 or 1;
R$^{13}$ is selected from the group consisting of —OR$^{13a}$ and substituted or unsubstituted alkyl;
R$^{13a}$ is selected from the group consisting of H and substituted or unsubstituted alkyl; and
R$^{14}$ is selected from the group consisting of H and substituted or unsubstituted alkyl.

2. The compound of claim 1, or a pharmaceutically acceptable salt thereof, wherein:
X is selected from the group consisting of —C(O)—, O, —SO$_2$, —N(R$^4$)—, and C(R$^{5a}$)(R$^{5b}$);
R$^1$ is selected from the group consisting of H, unsubstituted alkyl, and substituted or unsubstituted aryl;

R² is selected from the group consisting of H, substituted or unsubstituted alkyl, and unsubstituted aryl;

or R¹ and R² are taken together with the carbon to which they are attached to form a cycloalkyl, wherein the cycloalkyl is unsubstituted or fused with a ring selected from the group consisting of substituted or unsubstituted aryl;

R³ is t-butyl or isopropyl, or R³ is taken together with R⁶, when present, and the atoms to which they are attached, to form a substituted or unsubstituted heterocyclylene;

R⁴ is selected from the group consisting of H, substituted or unsubstituted $C_1$-$C_3$ alkyl, and unsubstituted aryl;

$R^{5a}$ and $R^{5b}$ are each independently unsubstituted $C_1$-$C_3$ alkyl; and Z is selected from the group consisting of —N(R⁶)$R^{6a}$, —N(R⁶)—SO₂—$R^{6b}$,

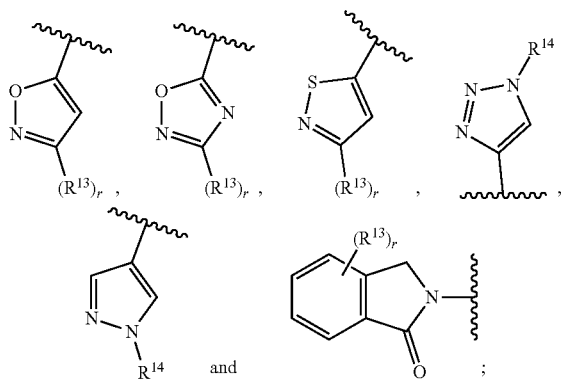

R⁶ is H; or R⁶ is taken together with R³ and the atoms to which they are attached to form a substituted or unsubstituted heterocyclylene;

each $R^{6a}$ is substituted or unsubstituted acyl;

$R^{6b}$ is unsubstituted alkyl;

R¹³ is selected from the group consisting of —OR$^{13a}$ and unsubstituted alkyl;

$R^{13a}$ is selected from the group consisting of H and unsubstituted alkyl; and R¹⁴ is unsubstituted alkyl.

3. The compound of claim 1, or a pharmaceutically acceptable salt thereof, wherein:

X is —C(O)— or O;

R¹ is

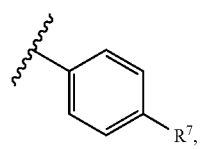

wherein R⁷ is selected from the group consisting of halo, substituted or unsubstituted heteroaryl, substituted or unsubstituted heterocyclyl, and substituted or unsubstituted aryl;

R² is a substituted or unsubstituted $C_1$-$C_3$ alkyl;

or R¹ and R² are taken together with the carbon to which they are attached to form a cycloalkyl, wherein the cycloalkyl is unsubstituted or fused with an unsubstituted aryl;

R³ is t-butyl or isopropyl; and

Z is selected from the group consisting of —N(R⁶)$R^{6a}$

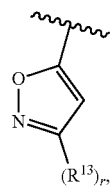

wherein

R⁶ is H;

$R^{6a}$ is a substituted or unsubstituted acyl;

r is 1; and

R¹³ is selected from the group consisting of —OR$^{13a}$ and unsubstituted alkyl, wherein $R^{13a}$ is selected from the group consisting of H and unsubstituted alkyl.

4. The compound of claim 3, or a pharmaceutically acceptable salt thereof, wherein:

R⁷ is selected from the group consisting of

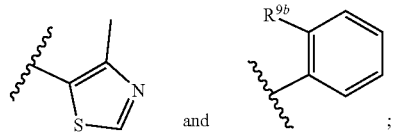

$R^{9b}$ is halo; and

Z is selected from the group consisting of —N(R⁶)$R^{6a}$ and

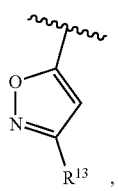

wherein R¹³ is selected from the group consisting of —CH₃ and —OR$^{13a}$, wherein $R^{13a}$ is H or —CH₃.

5. The compound of claim 1, or a pharmaceutically acceptable salt thereof, wherein the compound is selected from the group consisting of:

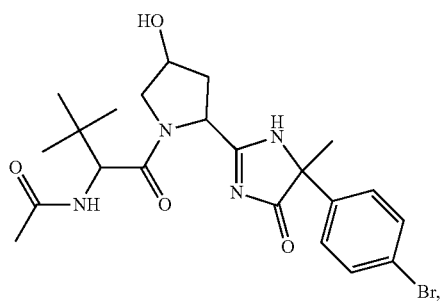

695
-continued
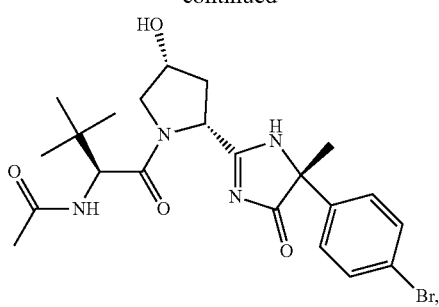
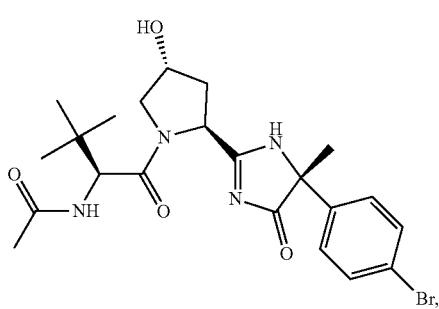
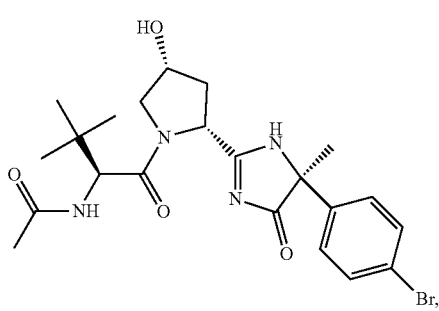
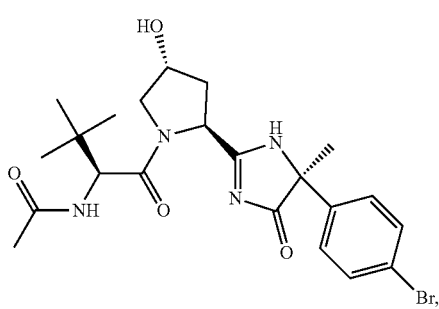
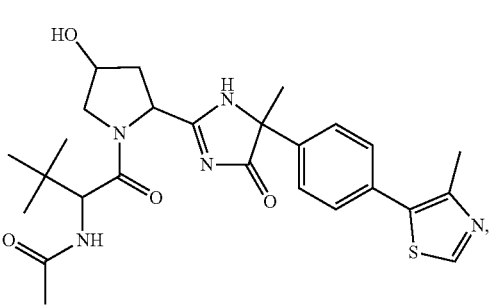
696
-continued
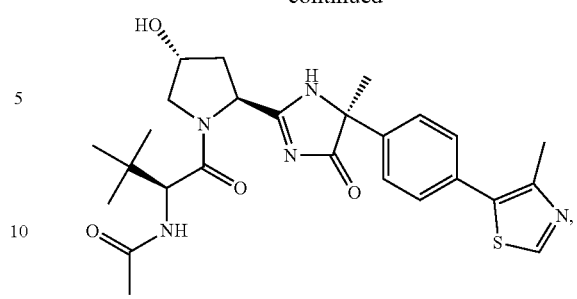
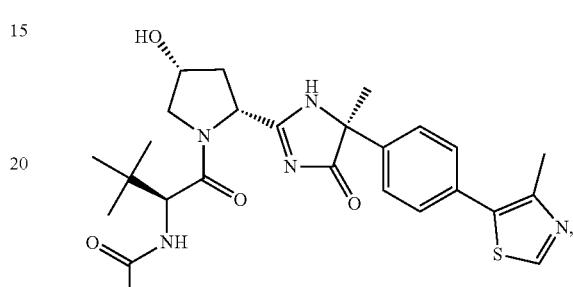
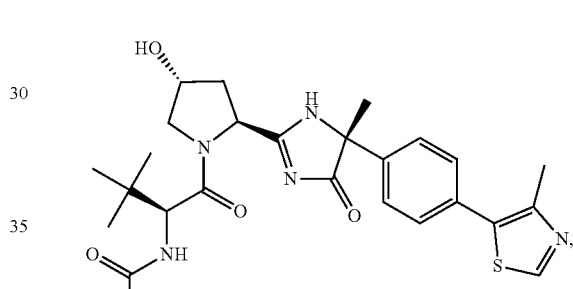
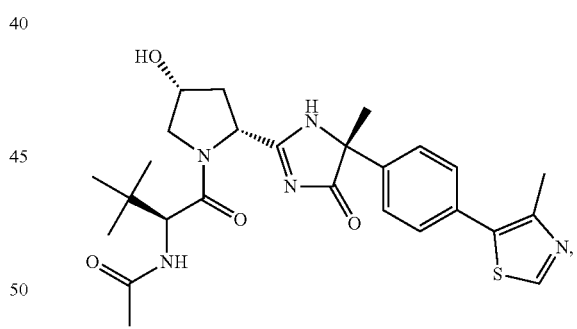
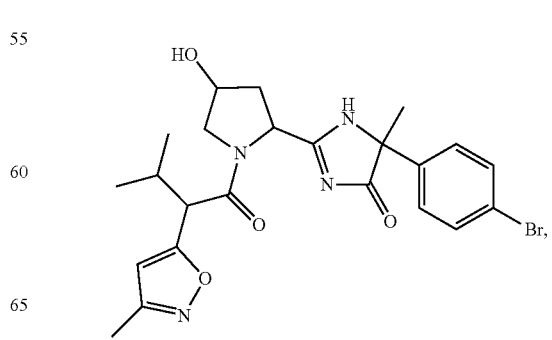

697
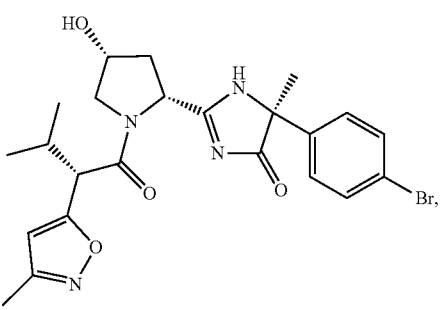
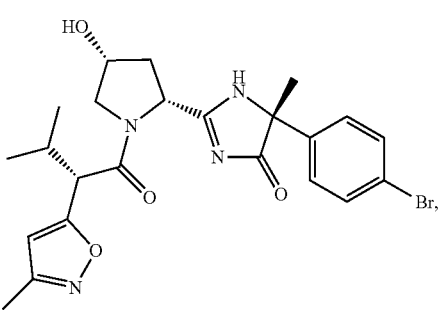
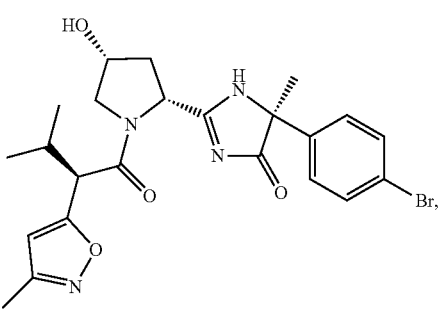
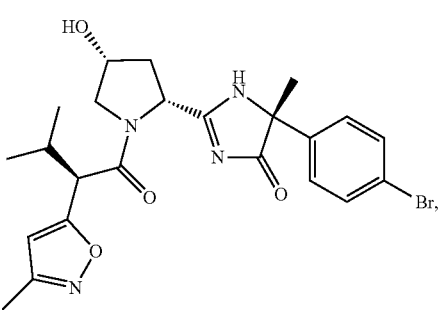
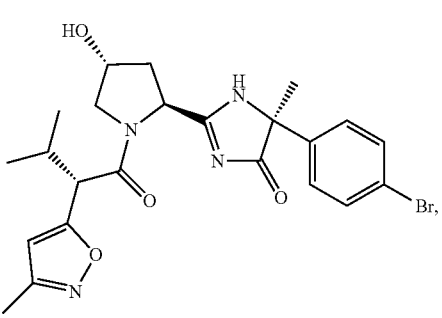
698
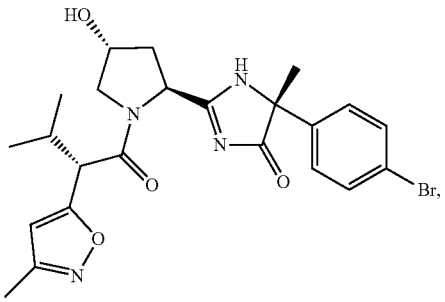
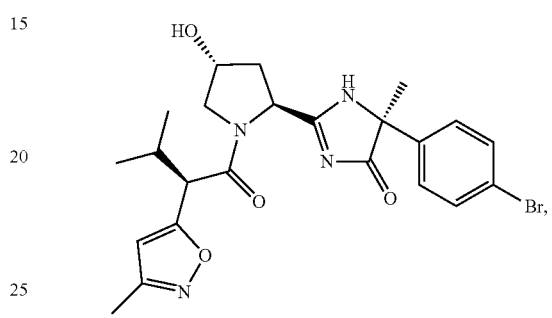
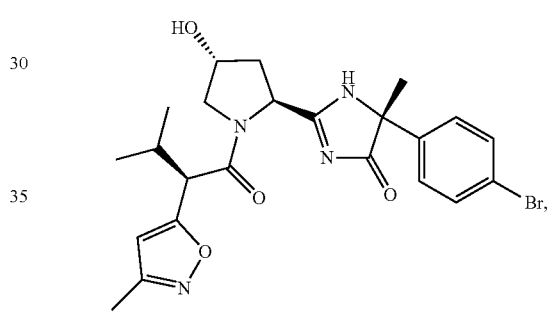
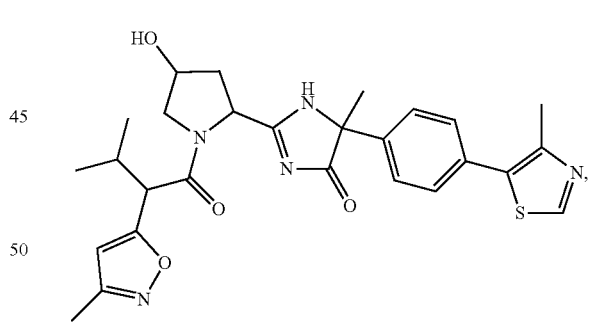
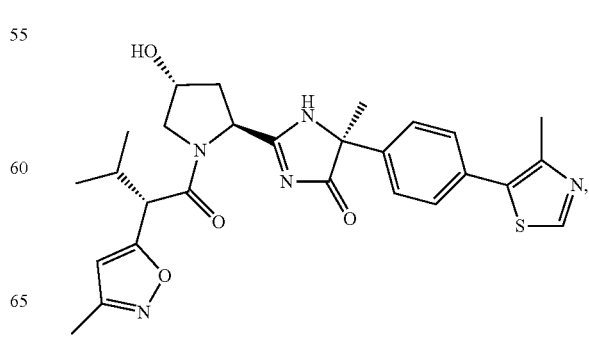

699
-continued
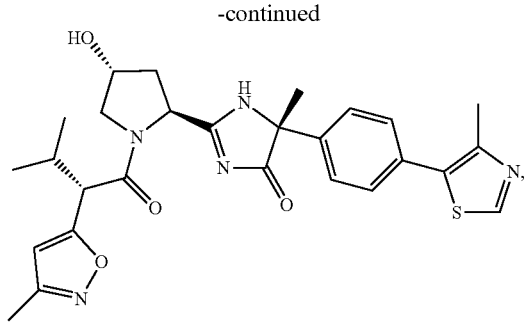
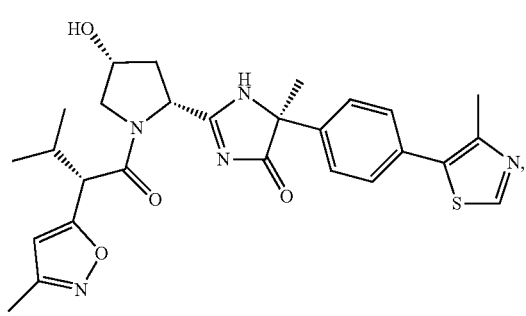
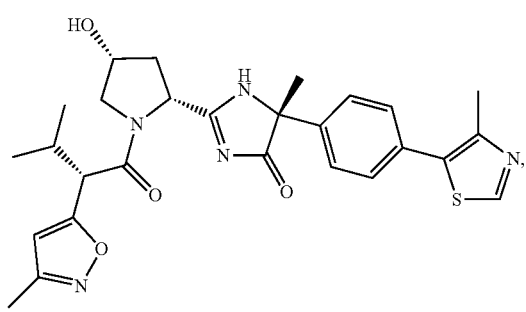
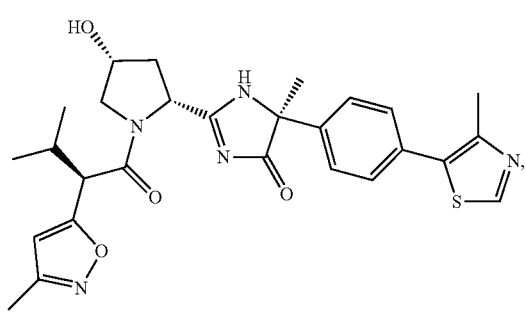
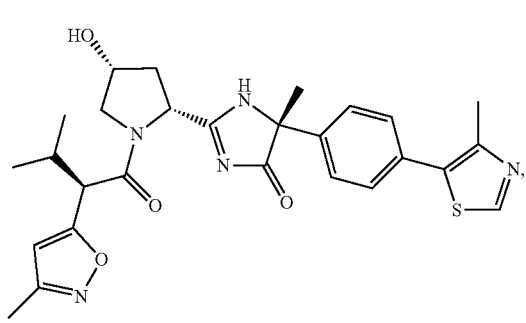
700
-continued
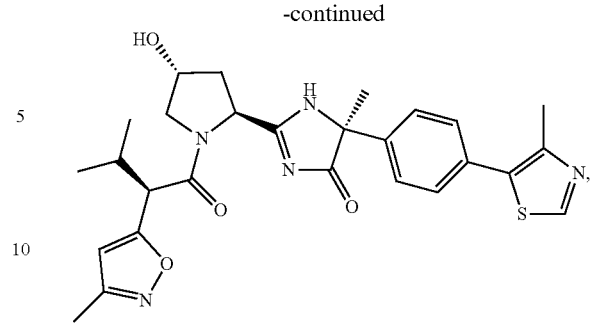
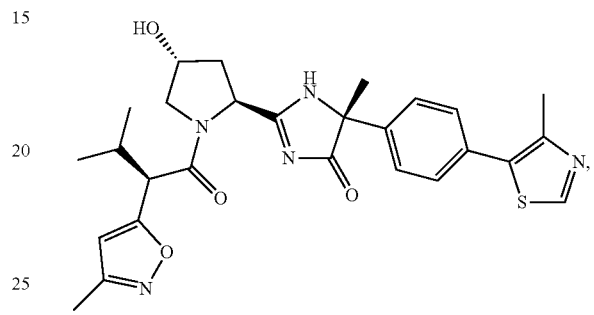
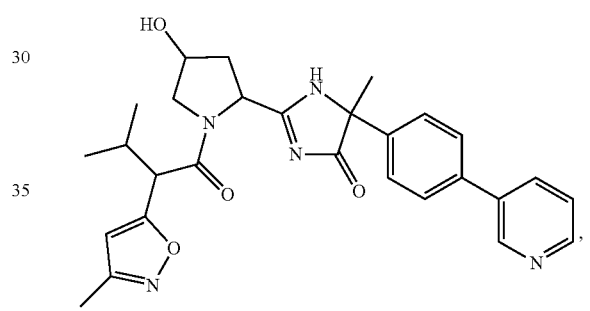
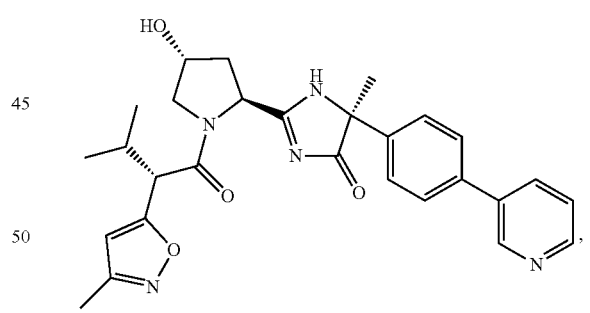
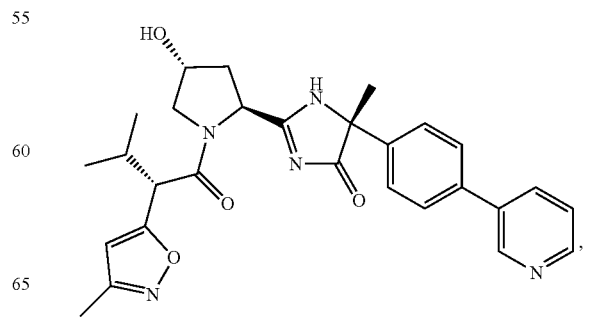

701
-continued
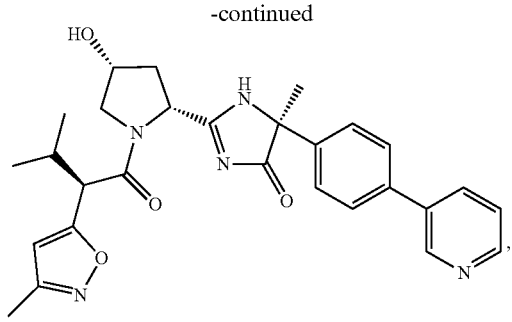
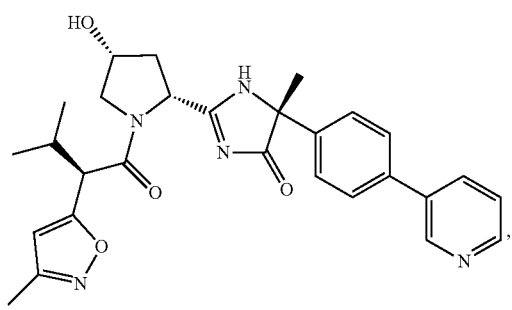
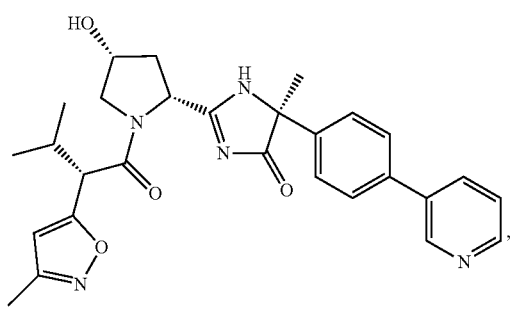
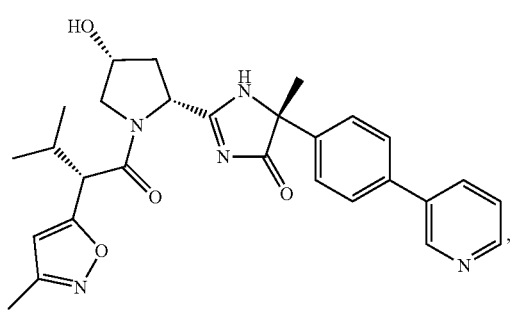
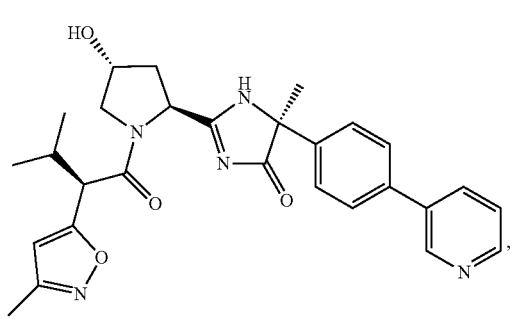
702
-continued
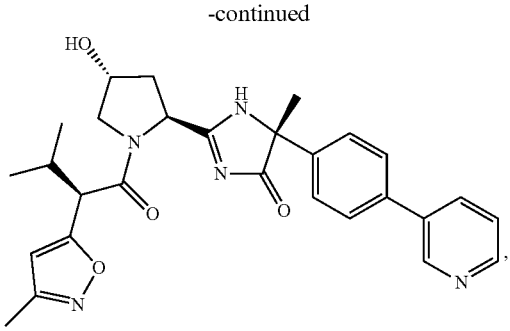
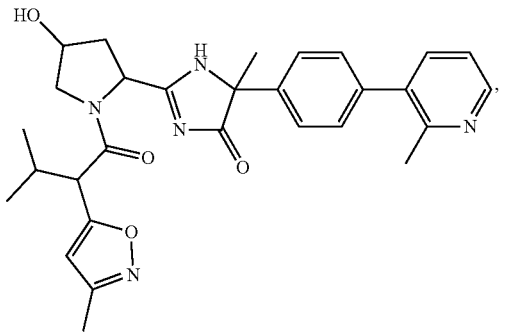
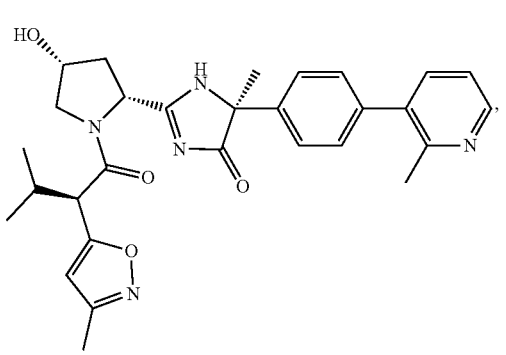
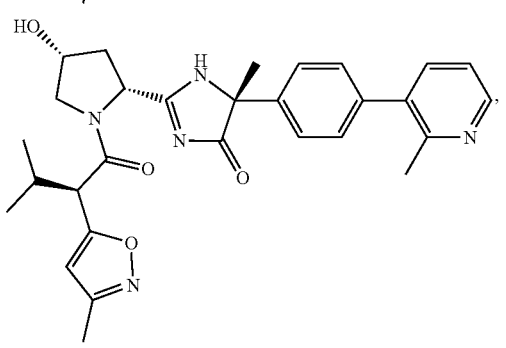
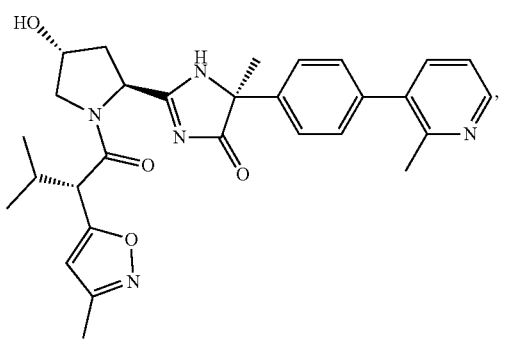

703
-continued
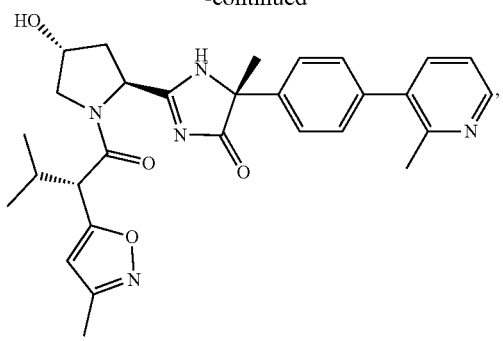
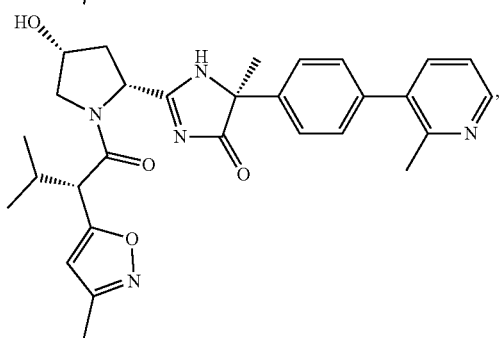
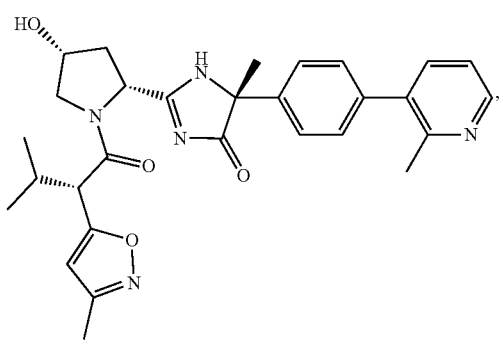
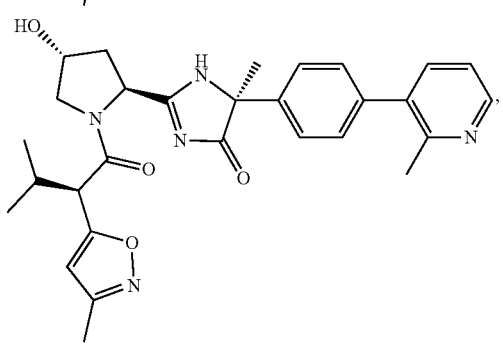
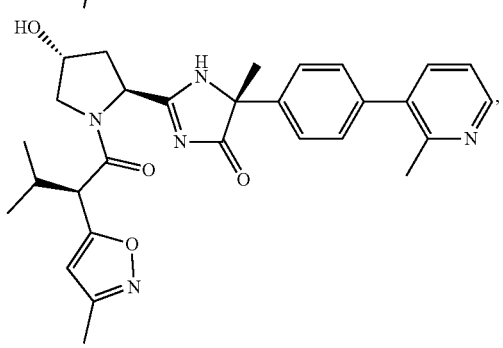
704
-continued
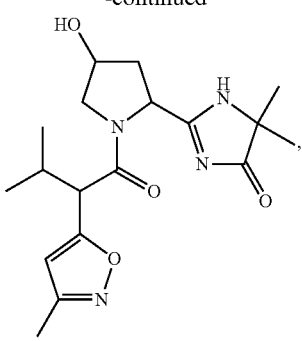
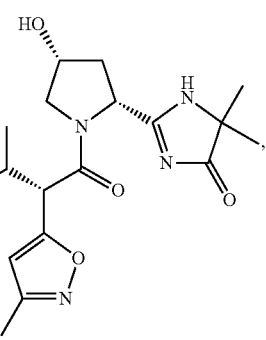
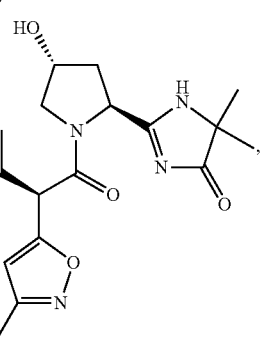
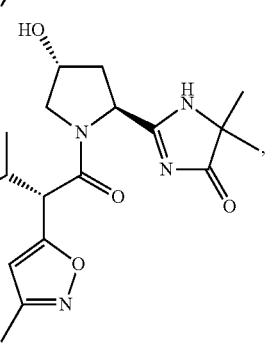
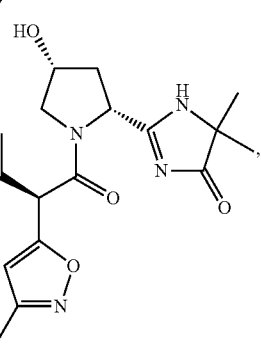

705
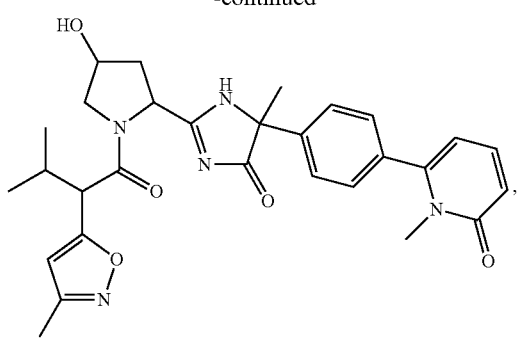
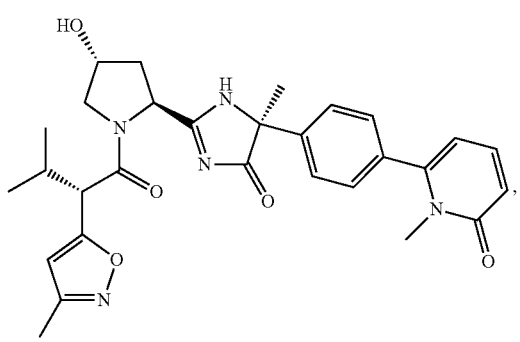
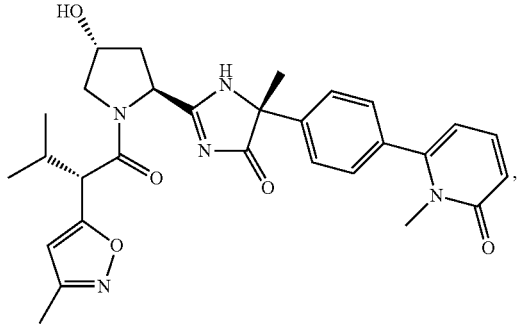
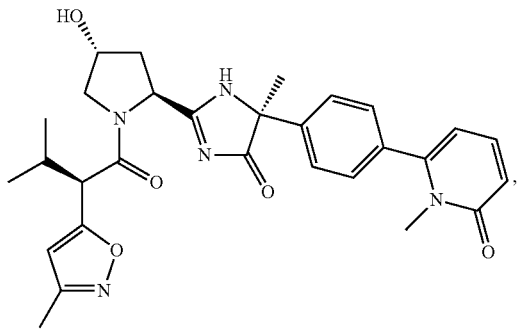
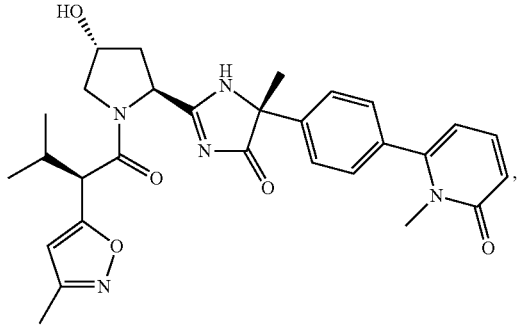
706
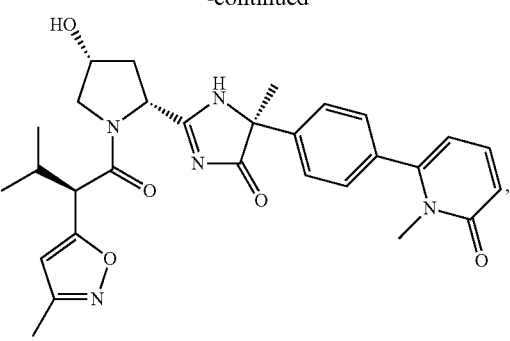
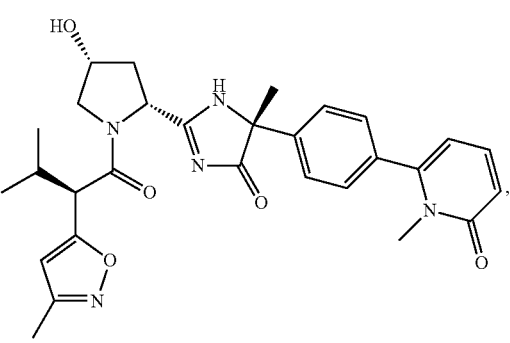
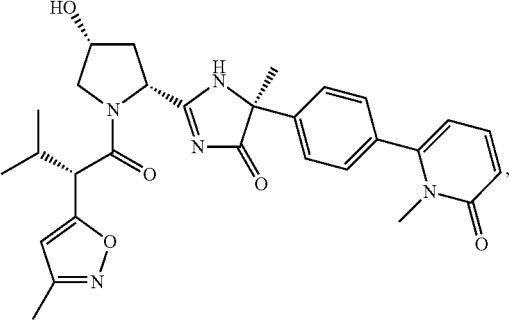
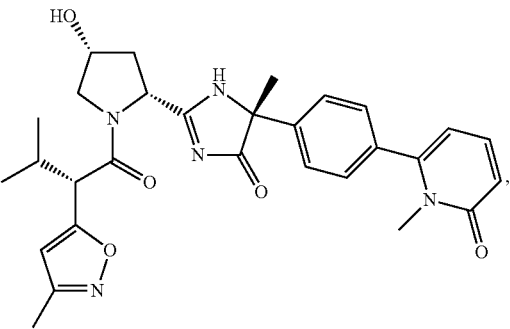
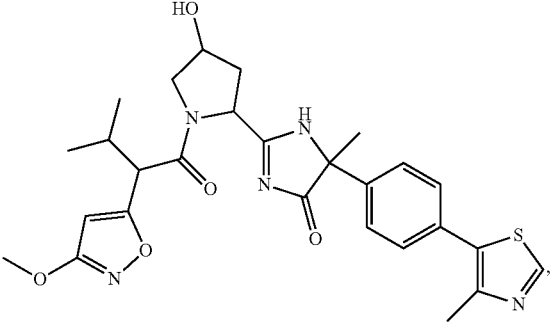

707
-continued
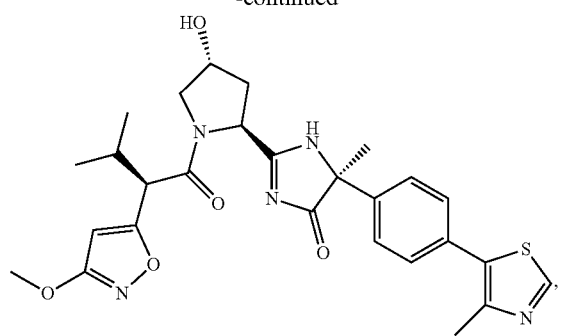
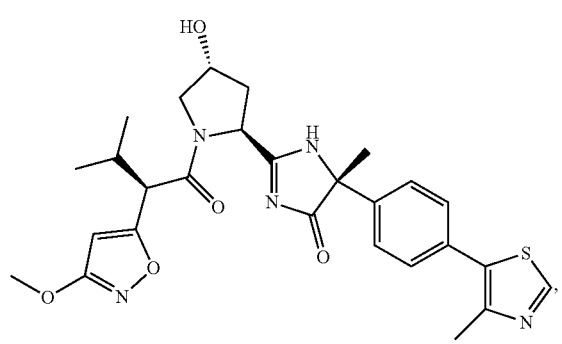
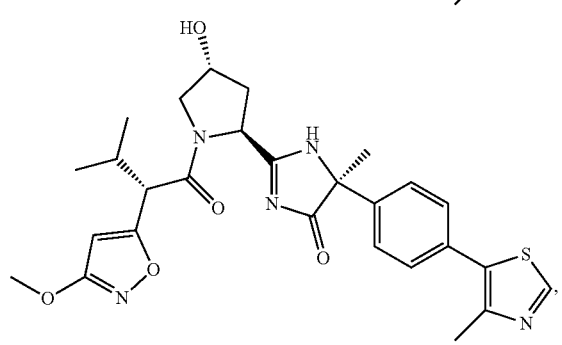
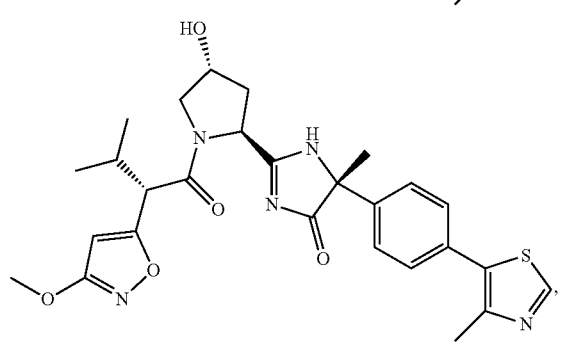
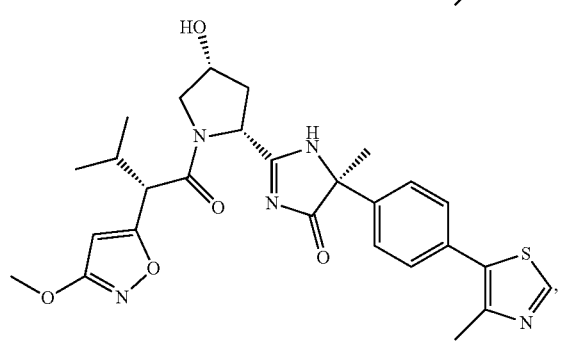
708
-continued
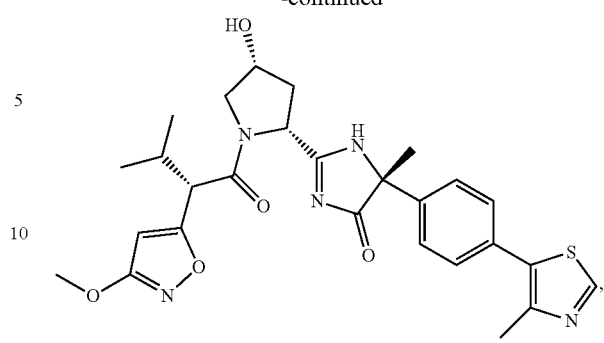
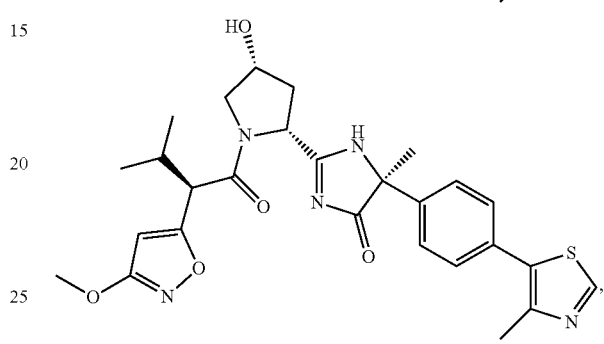
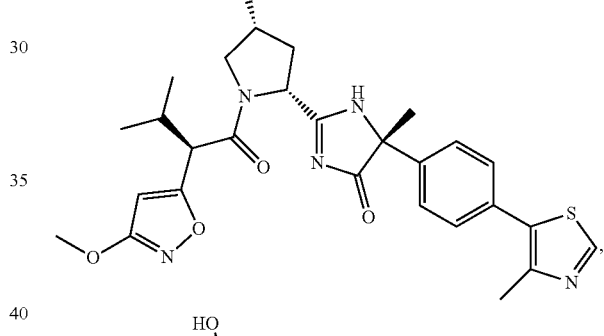
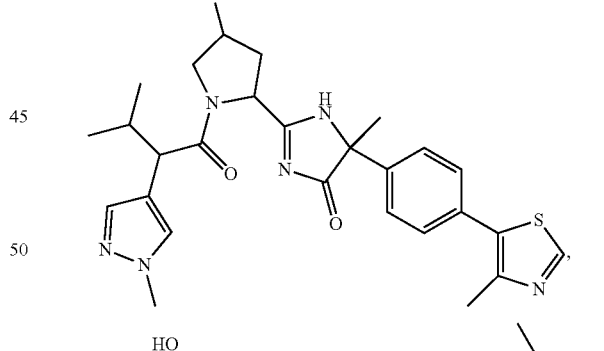
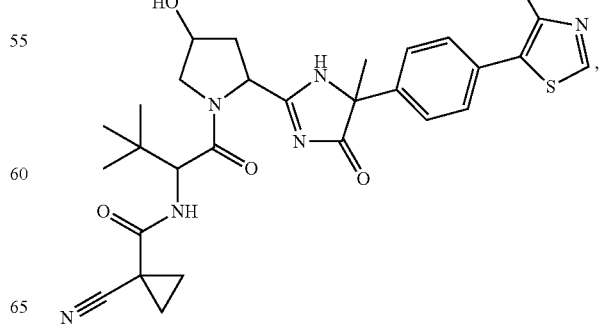

709
-continued
710
-continued
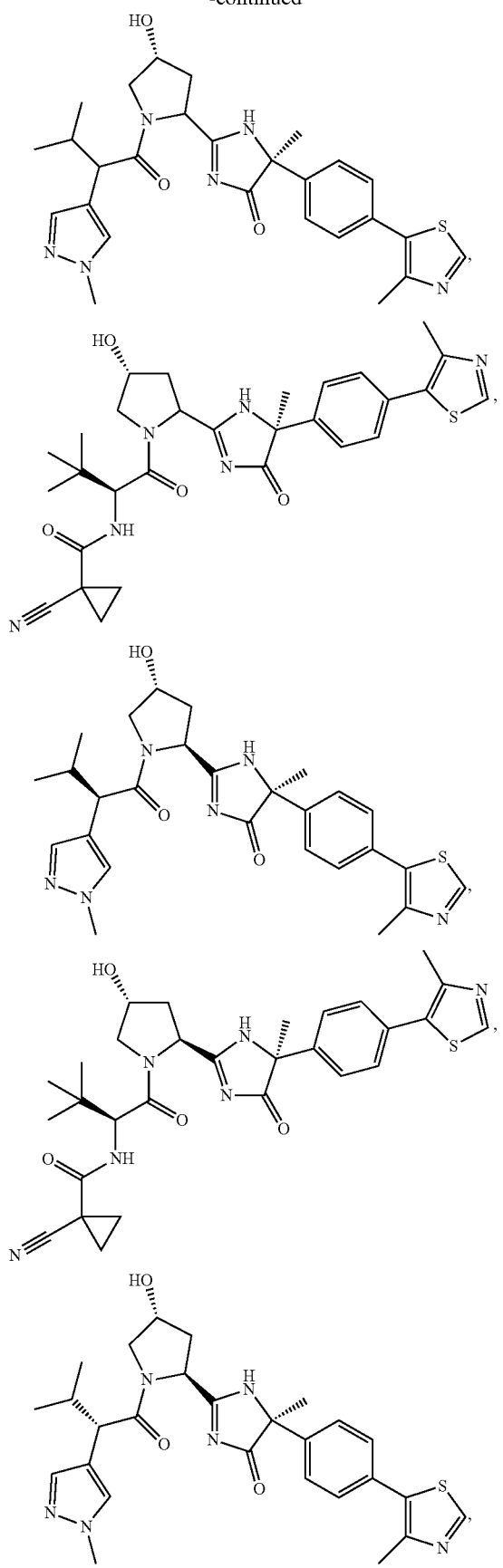
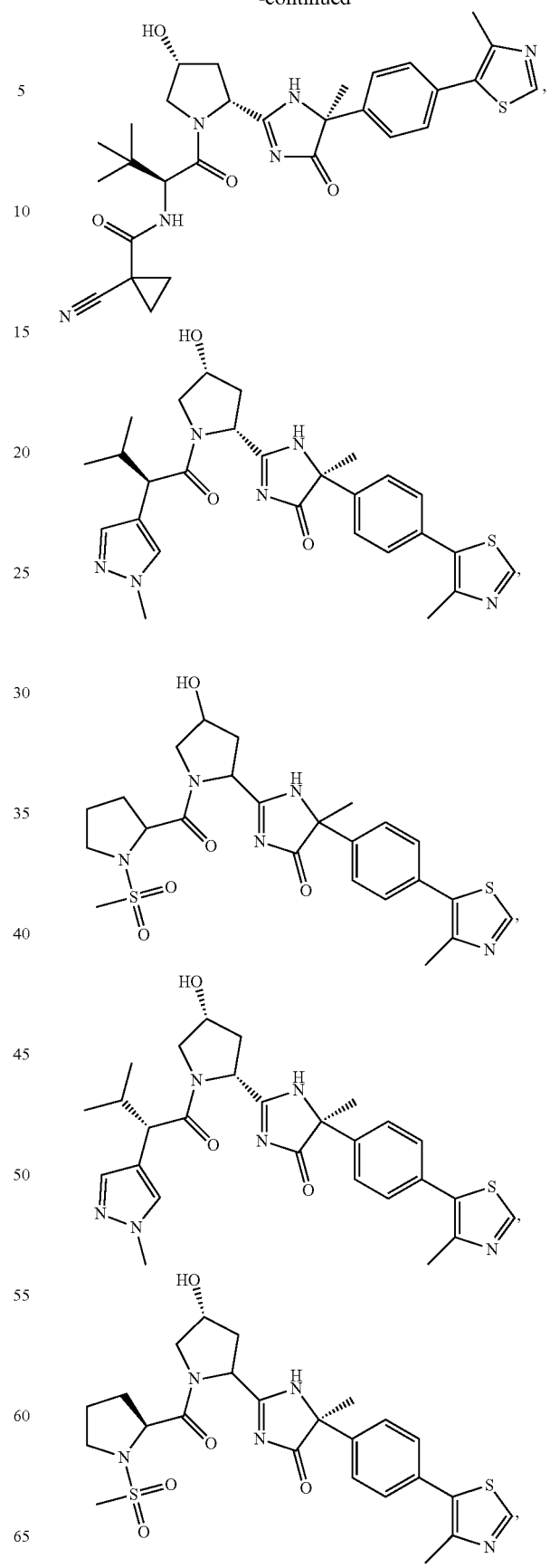

711
-continued
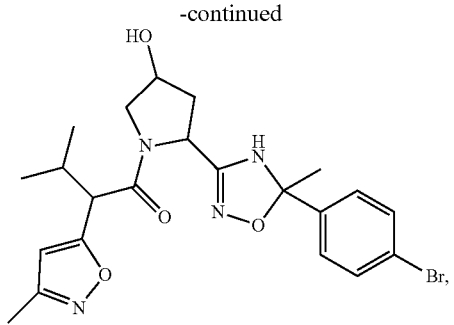
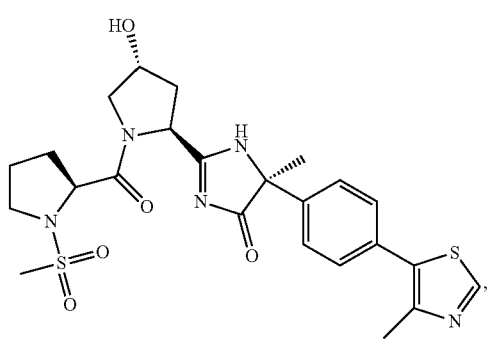
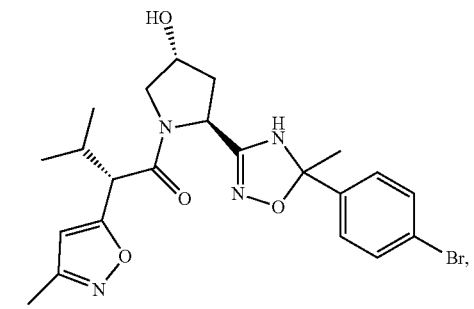
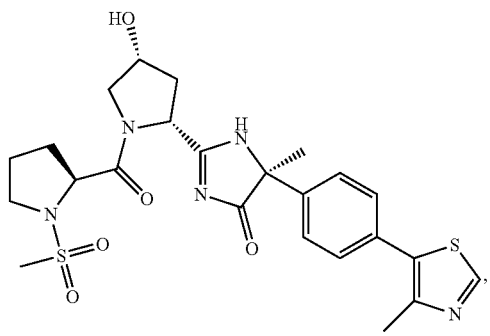
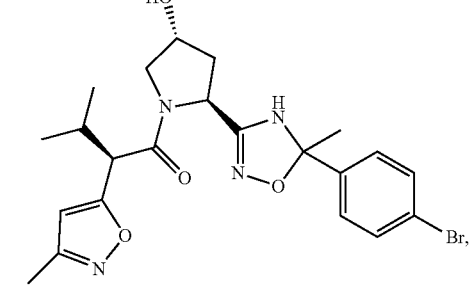
712
-continued
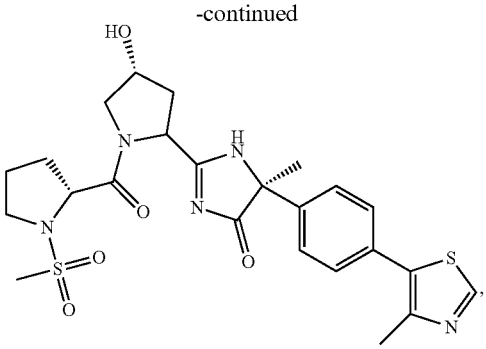
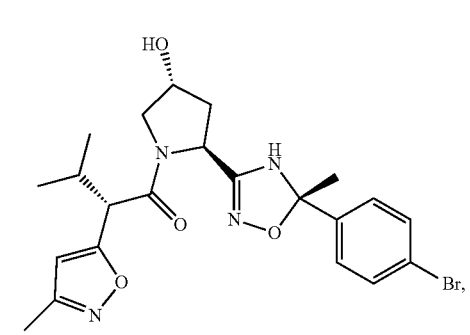
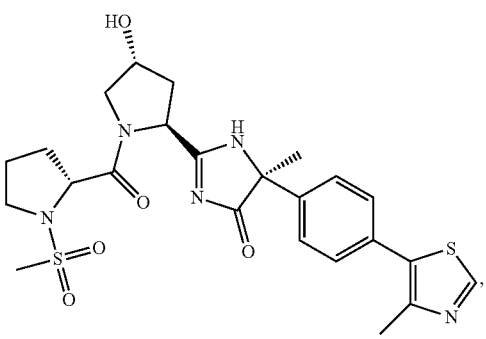
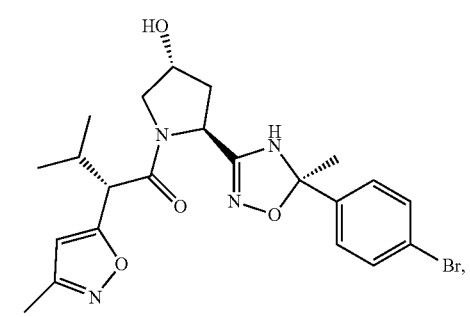
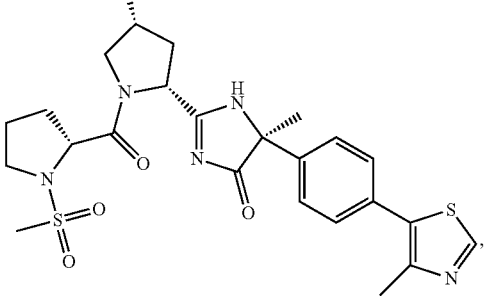

713
-continued
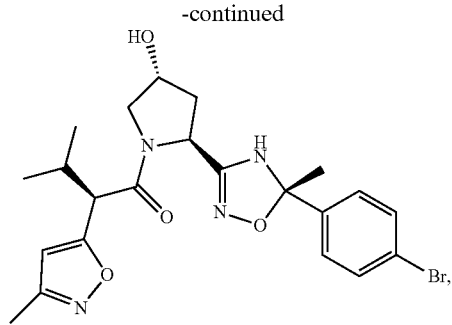
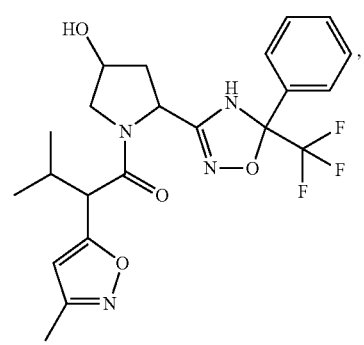
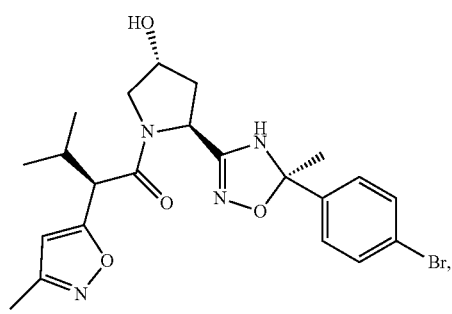
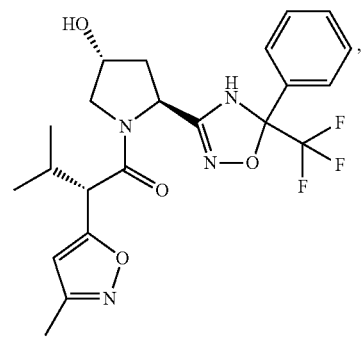
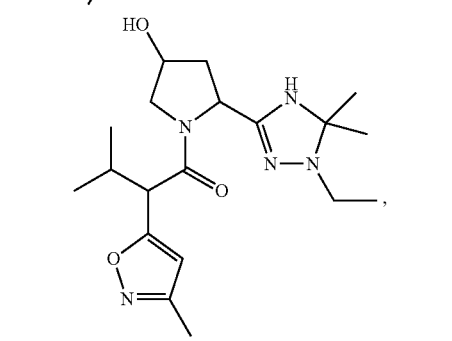
714
-continued
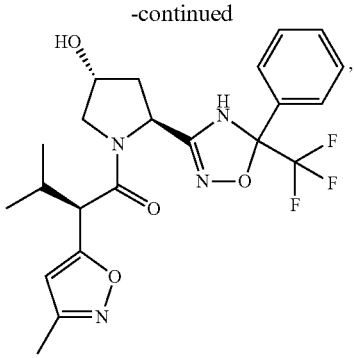
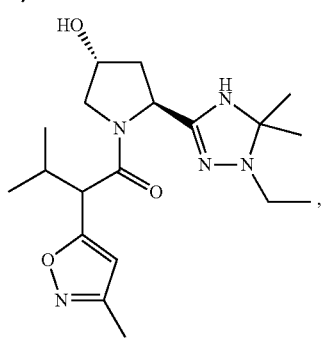
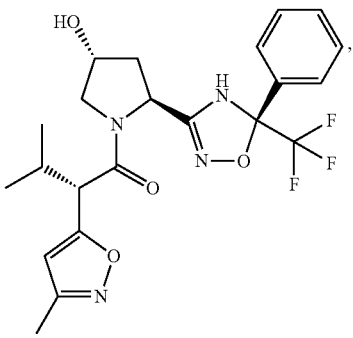
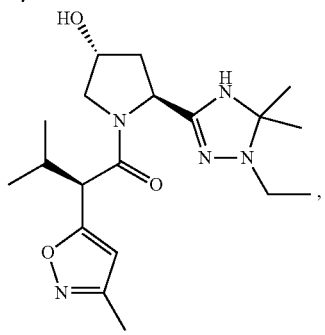
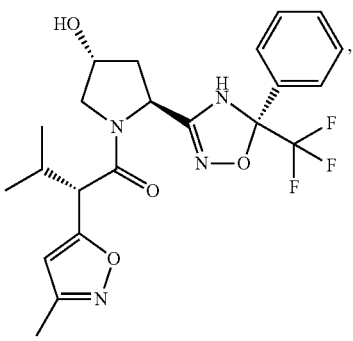

715
-continued
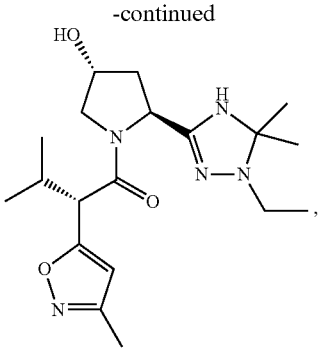
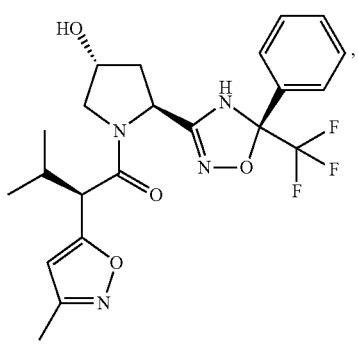
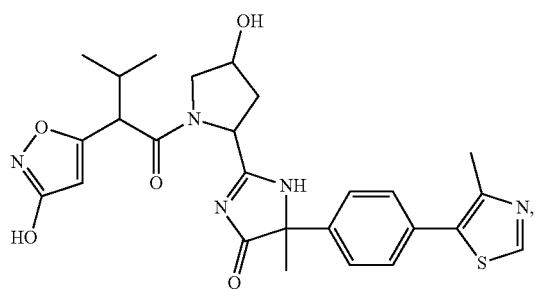
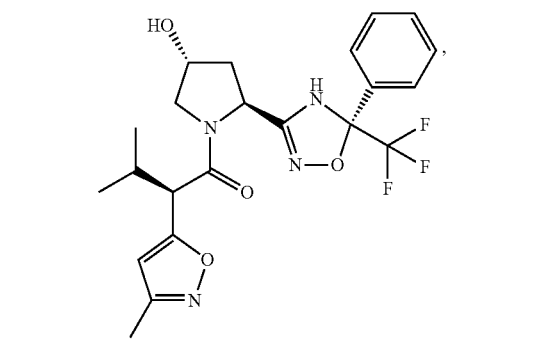
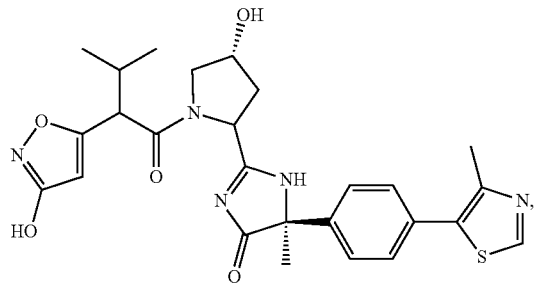
716
-continued
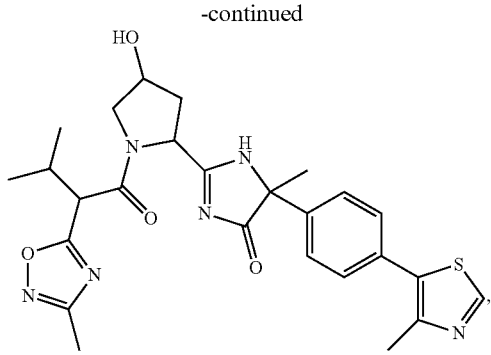
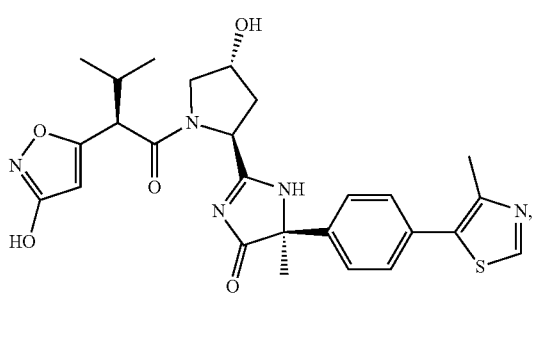
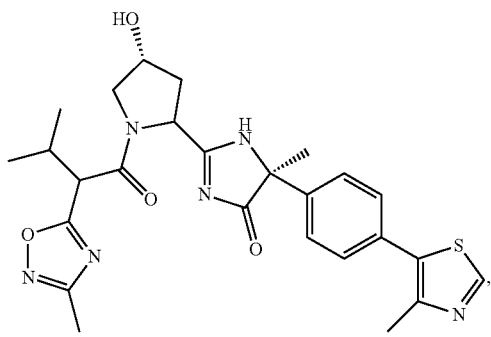
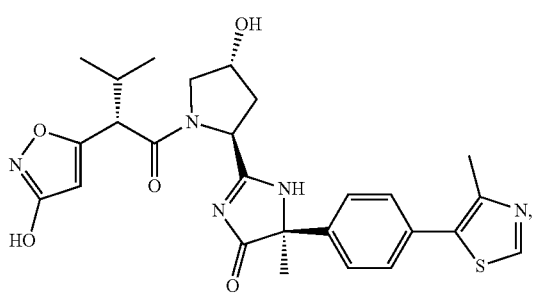
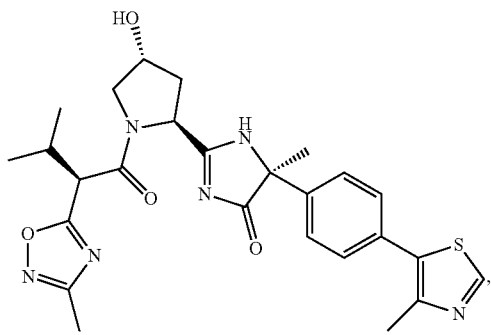

717
-continued
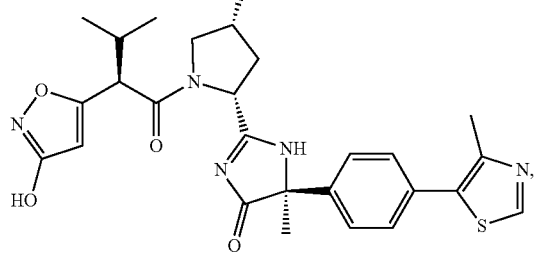
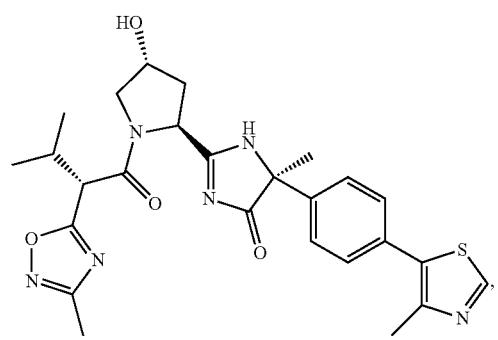
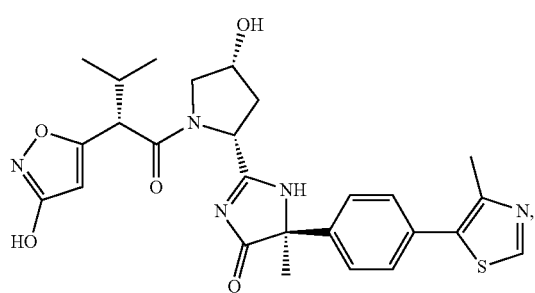
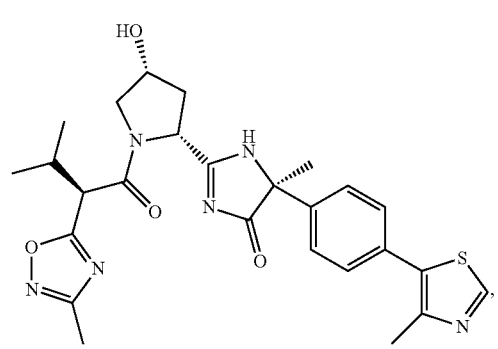
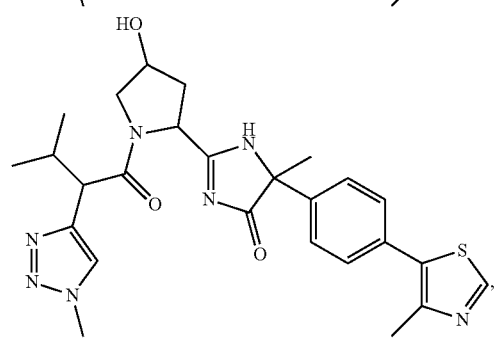
718
-continued
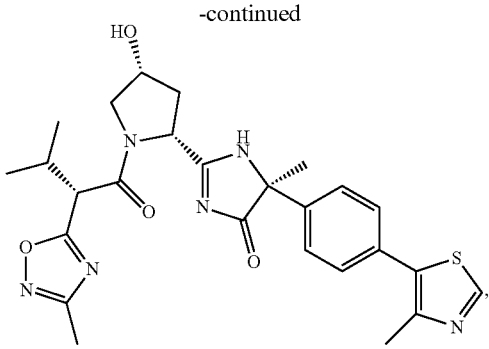
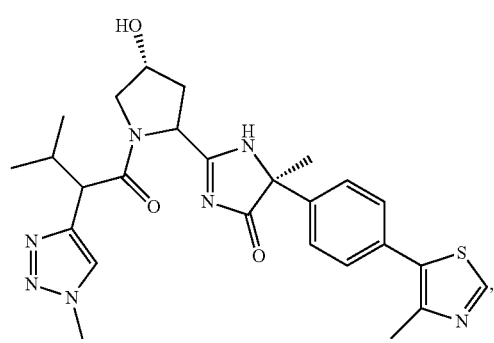
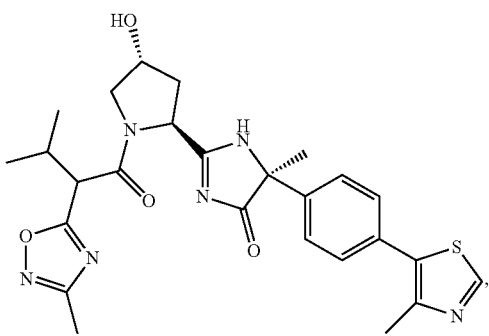
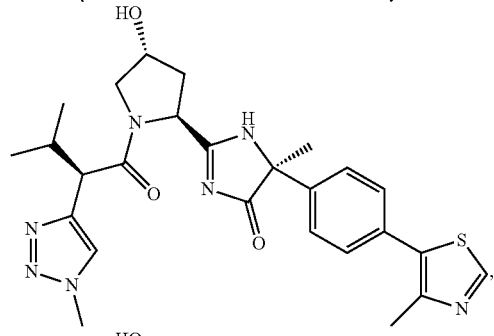
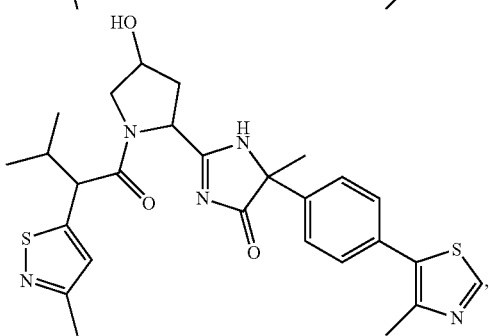

719
-continued
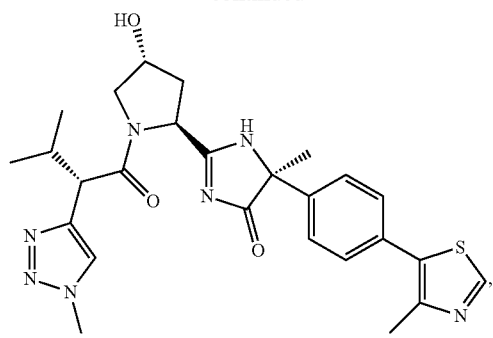
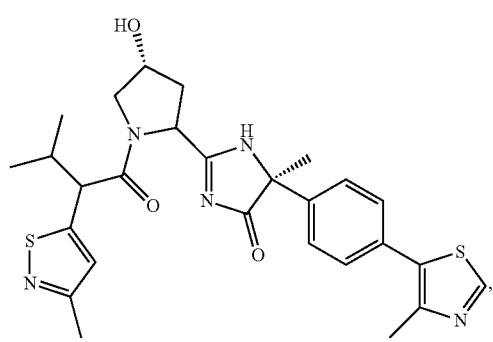
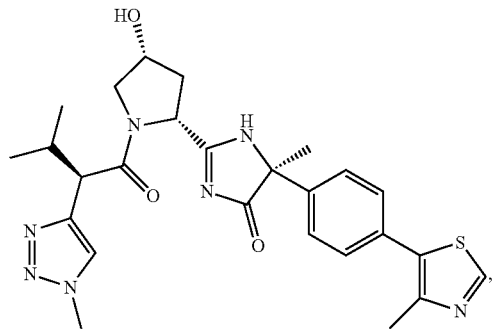
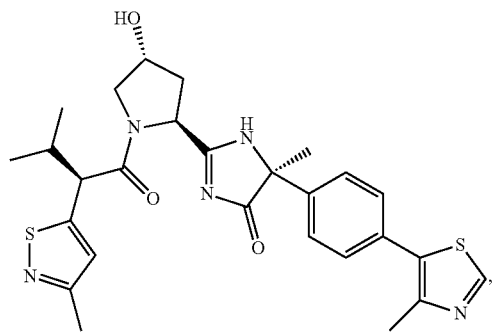
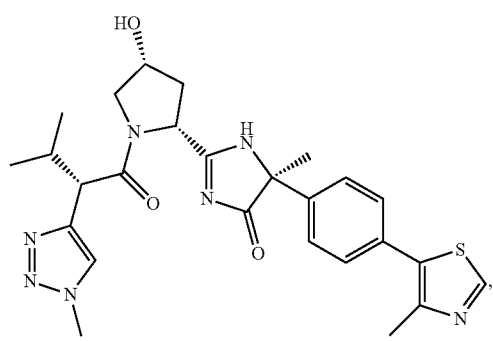
720
-continued
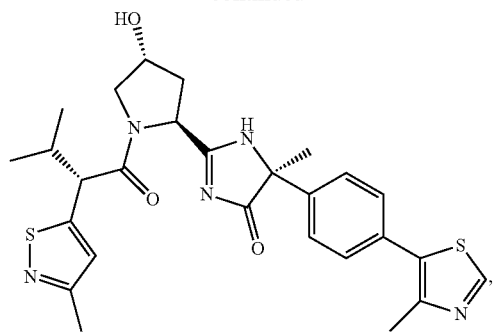
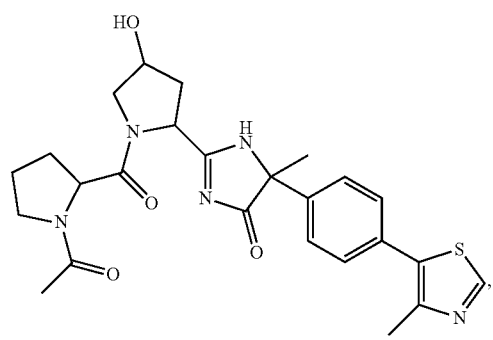
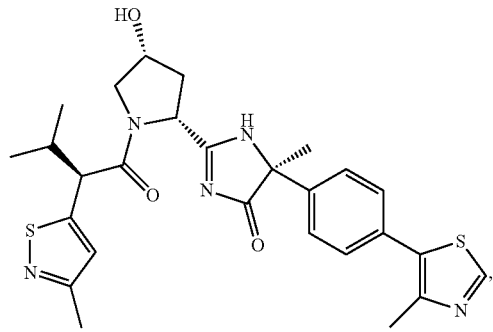
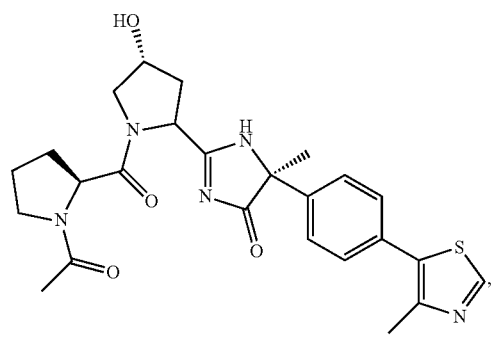
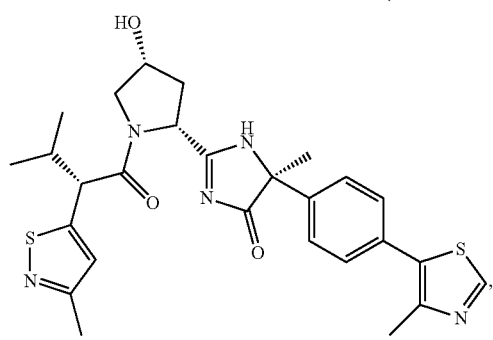

721
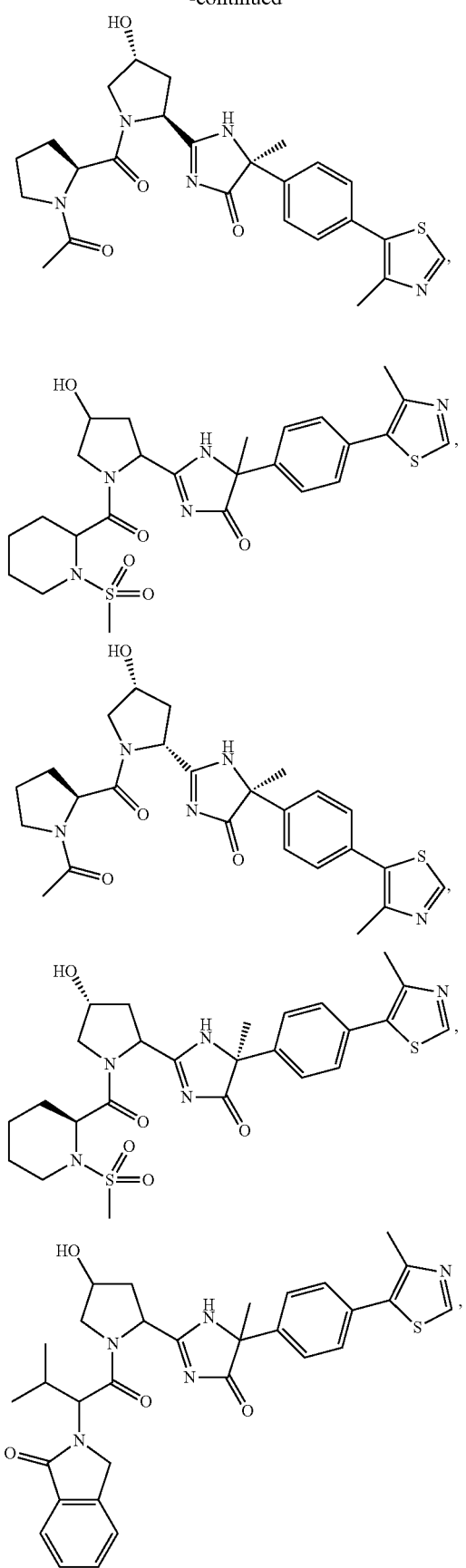
722
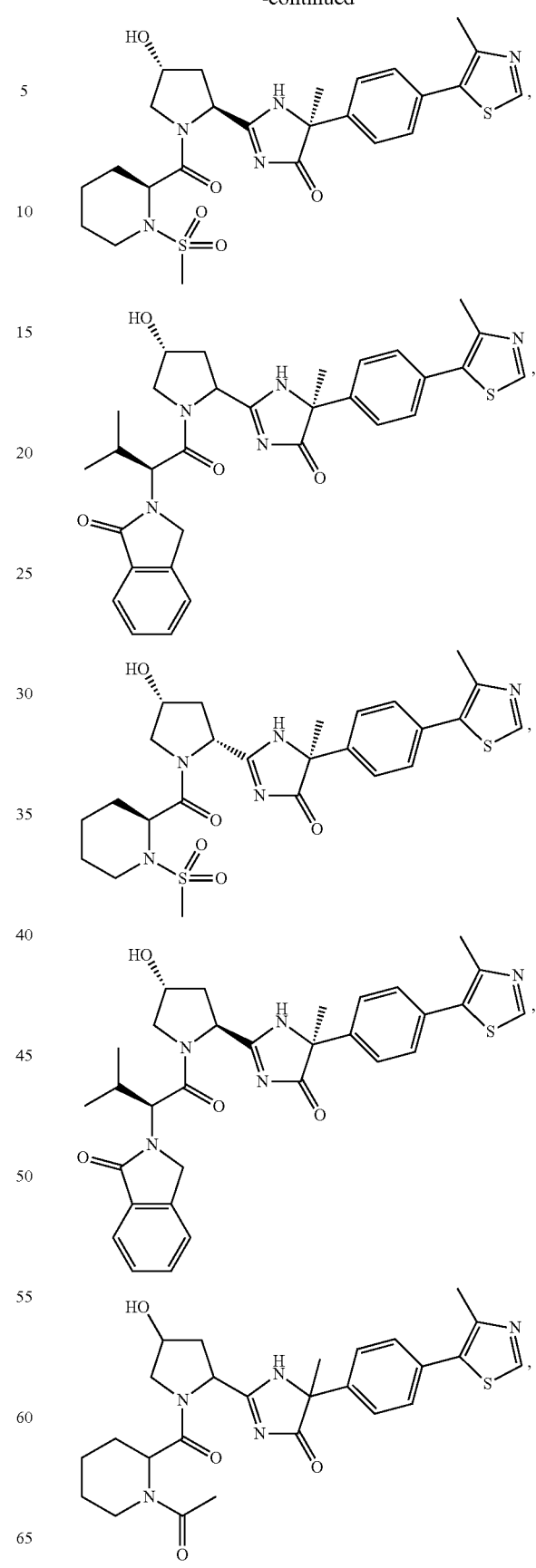

723
-continued
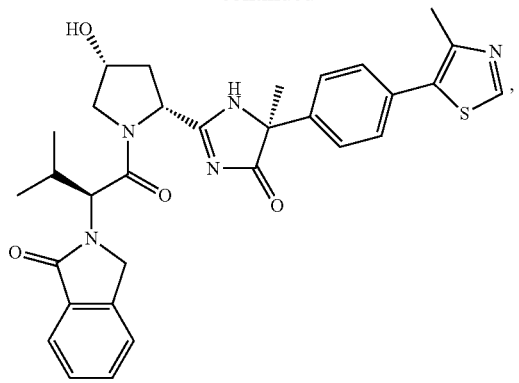
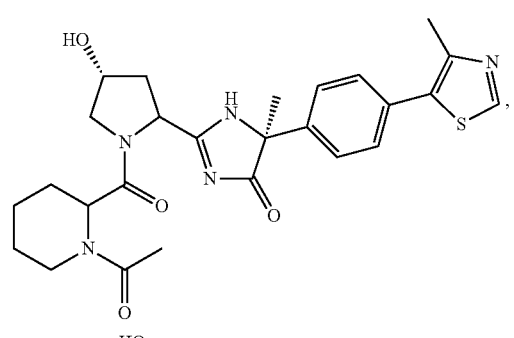
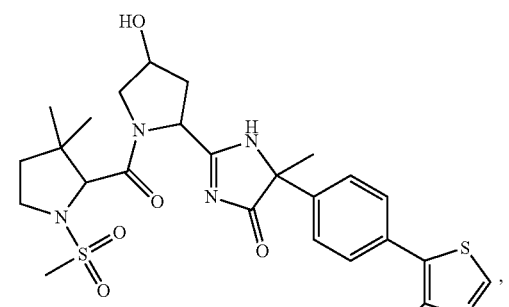
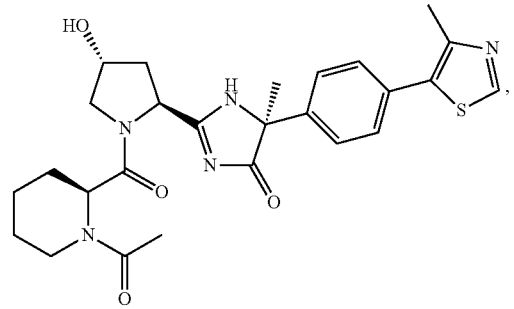
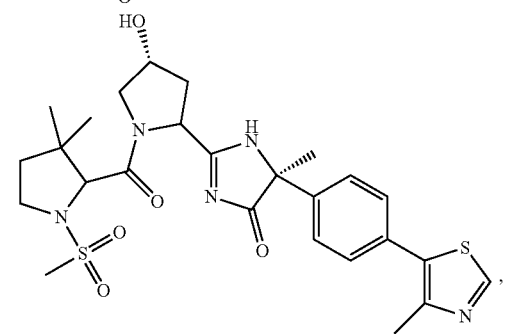
724
-continued
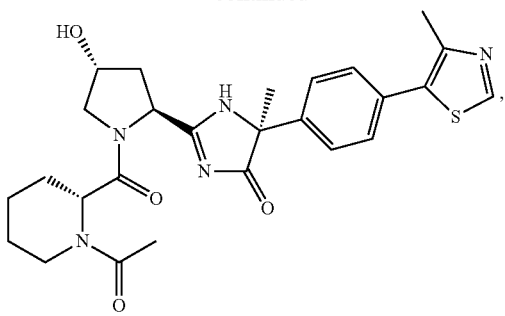
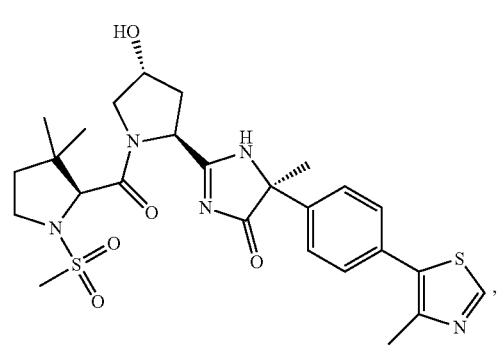
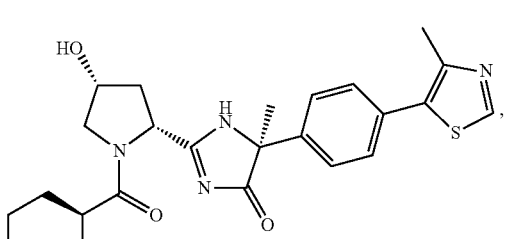
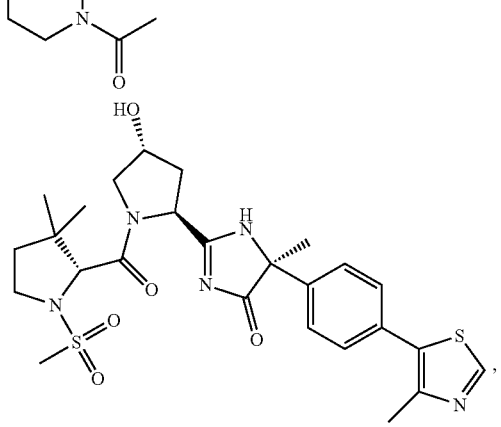
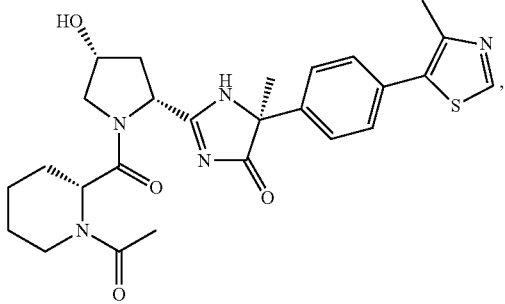

725
-continued
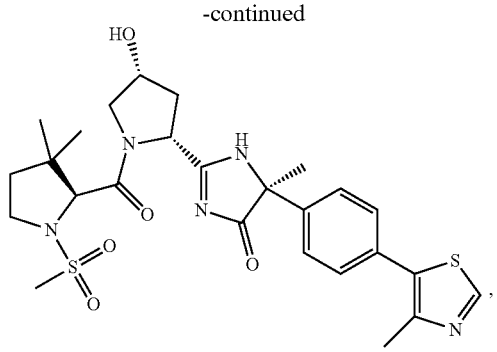
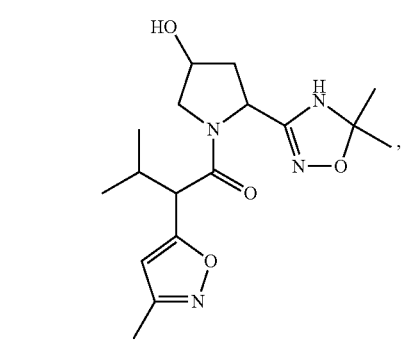
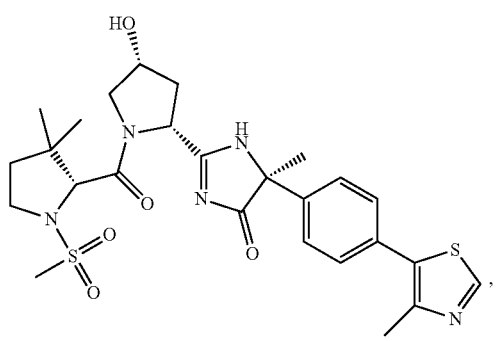
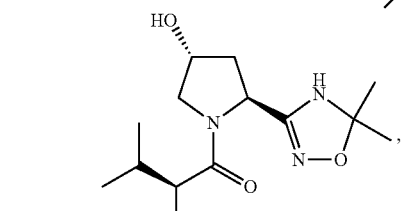
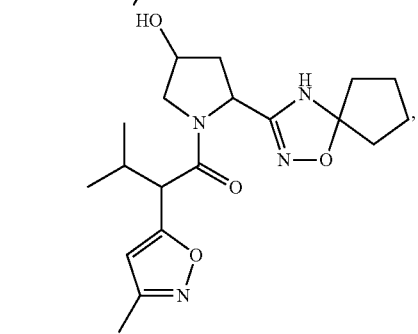
726
-continued
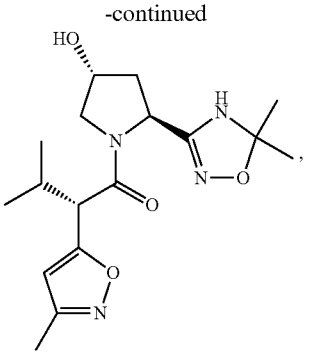
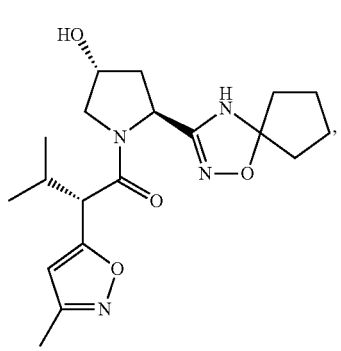
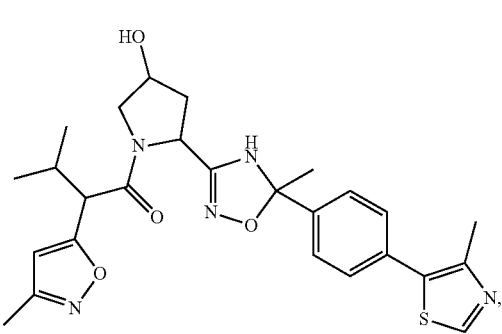
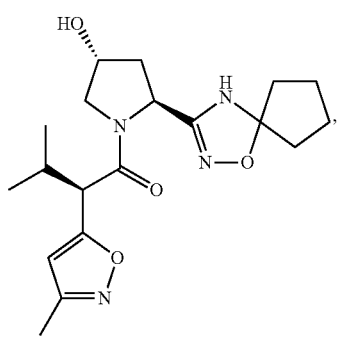
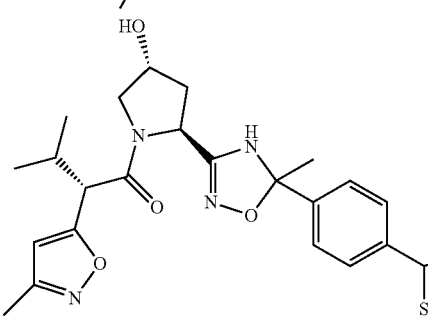

727
-continued
728
-continued
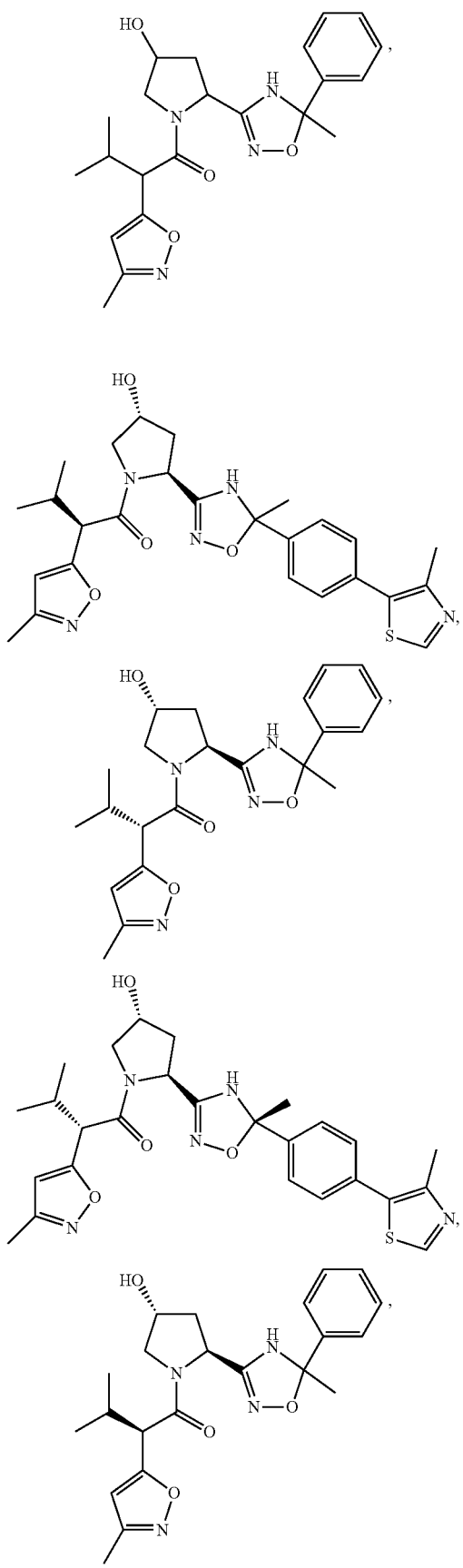
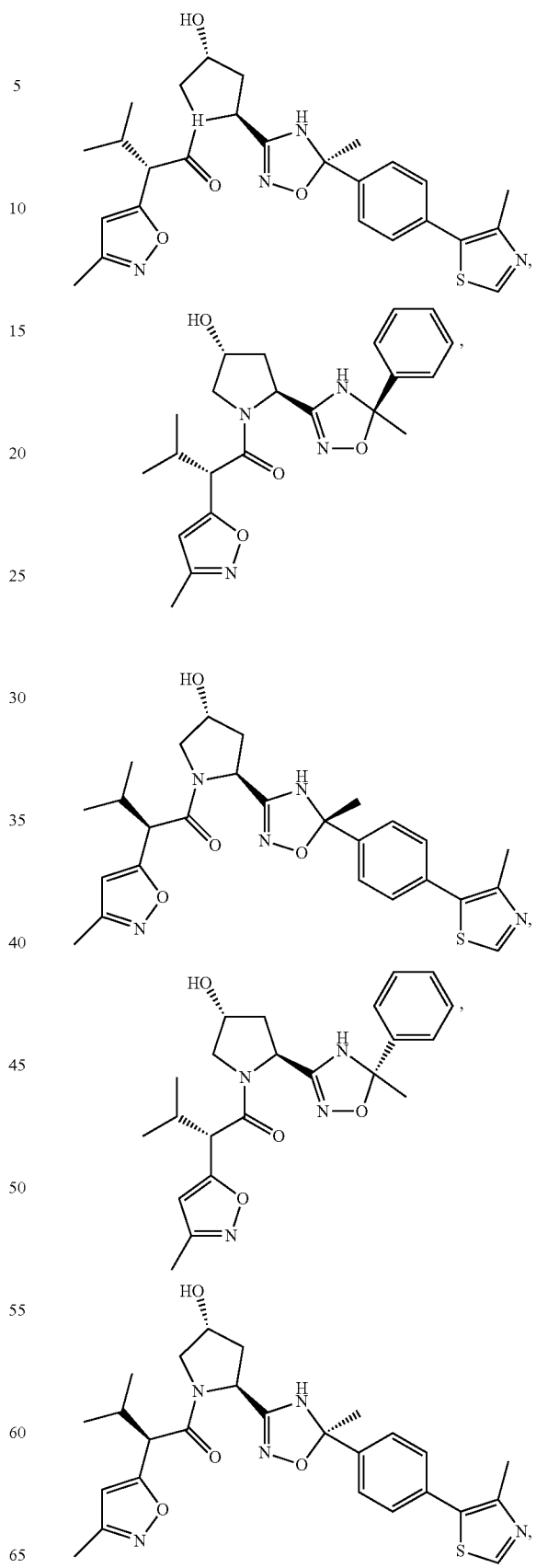

729
-continued
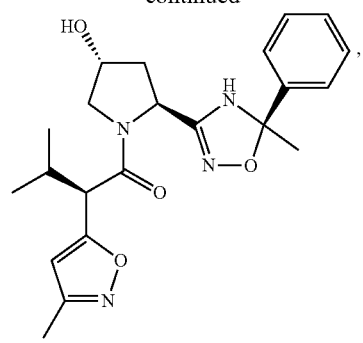,
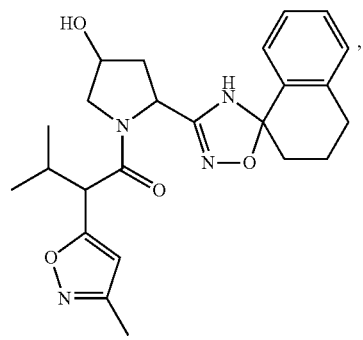,
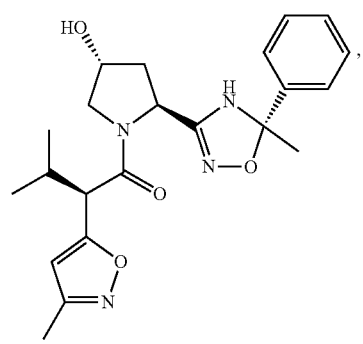,
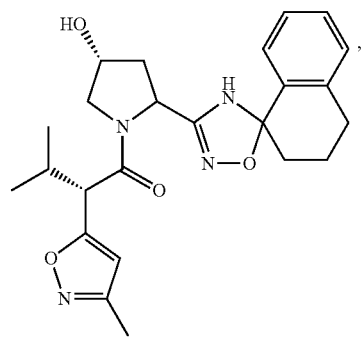,
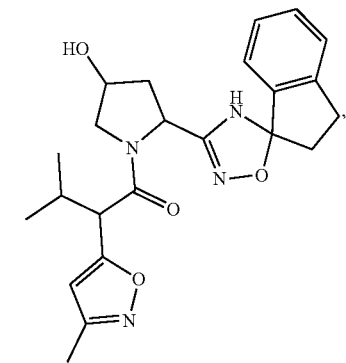,
730
-continued
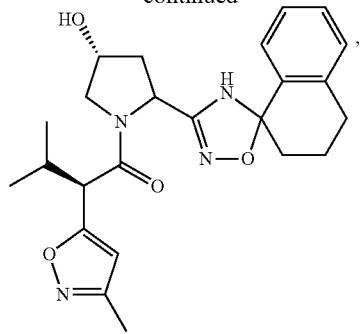,
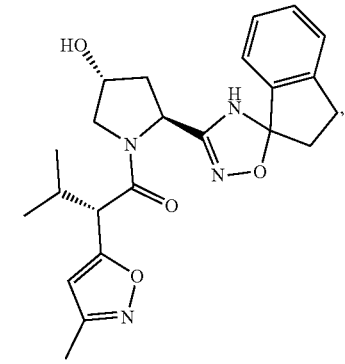,
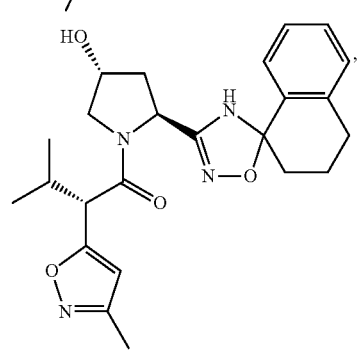,
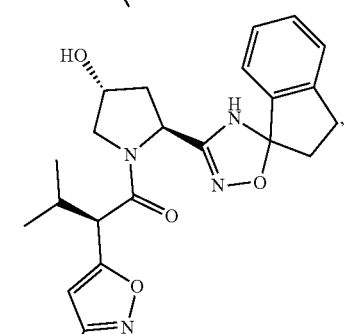,
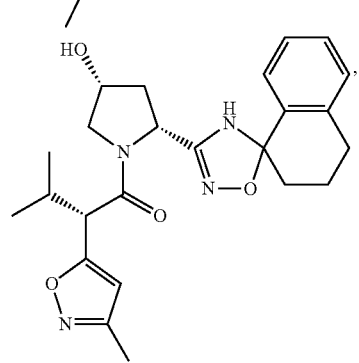, 731
-continued
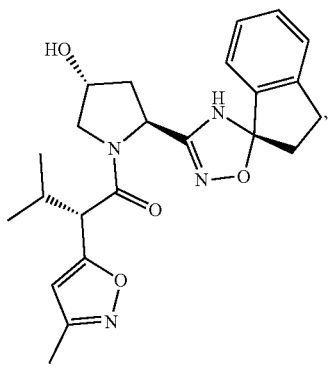
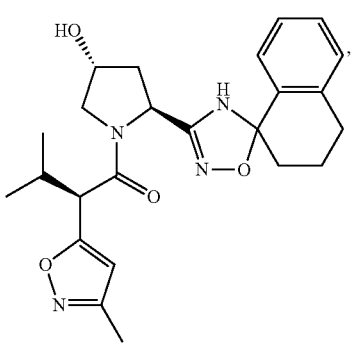
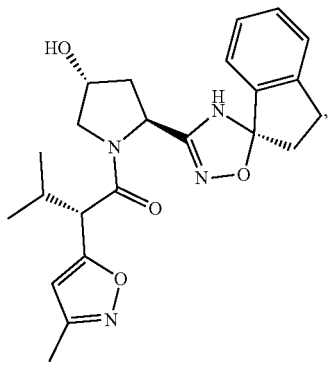
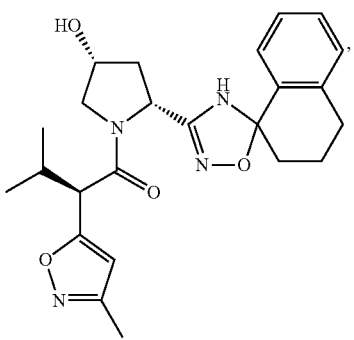
732
-continued
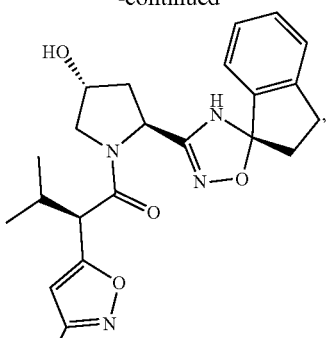
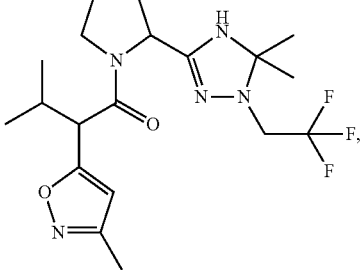
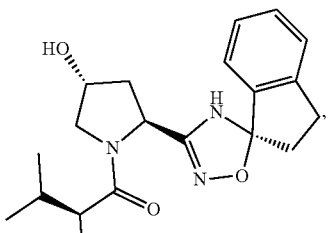
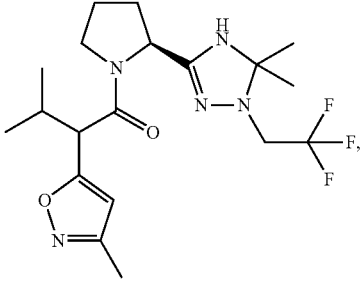
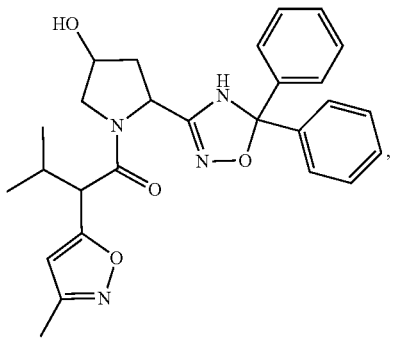

733
-continued
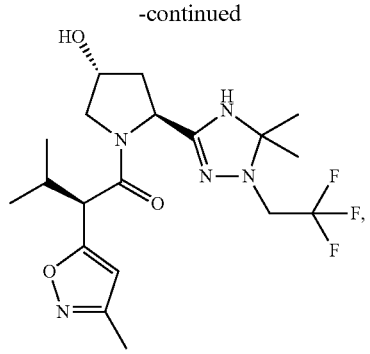
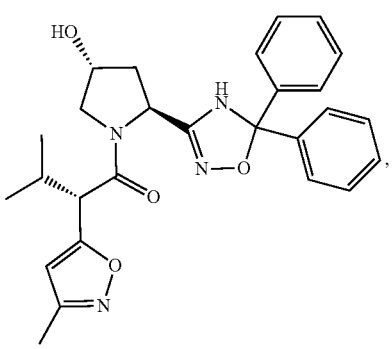
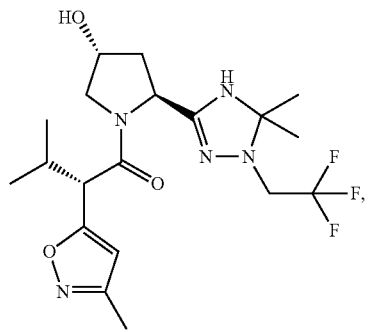
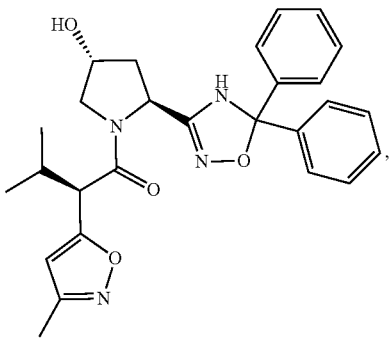
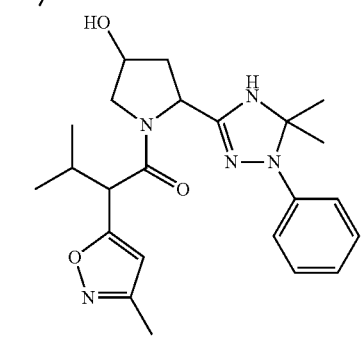
734
-continued
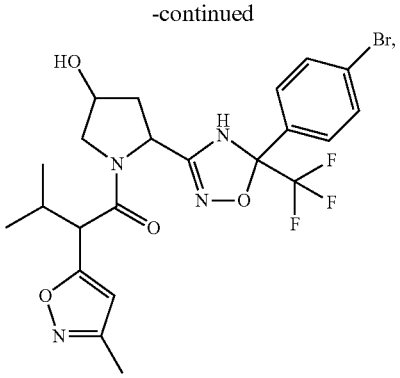
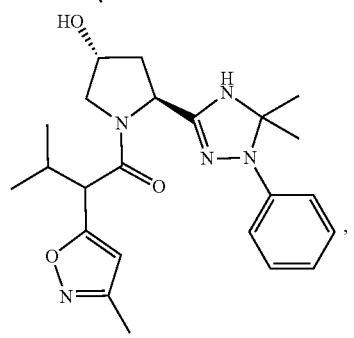
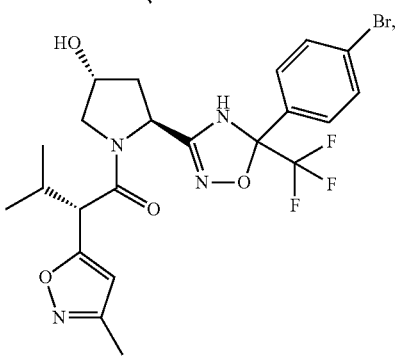
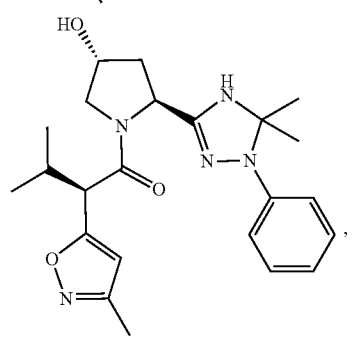
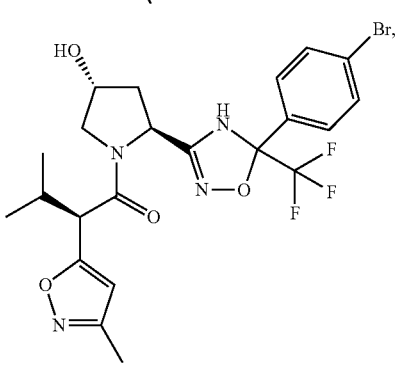

735
-continued
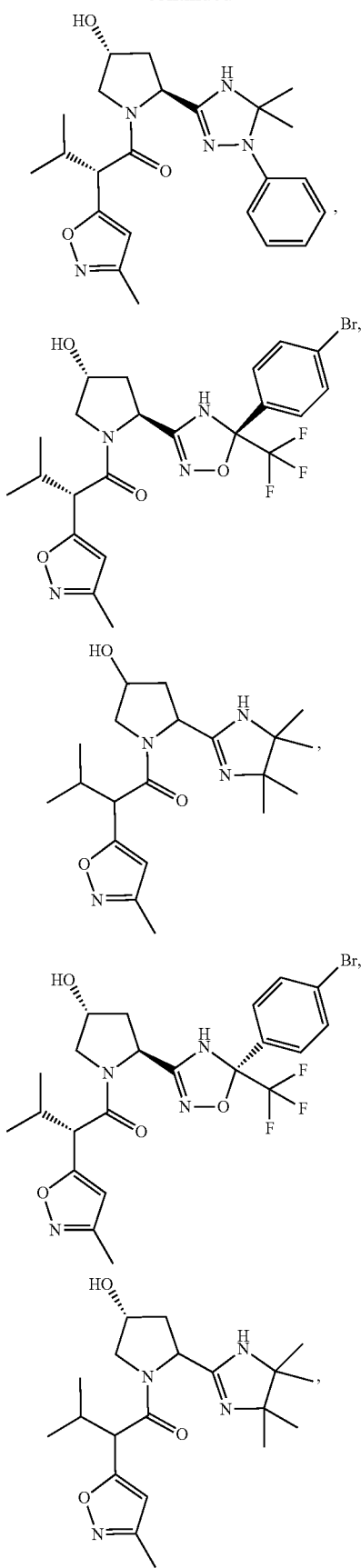
736
-continued
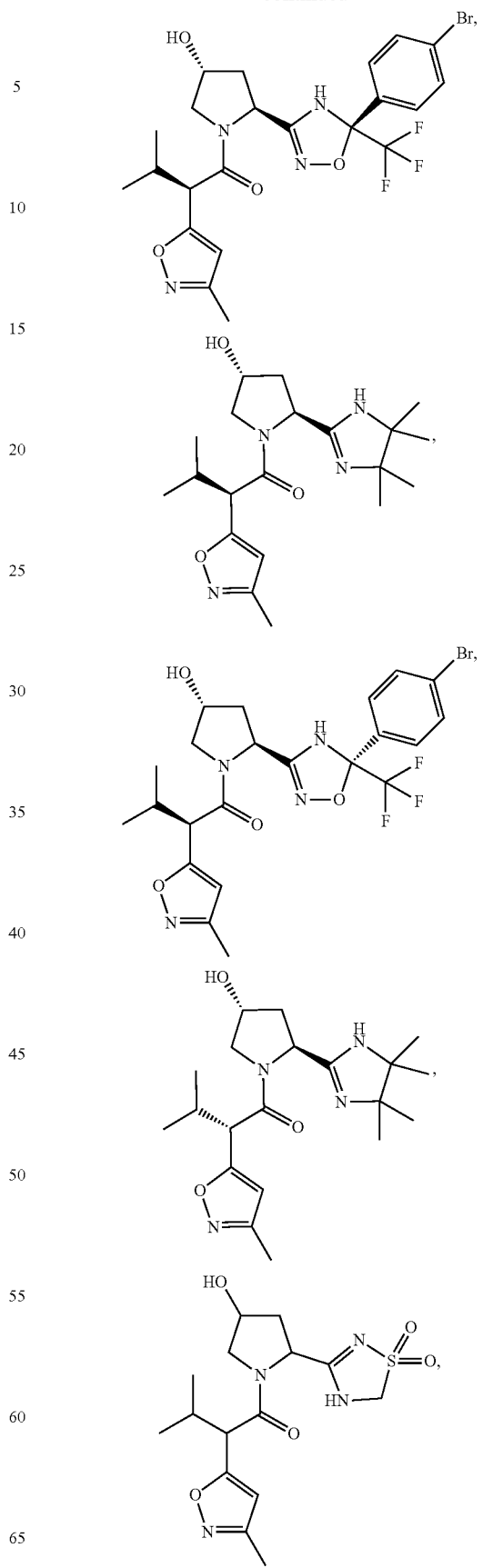

737
-continued
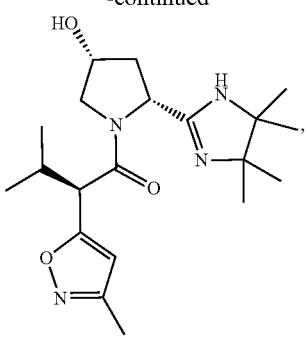
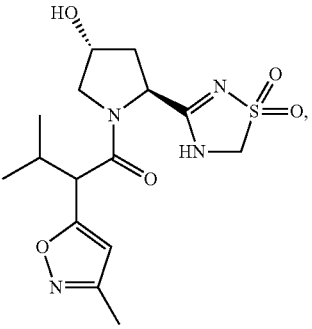
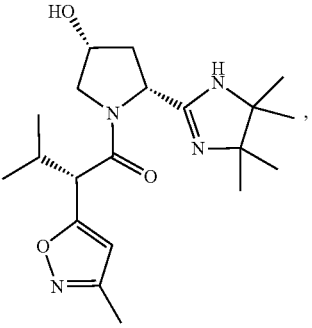
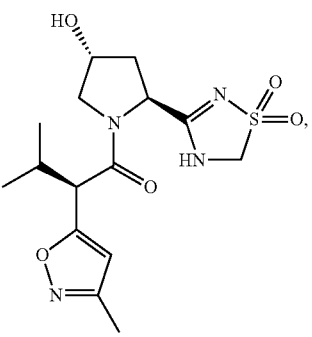
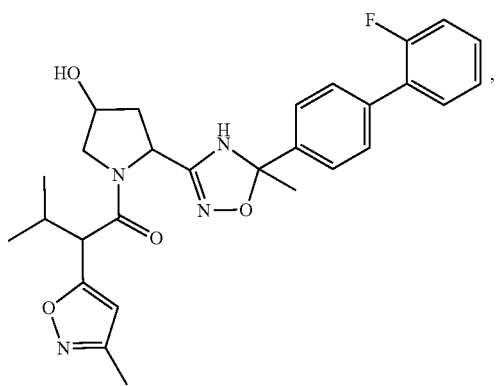
738
-continued
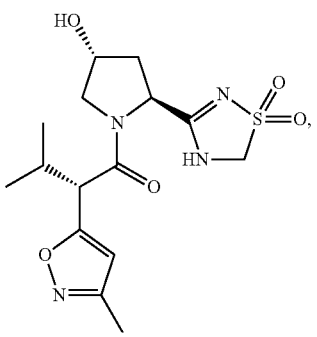
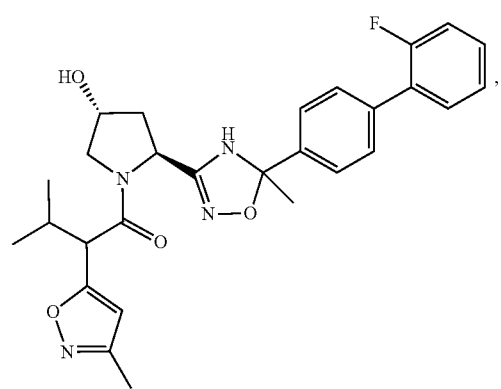
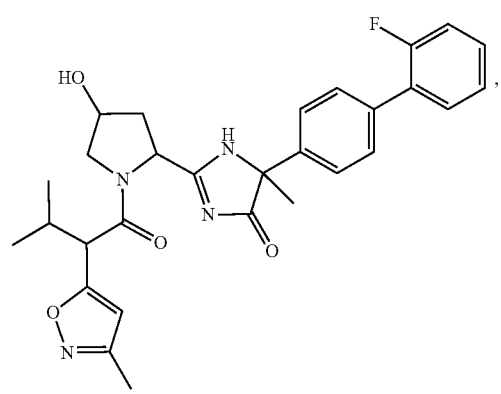
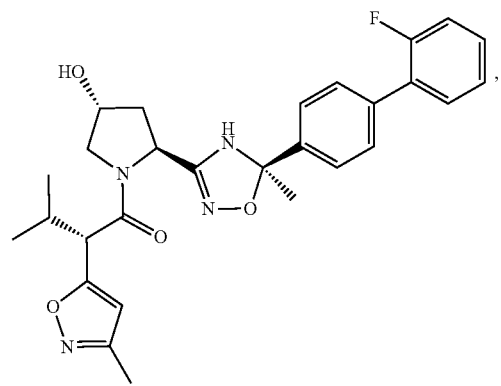

-continued
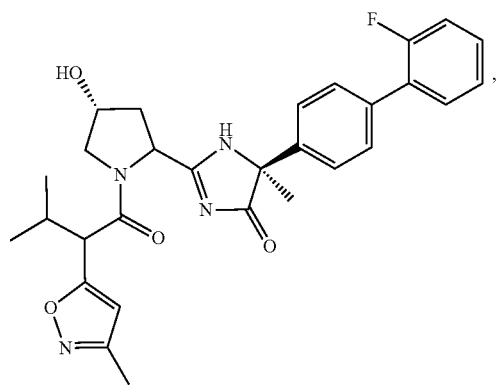
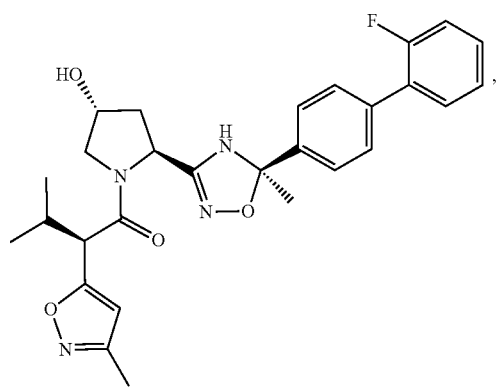
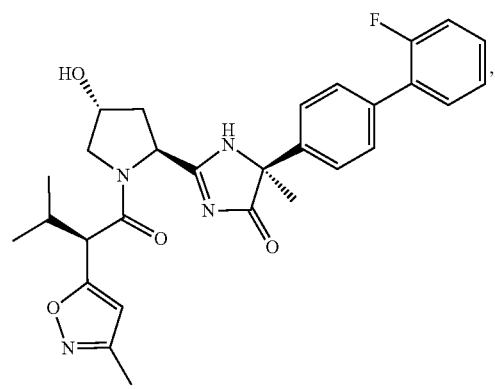
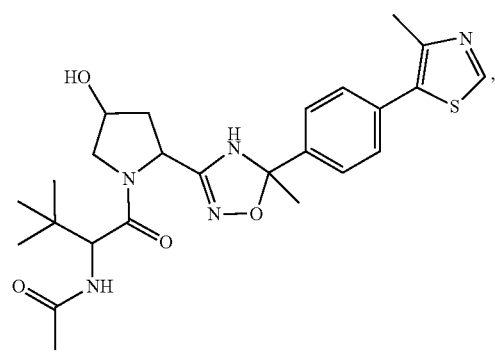
-continued
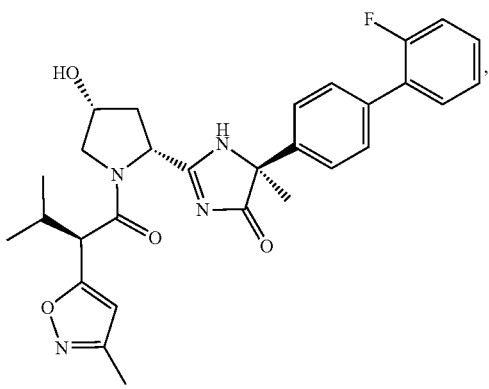
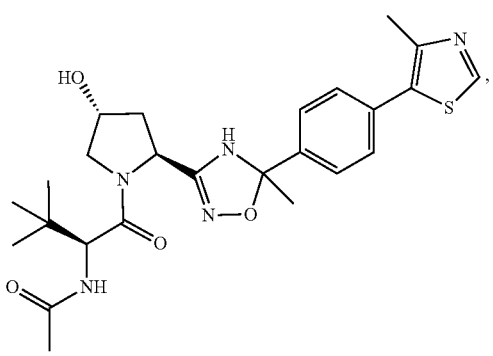
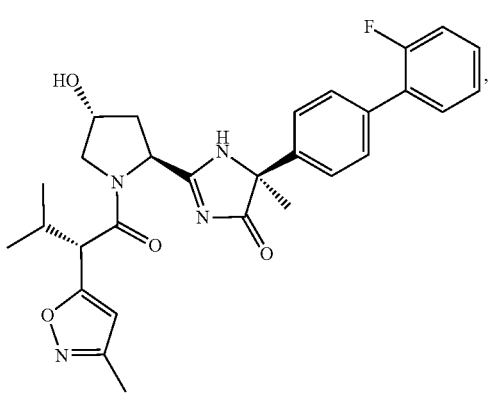
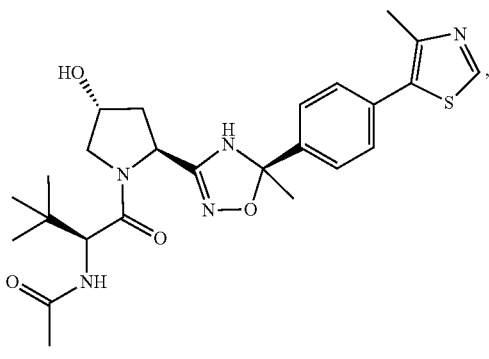

741
-continued
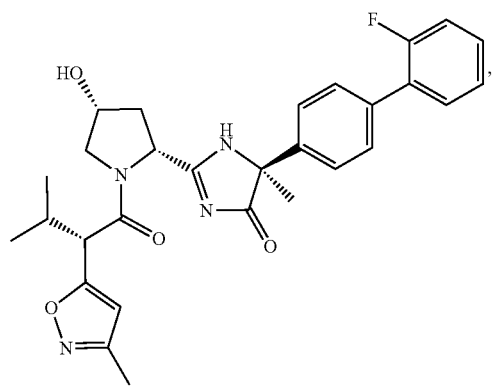
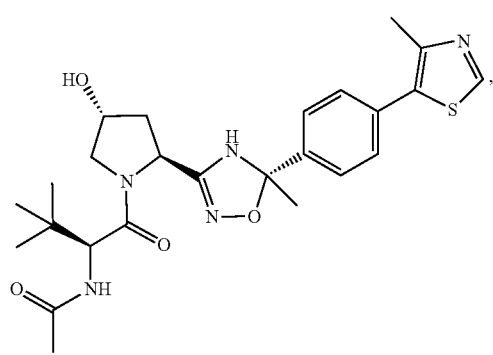
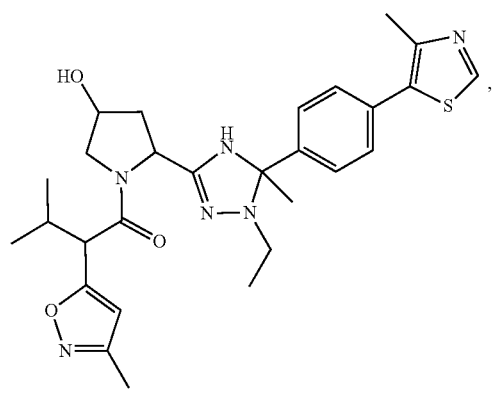
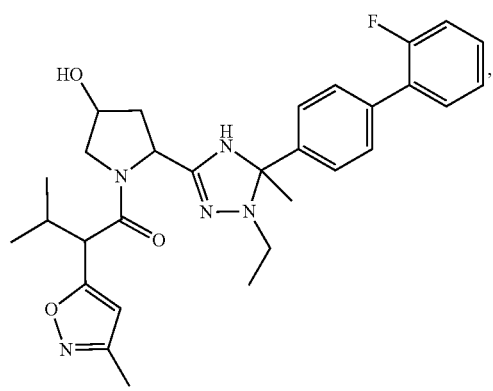
742
-continued
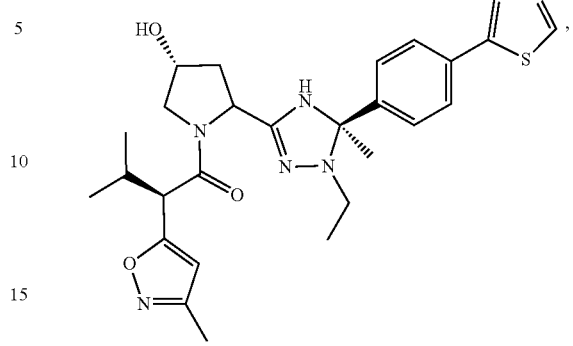
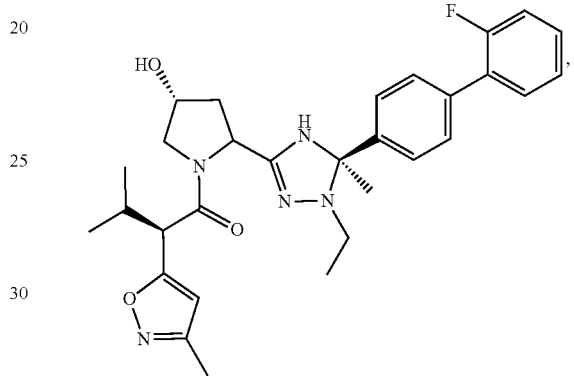
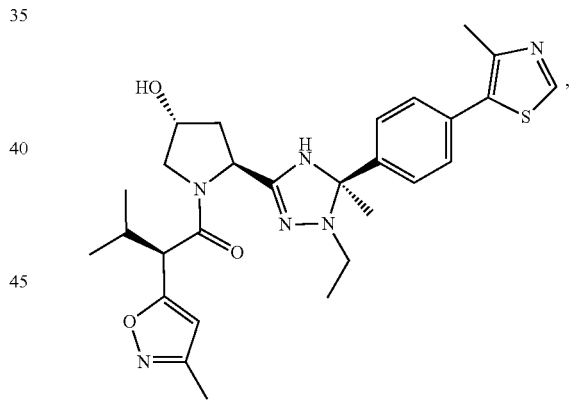
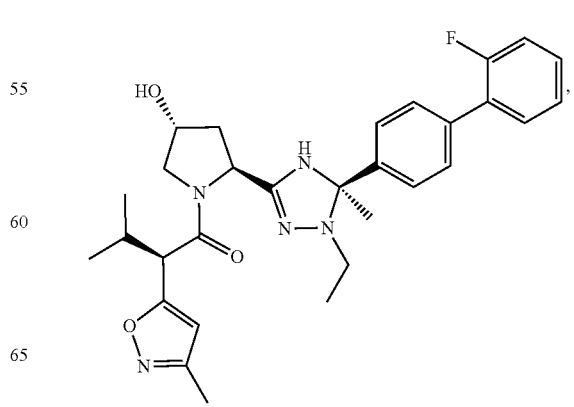

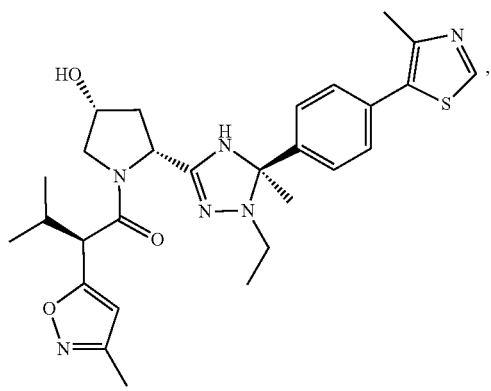
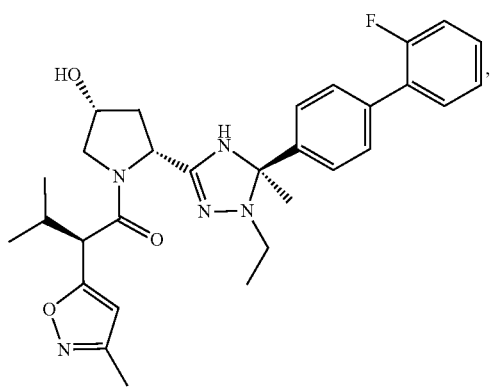
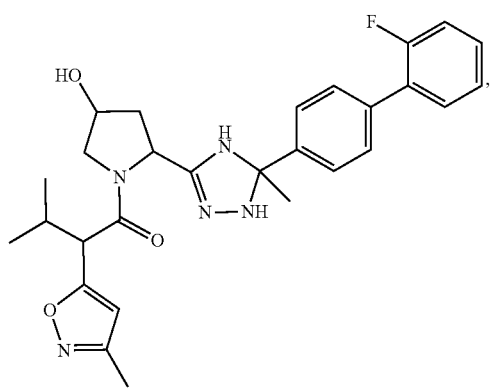
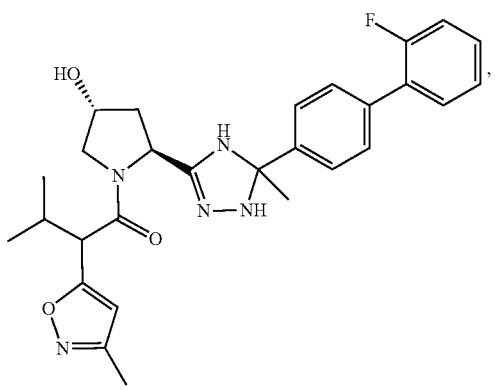 [SMILES: Cc1cc([C@@H](C(=O)N2C[C@H](O)C[C@H]2C2=NNC(C)(c3ccc(-c4ccccc4F)cc3)N2)C(C)C)on1]
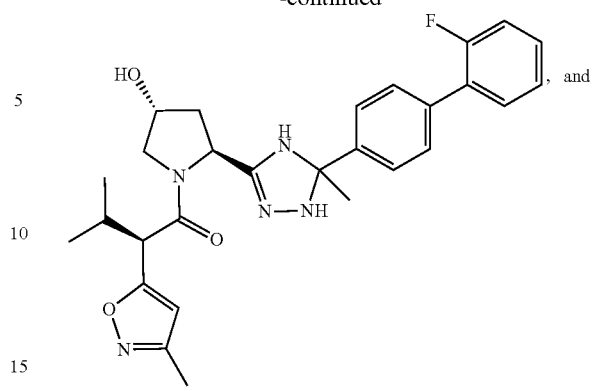
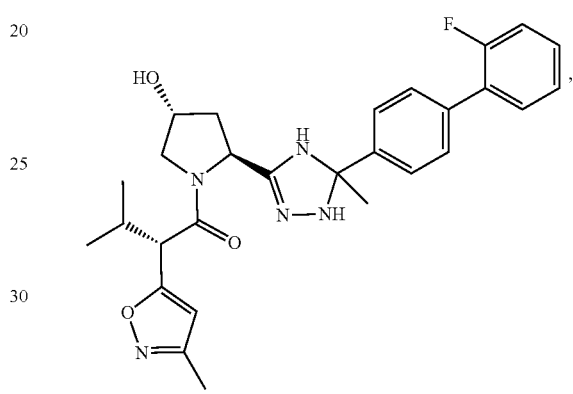
and tautomers thereof.
6. The compound of claim 1, or a pharmaceutically acceptable salt thereof, wherein the compound is selected from the group consisting of:
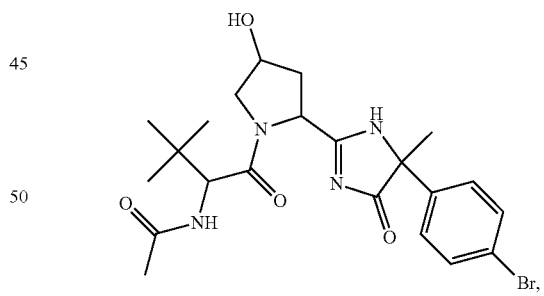
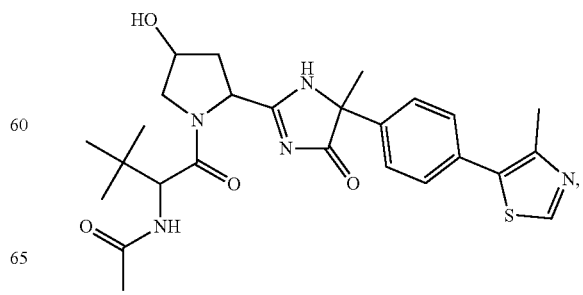

745
-continued
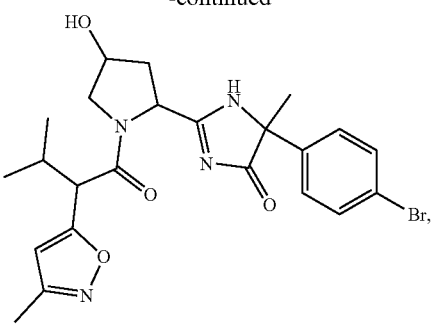
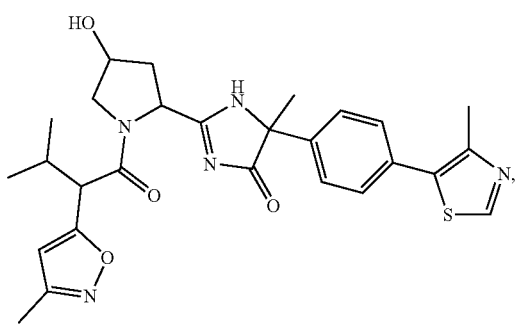
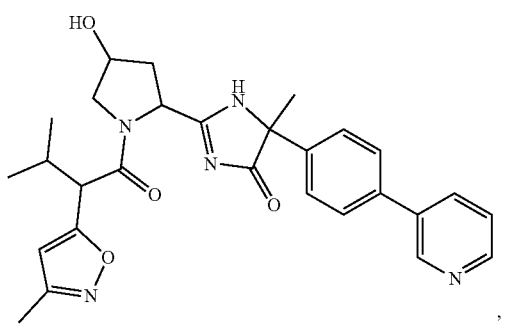
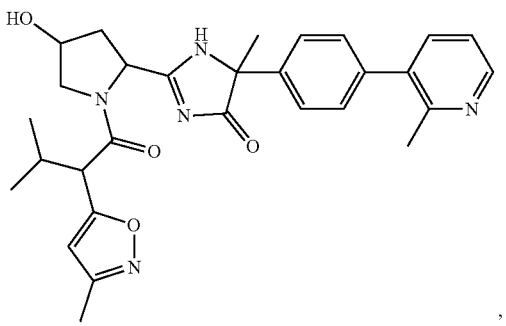
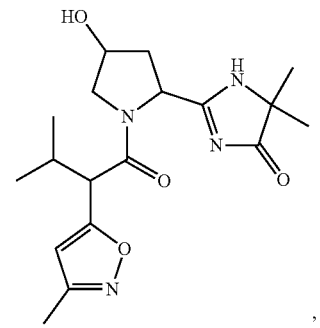
746
-continued
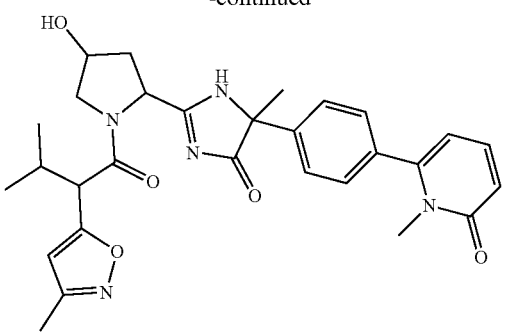
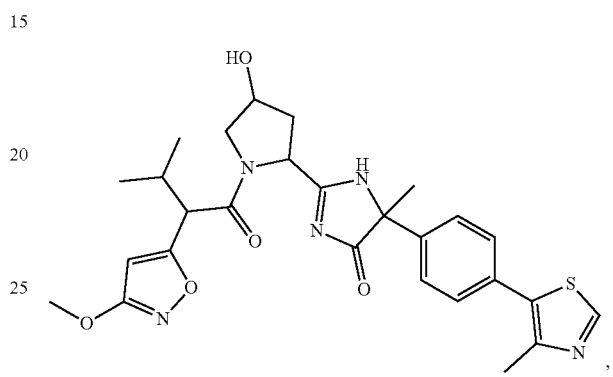
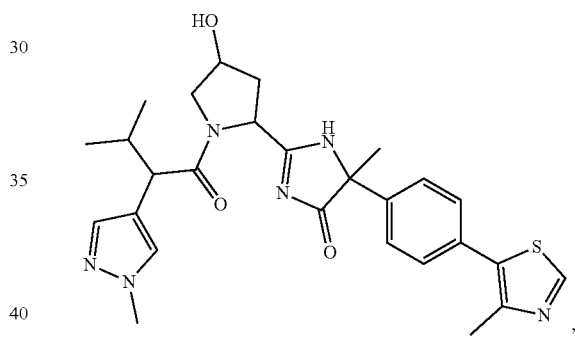
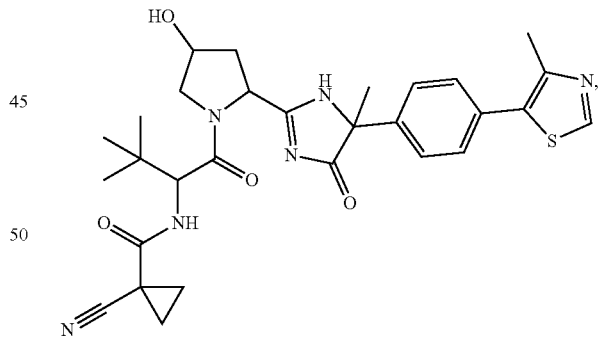
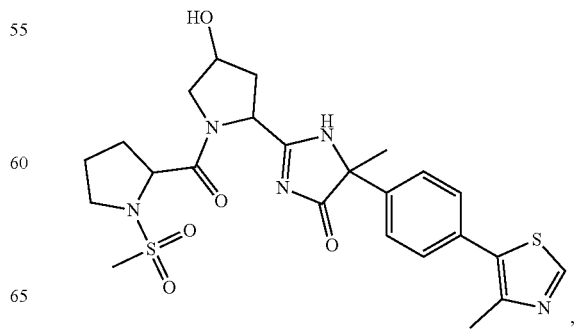

747
-continued
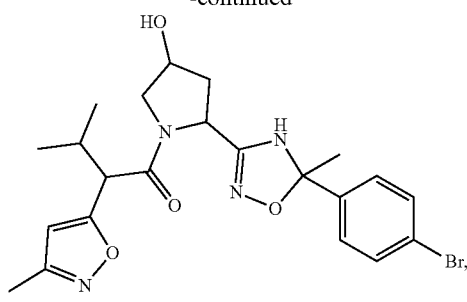
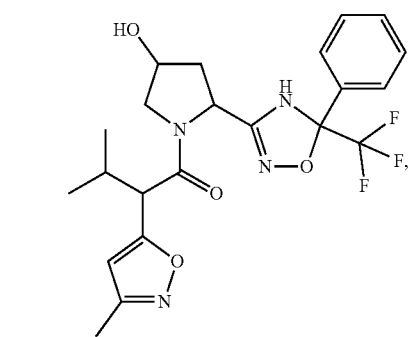
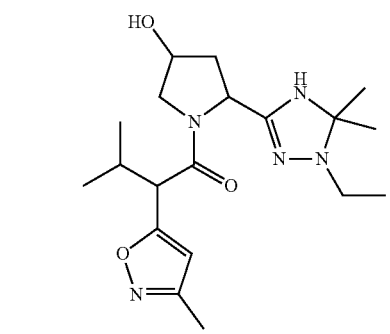
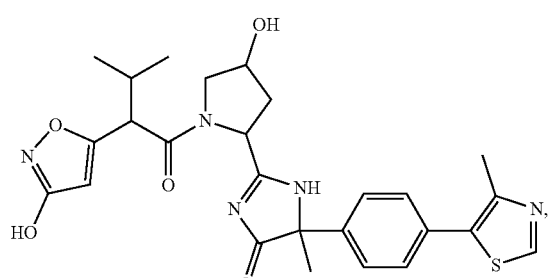
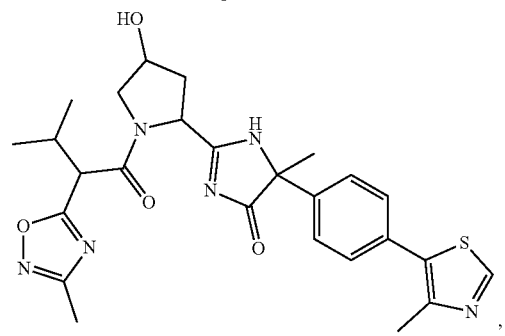
748
-continued
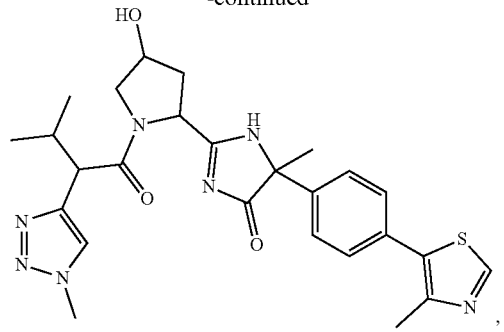
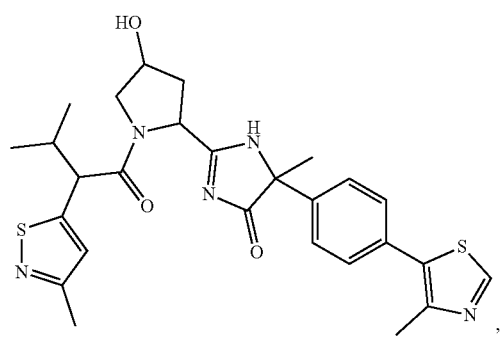
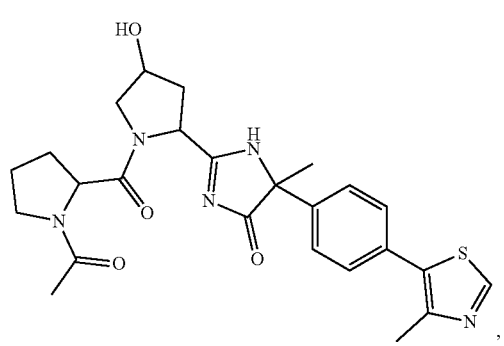
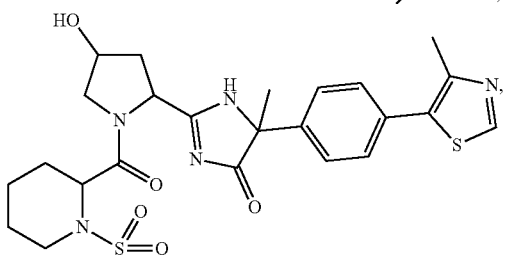
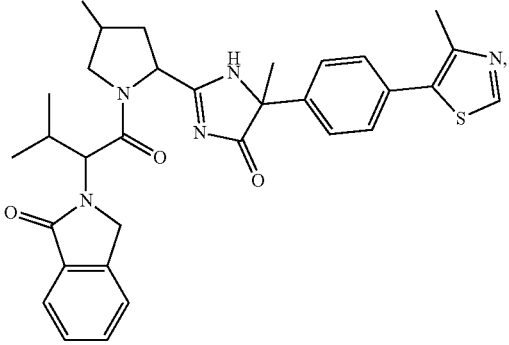

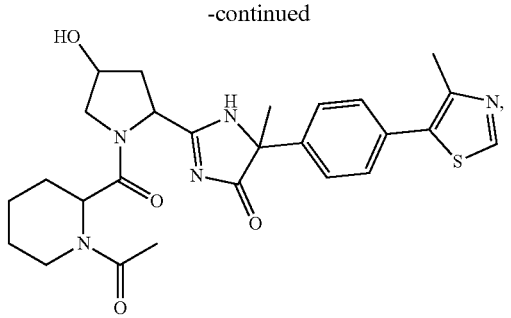
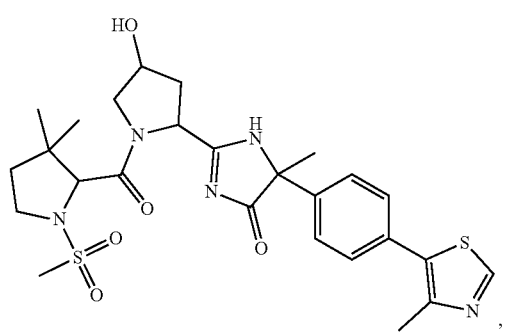
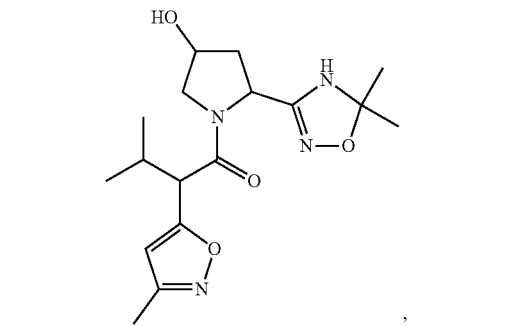
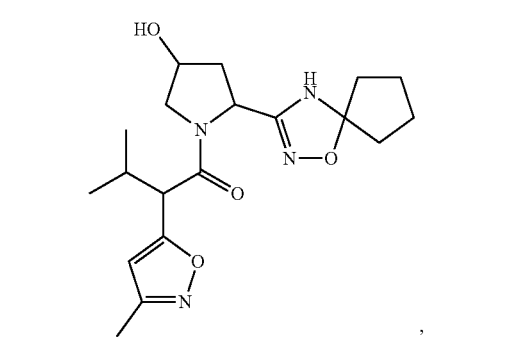
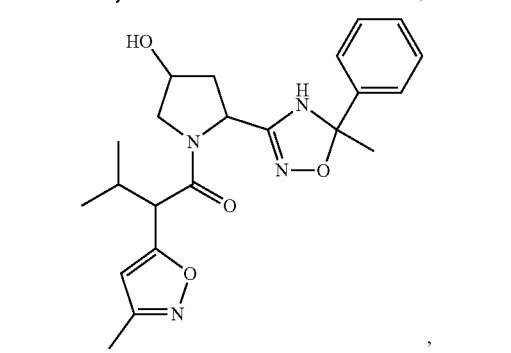
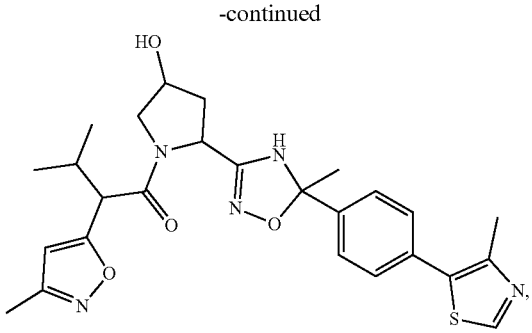
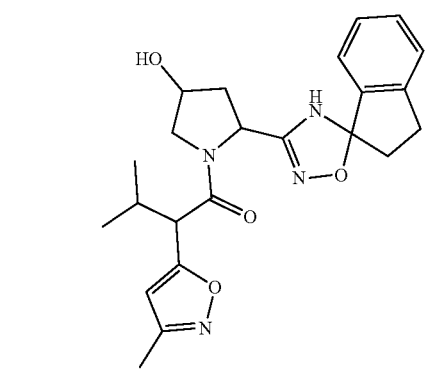
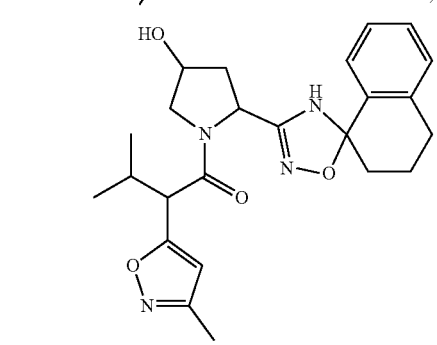
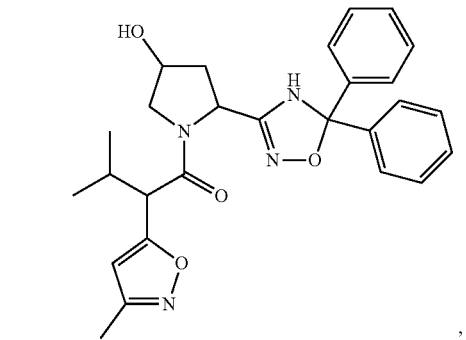
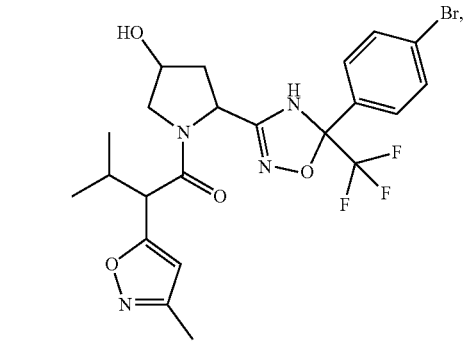

751
-continued
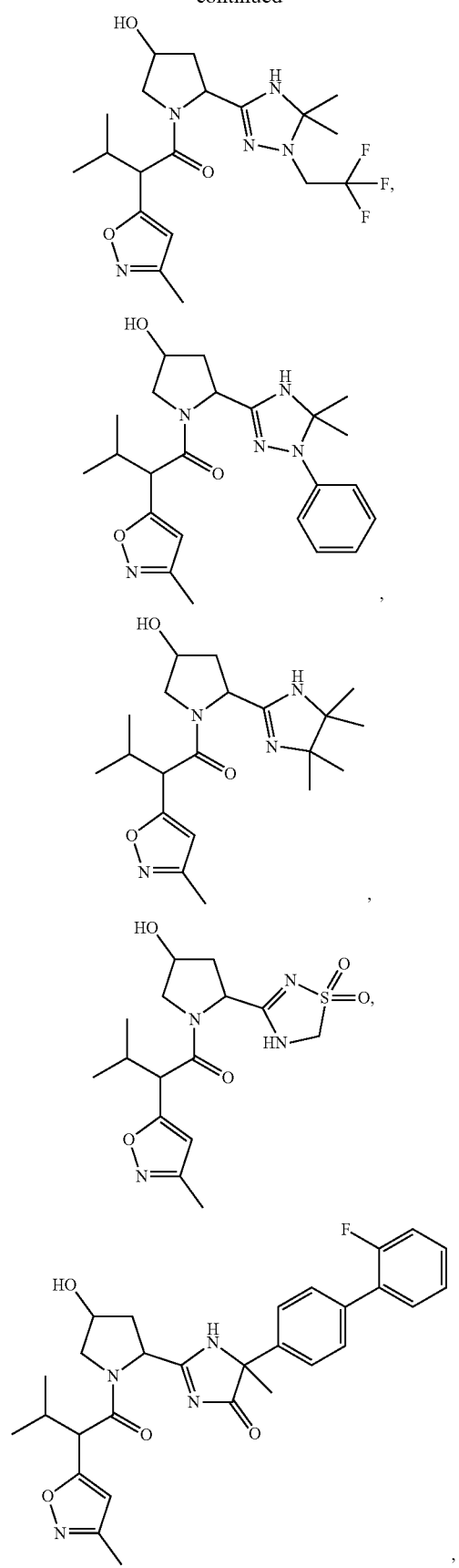
752
-continued
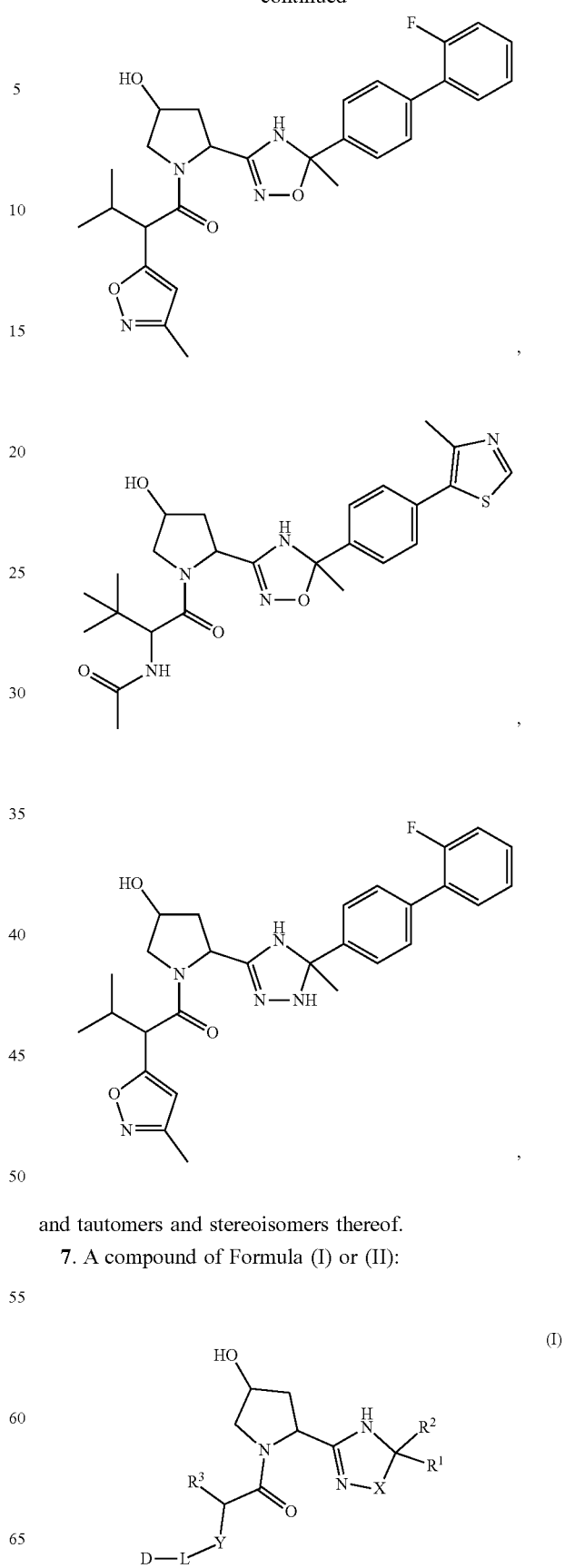
and tautomers and stereoisomers thereof.
7. A compound of Formula (I) or (II):
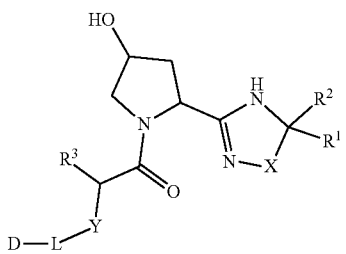

-continued

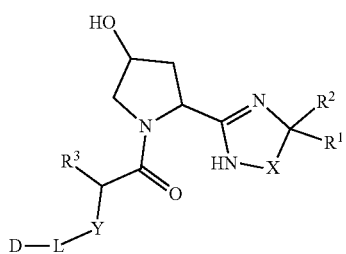

(II)

or a pharmaceutically acceptable salt thereof;
wherein:
X is selected from the group consisting of —C(O)—, O, S, —SO$_2$—, —N(R$^4$)—, and —C(R$^{5a}$)(R$^{5b}$)—;
R$^1$ is selected from the group consisting of H, substituted or unsubstituted alkyl, substituted or unsubstituted alkenyl, substituted or unsubstituted alkynyl, substituted or unsubstituted cycloalkyl, substituted or unsubstituted aryl, substituted or unsubstituted heterocyclyl, and substituted or unsubstituted heteroaryl;
R$^2$ is selected from the group consisting of H, substituted or unsubstituted alkyl, substituted or unsubstituted alkenyl, substituted or unsubstituted alkynyl, and substituted or unsubstituted aryl;
or R$^1$ and R$^2$ are taken together with the carbon to which they are attached to form a cycloalkyl or heterocyclyl, wherein the cycloalkyl or heterocyclyl is substituted or unsubstituted or fused with a ring selected from the group consisting of substituted or unsubstituted cycloalkyl, substituted or unsubstituted heterocyclyl, substituted or unsubstituted aryl, and substituted or unsubstituted heteroaryl;
R$^3$ is substituted or unsubstituted alkyl, or R$^3$ is taken together with R$^6$, when present, and the atoms to which they are attached, to form a substituted or unsubstituted heterocyclylene;
R$^4$, R$^{5a}$, and R$^{5b}$ are each independently selected from the group consisting of H, substituted or unsubstituted C$_1$-C$_3$ alkyl, and substituted or unsubstituted aryl;
Y is —N(R$^6$)—C(O)— or

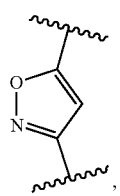

wherein ∿∿∿ indicates the point of attachment to the remaining structure of the compound or L, wherein Y may be attached to the compound in either orientation;
R$^6$ is selected from the group consisting of H and substituted or unsubstituted alkyl, or R$^6$ is taken together with R$^3$ and the atoms to which they are attached to form a substituted or unsubstituted heterocyclylene;
L is a linker moiety; and
D is a protein binding moiety.

8. The compound of claim 7, or a pharmaceutically acceptable salt thereof, wherein the compound is of Formula (Ia) or (IIa):

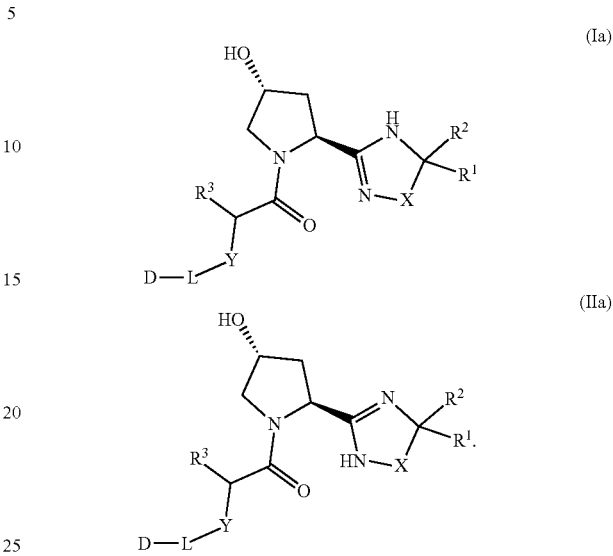

9. The compound of claim 7, or a pharmaceutically acceptable salt thereof, wherein X is —C(O)—.
10. The compound of claim 7, or a pharmaceutically acceptable salt thereof, wherein X is O.
11. The compound of claim 7, or a pharmaceutically acceptable salt thereof, wherein:
R$^1$ is —W—R$^7$;
W is selected from the group consisting of substituted or unsubstituted arylene, substituted or unsubstituted heteroarylene, substituted or unsubstituted heterocyclylene, and substituted or unsubstituted cycloalkylene;
R$^7$ is selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, —OR$^8$, —N(R$^{8a}$)R$^{8b}$, —C(O)R$^{8c}$, —C(O)N(R$^{8a}$)R$^{8b}$, —N(R$^{8a}$)C(O)R$^{8c}$, —SO$_2$N(R$^{8a}$)R$^{8b}$, and —SO$_2$R$^{8c}$;
R$^8$, R$^{8a}$, and R$^{8b}$ are independently selected from the group consisting of H and substituted or unsubstituted alkyl; and
R$^{8c}$ is selected from the group consisting of substituted or unsubstituted alkyl and substituted or unsubstituted aryl.
12. The compound of claim 11, or a pharmaceutically acceptable salt thereof, wherein R$^1$ is

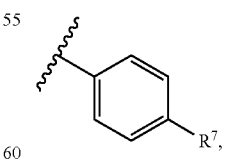

R$^7$, wherein R$^7$ is selected from the group consisting of halo, substituted or unsubstituted heteroaryl, substituted or unsubstituted heterocyclyl, and substituted or unsubstituted aryl.
13. The compound of claim 12, or a pharmaceutically acceptable salt thereof, wherein R$^7$ is selected from the group consisting of

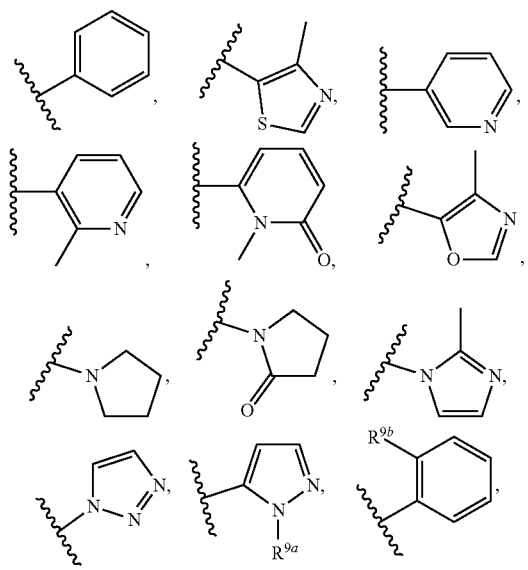

wherein R<sup>9a</sup> is alkyl and R<sup>9b</sup> is halo.

14. The compound of claim 7, or a pharmaceutically acceptable salt thereof, wherein R$^2$ is selected from the group consisting of substituted or unsubstituted alkyl and unsubstituted phenyl.

15. The compound of claim 7, or a pharmaceutically acceptable salt thereof, wherein R$^3$ is isopropyl or tert-butyl.

16. The compound of claim 7, or a pharmaceutically acceptable salt thereof, wherein Y is —N(R$^6$)—C(O)—, and R$^6$ is H.

17. The compound of claim 7, or a pharmaceutically acceptable salt thereof, wherein:
X is —C(O)—;
R$^1$ is unsubstituted alkyl or

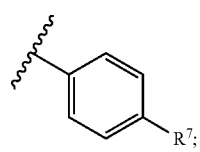

R$^2$ is unsubstituted alkyl;
R$^3$ is isopropyl or tert-butyl;
Y is —N(R$^6$)—C(O)— or

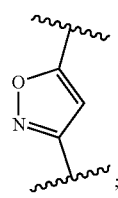 [SMILES: *c1cc(*)on1]

R$^6$ is H; and
R$^7$ is substituted or unsubstituted heteroaryl or halo.

18. The compound of claim 7, or a pharmaceutically acceptable salt thereof, wherein:
X is O;
R$^1$ is unsubstituted alkyl, phenyl, or

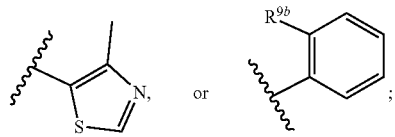

R$^2$ is unsubstituted alkyl, —CF$_3$, or phenyl;
R$^3$ is isopropyl or tert-butyl;
Y is —N(R$^6$)—C(O)— or;

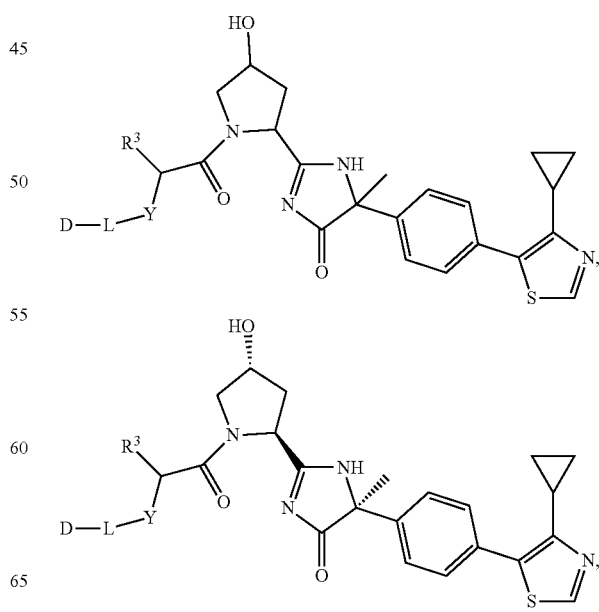

R$^6$ is H;
R$^7$ is halo, and

R$^{9b}$ is halo.

19. The compound of claim 7, or a pharmaceutically acceptable salt thereof, having a structure selected from the group consisting of 757
-continued
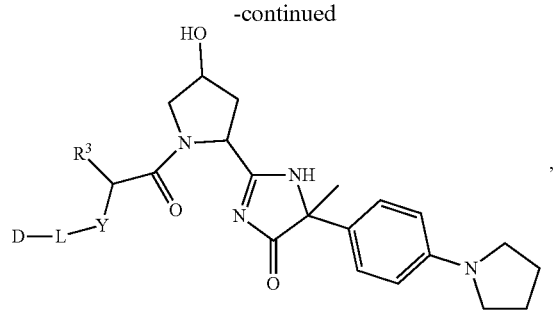
,
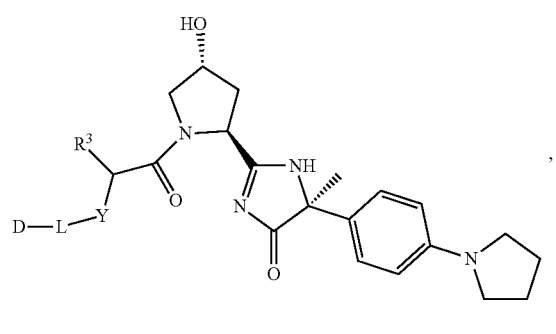
,
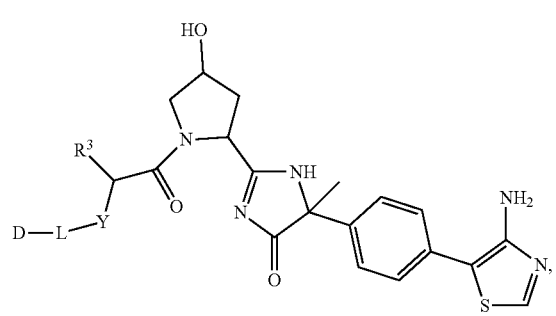
,
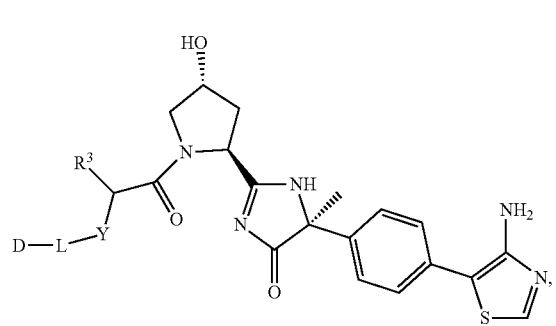
,
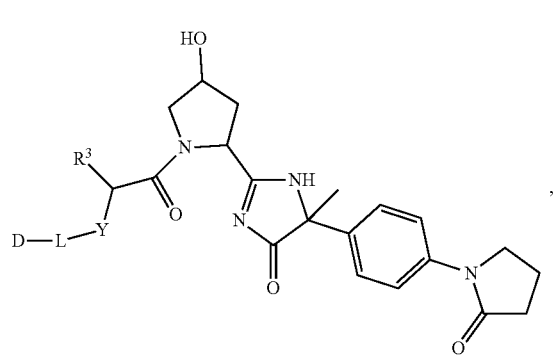
,
758
-continued
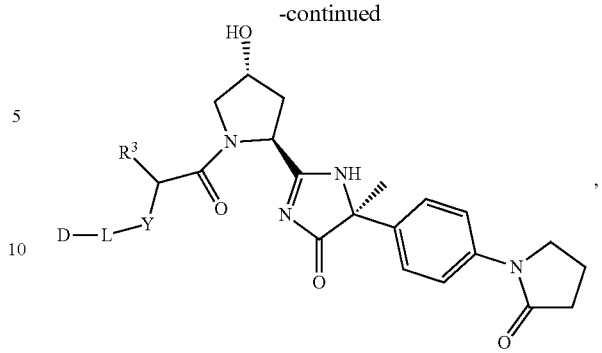
,
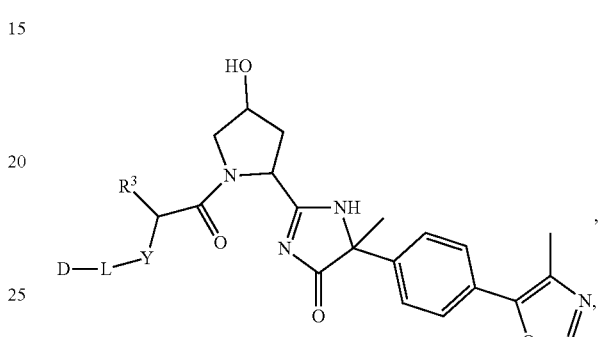
,
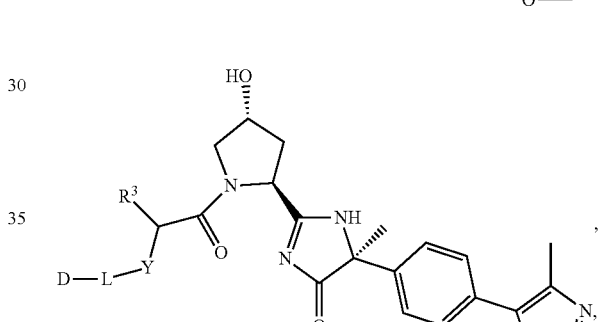
,
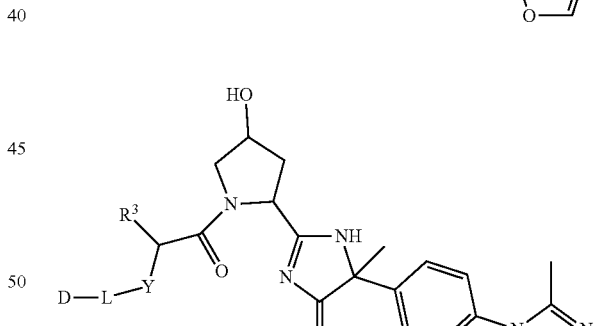
,
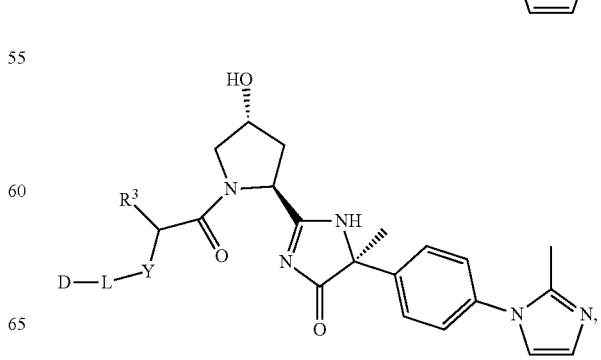
, 759
-continued
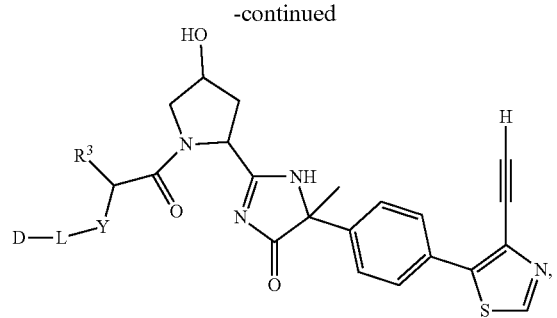
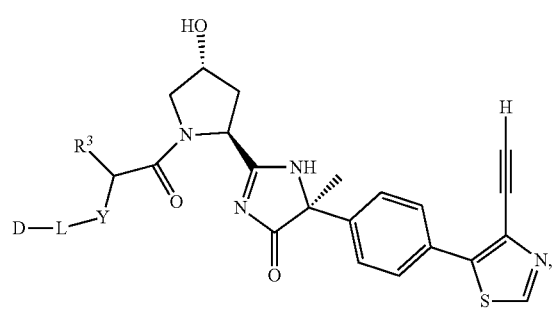
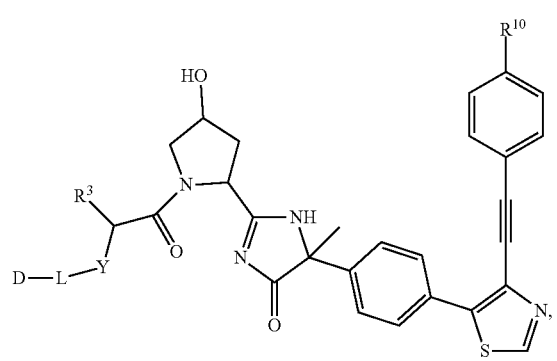
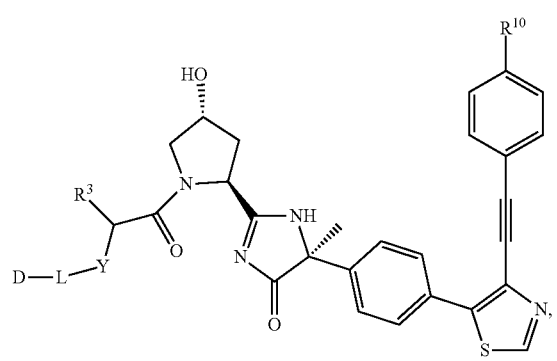
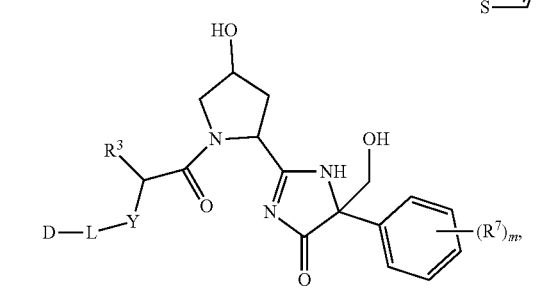
760
-continued
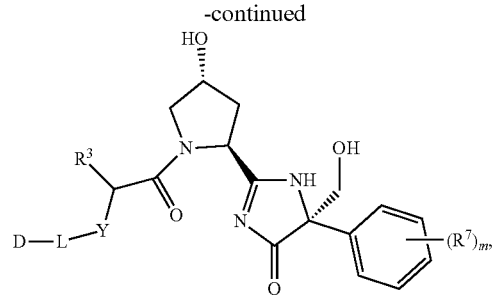
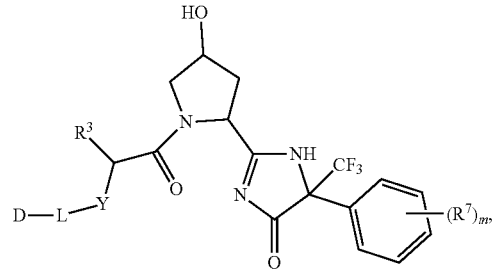
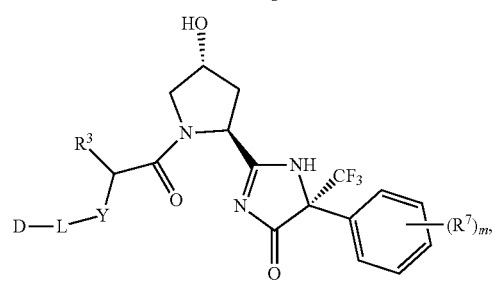
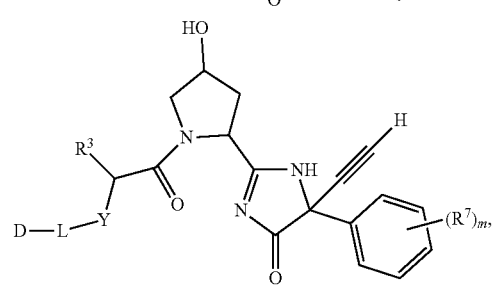
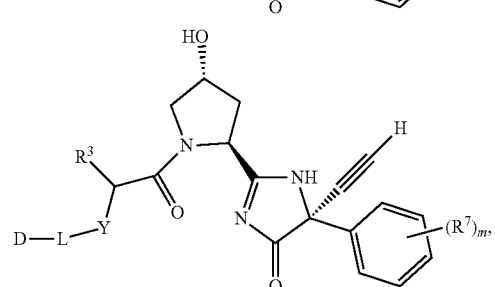
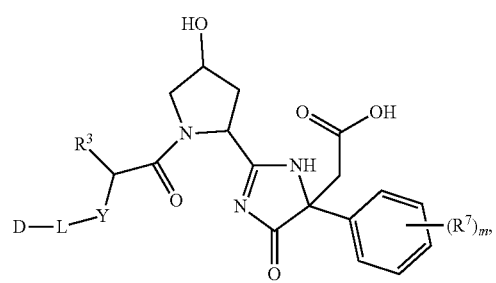

761
-continued
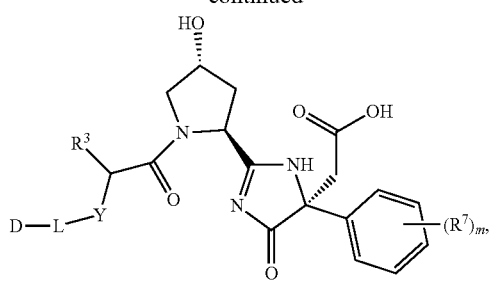
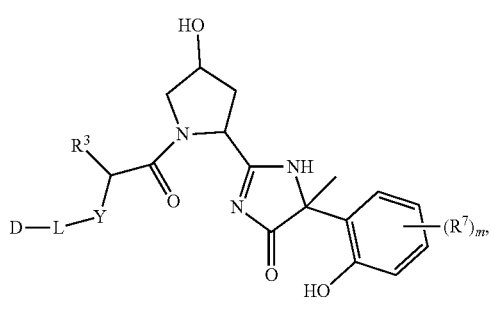
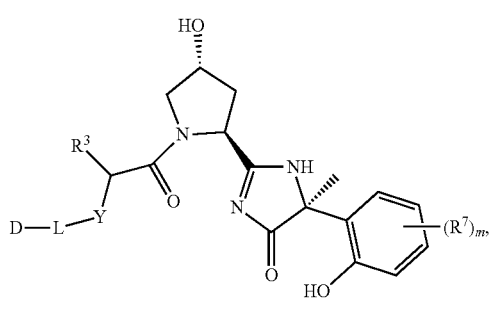
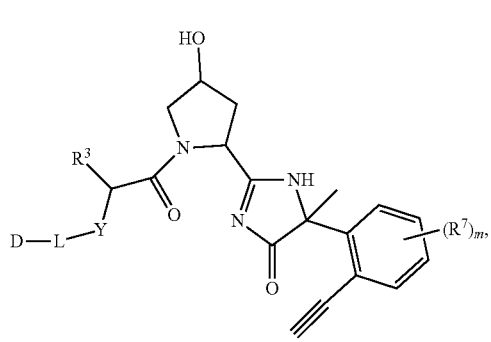
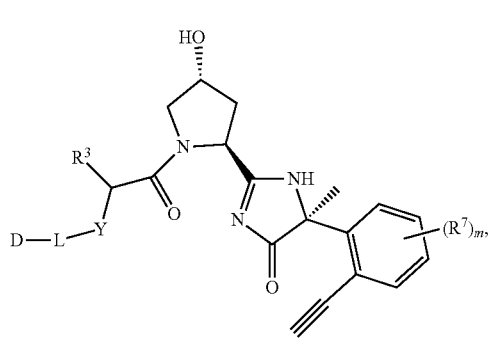
762
-continued
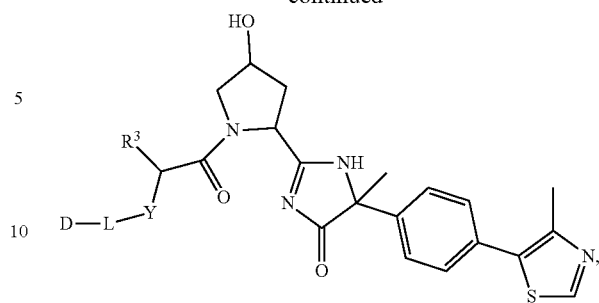
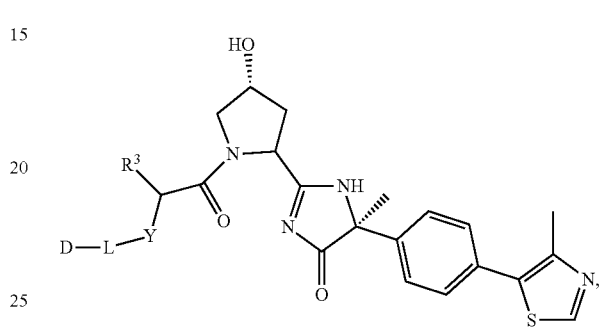
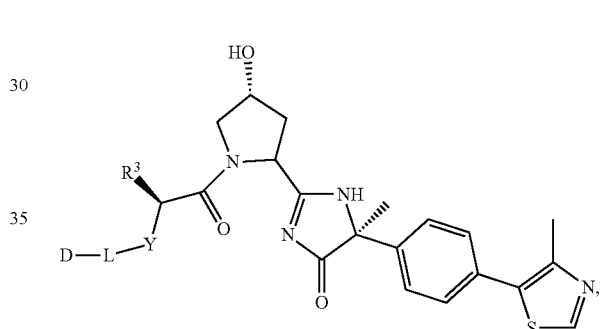
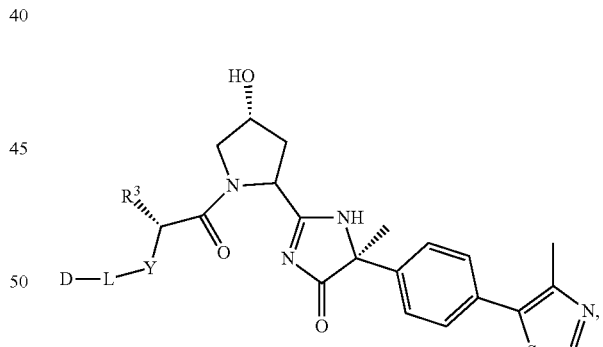
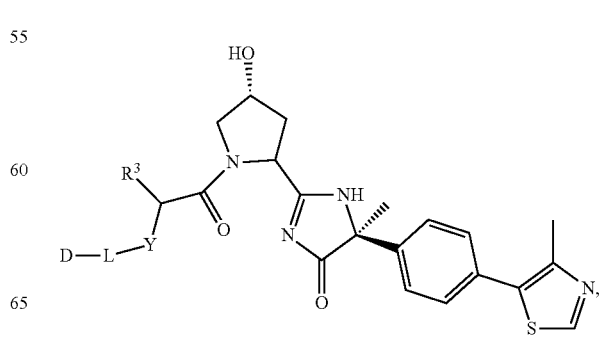

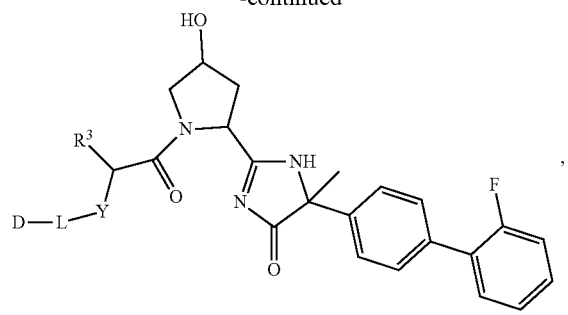,
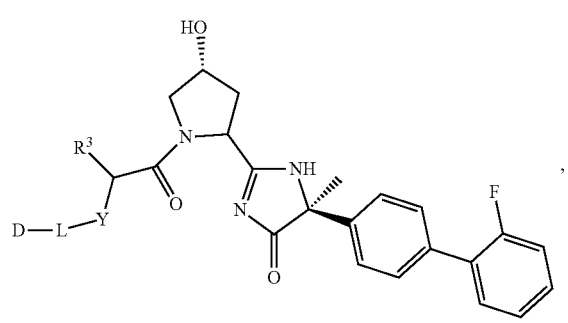,
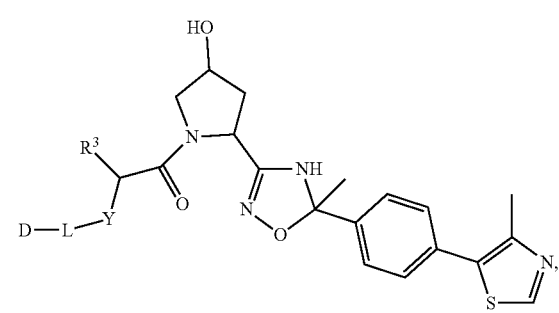,
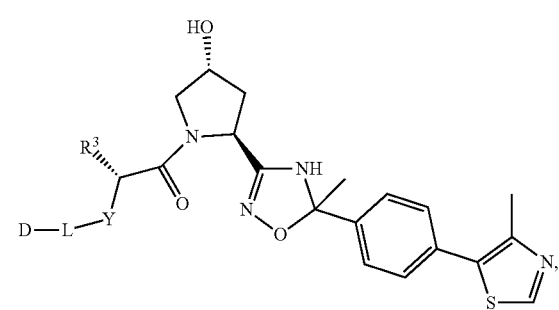,
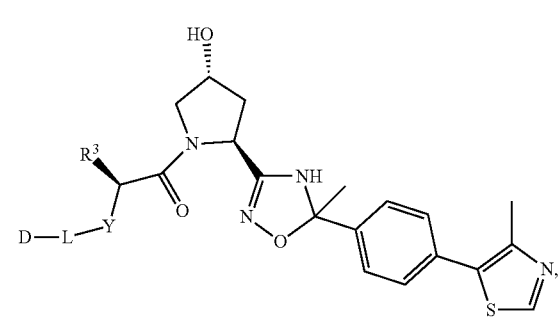,
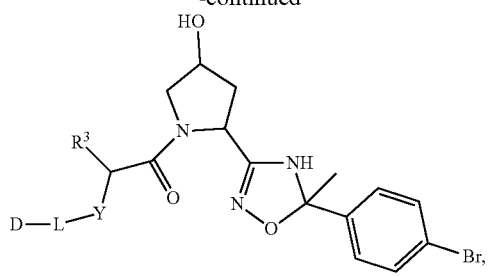,
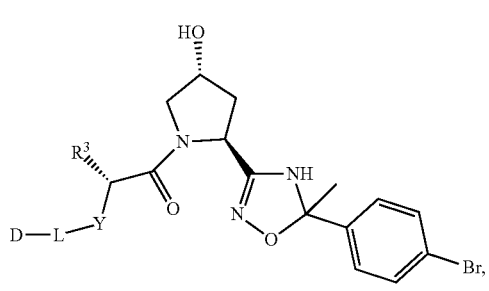,
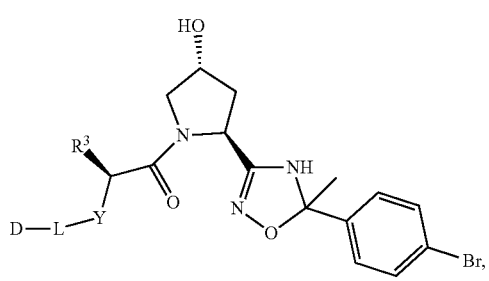,
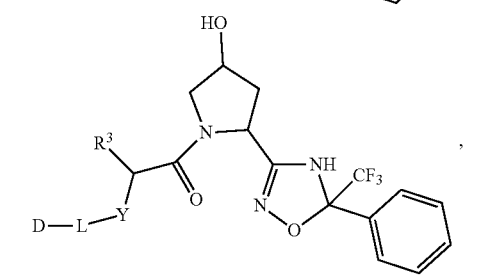,
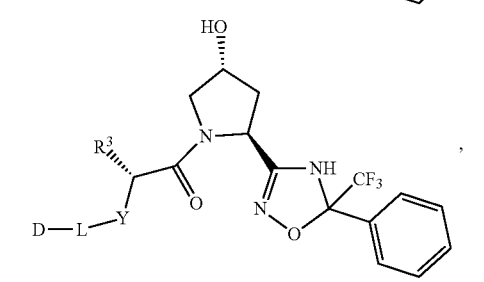,
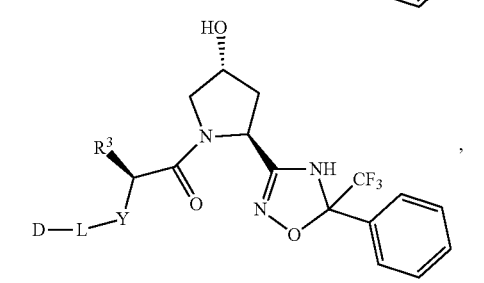, 765
-continued
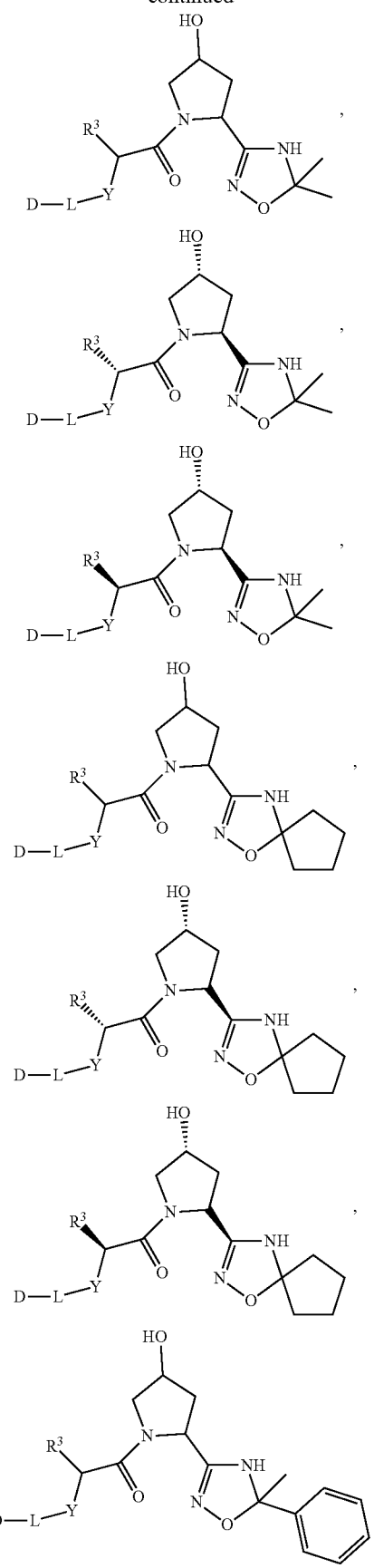
766
-continued
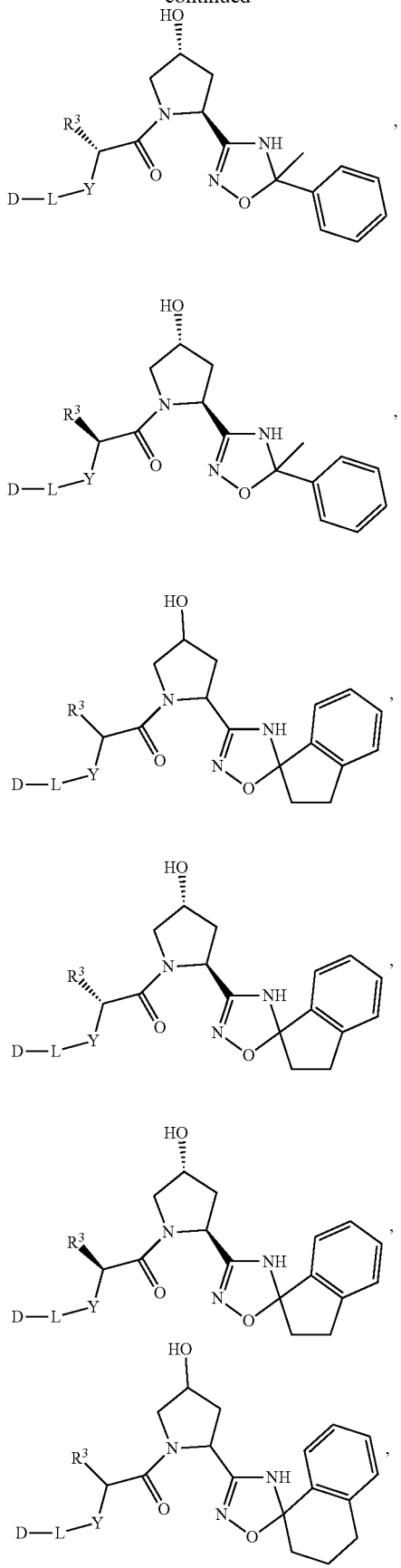

-continued
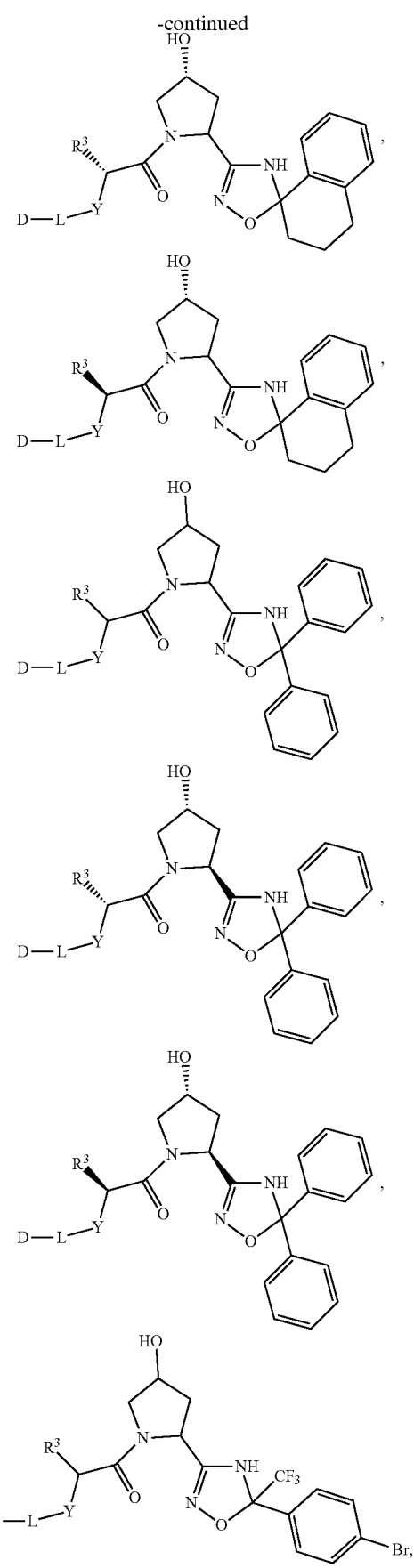
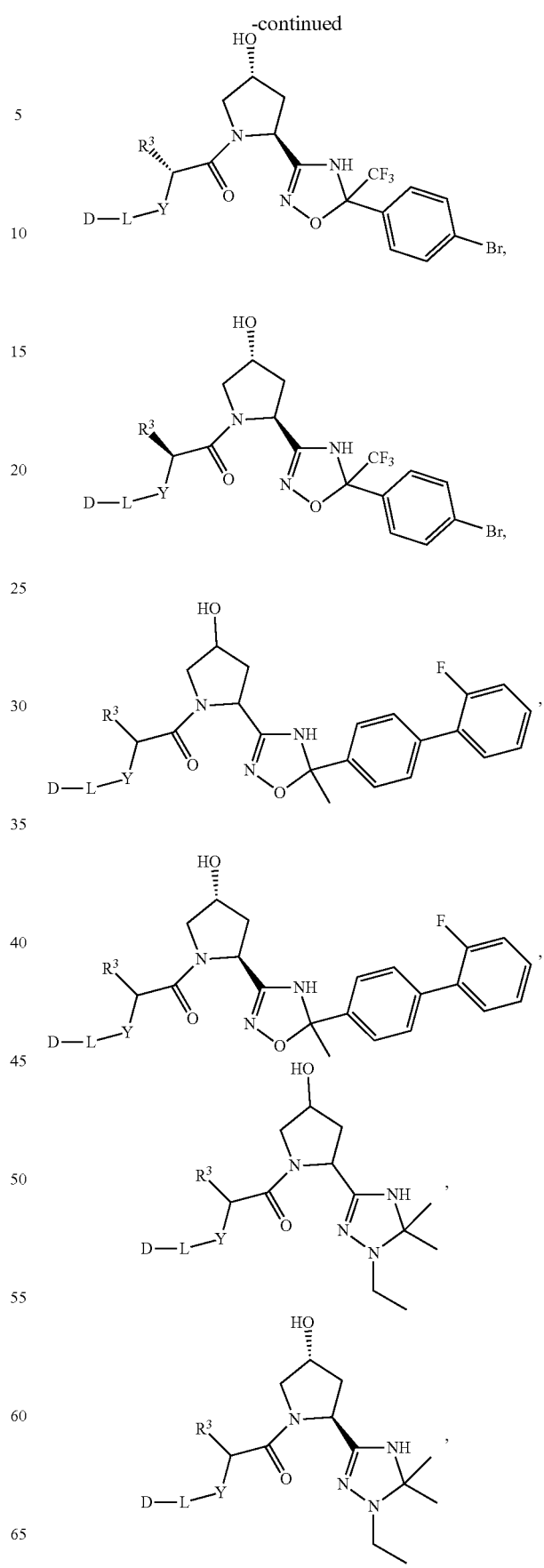

-continued
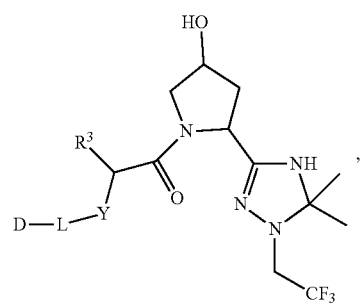
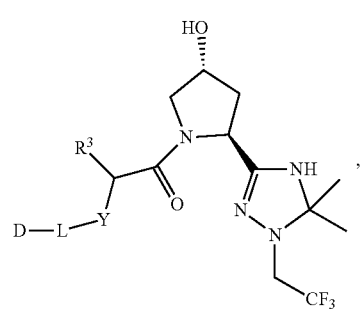
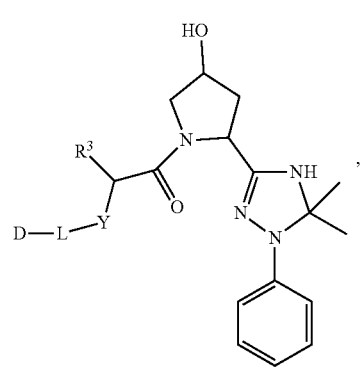
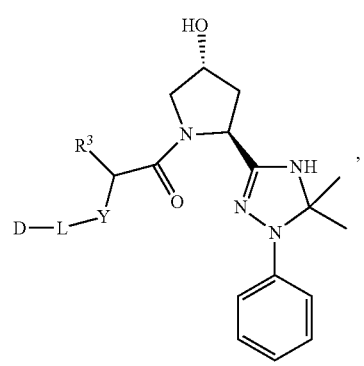
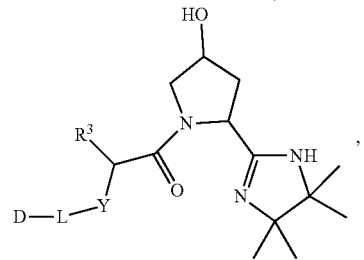
-continued
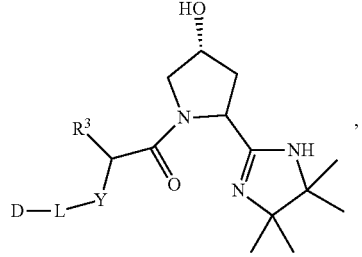
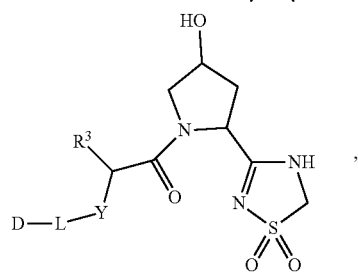
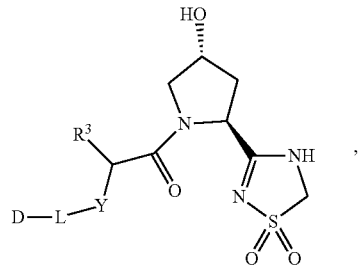
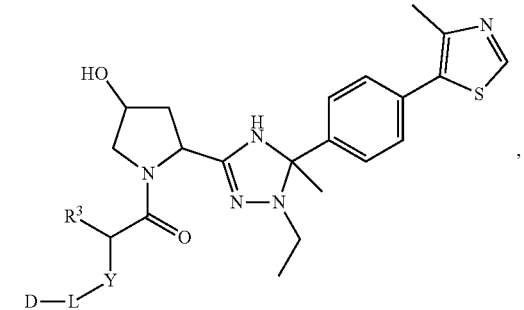
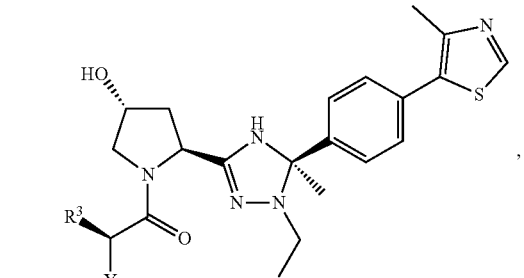
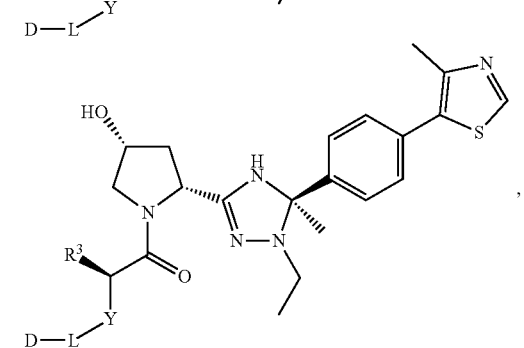

771
-continued

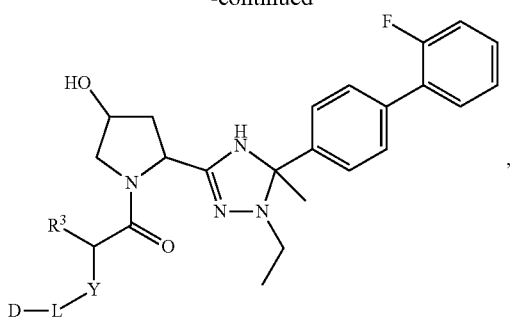,

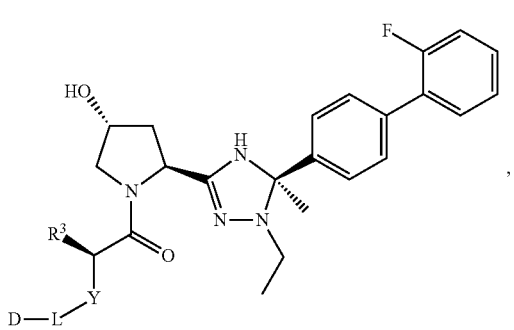,

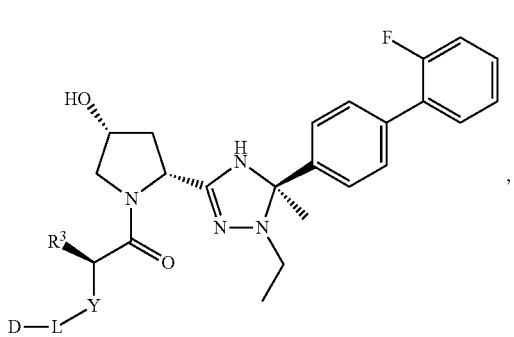,

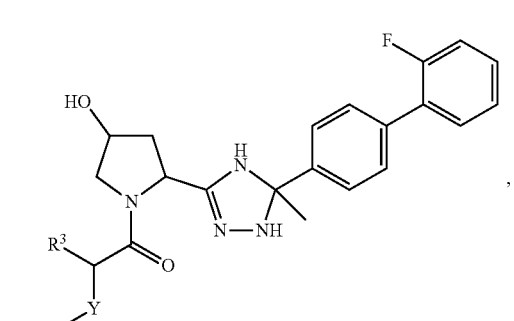,

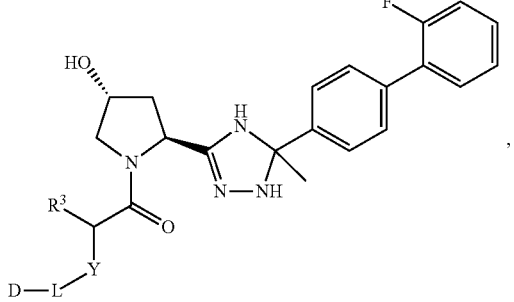,

772
-continued

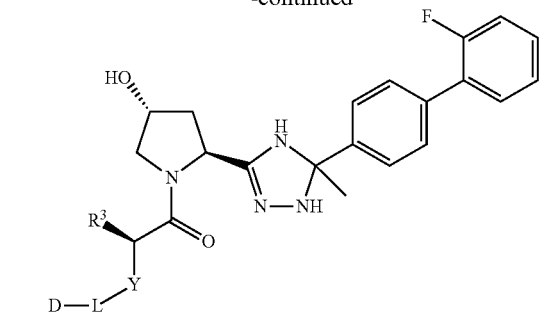, and tautomers thereof, wherein m is 0, 1, 2, 3, 4, or 5;

$R^7$ is selected from the group consisting of substituted or unsubstituted alkyl, substituted or unsubstituted cycloalkyl, substituted or unsubstituted aryl, substituted or unsubstituted heteroaryl, substituted or unsubstituted heterocyclyl, substituted or unsubstituted alkenyl, substituted or unsubstituted alkynyl, halo, —CN, —$OR^8$, —$N(R^{8a})R^{8b}$, —$C(O)R^{8c}$, —$C(O)N(R^{8a})R^{8b}$, —$N(R^{8a})C(O)R^{8c}$, —$SO_2N(R^{8a})R^{8b}$, and $SO_2R^{8c}$; wherein $R^8$, $R^{8a}$, and $R^{8b}$ are independently selected from the group consisting of H and substituted or unsubstituted alkyl; $R^{8c}$ is selected from the group consisting of substituted or unsubstituted alkyl and substituted or unsubstituted aryl; and $R^{10}$ is halo.

20. The compound of claim 7, or a pharmaceutically acceptable salt thereof, having a structure selected from the group consisting of

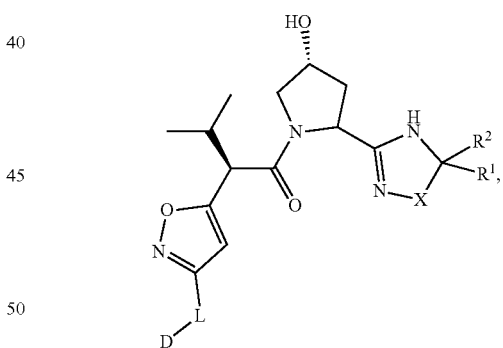,

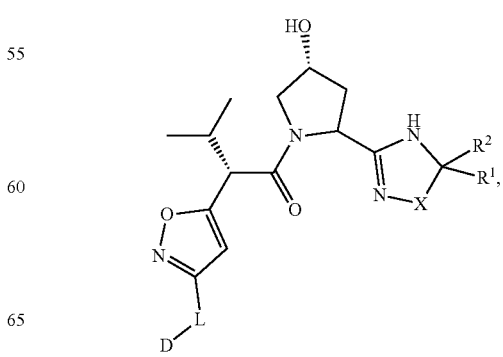,

773
-continued
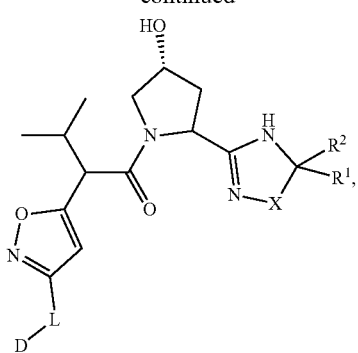
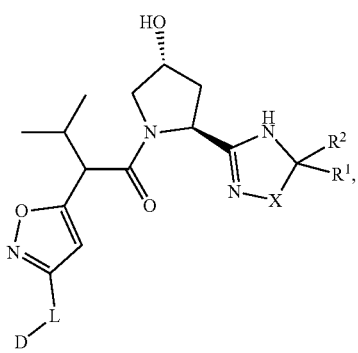
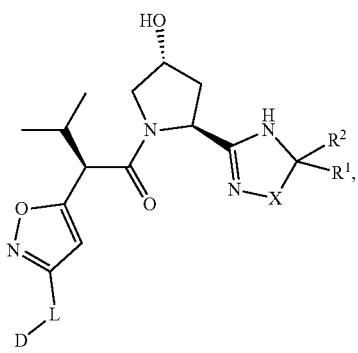
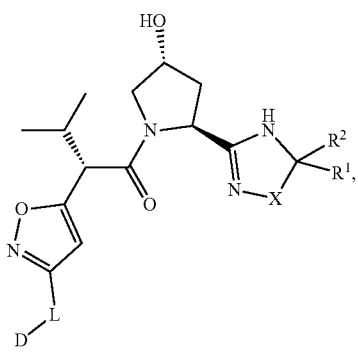
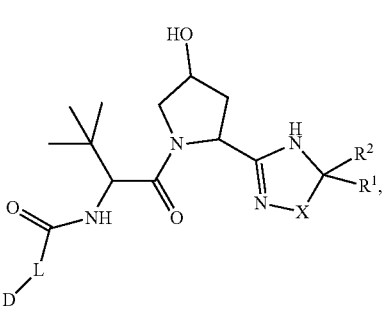
774
-continued
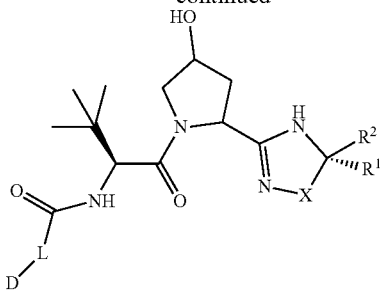
and
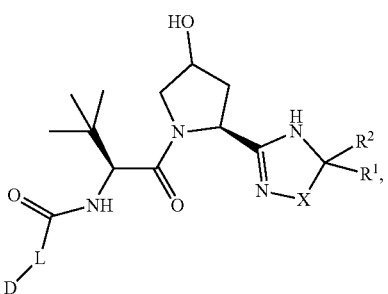
and tautomers thereof.
21. The compound of claim 7, or a pharmaceutically acceptable salt thereof, having a structure selected from the group consisting of
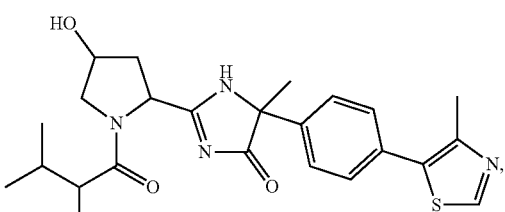
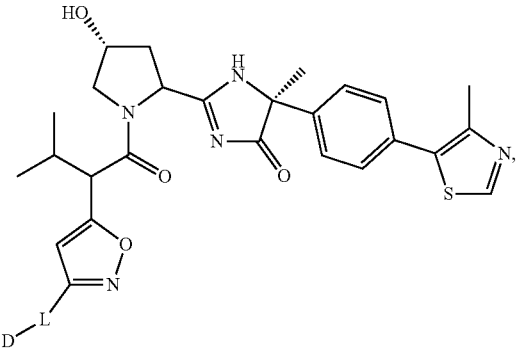

775
-continued
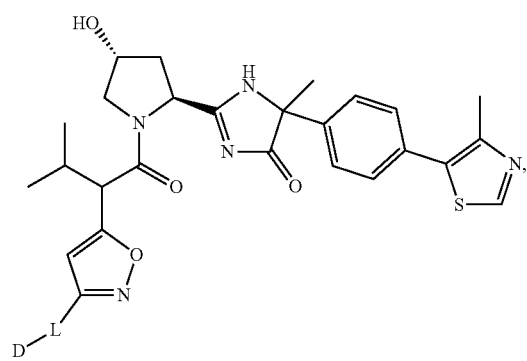
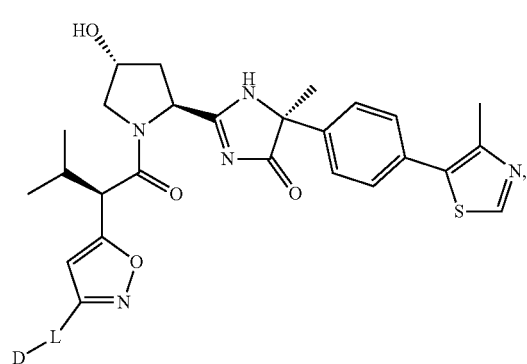
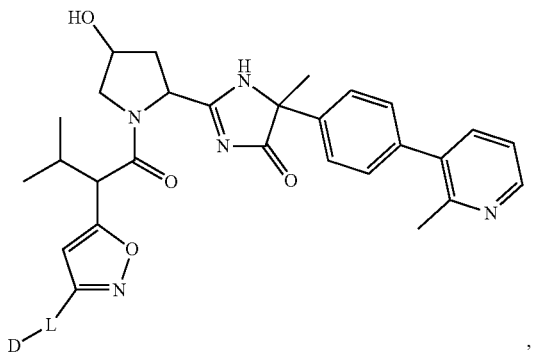
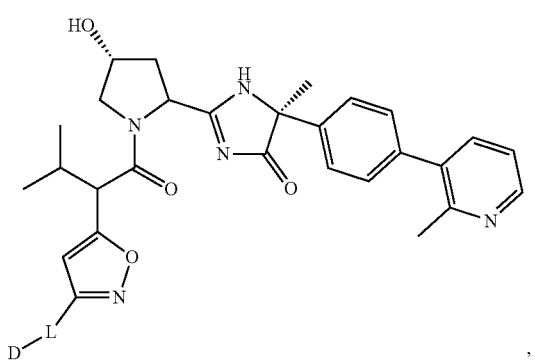
776
-continued
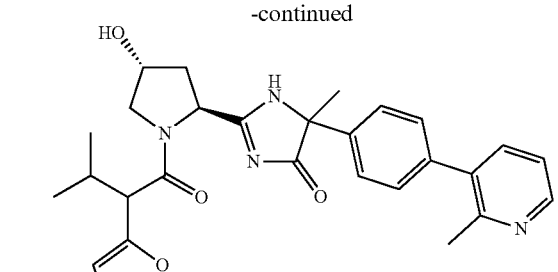
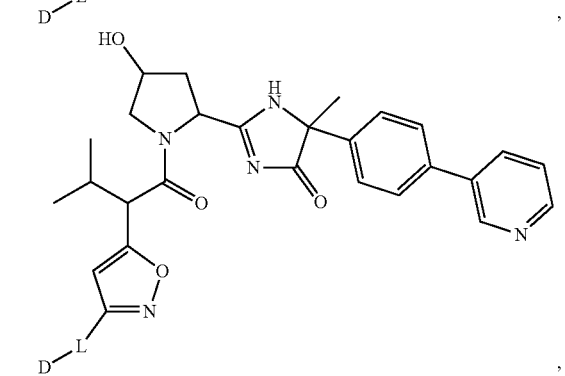
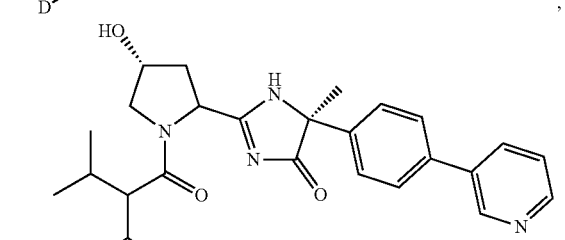
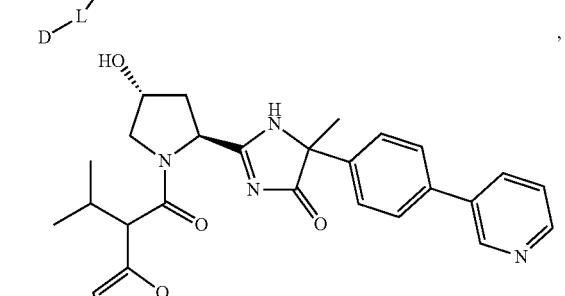
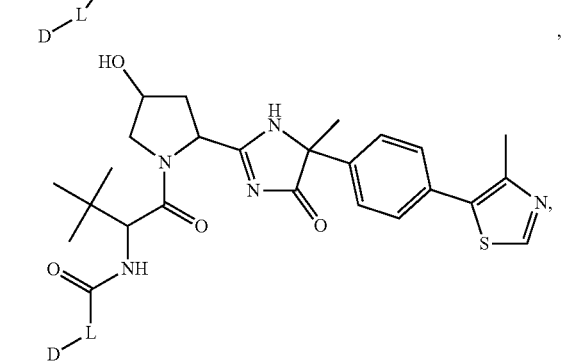

777
-continued
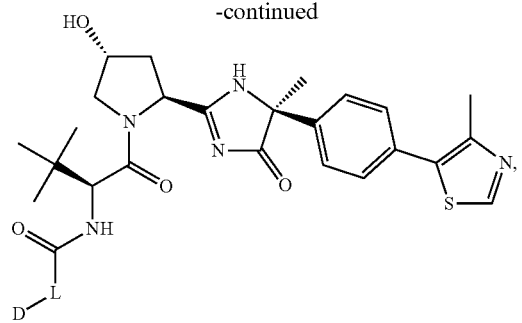
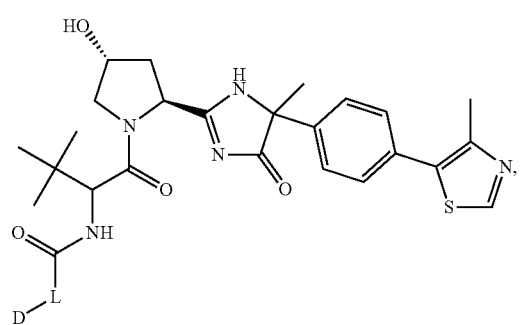
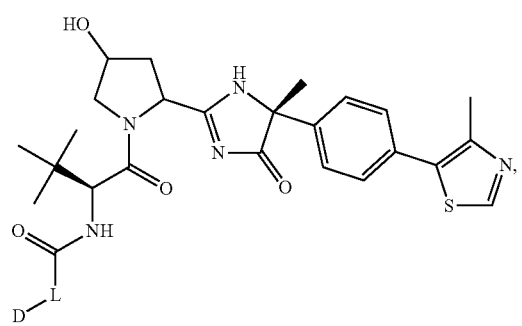
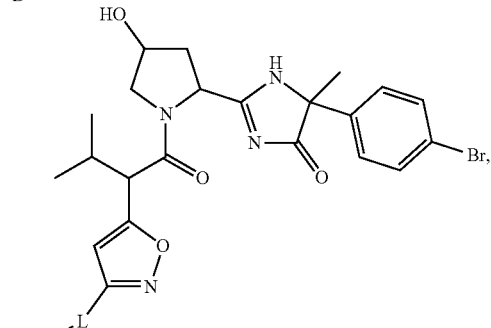
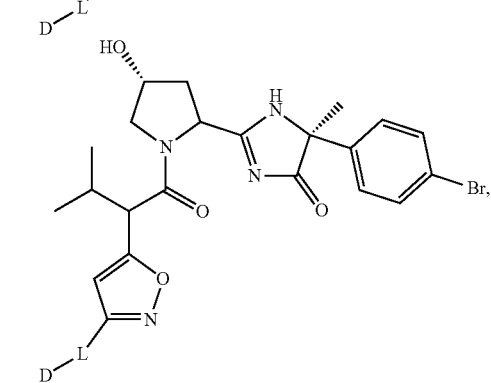
778
-continued
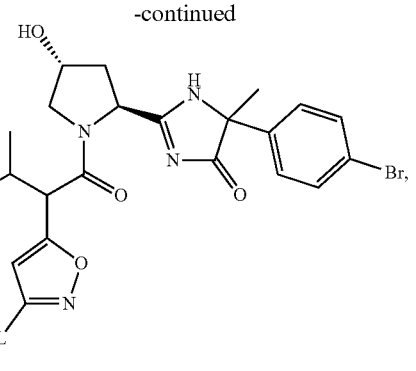
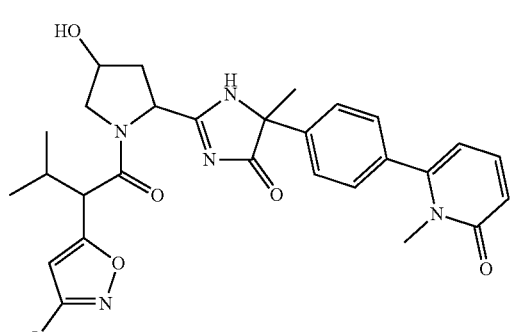
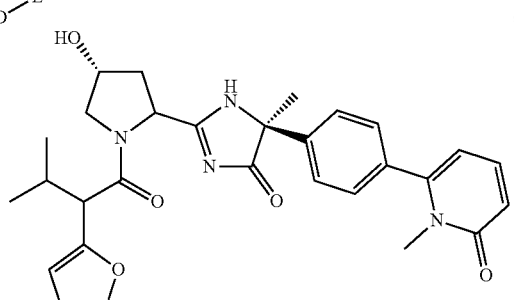
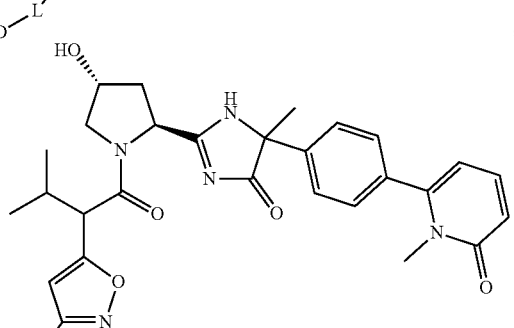
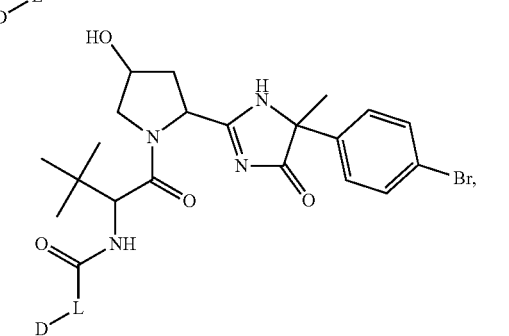

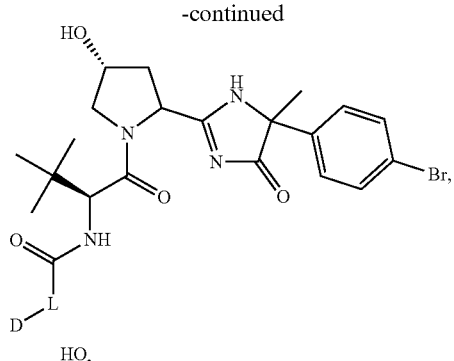
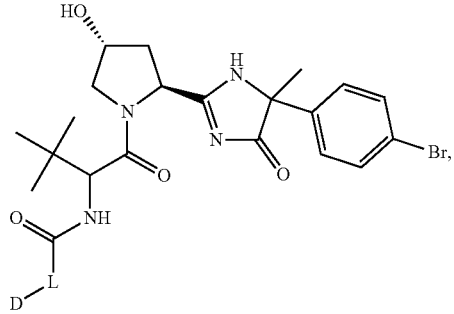
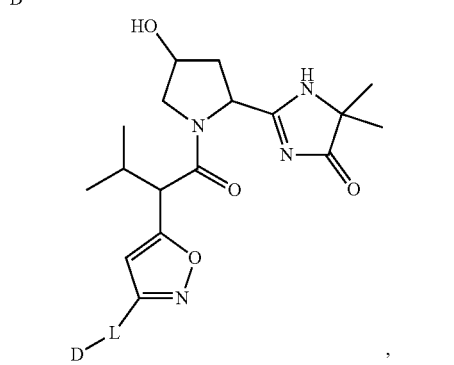
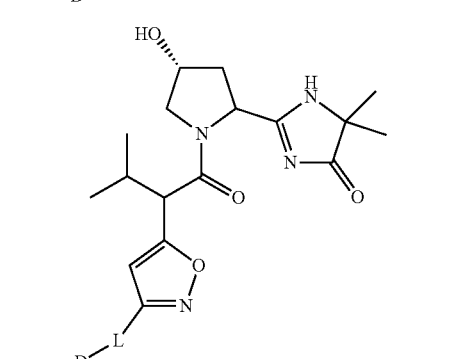
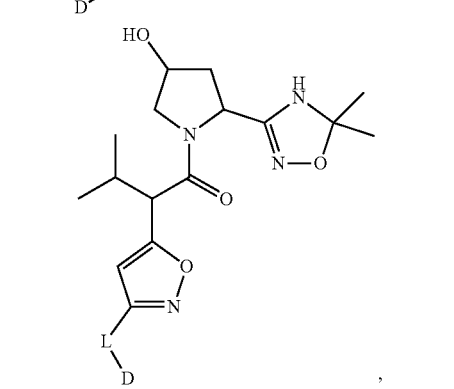
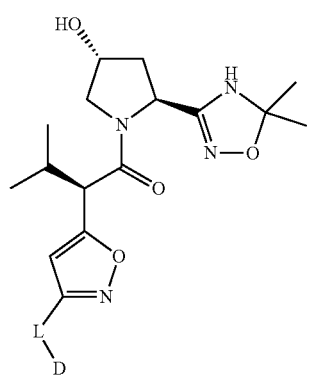
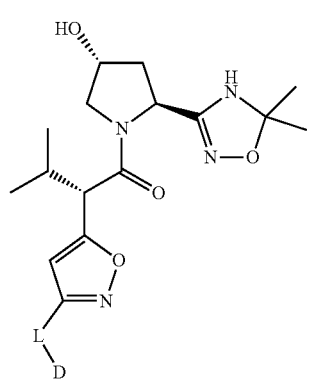
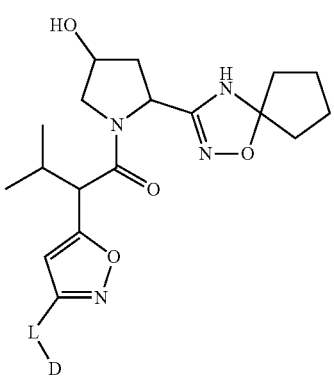
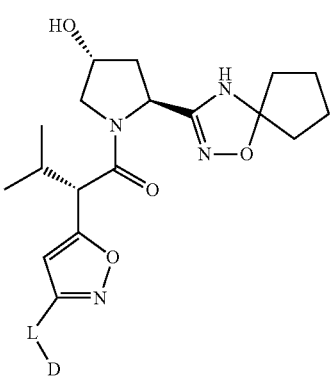

781
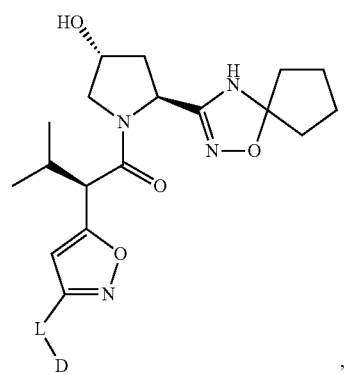
,
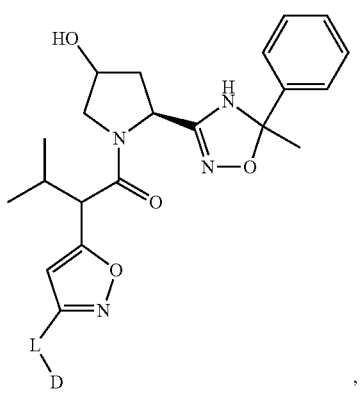
,
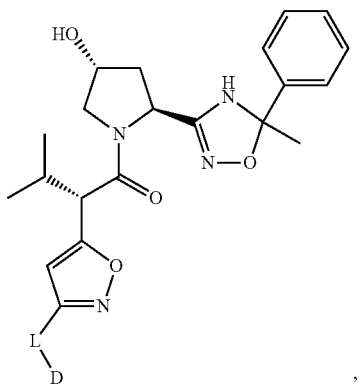
,
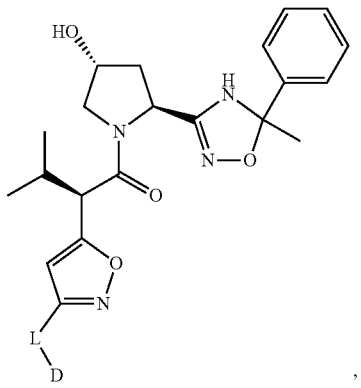
,
782
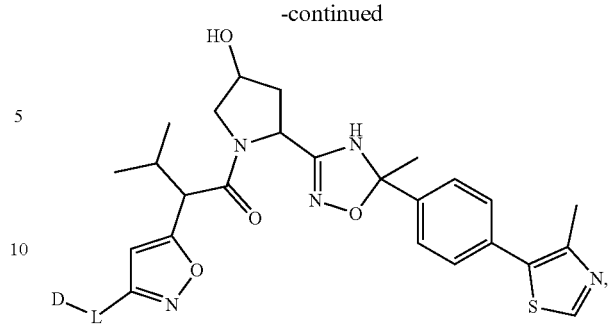
,
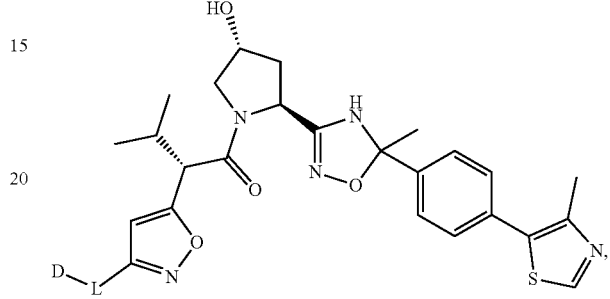
,
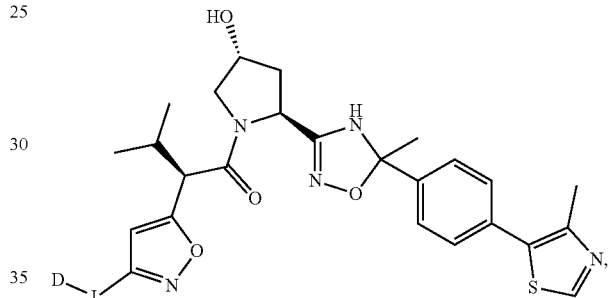
,
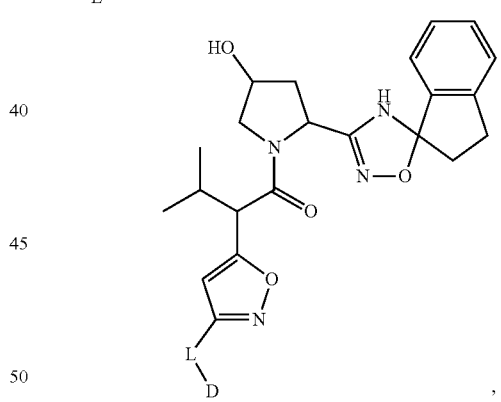
,
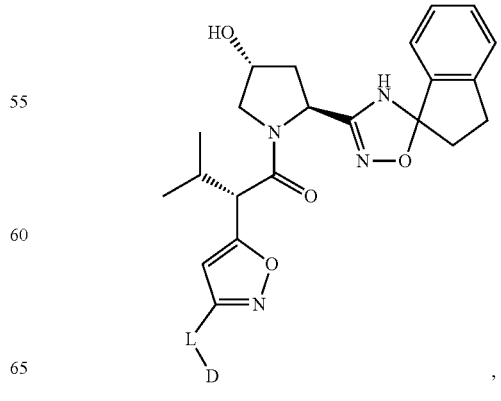
, 783
-continued
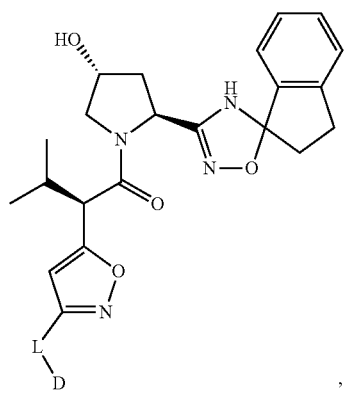
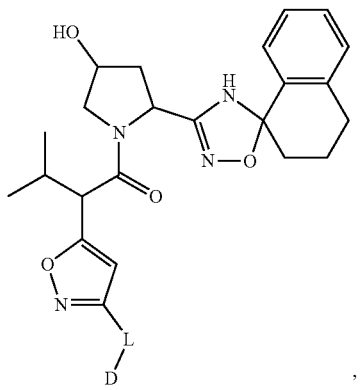
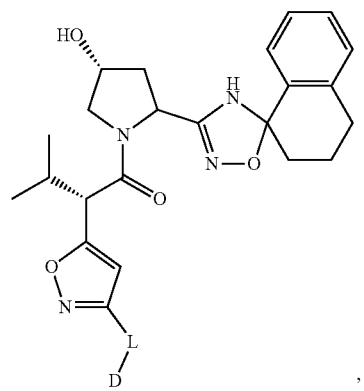
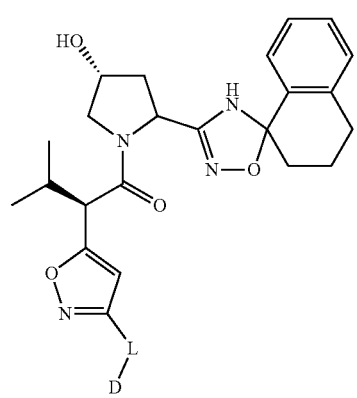
784
-continued
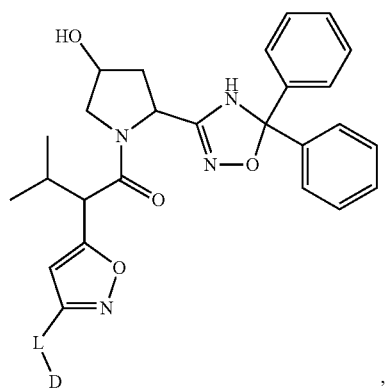
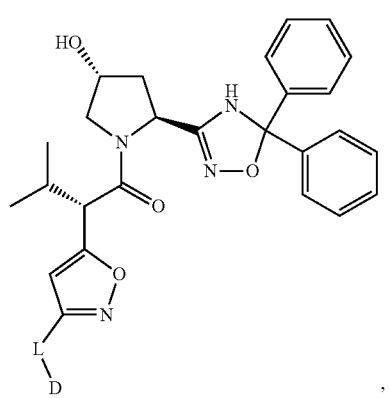
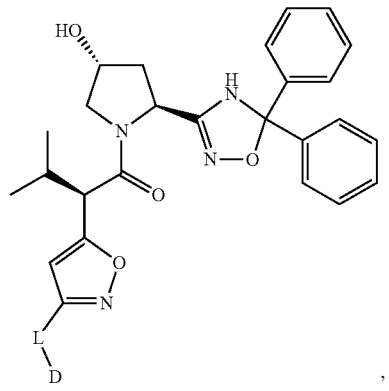
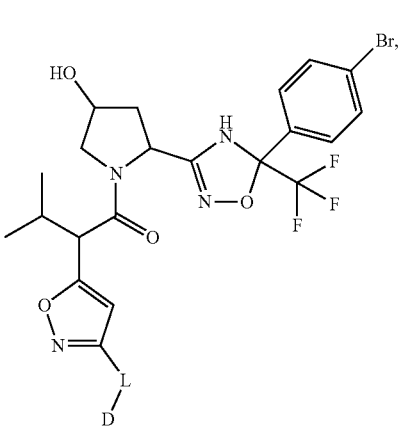

785
-continued
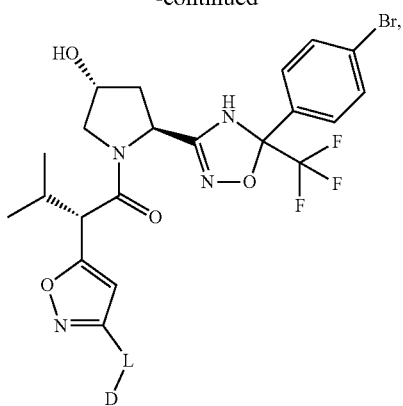
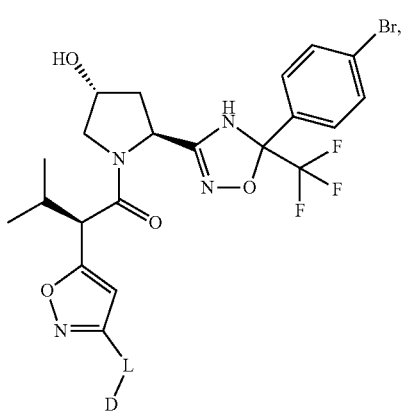
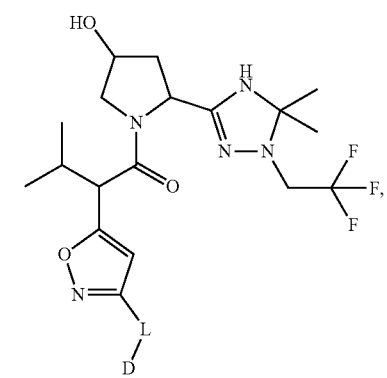
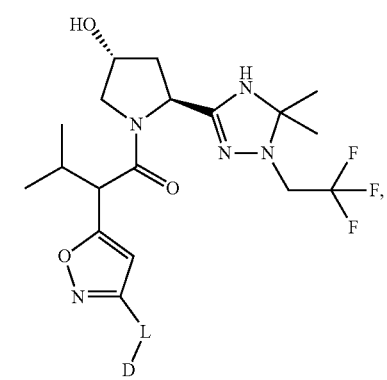
786
-continued
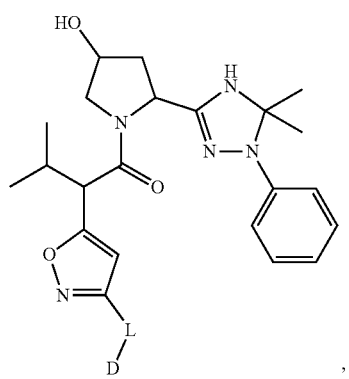
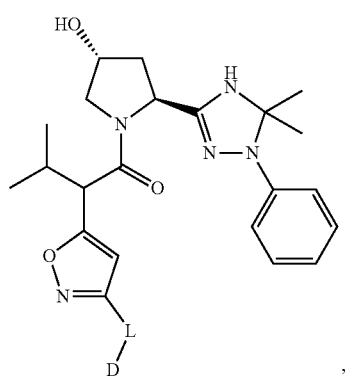
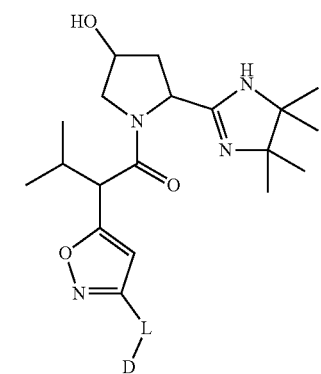
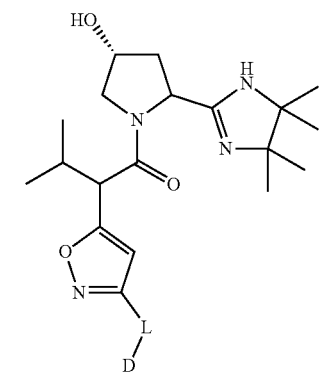

787
-continued
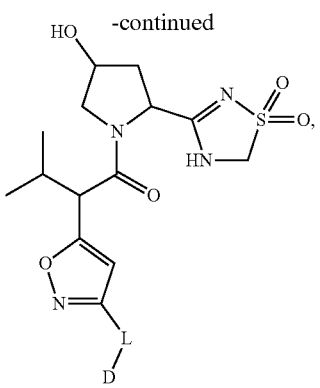
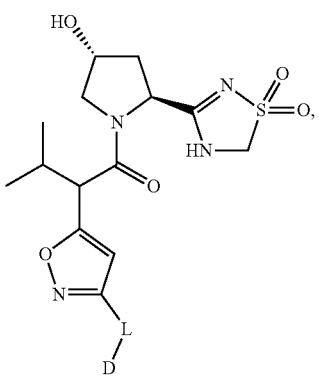
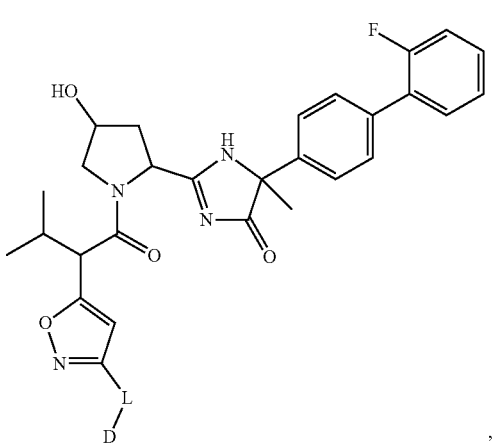
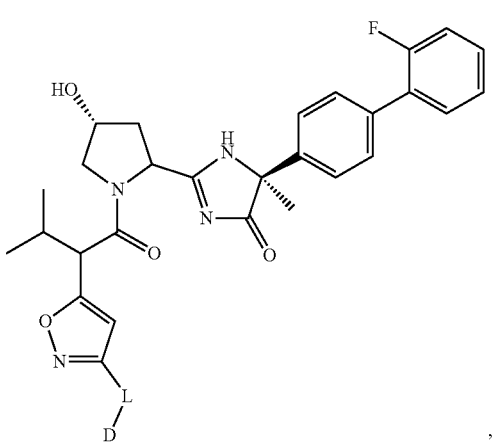
788
-continued
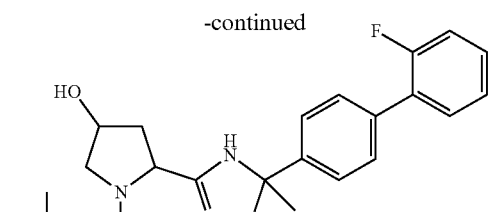
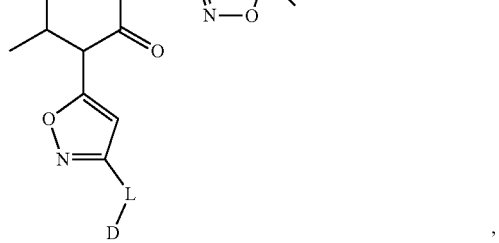
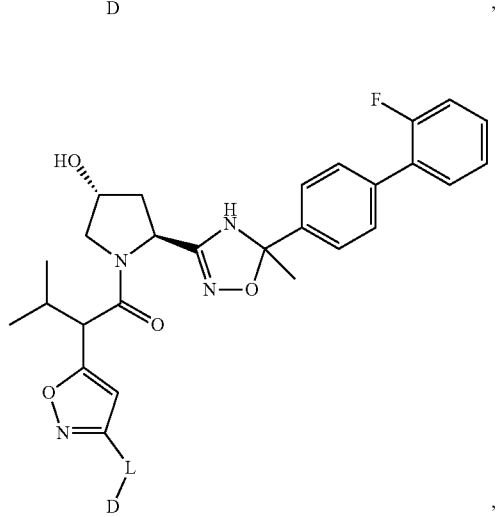
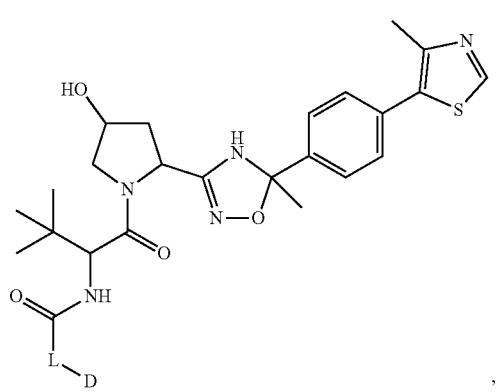
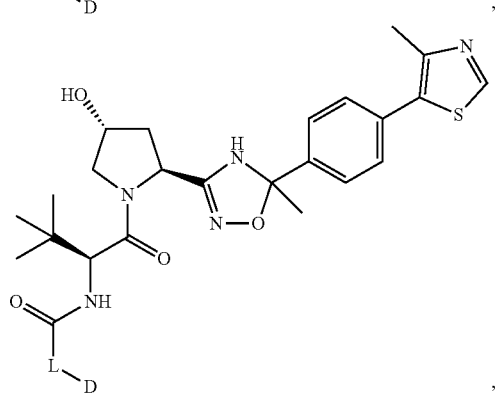

789
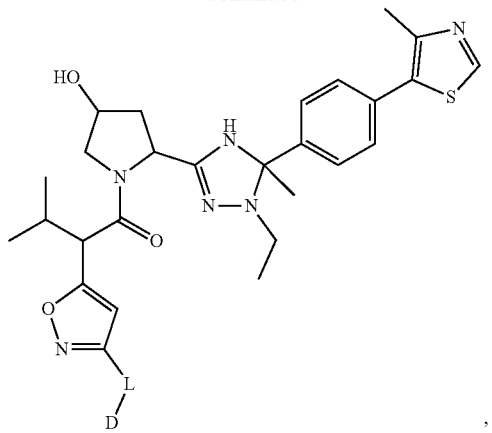
790
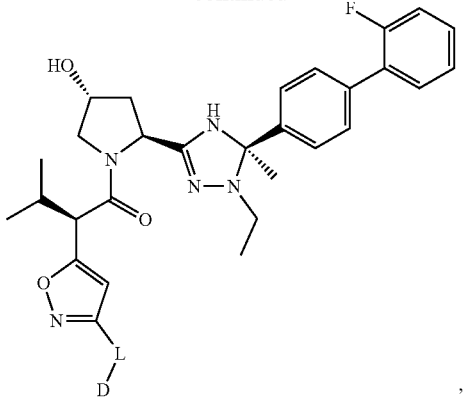
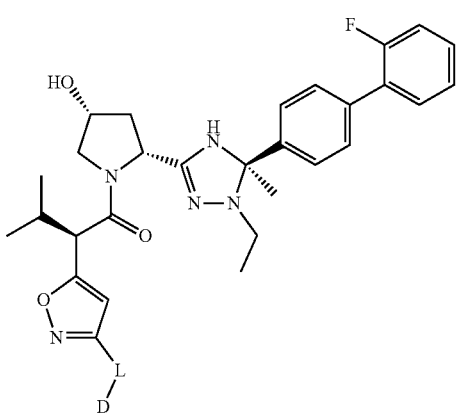
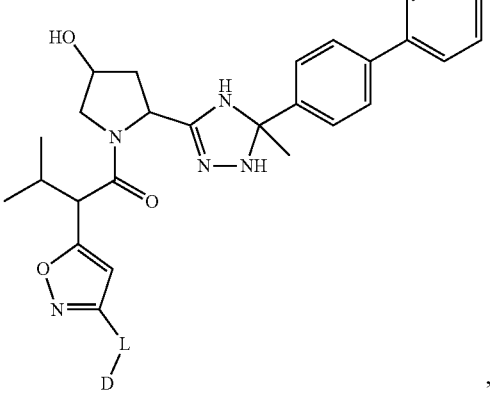
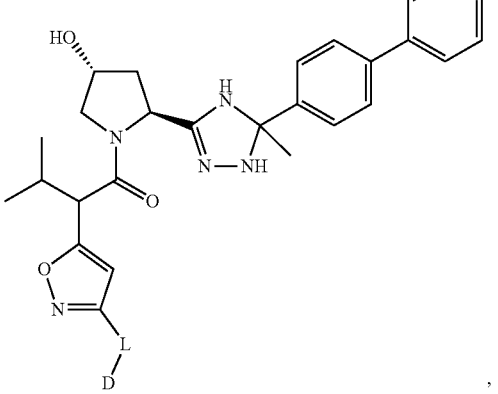
, and

791
-continued
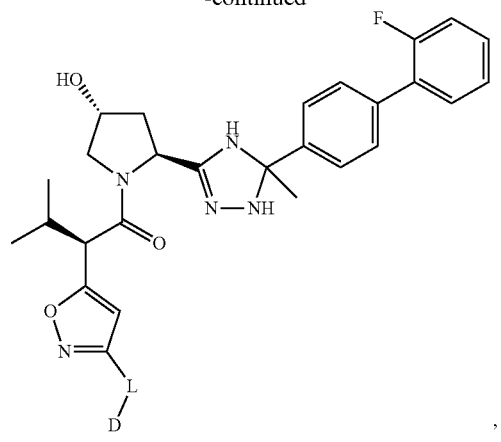
and tautomers thereof.
22. The compound of claim 7, or a pharmaceutically acceptable salt thereof, wherein L is selected from the group consisting of:
792
-continued
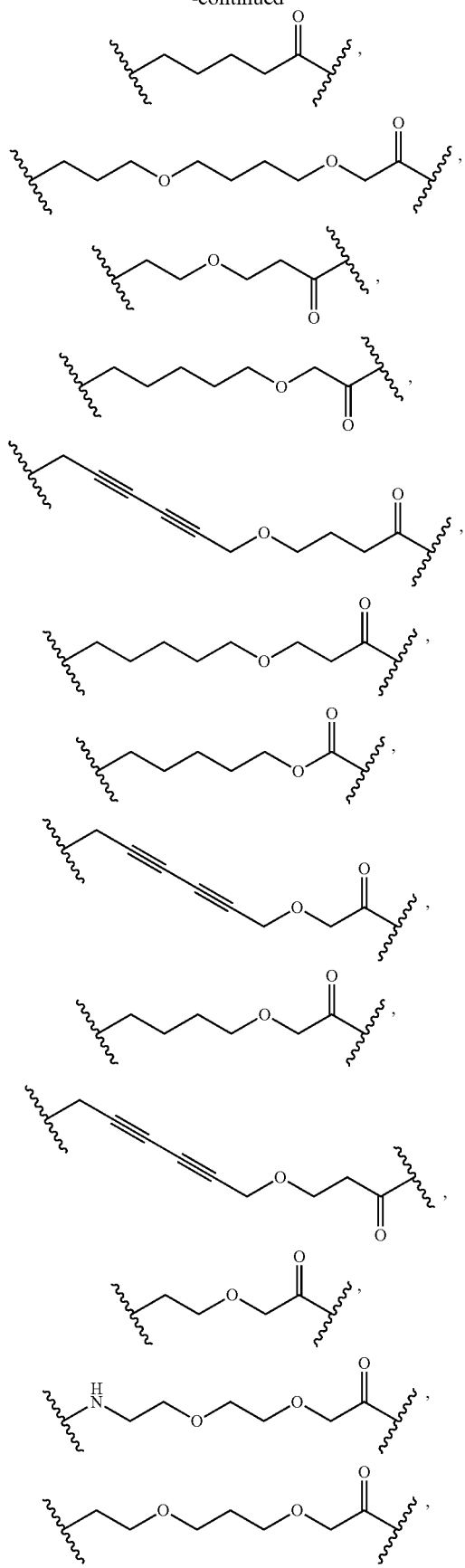

793
-continued
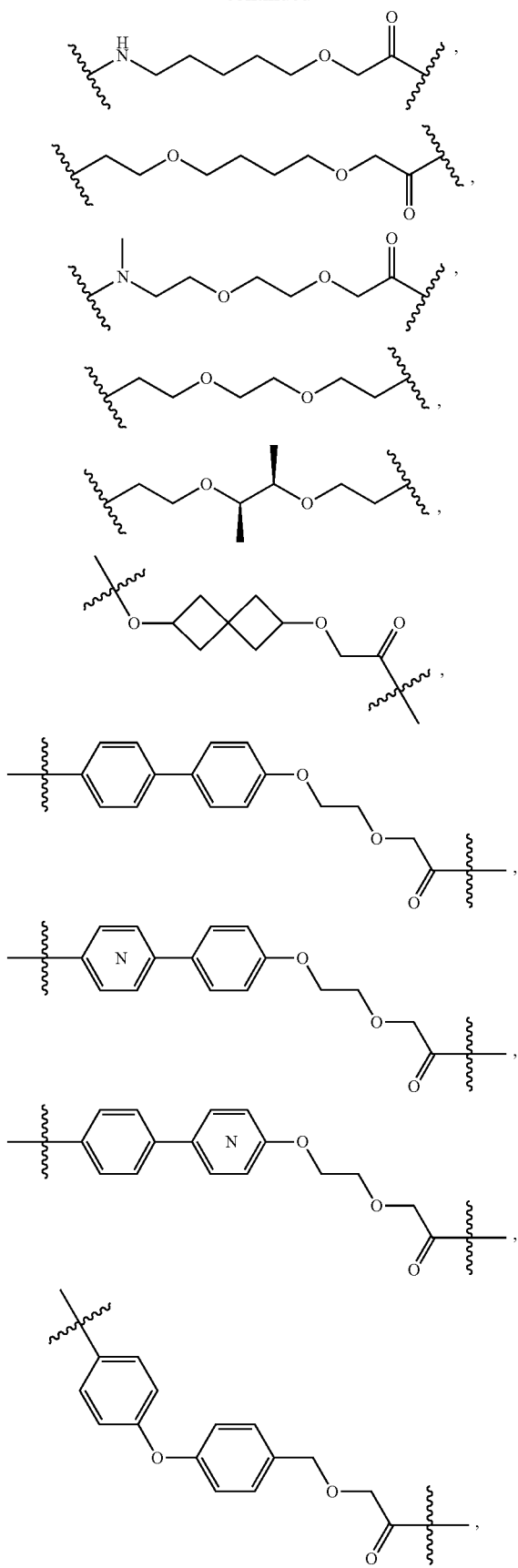
794
-continued
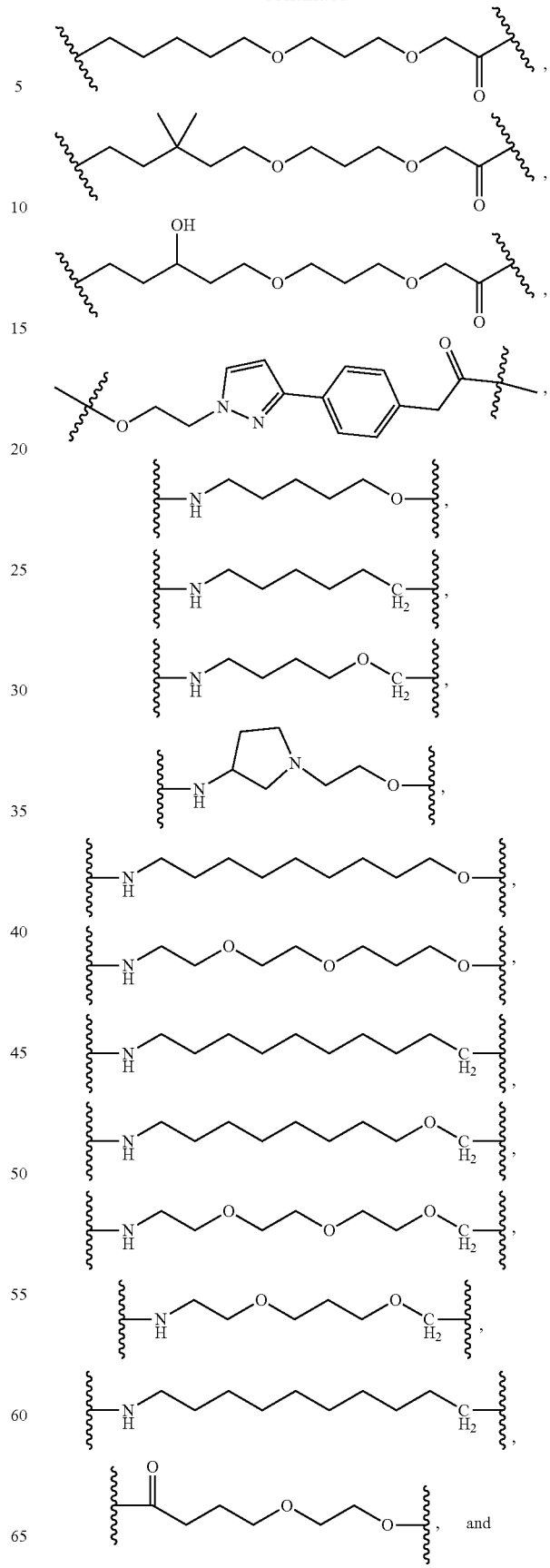

-continued

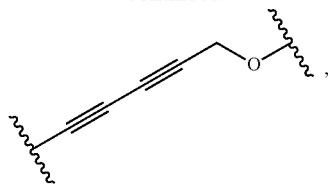 [SMILES: *C#CC#CCO*]

wherein ∿∿∿ indicates the point of attachment to the remaining structure of the compound or D; wherein L may be attached to the compound in either orientation.

23. The compound of claim 7, or a pharmaceutically acceptable salt thereof, wherein said compound is selected from the group consisting of:

7-(3,5-difluoropyridin-2-yl)-N-(5-((5-(1-(4-hydroxy-2-(5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide, 7-(3,5-difluoropyridin-2-yl)-N-(5-((5-((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide, 7-(3,5-difluoropyridin-2-yl)-N-(5-((5-((S)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide, 7-(3,5-difluoropyridin-2-yl)-N-(5-((5-((R)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide, 7-(3,5-difluoropyridin-2-yl)-N-(5-((5-((R)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide, 7-(3,5-difluoropyridin-2-yl)-N-(5-((5-((R)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide, 7-(3,5-difluoropyridin-2-yl)-N-(5-((5-((R)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide, 7-(3,5-difluoropyridin-2-yl)-N-(5-((5-((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide, 7-(3,5-difluoropyridin-2-yl)-N-(5-((5-((S)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)pentyl)-2-methyl-10-((methylsulfonyl)methyl)-3-oxo-3,4,6,7-tetrahydro-2H-2,4,7-triazadibenzo[cd,f]azulene-9-carboxamide, 4-(3,5-difluoropyridin-2-yl)-N-(1-(2-((5-(1-(4-hydroxy-2-(5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N—((S)-1-(2-((5-((R)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N—((S)-1-(2-((5-((R)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N—((S)-1-(2-((5-((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N—((S)-1-(2-((5-((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N—((S)-1-(2-((5-((R)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N—((S)-1-(2-((5-((R)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N—((S)-1-(2-((5-((S)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N—((S)-1-(2-((5-((S)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethyl)pyrrolidin-3-yl)-10-methyl-7-((methylsulfonyl)methyl)-11-oxo-3,4,10,11-tetrahydro-1H-1,4,10-triazadibenzo[cd,f]azulene-6-carboxamide, 4-(2-((5-(1-(4-hydroxy-2-(5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-(1-(4-hydroxyphenyl)-2-phenylbut-1-en-1-yl)phenoxy)ethyl)-N-methylbutanamide, 4-(2-((5-((R)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide, 4-(2-((5-((R)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide, 4-(2-((5-((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide, 4-(2-((5-((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide, 4-(2-((5-((R)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide, 4-(2-((5-((R)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide, 4-(2-((5-((S)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide, 4-(2-((5-((S)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((Z)-1-(4-hydroxyphenyl)-2-phenylbut-1-en-1-yl)phenoxy)ethyl)-N-methylbutanamide, 4-(2-((5-((R)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide, 4-(2-((5-((R)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide, 4-(2-((5-((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide, 4-(2-((5-((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide, 4-(2-((5-((R)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide, 4-(2-((5-((R)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide, 4-(2-((5-((S)-1-((2R,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide, 4-(2-((5-((S)-1-((2S,4R)-4-hydroxy-2-((R)-5-methyl-5-(4-(4-methylthiazol-5-yl)phenyl)-4-oxo-4,5-dihydro-1H-imidazol-2-yl)pyrrolidin-1-yl)-3-methyl-1-oxobutan-2-yl)isoxazol-3-yl)oxy)ethoxy)-N-(2-(4-((E)-1-(4-hydroxyphenyl)-2-phenylbut-1-en-1-yl)phenoxy)ethyl)-N-methylbutanamide, 2-(1-(2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one, (5S)-2-((4R)-1-(2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one, (S)-2-((2S,4R)-1-((R)-2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one, (S)-2-((2S,4R)-1-((S)-2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one, (S)-2-((2R,4R)-1-((R)-2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one, (S)-2-((2R,4R)-1-((S)-2-(3-((6-(2-((4-((3-ethynylphenyl)amino)-7-(2-methoxyethoxy)quinazolin-6-yl)oxy)ethoxy)hexa-2,4-diyn-1-yl)oxy)isoxazol-5-yl)-3-methylbutanoyl)-4-hydroxypyrrolidin-2-yl)-5-methyl-5-(4-(4-methylthiazol-5-yl)phenyl)-1,5-dihydro-4H-imidazol-4-one, 4-(3,5-difluoropyridin-2-yl)-N-(11-((1-(4-hydroxy-2-(5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(11-(((2S)-1-((4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(11-(((S)-1-((2S,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(11-(((S)-1-((2R,4R)-4-hydroxy-2-((S)-5-methyl-5-(4-(4-methylthiazol-5-yl)phenyl)-4-oxo-4,5-dihydro-1H-imidazol-2-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(11-((1-(4-hydroxy-2-(5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(11-(((2S)-1-((4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(11-((1-((2S,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(11-(((S)-1-((2S,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(11-(((S)-1-((2R,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(11-(((R)-1-((2S,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3,3-dimethyl-1-oxobutan-2-yl)amino)-11-oxoundecyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(5-((5-(1-(4-hydroxy-2-(5-methyl-5-(4-(4-methylthiazol-5-yl)phenyl)-4,5-dihydro-1,2,4-oxadiazol-3-yl)pyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(5-((5-((2R)-1-((4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(5-((5-((R)-1-((2S,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(5-((5-((R)-1-((2R,4R)-4-hydroxy-2-((R)-5-methyl-5-(4-(4-methylthiazol-5-yl)phenyl)-4,5-dihydro-1,2,4-oxadiazol-3-yl)pyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(5-((5-(1-(2-(1-ethyl-5-methyl-5-(4-(4-methylthiazol-5-yl)phenyl)-4,5-dihydro-1H-1,2,4-triazol-3-yl)-4-hydroxypyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide, 4-(3,5-difluoropyridin-2-yl)-N-(5-((5-((2R)-1-((4R)-2-((R)-1-ethyl-5-methyl-5-(4-(4-methylthiazol-5-yl)phenyl)-4,5-dihydro-1H-1,2,4-triazol-3-yl)-4-hydroxypyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide,

801

4-(3,5-difluoropyridin-2-yl)-N-(5-((5-((R)-1-((2S,4R)-2-((R)-1-ethyl-5-methyl-5-(4-(4-methylthiazol-5-yl)phenyl)-4,5-dihydro-1H-1,2,4-triazol-3-yl)-4-hydroxypyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide, and 4-(3,5-difluoropyridin-2-yl)-N-(5-((5-((R)-1-((2R,4R)-2-((R)-1-ethyl-5-methyl-5-(4-(4-methylthiazol-5-yl)phenyl)-4,5-dihydro-1H-1,2,4-triazol-3-yl)-4-hydroxypyrrolidin-1-yl)-3-methyl-1-oxobutan-2-yl)isoxazol-3-yl)oxy)pentyl)-10-methyl-7-((methylsulfonyl)methyl)-11-oxo-3,4,10,11-tetrahydro-1H-1,4,10-triazadibenzo[cd,f]azulene-6-carboxamide;

802 and tautomers thereof.

24. The compound of claim 7, or a pharmaceutically acceptable salt thereof, having a structure selected from the group consisting of

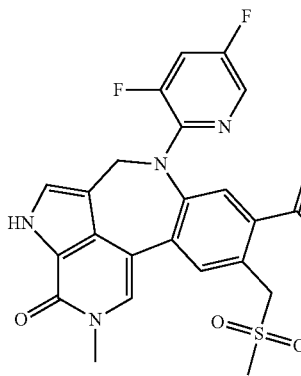
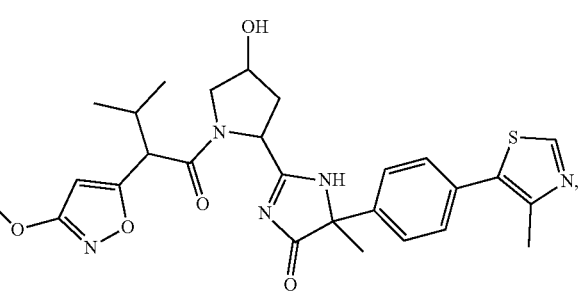

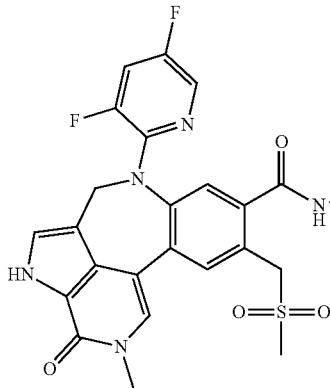
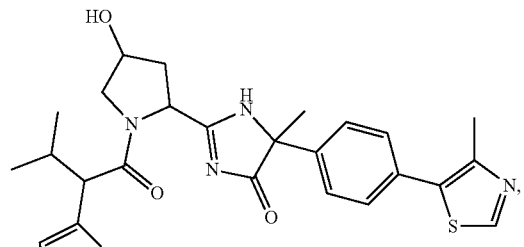

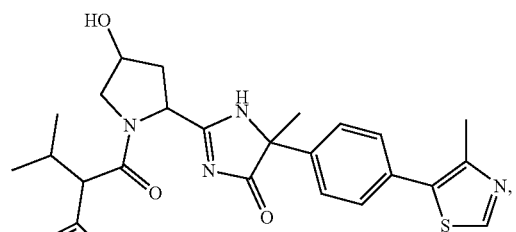

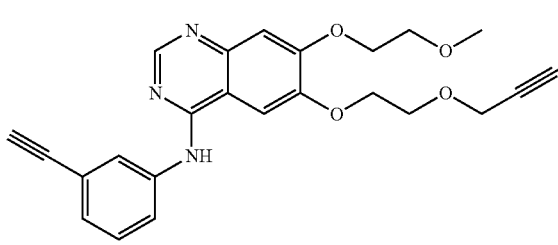

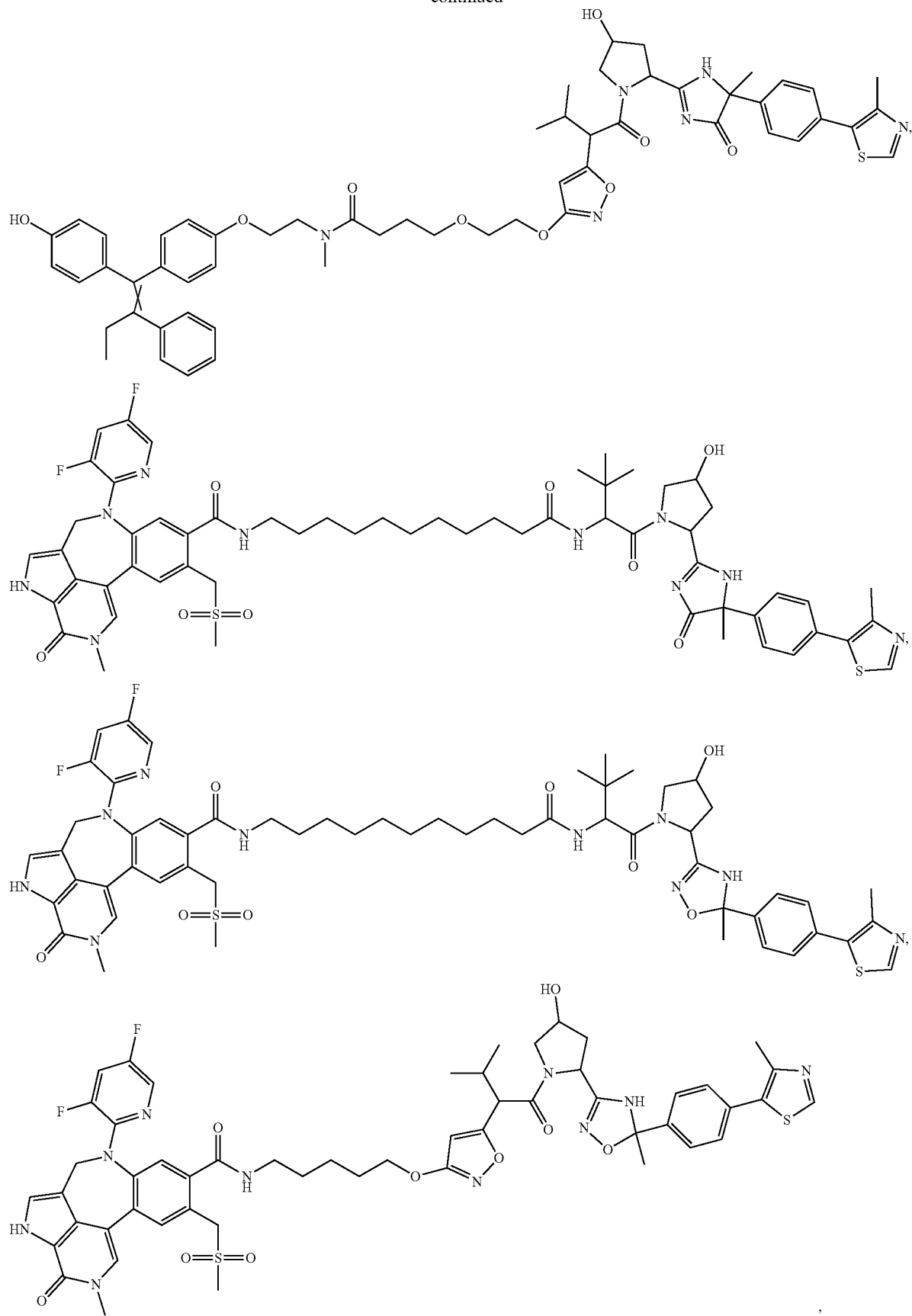

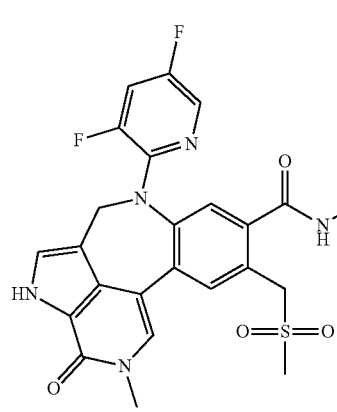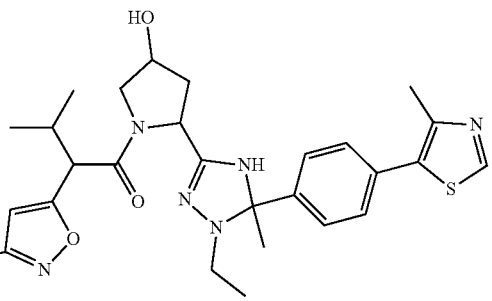
and tautomers and stereoisomers thereof.
25. The compound of claim 7, or a pharmaceutically acceptable salt thereof, having a structure selected from the group consisting of
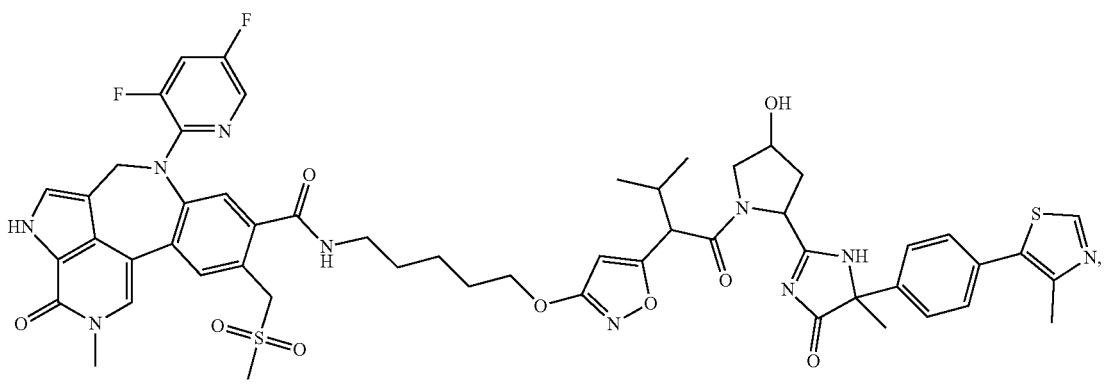
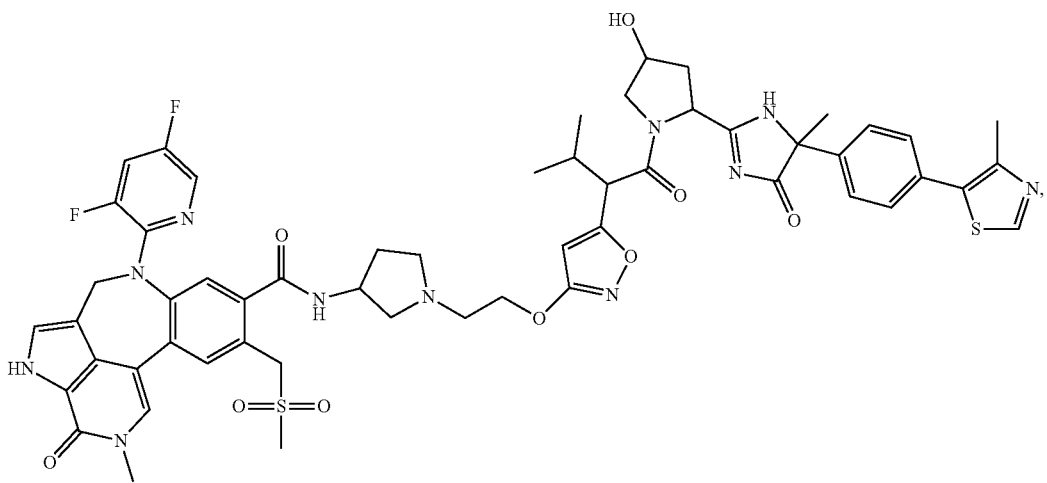

807 808
-continued
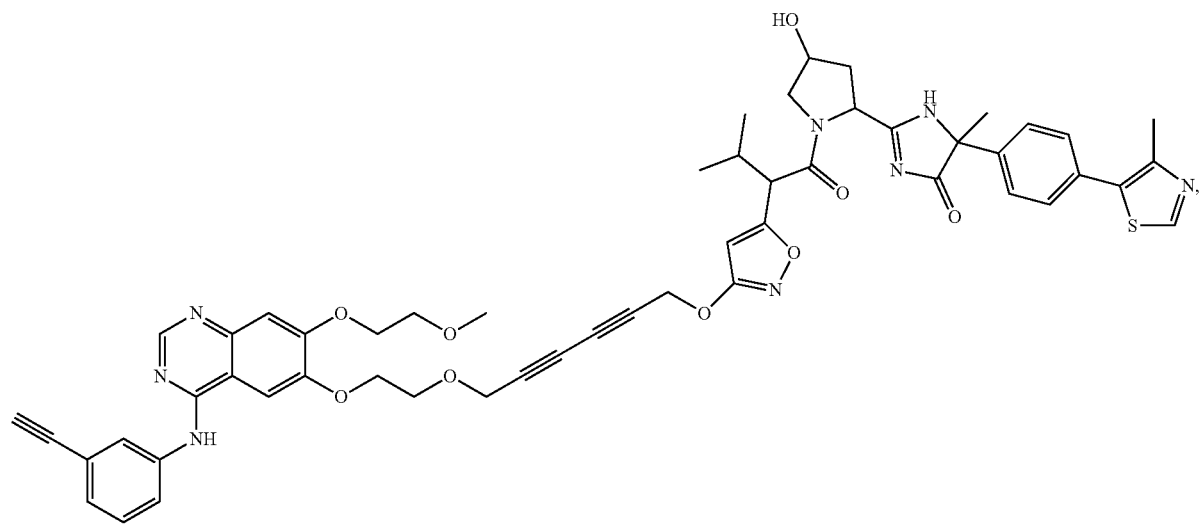
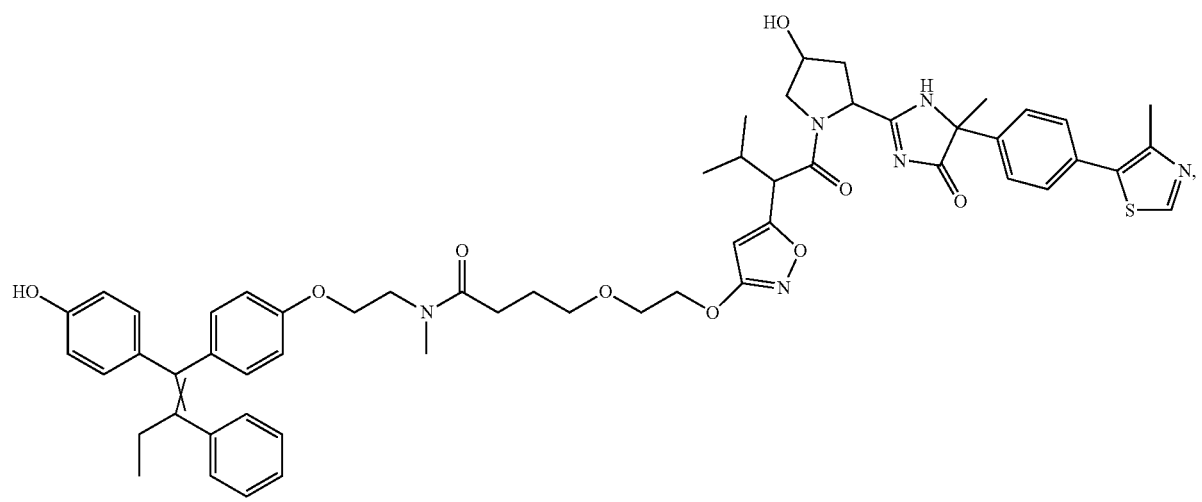
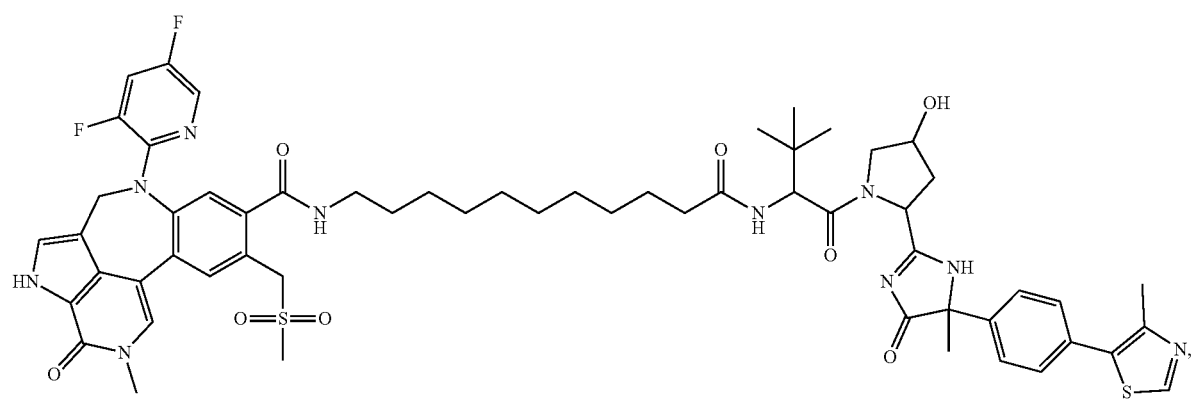

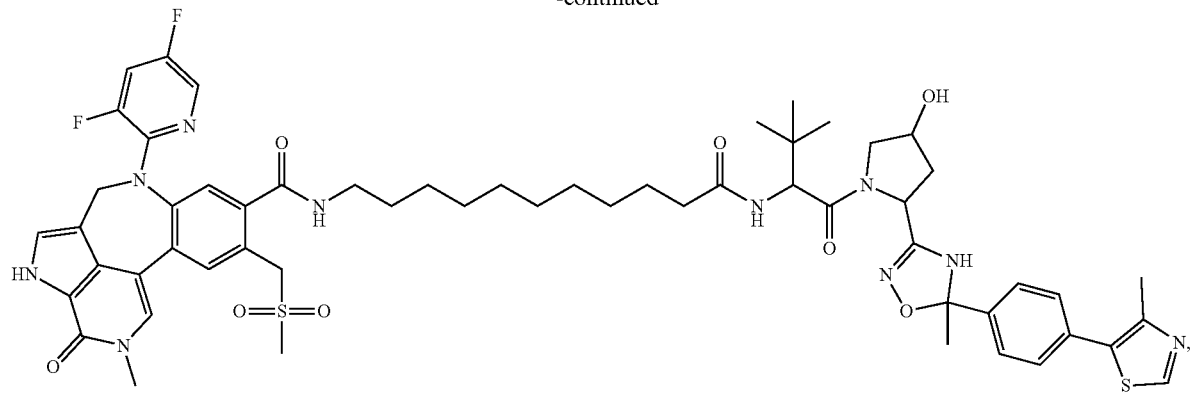

and tautomers and stereoisomers thereof.

26. A pharmaceutical composition comprising a compound of claim 7, or a pharmaceutically acceptable salt thereof, and one or more pharmaceutically acceptable excipients.

27. A method of degrading a target protein in a cell comprising exposing the cell to a composition comprising an effective amount of the compound of claim 7, or a pharmaceutically acceptable salt thereof, wherein the compound effectuates the degradation of the target protein.

28. The method of claim 27, wherein the target protein modulates a hyperproliferative disorder.

29. A method of treating a hyperproliferative disorder in a subject in need thereof during the course of said hyperproliferative disorder, comprising administering to said subject an effective amount of the compound of claim 7, or a pharmaceutically acceptable salt thereof, wherein the compound effectuates the degradation of a target protein that modulates the hyperproliferative disorder.

* * * * *